US009376422B2

(12) United States Patent
Kuntz et al.

(10) Patent No.: US 9,376,422 B2
(45) **Date of Patent: *Jun. 28, 2016**

(54) DIHIDROPYRIDIN-2-ONE BENZAMINE COMPOUNDS

(75) Inventors: Kevin Wayne Kuntz, Woburn, MA (US); Richard Chesworth, Concord, MA (US); Kenneth William Duncan, Norwood, MA (US); Heike Keilhack, Belmont, MA (US); Natalie Warholic, Brighton, MA (US); Christine Klaus, Weymouth, MA (US); Sarah K. Knutson, Cambridge, MA (US); Timothy James Nelson Wigle, Waltham, MA (US); Masashi Seki, Tsukuba (JP)

(73) Assignee: Epizyme, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/110,873

(22) PCT Filed: Apr. 13, 2012

(86) PCT No.: PCT/US2012/033662

§ 371 (c)(1),
(2), (4) Date: Jan. 30, 2014

(87) PCT Pub. No.: WO2012/142513

PCT Pub. Date: Oct. 18, 2012

(65) Prior Publication Data

US 2014/0142083 A1 May 22, 2014

Related U.S. Application Data

(60) Provisional application No. 61/474,825, filed on Apr. 13, 2011, provisional application No. 61/505,676, filed on Jul. 8, 2011.

(51) Int. Cl.

| | |
|---|---|
| ***C07D 213/64*** | (2006.01) |
| ***C07D 401/12*** | (2006.01) |
| ***C07D 401/14*** | (2006.01) |
| ***C07D 405/12*** | (2006.01) |
| ***C07D 405/14*** | (2006.01) |
| ***C07D 407/12*** | (2006.01) |
| ***C07D 409/12*** | (2006.01) |
| ***C07D 413/12*** | (2006.01) |
| ***C07D 413/14*** | (2006.01) |
| ***C07D 491/10*** | (2006.01) |
| ***C07D 491/113*** | (2006.01) |

(52) U.S. Cl.

CPC ............ *C07D 405/14* (2013.01); *C07D 213/64* (2013.01); *C07D 401/12* (2013.01); *C07D 401/14* (2013.01); *C07D 405/12* (2013.01); *C07D 407/12* (2013.01); *C07D 409/12* (2013.01); *C07D 413/12* (2013.01); *C07D 413/14* (2013.01); *C07D 491/10* (2013.01); *C07D 491/113* (2013.01)

(58) Field of Classification Search

CPC .. C07D 307/08; C07D 307/06; C07D 213/64; C07D 401/12; C07D 401/14; C07D 405/12; C07D 405/14; C07D 407/12; C07D 409/12; C07D 413/12; C07D 413/14

USPC ........................................................ 549/429

See application file for complete search history.

(56) References Cited

U.S. PATENT DOCUMENTS

| | | | | |
|---|---|---|---|---|
| 5,716,993 | A | 2/1998 | Ozaki et al. | |
| 5,948,803 | A | 9/1999 | Maeda et al. | |
| 7,122,547 | B1 | 10/2006 | Huth et al. | |
| 7,252,968 | B2 | 8/2007 | Jenuwein et al. | |
| 7,442,685 | B2 | 10/2008 | Zhang et al. | |
| 7,563,589 | B2 | 7/2009 | Zhang et al. | |
| 7,923,219 | B2 | 4/2011 | Wang et al. | |
| 8,410,088 | B2 * | 4/2013 | Kuntz et al. | 514/211.15 |
| 8,754,230 | B2 | 6/2014 | Livingston et al. | |
| 8,765,732 | B2 | 7/2014 | Kuntz et al. | |
| 8,895,245 | B2 | 11/2014 | Copeland et al. | |
| 2002/0183324 | A1 | 12/2002 | Jacobson et al. | |
| 2004/0082619 | A1 | 4/2004 | Tada et al. | |
| 2005/0266473 | A1 | 12/2005 | Zhang et al. | |
| 2008/0182844 | A1 | 7/2008 | Bjergarde et al. | |

(Continued)

FOREIGN PATENT DOCUMENTS

| | | | |
|---|---|---|---|
| CN | 101977905 | A | 2/2011 |
| EP | 1357111 | A1 | 10/2003 |

(Continued)

OTHER PUBLICATIONS

Braña et al. "Reaction of *N*-(2-Pyridylmethyl)-3,5-dimethylbenzamide and *N*-(3-Pyridylmethyl)-3,5-dimethylbenzamide *N*-Oxides With Acetic Anhydride." *Journal of Heterocyclic Chemistry*. 19.6(1982):1297-1300.
Chemical Abstracts Service Registry Nos. 1111568-29-6, 1111508-57-6, and 1111473-93-8 entered Feb. 25, 2009.
Chemical Abstracts Service Registry Nos. 1118856-92-0, 1118847-80-5, 1118847-59-8, 1118826-65-5, 1118826-02-0, 1118825-96-9, 1118825-75-4, 1118825-72-1, and 1118825-69-6 entered Mar. 11, 2009.
Chemical Abstracts Service Registry Nos. 1278089-60-3, 1277914-52-9, and 1277529-83-5, entered Apr. 10, 2011.
Chemical Abstracts Service Registry Nos. 1278854-92-4 and 127885491-3, entered Apr. 12, 2011.
Chemical Abstracts Service Registry Nos. 919939-47-2 and 919873-05-5 entered Feb. 8, 2007.
Chemical Abstracts Service Registry Nos. 923162-97-4, 923152-74-3, and 923111-85-7 entered Feb. 26, 2007.
Chemical Abstracts Service Registry Nos. 923774-47-4, 923730-10-3, and 923690-12-4 entered Feb. 28, 2007.

(Continued)

*Primary Examiner* — Valerie Rodriguez-Garcia

(74) *Attorney, Agent, or Firm* — Cooley LLP; Heidi A. Erlacher; Lian Ouyang

(57) ABSTRACT

The present invention relates to substituted benzene compounds. The present invention also relates to pharmaceutical compositions containing these compounds and methods of treating cancer by administering these compounds and pharmaceutical compositions to subjects in need thereof. The present invention also relates to the use of such compounds for research or other non-therapeutic purposes.

19 Claims, 4 Drawing Sheets

(56) References Cited

U.S. PATENT DOCUMENTS

| | | | |
|---|---|---|---|
| 2008/0222741 | A1 | 9/2008 | Chinnaiyan |
| 2008/0269289 | A1 | 10/2008 | Frank et al. |
| 2008/0312292 | A1 | 12/2008 | Yasui et al. |
| 2009/0012031 | A1 | 1/2009 | Chinnaiyan et al. |
| 2009/0061443 | A1 | 3/2009 | Zhang et al. |
| 2009/0203057 | A1 | 8/2009 | Zhang et al. |
| 2010/0035912 | A1 | 2/2010 | Debnath et al. |
| 2010/0113415 | A1 | 5/2010 | Rajapakse et al. |
| 2011/0021362 | A1 | 1/2011 | Trojer et al. |
| 2013/0004090 | A1 | 1/2013 | Kundu et al. |
| 2013/0040906 | A1 | 2/2013 | Kuntz et al. |
| 2013/0123234 | A1 | 5/2013 | Kuntz et al. |
| 2014/0107122 | A1 | 4/2014 | Kuntz et al. |
| 2014/0288041 | A1 | 9/2014 | Kuntz et al. |

FOREIGN PATENT DOCUMENTS

| | | | |
|---|---|---|---|
| JP | 7033729 | A | 2/1995 |
| TW | I287004 | B | 9/2007 |
| WO | WO-9640100 | A1 | 12/1996 |
| WO | WO-0018725 | A1 | 4/2000 |
| WO | WO-03079788 | A2 | 10/2003 |
| WO | WO-2006116713 | A1 | 11/2006 |
| WO | WO-2007045462 | A2 | 4/2007 |
| WO | WO-2007050347 | A1 | 5/2007 |
| WO | WO-2007070818 | A1 | 6/2007 |
| WO | WO-2007136592 | A2 | 11/2007 |
| WO | WO-2008073138 | A2 | 6/2008 |
| WO | WO-2008103277 | A2 | 8/2008 |
| WO | WO-2008104077 | A1 | 9/2008 |
| WO | WO-2008108825 | A2 | 9/2008 |
| WO | WO-2008113006 | A1 | 9/2008 |
| WO | WO-2009058298 | A1 | 5/2009 |
| WO | WO-2009077766 | A1 | 6/2009 |
| WO | WO 2009/094427 | A1 | 7/2009 |
| WO | WO-2009124137 | A2 | 10/2009 |
| WO | WO-2010018328 | A1 | 2/2010 |
| WO | WO 2010/039248 | A1 | 4/2010 |
| WO | WO-2010111653 | A2 | 9/2010 |
| WO | WO-2011082044 | A1 | 7/2011 |
| WO | WO-2011140324 | A1 | 11/2011 |
| WO | WO-2011140325 | A1 | 11/2011 |
| WO | WO-2012005805 | A1 | 1/2012 |
| WO | WO-2012034132 | A2 | 3/2012 |
| WO | WO-2012068589 | A2 | 5/2012 |
| WO | WO-2012075080 | A1 | 6/2012 |
| WO | WO-2012075500 | A2 | 6/2012 |
| WO | WO-2012118812 | A2 | 9/2012 |
| WO | WO-2012142504 | A1 | 10/2012 |
| WO | WO-2013173441 | A2 | 11/2013 |
| WO | WO 2014/062733 | | 4/2014 |

OTHER PUBLICATIONS

Chemical Abstracts Service Registry Nos. 941139-86-2 and 941091-93-6 entered Jul. 4, 2007.

Gura et al. "Systems for Identifying New Drugs are Often Faulty." *Science*. 278.5340(1997):1041-1042.

Johnson et al. "Relationships Between Drug Activity in NCI Preclinical in vitro and in vivo Models and Early Clinical Trials." *Brit. J. Cancer*. 84.10(2001):1424-1431.

Knutson et al. "A Selective Inhibitor of EZH2 Blocks H3K27 Methylation and Kills Mutant Lymphoma Cells." *Nat. Chem. Biol*. (2012):1-7. Epub: Sep. 30, 2012.

Lohr et al. "Discovery and Prioritization of Somatic Mutations in Diffuse Large B-Cell Lymphoma (DLBCL) by Whole-Exome Sequencing." *PNAS*. 109.10(2012):3879-3884. Epub Feb. 17, 2012.

Martinez-Garcia et al. "The MMSET Histone Methyl Transferase Switches Global Histone Methylation and Alters Gene Expression in t(4;14) Multiple Myeloma Cells." *Blood*. 117(2011):211-220.

McCabe et al. "EZH2 Inhibition as a Therapeutic Strategy for Lymphoma With EZH2-Activating Mutations." *Nature*. Epub: Oct. 10, 2012.

McCabe et al. "Mutation of A677 in Histone Methyltransferase EZH2 in Human B-Cell Lymphoma Promotes Hypertrimethylation of Histone H3 on Lysine 27 (H3K27)." *PNAS*. 109.8(2012):2989-2994.

Miranda et al. "DZNep is a Global Histone Methylation Inhibitor That Reactivates Developmental Genes not Silenced by DNA Methylation." *Mol. Cancer Ther*. 8.6(2009):1579-1588.

Morin et al. "Somatic Mutations Altering EZH2 (Tyr641) in Follicular and Diffuse Large B-Cell Lymphomas of Germinal-Center Origin." *Nat. Genet*. 42.2(2010):181-185.

Pearce et al. "Failure Modes in Anticancer Drug Discovery and Development." *Cancer Drug Design and Discovery*. Neidle, ed. Boston: Elsevier. (2008):424-435.

Sculley et al. "Some Amide Derivatives of Certain Aminomethylpyridines." *J. Am. Chem. Soc*. 75.14(1953):3400-3403.

Simone. "Oncology: Introduction." *Cecil Textbook of Medicine*. Bennett et al., eds. Philadelphia: W. B. Saunders Co. 20th ed. 1(1996):1004-1104.

Sneeringer et al. "Coordinated Activities of Wild-Type Plus Mutant EZH2 Drive Tumor-Associated Hypertrimethylation of Lysine 27 on Histone H3 (H3K27) in Human B-Cell Lymphomas." *PNAS*. 107.49(2010):20980-20985.

Wigle et al. "The Y641C Mutation of EZH2 Alters Substrate Specificity for Histone H3 Lysine 27 Methylation States." *FEBS Lett*. 585.19(2011):3011-3014.

Wilson et al. "Epigenetic Antagonism Between Polycomb and SWI/SNF Complexes During Oncogenic Transformation." *Cancer Cell*. 18(2010):316-328.

Yap et al. "Somatic Mutations at EZH2 Y641 Act Dominantly Through a Mechanism of Selectively Altered PRC2 Catalytic Activity, to Increase H3K27 Trimethylation." *Blood*. 117.8(2010):2451-2459.

* cited by examiner

SEQUENCE LISTING

```
<160> NUMBER OF SEQ ID NOS: 2

<210> SEQ ID NO 1
<211> LENGTH: 26
<212> TYPE: PRT
<213> ORGANISM: Artificial Sequence
<220> FEATURE:
<223> OTHER INFORMATION: Chemically synthesized polypeptide
<220> FEATURE:
<221> NAME/KEY: MISC_FEATURE
<222> LOCATION: (26)..(26)
<223> OTHER INFORMATION: wherein a biotin and an amide are conjugated

<400> SEQUENCE: 1

Ala Thr Lys Ala Ala Arg Lys Ser Ala Pro Ala Thr Gly Gly Val Lys
1               5                   10                  15

Lys Pro His Arg Tyr Arg Pro Gly Gly Lys
            20                  25


<210> SEQ ID NO 2
<211> LENGTH: 26
<212> TYPE: PRT
<213> ORGANISM: Artificial Sequence
<220> FEATURE:
<223> OTHER INFORMATION: Chemically synthesized polypeptide
<220> FEATURE:
<221> NAME/KEY: MISC_FEATURE
<222> LOCATION: (7)..(7)
<223> OTHER INFORMATION: wherein the lysine is dimethylated
<220> FEATURE:
<221> NAME/KEY: MISC_FEATURE
<222> LOCATION: (26)..(26)
<223> OTHER INFORMATION: wherein a biotin and an amide are conjugated

<400> SEQUENCE: 2

Ala Thr Lys Ala Ala Arg Lys Ser Ala Pro Ala Thr Gly Gly Val Lys
1               5                   10                  15

Lys Pro His Arg Tyr Arg Pro Gly Gly Lys
            20                  25
```

DIHIDROPYRIDIN-2-ONE BENZAMINE COMPOUNDS

RELATED APPLICATIONS

This application is a national stage application, filed under 35 U.S.C. §371, of International Application No. PCT/US2012/033662, filed Apr. 13, 2012, which claims priority to, and the benefit of, U.S. provisional application Nos. 61/474,825, filed Apr. 13, 2011, and 61/505,676 filed Jul. 8, 2011, the entire contents of each of which are incorporated herein by reference in their entireties.

INCORPORATION-BY-REFERENCE OF SEQUENCE LISTING

The contents of the text file named "41478508001 WOST25.txt," which was created on Mar. 28, 2012 and is 2 KB in size, are hereby incorporated by reference in their entireties.

BACKGROUND OF THE INVENTION

In eukaryotic cells DNA is packaged with histones to form chromatin. Changes in the ordered structure of chromatin can lead to alterations in transcription of associated genes. Control of changes in chromatin structure (and hence of transcription) is mediated by covalent modifications to histones, most notably of their N-terminal tails. These modifications are often referred to as epigenetic because they can lead to heritable changes in gene expression, but do not affect the sequence of the DNA itself. Covalent modifications (for example, methylation, acetylation, phosphorylation, and ubiquitination) of the side chains of amino acids are enzymatically mediated. The selective addition of methyl groups to specific amino acid sites on histones is controlled by the action of a unique family of enzymes known as histone methyltransferases (HMTs).

The orchestrated collection of biochemical systems behind transcriptional regulation must be tightly controlled in order for cell growth and differentiation to proceed optimally. Disease states result when these controls are disrupted by aberrant expression and/or activity of the enzymes responsible for DNA and histone modification. In human cancers, for example, there is a growing body of evidence to suggest that dysregulated epigenetic enzyme activity contributes to the uncontrolled cell proliferation associated with cancer as well as other cancer-relevant phenotypes such as enhanced cell migration and invasion. Beyond cancer, there is growing evidence for a role of epigenetic enzymes in a number of other human diseases, including metabolic diseases (such as diabetes), inflammatory diseases (such as Crohn's disease), neurodegenerative diseases (such as Alzheimer's disease) and cardiovascular diseases. Therefore, selectively modulating the aberrant action of epigenetic enzymes may hold promise for the treatment of a range of diseases.

Polycomb group (PcG) and trithorax group (trxG) proteins are known to be part of the cellular memory system. See, e.g., Francis et al. (2001) *Nat Rev Mol Cell Biol* 2:409-21 and Simon et al. (2002) *Curr Opin Genet Dev* 12:210-8. In general, PcG proteins are transcriptional repressors that maintain the "off state," and trxG proteins are transcriptional activators that maintain the "on state." Because members of PcG and trxG proteins contain intrinsic histone methyltransferase (HMTase) activity, PcG and trxG proteins may participate in cellular memory through methylation of core histones. See, e.g., Beisel et al. (2002) *Nature* 419:857-62; Cao et al. (2002) *Science* 298:1039-43; Czermin et al. (2002) *Cell* 111:185-96; Kuzmichev et al. (2002) *Genes Dev* 16:2893-905; Milne et al. (2002) *Mol Cell* 10:1107-17; Muller et al. (2002) *Cell* 111:197-208; and Nakamura et al. (2002) *Mol Cell* 10:1119-28.

Biochemical and genetic studies have provided evidence that *Drosophila* PcG proteins function in at least two distinct protein complexes, the Polycomb repressive complex 1 (PRC1) and the ESC-E(Z) complex (also known as Polycomb repressive complex 2 (PRC2)). Otte et al. (2003) *Curr Opin Genet Dev* 13:448-54. Studies in *Drosophila* have demonstrated that the ESC-E(Z)/EED-EZH2 (i.e., PRC2) complexes have intrinsic histone methyltransferase activity. Although the compositions of the complexes isolated by different groups are slightly different, they generally contain EED, EZH2, SUZ12, and RbAp48 or *Drosophila* homologs thereof. However, a reconstituted complex comprising only EED, EZH2, and SUZ12 retains histone methyltransferase activity for lysine 27 of histone H3. U.S. Pat. No. 7,563,589.

Of the various proteins making up PRC2 complexes, EZH2 (Enhancer of Zeste Homolog 2) is the catalytic subunit. The catalytic site of EZH2 in turn is present within a SET domain, a highly conserved sequence motif (named after Su(var)3-9, Enhancer of Zeste, Trithorax) that is found in several chromatin-associated proteins, including members of both the Trithorax group and Polycomb group. SET domain is characteristic of all known histone lysine methyltransferases except the H3-K79 methyltransferase DOT1.

In addition to Hox gene silencing, PRC2-mediated histone H3-K27 methylation has been shown to participate in X-inactivation. Plath et al. (2003) *Science* 300:131-5; Silva et al. (2003) *Dev Cell* 4:481-95. Recruitment of the PRC2 complex to Xi and subsequent trimethylation on histone H3-K27 occurs during the initiation stage of X-inactivation and is dependent on Xist RNA. Furthermore, EZH2 and its associated histone H3-K27 methyltransferase activity were found to mark differentially the pluripotent epiblast cells and the differentiated trophectoderm, and consistent with a role of EZH2 in maintaining the epigenetic modification patterns of pluripotent epiblast cells, Cre-mediated deletion of EZH2 results in loss of histone H3-K27 methylation in the cells. Erhardt et al. (2003) *Development* 130:4235-48). Further, studies in prostate and breast cancer cell lines and tissues have revealed a strong correlation between the levels of EZH2 and SUZ12 and the invasiveness of these cancers, indicating that dysfunction of the PRC2 complex may contribute to cancer. Bracken et al. (2003) *EMBO J* 22:5323-35; Kirmizis et al. (2003) *Mol Cancer Ther* 2:113-21; Kleer et al. (2003) *Proc Natl Acad Sci USA* 100:11606-11; Varambally et al. (2002) *Nature* 419:624-9.

Recently, somatic mutations of tyrosine 641 (Y641C, Y641F, Y641N, Y641S and Y641H; sometimes also referred to as Y646C, Y646F, Y646N, Y646S and Y646H, respectively) of EZH2 were reported to be associated with follicular lymphoma (FL) and the germinal center B cell-like (GCB) subtype of diffuse large B-cell lymphoma (DLBCL). Morin et al. (2010) *Nat Genet.* 42:181-5. In all cases, occurrence of the mutant EZH2 gene was found to be heterozygous, and expression of both wild-type and mutant alleles was detected in the mutant samples profiled by transcriptome sequencing. It was also demonstrated that all of the mutant forms of EZH2 could be incorporated into the multi-protein PRC2 complex, but that the resulting complexes lacked the ability to catalyze methylation of the H3-K27 equivalent residue of a peptidic substrate. Hence, it was concluded that the disease-associated changes at Tyr641 of EZH2 resulted in loss of function with respect to EZH2-catalyzed H3-K27 methylation.

SUMMARY OF THE INVENTION

In one aspect, the present invention features a substituted benzene compound of Formula (I) below or a pharmaceutically acceptable salt or ester thereof.

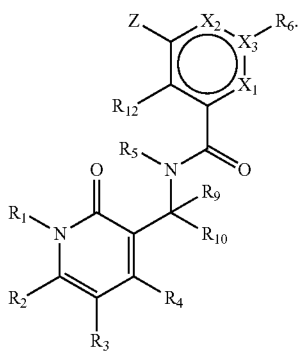

(I)

In this formula:

$X_1$ is N or $CR_{11}$;

$X_2$ is N or $CR_{13}$;

$X_3$ is N or C, and when $X_3$ is N, $R_6$ is absent;

Z is $NR_7R_8$, $OR_7$, $S(O)_aR_7$, or $CR_7R_8R_{14}$, in which a is 0, 1, or 2;

each of $R_1$, $R_5$, $R_9$, and $R_{10}$, independently, is H or $C_1$-$C_6$ alkyl optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

each of $R_2$, $R_3$, and $R_4$, independently, is -$Q_1$-$T_1$, in which $Q_1$ is a bond or $C_1$-$C_3$ alkyl linker optionally substituted with halo, cyano, hydroxyl or $C_1$-$C_6$ alkoxy, and $T_1$ is H, halo, hydroxyl, COOH, cyano, azido, or $R_{S1}$, in which $R_{S1}$ is $C_1$-$C_3$ alkyl, $C_2$-$C_6$ alkenyl, $C_2$-$C_6$ alkynyl, $C_1$-$C_6$ alkoxyl, C(O)O—$C_1$-$C_6$ alkyl, $C_3$-$C_8$ cycloalkyl, $C_6$-$C_{10}$ aryl, amino, mono-$C_1$-$C_6$ alkylamino, di-$C_1$-$C_6$ alkylamino, 4 to 12-membered heterocycloalkyl, or 5- or 6-membered heteroaryl, and $R_{S1}$ is optionally substituted with one or more substituents selected from the group consisting of halo, hydroxyl, oxo, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

$R_6$ is H, halo, cyano, azido, $OR_a$, —$NR_aR_b$, —$C(O)R_a$, —$C(O)OR_a$, —$C(O)NR_aR_b$, —$NR_bC(O)R_a$, —$S(O)_bR_a$, —$S(O)_bNR_aR_b$, or $R_{S2}$, in which $R_{S2}$ is $C_1$-$C_6$ alkyl, $C_2$-$C_6$ alkenyl, $C_2$-$C_6$ alkynyl, $C_3$-$C_8$ cycloalkyl, or 4 to 12-membered heterocycloalkyl; b is 0, 1, or 2; each of $R_a$ and $R_b$, independently is H or $R_{S3}$, and $R_{S3}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl; or $R_a$ and $R_b$, together with the N atom to which they are attached, form a 4 to 12-membered heterocycloalkyl ring having 0 or 1 additional heteroatom; and each of $R_{S2}$, $R_{S3}$, and the 4 to 12-membered heterocycloalkyl ring formed by $R_a$ and $R_b$, is optionally substituted with one or more -$Q_2$-$T_2$, wherein $Q_2$ is a bond or $C_1$-$C_3$ alkyl linker each optionally substituted with halo, cyano, hydroxyl or $C_1$-$C_6$ alkoxy, and $T_2$ is H, halo, cyano, —$OR_c$, —$NR_cR_d$, —$C(O)R_c$, —$C(O)OR_c$, —$C(O)NR_cR_d$, —$NR_dC(O)R_c$, —$NR_dC(O)OR_c$, —$S(O)_2R_c$, —$S(O)_2NR_cR_d$, or $R_{S4}$, in which each of $R_c$ and $R_d$, independently is H or $R_{S5}$, each of $R_{S4}$ and $R_{S5}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_c$ and $R_d$, together with the N atom to which they are attached, form a 4 to 12-membered heterocycloalkyl ring having 0 or 1 additional heteroatom, and each of $R_{S4}$, $R_{S5}$, and the 4 to 12-membered heterocycloalkyl ring formed by $R_c$ and $R_d$, is optionally substituted with one or more -$Q_3$-$T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_e$, $COOR_e$, —$S(O)_2R_e$, —$NR_eR_f$, and —$C(O)NR_eR_f$, each of $R_e$ and $R_f$ independently being H or $C_1$-$C_6$ alkyl, or -$Q_3$-$T_3$ is oxo; or -$Q_2$-$T_2$ is oxo;

$R_7$ is -$Q_4$-$T_4$, in which $Q_4$ is a bond, $C_1$-$C_4$ alkyl linker, or $C_2$-$C_4$ alkenyl linker, each linker optionally substituted with halo, cyano, hydroxyl or $C_1$-$C_6$ alkoxy, and $T_4$ is H, halo, cyano, $NR_gR_h$, —$OR_g$, —$C(O)R_g$, —$C(O)OR_g$, —$C(O)NR_gR_h$, —$C(O)NR_gOR_h$, —$NR_gC(O)R_h$, —$S(O)_2R_g$, or $R_{S6}$, in which each of $R_g$ and $R_h$, independently is H or $R_{S7}$, each of $R_{S6}$ and $R_{S7}$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 14-membered heterocycloalkyl, or 5- or 6-membered heteroaryl, and each of $R_{S6}$ and $R_{S7}$ is optionally substituted with one or more -$Q_5$-$T_5$, wherein $Q_5$ is a bond, C(O), $C(O)NR_k$, $NR_kC(O)$, $S(O)_2$, or $C_1$-$C_3$ alkyl linker, $R_k$ being H or $C_1$-$C_6$ alkyl, and $T_5$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or $S(O)_qR_q$ in which q is 0, 1, or 2 and $R_q$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_5$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_5$ is H, halo, hydroxyl, or cyano; or -$Q_5$-$T_5$ is oxo;

each of $R_8$, $R_{11}$, $R_{12}$, and $R_{13}$, independently, is H, halo, hydroxyl, COOH, cyano, $R_{S8}$, $OR_{S8}$, or $COOR_{S8}$, in which $R_{S8}$ is $C_1$-$C_6$ alkyl, $C_2$-$C_6$ alkenyl, $C_2$-$C_6$ alkynyl, $C_3$-$C_8$ cycloalkyl, 4 to 12-membered heterocycloalkyl, amino, mono-$C_1$-$C_6$ alkylamino, or di-$C_1$-$C_6$ alkylamino, and $R_{S8}$ is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino; or $R_7$ and $R_8$, together with the N atom to which they are attached, form a 4 to 12-membered heterocycloalkyl ring having 0 to 2 additional heteroatoms, or $R_7$ and $R_8$, together with the C atom to which they are attached, form $C_3$-$C_8$ cycloalkyl or a 4 to 12-membered heterocycloalkyl ring having 1 to 3 heteroatoms, and each of the 4 to 12-membered heterocycloalkyl ring or $C_3$-$C_8$ cycloalkyl formed by $R_7$ and $R_8$ is optionally substituted with one or more -$Q_6$-$T_6$, wherein $Q_6$ is a bond, C(O), C(O)NR$_m$, NR$_m$C(O), S(O)$_2$, or $C_1$-$C_3$ alkyl linker, R$_m$ being H or $C_1$-$C_6$ alkyl, and $T_6$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or S(O)$_p$R$_p$ in which p is 0, 1, or 2 and R$_p$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_6$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_6$ is H, halo, hydroxyl, or cyano; or -$Q_6$-$T_6$ is oxo; and $R_{14}$ is absent, H, or $C_1$-$C_6$ alkyl optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

provided that the compound is not

N-(5-(((4,6-dimethyl-2-oxo-1,2-dihydropyridin-3-yl)methyl)carbamoyl)-2-methylphenyl)furan-2-carboxamide, N,N'-(5-(((4,6-dimethyl-2-oxo-1,2-dihydropyridin-3-yl)methyl)carbamoyl)-1,3-phenylene)diacetamide, N-((4,6-dimethyl-2-oxo-1,2-dihydropyridin-3-yl)methyl)-3-pivalamidobenzamide, 3-(3,4-dihydro-2H-benzo[b][1,4]dioxepine-7-sulfonamido)-N-((4,6-dimethyl-2-oxo-1,2-dihydropyridin-3-yl)methyl) benzamide, N-((4,6-dimethyl-2-oxo-1,2-dihydropyridin-3-yl)methyl)-3,5-dimethoxybenzamide, N-((4,6-dimethyl-2-oxo-1,2-dihydropyridin-3-yl)methyl)-3,4,5-trimethoxybenzamide, 3-allyl-N-((4,6-dimethyl-2-oxo-1,2-dihydropyridin-3-yl) methyl)-4,5-dimethoxybenzamide, 4-(2-amino-2-oxoethoxy)-3-chloro-N-((4,6-dimethyl-2-oxo-1,2-dihydropyridin-3-yl)methyl)-5-methoxybenzamide, 3-chloro-N-((4,6-dimethyl-2-oxo-1,2-dihydropyridin-3-yl) methyl)-4-hydroxy-5-methoxybenzamide, or 3-bromo-N-((4,6-dimethyl-2-oxo-1,2-dihydropyridin-3-yl) methyl)-5-methoxy-4-propoxybenzamide.

In another aspect, the present invention features a substituted benzene compound of Formula (I) above or a pharmaceutically acceptable salt or ester thereof, in which $X_1$ is N or CR$_{11}$;

$X_2$ is N or CR$_{13}$;

$X_3$ is N or C, and when $X_3$ is N, $R_6$ is absent;

Z is NR$_7$R$_8$, OR$_7$, S(O)$_a$R$_7$, or CR$_7$R$_8$R$_{14}$, in which a is 0, 1, or 2;

each of $R_1$, $R_5$, $R_9$, and $R_{10}$, independently, is H or $C_1$-$C_6$ alkyl optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

each of $R_2$, $R_3$, and $R_4$, independently, is -$Q_1$-$T_1$, in which $Q_1$ is a bond or $C_1$-$C_3$ alkyl linker optionally substituted with halo, cyano, hydroxyl or $C_1$-$C_6$ alkoxy, and $T_1$ is H, halo, hydroxyl, COOH, cyano, azido, or R$_{S1}$, in which R$_{S1}$ is $C_1$-$C_3$ alkyl, $C_2$-$C_6$ alkenyl, $C_2$-$C_6$ alkynyl, $C_1$-$C_6$ alkoxyl, C(O)O—$C_1$-$C_6$ alkyl, $C_3$-$C_8$ cycloalkyl, $C_6$-$C_{10}$ aryl, amino, mono-$C_1$-$C_6$ alkylamino, di-$C_1$-$C_6$ alkylamino, 4 to 12-membered heterocycloalkyl, or 5- or 6-membered heteroaryl, and R$_{S1}$ is optionally substituted with one or more substituents selected from the group consisting of halo, hydroxyl, oxo, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

$R_6$ is H, halo, cyano, azido, —NR$_a$R$_b$, —C(O)R$_a$, —C(O)OR$_a$, —C(O)NR$_a$R$_b$, —NR$_b$C(O)R$_a$, —S(O)$_b$R$_a$, —S(O)$_b$NR$_a$R$_b$, or R$_{S2}$, in which R$_{S2}$ is $C_1$-$C_6$ alkyl, $C_2$-$C_6$ alkenyl, $C_2$-$C_6$ alkynyl, $C_3$-$C_8$ cycloalkyl, or 4 to 12-membered heterocycloalkyl, b is 0, 1, or 2, each of R$_a$ and R$_b$, independently is H or R$_{S3}$, and R$_{S3}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl; or R$_a$ and R$_b$, together with the N atom to which they are attached, form a 4 to 12-membered heterocycloalkyl ring having 0 or 1 additional heteroatom; and each of R$_{S2}$, R$_{S3}$, and the 4 to 12-membered heterocycloalkyl ring formed by R$_a$ and R$_b$, is optionally substituted with one or more -$Q_2$-$T_2$, wherein $Q_2$ is a bond or $C_1$-$C_3$ alkyl linker each optionally substituted with halo, cyano, hydroxyl or $C_1$-$C_6$ alkoxy, and $T_2$ is H, halo, cyano, —OR$_c$, —NR$_c$R$_d$, —C(O)R$_c$R$_d$, —C(O)OR$_c$, —C(O)NR$_c$R$_d$, —NR$_d$C(O)R$_c$, —NR$_d$C(O)OR$_c$, —S(O)$_2$R$_c$, —S(O)$_2$NR$_c$R$_d$, or R$_{S4}$, in which each of R$_c$ and R$_d$, independently is H or R$_{S5}$, each of R$_{S4}$ and R$_{S5}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or R$_c$ and R$_d$, together with the N atom to which they are attached, form a 4 to 12-membered heterocycloalkyl ring having 0 or 1 additional heteroatom, and each of R$_{S4}$, R$_{S5}$, and the 4 to 12-membered heterocycloalkyl ring formed by R$_c$ and R$_d$, is optionally substituted with one or more -$Q_3$-$T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, OR$_e$, COOR$_e$, —S(O)$_2$R$_e$, —NR$_e$R$_f$, and —C(O)NR$_e$R$_f$, each of R$_e$ and R$_f$ independently being H or $C_1$-$C_6$ alkyl, or -$Q_3$-$T_3$ is oxo; or -$Q_2$-$T_2$ is oxo;

$R_7$ is -$Q_4$-$T_4$, in which $Q_4$ is a bond, $C_1$-$C_4$ alkyl linker, or $C_2$-$C_4$ alkenyl linker, each linker optionally substituted with halo, cyano, hydroxyl or $C_1$-$C_6$ alkoxy, and $T_4$ is H, halo, cyano, NR$_g$R$_h$, —OR$_g$, —C(O)R$_g$, —O(O)OR$_g$, —C(O)NR$_g$R$_h$, —C(O)NR$_g$OR$_n$, —NR$_g$C(O)R$_h$, —S(O)$_2$R$_g$, or R$_{S6}$, in which each of R$_g$ and R$_h$, independently is H or R$_{S7}$, each of R$_{S6}$ and R$_{S7}$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 14-membered heterocycloalkyl, or 5- or 6-membered heteroaryl, and each of R$_{S6}$ and R$_{S7}$ is optionally substituted with one or more -$Q_5$-$T_5$, wherein $Q_5$ is a bond, C(O), C(O)$NR_k$, $NR_k$C(O), $S(O)_2$, or $C_1$-$C_3$ alkyl linker, $R_k$ being H or $C_1$-$C_6$ alkyl, and $T_5$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or $S(O)_qR_q$ in which q is 0, 1, or 2 and $R_q$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_5$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_5$ is H, halo, hydroxyl, or cyano; or -$Q_5$-$T_5$ is oxo; provided that (i) $R_7$ is not C(O)$R_g$ or —$S(O)_2R_g$ when Z is $NR_7R_8$; (ii) $R_7$ is not $C_1$-$C_6$ alkyl when Z is $OR_7$, and (iii) $R_7$ is not H;

each of $R_8$, $R_{11}$, $R_{12}$, and $R_{13}$, independently, is H, halo, hydroxyl, COOH, cyano, $R_{S8}$, $OR_{S8}$, or $COOR_{S8}$, in which $R_{S8}$ is $C_1$-$C_6$ alkyl, $C_2$-$C_6$ alkenyl, $C_2$-$C_6$ alkynyl, $C_3$-$C_8$ cycloalkyl, 4 to 12-membered heterocycloalkyl, amino, mono-$C_1$-$C_6$ alkylamino, or di-$C_1$-$C_6$ alkylamino, and $R_{S8}$ is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino; or $R_7$ and $R_8$, together with the N atom to which they are attached, form a 4 to 12-membered heterocycloalkyl ring having 0 to 2 additional heteroatoms, or $R_7$ and $R_8$, together with the C atom to which they are attached, form $C_3$-$C_8$ cycloalkyl or a 4 to 12-membered heterocycloalkyl ring having 1 to 3 heteroatoms, and each of the 4 to 12-membered heterocycloalkyl rings or $C_3$-$C_8$ cycloalkyl formed by $R_7$ and $R_8$ is optionally substituted with one or more -$Q_6$-$T_6$, wherein $Q_6$ is a bond, C(O), C(O)$NR_m$, $NR_m$C(O), $S(O)_2$, or $C_1$-$C_3$ alkyl linker, $R_m$ being H or $C_1$-$C_6$ alkyl, and $T_6$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or $S(O)_pR_p$ in which p is 0, 1, or 2 and $R_p$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_6$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_6$ is H, halo, hydroxyl, or cyano; or -$Q_6$-$T_6$ is oxo; and $R_{14}$ is absent, H, or $C_1$-$C_6$ alkyl optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl.

One subset of the compounds of Formula (I) includes those of Formula (Ia):

(Ia)

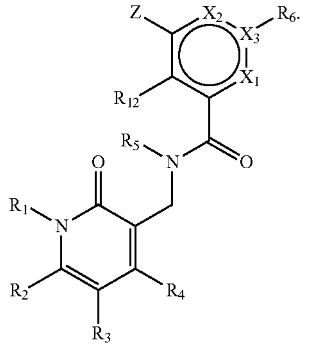

Another subset of the compounds of Formula (I) includes those of Formula (Ib), (Ic), or (Id):

(Ib)

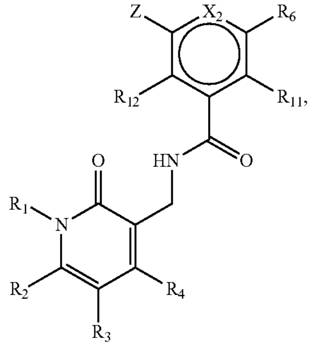

(Ic)

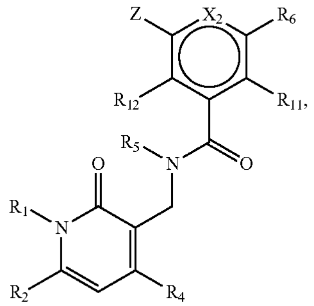

or (Id)

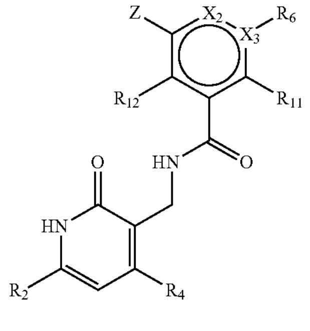

Still another subset of the compounds of Formula (I) includes those of Formula (Ie), (II) or (IIA):

(Ie)

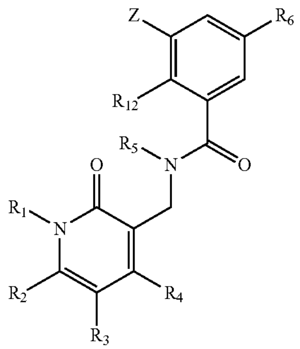

(II)

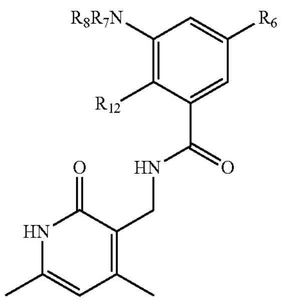

(IIA)

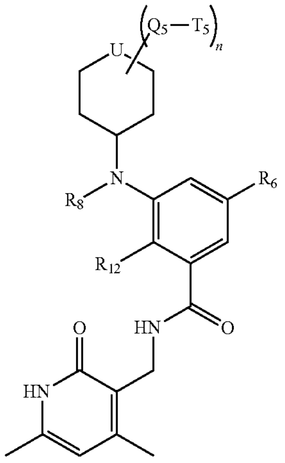

The compounds of Formulae (I), (Ia), (Ib), (Ic), (Id), (Ie), (II), and (IIA) can include one or more of the following features:

$X_1$ is $CR_{11}$ and $X_2$ is $CR_{13}$.

$X_1$ is $CR_{11}$ and $X_2$ is N.

$X_1$ is N and $X_2$ is $CR_{13}$.

$X_1$ is N and $X_2$ is N.

Z is $NR_7R_8$.

Z is $CR_7R_8R_{14}$.

Z is $OR_7$.

Z is $S(O)_aR_7$, in which a is 0, 1, or 2.

Z is $SR_7$.

$R_6$ is halo, $C_1$-$C_3$ alkyl, $C_2$-$C_6$ alkenyl, $C_3$-$C_6$ cycloalkyl, C(O)H, or —$C(O)R_a$, in which $R_a$ is $C_1$-$C_6$ alkyl or 4 to 12-membered (e.g., 4 to 7-membered) heterocycloalkyl.

$R_6$ is 4 to 12-membered (e.g., 4 to 7-membered) heterocycloalkyl optionally substituted with one or more -$Q_2$-$T_2$, in which -$Q_2$-$T_2$ is oxo or $Q_2$ is a bond and $T_2$ is $C_1$-$C_6$ alkyl, —$OR_c$, —$NR_cR_d$, —$C(O)R_c$, —$C(O)OR_c$, —$S(O)_2R_c$, or 4 to 12-membered (e.g., 4 to 7-membered) heterocycloalkyl optionally substituted with one or more -$Q_3$-$T_3$.

-$Q_2$-$T_2$ is not H.

$Q_3$ is a bond or $C_1$-$C_3$ alkyl linker and $T_3$ is selected from the group consisting of $C_1$-$C_3$ alkyl, $OR_e$, —$S(O)_2R_e$, or —$NR_eR_f$.

$R_6$ is piperidinyl, 2,2,6,6-tetramethyl-piperidinyl, 1,2,3,6-tetrahydropyridinyl, 2,2,6,6-tetramethyl-1,2,3,6-tetrahydropyridinyl, piperazinyl, morpholinyl, tetrahydro-2H-pyranyl, 3,6-dihydro-2H-pyranyl, or pyrrolidinyl.

$R_6$ is F, Br, or Cl.

$R_7$ is not H.

$R_7$ is $C_1$-$C_6$ alkyl, $C_3$-$C_8$ cycloalkyl or 4 to 14-membered (e.g., 4 to 7-membered) heterocycloalkyl, each optionally substituted with one or more -$Q_5$-$T_5$.

$R_7$ is piperidinyl, tetrahydropyran, tetrahydrothiopyran, oxetanyl, azetidinyl, pyrrolidinyl, 1,4-dioxaspiro[4.5]decanyl, 1-oxaspiro[4.5]decanyl, 3'H-spiro[cyclohexane-1,1'-isobenzofuran]-3'-one-4-yl, 7'H-spiro[cyclohexane-1,5'-furo[3,4-b]pyridin]-7'-one-4-yl, 3'H-spiro[cyclohexane-1,1'-furo[3,4-c]pyridin]-3'-one-4-yl, 1-azaspiro[4.5]decan-2-one-8-yl, cyclobutyl, cyclopentyl, or cyclohexyl, each optionally substituted with one or more -$Q_5$-$T_5$.

$T_5$ is H, halo, $C_1$-$C_6$ alkyl, $C_1$-$C_6$ alkoxyl, $C_3$-$C_8$ cycloalkyl, $C_6$-$C_{10}$ aryl, or 4 to 12-membered (e.g., 4 to 7-membered) heterocycloalkyl.

$Q_5$ is a bond and $T_5$ is $C_1$-$C_6$ alkyl, $C_3$-$C_8$ cycloalkyl, or 4 to 12-membered (e.g., 4 to 7-membered) heterocycloalkyl.

$Q_5$ is a bond and $T_5$ is H, $C_1$-$C_6$ alkyl, $C_3$-$C_8$ cycloalkyl, 4 to 12-membered heterocycloalkyl, 5- or 6-membered heteroaryl, amino, mono-$C_1$-$C_6$ alkylamino, or di-$C_1$-$C_6$ alkylamino, $T_5$ being optionally substituted with one or more substituents selected from the group consisting of halo, hydroxyl, $C_1$-$C_6$ alkoxyl, or $C_3$-$C_8$ cycloalkyl.

$Q_5$ is CO, $S(O)_2$, or NHC(O); and $T_5$ is $C_1$-$C_6$ alkyl, $C_1$-$C_6$ alkoxyl, $C_3$-$C_8$ cycloalkyl, or 4 to 12-membered (e.g., 4 to 7-membered) heterocycloalkyl.

$Q_5$ is $C_1$-$C_3$ alkyl linker and $T_5$ is H or $C_6$-$C_{10}$ aryl.

$Q_5$ is $C_1$-$C_3$ alkyl linker and $T_5$ is $C_3$-$C_8$ cycloalkyl, 4 to 12-membered (e.g., 4 to 7-membered) heterocycloalkyl, or $S(O)_qR_q$.

$R_{11}$ is H.

$R_7$ is cyclopentyl or cyclohexyl, each optionally substituted with one -$Q_5$-$T_5$.

$Q_5$ is NHC(O) and $T_5$ is $C_1$-$C_6$ alkyl or $C_1$-$C_6$ alkoxy.

$R_7$ is isopropyl.

Each of $R_2$ and $R_4$, independently is $C_1$-$C_3$ alkyl optionally substituted with $C_1$-$C_6$ alkoxyl.

Each of $R_2$ and $R_4$ is methyl.

$R_1$ is H.

$R_{12}$ is H, methyl, ethyl, ethenyl, or halo.

$R_{12}$ is methyl.

$R_{12}$ is ethyl.

$R_{12}$ is ethenyl.

$R_8$ is H, methyl, or ethyl.

$R_8$ is methyl.

$R_8$ is ethyl.

$R_8$ is ethenyl or propenyl.

$R_8$ is 4 to 12-membered (e.g., 4 to 7-membered) heterocycloalkyl, such as piperidinyl or tetrahydropyranyl.

Z is $NR_7R_8$ or $CR_7R_8R_{14}$ wherein $R_7$ and $R_8$, together with the atom to which they are attached, form a ring selected from the group consisting of piperidinyl, morpholinyl, piperazinyl, azetidinyl, pyrrolidinyl, 2-oxa-5-azabicyclo[2.2.1]heptan-5-yl, 1,4-dioxa-8-azaspiro[4.5]decanyl, and cyclohexenyl, each optionally substituted with one -$Q_6$-$T_6$.

$R_{13}$ is H or methyl.

$R_{13}$ is H.

$R_3$ is H.

Z is $NR_7R_8$, $OR_7$, or $S(O)_aR_7$; $R_1$ is H or $C_1$-$C_6$ alkyl optionally substituted with one or more substituents selected from hydroxyl, $C_1$-$C_6$ alkoxyl, amino, mono-$C_1$-$C_6$ alkylamino, di-$C_1$-$C_6$ alkylamino, and $C_6$-$C_{10}$ aryl; each of $R_2$ and $R_4$ independently, is -$Q_1$-$T_1$, in which $Q_1$ is a bond or $C_1$-$C_3$ alkyl linker optionally substituted with one or more substituents selected from halo and hydroxyl, and $T_1$ is H, halo, or azido; $R_3$ is H or halo; $R_5$ is H or $C_1$-$C_6$ alkyl; $R_6$ is H, halo, cyano, azido, $OR_a$, —$NR_aR_b$, —$C(O)NR_aR_b$, —$S(O)_bR_a$, or $R_{S2}$; wherein $R_{S2}$ is $C_1$-$C_6$ alkyl, $C_2$-$C_6$ alkenyl, $C_2$-$C_6$ alkynyl, or 4 to 12-membered heterocycloalkyl, and wherein each of $R_a$ and $R_b$, independently is H, $C_1$-$C_6$ alkyl, or 4 to 12-membered heterocycloalkyl; or $R_a$ and $R_b$, together with the N atom to which they are attached, form a 4 to 12-membered heterocycloalkyl ring having 0 or 1 additional heteroatom; and each of $R_a$, $R_{S2}$ and the 4 to 12-membered heterocycloalkyl ring formed by $R_a$ and $R_b$, is optionally substituted with one or more -$Q_2$-$T_2$; wherein $Q_2$ is a bond or $C_1$-$C_3$ alkyl linker, and $T_2$ is H, halo, —$OR_c$, —$NR_cR_d$, —$C(O)OR_c$, or $C_1$-$C_6$ alkyl, in which each of $R_c$ and $R_d$, independently is H or $C_1$-$C_6$ alkyl, or $R_c$ and $R_d$, together with the N atom to which they are attached, form a 4 to 12-membered heterocycloalkyl ring having 0 or 1 additional heteroatom and optionally substituted with $C_1$-$C_6$ alkyl; $R_7$ is -$Q_4$-$T_4$, in which $Q_4$ is a bond or $C_1$-$C_4$ alkyl linker and $T_4$ is H, $C_1$-$C_6$ alkyl, $C_3$-$C_8$ cycloalkyl, $C_6$-$C_{10}$ aryl, C(O)—$C_{1-6}$ alkyl, C(O)—$C_{3-6}$ cycloalkyl, or 4 to 14-membered heterocycloalkyl, each optionally substituted with one or more -$Q_5$-$T_5$; $R_8$ is H, $C_1$-$C_6$ alkyl optionally substituted with halo, hydroxyl or $C_1$-$C_6$ alkoxyl, $C_2$-$C_6$ alkenyl, $C_3$-$C_8$ cycloalkyl, or 4 to 7-membered heterocycloalkyl; or $R_7$ and $R_8$, together with the N atom to which they are attached, form a 4 to 12-membered heterocycloalkyl ring having 0 to 2 additional heteroatoms, and the 4 to 12-membered heterocycloalkyl ring formed by $R_7$ and $R_8$ is optionally substituted with one or more -$Q_6$-$T_6$; and $R_{12}$ is halo, $C_1$-$C_6$ alkoxyl, or $C_1$-$C_6$ alkyl optionally substituted with halo or $C_2$-$C_6$ alkenyl.

$R_1$ is H or $C_1$-$C_6$ alkyl optionally substituted one or more times with a substituent selected from hydroxyl, $C_1$-$C_6$ alkoxyl and $C_6$-$C_{10}$ aryl; $R_7$ is -$Q_4$-$T_4$, in which $Q_4$ is a bond or a $C_1$-$C_4$ alkyl linker, and $T_4$ is $C_1$-$C_6$ alkyl, $C_3$-$C_8$ cycloalkyl, $C_6$-$C_{10}$ aryl, C(O)—$C_1$-$C_6$ alkyl, C(O)—$C_3$-$C_6$ cycloalkyl, dihydropyranyl, tetrahydropyranyl, tetrahydrothiopyranyl, piperidinyl, pyrrolidinyl, azetidinyl and oxetanyl, each optionally substituted with one or more substituents independently selected from oxo and -$Q_5$-$T_5$; $R_8$ is H or $C_1$-$C_6$ alkyl, $C_1$-$C_6$ haloalkyl, $C_2$-$C_6$ alkenyl or $C_3$-$C_8$ cycloalkyl; and $R_{12}$ is halo, $C_1$-$C_6$ alkyl, $C_1$-$C_6$ haloalkyl or $C_1$-$C_6$ alkoxyl.

Z is $NR_7R_8$ or $SR_7$; $R_6$ is H, halo, cyano, $OR_a$, —C(O)$NR_aR_b$, —$S(O)_2R_a$, or $R_{S2}$; wherein $R_{S2}$ is $C_1$-$C_6$ alkyl, $C_2$-$C_6$ alkenyl, $C_2$-$C_6$ alkynyl, or 4 to 12-membered heterocycloalkyl, and wherein each of $R_a$ and $R_b$, independently is H or $C_1$-$C_6$ alkyl; or $R_a$ and $R_b$, together with the N atom to which they are attached, form a 4 to 12-membered heterocycloalkyl ring having 0 or 1 additional heteroatom; and each of $R_{S2}$ and the 4 to 12-membered heterocycloalkyl ring formed by $R_a$ and $R_b$, is optionally substituted with one or more -$Q_2$-$T_2$; wherein $Q_2$ is a bond or $C_1$-$C_3$ alkyl linker, and $T_2$ is H, halo, —$OR_c$, —$NR_cR_d$, —C(O)O$C_1$-$C_6$ alkyl, or $C_1$-$C_6$ alkyl, in which each of $R_c$ and $R_d$, independently is H or $C_1$-$C_6$ alkyl, or $R_c$ and $R_d$, together with the N atom to which they are attached, form a 4 to 12-membered heterocycloalkyl ring having 0 or 1 additional heteroatom and 0 or 1 $C_1$-$C_6$ alkyl substituents; $R_7$ is $C_1$-$C_6$ alkyl, $C_3$-$C_8$ cycloalkyl, dihydropyranyl, tetrahydropyranyl, tetrahydrothiopyranyl, piperidinyl, pyrrolidinyl, azetidinyl and oxetanyl, each optionally substituted with one or more substituents independently selected from oxo and -$Q_5$-$T_5$; and $R_{12}$ is halo or $C_1$-$C_6$ alkyl.

$R_2$, $R_4$ and $R_{12}$ are each independently $C_1$-$C_6$ alkyl and $R_5$ is H.

$R_7$ is cyclohexyl, dihydropyranyl, tetrahydropyranyl, tetrahydrothiopyranyl, piperidinyl, pyrrolidinyl, azetidinyl oxetanyl, 1,4-dioxaspiro[4.5]decan-8-yl, 1-oxaspiro[4.5]decan-8-yl, 3'H-spiro[cyclohexane-1,1'-isobenzofuran]-4-yl, 7'H-spiro[cyclohexane-1,5'-furo[3,4-b]pyridin]-4-yl, 3'H-spiro[cyclohexane-1,1'-furo[3,4-c]pyridin]-4-yl, or 1-azaspiro[4.5]decan-8-yl, each substituted with one or more -$Q_5$-$T_5$.

Z is selected from the group consisting of piperidinyl, morpholinyl, piperazinyl, azetidinyl, pyrrolidinyl, 2-oxa-5-azabicyclo[2.2.1]heptan-5-yl, 1,4-dioxa-8-azaspiro[4.5]decan-8-yl, and cyclohexenyl, each optionally substituted with one -$Q_6$-$T_6$.

$R_6$ is halo and Z is $S(O)_aR_7$, in which a is 0, 1, or 2 and $R_7$ is $C_1$-$C_6$ alkyl, $C_3$-$C_8$ cycloalkyl or 4 to 7-membered heterocycloalkyl and $R_7$ is optionally substituted with one or more -$Q_5$-$T_5$.

$R_6$ is halo and Z is $OR_7$, in which $R_7$ is 4 to 7-membered heterocycloalkyl optionally substituted with one or more -$Q_5$-$T_5$.

$R_6$ is —$S(O)_bR_a$ or azido, in which b is 0, 1, or 2 and $R_a$ is $C_1$-$C_6$ alkyl or $C_3$-$C_8$ cycloalkyl; and Z is $NR_7R_8$, in which $R_7$ is $C_3$-$C_8$ cycloalkyl or 4 to 14-membered heterocycloalkyl, each optionally substituted with one or more -$Q_5$-$T_5$; and $R_8$ is H or $C_1$-$C_6$ alkyl.

$R_6$ is halo and Z is $NR_7R_8$ or $CR_7R_8R_{14}$ wherein $R_7$ and $R_8$, together with the atom to which they are attached, form a 4 to 11-membered heterocycloalkyl ring having 1 to 3 heteroatoms or $C_3$-$C_8$ cycloalkyl, each optionally substituted with one or more -$Q_6$-$T_6$.

U is O, S, N-$Q_5$-$T_5$, or CH-$Q_5$-$T_5$.

n is 0, 1, or 2.

$R_{12}$ is Cl, Br, or methyl.

One or more -$Q_5$-$T_5$ are oxo.

U is CH-$Q_5$-$T_5$ and n is 0

One or more -$Q_6$-$T_6$ are oxo.

$Q_6$ is a bond or C(O) and $T_6$ is $C_1$-$C_6$ alkyl or $C_1$-$C_6$ alkoxy.

The present invention also provides pharmaceutical compositions comprising one or more pharmaceutically acceptable carriers and one or more compounds selected from those of any of the Formulae described herein, and N-(5-(((4,6-dimethyl-2-oxo-1,2-dihydropyridin-3-yl)methyl)carbamoyl)-2-methylphenyl)furan-2-carboxamide, N,N'-(5-(((4,6-dimethyl-2-oxo-1,2-dihydropyridin-3-yl)methyl) carbamoyl)-1,3-phenylene)diacetamide, N-((4,6-dimethyl-2-oxo-1,2-dihydropyridin-3-yl)methyl)-3-pivalamidobenzamide, 3-(3,4-dihydro-2H-benzo[b][1,4] dioxepine-7-sulfonamido)-N-((4,6-dimethyl-2-oxo-1,2-dihydropyridin-3-yl)methyl)benzamide, N-((4,6-dimethyl-2-oxo-1,2-dihydropyridin-3-yl)methyl)-3,5-dimethoxybenzamide, N-((4,6-dimethyl-2-oxo-1,2-dihydropyridin-3-yl)methyl)-3,4,5-trimethoxybenzamide, 3-allyl-N-((4,6-dimethyl-2-oxo-1,2-dihydropyridin-3-yl) methyl)-4,5-dimethoxybenzamide, 4-(2-amino-2-oxoethoxy)-3-chloro-N-((4,6-dimethyl-2-oxo-1,2-dihydropyridin-3-yl)methyl)-5-methoxybenzamide, 3-chloro-N-((4,6-dimethyl-2-oxo-1,2-dihydropyridin-3-yl)methyl)-4-hydroxy-5-methoxybenzamide, and 3-bromo-N-((4,6-dimethyl-2-oxo-1,2-dihydropyridin-3-yl)methyl)-5-methoxy-4-propoxybenzamide.

Another aspect of this invention is a method of treating or preventing cancer. The method includes administering to a subject in need thereof a therapeutically effective amount of one or more compounds selected from those of any of the Formulae described herein, and N-(5-(((4,6-dimethyl-2-oxo-1,2-dihydropyridin-3-yl)methyl)carbamoyl)-2-methylphenyl)furan-2-carboxamide, N,N'-(5-(((4,6-dimethyl-2-oxo-1,2-dihydropyridin-3-yl)methyl)carbamoyl)-1,3-phenylene) diacetamide, N-((4,6-dimethyl-2-oxo-1,2-dihydropyridin-3-yl)methyl)-3-pivalamidobenzamide, 3-(3,4-dihydro-2H-benzo[b][1,4]dioxepine-7-sulfonamido)-N-((4,6-dimethyl-2-oxo-1,2-dihydropyridin-3-yl)methyl)benzamide, N-((4,6-dimethyl-2-oxo-1,2-dihydropyridin-3-yl)methyl)-3,5-dimethoxybenzamide, N-((4,6-dimethyl-2-oxo-1,2-dihydropyridin-3-yl)methyl)-3,4,5-trimethoxybenzamide, 3-allyl-N-((4,6-dimethyl-2-oxo-1,2-dihydropyridin-3-yl) methyl)-4,5-dimethoxybenzamide, 4-(2-amino-2-oxoethoxy)-3-chloro-N-((4,6-dimethyl-2-oxo-1,2-dihydropyridin-3-yl)methyl)-5-methoxybenzamide, 3-chloro-N-((4,6-dimethyl-2-oxo-1,2-dihydropyridin-3-yl)methyl)-4-hydroxy-5-methoxybenzamide, and 3-bromo-N-((4,6-dimethyl-2-oxo-1,2-dihydropyridin-3-yl)methyl)-5-methoxy-4-propoxybenzamide.

Unless otherwise stated, any description of a method of treatment includes uses of the compounds to provide such treatment or prophylaxis as is described in the specification, as well as uses of the compounds to prepare a medicament to treat or prevent such condition. The treatment includes treatment of human or non-human animals including rodents and other disease models.

For example, the method comprises the step of administering to a subject having a cancer with aberrant H3-K27 methylation an effective amount of one or more compounds of Formulae described herein, wherein the compound(s) inhibits histone methyltransferase activity of EZH2, thereby treating the cancer. Examples of aberrant H3-K27 methylation may include a global increase in and/or altered distribution of H3-K27 di or tri-methylation within the cancer cell chromatin.

For example, the cancer is selected from the group consisting of cancers that overexpress EZH2 or other PRC2 subunits, contain loss-of-function mutations in H3-K27 demethylases such as UTX, or overexpress accessory proteins such as PHF19/PCL3 capable of increasing and or mislocalizing EZH2 activity (see references in Sneeringer et al. *Proc Natl Acad Sci USA* 107(49):20980-5, 2010).

For example, the method comprises the step of administering to a subject having a cancer overexpressing EZH2 a therapeutically effective amount of one or more compounds of Formulae described herein, wherein the compound(s) inhibits histone methyltransferase activity of EZH2, thereby treating the cancer.

For example, the method comprises the step of administering to a subject having a cancer with a loss-of-function mutation in the H3-K27 demethylase UTX a therapeutically effective amount of one or more compounds of Formulae described herein, wherein the compound(s) inhibits histone methyltransferase activity of EZH2, thereby treating the cancer For example, the method comprises the step of administering to a subject having a cancer overexpressing an accessory component(s) of the PRC2, such as PHF19/PCL3, a therapeutically effective amount of one or more compounds of Formulae described herein, wherein the compound(s) inhibits histone methyltransferase activity of EZH2, thereby treating the cancer In still another aspect, this invention relates to a method of modulating the activity of the wild-type EZH2, the catalytic subunit of the PRC2 complex which catalyzes the mono-through tri-methylation of lysine 27 on histone H3 (H3-K27). For example, the present invention relates to a method of inhibiting the activity of EZH2 in a cell. This method can be conducted either in vitro or in vivo.

In yet another aspect, this invention features to a method of inhibiting in a subject conversion of H3-K27 to trimethylated H3-K27. The method comprises administering to a subject a therapeutically effective amount of one or more of the compound of Formulae described herein to inhibit histone methyltransferase activity of EZH2, thereby inhibiting conversion of H3-K27 to trimethylated H3-K27 in the subject.

For example, the method comprises the step of administering to a subject having a cancer expressing a Y641 mutant of EZH2 a therapeutically effective amount of one or more compounds of Formulae described herein, wherein the compound(s) inhibits histone methyltransferase activity of EZH2, thereby treating the cancer.

For example, the cancer is selected from the group consisting of follicular lymphoma and diffuse large B-cell lymphoma (DLBCL) of germinal center B cell-like (GCB) subtype. For example, the cancer is lymphoma, leukemia or melanoma. Preferably, the lymphoma is non-Hodgkin lymphoma, follicular lymphoma or diffuse large B-cell lymphoma. Alternatively, the leukemia is chronic myelogenous leukemia (CML), acute myeloid leukemia, acute lymphocytic leukemia or mixed lineage leukemia.

The precancerous condition is myelodysplastic syndromes (MDS, formerly known as preleukemia).

For example, the cancer is a hematological cancer.

For example, the method comprises the step of administering to a subject having a cancer expressing a Y641 mutant of EZH2 a therapeutically effective amount of one or more compounds of Formulae described herein, wherein the compound(s) selectively inhibits histone methyltransferase activity of the Y641 mutant of EZH2, thereby treating the cancer.

For example, the method further comprises the steps of performing an assay to detect a Y641 mutant of EZH2 in a sample comprising cancer cells from a subject having a cancer.

In still another aspect, this invention relates to a method of modulating the activity of the wild-type and mutant histone methyltransferase EZH2, the catalytic subunit of the PRC2 complex which catalyzes the mono- through tri-methylation of lysine 27 on histone H3 (H3-K27). For example, the present invention relates to a method of inhibiting the activity of certain mutant forms of EZH2 in a cell. The mutant forms of EZH2 include a substitution of another amino acid residue for tyrosine 641 (Y641, also Tyr641) of wild-type EZH2. The method includes contacting the cell with an effective amount of one or more of the compound of any Formula described herein. This method can be conducted either in vitro or in vivo.

In yet another aspect, this invention features to a method of inhibiting in a subject conversion of H3-K27 to trimethylated H3-K27. The method comprises administering to a subject expressing a Y641 mutant of EZH2 a therapeutically effective amount of one or more of the compound of any Formula described herein to inhibit histone methyltransferase activity of EZH2, thereby inhibiting conversion of H3-K27 to trimethylated H3-K27 in the subject. For example, the histone methyltransferase activity inhibited is that of the Y641 mutant of EZH2. For example, the compound of this invention selectively inhibits histone methyltransferase activity of the Y641 mutant of EZH2. For example, the Y641 mutant of EZH2 is selected from the group consisting of Y641C, Y641F, Y641H, Y641N, and Y641S.

The method of inhibiting in a subject conversion of H3-K27 to trimethylated H3-K27 may also comprise performing an assay to detect a Y641 mutant of EZH2 in a sample from a subject before administering to the subject expressing a Y641 mutant of EZH2 a therapeutically effective amount of one or more of the compound of any Formula described herein. For example, performing the assay to detect the Y641 mutant of EZH2 includes whole-genome resequencing or target region resequencing that detects a nucleic acid encoding the Y641 mutant of EZH2. For example, performing the assay to detect the Y641 mutant of EZH2 includes contacting the sample with an antibody that binds specifically to a polypeptide or fragment thereof characteristic of the Y641 mutant of EZH2. For example, performing the assay to detect the Y641 mutant of EZH2 includes contacting the sample under highly stringent conditions with a nucleic acid probe that hybridizes to a nucleic acid encoding a polypeptide or fragment thereof characteristic of the Y641 mutant of EZH2.

Further, the invention also relates to a method of identifying an inhibitor of a Y641 mutant of EZH2. The method comprises the steps of combining an isolated Y641 mutant of EZH2 with a histone substrate, a methyl group donor, and a test compound, wherein the histone substrate comprises a form of H3-K27 selected from the group consisting of unmethylated H3-K27, monomethylated H3-K27, dimethylated H3-K27, and any combination thereof; and performing an assay to detect methylation of H3-K27 (e.g., formation of trimethylated H3-K27) in the histone substrate, thereby identifying the test compound as an inhibitor of the Y641 mutant of EZH2 when methylation of H3-K27 (e.g., formation of trimethylated H3-K27) in the presence of the test compound is less than methylation of H3-K27 (e.g., formation of trimethylated H3-K27) in the absence of the test compound.

In one embodiment, performing the assay to detect methylation of H3-K27 in the histone substrate comprises measuring incorporation of labeled methyl groups.

In one embodiment, the labeled methyl groups are isotopically labeled methyl groups.

In one embodiment, performing the assay to detect methylation of H3-K27 in the histone substrate comprises contacting the histone substrate with an antibody that binds specifically to trimethylated H3-K27.

Also within the scope of the invention is a method of identifying a selective inhibitor of a Y641 mutant of EZH2. The method comprises the steps of combining an isolated Y641 mutant of EZH2 with a histone substrate, a methyl group donor, and a test compound, wherein the histone substrate comprises a form of H3-K27 selected from the group consisting of monomethylated H3-K27, dimethylated H3-K27, and a combination of monomethylated H3-K27 and dimethylated H3-K27, thereby forming a test mixture; combining an isolated wild-type EZH2 with a histone substrate, a methyl group donor, and a test compound, wherein the histone substrate comprises a form of H3-K27 selected from the group consisting of monomethylated H3-K27, dimethylated H3-K27, and a combination of monomethylated H3-K27 and dimethylated H3-K27, thereby forming a control mixture; performing an assay to detect trimethylation of the histone substrate in each of the test mixture and the control mixture; calculating the ratio of (a) trimethylation with the Y641 mutant of EZH2 and the test compound (M+) to (b) trimethylation with the Y641 mutant of EZH2 without the test compound (M−); calculating the ratio of (c) trimethylation with wild-type EZH2 and the test compound (WT+) to (d) trimethylation with wild-type EZH2 without the test compound (WT−); comparing the ratio (a)/(b) with the ratio (c)/(d); and identifying the test compound as a selective inhibitor of the Y641 mutant of EZH2 when the ratio (a)/(b) is less than the ratio (c)/(d).

The present invention further provides a method of identifying a subject as a candidate for treatment with one or more compounds of the invention. The method comprises the steps of performing an assay to detect a Y641 mutant of EZH2 in a sample from a subject; and identifying a subject expressing a Y641 mutant of EZH2 as a candidate for treatment with one or more compounds of the invention, wherein the compound(s) inhibits histone methyltransferase activity of EZH2.

Still another aspect of the invention is a method of inhibiting conversion of H3-K27 to trimethylated H3-K27. The method comprises the step of contacting a Y641 mutant of EZH2 with a histone substrate comprising H3-K27 and an effective amount of a compound of the present invention, wherein the compound inhibits histone methyltransferase activity of EZH2, thereby inhibiting conversion of H3-K27 to trimethylated H3-K27.

Further, the compounds or methods described herein can be used for research (e.g., studying epigenetic enzymes) and other non-therapeutic purposes.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

Other features and advantages of the invention will be apparent from the following detailed description and claims.

BRIEF DESCRIPTIONS OF FIGURES

FIG. 1(B) is an idealized plot of ln(cell count) as a function of time for the data from panel (A).

Figure 2:
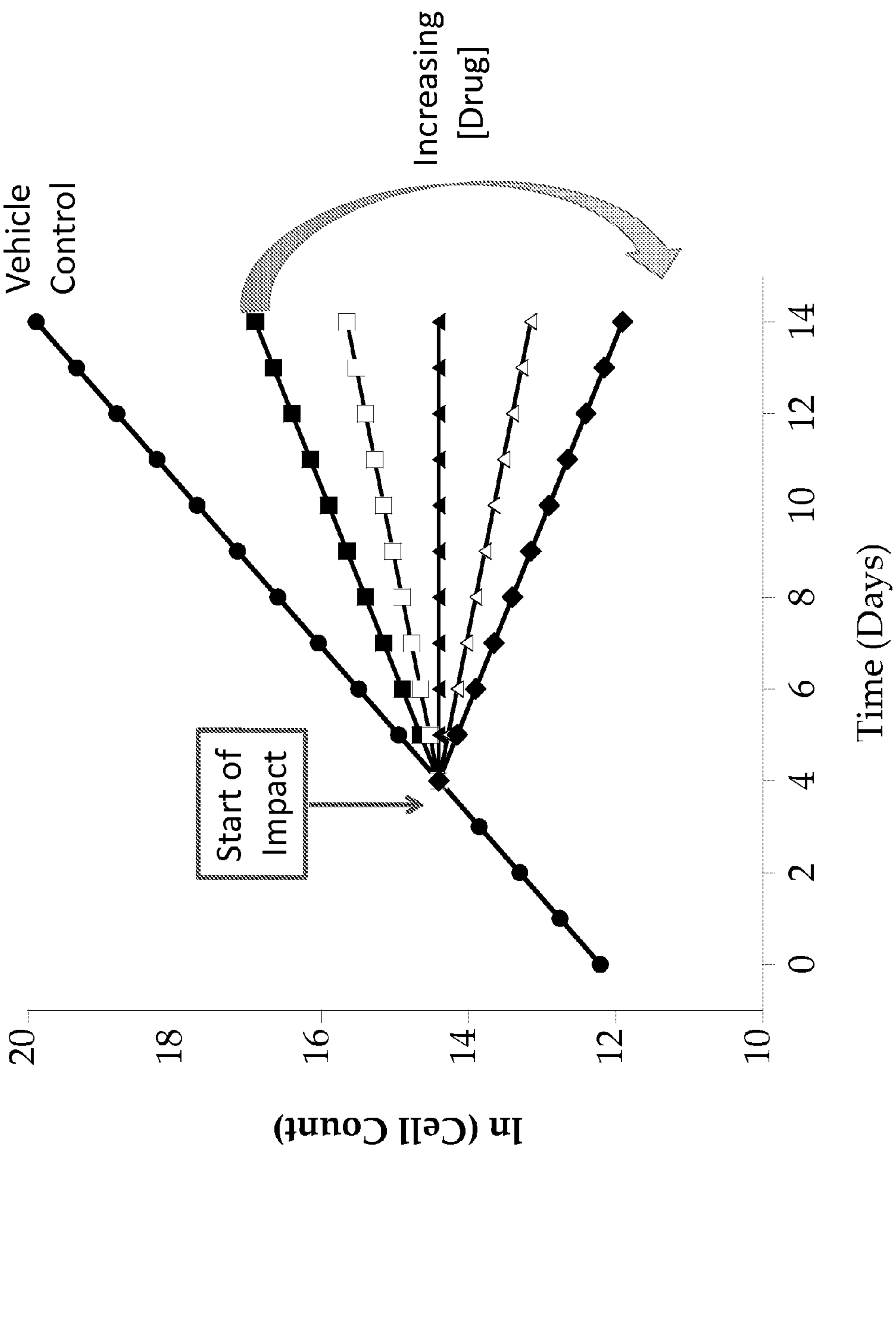

FIG. 2 is a graph showing biphasic cell growth curves in the presence of an antiproliferative compound for which there is a delay before the impact of the compound on cell growth is realized. The compound begins to affect cell growth at the time point labeled "start of impact." The solid circles represent idealized data for the vehicle (or solvent) control sample that is not treated with compound. The other symbols represent biphasic growth curves for cells treated with different concentrations of compound (i.e., drug).

Figure 3:
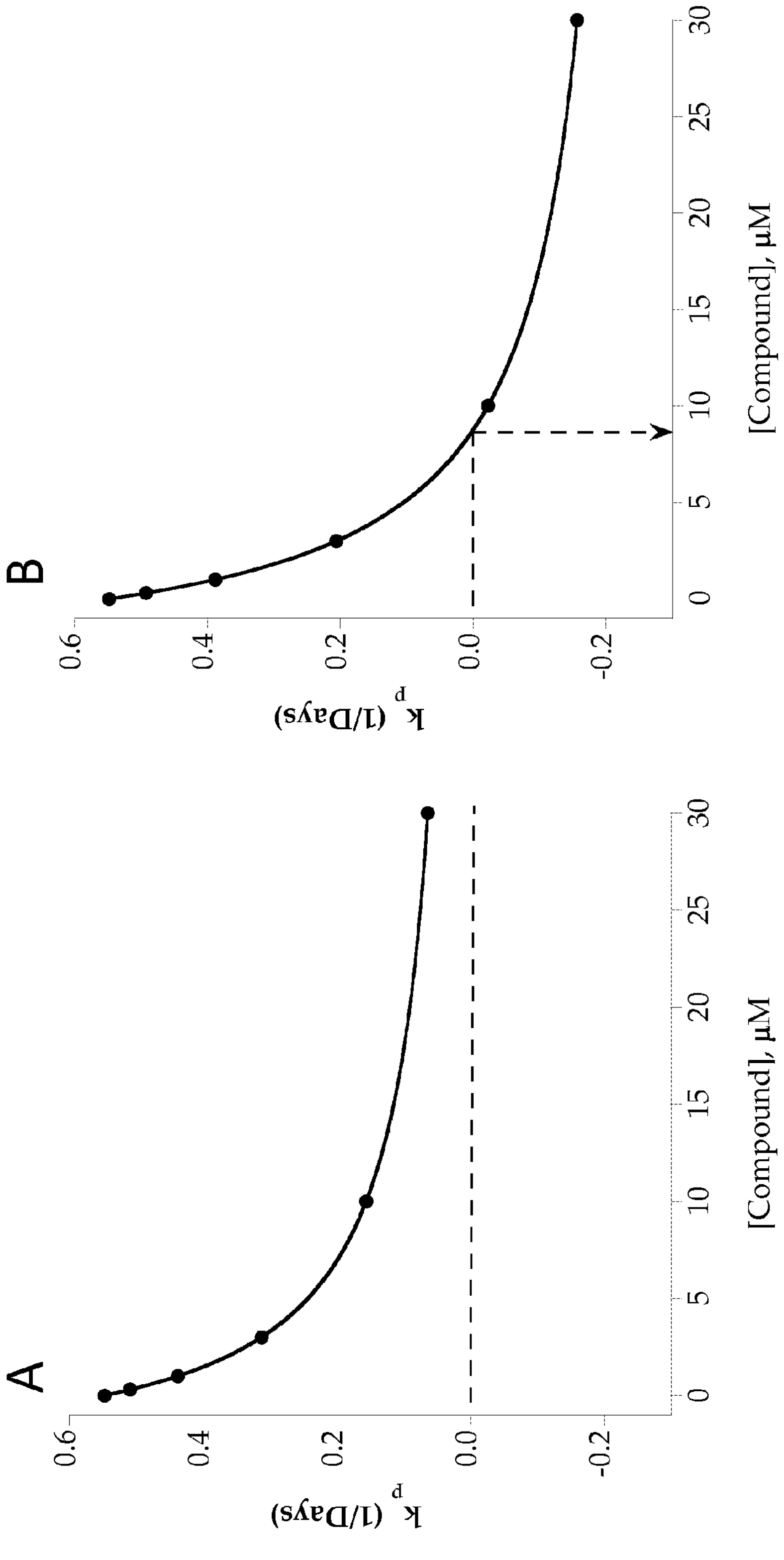

FIG. 3 is a replot of $k_p$ as a function of compound concentration for (A) a cytostatic and (B) a cytotoxic compound, illustrating the graphic determination of the LCC for a cytotoxic agent. Note that for a cytostatic compound (panel A), the value of $k_p$ can never drop below zero.

Figure 4:
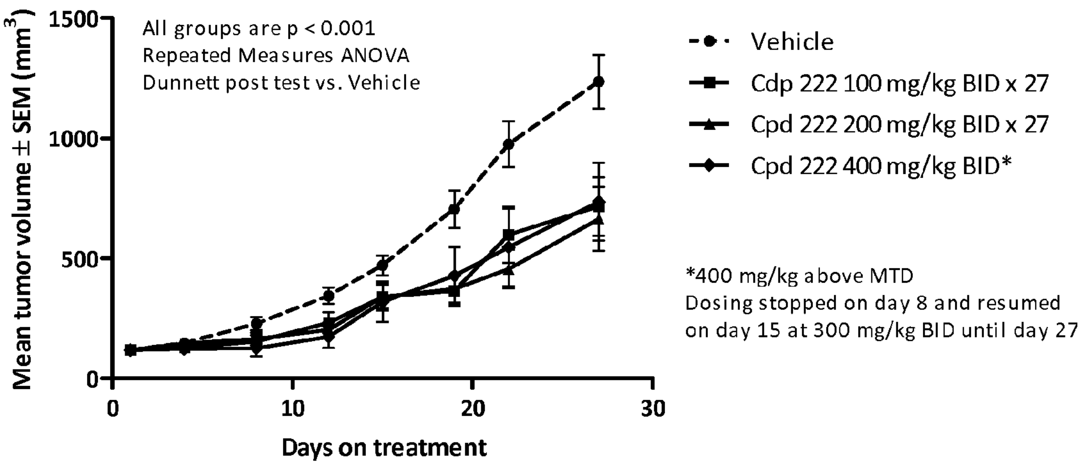

FIG. 4 is a diagram showing tumor growth of WSU-DLCL2 xenograft bearing mice treated with Compound 222 over 27 days.

Figure 5:
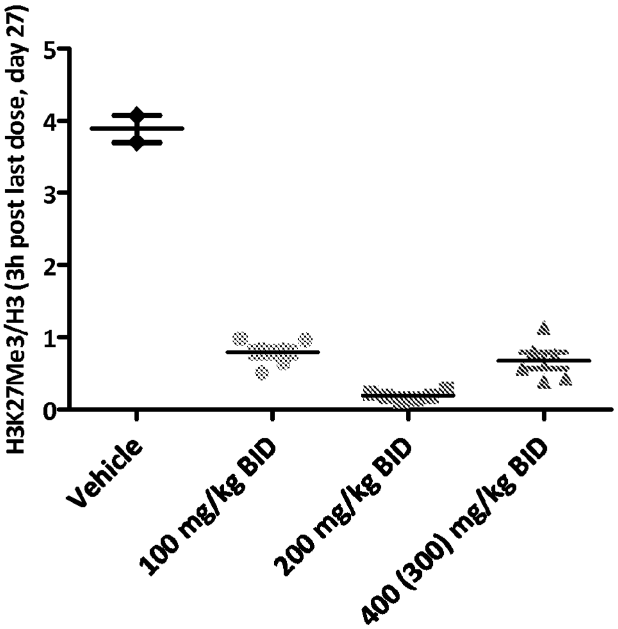

FIG. 5 is a diagram showing lobal H3K27me3 methylation in WSU-DLCL2 tumors from mice treated with Compound 222 or vehicle for 27 days.

DETAILED DESCRIPTION OF THE INVENTION

The present invention provides novel substituted benzene compounds, synthetic methods for making the compounds, pharmaceutical compositions containing them and various uses of the compounds.

1. Substituted Benzene Compounds

The present invention provides the compounds of Formula (I):

(I)

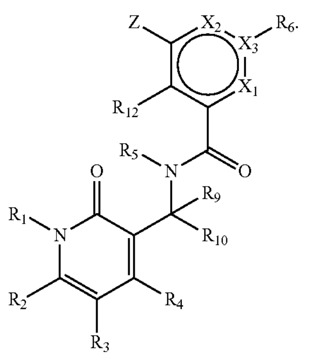

In this formula:

$X_1$ is N or $CR_{11}$;

$X_2$ is N or $CR_{13}$;

$X_3$ is N or C, and when $X_3$ is N, $R_6$ is absent;

Z is $NR_7R_8$, $OR_7$, $S(O)_aR_7$, or $CR_7R_8R_{14}$, in which a is 0, 1, or 2;

each of $R_1$, $R_5$, $R_9$, and $R_{10}$, independently, is H or $C_1$-$C_6$ alkyl optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

each of $R_2$, $R_3$, and $R_4$, independently, is -$Q_1$-$T_1$, in which $Q_1$ is a bond or $C_1$-$C_3$ alkyl linker optionally substituted with halo, cyano, hydroxyl or $C_1$-$C_6$ alkoxy, and $T_1$ is H, halo, hydroxyl, COOH, cyano, azido, or $R_{S1}$, in which $R_{S1}$ is $C_1$-$C_3$ alkyl, $C_2$-$C_6$ alkenyl, $C_2$-$C_6$ alkynyl, $C_1$-$C_6$ alkoxyl, C(O)O—$C_1$-$C_6$ alkyl, $C_3$-$C_8$ cycloalkyl, $C_6$-$C_{10}$ aryl, amino, mono-$C_1$-$C_6$ alkylamino, di-$C_1$-$C_6$ alkylamino, 4 to 12-membered heterocycloalkyl, or 5- or 6-membered heteroaryl, and $R_{S1}$ is optionally substituted with one or more substituents selected from the group consisting of halo, hydroxyl, oxo, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

$R_6$ is H, halo, cyano, azido, $OR_a$, —$NR_aR_b$, —C(O)$R_a$, —C(O)$OR_a$, —C(O)$NR_aR_b$, —$NR_b$C(O)$R_a$, —$S(O)_bR_a$, —$S(O)_bNR_aR_b$, or $R_{S2}$, in which $R_{S2}$ is $C_1$-$C_6$ alkyl, $C_2$-$C_6$ alkenyl, $C_2$-$C_6$ alkynyl, $C_3$-$C_8$ cycloalkyl, or 4 to 12-membered heterocycloalkyl; b is 0, 1, or 2, each of $R_a$ and $R_b$, independently is H or $R_{S3}$, and $R_{S3}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl; or $R_a$ and $R_b$, together with the N atom to which they are attached, form a 4 to 12-membered heterocycloalkyl ring having 0 or 1 additional heteroatom; and each of $R_{S2}$, $R_{S3}$, and the 4 to 12-membered heterocycloalkyl ring formed by $R_a$ and $R_b$, is optionally substituted with one or more -$Q_2T_2$, wherein $Q_2$ is a bond or $C_1$-$C_3$ alkyl linker each optionally substituted with halo, cyano, hydroxyl or $C_1$-$C_6$ alkoxy, and $T_2$ is H, halo, cyano, —$OR_c$, —$NR_cR_d$, —C(O)$R_c$, —C(O)$OR_c$, —C(O)$NR_cR_d$, —$NR_d$C(O)$R_c$, —$NR_d$C(O)$OR_c$, —$S(O)_2R_c$, —$S(O)_2NR_cR_d$, or $R_{S4}$, in which each of $R_c$ and $R_d$, independently is H or $R_{S5}$, each of $R_{S4}$ and $R_{S5}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_c$ and $R_d$, together with the N atom to which they are attached, form a 4 to 12-membered heterocycloalkyl ring having 0 or 1 additional heteroatom, and each of $R_{S4}$, $R_{S5}$, and the 4 to 12-membered heterocycloalkyl ring formed by $R_c$ and $R_d$, is optionally substituted with one or more -$Q_3$-$T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_e$, $COOR_e$, —$S(O)_2R_e$, —$NR_eR_f$, and —C(O)$NR_eR_f$, each of $R_e$ and $R_f$ independently being H or $C_1$-$C_6$ alkyl, or -$Q_3$-$T_3$ is oxo; or -$Q_2$-$T_2$ is oxo;

$R_7$ is -$Q_4$-$T_4$, in which $Q_4$ is a bond, $C_1$-$C_4$ alkyl linker, or $C_2$-$C_4$ alkenyl linker, each linker optionally substituted with halo, cyano, hydroxyl or $C_1$-$C_6$ alkoxy, and $T_4$ is H, halo, cyano, $NR_gR_h$, —$OR_g$, —C(O)$R_g$, —C(O)$OR_g$, —C(O)$NR_gR_h$, —C(O)$NR_gOR_h$, —$NR_g$C(O)$R_h$, —$S(O)_2R_g$, or $R_{S6}$, in which each of $R_g$ and $R_h$, independently is H or $R_{S7}$, each of $R_{S6}$ and $R_{S7}$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and each of $R_{S6}$ and $R_{S7}$ is optionally substituted with one or more -$Q_5$-$T_5$, wherein $Q_5$ is a bond, C(O), C(O)$NR_k$, $NR_k$C(O), $S(O)_2$, or $C_1$-$C_3$ alkyl linker, $R_k$ being H or $C_1$-$C_6$ alkyl, and $T_5$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or $S(O)_qR_q$ in which q is 0, 1, or 2 and $R_q$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_5$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_5$ is H, halo, hydroxyl, or cyano; or -$Q_5$-$T_5$ is oxo;

each of $R_8$, $R_{11}$, $R_{12}$, and $R_{13}$, independently, is H, halo, hydroxyl, COOH, cyano, $R_{S8}$, $OR_{S8}$, or $COOR_{S8}$, in which $R_{S8}$ is $C_1$-$C_6$ alkyl, $C_2$-$C_6$ alkenyl, $C_2$-$C_6$ alkynyl, $C_3$-$C_8$ cycloalkyl, 4 to 12-membered heterocycloalkyl, amino, mono-$C_1$-$C_6$ alkylamino, or di-$C_1$-$C_6$ alkylamino, and $R_{S8}$ is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino; or $R_7$ and $R_8$, together with the N atom to which they are attached, form a 4 to 12-membered heterocycloalkyl ring having 0 to 2 additional heteroatoms, or $R_7$ and $R_8$, together with the C atom to which they are attached, form $C_3$-$C_8$ cycloalkyl or a 4 to 12-membered heterocycloalkyl ring having 1 to 3 heteroatoms, and each of the 4 to 12-membered heterocycloalkyl rings or $C_3$-$C_8$ cycloalkyl formed by $R_7$ and $R_8$ is optionally substituted with one or more -$Q_6$-$T_6$, wherein $Q_6$ is a bond, C(O), C(O)$NR_m$, $NR_m$C(O), $S(O)_2$, or $C_1$-$C_3$ alkyl linker, $R_m$ being H or $C_1$-$C_6$ alkyl, and $T_6$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or $S(O)_pR_p$ in which p is 0, 1, or 2 and $R_p$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_6$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_6$ is H, halo, hydroxyl, or cyano; or -$Q_6$-$T_6$ is oxo; and $R_{14}$ is absent, H, or $C_1$-$C_6$ alkyl optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

provided that the compound is not

N-(5-(((4,6-dimethyl-2-oxo-1,2-dihydropyridin-3-yl)methyl)carbamoyl)-2-methylphenyl)furan-2-carboxamide, N,N'-(5-(((4,6-dimethyl-2-oxo-1,2-dihydropyridin-3-yl)methyl)carbamoyl)-1,3-phenylene)diacetamide, N-((4,6-dimethyl-2-oxo-1,2-dihydropyridin-3-yl)methyl)-3-pivalamidobenzamide, 3-(3,4-dihydro-2H-benzo[b][1,4]dioxepine-7-sulfonamido)-N-((4,6-dimethyl-2-oxo-1,2-dihydropyridin-3-yl)methyl)benzamide, N-((4,6-dimethyl-2-oxo-1,2-dihydropyridin-3-yl)methyl)-3,5-dimethoxybenzamide, N-((4,6-dimethyl-2-oxo-1,2-dihydropyridin-3-yl)methyl)-3,4,5-trimethoxybenzamide, 3-allyl-N-((4,6-dimethyl-2-oxo-1,2-dihydropyridin-3-yl)methyl)-4,5-dimethoxybenzamide, 4-(2-amino-2-oxoethoxy)-3-chloro-N-((4,6-dimethyl-2-oxo-1,2-dihydropyridin-3-yl)methyl)-5-methoxybenzamide, 3-chloro-N-((4,6-dimethyl-2-oxo-1,2-dihydropyridin-3-yl)methyl)-4-hydroxy-5-methoxybenzamide, or 3-bromo-N-((4,6-dimethyl-2-oxo-1,2-dihydropyridin-3-yl)methyl)-5-methoxy-4-propoxybenzamide.

For example, $X_1$ is $CR_{11}$ and $X_2$ is $CR_{13}$.

For example, $X_1$ is $CR_{11}$ and $X_2$ is N.

For example, $X_1$ is N and $X_2$ is $CR_{13}$.

For example, $X_1$ is N and $X_2$ is N.

For example, $X_3$ is C.

For example, $X_3$ is N and $R_6$ is absent.

For example, Z is $NR_7R_8$.

For example, Z is $CR_7R_8R_{14}$.

For example, Z is $OR_7$.

For example, Z is $S(O)_aR_7$, in which a is 0, 1, or 2

For example, Z is $SR_7$.

For example, $R_6$ is H.

For example, $R_6$ is halo (e.g., fluorine, chlorine, bromine, and iodine).

For example, $R_6$ is $C_1$-$C_3$ alkyl optionally substituted with one or more -$Q_2$-$T_2$.

For example, $R_6$ is $CF_3$.

For example, $R_6$ is $C_2$-$C_6$ alkenyl, $C_2$-$C_6$ alkynyl, or $C_3$-$C_6$ cycloalkyl each optionally substituted with one or more -$Q_2$-$T_2$.

For example, $R_6$ is ethenyl.

For example, $R_6$ is ethynyl.

For example, $R_6$ is ethynyl substituted with one or more -$Q_2$-$T_2$, in which $Q_2$ is a bond or $C_1$-$C_3$ alkyl linker and $T_2$ is $C_1$-$C_6$ alkyl, $C_3$-$C_6$ cycloalkyl, or 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, and morpholinyl, and the like) optionally substituted with one or more -$Q_3$-$T_3$.

For example, $R_6$ is azido.

For example, $R_6$ is cyano.

For example, $R_6$ is C(O)H.

For example, $R_6$ is $OR_a$ or —C(O)$R_a$.

For example, $R_a$ is $C_1$-$C_6$ alkyl or 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like), which is optionally substituted with one or more -$Q_2$-$T_2$.

For example, $R_6$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like) optionally substituted with one or more -$Q_2$-$T_2$.

For example, $R_6$ is piperidinyl, 2,2,6,6-tetramethyl-piperidinyl, 1,2,3,6-tetrahydropyridinyl, 2,2,6,6-tetramethyl-1,2,3,6-tetrahydropyridinyl, piperazinyl, morpholinyl, tetrahydro-2H-pyranyl, 3,6-dihydro-2H-pyranyl, or pyrrolidinyl, each of which is optionally substituted with one or more -$Q_2$-$T_2$.

For example, $R_6$ is 4 to 7-membered heterocycloalkyl optionally substituted with one or more -$Q_2$-$T_2$, and -$Q_2$-$T_2$ is oxo or $Q_2$ is a bond and $T_2$ is —$OR_c$, —$NR_cR_d$, —C(O)$R_c$, —C(O)$OR_c$, —$S(O)_2R_c$, $C_1$-$C_6$ alkyl, or 4 to 7-membered heterocycloalkyl, each of which is optionally substituted with one or more -$Q_3$-$T_3$ when $R_c$ or $R_d$ is not H.

For example, $R_6$ is —$NR_aR_b$, —C(O)$R_a$, —C(O)$OR_a$, —C(O)$NR_aR_b$, —$NR_b$C(O)$R_a$, —$SR_a$, —$S(O)_2R_a$, or —$S(O)_2NR_aR_b$.

For example, each of $R_a$ and $R_b$, independently is H, $C_1$-$C_6$ alkyl or $C_3$-$C_8$ cycloalkyl optionally substituted with one or more -$Q_2$-$T_2$.

For example, one of $R_a$ and $R_b$ is H.

For example, $R_a$ and $R_b$, together with the N atom to which they are attached, form a 4 to 7-membered heterocycloalkyl ring having 0 or 1 additional heteroatoms to the N atom (e.g., azetidinyl, pyrrolidinyl, imidazolidinyl, pyrazolidinyl, oxazolidinyl, isoxazolidinyl, triazolidinyl, piperidinyl, 1,2,3,6-tetrahydropyridinyl, piperazinyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like) and the ring is optionally substituted with one or more $-Q_2-T_2$.

For example, $-Q_2-T_2$ is not H.

For example, $-Q_2-T_2$ is oxo.

For example, $Q_2$ is a bond.

For example, $Q_2$ is an unsubstituted $C_1$-$C_3$ alkyl linker.

For example, $T_2$ is $C_1$-$C_6$ alkyl or $C_6$-$C_{10}$ aryl, each optionally substituted with one or more $-Q_3-T_3$.

For example, $T_2$ is an unsubstituted substituted straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl and n-hexyl.

For example, $T_2$ is phenyl.

For example, $T_2$ is halo (e.g., fluorine, chlorine, bromine, and iodine).

For example, $T_2$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like) optionally substituted with one or more $-Q_3-T_3$.

For example, $T_2$ is $—OR_c$, $—NR_cR_d$, $—C(O)R_c$, $—C(O)OR_c$, or $—S(O)_2R_c$.

For example, $R_c$ is $C_1$-$C_6$ alkyl or 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like), which is optionally substituted with one or more $-Q_3-T_3$.

For example, each of $R_c$ and $R_d$, independently is H or $C_1$-$C_6$ alkyl optionally substituted with one or more $-Q_3-T_3$.

For example, $R_c$ is H.

For example, $R_d$ is H.

For example, $R_c$ and $R_d$, together with the N atom to which they are attached, form a 4 to 7-membered heterocycloalkyl ring having 0 or 1 additional heteroatoms to the N atom (e.g., azetidinyl, pyrrolidinyl, imidazolidinyl, pyrazolidinyl, oxazolidinyl, isoxazolidinyl, triazolidinyl, piperidinyl, 1,2,3,6-tetrahydropyridinyl, piperazinyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like) and the ring is optionally substituted with one or more $-Q_3-T_3$.

For example, $Q_2$ is a bond and $T_2$ is $—OR_c$, $—NR_cR_d$, $—C(O)R_c$, $—C(O)OR_c$, $—S(O)_2R_c$, $C_1$-$C_6$ alkyl, or 4 to 7-membered heterocycloalkyl, each of which is optionally substituted with one or more $-Q_3-T_3$ when $R_c$ or $R_d$ is not H.

For example, $-Q_3-T_3$ is oxo.

For example, $T_2$ is 4 to 7-membered heterocycloalkyl or $C_3$-$C_8$ cycloalkyl and one or more $-Q_3-T_3$ are oxo.

For example, $Q_3$ is a bond or unsubstituted or substituted $C_1$-$C_3$ alkyl linker.

For example, $T_3$ is H, halo, 4 to 7-membered heterocycloalkyl, $C_1$-$C_3$ alkyl, $OR_e$, $COOR_e$, $—S(O)_2R_e$, $—NR_eR_f$, or $—C(O)NR_eR_f$.

For example, one of $R_d$ and $R_e$ is H.

For example, $Q_3$ is a bond or $C_1$-$C_3$ alkyl linker and $T_3$ is selected from the group consisting of $C_1$-$C_3$ alkyl, halo, $OR_e$, $—S(O)_2R_e$, $—NR_eR_f$, and $—C(O)NR_eR_f$.

For example, $Q_3$ is a bond or $C_1$-$C_3$ alkyl linker and $T_3$ is selected from the group consisting of $C_1$-$C_3$ alkyl, $OR_e$, $—S(O)_2R_e$, or $—NR_eR_f$.

For example, $R_e$ is H.

For example, $R_f$ is H.

For example, $R_7$ is not H.

For example, $R_7$ is $—C(O)R_g$.

For example, $R_7$ is $—C(O)R_g$, in which $R_g$ is $C_3$-$C_3$ cycloalkyl, or 4 to 7-membered heterocycloalkyl, $C_3$-$C_8$ cycloalkyl.

For example, $R_7$ is $C_6$-$C_{10}$ aryl substituted with one or more $-Q_5-T_5$.

For example, $R_7$ is phenyl optionally substituted with one or more $-Q_5-T_5$.

For example, $R_7$ is $C_1$-$C_6$ alkyl optionally substituted with one or more $-Q_5-T_5$.

For example, $R_7$ is $C_3$-$C_8$ cycloalkyl optionally substituted with one or more $-Q_5-T_5$.

For example, $R_7$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like) optionally substituted with one or more $-Q_5-T_5$.

For example, $R_7$ is 8 to 14-membered heterocycloalkyl such as 1,4-dioxaspiro[4.5]decanyl (e.g., 1,4-dioxaspiro[4.5]decan-8-yl), 1,4-dioxa-8-azaspiro[4.5]decanyl (e.g., 1,4-dioxa-8-azaspiro[4.5]decan-8-yl), 1-oxaspiro[4.5]decanyl (e.g., 1-oxaspiro[4.5]decan-8-yl or 1-oxaspiro[4.5]decan-2-one-8-yl), 1-azaspiro[4.5]decanyl (e.g., 1-azaspiro[4.5]decan-8-yl or 1-azaspiro[4.5]decan-2-one-8-yl), 3'H-spiro[cyclohexane-1,1'-isobenzofuran]-yl (e.g., 3'H-spiro[cyclohexane-1,1'-isobenzofuran]-4-yl or 3'H-spiro[cyclohexane-1,1'-isobenzofuran]-3'-one-4-yl), 7'H-spiro[cyclohexane-1,5'-furo[3,4-b]pyridin]-yl (e.g., 7'H-spiro[cyclohexane-1,5'-furo[3,4-b]pyridin]-4-yl or 7'H-spiro[cyclohexane-1,5'-furo[3,4-b]pyridin]-7'-one-4-yl), or 3'H-spiro[cyclohexane-1,1'-furo[3,4-c]pyridin]-yl (e.g., 3'H-spiro[cyclohexane-1,1'-furo[3,4-c]pyridin]-4-yl or 3'H-spiro[cyclohexane-1,1'-furo[3,4-c]pyridin]-3'-one-4-yl), each optionally substituted with one or more $-Q_5-T_5$.

For example, $R_7$ is 5 to 6-membered heterocycloalkyl optionally substituted with one or more $-Q_5-T_5$.

For example, $R_7$ is isopropyl.

For example, $R_7$ is pyrrolidinyl, piperidinyl, tetrahydropyran, cyclopentyl, or cyclohexyl, cycloheptyl, each optionally substituted with one $-Q_5-T_5$.

For example, $R_7$ is cyclopentyl or cyclohexyl, each optionally substituted with one $-Q_5-T_5$.

For example, $Q_5$ is NHC(O) and $T_5$ is $C_1$-$C_6$ alkyl or $C_1$-$C_6$ alkoxy.

For example, $-Q_5-T_5$ is oxo.

For example, $T_4$ is 4 to 7-membered heterocycloalkyl or $C_3$-$C_8$ cycloalkyl or $C_6$-$C_{10}$ aryl, and one or more -$Q_5$-$T_5$ are oxo.

For example, $R_7$ is 1-oxide-tetrahydro-2H-thiopyranyl or 1,1-dioxide-tetrahydro-2H-thiopyranyl.

For example, $R_7$ is cyclohexanonyl, e.g., cyclohexanon-4-yl.

For example, $T_5$ is H, halo, $C_1$-$C_6$ alkyl, $C_1$-$C_6$ alkoxyl, $C_3$-$C_8$ cycloalkyl, $C_6$-$C_{10}$ aryl, or 4 to 7-membered heterocycloalkyl.

For example, $Q_5$ is a bond and $T_5$ is $C_1$-$C_6$ alkyl, $C_3$-$C_8$ cycloalkyl, or 4 to 7-membered heterocycloalkyl.

For example, $Q_5$ is a bond and $T_5$ is 5- or 6-membered heteroaryl, amino, mono-$C_1$-$C_6$ alkylamino, di-$C_1$-$C_6$ alkylamino, $T_5$ being optionally substituted with one or more substituents selected from the group consisting of halo, hydroxyl, $C_1$-$C_6$ alkoxyl, or $C_3$-$C_8$ cycloalkyl.

For example, $Q_5$ is CO, $S(O)_2$, or NHC(O); and $T_5$ is $C_1$-$C_6$ alkyl, $C_1$-$C_6$ alkoxyl, $C_3$-$C_8$ cycloalkyl, or 4 to 7-membered heterocycloalkyl.

For example, $T_5$ is $C_1$-$C_6$ alkyl or $C_1$-$C_6$ alkoxyl, each optionally substituted with halo, hydroxyl, cyano, $C_1$-$C_6$ alkoxyl, amino, mono-$C_1$-$C_6$ alkylamino, di-$C_1$-$C_6$ alkylamino, or $C_3$-$C_8$ cycloalkyl.

For example, $Q_5$ is $C_1$-$C_3$ alkyl linker and $T_5$ is H or $C_6$-$C_{10}$ aryl.

For example, $Q_5$ is $C_1$-$C_3$ alkyl linker and $T_5$ is $C_3$-$C_8$ cycloalkyl, 4 to 7-membered heterocycloalkyl, or $S(O)_qR_q$.

For example, $R_6$ is halo (e.g., fluorine, chlorine, bromine, and iodine) and Z is $S(O)_aR_7$, in which a is 0, 1, or 2 and $R_7$ is $C_1$-$C_6$ alkyl (e.g., methyl, ethyl, n-propyl, i-propyl, butyl, or t-butyl), $C_3$-$C_8$ cycloalkyl (e.g., cyclopentyl, cyclohexyl, or cycloheptyl) or 4 to 14-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, morpholinyl, 1,4-dioxaspiro[4.5]decanyl, 1,4-dioxa-8-azaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, or 3'H-spiro[cyclohexane-1,1'-furo[3,4-c]pyridin]-yl, and the like) and $R_7$ is optionally substituted with one or more -$Q_5$-$T_5$.

For example, $R_6$ is halo (e.g., fluorine, chlorine, bromine, and iodine) and Z is $OR_7$ in which $R_7$ is 4 to 14-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, morpholinyl, 1,4-dioxaspiro[4.5]decanyl, 1,4-dioxa-8-azaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, or 3'H-spiro[cyclohexane-1,1'-furo[3,4-c]pyridin]-yl, and the like) and $R_7$ is optionally substituted with one or more -$Q_5$-$T_5$.

For example, $R_{11}$ is H.

For example, each of $R_2$ and $R_4$, independently, is H or $C_1$-$C_6$ alkyl optionally substituted with amino, azido, halo, mono-$C_1$-$C_6$ alkylamino, di-$C_1$-$C_6$ alkylamino, or $C_6$-$C_{10}$ aryl.

For example, each of $R_2$ and $R_4$, independently is $C_1$-$C_3$ alkyl optionally substituted with $C_1$-$C_6$ alkoxyl.

For example, each of $R_2$ and $R_4$ is methyl.

For example, $R_1$ is H.

For example, $R_1$ is $C_1$-$C_6$ alkyl optionally substituted with azido, halo, amino, mono-$C_1$-$C_6$ alkylamino, di-$C_1$-$C_6$ alkylamino, or $C_6$-$C_{10}$ aryl.

For example, $R_{12}$ is H, methyl, ethyl, ethenyl, or halo.

For example, $R_{12}$ is methyl.

For example, $R_{12}$ is ethyl or propenyl.

For example, $R_{12}$ is methoxyl.

For example, $R_{12}$ is ethenyl.

For example, $R_8$ is H, methyl, ethyl, or ethenyl.

For example, $R_8$ is methyl.

For example, $R_8$ is ethyl.

For example, $R_8$ is propyl.

For example, $R_8$ is ethenyl or propenyl.

For example, $R_8$ is $C_1$-$C_6$ alkyl substituted with one or more substituents selected from the group consisting of halo (e.g., F, Cl, or Br), hydroxyl, or $C_1$-$C_6$ alkoxyl.

For example, $R_8$ is 4 to 7-membered optionally substituted heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like).

For example, $R_8$ is piperidinyl.

For example, $R_8$ is 4 to 7-membered optionally substituted heterocycloalkyl and $R_7$ is -$Q_4$-$T_4$, in which $Q_4$ is a bond or $C_1$-$C_4$ alkyl linker and $T_4$ is H, $C_1$-$C_6$ alkyl, $C_3$-$C_8$ cycloalkyl or 4 to 7-membered heterocycloalkyl.

For example, Z is $NR_7R_8$ or $CR_7R_8R_{14}$ wherein $R_7$ and $R_8$, together with the atom to which they are attached, form a 4 to 11-membered heterocycloalkyl ring having 1 to 3 heteroatoms (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, morpholinyl, 1,4-dioxa-8-azaspiro[4.5]decanyl, and the like) or $C_3$-$C_8$ cycloalkyl, each optionally substituted with one or more -$Q_6$-$T_6$.

For example, the ring formed by $R_7$ and $R_8$ is selected from the group consisting of azetidinyl, pyrrolidinyl, piperidinyl, morpholinyl, piperazinyl, 1,4-dioxa-8-azaspiro[4.5]decanyl, and cyclohexenyl, each optionally substituted with one -$Q_6$-$T_6$.

For example, Z is 1,4-dioxa-8-azaspiro[4.5]decan-8-yl, pyrrolidine-2,5-dione-1-yl, or piperidine-2,6-dione-1-yl.

For example, one or more -$Q_6$-$T_6$ is oxo.

For example, $T_6$ is H, halo, $C_1$-$C_6$ alkyl, $C_1$-$C_6$ alkoxyl, $C_3$-$C_8$ cycloalkyl, $C_6$-$C_{10}$ aryl, or 4 to 7-membered heterocycloalkyl.

For example, $Q_6$ is a bond and $T_6$ is $C_1$-$C_6$ alkyl, $C_3$-$C_8$ cycloalkyl, or 4 to 7-membered heterocycloalkyl.

For example, $Q_6$ is CO, $S(O)_2$, or NHC(O); and $T_6$ is $C_1$-$C_6$ alkyl, $C_1$-$C_6$ alkoxyl, $C_3$-$C_8$ cycloalkyl, or 4 to 7-membered heterocycloalkyl.

For example, $T_6$ is $C_1$-$C_6$ alkyl or $C_1$-$C_6$ alkoxyl, each optionally substituted with halo, hydroxyl, cyano, $C_1$-$C_6$ alkoxyl, amino, mono-$C_1$-$C_6$ alkylamino, di-$C_1$-$C_6$ alkylamino, or $C_3$-$C_8$ cycloalkyl.

For example, $Q_6$ is $C_1$-$C_3$ alkyl linker and $T_6$ is H or $C_6$-$C_{10}$ aryl.

For example, $Q_6$ is $C_1$-$C_3$ alkyl linker and $T_6$ is $C_3$-$C_8$ cycloalkyl, 4 to 7-membered heterocycloalkyl, or $S(O)_pR_p$.

For example, each of $R_p$ and $R_q$, independently, is $C_1$-$C_6$ alkyl.

For example, $R_6$ is —$S(O)_bR_a$ or azido, in which b is 0, 1, or 2 and $R_a$ is $C_1$-$C_6$ alkyl or $C_3$-$C_8$ cycloalkyl; and Z is $NR_7R_8$, in which $R_7$ is $C_3$-$C_8$ cycloalkyl (e.g., cyclopentyl, cyclohexyl, or cycloheptyl) or 4 to 14-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, morpholinyl, 1,4-dioxaspiro[4.5]decanyl, 1,4-dioxa-8-azaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, or 3'H-spiro[cyclohexane-1,1'-furo[3,4-c]pyridin]-yl, and the like), each optionally substituted with one or more -$Q_5$-$T_5$; and $R_8$ is H or $C_1$-$C_6$ alkyl (e.g., methyl, ethyl, n-propyl, i-propyl, butyl, or t-butyl).

For example, $R_6$ is halo (e.g., fluorine, chlorine, bromine, and iodine) and Z is $NR_7R_8$ or $CR_7R_8R_{14}$ wherein $R_7$ and $R_8$, together with the atom to which they are attached, form a 4 to 11-membered heterocycloalkyl ring having 1 to 3 heteroatoms (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, morpholinyl, 2-oxa-6-azaspiro[3.3]heptanyl, 2,6-diazaspiro[3.3]heptanyl, 1,4-dioxa-8-azaspiro[4.5]decanyl, 1,4-dioxa-8-azaspiro[4.5]decan-8-yl, pyrrolidine-2,5-dione-1-yl, piperidine-2,6-dione-1-yl, and the like) or $C_3$-$C_8$ cycloalkyl, each optionally substituted with one or more -$Q_6$-$T_6$.

For example, $R_{13}$ is H or methyl.

For example, $R_{13}$ is H.

For example, $R_3$ is H.

For example, each of $R_5$, $R_9$, and $R_{10}$ is H.

In another aspect, the present invention features a substituted benzene compound of Formula (I) above or a pharmaceutically acceptable salt or ester thereof, in which $X_1$ is N or $CR_{11}$;

$X_2$ is N or $CR_{13}$;

$X_3$ is N or C, and when $X_3$ is N, $R_6$ is absent;

Z is $NR_7R_8$, $OR_7$, $S(O)_aR_7$, or $CR_7R_8R_{14}$, in which a is 0, 1, or 2;

each of $R_1$, $R_5$, $R_9$, and $R_{10}$, independently, is H or $C_1$-$C_6$ alkyl optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

each of $R_2$, $R_3$, and $R_4$, independently, is -$Q_1$-$T_1$, in which $Q_1$ is a bond or $C_1$-$C_3$ alkyl linker optionally substituted with halo, cyano, hydroxyl or $C_1$-$C_6$ alkoxy, and $T_1$ is H, halo, hydroxyl, COOH, cyano, azido, or $R_{S1}$, in which $R_{S1}$ is $C_1$-$C_3$ alkyl, $C_2$-$C_6$ alkenyl, $C_2$-$C_6$ alkynyl, $C_1$-$C_6$ alkoxyl, C(O)O—$C_1$-$C_6$ alkyl, $C_3$-$C_8$ cycloalkyl, $C_6$-$C_{10}$ aryl, amino, mono-$C_1$-$C_6$ alkylamino, di-$C_1$-$C_6$ alkylamino, 4 to 12-membered heterocycloalkyl, or 5- or 6-membered heteroaryl, and $R_{S1}$ is optionally substituted with one or more substituents selected from the group consisting of halo, hydroxyl, oxo, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

$R_6$ is H, halo, cyano, azido, $OR_a$, —$NR_aR_b$, —$C(O)R_a$, —$C(O)OR_a$, —$C(O)NR_aR_b$, —$NR_bC(O)R_a$, —$S(O)_bR_a$, —$S(O)_bNR_aR_b$, or $R_{S2}$, in which $R_{S2}$ is $C_1$-$C_6$ alkyl, $C_2$-$C_6$ alkenyl, $C_2$-$C_6$ alkynyl, $C_3$-$C_8$ cycloalkyl, or 4 to 12-membered heterocycloalkyl; b is 0, 1, or 2, each of $R_a$ and $R_b$, independently is H or $R_{S3}$, and $R_{S3}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl; or $R_a$ and $R_b$, together with the N atom to which they are attached, form a 4 to 12-membered heterocycloalkyl ring having 0 or 1 additional heteroatom; and each of $R_{S2}$, $R_{S3}$, and the 4 to 12-membered heterocycloalkyl ring formed by $R_a$ and $R_b$, is optionally substituted with one or more -$Q_2$-$T_2$, wherein $Q_2$ is a bond or $C_1$-$C_3$ alkyl linker each optionally substituted with halo, cyano, hydroxyl or $C_1$-$C_6$ alkoxy, and $T_2$ is H, halo, cyano, —$NR_cR_d$, —$C(O)R_c$, —$C(O)OR_c$, —$C(O)NR_cR_d$, —$NR_dC(O)R_c$, —$NR_dC(O)OR_c$, —$S(O)_2R_c$, —$S(O)_2NR_cR_d$, or $R_{S4}$, in which each of $R_c$ and $R_d$, independently is H or $R_{S5}$, each of $R_{S4}$ and $R_{S5}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_c$ and $R_d$, together with the N atom to which they are attached, form a 4 to 12-membered heterocycloalkyl ring having 0 or 1 additional heteroatom, and each of $R_{S4}$, $R_{S5}$, and the 4 to 12-membered heterocycloalkyl ring formed by $R_c$ and $R_d$, is optionally substituted with one or more -$Q_3$-$T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_e$, $COOR_e$, —$S(O)_2R_e$, —$NR_eR_f$, and —$C(O)NR_eR_f$, each of $R_e$ and $R_f$ independently being H or $C_1$-$C_6$ alkyl, or -$Q_3$-$T_3$ is oxo; or -$Q_2$-$T_2$ is oxo;

$R_7$ is -$Q_4$-$T_4$, in which $Q_4$ is a bond, $C_1$-$C_4$ alkyl linker, or $C_2$-$C_4$ alkenyl linker, each linker optionally substituted with halo, cyano, hydroxyl or $C_1$-$C_6$ alkoxy, and $T_4$ is H, halo, cyano, $NR_gR_h$, —$OR_g$, —$C(O)R_g$, —$C(O)OR_g$, —$C(O)NR_gR_h$, —$C(O)NR_gOR_h$, —$NR_gC(O)R_h$, —$S(O)_2R_g$, or $R_{S6}$, in which each of $R_g$ and $R_h$, independently is H or $R_{S7}$, each of $R_{S6}$ and $R_{S7}$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and each of $R_{S6}$ and $R_{S7}$ is optionally substituted with one or more -$Q_5$-$T_5$, wherein $Q_5$ is a bond, C(O), $C(O)NR_k$, $NR_kC(O)$, $S(O)_2$, or $C_1$-$C_3$ alkyl linker, $R_k$ being H or $C_1$-$C_6$ alkyl, and $T_5$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or $S(O)_qR_q$ in which q is 0, 1, or 2 and $R_q$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_5$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_5$ is H, halo, hydroxyl, or cyano; or -$Q_5$-$T_5$ is oxo; provided that (i) $R_7$ is not $C(O)R_g$ or —$S(O)_2R_g$ when Z is $NR_7R_8$; (ii) $R_7$ is not $C_1$-$C_6$ alkyl when Z is $OR_7$, and (iii) $R_7$ is not H;

each of $R_8$, $R_{11}$, $R_{12}$, and $R_{13}$, independently, is H, halo, hydroxyl, COOH, cyano, $R_{S8}$, $OR_{S8}$, or $COOR_{S8}$, in which $R_{S8}$ is $C_1$-$C_6$ alkyl, $C_2$-$C_6$ alkenyl, $C_2$-$C_6$ alkynyl, $C_3$-$C_8$ cycloalkyl, 4 to 12-membered heterocycloalkyl, amino, mono-$C_1$-$C_6$ alkylamino, or di-$C_1$-$C_6$ alkylamino, and $R_{S8}$ is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino; or $R_7$ and $R_8$, together with the N atom to which they are attached, form a 4 to 12-membered heterocycloalkyl ring having 0 to 2 additional heteroatoms, or $R_7$ and $R_8$, together with the C atom to which they are attached, form $C_3$-$C_8$ cycloalkyl or a 4 to 12-membered heterocycloalkyl ring having 1 to 3 heteroatoms, and each of the 4 to 12-membered heterocycloalkyl rings or $C_3$-$C_8$ cycloalkyl formed by $R_7$ and $R_8$ is optionally substituted with one or more -$Q_6$-$T_6$, wherein $Q_6$ is a bond, C(O), $C(O)NR_m$, $NR_mC(O)$, $S(O)_2$, or $C_1$-$C_3$ alkyl linker, $R_m$ being H or $C_1$-$C_6$ alkyl, and $T_6$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or $S(O)_pR_p$ in which p is 0, 1, or 2 and $R_p$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_6$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_6$ is H, halo, hydroxyl, or cyano; or -$Q_6$-$T_6$ is oxo; and $R_{14}$ is absent, H, or $C_1$-$C_6$ alkyl optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl.

For example, $X_1$ is $CR_{11}$ and $X_2$ is $CR_{13}$.

For example, $X_1$ is $CR_{11}$ and $X_2$ is N.

For example, $X_1$ is N and $X_2$ is $CR_{13}$.

For example, $X_1$ is N and $X_2$ is N.

For example, $X_3$ is C.

For example, $X_3$ is N and $R_6$ is absent.

For example, Z is $NR_7R_8$.

For example, Z is $CR_7R_8R_{14}$.

For example, Z is $OR_7$.

For example, Z is $S(O)_aR_7$, in which a is 0, 1, or 2

For example, Z is $SR_7$.

For example, $R_6$ is H.

For example, $R_6$ is halo (e.g., fluorine, chlorine, bromine, and iodine).

For example, $R_6$ is $C_1$-$C_3$ alkyl optionally substituted with one or more -$Q_2$-$T_2$.

For example, $R_6$ is $CF_3$.

For example, $R_6$ is $C_2$-$C_6$ alkenyl, $C_2$-$C_6$ alkynyl, or $C_3$-$C_6$ cycloalkyl each optionally substituted with one or more -$Q_2$-$T_2$.

For example, $R_6$ is ethenyl.

For example, $R_6$ is ethynyl.

For example, $R_6$ is ethynyl substituted with one or more -$Q_2$-$T_2$, in which $Q_2$ is a bond or $C_1$-$C_3$ alkyl linker and $T_2$ is $C_1$-$C_6$ alkyl, $C_3$-$C_6$ cycloalkyl, or 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, and morpholinyl, and the like) optionally substituted with one or more -$Q_3$-$T_3$.

For example, $R_6$ is azido.

For example, $R_6$ is cyano.

For example, $R_6$ is C(O)H.

For example, $R_6$ is —$C(O)R_a$.

For example, $R_a$ is $C_1$-$C_6$ alkyl or 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like), which is optionally substituted with one or more -$Q_2$-$T_2$.

For example, $R_6$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like) optionally substituted with one or more -$Q_2$-$T_2$.

For example, $R_6$ is piperidinyl, 2,2,6,6-tetramethyl-piperidinyl, 1,2,3,6-tetrahydropyridinyl, 2,2,6,6-tetramethyl-1,2,3,6-tetrahydropyridinyl, piperazinyl, morpholinyl, tetrahydro-2H-pyranyl, 3,6-dihydro-2H-pyranyl, or pyrrolidinyl, each of which is optionally substituted with one or more -$Q_2$-$T_2$.

For example, $R_6$ is 4 to 7-membered heterocycloalkyl optionally substituted with one or more -$Q_2$-$T_2$, and -$Q_2$-$T_2$ is oxo or $Q_2$ is a bond and $T_2$ is —$OR_c$, —$NR_cR_d$, —$C(O)R_c$, —$C(O)OR_c$, —$S(O)_2R_c$, $C_1$-$C_6$ alkyl, or 4 to 7-membered heterocycloalkyl, each of which is optionally substituted with one or more -$Q_3$-$T_3$ when $R_c$ or $R_d$ is not H.

For example, $R_6$ is —$NR_aR_b$, —$C(O)R_a$, —$C(O)OR_a$, —$C(O)NR_aR_b$, —$NR_bC(O)R_a$, —$SR_a$, —$S(O)_2R_a$, or —$S(O)_2NR_aR_b$.

For example, each of $R_a$ and $R_b$, independently is H, $C_1$-$C_6$ alkyl or $C_3$-$C_8$ cycloalkyl optionally substituted with one or more -$Q_2$-$T_2$.

For example, one of $R_a$ and $R_b$ is H.

For example, $R_a$ and $R_b$, together with the N atom to which they are attached, form a 4 to 7-membered heterocycloalkyl ring having 0 or 1 additional heteroatoms to the N atom (e.g., azetidinyl, pyrrolidinyl, imidazolidinyl, pyrazolidinyl, oxazolidinyl, isoxazolidinyl, triazolidinyl, piperidinyl, 1,2,3,6-tetrahydropyridinyl, piperazinyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like) and the ring is optionally substituted with one or more $-Q_2-T_2$.

For example, $-Q_2-T_2$ is not H.

For example, $-Q_2-T_2$ is oxo.

For example, $Q_2$ is a bond.

For example, $Q_2$ is an unsubstituted $C_1$-$C_3$ alkyl linker.

For example, $T_2$ is $C_1$-$C_6$ alkyl or $C_6$-$C_{10}$ aryl, each optionally substituted with one or more $-Q_3-T_3$.

For example, $T_2$ is an unsubstituted substituted straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl and n-hexyl.

For example, $T_2$ is phenyl.

For example, $T_2$ is halo (e.g., fluorine, chlorine, bromine, and iodine).

For example, $T_2$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like) optionally substituted with one or more $-Q_3-T_3$.

For example, $T_2$ is $-OR_c$, $-NR_cR_d$, $-C(O)R_c$, $-C(O)OR_c$, or $-S(O)_2R_c$.

For example, $R_c$ is $C_1$-$C_6$ alkyl or 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like), which is optionally substituted with one or more $-Q_3-T_3$.

For example, each of $R_c$ and $R_d$, independently is H or $C_1$-$C_6$ alkyl optionally substituted with one or more $-Q_3-T_3$.

For example, $R_c$ is H.

For example, $R_d$ is H.

For example, $R_c$ and $R_d$, together with the N atom to which they are attached, form a 4 to 7-membered heterocycloalkyl ring having 0 or 1 additional heteroatoms to the N atom (e.g., azetidinyl, pyrrolidinyl, imidazolidinyl, pyrazolidinyl, oxazolidinyl, isoxazolidinyl, triazolidinyl, piperidinyl, 1,2,3,6-tetrahydropyridinyl, piperazinyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like) and the ring is optionally substituted with one or more $-Q_3-T_3$.

For example, $Q_2$ is a bond and $T_2$ is $-OR_c$, $-NR_cR_d$, $-C(O)R_c$, $-C(O)OR_c$, $-S(O)_2R_c$, $C_1$-$C_6$ alkyl, or 4 to 7-membered heterocycloalkyl, each of which is optionally substituted with one or more $-Q_3-T_3$ when $R_c$ or $R_d$ is not H.

For example, $-Q_3-T_3$ is oxo.

For example, $T_2$ is 4 to 7-membered heterocycloalkyl or $C_3$-$C_8$ cycloalkyl and one or more $-Q_3-T_3$ are oxo.

For example, $Q_3$ is a bond or unsubstituted or substituted $C_1$-$C_3$ alkyl linker.

For example, $T_3$ is H, halo, 4 to 7-membered heterocycloalkyl, $C_1$-$C_3$ alkyl, $OR_e$, $COOR_e$, $-S(O)_2R_e$, $-NR_eR_f$, or $-C(O)NR_eR_f$.

For example, one of $R_d$ and $R_e$ is H.

For example, $Q_3$ is a bond or $C_1$-$C_3$ alkyl linker and $T_3$ is selected from the group consisting of $C_1$-$C_3$ alkyl, halo, $OR_e$, $-S(O)_2R_e$, $-NR_eR_f$, and $-C(O)NR_eR_f$.

For example, $Q_3$ is a bond or $C_1$-$C_3$ alkyl linker and $T_3$ is selected from the group consisting of $C_1$-$C_3$ alkyl, $OR_e$, $-S(O)_2R_e$, or $-NR_eR_f$.

For example, $R_e$ is H.

For example, $R_f$ is H.

For example, $R_7$ is not H.

For example, $R_7$ is $-C(O)R_g$.

For example, $R_7$ is $-C(O)R_g$, in which $R_g$ is $C_3$-$C_8$ cycloalkyl, or 4 to 7-membered heterocycloalkyl, $C_3$-$C_8$ cycloalkyl.

For example, $R_7$ is $C_6$-$C_{10}$ aryl substituted with one or more $-Q_5-T_5$.

For example, $R_7$ is phenyl optionally substituted with one or more $-Q_5-T_5$.

For example, $R_7$ is $C_1$-$C_6$ alkyl optionally substituted with one or more $-Q_5-T_5$.

For example, $R_7$ is $C_3$-$C_8$ cycloalkyl optionally substituted with one or more $-Q_5-T_5$.

For example, $R_7$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like) optionally substituted with one or more $-Q_5-T_5$.

For example, $R_7$ is 8 to 14-membered heterocycloalkyl such as 1,4-dioxaspiro[4.5]decanyl (e.g., 1,4-dioxaspiro[4.5]decan-8-yl), 1,4-dioxa-8-azaspiro[4.5]decanyl (e.g., 1,4-dioxa-8-azaspiro[4.5]decan-8-yl), 1-oxaspiro[4.5]decanyl (e.g., 1-oxaspiro[4.5]decan-8-yl or 1-oxaspiro[4.5]decan-2-one-8-yl), 1-azaspiro[4.5]decanyl (e.g., 1-azaspiro[4.5]decan-8-yl or 1-azaspiro[4.5]decan-2-one-8-yl), 3'H-spiro[cyclohexane-1,1'-isobenzofuran]-yl (e.g., 3'H-spiro[cyclohexane-1,1'-isobenzofuran]-4-yl or 3'H-spiro[cyclohexane-1,1'-isobenzofuran]-3'-one-4-yl), 7'H-spiro[cyclohexane-1,5'-furo[3,4-b]pyridin]-yl (e.g., 7'H-spiro[cyclohexane-1,5'-furo[3,4-b]pyridin]-4-yl or 7'H-spiro[cyclohexane-1,5'-furo[3,4-b]pyridin]-7'-one-4-yl), or 3'H-spiro[cyclohexane-1,1'-furo[3,4-c]pyridin]-yl (e.g., 3'H-spiro[cyclohexane-1,1'-furo[3,4-c]pyridin]-4-yl or 3'H-spiro[cyclohexane-1,1'-furo[3,4-c]pyridin]-3'-one-4-yl), each optionally substituted with one or more $-Q_5-T_5$.

For example, $R_7$ is 5 to 6-membered heterocycloalkyl optionally substituted with one or more $-Q_5-T_5$.

For example, $R_7$ is isopropyl.

For example, $R_7$ is pyrrolidinyl, piperidinyl, tetrahydropyran, cyclopentyl, or cyclohexyl, cycloheptyl, each optionally substituted with one $-Q_5-T_5$.

For example, $R_7$ is cyclopentyl or cyclohexyl, each optionally substituted with one $-Q_5-T_5$.

For example, $Q_5$ is NHC(O) and $T_5$ is $C_1$-$C_6$ alkyl or $C_1$-$C_6$ alkoxy.

For example, $-Q_5-T_5$ is oxo.

For example, $T_4$ is 4 to 7-membered heterocycloalkyl or $C_3$-$C_8$ cycloalkyl or $C_6$-$C_{10}$ aryl, and one or more $-Q_5-T_5$ are oxo.

For example, $R_7$ is 1-oxide-tetrahydro-2H-thiopyranyl or 1,1-dioxide-tetrahydro-2H-thiopyranyl.

For example, $R_7$ is cyclohexanonyl, e.g., cyclohexanon-4-yl.

For example, $T_5$ is H, halo, $C_1$-$C_6$ alkyl, $C_1$-$C_6$ alkoxyl, $C_3$-$C_8$ cycloalkyl, $C_6$-$C_{10}$ aryl, or 4 to 7-membered heterocycloalkyl.

For example, $Q_5$ is a bond and $T_5$ is $C_1$-$C_6$ alkyl, $C_3$-$C_8$ cycloalkyl, or 4 to 7-membered heterocycloalkyl.

For example, $Q_5$ is a bond and $T_5$ is 5- or 6-membered heteroaryl, amino, mono-$C_1$-$C_6$ alkylamino, di-$C_1$-$C_6$ alkylamino, $T_5$ being optionally substituted with one or more substituents selected from the group consisting of halo, hydroxyl, $C_1$-$C_6$ alkoxyl, or $C_3$-$C_8$ cycloalkyl.

For example, $Q_5$ is CO, $S(O)_2$, or NHC(O); and $T_5$ is $C_1$-$C_6$ alkyl, $C_1$-$C_6$ alkoxyl, $C_3$-$C_8$ cycloalkyl, or 4 to 7-membered heterocycloalkyl.

For example, $T_5$ is $C_1$-$C_6$ alkyl or $C_1$-$C_6$ alkoxyl, each optionally substituted with halo, hydroxyl, cyano, $C_1$-$C_6$ alkoxyl, amino, mono-$C_1$-$C_6$ alkylamino, di-$C_1$-$C_6$ alkylamino, or $C_3$-$C_8$ cycloalkyl.

For example, $Q_5$ is $C_1$-$C_3$ alkyl linker and $T_5$ is H or $C_6$-$C_{10}$ aryl.

For example, $Q_5$ is $C_1$-$C_3$ alkyl linker and $T_5$ is $C_3$-$C_8$ cycloalkyl, 4 to 7-membered heterocycloalkyl, or $S(O)_qR_q$.

For example, $R_6$ is halo (e.g., fluorine, chlorine, bromine, and iodine) and Z is $S(O)_aR_7$, in which a is 0, 1, or 2 and $R_7$ is $C_1$-$C_6$ alkyl (e.g., methyl, ethyl, n-propyl, i-propyl, butyl, or t-butyl), $C_3$-$C_8$ cycloalkyl (e.g., cyclopentyl, cyclohexyl, or cycloheptyl) or 4 to 14-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, morpholinyl, 1,4-dioxaspiro[4.5]decanyl, 1,4-dioxa-8-azaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, or 3'H-spiro[cyclohexane-1,1'-furo[3,4-c]pyridin]-yl, and the like) and $R_7$ is optionally substituted with one or more -$Q_5$-$T_5$.

For example, $R_6$ is halo (e.g., fluorine, chlorine, bromine, and iodine) and Z is $OR_7$ in which $R_7$ is 4 to 14-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, morpholinyl, 1,4-dioxaspiro[4.5]decanyl, 1,4-dioxa-8-azaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, or 3'H-spiro[cyclohexane-1,1'-furo[3,4-c]pyridin]-yl, and the like) and $R_7$ is optionally substituted with one or more -$Q_5$-$T_5$.

For example, $R_{11}$ is H.

For example, each of $R_2$ and $R_4$, independently, is H or $C_1$-$C_6$ alkyl optionally substituted with amino, azido, halo, mono-$C_1$-$C_6$ alkylamino, di-$C_1$-$C_6$ alkylamino, or $C_6$-$C_{10}$ aryl.

For example, each of $R_2$ and $R_4$, independently is $C_1$-$C_3$ alkyl optionally substituted with $C_1$-$C_6$ alkoxyl.

For example, each of $R_2$ and $R_4$ is methyl.

For example, $R_1$ is H.

For example, $R_1$ is $C_1$-$C_6$ alkyl optionally substituted with azido, halo, amino, mono-$C_1$-$C_6$ alkylamino, di-$C_1$-$C_6$ alkylamino, or $C_6$-$C_{10}$ aryl.

For example, $R_{12}$ is H, methyl, ethyl, ethenyl, or halo.

For example, $R_{12}$ is methyl.

For example, $R_{12}$ is ethyl or propenyl.

For example, $R_{12}$ is methoxyl.

For example, $R_{12}$ is ethenyl.

For example, $R_8$ is H, methyl, ethyl, or ethenyl.

For example, $R_8$ is methyl.

For example, $R_8$ is ethyl.

For example, $R_8$ is propyl.

For example, $R_8$ is ethenyl or propenyl.

For example, $R_8$ is $C_1$-$C_6$ alkyl substituted with one or more substituents selected from the group consisting of halo (e.g., F, Cl, or Br), hydroxyl, or $C_1$-$C_6$ alkoxyl.

For example, $R_8$ is 4 to 7-membered optionally substituted heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like).

For example, $R_8$ is piperidinyl.

For example, $R_8$ is 4 to 7-membered optionally substituted heterocycloalkyl and $R_7$ is -$Q_4$-$T_4$, in which $Q_4$ is a bond or $C_1$-$C_4$ alkyl linker and $T_4$ is H, $C_1$-$C_6$ alkyl, $C_3$-$C_8$ cycloalkyl or 4 to 7-membered heterocycloalkyl.

For example, Z is $NR_7R_8$ or $CR_7R_8R_{14}$ wherein $R_7$ and $R_8$, together with the atom to which they are attached, form a 4 to 11-membered heterocycloalkyl ring having 1 to 3 heteroatoms (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, morpholinyl, 1,4-dioxa-8-azaspiro[4.5]decanyl, and the like) or $C_3$-$C_8$ cycloalkyl, each optionally substituted with one or more -$Q_6$-$T_6$.

For example, the ring formed by $R_7$ and $R_8$ is selected from the group consisting of azetidinyl, pyrrolidinyl, piperidinyl, morpholinyl, piperazinyl, 1,4-dioxa-8-azaspiro[4.5]decanyl, and cyclohexenyl, each optionally substituted with one -$Q_6$-$T_6$.

For example, Z is 1,4-dioxa-8-azaspiro[4.5]decan-8-yl, pyrrolidine-2,5-dione-1-yl, or piperidine-2,6-dione-1-yl.

For example, one or more -$Q_6$-$T_6$ is oxo.

For example, $T_6$ is H, halo, $C_1$-$C_6$ alkyl, $C_1$-$C_6$ alkoxyl, $C_3$-$C_8$ cycloalkyl, $C_6$-$C_{10}$ aryl, or 4 to 7-membered heterocycloalkyl.

For example, $Q_6$ is a bond and $T_6$ is $C_1$-$C_6$ alkyl, $C_3$-$C_8$ cycloalkyl, or 4 to 7-membered heterocycloalkyl.

For example, $Q_6$ is CO, $S(O)_2$, or NHC(O); and $T_6$ is $C_1$-$C_6$ alkyl, $C_1$-$C_6$ alkoxyl, $C_3$-$C_8$ cycloalkyl, or 4 to 7-membered heterocycloalkyl.

For example, $T_6$ is $C_1$-$C_6$ alkyl or $C_1$-$C_6$ alkoxyl, each optionally substituted with halo, hydroxyl, cyano, $C_1$-$C_6$ alkoxyl, amino, mono-$C_1$-$C_6$ alkylamino, di-$C_1$-$C_6$ alkylamino, or $C_3$-$C_8$ cycloalkyl.

For example, $Q_6$ is $C_1$-$C_3$ alkyl linker and $T_6$ is H or $C_6$-$C_{10}$ aryl.

For example, $Q_6$ is $C_1$-$C_3$ alkyl linker and $T_6$ is $C_3$-$C_8$ cycloalkyl, 4 to 7-membered heterocycloalkyl, or $S(O)_pR_p$.

For example, each of $R_p$ and $R_q$, independently, is $C_1$-$C_6$ alkyl.

For example, $R_6$ is —$S(O)_bR_a$ or azido, in which b is 0, 1, or 2 and $R_a$ is $C_1$-$C_6$ alkyl or $C_3$-$C_8$ cycloalkyl; and Z is $NR_7R_8$, in which $R_7$ is $C_3$-$C_8$ cycloalkyl (e.g., cyclopentyl, cyclohexyl, or cycloheptyl) or 4 to 14-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, morpholinyl, 1,4-dioxaspiro[4.5]decanyl, 1,4-dioxa-8-azaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, or 3'H-spiro[cyclohexane-1,1'-furo[3,4-c]pyridin]-yl, and the like), each optionally substituted with one or more -$Q_5$-$T_5$; and $R_8$ is H or $C_1$-$C_6$ alkyl (e.g., methyl, ethyl, n-propyl, i-propyl, butyl, or t-butyl).

For example, $R_6$ is halo (e.g., fluorine, chlorine, bromine, and iodine) and Z is $NR_7R_8$ or $CR_7R_8R_{14}$ wherein $R_7$ and $R_8$, together with the atom to which they are attached, form a 4 to 11-membered heterocycloalkyl ring having 1 to 3 heteroatoms (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, morpholinyl, 2-oxa-6-azaspiro[3.3]heptanyl, 2,6-diazaspiro[3.3]heptanyl, 1,4-dioxa-8-azaspiro[4.5]decanyl, 1,4-dioxa-8-azaspiro[4.5]decan-8-yl, pyrrolidine-2,5-dione-1-yl, piperidine-2,6-dione-1-yl, and the like) or $C_3$-$C_8$ cycloalkyl, each optionally substituted with one or more -$Q_6$-$T_6$.

For example, $R_{13}$ is H or methyl.

For example, $R_{13}$ is H.

For example, $R_3$ is H.

For example, each of $R_5$, $R_9$, and $R_{10}$ is H.

The present invention provides the compounds of Formula (Ia)

(Ia)

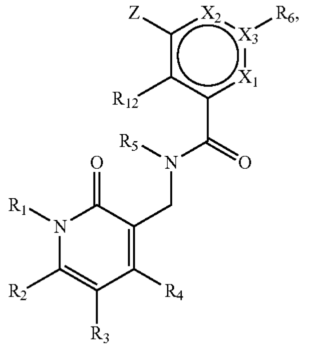

or a pharmaceutically acceptable salt or ester thereof, wherein:

$X_1$ is N or $CR_{11}$;

$X_2$ is N or $CR_{13}$;

$X_3$ is N or C, and when $X_3$ is N, $R_6$ is absent;

Z is $NR_7R_8$, $OR_7$, $S(O)_aR_7$, or $CR_7R_8R_{14}$, in which a is 0, 1, or 2;

each of $R_1$ and $R_5$, independently, is H or $C_1$-$C_6$ alkyl optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

each of $R_2$, $R_3$, and $R_4$, independently, is -$Q_1$-$T_1$, in which $Q_1$ is a bond or $C_1$-$C_3$ alkyl linker optionally substituted with halo, cyano, hydroxyl or $C_1$-$C_6$ alkoxy, and $T_1$ is H, halo, hydroxyl, COOH, cyano, azido, or $R_{S1}$, in which $R_{S1}$ is $C_1$-$C_3$ alkyl, $C_2$-$C_6$ alkenyl, $C_2$-$C_6$ alkynyl, $C_1$-$C_6$ alkoxyl, C(O)O—$C_1$-$C_6$ alkyl, $C_3$-$C_8$ cycloalkyl, $C_6$-$C_{10}$ aryl, amino, mono-$C_1$-$C_6$ alkylamino, di-$C_1$-$C_6$ alkylamino, 4 to 12-membered heterocycloalkyl, or 5- or 6-membered heteroaryl, and $R_{S1}$ is optionally substituted with one or more substituents selected from the group consisting of halo, hydroxyl, oxo, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

$R_6$ is H, halo, cyano, azido, $OR_a$, —$NR_aR_b$, —$C(O)R_a$, —$C(O)OR_a$, —$C(O)NR_aR_b$, —$NR_bC(O)R_a$, —$S(O)_bR_a$, —$S(O)_bNR_aR_b$, or $R_{S2}$, in which $R_{S2}$ is $C_1$-$C_6$ alkyl, $C_2$-$C_6$ alkenyl, $C_2$-$C_6$ alkynyl, $C_3$-$C_8$ cycloalkyl, or 4 to 12-membered heterocycloalkyl, b is 0, 1, or 2, each of $R_a$ and $R_b$, independently is H or $R_{S3}$, and $R_{S3}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl; or $R_a$ and $R_b$, together with the N atom to which they are attached, form a 4 to 12-membered heterocycloalkyl ring having 0 or 1 additional heteroatom; and each of $R_{S2}$, $R_{S3}$, and the 4 to 12-membered heterocycloalkyl ring formed by $R_a$ and $R_b$, is optionally substituted with one or more -$Q_2$-$T_2$, wherein $Q_2$ is a bond or $C_1$-$C_3$ alkyl linker each optionally substituted with halo, cyano, hydroxyl or $C_1$-$C_6$ alkoxy, and $T_2$ is H, halo, cyano, —$OR_c$, —$NR_cR_d$, —$C(O)R_c$, —$C(O)OR_c$, —$C(O)NR_cR_d$, —$NR_dC(O)R_c$, —$NR_dC(O)OR_c$, —$S(O)_2R_c$, —$S(O)_2NR_cR_d$, or $R_{S4}$, in which each of $R_c$ and $R_d$, independently is H or $R_{S5}$, each of $R_{S4}$ and $R_{S5}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_c$ and $R_d$, together with the N atom to which they are attached, form a 4 to 12-membered heterocycloalkyl ring having 0 or 1 additional heteroatom, and each of $R_{S4}$, $R_{S5}$, and the 4 to 12-membered heterocycloalkyl ring formed by $R_c$ and $R_d$, is optionally substituted with one or more -$Q_3$-$T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_e$, $COOR_e$, —$S(O)_2R_e$, —$NR_eR_f$, and —$C(O)NR_eR_f$, each of $R_e$ and $R_f$ independently being H or $C_1$-$C_6$ alkyl, or -$Q_3$-$T_3$ is oxo; or -$Q_2$-$T_2$ is oxo; or $R_6$ is H, halo, cyano, azido, —$NR_aR_b$, —$C(O)R_a$, —$C(O)OR_a$, —$C(O)NR_aR_b$, —$NR_bC(O)R_a$, —$S(O)_bR_a$, —$S(O)_bNR_aR_b$, or $R_{S2}$, in which $R_{S2}$ is $C_1$-$C_6$ alkyl, $C_2$-$C_6$ alkenyl, $C_2$-$C_6$ alkynyl, $C_3$-$C_8$ cycloalkyl, or 4 to 12-membered heterocycloalkyl, b is 0, 1, or 2, each of $R_a$ and $R_b$, independently is H or $R_{S3}$, and $R_{S3}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl; or $R_a$ and $R_b$, together with the N atom to which they are attached, form a 4 to 12-membered heterocycloalkyl ring having 0 or 1 additional heteroatom; and each of $R_{S2}$, $R_{S3}$, and the 4 to 12-membered heterocycloalkyl ring formed by $R_a$ and $R_b$, is optionally substituted with one or more -$Q_2$-$T_2$, wherein $Q_2$ is a bond or $C_1$-$C_3$ alkyl linker each optionally substituted with halo, cyano, hydroxyl or $C_1$-$C_6$ alkoxy, and $T_2$ is H, halo, cyano, —$OR_c$, —$NR_cR_d$, —C(O)$R_c$, —C(O)$OR_c$, —C(O)$NR_cR_d$, —$NR_d$C(O)$R_c$, —$NR_d$C(O)$OR_c$, —S(O)$_2R_c$, —S(O)$_2NR_cR_d$, or $R_{S4}$, in which each of $R_c$ and $R_d$, independently is H or $R_{S5}$, each of $R_{S4}$ and $R_{S5}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_c$ and $R_d$, together with the N atom to which they are attached, form a 4 to 12-membered heterocycloalkyl ring having 0 or 1 additional heteroatom, and each of $R_{S4}$, $R_{S5}$, and the 4 to 12-membered heterocycloalkyl ring formed by $R_c$ and $R_d$, is optionally substituted with one or more -$Q_3$-$T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_e$, $COOR_e$, —S(O)$_2R_e$, —$NR_eR_f$, and —C(O)$NR_eR_f$, each of $R_e$ and $R_f$ independently being H or $C_1$-$C_6$ alkyl, or -$Q_3$-$T_3$ is oxo; or -$Q_2$-$T_2$ is oxo;

$R_7$ is -$Q_4$-$T_4$, in which $Q_4$ is a bond, $C_1$-$C_4$ alkyl linker, or $C_2$-$C_4$ alkenyl linker, each linker optionally substituted with halo, cyano, hydroxyl or $C_1$-$C_6$ alkoxy, and $T_4$ is H, halo, cyano, $NR_gR_h$, —$OR_g$, —C(O)$R_g$, —C(O)$OR_g$, —C(O)$NR_gR_h$, —C(O)$NR_gOR_h$, —$NR_g$C(O)$R_h$, —S(O)$_2R_g$, or $R_{S6}$, in which each of $R_g$ and $R_h$, independently is H or $R_{S7}$, each of $R_{S6}$ and $R_{S7}$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 14-membered heterocycloalkyl, or 5- or 6-membered heteroaryl, and each of $R_{S6}$ and $R_{S7}$ is optionally substituted with one or more -$Q_5$-$T_5$, wherein $Q_5$ is a bond, C(O), C(O)$NR_k$, $NR_k$C(O), S(O)$_2$, or $C_1$-$C_3$ alkyl linker, $R_k$ being H or $C_1$-$C_6$ alkyl, and $T_5$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or S(O)$_qR_q$ in which q is 0, 1, or 2 and $R_q$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_5$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_5$ is H, halo, hydroxyl, or cyano; or -$Q_5$-$T_5$ is oxo; or $R_7$ is -$Q_4$-$T_4$, in which $Q_4$ is a bond, $C_1$-$C_4$ alkyl linker, or $C_2$-$C_4$ alkenyl linker, each linker optionally substituted with halo, cyano, hydroxyl or $C_1$-$C_6$ alkoxy, and $T_4$ is H, halo, cyano, $NR_gR_h$, —$OR_g$, —C(O)$R_g$, —C(O)$OR_g$, —C(O)$NR_gR_h$, —C(O)$NR_gOR_h$, —$NR_g$C(O)$R_h$, —S(O)$_2R_g$, or $R_{S6}$, in which each of $R_g$ and $R_h$, independently is H or $R_{S7}$, each of $R_{S6}$ and $R_{S7}$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and each of $R_{S6}$ and $R_{S7}$ is optionally substituted with one or more -$Q_5$-$T_5$, wherein $Q_5$ is a bond, C(O), C(O)$NR_k$, $NR_k$C(O), S(O)$_2$, or $C_1$-$C_3$ alkyl linker, $R_k$ being H or $C_1$-$C_6$ alkyl, and $T_5$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or S(O)$_qR_q$ in which q is 0, 1, or 2 and $R_q$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_5$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_5$ is H, halo, hydroxyl, or cyano; or -$Q_5$-$T_5$ is oxo; provided that (i) $R_7$ is not C(O)$R_g$ or —S(O)$_2R_g$ when Z is $NR_7R_8$; (ii) $R_7$ is not $C_1$-$C_6$ alkyl when Z is $OR_7$, and (iii) $R_7$ is not H;

each of $R_8$, $R_{11}$, $R_{12}$, and $R_{13}$, independently, is H, halo, hydroxyl, COOH, cyano, $R_{S8}$, $OR_{S8}$, or $COOR_{S8}$, in which $R_{S8}$ is $C_1$-$C_6$ alkyl, $C_2$-$C_6$ alkenyl, $C_2$-$C_6$ alkynyl, $C_3$-$C_8$ cycloalkyl, 4 to 12-membered heterocycloalkyl, amino, mono-$C_1$-$C_6$ alkylamino, or di-$C_1$-$C_6$ alkylamino, and $R_{S8}$ is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino; or $R_7$ and $R_8$, together with the N atom to which they are attached, form a 4 to 12-membered heterocycloalkyl ring having 0 to 2 additional heteroatoms, or $R_7$ and $R_8$, together with the C atom to which they are attached, form $C_3$-$C_8$ cycloalkyl or a 4 to 12-membered heterocycloalkyl ring having 1 to 3 heteroatoms, and each of the 4 to 12-membered heterocycloalkyl rings or $C_3$-$C_8$ cycloalkyl formed by $R_7$ and $R_8$ is optionally substituted with one or more -$Q_6$-$T_6$, wherein $Q_6$ is a bond, C(O), C(O)$NR_m$, $NR_m$C(O), S(O)$_2$, or $C_1$-$C_3$ alkyl linker, $R_m$ being H or $C_1$-$C_6$ alkyl, and $T_6$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or S(O)$_pR_p$ in which p is 0, 1, or 2 and $R_p$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_6$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_6$ is H, halo, hydroxyl, or cyano; or -$Q_6$-$T_6$ is oxo; and $R_{14}$ is absent, H, or $C_1$-$C_6$ alkyl optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

provided that the compound is not

N-(5-(((4,6-dimethyl-2-oxo-1,2-dihydropyridin-3-yl)methyl)carbamoyl)-2-methylphenyl)furan-2-carboxamide, N,N'-(5-(((4,6-dimethyl-2-oxo-1,2-dihydropyridin-3-yl)methyl)carbamoyl)-1,3-phenylene)diacetamide, N-((4,6-dimethyl-2-oxo-1,2-dihydropyridin-3-yl)methyl)-3-pivalamidobenzamide, 3-(3,4-dihydro-2H-benzo[b][1,4]dioxepine-7-sulfonamido)-N-((4,6-dimethyl-2-oxo-1,2-dihydropyridin-3-yl)methyl)benzamide, N-((4,6-dimethyl-2-oxo-1,2-dihydropyridin-3-yl)methyl)-3,5-dimethoxybenzamide, N-((4,6-dimethyl-2-oxo-1,2-dihydropyridin-3-yl)methyl)-3,4,5-trimethoxybenzamide, 3-allyl-N-((4,6-dimethyl-2-oxo-1,2-dihydropyridin-3-yl)methyl)-4,5-dimethoxybenzamide, 4-(2-amino-2-oxoethoxy)-3-chloro-N-((4,6-dimethyl-2-oxo-1,2-dihydropyridin-3-yl)methyl)-5-methoxybenzamide, 3-chloro-N-((4,6-dimethyl-2-oxo-1,2-dihydropyridin-3-yl)methyl)-4-hydroxy-5-methoxybenzamide, or 3-bromo-N-((4,6-dimethyl-2-oxo-1,2-dihydropyridin-3-yl)methyl)-5-methoxy-4-propoxybenzamide.

For example, $X_1$ is $CR_{11}$ and $X_2$ is $CR_{13}$.

For example, $X_1$ is $CR_{11}$ and $X_2$ is N.

For example, $X_1$ is N and $X_2$ is $CR_{13}$.

For example, $X_1$ is N and $X_2$ is N.

For example, $X_3$ is C.

For example, $X_3$ is N and $R_6$ is absent.

For example, Z is $NR_7R_8$.

For example, Z is $CR_7R_8R_{14}$.

For example, Z is $OR_7$.

For example, Z is $S(O)_aR_7$, in which a is 0, 1, or 2

For example, Z is $SR_7$.

For example, $R_6$ is H.

For example, $R_6$ is halo (e.g., fluorine, chlorine, bromine, and iodine).

For example, $R_6$ is $C_1$-$C_3$ alkyl optionally substituted with one or more -$Q_2$-$T_2$.

For example, $R_6$ is $CF_3$.

For example, $R_6$ is $C_2$-$C_6$ alkenyl, $C_2$-$C_6$ alkynyl, or $C_3$-$C_6$ cycloalkyl each optionally substituted with one or more -$Q_2$-$T_2$.

For example, $R_6$ is ethenyl.

For example, $R_6$ is ethynyl.

For example, $R_6$ is ethynyl substituted with one or more -$Q_2$-$T_2$, in which $Q_2$ is a bond or $C_1$-$C_3$ alkyl linker and $T_2$ is $C_1$-$C_6$ alkyl, $C_3$-$C_6$ cycloalkyl, or 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, and morpholinyl, and the like) optionally substituted with one or more -$Q_3$-$T_3$.

For example, $R_6$ is azido.

For example, $R_6$ is cyano.

For example, $R_6$ is C(O)H.

For example, $R_6$ is OR, or —C(O)$R_a$.

For example, $R_a$ is $C_1$-$C_6$ alkyl or 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like), which is optionally substituted with one or more -$Q_2$-$T_2$.

For example, $R_6$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like) optionally substituted with one or more -$Q_2$-$T_2$.

For example, $R_6$ is piperidinyl, 2,2,6,6-tetramethyl-piperidinyl, 1,2,3,6-tetrahydropyridinyl, 2,2,6,6-tetramethyl-1,2,3,6-tetrahydropyridinyl, piperazinyl, morpholinyl, tetrahydro-2H-pyranyl, 3,6-dihydro-2H-pyranyl, or pyrrolidinyl, each of which is optionally substituted with one or more -$Q_2$-$T_2$.

For example, $R_6$ is 4 to 7-membered heterocycloalkyl optionally substituted with one or more -$Q_2$-$T_2$, and -$Q_2$-$T_2$ is oxo or $Q_2$ is a bond and $T_2$ is —$OR_c$, —$NR_cR_d$, —C(O)$R_c$, —C(O)$OR_c$, —S(O)$_2R_c$, $C_1$-$C_6$ alkyl, or 4 to 7-membered heterocycloalkyl, each of which is optionally substituted with one or more -$Q_3$-$T_3$ when $R_c$ or $R_d$ is not H.

For example, $R_6$ is —$NR_aR_b$, —C(O)$R_a$, —C(O)$OR_a$, —C(O)$NR_aR_b$, —$NR_b$C(O)$R_a$, —$SR_a$, —S(O)$_2R_a$, or —S(O)$_2NR_aR_b$.

For example, each of $R_a$ and $R_b$, independently is H, $C_1$-$C_6$ alkyl or $C_3$-$C_8$ cycloalkyl optionally substituted with one or more -$Q_2$-$T_2$.

For example, one of $R_a$ and $R_b$ is H.

For example, $R_a$ and $R_b$, together with the N atom to which they are attached, form a 4 to 7-membered heterocycloalkyl ring having 0 or 1 additional heteroatoms to the N atom (e.g., azetidinyl, pyrrolidinyl, imidazolidinyl, pyrazolidinyl, oxazolidinyl, isoxazolidinyl, triazolidinyl, piperidinyl, 1,2,3,6-tetrahydropyridinyl, piperazinyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like) and the ring is optionally substituted with one or more -$Q_2$-$T_2$.

For example, -$Q_2$-$T_2$ is not H.

For example, -$Q_2$-$T_2$ is oxo.

For example, $Q_2$ is a bond.

For example, $Q_2$ is an unsubstituted $C_1$-$C_3$ alkyl linker.

For example, $T_2$ is $C_1$-$C_6$ alkyl or $C_6$-$C_{10}$ aryl, each optionally substituted with one or more -$Q_3$-$T_3$.

For example, $T_2$ is an unsubstituted substituted straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl and n-hexyl.

For example, $T_2$ is phenyl.

For example, $T_2$ is halo (e.g., fluorine, chlorine, bromine, and iodine).

For example, $T_2$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like) optionally substituted with one or more -$Q_3$-$T_3$.

For example, $T_2$ is —$OR_c$, —$NR_cR_d$, —C(O)$R_c$, —C(O)$OR_c$, or —S(O)$_2R_c$.

For example, $R_c$ is $C_1$-$C_6$ alkyl or 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like), which is optionally substituted with one or more $-Q_3-T_3$.

For example, each of $R_c$ and $R_d$, independently is H or $C_1-C_6$ alkyl optionally substituted with one or more $-Q_3-T_3$.

For example, $R_c$ is H.

For example, $R_d$ is H.

For example, $R_c$ and $R_d$, together with the N atom to which they are attached, form a 4 to 7-membered heterocycloalkyl ring having 0 or 1 additional heteroatoms to the N atom (e.g., azetidinyl, pyrrolidinyl, imidazolidinyl, pyrazolidinyl, oxazolidinyl, isoxazolidinyl, triazolidinyl, piperidinyl, 1,2,3,6-tetrahydropyridinyl, piperazinyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like) and the ring is optionally substituted with one or more $-Q_3-T_3$.

For example, $Q_2$ is a bond and $T_2$ is $—OR_c$, $—NR_cR_d$, $—C(O)R_c$, $—C(O)OR_c$, $—S(O)_2R_c$, $C_1-C_6$ alkyl, or 4 to 7-membered heterocycloalkyl, each of which is optionally substituted with one or more $-Q_3-T_3$ when $R_c$ or $R_d$ is not H.

For example, $-Q_3-T_3$ is oxo.

For example, $T_2$ is 4 to 7-membered heterocycloalkyl or $C_3-C_8$ cycloalkyl and one or more $-Q_3-T_3$ are oxo.

For example, $Q_3$ is a bond or unsubstituted or substituted $C_1-C_3$ alkyl linker.

For example, $T_3$ is H, halo, 4 to 7-membered heterocycloalkyl, $C_1-C_3$ alkyl, $OR_e$, $COOR_e$, $—S(O)_2R_e$, $—NR_eR_f$, or $—C(O)NR_eR_f$.

For example, one of $R_d$ and $R_e$ is H.

For example, $Q_3$ is a bond or $C_1-C_3$ alkyl linker and $T_3$ is selected from the group consisting of $C_1-C_3$ alkyl, halo, $OR_e$, $—S(O)_2R_e$, $—NR_eR_f$, and $—C(O)NR_eR_f$.

For example, $Q_3$ is a bond or $C_1-C_3$ alkyl linker and $T_3$ is selected from the group consisting of $C_1-C_3$ alkyl, $OR_e$, $—S(O)_2R_e$, or $—NR_eR_f$.

For example, $R_e$ is H.

For example, $R_f$ is H.

For example, $R_7$ is not H.

For example, $R_7$ is $—C(O)R_g$.

For example, $R_7$ is $—C(O)R_g$, in which $R_g$ is $C_3-C_8$ cycloalkyl, or 4 to 7-membered heterocycloalkyl, $C_3-C_8$ cycloalkyl.

For example, $R_7$ is $C_6-C_{10}$ aryl substituted with one or more $-Q_5-T_5$.

For example, $R_7$ is phenyl optionally substituted with one or more $-Q_5-T_5$.

For example, $R_7$ is $C_1-C_6$ alkyl optionally substituted with one or more $-Q_5-T_5$.

For example, $R_7$ is $C_3-C_8$ cycloalkyl optionally substituted with one or more $-Q_5-T_5$.

For example, $R_7$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like) optionally substituted with one or more $-Q_5-T_5$.

For example, $R_7$ is 8 to 14-membered heterocycloalkyl such as 1,4-dioxaspiro[4.5]decanyl (e.g., 1,4-dioxaspiro[4.5]decan-8-yl), 1,4-dioxa-8-azaspiro[4.5]decanyl (e.g., 1,4-dioxa-8-azaspiro[4.5]decan-8-yl), 1-oxaspiro[4.5]decanyl (e.g., 1-oxaspiro[4.5]decan-8-yl or 1-oxaspiro[4.5]decan-2-one-8-yl), 1-azaspiro[4.5]decanyl (e.g., 1-azaspiro[4.5]decan-8-yl or 1-azaspiro[4.5]decan-2-one-8-yl), 3'H-spiro[cyclohexane-1,1'-isobenzofuran]-yl (e.g., 3'H-spiro[cyclohexane-1,1'-isobenzofuran]-4-yl or 3'H-spiro[cyclohexane-1,1'-isobenzofuran]-3'-one-4-yl), 7'H-spiro[cyclohexane-1,5'-furo[3,4-b]pyridin]-yl (e.g., 7'H-spiro[cyclohexane-1,5'-furo[3,4-b]pyridin]-4-yl or 7'H-spiro[cyclohexane-1,5'-furo[3,4-b]pyridin]-7'-one-4-yl), or 3'H-spiro[cyclohexane-1,1'-furo[3,4-c]pyridin]-yl (e.g., 3'H-spiro[cyclohexane-1,1'-furo[3,4-c]pyridin]-4-yl or 3'H-spiro[cyclohexane-1,1'-furo[3,4-c]pyridin]-3'-one-4-yl), each optionally substituted with one or more $-Q_5-T_5$.

For example, $R_7$ is 5 to 6-membered heterocycloalkyl optionally substituted with one or more $-Q_5-T_5$.

For example, $R_7$ is isopropyl.

For example, $R_7$ is pyrrolidinyl, piperidinyl, tetrahydropyran, cyclopentyl, or cyclohexyl, cycloheptyl, each optionally substituted with one $-Q_5-T_5$.

For example, $R_7$ is cyclopentyl or cyclohexyl, each optionally substituted with one $-Q_5-T_5$.

For example, $Q_5$ is NHC(O) and $T_5$ is $C_1-C_6$ alkyl or $C_1-C_6$ alkoxy.

For example, $-Q_5-T_5$ is oxo.

For example, $T_4$ is 4 to 7-membered heterocycloalkyl or $C_3-C_8$ cycloalkyl or $C_6-C_{10}$ aryl, and one or more $-Q_5-T_5$ are oxo.

For example, $R_7$ is 1-oxide-tetrahydro-2H-thiopyranyl or 1,1-dioxide-tetrahydro-2H-thiopyranyl.

For example, $R_7$ is cyclohexanonyl, e.g., cyclohexanon-4-yl.

For example, $T_5$ is H, halo, $C_1-C_6$ alkyl, $C_1-C_6$ alkoxyl, $C_3-C_8$ cycloalkyl, $C_6-C_{10}$ aryl, or 4 to 7-membered heterocycloalkyl.

For example, $Q_5$ is a bond and $T_5$ is $C_1-C_6$ alkyl, $C_3-C_8$ cycloalkyl, or 4 to 7-membered heterocycloalkyl.

For example, $Q_5$ is a bond and $T_5$ is 5- or 6-membered heteroaryl, amino, mono-$C_1-C_6$ alkylamino, di-$C_1-C_6$ alkylamino, $T_5$ being optionally substituted with one or more substituents selected from the group consisting of halo, hydroxyl, $C_1-C_6$ alkoxyl, or $C_3-C_8$ cycloalkyl.

For example, $Q_5$ is CO, $S(O)_2$, or NHC(O); and $T_5$ is $C_1-C_6$ alkyl, $C_1-C_6$ alkoxyl, $C_3-C_8$ cycloalkyl, or 4 to 7-membered heterocycloalkyl.

For example, $T_5$ is $C_1-C_6$ alkyl or $C_1-C_6$ alkoxyl, each optionally substituted with halo, hydroxyl, cyano, $C_1-C_6$ alkoxyl, amino, mono-$C_1-C_6$ alkylamino, di-$C_1-C_6$ alkylamino, or $C_3-C_8$ cycloalkyl.

For example, $Q_5$ is $C_1-C_3$ alkyl linker and $T_5$ is H or $C_6-C_{10}$ aryl.

For example, $Q_5$ is $C_1-C_3$ alkyl linker and $T_5$ is $C_3-C_8$ cycloalkyl, 4 to 7-membered heterocycloalkyl, or $S(O)_qR_q$.

For example, $R_6$ is halo (e.g., fluorine, chlorine, bromine, and iodine) and Z is $S(O)_aR_7$, in which a is 0, 1, or 2 and $R_7$ is $C_1-C_6$ alkyl (e.g., methyl, ethyl, n-propyl, i-propyl, butyl, or t-butyl), $C_3-C_8$ cycloalkyl (e.g., cyclopentyl, cyclohexyl, or cycloheptyl) or 4 to 14-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, morpholinyl, 1,4-dioxaspiro[4.5]decanyl, 1,4-dioxa-8-azaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, or 3'H-spiro[cyclohexane-1,1'-furo[3,4-c]pyridin]-yl, and the like) and $R_7$ is optionally substituted with one or more -$Q_5$-$T_5$.

For example, $R_6$ is halo (e.g., fluorine, chlorine, bromine, and iodine) and Z is $OR_7$ in which $R_7$ is 4 to 14-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, morpholinyl, 1,4-dioxaspiro[4.5]decanyl, 1,4-dioxa-8-azaspiro[4.5]decanyl, 1-oxaspiro[4.5]decanyl, 1-azaspiro[4.5]decanyl, 3'H-spiro[cyclohexane-1,1'-isobenzofuran]-yl, 7H-spiro[cyclohexane-1,5'-furo[3,4-b]pyridin]-yl, or 3'H-spiro[cyclohexane-1,1'-furo[3,4-c]pyridin]-yl, and the like) and $R_7$ is optionally substituted with one or more -$Q_5$-$T_5$.

For example, $R_{11}$ is H.

For example, each of $R_2$ and $R_4$, independently, is H or $C_1$-$C_6$ alkyl optionally substituted with amino, azido, halo, mono-$C_1$-$C_6$ alkylamino, di-$C_1$-$C_6$ alkylamino, or $C_6$-$C_{10}$ aryl.

For example, each of $R_2$ and $R_4$, independently is $C_1$-$C_3$ alkyl optionally substituted with $C_1$-$C_6$ alkoxyl.

For example, each of $R_2$ and $R_4$ is methyl.

For example, $R_1$ is H.

For example, $R_1$ is $C_1$-$C_6$ alkyl optionally substituted with azido, halo, amino, mono-$C_1$-$C_6$ alkylamino, di-$C_1$-$C_6$ alkylamino, or $C_6$-$C_{10}$ aryl.

For example, $R_{12}$ is H, methyl, ethyl, ethenyl, or halo.

For example, $R_{12}$ is methyl.

For example, $R_{12}$ is ethyl or propenyl.

For example, $R_{12}$ is methoxyl.

For example, $R_{12}$ is ethenyl.

For example, $R_8$ is H, methyl, ethyl, or ethenyl.

For example, $R_8$ is methyl.

For example, $R_8$ is ethyl.

For example, $R_8$ is propyl.

For example, $R_8$ is ethenyl or propenyl.

For example, $R_8$ is $C_1$-$C_6$ alkyl substituted with one or more substituents selected from the group consisting of halo (e.g., F, Cl, or Br), hydroxyl, or $C_1$-$C_6$ alkoxyl.

For example, $R_8$ is 4 to 7-membered optionally substituted heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and morpholinyl, and the like).

For example, $R_8$ is piperidinyl.

For example, $R_8$ is 4 to 7-membered optionally substituted heterocycloalkyl and $R_7$ is -$Q_4$-$T_4$, in which $Q_4$ is a bond or $C_1$-$C_4$ alkyl linker and $T_4$ is H, $C_1$-$C_6$ alkyl, $C_3$-$C_8$ cycloalkyl or 4 to 7-membered heterocycloalkyl.

For example, Z is $NR_7R_8$ or $CR_7R_8R_{14}$ wherein $R_7$ and $R_8$, together with the atom to which they are attached, form a 4 to 11-membered heterocycloalkyl ring having 1 to 3 heteroatoms (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, morpholinyl, 1,4-dioxa-8-azaspiro[4.5]decanyl, and the like) or $C_3$-$C_8$ cycloalkyl, each optionally substituted with one or more -$Q_6$-$T_6$.

For example, the ring formed by $R_7$ and $R_8$ is selected from the group consisting of azetidinyl, pyrrolidinyl, piperidinyl, morpholinyl, piperazinyl, 1,4-dioxa-8-azaspiro[4.5]decanyl, and cyclohexenyl, each optionally substituted with one -$Q_6$-$T_6$.

For example, Z is 1,4-dioxa-8-azaspiro[4.5]decan-8-yl, pyrrolidine-2,5-dione-1-yl, or piperidine-2,6-dione-1-yl.

For example, one or more -$Q_6$-$T_6$ is oxo.

For example, $T_6$ is H, halo, $C_1$-$C_6$ alkyl, $C_1$-$C_6$ alkoxyl, $C_3$-$C_8$ cycloalkyl, $C_6$-$C_{10}$ aryl, or 4 to 7-membered heterocycloalkyl.

For example, $Q_6$ is a bond and $T_6$ is $C_1$-$C_6$ alkyl, $C_3$-$C_8$ cycloalkyl, or 4 to 7-membered heterocycloalkyl.

For example, $Q_6$ is CO, $S(O)_2$, or NHC(O); and $T_6$ is $C_1$-$C_6$ alkyl, $C_1$-$C_6$ alkoxyl, $C_3$-$C_8$ cycloalkyl, or 4 to 7-membered heterocycloalkyl.

For example, $T_6$ is $C_1$-$C_6$ alkyl or $C_1$-$C_6$ alkoxyl, each optionally substituted with halo, hydroxyl, cyano, $C_1$-$C_6$ alkoxyl, amino, mono-$C_1$-$C_6$ alkylamino, di-$C_1$-$C_6$ alkylamino, or $C_3$-$C_8$ cycloalkyl.

For example, $Q_6$ is $C_1$-$C_3$ alkyl linker and $T_6$ is H or $C_6$-$C_{10}$ aryl.

For example, $Q_6$ is $C_1$-$C_3$ alkyl linker and $T_6$ is $C_3$-$C_8$ cycloalkyl, 4 to 7-membered heterocycloalkyl, or $S(O)_pR_p$.

For example, each of $R_p$ and $R_q$, independently, is $C_1$-$C_6$ alkyl.

For example, $R_6$ is —$S(O)_bR_a$ or azido, in which b is 0, 1, or 2 and $R_a$ is $C_1$-$C_6$ alkyl or $C_3$-$C_8$ cycloalkyl; and Z is $NR_7R_8$, in which $R_7$ is $C_3$-$C_8$ cycloalkyl (e.g., cyclopentyl, cyclohexyl, or cycloheptyl) or 4 to 14-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, morpholinyl, 1,4-dioxaspiro[4.5]decanyl, 1,4-dioxa-8-azaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, or 3'H-spiro[cyclohexane-1,1'-furo[3,4-c]pyridin]-yl, and the like), each optionally substituted with one or more -$Q_5$-$T_5$; and $R_8$ is H or $C_1$-$C_6$ alkyl (e.g., methyl, ethyl, n-propyl, i-propyl, butyl, or t-butyl).

For example, $R_6$ is halo (e.g., fluorine, chlorine, bromine, and iodine) and Z is $NR_7R_8$ or $CR_7R_8R_{14}$ wherein $R_7$ and $R_8$, together with the atom to which they are attached, form a 4 to 11-membered heterocycloalkyl ring having 1 to 3 heteroatoms (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, morpholinyl, 2-oxa-6-azaspiro[3.3]heptanyl, 2,6-diazaspiro[3.3]heptanyl, 1,4-dioxa-8-azaspiro[4.5]decanyl, 1,4-dioxa-8-azaspiro[4.5]decan-8-yl, pyrrolidine-2,5-dione-1-yl, piperidine-2,6-dione-1-yl, and the like) or $C_3$-$C_8$ cycloalkyl, each optionally substituted with one or more -$Q_6$-$T_6$.

For example, $R_{13}$ is H or methyl.

For example, $R_{13}$ is H.

For example, $R_3$ is H.

For example, each of $R_5$, $R_9$, and $R_{10}$ is H.

Another subset of the compounds of Formula (I) includes those of Formula (Ib), (Ic), or (Id):

(Ib)

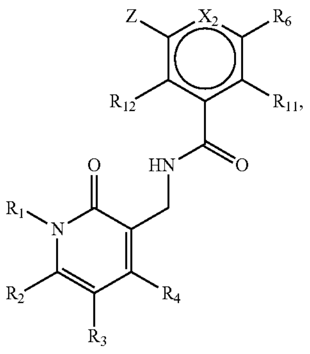

(Ic)

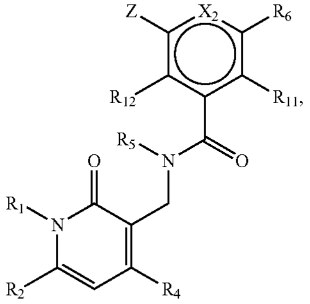

or (Id)

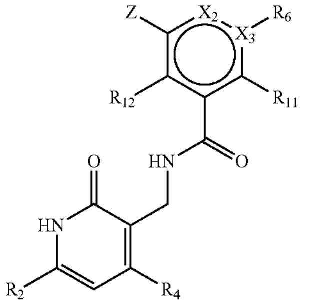

or a pharmaceutically acceptable salt or ester thereof, wherein Z, $X_2$, $X_3$, $R_1$, $R_2$, $R_3$, $R_4$, $R_5$, $R_6$, $R_{11}$, and $R_{12}$ are as defined herein for Formula (I).

Yet another subset of the compounds of Formula (I) is those of Formula (Ie):

(Ie)

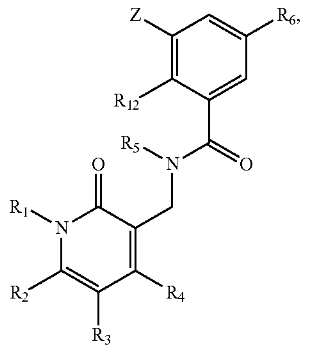

wherein

Z is $NR_7R_8$, $OR_7$, or $S(O)_aR_7$;

$R_1$ is H or $C_1$-$C_6$ alkyl optionally substituted with one or more substituents selected from hydroxyl, $C_1$-$C_6$ alkoxyl, amino, mono-$C_1$-$C_6$ alkylamino, di-$C_1$-$C_6$ alkylamino, and $C_6$-$C_{10}$ aryl;

each of $R_2$ and $R_4$ independently, is -$Q_1$-$T_1$, in which $Q_1$ is a bond or $C_1$-$C_3$ alkyl linker optionally substituted with one or more substituents selected from halo and hydroxyl, and $T_1$ is H, halo, or azido;

$R_3$ is H or halo;

$R_5$ is H or $C_1$-$C_6$ alkyl;

$R_6$ is H, halo, cyano, azido, $OR_a$, —$NR_aR_b$, —C(O)$NR_aR_b$, —$S(O)_bR_a$, or $R_{S2}$); wherein $R_{S2}$ is $C_1$-$C_6$ alkyl, $C_2$-$C_6$ alkenyl, $C_2$-$C_6$ alkynyl, or 4 to 12-membered heterocycloalkyl, and wherein each of $R_a$ and $R_b$, independently is H, $C_1$-$C_6$ alkyl, or 4 to 12-membered heterocycloalkyl; or $R_a$ and $R_b$, together with the N atom to which they are attached, form a 4 to 12-membered heterocycloalkyl ring having 0 or 1 additional heteroatom; and each of $R_a$, $R_{S2}$ and the 4 to 12-membered heterocycloalkyl ring formed by $R_a$ and $R_b$, is optionally substituted with one or more -$Q_2$-$T_2$; wherein $Q_2$ is a bond or $C_1$-$C_3$ alkyl linker, and $T_2$ is H, halo, —$OR_c$, —$NR_cR_d$, —C(O)$OR_c$, or $C_1$-$C_6$ alkyl, in which each of $R_c$ and $R_d$, independently is H or $C_1$-$C_6$ alkyl, or $R_c$ and $R_d$, together with the N atom to which they are attached, form a 4 to 12-membered heterocycloalkyl ring having 0 or 1 additional heteroatom and optionally substituted with $C_1$-$C_6$ alkyl;

$R_7$ is -$Q_4$-$T_4$, in which $Q_4$ is a bond or $C_1$-$C_4$ alkyl linker and $T_4$ is H, $C_1$-$C_6$ alkyl, $C_3$-$C_8$ cycloalkyl, $C_6$-$C_{10}$ aryl, C(O)—$C_{1-6}$ alkyl, C(O)—$C_{3-6}$ cycloalkyl, or 4 to 14-membered heterocycloalkyl, each optionally substituted with one or more -$Q_5$-$T_5$;

$R_8$ is H, $C_1$-$C_6$ alkyl optionally substituted with halo, hydroxyl or $C_1$-$C_6$ alkoxyl, $C_2$-$C_6$ alkenyl, $C_3$-$C_8$ cycloalkyl, or 4 to 7-membered heterocycloalkyl; or $R_7$ and $R_8$, together with the N atom to which they are attached, form a 4 to 12-membered heterocycloalkyl ring having 0 to 2 additional heteroatoms, and the 4 to 12-membered heterocycloalkyl ring formed by $R_7$ and $R_8$ is optionally substituted with one or more -$Q_6$-$T_6$; and $R_{12}$ is halo, $C_1$-$C_6$ alkoxyl, or $C_1$-$C_6$ alkyl optionally substituted with halo or $C_2$-$C_6$ alkenyl.

In addition to the above-described features of the compounds of this invention where applicable, the compounds of Formula (Ie) can include one or more of the following features:

For example, $R_1$ is H or $C_1$-$C_6$ alkyl optionally substituted one or more times with a substituent selected from hydroxyl, $C_1$-$C_6$ alkoxyl and $C_6$-$C_{10}$ aryl; $R_7$ is -$Q_4$-$T_4$, in which $Q_4$ is a bond or a $C_1$-$C_4$ alkyl linker, and $T_4$ is $C_1$-$C_6$ alkyl, $C_3$-$C_8$ cycloalkyl, $C_6$-$C_{10}$ aryl, C(O)—$C_1$-$C_6$ alkyl, C(O)—$C_3$-$C_6$ cycloalkyl, dihydropyranyl, tetrahydropyranyl, tetrahydrothiopyranyl, piperidinyl, pyrrolidinyl, azetidinyl and oxetanyl, each optionally substituted with one or more substituents independently selected from oxo and -$Q_5$-$T_5$; $R_8$ is H or $C_1$-$C_6$ alkyl, $C_1$-$C_6$ haloalkyl, $C_2$-$C_6$ alkenyl or $C_3$-$C_8$ cycloalkyl; and $R_{12}$ is halo, $C_1$-$C_6$ alkyl, $C_1$-$C_6$ haloalkyl or $C_1$-$C_6$ alkoxyl.

For example, Z is $NR_7R_8$ or $SR_7$; $R_6$ is H, halo, cyano, $OR_a$, —C(O)$NR_aR_b$, —S(O)$_2R_a$, or $R_{S2}$; wherein $R_{S2}$ is $C_1$-$C_6$ alkyl, $C_2$-$C_6$ alkenyl, $C_2$-$C_6$ alkynyl, or 4 to 12-membered heterocycloalkyl, and wherein each of $R_a$ and $R_b$, independently is H or $C_1$-$C_6$ alkyl; or $R_a$ and $R_b$, together with the N atom to which they are attached, form a 4 to 12-membered heterocycloalkyl ring having 0 or 1 additional heteroatom; and each of $R_{S2}$ and the 4 to 12-membered heterocycloalkyl ring formed by $R_a$ and $R_b$, is optionally substituted with one or more -$Q_2$-$T_2$; wherein $Q_2$ is a bond or $C_1$-$C_3$ alkyl linker, and $T_2$ is H, halo, —$OR_c$, —$NR_cR_d$, —C(O)O$C_1$-$C_6$ alkyl, or $C_1$-$C_6$ alkyl, in which each of $R_c$ and $R_d$, independently is H or $C_1$-$C_6$ alkyl, or $R_c$ and $R_d$, together with the N atom to which they are attached, form a 4 to 12-membered heterocycloalkyl ring having 0 or 1 additional heteroatom and 0 or 1 $C_1$-$C_6$ alkyl substituents; $R_7$ is $C_1$-$C_6$ alkyl, $C_3$-$C_8$ cycloalkyl, dihydropyranyl, tetrahydropyranyl, tetrahydrothiopyranyl, piperidinyl, pyrrolidinyl, azetidinyl and oxetanyl, each optionally substituted with one or more substituents independently selected from oxo and -$Q_5$-$T_5$; and $R_{12}$ is halo or $C_1$-$C_6$ alkyl.

For example, $R_2$, $R_4$ and $R_{12}$ are each independently $C_1$-$C_6$ alkyl and $R_5$ is H.

For example, $R_7$ is cyclohexyl, dihydropyranyl, tetrahydropyranyl, tetrahydrothiopyranyl, piperidinyl, pyrrolidinyl, azetidinyl oxetanyl, 1,4-dioxaspiro[4.5]decan-8-yl, 1-oxaspiro[4.5]decan-8-yl, 3'H-spiro[cyclohexane-1,1'-isobenzofuran]-4-yl, 7'H-spiro[cyclohexane-1,5'-furo[3,4-b]pyridin]-4-yl, 3'H-spiro[cyclohexane-1,1'-furo[3,4-c]pyridin]-4-yl, or 1-azaspiro[4.5]decan-8-yl, each substituted with one or more -$Q_5$-$T_5$.

For example, Z is selected from the group consisting of piperidinyl, morpholinyl, piperazinyl, azetidinyl, pyrrolidinyl, 2-oxa-5-azabicyclo[2.2.1]heptan-5-yl, 1,4-dioxa-8-azaspiro[4.5]decan-8-yl, and cyclohexenyl, each optionally substituted with one -$Q_6$-$T_6$.

For example, $R_6$ is halo (e.g., fluorine, chlorine, bromine, and iodine) and Z is S(O)$_aR_7$, in which a is 0, 1, or 2 and $R_7$ is $C_1$-$C_6$ alkyl (e.g., methyl, ethyl, n-propyl, i-propyl, butyl, or t-butyl), $C_3$-$C_8$ cycloalkyl (e.g., cyclopentyl, cyclohexyl, or cycloheptyl) or 4 to 14-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, morpholinyl, 1,4-dioxaspiro[4.5]decanyl, 1,4-dioxa-8-azaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, or 3'H-spiro[cyclohexane-1,1'-furo[3,4-c]pyridin]-yl, and the like) and $R_7$ is optionally substituted with one or more -$Q_5$-$T_5$.

For example, $R_6$ is halo (e.g., fluorine, chlorine, bromine, and iodine) and Z is $OR_7$ in which $R_7$ is 4 to 14-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, morpholinyl, 1,4-dioxaspiro[4.5]decanyl, 1,4-dioxa-8-azaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, or 3'H-spiro[cyclohexane-1,1'-furo[3,4-c]pyridin]-yl, and the like) and $R_7$ is optionally substituted with one or more -$Q_5$-$T_5$.

For example, $R_6$ is —S(O)$_bR_a$ or azido, in which b is 0, 1, or 2 and $R_a$ is $C_1$-$C_6$ alkyl or $C_3$-$C_8$ cycloalkyl; and Z is $NR_7R_8$, in which $R_7$ is $C_3$-$C_8$ cycloalkyl (e.g., cyclopentyl, cyclohexyl, or cycloheptyl) or 4 to 14-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, morpholinyl, 1,4-dioxaspiro[4.5]decanyl, 1,4-dioxa-8-azaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, or 3'H-spiro[cyclohexane-1,1'-furo[3,4-c]pyridin]-yl, and the like), each optionally substituted with one or more -$Q_5$-$T_5$; and $R_8$ is H or $C_1$-$C_6$ alkyl (e.g., methyl, ethyl, n-propyl, i-propyl, butyl, or t-butyl).

For example, $R_6$ is halo (e.g., fluorine, chlorine, bromine, and iodine) and Z is $NR_7R_8$ or $CR_7R_8R_{14}$ wherein $R_7$ and $R_8$, together with the atom to which they are attached, form a 4 to 11-membered heterocycloalkyl ring having 1 to 3 heteroatoms (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, 1,4-diazepanyl, 1,4-oxazepanyl, 2-oxa-5-azabicyclo[2.2.1]heptanyl, 2,5-diazabicyclo[2.2.1]heptanyl, morpholinyl, 2-oxa-6-azaspiro[3.3]heptanyl, 2,6-diazaspiro[3.3]heptanyl, 1,4-dioxa-8-azaspiro[4.5]decanyl, 1,4-dioxa-8-azaspiro[4.5]decan-8-yl, pyrrolidine-2,5-dione-1-yl, piperidine-2,6-dione-1-yl, and the like) or $C_3$-$C_8$ cycloalkyl, each optionally substituted with one or more -$Q_6$-$T_6$.

Another subset of the compounds of Formula (I) includes those of Formula (II):

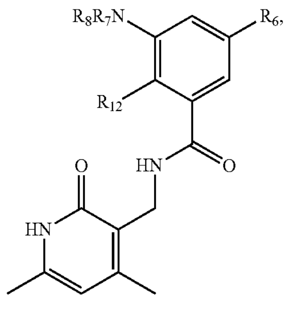

(II)

or a pharmaceutically acceptable salts or esters thereof, wherein $R_6$, $R_7$, $R_8$, and $R_{12}$ are defined herein.

Yet another subset of the compounds of Formula (I) includes those of Formula (IIA):

(IIA)

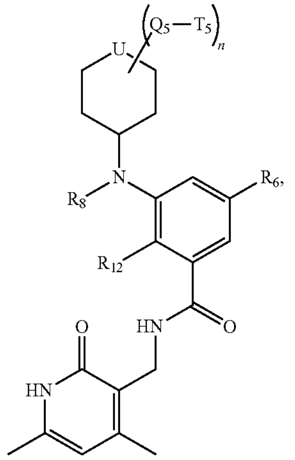

or a pharmaceutically acceptable salts or esters thereof, wherein n is 0, 1, or 2; U is O, S, N-$Q_5$-$T_5$, or CH-$Q_5$-$T_5$; $R_{12}$ is Cl, Br, or methyl; and $R_6$, $R_7$, $R_8$, $Q_5$ and $T_5$ are defined herein.

In addition to the above-described features of the compounds of this invention where applicable, the compounds of Formula (II) or (IIA) can include one or more of the following features:

For example, $Q_5$ is a bond and $T_5$ is H, $C_1$-$C_6$ alkyl, $C_3$-$C_8$ cycloalkyl, 4 to 12-membered heterocycloalkyl, 5- or 6-membered heteroaryl, amino, mono-$C_1$-$C_6$ alkylamino, or di-$C_1$-$C_6$ alkylamino, $T_5$ being optionally substituted with one or more substituents selected from the group consisting of halo, hydroxyl, $C_1$-$C_6$ alkoxyl, or $C_3$-$C_8$ cycloalkyl.

For example, $Q_5$ is CO, $S(O)_2$, or NHC(O); and $T_5$ is $C_1$-$C_6$ alkyl, $C_1$-$C_6$ alkoxyl, $C_3$-$C_8$ cycloalkyl, or 4 to 12-membered heterocycloalkyl.

For example, $Q_5$ is $C_1$-$C_3$ alkyl linker and $T_5$ is H or $C_6$-$C_{10}$ aryl.

For example, $Q_5$ is $C_1$-$C_3$ alkyl linker and $T_5$ is $C_3$-$C_8$ cycloalkyl, 4 to 12-membered heterocycloalkyl, or $S(O)_qR_q$.

For example, $Q_5$ is NHC(O) and $T_5$ is $C_1$-$C_6$ alkyl or $C_1$-$C_6$ alkoxy.

For example, one or more -$Q_5$-$T_5$ are oxo.

For example, U is CH-$Q_5$-$T_5$ and n is 0

For example, one or more -$Q_6$-$T_6$ are oxo.

For example, $Q_6$ is a bond or C(O) and $T_6$ is $C_1$-$C_6$ alkyl or $C_1$-$C_6$ alkoxy.

Still another subset of the compounds of Formula (I) includes those of Formula (III):

(III)

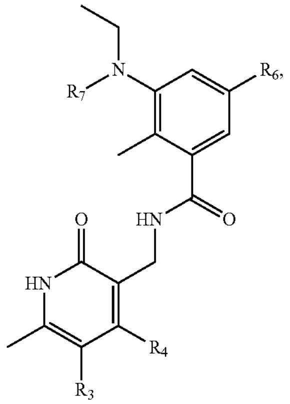

or a pharmaceutically acceptable salts or esters thereof, wherein $R_7$ is a 4 or 6-membered heterocycloalkyl having one nitrogen atom in the ring and is substituted with one or two methyl groups or one i-propyl group; $R^3$ is H or F; $R_4$ is methyl, ethyl, n-propyl, isopropyl, or $CF_3$, and $R_6$ is $CF_3$, Cl, or F, provided that when $R_4$ is methyl, (1) $R_6$ is $CF_3$, or (2) $R_3$ is F, or (3) $R_6$ is $CF_3$ and $R_3$ is F, or (4) $R_6$ is F or $C_1$ and $R_7$ is a 6-membered heterocycloalkyl having only one nitrogen and is substituted with two methyl groups.

In addition to the above-described features of the compounds of this invention where applicable, the compounds of Formula (III) can include one or more of the following features:

For example, $R_7$ is a 4 or 6-membered heterocycloalkyl having one and only one heteroatom in the ring and the heteroatom is nitrogen.

For example, $R_7$ is not further substituted besides the one or two methyl groups or the one i-propyl group.

For example, $R_7$ is

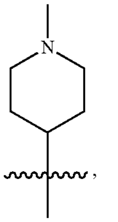,
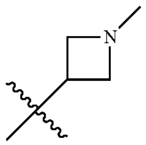, or
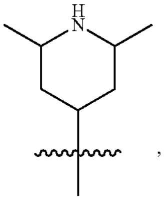,

For example, $R_7$ is

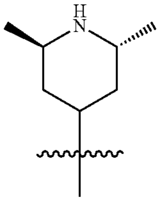 or 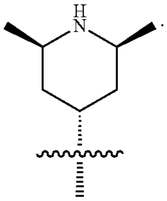.

For example, $R_7$ is

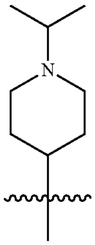 [SMILES: *C1CCN(C(C)C)CC1]

Representative compounds of the present invention include compounds listed in Table 1. In the table below, each occurrence of

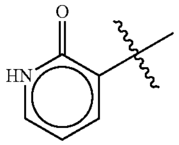

should be construed as

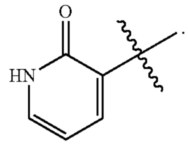 [SMILES: *c1ccc[nH]c1=O ; "."]

TABLE 1

| Compound Number | Structure | Name | MS† |
|---|---|---|---|
| 1 | 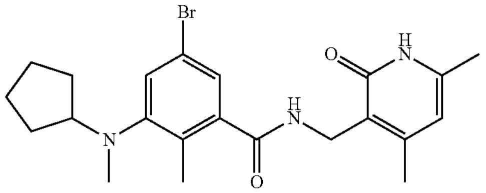 | 5-bromo-3-(cyclopentyl(methyl)amino)-N-((4,6-dimethyl-2-oxo-1,2-dihydropyridin-3-yl)methyl)-2-methylbenzamide | 446.2 |
| 2 | 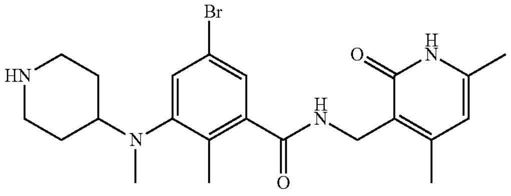 | 5-bromo-N-((4,6-dimethyl-2-oxo-1,2-dihydropyridin-3-yl)methyl)-2-methyl-3-(methyl(piperidin-4-yl)amino)benzamide | 462.2 |
| 3 | 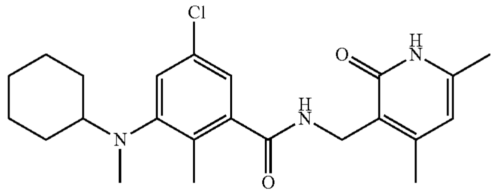 [SMILES: Cc1cc(C)c(CNC(=O)c2cc(Cl)cc(N(C)C3CCCCC3)c2C)c(=O)[nH]1] | 5-chloro-3-(cyclohexyl(methyl)amino)-N-((4,6-dimethyl-2-oxo-1,2-dihydropyridin-3-yl)methyl)-2-methyl-benzamide | 416.4 |
| 4 | 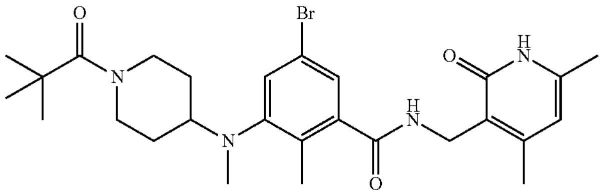 [SMILES: Cc1cc(C)c(CNC(=O)c2cc(Br)cc(N(C)C3CCN(C(=O)C(C)(C)C)CC3)c2C)c(=O)[nH]1] | 5-bromo-N-((4,6-dimethyl-2-oxo-1,2-dihydropyridin-3-yl)methyl)-2-methyl-3-(methyl(1-pivaloylpiperidin-4-yl)amino)benzamide | 545.2 |
| 5 | 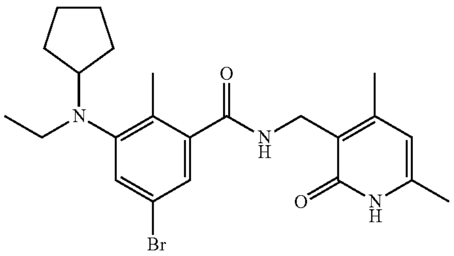 [SMILES: CCN(c1cc(Br)cc(C(=O)NCc2c(C)cc(C)[nH]c2=O)c1C)C1CCCC1] | 5-bromo-3-(cyclopentyl(ethyl)amino)-N-((4,6-dimethyl-2-oxo-1,2-dihydropyridin-3-yl)methyl)-2-methylbenzamide | 460.1 |

TABLE 1-continued

| Compound Number | Structure | Name | MS† |
|---|---|---|---|
| 6 | 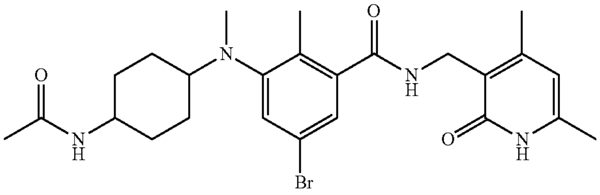 [SMILES: CC(=O)NC1CCC(N(C)c2cc(Br)cc(C(=O)NCc3c(C)cc(C)[nH]c3=O)c2C)CC1] | 3-((4-acetamidocyclo-hexyl)(methyl) amino)-5-bromo-N-((4,6-dimethyl-2-oxo-1,2-dihydropyridin-3-yl)methyl)-2-methylbenzamide | 516.9 |
| 7 | 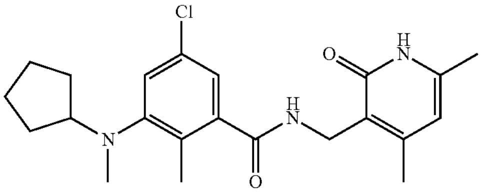 | 5-chloro-3-(cyclopentyl(methyl) amino)-N-((4,6-dimethyl-2-oxo-1,2-dihydropyridin-3-yl)methyl)-2-methylbenzamide | 402.2 |
| 8 | 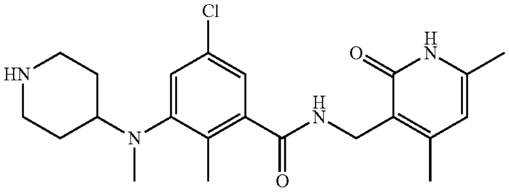 | 5-chloro-N-((4,6-dimethyl-2-oxo-1,2-dihydropyridin-3-yl)methyl)-2-methyl-3-(methyl(piperidin-4-yl)amino)benzamide | 417.3 |
| 9 | 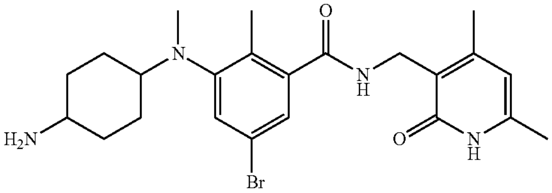 [SMILES: Cc1cc(C)c(CNC(=O)c2cc(Br)cc(N(C)C3CCC(N)CC3)c2C)c(=O)[nH]1] | 3-((4-aminocyclohexyl) (methyl)amino)-5-bromo-N-((4,6-dimethyl-2-oxo-1,2-dihydropyridin-3-yl)methyl)-2-methylbenzamide | 475.1 |
| 10 | 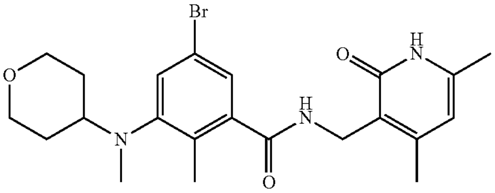 [SMILES: Cc1cc(C)c(CNC(=O)c2cc(Br)cc(N(C)C3CCOCC3)c2C)c(=O)[nH]1] | 5-bromo-N-((4,6-dimethyl-2-oxo-1,2-dihydropyridin-3-yl) methyl)-2-methyl-3-(methyl(tetrahydro-2H-pyran-4-yl)amino)benzamide | 462.2 |
| 11 | 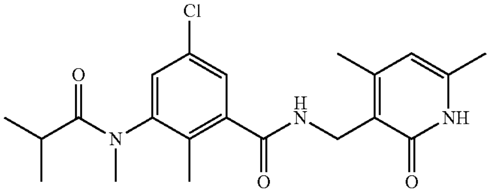 [SMILES: Cc1cc(C)c(CNC(=O)c2cc(Cl)cc(N(C)C(=O)C(C)C)c2C)c(=O)[nH]1] | 5-chloro-N-((4,6-dimethyl-2-oxo-1,2-dihydropyridin-3-yl)methyl)-2-methyl-3-(N-methylisobutyramido) benzamide | 404.2 |
| 12 | 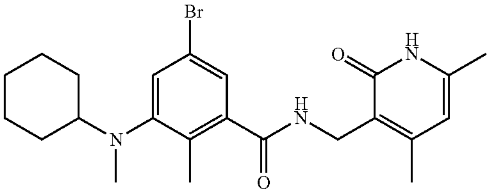 [SMILES: Cc1cc(C)c(CNC(=O)c2cc(Br)cc(N(C)C3CCCCC3)c2C)c(=O)[nH]1] | 5-bromo-3-(cyclohexyl(methyl) amino)-N-((4,6-dimethyl-2-oxo-1,2-dihydropyridin-3-yl)methyl)-2-methylbenzamide | 460.1 |

TABLE 1-continued

| Compound Number | Structure | Name | MS† |
|---|---|---|---|
| 13 | 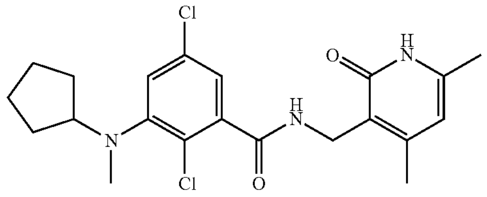 | 2,5-dichloro-3-(cyclopentyl(methyl)amino)-N-((4,6-dimethyl-2-oxo-1,2-dihydropyridin-3-yl)methyl)benzamide | 422.1 |
| 14 | 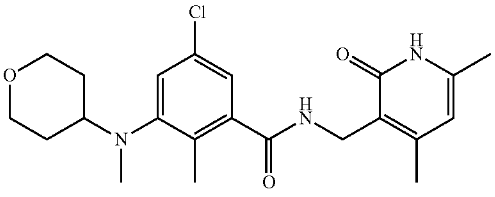 [SMILES: Cc1cc(C)c(CNC(=O)c2cc(Cl)cc(N(C)C3CCOCC3)c2C)c(=O)[nH]1] | 5-chloro-N-((4,6-dimethyl-2-oxo-1,2-dihydropyridin-3-yl)methyl)-2-methyl-3-(methyl(tetrahydro-2H-pyran-4-yl)amino)benzamide | 418.3 |
| 15 | 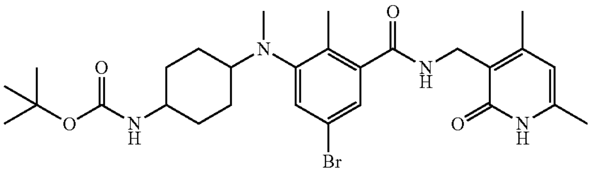 [SMILES: Cc1cc(C)c(CNC(=O)c2cc(Br)cc(N(C)C3CCC(NC(=O)OC(C)(C)C)CC3)c2C)c(=O)[nH]1] | tert-butyl (4-((5-bromo-3-(((4,6-dimethyl-2-oxo-1,2-dihydropyridin-3-yl)methyl)carbamoyl)-2-methylphenyl)(methyl)amino)cyclohexyl)carbamate | 575.8 |
| 16 | 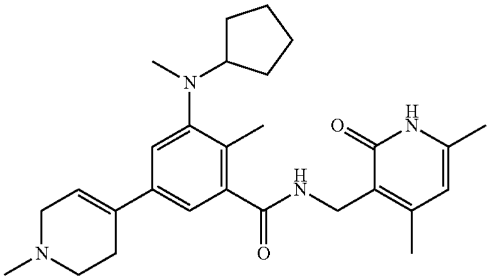 | 3-(cyclopentyl(methyl)amino)-N-((4,6-dimethyl-2-oxo-1,2-dihydro-pyridin-3-yl)methyl)-2-methyl-5-(1-methyl-1,2,3,6-tetrahydro-pyridin-4-yl)benzamide | 463.4 |
| 17 | 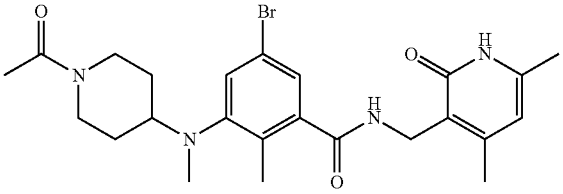 [SMILES: CC(=O)N1CCC(N(C)c2cc(Br)cc(C(=O)NCc3c(C)cc(C)[nH]c3=O)c2C)CC1] | 3-((1-acetylpiperidin-4-yl)(methyl)amino)-5-bromo-N-((4,6-dimethyl-2-oxo-1,2-dihydropyridin-3-yl)methyl)-2-methylbenzamide | 503.2 |
| 18 | 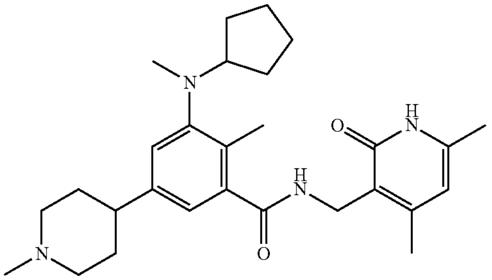 | 3-(cyclopentyl(methyl)amino)-N-((4,6-dimethyl-2-oxo-1,2-dihydropyridin-3-yl)methyl)-2-methyl-5-(1-methylpiperidin-4-yl)benzamide | 465.4 |
| 19 | 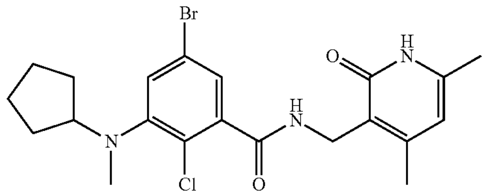 | 5-bromo-2-chloro-3-(cyclopentyl(methyl)amino)-N-((4,6-dimethyl-2-oxo-1,2-dihydropyridin-3-yl)methyl)benzamide | 466.1 |

TABLE 1-continued

| Compound Number | Structure | Name | MS† |
|---|---|---|---|
| 20 | 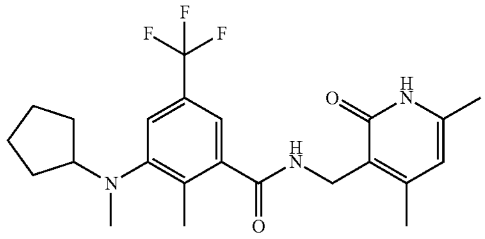 [SMILES: Cc1cc(C)c(CNC(=O)c2cc(C(F)(F)F)cc(N(C)C3CCCC3)c2C)c(=O)[nH]1] | 3-(cyclopentyl(methyl)amino)-N-((4,6-dimethyl-2-oxo-1,2-dihydropyridin-3-yl)methyl)-2-methyl-5-(trifluoromethyl)benzamide | 436.2 |
| 21 | 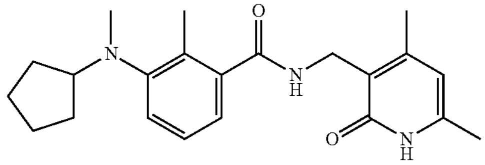 [SMILES: Cc1cc(C)c(CNC(=O)c2cccc(N(C)C3CCCC3)c2C)c(=O)[nH]1] | 3-(cyclopentyl(methyl)amino)-N-((4,6-dimethyl-2-oxo-1,2-dihydropyridin-3-yl)methyl)-2-methyl-5-(trifluoromethyl)benzamide | 368.2 |
| 22 | 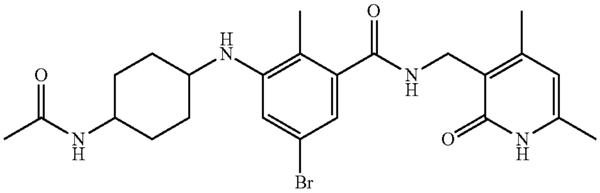 [SMILES: CC(=O)NC1CCC(Nc2cc(Br)cc(C(=O)NCc3c(C)cc(C)[nH]c3=O)c2C)CC1] | 3-((4-acetamidocyclohexyl)amino)-5-bromo-N-((4,6-dimethyl-2-oxo-1,2-dihydropyridin-3-yl)methyl)-2-methylbenzamide | 503.1 |
| 23 | 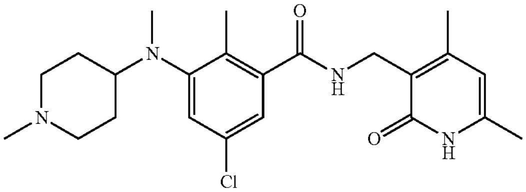 | 5-chloro-N-((4,6-dimethyl-2-oxo-1,2-dihydropyridin-3-yl)methyl)-2-methyl-3-(methyl(1-methylpiperidin-4-yl)amino)benzamide | 431.3 |
| 24 | 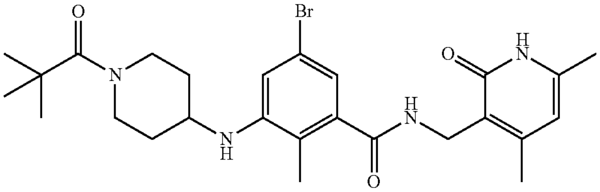 [SMILES: Cc1cc(C)c(CNC(=O)c2cc(Br)cc(NC3CCN(C(=O)C(C)(C)C)CC3)c2C)c(=O)[nH]1] | 5-bromo-N-((4,6-dimethyl-2-oxo-1,2-dihydropyridin-3-yl)methyl)-2-methyl-3-((1-pivaloylpiperidin-4-yl)amino)benzamide | 531.1 |
| 25 | 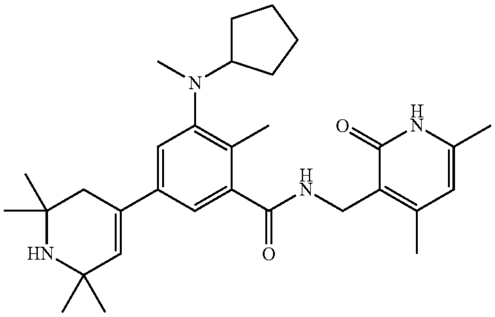 | 3-(cyclopentyl(methyl)amino)-N-((4,6-dimethyl-2-oxo-1,2-dihydropyridin-3-yl)methyl)-2-methyl-5-(2,2,6,6-tetramethyl-1,2,3,6-tetrahydro-pyridin-4-yl)benzamide | 505.4 |
| 26 | 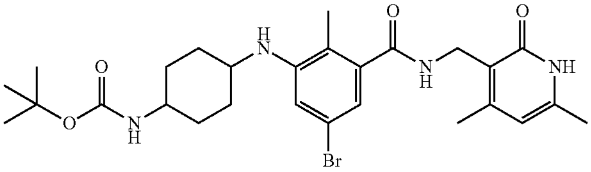 [SMILES: Cc1cc(C)c(CNC(=O)c2cc(Br)cc(NC3CCC(NC(=O)OC(C)(C)C)CC3)c2C)c(=O)[nH]1] | tert-butyl (4-((5-bromo-3-(((4,6-dimethyl-2-oxo-1,2-dihydropyridin-3-yl)methyl)carbamoyl)-2-methylphenyl)amino)cyclohexyl)carbamate | 562.2 |

TABLE 1-continued

| Compound Number | Structure | Name | MS† |
|---|---|---|---|
| 27 | 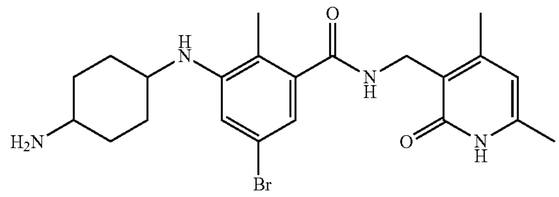 [SMILES: Cc1cc(C)c(CNC(=O)c2cc(Br)cc(NC3CCC(N)CC3)c2C)c(=O)[nH]1] | 3-((4-aminocyclohexyl)amino)-5-bromo-N-((4,6-dimethyl-2-oxo-1,2-dihydro-pyridin-3-yl)methyl)-2-methylbenzamide | 461.1 |
| 28 | 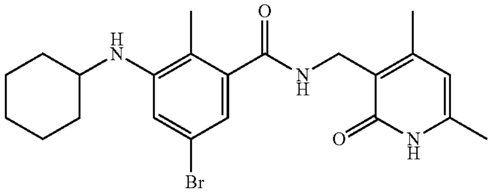 [SMILES: Cc1cc(C)c(CNC(=O)c2cc(Br)cc(NC3CCCCC3)c2C)c(=O)[nH]1] | 5-bromo-3-(cyclohexylamino)-N-((4,6-dimethyl-2-oxo-1,2-dihydropyridin-3-yl)methyl)-2-methylbenzamide | 446.2 |
| 29 | 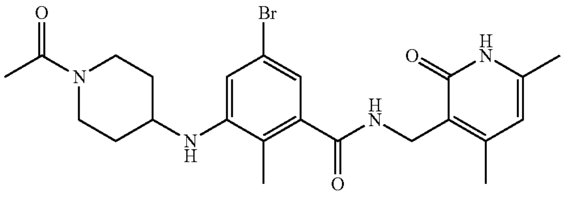 | 3-((1-acetylpiperidin-4-yl)amino)-5-bromo-N-((4,6-dimethyl-2-oxo-1,2-dihydropyridin-3-yl)methyl)-2-methylbenzamide | 489.2 |
| 30 | 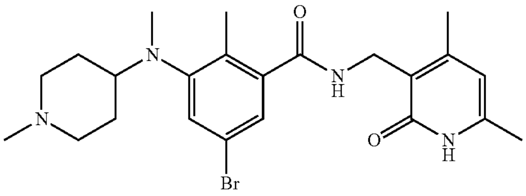 | 5-bromo-N-((4,6-dimethyl-2-oxo-1,2-dihydropyridin-3-yl)methyl)-2-methyl-3-(methyl(1-methyl-piperidin-4-yl)amino)benzamide | 475.02 |
| 31 | 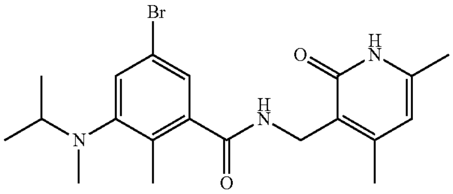 [SMILES: Cc1cc(C)c(CNC(=O)c2cc(Br)cc(N(C)C(C)C)c2C)c(=O)[nH]1] | 5-bromo-N-((4,6-dimethyl-2-oxo-1,2-dihydropyridin-3-yl)methyl)-3-(isopropyl(methyl)amino)-2-methylbenzamide | 420.2 |
| 32 | 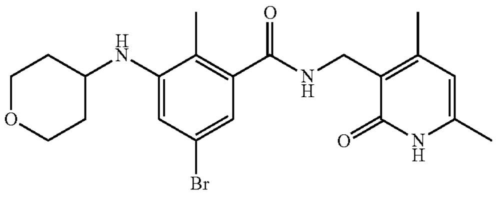 [SMILES: Cc1cc(C)c(CNC(=O)c2cc(Br)cc(NC3CCOCC3)c2C)c(=O)[nH]1] | 5-bromo-N-((4,6-dimethyl-2-oxo-1,2-dihydropyridin-3-yl)methyl)-2-methyl-3-((tetrahydro-2H-pyran-4-yl)amino)benzamide | 447.9 |
| 33 | 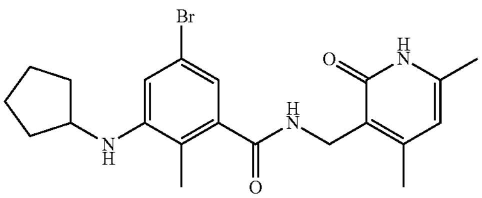 | 5-bromo-3-(cyclopentylamino)-N-((4,6-dimethyl-2-oxo-1,2-dihydropyridin-3-yl)methyl)-2-methylbenzamide | 432.1 |

TABLE 1-continued

| Compound Number | Structure | Name | MS† |
|---|---|---|---|
| 34 | 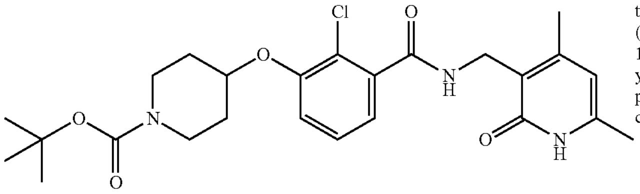 | tert-butyl 4-(2-chloro-3-(((4,6-dimethyl-2-oxo-1,2-dihydropyridin-3-yl)methyl)carbamoyl) phenoxy)piperidine-1-carboxylate | 490.3 |
| 35 | 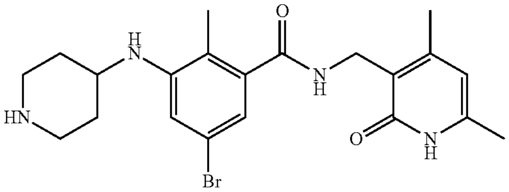 [SMILES: Cc1cc(C)c(CNC(=O)c2cc(Br)cc(NC3CCNCC3)c2C)c(=O)[nH]1] | 5-bromo-N-((4,6-dimethyl-2-oxo-1,2-dihydropyridin-3-yl)methyl)-2-methyl-3-(piperidin-4-ylamino)benzamide | 447.1 |
| 36 | 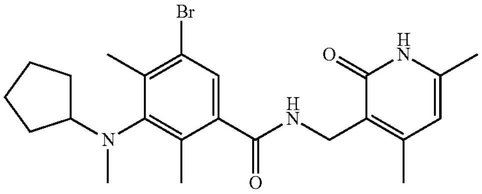 [SMILES: Cc1cc(C)c(CNC(=O)c2cc(Br)c(C)c(N(C)C3CCCC3)c2C)c(=O)[nH]1] | 5-bromo-3-(cyclopentyl(methyl) amino)-N-((4,6-dimethyl-2-oxo-1,2-dihydropyridin-3-yl)methyl)-2,4-dimethylbenzamide | 460.1 |
| 37 | 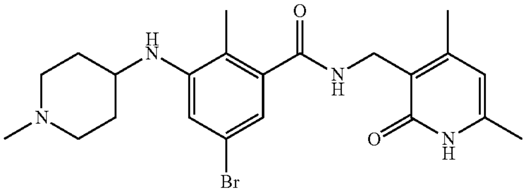 | 5-bromo-N-((4,6-dimethyl-2-oxo-1,2-dihydropyridin-3-yl)methyl)-2-methyl-3-((1-methylpiperidin-4-yl)amino)benzamide | 460.96 |
| 38 | 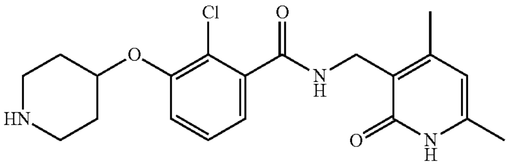 [SMILES: Cc1cc(C)c(CNC(=O)c2cccc(OC3CCNCC3)c2Cl)c(=O)[nH]1] | 2-chloro-N-((4,6-dimethyl-2-oxo-1,2-dihydropyridin-3-yl)methyl)-3-(piperidin-4-yloxy)benzamide | 390.1 |
| 39 | 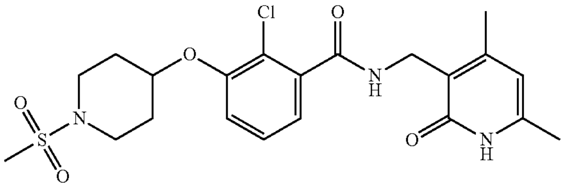 | 2-chloro-N-((4,6-dimethyl-2-oxo-1,2-dihydropyridin-3-yl)methyl)-3-((1-(methylsulfonyl) piperidin-4-yl)oxy) benzamide | 468.1 |
| 40 | 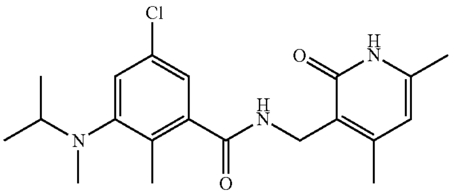 | 5-chloro-N-((4,6-dimethyl-2-oxo-1,2-dihydropyridin-3-yl)methyl)-2-methyl-3-(N-methylacetamido) benzamide | 376.2 |

TABLE 1-continued

| Compound Number | Structure | Name | MS† |
|---|---|---|---|
| 41 | 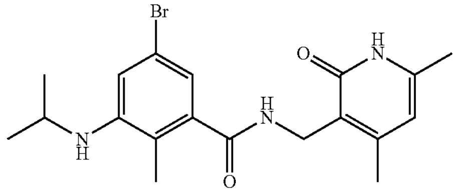 [SMILES: Cc1cc(C)c(CNC(=O)c2cc(Br)cc(NC(C)C)c2C)c(=O)[nH]1] | 5-bromo-N-((4,6-dimethyl-2-oxo-1,2-dihydropyridin-3-yl)methyl)-3-(isopropylamino)-2-methylbenzamide | 406.1 |
| 42 | 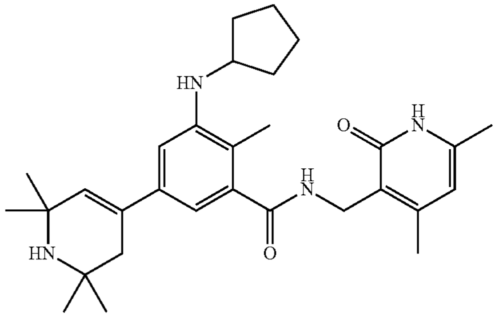 | 3-(cyclopentylamino)-N-((4,6-dimethyl-2-oxo-1,2-dihydropyridin-3-yl)methyl)-2-methyl-5-(2,2,6,6-tetramethyl-1,2,3,6-tetrahydropyridin-4-yl) benzamide | 491.2 |
| 43 | 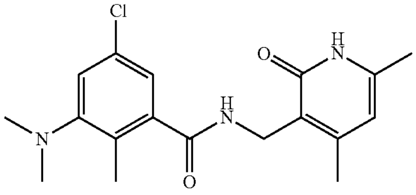 | 5-chloro-N-((4,6-dimethyl-2-oxo-1,2-dihydropyridin-3-yl)methyl)-3-(dimethylamino)-2-methylbenzamide | 348.2 |
| 44 | 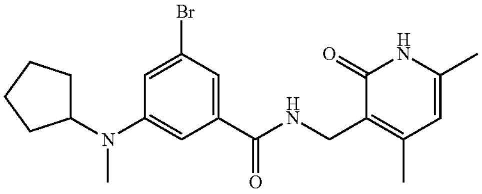 [SMILES: Cc1cc(C)c(CNC(=O)c2cc(Br)cc(N(C)C3CCCC3)c2)c(=O)[nH]1] | 3-bromo-5-(cyclopentyl(methyl) amino)-N-((4,6-dimethyl-2-oxo-1,2-dihydropyridin-3-yl) methyl)benzamide | 432 |
| 45 | 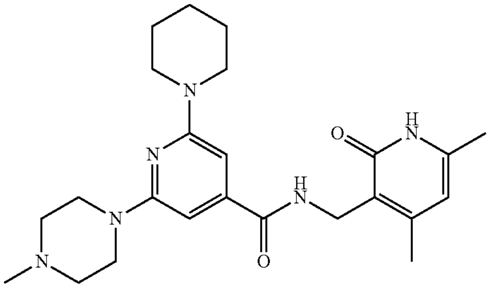 | N-((4,6-dimethyl-2-oxo-1,2-dihydropyridin-3-yl)methyl)-2-(4-methylpiperazin-1-yl)-6-(piperidin-1-yl)isonicotinamide | 438.3 |
| 46 | 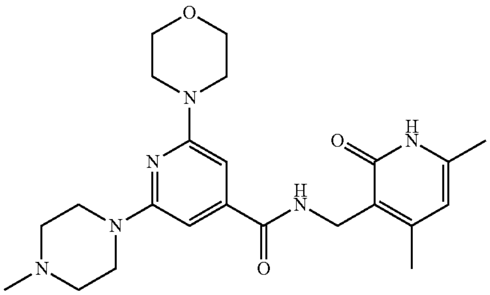 | N-((4,6-dimethyl-2-oxo-1,2-dihydropyridin-3-yl)methyl)-2-(4-methylpiperazin-1-yl)-6-morpholinoiso-nicotinamide | 441.2 |

TABLE 1-continued

| Compound Number | Structure | Name | MS† |
|---|---|---|---|
| 47 | 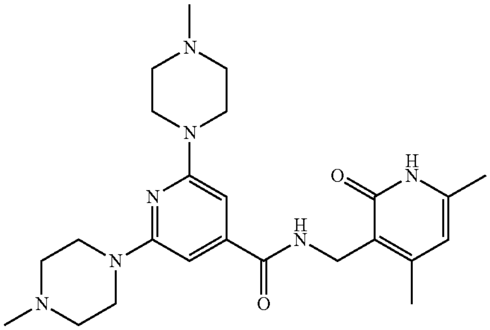 | N-((4,6-dimethyl-2-oxo-1,2-dihydropyridin-3-yl)methyl)-2,6-bis(4-methylpiperazin-1-yl)isonicotinamide | 454.2 |
| 48 | 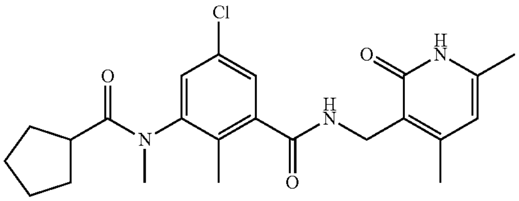 [SMILES: Cc1cc(C)c(CNC(=O)c2cc(Cl)cc(N(C)C(=O)C3CCCC3)c2C)c(=O)[nH]1] | N-((4,6-dimethyl-2-oxo-1,2-dihydropyridin-3-yl)methyl)-2,6-bis(4-methylpiperazin-1-yl)isonicotinamide | 430.2 |
| 49 | 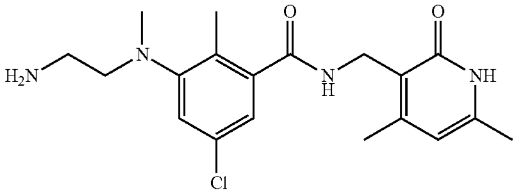 [SMILES: Cc1cc(C)c(CNC(=O)c2cc(Cl)cc(N(C)CCN)c2C)c(=O)[nH]1] | 5-chloro-N-((4,6-dimethyl-2-oxo-1,2-dihydropyridin-3-yl)methyl)-2-methyl-3-(N-methylcyclo-pentanecarboxamido) benzamide | 377.2 |
| 50 | 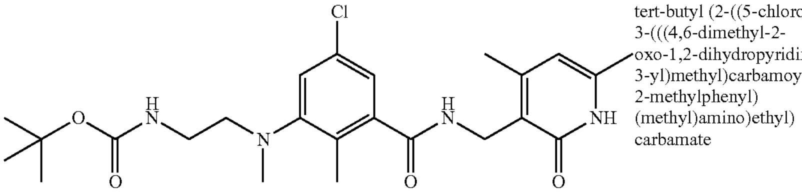 | tert-butyl (2-((5-chloro-3-(((4,6-dimethyl-2-oxo-1,2-dihydropyridin-3-yl)methyl)carbamoyl)-2-methylphenyl) (methyl)amino)ethyl) carbamate | 477.3 |
| 51 | 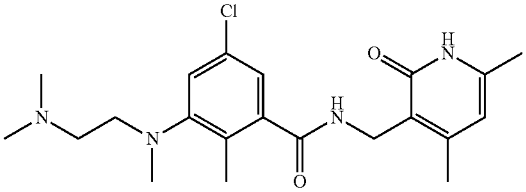 | 5-chloro-N-((4,6-dimethyl-2-oxo-1,2-dihydropyridin-3-yl)methyl)-3-((2-(dimethylamino)ethyl) (methyl)amino)-2-methylbenzamide | 405.3 |
| 52 | 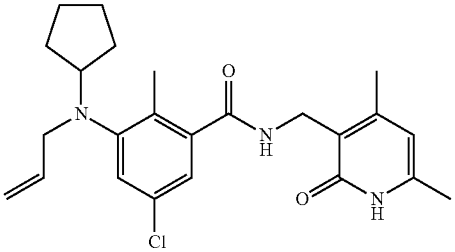 [SMILES: C=CCN(c1cc(Cl)cc(C(=O)NCc2c(C)cc(C)[nH]c2=O)c1C)C1CCCC1] | 3-(allyl(cyclopentyl) amino)-5-chloro-N-((4,6-dimethyl-2-oxo-1,2-dihydropyridin-3-yl)methyl)-2-methylbenzamide | 428.3 |

TABLE 1-continued

| Compound Number | Structure | Name | MS† |
|---|---|---|---|
| 53 | 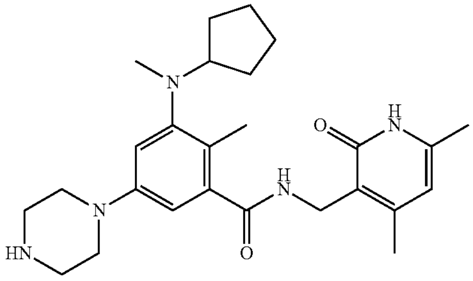 [SMILES: Cc1cc(C)c(CNC(=O)c2cc(N3CCNCC3)cc(N(C)C3CCCC3)c2C)c(=O)[nH]1] | 3-(cyclopentyl(methyl) amino)-N-((4,6-dimethyl-2-oxo-1,2-dihydropyridin-3-yl) methyl)-2-methyl-5-(piperazin-1-yl)benzamide | 452.4 |
| 54 | 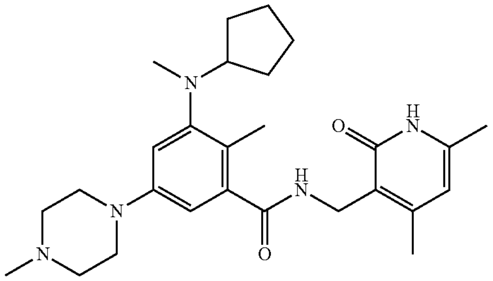 | 3-(cyclopentyl(methyl) amino)-N-((4,6-dimethyl-2-oxo-1,2-dihydropyridin-3-yl) methyl)-2-methyl-5-(4-methylpiperazin-1-yl)benzamide | 466.4 |
| 55 | 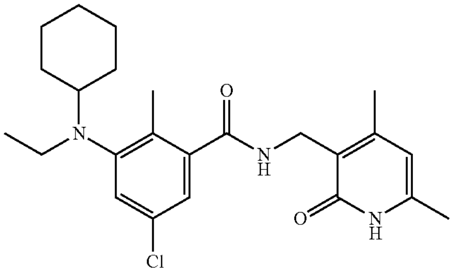 [SMILES: CCN(c1cc(Cl)cc(C(=O)NCc2c(C)cc(C)[nH]c2=O)c1C)C1CCCCC1] | 5-chloro-3-(cyclohexyl(ethyl) amino)-N-((4,6-dimethyl-2-oxo-1,2-dihydropyridin-3-yl)methyl)-2-methylbenzamide | 430.2 |
| 56 | 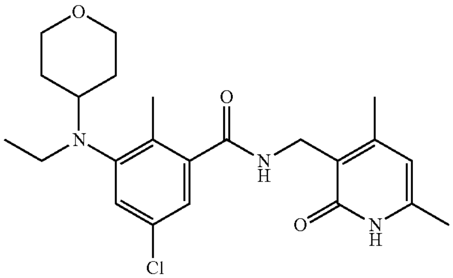 [SMILES: CCN(c1cc(Cl)cc(C(=O)NCc2c(C)cc(C)[nH]c2=O)c1C)C1CCOCC1] | 5-chloro-N-((4,6-dimethyl-2-oxo-1,2-dihydropyridin-3-yl)methyl)-3-(ethyl(tetrahydro-2H-pyran-4-yl)amino)-2-methylbenzamide | 432.3 |
| 57 | 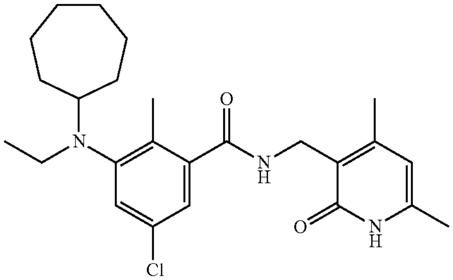 [SMILES: CCN(c1cc(Cl)cc(C(=O)NCc2c(C)cc(C)[nH]c2=O)c1C)C1CCCCCC1] | 5-chloro-3-(cycloheptyl(ethyl) amino)-N-((4,6-dimethyl-2-oxo-1,2-dihydropyridin-3-yl)methyl)-2-methylbenzamide | 444.3 |

TABLE 1-continued

| Compound Number | Structure | Name | MS† |
|---|---|---|---|
| 58 | 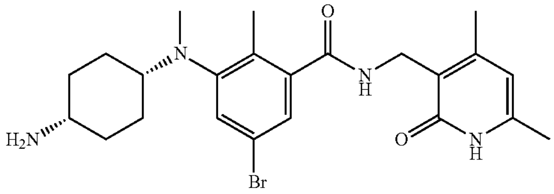 [SMILES: Cc1cc(C)c(CNC(=O)c2cc(Br)cc(N(C)[C@H]3CC[C@@H](N)CC3)c2C)c(=O)[nH]1] | 3-(((1s,4s)-4-aminocyclohexyl)(methyl)amino)-5-bromo-N-((4,6-dimethyl-2-oxo-1,2-dihydropyridin-3-yl)methyl)-2-methylbenzamide | 475.2 |
| 59 | 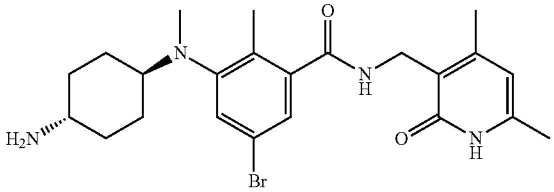 [SMILES: Cc1cc(C)c(CNC(=O)c2cc(Br)cc(N(C)[C@H]3CC[C@H](N)CC3)c2C)c(=O)[nH]1] | 3-(((1r,4r)-4-aminocyclohexyl)(methyl)amino)-5-bromo-N-((4,6-dimethyl-2-oxo-1,2-dihydropyridin-3-yl)methyl)-2-methylbenzamide | 475.2 |
| 60 | 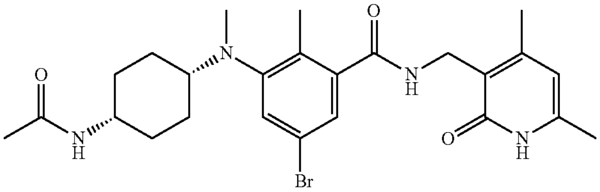 [SMILES: CC(=O)N[C@H]1CC[C@@H](N(C)c2cc(Br)cc(C(=O)NCc3c(C)cc(C)[nH]c3=O)c2C)CC1] | 3-(((1s,4s)-4-acetamidocyclohexyl)(methyl)amino)-5-bromo-N-((4,6-dimethyl-2-oxo-1,2-dihydropyridin-3-yl)methyl)-2-methylbenzamide | 517.3 |
| 61 | 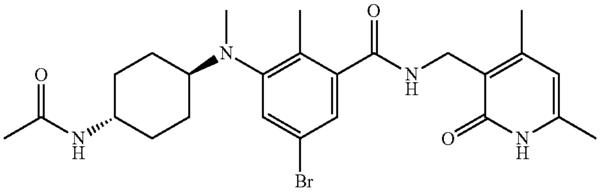 [SMILES: CC(=O)N[C@H]1CC[C@H](N(C)c2cc(Br)cc(C(=O)NCc3c(C)cc(C)[nH]c3=O)c2C)CC1] | 3-(((1r,4r)-4-acetamidocyclohexyl)(methyl)amino)-5-bromo-N-((4,6-dimethyl-2-oxo-1,2-dihydropyridin-3-yl)methyl)-2-methylbenzamide | 517.3 |
| 62 | 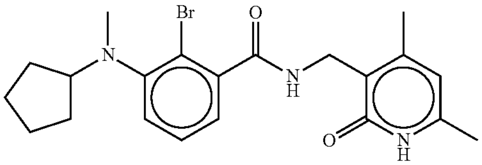 | 2-bromo-3-(cyclopentyl(methyl)amino)-N-((4,6-dimethyl-2-oxo-1,2-dihydropyridin-3-yl)methyl)benzamide | 432.1 |
| 63 | 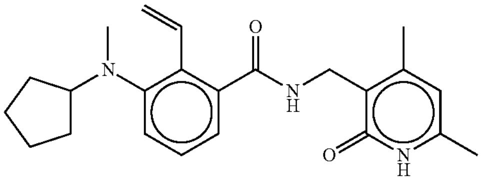 | 3-(cyclopentyl(methyl)amino)-N-((4,6-dimethyl-2-oxo-1,2-dihydropyridin-3-yl)methyl)-2-vinylbenzamide | 380.3 |
| 64 | 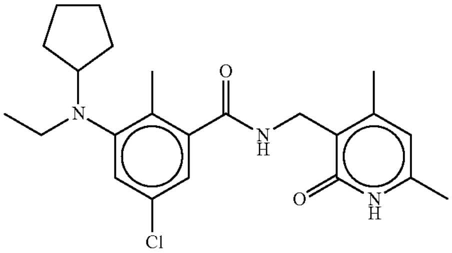 | 5-chloro-3-(cyclopentyl(ethyl)amino)-N-((4,6-dimethyl-2-oxo-1,2-dihydropyridin-3-yl)methyl)-2-methylbenzamide | 416.3 |

TABLE 1-continued

| Compound Number | Structure | Name | MS† |
| --- | --- | --- | --- |
| 65 | 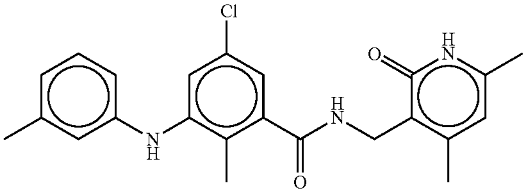 | 5-chloro-N-((4,6-dimethyl-2-oxo-1,2-dihydropyridin-3-yl)methyl)-2-methyl-3-(m-tolylamino)benzamide | 410.3 |
| 66 | 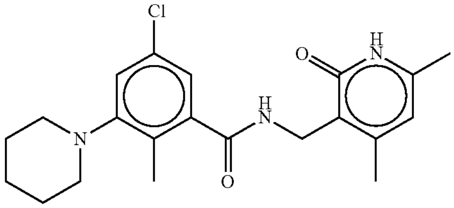 | 5-chloro-N-((4,6-dimethyl-2-oxo-1,2-dihydropyridin-3-yl)methyl)-2-methyl-3-(piperidin-1-yl)benzamide | 388.2 |
| 67 | 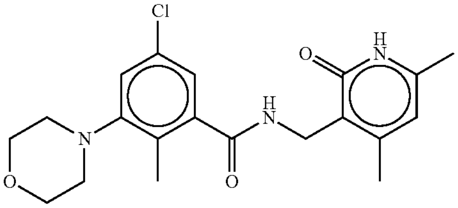 | 5-chloro-N-((4,6-dimethyl-2-oxo-1,2-dihydropyridin-3-yl)methyl)-2-methyl-3-morpholinobenzamide | 390.2 |
| 68 | 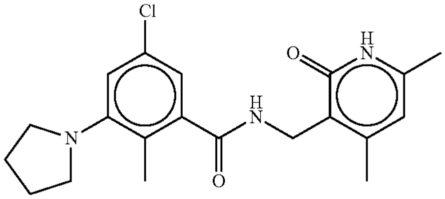 | 5-chloro-N-((4,6-dimethyl-2-oxo-1,2-dihydropyridin-3-yl)methyl)-2-methyl-3-(pyrrolidin-1-yl)benzamide | 374.2 |
| 69 | 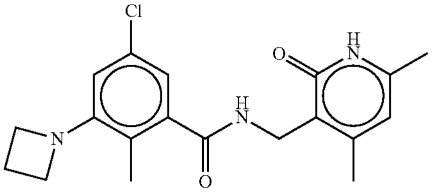 | 3-(azetidin-1-yl)-5-chloro-N-((4,6-dimethyl-2-oxo-1,2-dihydropyridin-3-yl)methyl)-2-methylbenzamide | 360.2 |
| 70 | 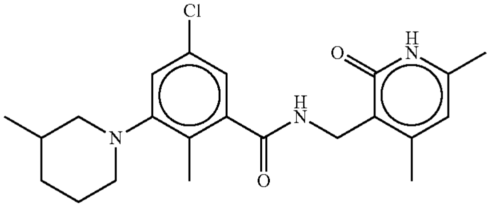 | 5-chloro-N-((4,6-dimethyl-2-oxo-1,2-dihydropyridin-3-yl)methyl)-2-methyl-3-(3-methylpiperidin-1-yl)benzamide | 402.3 |
| 71 | 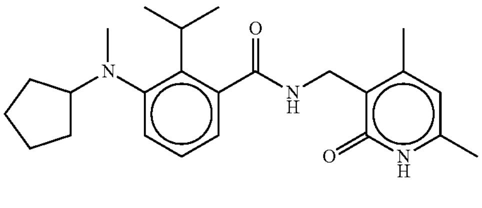 | 3-(cyclopentyl (methyl)amino)-N-((4,6-dimethyl-2-oxo-1,2-dihydropyridin-3-yl)methyl)-2-isopropylbenzamide | 396.25 |

TABLE 1-continued

| Compound Number | Structure | Name | MS† |
|---|---|---|---|
| 72 | 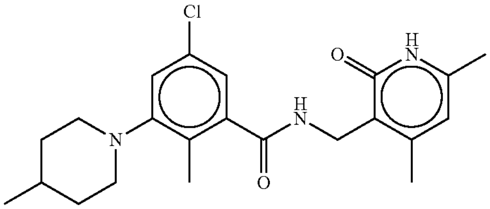 | 5-chloro-N-((4,6-dimethyl-2-oxo-1,2-dihydropyridin-3-yl)methyl)-2-methyl-3-(4-methylpiperidin-1-yl)benzamide | 402.2 |
| 73 | 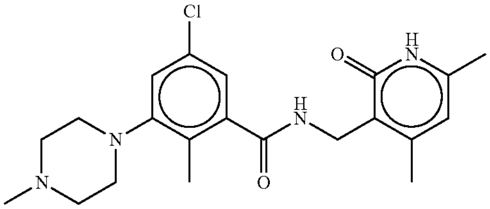 | 5-chloro-N-((4,6-dimethyl-2-oxo-1,2-dihydropyridin-3-yl)methyl)-2-methyl-3-(4-methylpiperazin-1-yl)benzamide | 403.2 |
| 74 | 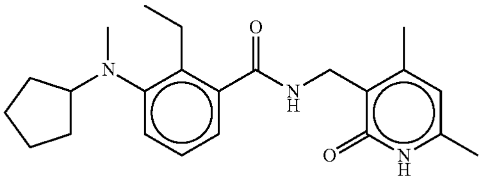 | 3-(cyclopentyl(methyl) amino)-N-((4,6-dimethyl-2-oxo-1,2-dihydropyridin-3-yl)methyl)-2-ethylbenzamide | 382.3 |
| 75 | 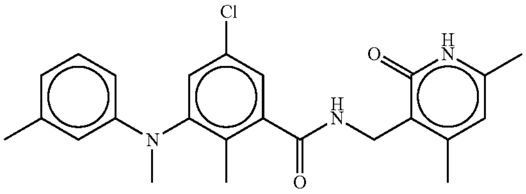 | 5-chloro-N-((4,6-dimethyl-2-oxo-1,2-dihydropyridin-3-yl)methyl)-2-methyl-3-(methyl(m-tolyl) amino)benzamide | 424.2 |
| 76 | 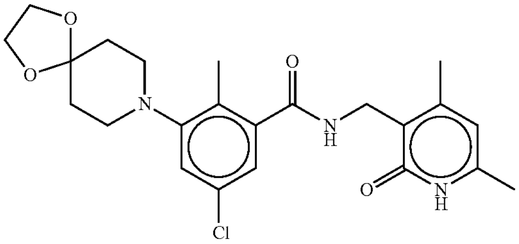 | 5-chloro-N-((4,6-dimethyl-2-oxo-1,2-dihydropyridin-3-yl)methyl)-2-methyl-3-(1,4-dioxa-8-azaspiro[4.5]decan-8-yl)benzamide | 446.2 |
| 77 | 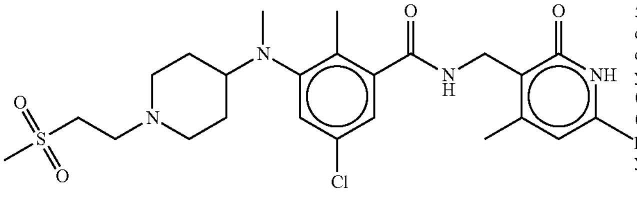 | 5-chloro-N-((4,6-dimethyl-2-oxo-1,2-dihydropyridin-3-yl)methyl)-2-methyl-3-(methyl(1-(2-(methylsulfonyl)ethyl) piperidin-4-yl)amino)benzamide | 523.2 |
| 78 | 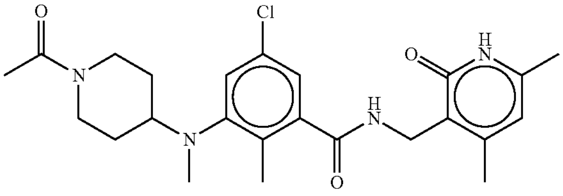 | 3-((1-acetylpiperidin-4-yl)(methyl)amino)-5-chloro-N-((4,6-dimethyl-2-oxo-1,2-dihydropyridin-3-yl)methyl)-2-methylbenzamide | 459.3 |

TABLE 1-continued

| Compound Number | Structure | Name | MS† |
|---|---|---|---|
| 79 | 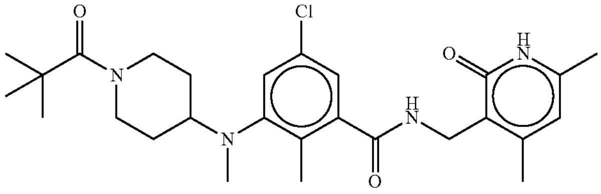 | 5-chloro-N-((4,6-dimethyl-2-oxo-1,2-dihydropyridin-3-yl)methyl)-2-methyl-3-(methyl(1-pivaloylpiperidin-4-yl)amino)benzamide | 501.2 |
| 80 | 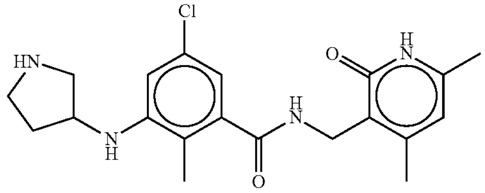 | 5-chloro-N-((4,6-dimethyl-2-oxo-1,2-dihydropyridin-3-yl)methyl)-2-methyl-3-(pyrrolidin-3-ylamino)benzamide | 389.2 |
| 81 | | [[Duplicate with #19]] | |
| 82 | 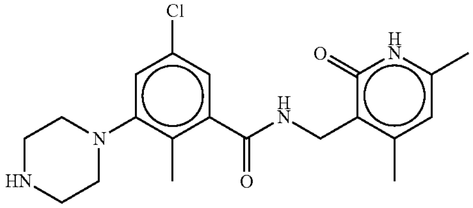 | 5-chloro-N-((4,6-dimethyl-2-oxo-1,2-dihydropyridin-3-yl)methyl)-2-methyl-3-(piperazin-1-yl)benzamide | 389.1 |
| 83 | 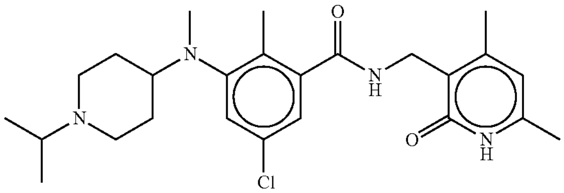 | 5-chloro-N-((4,6-dimethyl-2-oxo-1,2-dihydropyridin-3-yl)methyl)-3-((1-isopropylpiperidin-4-yl)(methyl)amino)-2-methylbenzamide | 459.3 |
| 84 | 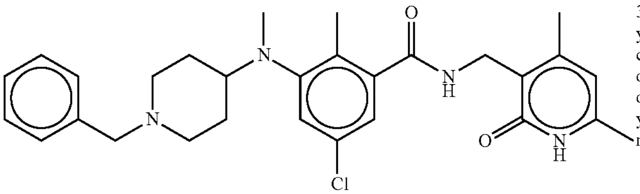 | 3-((1-benzylpiperidin-4-yl)(methyl)amino)-5-chloro-N-((4,6-dimethyl-2-oxo-1,2-dihydropyridin-3-yl)methyl)-2-methylbenzamide | 507.2 |
| 85 | 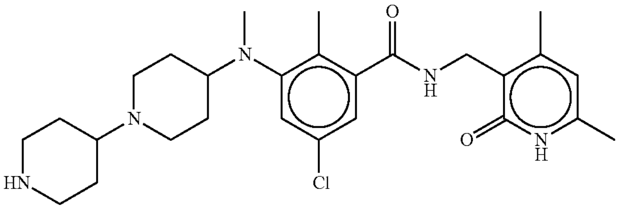 | 3-([1,4'-bipiperidin]-4-yl(methyl)amino)-5-chloro-N-((4,6-dimethyl-2-oxo-1,2-dihydropyridin-3-yl)methyl)-2-methylbenzamide | 500.2 |
| 86 | 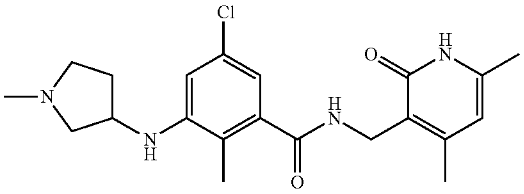 | 5-chloro-N-((4,6-dimethyl-2-oxo-1,2-dihydropyridin-3-yl)methyl)-2-methyl-3-((1-methylpyrrolidin-3-yl)amino)benzamide | 403.1 |

TABLE 1-continued

| Compound Number | Structure | Name | MS† |
|---|---|---|---|
| 87 | 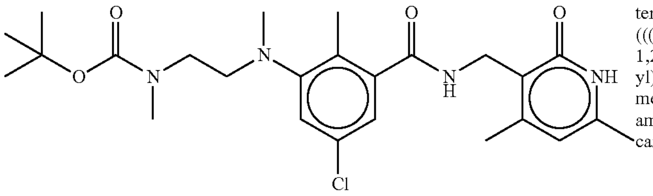 | tert-butyl (2-((5-chloro-3-(((4,6-dimethyl-2-oxo-1,2-dihydropyridin-3-yl)methyl)carbamoyl)-2-methylphenyl)(methyl)amino)ethyl)(methyl)carbamate | 391.2 |
| 88 | 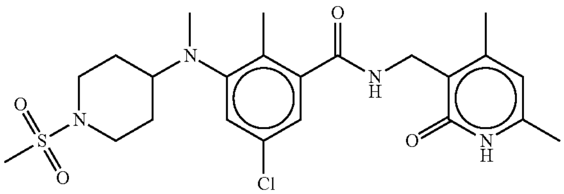 | 5-chloro-N-((4,6-dimethyl-2-oxo-1,2-dihydropyridin-3-yl)methyl)-2-methyl-3-(methyl(1-(methylsulfonyl)piperidin-4-yl)amino)benzamide | 494.9 |
| 89 | 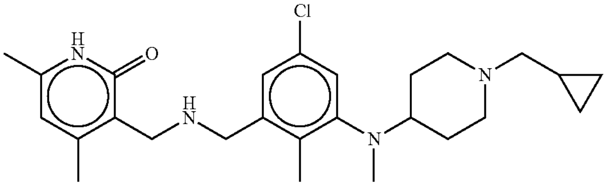 | 5-chloro-3-((1-(cyclopropylmethyl)piperidin-4-yl)(methyl)amino)-N-((4,6-dimethyl-2-oxo-1,2-dihydropyridin-3-yl)methyl)-2-methylbenzamide | 471.2 |
| 90 | 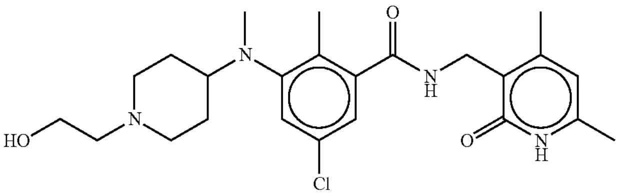 | 5-chloro-N-((4,6-dimethyl-2-oxo-1,2-dihydropyridin-3-yl)methyl)-3-((1-(2-hydroxyethyl)piperidin-4-yl)(methyl)amino)-2-methylbenzamide | 461.2 |
| 91 | 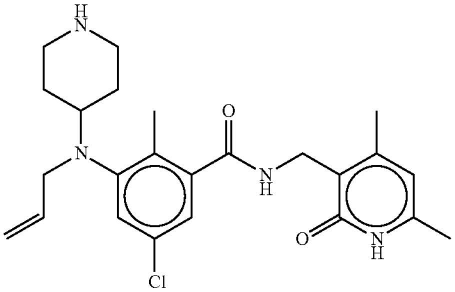 | 3-(allyl(piperidin-4-yl)amino)-5-chloro-N-((4,6-dimethyl-2-oxo-1,2-dihydropyridin-3-yl)methyl)-2-methylbenzamide | 443.3 |
| 92 | 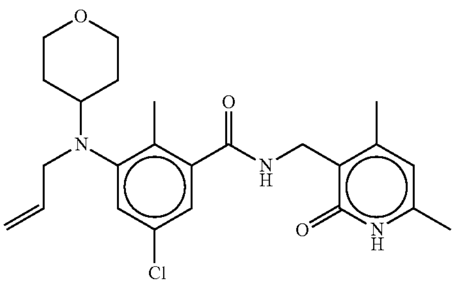 | 3-(allyl(tetrahydro-2H-pyran-4-yl)amino)-5-chloro-N-((4,6-dimethyl-2-oxo-1,2-dihydropyridin-3-yl)methyl)-2-methylbenzamide | 444.3 |

TABLE 1-continued

| Compound Number | Structure | Name | MS† |
|---|---|---|---|
| 93 | 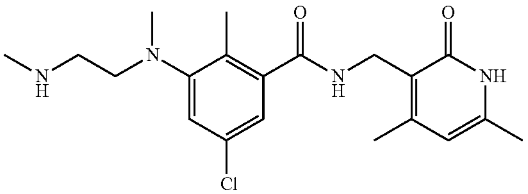 | 5-chloro-N-((4,6-dimethyl-2-oxo-1,2-dihydropyridin-3-yl)methyl)-2-methyl-3-(methyl(2-(methyl-amino)ethyl)amino) benzamide | 391.2 |
| 94 | 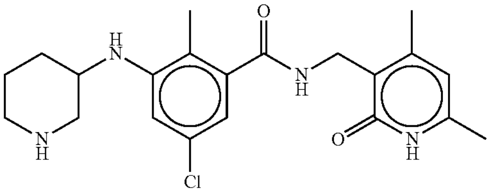 | 5-chloro-N-((4,6-dimethyl-2-oxo-1,2-dihydropyridin-3-yl)methyl)-2-methyl-3-(piperidin-3-ylamino)benzamide | 403.3 |
| 95 | 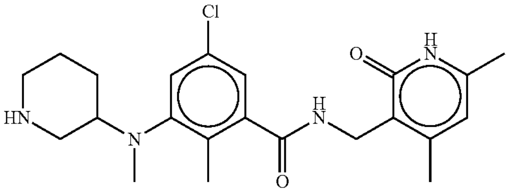 | 5-chloro-N-((4,6-dimethyl-2-oxo-1,2-dihydropyridin-3-yl)methyl)-2-methyl-3-(methyl(piperidin-3-yl)amino)benzamide | 417.3 |
| 96 | 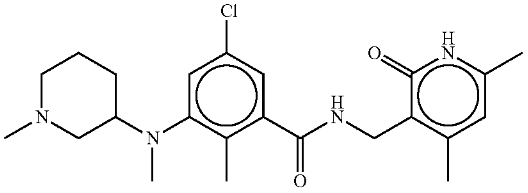 | 5-chloro-N-((4,6-dimethyl-2-oxo-1,2-dihydropyridin-3-yl)methyl)-2-methyl-3-(methyl(1-methyl-piperidin-3-yl)amino) benzamide | 431.2 |
| 97 | 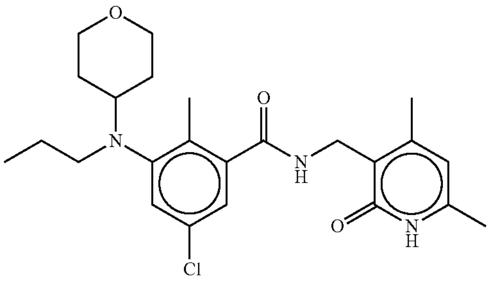 | 5-chloro-N-((4,6-dimethyl-2-oxo-1,2-dihydropyridin-3-yl)methyl)-2-methyl-3-(piperidin-4-yl(propyl) amino)benzamide | 445.3 |
| 98 | 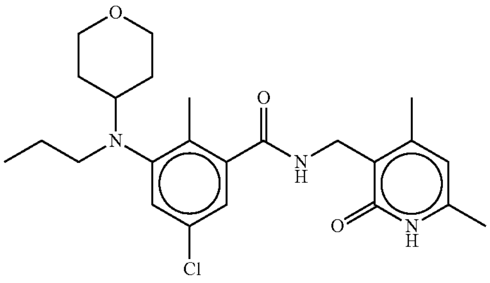 | 5-chloro-N-((4,6-dimethyl-2-oxo-1,2-dihydropyridin-3-yl)methyl)-2-methyl-3-(propyl(tetrahydro-2H-pyran-4-yl)amino) benzamide | 445.3 |

TABLE 1-continued

| Compound Number | Structure | Name | MS† |
|---|---|---|---|
| 99 | 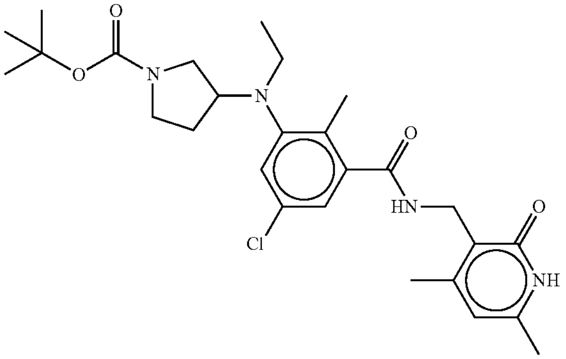 | tert-butyl 3-((5-chloro-3-(((4,6-dimethyl-2-oxo-1,2-dihydro-pyridin-3-yl)methyl) carbamoyl)-2-methyl-phenyl)(ethyl)amino) pyrrolidine-1-carboxylate | 517.4 |
| 100 | 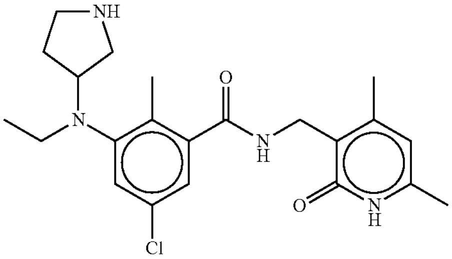 | 5-chloro-N-((4,6-dimethyl-2-oxo-1,2-dihydropyridin-3-yl)methyl)-3-(ethyl(pyrrolidin-3-yl)amino)-2-methylbenzamide | 417.3 |
| 101 | 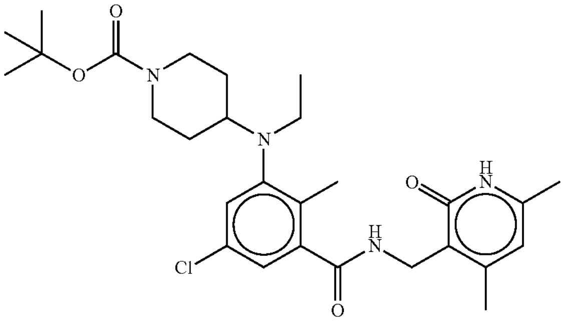 | tert-butyl 4-((5-chloro-3-(((4,6-dimethyl-2-oxo-1,2-dihydropyridin-3-yl)methyl)carbamoyl)-2-methylphenyl) (ethyl)amino)piperidine-1-carboxylate | 531.4 |
| 102 | 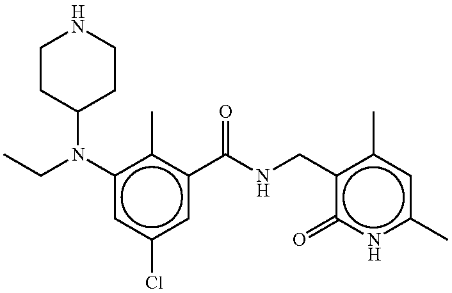 | 5-chloro-N-((4,6-dimethyl-2-oxo-1,2-dihydropyridin-3-yl)methyl)-3-(ethyl(piperidin-4-yl)amino)-2-methylbenzamide | 431.2 |
| 103 | 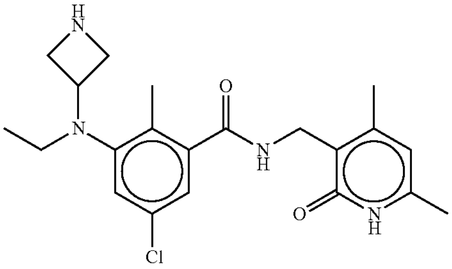 | 3-(azetidin-3-yl(ethyl)amino)-5-chloro-N-((4,6-dimethyl-2-oxo-1,2-dihydropyridin-3-yl)methyl)-2-methylbenzamide | 403.2 |

TABLE 1-continued

| Compound Number | Structure | Name | MS† |
|---|---|---|---|
| 104 | 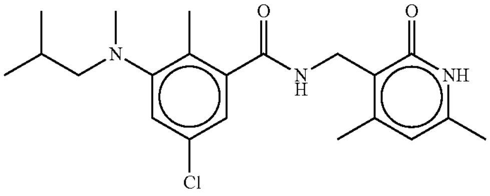 | 5-chloro-N-((4,6-dimethyl-2-oxo-1,2-dihydropyridin-3-yl)methyl)-3-(isobutyl(methyl)amino)-2-methyl-benzamide | 390.3 |
| 105 | 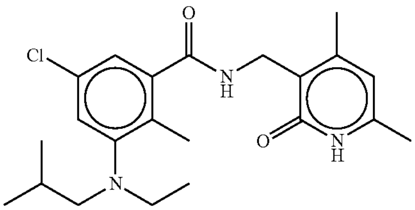 | 5-chloro-N-((4,6-dimethyl-2-oxo-1,2-dihydropyridin-3-yl)methyl)-3-(ethyl(isobutyl)amino)-2-methylbenzamide | 404.3 |
| 106 | 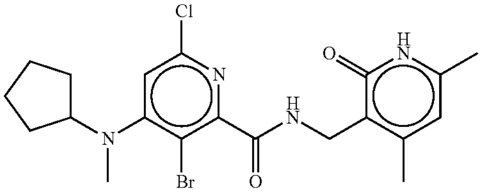 | 3-bromo-6-chloro-4-(cyclopentyl(methyl)amino)-N-((4,6-dimethyl-2-oxo-1,2-dihydropyridin-3-yl)methyl)picolinamide | 469.2 |
| 107 | 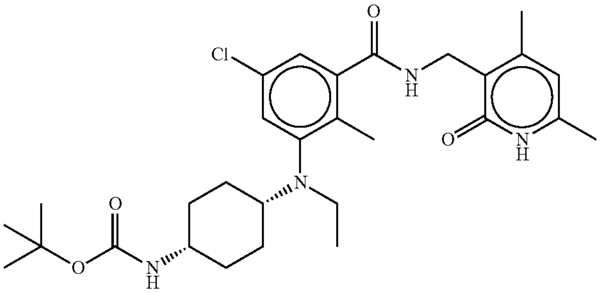 | tert-butyl ((1s,4s)-4-((5-chloro-3-(((4,6-dimethyl-2-oxo-1,2-dihydropyridin-3-yl)methyl)carbamoyl)-2-methylphenyl)(ethyl)amino)cyclohexyl)carbamate | 545.4 |
| 108 | 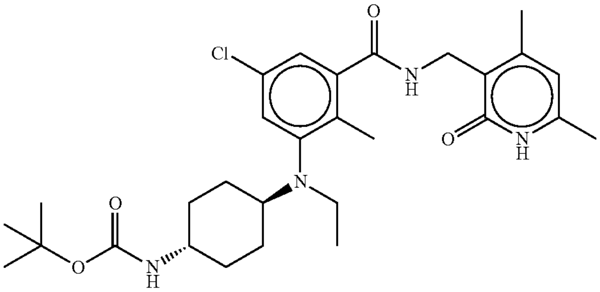 | tert-butyl ((1r,4r)-4-((5-chloro-3-(((4,6-dimethyl-2-oxo-1,2-dihydropyridin-3-yl)methyl)carbamoyl)-2-methylphenyl)(ethyl)amino)cyclohexyl)carbamate | 545.3 |

TABLE 1-continued

| Compound Number | Structure | Name | MS† |
|---|---|---|---|
| 109 | 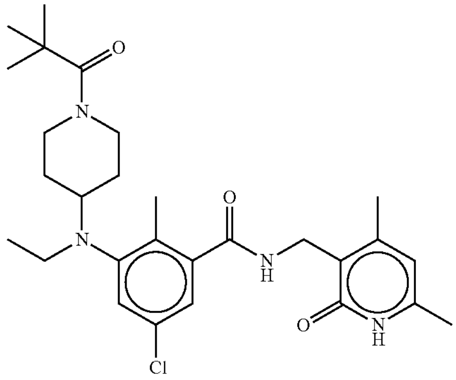 | 5-chloro-N-((4,6-dimethyl-2-oxo-1,2-dihydropyridin-3-yl)methyl)-3-(ethyl(1-pivaloylpiperidin-4-yl)amino)-2-methylbenzamide | 515.4 |
| 110 | 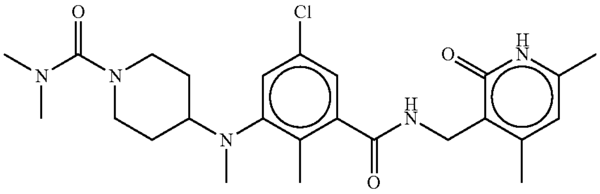 | 4-((5-chloro-3-(((4,6-dimethyl-2-oxo-1,2-dihydropyridin-3-yl)methyl)carbamoyl)-2-methylphenyl)(methyl) amino)-N,N-dimethylpiperidine-1-carboxamide | 488.2 |
| 111 | 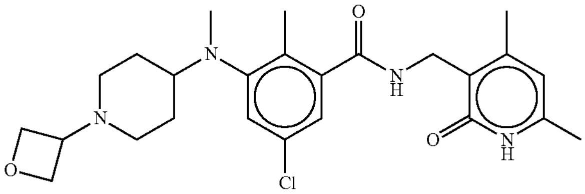 | 5-chloro-N-((4,6-dimethyl-2-oxo-1,2-dihydropyridin-3-yl)methyl)-2-methyl-3-(methyl(1-(oxetan-3-yl)piperidin-4-yl)amino)benzamide | 473.3 |
| 112 | 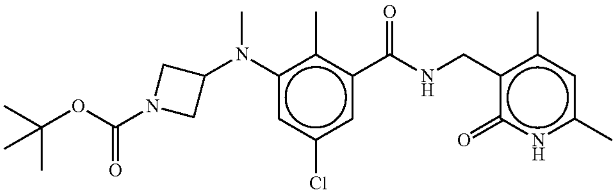 | tert-butyl 3-((5-chloro-3-(((4,6-dimethyl-2-oxo-1,2-dihydro-pyridin-3-yl)methyl) carbamoyl)-2-methylphenyl)(methyl) amino)azetidine-1-carboxylate | 489.3 |
| 113 | 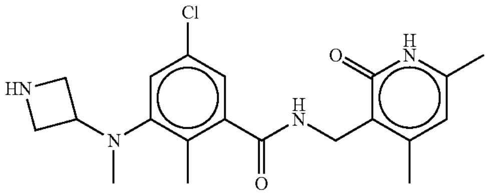 | 3-(azetidin-3-yl(methyl)amino)-5-chloro-N-((4,6-dimethyl-2-oxo-1,2-dihydropyridin-3-yl)methyl)-2-methylbenzamide | 389.3 |
| 114 | 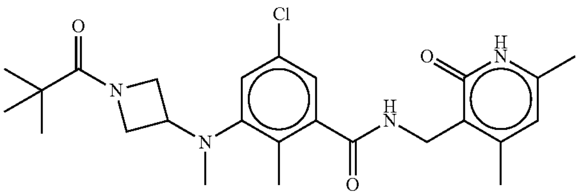 | 5-chloro-N-((4,6-dimethyl-2-oxo-1,2-dihydropyridin-3-yl)methyl)-2-methyl-3-(methyl(1-pivaloylazetidin-3-yl)amino)benzamide | 473.2 |

TABLE 1-continued

| Compound Number | Structure | Name | MS† |
|---|---|---|---|
| 115 | 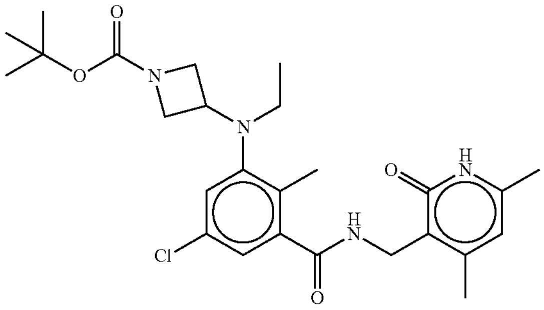 | tert-butyl 3-((5-chloro-3-(((4,6-dimethyl-2-oxo-1,2-dihydropyridin-3-yl)methyl)carbamoyl)-2-methylphenyl)(ethyl)amino)azetidine-1-carboxylate | 503.3 |
| 116 | 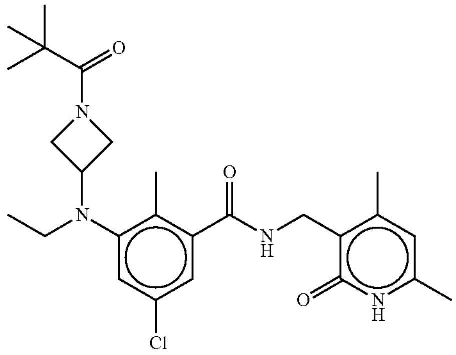 | 5-chloro-N-((4,6-dimethyl-2-oxo-1,2-dihydropyridin-3-yl)methyl)-3-(ethyl(1-pivaloylazetidin-3-yl)amino)-2-methylbenzamide | 487.2 |
| 117 | 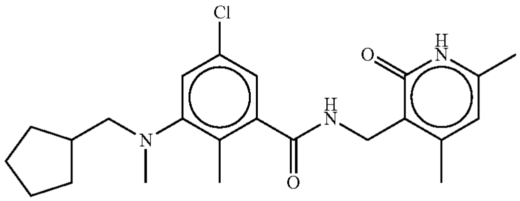 | 5-chloro-3-((cyclopentylmethyl)(methyl)amino)-N-((4,6-dimethyl-2-oxo-1,2-dihydropyridin-3-yl)methyl)-2-methylbenzamide | 416.2 |
| 118 | 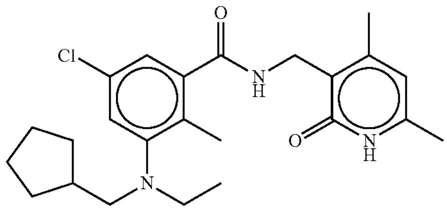 | 5-chloro-3-((cyclopentylmethyl)(ethyl)amino)-N-((4,6-dimethyl-2-oxo-1,2-dihydropyridin-3-yl)methyl)-2-methylbenzamide | 430.2 |
| 119 | 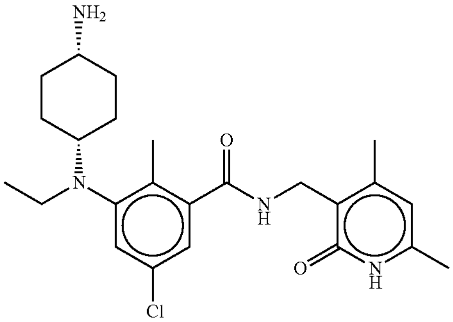 | 3-(((1s,4s)-4-aminocyclohexyl)(ethyl)amino)-5-chloro-N-((4,6-dimethyl-2-oxo-1,2-dihydropyridin-3-yl)methyl)-2-methylbenzamide | 445.3 |

TABLE 1-continued

| Compound Number | Structure | Name | MS† |
|---|---|---|---|
| 120 | 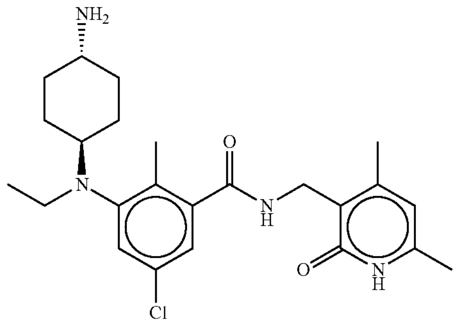 | 3-(((1r,4r)-4-aminocyclohexyl)(ethyl)amino)-5-chloro-N-((4,6-dimethyl-2-oxo-1,2-dihydropyridin-3-yl)methyl)-2-methylbenzamide | 445.2 |
| 121 | 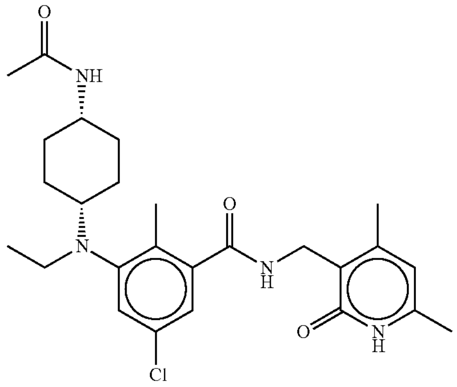 | 3-(((1s,4s)-4-acetamidocyclohexyl)(ethyl)amino)-5-chloro-N-((4,6-dimethyl-2-oxo-1,2-dihydropyridin-3-yl)methyl)-2-methylbenzamide | 487.3 |
| 122 | 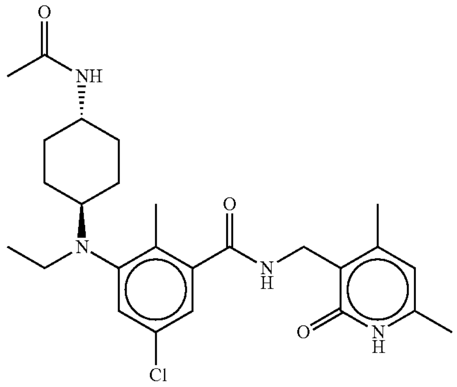 | 3-(((1r,4r)-4-acetamidocyclohexyl)(ethyl)amino)-5-chloro-N-((4,6-dimethyl-2-oxo-1,2-dihydropyridin-3-yl)methyl)-2-methylbenzamide | 487.3 |
| 123 | 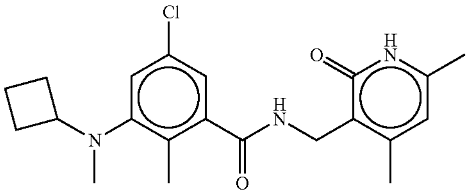 | 5-chloro-3-(cyclobutyl(methyl)amino)-N-((4,6-dimethyl-2-oxo-1,2-dihydropyridin-3-yl)methyl)-2-methylbenzamide | 388.1 |
| 124 | 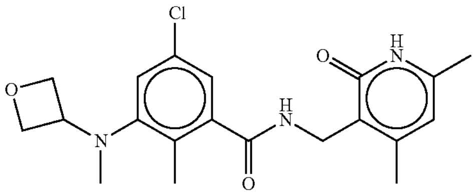 | 5-chloro-N-((4,6-dimethyl-2-oxo-1,2-dihydropyridin-3-yl)methyl)-2-methyl-3-(methyl(oxetan-3-yl)amino)benzamide | 390.2 |

TABLE 1-continued

| Compound Number | Structure | Name | MS† |
|---|---|---|---|
| 125 | 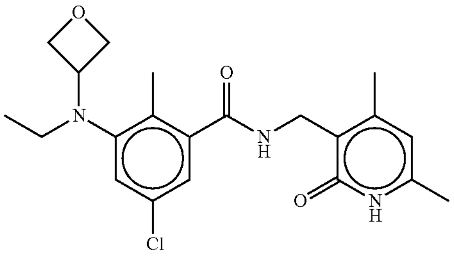 | 5-chloro-N-((4,6-dimethyl-2-oxo-1,2-dihydropyridin-3-yl)methyl)-3-(ethyl(oxetan-3-yl)amino)-2-methylbenzamide | 404.2 |
| 126 | 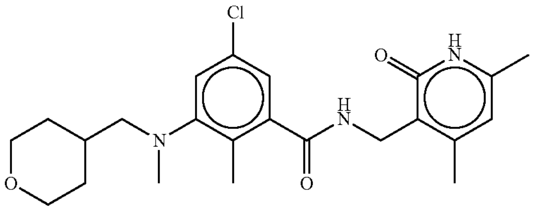 | 5-chloro-N-((4,6-dimethyl-2-oxo-1,2-dihydropyridin-3-yl)methyl)-2-methyl-3-(methyl((tetrahydro-2H-pyran-4-yl)methyl)amino) benzamide | 432.3 |
| 127 | 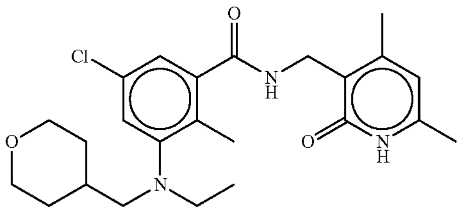 | 5-chloro-N-((4,6-dimethyl-2-oxo-1,2-dihydropyridin-3-yl)methyl)-3-(ethyl((tetrahydro-2H-pyran-4-yl)methyl)amino)-2-methylbenzamide | 446.2 |
| 128 | 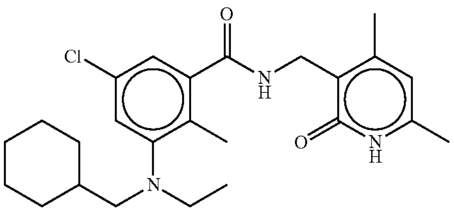 | 5-chloro-3-((cyclohexylmethyl) (ethyl)amino)-N-((4,6-dimethyl-2-oxo-1,2-dihydropyridin-3-yl)methyl)-2-methylbenzamide | 444.3 |
| 129 | 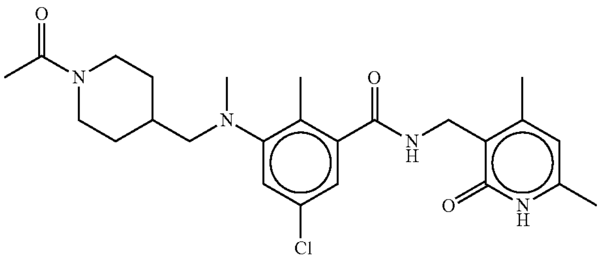 | 3-(((1-acetylpiperidin-4-yl)methyl)(methyl) amino)-5-chloro-N-((4,6-dimethyl-2-oxo-1,2-dihydropyridin-3-yl)methyl)-2-methylbenzamide | 473.3 |
| 130 | 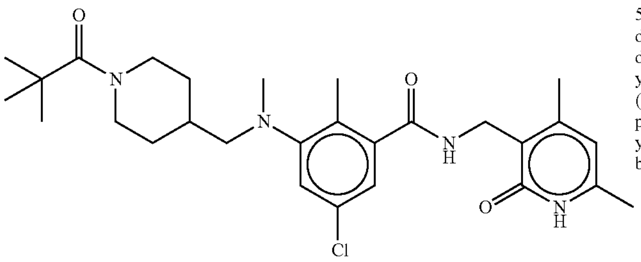 | 5-chloro-N-((4,6-dimethyl-2-oxo-1,2-dihydropyridin-3-yl)methyl)-2-methyl-3-(methyl((1-pivaloylpiperidin-4-yl)methyl)amino) benzamide | 515.3 |

TABLE 1-continued

| Compound Number | Structure | Name | MS† |
|---|---|---|---|
| 131 | 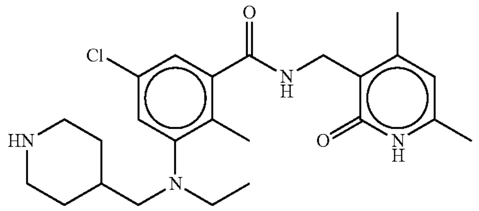 | 5-chloro-N-((4,6-dimethyl-2-oxo-1,2-dihydropyridin-3-yl)methyl)-3-(ethyl(piperidin-4-ylmethyl)amino)-2-methylbenzamide | 445.2 |
| 132 | 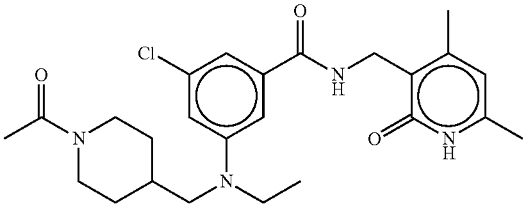 | 3-(((1-acetylpiperidin-4-yl)methyl)(ethyl)amino)-5-chloro-N-((4,6-dimethyl-2-oxo-1,2-dihydropyridin-3-yl)methyl)-2-methylbenzamide | 487.3 |
| 133 | 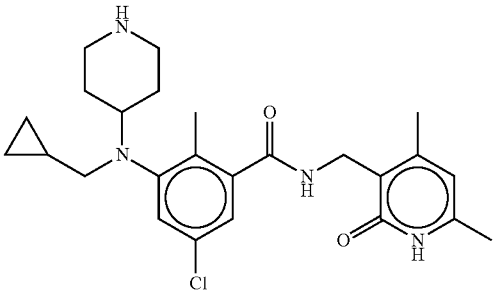 | 5-chloro-3-((cyclopropylmethyl)(piperidin-4-yl)amino)-N-((4,6-dimethyl-2-oxo-1,2-dihydropyridin-3-yl)methyl)-2-methylbenzamide | 457.2 |
| 134 | 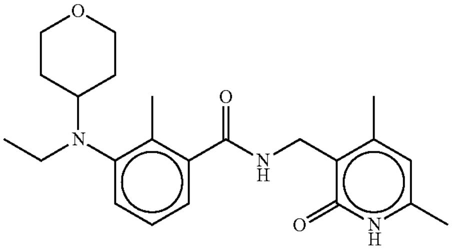 | N-((4,6-dimethyl-2-oxo-1,2-dihydropyridin-3-yl)methyl)-3-(ethyl(tetrahydro-2H-pyran-4-yl)amino)-2-methylbenzamide | 398.3 |
| 135 | 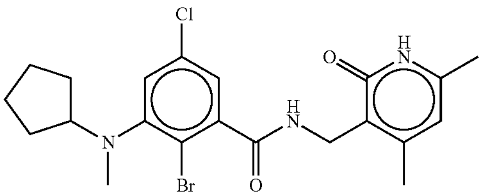 | 2-bromo-5-chloro-3-(cyclopentyl(methyl)amino)-N-((4,6-dimethyl-2-oxo-1,2-dihydropyridin-3-yl)methyl)benzamide | 466.1 |
| 136 | 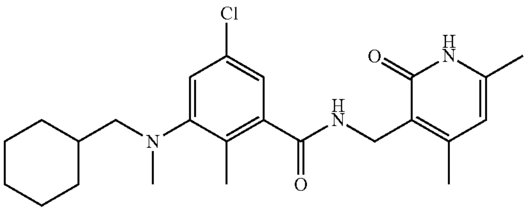 [SMILES: Cc1cc(C)c(CNC(=O)c2cc(Cl)cc(N(C)CC3CCCCC3)c2C)c(=O)[nH]1] | 5-chloro-3-((cyclohexylmethyl)(methyl)amino)-N-((4,6-dimethyl-2-oxo-1,2-dihydropyridin-3-yl)methyl)-2-methylbenzamide | 430.2 |

TABLE 1-continued

| Compound Number | Structure | Name | MS† |
|---|---|---|---|
| 137 | 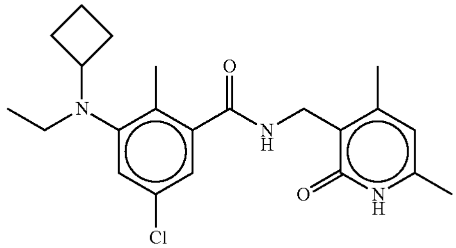 | 5-chloro-3-(cyclobutyl(ethyl)amino)-N-((4,6-dimethyl-2-oxo-1,2-dihydropyridin-3-yl)methyl)-2-methylbenzamide | 402.2 |
| 138 | 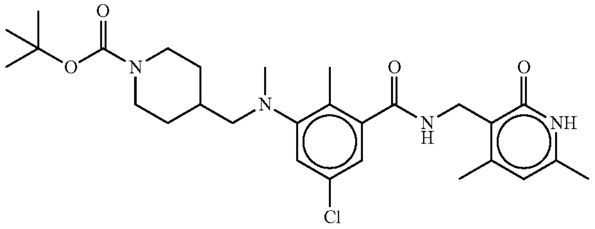 | tert-butyl 4-(((5-chloro-3-(((4,6-dimethyl-2-oxo-1,2-dihydropyridin-3-yl)methyl)carbamoyl)-2-methylphenyl)(methyl) amino)methyl) piperidine-1-carboxylate | 531.3 |
| 139 | 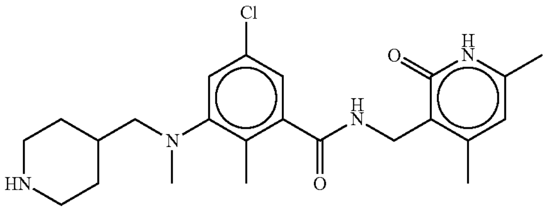 | 5-chloro-N-((4,6-dimethyl-2-oxo-1,2-dihydropyridin-3-yl)methyl)-2-methyl-3-(methyl(piperidin-4-ylmethyl)amino) benzamide | 431.2 |
| 140 | 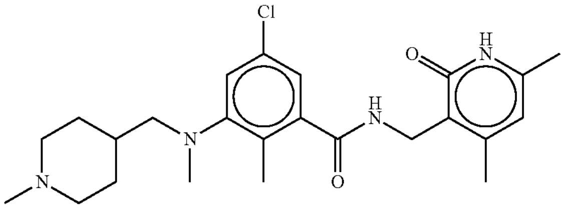 | 5-chloro-N-((4,6-dimethyl-2-oxo-1,2-dihydropyridin-3-yl)methyl)-2-methyl-3-(methyl((1-methylpiperidin-4-yl)methyl)amino) benzamide | 445.2 |
| 141 | 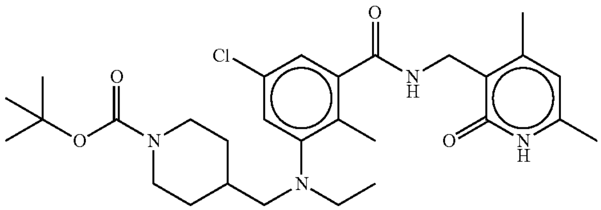 | tert-butyl 4-(((5-chloro-3-(((4,6-dimethyl-2-oxo-1,2-dihydropyridin-3-yl)methyl)carbamoyl)-2-methylphenyl)(ethyl) amino)methyl) piperidine-1-carboxylate | 545.3 |
| 142 | 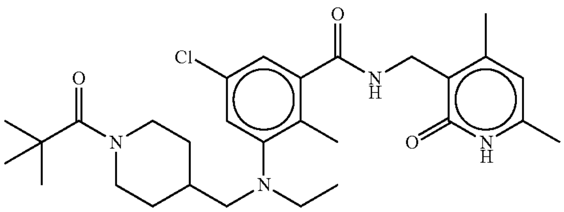 | 5-chloro-N-((4,6-dimethyl-2-oxo-1,2-dihydropyridin-3-yl)methyl)-3-(ethyl((1-pivaloylpiperidin-4-yl)methyl)amino)-2-methylbenzamide | 530.4 |
| 143 | 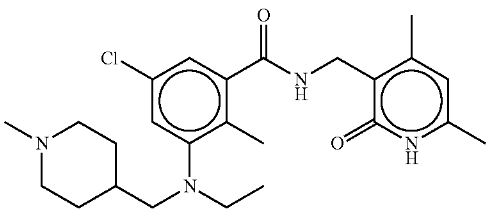 | 5-chloro-N-((4,6-dimethyl-2-oxo-1,2-dihydropyridin-3-yl)methyl)-3-(ethyl((1-methylpiperidin-4-yl)methyl)amino)-2-methylbenzamide | 459.3 |

TABLE 1-continued

| Compound Number | Structure | Name | MS† |
|---|---|---|---|
| 144 | 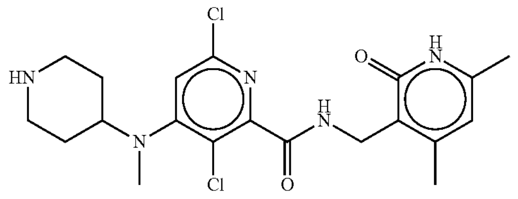 | 3,6-dichloro-N-((4,6-dimethyl-2-oxo-1,2-dihydropyridin-3-yl)methyl)-4-(methyl(piperidin-4-yl)amino)picolinamide | 439.8 |
| 145 | 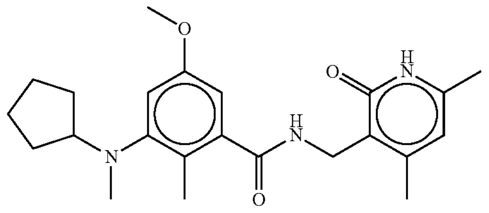 | 3-(cyclopentyl(methyl)amino)-N-((4,6-dimethyl-2-oxo-1,2-dihydropyridin-3-yl)methyl)-5-methoxy-2-methylbenzamide | 398.1 |
| 146 | 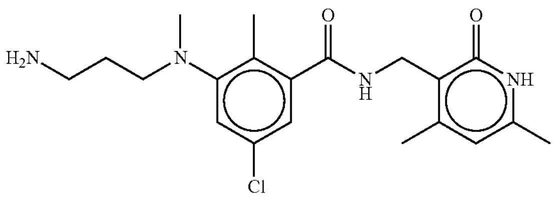 | 3-((3-aminopropyl)(methyl)amino)-5-chloro-N-((4,6-dimethyl-2-oxo-1,2-dihydropyridin-3-yl)methyl)-2-methylbenzamide | 391.1 |
| 147 | 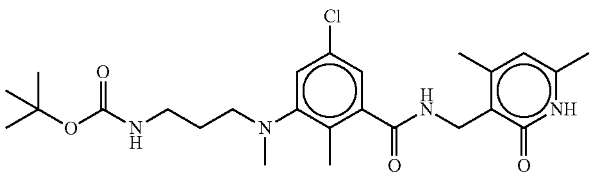 | tert-butyl (3-((5-chloro-3-(((4,6-dimethyl-2-oxo-1,2-dihydropyridin-3-yl)methyl)carbamoyl)-2-methylphenyl)(methyl)amino)propyl)carbamate | 491.1 |
| 148 | 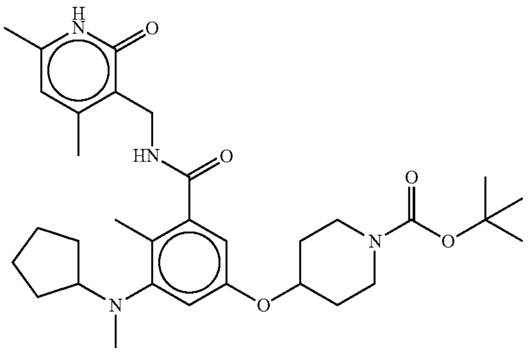 | tert-butyl 4-(3-(cyclopentyl(methyl)amino)-5-(((4,6-dimethyl-2-oxo-1,2-dihydropyridin-3-yl)methyl)carbamoyl)-4-methylphenoxy)piperidine-1-carboxylate | 567.3 |
| 149 | 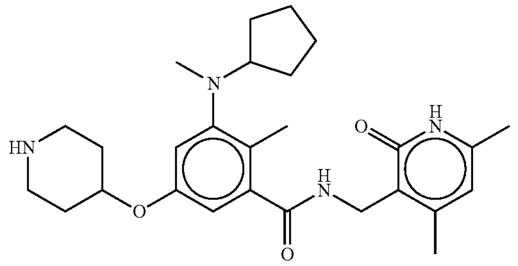 | 3-(cyclopentyl(methyl)amino)-N-((4,6-dimethyl-2-oxo-1,2-dihydropyridin-3-yl)methyl)-2-methyl-5-(piperidin-4-yloxy)benzamide | 467.2 |

TABLE 1-continued

| Compound Number | Structure | Name | MS† |
|---|---|---|---|
| 150 | 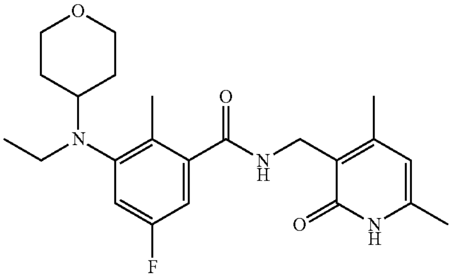 [SMILES: CCN(c1cc(F)cc(C(=O)NCc2c(C)cc(C)[nH]c2=O)c1C)C1CCOCC1] | N-((4,6-dimethyl-2-oxo-1,2-dihydropyridin-3-yl)methyl)-3-(ethyl(tetrahydro-2H-pyran-4-yl)amino)-5-fluoro-2-methylbenzamide | 416.1 |
| 151 | 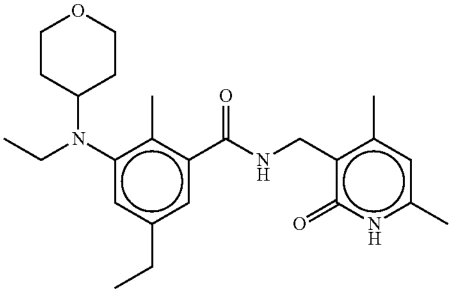 | N-((4,6-dimethyl-2-oxo-1,2-dihydropyridin-3-yl)methyl)-5-ethyl-3-(ethyl(tetrahydro-2H-pyran-4-yl)amino)-2-methylbenzamide | 446.2 |
| 152 | 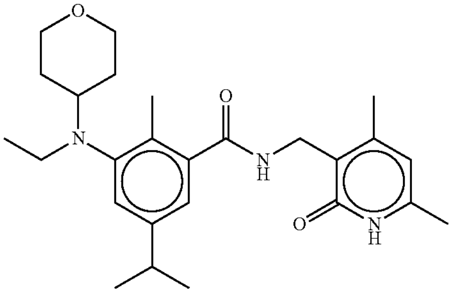 | N-((4,6-dimethyl-2-oxo-1,2-dihydropyridin-3-yl)methyl)-3-(ethyl(tetrahydro-2H-pyran-4-yl)amino)-5-isopropyl-2-methylbenzamide | 440.2 |
| 153 | 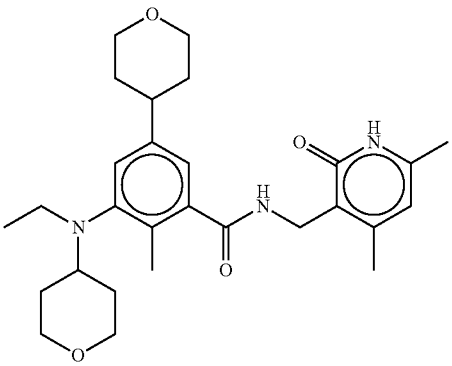 | N-((4,6-dimethyl-2-oxo-1,2-dihydropyridin-3-yl)methyl)-3-(ethyl(tetrahydro-2H-pyran-4-yl)amino)-2-methyl-5-(tetrahydro-2H-pyran-4-yl)benzamide | 482.2 |

TABLE 1-continued

| Compound Number | Structure | Name | MS† |
|---|---|---|---|
| 154 | 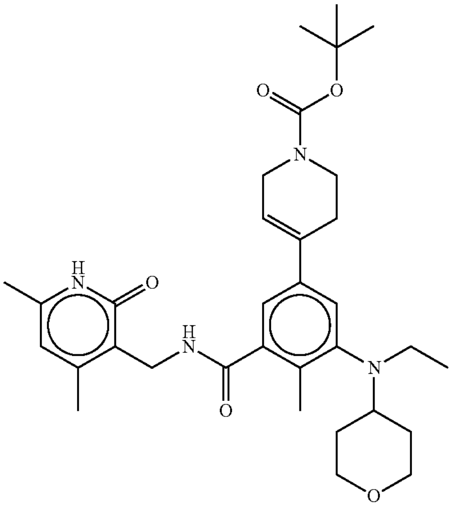 | tert-butyl 4-(3-(((4,6-dimethyl-2-oxo-1,2-dihydropyridin-3-yl)methyl)carbamoyl)-5-(ethyl(tetrahydro-2H-pyran-4-yl)amino)-4-methylphenyl)-5,6-dihydropyridine-1(2H)-carboxylate | 579.3 |
| 155 | 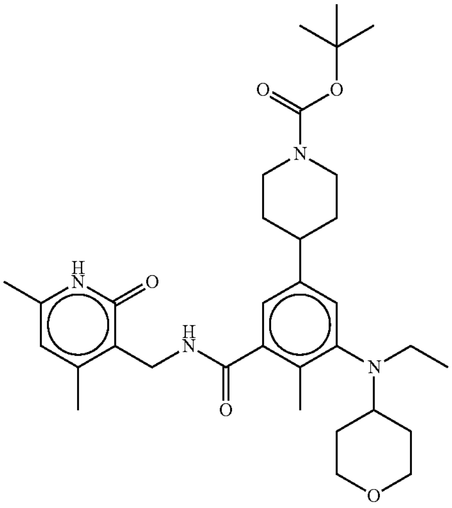 | tert-butyl 4-(3-(((4,6-dimethyl-2-oxo-1,2-dihydropyridin-3-yl)methyl)carbamoyl)-5-(ethyl(tetrahydro-2H-pyran-4-yl)amino)-4-methylphenyl)piperidine-1-carboxylate | 581.2 |
| 156 | 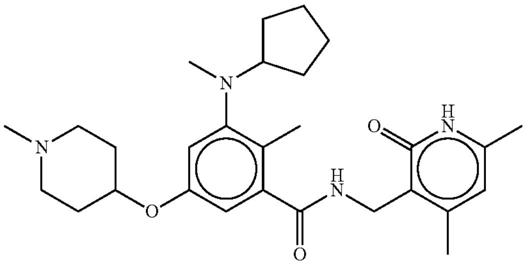 | 3-(cyclopentyl (methyl)amino)-N-((4,6-dimethyl-2-oxo-1,2-dihydropyridin-3-yl)methyl)-2-methyl-5-((1-methylpiperidin-4-yl)oxy)benzamide | 481.3 |
| 157 | 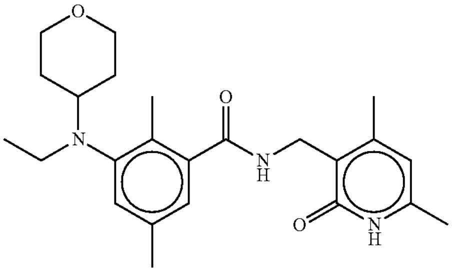 | N-((4,6-dimethyl-2-oxo-1,2-dihydropyridin-3-yl)methyl)-3-(ethyl(tetrahydro-2H-pyran-4-yl)amino)-2,5-dimethylbenzamide | 412.2 |

TABLE 1-continued

| Compound Number | Structure | Name | MS† |
| --- | --- | --- | --- |
| 158 | 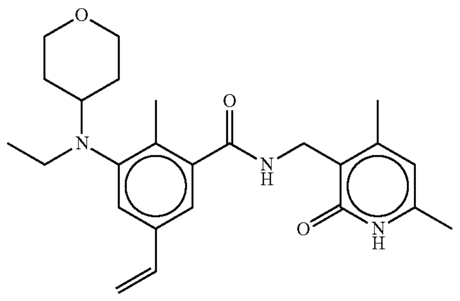 | N-((4,6-dimethyl-2-oxo-1,2-dihydropyridin-3-yl)methyl)-3-(ethyl(tetrahydro-2H-pyran-4-yl)amino)-2-methyl-5-vinylbenzamide | 424.1 |
| 159 | 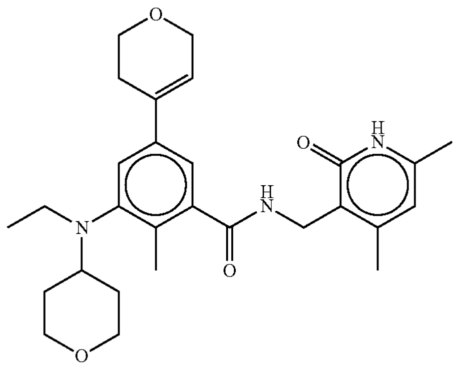 | 5-(3,6-dihydro-2H-pyran-4-yl)-N-((4,6-dimethyl-2-oxo-1,2-dihydropyridin-3-yl)methyl)-3-(ethyl(tetrahydro-2H-pyran-4-yl)amino)-2-methylbenzamide | 480.3 |
| 160 | 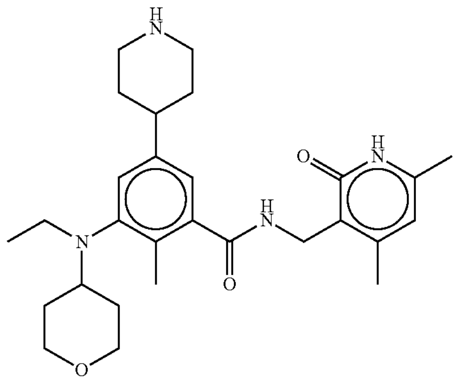 | N-((4,6-dimethyl-2-oxo-1,2-dihydropyridin-3-yl)methyl)-3-(ethyl(tetrahydro-2H-pyran-4-yl)amino)-2-methyl-5-(piperidin-4-yl)benzamide | 481.3 |
| 161 | 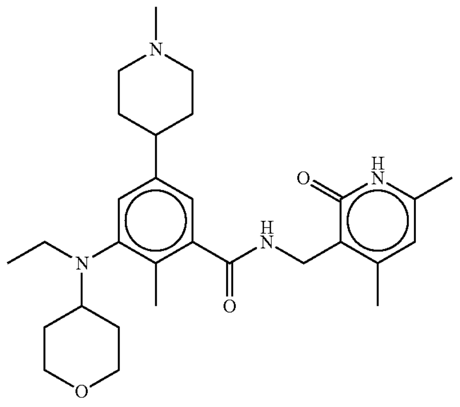 | N-((4,6-dimethyl-2-oxo-1,2-dihydropyridin-3-yl)methyl)-3-(ethyl(tetrahydro-2H-pyran-4-yl)amino)-2-methyl-5-(1-methylpiperidin-4-yl)benzamide | 495.3 |

TABLE 1-continued

| Compound Number | Structure | Name | MS† |
|---|---|---|---|
| 162 | 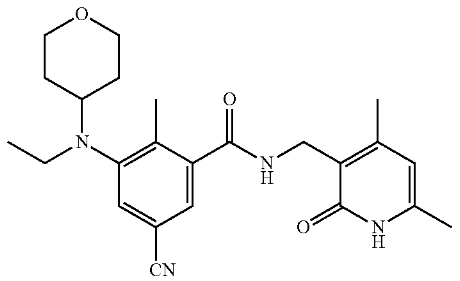 [SMILES: CCN(c1cc(C#N)cc(C(=O)NCc2c(C)cc(C)[nH]c2=O)c1C)C1CCOCC1] | 5-cyano-N-((4,6-dimethyl-2-oxo-1,2-dihydropyridin-3-yl)methyl)-3-(ethyl(tetrahydro-2H-pyran-4-yl)amino)-2-methylbenzamide | 423.2 |
| 163 | 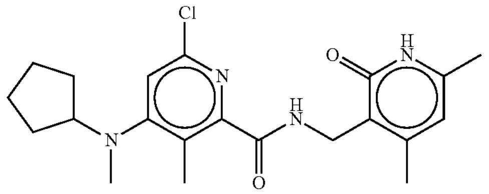 | 6-chloro-4-(cyclopentyl(methyl)amino)-N-((4,6-dimethyl-2-oxo-1,2-dihydropyridin-3-yl)methyl)-3-methylpicolinamide | 403.2 |
| 164 | 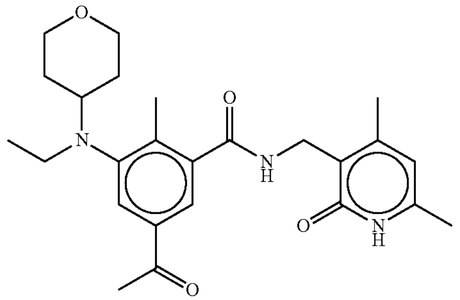 | 5-acetyl-N-((4,6-dimethyl-2-oxo-1,2-dihydropyridin-3-yl)methyl)-3-(ethyl(tetrahydro-2H-pyran-4-yl)amino)-2-methylbenzamide | 440.2 |
| 165 | 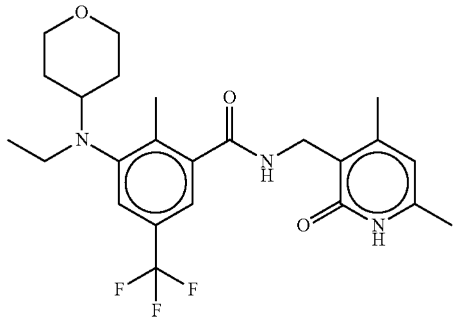 | N-((4,6-dimethyl-2-oxo-1,2-dihydropyridin-3-yl)methyl)-3-(ethyl(tetrahydro-2H-pyran-4-yl)amino)-2-methyl-5-(trifluoromethyl)benzamide | 466.2 |
| 166 | 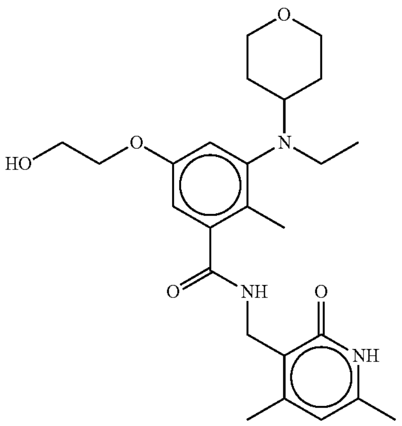 | N-((4,6-dimethyl-2-oxo-1,2-dihydropyridin-3-yl)methyl)-3-(ethyl(tetrahydro-2H-pyran-4-yl)amino)-5-(2-hydroxyethoxy)-2-methylbenzamide | 458.2 |

TABLE 1-continued

| Compound Number | Structure | Name | MS† |
|---|---|---|---|
| 167 | 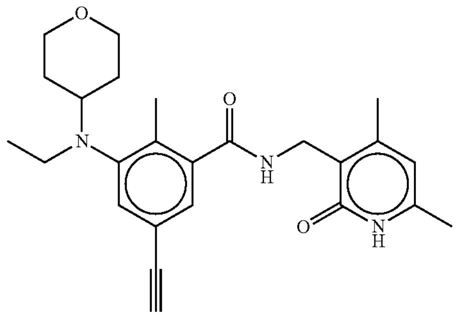 | N-((4,6-dimethyl-2-oxo-1,2-dihydropyridin-3-yl)methyl)-3-(ethyl(tetrahydro-2H-pyran-4-yl)amino)-5-ethynyl-2-methylbenzamide | 422.3 |
| 168 | 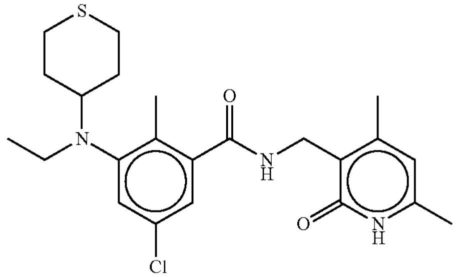 | 5-chloro-N-((4,6-dimethyl-2-oxo-1,2-dihydropyridin-3-yl)methyl)-3-(ethyl(tetrahydro-2H-thiopyran-4-yl)amino)-methylbenzamide | 448.1 |
| 169 | 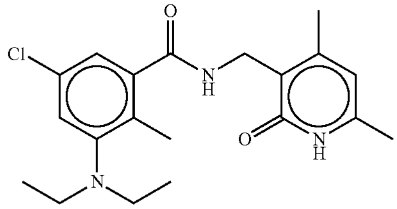 | 5-chloro-3-(diethylamino)-N-((4,6-dimethyl-2-oxo-1,2-dihydropyridin-3-yl)methyl)-2-methylbenzamide | 376 |
| 170 | 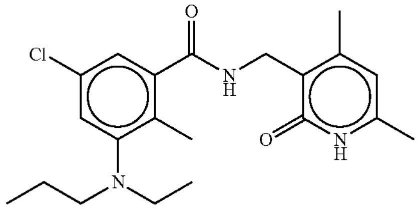 | 5-chloro-N-((4,6-dimethyl-2-oxo-1,2-dihydropyridin-3-yl)methyl)-3-(ethyl(propyl)amino)-2-methylbenzamide | 390.2 |
| 171 | 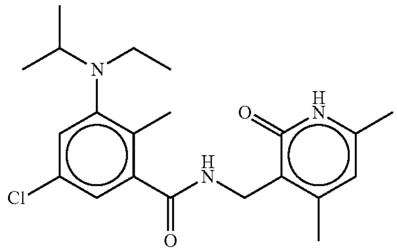 | 5-chloro-N-((4,6-dimethyl-2-oxo-1,2-dihydropyridin-3-yl)methyl)-3-(ethyl(isopropyl)amino)-2-methylbenzamide | 390.1 |
| 172 | 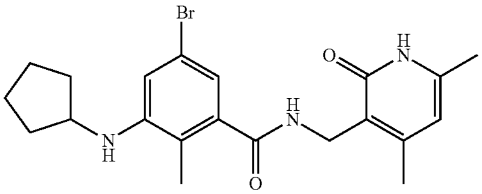 | 5-bromo-3-(cyclopentylamino)-N-((4,6-dimethyl-2-oxo-dihydropyridin-3-yl)methyl)-2-methylbenzamide | 432.1 |

TABLE 1-continued

| Compound Number | Structure | Name | MS† |
|---|---|---|---|
| 173 | 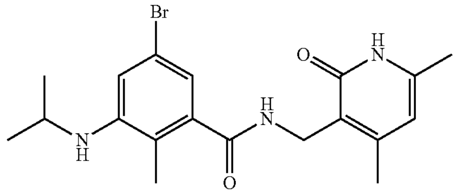 | 5-bromo-N-((4,6-dimethyl-2-oxo-1,2-dihydropyridin-3-yl)methyl)-3-(isopropylamino)-2-methylbenzamide | 406.1 |
| 174 | 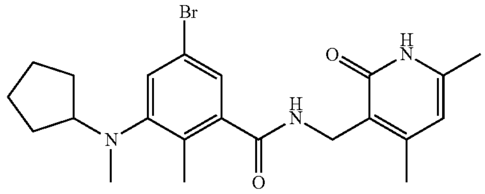 [SMILES: Cc1cc(C)c(CNC(=O)c2cc(Br)cc(N(C)C3CCCC3)c2C)c(=O)[nH]1] | 5-bromo-3-(cyclopentyl(methyl)amino)-N-((4,6-dimethyl-2-oxo-1,2-dihydropyridin-3-yl)methyl)-2-methylbenzamide | 446.2 |
| 175 | 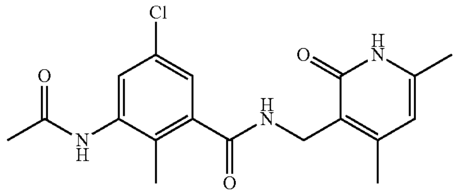 | 3-acetamido-5-chloro-N-((4,6-dimethyl-2-oxo-1,2-dihydropyridin-3-yl)methyl)-2-methylbenzamide | 362.1 |
| 176 | 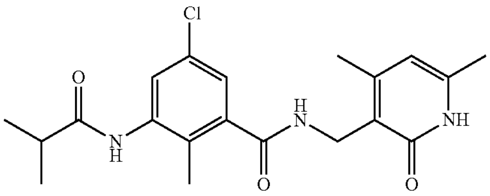 [SMILES: Cc1cc(C)c(CNC(=O)c2cc(Cl)cc(NC(=O)C(C)C)c2C)c(=O)[nH]1] | 5-chloro-N-((4,6-dimethyl-2-oxo-1,2-dihydropyridin-3-yl)methyl)-3-isobutyramido-2-methylbenzamide | 390.1 |
| 177 | 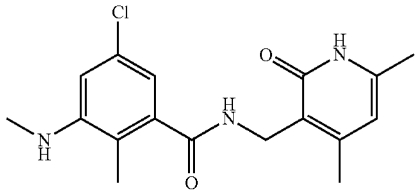 | 5-chloro-N-((4,6-dimethyl-2-oxo-1,2-dihydropyridin-3-yl)methyl)-2-methyl-3-(methylamino)benzamide | 334.2 |
| 178 | 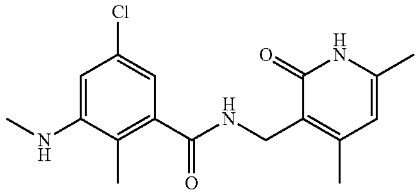 | 5-chloro-N-((4,6-dimethyl-2-oxo-1,2-dihydropyridin-3-yl)methyl)-2-methyl-3-(methylamino)benzamide | 334.2 |
| 179 | 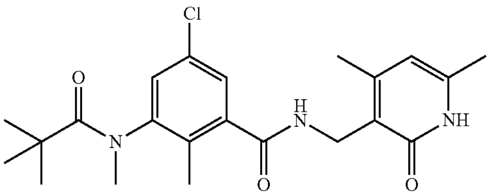 [SMILES: Cc1cc(C)c(CNC(=O)c2cc(Cl)cc(N(C)C(=O)C(C)(C)C)c2C)c(=O)[nH]1] | 5-chloro-N-((4,6-dimethyl-2-oxo-1,2-dihydropyridin-3-yl)methyl)-2-methyl-3-(N-methylpivalamido)benzamide | 418.2 |

TABLE 1-continued

| Compound Number | Structure | Name | MS† |
|---|---|---|---|
| 180 | 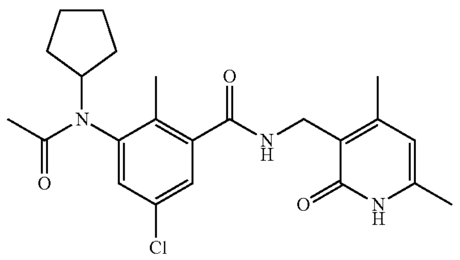 [SMILES: CC(=O)N(c1cc(Cl)cc(C(=O)NCc2c(C)cc(C)[nH]c2=O)c1C)C1CCCC1] | 5-chloro-3-(N-cyclopentylacetamido)-N-((4,6-dimethyl-2-oxo-1,2-dihydropyridin-3-yl)methyl)-2-methylbenzamide | 430.3 |
| 181 | 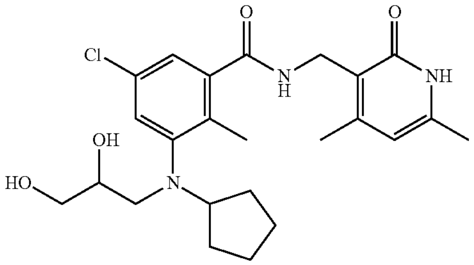 [SMILES: Cc1cc(C)c(CNC(=O)c2cc(Cl)cc(N(CC(O)CO)C3CCCC3)c2C)c(=O)[nH]1] | 5-chloro-3-(cyclopentyl(2,3-dihydroxypropyl)amino)-N-((4,6-dimethyl-2-oxo-1,2-dihydropyridin-3-yl)methyl)-2-methylbenzamide | 462.2 |
| 182 | 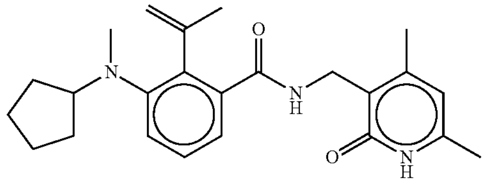 | 3-(cyclopentyl(methyl)amino)-N-((4,6-dimethyl-2-oxo-1,2-dihydropyridin-3-yl)methyl)-2-(prop-1-en-2-yl)benzamide | 394.3 |
| 183 | 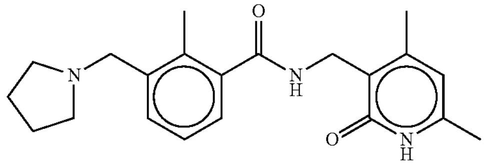 | N-((4,6-dimethyl-2-oxo-1,2-dihydropyridin-3-yl)methyl)-2-methyl-3-(pyrrolidin-1-ylmethyl)benzamide | 354.3 |
| 184 | 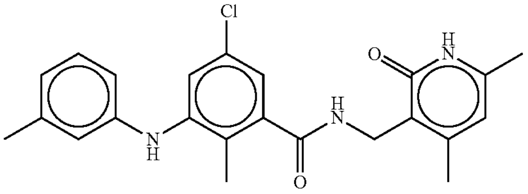 | 5-chloro-N-((4,6-dimethyl-2-oxo-1,2-dihydropyridin-3-yl)methyl)-2-methyl-3-(m-tolylamino)benzamide | 410.3 |
| 185 | | [[Duplicate with #184]] | |
| 186 | 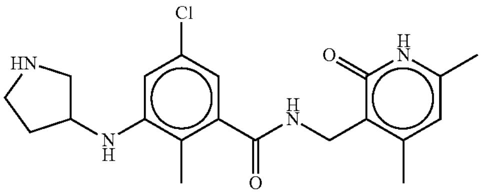 | 5-chloro-N-((4,6-dimethyl-2-oxo-1,2-dihydropyridin-3-yl)methyl)-2-methyl-3-(pyrrolidin-3-ylamino)benzamide | 389.2 |
| 187 | 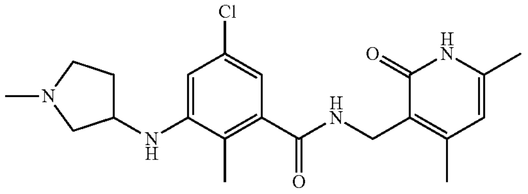 | 5-chloro-N-((4,6-dimethyl-2-oxo-1,2-dihydropyridin-3-yl)methyl)-2-methyl-3-((1-methylpyrrolidin-3-yl)amino)benzamide | 403.1 |

TABLE 1-continued

| Compound Number | Structure | Name | MS† |
| --- | --- | --- | --- |
| 188 | 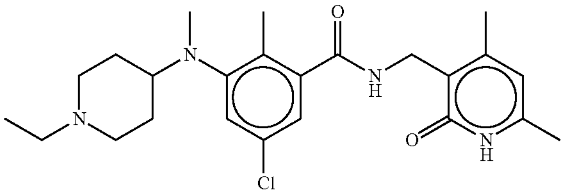 | 5-chloro-N-((4,6-dimethyl-2-oxo-1,2-dihydropyridin-3-yl)methyl)-3-((1-ethylpiperidin-4-yl)(methyl)amino)-2-methylbenzamide | 445.4 |
| 189 | 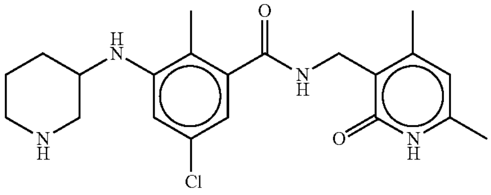 | 5-chloro-N-((4,6-dimethyl-2-oxo-1,2-dihydropyridin-3-yl)methyl)-2-methyl-3-(piperidin-3-ylamino)benzamide | 403.3 |
| 190 | 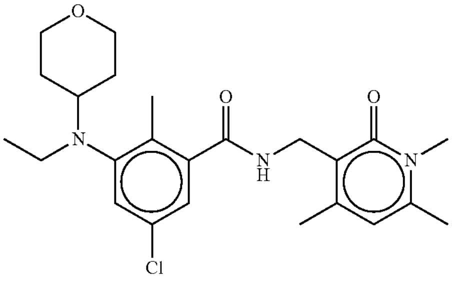 | 5-chloro-3-(ethyl(tetrahydro-2H-pyran-4-yl)amino)-2-methyl-N-((1,4,6-trimethyl-2-oxo-1,2-dihydropyridin-3-yl)methyl)benzamide | 446.3 |
| 191 | 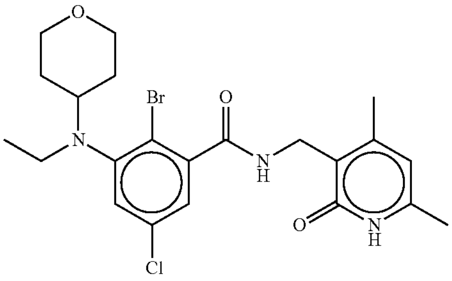 | 2-bromo-5-chloro-N-((4,6-dimethyl-2-oxo-1,2-dihydropyridin-3-yl)methyl)-3-(ethyl(tetrahydro-2H-pyran-4-yl)amino)benzamide | 498 |
| 192 | 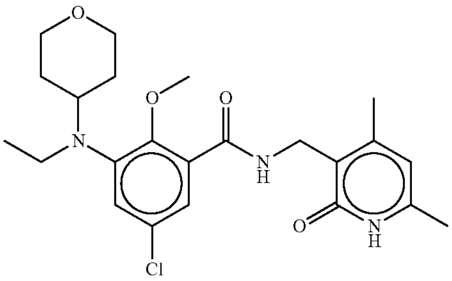 | 5-chloro-N-((4,6-dimethyl-2-oxo-1,2-dihydropyridin-3-yl)methyl)-3-(ethyl(tetrahydro-2H-pyran-4-yl)amino)-2-methoxybenzamide | 449.5 |
| 193 | 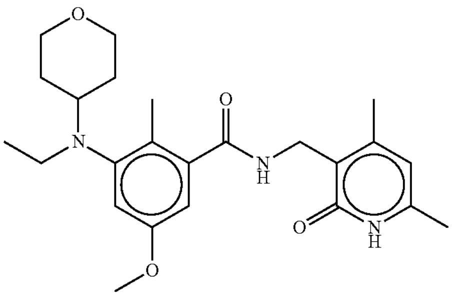 | N-((4,6-dimethyl-2-oxo-1,2-dihydropyridin-3-yl)methyl)-3-(ethyl(tetrahydro-2H-pyran-4-yl)amino)-5-methoxy-2-methylbenzamide | 428.2 |

TABLE 1-continued

| Compound Number | Structure | Name | MS† |
|---|---|---|---|
| 194 | 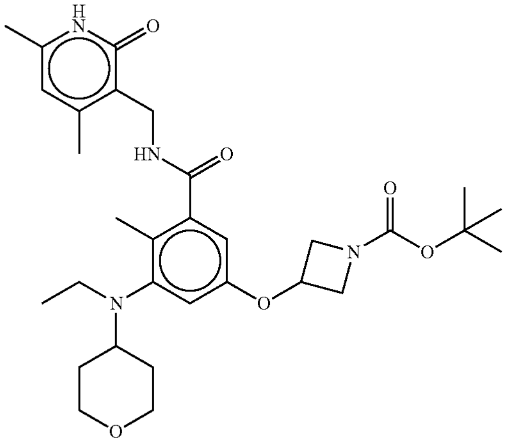 | tert-butyl 3-(3-(((4,6-dimethyl-2-oxo-1,2-dihydropyridin-3-yl)methyl)carbamoyl)-5-(ethyl(tetrahydro-2H-pyran-4-yl)amino)-4-methylphenoxy) azetidine-1-carboxylate | 569.3 |
| 195 | 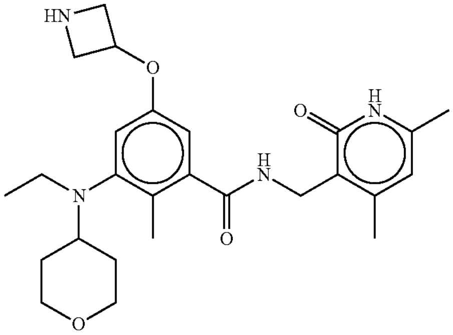 | 5-(azetidin-3-yloxy)-N-((4,6-dimethyl-2-oxo-1,2-dihydropyridin-3-yl)methyl)-3-(ethyl(tetrahydro-2H-pyran-4-yl)amino)-2-methylbenzamide | 469.3 |
| 196 | 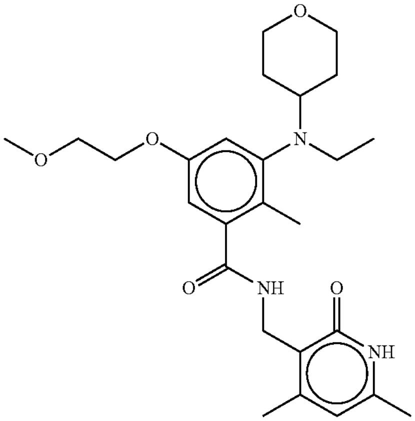 | N-((4,6-dimethyl-2-oxo-1,2-dihydropyridin-3-yl)methyl)-3-(ethyl(tetrahydro-2H-pyran-4-yl)amino)-5-(2-methoxyethoxy)-2-methylbenzamide | 472.2 |
| 197 | 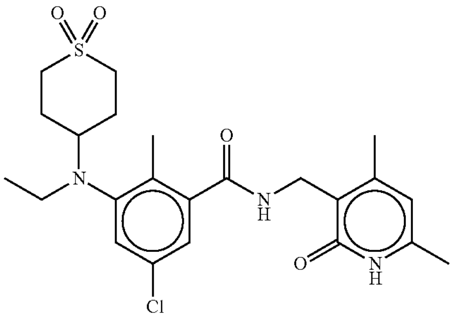 | 5-chloro-N-((4,6-dimethyl-2-oxo-1,2-dihydropyridin-3-yl)methyl)-3-((1,1-dioxidotetrahydro-2H-thiopyran-4-yl)(ethyl)amino)-2-methylbenzamide | 480.1 |

TABLE 1-continued

| Compound Number | Structure | Name | MS† |
|---|---|---|---|
| 198 | 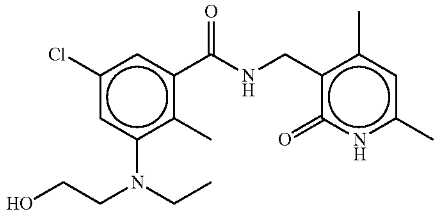 | 5-chloro-N-((4,6-dimethyl-2-oxo-1,2-dihydropyridin-3-yl)methyl)-3-(ethyl(2-hydroxyethyl)amino)-2-methylbenzamide | 392.1 |
| 199 | 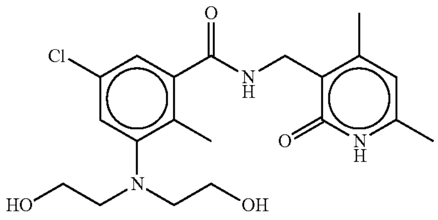 | 3-(bis(2-hydroxyethyl)amino)-5-chloro-N-((4,6-dimethyl-2-oxo-1,2-dihydropyridin-3-yl)methyl)-2-methylbenzamide | 408.1 |
| 200 | 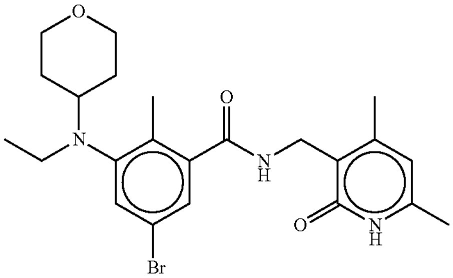 | 5-bromo-N-((4,6-dimethyl-2-oxo-1,2-dihydropyridin-3-yl)methyl)-3-(ethyl(tetrahydro-2H-pyran-4-yl)amino)-2-methylbenzamide | 476.1 |
| 201 | 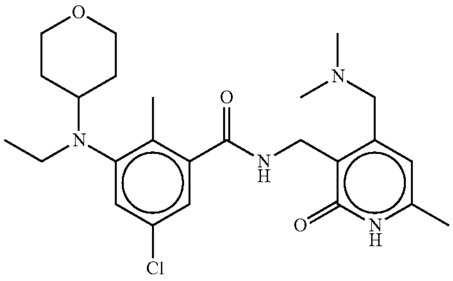 | 5-chloro-N-((4-((dimethylamino) methyl)-6-methyl-2-oxo-1,2-dihydropyridin-3-yl)methyl)-3-(ethyl(tetrahydro-2H-pyran-4-yl)amino)-2-methylbenzamide | 475.2 |
| 202 | 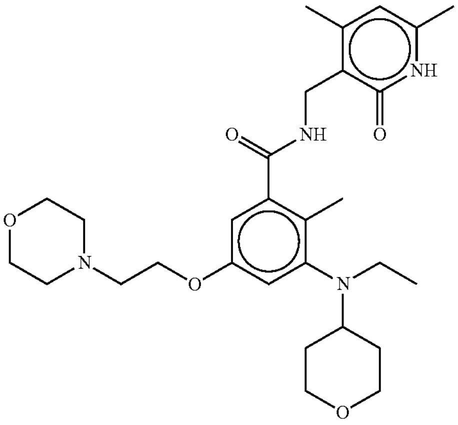 | N-((4,6-dimethyl-2-oxo-1,2-dihydropyridin-3-yl)methyl)-3-(ethyl(tetrahydro-2H-pyran-4-yl)amino)-2-methyl-5-(2-morpholinoethoxy) benzamide | 527.4 |

TABLE 1-continued

| Compound Number | Structure | Name | MS† |
|---|---|---|---|
| 203 | 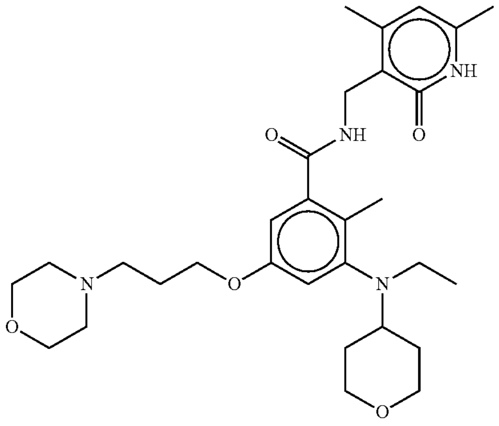 | N-((4,6-dimethyl-2-oxo-1,2-dihydropyridin-3-yl)methyl)-3-(ethyl(tetrahydro-2H-pyran-4-yl)amino)-2-methyl-5-(3-morpholinopropoxy) benzamide | 541.4 |
| 204 | 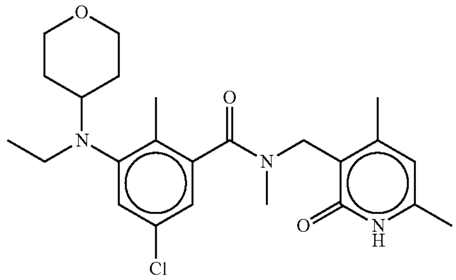 | 5-chloro-N-((4,6-dimethyl-2-oxo-1,2-dihydropyridin-3-yl)methyl)-3-(ethyl(tetrahydro-2H-pyran-4-yl)amino)-N,2-dimethylbenzamide | 446.1 |
| 205 | 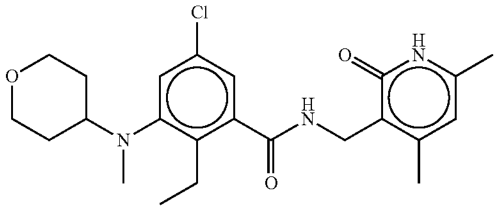 | 5-chloro-N-((4,6-dimethyl-2-oxo-1,2-dihydropyridin-3-yl)methyl)-2-ethyl-3-(methyl(tetrahydro-2H-pyran-4-yl)amino)benzamide | 432.1 |
| 206 | 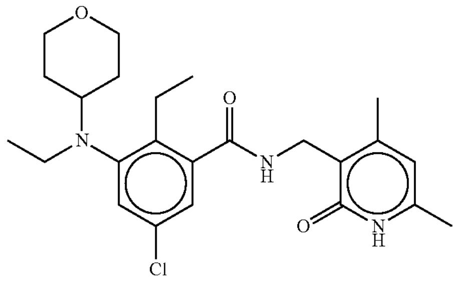 | 5-chloro-N-((4,6-dimethyl-2-oxo-1,2-dihydropyridin-3-yl)methyl)-2-ethyl-3-(ethyl(tetrahydro-2H-pyran-4-yl)amino)benzamide | 446.1 |
| 207 | 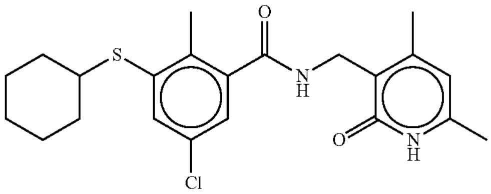 | 5-chloro-3-(cyclohexylthio)-N-((4,6-dimethyl-2-oxo-1,2-dihydropyridin-3-yl)methyl)-2-methylbenzamide | 419.2 |

TABLE 1-continued

| Compound Number | Structure | Name | MS† |
|---|---|---|---|
| 208 | 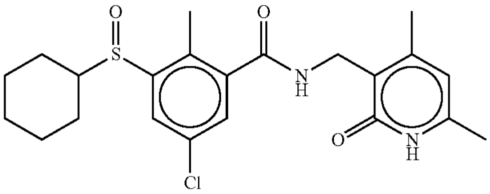 | 5-chloro-3-(cyclohexylsulfinyl)-N-((4,6-dimethyl-2-oxo-1,2-dihydropyridin-3-yl)methyl)-2-methylbenzamide | 435.1 |
| 209 | 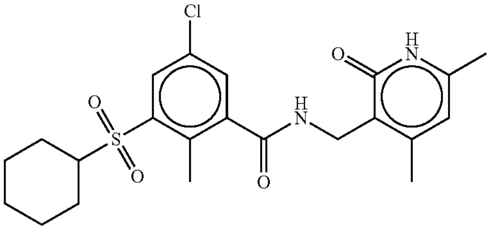 | 5-chloro-3-(cyclohexylsulfonyl)-N-((4,6-dimethyl-2-oxo-1,2-dihydropyridin-3-yl)methyl)-2-methylbenzamide | 451.1 |
| 210 | 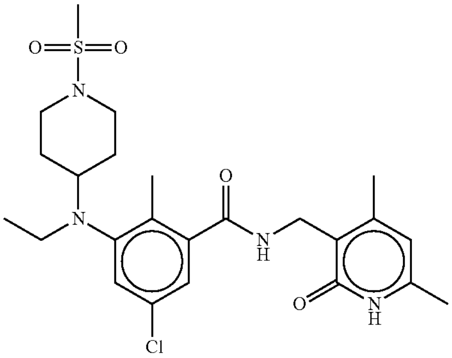 | 5-chloro-N-((4,6-dimethyl-2-oxo-1,2-dihydropyridin-3-yl)methyl)-3-(ethyl(1-(methylsulfonyl) piperidin-4-yl)amino)-2-methylbenzamide | 509.2 |
| 211 | 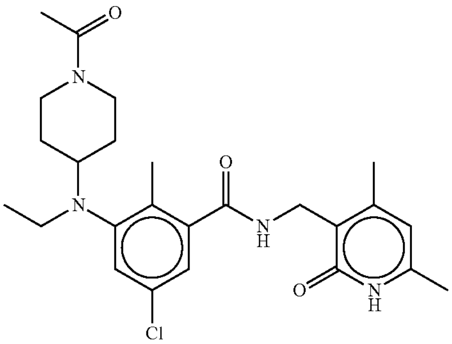 | 3-((1-acetylpiperidin-4-yl)(ethyl)amino)-5-chloro-N-((4,6-dimethyl-2-oxo-1,2-dihydropyridin-3-yl)methyl)-2-methylbenzamide | 495.1 |
| 212 | 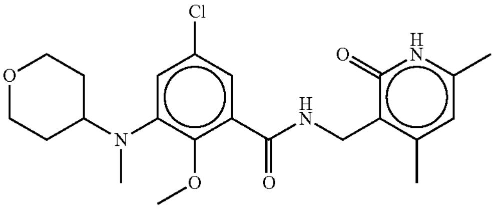 | 5-chloro-N-((4,6-dimethyl-2-oxo-1,2-dihydropyridin-3-yl)methyl)-2-methoxy-3-(methyl (tetrahydro-2H-pyran-4-yl)amino)benzamide | 434.1 |

TABLE 1-continued

| Compound Number | Structure | Name | MS† |
|---|---|---|---|
| 213 | 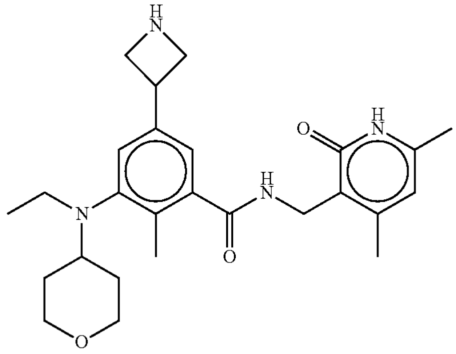 | 5-(azetidin-3-yl)-N-((4,6-dimethyl-2-oxo-1,2-dihydropyridin-3-yl)methyl)-3-(ethyl(tetrahydro-2H-pyran-4-yl)amino)-2-methylbenzamide | 453.2 |
| 214 | 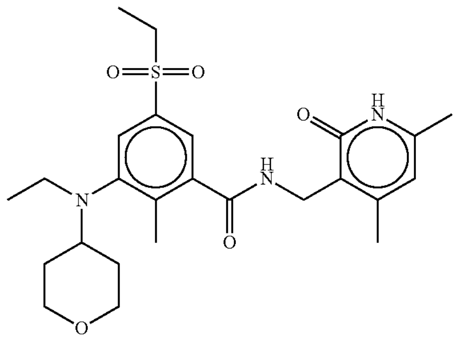 | N-((4,6-dimethyl-2-oxo-1,2-dihydropyridin-3-yl)methyl)-3-(ethyl(tetrahydro-2H-pyran-4-yl)amino)-5-(ethylsulfonyl)-2-methylbenzamide | 490.3 |
| 215 | 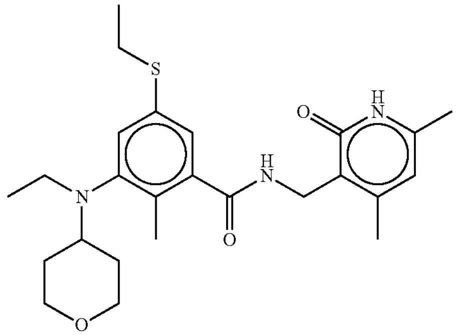 | N-((4,6-dimethyl-2-oxo-1,2-dihydropyridin-3-yl)methyl)-3-(ethyl(tetrahydro-2H-pyran-4-yl)amino)-5-(ethylthio)-2-methylbenzamide | 458.2 |
| 216 | 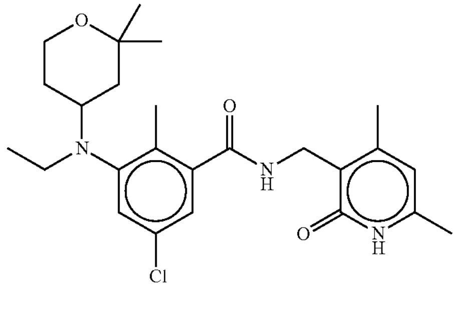 | 5-chloro-N-((4,6-dimethyl-2-oxo-1,2-dihydropyridin-3-yl)methyl)-3-((2,2-dimethyltetrahydro-2H-pyran-4-yl)(ethyl)amino)-2-methylbenzamide | 460.3 |

TABLE 1-continued

| Compound Number | Structure | Name | MS† |
|---|---|---|---|
| 217 | 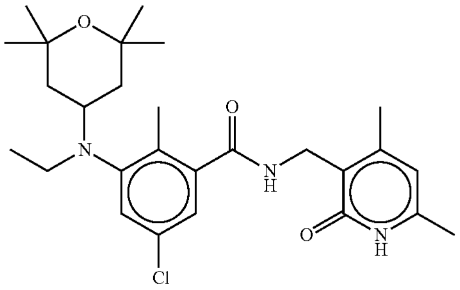 | 5-chloro-N-((4,6-dimethyl-2-oxo-1,2-dihydropyridin-3-yl)methyl)-3-(ethyl(2,2,6,6-tetramethyltetrahydro-2H-pyran-4-yl)amino)-2-methylbenzamide | 488.5 |
| 218 | 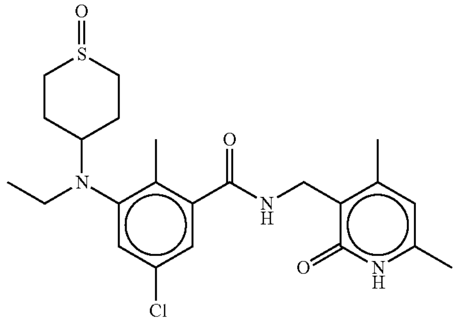 | 5-chloro-N-((4,6-dimethyl-2-oxo-1,2-dihydropyridin-3-yl)methyl)-3-(ethyl(1-oxidotetrahydro-2H-thiopyran-4-yl)amino)-2-methylbenzamide | 464.1 |
| 219 | 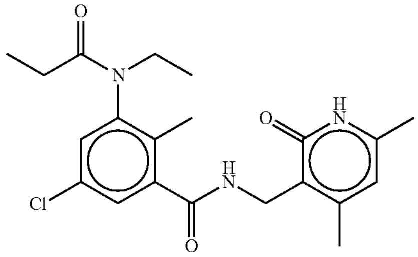 | 5-chloro-N-((4,6-dimethyl-2-oxo-1,2-dihydropyridin-3-yl)methyl)-3-(N-ethylpropionamido)-2-methylbenzamide | 404.2 |
| 220 | 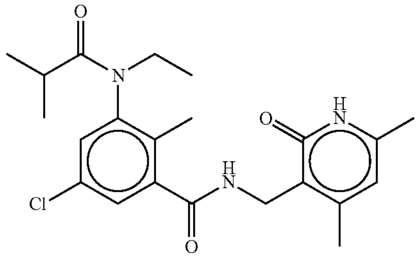 | 5-chloro-N-((4,6-dimethyl-2-oxo-1,2-dihydropyridin-3-yl)methyl)-3-(N-ethylisobutyramido)-2-methylbenzamide | 418.2 |
| 221 | 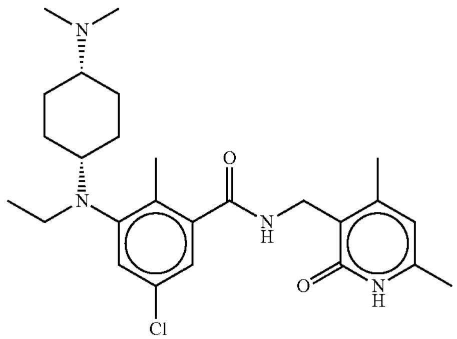 | 5-chloro-N-((4,6-dimethyl-2-oxo-1,2-dihydropyridin-3-yl)methyl)-3-(((1s,4s)-4-(dimethylamino) cyclohexyl)(ethyl) amino)-2-methylbenzamide | 473.3 |

TABLE 1-continued

| Compound Number | Structure | Name | MS† |
|---|---|---|---|
| 222 | 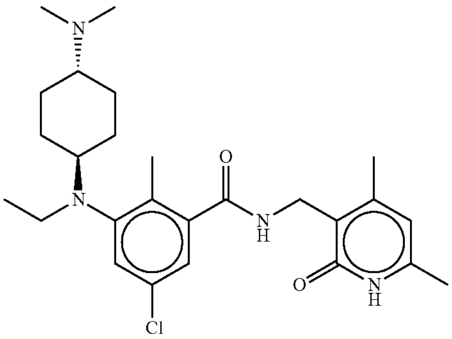 | 5-chloro-N-((4,6-dimethyl-2-oxo-1,2-dihydropyridin-3-yl)methyl)-3-(((1r,4r)-4-(dimethylamino) cyclohexyl)(ethyl) amino)-2-methylbenzamide | 473.4 |
| 223 | 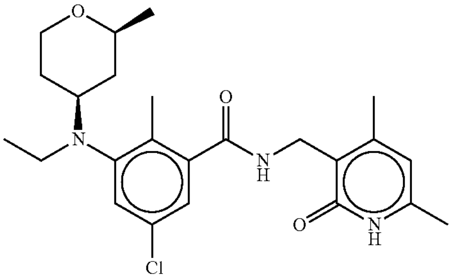 | 5-chloro-N-((4,6-dimethyl-2-oxo-1,2-dihydropyridin-3-yl)methyl)-3-(ethyl((2S,4S)-2-methyltetrahydro-2H-pyran-4-yl)amino)-2-methylbenzamide | 446.2 |
| 224 | 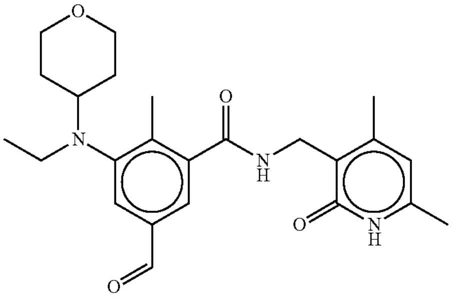 | N-((4,6-dimethyl-2-oxo-1,2-dihydropyridin-3-yl)methyl)-3-(ethyl(tetrahydro-2H-pyran-4-yl)amino)-5-formyl-2-methylbenzamide | 426.2 |
| 225 | 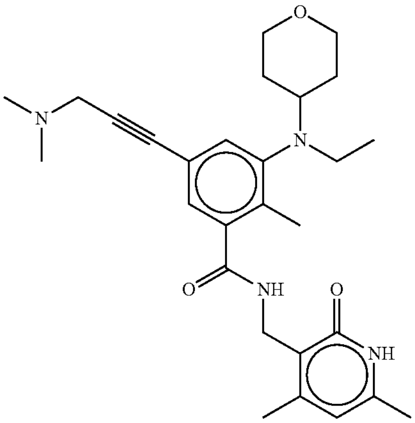 | N-((4,6-dimethyl-2-oxo-1,2-dihydropyridin-3-yl)methyl)-5-(3-(dimethylamino)prop-1-yn-1-yl)-3-(ethyl(tetrahydro-2H-pyran-4-yl)amino)-2-methylbenzamide | 479.2 |

TABLE 1-continued

| Compound Number | Structure | Name | MS† |
|---|---|---|---|
| 226 | 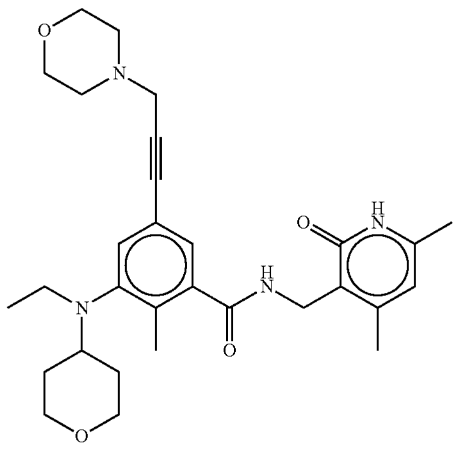 | N-((4,6-dimethyl-2-oxo-1,2-dihydropyridin-3-yl)methyl)-3-(ethyl(tetrahydro-2H-pyran-4-yl)amino)-2-methyl-5-(3-morpholinoprop-1-yn-1-yl)benzamide | 521.3 |
| 227 | 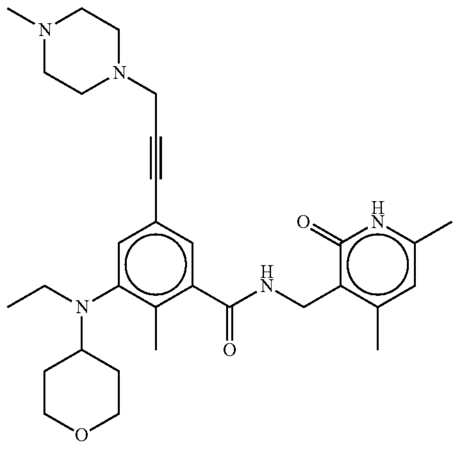 | N-((4,6-dimethyl-2-oxo-1,2-dihydropyridin-3-yl)methyl)-3-(ethyl(tetrahydro-2H-pyran-4-yl)amino)-2-methyl-5-(3-(4-methylpiperazin-1-yl)prop-1-yn-1-yl)benzamide | 534.4 |
| 228 | 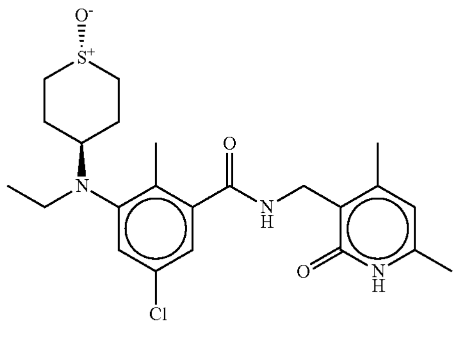 | 5-chloro-N-((4,6-dimethyl-2-oxo-1,2-dihydropyridin-3-yl)methyl)-3-(ethyl((1r,4r)-1-oxidotetrahydro-2H-thiopyran-4-yl)amino)-2-methylbenzamide | 464.1 |
| 229 | 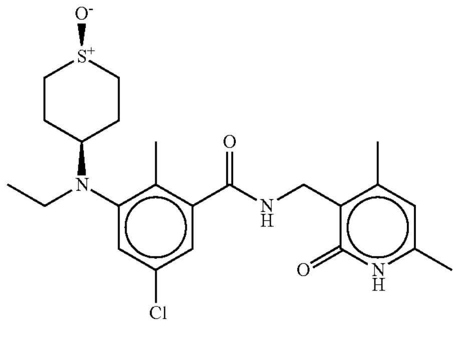 | 5-chloro-N-((4,6-dimethyl-2-oxo-1,2-dihydropyridin-3-yl)methyl)-3-(ethyl((1s,4s)-1-oxidotetrahydro-2H-thiopyran-4-yl)amino)-2-methylbenzamide | 464.2 |

TABLE 1-continued

| Compound Number | Structure | Name | MS† |
|---|---|---|---|
| 230 | 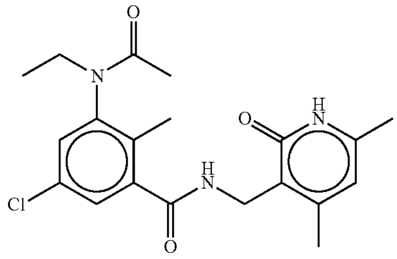 | 5-chloro-N-((4,6-dimethyl-2-oxo-1,2-dihydropyridin-3-yl)methyl)-3-(N-ethylacetamido)-2-methylbenzamide | 390.2 |
| 231 | 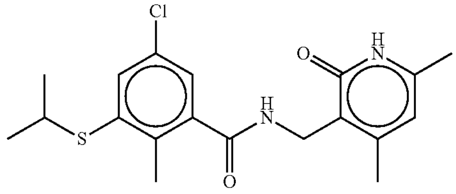 | 5-chloro-N-((4,6-dimethyl-2-oxo-1,2-dihydropyridin-3-yl)methyl)-3-(isopropylthio)-2-methylbenzamide | 379.1 |
| 232 | 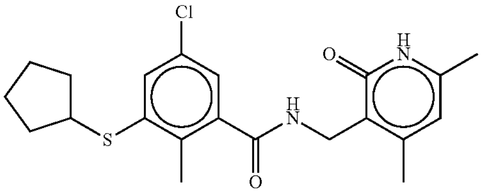 | 5-chloro-3-(cyclopentylthio)-N-((4,6-dimethyl-2-oxo-1,2-dihydropyridin-3-yl)methyl)-2-methylbenzamide | 405.1 |
| 233 | 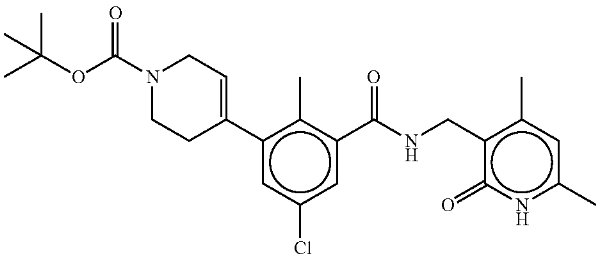 | tert-butyl 4-(5-chloro-3-(((4,6-dimethyl-2-oxo-1,2-dihydropyridin-3-yl)methyl)carbamoyl)-2-methylphenyl)-5,6-dihydropyridine-1(2H)-carboxylate | 486.2 |
| 234 | 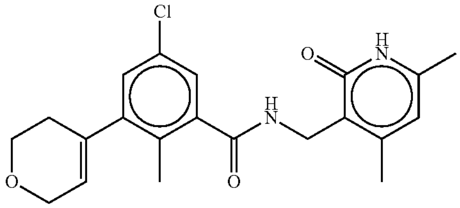 | 5-chloro-3-(3,6-dihydro-2H-pyran-4-yl)-N-((4,6-dimethyl-2-oxo-1,2-dihydropyridin-3-yl)methyl)-2-methylbenzamide | 387.1 |
| 235 | 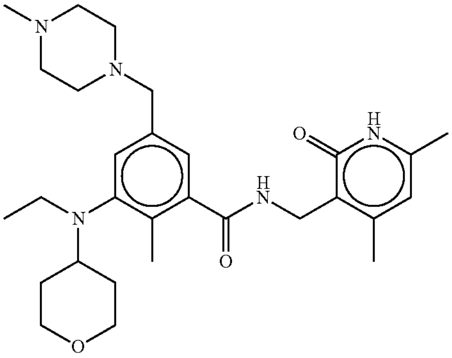 | N-((4,6-dimethyl-2-oxo-1,2-dihydropyridin-3-yl)methyl)-3-(ethyl(tetrahydro-2H-pyran-4-yl)amino)-2-methyl-5-((4-methylpiperazin-1-yl)methyl)benzamide | 510.4 |

TABLE 1-continued

| Compound Number | Structure | Name | MS† |
| --- | --- | --- | --- |
| 236 | 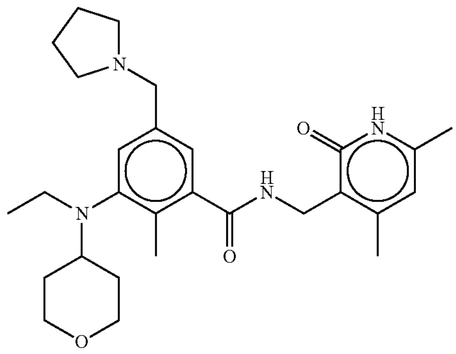 | N-((4,6-dimethyl-2-oxo-1,2-dihydropyridin-3-yl)methyl)-3-(ethyl(tetrahydro-2H-pyran-4-yl)amino)-2-methyl-5-(pyrrolidin-1-ylmethyl)benzamide | 481.3 |
| 237 | 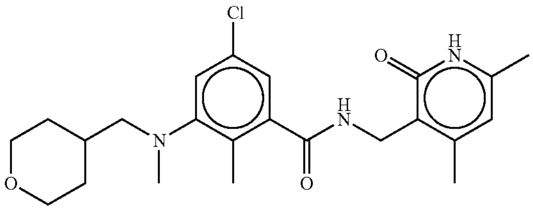 | N-(5-chloro-3-(((4,6-dimethyl-2-oxo-1,2-dihydropyridin-3-yl)methyl)carbamoyl)-2-methylphenyl)-N-methyltetrahydro-2H-pyran-4-carboxamide | 446.1 |
| 238 | 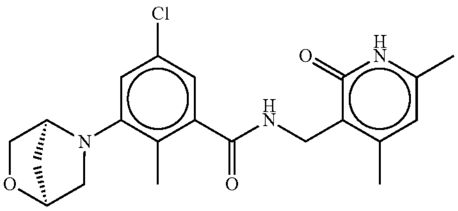 | 3-((1S,4S)-2-oxa-5-azabicyclo[2.2.1]heptan-5-yl)-5-chloro-N-((4,6-dimethyl-2-oxo-1,2-dihydropyridin-3-yl)methyl)-2-methylbenzamide | 402.1 |
| 239 | 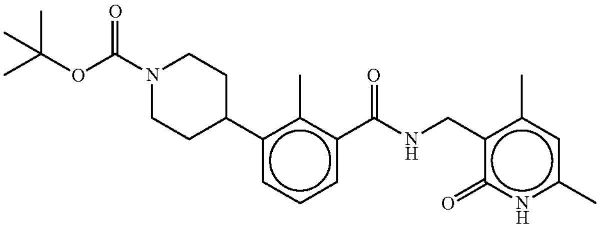 | tert-butyl 4-(3-(((4,6-dimethyl-2-oxo-1,2-dihydropyridin-3-yl)methyl)carbamoyl)-2-methylphenyl)piperidine-1-carboxylate | 454.2 |
| 240 | 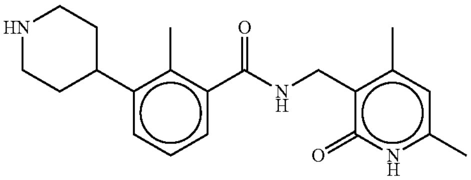 | N-((4,6-dimethyl-2-oxo-1,2-dihydropyridin-3-yl)methyl)-2-methyl-3-(piperidin-4-yl)benzamide | 354.2 |
| 241 | 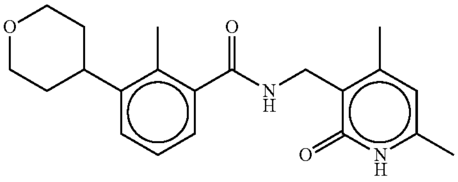 | N-((4,6-dimethyl-2-oxo-1,2-dihydropyridin-3-yl)methyl)-2-methyl-3-(tetrahydro-2H-pyran-4-yl)benzamide | 355.2 |

TABLE 1-continued

| Compound Number | Structure | Name | MS† |
|---|---|---|---|
| 242 | 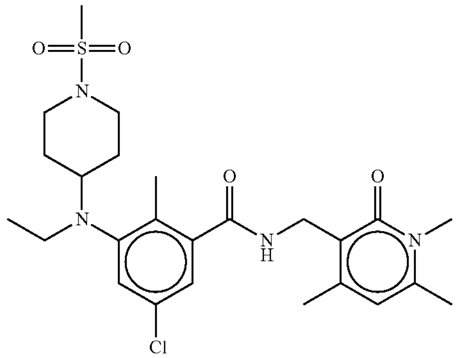 | 5-chloro-3-(ethyl(1-(methylsulfonyl) piperidin-4-yl) amino)-2-methyl-N-((1,4,6-trimethyl-2-oxo-1,2-dihydropyridin-3-yl)methyl)benzamide | 522.2 |
| 243 | 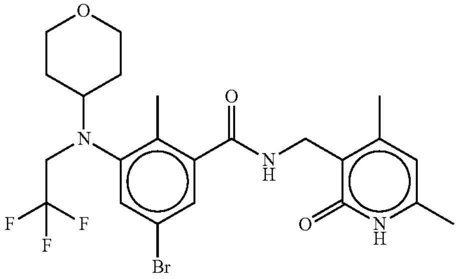 | 5-bromo-N-((4,6-dimethyl-2-oxo-1,2-dihydropyridin-3-yl)methyl)-2-methyl-3-((tetrahydro-2H-pyran-4-yl)(2,2,2-trifluoroethyl)amino) benzamide | 531 |
| 244 | 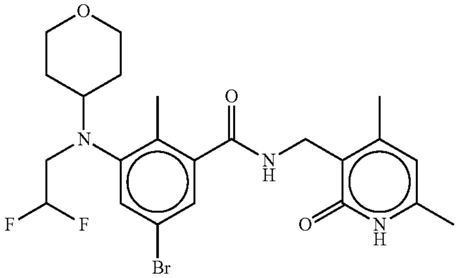 | 5-bromo-3-((2,2-difluoroethyl)(tetrahydro-2H-pyran-4-yl)amino)-N-((4,6-dimethyl-2-oxo-1,2-dihydropyridin-3-yl)methyl)-2-methylbenzamide | 513 |
| 245 | 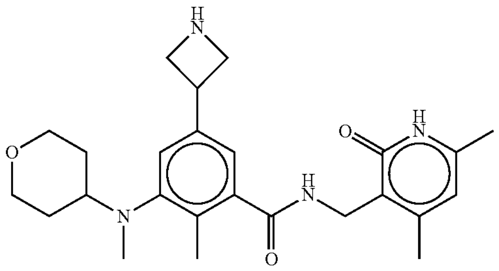 | 5-(azetidin-3-yl)-N-((4,6-dimethyl-2-oxo-1,2-dihydropyridin-3-yl)methyl)-2-methyl-3-(methyl(tetrahydro-2H-pyran-4-yl)amino)benzamide | 439.3 |
| 246 | 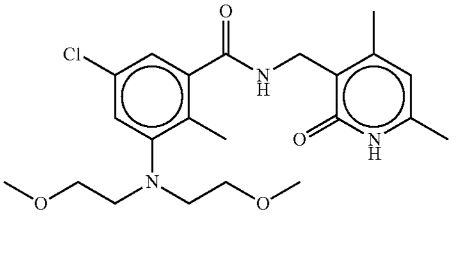 | 3-(bis(2-methoxyethyl)amino)-5-chloro-N-((4,6-dimethyl-2-oxo-1,2-dihydropyridin-3-yl)methyl)-2-methylbenzamide | 436.2 |

TABLE 1-continued

| Compound Number | Structure | Name | MS† |
|---|---|---|---|
| 247 | 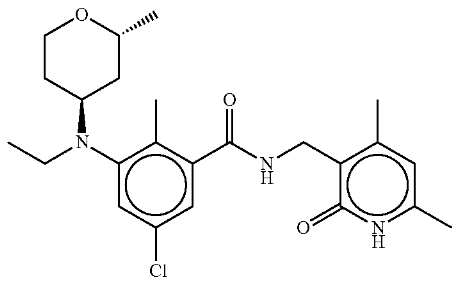 | 5-chloro-N-((4,6-dimethyl-2-oxo-1,2-dihydropyridin-3-yl)methyl)-3-(ethyl((2R,4S)-2-methyltetrahydro-2H-pyran-4-yl)amino)-2-methylbenzamide | 446.2 |
| 248 | 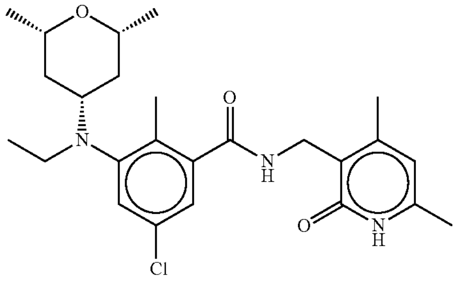 | 5-chloro-N-((4,6-dimethyl-2-oxo-1,2-dihydropyridin-3-yl)methyl)-3-(((2R,4r,6S)-2,6-dimethyltetrahydro-2H-pyran-4-yl)(ethyl)amino)-2-methylbenzamide | 460.3 |
| 249 | 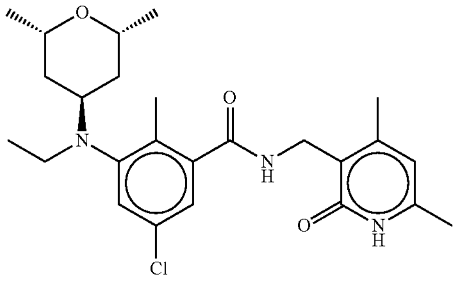 | 5-chloro-N-((4,6-dimethyl-2-oxo-1,2-dihydropyridin-3-yl)methyl)-3-(((2R,4s,6S)-2,6-dimethyltetrahydro-2H-pyran-4-yl)(ethyl)amino)-2-methylbenzamide | 460.3 |
| 250 | 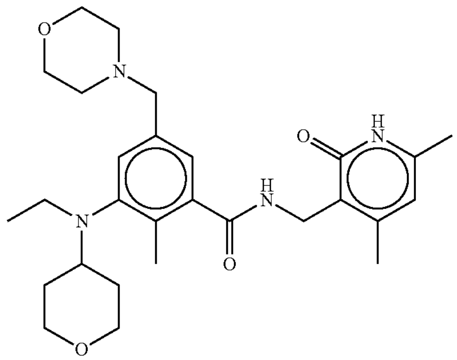 | N-((4,6-dimethyl-2-oxo-1,2-dihydropyridin-3-yl)methyl)-3-(ethyl(tetrahydro-2H-pyran-4-yl)amino)-2-methyl-5-(morpholinomethyl) benzamide | 497.3 |
| 251 | 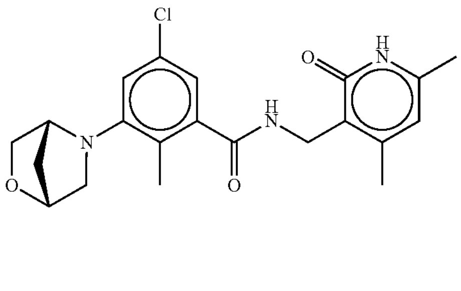 | 3-((1R,4R)-2-oxa-5-azabicyclo[2.2.1]heptan-5-yl)-5-chloro-N-((4,6-dimethyl-2-oxo-1,2-dihydropyridin-3-yl)methyl)-2-methylbenzamide | 402.2 |

TABLE 1-continued

| Compound Number | Structure | Name | MS† |
|---|---|---|---|
| 252 | 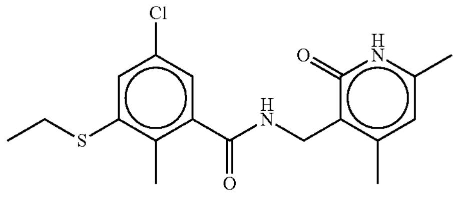 | 5-chloro-N-((4,6-dimethyl-2-oxo-1,2-dihydropyridin-3-yl)methyl)-3-(ethylthio)-2-methylbenzamide | 365.2 |
| 253 | 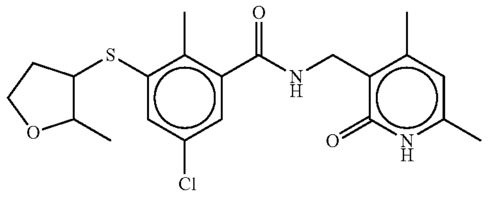 | 5-chloro-N-((4,6-dimethyl-2-oxo-1,2-dihydropyridin-3-yl)methyl)-2-methyl-3-((2-methyltetra-hydrofuran-3-yl)thio)benzamide | 421.1 |
| 254 | 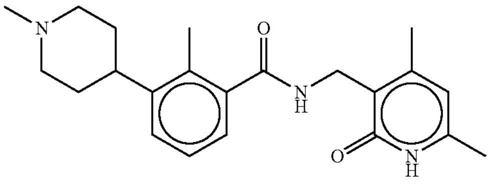 | N-((4,6-dimethyl-2-oxo-1,2-dihydropyridin-3-yl)methyl)-2-methyl-3-(1-methylpiperidin-4-yl)benzamide | 368.3 |
| 255 | 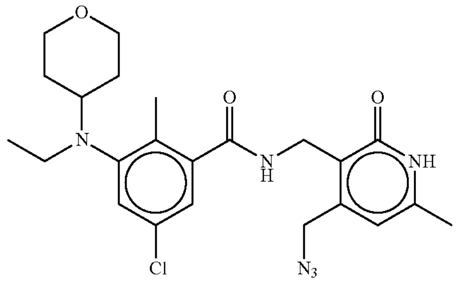 | N-((4-(azidomethyl)-6-methyl-2-oxo-1,2-dihydropyridin-3-yl)methyl)-5-chloro-3-(ethyl(tetrahydro-2H-pyran-4-yl)amino)-2-methylbenzamide | 473.2 |
| 256 | 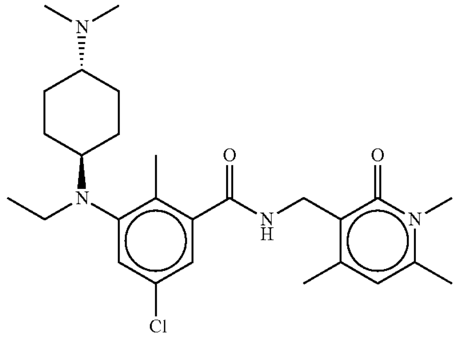 | 5-chloro-3-(((1r,4r)-4-(dimethylamino) cyclohexyl)(ethyl) amino)-2-methyl-N-((1,4,6-trimethyl-2-oxo-1,2-dihydropyridin-3-yl)methyl)benzamide | 487.4 |
| 257 | 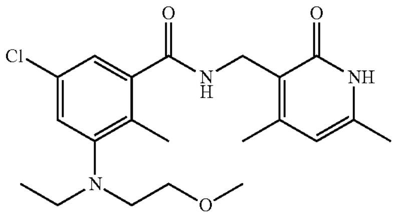 [SMILES: CCN(CCOC)c1cc(Cl)cc(C(=O)NCc2c(C)cc(C)[nH]c2=O)c1C] | 5-chloro-N-((4,6-dimethyl-2-oxo-1,2-dihydropyridin-3-yl)methyl)-3-(ethyl(2-methoxyethyl)amino)-2-methylbenzamide | 406.2 |

TABLE 1-continued

| Compound Number | Structure | Name | MS† |
|---|---|---|---|
| 258 | 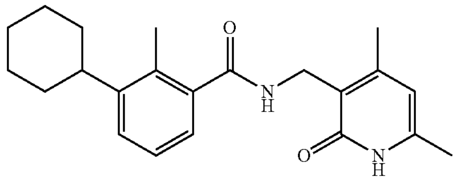 [SMILES: Cc1cc(C)c(CNC(=O)c2cccc(C3CCCCC3)c2C)c(=O)[nH]1] | 3-cyclohexyl-N-((4,6-dimethyl-2-oxo-1,2-dihydropyridin-3-yl)methyl)-2-methylbenzamide | 353.2 |
| 259 | 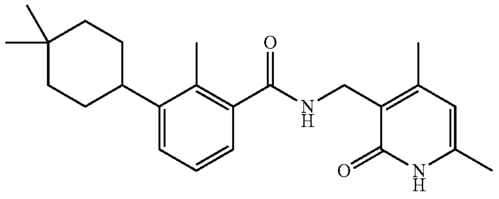 | N-((4,6-dimethyl-2-oxo-1,2-dihydropyridin-3-yl)methyl)-3-(4,4-dimethylcyclohexyl)-2-methylbenzamide | 381.3 |
| 260 | 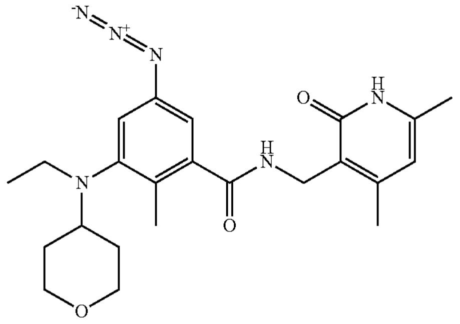 | 5-azido-N-((4,6-dimethyl-2-oxo-1,2-dihydropyridin-3-yl)methyl)-3-(ethyl(tetrahydro-2H-pyran-4-yl)amino)-2-methylbenzamide | 439.3 |
| 261 | 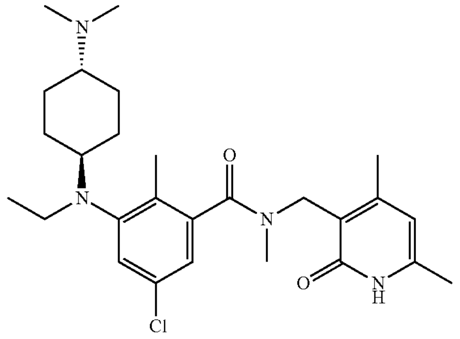 [SMILES: CCN(c1cc(Cl)cc(C(=O)N(C)Cc2c(C)cc(C)[nH]c2=O)c1C)[C@H]1CC[C@H](N(C)C)CC1] | 5-chloro-N-((4,6-dimethyl-2-oxo-1,2-dihydropyridin-3-yl)methyl)-3-(((1r,4r)-4-(dimethylamino)cyclohexyl)(ethyl)amino)-N,2-dimethylbenzamide | 487.2 |
| 262 | 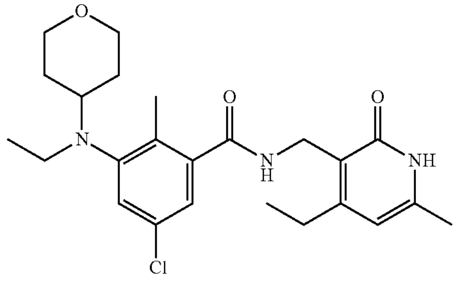 [SMILES: CCc1cc(C)[nH]c(=O)c1CNC(=O)c1cc(Cl)cc(N(CC)C2CCOCC2)c1C] | 5-chloro-3-(ethyl(tetrahydro-2H-pyran-4-yl)amino)-N-((4-ethyl-6-methyl-2-oxo-1,2-dihydropyridin-3-yl)methyl)-2-methylbenzamide | 446.1 |
| 263 | 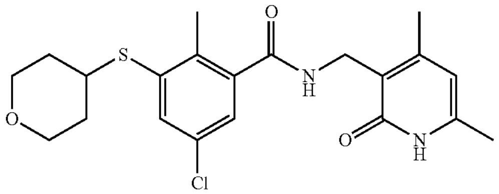 | 5-chloro-N-((4,6-dimethyl-2-oxo-1,2-dihydropyridin-3-yl)methyl)-2-methyl-3-((tetrahydro-2H-pyran-4-yl)thio)benzamide | 421 |

TABLE 1-continued

| Compound Number | Structure | Name | MS† |
|---|---|---|---|
| 264 | 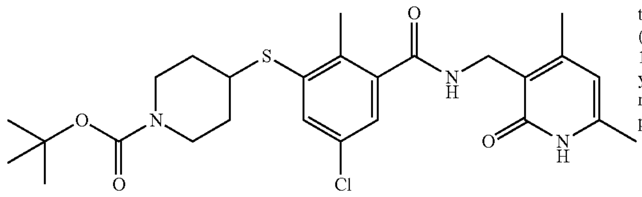 | tert-butyl 4-((5-chloro-3-(((4,6-dimethyl-2-oxo-1,2-dihydropyridin-3-yl)methyl)carbamoyl)-2-methylphenyl)thio) piperidine-1-carboxylate | 542.2 |
| 265 | 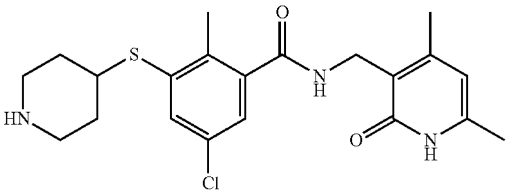 [SMILES: Cc1cc(C)c(CNC(=O)c2cc(Cl)cc(SC3CCNCC3)c2C)c(=O)[nH]1] | 5-chloro-N-((4,6-dimethyl-2-oxo-1,2-dihydropyridin-3-yl)methyl)-2-methyl-3-(piperidin-4-ylthio)benzamide | 420.1 |
| 266 | 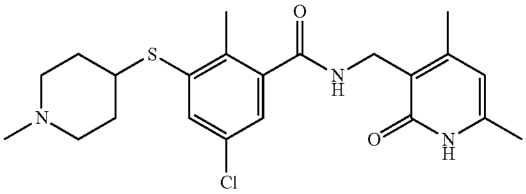 | 5-chloro-N-((4,6-dimethyl-2-oxo-1,2-dihydropyridin-3-yl)methyl)-2-methyl-3-((1-methylpiperidin-4-yl)thio)benzamide | 434.1 |
| 267 | 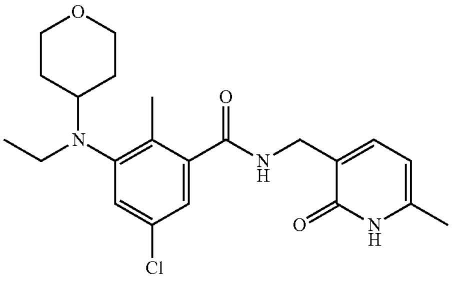 [SMILES: CCN(c1cc(Cl)cc(C(=O)NCc2ccc(C)[nH]c2=O)c1C)C1CCOCC1] | 5-chloro-3-(ethyl(tetrahydro-2H-pyran-4-yl)amino)-2-methyl-N-((6-methyl-2-oxo-1,2-dihydropyridin-3-yl)methyl)benzamide | 418.1 |
| 268 | 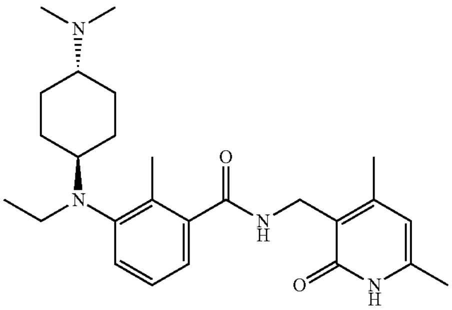 [SMILES: CCN(c1cccc(C(=O)NCc2c(C)cc(C)[nH]c2=O)c1C)[C@H]1CC[C@H](N(C)C)CC1] | N-((4,6-dimethyl-2-oxo-1,2-dihydropyridin-3-yl)methyl)-3-(((1r,4r)-4-(dimethylamino) cyclohexyl)(ethyl) amino)-2-methylbenzamide | 439.3 |
| 269 | 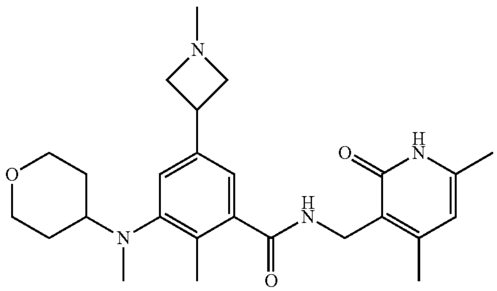 [SMILES: Cc1cc(C)c(CNC(=O)c2cc(C3CN(C)C3)cc(N(C)C3CCOCC3)c2C)c(=O)[nH]1] | N-((4,6-dimethyl-2-oxo-1,2-dihydropyridin-3-yl)methyl)-2-methyl-3-(methyl(tetrahydro-2H-pyran-4-yl)amino)-5-(1-methylazetidin-3-yl)benzamide | 453.2 |

TABLE 1-continued

| Compound Number | Structure | Name | MS† |
|---|---|---|---|
| 270 | 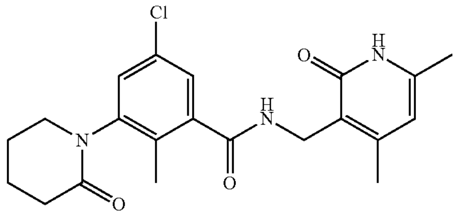 [SMILES: Cc1cc(C)c(CNC(=O)c2cc(Cl)cc(N3CCCCC3=O)c2C)c(=O)[nH]1] | 5-chloro-N-((4,6-dimethyl-2-oxo-1,2-dihydropyridin-3-yl)methyl)-2-methyl-3-(2-oxopiperidin-1-yl)benzamide | 402.1 |
| 271 | 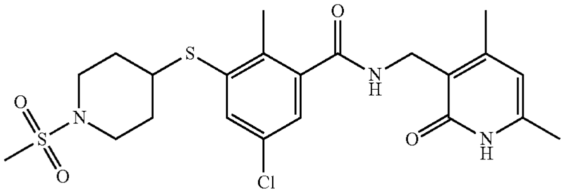 | 5-chloro-N-((4,6-dimethyl-2-oxo-1,2-dihydropyridin-3-yl)methyl)-2-methyl-3-((1-(methylsulfonyl) piperidin-4-yl)thio) benzamide | 498 |
| 272 | 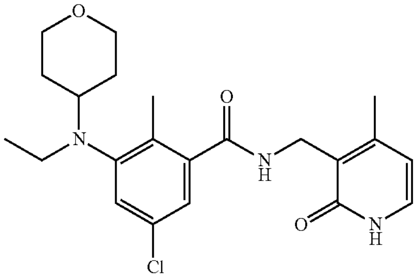 [SMILES: CCN(c1cc(Cl)cc(C(=O)NCc2c(C)cc[nH]c2=O)c1C)C1CCOCC1] | 5-chloro-3-(ethyl(tetrahydro-2H-pyran-4-yl)amino)-2-methyl-N-((4-methyl-2-oxo-1,2-dihydropyridin-3-yl)methyl)benzamide | 418.2 |
| 273 | 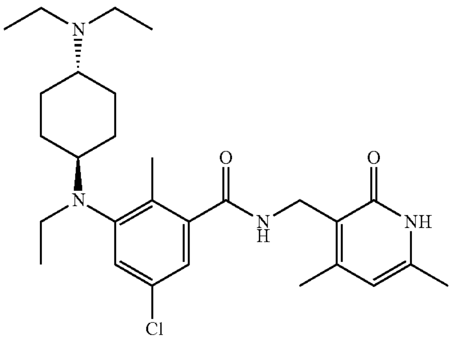 [SMILES: CCN(CC)[C@H]1CC[C@H](N(CC)c2cc(Cl)cc(C(=O)NCc3c(C)cc(C)[nH]c3=O)c2C)CC1] | 5-chloro-3-(((1r,4r)-4-(diethylamino) cyclohexyl)(ethyl) amino)-N-((4,6-dimethyl-2-oxo-1,2-dihydropyridin-3-yl)methyl)-2-methylbenzamide | 501.5 |
| 274 | 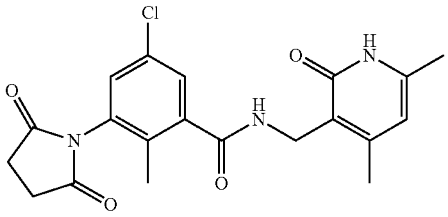 [SMILES: Cc1cc(C)c(CNC(=O)c2cc(Cl)cc(N3C(=O)CCC3=O)c2C)c(=O)[nH]1] | 5-chloro-N-((4,6-dimethyl-2-oxo-1,2-dihydropyridin-3-yl)methyl)-3-(2,5-dioxopyrrolidin-1-yl)-2-methylbenzamide | 402.3 |
| 275 | 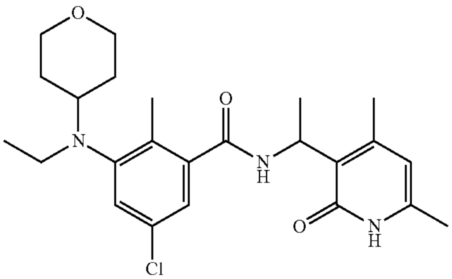 [SMILES: CCN(c1cc(Cl)cc(C(=O)NC(C)c2c(C)cc(C)[nH]c2=O)c1C)C1CCOCC1] | 5-chloro-N-(1-(4,6-dimethyl-2-oxo-1,2-dihydropyridin-3-yl)ethyl)-3-(ethyl(tetrahydro-2H-pyran-4-yl)amino)-2-methylbenzamide | 446.2 |

TABLE 1-continued

| Compound Number | Structure | Name | MS† |
|---|---|---|---|
| 276 | 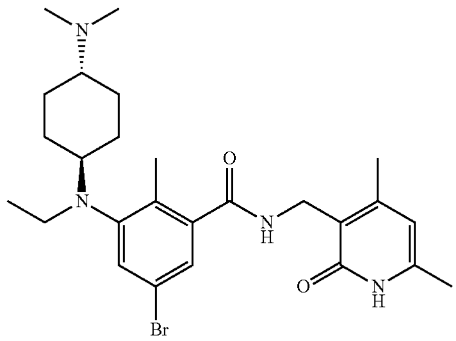 [SMILES: CCN(c1cc(Br)cc(C(=O)NCc2c(C)cc(C)[nH]c2=O)c1C)[C@H]1CC[C@H](N(C)C)CC1] | 5-bromo-N-((4,6-dimethyl-2-oxo-1,2-dihydropyridin-3-yl)methyl)-3-(((1r,4r)-4-(dimethylamino)cyclohexyl)(ethyl)amino)-2-methylbenzamide | 519.3 |
| 277 | 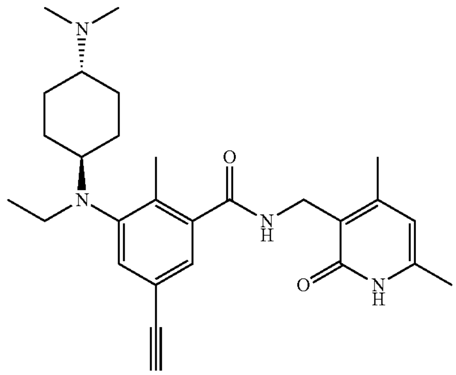 [SMILES: C#Cc1cc(C(=O)NCc2c(C)cc(C)[nH]c2=O)c(C)c(N(CC)[C@H]2CC[C@H](N(C)C)CC2)c1] | N-((4,6-dimethyl-2-oxo-1,2-dihydropyridin-3-yl)methyl)-3-(((1r,4r)-4-(dimethylamino)cyclohexyl)(ethyl)amino)-5-ethynyl-2-methylbenzamide | 463.5 |
| 278 | 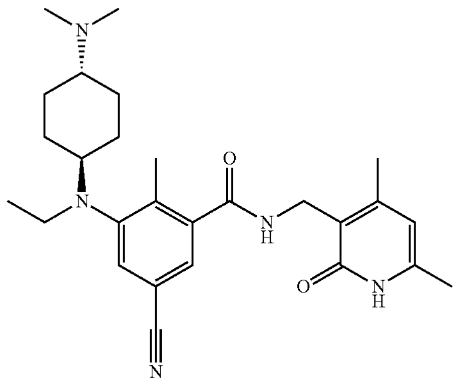 [SMILES: CCN(c1cc(C#N)cc(C(=O)NCc2c(C)cc(C)[nH]c2=O)c1C)[C@H]1CC[C@H](N(C)C)CC1] | 5-cyano-N-((4,6-dimethyl-2-oxo-1,2-dihydropyridin-3-yl)methyl)-3-(((1r,4r)-4-(dimethylamino)cyclohexyl)(ethyl)amino)-2-methylbenzamide | 464.3 |
| 279 | 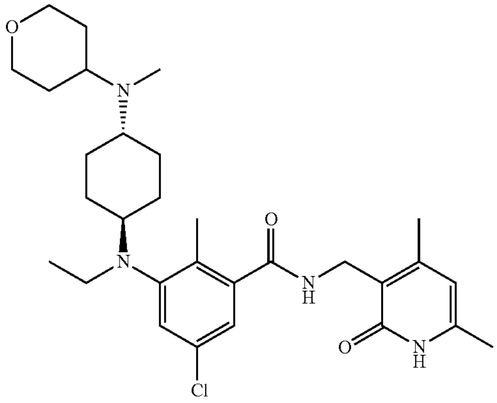 [SMILES: CCN(c1cc(Cl)cc(C(=O)NCc2c(C)cc(C)[nH]c2=O)c1C)[C@H]1CC[C@H](N(C)C2CCOCC2)CC1] | 5-chloro-N-((4,6-dimethyl-2-oxo-1,2-dihydropyridin-3-yl)methyl)-3-(ethyl((1r,4r)-4-(methyl(tetrahydro-2H-pyran-4-yl)amino)cyclohexyl)amino)-2-methylbenzamide | 543.7 |

TABLE 1-continued

| Compound Number | Structure | Name | MS† |
|---|---|---|---|
| 280 | 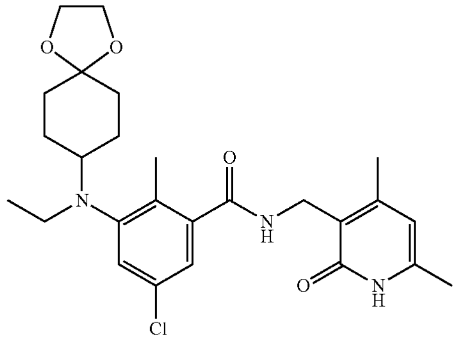 | 5-chloro-N-((4,6-dimethyl-2-oxo-1,2-dihydropyridin-3-yl)methyl)-3-(ethyl(1,4-dioxaspiro[4.5]decan-8-yl)amino)-2-methylbenzamide | 488.3 |
| 281 | 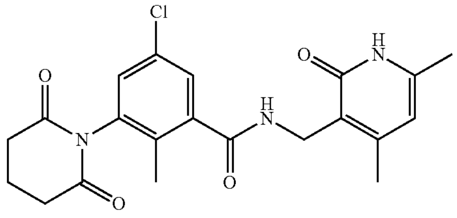 [SMILES: Cc1cc(C)c(CNC(=O)c2cc(Cl)cc(N3C(=O)CCCC3=O)c2C)c(=O)[nH]1] | 5-chloro-N-((4,6-dimethyl-2-oxo-1,2-dihydropyridin-3-yl)methyl)-3-(2,6-dioxopiperidin-1-yl)-2-methylbenzamide | 416.1 |
| 282 | 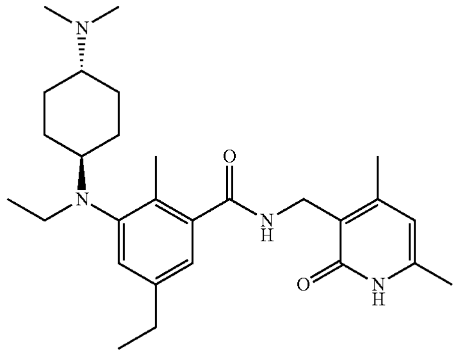 [SMILES: CCc1cc(C(=O)NCc2c(C)cc(C)[nH]c2=O)c(C)c(N(CC)[C@H]2CC[C@H](N(C)C)CC2)c1] | N-((4,6-dimethyl-2-oxo-1,2-dihydropyridin-3-yl)methyl)-3-(((1r,4r)-4-(dimethylamino)cyclohexyl)(ethyl)amino)-5-ethyl-2-methylbenzamide | 467.4 |
| 283 | 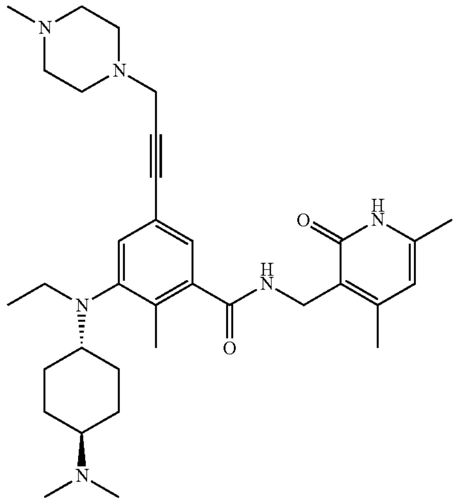 [SMILES: CCN(c1cc(C#CCN2CCN(C)CC2)cc(C(=O)NCc2c(C)cc(C)[nH]c2=O)c1C)[C@H]1CC[C@H](N(C)C)CC1] | N-((4,6-dimethyl-2-oxo-1,2-dihydropyridin-3-yl)methyl)-3-(((1r,4r)-4-(dimethylamino)cyclohexyl)(ethyl)amino)-2-methyl-5-(3-(4-methylpiperazin-1-yl)prop-1-yn-1-yl)benzamide | 575.5 |

TABLE 1-continued

| Compound Number | Structure | Name | MS† |
|---|---|---|---|
| 284 | 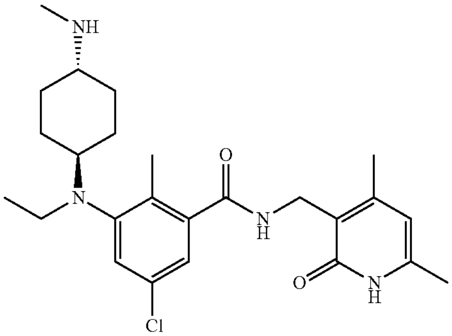 [SMILES: CCN(c1cc(Cl)cc(C(=O)NCc2c(C)cc(C)[nH]c2=O)c1C)[C@H]1CC[C@H](NC)CC1] | 5-chloro-N-((4,6-dimethyl-2-oxo-1,2-dihydropyridin-3-yl)methyl)-3-(ethyl((1r,4r)-4-(methylamino)cyclohexyl)amino)-2-methylbenzamide | 459.4 |
| 285 | 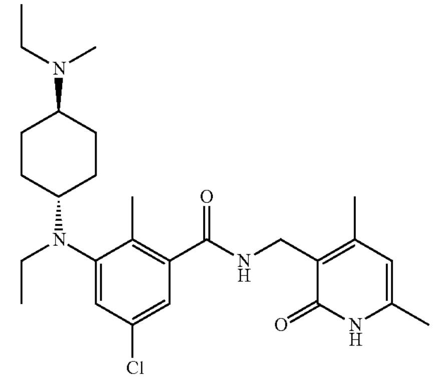 [SMILES: CCN(C)[C@H]1CC[C@H](N(CC)c2cc(Cl)cc(C(=O)NCc3c(C)cc(C)[nH]c3=O)c2C)CC1] | 5-chloro-N-((4,6-dimethyl-2-oxo-1,2-dihydropyridin-3-yl)methyl)-3-(ethyl((1r,4r)-4-(ethyl(methyl)amino)cyclohexyl)amino)-2-methylbenzamide | 487.4 |
| 286 | 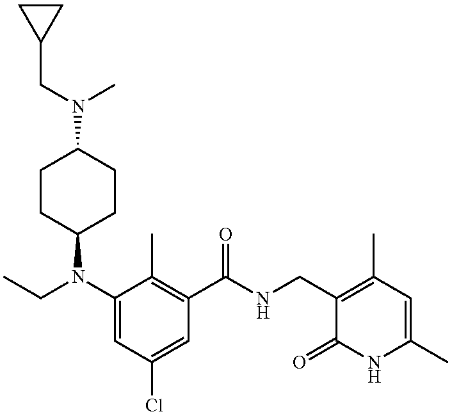 [SMILES: CCN(c1cc(Cl)cc(C(=O)NCc2c(C)cc(C)[nH]c2=O)c1C)[C@H]1CC[C@H](N(C)CC2CC2)CC1] | 5-chloro-3-(((1r,4r)-4-((cyclopropylmethyl)(methyl)amino)cyclohexyl)(ethyl)amino)-N-((4,6-dimethyl-2-oxo-1,2-dihydropyridin-3-yl)methyl)-2-methylbenzamide | 513.4 |
| 287 | 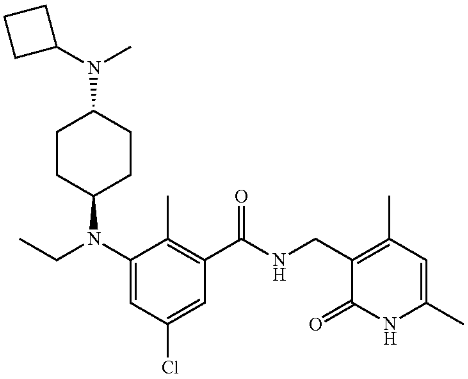 [SMILES: CCN(c1cc(Cl)cc(C(=O)NCc2c(C)cc(C)[nH]c2=O)c1C)[C@H]1CC[C@H](N(C)C2CCC2)CC1] | 5-chloro-3-(((1r,4r)-4-(cyclobutyl(methyl)amino)cyclohexyl)(ethyl)amino)-N-((4,6-dimethyl-2-oxo-1,2-dihydropyridin-3-yl)methyl)-2-methylbenzamide | 513.3 |

TABLE 1-continued

| Compound Number | Structure | Name | MS† |
|---|---|---|---|
| 288 | 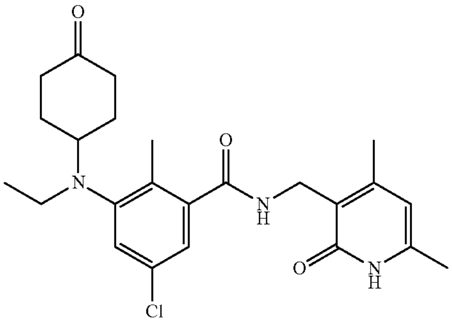 [SMILES: CCN(c1cc(Cl)cc(C(=O)NCc2c(C)cc(C)[nH]c2=O)c1C)C1CCC(=O)CC1] | 5-chloro-N-((4,6-dimethyl-2-oxo-1,2-dihydropyridin-3-yl)methyl)-3-(ethyl(4-oxocyclohexyl)amino)-2-methylbenzamide | 444.3 |
| 289 | 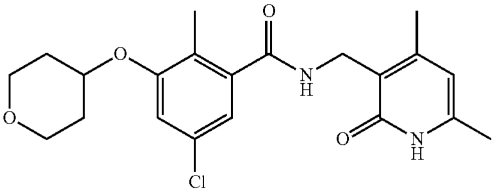 [SMILES: Cc1cc(C)c(CNC(=O)c2cc(Cl)cc(OC3CCOCC3)c2C)c(=O)[nH]1] | 5-chloro-N-((4,6-dimethyl-2-oxo-1,2-dihydropyridin-3-yl)methyl)-2-methyl-3-((tetrahydro-2H-pyran-4-yl)oxy)benzamide | 405.2 |
| 290 | 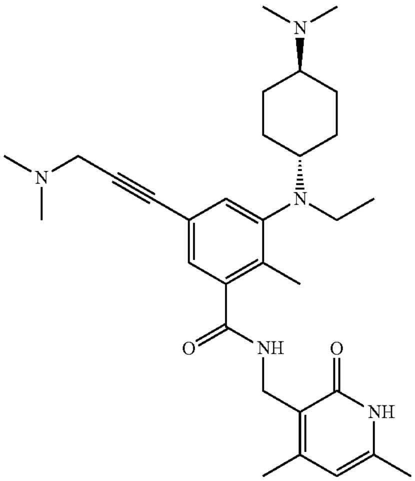 | N-((4,6-dimethyl-2-oxo-1,2-dihydropyridin-3-yl)methyl)-3-(((1r,4r)-4-(dimethylamino)cyclohexyl)ethyl)amino)-5-(3-(dimethylamino)prop-1-yn-1-yl)-2-methylbenzamide | 520.6 |
| 291 | 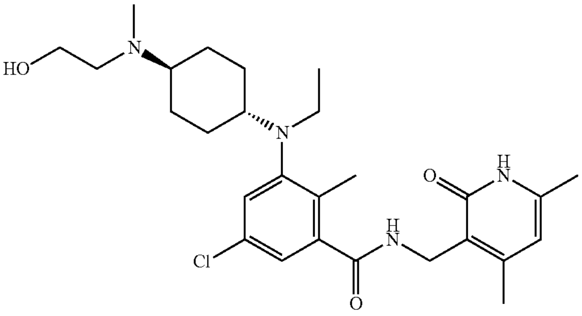 [SMILES: CCN(c1cc(Cl)cc(C(=O)NCc2c(C)cc(C)[nH]c2=O)c1C)[C@H]1CC[C@H](N(C)CCO)CC1] | 5-chloro-N-((4,6-dimethyl-2-oxo-1,2-dihydropyridin-3-yl)methyl)-3-(ethyl((1r,4r)-4-((2-hydroxyethyl)(methyl)amino)cyclohexyl)amino)-2-methylbenzamide | 503.3 |

TABLE 1-continued

| Compound Number | Structure | Name | MS† |
|---|---|---|---|
| 292 | 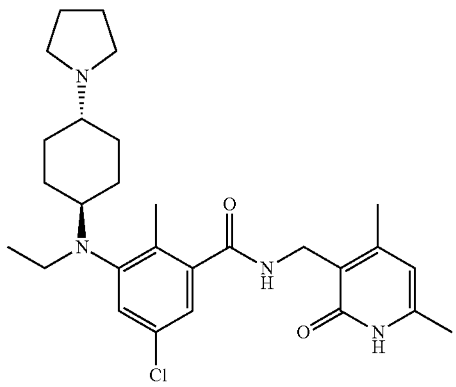 [SMILES: CCN(c1cc(Cl)cc(C(=O)NCc2c(C)cc(C)[nH]c2=O)c1C)[C@H]1CC[C@H](N2CCCC2)CC1] | 5-chloro-N-((4,6-dimethyl-2-oxo-1,2-dihydropyridin-3-yl)methyl)-3-(ethyl((1r,4r)-4-(pyrrolidin-1-yl)cyclohexyl)amino)-2-methylbenzamide | 499.3 |
| 293 | 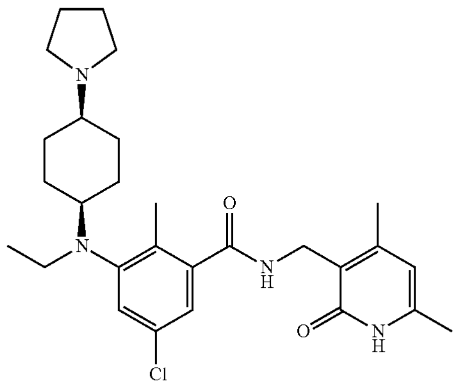 [SMILES: CCN(c1cc(Cl)cc(C(=O)NCc2c(C)cc(C)[nH]c2=O)c1C)[C@H]1CC[C@@H](N2CCCC2)CC1] | 5-chloro-N-((4,6-dimethyl-2-oxo-1,2-dihydropyridin-3-yl)methyl)-3-(ethyl((1s,4s)-4-(pyrrolidin-1-yl)cyclohexyl)amino)-2-methylbenzamide | 499.3 |
| 294 | 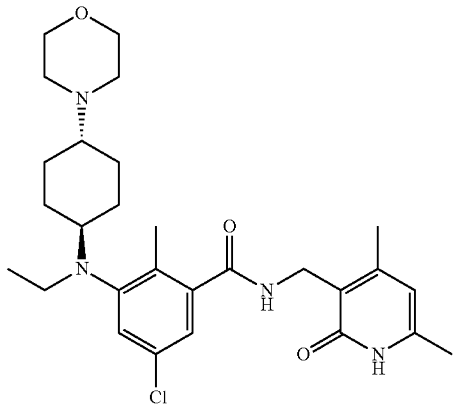 [SMILES: CCN(c1cc(Cl)cc(C(=O)NCc2c(C)cc(C)[nH]c2=O)c1C)[C@H]1CC[C@H](N2CCOCC2)CC1] | 5-chloro-N-((4,6-dimethyl-2-oxo-1,2-dihydropyridin-3-yl)methyl)-3-(ethyl((1r,4r)-4-morpholinocyclohexyl)amino)-2-methylbenzamide | 515.3 |
| 295 | 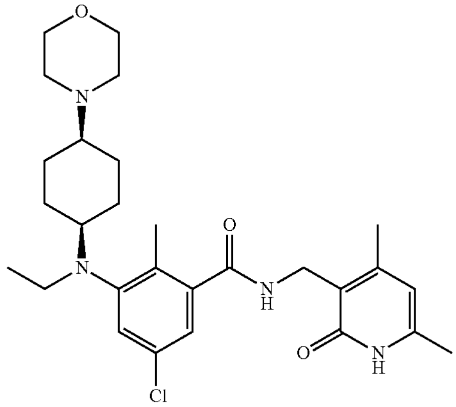 [SMILES: CCN(c1cc(Cl)cc(C(=O)NCc2c(C)cc(C)[nH]c2=O)c1C)[C@H]1CC[C@@H](N2CCOCC2)CC1] | 5-chloro-N-((4,6-dimethyl-2-oxo-1,2-dihydropyridin-3-yl)methyl)-3-(ethyl((1s,4s)-4-morpholinocyclohexyl)amino)-2-methylbenzamide | 515.3 |

TABLE 1-continued

| Compound Number | Structure | Name | MS† |
|---|---|---|---|
| 296 | 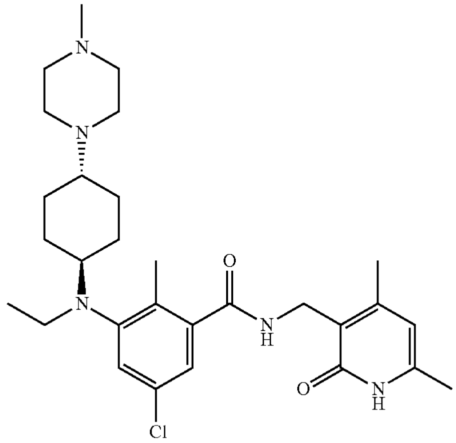 [SMILES: CCN(c1cc(Cl)cc(C(=O)NCc2c(C)cc(C)[nH]c2=O)c1C)[C@H]1CC[C@H](N2CCN(C)CC2)CC1] | 5-chloro-N-((4,6-dimethyl-2-oxo-1,2-dihydropyridin-3-yl)methyl)-3-(ethyl((1r,4r)-4-(4-methylpiperazin-1-yl)cyclohexyl)amino)-2-methylbenzamide | 528.4 |
| 297 | 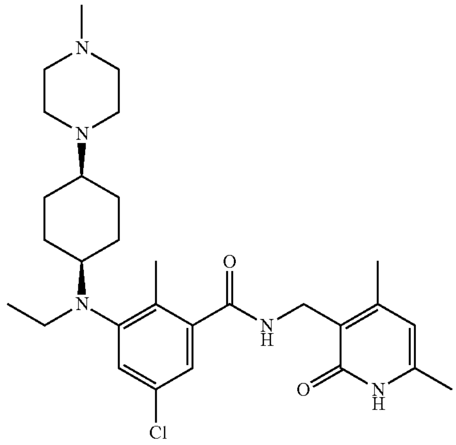 [SMILES: CCN(c1cc(Cl)cc(C(=O)NCc2c(C)cc(C)[nH]c2=O)c1C)[C@H]1CC[C@@H](N2CCN(C)CC2)CC1] | 5-chloro-N-((4,6-dimethyl-2-oxo-1,2-dihydropyridin-3-yl)methyl)-3-(ethyl((1s,4s)-4-(4-methylpiperazin-1-yl)cyclohexyl)amino)-2-methylbenzamide | 528.3 |
| 298 | 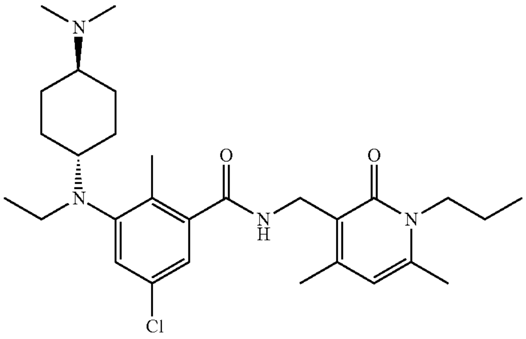 [SMILES: CCCn1c(C)cc(C)c(CNC(=O)c2cc(Cl)cc(N(CC)[C@H]3CC[C@H](N(C)C)CC3)c2C)c1=O] | 5-chloro-N-((4,6-dimethyl-2-oxo-1-propyl-1,2-dihydropyridin-3-yl)methyl)-3-(((1r,4r)-4-(dimethylamino) cyclohexyl)(ethyl) amino)-2-methylbenzamide | 515.3 |
| 299 | 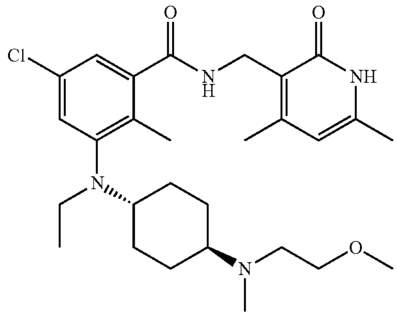 [SMILES: CCN(c1cc(Cl)cc(C(=O)NCc2c(C)cc(C)[nH]c2=O)c1C)[C@H]1CC[C@H](N(C)CCOC)CC1] | 5-chloro-N-((4,6-dimethyl-2-oxo-1,2-dihydropyridin-3-yl)methyl)-3-(ethyl((1r,4r)-4-((2-methoxyethyl)(methyl) amino)cyclohexyl) amino)-2-methylbenzamide | 517.4 |

TABLE 1-continued

| Compound Number | Structure | Name | MS† |
|---|---|---|---|
| 300 | 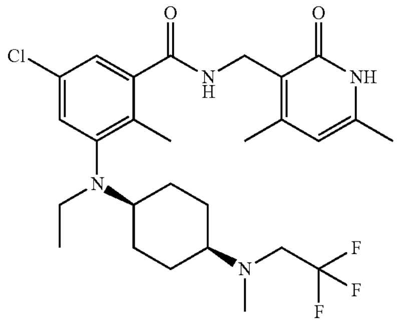 [SMILES: CCN(c1cc(Cl)cc(C(=O)NCc2c(C)cc(C)[nH]c2=O)c1C)[C@H]1CC[C@@H](N(C)CC(F)(F)F)CC1] | 5-chloro-N-((4,6-dimethyl-2-oxo-1,2-dihydropyridin-3-yl)methyl)-3-(ethyl((1s,4s)-4-(methyl(2,2,2-trifluoroethyl)amino) cyclohexyl)amino)-2-methylbenzamide | 541.4 |
| 301 | 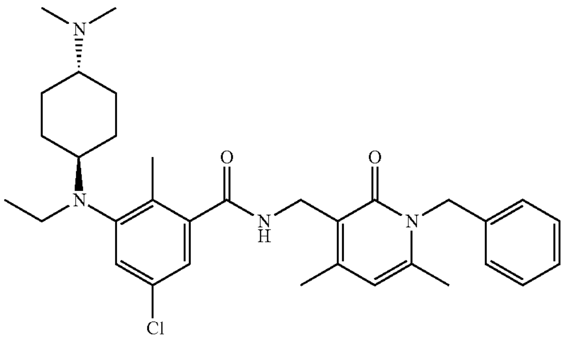 [SMILES: CCN(c1cc(Cl)cc(C(=O)NCc2c(C)cc(C)n(Cc3ccccc3)c2=O)c1C)[C@H]1CC[C@H](N(C)C)CC1] | N-((1-benzyl-4,6-dimethyl-2-oxo-1,2-dihydropyridin-3-yl)methyl)-5-chloro-3-(((1r,4r)-4-(dimethylamino) cyclohexyl)(ethyl) amino)-2-methylbenzamide | 563.4 |
| 302 | 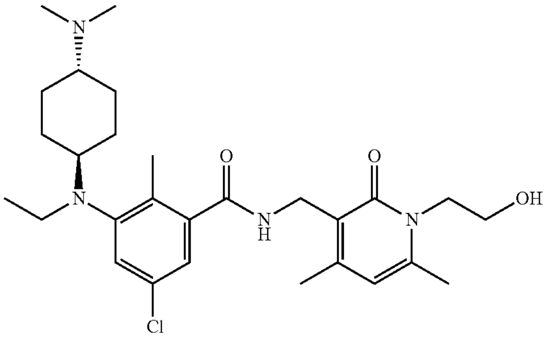 [SMILES: CCN(c1cc(Cl)cc(C(=O)NCc2c(C)cc(C)n(CCO)c2=O)c1C)[C@H]1CC[C@H](N(C)C)CC1] | 5-chloro-3-(((1r,4r)-4-(dimethylamino) cyclohexyl)(ethyl) amino)-N-((1-(2-hydroxyethyl)-4,6-dimethyl-2-oxo-1,2-dihydropyridin-3-yl)methyl)-2-methylbenzamide | 517.4 |
| 303 | 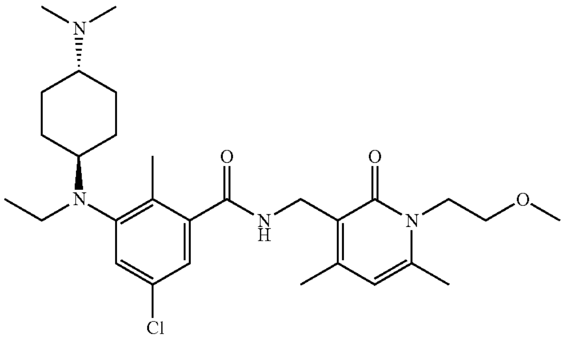 [SMILES: CCN(c1cc(Cl)cc(C(=O)NCc2c(C)cc(C)n(CCOC)c2=O)c1C)[C@H]1CC[C@H](N(C)C)CC1] | 5-chloro-3-(((1r,4r)-4-(dimethylamino) cyclohexyl)(ethyl) amino)-N-((1-(2-methoxyethyl)-4,6-dimethyl-2-oxo-1,2-dihydropyridin-3-yl)methyl)-2-methylbenzamide | 531.4 |

TABLE 1-continued

| Compound Number | Structure | Name | MS† |
|---|---|---|---|
| 304 | 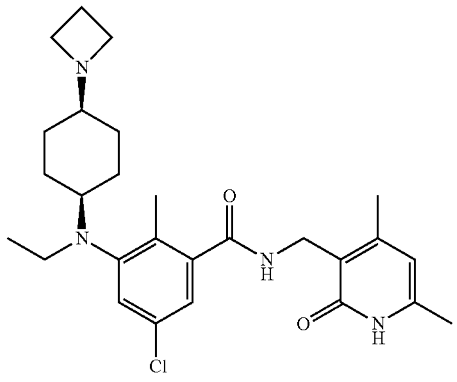 [SMILES: CCN(c1cc(Cl)cc(C(=O)NCc2c(C)cc(C)[nH]c2=O)c1C)[C@H]1CC[C@@H](N2CCC2)CC1] | 3-(((1s,4s)-4-(azetidin-1-yl)cyclohexyl)(ethyl) amino)-5-chloro-N-((4,6-dimethyl-2-oxo-1,2-dihydropyridin-3-yl)methyl)-2-methylbenzamide | 485.2 |
| 305 | 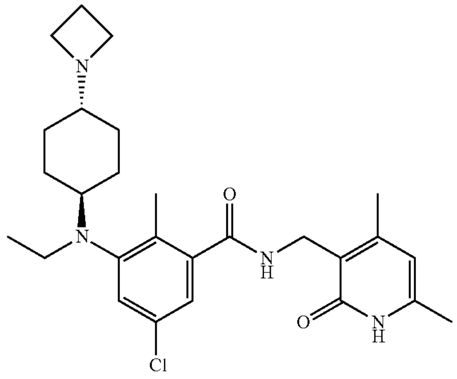 [SMILES: CCN(c1cc(Cl)cc(C(=O)NCc2c(C)cc(C)[nH]c2=O)c1C)[C@H]1CC[C@H](N2CCC2)CC1] | 3-(((1r,4r)-4-(azetidin-1-yl)cyclohexyl)(ethyl) amino)-5-chloro-N-((4,6-dimethyl-2-oxo-1,2-dihydropyridin-3-yl)methyl)-2-methylbenzamide | 485.2 |
| 306 | 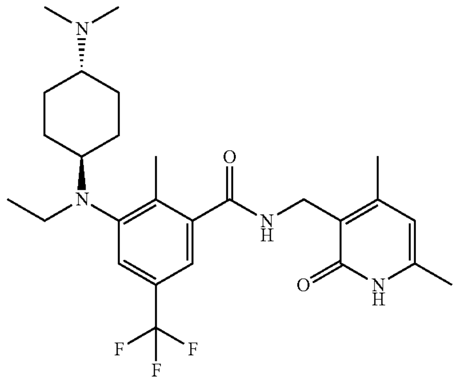 [SMILES: CCN(c1cc(C(F)(F)F)cc(C(=O)NCc2c(C)cc(C)[nH]c2=O)c1C)[C@H]1CC[C@H](N(C)C)CC1] | N-((4,6-dimethyl-2-oxo-1,2-dihydropyridin-3-yl)methyl)-3-(((1r,4r)-4-(dimethylamino) cyclohexyl)(ethyl) amino)-2-methyl-5-(trifluoromethyl) benzamide | 507.5 |
| 307 | 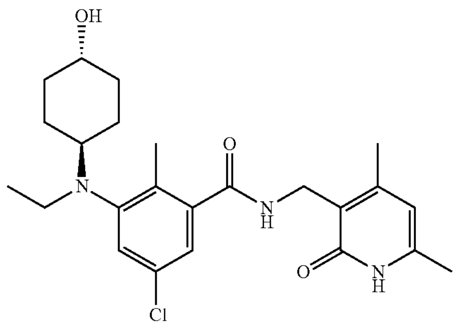 [SMILES: CCN(c1cc(Cl)cc(C(=O)NCc2c(C)cc(C)[nH]c2=O)c1C)[C@H]1CC[C@H](O)CC1] | 5-chloro-N-((4,6-dimethyl-2-oxo-1,2-dihydropyridin-3-yl)methyl)-3-(ethyl((1r,4r)-4-hydroxycyclohexyl) amino)-2-methylbenzamide | 446.3 |

TABLE 1-continued

| Compound Number | Structure | Name | MS† |
|---|---|---|---|
| 308 | 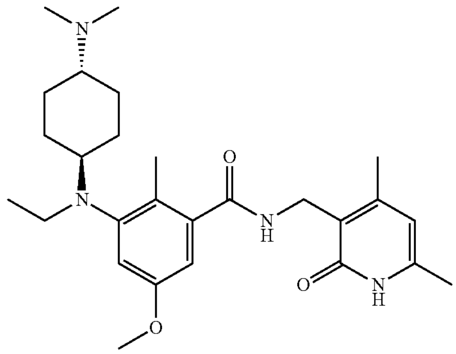 [SMILES: CCN(c1cc(OC)cc(C(=O)NCc2c(C)cc(C)[nH]c2=O)c1C)[C@H]1CC[C@H](N(C)C)CC1] | N-((4,6-dimethyl-2-oxo-1,2-dihydropyridin-3-yl)methyl)-3-(((1r,4r)-4-(dimethylamino) cyclohexyl)(ethyl) amino)-5-methoxy-2-methylbenzamide | 469.8 |
| 309 | 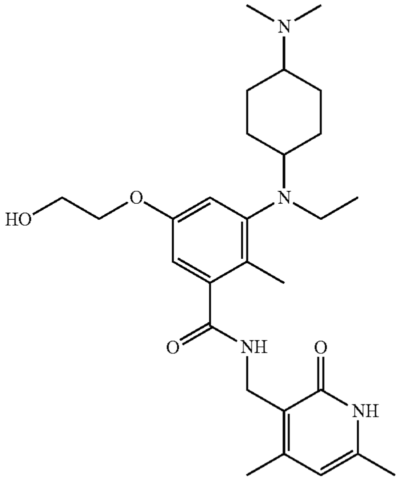 [SMILES: CCN(c1cc(OCCO)cc(C(=O)NCc2c(C)cc(C)[nH]c2=O)c1C)C1CCC(N(C)C)CC1] | N-((4,6-dimethyl-2-oxo-1,2-dihydropyridin-3-yl)methyl)-3-((4-(dimethylamino) cyclohexyl)ethyl) amino)-5-(2-hydroxyethoxy)-2-methylbenzamide | 499.6 |
| 310 | 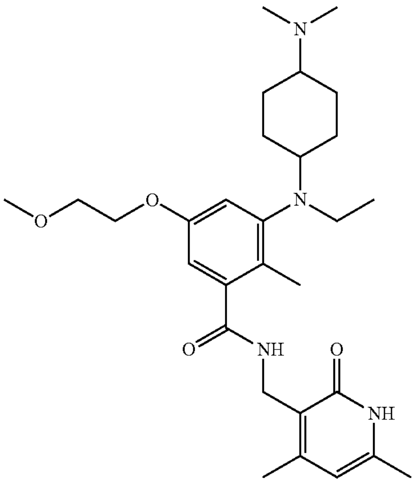 | N-((4,6-dimethyl-2-oxo-1,2-dihydropyridin-3-yl)methyl)-3-((4-(dimethylamino) cyclohexyl)(ethyl) amino)-5-(2-methoxyethoxy)-2-methylbenzamide | 513.6 |

TABLE 1-continued

| Compound Number | Structure | Name | MS† |
| --- | --- | --- | --- |
| 311 | 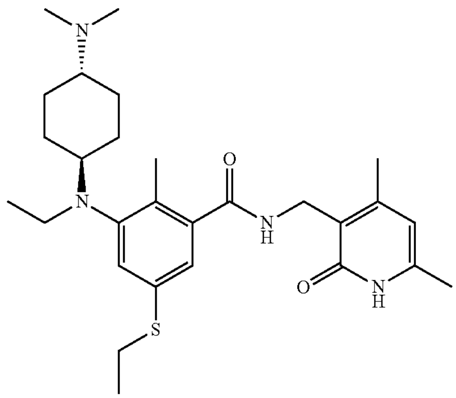 [SMILES: CCSc1cc(C(=O)NCc2c(C)cc(C)[nH]c2=O)c(C)c(N(CC)[C@H]2CC[C@H](N(C)C)CC2)c1] | N-((4,6-dimethyl-2-oxo-1,2-dihydropyridin-3-yl)methyl)-3-(((1r,4r)-4-(dimethylamino) cyclohexyl)(ethyl) amino)-5-(ethylthio)-2-methylbenzamide | 499.6 |
| 312 | 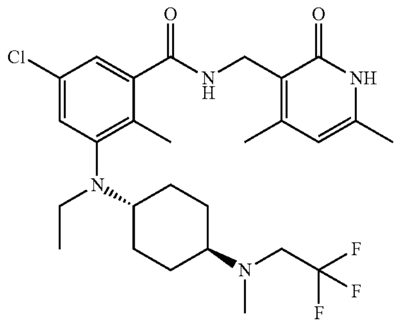 [SMILES: CCN(c1cc(Cl)cc(C(=O)NCc2c(C)cc(C)[nH]c2=O)c1C)[C@H]1CC[C@H](N(C)CC(F)(F)F)CC1] | 5-chloro-N-((4,6-dimethyl-2-oxo-1,2-dihydropyridin-3-yl)methyl)-3-(ethyl((1r,4r)-4-(methyl(2,2,2-trifluoroethyl)amino) cyclohexyl)amino)-2-methylbenzamide | 541.5 |
| 313 | 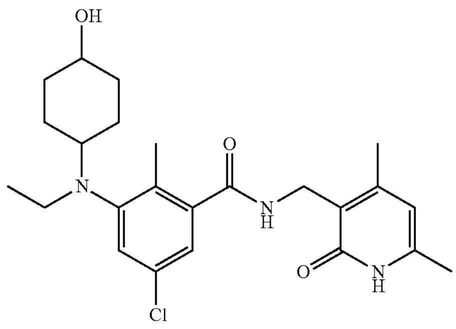 [SMILES: CCN(c1cc(Cl)cc(C(=O)NCc2c(C)cc(C)[nH]c2=O)c1C)C1CCC(O)CC1] | 5-chloro-N-((4,6-dimethyl-2-oxo-1,2-dihydropyridin-3-yl)methyl)-3-(ethyl(4-hydroxycyclohexyl) amino)-2-methylbenzamide | 446.3 |
| 314 | 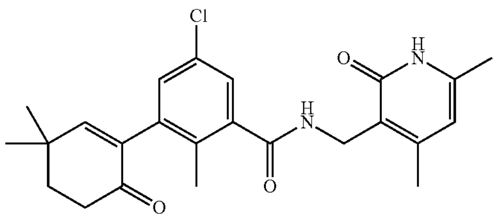 | 5-chloro-N-((4,6-dimethyl-2-oxo-1,2-dihydropyridin-3-yl)methyl)-2,5',5'-trimethyl-2'-oxo-2',3',4',5'-tetrahydro-[1,1'-biphenyl]-3-carboxamide | 427.4 |

TABLE 1-continued

| Compound Number | Structure | Name | MS† |
|---|---|---|---|
| 315 | 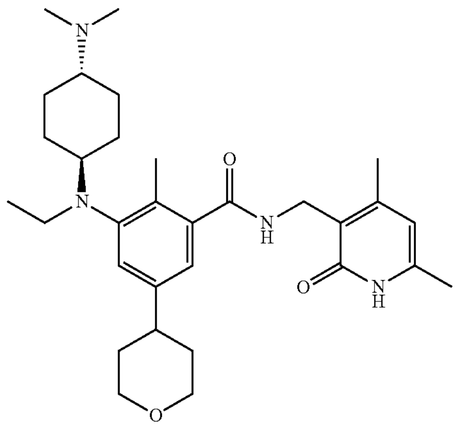 [SMILES: CCN(c1cc(C2CCOCC2)cc(C(=O)NCc2c(C)cc(C)[nH]c2=O)c1C)[C@H]1CC[C@H](N(C)C)CC1] | N-((4,6-dimethyl-2-oxo-1,2-dihydropyridin-3-yl)methyl)-3-(((1r,4r)-4-(dimethylamino) cyclohexyl)(ethyl) amino)-2-methyl-5-(tetrahydro-2H-pyran-4-yl) benzamide | 523.6 |
| 316 | 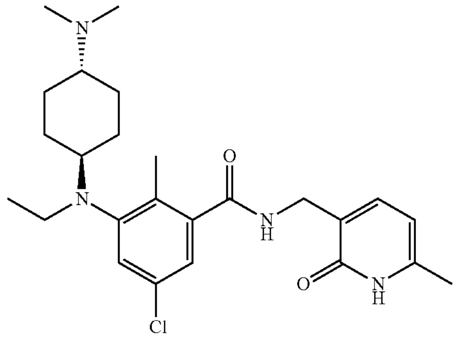 [SMILES: CCN(c1cc(Cl)cc(C(=O)NCc2ccc(C)[nH]c2=O)c1C)[C@H]1CC[C@H](N(C)C)CC1] | 5-chloro-3-(((1r,4r)-4-(dimethylamino) cyclohexyl)(ethyl) amino)-2-methyl-N-((6-methyl-2-oxo-1,2-dihydropyridin-3-yl)methyl)benzamide | 459.5 |
| 317 | 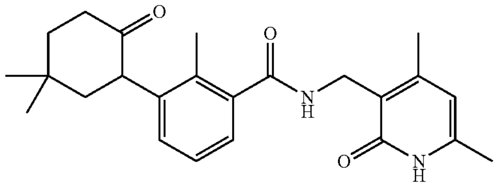 | N-((4,6-dimethyl-2-oxo-1,2-dihydropyridin-3-yl)methyl)-3-(5,5-dimethyl-2-oxocyclohexyl)-2-methylbenzamide | 395.4 |
| 318 | 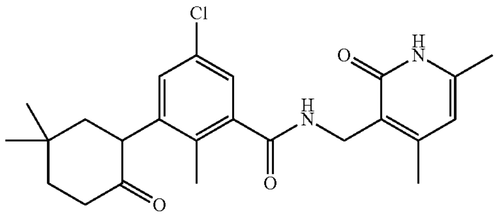 | 5-chloro-N-((4,6-dimethyl-2-oxo-1,2-dihydropyridin-3-yl)methyl)-3-(5,5-dimethyl-2-oxocyclohexyl)-2-methylbenzamide | 429.4 |
| 319 | 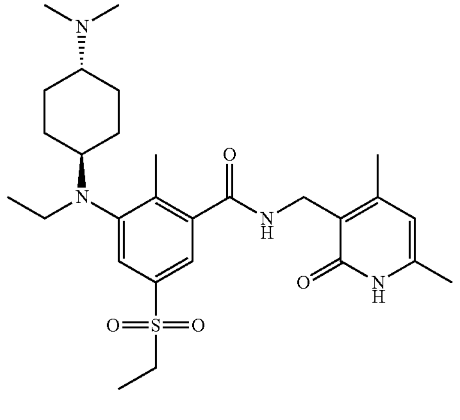 [SMILES: CCN(c1cc(S(=O)(=O)CC)cc(C(=O)NCc2c(C)cc(C)[nH]c2=O)c1C)[C@H]1CC[C@H](N(C)C)CC1] | N-((4,6-dimethyl-2-oxo-1,2-dihydropyridin-3-yl)methyl)-3-(((1r,4r)-4-(dimethylamino) cyclohexyl)(ethyl) amino)-5-(ethylsulfonyl)-2-methylbenzamide | 531.6 |

TABLE 1-continued

| Compound Number | Structure | Name | MS† |
|---|---|---|---|
| 320 | 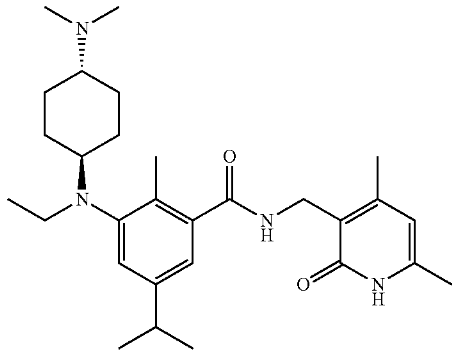 [SMILES: CCN(c1cc(C(C)C)cc(C(=O)NCc2c(C)cc(C)[nH]c2=O)c1C)[C@H]1CC[C@H](N(C)C)CC1] | N-((4,6-dimethyl-2-oxo-1,2-dihydropyridin-3-yl)methyl)-3-(((1r,4r)-4-(dimethylamino) cyclohexyl)(ethyl) amino)-5-isopropyl-2-methylbenzamide | 481.4 |
| 321 | 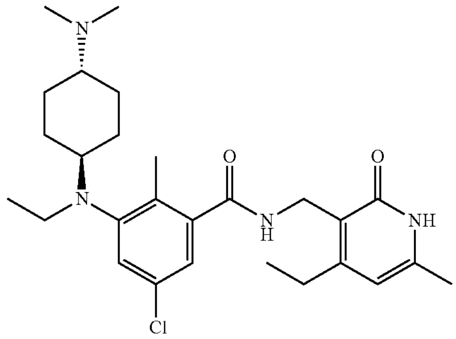 [SMILES: CCc1cc(C)[nH]c(=O)c1CNC(=O)c1cc(Cl)cc(N(CC)[C@H]2CC[C@H](N(C)C)CC2)c1C] | 5-chloro-3-(((1r,4r)-4-(dimethylamino) cyclohexyl)ethyl) amino)-N-((4-ethyl-6-methyl-2-oxo-1,2-dihydropyridin-3-yl)methyl)-2-methylbenzamide | 487.5 |
| 322 | 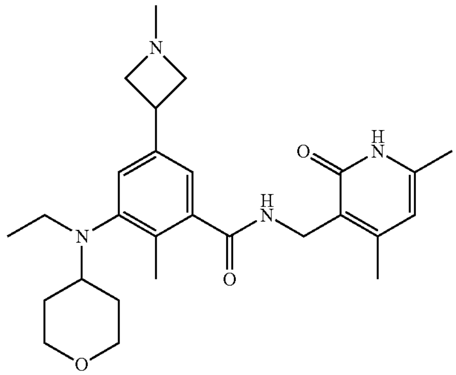 [SMILES: CCN(c1cc(C2CN(C)C2)cc(C(=O)NCc2c(C)cc(C)[nH]c2=O)c1C)C1CCOCC1] | N-((4,6-dimethyl-2-oxo-1,2-dihydropyridin-3-yl)methyl)-3-(ethyl(tetrahydro-2H-pyran-4-yl)amino)-2-methyl-5-(1-methylazetidin-3-yl)benzamide | 467.3 |
| 323 | 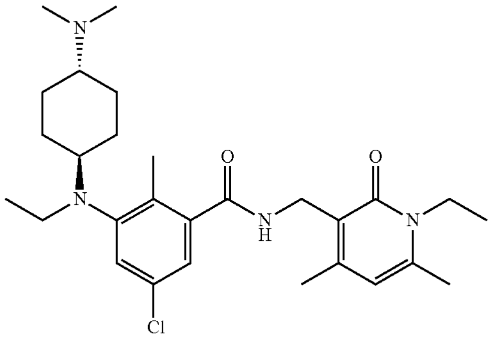 [SMILES: CCn1c(C)cc(C)c(CNC(=O)c2cc(Cl)cc(N(CC)[C@H]3CC[C@H](N(C)C)CC3)c2C)c1=O] | 5-chloro-3-(((1r,4r)-4-(dimethylamino) cyclohexyl)(ethyl) amino)-N-((1-ethyl-4,6-dimethyl-2-oxo-1,2-dihydropyridin-3-yl)methyl)-2-methylbenzamide | 501.5 |

TABLE 1-continued

| Compound Number | Structure | Name | MS† |
|---|---|---|---|
| 324 | 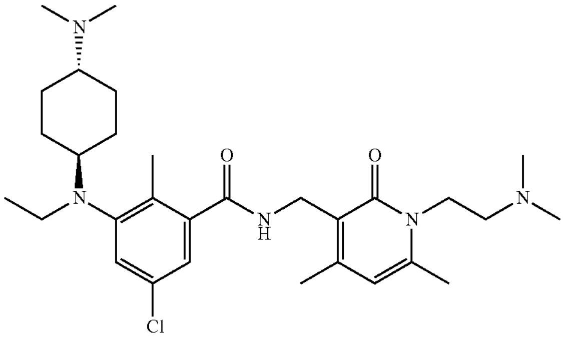 [SMILES: CCN(c1cc(Cl)cc(C(=O)NCc2c(C)cc(C)n(CCN(C)C)c2=O)c1C)[C@H]1CC[C@H](N(C)C)CC1] | 5-chloro-3-(((1r,4r)-4-(dimethylamino) cyclohexyl)(ethyl) amino)-N-((1-(2-(dimethylamino) ethyl)-4,6-dimethyl-2-oxo-1,2-dihydropyridin-3-yl)methyl)-2-methylbenzamide | 544.6 |
| 325 | 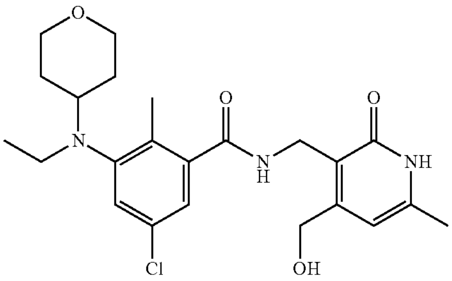 [SMILES: CCN(c1cc(Cl)cc(C(=O)NCc2c(CO)cc(C)[nH]c2=O)c1C)C1CCOCC1] | 5-chloro-3-(ethyl(tetrahydro-2H-pyran-4-yl)amino)-N-((4-(hydroxymethyl)-6-methyl-2-oxo-1,2-dihydropyridin-3-yl)methyl)-2-methylbenzamide | 448.4 |
| 326 | 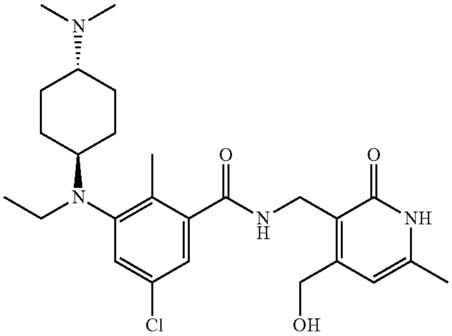 [SMILES: CCN(c1cc(Cl)cc(C(=O)NCc2c(CO)cc(C)[nH]c2=O)c1C)[C@H]1CC[C@H](N(C)C)CC1] | 5-chloro-3-(((1r,4r)-4-(dimethylamino) cyclohexyl)(ethyl) amino)-N-((4-(hydroxymethyl)-6-methyl-2-oxo-1,2-dihydropyridin-3-yl)methyl)-2-methylbenzamide | 489.5 |
| 327 | 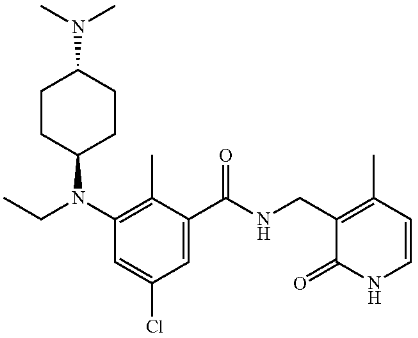 [SMILES: CCN(c1cc(Cl)cc(C(=O)NCc2c(C)cc[nH]c2=O)c1C)[C@H]1CC[C@H](N(C)C)CC1] | 5-chloro-3-(((1r,4r)-4-(dimethylamino) cyclohexyl)(ethyl) amino)-2-methyl-N-((4-methyl-2-oxo-1,2-dihydropyridin-3-yl)methyl)benzamide | 459.4 |
| 328 | 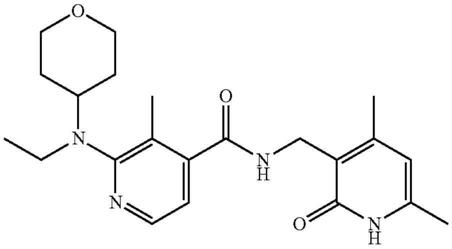 [SMILES: CCN(c1nccc(C(=O)NCc2c(C)cc(C)[nH]c2=O)c1C)C1CCOCC1] | N-((4,6-dimethyl-2-oxo-1,2-dihydropyridin-3-yl)methyl)-2-(ethyl(tetrahydro-2H-pyran-4-yl)amino)-3-methylisonicotinamide | 399.1 |

TABLE 1-continued

| Compound Number | Structure | Name | MS† |
|---|---|---|---|
| 329 | 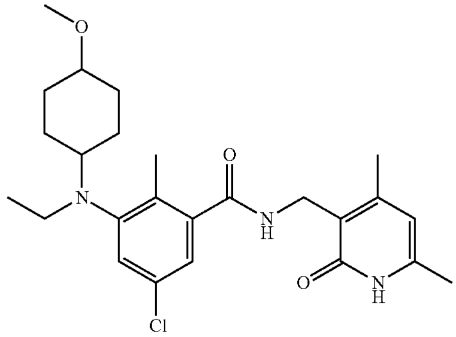 | 5-chloro-N-((4,6-dimethyl-2-oxo-1,2-dihydropyridin-3-yl)methyl)-3-(ethyl(4-methoxycyclohexyl) amino)-2-methylbenzamide | 460.4 |
| 330 | 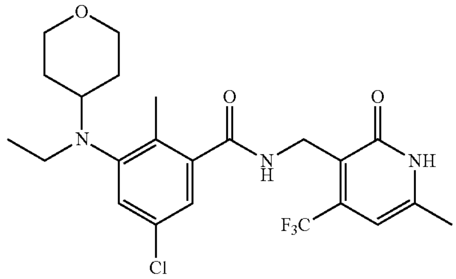 [SMILES: CCN(c1cc(Cl)cc(C(=O)NCc2c(C(F)(F)F)cc(C)[nH]c2=O)c1C)C1CCOCC1] | 5-chloro-3-(ethyl(tetrahydro-2H-pyran-4-yl)amino)-2-methyl-N-((6-methyl-2-oxo-4-(trifluoromethyl)-1,2-dihydropyridin-3-yl)methyl)benzamide | 486.4 |
| 331 | 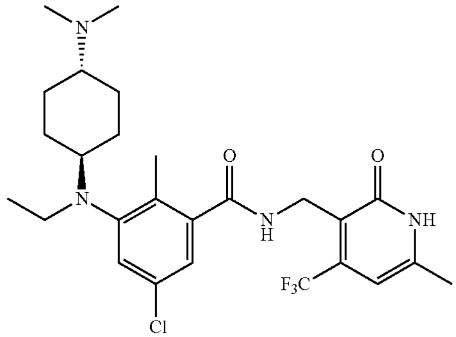 [SMILES: CCN(c1cc(Cl)cc(C(=O)NCc2c(C(F)(F)F)cc(C)[nH]c2=O)c1C)[C@H]1CC[C@H](N(C)C)CC1] | 5-chloro-3-(((1r,4r)-4-(dimethylamino) cyclohexyl)(ethyl) amino)-2-methyl-N-((6-methyl-2-oxo-4-(trifluoromethyl)-1,2-dihydropyridin-3-yl)methyl)benzamide | 527.5 |
| 332 | 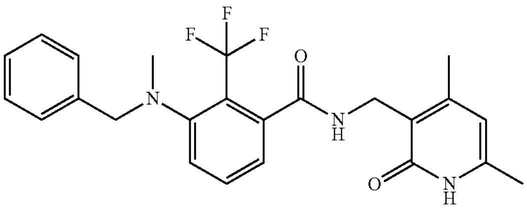 [SMILES: Cc1cc(C)c(CNC(=O)c2cccc(N(C)Cc3ccccc3)c2C(F)(F)F)c(=O)[nH]1] | 3-(benzyl(methyl) amino)-N-((4,6-dimethyl-2-oxo-1,2-dihydropyridin-3-yl)methyl)-2-(trifluoromethyl) benzamide | 444.2 |
| 333 | 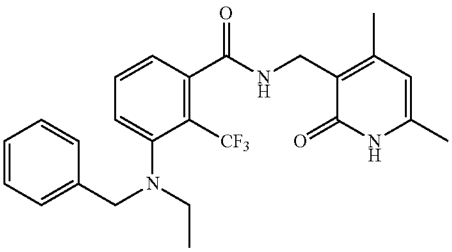 [SMILES: CCN(Cc1ccccc1)c1cccc(C(=O)NCc2c(C)cc(C)[nH]c2=O)c1C(F)(F)F] | 3-(benzyl(ethyl)amino)-N-((4,6-dimethyl-2-oxo-1,2-dihydropyridin-3-yl)methyl)-2-(trifluoromethyl) benzamide | 458.3 |

TABLE 1-continued

| Compound Number | Structure | Name | MS† |
|---|---|---|---|
| 334 | 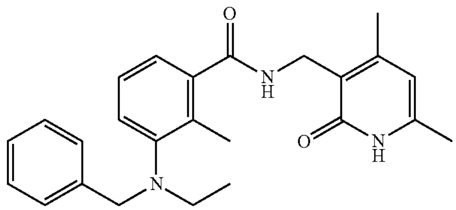 [SMILES: CCN(Cc1ccccc1)c1cccc(C(=O)NCc2c(C)cc(C)[nH]c2=O)c1C] | 3-(benzyl(ethyl)amino)-N-((4,6-dimethyl-2-oxo-1,2-dihydropyridin-3-yl)methyl)-2-methylbenzamide | 404.3 |
| 335 | 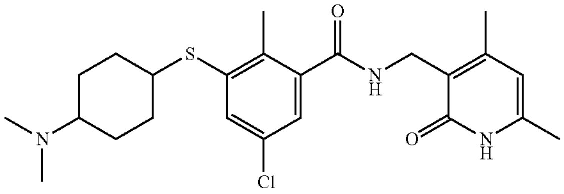 | 5-chloro-N-((4,6-dimethyl-2-oxo-1,2-dihydropyridin-3-yl)methyl)-3-((4-(dimethylamino) cyclohexyl)thio)-2-methylbenzamide | 462.4 |
| 336 | 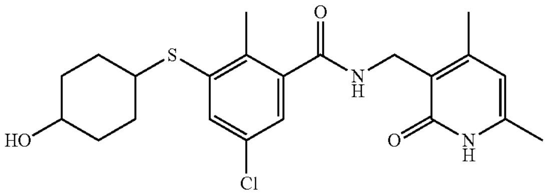 [SMILES: Cc1cc(C)c(CNC(=O)c2cc(Cl)cc(SC3CCC(O)CC3)c2C)c(=O)[nH]1] | 5-chloro-N-((4,6-dimethyl-2-oxo-1,2-dihydropyridin-3-yl)methyl)-3-((4-hydroxycyclohexyl)thio)-2-methylbenzamide | 435.3 |
| 337 | 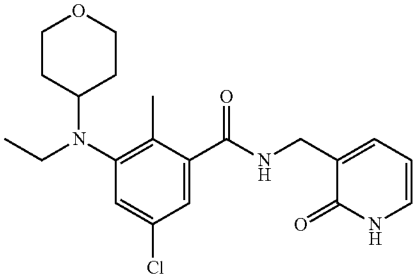 [SMILES: CCN(c1cc(Cl)cc(C(=O)NCc2ccc[nH]c2=O)c1C)C1CCOCC1] | 5-chloro-3-(ethyl(tetrahydro-2H-pyran-4-yl)amino)-2-methyl-N-((2-oxo-1,2-dihydropyridin-3-yl)methyl)benzamide | 404.3 |
| 338 | 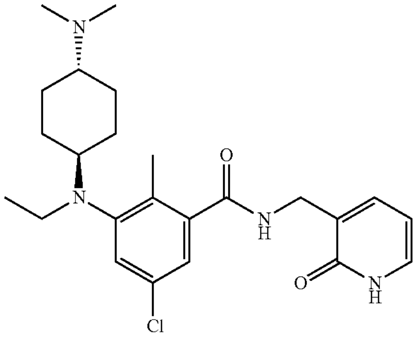 [SMILES: CCN(c1cc(Cl)cc(C(=O)NCc2ccc[nH]c2=O)c1C)[C@H]1CC[C@H](N(C)C)CC1] | 5-chloro-3-(((1r,4r)-4-(dimethylamino) cyclohexyl)(ethyl) amino)-2-methyl-N-((2-oxo-1,2-dihydropyridin-3-yl)methyl)benzamide | 445.5 |
| 339 | 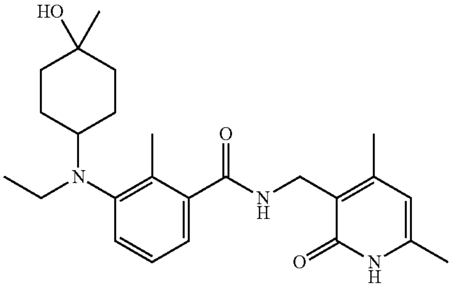 | N-((4,6-dimethyl-2-oxo-1,2-dihydropyridin-3-yl)methyl)-3-(ethyl(4-hydroxy-4-methylcyclohexyl) amino)-2-methylbenzamide | 426.5 |

TABLE 1-continued

| Compound Number | Structure | Name | MS† |
|---|---|---|---|
| 340 | 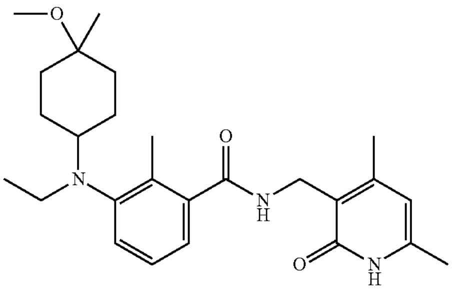 [SMILES: CCN(c1cccc(C(=O)NCc2c(C)cc(C)[nH]c2=O)c1C)C1CCC(C)(OC)CC1] | N-((4,6-dimethyl-2-oxo-1,2-dihydropyridin-3-yl)methyl)-3-(ethyl(4-methoxy-4-methylcyclohexyl) amino)-2-methylbenzamide | 440.45 |
| 341 | 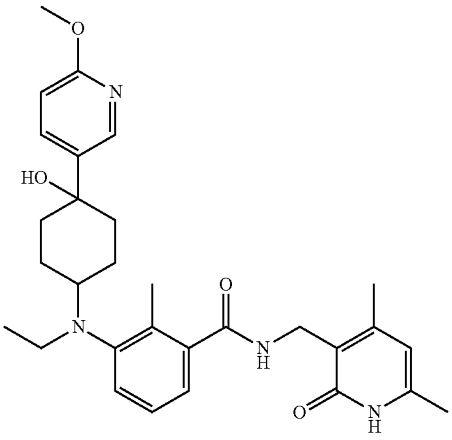 [SMILES: CCN(c1cccc(C(=O)NCc2c(C)cc(C)[nH]c2=O)c1C)C1CCC(O)(c2ccc(OC)nc2)CC1] | N-((4,6-dimethyl-2-oxo-1,2-dihydropyridin-3-yl)methyl)-3-(ethyl(4-hydroxy-4-(6-methoxypyridin-3-yl)cyclohexyl)amino)-2-methylbenzamide | 519.3 |
| 342 | 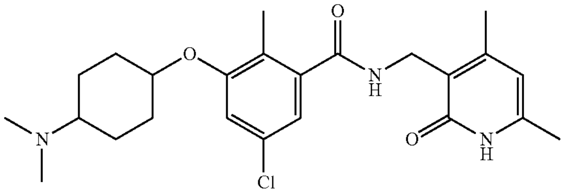 | 5-chloro-N-((4,6-dimethyl-2-oxo-1,2-dihydropyridin-3-yl)methyl)-3-((4-(dimethylamino) cyclohexyl)oxy)-2-methylbenzamide | 446.3 |
| 343 | 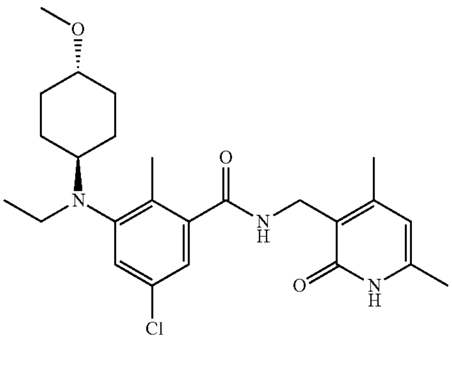 [SMILES: CCN(c1cc(Cl)cc(C(=O)NCc2c(C)cc(C)[nH]c2=O)c1C)[C@H]1CC[C@H](OC)CC1] | 5-chloro-N-((4,6-dimethyl-2-oxo-1,2-dihydropyridin-3-yl)methyl)-3-(ethyl((1r,4r)-4-methoxycyclohexyl) amino)-2-methylbenzamide | 460.4 |

TABLE 1-continued

| Compound Number | Structure | Name | MS† |
|---|---|---|---|
| 344 | 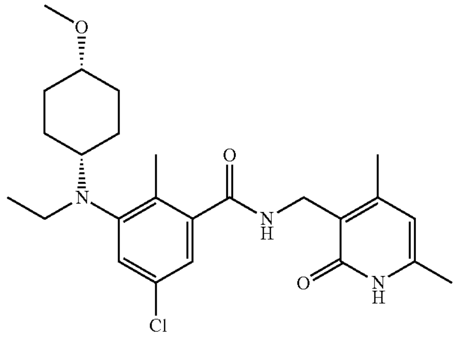 [SMILES: CCN(c1cc(Cl)cc(C(=O)NCc2c(C)cc(C)[nH]c2=O)c1C)[C@H]1CC[C@@H](OC)CC1] | 5-chloro-N-((4,6-dimethyl-2-oxo-1,2-dihydropyridin-3-yl)methyl)-3-(ethyl((1s,4s)-4-methoxycyclohexyl) amino)-2-methylbenzamide | 460.3 |
| 345 | 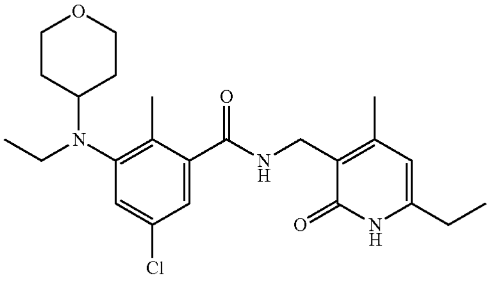 [SMILES: CCc1cc(C)c(CNC(=O)c2cc(Cl)cc(N(CC)C3CCOCC3)c2C)c(=O)[nH]1] | 5-chloro-3-(ethyl(tetrahydro-2H-pyran-4-yl)amino)-N-((6-ethyl-4-methyl-2-oxo-1,2-dihydropyridin-3-yl)methyl)-2-methylbenzamide | 446.3 |
| 346 | 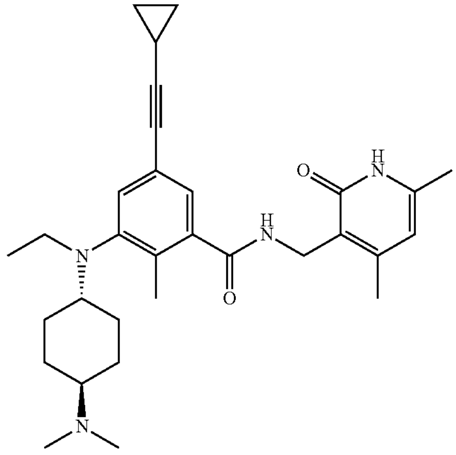 [SMILES: CCN(c1cc(C#CC2CC2)cc(C(=O)NCc2c(C)cc(C)[nH]c2=O)c1C)[C@H]1CC[C@H](N(C)C)CC1] | 5-(cyclopropylethynyl)-N-((4,6-dimethyl-2-oxo-1,2-dihydropyridin-3-yl)methyl)-3-(((1r,4r)-4-(dimethylamino) cyclohexyl)(ethyl) amino)-2-methylbenzamide | 503.5 |
| 347 | 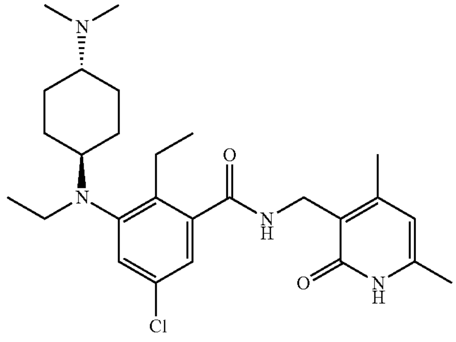 [SMILES: CCc1c(C(=O)NCc2c(C)cc(C)[nH]c2=O)cc(Cl)cc1N(CC)[C@H]1CC[C@H](N(C)C)CC1] | 5-chloro-N-((4,6-dimethyl-2-oxo-1,2-dihydropyridin-3-yl)methyl)-3-(((1r, 4r)-4-(dimethylamino) cyclohexyl) (ethyl)amino)-2-ethylbenzamide | 487.2 |

TABLE 1-continued

| Compound Number | Structure | Name | MS† |
|---|---|---|---|
| 348 | 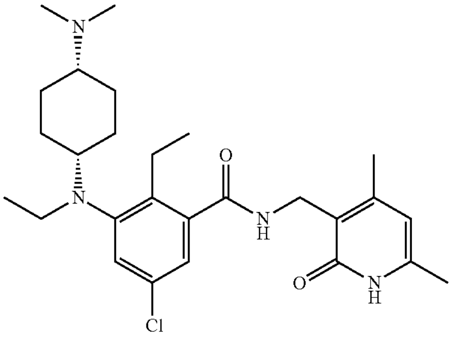 [SMILES: CCc1c(C(=O)NCc2c(C)cc(C)[nH]c2=O)cc(Cl)cc1N(CC)[C@H]1CC[C@@H](N(C)C)CC1] | 5-chloro-N-((4,6-dimethyl-2-oxo-1,2-dihydropyridin-3-yl)methyl)-3-(((1s,4s)-4-(dimethylamino) cyclohexyl)(ethyl) amino)-2-ethylbenzamide | 487.2 |
| 349 | 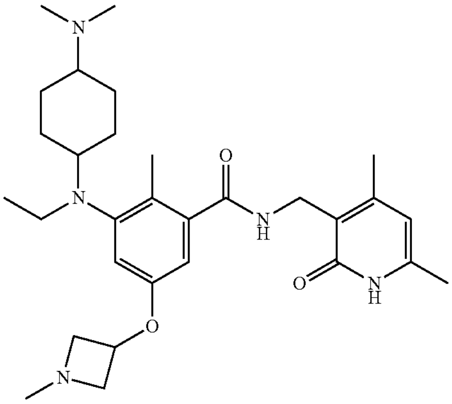 [SMILES: CCN(c1cc(OC2CN(C)C2)cc(C(=O)NCc2c(C)cc(C)[nH]c2=O)c1C)C1CCC(N(C)C)CC1] | N-((4,6-dimethyl-2-oxo-1,2-dihydropyridin-3-yl)methyl)-3-((4-(dimethylamino) cyclohexyl)(ethyl) amino)-2-methyl-5-((1-methylazetidin-3-yl)oxy)benzamide | 524.6 |
| 350 | 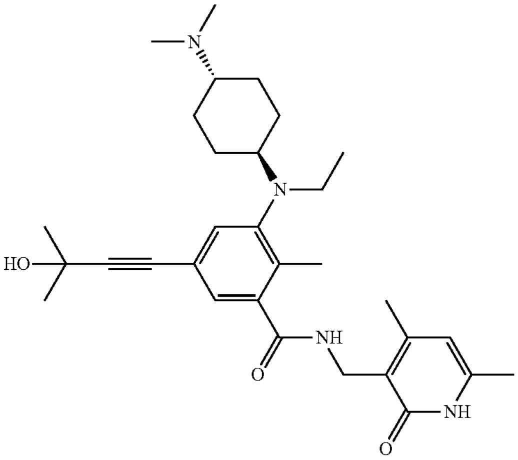 [SMILES: CCN(c1cc(C#CC(C)(C)O)cc(C(=O)NCc2c(C)cc(C)[nH]c2=O)c1C)[C@H]1CC[C@H](N(C)C)CC1] | N-((4,6-dimethyl-2-oxo-1,2-dihydropyridin-3-yl)methyl)-3-(((1r,4r)-4-(dimethylamino) cyclohexyl)(ethyl) amino)-5-(3-hydroxy-3-methylbut-1-yn-1-yl)-2-methylbenzamide | 521.5 |

TABLE 1-continued

| Compound Number | Structure | Name | MS† |
|---|---|---|---|
| 351 | 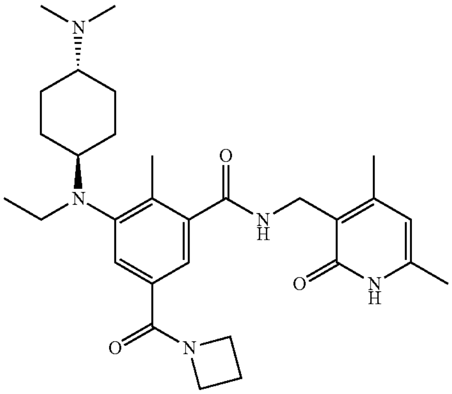 [SMILES: CCN(c1cc(C(=O)N2CCC2)cc(C(=O)NCc2c(C)cc(C)[nH]c2=O)c1C)[C@H]1CC[C@H](N(C)C)CC1] | 5-(azetidine-1-carbonyl)-N-((4,6-dimethyl-2-oxo-1,2-dihydropyridin-3-yl)methyl)-3-(((1r,4r)-4-(dimethylamino)cyclohexyl)(ethyl)amino)-2-methylbenzamide | 522.8 |
| 352 | 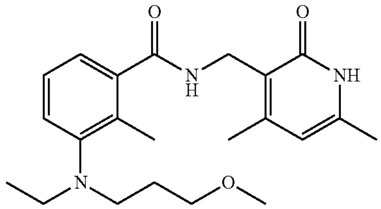 [SMILES: CCN(CCCOC)c1cccc(C(=O)NCc2c(C)cc(C)[nH]c2=O)c1C] | N-((4,6-dimethyl-2-oxo-1,2-dihydropyridin-3-yl)methyl)-3-(ethyl(3-methoxypropyl)amino)-2-methylbenzamide | 386.4 |
| 353 | 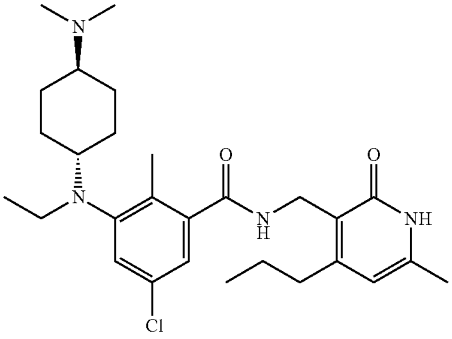 [SMILES: CCCc1cc(C)[nH]c(=O)c1CNC(=O)c1cc(Cl)cc(N(CC)[C@H]2CC[C@H](N(C)C)CC2)c1C] | 5-chloro-3-(((1r,4r)-4-(dimethylamino)cyclohexyl)(ethyl)amino)-2-methyl-N-((6-methyl-2-oxo-4-propyl-1,2-dihydropyridin-3-yl)methyl)benzamide | 501.5 |
| 354 | 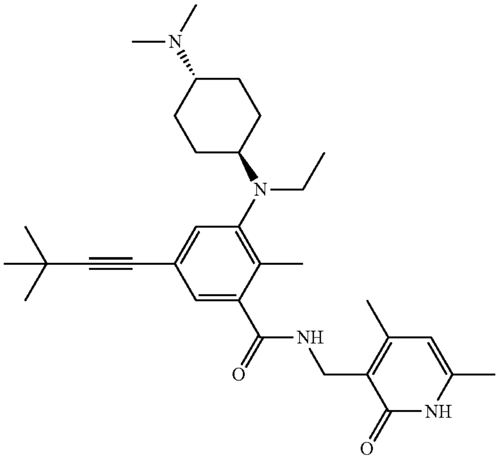 [SMILES: CCN(c1cc(C#CC(C)(C)C)cc(C(=O)NCc2c(C)cc(C)[nH]c2=O)c1C)[C@H]1CC[C@H](N(C)C)CC1] | N-((4,6-dimethyl-2-oxo-1,2-dihydropyridin-3-yl)methyl)-3-(((1r,4r)-4-(dimethylamino)cyclohexyl)(ethyl)amino)-5-(3,3-dimethylbut-1-yn-1-yl)-2-methylbenzamide | 519.6 |

TABLE 1-continued

| Compound Number | Structure | Name | MS† |
|---|---|---|---|
| 355 | 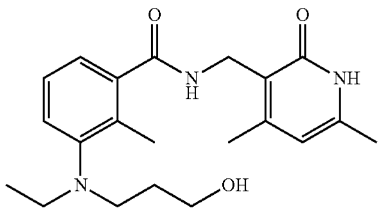 [SMILES: CCN(CCCO)c1cccc(C(=O)NCc2c(C)cc(C)[nH]c2=O)c1C] | N-((4,6-dimethyl-2-oxo-1,2-dihydropyridin-3-yl)methyl)-3-(ethyl(3-hydroxypropyl)amino)-2-methylbenzamide | 372.3 |
| 356 | 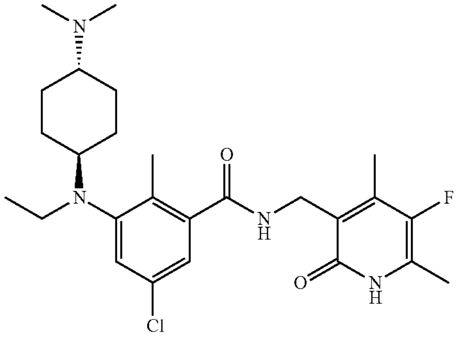 [SMILES: CCN(c1cc(Cl)cc(C(=O)NCc2c(C)c(F)c(C)[nH]c2=O)c1C)[C@H]1CC[C@H](N(C)C)CC1] | 5-chloro-3-(((1r,4r)-4-(dimethylamino) cyclohexyl)(ethyl) amino)-N-((5-fluoro-4,6-dimethyl-2-oxo-1,2-dihydropyridin-3-yl)methyl)-2-methylbenzamide | 491.1 |
| 357 | 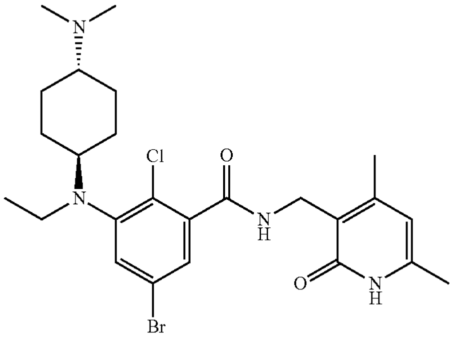 | 5-bromo-2-chloro-N-((4,6-dimethyl-2-oxo-1,2-dihydropyridin-3-yl)methyl)-3-(((1r,4r)-4-(dimethylamino) cyclohexyl)(ethyl) amino)benzamide | 539.25 |
| 358 | 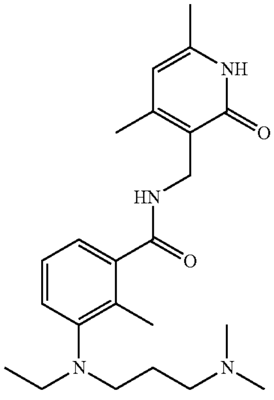 [SMILES: CCN(CCCN(C)C)c1cccc(C(=O)NCc2c(C)cc(C)[nH]c2=O)c1C] | N-((4,6-dimethyl-2-oxo-1,2-dihydropyridin-3-yl)methyl)-3-((3-(dimethylamino)propyl) (ethyl)amino)-2-methylbenzamide | 399.4 |

TABLE 1-continued

| Compound Number | Structure | Name | MS† |
|---|---|---|---|
| 359 | 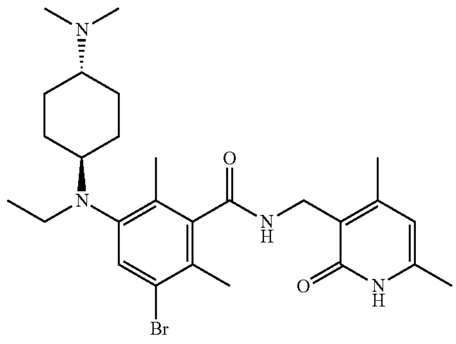 [SMILES: CCN(c1cc(Br)c(C)c(C(=O)NCc2c(C)cc(C)[nH]c2=O)c1C)[C@H]1CC[C@H](N(C)C)CC1] | 3-bromo-N-((4,6-dimethyl-2-oxo-1,2-dihydropyridin-3-yl)methyl)-5-(((1r,4r)-4-(dimethylamino) cyclohexyl)(ethyl) amino)-2,6-dimethylbenzamide | 531.4 |
| 360 | 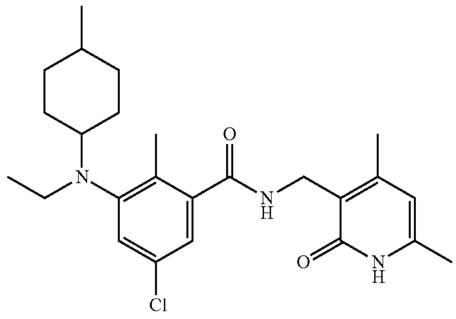 [SMILES: CCN(c1cc(Cl)cc(C(=O)NCc2c(C)cc(C)[nH]c2=O)c1C)C1CCC(C)CC1] | 5-chloro-N-((4,6-dimethyl-2-oxo-1,2-dihydropyridin-3-yl)methyl)-3-(ethyl(4-methylcyclohexyl) amino)-2-methylbenzamide | 444.4 |
| 361 | 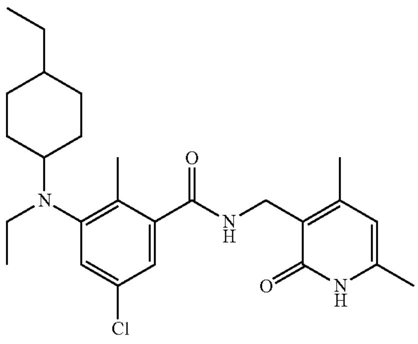 [SMILES: CCC1CCC(N(CC)c2cc(Cl)cc(C(=O)NCc3c(C)cc(C)[nH]c3=O)c2C)CC1] | 5-chloro-N-((4,6-dimethyl-2-oxo-1,2-dihydropyridin-3-yl)methyl)-3-(ethyl(4-ethylcyclohexyl)amino)-2-methylbenzamide | 458.4 |
| 362 | 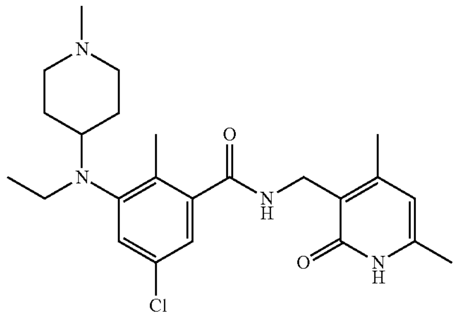 [SMILES: CCN(c1cc(Cl)cc(C(=O)NCc2c(C)cc(C)[nH]c2=O)c1C)C1CCN(C)CC1] | 5-chloro-N-((4,6-dimethyl-2-oxo-1,2-dihydropyridin-3-yl)methyl)-3-(ethyl(1-methylpiperidin-4-yl)amino)-2-methylbenzamide | 445.4 |

TABLE 1-continued

| Compound Number | Structure | Name | MS† |
|---|---|---|---|
| 363 | 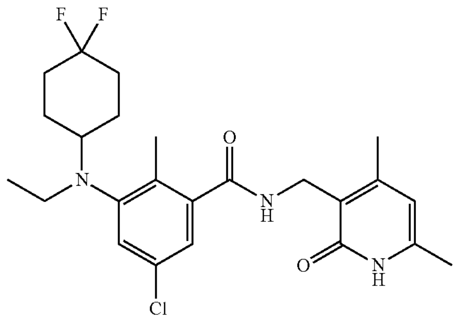 [SMILES: CCN(c1cc(Cl)cc(C(=O)NCc2c(C)cc(C)[nH]c2=O)c1C)C1CCC(F)(F)CC1] | 5-chloro-3-((4,4-difluorocyclohexyl)(ethyl)amino)-N-((4,6-dimethyl-2-oxo-1,2-dihydropyridin-3-yl)methyl)-2-methylbenzamide | 466.2 |
| 364 | 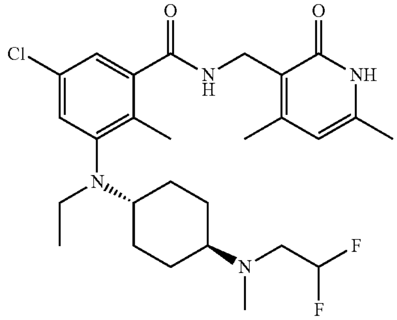 [SMILES: CCN(c1cc(Cl)cc(C(=O)NCc2c(C)cc(C)[nH]c2=O)c1C)[C@H]1CC[C@H](N(C)CC(F)F)CC1] | 5-chloro-3-(((1r,4r)-4-((2,2-difluoroethyl)(methyl)amino)cyclohexyl)(ethyl)amino)-N-((4,6-dimethyl-2-oxo-1,2-dihydropyridin-3-yl)methyl)-2-methylbenzamide | 523.5 |
| 365 | 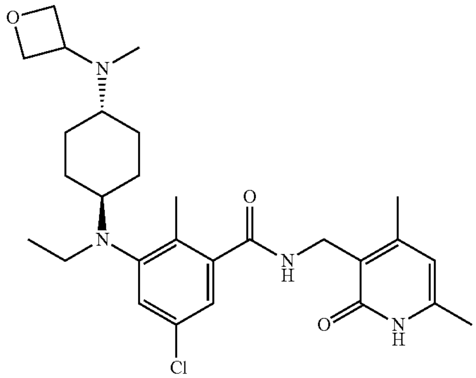 [SMILES: CCN(c1cc(Cl)cc(C(=O)NCc2c(C)cc(C)[nH]c2=O)c1C)[C@H]1CC[C@H](N(C)C2COC2)CC1] | 5-chloro-N-((4,6-dimethyl-2-oxo-1,2-dihydropyridin-3-yl)methyl)-3-(ethyl((1r,4r)-4-(methyl(oxetan-3-yl)amino)cyclohexyl)amino)-2-methylbenzamide | 515.4 |
| 366 | 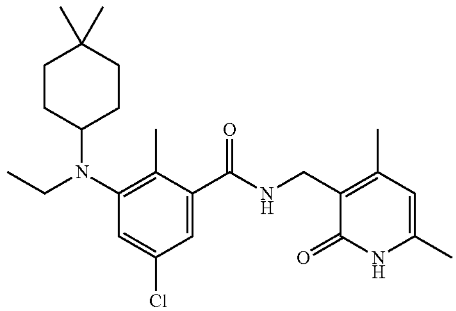 [SMILES: CCN(c1cc(Cl)cc(C(=O)NCc2c(C)cc(C)[nH]c2=O)c1C)C1CCC(C)(C)CC1] | 5-chloro-N-((4,6-dimethyl-2-oxo-1,2-dihydropyridin-3-yl)methyl)-3-((4,4-dimethylcyclohexyl)(ethyl)amino)-2-methylbenzamide | 458.4 |

TABLE 1-continued

| Compound Number | Structure | Name | MS† |
|---|---|---|---|
| 367 | 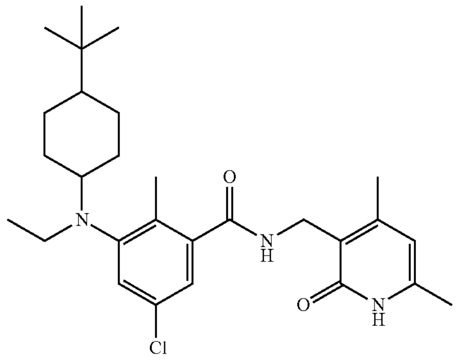 [SMILES: CCN(c1cc(Cl)cc(C(=O)NCc2c(C)cc(C)[nH]c2=O)c1C)C1CCC(C(C)(C)C)CC1] | 3-((4-(tert-butyl) cyclohexyl)(ethyl) amino)-5-chloro-N-((4,6-dimethyl-2-oxo-1,2-dihydropyridin-3-yl)methyl)-2-methylbenzamide | 486.5 |
| 368 | 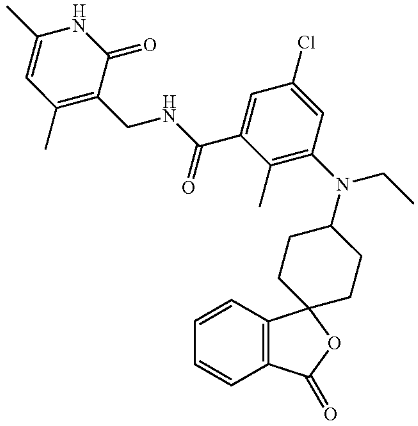 [SMILES: CCN(c1cc(Cl)cc(C(=O)NCc2c(C)cc(C)[nH]c2=O)c1C)C1CCC2(CC1)OC(=O)c1ccccc12] | 5-chloro-N-((4,6-dimethyl-2-oxo-1,2-dihydropyridin-3-yl)methyl)-3-(ethyl(3'-oxo-3'H-spiro[cyclohexane-1,1'-isobenzofuran]-4-yl)amino)-2-methylbenzamide | 548.5 |
| 369 | 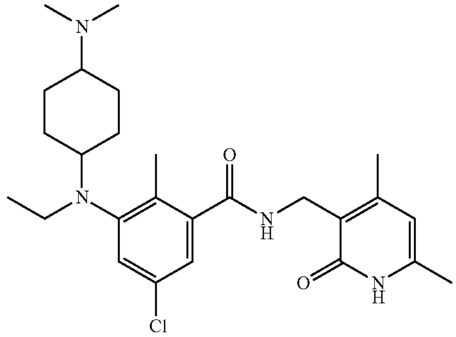 | 5-chloro-N-((4,6-dimethyl-2-oxo-1,2-dihydropyridin-3-yl)methyl)-3-(ethyl(1-isopropylpiperidin-4-yl)amino)-2-methylbenzamide | 473.5 |
| 370 | 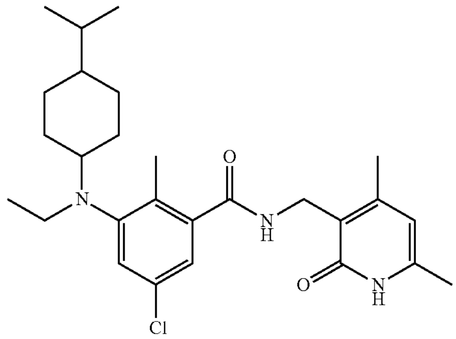 [SMILES: CCN(c1cc(Cl)cc(C(=O)NCc2c(C)cc(C)[nH]c2=O)c1C)C1CCC(C(C)C)CC1] | 5-chloro-N-((4,6-dimethyl-2-oxo-1,2-dihydropyridin-3-yl)methyl)-3-(ethyl(4-isopropylcyclohexyl) amino)-2-methylbenzamide | 472.3 |

TABLE 1-continued

| Compound Number | Structure | Name | MS† |
|---|---|---|---|
| 371 | 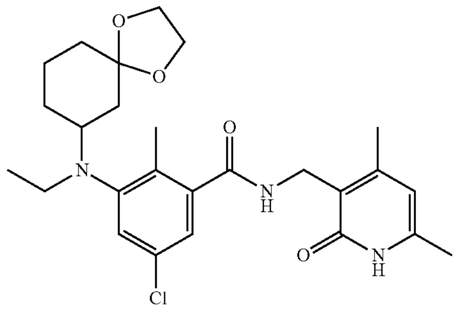 [SMILES: CCN(c1cc(Cl)cc(C(=O)NCc2c(C)cc(C)[nH]c2=O)c1C)C1CCCC2(C1)OCCO2] | 5-chloro-N-((4,6-dimethyl-2-oxo-1,2-dihydropyridin-3-yl)methyl)-3-(ethyl(1,4-dioxaspiro[4.5]decan-7-yl)amino)-2-methylbenzamide | 488.4 |
| 372 | 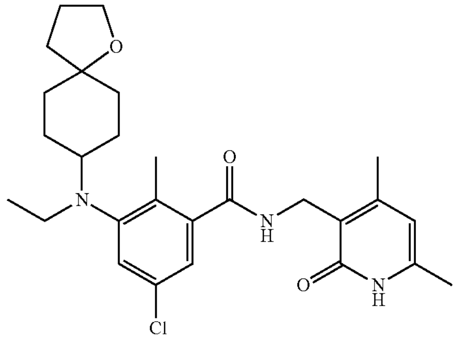 [SMILES: CCN(c1cc(Cl)cc(C(=O)NCc2c(C)cc(C)[nH]c2=O)c1C)C1CCC2(CCCO2)CC1] | 5-chloro-N-((4,6-dimethyl-2-oxo-1,2-dihydropyridin-3-yl)methyl)-3-(ethyl(1-oxaspiro[4.5]decan-8-yl)amino)-2-methylbenzamide | 486.35 |
| 373 | 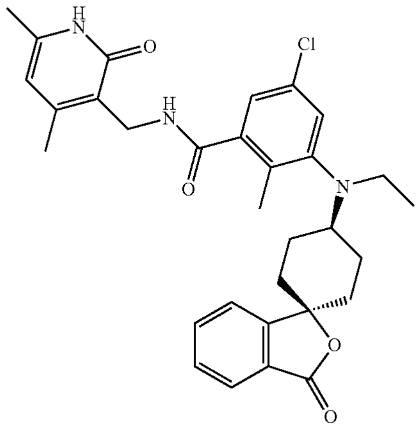 [SMILES: CCN(c1cc(Cl)cc(C(=O)NCc2c(C)cc(C)[nH]c2=O)c1C)[C@H]1CC[C@]2(CC1)OC(=O)c1ccccc12] | 5-chloro-N-((4,6-dimethyl-2-oxo-1,2-dihydropyridin-3-yl)methyl)-3-(ethyl((1s,4s)-3'-oxo-3'H-spiro[cyclohexane-1,1'-isobenzofuran]-4-yl)amino)-2-methylbenzamide | 548.4 |
| 374 | 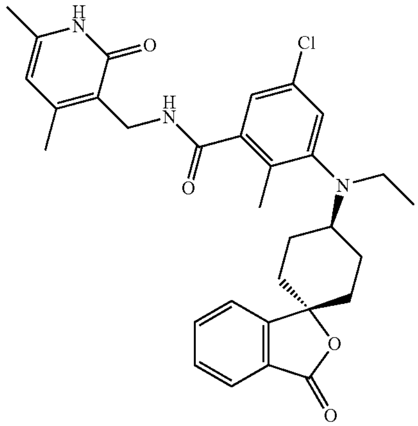 [SMILES: CCN(c1cc(Cl)cc(C(=O)NCc2c(C)cc(C)[nH]c2=O)c1C)[C@H]1CC[C@@]2(CC1)OC(=O)c1ccccc12] | 5-chloro-N-((4,6-dimethyl-2-oxo-1,2-dihydropyridin-3-yl)methyl)-3-(ethyl((1r,4r)-3'-oxo-3'H-spiro[cyclohexane-1,1'-isobenzofuran]-4-yl)amino)-2-methylbenzamide | 548.4 |

TABLE 1-continued

| Compound Number | Structure | Name | MS† |
|---|---|---|---|
| 375 | 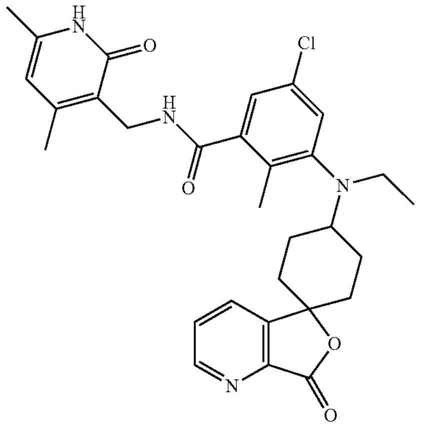 [SMILES: CCN(c1cc(Cl)cc(C(=O)NCc2c(C)cc(C)[nH]c2=O)c1C)C1CCC2(CC1)OC(=O)c1ncccc12] | 5-chloro-N-((4,6-dimethyl-2-oxo-1,2-dihydropyridin-3-yl)methyl)-3-(ethyl(7'-oxo-7'H-spiro[cyclohexane-1,5'-furo[3,4-b]pyridin]-4-yl)amino)-2-methylbenzamide | 549.3 |
| 376 | 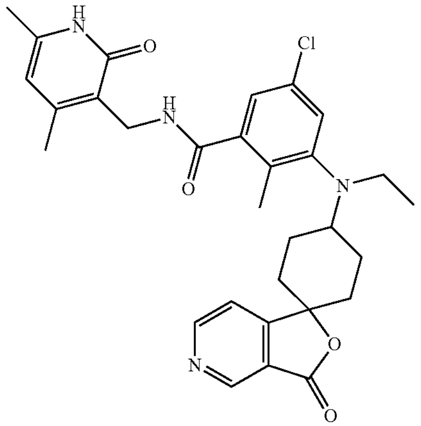 [SMILES: CCN(c1cc(Cl)cc(C(=O)NCc2c(C)cc(C)[nH]c2=O)c1C)C1CCC2(CC1)OC(=O)c1cnccc12] | 5-chloro-N-((4,6-dimethyl-2-oxo-1,2-dihydropyridin-3-yl)methyl)-3-(ethyl(3'-oxo-3'H-spiro[cyclohexane-1,1'-furo[3,4-c]pyridin]-4-yl)amino)-2-methylbenzamide | 549.5 |
| 377 | 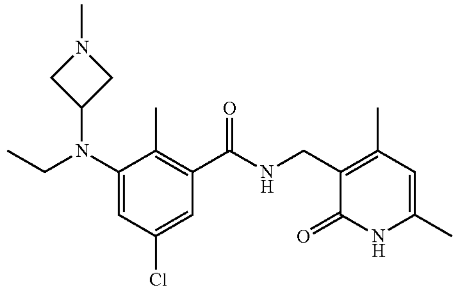 [SMILES: CCN(c1cc(Cl)cc(C(=O)NCc2c(C)cc(C)[nH]c2=O)c1C)C1CN(C)C1] | 5-chloro-N-((4,6-dimethyl-2-oxo-1,2-dihydropyridin-3-yl)methyl)-3-(ethyl(1-methylazetidin-3-yl)amino)-2-methylbenzamide | 417.3 |
| 378 | 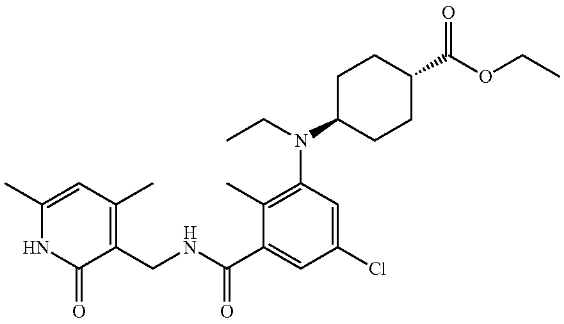 [SMILES: CCOC(=O)[C@H]1CC[C@H](N(CC)c2cc(Cl)cc(C(=O)NCc3c(C)cc(C)[nH]c3=O)c2C)CC1] | (1r,4r)-ethyl 4-((5-chloro-3-(((4,6-dimethyl-2-oxo-1,2-dihydropyridin-3-yl)methyl)carbamoyl)-2-methylphenyl)(ethyl)amino)cyclohexanecarboxylate | 502.5 |

TABLE 1-continued

| Compound Number | Structure | Name | MS† |
|---|---|---|---|
| 379 | 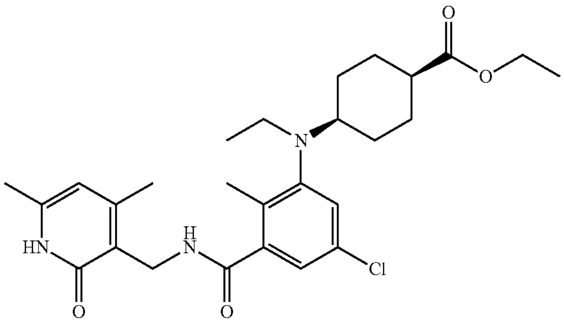 [SMILES: CCOC(=O)[C@H]1CC[C@@H](N(CC)c2cc(Cl)cc(C(=O)NCc3c(C)cc(C)[nH]c3=O)c2C)CC1] | (1s,4s)-ethyl 4-((5-chloro-3-(((4,6-dimethyl-2-oxo-1,2-dihydropyridin-3-yl)methyl)carbamoyl)-2-methylphenyl)(ethyl)amino)cyclohexane-carboxylate | 502.4 |
| 380 | 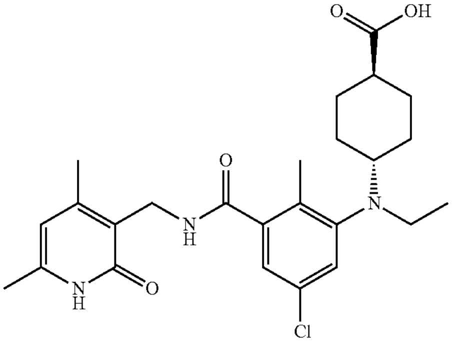 [SMILES: CCN(c1cc(Cl)cc(C(=O)NCc2c(C)cc(C)[nH]c2=O)c1C)[C@H]1CC[C@H](C(=O)O)CC1] | (1r,4r)-4-((5-chloro-3-(((4,6-dimethyl-2-oxo-1,2-dihydropyridin-3-yl)methyl)carbamoyl)-2-methylphenyl)(ethyl)amino)cyclohexanecarboxylic acid | 474.3 |
| 381 | 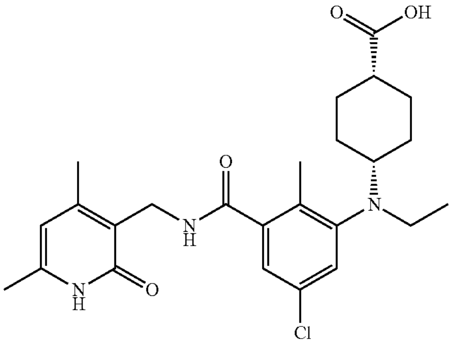 [SMILES: CCN(c1cc(Cl)cc(C(=O)NCc2c(C)cc(C)[nH]c2=O)c1C)[C@H]1CC[C@@H](C(=O)O)CC1] | (1s,4s)-4-((5-chloro-3-(((4,6-dimethyl-2-oxo-1,2-dihydropyridin-3-yl)methyl)carbamoyl)-2-methylphenyl)(ethyl)amino)cyclohexanecarboxylic acid | 474.4 |
| 382 | 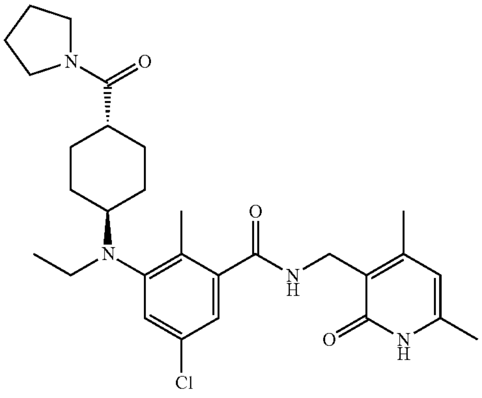 [SMILES: CCN(c1cc(Cl)cc(C(=O)NCc2c(C)cc(C)[nH]c2=O)c1C)[C@H]1CC[C@H](C(=O)N2CCCC2)CC1] | 5-chloro-N-((4,6-dimethyl-2-oxo-1,2-dihydropyridin-3-yl)methyl)-3-(ethyl((1r,4r)-4-(pyrrolidine-1-carbonyl)cyclohexyl)amino)-2-methylbenzamide | 527.5 |

TABLE 1-continued

| Compound Number | Structure | Name | MS† |
|---|---|---|---|
| 383 | 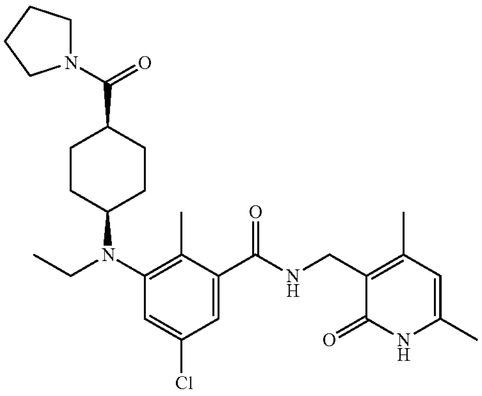 [SMILES: CCN(c1cc(Cl)cc(C(=O)NCc2c(C)cc(C)[nH]c2=O)c1C)[C@H]1CC[C@@H](C(=O)N2CCCC2)CC1] | 5-chloro-N-((4,6-dimethyl-2-oxo-1,2-dihydropyridin-3-yl)methyl)-3-(ethyl((1s,4s)-4-(pyrrolidine-1-carbonyl)cyclohexyl)amino)-2-methylbenzamide | 527.4 |
| 384 | 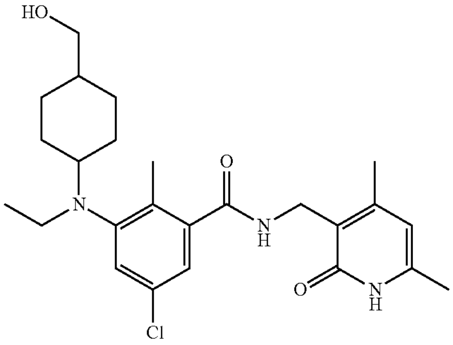 [SMILES: CCN(c1cc(Cl)cc(C(=O)NCc2c(C)cc(C)[nH]c2=O)c1C)C1CCC(CO)CC1] | 5-chloro-N-((4,6-dimethyl-2-oxo-1,2-dihydropyridin-3-yl)methyl)-3-(ethyl(4-(hydroxymethyl)cyclohexyl)amino)-2-methylbenzamide | 460.2 |
| 385 | 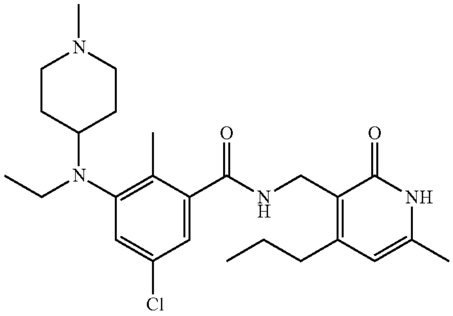 [SMILES: CCCc1cc(C)[nH]c(=O)c1CNC(=O)c1cc(Cl)cc(N(CC)C2CCN(C)CC2)c1C] | 5-chloro-3-(ethyl(1-methylpiperidin-4-yl)amino)-2-methyl-N-((6-methyl-2-oxo-4-propyl-1,2-dihydropyridin-3-yl)methyl)benzamide | 473.4 |
| 386 | 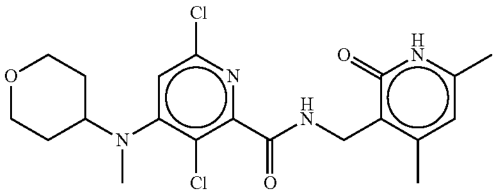 | 3,6-dichloro-N-((4,6-dimethyl-2-oxo-1,2-dihydropyridin-3-yl)methyl)-4-(methyl(tetrahydro-2H-pyran-4-yl)amino)picolinamide | 440.8 |
| 387 | 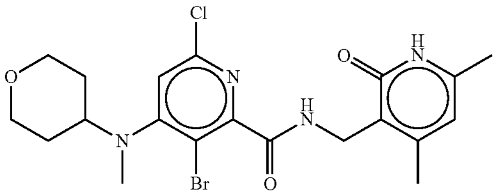 | 3-bromo-6-chloro-N-((4,6-dimethyl-2-oxo-1,2-dihydropyridin-3-yl)methyl)-4-(methyl(tetrahydro-2H-pyran-4-yl)amino)picolinamide | 485 |

TABLE 1-continued

| Compound Number | Structure | Name | MS† |
|---|---|---|---|
| 388 | 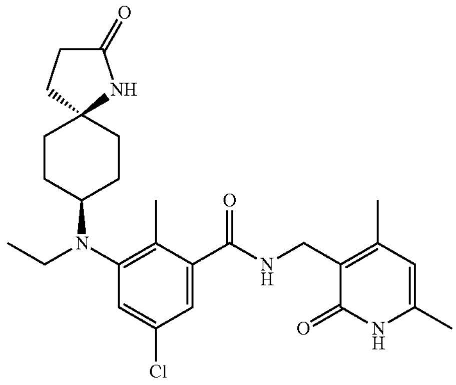 [SMILES: CCN(c1cc(Cl)cc(C(=O)NCc2c(C)cc(C)[nH]c2=O)c1C)[C@H]1CC[C@]2(CCC(=O)N2)CC1] | 5-chloro-N-((4,6-dimethyl-2-oxo-1,2-dihydropyridin-3-yl)methyl)-3-(ethyl((5s,8s)-2-oxo-1-azaspiro[4.5]decan-8-yl)amino)-2-methylbenzamide | 499.35 |
| 389 | 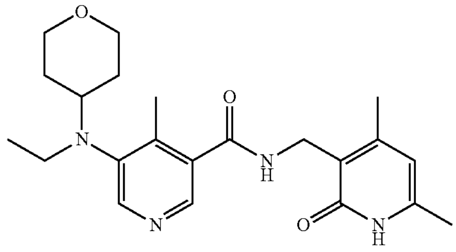 [SMILES: CCN(c1cncc(C(=O)NCc2c(C)cc(C)[nH]c2=O)c1C)C1CCOCC1] | N-((4,6-dimethyl-2-oxo-1,2-dihydropyridin-3-yl)methyl)-5-(ethyl(tetrahydro-2H-pyran-4-yl)amino)-4-methylnicotinamide | 399.5 |
| 390 | 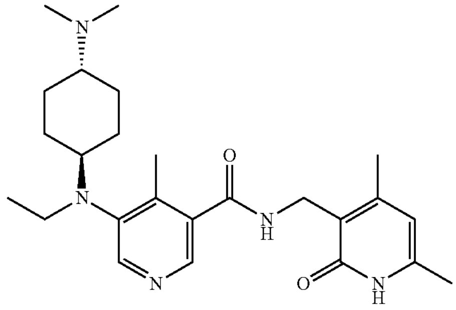 | N-((4,6-dimethyl-2-oxo-1,2-dihydropyridin-3-yl)methyl)-5-(((1r,4r)-4-(dimethylamino)cyclohexyl)(ethyl)amino)-4-methylnicotinamide | 440.5 |
| 391 | 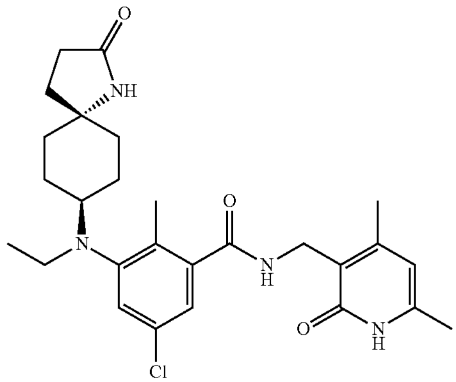 [SMILES: CCN(c1cc(Cl)cc(C(=O)NCc2c(C)cc(C)[nH]c2=O)c1C)[C@H]1CC[C@@]2(CCC(=O)N2)CC1] | 5-chloro-N-((4,6-dimethyl-2-oxo-1,2-dihydropyridin-3-yl)methyl)-3-(ethyl((5r,8r)-2-oxo-1-azaspiro[4.5]decan-8-yl)amino)-2-methylbenzamide | 499.4 |

TABLE 1-continued

| Compound Number | Structure | Name | MS† |
| --- | --- | --- | --- |
| 392 | 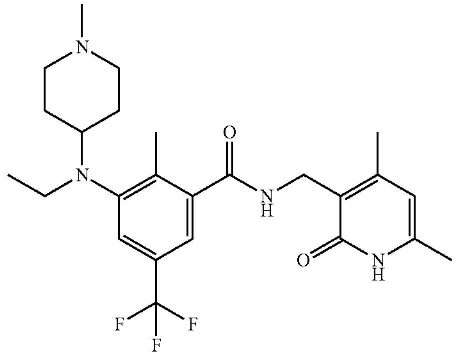 [SMILES: CCN(c1cc(C(F)(F)F)cc(C(=O)NCc2c(C)cc(C)[nH]c2=O)c1C)C1CCN(C)CC1] | N-((4,6-dimethyl-2-oxo-1,2-dihydropyridin-3-yl)methyl)-3-(ethyl(1-methylpiperidin-4-yl)amino)-2-methyl-5-(trifluoromethyl) benzamide | 501.3 |
| 393 | 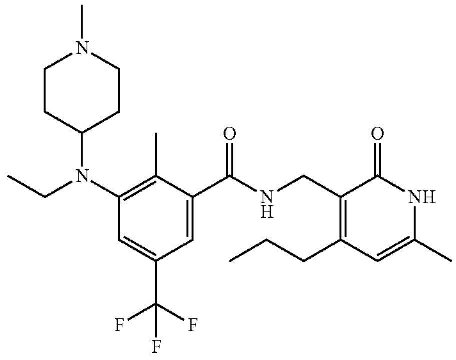 | 3-(ethyl(1-methylpiperidin-4-yl)amino)-2-methyl-N-((6-methyl-2-oxo-4-propyl-1,2-dihydropyridin-3-yl)methyl)-5-(trifluoromethyl) benzamide | 505.2 |
| 394 | 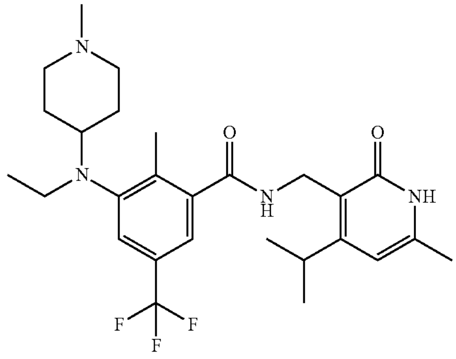 | 3-(ethyl(1-methylpiperidin-4-yl)amino)-N-((4-isopropyl-6-methyl-2-oxo-1,2-dihydropyridin-3-yl)methyl)-2-methyl-5-(trifluoromethyl) benzamide | 529.2 |
| 395 | 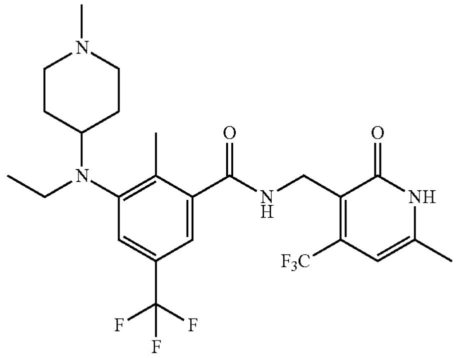 | 3-(ethyl(1-methylpiperidin-4-yl)amino)-2-methyl-N-((6-methyl-2-oxo-4-(trifluoromethyl)-1,2-dihydropyridin-3-yl)methyl)-5-(trifluoromethyl) benzamide | 555.2 |

TABLE 1-continued

| Compound Number | Structure | Name | MS† |
|---|---|---|---|
| 396 | 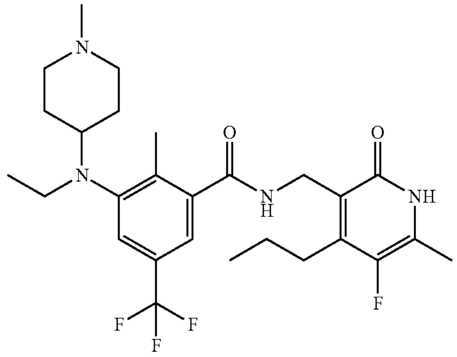 [SMILES: CCCc1c(F)c(C)[nH]c(=O)c1CNC(=O)c1cc(C(F)(F)F)cc(N(CC)C2CCN(C)CC2)c1C] | 3-(ethyl(1-methylpiperidin-4-yl)amino)-N-((5-fluoro-6-methyl-2-oxo-4-propyl-1,2-dihydropyridin-3-yl)methyl)-2-methyl-5-(trifluoromethyl) benzamide | 525.6 |
| 397 | 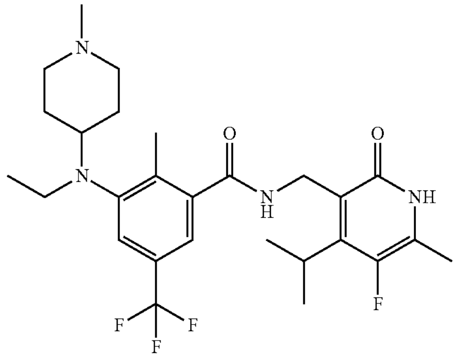 [SMILES: CCN(c1cc(C(F)(F)F)cc(C(=O)NCc2c(C(C)C)c(F)c(C)[nH]c2=O)c1C)C1CCN(C)CC1] | 3-(ethyl(1-methylpiperidin-4-yl)amino)-N-((5-fluoro-4-isopropyl-6-methyl-2-oxo-1,2-dihydropyridin-3-yl)methyl)-2-methyl-5-(trifluoromethyl) benzamide | 525.6 |
| 398 | 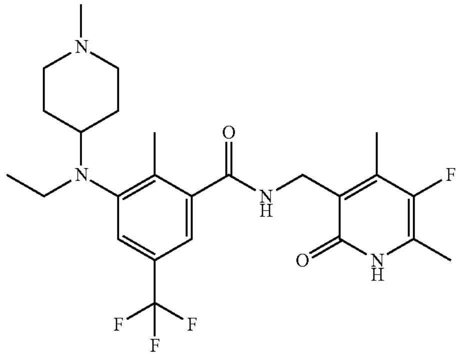 [SMILES: CCN(c1cc(C(F)(F)F)cc(C(=O)NCc2c(C)c(F)c(C)[nH]c2=O)c1C)C1CCN(C)CC1] | 3-(ethyl(1-methylpiperidin-4-yl)amino)-N-((5-fluoro-4,6-dimethyl-2-oxo-1,2-dihydropyridin-3-yl)methyl)-2-methyl-5-(trifluoromethyl) benzamide | 497.5 |
| 399 | 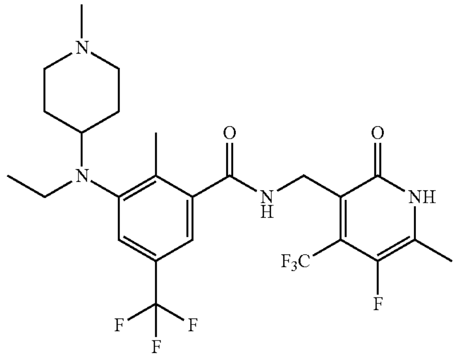 [SMILES: CCN(c1cc(C(F)(F)F)cc(C(=O)NCc2c(C(F)(F)F)c(F)c(C)[nH]c2=O)c1C)C1CCN(C)CC1] | 3-(ethyl(1-methylpiperidin-4-yl)amino)-N-((5-fluoro-6-methyl-2-oxo-4-(trifluoromethyl)-1,2-dihydropyridin-3-yl)methyl)-2-methyl-5-(trifluoromethyl) benzamide | 551.5 |

TABLE 1-continued

| Compound Number | Structure | Name | MS† |
|---|---|---|---|
| 400 | 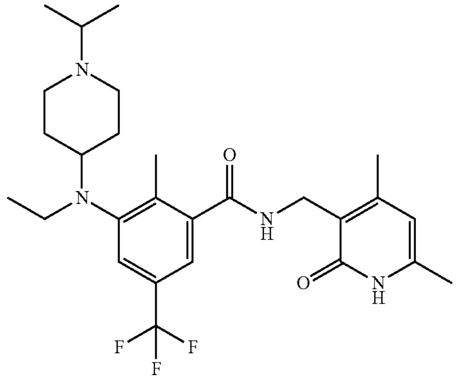 [SMILES: CCN(c1cc(C(F)(F)F)cc(C(=O)NCc2c(C)cc(C)[nH]c2=O)c1C)C1CCN(C(C)C)CC1] | N-((4,6-dimethyl-2-oxo-1,2-dihydropyridin-3-yl)methyl)-3-(ethyl(1-isopropylpiperidin-4-yl)amino)-2-methyl-5-(trifluoromethyl) benzamide | 507.2 |
| 401 | 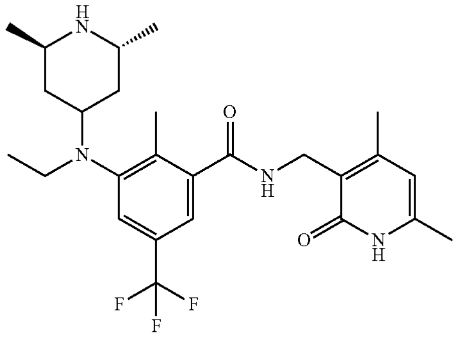 [SMILES: CCN(c1cc(C(F)(F)F)cc(C(=O)NCc2c(C)cc(C)[nH]c2=O)c1C)C1C[C@@H](C)N[C@H](C)C1] | N-((4,6-dimethyl-2-oxo-1,2-dihydropyridin-3-yl)methyl)-3-(((2R,6R)-2,6-dimethylpiperidin-4-yl)(ethyl)amino)-2-methyl-5-(trifluoromethyl) benzamide | 493.1 |
| 402 | 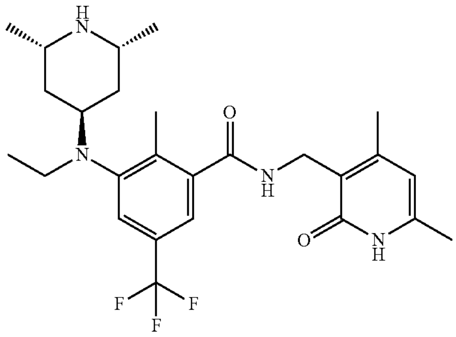 [SMILES: CCN(c1cc(C(F)(F)F)cc(C(=O)NCc2c(C)cc(C)[nH]c2=O)c1C)[C@@H]1C[C@@H](C)N[C@@H](C)C1] | N-((4,6-dimethyl-2-oxo-1,2-dihydropyridin-3-yl)methyl)-3-(((2S,4s,6R)-2,6-dimethylpiperidin-4-yl)(ethyl)amino)-2-methyl-5-(trifluoromethyl) benzamide | 493.2 |
| 403 | 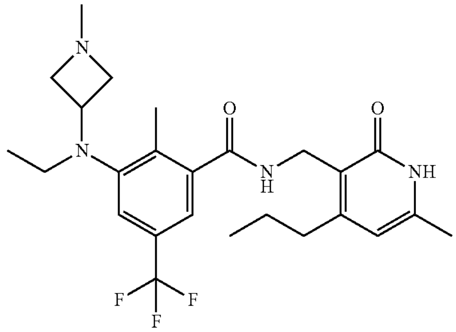 [SMILES: CCCc1cc(C)[nH]c(=O)c1CNC(=O)c1cc(C(F)(F)F)cc(N(CC)C2CN(C)C2)c1C] | 3-(ethyl(1-methylazetidin-3-yl)amino)-2-methyl-N-((6-methyl-2-oxo-4-propyl-1,2-dihydropyridin-3-yl)methyl)-5-(trifluoromethyl) benzamide | 480.5 |

TABLE 1-continued

| Compound Number | Structure | Name | MS† |
|---|---|---|---|
| 404 | 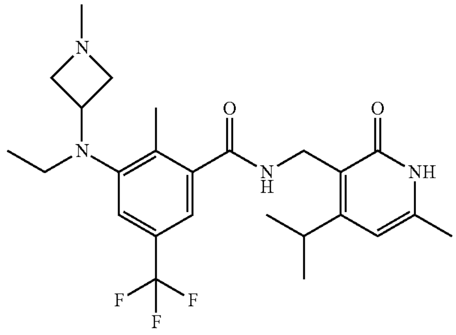 [SMILES: CCN(c1cc(C(F)(F)F)cc(C(=O)NCc2c(C(C)C)cc(C)[nH]c2=O)c1C)C1CN(C)C1] | 3-(ethyl(1-methylazetidin-3-yl)amino)-N-((4-isopropyl-6-methyl-2-oxo-1,2-dihydropyridin-3-yl)methyl)-2-methyl-5-(trifluoromethyl) benzamide | 479.5 |
| 405 | 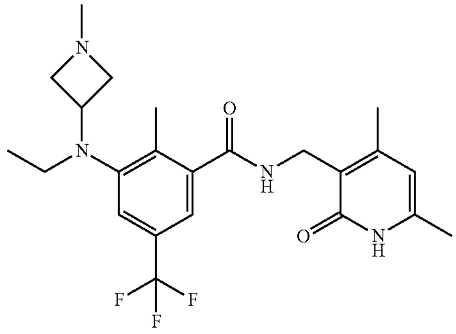 [SMILES: CCN(c1cc(C(F)(F)F)cc(C(=O)NCc2c(C)cc(C)[nH]c2=O)c1C)C1CN(C)C1] | N-((4,6-dimethyl-2-oxo-1,2-dihydropyridin-3-yl)methyl)-3-(ethyl(1-methylazetidin-3-yl)amino)-2-methyl-5-(trifluoromethyl) benzamide | 451.5 |
| 406 | 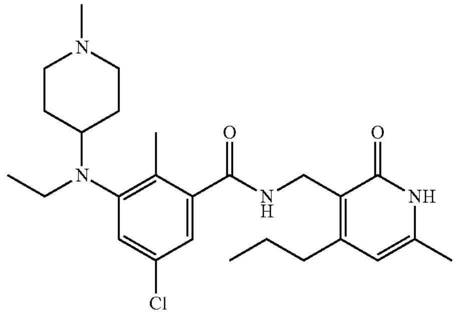 | 5-chloro-3-(ethyl(1-methylpiperidin-4-yl)amino)-2-methyl-N-((6-methyl-2-oxo-4-propyl-1,2-dihydropyridin-3-yl)methyl)benzamide | 473.1 |
| 407 | 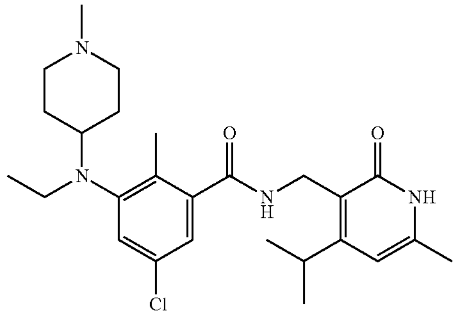 [SMILES: CCN(c1cc(Cl)cc(C(=O)NCc2c(C(C)C)cc(C)[nH]c2=O)c1C)C1CCN(C)CC1] | 5-chloro-3-(ethyl(1-methylpiperidin-4-yl)amino)-N-((4-isopropyl-6-methyl-2-oxo-1,2-dihydropyridin-3-yl)methyl)-2-methylbenzamide | 495.2 |

TABLE 1-continued

| Compound Number | Structure | Name | MS† |
|---|---|---|---|
| 408 | 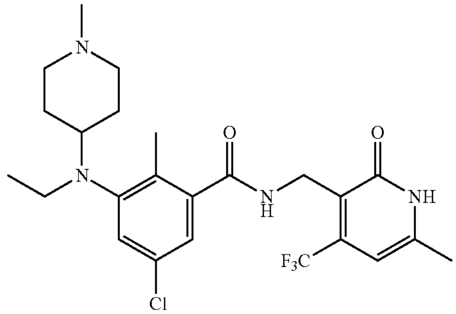 [SMILES: CCN(c1cc(Cl)cc(C(=O)NCc2c(C(F)(F)F)cc(C)[nH]c2=O)c1C)C1CCN(C)CC1] | 5-chloro-3-(ethyl(1-methylpiperidin-4-yl)amino)-2-methyl-N-((6-methyl-2-oxo-4-(trifluoromethyl)-1,2-dihydropyridin-3-yl)methyl)benzamide | 499.1 |
| 409 | 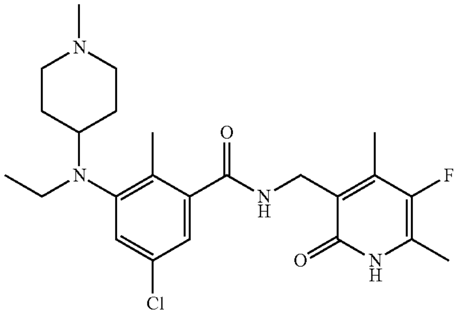 [SMILES: CCN(c1cc(Cl)cc(C(=O)NCc2c(C)c(F)c(C)[nH]c2=O)c1C)C1CCN(C)CC1] | 5-chloro-3-(ethyl(1-methylpiperidin-4-yl)amino)-N-((5-fluoro-4,6-dimethyl-2-oxo-1,2-dihydropyridin-3-yl)methyl)-2-methylbenzamide | 463.5 |
| 410 | 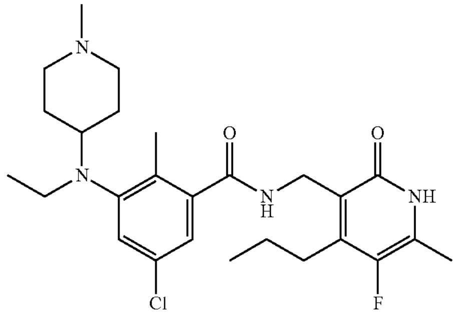 | 5-chloro-3-(ethyl(1-methylpiperidin-4-yl)amino)-N-((5-fluoro-6-methyl-2-oxo-4-propyl-1,2-dihydropyridin-3-yl)methyl)-2-methylbenzamide | 491.5 |
| 411 | 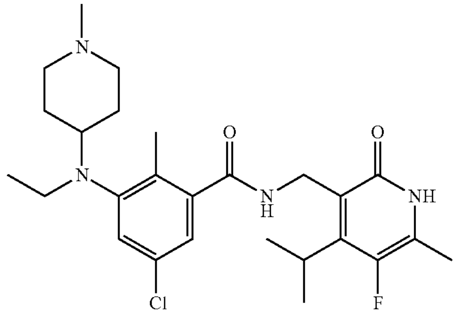 [SMILES: CCN(c1cc(Cl)cc(C(=O)NCc2c(C(C)C)c(F)c(C)[nH]c2=O)c1C)C1CCN(C)CC1] | 5-chloro-3-(ethyl(1-methylpiperidin-4-yl)amino)-N-((5-fluoro-4-isopropyl-6-methyl-2-oxo-1,2-dihydropyridin-3-yl)methyl)-2-methylbenzamide | 491.5 |
| 412 | 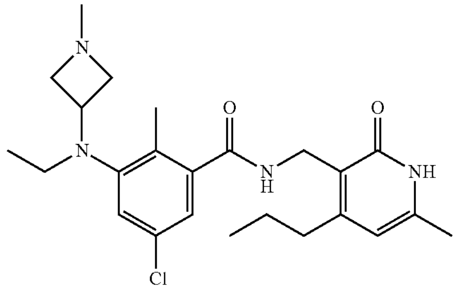 [SMILES: CCCc1cc(C)[nH]c(=O)c1CNC(=O)c1cc(Cl)cc(N(CC)C2CN(C)C2)c1C] | 5-chloro-3-(ethyl(1-methylazetidin-3-yl)amino)-2-methyl-N-((6-methyl-2-oxo-4-propyl-1,2-dihydropyridin-3-yl)methyl)benzamide | 445.5 |

TABLE 1-continued

| Compound Number | Structure | Name | MS† |
|---|---|---|---|
| 413 | 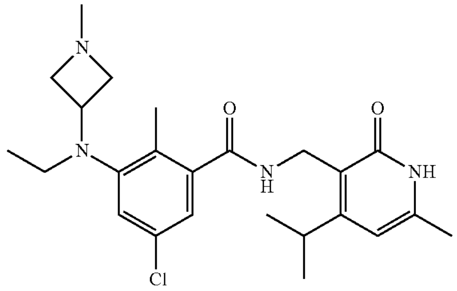 [SMILES: CCN(c1cc(Cl)cc(C(=O)NCc2c(C(C)C)cc(C)[nH]c2=O)c1C)C1CN(C)C1] | 5-chloro-3-(ethyl(2-methylazetidin-3-yl)amino)-N-((4-isopropyl-6-methyl-2-oxo-1,2-dihydropyridin-3-yl)methyl)-2-methylbenzamide | 445.6 |
| 414 | 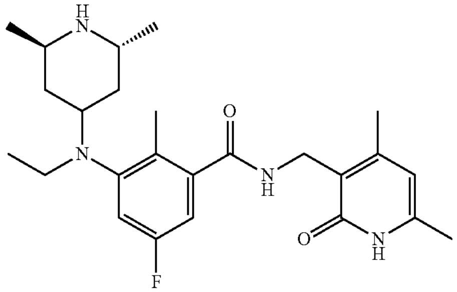 [SMILES: CCN(c1cc(F)cc(C(=O)NCc2c(C)cc(C)[nH]c2=O)c1C)C1C[C@@H](C)N[C@H](C)C1] | N-((4,6-dimethyl-2-oxo-1,2-dihydropyridin-3-yl)methyl)-3-(((2R,6R)-2,6-dimethylpiperidin-4-yl)(ethyl)amino)-5-fluoro-2-methylbenzamide | 443.1 |
| 415 | 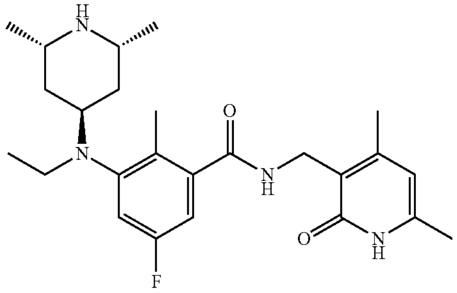 [SMILES: CCN(c1cc(F)cc(C(=O)NCc2c(C)cc(C)[nH]c2=O)c1C)[C@@H]1C[C@@H](C)N[C@@H](C)C1] | N-((4,6-dimethyl-2-oxo-1,2-dihydropyridin-3-yl)methyl)-3-(((2S,4s,6R)-2,6-dimethylpiperidin-4-yl)(ethyl)amino)-5-fluoro-2-methylbenzamide | 443.2 |
| 416 | 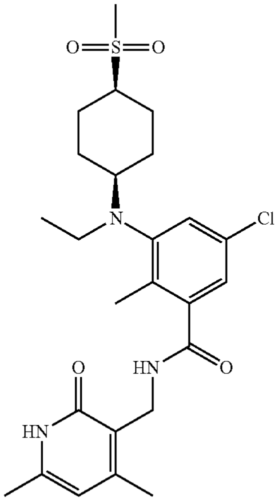 [SMILES: CCN(c1cc(Cl)cc(C(=O)NCc2c(C)cc(C)[nH]c2=O)c1C)[C@H]1CC[C@@H](S(C)(=O)=O)CC1] | 5-chloro-N-((4,6-dimethyl-2-oxo-1,2-dihydropyridin-3-yl)methyl)-3-(ethyl((1s,4s)-4-(methylsulfonyl)cyclohexyl)amino)-2-methylbenzamide | 508.1 |

TABLE 1-continued

| Compound Number | Structure | Name | MS† |
|---|---|---|---|
| 417 | 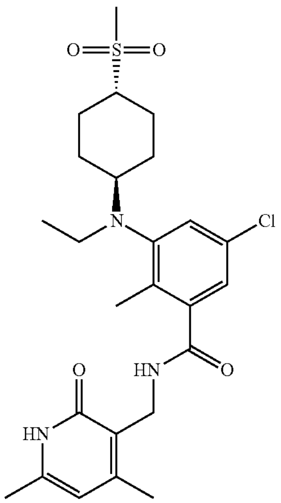 [SMILES: CCN(c1cc(Cl)cc(C(=O)NCc2c(C)cc(C)[nH]c2=O)c1C)[C@H]1CC[C@H](S(C)(=O)=O)CC1] | 5-chloro-N-((4,6-dimethyl-2-oxo-1,2-dihydropyridin-3-yl)methyl)-3-(ethyl((1r,4r)-4-(methylsulfonyl)cyclohexyl)amino)-2-methylbenzamide | 508 |
| 418 | 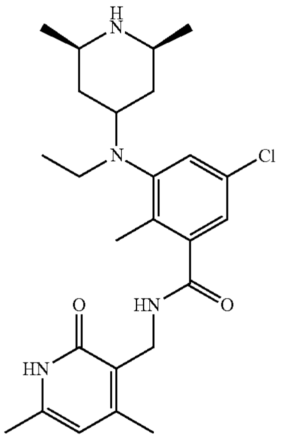 [SMILES: CCN(c1cc(Cl)cc(C(=O)NCc2c(C)cc(C)[nH]c2=O)c1C)C1C[C@@H](C)N[C@@H](C)C1] | 5-chloro-N-((4,6-dimethyl-2-oxo-1,2-dihydropyridin-3-yl)methyl)-3-(((2S,6R)-2,6-dimethylpiperidin-4-yl)(ethyl)amino)-2-methylbenzamide | |

*The cis/trans stereochemical assignments of Compounds 58/59, 60/61, 107/108, and 416/417 are arbitrarily assigned.

†MS—Mass spectrometry of sample. This can be recorded in positive or negative ion modes and potential ions include M, M + 1, M + 23 (M + Na) and M − 1.

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl or n-hexyl.

In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "cycloalkyl" refers to a saturated or unsaturated nonaromatic hydrocarbon mono- or multi-ring (e.g., fused, bridged, or spiro rings) system having 3 to 30 carbon atoms (e.g., $C_3$-$C_{10}$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, and adamantyl. The term "heterocycloalkyl" refers to a saturated or unsaturated nonaromatic 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, or Se), unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, tetrahyrofuranyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl, 1,4-dioxaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, 3'H-spiro[cyclohexane-1,1'-furo[3,4-c]pyridin]-yl, and the like.

The term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

An "arylalkyl" or an "aralkyl" moiety is an alkyl substituted with an aryl (e.g., phenylmethyl (benzyl)). An "alkylaryl" moiety is an aryl substituted with an alkyl (e.g., methylphenyl).

As used herein, "alkyl linker" is intended to include $C_1$, $C_2$, $C_3$, $C_4$, $C_5$ or $C_6$ straight chain (linear) saturated divalent aliphatic hydrocarbon groups and $C_3$, $C_4$, $C_5$ or $C_6$ branched saturated aliphatic hydrocarbon groups. For example, $C_1$-$C_6$ alkyl linker is intended to include $C_1$, $C_2$, $C_3$, $C_4$, $C_5$ and $C_6$ alkyl linker groups. Examples of alkyl linker include, moieties having from one to six carbon atoms, such as, but not limited to, methyl ($-CH_2-$), ethyl ($-CH_2CH_2-$), n-propyl ($-CH_2CH_2CH_2-$), i-propyl ($-CHCH_3CH_2-$), n-butyl ($-CH_2CH_2CH_2CH_2-$), s-butyl ($-CHCH_3CH_2CH_2-$), i-butyl ($-C(CH_3)_2CH_2-$), n-pentyl ($-CH_2CH_2CH_2CH_2CH_2-$), s-pentyl ($-CHCH_3CH_2CH_2CH_2-$) or n-hexyl ($-CH_2CH_2CH_2CH_2CH_2CH_2-$).

"Alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

The term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

The term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

"Aryl" includes groups with aromaticity, including "conjugated," or multicyclic systems with at least one aromatic ring and do not contain any heteroatom in the ring structure. Examples include phenyl, benzyl, 1,2,3,4-tetrahydronaphthalenyl, etc.

"Heteroaryl" groups are aryl groups, as defined above, except having from one to four heteroatoms in the ring structure, and may also be referred to as "aryl heterocycles" or "heteroaromatics." As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and $S(O)_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthrydine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl).

As used herein, "carbocycle" or "carbocyclic ring" is intended to include any stable monocyclic, bicyclic or tricyclic ring having the specified number of carbons, any of which may be saturated, unsaturated, or aromatic. Carbocycle includes cycloalkyl and aryl. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]bicyclooctane, [4.3.0]bicyclononane, and [4.4.0]bicyclodecane and [2.2.2] bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included.

As used herein, "heterocycle" or "heterocyclic group" includes any ring structure (saturated, unsaturated, or aromatic) which contains at least one ring heteroatom (e.g., N, O or S). Heterocycle includes heterocycloalkyl and heteroaryl. Examples of heterocycles include, but are not limited to, morpholine, pyrrolidine, tetrahydrothiophene, piperidine, piperazine, oxetane, pyran, tetrahydropyran, azetidine, and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thenooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

The term "substituted," as used herein, means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., $R_1$) occurs more than one time in any constituent or formula for a compound, its definition at each occurrence is independent of its definition at every other occurrence. Thus, for example, if a group is shown to be substituted with 0-2 $R_1$ moieties, then the group may optionally be substituted with up to two $R_1$ moieties and $R_1$ at each occurrence is selected independently from the definition of $R_1$. Also, combinations of substituents and/or variables are permissible, but only if such combinations result in stable compounds.

The term "hydroxy" or "hydroxyl" includes groups with an —OH or —$O^-$.

As used herein, "halo" or "halogen" refers to fluoro, chloro, bromo and iodo. The term "perhalogenated" generally refers to a moiety wherein all hydrogen atoms are replaced by halogen atoms. The term "haloalkyl" or "haloalkoxyl" refers to an alkyl or alkoxyl substituted with one or more halogen atoms.

The term "carbonyl" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

The term "carboxyl" refers to —COOH or its $C_1$-$C_6$ alkyl ester.

"Acyl" includes moieties that contain the acyl radical (R—C(O)—) or a carbonyl group. "Substituted acyl" includes acyl groups where one or more of the hydrogen atoms are replaced by, for example, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aroyl" includes moieties with an aryl or heteroaromatic moiety bound to a carbonyl group. Examples of aroyl groups include phenylcarboxy, naphthyl carboxy, etc.

"Alkoxyalkyl," "alkylaminoalkyl," and "thioalkoxyalkyl" include alkyl groups, as described above, wherein oxygen, nitrogen, or sulfur atoms replace one or more hydrocarbon backbone carbon atoms.

The term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

The term "ether" or "alkoxy" includes compounds or moieties which contain an oxygen bonded to two carbon atoms or heteroatoms. For example, the term includes "alkoxyalkyl," which refers to an alkyl, alkenyl, or alkynyl group covalently bonded to an oxygen atom which is covalently bonded to an alkyl group.

The term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

The term "thioalkyl" includes compounds or moieties which contain an alkyl group connected with a sulfur atom. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties.

The term "thiocarbonyl" or "thiocarboxy" includes compounds and moieties which contain a carbon connected with a double bond to a sulfur atom.

The term "thioether" includes moieties which contain a sulfur atom bonded to two carbon atoms or heteroatoms. Examples of thioethers include, but are not limited to alkthioalkyls, alkthioalkenyls, and alkthioalkynyls. The term "alkthioalkyls" include moieties with an alkyl, alkenyl, or alkynyl group bonded to a sulfur atom which is bonded to an alkyl group. Similarly, the term "alkthioalkenyls" refers to moieties wherein an alkyl, alkenyl or alkynyl group is bonded to a sulfur atom which is covalently bonded to an alkenyl group; and alkthioalkynyls" refers to moieties wherein an alkyl, alkenyl or alkynyl group is bonded to a sulfur atom which is covalently bonded to an alkynyl group.

As used herein, "amine" or "amino" refers to unsubstituted or substituted $—NH_2$. "Alkylamino" includes groups of compounds wherein nitrogen of $—NH_2$ is bound to at least one alkyl group. Examples of alkylamino groups include benzylamino, methylamino, ethylamino, phenethylamino, etc. "Dialkylamino" includes groups wherein the nitrogen of $—NH_2$ is bound to at least two additional alkyl groups. Examples of dialkylamino groups include, but are not limited to, dimethylamino and diethylamino. "Arylamino" and "diarylamino" include groups wherein the nitrogen is bound to at least one or two aryl groups, respectively. "Aminoaryl" and "aminoaryloxy" refer to aryl and aryloxy substituted with amino. "Alkylarylamino," "alkylaminoaryl" or "arylaminoalkyl" refers to an amino group which is bound to at least one alkyl group and at least one aryl group. "Alkaminoalkyl" refers to an alkyl, alkenyl, or alkynyl group bound to a nitrogen atom which is also bound to an alkyl group. "Acylamino" includes groups wherein nitrogen is bound to an acyl group. Examples of acylamino include, but are not limited to, alkylcarbonylamino, arylcarbonylamino, carbamoyl and ureido groups.

The term "amide" or "aminocarboxy" includes compounds or moieties that contain a nitrogen atom that is bound to the carbon of a carbonyl or a thiocarbonyl group. The term includes "alkaminocarboxy" groups that include alkyl, alkenyl or alkynyl groups bound to an amino group which is bound to the carbon of a carbonyl or thiocarbonyl group. It also includes "arylaminocarboxy" groups that include aryl or heteroaryl moieties bound to an amino group that is bound to the carbon of a carbonyl or thiocarbonyl group. The terms "alkylaminocarboxy", "alkenylaminocarboxy", "alkynylaminocarboxy" and "arylaminocarboxy" include moieties wherein alkyl, alkenyl, alkynyl and aryl moieties, respectively, are bound to a nitrogen atom which is in turn bound to the carbon of a carbonyl group. Amides can be substituted with substituents such as straight chain alkyl, branched alkyl, cycloalkyl, aryl, heteroaryl or heterocycle. Substituents on amide groups may be further substituted.

Compounds of the present invention that contain nitrogens can be converted to N-oxides by treatment with an oxidizing agent (e.g., 3-chloroperoxybenzoic acid (mCPBA) and/or hydrogen peroxides) to afford other compounds of the present invention. Thus, all shown and claimed nitrogen-containing compounds are considered, when allowed by valency and structure, to include both the compound as shown and its N-oxide derivative (which can be designated as $N \rightarrow O$ or $N^+—O^-$). Furthermore, in other instances, the nitrogens in the compounds of the present invention can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

In the present specification, the structural formula of the compound represents a certain isomer for convenience in some cases, but the present invention includes all isomers, such as geometrical isomers, optical isomers based on an asymmetrical carbon, stereoisomers, tautomers, and the like, it being understood that not all isomers may have the same level of activity. In addition, a crystal polymorphism may be present for the compounds represented by the formula. It is noted that any crystal form, crystal form mixture, or anhydride or hydrate thereof is included in the scope of the present invention. Furthermore, so-called metabolite which is produced by degradation of the present compound in vivo is included in the scope of the present invention.

"Isomerism" means compounds that have identical molecular formulae but differ in the sequence of bonding of their atoms or in the arrangement of their atoms in space. Isomers that differ in the arrangement of their atoms in space are termed "stereoisomers."Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

A carbon atom bonded to four nonidentical substituents is termed a "chiral center."

"Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds or a cycloalkyl linker (e.g., 1,3-cyclobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present invention may be depicted as different chiral isomers or geometric isomers. It should also be understood that when compounds have chiral isomeric or geometric isomeric forms, all isomeric forms are intended to be included in the scope of the present invention, and the naming of the compounds does not exclude any isomeric forms, it being understood that not all isomers may have the same level of activity.

Furthermore, the structures and other compounds discussed in this invention include all atropic isomers thereof, it being understood that not all atropic isomers may have the same level of activity. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), imine-enamine and enamine-enamine. An example of keto-enol equilibria is between pyridin-2(1H)-ones and the corresponding pyridin-2-ols, as shown below.

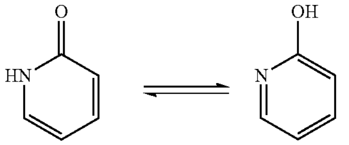

pyridin-2(1H)-one pyridin-2-ol

It is to be understood that the compounds of the present invention may be depicted as different tautomers. It should also be understood that when compounds have tautomeric forms, all tautomeric forms are intended to be included in the scope of the present invention, and the naming of the compounds does not exclude any tautomer form. It will be understood that certain tautomers may have a higher level of activity than others.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The compounds of any Formula described herein include the compounds themselves, as well as their salts, their solvates, and their prodrugs, if applicable. A salt, for example, can be formed between an anion and a positively charged group (e.g., amino) on a substituted benzene compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate) . The term "pharmaceutically acceptable anion" refers to an anion suitable for forming a pharmaceutically acceptable salt. Likewise, a salt can also be formed between a cation and a negatively charged group (e.g., carboxylate) on a substituted benzene compound. Suitable cations include sodium ion, potassium ion, magnesium ion, calcium ion, and an ammonium cation such as tetramethylammonium ion. The substituted benzene compounds also include those salts containing quaternary nitrogen atoms.

Examples of prodrugs include esters and other pharmaceutically acceptable derivatives, which, upon administration to a subject, are capable of providing active substituted benzene compounds.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative" refers to compounds that have a common core structure, and are substituted with various groups as described herein. For example, all of the compounds represented by Formula (I) are substituted benzene compounds, and have Formula (I) as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonimides, tetrazoles, sulfonates and phosphonates. See, e.g., Patani and LaVoie, *Chem. Rev.* 96, 3147-3176, 1996.

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

2. Synthesis of Substituted Benzene Compounds

The present invention provides methods for the synthesis of the compounds of any of the Formulae described herein. The present invention also provides detailed methods for the synthesis of various disclosed compounds of the present invention according to the following schemes as shown in the Examples.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes of the invention can tolerate a wide variety of functional groups, therefore various substituted starting materials can be used. The processes generally provide the desired final compound at or near the end of the overall process, although it may be desirable in certain instances to further convert the compound to a pharmaceutically acceptable salt, ester, or prodrug thereof.

Compounds of the present invention can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry. Reactions, Mechanisms, and Structure,* 5th edition, John Wiley & Sons: New York, 2001; Greene, T. W., Wuts, P. G. M., *Protective Groups in Organic Synthesis,* 3rd edition, John Wiley & Sons: New York, 1999; R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), incorporated by reference herein, are useful and recognized reference textbooks of organic synthesis known to those in the art. The following descriptions of synthetic methods are designed to illustrate, but not to limit, general procedures for the preparation of compounds of the present invention.

Compounds of the present invention can be conveniently prepared by a variety of methods familiar to those skilled in the art. The compounds of this invention with any of the Formulae described herein may be prepared according to the procedures illustrated in Schemes 1-10 below, from commercially available starting materials or starting materials which can be prepared using literature procedures. The Z and R groups (such as $R_1$, $R_2$, $R_3$, $R_4$, $R_6$, $R_7$, $R_8$, and $R_{12}$) in Schemes 1-10 are as defined in any Formula described herein, unless otherwise specified.

One of ordinary skill in the art will note that, during the reaction sequences and synthetic schemes described herein, the order of certain steps may be changed, such as the introduction and removal of protecting groups.

One of ordinary skill in the art will recognize that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M., *Protective Groups in Organic Synthesis,* $3^{rd}$ edition, John Wiley & Sons: New York, 1999.

Preferred protecting groups include, but are not limited to:

For a hydroxyl moiety: TBS, benzyl, THP, Ac

For carboxylic acids: benzyl ester, methyl ester, ethyl ester, allyl ester

For amines: Cbz, BOC, DMB

For diols: Ac (×2) TBS (×2), or when taken together acetonides

For thiols: Ac

For benzimidazoles: SEM, benzyl, PMB, DMB

For aldehydes: di-alkyl acetals such as dimethoxy acetal or diethyl acetyl.

In the reaction schemes described herein, multiple stereoisomers may be produced. When no particular stereoisomer is indicated, it is understood to mean all possible stereoisomers that could be produced from the reaction. A person of ordinary skill in the art will recognize that the reactions can be optimized to give one isomer preferentially, or new schemes may be devised to produce a single isomer. If mixtures are produced, techniques such as preparative thin layer chromatography, preparative HPLC, preparative chiral HPLC, or preparative SFC may be used to separate the isomers.

The following abbreviations are used throughout the specification and are defined below:

AA ammonium acetate
ACN acetonitrile
Ac acetyl
AcOH acetic acid
atm atmosphere
aq. Aqueous
BID or b.i.d. bis in die (twice a day)
tBuOK potassium t-butoxide
Bn benzyl
BOC tert-butoxy carbonyl
BOP (benzotriazol-1-yloxy)tris(dimethylamino)-phosphoniumhexafluorophosphate
Cbz benzyloxy carbonyl
$CDCl_3$ deuterated chloroform
$CH_2Cl_2$ dichloromethane
COMU (1-Cyano-2-ethoxy-2-oxoethylidenaminooxy) dimethyl-amino-morpholino-carbenium hexafluorophosphate
d days
DBU 1,8-diazabicyclo[5.4.0]undec-7-ene
DCE 1,2 dichloroethane
DCM dichloromethane
DEAD Diethyl azodicarboxylate
DIAD Diisopropyl azodicarboxylate
DiBAL-H diisobutyl aluminium hydride
DIPEA N,N-diisopropylethylamine (Hunig's base)
DMA Dimethylacetamide
DMAP N,N dimethyl-4-aminopyridine
DMB 2,4 dimethoxy benzyl
DMF N,N-Dimethylformamide
DMSO Dimethyl sulfoxide
DPPA Diphenylphosphonic azide
EA or EtOAc Ethyl acetate
EDC or EDCI N-(3-Dimethylaminopropyl)-N'-ethylcarbodiimide
$Et_2O$ diethyl ether
ELS Evaporative Light Scattering
ESI− Electrospray negative mode
ESI+ Electrospray positive mode
$Et_3N$ or TEA triethylamine
EtOH ethanol
FA formic acid
FC or FCC Flash chromatography
h hours
$H_2O$ water
HATU O-(7-Azabenzotriazol-1-yl)-N,N,N',N'-tetramethyluronium hexafluorophosphate
HOAT 1-Hydroxy-7-azabenzotriazole
HOBt 1-Hydroxybenzotriazole
HO-Su N-Hydroxysuccinimide
HCl hydrogen chloride or hydrochloric acid
HPLC High performance liquid chromatography
$K_2CO_3$ potassium carbonate
KHMDs Potassium hexamethyldisilazide
LC/MS or LC-MS Liquid chromatography mass spectrum
LDA Lithium diisopropylamide
LiHMDs Lithium hexamethyldisilazide
LG leaving group
M Molar
m/z mass/charge ratio
m-CPBA meta-chloroperbenzoic acid
MeCN Acetonitrile
MeOD d4-methanol
MeI Methyl iodide
MS3 Å 3 Å molecular sieves
$MgSO_4$ Magnesium Sulfate
min minutes
Ms Mesyl
MsCl Mesyl chloride
MsO Mesylate
MS Mass Spectrum
MWI microwave irradiation
$Na_2CO_3$ sodium carbonate
$Na_2SO_4$ sodium sulfate
$NaHCO_3$ sodium bicarbonate
NaHMDs Sodium hexamethyldisilazide
NaOH sodium hydroxide
$NaHCO_3$ sodium bicarbonate
$Na_2SO_4$ sodium sulfate
NIS N-iodosuccinimide
NMR Nuclear Magnetic Resonance
o/n or O/N overnight
Pd/C Palladium on carbon
$Pd(dppf)Cl_2$.DCM [1,1'-Bis(diphenylphosphino)ferrocene]dichloropalladium(II), complex with dichloromethane
PPAA 1-Propanephosphonic acid cyclic anhydride
$Pd(OH)_2$ Palladium dihydroxide
PE Petroleum Ether
PG protecting group
PMB para methoxybenzyl
ppm parts per million
p.o. per os (oral administration)
prep HPLC preparative High Performance Liquid Chromatography
prep TLC preparative thin layer chromatography
p-TsOH para-toluenesulfonic acid
PyBOP (Benzotriazol-1-yloxy)tripyrrolidinophosphonium Hexafluorophosphate
QD or q.d. quaque die (once a day)
RBF round bottom flask
RP-HPLC Reverse phase High Performance liquid chromatography
Rt or RT Room temperature
SEM (Trimethylsilyl)ethoxymethyl
SEMCl (Trimethylsilyl)ethoxymethyl chloride
SFC Super critical chromatography
SGC silica gel chromatography STAB Sodium triacetoxy borohydride
TBAF tetra-n-butylammonium fluoride
TBME tert-Butyl methyl ether
TEA Triethylamine
TFA trifluoroacetic acid
TfO triflate
THF tetrahydrofuran
THP tetrahydropyran
TID or t.i.d ter in die (three times a day)
TLC thin layer chromatography
TMSCl Trimethylsilyl chloride
Ts tosyl
TsOH tosic acid
UV ultraviolet Scheme 1

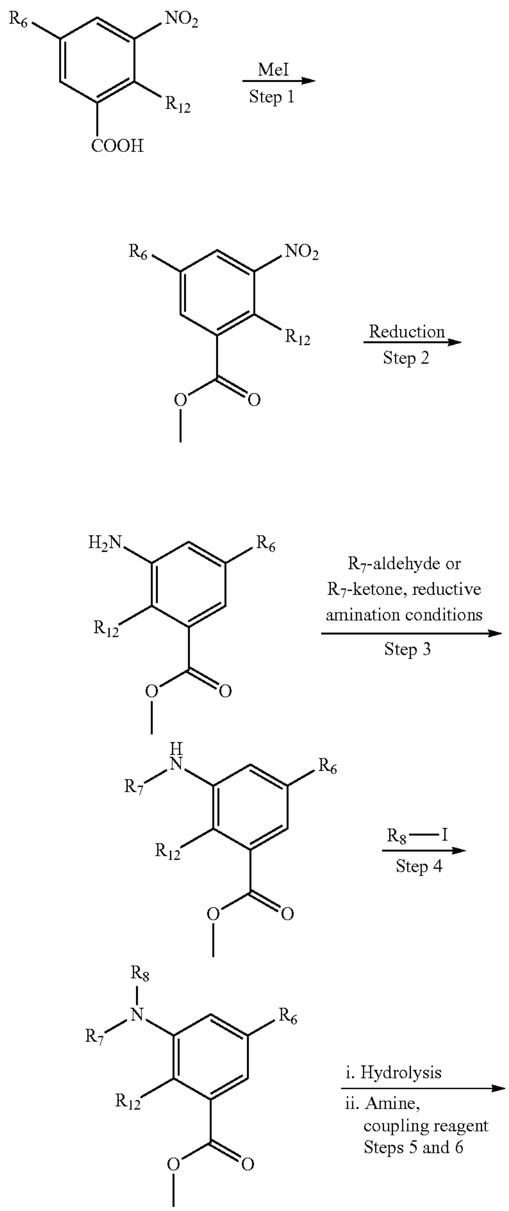

-continued

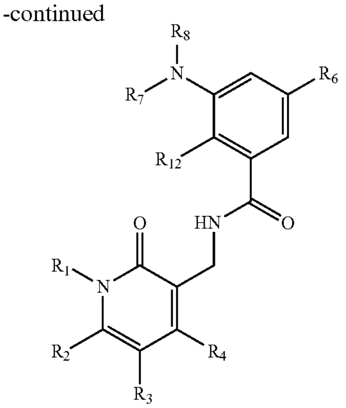

Scheme 1 shows the synthesis of benzene analogs wherein Z=—N($R_7$)($R_8$) following a general route that utilizes well-established chemistry. Substituted nitrobenzoic acids, many of which are commercially available or can be prepared by nitrations of the appropriate substituted benzoic acids or other chemistry known to one skilled in the art, can be converted to their methyl esters by treatment with methyl iodide in a polar solvent such as DMF in the presence of an appropriate base such as sodium carbonate at an appropriate temperature such as 60° C. (Step 1). The nitro group can be reduced to an amine using an appropriate reducing agent such as iron in the presence of an acid such as ammonium chloride in a protic solvent such as ethanol at an appropriate temperature such as 80° C. (Step 2). Introduction of the $R_7$ can be done using a reductive amination with an appropriate $R_7$-ketone or $R_7$-aldehyde in the presence of an appropriate reducing agent such as sodium cyanoborohydride and catalytic acid such as acetic acid in an appropriate solvent such as methanol. A variety of $R_8$ groups can be introduced by alkylation using $R_8$-LG, where LG is a leaving group such as iodine, in the presence of a mild base such as cesium carbonate in an appropriate polar solvent such as acetonitrile at an appropriate temperature such as 80° C. (Step 4). Alternatively, $R_8$ groups can be introduced by reductive amination with $R_8$-ketone or $R_8$-aldehyde in the presence of an appropriate reducing agent such as sodium cyanoborohydride and catalytic acid such as acetic acid in an appropriate solvent such as methanol. The ester moiety can be converted to an amide using a standard two step protocol. The ester can be hydrolyzed to the corresponding acid using a suitable base such as sodium hydroxide in a polar solvent such as ethanol (Step 5). The acid would then be subjecting to a standard amide coupling reaction whereupon the appropriate amine would be added along with a suitable amide coupling reagent such as PYBOP in a suitable solvent such as DMSO to give the desired amide (Step 6).

Scheme 2

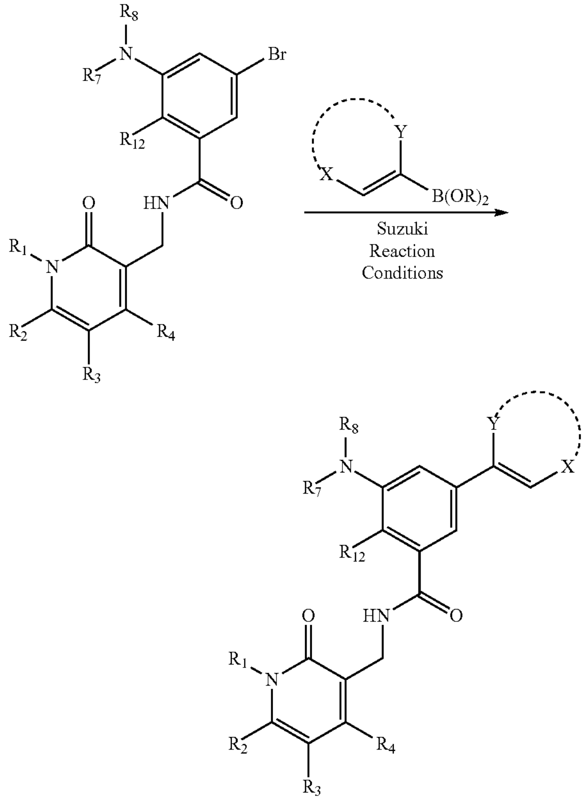

Depending upon the nature of the $R_6$ substituent, further chemical modification could be employed to convert the $R_6$ substituent into an alternative $R_6$ substituent. A representative sampling of such modifications could include hydrogenation, protecting group removal followed by additional amide coupling reactions, palladium catalyzed coupling reactions, reductive amination reactions or alkylation reactions. For example, if $R_6$ is a bromide, alternative $R_6$ substituents could then be introduced using standard transition metal-based protocols that rely upon a leaving group such as a bromide as a connection point.

In one such protocol as depicted in Scheme 2 non-aromatic $R_6$ substituents attached via a carbon-carbon bond may be introduced by Suzuki reaction of a compound where $R_6$=Br with an appropriate unsaturated non-aromatic boronic ester derivative (e.g. an olefinic boronic ester derivative such as vinyl 4,4,5,5-tetramethyl-2-vinyl-1,3,2-dioxaborolane) in the presence of a mild base and a palladium catalyst in a polar solvent such as dioxane/water, at elevated temperature to give the desired new $R_6$ substituent. Depending upon the nature of the $R_6$ substituent, further chemical modification could be employed to convert the unsaturated $R_6$ substituent into an alternative $R_6$ substituent. A representative sampling of such modifications could include hydrogenation, protecting group removal followed by additional amide coupling reactions, palladium catalyzed coupling reactions, reductive amination reactions or alkylation reactions. For example, in cases where an unsaturated non-aromatic $R_6$ group is introduced, further modification by hydrogenation can give the corresponding saturated $R_6$ group (e.g. conversion of a vinyl group to an ethyl group). In cases of where $R_6$ groups introduced have protected amine functionality further modifications include deprotection to give amines which may in subsequent steps be further modified for example by amide formation or reductive amination reactions.

In another protocol as depicted in Scheme 3, non-aromatic $R_6$ substituents attached via a carbon-carbon bond may be introduced by Sonogashira reaction of a compound where $R_6$=Br optionally followed by further modification of the introduced alkynyl group. In the Sonogashira reaction, a compound where $R_6$=Br is coupled with a terminal alkyne derivative in the presence of a mild base, a copper catalyst and a palladium catalyst in an organic solvent such as toluene at elevated temperature. This results in the replacement of the Br group with an alkynyl group. The resulting compound wherein the $R_6$ substituent is an alkynyl group may be subject to subsequent suitable modifications to give an alternative $R_6$ substituent. A representative sampling of such modifications could include hydrogenation, protecting group removal followed by additional amide coupling reactions, reductive amination reactions or alkylation reactions.

Scheme 3

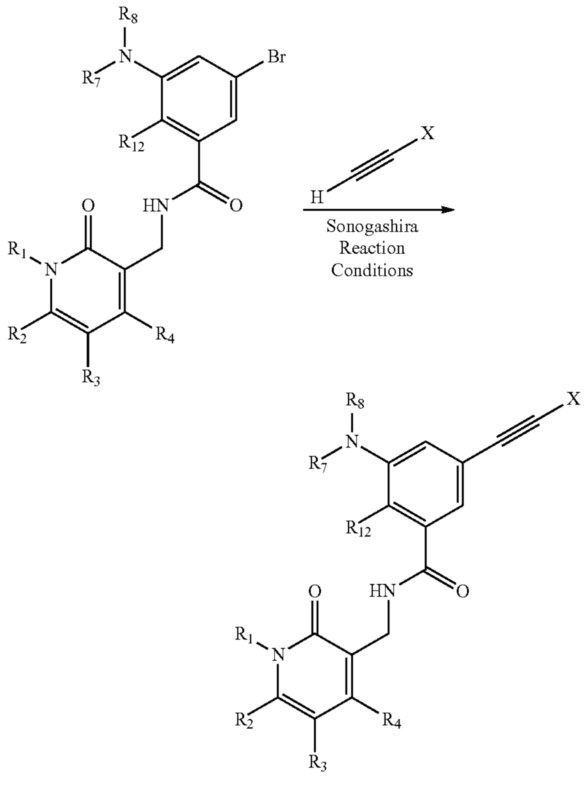

In another protocol non-aromatic $R_6$ substituents attached via a carbon-carbon bond may be prepared by other substitution reactions of the bromine atom compounds where $R_6$=Br, optionally followed by further modification of the introduced $R_6$ group. Examples of such substitution reactions include coupling reactions with zinc reagents such as cyanation and Negishi reactions. In the case of cyanation reaction, compounds where $R_6$=Br may be reacted with zinc cyanide under standard palladium catalyst mediated reaction conditions to give compounds where $R_6$=CN. The cyano group in such compounds may be subject to further modification to give other $R_6$ groups. Such cyano modifications include i. reduction to an amine which may be subsequently converted to an amide by acylation or alkylation, reduction to an aldehyde which may be subjected to reductive amination reaction to give corresponding derivatives. In Negishi reactions alkylzinc reagents which may be prepared from alkyl iodides (e.g. N-Boc-3-iodoazetidine) are coupled to compounds where $R_6$=Br using palladium or nickel catalysts. In the resulting products the introduced $R_6$ group may be converted to an alternative group by further modifications of the $R_6$ group in subsequent steps such as deprotection, amide formation or alkylation.

Compounds with $R_6$ substituents which are amines attached via a nitrogen-carbon bond may be introduced by Buchwald coupling reaction of compounds where $R_6$=Br followed by optional modification of the $R_6$ group as depicted in Scheme 4. In the Buchwald reaction compounds where $R_6$=Br are treated with a primary or secondary amine (e.g. tert-butyl piperazine-1-carboxylate) in the presence of a palladium catalyst (e.g. $Pd(dba)_2$/BINAP) and a base (e.g. cesium carbonate) in an organic solvent (e.g. toluene) at elevated temperature. The Buchwald coupling product may be subjected to subsequent suitable modifications to give an alternative $R_6$ substituent. Such modifications are exemplified by protecting group removal, amide coupling reactions, reductive amination reactions or alkylation reactions.

Scheme 4

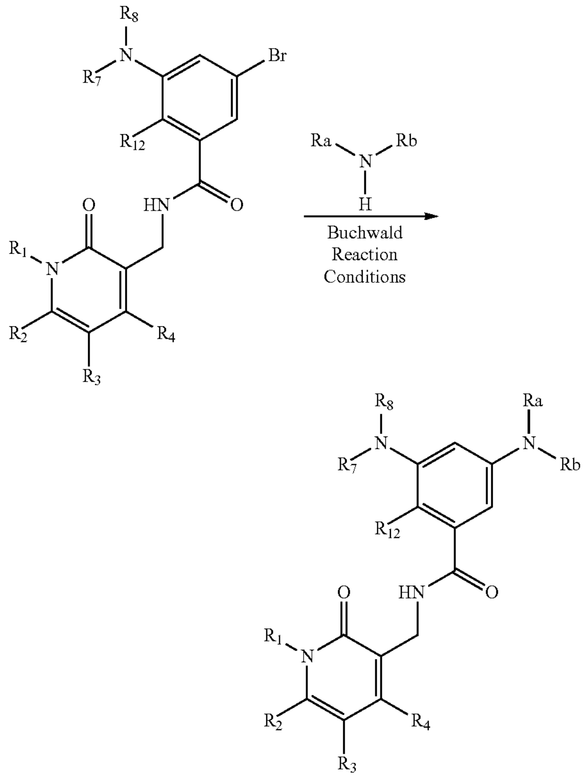

Compounds with $R_6$ substituents which are alkylthio groups attached via a sulfur-carbon bond may be prepared by coupling reaction of compounds where $R_6$=Br with thiols in the presence of a palladium catalyst and a weak base (e.g. DIPEA) in an organic solvent at elevated temperature. The coupling product sulfides may be subject to subsequent suitable modifications to give an alternative $R_6$ substituent. Such modifications include sulfur oxidation reactions to give sulfoxides and sulfones, protecting group removal, amide coupling reactions, reductive amination reactions or alkylation reactions.

In a modification of the general synthesis in Scheme 1, depending upon the nature of the $R_7$ substituent, further chemical modification subsequent to Step 6 of Scheme 1 could be employed to convert the $R_7$ substituent into an alternative $R_7$ substituent. For example a protected amino group contained within $R_7$ may be subjected to deprotection reaction (e.g. Boc group cleavage) to give free amino groups. Such free amino groups may be subjected to reductive amination reactions or alkylation reactions to give substituted amines.

Scheme 5 shows the general synthesis of picolinamide compounds. Starting from methyl 3-bromo-6-chloropicolinate oxidation to the N-oxide followed by chlorination with phosphorus oxychloride gives methyl 3-bromo-4,6-dichloropicolinate. The 4-chloro group can be selectively substituted with diverse mono and dialkyl amines which may also contain functional or protected functional groups that may be unmasked at a later stage. The 3-bromo group may be retained or may be optionally converted into an alternative $R_{12}$ group by suitable substitution reaction and further functional group modifications. Such reactions include coupling reactions mediated with palladium catalysts. For example the 3-bromo group may be converted to an $R_{12}$=methyl group by Stille reaction with tetramethyltin. Ester hydrolysis followed by amide coupling with appropriate 3-(aminomethyl)-pyridin-2-ones yields picolinamide compounds wherein $R_6$ is a chloro group. The chloro group may optionally be converted to alternative $R_6$ groups by suitable substitution reactions either in a final step or alternatively prior to ester hydrolysis Step 6. Examples of such substitution reactions include cyanation and amination reactions either directly or mediated with palladium catalysts. Analogous compounds wherein $R_{12}$ is chloro may be prepared in analogous fashion from methyl 3,4,6-trichloropyridine-2-carboxylate.

Scheme 5

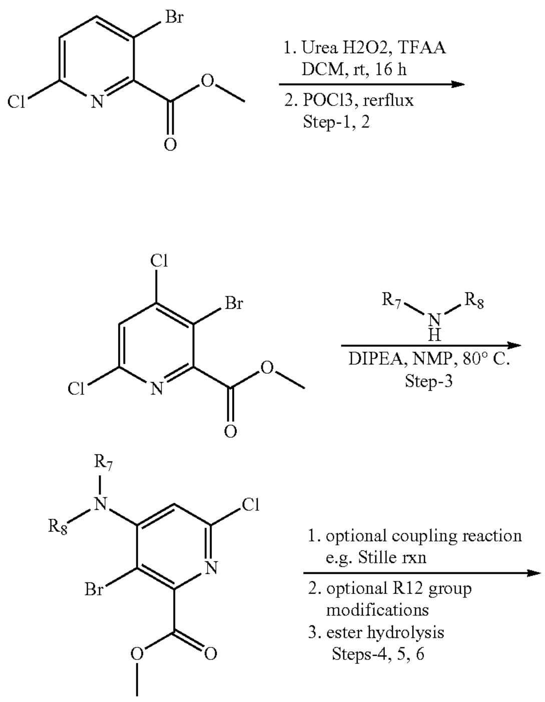

-continued

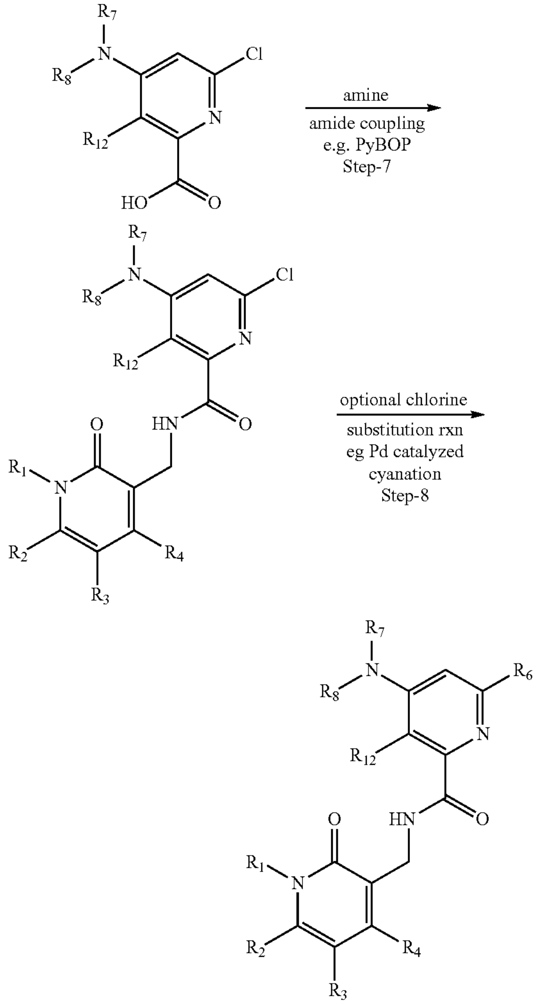

General syntheses of 3-(aminomethyl)-pyridin-2(1H)-ones intermediates for the amide coupling reaction from Scheme 1 are depicted in Scheme 6. In one method, a diketone can be condensed with 2-cyanoacetamide in the presence of an appropriate reagent such as piperidine acetate in a polar solvent such as ethanol to provide a cyanopyridone (Step 9). In another method, when $R_3$ is H, an appropriately substituted alkynyl ketone can be condensed with 2-cyanoacetamide in the presence of an appropriate reagent such as piperidine acetate in a polar solvent such as ethanol to provide a cyanopyridone (Step 11). The cyano group can be reduced under appropriate conditions such as hydrogenation in the presence of catalytic Raney nickel in a polar solvent such as ammonium in methanol to provide the amine (Step 10).

Scheme 6

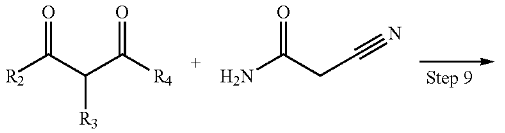

-continued

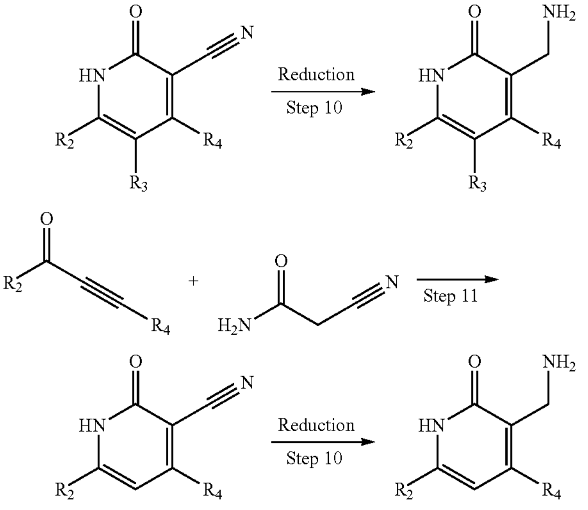

Additionally, depending upon the nature of the $R_2$, $R_3$, or $R_4$ group, further chemical modification can be employed to convert each of them independently into an alternative substituent. A representative sampling of such modifications can include hydrogenation, protecting group removal followed by additional amide coupling reactions, palladium catalyzed coupling reactions, reductive amination reactions, and alkylation reactions.

Scheme 7 depicts a variant of the general synthesis route of Scheme 1 based on 2-substituted (substituent is an $R_{12}$ group) methyl 3-amino-5-bromo-benzoate starting materials. These starting materials can in turn be prepared from 2-substituted 3-nitro-benzoic acids which are commercially available or can be prepared by nitration of 2-substituted benzoic acids. Thus, bromination of 2-substituted 3-nitro-benzoic acids with a suitable reagent such as 1,3-dibromo-5,5-dimethyl-2,4-imidazolidinedione yields the appropriate 2-substituted 3-nitro-5-bromo-benzoic acids. A variety of esterification and then nitro group reduction methods can then be sequentially implemented to prepare the 2-substituted methyl 3-amino-5-bromo-benzoate starting materials from the 2-substituted 3-nitro-5-bromo-benzoic acids.

Scheme 7

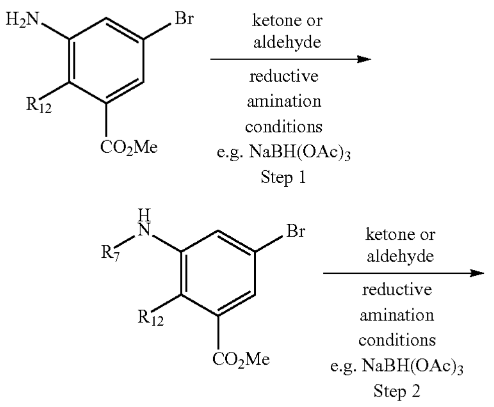

-continued

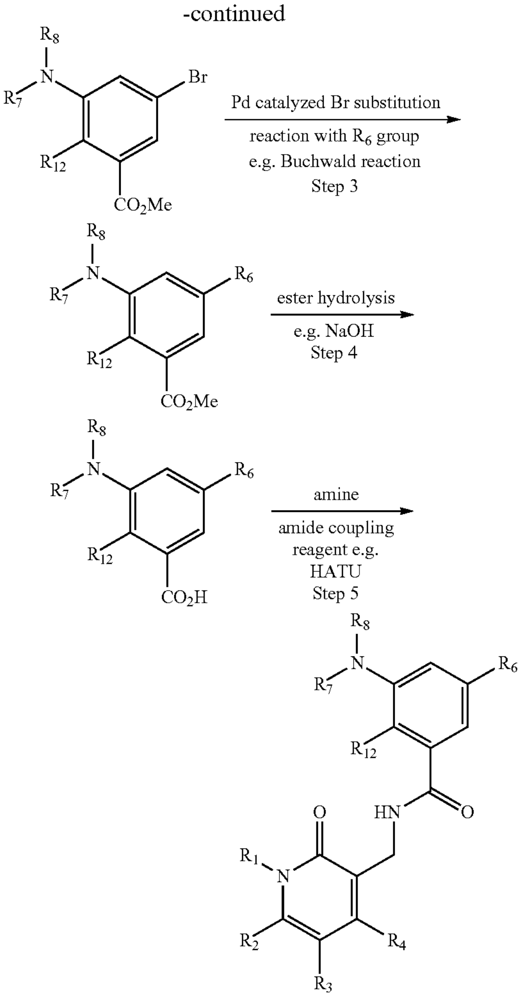

As depicted in Scheme 7 the $R_7$ group can be introduced from 2-substituted methyl 3-amino-5-bromo-benzoates in Step 1 using a reductive amination with an appropriate $R_7$-ketone or $R_7$-aldehyde in the presence of an appropriate reducing agent such as sodium cyanoborohydride and catalytic acid such as acetic acid in an appropriate solvent such as methanol. Similarly, $R_8$ groups can be introduced in Step 2 by reductive amination with $R_8$-ketone or $R_8$-aldehyde in the presence of an appropriate reducing agent such as sodium cyanoborohydride and catalytic acid such as acetic acid in an appropriate solvent such as methanol. Alternatively, a variety of $R_8$ groups can be introduced by alkylation using $R_8$-LG, where LG is a leaving group such as iodine, in the presence of a mild base such as cesium carbonate in an appropriate polar solvent such as acetonitrile at an appropriate temperature such as 80° C. In Step 3, $R_6$ groups other than bromine can be introduced via palladium catalyzed coupling reactions. Examples of such $R_6$ groups and methods have been described above. For example amines may be introduced by Buchwald reactions and unsaturated groups may be introduced by Suzuki or Sonogashiri reactions. The $R_6$ substituent may be subject to subsequent suitable modifications to give an alternative $R_6$ substituent. A representative sampling of such modifications could include hydrogenation (e.g. to saturate unsaturated groups), protecting group removal followed by additional amide coupling reactions, reductive amination reactions or alkylation reactions. In Step 4 the ester moiety can be hydrolyzed to the corresponding acid using a suitable base such as sodium hydroxide in a polar solvent such as ethanol. In Step 5, the acid can be subjected to a standard amide coupling reaction whereupon the appropriate 3-(aminomethyl)-pyridin-2-one would be added along with a suitable amide coupling reagent such as PYBOP in a suitable solvent such as DMSO to give the desired amide. Depending upon the nature of the $R_7$ substituent, further chemical modification subsequent to Step 5 of Scheme 4 could be employed to convert the $R_7$ substituent into an alternative $R_7$ substituent. For example a protected amino group contained within $R_7$ may be subjected to deprotection reaction (e.g. Boc group cleavage) to give free amino groups. Such free amino groups may be subjected to reductive amination reactions or alkylation reactions to give substituted amines.

Scheme 8 below depicts the general synthesis of 2-monoalkylamino and 2-dialkylamino-3,6-disubstituted-isonicotinamides wherein the 3-substituent corresponds to $R_{12}$ and the 6-substituent corresponds to $R_6$. In Step 1 the 3-substituent may be introduced by the method described by Epsztain J. et al. *Tetrahedron,* 1991, v. 47, 1697-16708, by metalation of 2-chloro-isonicotinanilide with n-butyllithium followed by trapping with an alkyliodide such as methyl iodide or aldehyde or other electrophilic group.

Scheme 8

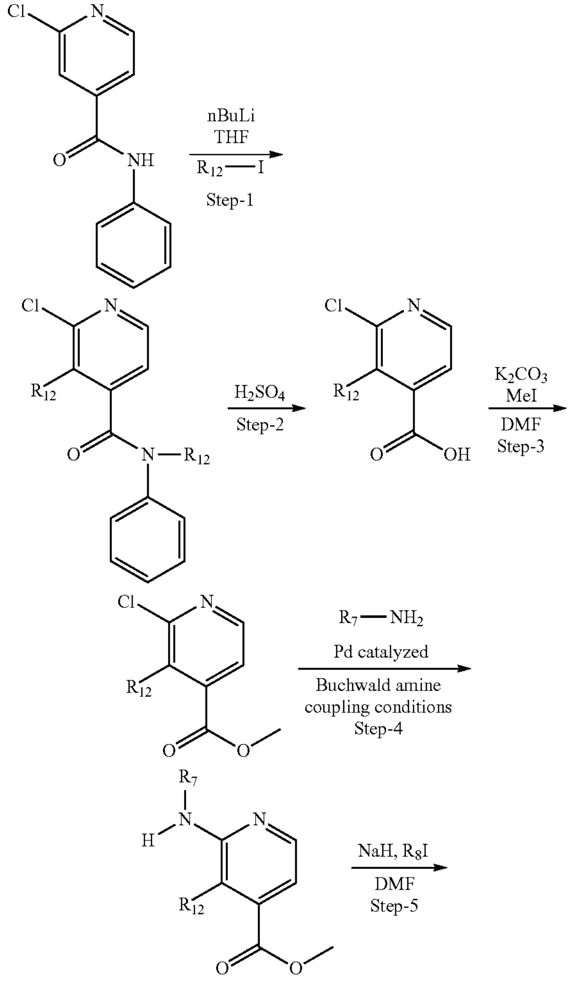

-continued

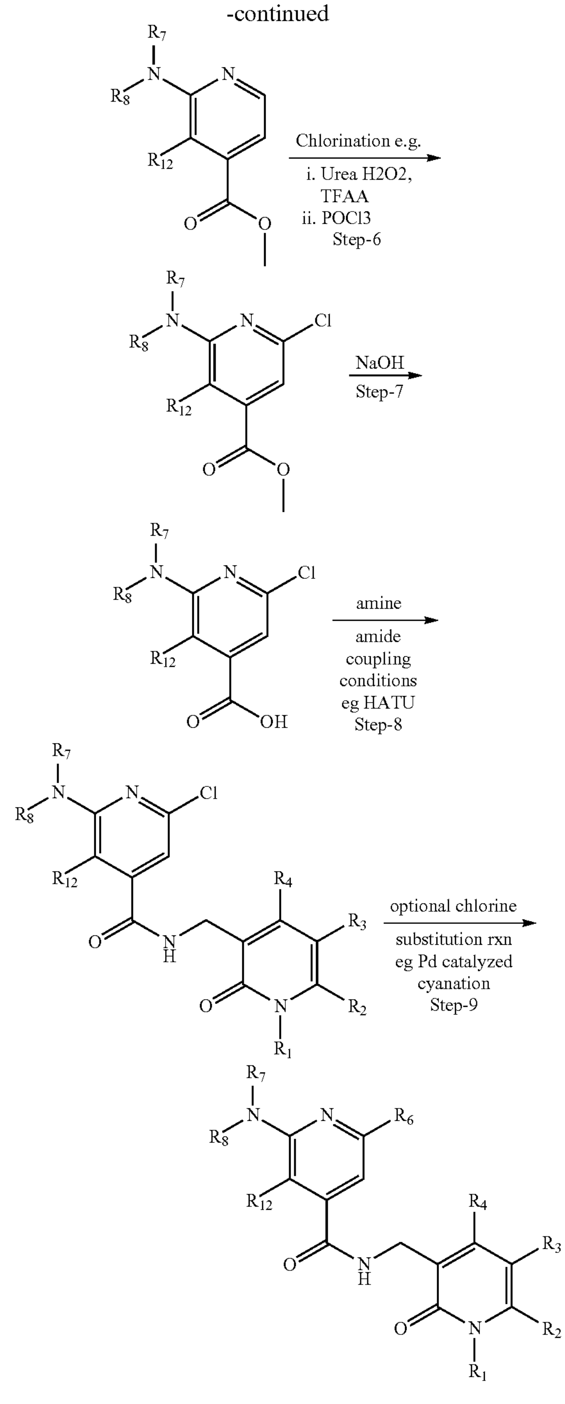

In cases where the trapping reagent yields a substituent with a functional group this group may be masked or converted into another functional group compatible with the subsequent chemical steps. In Step 2 anilide amide hydrolysis under standard acidic conditions may be conducted followed by methyl ester synthesis under standard conditions for example as shown with methyl iodide and base gives corresponding methyl 2-chloro-3-substituted isonicotinates. In Step 4 an alkylamino group can be introduced by Buchwald coupling reaction of an $R_7NH_2$ monoalkylamine with the methyl 2-chloro-3-substituted isonicotinates. This reaction is well precedented for diverse 2-chloropyridine systems in the chemical literature. In an optional Step 5 for dialkylamino compounds $R_8$ groups can be introduced by reductive amination with $R_8$-ketone or $R_8$-aldehyde in the presence of an appropriate reducing agent such as sodium cyanoborohydride and catalytic acid such as acetic acid in an appropriate solvent such as methanol. Alternatively, a variety of $R_8$ groups can be introduced by alkylation using $R_8$-LG, where LG is a leaving group such as iodine, in the presence of a mild base such as cesium carbonate in an appropriate polar solvent such as acetonitrile at an appropriate temperature such as 80° C. In Step 6, oxidation to the N-oxide followed by chlorination with phosphorus oxychloride gives methyl 6-chloro-2-mono or dialkylamino-3-substituted isonicotinates. In Step 7 the ester moiety can be hydrolyzed to the corresponding acid using a suitable base such as sodium hydroxide in a polar solvent such as ethanol. In Step 8, the acid can be subjected to a standard amide coupling reaction whereupon the appropriate substituted 3-(aminomethyl)-pyridin-2-one would be added along with a suitable amide coupling reagent such as PYBOP in a suitable solvent such as DMSO to give the desired amide. In Step 9, the chloro group may optionally be converted to alternative $R_6$ groups by suitable substitution reactions either in a final step or alternatively prior to ester hydrolysis Step 6. Examples of such substitution reactions include cyanation and amination reactions either directly or mediated with palladium catalysts. The $R_6$ substituent may be subject to subsequent suitable modifications to give an alternative $R_6$ substituent. A representative sampling of such modifications could include hydrogenation (e.g. to saturate unsaturated groups), protecting group removal followed by additional amide coupling reactions, reductive amination reactions or alkylation reactions. Depending upon the nature of the $R_7$ substituent, further chemical modification steps may be employed to convert the $R_7$ substituent into an alternative $R_7$ substituent. For example a protected amino group contained within $R_7$ may be subjected to deprotection reaction (e.g. Boc group cleavage) to give free amino groups. Such free amino groups may be subjected to reductive amination reactions or alkylation reactions to give substituted amines.

Scheme 9

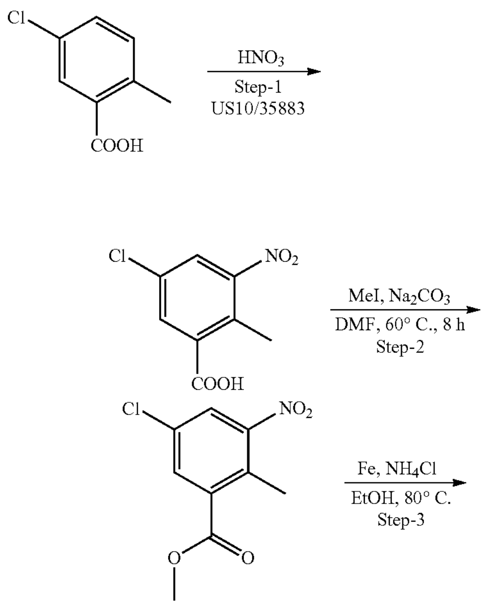

-continued

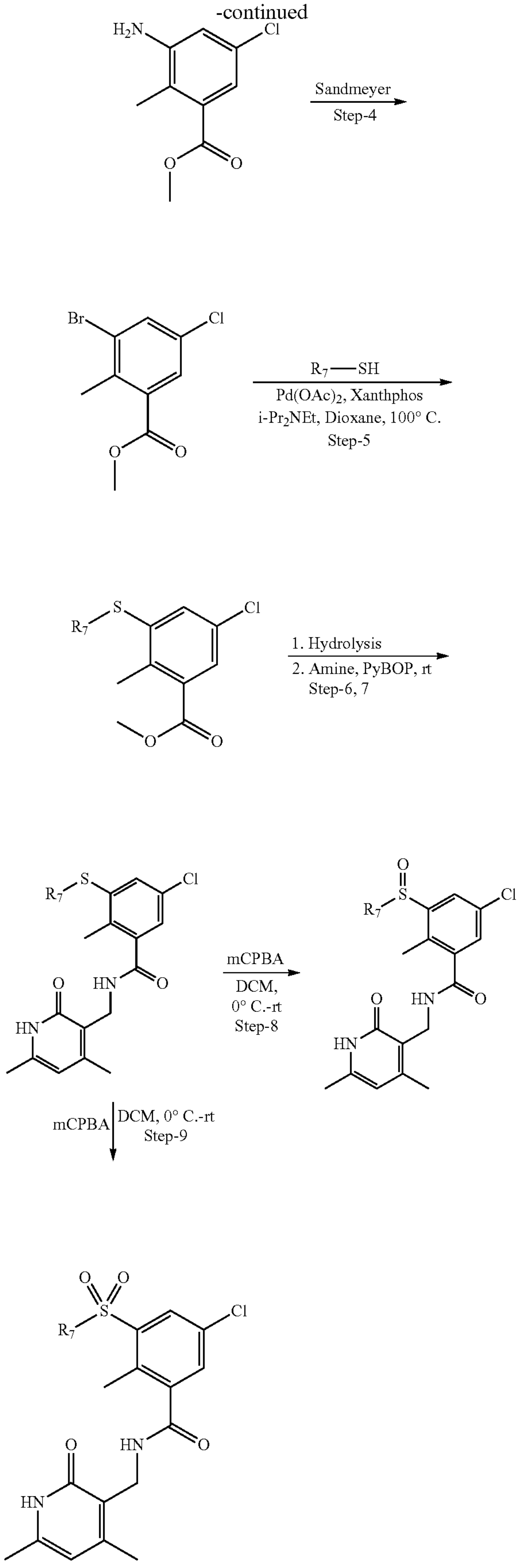

-continued

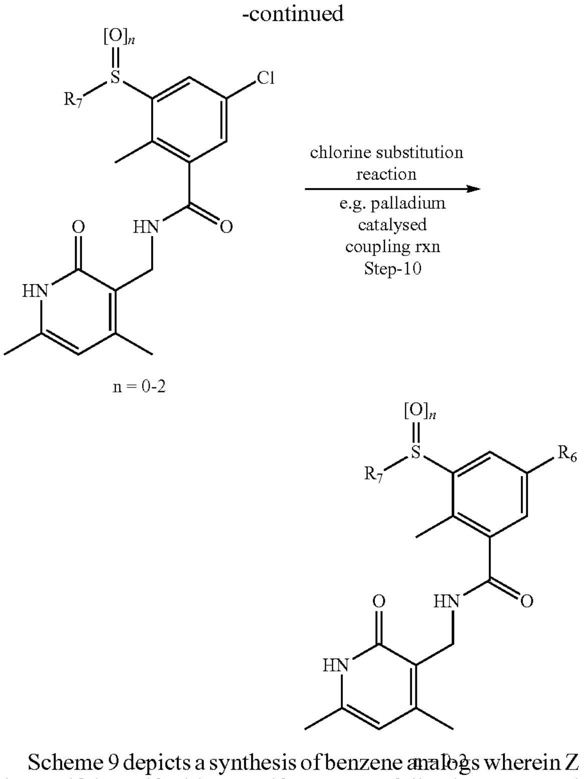

Scheme 9 depicts a synthesis of benzene analogs wherein Z is a sulfide, sulfoxide or sulfone group following a general route that utilizes well-established chemistry. Starting with a substituted benzoic acid such as 5-chloro-2-methylbenzoic acid, nitration using standard conditions such as treatment with conc. $H_2SO_4$ and conc. $HNO_3$ can provide the nitro analog. Esterification of the acid can be achieved using an alkylating agent such as methyl iodide in the presence of a base such as sodium carbonate in a polar solvent such as DMF. The nitro group can be reduced using conditions such iron and ammonium chloride in a protic solvent such as ethanol with heating to a temperature such as 80° C. The resulting aniline can be converted to a bromide using a Sandmeyer reaction such treatment with $CuBr_2$ and t-butyl nitrite in a solvent such as acetonitrile. A palladium catalyzed coupling of a thiol with the bromide can be achieved using a palladium source such as $Pd(OAc)_2$ with a ligand such as Xanthphos in the presence of a base such as N,N-diisopropyl ethylamine in a solvent such as 1,4-dioxane optionally heating to a temperature such as 100° C. The ester can be hydrolyzed with an aqueous base such as NaOH in water. The resulting acid can be coupled to the appropriate substituted 3-(aminomethyl)-pyridin-2-one (e.g. 3-(amino methyl)-4,6-dimethylpyridin-2(1H)-one as depicted in Scheme 9) using standard amino acid coupling conditions such as PyBOP in DMSO. The resulting thioether may be oxidized to the corresponding sulfoxide or sulfone by using the appropriate equivalents of an oxidant such as m-CPBA in a solvent such as DCM. The $R_6$ chloro group may be replaced with an alternative $R_6$ group in an additional Step 10 or after Step 5 or prior to amide coupling. Examples of alternative $R_6$ groups include substituents that can be incorporated by using palladium couplings such as a Buchwald reaction to give amine groups (e.g. morpholino). The $R_6$ substituent may be subject to subsequent suitable modifications to give an alternative $R_6$ substituent. A representative sampling of such modifications includes protecting group removal followed by additional amide coupling reactions, reductive amination reactions or alkylation reactions.

Scheme 10

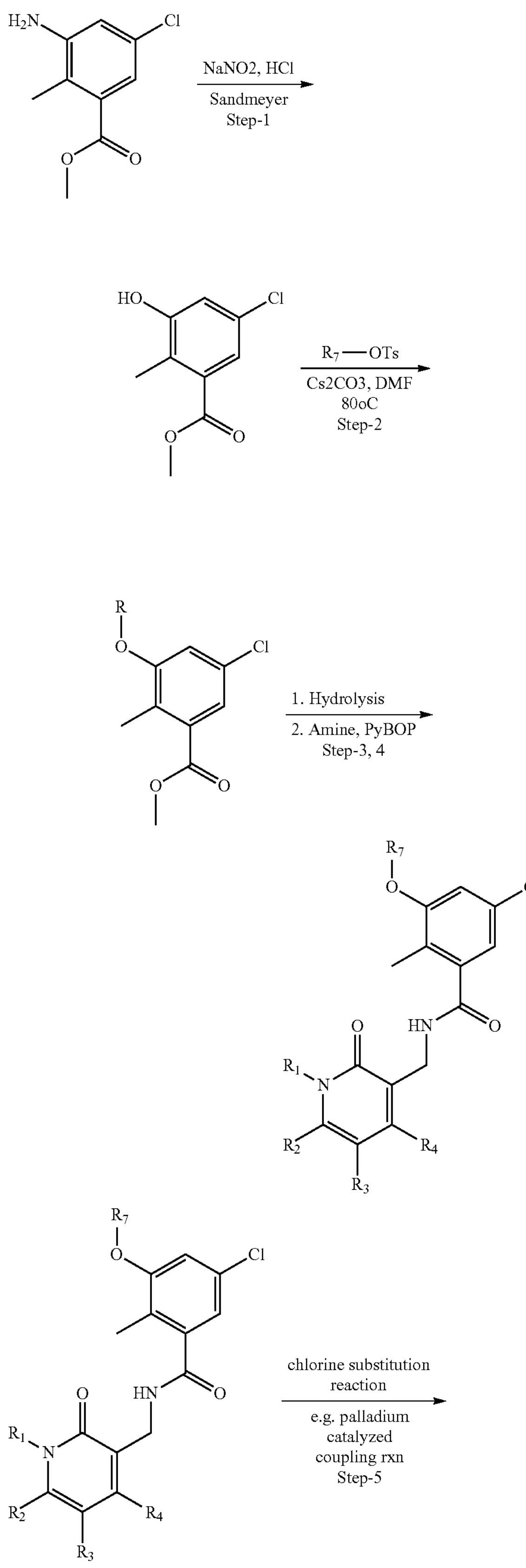

-continued

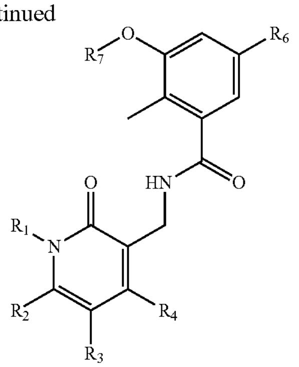

Scheme 10 depicts a synthesis of modified benzene analogs wherein Z is an ether group following a general route that utilizes well-established chemistry. Starting with a substituted aniline such as methyl 3-amino-5-chloro-2-methylbenzoate, the aniline can be converted to a phenol using a Sandmeyer reaction such as treatment with aqueous $NaNO_2$ solution in a aqueous acid such as 50% $H_2SO_4$. The phenol can be alkylated using an alkylating agent such as tetrahydro-2H-pyran-4-yl 4-methylbenzenesulfonate in the presence of an appropriate base such as cesium carbonate in as polar solvent such as DMF optionally heating to a temperature such as 80° C. The ester can be hydrolyzed with an aqueous base such as NaOH in water. The resulting acid can be coupled to the appropriate substituted 3-(aminomethyl)-pyridin-2-one using standard amino acid coupling conditions such as PyBOP in DMSO. The $R_6$ chloro group may be replaced with an alternative $R_6$ group in an additional after Step 5 or prior to amide coupling. Examples of alternative $R_6$ groups include substituents that can be incorporated by using palladium couplings such as a Buchwald reaction to give amine groups (e.g. morpholino). The $R_6$ substituent may be subject to subsequent suitable modifications to give an alternative $R_6$ substituent. A representative sampling of such modifications includes protecting group removal followed by additional amide coupling reactions, reductive amination reactions or alkylation.

A person of ordinary skill in the art will recognize that in the above schemes the order of many of the steps are interchangeable.

3. Methods of Treatment

Compounds of the present invention inhibit the histone methyltransferase activity of EZH2 or a mutant thereof and, accordingly, the present invention also provides methods for treating conditions and diseases the course of which can be influenced by modulating the methylation status of histones or other proteins, wherein said methylation status is mediated at least in part by the activity of EZH2. In one aspect of the invention, certain compounds disclosed herein are candidates for treating, or preventing certain conditions and diseases. Modulation of the methylation status of histones can in turn influence the level of expression of target genes activated by methylation, and/or target genes suppressed by methylation. The method includes administering to a subject in need of such treatment, a therapeutically effective amount of a compound of the present invention, or a pharmaceutically acceptable salt, prodrug, metabolite, polymorph, solvate, or stereoisomeror thereof.

The disorder in which EZH2-mediated protein methylation plays a part can be cancer or a precancerous condition. The present invention further provides the use of a compound of the present invention, or a pharmaceutically acceptable salt, prodrug, metabolite, polymorph or solvate thereof in the treatment of cancer or pre-cancer the course of which can be influenced by modulating EZH2-mediated protein methylation, or, for the preparation of a medicament useful for the treatment of such cancer or pre-cancer. Exemplary cancers that may be treated include lymphomas, including non-Hodgkin lymphoma, follicular lymphoma (FL) and diffuse large B-cell lymphoma (DLBCL); melanoma; and leukemia, including CML. Exemplary precancerous condition includes myelodysplastic syndrome (MDS; formerly known as preleukemia).

The present invention also provides methods of protecting against a disorder in which EZH2-mediated protein methylation plays a part in a subject in need thereof by administering a therapeutically effective amount of compound of the present invention, or a pharmaceutically acceptable salt, prodrug, metabolite, polymorph or solvate thereof, to a subject in need of such treatment. The disorder can be cancer, e.g., cancer in which EZH2-mediated protein methylation plays a role. The present invention also provides the use of compound of the present invention, or a pharmaceutically acceptable salt, prodrug, metabolite, polymorph, solvate, or stereoisomeror thereof, for the preparation of a medicament useful for the prevention of a cell proliferative disorder associated, at least in part, with EZH2-mediated protein methylation.

The compounds of this invention can or may be used to modulate protein (e.g., histone) methylation, e.g., to modulate histone methyltransferase or histone demethylase enzyme activity. At least some of the compounds of the invention can be used in vivo or in vitro for modulating protein methylation. Histone methylation has been reported to be involved in aberrant expression of certain genes in cancers, and in silencing of neuronal genes in non-neuronal cells. At least some compounds described herein are suitable candidates for treating these diseases, i.e., to decrease methylation or restore methylation to roughly its level in counterpart normal cells.

Compounds that are methylation modulators can or may be used for modulating cell proliferation. For example, in some cases excessive proliferation may be reduced with agents that decrease methylation, whereas insufficient proliferation may be stimulated with agents that increase methylation. Accordingly, diseases that may be treated by the compounds of the invention could include hyperproliferative diseases, such as benign cell growth and malignant cell growth.

As used herein, a “subject in need thereof” is a subject having a disorder in which EZH2-mediated protein methylation plays a part, or a subject having an increased risk of developing such disorder relative to the population at large. A subject in need thereof can have a precancerous condition. Preferably, a subject in need thereof has cancer. A “subject” includes a mammal. The mammal can be e.g., a human or appropriate non-human mammal, such as primate, mouse, rat, dog, cat, cow, horse, goat, camel, sheep or a pig. The subject can also be a bird or fowl. In one embodiment, the mammal is a human.

As used herein, the term “cell proliferative disorder” refers to conditions in which unregulated or abnormal growth, or both, of cells can lead to the development of an unwanted condition or disease, which may or may not be cancerous. Exemplary cell proliferative disorders that may be treated with the compounds of the invention encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term “rapidly dividing cell” as used herein is defined as any cell that divides at a rate that exceeds or is greater than what is expected or observed among neighboring or juxtaposed cells within the same tissue. A cell proliferative disorder includes a precancer or a precancerous condition. A cell proliferative disorder includes cancer. The methods and uses provided herein can be or may be used to treat or alleviate a symptom of cancer or to identify suitable candidates for such purposes. The term “cancer” includes solid tumors, as well as, hematologic tumors and/or malignancies. A “precancer cell” or “precancerous cell” is a cell manifesting a cell proliferative disorder that is a precancer or a precancerous condition. A “cancer cell” or “cancerous cell” is a cell manifesting a cell proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers.

Exemplary non-cancerous conditions or disorders that may be treated using one or more compounds of the present invention include, but are not limited to, rheumatoid arthritis; inflammation; autoimmune disease; lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn’s disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer’s disease; Huntington’s disease; Parkinson’s disease; acute and chronic pain; allergic rhinitis; allergic conjunctivitis; chronic heart failure; acute coronary syndrome; cachexia; malaria; leprosy; leishmaniasis; Lyme disease; Reiter’s syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; Multiple Sclerosis; lupus; fibromyalgia; AIDS and other viral diseases such as Herpes Zoster, Herpes Simplex I or II, influenza virus and cytomegalovirus; and diabetes mellitus.

Exemplary cancers that may be treated using one or more compounds of the present invention include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

A "cell proliferative disorder of the hematologic system" is a cell proliferative disorder involving cells of the hematologic system. A cell proliferative disorder of the hematologic system can include lymphoma, leukemia, myeloid neoplasms, mast cell neoplasms, myelodysplasia, benign monoclonal gammopathy, lymphomatoid granulomatosis, lymphomatoid papulosis, polycythemia vera, chronic myelocytic leukemia, agnogenic myeloid metaplasia, and essential thrombocythemia. A cell proliferative disorder of the hematologic system can include hyperplasia, dysplasia, and metaplasia of cells of the hematologic system. In one aspect, compositions of the present invention may be used to treat a cancer selected from the group consisting of a hematologic cancer of the present invention or a hematologic cell proliferative disorder of the present invention, or used to identify suitable candidates for such purposes. A hematologic cancer of the present invention can include multiple myeloma, lymphoma (including Hodgkin's lymphoma, non-Hodgkin's lymphoma, childhood lymphomas, and lymphomas of lymphocytic and cutaneous origin), leukemia (including childhood leukemia, hairy-cell leukemia, acute lymphocytic leukemia, acute myelocytic leukemia, chronic lymphocytic leukemia, chronic myelocytic leukemia, chronic myelogenous leukemia, and mast cell leukemia), myeloid neoplasms and mast cell neoplasms.

A "cell proliferative disorder of the lung" is a cell proliferative disorder involving cells of the lung. Cell proliferative disorders of the lung can include all forms of cell proliferative disorders affecting lung cells. Cell proliferative disorders of the lung can include lung cancer, a precancer or precancerous condition of the lung, benign growths or lesions of the lung, and malignant growths or lesions of the lung, and metastatic lesions in tissue and organs in the body other than the lung. In one aspect, compositions of the present invention may be used to treat lung cancer or cell proliferative disorders of the lung, or used to identify suitable candidates for such purposes. Lung cancer can include malignant lung neoplasms, carcinoma in situ, typical carcinoid tumors, and atypical carcinoid tumors. Lung cancer can include small cell lung cancer ("SCLC"), non-small cell lung cancer ("NSCLC"), squamous cell carcinoma, adenocarcinoma, small cell carcinoma, large cell carcinoma, adenosquamous cell carcinoma, and mesothelioma. Lung cancer can include "scar carcinoma," bronchioalveolar carcinoma, giant cell carcinoma, spindle cell carcinoma, and large cell neuroendocrine carcinoma. Lung cancer can include lung neoplasms having histologic and ultrastructual heterogeneity (e.g., mixed cell types).

Cell proliferative disorders of the lung can include all forms of cell proliferative disorders affecting lung cells. Cell proliferative disorders of the lung can include lung cancer, precancerous conditions of the lung. Cell proliferative disorders of the lung can include hyperplasia, metaplasia, and dysplasia of the lung. Cell proliferative disorders of the lung can include asbestos-induced hyperplasia, squamous metaplasia, and benign reactive mesothelial metaplasia. Cell proliferative disorders of the lung can include replacement of columnar epithelium with stratified squamous epithelium, and mucosal dysplasia. Individuals exposed to inhaled injurious environmental agents such as cigarette smoke and asbestos may be at increased risk for developing cell proliferative disorders of the lung. Prior lung diseases that may predispose individuals to development of cell proliferative disorders of the lung can include chronic interstitial lung disease, necrotizing pulmonary disease, scleroderma, rheumatoid disease, sarcoidosis, interstitial pneumonitis, tuberculosis, repeated pneumonias, idiopathic pulmonary fibrosis, granulomata, asbestosis, fibrosing alveolitis, and Hodgkin's disease.

A "cell proliferative disorder of the colon" is a cell proliferative disorder involving cells of the colon. In one aspect, compositions of the present invention may be used to treat colon cancer or cell proliferative disorders of the colon, or used to identify suitable candidates for such purposes. Colon cancer can include all forms of cancer of the colon. Colon cancer can include sporadic and hereditary colon cancers. Colon cancer can include malignant colon neoplasms, carcinoma in situ, typical carcinoid tumors, and atypical carcinoid tumors. Colon cancer can include adenocarcinoma, squamous cell carcinoma, and adenosquamous cell carcinoma. Colon cancer can be associated with a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis. Colon cancer can be caused by a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis.

Cell proliferative disorders of the colon can include all forms of cell proliferative disorders affecting colon cells. Cell proliferative disorders of the colon can include colon cancer, precancerous conditions of the colon, adenomatous polyps of the colon and metachronous lesions of the colon. A cell proliferative disorder of the colon can include adenoma. Cell proliferative disorders of the colon can be characterized by hyperplasia, metaplasia, and dysplasia of the colon. Prior colon diseases that may predispose individuals to development of cell proliferative disorders of the colon can include prior colon cancer. Current disease that may predispose individuals to development of cell proliferative disorders of the colon can include Crohn's disease and ulcerative colitis. A cell proliferative disorder of the colon can be associated with a mutation in a gene selected from the group consisting of p53, ras, FAP and DCC. An individual can have an elevated risk of developing a cell proliferative disorder of the colon due to the presence of a mutation in a gene selected from the group consisting of p53, ras, FAP and DCC.

A "cell proliferative disorder of the pancreas" is a cell proliferative disorder involving cells of the pancreas. Cell proliferative disorders of the pancreas can include all forms of cell proliferative disorders affecting pancreatic cells. Cell proliferative disorders of the pancreas can include pancreas cancer, a precancer or precancerous condition of the pancreas, hyperplasia of the pancreas, and dysaplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas. Pancreatic cancer can include ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma. Pancreatic cancer can also include pancreatic neoplasms having histologic and ultrastructual heterogeneity (e.g., mixed cell types).

A "cell proliferative disorder of the prostate" is a cell proliferative disorder involving cells of the prostate. Cell proliferative disorders of the prostate can include all forms of cell proliferative disorders affecting prostate cells. Cell proliferative disorders of the prostate can include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate can include hyperplasia, metaplasia, and dysplasia of the prostate.

A "cell proliferative disorder of the skin" is a cell proliferative disorder involving cells of the skin. Cell proliferative disorders of the skin can include all forms of cell proliferative disorders affecting skin cells. Cell proliferative disorders of the skin can include a precancer or precancerous condition of the skin, benign growths or lesions of the skin, melanoma, malignant melanoma and other malignant growths or lesions of the skin, and metastatic lesions in tissue and organs in the body other than the skin. Cell proliferative disorders of the skin can include hyperplasia, metaplasia, and dysplasia of the skin.

A "cell proliferative disorder of the ovary" is a cell proliferative disorder involving cells of the ovary. Cell proliferative disorders of the ovary can include all forms of cell proliferative disorders affecting cells of the ovary. Cell proliferative disorders of the ovary can include a precancer or precancerous condition of the ovary, benign growths or lesions of the ovary, ovarian cancer, malignant growths or lesions of the ovary, and metastatic lesions in tissue and organs in the body other than the ovary. Cell proliferative disorders of the skin can include hyperplasia, metaplasia, and dysplasia of cells of the ovary.

A "cell proliferative disorder of the breast" is a cell proliferative disorder involving cells of the breast. Cell proliferative disorders of the breast can include all forms of cell proliferative disorders affecting breast cells. Cell proliferative disorders of the breast can include breast cancer, a precancer or precancerous condition of the breast, benign growths or lesions of the breast, and malignant growths or lesions of the breast, and metastatic lesions in tissue and organs in the body other than the breast. Cell proliferative disorders of the breast can include hyperplasia, metaplasia, and dysplasia of the breast.

A cell proliferative disorder of the breast can be a precancerous condition of the breast. Compositions of the present invention may be used to treat a precancerous condition of the breast. A precancerous condition of the breast can include atypical hyperplasia of the breast, ductal carcinoma in situ (DCIS), intraductal carcinoma, lobular carcinoma in situ (LCIS), lobular neoplasia, and stage 0 or grade 0 growth or lesion of the breast (e.g., stage 0 or grade 0 breast cancer, or carcinoma in situ). A precancerous condition of the breast can be staged according to the TNM classification scheme as accepted by the American Joint Committee on Cancer (AJCC), where the primary tumor (T) has been assigned a stage of T0 or T is; and where the regional lymph nodes (N) have been assigned a stage of NO; and where distant metastasis (M) has been assigned a stage of M0.

The cell proliferative disorder of the breast can be breast cancer. In one aspect, compositions of the present invention may be used to treat breast cancer, or used to identify suitable candidates for such purposes. Breast cancer may include all forms of cancer of the breast. Breast cancer includes all forms of cancer of the breast. Breast cancer can include primary epithelial breast cancers. Breast cancer can include cancers in which the breast is involved by other tumors such as lymphoma, sarcoma or melanoma. Breast cancer can include carcinoma of the breast, ductal carcinoma of the breast, lobular carcinoma of the breast, undifferentiated carcinoma of the breast, cystosarcoma phyllodes of the breast, angiosarcoma of the breast, and primary lymphoma of the breast. Breast cancer can include Stage I, II, IIIA, IIIB, IIIC and IV breast cancer. Ductal carcinoma of the breast can include invasive carcinoma, invasive carcinoma in situ with predominant intraductal component, inflammatory breast cancer, and a ductal carcinoma of the breast with a histologic type selected from the group consisting of comedo, mucinous (colloid), medullary, medullary with lymphcytic infiltrate, papillary, scirrhous, and tubular. Lobular carcinoma of the breast can include invasive lobular carcinoma with predominant in situ component, invasive lobular carcinoma, and infiltrating lobular carcinoma. Breast cancer can include Paget's disease, Paget's disease with intraductal carcinoma, and Paget's disease with invasive ductal carcinoma. Breast cancer can include breast neoplasms having histologic and ultrastructual heterogeneity (e.g., mixed cell types).

A compound of the present invention, or a pharmaceutically acceptable salt, prodrug, metabolite, polymorph, or solvate thereof, may be used to treat breast cancer, or used to identify suitable candidates for such purposes. A breast cancer that is to be treated can include familial breast cancer. A breast cancer that is to be treated can include sporadic breast cancer. A breast cancer that is to be treated can arise in a male subject. A breast cancer that is to be treated can arise in a female subject. A breast cancer that is to be treated can arise in a premenopausal female subject or a postmenopausal female subject. A breast cancer that is to be treated can arise in a subject equal to or older than 30 years old, or a subject younger than 30 years old. A breast cancer that is to be treated has arisen in a subject equal to or older than 50 years old, or a subject younger than 50 years old. A breast cancer that is to be treated can arise in a subject equal to or older than 70 years old, or a subject younger than 70 years old.

A breast cancer that is to be treated can be typed to identify a familial or spontaneous mutation in BRCA1, BRCA2, or p53. A breast cancer that is to be treated can be typed as having a HER2/neu gene amplification, as overexpressing HER2/neu, or as having a low, intermediate or high level of HER2/neu expression. A breast cancer that is to be treated can be typed for a marker selected from the group consisting of estrogen receptor (ER), progesterone receptor (PR), human epidermal growth factor receptor-2, Ki-67, CA 15-3, CA 27-29, and c-Met. A breast cancer that is to be treated can be typed as ER-unknown, ER-rich or ER-poor. A breast cancer that is to be treated can be typed as ER-negative or ER-positive. ER-typing of a breast cancer may be performed by any reproducible means. ER-typing of a breast cancer may be performed as set forth in Onkologie 27: 175-179 (2004). A breast cancer that is to be treated can be typed as PR-unknown, PR-rich, or PR-poor. A breast cancer that is to be treated can be typed as PR-negative or PR-positive. A breast cancer that is to be treated can be typed as receptor positive or receptor negative. A breast cancer that is to be treated can be typed as being associated with elevated blood levels of CA 15-3, or CA 27-29, or both.

A breast cancer that is to be treated can include a localized tumor of the breast. A breast cancer that is to be treated can include a tumor of the breast that is associated with a negative sentinel lymph node (SLN) biopsy. A breast cancer that is to be treated can include a tumor of the breast that is associated with a positive sentinel lymph node (SLN) biopsy. A breast cancer that is to be treated can include a tumor of the breast that is associated with one or more positive axillary lymph nodes, where the axillary lymph nodes have been staged by any applicable method. A breast cancer that is to be treated can include a tumor of the breast that has been typed as having nodal negative status (e.g., node-negative) or nodal positive status (e.g., node-positive). A breast cancer that is to be treated can include a tumor of the breast that has metastasized to other locations in the body. A breast cancer that is to be treated can be classified as having metastasized to a location selected from the group consisting of bone, lung, liver, or brain. A breast cancer that is to be treated can be classified according to a characteristic selected from the group consisting of metastatic, localized, regional, local-regional, locally advanced, distant, multicentric, bilateral, ipsilateral, contralateral, newly diagnosed, recurrent, and inoperable.

A compound of the present invention, or a pharmaceutically acceptable salt, prodrug, metabolite, polymorph or solvate thereof, may be used to treat or prevent a cell proliferative disorder of the breast, or to treat or prevent breast cancer, in a subject having an increased risk of developing breast cancer relative to the population at large, or used to identify suitable candidates for such purposes. A subject with an increased risk of developing breast cancer relative to the population at large is a female subject with a family history or personal history of breast cancer. A subject with an increased risk of developing breast cancer relative to the population at large is a female subject having a germ-line or spontaneous mutation in BRCA1 or BRCA2, or both. A subject with an increased risk of developing breast cancer relative to the population at large is a female subject with a family history of breast cancer and a germ-line or spontaneous mutation in BRCA1 or BRCA2, or both. A subject with an increased risk of developing breast cancer relative to the population at large is a female who is greater than 30 years old, greater than 40 years old, greater than 50 years old, greater than 60 years old, greater than 70 years old, greater than 80 years old, or greater than 90 years old. A subject with an increased risk of developing breast cancer relative to the population at large is a subject with atypical hyperplasia of the breast, ductal carcinoma in situ (DCIS), intraductal carcinoma, lobular carcinoma in situ (LCIS), lobular neoplasia, or a stage 0 growth or lesion of the breast (e.g., stage 0 or grade 0 breast cancer, or carcinoma in situ).

A breast cancer that is to be treated can histologically graded according to the Scarff-Bloom-Richardson system, wherein a breast tumor has been assigned a mitosis count score of 1, 2, or 3; a nuclear pleiomorphism score of 1, 2, or 3; a tubule formation score of 1, 2, or 3; and a total Scarff-Bloom-Richardson score of between 3 and 9. A breast cancer that is to be treated can be assigned a tumor grade according to the International Consensus Panel on the Treatment of Breast Cancer selected from the group consisting of grade 1, grade 1-2, grade 2, grade 2-3, or grade 3.

A cancer that is to be treated can be staged according to the American Joint Committee on Cancer (AJCC) TNM classification system, where the tumor (T) has been assigned a stage of TX, T1, T1mic, T1a, T1b, T1c, T2, T3, T4, T4a, T4b, T4c, or T4d; and where the regional lymph nodes (N) have been assigned a stage of NX, N0, N1, N2, N2a, N2b, N3, N3a, N3b, or N3c; and where distant metastasis (M) can be assigned a stage of MX, M0, or M1. A cancer that is to be treated can be staged according to an American Joint Committee on Cancer (AJCC) classification as Stage I, Stage IIA, Stage IIB, Stage IIIA, Stage IIIB, Stage IIIC, or Stage IV. A cancer that is to be treated can be assigned a grade according to an AJCC classification as Grade GX (e.g., grade cannot be assessed), Grade 1, Grade 2, Grade 3 or Grade 4. A cancer that is to be treated can be staged according to an AJCC pathologic classification (pN) of pNX, pN0, PN0 (1−), PN0 (1+), PN0 (mol−), PN0 (mol+), PN1, PN1 (mi), PN1a, PN1b, PN1c, pN2, pN2a, pN2b, pN3, pN3a, pN3b, or pN3c.

A cancer that is to be treated can include a tumor that has been determined to be less than or equal to about 2 centimeters in diameter. A cancer that is to be treated can include a tumor that has been determined to be from about 2 to about 5 centimeters in diameter. A cancer that is to be treated can include a tumor that has been determined to be greater than or equal to about 3 centimeters in diameter. A cancer that is to be treated can include a tumor that has been determined to be greater than 5 centimeters in diameter. A cancer that is to be treated can be classified by microscopic appearance as well differentiated, moderately differentiated, poorly differentiated, or undifferentiated. A cancer that is to be treated can be classified by microscopic appearance with respect to mitosis count (e.g., amount of cell division) or nuclear pleiomorphism (e.g., change in cells). A cancer that is to be treated can be classified by microscopic appearance as being associated with areas of necrosis (e.g., areas of dying or degenerating cells). A cancer that is to be treated can be classified as having an abnormal karyotype, having an abnormal number of chromosomes, or having one or more chromosomes that are abnormal in appearance. A cancer that is to be treated can be classified as being aneuploid, triploid, tetraploid, or as having an altered ploidy. A cancer that is to be treated can be classified as having a chromosomal translocation, or a deletion or duplication of an entire chromosome, or a region of deletion, duplication or amplification of a portion of a chromosome.

A cancer that is to be treated can be evaluated by DNA cytometry, flow cytometry, or image cytometry. A cancer that is to be treated can be typed as having 10%, 20%, 30%, 40%, 50%, 60%, 70%, 80%, or 90% of cells in the synthesis stage of cell division (e.g., in S phase of cell division). A cancer that is to be treated can be typed as having a low S-phase fraction or a high S-phase fraction.

As used herein, a "normal cell" is a cell that cannot be classified as part of a "cell proliferative disorder". A normal cell lacks unregulated or abnormal growth, or both, that can lead to the development of an unwanted condition or disease. Preferably, a normal cell possesses normally functioning cell cycle checkpoint control mechanisms.

As used herein, "contacting a cell" refers to a condition in which a compound or other composition of matter is in direct contact with a cell, or is close enough to induce a desired biological effect in a cell.

As used herein, "candidate compound" refers to a compound of the present invention, or a pharmaceutically acceptable salt, prodrug, metabolite, polymorph or solvate thereof, that has been or will be tested in one or more in vitro or in vivo biological assays, in order to determine if that compound is likely to elicit a desired biological or medical response in a cell, tissue, system, animal or human that is being sought by a researcher or clinician. A candidate compound is a compound of the present invention, or a pharmaceutically acceptable salt, prodrug, metabolite, polymorph or solvate thereof. The biological or medical response can be the treatment of cancer. The biological or medical response can be treatment or prevention of a cell proliferative disorder. The biological response or effect can also include a change in cell proliferation or growth that occurs in vitro or in an animal model, as well as other biological changes that are observable in vitro. In vitro or in vivo biological assays can include, but are not limited to, enzymatic activity assays, electrophoretic mobility shift assays, reporter gene assays, in vitro cell viability assays, and the assays described herein.

As used herein, "monotherapy" refers to the administration of a single active or therapeutic compound to a subject in need thereof. Preferably, monotherapy will involve administration of a therapeutically effective amount of an active compound. For example, cancer monotherapy with one of the compound of the present invention, or a pharmaceutically acceptable salt, prodrug, metabolite, analog or derivative thereof, to a subject in need of treatment of cancer. Monotherapy may be contrasted with combination therapy, in which a combination of multiple active compounds is administered, preferably with each component of the combination present in a therapeutically effective amount. Monotherapy with a compound of the present invention, or a pharmaceutically acceptable salt, prodrug, metabolite, polymorph or solvate thereof, may be more effective than combination therapy in inducing a desired biological effect.

As used herein, "treating" or "treat" describes the management and care of a patient for the purpose of combating a disease, condition, or disorder and includes the administration of a compound of the present invention, or a pharmaceutically acceptable salt, prodrug, metabolite, polymorph or solvate thereof, to alleviate the symptoms or complications of a disease, condition or disorder, or to eliminate the disease, condition or disorder. The term "treat" can also include treatment of a cell in vitro or an animal model.

A compound of the present invention, or a pharmaceutically acceptable salt, prodrug, metabolite, polymorph or solvate thereof, can or may also be used to prevent a relevant disease, condition or disorder, or used to identify suitable candidates for such purposes. As used herein, "preventing" or "prevent" describes reducing or eliminating the onset of the symptoms or complications of such disease, condition or disorder.

As used herein, the term "alleviate" is meant to describe a process by which the severity of a sign or symptom of a disorder is decreased. Importantly, a sign or symptom can be alleviated without being eliminated. The administration of pharmaceutical compositions of the invention can or may lead to the elimination of a sign or symptom, however, elimination is not required. Effective dosages should be expected to decrease the severity of a sign or symptom. For instance, a sign or symptom of a disorder such as cancer, which can occur in multiple locations, is alleviated if the severity of the cancer is decreased within at least one of multiple locations.

As used herein, the term "severity" is meant to describe the potential of cancer to transform from a precancerous, or benign, state into a malignant state. Alternatively, or in addition, severity is meant to describe a cancer stage, for example, according to the TNM system (accepted by the International Union Against Cancer (UICC) and the American Joint Committee on Cancer (AJCC)) or by other art-recognized methods. Cancer stage refers to the extent or severity of the cancer, based on factors such as the location of the primary tumor, tumor size, number of tumors, and lymph node involvement (spread of cancer into lymph nodes). Alternatively, or in addition, severity is meant to describe the tumor grade by art-recognized methods (see, National Cancer Institute, www.cancer.gov). Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade vary with each type of cancer. Severity also describes a histologic grade, also called differentiation, which refers to how much the tumor cells resemble normal cells of the same tissue type (see, National Cancer Institute, www.cancer.gov). Furthermore, severity describes a nuclear grade, which refers to the size and shape of the nucleus in tumor cells and the percentage of tumor cells that are dividing (see, National Cancer Institute, www.cancer.gov).

Severity can also describe the degree to which a tumor has secreted growth factors, degraded the extracellular matrix, become vascularized, lost adhesion to juxtaposed tissues, or metastasized. Moreover, severity can describe the number of locations to which a primary tumor has metastasized. Finally, severity can include the difficulty of treating tumors of varying types and locations. For example, inoperable tumors, those cancers which have greater access to multiple body systems (hematological and immunological tumors), and those which are the most resistant to traditional treatments are considered most severe. In these situations, prolonging the life expectancy of the subject and/or reducing pain, decreasing the proportion of cancerous cells or restricting cells to one system, and improving cancer stage/tumor grade/histological grade/nuclear grade are considered alleviating a sign or symptom of the cancer.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

Cancer is a group of diseases that may cause almost any sign or symptom. The signs and symptoms will depend on where the cancer is, the size of the cancer, and how much it affects the nearby organs or structures. If a cancer spreads (metastasizes), then symptoms may appear in different parts of the body.

As a cancer grows, it begins to push on nearby organs, blood vessels, and nerves. This pressure creates some of the signs and symptoms of cancer. If the cancer is in a critical area, such as certain parts of the brain, even the smallest tumor can cause early symptoms.

But sometimes cancers start in places where it does not cause any symptoms until the cancer has grown quite large. Pancreas cancers, for example, do not usually grow large enough to be felt from the outside of the body. Some pancreatic cancers do not cause symptoms until they begin to grow around nearby nerves (this causes a backache). Others grow around the bile duct, which blocks the flow of bile and leads to a yellowing of the skin known as jaundice. By the time a pancreatic cancer causes these signs or symptoms, it has usually reached an advanced stage.

A cancer may also cause symptoms such as fever, fatigue, or weight loss. This may be because cancer cells use up much of the body's energy supply or release substances that change the body's metabolism. Or the cancer may cause the immune system to react in ways that produce these symptoms.

Sometimes, cancer cells release substances into the bloodstream that cause symptoms not usually thought to result from cancers. For example, some cancers of the pancreas can release substances which cause blood clots to develop in veins of the legs. Some lung cancers make hormone-like substances that affect blood calcium levels, affecting nerves and muscles and causing weakness and dizziness.

Cancer presents several general signs or symptoms that occur when a variety of subtypes of cancer cells are present. Most people with cancer will lose weight at some time with their disease. An unexplained (unintentional) weight loss of 10 pounds or more may be the first sign of cancer, particularly cancers of the pancreas, stomach, esophagus, or lung.

Fever is very common with cancer, but is more often seen in advanced disease. Almost all patients with cancer will have fever at some time, especially if the cancer or its treatment affects the immune system and makes it harder for the body to fight infection. Less often, fever may be an early sign of cancer, such as with leukemia or lymphoma.

Fatigue may be an important symptom as cancer progresses. It may happen early, though, in cancers such as with leukemia, or if the cancer is causing an ongoing loss of blood, as in some colon or stomach cancers.

Pain may be an early symptom with some cancers such as bone cancers or testicular cancer. But most often pain is a symptom of advanced disease.

Along with cancers of the skin (see next section), some internal cancers can cause skin signs that can be seen. These changes include the skin looking darker (hyperpigmentation), yellow (jaundice), or red (erythema); itching; or excessive hair growth.

Alternatively, or in addition, cancer subtypes present specific signs or symptoms. Changes in bowel habits or bladder function could indicate cancer. Long-term constipation, diarrhea, or a change in the size of the stool may be a sign of colon cancer. Pain with urination, blood in the urine, or a change in bladder function (such as more frequent or less frequent urination) could be related to bladder or prostate cancer.

Changes in skin condition or appearance of a new skin condition could indicate cancer. Skin cancers may bleed and look like sores that do not heal. A long-lasting sore in the mouth could be an oral cancer, especially in patients who smoke, chew tobacco, or frequently drink alcohol. Sores on the penis or vagina may either be signs of infection or an early cancer.

Unusual bleeding or discharge could indicate cancer. Unusual bleeding can happen in either early or advanced cancer. Blood in the sputum (phlegm) may be a sign of lung cancer. Blood in the stool (or a dark or black stool) could be a sign of colon or rectal cancer. Cancer of the cervix or the endometrium (lining of the uterus) can cause vaginal bleeding. Blood in the urine may be a sign of bladder or kidney cancer. A discharge from the nipple may be a sign of breast cancer.

A thickening or lump in the breast or in other parts of the body could indicate the presence of a cancer. Many cancers can be felt through the skin, mostly in the breast, testicle, lymph nodes (glands), and the soft tissues of the body. A lump or thickening may be an early or late sign of cancer. Any lump or thickening could be indicative of cancer, especially if the formation is new or has grown in size.

Indigestion or trouble swallowing could indicate cancer. While these symptoms commonly have other causes, indigestion or swallowing problems may be a sign of cancer of the esophagus, stomach, or pharynx (throat).

Recent changes in a wart or mole could be indicative of cancer. Any wart, mole, or freckle that changes in color, size, or shape, or loses its definite borders indicates the potential development of cancer. For example, the skin lesion may be a melanoma.

A persistent cough or hoarseness could be indicative of cancer. A cough that does not go away may be a sign of lung cancer. Hoarseness can be a sign of cancer of the larynx (voice box) or thyroid.

While the signs and symptoms listed above are the more common ones seen with cancer, there are many others that are less common and are not listed here.

Treating cancer may result in or can result in a reduction in size of a tumor. A reduction in size of a tumor may also be referred to as "tumor regression". Preferably, after treatment, tumor size would be reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer may result in or can result in a reduction in tumor volume. Preferably, after treatment, tumor volume would be reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer may result in or can result in a decrease in number of tumors. Preferably, after treatment, tumor number would be reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer may result in or can result in a decrease in number of metastatic lesions in other tissues or organs distant from the primary tumor site. Preferably, after treatment, the number of metastatic lesions would be reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer may result in or can result in an increase in average survival time of a population of treated subjects in comparison to a population receiving carrier alone. Preferably, the average survival time would be increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer may result in or can result in an increase in average survival time of a population of treated subjects in comparison to a population of untreated subjects. Preferably, the average survival time would be increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer may result in or can result in increase in average survival time of a population of treated subjects in comparison to a population receiving monotherapy with a drug that is not a compound of the present invention, or a pharmaceutically acceptable salt, prodrug, metabolite, analog or derivative thereof. Preferably, the average survival time would be increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer may result in or can result in a decrease in the mortality rate of a population of treated subjects in comparison to a population receiving carrier alone. Treating cancer may result in or can result in a decrease in the mortality rate of a population of treated subjects in comparison to an untreated population. Treating cancer may result in or can result in a decrease in the mortality rate of a population of treated subjects in comparison to a population receiving monotherapy with a drug that is not a compound of the present invention, or a pharmaceutically acceptable salt, prodrug, metabolite, analog or derivative thereof. Preferably, the mortality rate would be decreased by more than 2%; more preferably, by more than 5%; more preferably, by more than 10%; and most preferably, by more than 25% decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer may result in or can result in a decrease in tumor growth rate. Preferably, after treatment, tumor growth rate would be reduced by at least 5% relative to number prior to treatment; more preferably, tumor growth rate would be reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer may result in or can result in a decrease in tumor regrowth. Preferably, after treatment, tumor regrowth would be less than 5%; more preferably, tumor regrowth would be less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder may result in or can result in a reduction in the rate of cellular proliferation. Preferably, after treatment, the rate of cellular proliferation would be reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder may result in or can result in a reduction in the proportion of proliferating cells. Preferably, after treatment, the proportion of proliferating cells would be reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating or preventing a cell proliferative disorder may result in or can result in a decrease in size of an area or zone of cellular proliferation. Preferably, after treatment, size of an area or zone of cellular proliferation would be reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder may result in or can result in a decrease in the number or proportion of cells having an abnormal appearance or morphology. Preferably, after treatment, the number of cells having an abnormal morphology would be reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

As used herein, the term "selectively" means tending to occur at a higher frequency in one population than in another population. The compared populations can be cell populations. A compound of the present invention, or a pharmaceutically acceptable salt, prodrug, metabolite, polymorph or solvate thereof, may or can act selectively on a cancer or precancerous cell but not on a normal cell. A compound of the present invention, or a pharmaceutically acceptable salt, prodrug, metabolite, polymorph or solvate thereof, may or can act selectively to modulate one molecular target (e.g., a target protein methyltransferase) but does not significantly modulate another molecular target (e.g., a non-target protein methyltransferase). The invention also provides a method for selectively inhibiting the activity of an enzyme, such as a protein methyltransferase. Preferably, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in cancer cells if it occurred greater than twice as frequently in cancer cells as compared to normal cells.

A compound of the present invention, or a pharmaceutically acceptable salt, prodrug, metabolite, polymorph or solvate thereof, may or can modulate the activity of a molecular target (e.g., a target protein methyltransferase). Modulating refers to stimulating or inhibiting an activity of a molecular target. Preferably, a compound of the present invention, or a pharmaceutically acceptable salt, prodrug, metabolite, polymorph or solvate thereof, modulates the activity of a molecular target if it stimulates or inhibits the activity of the molecular target by at least 2-fold relative to the activity of the molecular target under the same conditions but lacking only the presence of said compound. More preferably, a compound of the present invention, or a pharmaceutically acceptable salt, prodrug, metabolite, polymorph or solvate thereof, modulates the activity of a molecular target if it stimulates or inhibits the activity of the molecular target by at least 5-fold, at least 10-fold, at least 20-fold, at least 50-fold, at least 100-fold relative to the activity of the molecular target under the same conditions but lacking only the presence of said compound. The activity of a molecular target may be measured by any reproducible means. The activity of a molecular target may be measured in vitro or in vivo. For example, the activity of a molecular target may be measured in vitro by an enzymatic activity assay or a DNA binding assay, or the activity of a molecular target may be measured in vivo by assaying for expression of a reporter gene.

A compound of the present invention, or a pharmaceutically acceptable salt, prodrug, metabolite, polymorph or solvate thereof, does not significantly modulate the activity of a molecular target if the addition of the compound does not stimulate or inhibit the activity of the molecular target by greater than 10% relative to the activity of the molecular target under the same conditions but lacking only the presence of said compound.

As used herein, the term "isozyme selective" means preferential inhibition or stimulation of a first isoform of an enzyme in comparison to a second isoform of an enzyme (e.g., preferential inhibition or stimulation of a protein methyltransferase isozyme alpha in comparison to a protein methyltransferase isozyme beta). Preferably, a compound of the present invention, or a pharmaceutically acceptable salt, prodrug, metabolite, polymorph or solvate thereof, demonstrates a minimum of a fourfold differential, preferably a tenfold differential, more preferably a fifty fold differential, in the dosage required to achieve a biological effect. Preferably, a compound of the present invention, or a pharmaceutically acceptable salt, prodrug, metabolite, polymorph or solvate thereof, demonstrates this differential across the range of inhibition, and the differential is exemplified at the $IC_{50}$, i.e., a 50% inhibition, for a molecular target of interest.

Administering a compound of the present invention, or a pharmaceutically acceptable salt, prodrug, metabolite, polymorph or solvate thereof, to a cell or a subject in need thereof may result in or can result in modulation (i.e., stimulation or inhibition) of an activity of a protein methyltransferase of interest.

The present invention provides methods to assess biological activity of a compound of the present invention, or a pharmaceutically acceptable salt, prodrug, metabolite, polymorph or solvate thereof or methods of identifying a test compound as an inhibitor of a Y641 mutant of EZH2. In one embodiment the method includes combining an isolated Y641 mutant of EZH2 with a histone substrate a methyl group donor (such as S-adenosylmethionine (SAM)), and a test compound, wherein the histone substrate comprises a form of H3-K27 selected from the group consisting of unmethylated H3-K27, monomethylated H3-K27, dimethylated H3-K27, and any combination thereof; and performing an assay to detect methylation of H3-K27 in the histone substrate, thereby identifying the test compound as an inhibitor of the Y641 mutant of EZH2 when methylation of H3-K27 in the presence of the test compound is less than methylation of H3-K27 in the absence of the test compound. The assay to detect methylation of H3-K27 can be selected to measure the rate of methylation, the extent of methylation, or both the rate and extent of methylation.

The Y641 mutant of EZH2 is isolated as a PRC2 complex or functional equivalent thereof. As used herein, the term "isolated" means substantially separated from other components with which the complex may be found as it occurs in nature. A compound can be isolated without necessarily being purified. In one embodiment the mutant of EZH2 is isolated as a complex of a Y641 mutant of EZH2 together with EED and SUZ12. In another embodiment the mutant of EZH2 is isolated as a complex of a Y641 mutant of EZH2 together with EED, SUZ12, and RbAp48. Under appropriate conditions, a PRC2 complex or functional equivalent thereof exhibits histone methyltransferase activity for H3-K27. In one embodiment the complex is composed of recombinantly expressed component polypeptides, e.g., EZH2, EED, SUZ12, with or without RbAp48.

The isolated Y641 mutant of EZH2 is combined with a histone substrate. A histone substrate includes any suitable source of histone polypeptides or fragments thereof that can serve as substrate for EZH2. In one embodiment the histone substrate includes histones isolated from a subject. The histones can be isolated from cells of a subject using any suitable method; such methods are well known to persons skilled in the art and need not be further specified here. See, for example, Fang et al. (2004) *Methods Enzymol* 377:213-26. In accordance with the Examples below, in one embodiment the histone substrate is provided as nucleosomes. In accordance with the Examples below, in one embodiment the histone substrate is provided as avian (chicken) erythrocyte nucleosomes.

Histone substrate so provided may include an admixture of states of histone modification, including various states of H3-K27 methylation as judged by Western blotting with H3-K27 methylation state-specific antibodies. In one embodiment the histone substrate may be provided as purified full-length histone H3. Such purified full-length histone H3 may be provided as a homogeneous preparation in respect of states of H3-K27 methylation, or as an admixture of various states of H3-K27 methylation. Homogeneous preparations of isolated histone H3 in respect of states of H3-K27 methylation may be prepared in part by passage over an immunoaffinity column loaded with suitable H3-K27 methylation state-specific antibodies or by immunoprecipitation using magnetic beads coated with suitable H3-K27 methylation state-specific antibodies. Alternatively or in addition, the methylation state of H3-K27 can be characterized as part of performing the assay. For example, the starting material histone substrate might be characterized as containing 50 percent unmethylated H3-K27, 40 percent monomethylated H3-K27, 10 percent dimethylated H3-K27, and 0 percent trimethylated H3-K27.

In one embodiment the histone substrate includes a peptide library or a suitable peptide comprising one or more amino acid sequences related to histone H3, including, in particular, a sequence that encompasses H3-K27. For example, in one embodiment, the histone substrate is a peptide fragment that corresponds to amino acid residues 21-44 of histone H3. The peptide library or peptide can be prepared by peptide synthesis according to techniques well known in the art and optionally modified so as to incorporate any desired degree of methylation of lysine corresponding to H3-K27. As described in the Examples below, such peptides can also be modified to incorporate a label, such as biotin, useful in performing downstream assays. In one embodiment the label is appended to the amino (N)-terminus of the peptide(s). In one embodiment the label is appended to the carboxy (C)-terminus of the peptide(s).

Detection of methylation of H3-K27 can be accomplished using any suitable method. In one embodiment, the source of donor methyl groups includes methyl groups that are labeled with a detectable label. The detectable label in one embodiment is an isotopic label, e.g., tritium. Other types of labels may include, for example, fluorescent labels.

Detection of formation of trimethylated H3-K27 can be accomplished using any suitable method. For example, detection of formation of trimethylated H3-K27 can be accomplished using an assay to detect incorporation of labeled methyl groups, such as described above, optionally combined with a chromatographic or other method to separate labeled products by size, e.g., polyacrylamide gel electrophoresis (PAGE), capillary electrophoresis (CE), or high pressure liquid chromatography (HPLC). Alternatively or in addition, detection of formation of trimethylated H3-K27 can be accomplished using antibodies that are specific for trimethylated H3-K27.

Detection of conversion of monomethylated H3-K27 to dimethylated H3-K27 can be accomplished using any suitable method. In one embodiment the conversion is measured using antibodies specific for monomethylated H3-K27 and dimethylated H3-K27. For example, starting amounts or concentrations of monomethylated H3-K27 and dimethylated H3-K27 may be determined using appropriate antibodies specific for monomethylated H3-K27 and dimethylated H3-K27. Following the combination of enzyme, substrate, methyl group donor, and test compound, resulting amounts or concentrations of monomethylated H3-K27 and dimethylated H3-K27 may then be determined using appropriate antibodies specific for monomethylated H3-K27 and dimethylated H3-K27. The beginning and resulting amounts or concentrations of monomethylated H3-K27 and dimethylated H3-K27 can then be compared. Alternatively or in addition, beginning and resulting amounts or concentrations of monomethylated H3-K27 and dimethylated H3-K27 can then be compared to corresponding amounts of concentrations from a negative control. A negative control reaction, in which no test agent is included in the assay, can be run in parallel or as a historical control. Results of such control reaction can optionally be subtracted from corresponding results of the experimental reaction prior to or in conjunction with making the comparison mentioned above.

Because the dimethylated form of H3-K27 may be further methylated in the same assay, a reduction in the amount or concentration of monomethylated H3-K27 may not appear to correspond directly to an increase in dimethylated H3-K27. In this instance, it may be presumed, however, that a reduction in the amount or concentration of monomethylated H3-K27 is, by itself, reflective of conversion of monomethylated H3-K27 to dimethylated H3-K27.

Detection of conversion of dimethylated H3-K27 to trimethylated H3-K27 can be accomplished using any suitable method. In one embodiment the conversion is measured using antibodies specific for dimethylated H3-K27 and trimethylated H3-K27. For example, starting amounts or concentrations of dimethylated H3-K27 and trimethylated H3-K27 may be determined using appropriate antibodies specific for dimethylated H3-K27 and trimethylated H3-K27. Following the combination of enzyme, substrate, and test compound, resulting amounts or concentrations of dimethylated H3-K27 and trimethylated H3-K27 may then be determined using appropriate antibodies specific for dimethylated H3-K27 and trimethylated H3-K27. The beginning and resulting amounts or concentrations of dimethylated H3-K27 and trimethylated H3-K27 can then be compared. Alternatively or in addition, beginning and resulting amounts or concentrations of dimethylated H3-K27 and trimethylated H3-K27 can then be compared to corresponding amounts of concentrations from a negative control. A negative control reaction, in which no test agent is included in the assay, can be run in parallel or as a historical control. Results of such control reaction can optionally be subtracted from corresponding results of the experimental reaction prior to or in conjunction with making the comparison mentioned above.

A test agent is identified as an inhibitor of the Y641 mutant of EZH2 when methylation of H3-K27 with the test compound is less than methylation of H3-K27 without the test compound. In one embodiment, a test agent is identified as an inhibitor of the Y641 mutant of EZH2 when formation of trimethylated H3-K27 in the presence of the test compound is less than formation of trimethylated H3-K27 in the absence of the test compound.

The present invention also provides a method for identifying a selective inhibitor of a Y641 mutant of EZH2. In one embodiment the method includes combining an isolated Y641 mutant of EZH2 with a histone substrate, a methyl group donor (e.g., SAM), and a test compound, wherein the histone substrate comprises a form of H3-K27 selected from the group consisting of monomethylated H3-K27, dimethylated H3-K27, and a combination of monomethylated H3-K27 and dimethylated H3-K27, thereby forming a test mixture; combining an isolated wild-type EZH2 with a histone substrate, a methyl group donor (e.g., SAM), and a test compound, wherein the histone substrate comprises a form of H3-K27 selected from the group consisting of monomethylated H3-K27, dimethylated H3-K27, and a combination of monomethylated H3-K27 and dimethylated H3-K27, thereby forming a control mixture; performing an assay to detect trimethylation of the histone substrate in each of the test mixture and the control mixture; calculating the ratio of (a) trimethylation with the Y641 mutant of EZH2 and the test compound (M+) to (b) trimethylation with the Y641 mutant of EZH2 without the test compound (M−); calculating the ratio of (c) trimethylation with wild-type EZH2 and the test compound (WT+) to (d) trimethylation with wild-type EZH2 without the test compound (WT−); comparing the ratio (a)/(b) with the ratio (c)/(d); and identifying the test compound as a selective inhibitor of the Y641 mutant of EZH2 when the ratio (a)/(b) is less than the ratio (c)/(d). In one embodiment the method further includes taking into account a negative control without test compound for either or both of the test mixture and the control mixture.

In some assays, immunological reagents, e.g., antibodies and antigens, are employed. Fluorescence can be utilized in the measurement of enzymatic activity in some assays. As used herein, "fluorescence" refers to a process through which a molecule emits a photon as a result of absorbing an incoming photon of higher energy by the same molecule. Specific methods for assessing the biological activity of the disclosed compounds are described in the examples.

Administering a compound of the present invention, or a pharmaceutically acceptable salt, prodrug, metabolite, polymorph or solvate thereof, to a cell or a subject in need thereof may or can result in modulation (i.e., stimulation or inhibition) of an activity of an intracellular target (e.g., substrate). Several intracellular targets may or can be modulated with the compounds of the present invention, including, but not limited to, protein methyltransferase.

Activating refers to placing a composition of matter (e.g., protein or nucleic acid) in a state suitable for carrying out a desired biological function. A composition of matter capable of being activated also has an unactivated state. An activated composition of matter may have an inhibitory or stimulatory biological function, or both.

Elevation refers to an increase in a desired biological activity of a composition of matter (e.g., a protein or a nucleic acid). Elevation may occur through an increase in concentration of a composition of matter.

As used herein, "a cell cycle checkpoint pathway" refers to a biochemical pathway that is involved in modulation of a cell cycle checkpoint. A cell cycle checkpoint pathway may have stimulatory or inhibitory effects, or both, on one or more functions comprising a cell cycle checkpoint. A cell cycle checkpoint pathway is comprised of at least two compositions of matter, preferably proteins, both of which contribute to modulation of a cell cycle checkpoint. A cell cycle checkpoint pathway may be activated through an activation of one or more members of the cell cycle checkpoint pathway. Preferably, a cell cycle checkpoint pathway is a biochemical signaling pathway.

As used herein, "cell cycle checkpoint regulator" refers to a composition of matter that can function, at least in part, in modulation of a cell cycle checkpoint. A cell cycle checkpoint regulator may have stimulatory or inhibitory effects, or both, on one or more functions comprising a cell cycle checkpoint. A cell cycle checkpoint regulator can be a protein or not a protein.

Treating cancer or a cell proliferative disorder may result in or can result in cell death, and preferably, cell death would result in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. A number of cells in a population can be measured by fluorescence activated cell sorting (FACS), immunofluorescence microscopy and light microscopy. Methods of measuring cell death are as shown in Li et al., *Proc Natl Acad Sci USA.* 100(5): 2674-8, 2003. In an aspect, cell death occurs by apoptosis.

Preferably, an effective amount of a compound of the present invention, or a pharmaceutically acceptable salt, prodrug, metabolite, polymorph or solvate thereof, would not be significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells. In an aspect, cell death occurs by apoptosis.

Contacting a cell with a compound of the present invention, or a pharmaceutically acceptable salt, prodrug, metabolite, polymorph or solvate thereof, may or can induce or activate cell death selectively in cancer cells. Administering to a subject in need thereof a compound of the present invention, or a pharmaceutically acceptable salt, prodrug, metabolite, polymorph or solvate thereof, may or can induce or activate cell death selectively in cancer cells. Contacting a cell with a compound of the present invention, or a pharmaceutically acceptable salt, prodrug, metabolite, polymorph or solvate thereof, may or can induce cell death selectively in one or more cells affected by a cell proliferative disorder. Preferably, administering to a subject in need thereof a compound of the present invention, or a pharmaceutically acceptable salt, prodrug, metabolite, polymorph or solvate thereof, would induce cell death selectively in one or more cells affected by a cell proliferative disorder.

One aspect of the present invention relates to a method of treating or preventing cancer (e.g., the course of which can be influenced by modulating EZH2-mediated protein methylation) by administering a compound of the present invention, or a pharmaceutically acceptable salt, prodrug, metabolite, polymorph or solvate thereof, to a subject in need thereof, where administration of the compound of the present invention, or a pharmaceutically acceptable salt, prodrug, metabolite, polymorph or solvate thereof, results in one or more of the following: prevention of cancer cell proliferation by accumulation of cells in one or more phases of the cell cycle (e.g. G1, G1/S, G2/M), or induction of cell senescence, or promotion of tumor cell differentiation; promotion of cell death in cancer cells via cytotoxicity, necrosis or apoptosis, without a significant amount of cell death in normal cells, antitumor activity in animals with a therapeutic index of at least 2. As used herein, "therapeutic index" is the maximum tolerated dose divided by the efficacious dose. The present invention also relates to a method used to identify suitable candidates for treating or preventing cancer.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* ($3^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., $18^{th}$ edition (1990). These texts can, of course, also be referred to in making or using an aspect of the invention.

As used herein, "combination therapy" or "co-therapy" includes the administration of a compound of the present invention, or a pharmaceutically acceptable salt, prodrug, metabolite, polymorph or solvate thereof, and at least a second agent as part of a specific treatment regimen intended to provide the beneficial effect from the co-action of these therapeutic agents. The beneficial effect of the combination may include, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may be, but generally is not, intended to encompass the administration of two or more of these therapeutic agents as part of separate monotherapy regimens that incidentally and arbitrarily result in the combinations of the present invention.

"Combination therapy" is intended to embrace administration of these therapeutic agents in a sequential manner, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

A compound of the present invention, or a pharmaceutically acceptable salt, prodrug, metabolite, analog or derivative thereof, may be administered in combination with a second chemotherapeutic agent. The second chemotherapeutic agent (also referred to as an anti-neoplastic agent or anti-proliferative agent) can be an alkylating agent; an antibiotic; an anti-metabolite; a detoxifying agent; an interferon; a polyclonal or monoclonal antibody; an EGFR inhibitor; a HER2 inhibitor; a histone deacetylase inhibitor; a hormone; a mitotic inhibitor; an MTOR inhibitor; a multi-kinase inhibitor; a serine/threonine kinase inhibitor; a tyrosine kinase inhibitors; VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase or a protein methyltransferase), a cytidine analogue drug or any chemotherapeutic, anti-neoplastic or anti-proliferative agent listed in www.cancer.org/docroot/cdg/cdg_0.asp.

Exemplary alkylating agents include, but are not limited to, cyclophosphamide (Cytoxan; Neosar); chlorambucil (Leukeran); melphalan (Alkeran); carmustine (BiCNU); busulfan (Busulfex); lomustine (CeeNU); dacarbazine (DTIC-Dome); oxaliplatin (Eloxatin); carmustine (Gliadel); ifosfamide (Ifex); mechlorethamine (Mustargen); busulfan (Myleran);

carboplatin (Paraplatin); cisplatin (CDDP; Platinol); temozolomide (Temodar); thiotepa (Thioplex); bendamustine (Treanda); or streptozocin (Zanosar).

Exemplary antibiotics include, but are not limited to, doxorubicin (Adriamycin); doxorubicin liposomal (Doxil); mitoxantrone (Novantrone); bleomycin (Blenoxane); daunorubicin (Cerubidine); daunorubicin liposomal (DaunoXome); dactinomycin (Cosmegen); epirubicin (Ellence); idarubicin (Idamycin); plicamycin (Mithracin); mitomycin (Mutamycin); pentostatin (Nipent); or valrubicin (Valstar).

Exemplary anti-metabolites include, but are not limited to, fluorouracil (Adrucil); capecitabine (Xeloda); hydroxyurea (Hydrea); mercaptopurine (Purinethol); pemetrexed (Alimta); fludarabine (Fludara); nelarabine (Arranon); cladribine (Cladribine Novaplus); clofarabine (Clolar); cytarabine (Cytosar-U); decitabine (Dacogen); cytarabine liposomal (DepoCyt); hydroxyurea (Droxia); pralatrexate (Folotyn); floxuridine (FUDR); gemcitabine (Gemzar); cladribine (Leustatin); fludarabine (Oforta); methotrexate (MTX; Rheumatrex); methotrexate (Trexall); thioguanine (Tabloid); TS-1 or cytarabine (Tarabine PFS).

Exemplary detoxifying agents include, but are not limited to, amifostine (Ethyol) or mesna (Mesnex).

Exemplary interferons include, but are not limited to, interferon alfa-2b (Intron A) or interferon alfa-2a (Roferon-A).

Exemplary polyclonal or monoclonal antibodies include, but are not limited to, trastuzumab (Herceptin); ofatumumab (Arzerra); bevacizumab (Avastin); rituximab (Rituxan); cetuximab (Erbitux); panitumumab (Vectibix); tositumomab/iodine131 tositumomab (Bexxar); alemtuzumab (Campath); ibritumomab (Zevalin; In-111; Y-90 Zevalin); gemtuzumab (Mylotarg); eculizumab (Soliris) ordenosumab.

Exemplary EGFR inhibitors include, but are not limited to, gefitinib (Iressa); lapatinib (Tykerb); cetuximab (Erbitux); erlotinib (Tarceva); panitumumab (Vectibix); PKI-166; canertinib (CI-1033); matuzumab (Emd7200) or EKB-569.

Exemplary HER2 inhibitors include, but are not limited to, trastuzumab (Herceptin); lapatinib (Tykerb) or AC-480.

Histone Deacetylase Inhibitors include, but are not limited to, vorinostat (Zolinza).

Exemplary hormones include, but are not limited to, tamoxifen (Soltamox; Nolvadex); raloxifene (Evista); megestrol (Megace); leuprolide (Lupron; Lupron Depot; Eligard; Viadur); fulvestrant (Faslodex); letrozole (Femara); triptorelin (Trelstar LA; Trelstar Depot); exemestane (Aromasin); goserelin (Zoladex); bicalutamide (Casodex); anastrozole (Arimidex); fluoxymesterone (Androxy; Halotestin); medroxyprogesterone (Provera; Depo-Provera); estramustine (Emcyt); flutamide (Eulexin); toremifene (Fareston); degarelix (Firmagon); nilutamide (Nilandron); abarelix (Plenaxis); or testolactone (Teslac).

Exemplary mitotic inhibitors include, but are not limited to, paclitaxel (Taxol; Onxol; Abraxane); docetaxel (Taxotere); vincristine (Oncovin; Vincasar PFS); vinblastine (Velban); etoposide (Toposar; Etopophos; VePesid); teniposide (Vumon); ixabepilone (Ixempra); nocodazole; epothilone; vinorelbine (Navelbine); camptothecin (CPT); irinotecan (Camptosar); topotecan (Hycamtin); amsacrine or lamellarin D (LAM-D).

Exemplary MTOR inhibitors include, but are not limited to, everolimus (Afinitor) or temsirolimus (Torisel); rapamune, ridaforolimus; or AP23573.

Exemplary multi-kinase inhibitors include, but are not limited to, sorafenib (Nexavar); sunitinib (Sutent); BIBW 2992; E7080; Zd6474; PKC-412; motesanib; or AP24534.

Exemplary serine/threonine kinase inhibitors include, but are not limited to, ruboxistaurin; eril/easudil hydrochloride; flavopiridol; seliciclib (CYC202; Roscovitrine); SNS-032 (BMS-387032); Pkc412; bryostatin; KAI-9803; SF1126; VX-680; Azd1152; Arry-142886 (AZD-6244); SC10-469; GW681323; CC-401; CEP-1347 or PD 332991.

Exemplary tyrosine kinase inhibitors include, but are not limited to, erlotinib (Tarceva); gefitinib (Iressa); imatinib (Gleevec); sorafenib (Nexavar); sunitinib (Sutent); trastuzumab (Herceptin); bevacizumab (Avastin); rituximab (Rituxan); lapatinib (Tykerb); cetuximab (Erbitux); panitumumab (Vectibix); everolimus (Afinitor); alemtuzumab (Campath); gemtuzumab (Mylotarg); temsirolimus (Torisel); pazopanib (Votrient); dasatinib (Sprycel); nilotinib (Tasigna); vatalanib (Ptk787; ZK222584); CEP-701; SU5614; MLN518; XL999; VX-322; Azd0530; BMS-354825; SKI-606 CP-690; AG-490; WH1-P154; WH1-P131; AC-220; or AMG888.

Exemplary VEGF/VEGFR inhibitors include, but are not limited to, bevacizumab (Avastin); sorafenib (Nexavar); sunitinib (Sutent); ranibizumab; pegaptanib; or vandetinib.

Exemplary microtubule targeting drugs include, but are not limited to, paclitaxel, docetaxel, vincristin, vinblastin, nocodazole, epothilones and navelbine.

Exemplary topoisomerase poison drugs include, but are not limited to, teniposide, etoposide, adriamycin, camptothecin, daunorubicin, dactinomycin, mitoxantrone, amsacrine, epirubicin and idarubicin.

Exemplary taxanes or taxane derivatives include, but are not limited to, paclitaxel and docetaxol.

Exemplary general chemotherapeutic, anti-neoplastic, anti-proliferative agents include, but are not limited to, altretamine (Hexylen); isotretinoin (Accutane; Amnesteem; Claravis; Sotret); tretinoin (Vesanoid); azacitidine (Vidaza); bortezomib (Velcade) asparaginase (Elspar); levamisole (Ergamisol); mitotane (Lysodren); procarbazine (Matulane); pegaspargase (Oncaspar); denileukin diftitox (Ontak); porfimer (Photofrin); aldesleukin (Proleukin); lenalidomide (Revlimid); bexarotene (Targretin); thalidomide (Thalomid); temsirolimus (Torisel); arsenic trioxide (Trisenox); verteporfin (Visudyne); mimosine (Leucenol); (1M tegafur-0.4 M 5-chloro-2,4-dihydroxypyrimidine-1 M potassium oxonate) or lovastatin.

In another aspect, the second chemotherapeutic agent can be a cytokine such as G-CSF (granulocyte colony stimulating factor). In another aspect, a compound of the present invention, or a pharmaceutically acceptable salt, prodrug, metabolite, analog or derivative thereof, may be administered in combination with radiation therapy. Radiation therapy can also be administered in combination with a compound of the present invention and another chemotherapeutic agent described herein as part of a multiple agent therapy. In yet another aspect, a compound of the present invention, or a pharmaceutically acceptable salt, prodrug, metabolite, analog or derivative thereof, may be administered in combination with standard chemotherapy combinations such as, but not restricted to, CMF (cyclophosphamide, methotrexate and 5-fluorouracil), CAF (cyclophosphamide, adriamycin and 5-fluorouracil), AC (adriamycin and cyclophosphamide), FEC (5-fluorouracil, epirubicin, and cyclophosphamide), ACT or ATC (adriamycin, cyclophosphamide, and paclitaxel), rituximab, Xeloda (capecitabine), Cisplatin (CDDP), Carboplatin, TS-1 (tegafur, gimestat and otastat potassium at a molar ratio of 1:0.4:1), Camptothecin-11 (CPT-11, Irinotecan or Camptosar™), CHOP (cyclophosphamide, hydroxydaunorubicin, oncovin, and prednisone or prednisolone), R—CHOP (rituximab, cyclophosphamide, hydroxydaunorubicin, oncovin, prednisone or prednisolone), or CMFP (cyclophosphamide, methotrexate, 5-fluorouracil and prednisone).

In preferred embodiments, a compound of the present invention, or a pharmaceutically acceptable salt, prodrug, metabolite, polymorph or solvate thereof, may be administered with an inhibitor of an enzyme, such as a receptor or non-receptor kinase. Receptor and non-receptor kinases are, for example, tyrosine kinases or serine/threonine kinases. Kinase inhibitors described herein are small molecules, polynucleic acids, polypeptides, or antibodies.

Exemplary kinase inhibitors include, but are not limited to, Bevacizumab (targets VEGF), BIBW 2992 (targets EGFR and Erb2), Cetuximab/Erbitux (targets Erb1), Imatinib/Gleevic (targets Bcr-Abl), Trastuzumab (targets Erb2), Gefitinib/Iressa (targets EGFR), Ranibizumab (targets VEGF), Pegaptanib (targets VEGF), Erlotinib/Tarceva (targets Erb1), Nilotinib (targets Bcr-Abl), Lapatinib (targets Erb1 and Erb2/Her2), GW-572016/lapatinib ditosylate (targets HER2/Erb2), Panitumumab/Vectibix (targets EGFR), Vandetinib (targets RET/VEGFR), E7080 (multiple targets including RET and VEGFR), Herceptin (targets HER2/Erb2), PKI-166 (targets EGFR), Canertinib/CI-1033 (targets EGFR), Sunitinib/SU-11464/Sutent (targets EGFR and FLT3), Matuzumab/Emd7200 (targets EGFR), EKB-569 (targets EGFR), Zd6474 (targets EGFR and VEGFR), PKC-412 (targets VEGR and FLT3), Vatalanib/Ptk787/ZK222584 (targets VEGR), CEP-701 (targets FLT3), SU5614 (targets FLT3), MLN518 (targets FLT3), XL999 (targets FLT3), VX-322 (targets FLT3), Azd0530 (targets SRC), BMS-354825 (targets SRC), SKI-606 (targets SRC), CP-690 (targets JAK), AG-490 (targets JAK), WH1-P154 (targets JAK), WH1-P131 (targets JAK), sorafenib/Nexavar (targets RAF kinase, VEGFR-1, VEGFR-2, VEGFR-3, PDGFR-13, KIT, FLT-3, and RET), Dasatinib/Sprycel (BCR/ABL and Src), AC-220 (targets Flt3), AC-480 (targets all HER proteins, "panHER"), Motesanib diphosphate (targets VEGF1-3, PDGFR, and c-kit), Denosumab (targets RANKL, inhibits SRC), AMG888 (targets HER3), and AP24534 (multiple targets including Flt3).

Exemplary serine/threonine kinase inhibitors include, but are not limited to, Rapamune (targets mTOR/FRAP1), Deforolimus (targets mTOR), Certican/Everolimus (targets mTOR/FRAP1), AP23573 (targets mTOR/FRAP1), Eril/Fasudil hydrochloride (targets RHO), Flavopiridol (targets CDK), Seliciclib/CYC202/Roscovitrine (targets CDK), SNS-032/BMS-387032 (targets CDK), Ruboxistaurin (targets PKC), Pkc412 (targets PKC), Bryostatin (targets PKC), KAI-9803 (targets PKC), SF1126 (targets PI3K), VX-680 (targets Aurora kinase), Azd1152 (targets Aurora kinase), Arry-142886/AZD-6244 (targets MAP/MEK), SCIO-469 (targets MAP/MEK), GW681323 (targets MAP/MEK), CC-401 (targets JNK), CEP-1347 (targets JNK), and PD 332991 (targets CDK).

The disorder in which EZH2-mediated protein methylation plays a part can be a neurological disease. The compounds of this invention may thus also be used for treating or studying neurologic diseases such as epilepsy, schizophrenia, bipolar disorder or other psychological and/or psychiatric disorders, neuropathies, skeletal muscle atrophy, and neurodegenerative diseases, e.g., a neurodegenerative disease. Exemplary neurodegenerative diseases include: Alzheimer's, Amyotrophic Lateral Sclerosis (ALS), and Parkinson's disease. Another class of neurodegenerative diseases includes diseases caused at least in part by aggregation of poly-glutamine. Diseases of this class include: Huntington's Diseases, Spinalbulbar Muscular Atrophy (SBMA or Kennedy's Disease) Dentatorubropallidoluysian Atrophy (DRPLA), Spinocerebellar Ataxia 1 (SCA1), Spinocerebellar Ataxia 2 (SCA2), Machado-Joseph Disease (MJD; SCA3), Spinocerebellar Ataxia 6 (SCA6), Spinocerebellar Ataxia 7 (SCAT), and Spinocerebellar Ataxia 12 (SCA12).

Any other disease in which epigenetic methylation, which is mediated by EZH2, plays a role may be treatable or preventable using compounds and methods described herein, or such diseases and potential treatments thereof may be studied with the compounds described herein.

4. Pharmaceutical Compositions

The present invention also provides pharmaceutical compositions comprising a compound of any of the Formulae described herein in combination with at least one pharmaceutically acceptable excipient or carrier.

A "pharmaceutical composition" is a formulation containing the compounds of the present invention in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the phrase "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the invention can be administered to a subject in many of the well-known methods currently used for chemotherapeutic treatment. For example, for treatment of cancers, a compound of the invention may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The compounds of the present invention are capable of further forming salts. All of these forms are also contemplated within the scope of the claimed invention.

As used herein, "pharmaceutically acceptable salts" refer to derivatives of the compounds of the present invention wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ration other than 1:1, e.g., 3:1, 2:1, 1:2, or 1:3.

It should be understood that all references to pharmaceutically acceptable salts include solvent addition forms (solvates) or crystal forms (polymorphs) as defined herein, of the same salt.

The compounds of the present invention can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., acetate, propionate or other ester.

The compounds of the present invention can also be prepared as prodrugs, for example, pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.), the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject. Prodrugs in the present invention are prepared by modifying functional groups present in the compound in such a way that the modifications are cleaved, either in routine manipulation or in vivo, to the parent compound. Prodrugs include compounds of the present invention wherein a hydroxy, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of the invention, and the like, See Bundegaard, H., *Design of Prodrugs*, p 1-92, Elesevier, New York-Oxford (1985).

The compounds, or pharmaceutically acceptable salts, esters or prodrugs thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the invention can be found in *Remington: the Science and Practice of Pharmacy,* $19^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

In the synthetic schemes described herein, compounds may be drawn with one particular configuration for simplicity. Such particular configurations are not to be construed as limiting the invention to one or another isomer, tautomer, regioisomer or stereoisomer, nor does it exclude mixtures of isomers, tautomers, regioisomers or stereoisomers; however, it will be understood that a given isomer, tautomer, regioisomer or stereoisomer may have a higher level of activity than another isomer, tautomer, regioisomer or stereoisomer.

Compounds designed, selected and/or optimized by methods described above, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

5. EXAMPLES

General Experimental

NMR $^1$H-NMR spectra were taken using $CDCl_3$ unless otherwise stated and were recorded at 400 or 500 MHz using a Varian or Oxford instruments magnet (500 MHz) instruments. Multiplicities indicated are s=singlet, d=doublet, t=triplet, q=quartet, quint=quintet, sxt=sextet, m=multiplet, dd=doublet of doublets, dt=doublet of triplets; br indicates a broad signal.

LCMS and HPLC

Shimadzu LC-Q, Shimadzu LCMS-2010EV or Waters Acquity Ultra Performance LC. HPLC: Products were analyzed by Shimadzu SPD-20A with 150×4.5 mm YMC ODS-M80 column or 150×4.6 mm YMC-Pack Pro C18 column at 1.0 ml/min.

Mobile phase was MeCN:H2O=3:2 (containing 0.3% SDS and 0.05% $H_3PO_4$), 0.05% TFA in water, 0.05% TFA in acetonitrile (gradient Initial 20%, then 0.05% TFA/MeCN to conc. to 95% in 3 min. holds for 0.5 min. at 3.51 to 4.50 min then 0.05% TFA/MeCN conc. 20).

Alternatively the LCMS, 2 different methods were used; the one we use the most is the high pH (METCR1600) and the other one for more standard compounds (METCR1416).

0.1% Formic acid in water-Mobile phase "A" 0.1% Formic acid in acetonitrile-Mobile phase "B" utilizing Waters Atlantis dC18, 2.1 mm×100 mm, 3 μm column, with a flow rate=0.6 ml/min Column temperature=40° C.; Time (mins) % B 0.00 min 5% B. 5.0 mins 100% B, 5.4 mins 100% B and 0.42 mins 5% B 3.5 minute method refers to Atlantis dC18, 2.1 mm×50 mm, 3 μm column, flow rate of 1 ml/min at 40 C. Mobile phase A Formic acid (aq.) 0.1% mobile phase B formic acid (MeCN) 0.1%, injection 3 μL, gradient 0 mins (5% organic), 2.5 min (100% organic), 2.7 mins (100% organic), 2.71 min (5% organic), 3.5 min (5% organic)

7.0 minute method refers to Atlantis dC18, 2.1 mm×100 mm, 3 μm column, flow rate of 0.6 ml/min at 40 C. Mobile phase A Formic acid (aq.) 0.1% mobile phase B formic acid (MeCN) 0.1%, injection 3 μL, gradient 0 mins (5% organic) 5 min (100% organic), 5.4 mins (100% organic), 5.42 min (5% organic), 7 min (5% organic)

Both the 3. 5 and 7 minute methods were performed on a MS18 Shimadzu LCMS-2010EV or a MS19 Shimadzu LCMS-2010EV system utilizing LC-20AB pumps and SPD-M20A PDA detectors.

Products were purified by HPLC/MS using Waters AutoPurification System with 3100 Mass Detector.

HPLC analyses may also be performed on a Shimdazu LC-2010 CHT using an YMC ODS-A, C18, (150×4.6×5 μm) column at ambient temperature with a flow Rate of 1.4 ml/min. An injection volume of 10 μl is utilized and detection occurs via UV/PDA. Mobile Phase A is 0.05% TFA in water and Mobile Phase B is 0.05% TFA in acetonitrile with a gradient program of Initial 5% B to 95% B in 8 min, hold for 1.5 min, at 9.51 to 12 min B. conc. 0.5%. The diluent is the mobile phase Other Automated flash column chromatography was performed on a Biotage Isolera version 4. 10 g SNAP cartridge running at 12 ml/min or a 25 g SNAP cartridge running at 25 ml/min and detecting at 254 nm and 280 nm.

Select Nitrile reductions may be performed on a ThalesNano H-Cube® according to the conditions described in the experimental procedure.

General Procedure for the Synthesis of the Pyridone Amines

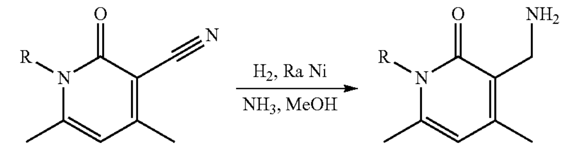

R = e.g. —$CH_2Ph$, —$CH_2CH_2OH$, $CH_2CH_2OMe$

To a solution of the cyano compound (1 eq.) in MeOH, a catalytic amount of Raney Nickel and ammonia solution were added. The mixture was stirred at RT under hydrogen (balloon pressure) for 1 hr. On completion of the reaction, the mixture was filtered through a celite bed washing with MeOH. The filtrate was concentrated under reduced pressure to afford the desired amine. This procedure is applicable to a wide variety of R groups described within the examples: In general the cyano pyridines care available from commercial vendors or can be synthesized via methods known to those of ordinary skill in the art.

Syntheses of Starting Materials or Intermediates 3-(Aminomethyl)-6-methyl-4-propyl-1,2-dihydropyridin-2-one HCl salt

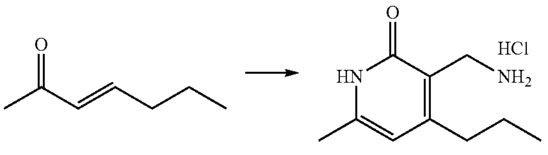

To a stirred solution of t-BuOK (20.0 g, 179 mmol) and cyanoacetamide (16.5 g, 196 mmol) in DMSO (300 mL) was added (3E)-3-hepten-2-one (20.0 g, 178 mmol). The reaction mixture was stirred at 23° C. for 30 minutes and then additional t-BuOK (60.0 g, 712 mmol) was added to the reaction mixture. The reaction mixture was placed under oxygen atmosphere and stirred for 16 h. The reaction mixture was then purged with argon and was cooled to 0° C. The mixture was diluted with aq. HCl and the resulting precipitate was collected. The solid was washed with water and dried to give 6-methyl-2-oxo-4-propyl-1,2-dihydropyridine-3-carbonitrile (15.0 g, 47% yield).

To a stirred solution of 6-methyl-2-oxo-4-propyl-1,2-dihydropyridine-3-carbonitrile (15.0 g, 85.1 mmol) in methanol (600 mL) and concentrated HCl (15 mL) was added $Pd(OH)_2$ (15.0 g). The mixture was stirred for 48 hours under $H_2$ atmosphere. The reaction mixture was filtered and filtrate was concentrated in vacuo. Ethanol was added to the residue, the resulting precipitate was collected and dried to give the titled compound as a white solid (13.0 g, 60% yield). $^1$H-NMR (400 MHz, $CDCl_3$) δppm; 11.86 (br. s., 1H), 6.00 (s, 1H), 3.78 (q, J=5.5 Hz, 2H), 3.61 (br. s., 2H), 2.46 (m, 2H), 2.17 (s, 3H), 1.50 (sxt, J=7.4 Hz, 2H), 0.91 (t, J=7.4 Hz, 3H).

6-Methyl-2-oxo-4-(propan-2-yl)-1,2-dihydropyridine-3-carbonitrile

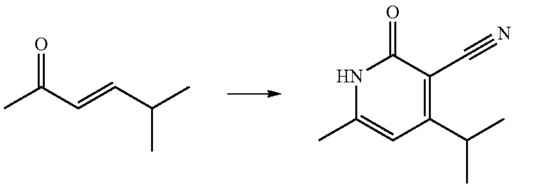

To a solution of 2-cyanoacetamide (35.1 g, 417 mmol) and t-BuOK (42.5 g, 379 mmol) in DMSO (631 ml) was added 5-methyl-3-hexen-2-one (50.0 ml, 379 mmol) under $N_2$ atmosphere. The mixture was stirred at 23° C. for 30 min and then additional t-BuOK (127 g, 1137 mmol) was added. The $N_2$ gas was displaced by $O_2$ gas and the mixture was stirred for 45 h at 23° C. under oxygen. The mixture was cooled to 0° C., diluted with $H_2O$ (200 ml) and HCl (5N, 227 ml, slowly added). The mixture was stirred for 15 min at 0° C. and the solid was filtered with Buchner funnel. The solid was washed with $H_2O$ (1500 ml) and dried with hot-air (55° C., 16 h) to give 6-methyl-2-oxo-4-(propan-2-yl)-1,2-dihydropyridine- 3-carbonitrile (26.6 g, 40% yield). $^1$H NMR (400 MHz, $CDCl_3$): δ 6.14 ppm (s, 1H), 3.25-3.29 (m, 1H), 2.45 (s, 3H), 1.26 (d, J=6.8 Hz, 6H); LC-MS: m/z 177.1 [M+1], 198.9 [M+23].

3-(Aminomethyl)-6-methyl-4-(propan-2-yl)-1,2-dihydropyridin-2-one HCl salt

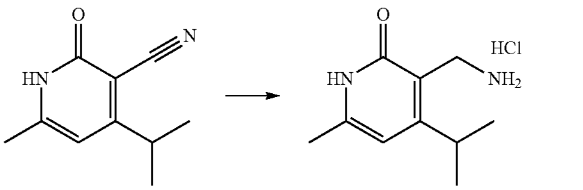

To a solution of 6-methyl-2-oxo-4-(propan-2-yl)-1,2-dihydropyridine-3-carbonitrile (5.00 g, 28.4 mmol) and in MeOH (400 ml) and HCl (8.8 ml, 12 M) was added 10% $Pd(OH)_2$ (5.17 g, 3.68 mmol) under $N_2$ atmosphere. The $N_2$ gas was displaced by $H_2$ gas and the mixture was stirred for 24 h at 23° C. under hydrogen. The $H_2$ gas was displaced by $N_2$ gas and the mixture was filtered through celite, washed with MeOH and concentrated. The residue was triturated with EtOH-TBME, the solid was collected with Buchner funnel and dried in vacuo to give the titled compound (6.15 g, 100%). $^1$H NMR (400 MHz, DMSO-$d_6$): δ ppm 11.9 (br-s, 1H), 8.03 (br-s, 2H), 6.12 (s, 1H), 3.82-3.84 (m, 2H), 3.08-3.12 (m, 1H), 2.19 (s, 3H), 1.12 (d, J=6.8 Hz, 6H).

6-Methyl-2-oxo-4-(trifluoromethyl)-1,2-dihydropyridine-3-carbonitrile

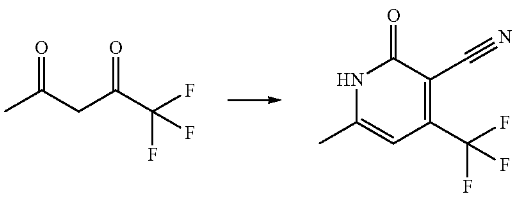

To a solution of 2-cyanoacetamide (14.0 g, 166 mmol) and trifluoroacetylacetone (20.0 ml, 166 mmol) in $H_2O$ (332 ml) was added $K_2CO_3$ (6.60 g, 47.9 mmol). The mixture was stirred at 23° C. for 15 h. The precipitated solid was filtered with Buchner funnel, washed with ice cold $H_2O$, and dried with hot air (60° C., 16 h) to give the titled compound (17.6 g, 52%). $^1$H NMR (400 MHz, DMSO-$d_6$): δ ppm 2.38 (s, 3H), 6.66 (s, 1H).

3-(Aminomethyl)-6-methyl-4-(trifluoromethyl)-1,2-dihydropyridin-2-one hydrochloride HCl salt

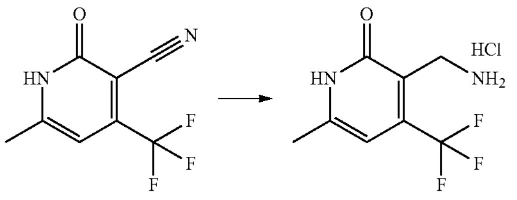

To a solution of 6-methyl-2-oxo-4-(trifluoromethyl)-1,2-dihydropyridine-3-carbonitrile (400 mg, 1.98 mmol) in MeOH (19.8 ml) and HCl (436 ul, 12M) was added 10% $Pd(OH)_2$ (361 mg, 0.257 mmol) under $N_2$ atmosphere. The $N_2$ gas was displaced by $H_2$ gas and the mixture was stirred for 18 h at 23° C. under hydrogen. The $H_2$ gas was displaced by $N_2$ gas. The mixture was filtered through Celite, washed with MeOH and concentrated. The residue was triturated with MeOH-$Et_2O$, collected with Buchner funnel, and dried in vacuo to give the titled compound (433 mg, 100%). $^1$H NMR (400 MHz, DMSO-$d_6$): δ ppm 2.31 (s, 3H), 3.88 (s, 2H), 6.43 (s, 1H).

5-Fluoro-4-isopropyl-6-methyl-2-oxo-1,2-dihydropyridine-3-carbonitrile

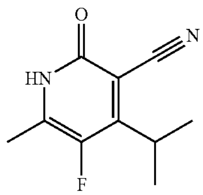

To a stirred solution of 6-methyl-2-oxo-4-(propan-2-yl)-1,2-dihydropyridine-3-carbonitrile (225 mg, 1.277 mmol) in MeCN (6 mL) was added Selectfluor (620 mg, 1.75 mmol). The reaction mixture was stirred at 50° C. for 3 h. After cooling to 23° C., the reaction mixture was concentrated in vacuo. The residue was purified by column chromatography (50% to 100% EtOAc-heptane to obtain the titled compound (90 mg, 36%). $^1$H NMR (400 MHz, $CDCl_3$) δ ppm 3.39 (m, 1H), 2.44 (d, J=3.1 Hz, 3H), 1.41 (dd, J=7.0, 3.1 Hz, 6H); LCMS E-S (M+H)=195.2.

5-Fluoro-6-methyl-2-oxo-4-propyl-1,2-dihydropyridine-3-carbonitrile

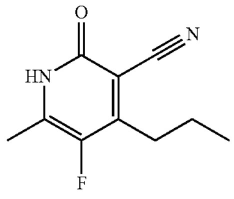

The title compound was prepared in the same manner as described for 5-Fluoro-4-isopropyl-6-methyl-2-oxo-1,2-dihydropyridine-3-carbonitrile (20% yield). $^1$H NMR (400 MHz, $CDCl_3$) δ ppm 2.80 (dt, J=7.9, 1.9 Hz 2H), 2.31 (d, J=2.1 Hz, 3H), 1.73 (tq, J=7.4, 7.4 Hz, 2H), 1.06 (t, J=7.3 Hz, 3H); LCMS E-S (M+H)=195.2.

5-Fluoro-4,6-dimethyl-2-oxo-1,2-dihydropyridine-3-carbonitrile

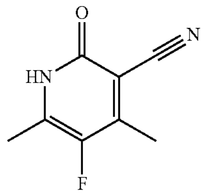

The title compound was prepared in the same manner as described for 5-Fluoro-4-isopropyl-6-methyl-2-oxo-1,2-dihydropyridine-3-carbonitrile (15% yield). $^1H$ NMR (400 MHz, $CDCl_3$) δ ppm 2.46 (d, J=3.1 Hz, 3H), 2.44 (d, J=7.4, 3.1 Hz, 3H); LCMS E-S (M+H)=167.2.

3-(Aminomethyl)-5-fluoro-4-isopropyl-6-methylpyridin-2(1H)-one

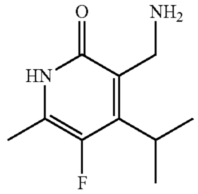

5-Fluoro-4-isopropyl-6-methyl-2-oxo-1,2-dihydropyridine-3-carbonitrile (100 mg, 0.515 mmol) in 100 mL flask was dissolved in a mixture of MeOH (6 mL) and 2 mL $NH_{3aq}$ (2 mL, 25%). Reduction was conducted using H-Cube with Raney-Ni as a catalyst at room temperature for 3-4 h. On completion of reaction (monitored by TLC), reaction was concentrated under reduced pressure to afford titled compound as a grey solid (90 mg, 90%). $^1H$ NMR (400 MHz, $CD_3OD$) δ ppm 4.04 (s, 2H), 3.22 (m, 1H), 2.24 (d, J=3.4 Hz, 3H), 1.32 (dd, J=7.0, 1.8 Hz, 6H); LCMS E-S (M+H)=199.2.

3-(Aminomethyl)-5-fluoro-6-methyl-4-propylpyridin-2(1H)-one

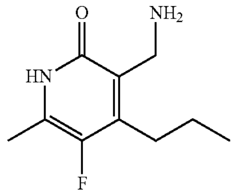

The titled compound was prepared in the same manner as described for 3-(aminomethyl)-5-fluoro-4-isopropyl-6-methylpyridin-2(1H)-one (92% yield). $^1H$ NMR (400 MHz, $CDCl_3$) δ ppm 3.76 (s, 2H), 2.61 (dt, J=7.2, 1.8 Hz 2H), 2.31 (d, J=2.8 Hz, 3H), 1.57 (tq, J=7.6, 7.6 Hz, 2H), 1.00 (t, J=7.3 Hz, 3H); LCMS E-S (M+H)=199.2.

3-(Aminomethyl)-5-fluoro-4,6-dimethylpyridin-2(1H)-one

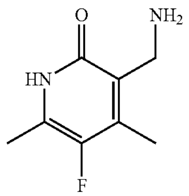

The title compound was prepared in the same manner as described for 3-(Aminomethyl)-5-fluoro-4-isopropyl-6-methylpyridin-2(1H)-one (92% yield). $^1H$ NMR (400 MHz, $CDCl_3$) δ ppm 3.79 (s, 2H), 2.29 (d, J=3.3 Hz, 3H), 2.24 (d, J=2.1 Hz, 3H); LCMS E-S (M+H)=171.2.

2-Methyl-3-nitro-5-(trifluoromethyl)benzoic acid

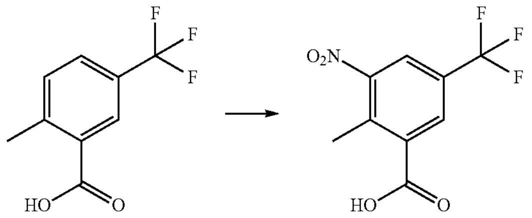 [SMILES: Cc1ccc(C(F)(F)F)cc1C(=O)O ; Cc1c(C(=O)O)cc(C(F)(F)F)cc1[N+](=O)[O-]]

To a stirred solution of 2-methyl-5-(trifluoromethyl)benzoic acid (2.00 g, 9.80 mmol) in $H_2SO_4$ (20 mL, 12 N) was added $HNO_3$ (2 mL, 12N) at 0° C. After stirring for 3 hours, water was added and resulting precipitate was collected. The solid was washed with water and dried to give the titled compound as a white solid (1.90 g, 76% yield). $^1H$-NMR (400 MHz, $CDCl_3$) δppm; 8.43 (s, 1H), 8.15 (s, 1H), 2.77 (s, 3H); MS (ES) [M−H] 247.8.

Methyl 2-methyl-3-nitro-5-(trifluoromethyl)benzoate

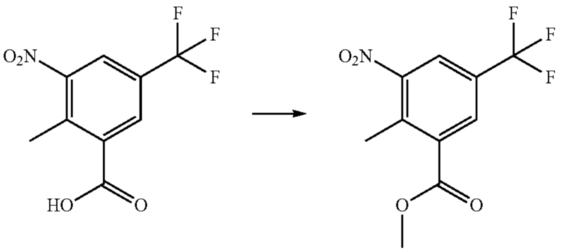 [SMILES: Cc1c(C(=O)O)cc(C(F)(F)F)cc1[N+](=O)[O-] ; COC(=O)c1cc(C(F)(F)F)cc([N+](=O)[O-])c1C]

To a solution of 2-methyl-3-nitro-5-(trifluoromethyl)benzoic acid (21.0 g, 84.3 mmol) in DMF (200 mL) was added potassium carbonate (35.0 g, 253 mmol) and methyl iodide (24.0 g, 169 mmol). The mixture was stirred at 60° C. and after stirring for 6 h the reaction mixture was cooled to 23° C. and was filtered. The filtrate was concentrated in vacuo and the residue was dissolved in EtOAc and water. The aqueous phase was extracted with EtOAc (2×250 mL and the combined organic layers were concentrated in vacuo. The residue was purified by column chromatography ($SiO_2$ heptane-EtOac=4/1) to give the titled compound (20.0 g, 90% yield). $^1$H-NMR (400 MHz, $CDCl_3$) δ (ppm); 8.27 (s, 1H), 8.11 (s, 1H), 3.99 (s, 3H), 2.71 (s, 3H); MS (ES) [M−H] 261.9.

Methyl 3-amino-2-methyl-5-(trifluoromethyl)benzoate

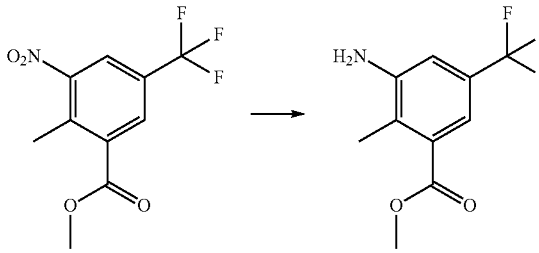

To a stirred solution of methyl 2-methyl-3-nitro-5-(trifluoromethyl)benzoate (20.0 g, 76.0 mmol) in MeOH (400 ml) was added $Pd(OH)_2$ (2.00 g). The reaction mixture was stirred for 3 hours under hydrogen atmosphere. After purging with nitrogen, the mixture was filtered and the filtrate was concentrated in vacuo to give the titled compound as an orange solid (10.2 g, 58% yield). $^1$H-NMR (400 MHz, $CDCl_3$) δppm; 7.47 (brs, 1H), 7.01 (d, J=2.0 Hz, 1H), 3.92 (m, 2H), 3.91 (s, 3H), 2.39 (s, 3H).

tert-Butyl-4-{[3-(methoxycarbonyl)-2-methyl-5-(trifluoromethyl)phenyl]amino}piperidine-1-carboxylate

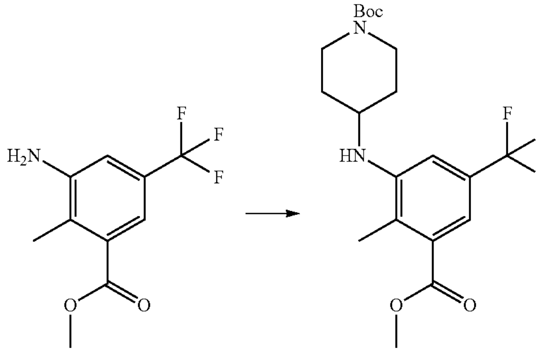

To a stirred solution of methyl 3-amino-2-methyl-5-(trifluoromethyl)benzoate (6.00 g, 25.7 mmol) in $CH_2Cl_2$ (120 mL) and AcOH (6 mL) was added N-Boc piperidinone (6.70 g, 33.4 mmol) and sodium triacetoxyborohydride (13.6 g, 64.3 mmol). The reaction mixture was stirred at 23° C. for 20 hours. Then saturated $NaHCO_3$ was added and the mixture was separated. The aqueous layer was extracted with $CH_2Cl_2$ (3×50 mL) and the combined organic layer were concentrated in vacuo. The residue was purified by silica gel column chromatography ($SiO_2$ heptane/EtOAc=4/1) to give the titled compound (10.6 g, 98% yield). $^1$H-NMR (400 MHz, $CDCl_3$) δppm; 7.37 (s, 1H), 6.88 (s, 1H), 4.05 (m, 2H), 3.90 (s, 3H), 3.01 (m, 3H), 2.32 (s, 3H), 1.71 (m, 2H), 1.48-1.61 (m, 2H), 1.45 (s, 9H); MS (ES) [M−H] 415.1.

tert-Butyl-4-{ethyl[3-(methoxycarbonyl)-2-methyl-5-(trifluoromethyl)phenyl]amino}piperidine-1-carboxylate

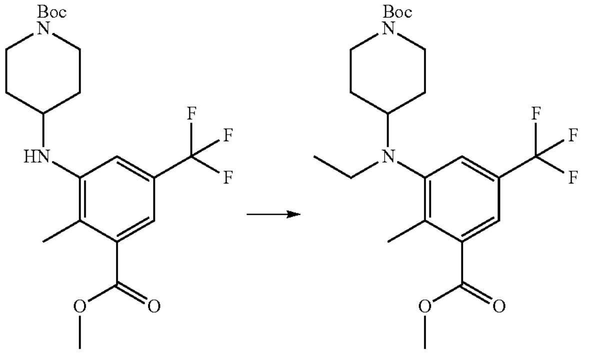 [SMILES: COC(=O)c1cc(C(F)(F)F)cc(NC2CCNCC2)c1C ; CCN(c1cc(C(F)(F)F)cc(C(=O)OC)c1C)C1CCNCC1 ; "Boc" ; "Boc"]

To a stirred solution of tert-butyl 4-{[3-(methoxycarbonyl)-2-methyl-5-(trifluoromethyl)phenyl]amino}piperidine-1-carboxylate (10.6 g, 25.4 mmol) in $CH_2Cl_2$ (200 mL) and AcOH (10 mL) was added acetaldehyde (2.80 g, 63.5 mmol) and sodium triacetoxyborohydride (13.4 g, 63.5 mmol). The reaction mixture was stirred at 23° C. for 24 hours. Then saturated $NaHCO_3$ was added and the mixture was separated. The aqueous layer was extracted with $CH_2Cl_2$ (3×50 mL) and the combined organic layer was concentrated in vacuo. The residue was purified by silica gel column chromatography ($SiO_2$ Heptane/EtOAc=5/1) to give the titled compound as oil (4.50 g, 40% yield). $^1$H-NMR (400 MHz, $CDCl_3$) δppm; 7.82 (br. s., 1H), 7.45 (d, J=1.6 Hz, 1H), 3.96-4.18 (m, 2H), 3.92 (s, 3H), 3.08 (q, J=7.0 Hz, 2H), 2.89 (tt, J=11.0, 3.7 Hz, 1H), 2.69 (m, 2H), 2.55 (s, 3H), 1.73 (m, 2H), 1.49-1.56 (m, 2H), 1.45 (s, 9H), 0.86 (t, J=7.0 Hz, 3H); MS (ES) [M+Na] 467.0.

Methyl 3-[ethyl(piperidin-4-yl)amino]-2-methyl-5-(trifluoromethyl)benzoate TFA salt

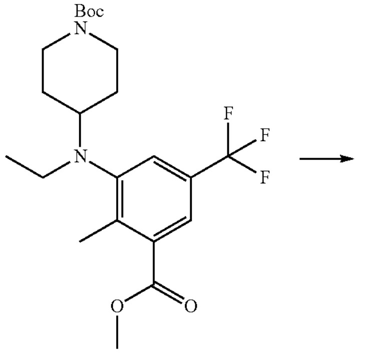

-continued

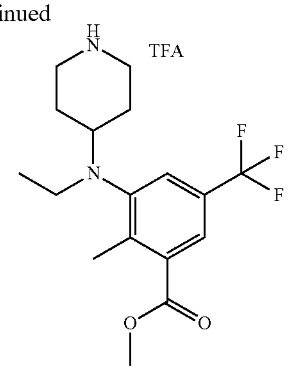

To a stirred solution of tert-butyl 4-{ethyl[3-(methoxycarbonyl)-2-methyl-5-(trifluoromethyl)phenyl] amino}piperidine-1-carboxylate (4.50 g, 10.1 mmol) in $CH_2Cl_2$ (50 mL) was added TFA (5 mL). The reaction mixture was stirred at rt for 18 hours. Then reaction mixture was concentrated in vacuo to give the titled compound as a crude product (7.70 g).

Methyl 3-[ethyl(1-methylpiperidin-4-yl)amino]-2-methyl-5-(trifluoromethyl)benzoate

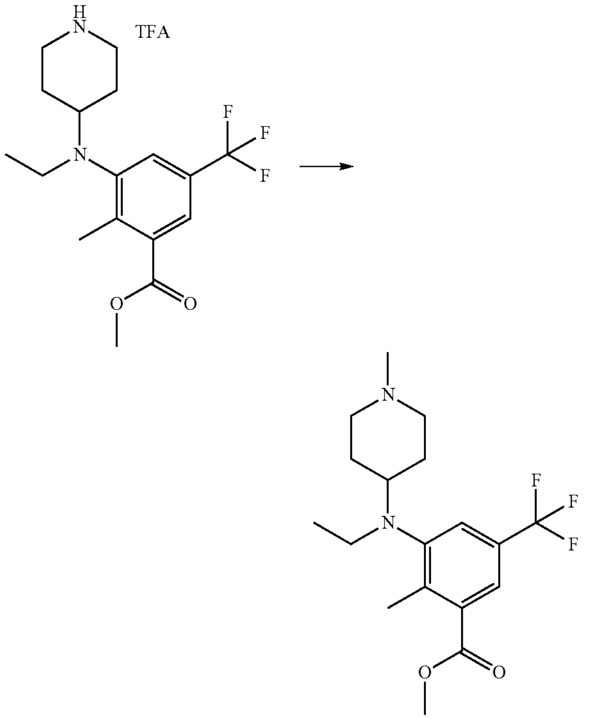

To a stirred solution of methyl 3-[ethyl(piperidin-4-yl) amino]-2-methyl-5-(trifluoromethyl)benzoate TFA salt (crude material, 5.30 g, 12.0 mmol) in $CH_2Cl_2$ (150 mL) and AcOH (10 mL) was added formaldehyde (15 mL, 44% aqueous solution) and sodium triacetoxyborohydride (6.40 g, 30.0 mmol). The reaction mixture was stirred at 23° C. for 2.5 days. Then saturated $NaHCO_3$ was added and the mixture was separated. The aqueous layer was extracted with $CH_2Cl_2$ (3×50 mL) and the combined organic layers were concentrated in vacuo. The residue was purified by silica gel column chromatography (NH—$SiO_2$ heptane/EtOAc=2/1) to give the titled compound as oil (1.20 cg, 28% yield). $^1$H-NMR (400 cMHz, $CDCl_3$) δppm; 7.81 (br. s., 1H), 7.45 (d, J=2.0 Hz, 1H), 3.92 (s, 3H), 3.10 (q, J=7.0 Hz, 2H), 2.83 (m, 2H), 2.66-2.77 (m, 1H), 2.54 (s, 3H), 2.24 (s, 3H), 1.84-1.94 (m, 2H), 1.63-1.78 (m, 4H), 0.86 (t, J=7.0 Hz, 3H); MS (ES) [M+H] 359.1.

Methyl 3-{ethyl[1-(propan-2-yl)piperidin-4-yl] amino}-2-methyl-5-(trifluoromethyl)benzoate

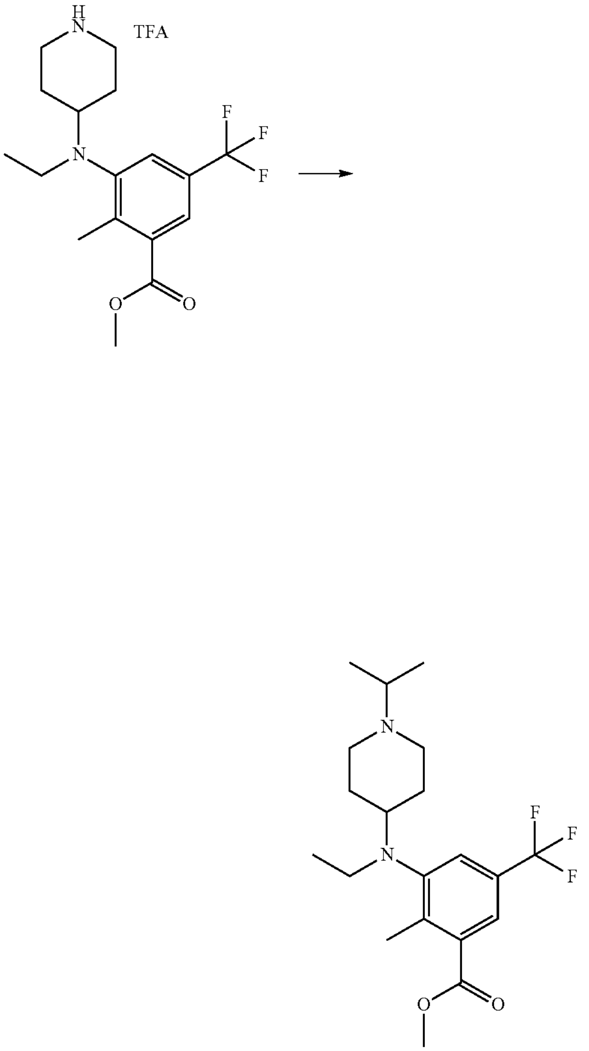

To a stirred solution of methyl 3-[ethyl(piperidin-4-yl) amino]-2-methyl-5-(trifluoromethyl)benzoate TFA salt (crude material, 1.30 g, 3.36 mmol) in $CH_2Cl_2$ (20 mL) and AcOH (5 mL) was added acetone (590 mg, 10.1 mmol) and sodium triacetoxyborohydride (1.80 g, 8.40 mmol). The reaction mixture was stirred at 23° C. for 6 days and then saturated $NaHCO_3$ was added and the mixture was separated. The aqueous layer was extracted with $CH_2Cl_2$ (3×30 mL) and the combined organic layer was concentrated in vacuo. The residue was purified by silica gel column chromatography (NH—$SiO_2$ heptane/ethylacetate=5/1) to give the titled compound as oil (220 mg, 17% yield). $^1$HNMR (400 MHz, $CDCl_3$) δppm; 7.79 (br. s., 1H), 7.44 (d, J=1.6 Hz, 1H), 3.91 (s, 3H), 3.10 (q, J=7.0 Hz, 2H), 2.86 (m, 2H), 2.61-2.75 (m, 2H), 2.53

(s, 3H), 2.06 (m, 2H), 1.70-1.80 (m, 2H), 1.58-1.69 (m, 2H), 1.00 (s×2, 6H), 0.84 (t, J=7.0 Hz, 3H); MS (ES) [M+H] 387.2.

3-[Ethyl(1-methylpiperidin-4-yl)amino]-2-methyl-5-(trifluoromethyl)benzoic acid

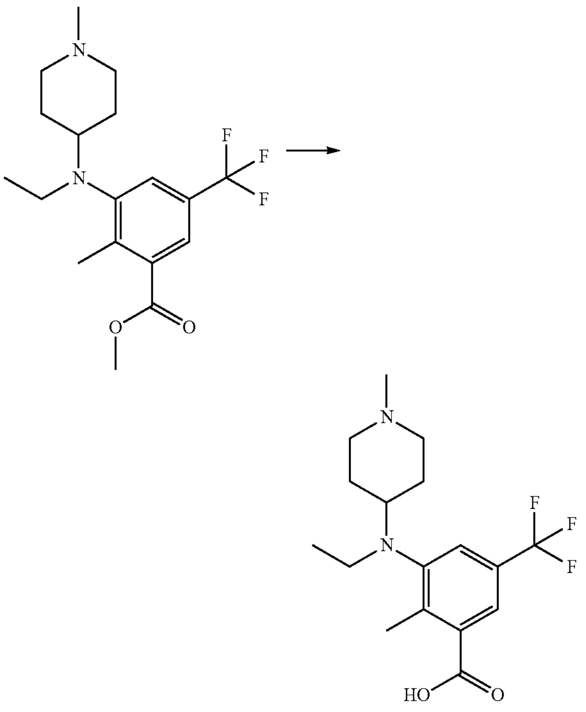

To a stirred solution of methyl 3-[ethyl(1-methylpiperidin-4-yl)amino]-2-methyl-5-(trifluoromethyl)benzoate (700 mg, 1.95 mmol) in methanol (15 mL) was added aq. NaOH (5M, 590 ul, 2.93 mmol). The reaction mixture was stirred at 50° C. for 3 hours. After cooling to 23° C., HCl (2 M) was added to the mixture. The mixture was acidified to pH=5 and was concentrated in vacuo to give the titled compound as crude products (1.26 g).

Following the same preparation method for 3-[ethyl(1-methylpiperidin-4-yl)amino]-2-methyl-5-(trifluoromethyl) benzoic acid, the following titled compounds were prepared from methyl 3-amino-2-methyl-5-(trifluoromethyl)benzoate and tert-butyl 3-oxoazetidine-1-carboxylate.

t-butyl 3-((3-(methoxycarbonyl)-2-methyl-5-(trifluoromethyl)phenyl)amino)azetidine-1-carboxylate

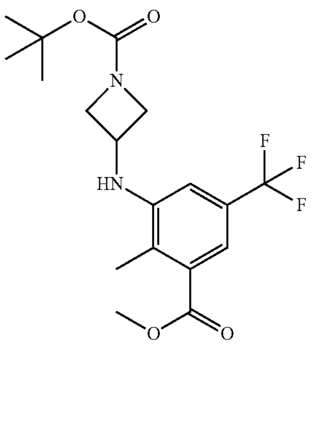 [SMILES: COC(=O)c1cc(C(F)(F)F)cc(NC2CN(C(=O)OC(C)(C)C)C2)c1C]

$^1$H NMR (400 MHz, $CDCl_3$) δ ppm 7.49 (s, 1H), 6.60 (s, 1H), 4.39 (dd, J=7.2 Hz, 8.8 Hz, 2H), 4.26 (m, 1H), 4.19 (br, d, J=5.6 Hz, 1H), 3.93 (s, 3H), 3.78 (m, 2H), 2.41 (s, 3H), 1.47 (s, 9H).

tert-butyl 3-(ethyl(3-(methoxycarbonyl)-2-methyl-5-(trifluoromethyl)phenyl)amino)azetidine-1-carboxylate

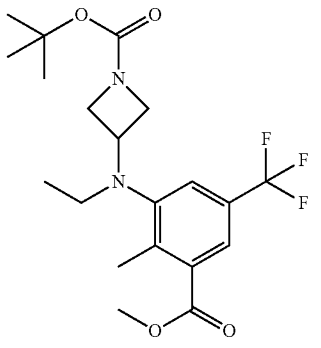 [SMILES: CCN(c1cc(C(F)(F)F)cc(C(=O)OC)c1C)C1CN(C(=O)OC(C)(C)C)C1]

$^1$H NMR (400 MHz, $CDCl_3$) δ ppm 7.86 (s, 1H), 7.20 (s, 1H), 4.15 (m, 1H), 3.99 (dd, J=8.4 Hz, J=8.4 Hz, 2H), 3.94 (s, 3H), 3.65 (br, 2H), 3.00 (q, J=7.2 Hz, 2H), 2.60 (s, 3H), 1.43 (s, 9H), 0.90 (t, J=6.8 Hz, 3H); MS (ES) (M+1) 417.41.

Methyl 3-(azetidin-3-yl(ethyl)amino)-2-methyl-5-(trifluoromethyl)benzoate

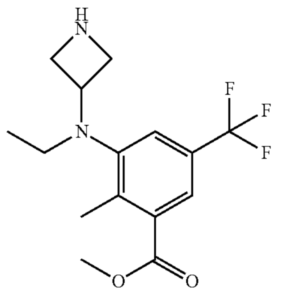 [SMILES: CCN(c1cc(C(F)(F)F)cc(C(=O)OC)c1C)C1CNC1]

$^1$H NMR (400 MHz, $CDCl_3$) δ ppm 7.89 (s, 1H), 7.20 (s, 1H), 4.39 (m, 1H), 3.94 (s, 3H), 3.87 (m, 2H), 3.68 (br, 2H), 2.99 (q, J=6.8 Hz, 2H), 2.64 (s, 3H), 0.92 (t, J=6.8 Hz, 3H); MS (ES) (M+1) 317.32.

Methyl 3-(ethyl(1-methylazetidin-3-yl)amino)-2-methyl-5-(trifluoromethyl)benzoate

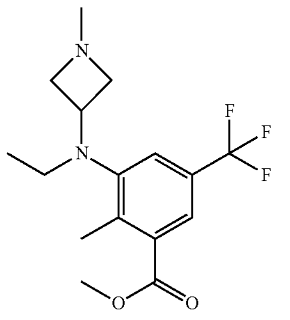 [SMILES: CCN(c1cc(C(F)(F)F)cc(C(=O)OC)c1C)C1CN(C)C1]

$^1$H NMR (400 MHz, $CDCl_3$) δ ppm 7.83 (s, 1H), 7.24 (s, 1H), 4.03 (m, 1H), 3.94 (s, 3H), 3.60 (br, dd, J=7.2, 7.2 Hz, 2H), 2.94 (q, J=7.6 Hz, 2H), 2.72 (br, t, J=6.8 Hz, 2H), 2.59 (s, 3H), 2.33 (s, 3H), 0.90 (t, J=7.2 Hz, 3H); MS (ES) (M+1) 331.09.

3-(ethyl(1-methylazetidin-3-yl)amino)-2-methyl-5-(trifluoromethyl)benzoic acid

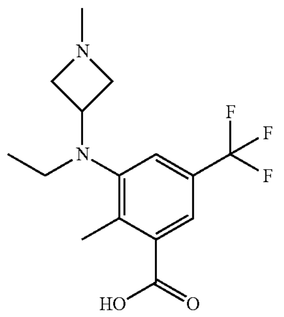 [SMILES: CCN(c1cc(C(F)(F)F)cc(C(=O)O)c1C)C1CN(C)C1]

$^1$H NMR (400 MHz, $CD_3OD$) δ ppm 7.83 (s, 1H), 7.37 (s, 1H), 4.44 (br, 1H), 3.86 (br, 2H), 3.33 (s, 2H), 3.04 (q, J=6.8 Hz, 2H), 3.03 (s, 3H), 2.64 (s, 3H), 0.90 (t, J=7.2 Hz, 3H); MS (ES) (M+1) 317.32.

tert-butyl 3-((5-Chloro-3-(methoxycarbonyl)-2-methylphenyl)amino)azetidine-1-carboxylate

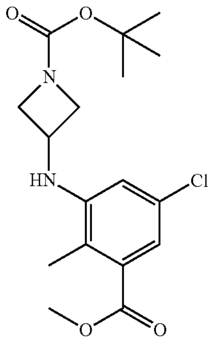 [SMILES: COC(=O)c1cc(Cl)cc(NC2CN(C(=O)OC(C)(C)C)C2)c1C]

$^1$H-NMR (500 MHz, $CD_3OD$) δ ppm 7.05 (d, J=2.0 Hz, 1H), 6.48 (d, J=2.0 Hz, 1H), 4.31 (dd, J=7.2, 7.8 Hz, 2H), 4.26-4.21 (m, 1H), 3.87 (s, 3H), 3.82 (dd, J=4.4, 8.3 Hz, 2H), 2.29 (s, 3H), 1.45 (s, 9H).

tert-butyl 3-((5-Chloro-3-(methoxycarbonyl)-2-methylphenyl)(ethyl)amino)azetidine-1-carboxylate

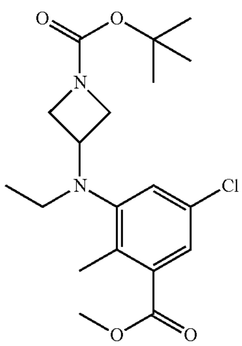 [SMILES: CCN(c1cc(Cl)cc(C(=O)OC)c1C)C1CN(C(=O)OC(C)(C)C)C1]

$^1$H-NMR (500 MHz, $CD_3OD$) δ ppm 7.57 (d, J=2.0 Hz, 1H), 7.18 (d, J=2.0 Hz, 1H), 4.19-4.14 (m, 1H), 3.98 (dd, J=8.0, 7.5 Hz, 2H), 3.89 (s, 3H), 3.62-3.56 (br, 2H), 2.98 (q, J=6.7 Hz, 2H), 2.49 (s, 3H), 1.42 (s, 9H), 0.88 (t, J=7.2 Hz, 3H).

Methyl 5-chloro-3-(ethyl(1-methylazetidin-3-yl)amino)-2-methylbenzoate

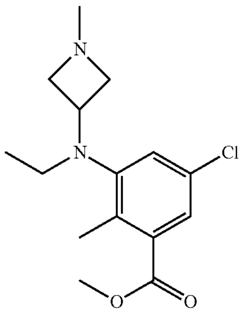 [SMILES: CCN(c1cc(Cl)cc(C(=O)OC)c1C)C1CN(C)C1]

$^1$H-NMR (500 MHz, $CD_3OD$) δ ppm 7.53 (d, J=2.0 Hz, 1H), 7.17 (d, J=2.0 Hz, 1H), 4.01 (m, 1H), 3.89 (s, 3H), 3.57 (dd, J=6.5, 8.0 Hz, 2H), 2.93 (q, J=7.5 Hz, 2H), 2.83 (bt, J=7.0 Hz, 2H), 2.49 (s, 3H), 2.33 (s, 3H), 0.90 (t, J=7.0 Hz, 3H); LCMS (M+H)=297.30.

3-{Ethyl[1-(propan-2-yl)piperidin-4-yl]amino}-2-methyl-5-(trifluoromethyl)benzoic acid

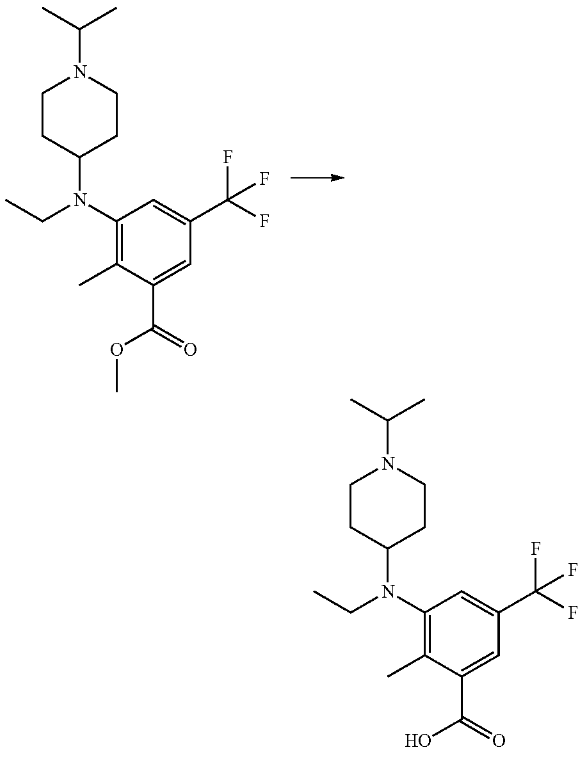

To a stirred solution of methyl 3-{ethyl[1-(propan-2-yl)piperidin-4-yl]amino}-2-methyl-5-(trifluoromethyl)benzoate (220 mg, 0.569 mmol) in methanol (4 mL) was added aq. NaOH (5M, 170 ul, 0.854 mmol). The reaction mixture was stirred at 50° C. for 2 hours. After cooling to 23° C. HCl (2 M) was added to the mixture. The mixture was acidified to pH=5 and was concentrated in vacuo to give the titled compound as crude products (510 mg).

Methyl 3-{[(2R*,6R*)-1-benzyl-2,6-dimethylpiperidin-4-yl]amino}-2-methyl-5-(trifluoromethyl)benzoate

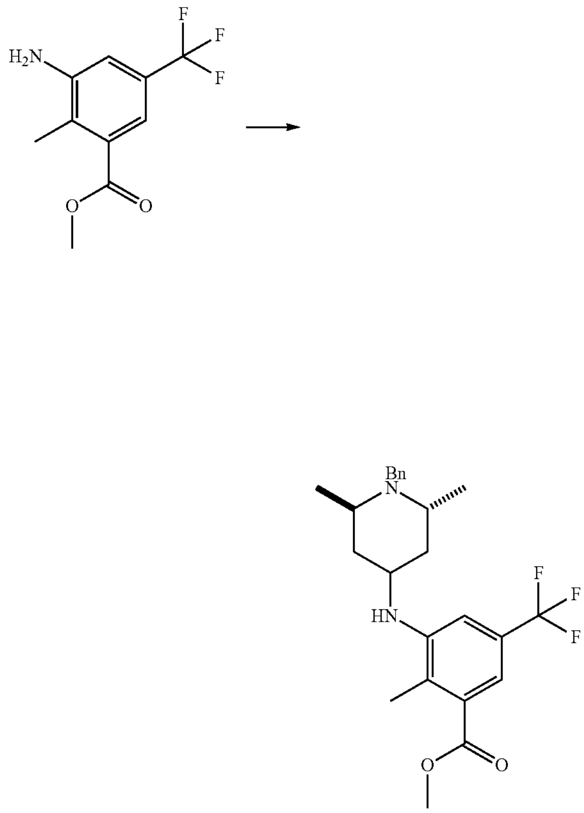 [SMILES: COC(=O)c1cc(C(F)(F)F)cc(N)c1C ; COC(=O)c1cc(C(F)(F)F)cc(NC2C[C@@H](C)N(Cc3ccccc3)[C@H](C)C2)c1C]

To a stirred solution of methyl 3-amino-2-methyl-5-(trifluoromethyl)benzoate (400 mg, 1.72 mmol) in THF (15 mL) and TFA (491 uL) was added (2R,6S)-1-benzyl-2,6-dimethylpiperidin-4-one (410 mg, 1.89 mmol) at 0° C. The mixture was stirred at 60° C. for 1 hour under nitrogen atmosphere. Then the mixture was cooled to 0° C. in an ice bath, sodium triacetoxyborohydride (765 mg, 3.43 mmol) was added. The reaction mixture was stirred at 23° C. for 2 hours. Then aq. $NaHCO_3$ was added at 0° C. until pH8-9, and the content was extracted with ethylacetate. The organic layer was dried over $MgSO_4$ and filtered. The filtrate was concentrated in vacuo. The residue was purified by silica gel column chromatography (NH—$SiO_2$; heptane/ethylacetate=3/1) to give the titled compound as a colorless oil. (278 mg, 37% yield). $^1$H-NMR (400M Hz, $CDCl_3$) δppm; 7.21-7.40 (m, 6H), 6.90 (s, 1H), 3.95 (d, J=14.0 Hz, 1H), 3.90 (s, 3H), 3.60-3.73 (m, 2H), 3.46 (d, J=14.0 Hz, 1H), 3.08-3.12 (m, 1H), 2.98-3.03 (m, 1H), 2.30 (s, 3H), 2.02-2.08 (m, 1H), 1.83-1.88 (m, 1H), 1.52-1.60 (m, 1H), 1.17-1.26 (m, 1H), 1.11 (d, J=6.8 Hz, 3H), 1.13 (d, J=6.4 Hz, 3H).

Methyl 3-{[(2R*,6S*)-1-benzyl-2,6-dimethylpiperidin-4-yl]amino}-2-methyl-5-(trifluoromethyl)benzoate (Diastereomeric Mixture)

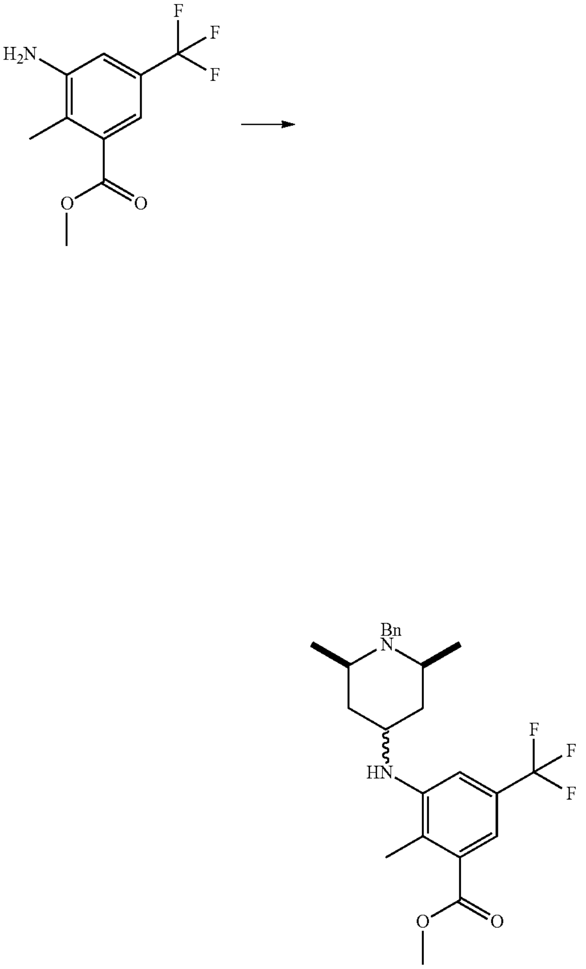

To a stirred mixture of MS3A (1.0 g), methyl 3-amino-2-methyl-5-(trifluoromethyl)benzoate (350 mg, 1.50 mmol) and (2R,6S)-1-benzyl-2,6-dimethylpiperidin-4-one (359 mg, 1.65 mmol) in chloroform (10 mL) was added acetic acid (500 uL) at 0° C. and stirred at r.t. for 7 hours. To the reaction mixture was added sodium triacetoxyborohydride (670 mg, 3.00 mmol) at 0° C. The reaction mixture was stirred at 23° C. for 1.5 hours. Then the reaction mixture was quenched with aq. $NaHCO_3$ until pH8-9. The MS 3 Å was removed by Celite filtration and the content was extracted with ethylacetate, dried over $MgSO_4$, filtered and the filtrate was concentrated in vacuo. The residue was purified by silica gel column chromatography (heptane/ethylacetate=5/1 to 3/1). Target fractions were collected and concentrated in vacuo. The residue was purified by silica gel column chromatography (NH—$SiO_2$; heptane/ethylacetate=5/1) to give the titled compound as a light yellow oil (223 mg, 62% yield.). For major isomer; $^1$H-NMR (400 MHz, $CDCl_3$) δppm; 7.40-7.21 (m, 6H), 6.85

(s, 1H), 4.00-3.95 (m, 1H), 3.91 (s, 3H), 3.88 (d, 2H), 3.84-3.76 (m, 1H), 2.83-2.73 (m, 2H), 2.25 (s, 3H), 1.83-1.69 (m, 4H), 1.13 (d, J=6.4 Hz, 6H).

Methyl 3-{[(2R*,6R*)-1-benzyl-2,6-dimethylpiperidin-4-yl](ethyl)amino}-2-methyl-5-(trifluoromethyl) benzoate

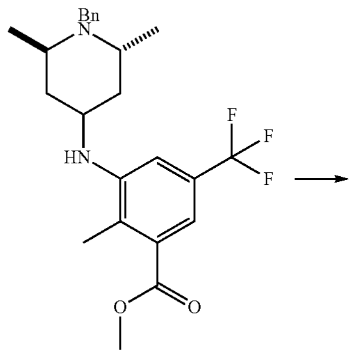

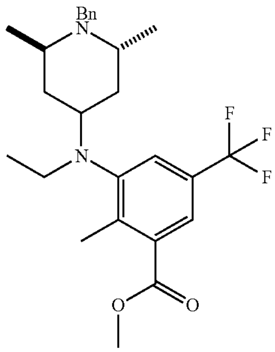

To a stirred solution of methyl 3-{[(2R,6R)-1-benzyl-2,6-dimethylpiperidin-4-yl]amino}-2-methyl-5-(trifluoromethyl)benzoate (278 mg, 0.640 mmol) in $CH_2Cl_2$ (5 mL) and AcOH (500 uL) was added acetaldehyde (359 mg, 6.40 mmol) and sodium triacetoxyborohydride (428 mg, 1.92 mmol) at 0° C. The reaction mixture was stirred at 23° C. for 7 hours. Then the reaction mixture was quenched with aq. $NaHCO_3$ until pH8-9. The content was extracted with ethylacetate, dried over $MgSO_4$ and filtered. The filtrate was concentrated in vacuo. The residue was purified by silica gel column chromatography (NH—$SiO_2$; heptane/ethylacetate=5/1) to give the titled compound as a light yellow oil (236 mg, 80% yield.). $^1$H-NMR (400 MHz, $CDCl_3$) δppm; 7.79 (s, 1H), 7.43 (s, 1H), 7.21-7.36 (m, 5H), 3.92 (s, 3H), 3.87 (d, J=14.0 Hz, 1H), 3.38 (d, J=14.0 Hz, 1H), 3.04-3.15 (m, 4H), 2.73-2.80 (m, 1H), 2.53 (s, 3H), 1.76-1.82 (m, 1H), 1.51-1.63 (m, 2H), 1.34-1.42 (m, 1H), 1.06 (d, J=6.0 Hz, 3H), 0.93 (d, J=6.8 Hz, 3H), 0.86 (t, J=6.8 Hz, 3H).

Methyl 3-{[(2R*,6S*)-1-benzyl-2,6-dimethylpiperidin-4-yl](ethyl)amino}-2-methyl-5-(trifluoromethyl) benzoate (Diastereomeric Mixture)

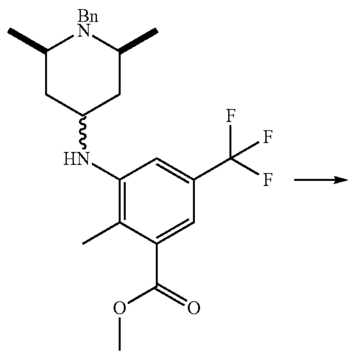

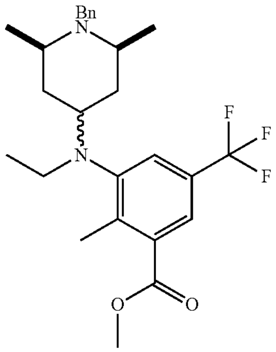

To a stirred solution of methyl 3-{[(2R,6S)-1-benzyl-2,6-dimethylpiperidin-4-yl]amino}-2-methyl-5-(trifluoromethyl)benzoate (223 mg, 0.513 mmol) in chloroform (4 mL) and acetic acid (500 uL) was added acetaldehyde (1.0 ml) and stirred for 30 min at 0° C. Then sodium triacetoxyborohydride (343 mg, 1.54 mmol) was added to the reaction mixture at 0° C. The reaction mixture was stirred at 23° C. for 4 hours. Then the reaction mixture was quenched with aq. $NaHCO_3$ until pH8-9. The content was extracted with ethylacetate. The organic layer was washed with brine. The organic layer was dried over $MgSO_4$ and filtered. The filtrate was concentrated in vacuo. The residue was purified by silica gel column chromatography (heptane/ethylacetate=4/1 to 1/2) to give the titled compound as a colorless oil. (105.5 mg, 44% yield). MS (ES) [M+H] 463.3.

3-{[(2R*,4S*,6R*)-1-Benzyl-2,6-dimethylpiperidin-4-yl](ethyl)amino}-N-[(4,6-dimethyl-2-oxo-1,2-dihydropyridin-3-yl)methyl]-2-methyl-5-(trifluoromethyl)benzamide

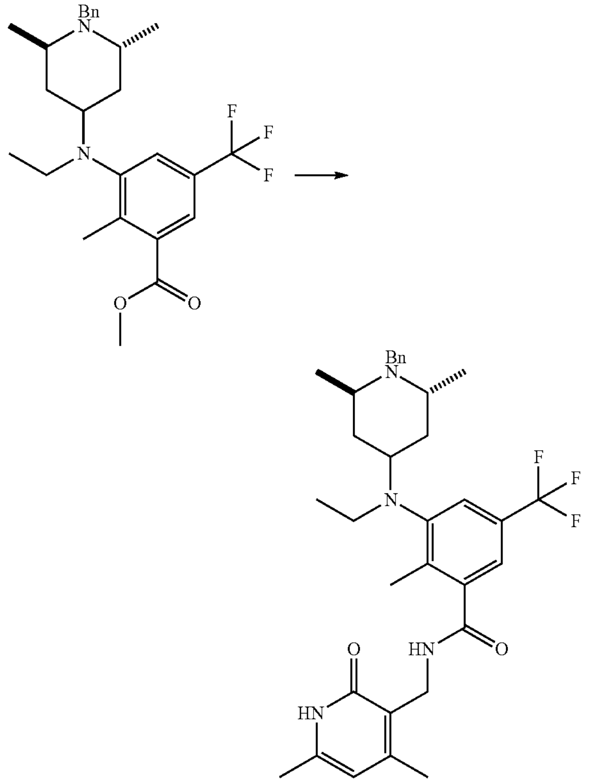

To a stirred solution of methyl 3-{[(2R,6R)-1-benzyl-2,6-dimethylpiperidin-4-yl](ethyl)amino}-2-methyl-5-(trifluoromethyl)benzoate (236 mg, 0.510 mmol) in ethanol (5 mL) was added aq. NaOH (5 M, 269 ul, 1.02 mmol). The reaction mixture was stirred at 80° C. for 2 hours. After cooling to rt, the reaction mixture was concentrated in vacuo and dried under reduced pressure to give crude carboxylic acid sodium salt.

To a stirred solution of crude carboxylic acid sodium salt and 3-(aminomethyl)-4,6-dimethyl-1,2-dihydropyridin-2-one HCl salt (125 mg, 0.664 mmol) in DMSO (5 mL) was added PyBOP (398 mg, 0.766 mmol) and Hunig's base (445 ul, 2.55 mmol). The reaction mixture was stirred at 23° C. for 19 hours. The reaction mixture was quenched with water and extracted with ethylacetate. The organic layer was washed with water (twice) and brine. The organic layer was dried over $MgSO_4$ and filtered. The combined organic layer was concentrated in vacuo. The residue was purified by silica gel column chromatography (NH—$SiO_2$; ethylacetate/MeOH=50/1-8/1) to give the titled compound as a white amorphous (267 mg, 90% yield). $^1$H-NMR (400 MHz, $CDCl_3$) δppm; 7.14-7.36 (m, 8H), 5.94 (s, 1H), 4.53-4.56 (m, 2H), 3.85 (d, J=14.0 Hz, 1H), 3.58 (d, J=14.0 Hz, 1H), 3.02-3.14 (m, 4H), 2.72-2.80 (m, 1H), 2.40 (s, 3H), 2.32 (s, 3H), 2.21 (s, 3H), 1.32-1.82 (m, 4H), 1.05 (d, J=6.4 Hz, 3H), 0.92 (d, J=6.8 Hz, 3H), 0.84 (t, J=6.8 Hz, 3H).

3-{[(2R*,4R*,6S)-1-Benzyl-2,6-dimethylpiperidin-4-yl](ethyl)amino}-N-[(4,6-dimethyl-2-oxo-1,2-dihydropyridin-3-yl)methyl]-2-methyl-5-(trifluoromethyl)benzamide

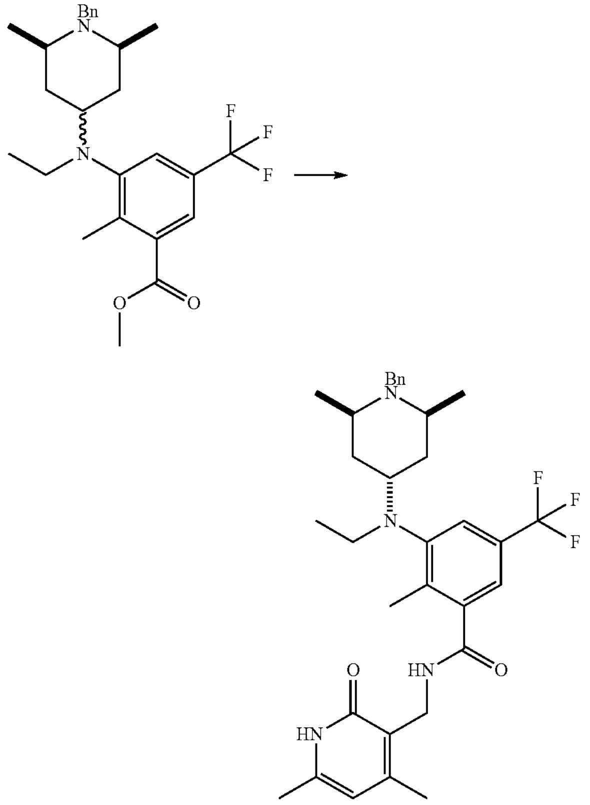

To a stirred solution of methyl 3-{[(2R,6S)-1-benzyl-2,6-dimethylpiperidin-4-yl](ethyl)amino}-2-methyl-5-(trifluoromethyl)benzoate (106 mg, 0.228 mmol) in ethanol (2.0 mL) was added aq. NaOH (5 M, 91.2 ul, 0.456 mmol). The reaction mixture was stirred at 80° C. for 1.5 hours. After cooling to rt, solvent was removed in vacuo and dried under reduced pressure. To a stirred solution of this residue and 3-(aminomethyl)-4,6-dimethyl-1,2-dihydropyridin-2-one HCl salt (55.9 mg, 0.297 mmol) in DMSO (2 mL) was added Hunig's base (199 ul, 1.14 mmol) and PyBOP (178 mg, 0.342 mmol). The reaction mixture was stirred at rt for 4 hours. The reaction mixture was quenched with water. The content was extracted with ethylacetate. The organic layer was washed with water twice and brine. The organic layer was dried over $MgSO_4$ and filtered. The filtrate was concentrated in vacuo. The residue was purified by silica gel column chromatography (NH $SiO_2$, ethylacetate/MeOH=50/1 to 40/1) to give the titled compound as a colorless oil (35.6 mg, 27% yield). $^1$H-NMR (400 MHz, $CDCl_3$) δppm; 7.34-7.08 (m, 7H), 5.96 (s, 1H), 4.54 (d, J=6.0 Hz, 2H), 3.81 (s, 2H), 3.53 (m, 1H), 2.99-2.91 (m, 2H), 2.81 (m, 2H), 2.41 (s, 3H), 2.24 (s, 3H), 2.20 (s, 3H), 1.82-1.47 (m, 4H), 1.00 (d, J=6.4 Hz, 6H), 0.81 (t, J=6.8 Hz, 3H); MS (ES) [M+H] 583.0.

tert-Butyl 4-{[5-chloro-3-(methoxycarbonyl)-2-methylphenyl]amino}piperidine-1-carboxylate

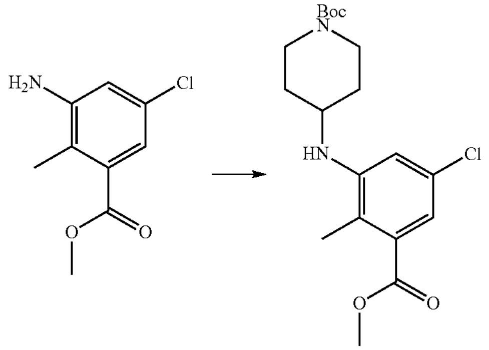 [SMILES: COC(=O)c1cc(Cl)cc(N)c1C ; COC(=O)c1cc(Cl)cc(NC2CCN(C(=O)OC(C)(C)C)CC2)c1C]

To a stirred solution of methyl 3-amino-5-chloro-2-methylbenzoate (1.40 g, 7.04 mmol) in $CH_2Cl_2$ (30 mL) and AcOH (2.50 g, 42.2 mmol) was added N-Boc piperidinone (1.96 g, 9.85 mmol) and sodium triacetoxyborohydride (4.40 g, 21.1 mmol). The reaction mixture was stirred at 23° C. for 18 hours and then saturated $NaHCO_3$ was added and the mixture was separated. The aqueous layer was extracted with $CH_2Cl_2$ (3×20 mL) and the combined organic layers were concentrated in vacuo. The residue was purified by silica gel column chromatography ($SiO_2$ heptane/ethylacetate=10/1 to 1/1) to give the titled compound as oil (2.40 g, 89% yield). $^1$H-NMR (400 MHz, $CDCl_3$) δppm; 7.09 (s, 1H), 6.69 (s, 1H), 4.05 (m, 2H), 3.88 (s, 3H), 3.63 (m, 1H), 3.42 (m, 1H), 2.97 (m, 2H), 2.23 (s, 3H), 2.05 (m, 2H), 1.45 (s, 9H), 1.27 (m, 2H).

tert-Butyl 4-{[5-chloro-3-(methoxycarbonyl)-2-methylphenyl](ethyl)amino}piperidine-1-carboxylate

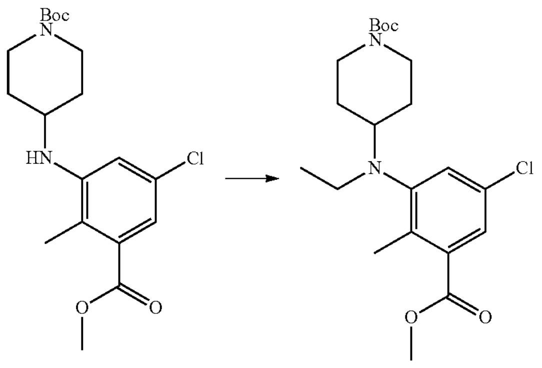 [SMILES: COC(=O)c1cc(Cl)cc(NC2CCN(C(=O)OC(C)(C)C)CC2)c1C ; CCN(c1cc(Cl)cc(C(=O)OC)c1C)C1CCN(C(=O)OC(C)(C)C)CC1]

To a stirred solution of tert-butyl 4-{[5-chloro-3-(methoxycarbonyl)-2-methylphenyl]amino}piperidine-1-carboxylate (2.40 g, 6.28 mmol) in dichloromethane (50 mL) and acetic acid (1.8 mL) was added acetaldehyde (830 ul, 12.6 mmol) and sodium triacetoxyborohydride (4.00 g, 18.8 mmol). The reaction mixture was stirred at rt for 18 hours. Then aq. $NaHCO_3$ was added and the mixture was separated. The aqueous layer was extracted with dichloromethane. The combined organic layer was concentrated in vacuo. The residue was purified by silica gel column chromatography ($SiO_2$ heptane/ethylacetate=10/1) to give the titled compound as oil (2.40 g, 89% yield). $^1$H-NMR (400 MHz, $CDCl_3$) δppm; 7.56 (s, 1H), 7.21 (d, J=1.6 Hz, 1H), 4.04 (m, 2H), 3.89 (s, 3H), 3.02 (q, J=7.0 Hz, 2H), 2.88 (m, 1H), 2.68 (m, 2H), 2.44 (s, 3H), 1.71 (m, 2H), 1.48-1.61 (m, 2H), 1.45 (s, 9H), 0.83-0.89 (t, J=7.0 Hz, 3H); MS (ES) [M+Na] 433.0.

Methyl 5-chloro-3-[ethyl(1-methylpiperidin-4-yl)amino]-2-methylbenzoate

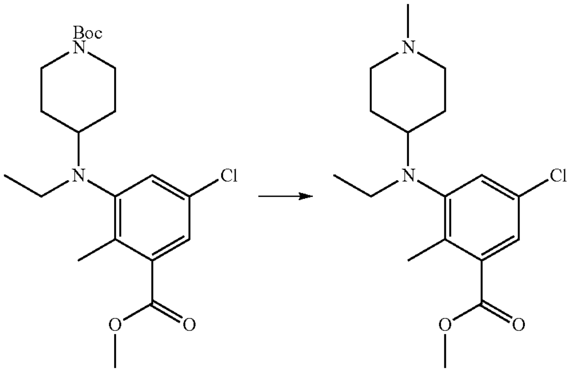 [SMILES: CCN(c1cc(Cl)cc(C(=O)OC)c1C)C1CCN(C(=O)OC(C)(C)C)CC1 ; CCN(c1cc(Cl)cc(C(=O)OC)c1C)C1CCN(C)CC1]

To a stirred solution of tert-butyl 4-{ethyl[3-(methoxycarbonyl)-2-methyl-5-chlorophenyl]amino}piperidine-1-carboxylate (2.20 g, 5.35 mmol) in dichloromethane (20 mL) was added TFA (4 mL). The reaction mixture was stirred at rt for 2 hours. Then reaction mixture was concentrated in vacuo to give TFA salt as a crude product.

To a stirred solution of TFA salt in THF (20 mL) and acetic acid (305 ul) was added formaldehyde (3 mL, 44% aqueous solution) and sodium triacetoxyborohydride (3.40 g, 16.1 mmol) at 0° C. The reaction mixture was stirred at 23° C. for 19 hours and then saturated $NaHCO_3$ was added and the mixture was separated. The aqueous layer was extracted with EtOAc (50 mL) and the combined organic layer was washed with brine, dried over $Na_2SO_4$ and filtered and the filtrate concentrated in vacuo. The residue was purified by silica gel column chromatography (NH—$SiO_2$ heptane/ethylacetate=1/1) to give title compound as oil (1.54 g, 89% yield). $^1$H-NMR (400 MHz, $CDCl_3$) δppm; 7.54 (d, J=2.4 Hz, 1H), 7.21 (d, J=2.4 Hz, 1H), 3.89 (s, 3H), 3.07 (q, J=6.8 Hz, 2H), 2.81-2.85 (m, 2H), 2.66-2.70 (m, 1H), 2.44 (s, 3H), 2.24 (s, 3H), 1.86-1.93 (m, 2H), 1.65-1.75 (m, 4H), 0.86 (t, J=6.8 Hz, 3H).

5-Chloro-3-[ethyl(1-methylpiperidin-4-yl)amino]-2-methylbenzoic acid

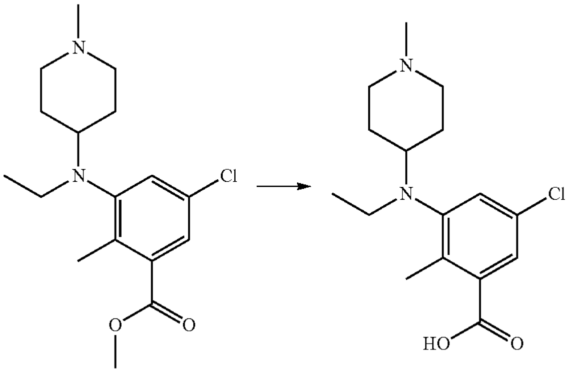 [SMILES: CCN(c1cc(Cl)cc(C(=O)OC)c1C)C1CCN(C)CC1 ; CCN(c1cc(Cl)cc(C(=O)O)c1C)C1CCN(C)CC1]

To a stirred solution of methyl 5-chloro-3-[ethyl(1-methylpiperidin-4-yl)amino]-2-methylbenzoate (1.06 g, 3.26 mmol) in methanol (10 mL) was added aq. NaOH (5 M, 780 ul, 3.92 mmol). The reaction mixture was stirred at 50° C. for 18 hours. After cooling to 23° C., HCl (2 M, 2 mL)) was added to the mixture and the mixture was acidified to pH=5 and was concentrated in vacuo to give the titled compound as crude products (1.80 g).

Methyl 3-{[(2R,6R)-1-benzyl-2,6-dimethylpiperidin-4-yl]amino}-5-fluoro-2-methylbenzoate

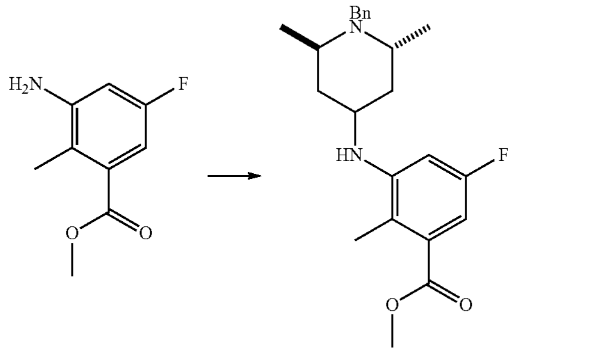 [SMILES: COC(=O)c1cc(F)cc(N)c1C ; COC(=O)c1cc(F)cc(NC2C[C@@H](C)N(Cc3ccccc3)[C@H](C)C2)c1C]

To a stirred solution of methyl 3-amino-5-fluoro-2-methylbenzoate (520 mg, 2.84 mmol) in THF (20 mL) and TFA (813 uL) was added (2R,6S)-1-benzyl-2,6-dimethylpiperidin-4-one (679 mg, 3.12 mmol) at 0° C. The mixture was stirred at 60° C. for 1 hour under nitrogen atmosphere. Then the mixture was cooled to 0° C. in an ice bath, sodium triacetoxyborohydride (1.27 g, 5.68 mmol) was added. The reaction mixture was stirred at rt for 2 hours. Then aq. $NaHCO_3$ was added at 0° C. until pH8-9, and the content was extracted with ethylacetate. The organic layer was dried over $MgSO_4$ and filtered. The filtrate was concentrated in vacuo. The residue was purified by silica gel column chromatography (NH—$SiO_2$; heptane/ethylacetate=5/1) to give titled compound as a colorless oil (331 mg, 30% yield.). $^1$H-NMR (400 MHz, $CDCl_3$) δppm; 7.35-7.39 (m, 2H), 7.27-7.30 (m, 2H), 7.21-7.26 (m, 1H), 6.76 (dd, J=2.4, 9.2 Hz, 1H), 6.45 (dd, J=2.4, 11.2 Hz, 1H), 3.94 (d, J=14.4 Hz, 1H), 3.87 (s, 3H), 3.58-3.65 (m, 2H), 3.46 (d, J=14.4 Hz, 1H), 3.06-3.12 (m, 1H), 2.94-3.01 (m, 1H), 2.21 (s, 3H), 2.02-2.07 (m, 1H), 1.82-1.89 (m, 1H), 1.15-1.22 (m, 1H), 1.12 (d, J=6.0 Hz, 3H), 1.09 (d, J=7.2 Hz, 3H).

Methyl 3-{[(2R,4R,6S)-1-benzyl-2,6-dimethylpiperidin-4-yl]amino}-5-fluoro-2-methylbenzoate

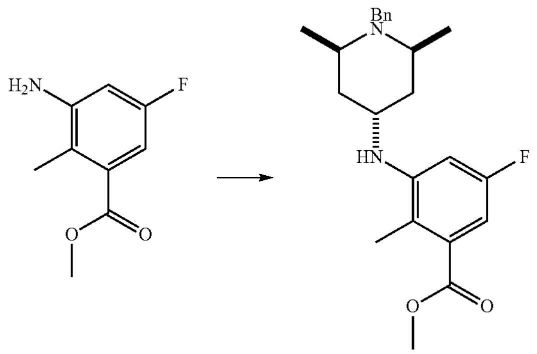

To a stirred solution of methyl 3-amino-5-fluoro-2-methylbenzoate (171 mg, 0.931 mmol) in chloroform (6 mL) and AcOH (266 uL) was added (2R,6S)-1-benzyl-2,6-dimethylpiperidin-4-one (212 mg, 0.980 mmol) and MS3A (500 mg) at 0° C. The mixture was stirred at rt for 2 hour under nitrogen atmosphere. Then the mixture was cooled to 0° C. in an ice bath and sodium triacetoxyborohydride (415 mg, 1.86 mmol) was added. The reaction mixture was stirred at rt for 5 hours. Then aq. $NaHCO_3$ was added at 0° C. until pH8-9, and the content was extracted with ethylacetate. The organic layer was dried over $MgSO_4$ and filtered. The filtrate was concentrated in vacuo. The residue was purified by silica gel column chromatography (1. $SiO_2$; heptane/ethylacetate=5/1 to 3/1, 2. NH—$SiO_2$; heptane/ethylacetate=5/1, 3. NH—$SiO_2$; heptane/ethylacetate=10/1 to 6/1) to give the titled compound as a colorless oil (85.0 mg, 24% yield.). $^1$H-NMR (400 MHz, $CDCl_3$) δppm; 7.38-7.20 (m, 5H), 6.77 (dd, J=2.4, 9.2 Hz, 1H), 6.40 (dd, J=2.4, 11.6 Hz, 1H), 3.95-3.90 (m, 1H), 3.88 (s, 3H), 3.87 (s, 2H), 2.84-2.74 (m, 2H), 2.16 (s, 3H), 1.81-1.66 (m, 4H), 1.11 (d, J=6.0 Hz, 6H).

Methyl 3-{[(2R,6R)-1-benzyl-2,6-dimethylpiperidin-4-yl](ethyl)amino}-5-fluoro-2-methylbenzoate

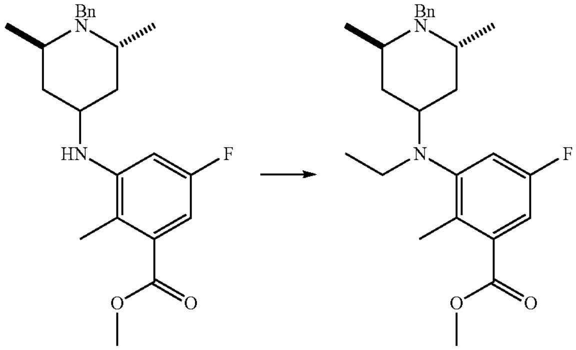 [SMILES: COC(=O)c1cc(F)cc(NC2C[C@@H](C)N(Cc3ccccc3)[C@H](C)C2)c1C ; CCN(c1cc(F)cc(C(=O)OC)c1C)C1C[C@@H](C)N(Cc2ccccc2)[C@H](C)C1]

To a stirred solution of methyl 3-{[(2R,6R)-1-benzyl-2,6-dimethylpiperidin-4-yl]amino}-5-fluoro-2-methylbenzoate (269 mg, 0.701 mmol) in dichloromethane (5 mL) and acetic acid (500 uL) was added acetaldehyde (124 mg, 2.80 mmol) and sodium triacetoxyborohydride (469 mg, 2.10 mmol) at 0° C. The reaction mixture was stirred at rt for 12 hours. Then the reaction mixture was quenched with aq. $NaHCO_3$ until pH8-9. The content was extracted with ethylacetate. The organic layer was dried over $MgSO_4$ and filtered. The filtrate was concentrated in vacuo. The residue was purified by silica gel column chromatography (NH—$SiO_2$; heptane/ethylacetate=5/1) to give the titled compound as a light yellow oil (277 mg, 96% yield). $^1$HNMR (400 MHz, $CDCl_3$) δppm; 7.19-7.36 (m, 6H), 6.97 (dd, J=2.4, 10.4 Hz, 1H), 3.89 (s, 3H), 3.86 (d, J=10.4 Hz, 1H), 3.39 (d, J=10.4 Hz, 1H), 3.02-3.10 (m, 4H), 2.74-2.80 (m, 1H), 2.43 (s, 3H), 1.74-1.82 (m, 1H), 1.51-1.63 (m, 2H), 1.32-1.40 (m, 1H), 1.05 (d, J=6.4 Hz, 3H), 0.93 (d, J=7.2 Hz, 3H), 0.86 (t, J=6.8 Hz, 3H); MS (ES) [M+H] 413.0.

Methyl 3-{[(2R,4R,6S)-1-benzyl-2,6-dimethylpiperidin-4-yl](ethyl)amino}-5-fluoro-2-methylbenzoate

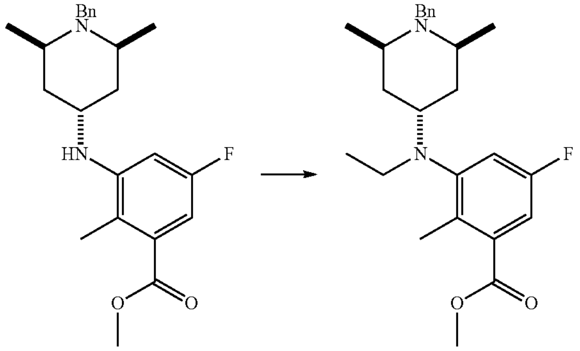

To a stirred solution of methyl 3-{[(2R,4R,6S)-1-benzyl-2,6-dimethylpiperidin-4-yl]amino}-5-fluoro-2-methylbenzoate (84.9 mg, 0.221 mmol) and acetaldehyde (124 mg, 2.21 mmol) in chloroform (2 mL), was added acetic acid (200 uL) at 0° C. and stirred at 23° C. for 1 hour. To the reaction mixture was added sodium triacetoxyborohydride (148 mg, 0.662 mmol) at 0° C. The reaction mixture was stirred at RT for 3.5 hours. To the reaction mixture were added MS 3 Å (200 mg) and acetaldehyde (500 ul) at 0° C. and stirred at r.t. for 25 minutes. To the reaction mixture was added sodium triacetoxyborohydride (148 mg, 0.662 mmol) at 0° C. and stirred at rt for 12 hours. Then the reaction mixture was then quenched with saturated $NaHCO_3$ until pH=8-9. The content was extracted with EtOAc. The organic layer was washed with brine. The organic layer was dried over $MgSO_4$ and filtered. The filtrate was concentrated in vacuo. The residue was purified by silica gel column chromatography (NH—SiO2; heptane/ethylacetate=5/1) to give title compound as a colorless oil (48.5 mg, 53% yield). $^1$HNMR (400 MHz, $CDCl_3$) δppm; 7.36-7.19 (m, 6H), 6.96 (dd, J=2.8, 9.6 Hz, 1H), 3.90 (s, 3H), 3.82 (s, 2H), 3.44 (m, 1H), 2.98-2.91 (m, 2H), 2.88-2.87 (m, 2H), 2.31 (s, 3H), 1.82-1.70 (m, 2H), 1.57-1.4 7 (m, 2H), 0.99 (d, J=6.4 Hz, 6H), 0.83 (t, J=6.8 Hz, 3H).3-{[(2R,6R)-1-Benzyl-2,6-dimethylpiperidin-4-yl](ethyl)amino}-N-[(4,6-dimethyl-2-oxo-1,2-dihydropyridin-3-yl)methyl]-5-fluoro-2-methylbenzamide

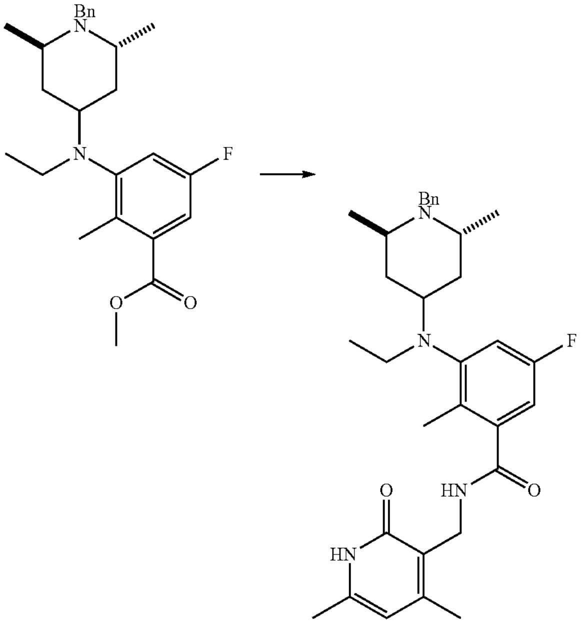

To a stirred solution of methyl 3-{[(2R,6R)-1-benzyl-2,6-dimethylpiperidin-4-yl](ethyl)amino}-5-fluoro-2-methylbenzoate (277 mg, 0.672 mmol) in ethanol (5 mL) was added aq. NaOH (5 M, 269 ul, 1.35 mmol). The reaction mixture was stirred at 80° C. for 2 hours. After cooling to rt, the reaction mixture was concentrated in vacuo and dried under reduced pressure to give crude carboxylic acid sodium salt.

To a stirred solution of crude carboxylic acid sodium salt and 3-(aminomethyl)-4,6-dimethyl-1,2-dihydropyridin-2-one HCl salt (165 mg, 0.874 mmol) in DMSO (5 mL) was added PyBOP (525 mg, 1.01 mmol) and Hunig's base (586 ul, 3.36 mmol). The reaction mixture was stirred at 23° C. for 5 hours. The reaction mixture was quenched with water and extracted with ethylacetate. The organic layer was washed with water (2×10 mL) and brine (1×10 mL). The organic layer was dried over $MgSO_4$ and filtered and the filtrate concentrated in vacuo. The residue was purified by silica gel column chromatography (NH—$SiO_2$; ethylacetate only to ethylacetate/MeOH=50/1-8/1) to give titled compound as a white solid (378 mg, quantitative yield). $^1$HNMR (400 MHz, $CDCl_3$) δppm; 7.20-7.38 (m, 5H), 7.02-7.10 (m, 1H), 6.80-6.84 (m, 1H), 6.73-6.78 (m, 1H), 5.93 (s, 1H), 4.51 (d, J=6.0 Hz, 2H), 3.85 (d, J=10.0 Hz, 1H), 3.38 (d, J=10.0 Hz, 1H), 3.01-3.05 (m, 4H), 2.67-2.81 (m, 1H), 2.40 (s, 3H), 2.23 (s, 3H), 2.23 (s, 3H), 1.52-1.83 (m, 3H), 1.32-1.39 (m, 1H), 1.05 (d, J=6.4 Hz, 3H), 0.93 (d, J=6.8 Hz, 3H), 0.84 (t, J=6.8 Hz, 3H).

3-{[(2R,4R,6S)-1-Benzyl-2,6-dimethylpiperidin-4-yl](ethyl)amino}-N-[(4,6-dimethyl-2-oxo-1,2-dihydropyridin-3-yl)methyl]-5-fluoro-2-methylbenzamide

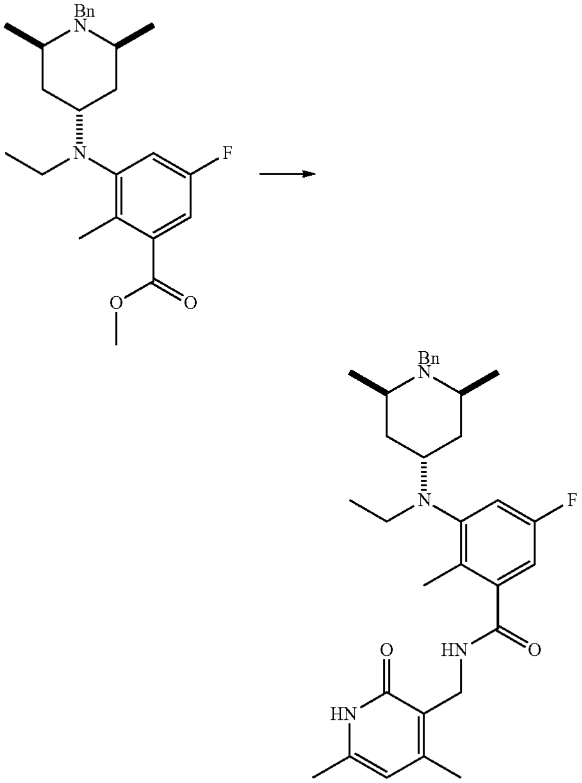

To a stirred solution of methyl 3-{[(2R,4R,6S)-1-benzyl-2,6-dimethylpiperidin-4-yl](ethyl)amino}-5-fluoro-2-methylbenzoate (48.5 mg, 0.118 mmol) in ethanol (1.5 mL) was added aq. NaOH (5 M, 47.0 ul, 0.235 mmol). The reaction mixture was stirred at 80° C. for 1.5 hours. After cooling to rt, solvent was removed in vacuo and dried under reduced pressure. To a stirred solution of this residue and 3-(aminomethyl)-4,6-dimethyl-1,2-dihydropyridin-2-one HCl salt (28.8 mg, 0.153 mmol) in DMSO (1 mL) was added PyBOP (91.8 mg, 0.176 mmol) and Hunig's base (102 ul, 0.588 mmol). The reaction mixture was stirred at 23° C. for 13.5 hours. The reaction mixture was quenched with water, and the mixture was extracted with ethylacetate. The organic layer was washed with water (2×10 mL) and brine (1×10 mL). The organic layer was dried over $MgSO_4$, filtered and the filtrate was concentrated in vacuo. The residue was purified by silica gel column chromatography (NH $SiO_2$, ethylacetate/MeOH=50/1 to 8/1) to give title compound as a white solid (50.1 mg, 79% yield). MS (ES) [M+H] 533.3.

Example 1

Synthesis of Compound 1: 5-bromo-3-(cyclopentylamino)-N-((4,6-dimethyl-2-oxo-1,2-dihydropyridin-3-yl)methyl)-2-methylbenzamide Compound 1

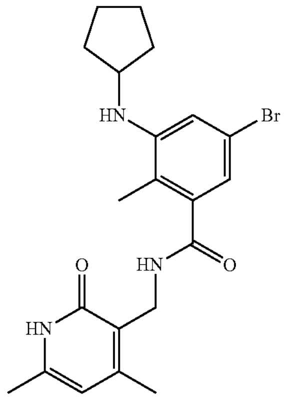

Step 1: Synthesis of methyl 5-bromo-3-(cyclopentyl(methyl)amino)-2-methylbenzoate

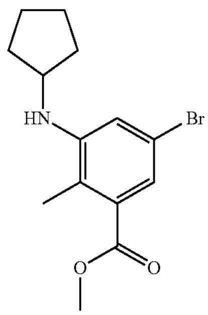 [SMILES: COC(=O)c1cc(Br)cc(NC2CCCC2)c1C]

To a stirred solution of methyl 5-bromo-3-(cyclopentylamino)-2-methylbenzoate (0.5 g, 1.75 mmol) in acetonitrile (10 mL), $Cs_2CO_3$ (1.02 g, 2.63 mmol) and methyl iodide (1.45 g, 3.5 mmol) were added to it. The resulting reaction mixture was stirred at 80° C. for 4 h. Upon completion, the solvent was removed under reduced pressure and residue dissolved in water and extracted with ethyl acetate. Crude material obtained was purified by column chromatography over silica gel affording the desired compound product without further purification (0.39 g).

Step 2: Synthesis of 5-bromo-3-(cyclopentylamino)-N-((4,6-dimethyl-2-oxo-1,2-dihydropyridin-3-yl)methyl)-2-methylbenzamide

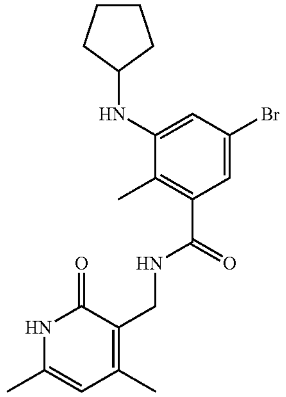 [SMILES: Cc1cc(C)c(CNC(=O)c2cc(Br)cc(NC3CCCC3)c2C)c(=O)[nH]1]

To a stirred solution of methyl 5-bromo-3-(cyclopentyl(methyl)amino)-2-methylbenzoate (1 equiv.) in ethanol (5 mL), aqueous NaOH solution (1 equiv.) was added and reaction stirred at 60° C. for 4 h. On completion, ethanol was removed under reduced pressure and residue acidified with 1N HCl to pH 6. The aqueous phase was extracted with 10% MeOH/DCM. Combined organic layers were dried over sodium sulfate and solvent removed under reduced pressure affording pure acid (yield 50-60%). To a solution of this acid (1 equiv.) in DMSO (1.5 mL), PyBOP (1.5 equiv.) was added and reaction stirred at room temperature for 15 min. Then 3-(aminomethyl)-4,6-dimethylpyridin-2(1H)-one (2 equiv.) was added and reaction stirred overnight. On completion, water was added and the resulting solid precipitate filtered and washed with water. Then this solid was stirred with acetonitrile for 10 min and filtered again to obtain pure target molecule (yield 50-60%). LCMS: 446.15 $(M+1)^+$; HPLC: 94.48% (@ 254 nm) ($R_t$; 5.257); $^1H$ NMR (DMSO-$d_6$, 400 MHz) δ 11.47 (s, 1H), 8.20 (t, 1H, J=4.8 Hz), 7.25 (s, 1H), 7.04 (s, 1H), 5.85 (s, 1H), 4.23 (d, 2H, J=4.8 Hz), 3.37-3.45 (m, 1H), 2.49 (3H merged in solvent peak), 2.17 (s, 3H), 2.13 (s, 3H), 2.10 (s, 3H), 1.53-1.67 (m, 4H), 1.38-1.50 (m, 4H).

Example 2

Synthesis of Compound 2: 5-bromo-N-((4,6-dimethyl-2-oxo-1,2-dihydropyridin-3-yl)methyl)-2-methyl-3-(methyl(piperidine-4-yl)amino)benzamide Compound 2

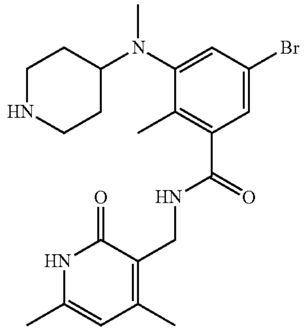

Step 1: 5-bromo-2-methyl-3-nitrobenzoic acid

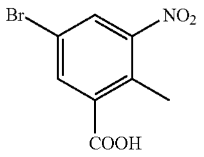

To stirred solution of 2-methyl-3-nitrobenzoic acid (50 g, 276.2 mmol) in conc. $H_2SO_4$ (200 mL), 1,3-dibromo-5,5-dimethyl-2,4-imidazolidinedione (43.4 g, 151.8 mmol) was added portion wise at room temperature and reaction mass was stirred at room temperature for 5 h. On completion, reaction mass was poured on ice cold water, solid precipitated was filtered, resulting residue was washed with water and dried under vacuum giving the desired compound (71.7 g, 99.9%) which was used for further reaction.

Step 2: methyl 5-bromo-2-methyl-3-nitrobenzene

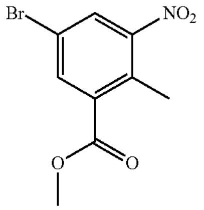

To a stirred solution of 5-bromo-2-methyl-3-nitrobenzoic acid (287 g, 1103 mmol) in DMF (150 mL), sodium carbonate (468 g, 4415 mmol) and methyl iodide (626.63 g, 4415 mmol) were added. Resulting reaction mass was heated at 60° C. for 8 h. On completion, solid precipitated was filtered, residue washed with diethyl ether (5 times). Combined organic layers were dried, concentrated under reduced pressure giving the desired compound (302 g, 99%) which was used for further reaction.

Step 3: methyl 3-amino-5-bromo-2-methylbenzoate

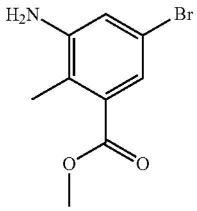

To a stirred solution of methyl 5-bromo-2-methyl-3-nitrobenzene (150 g, 544 mmol) in ethanol (750 mL), ammonium chloride (150 g, 2777 mmol) dissolved in water (750 mL) and iron powder (93.3 g, 1636 mmol) were added under stirring. Resulting reaction mass was heated at 80° C. for 7 h. On completion, reaction mass was filtered through celite giving washing of water and ethyl acetate, filtrate was extracted with ethyl acetate. The combined organic layers were dried, concentrated under reduced pressure giving the desired compound.

Step 4: tert-butyl 4-((5-bromo-3-(methoxycarbonyl) amino)piperidine-1-carboxylate

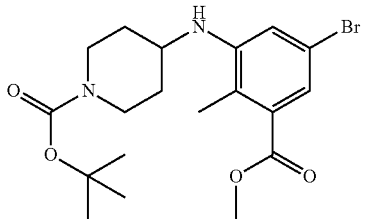 [SMILES: COC(=O)c1cc(Br)cc(NC2CCN(C(=O)OC(C)(C)C)CC2)c1C]

To a stirred solution of above crude methyl 3-amino-5-bromo-2-methylbenzoate (5 g, 20.57 mmol) and tert-butyl 4-oxopiperidine-1-carboxylate (8.2 g, 41.15 mmol) in methanol (50 mL), acetic acid (1.2 g, 20.57 mmol) was added and reaction stirred at room temperature for 3 h. Then sodium cyanoborohydride (1.55 g, 24.6 mmol) was added at 0° C. and reaction stirred overnight at room temperature. On completion, solvent was removed under reduced pressure and crude material was purified by column chromatography to afford compound 5 (5 g, 57%).

Step 5: tert-butyl 4-((5-bromo-3-(methoxycarbonyl)-2-methylphenyl(methyl)amino)piperidine-1-carboxylate

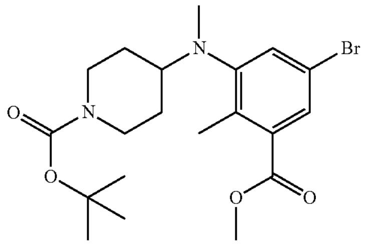 [SMILES: COC(=O)c1cc(Br)cc(N(C)C2CCN(C(=O)OC(C)(C)C)CC2)c1C]

To a stirred solution of tert-butyl 4-((5-bromo-3-(methoxycarbonyl)amino)piperidine-1-carboxylate (3 g, 7.06 mmol) in acetonitrile (25 mL), cesium carbonate (4.57 g, 14.11 mmol) and methyl iodide (5 g, 35.2 mmol) were added; resulting reaction mass was heated at 80° C. for 7 h. On completion, reaction mass was cooled to room temperature and filtered, residue was washed with ethyl acetate and filtrate was concentrated and then purified by column chromatography to afford the desired compound (2.5 g, 81%).

Step 6: tert-butyl 4-((5-bromo-3-(((4,6-dimethyl-2-oxo-1,2-dihydropyridin-3-yl)methyl)carbamoyl)-2-methylphenyl)(methyl)amino)piperidin-1-carboxylate

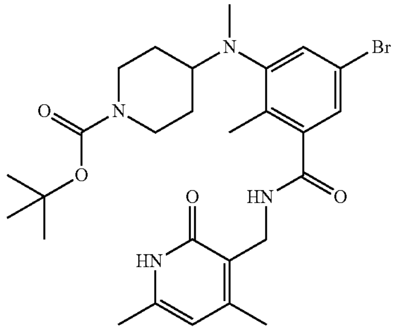 [SMILES: Cc1cc(C)c(CNC(=O)c2cc(Br)cc(N(C)C3CCN(C(=O)OC(C)(C)C)CC3)c2C)c(=O)[nH]1]

Aqueous NaOH (0.37 g, 9.38 mmol) was added to a solution of tert-butyl 4-((5-bromo-3-(methoxycarbonyl)-2-methylphenyl(methyl)amino)piperidine-1-carboxylate (2 g, 4.69 mmol) in MeOH (20 mL) and stirred at 60° C. for 1 h. After completion of the reaction, ethanol was removed under reduced pressure and acidified using dilute HCl up to pH 6 and pH 4 was adjusted using citric acid. Extraction was carried out using ethyl acetate. Combined organic layers were dried concentrated giving respective acid (1.7 g, 90%).

The acid (1.7 g, 4.22 mmol) was then dissolved in DMSO (10 mL) and 3-(amino methyl)-4,6-dimethylpyridin-2(1H)-one (1.42 g, 9.38 mmol) was added to it. The reaction mixture was stirred at room temperature for 15 min before PYBOP (3.66 g, 7.04 mmol) was added to it and stirring was continued for overnight. After completion, reaction mass was poured into ice to obtain solid, this was filtered and washed with acetonitrile followed by purification with column chromatography to afford the desired compound (1.3 g, 50%).

Step 7: 5-bromo-N-((4,6-dimethyl-2-oxo-1,2-dihydropyridin-3-yl)methyl)-2-methyl-3-(methyl(piperidine-4-yl)amino)benzamide

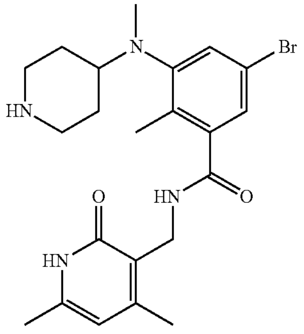 [SMILES: Cc1cc(C)c(CNC(=O)c2cc(Br)cc(N(C)C3CCNCC3)c2C)c(=O)[nH]1]

A stirred solution of tert-butyl 4-((5-bromo-3-(((4,6-dimethyl-2-oxo-1,2-dihydropyridin-3-yl)methyl)carbamoyl)-2-methylphenyl)(methyl)amino)piperidin-1-carboxylate (1.3 g, 2.39 mmol) in DCM (10 mL) was cooled to 0° C. and TFA (2 mL) was added to it. Reaction mass was stirred at room temperature for 1 h. On completion, reaction was concentrated to dryness. Residue was basified with aqueous sodium bicarbonate till pH 8 and aqueous layer extracted with 20% MeOH/DCM. Combined organic layers were dried over sodium sulfate and concentrated to afford the desired compound (0.9 g, 85%). LCMS: 461.15 $(M+1)^+$; HPLC: 98.52% (@ 254 nm) ($R_t$; 4.673; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 8.22 (t, 1H), 7.19 (s, 1H), 7.01 (s, 1H), 5.85 (s, 1H), 4.23 (d, 2H, J=4 Hz), 2.91 (d, 2H, J=11.6 Hz), 2.78 (bs, 1H), 2.55 (s, 3H), 2.32-2.35 (m, 2H), 2.18 (s, 3H), 2.10 (s, 6H), 1.44-1.50 (m, 4H).

Example 3

Synthesis of Compound 3: 5-chloro-3-(cyclohexyl(methyl)amino)-N-((4,6-dimethyl-2-oxo-1,2-dihydropyridin-3-yl)methyl)-2-methylbenzamide Compound 3

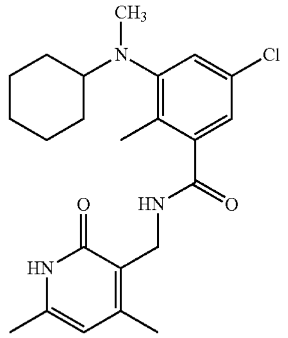

Step 1: 5-chloro-2-methyl-3-nitrobenzoic acid

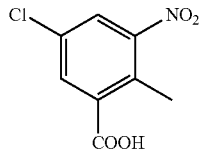

5-Chloro-2-methylbenzoic acid (4 g, 23.39 mmol) was added to cooled conc. $H_2SO_4$ (27 mL) at −10° C. lot wise. After 10 minutes nitrating mixture {prepared as mixing Conc. HNO3 (3.3 g, 52.68 mmol) with conc.$H_2SO_4$ (4.4 mL)} was added drop wise at −10° C. Resulting reaction mass was stirred at −10° C. for 30 minutes. On completion, reaction mixture was poured on ice cold water, solid precipitated was filtered, washed with water and dried under vacuum giving desired compound (4.95 g, 99%).

Step 2: methyl 5-chloro-2-methyl-3-nitrobenzoate

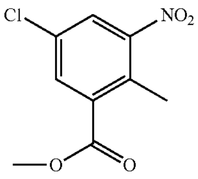

To stirred solution of 5-chloro-2-methyl-3-nitrobenzoic acid (6.75 g, 31.25 mmol) in DMF (33 mL), sodium carbonate (13.23 g, 125.18 mmol) and methyl iodide (17.77 g, 125.2 mmol) were added. Resulting reaction mass was heated at 60° C. for 4 h. On completion, water was added to the reaction mass and extraction was carried out using DCM. Combined organic layers were dried, concentrated under reduced pressure and purified by column chromatography over silica (60-120 mesh size) giving desired compound (6 g, 83%).

Step 3: methyl 3-amino-5-chloro-2-methyl benzoate

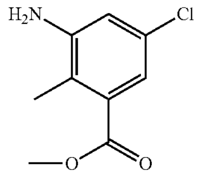

To stirred solution of methyl 5-chloro-2-methyl-3-nitrobenzoate (6 g, 26.13 mmol) in ethanol (60 mL), ammonium chloride (6 g, 112.1 mmol) dissolved in water (60 mL) and iron powder (11.88 g, 208.4 mmol) were added under stirring. Resulting reaction mass was heated at 80° C. for 1 h. On completion, water was added to reaction mass and reaction mixture was filtered through celite, filtrate was extracted with ethyl acetate. Combined organic layers were washed with water, dried, concentrated under reduced pressure giving desired compound.

Step 4: methyl 5-chloro-3-(cyclohexylamino)-2-methylbenzoate

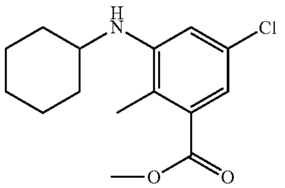 [SMILES: COC(=O)c1cc(Cl)cc(NC2CCCCC2)c1C]

To a stirred solution of methyl 3-amino-5-chloro-2-methyl benzoate (1 g, 5.025 mmol) and cyclohexanone (0.739 g, 7.75 mmol) in methanol (10 mL), acetic acid (0.301 g, 5.02 mmol) was added and reaction stirred at room temperature for 3 h. Then sodium cyanoborohydride (390 mg, 0.00621 mmol) was added and reaction stirred overnight. On completion, solvent was removed under reduced pressure and crude material was purified by column chromatography to afford the desired compound (1.4 g, contaminated with cyclohexanone).

Step 5: methyl 5-chloro-3-(cyclohexyl(methyl) amino)-2-methylbenzoate (6)

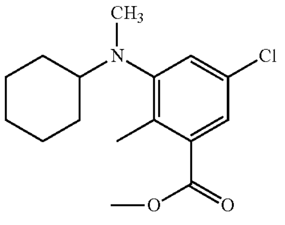 [SMILES: COC(=O)c1cc(Cl)cc(N(C)C2CCCCC2)c1C]

To a stirred solution of methyl 5-chloro-3-(cyclohexylamino)-2-methylbenzoate (1.4 g, 0.0049 mole) in acetonitrile (10 mL), cesium carbonate (3.2 g, 0.0099 mole) and methyl iodide (3.5 g, 0.0024 mole) were added; resulting reaction mass was heated at 80° C. for 13 h. On completion, reaction mass was cooled to room temperature and filtered, residue was washed with ethyl acetate and filtrate was concentrated and then purified by column chromatography to afford desired compound (800 mg, 55%).

Step 6: 5-chloro-3-(cyclohexyl(methyl)amino)-N-((4,6-dimethyl-2-oxo-1,2-dihydropyridin-3-yl)methyl)-2-methylbenzamide

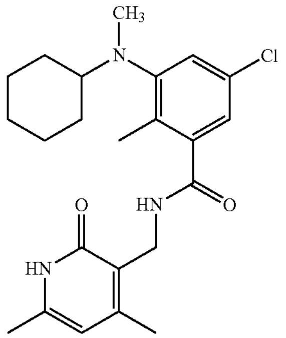 [SMILES: Cc1cc(C)c(CNC(=O)c2cc(Cl)cc(N(C)C3CCCCC3)c2C)c(=O)[nH]1]

Aqueous NaOH (0.16 g, 4.06 mmol) was added to a solution of compound 6 (0.8 g, 2.71 mmol) in EtOH (5 mL) and stirred at 60° C. for 1 h. After completion of the reaction, ethanol was removed under reduced pressure and acidified using dilute HCl up to pH 6 and pH 4 was adjusted using citric acid. Extraction was carried out using ethyl acetate. Combined organic layers were dried concentrated giving respective acid (0.7 g, 91%).

The acid (0.7 g, 2.49 mmol) was then dissolved in DMSO (2 mL) and 3-(amino methyl)-4,6-dimethylpyridin-2(1H)-one (0.752 g, 4.98 mmol) was added to it. The reaction mixture was stirred at room temperature for 15 min before PYBOP (1.9 g, 3.73 mmol) was added to it and stirring was continued for overnight. After completion of the reaction, reaction mass was poured into ice to obtain solid, this was filtered and washed with acetonitrile followed column purification to provide the title compound (0.250 g, 25%).

LCMS: 416.35 $(M+1)^+$; HPLC: 99.01% (@ 254 nm) ($R_t$; 5.408; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-$d_6$, 400 MHz) δ 11.46 (s, 1H), 8.20 (t, 1H, J=4.8 Hz), 7.05 (d, 1H, J=2 Hz), 6.88 (d, 1H, J=2 Hz), 5.85 (s, 1H), 4.24 (d, 2H, J=4.8 Hz), 2.70 (m, 1H), 2.56 (s, 3H), 2.18 (s, 3H), 2.12 (s, 3H), 2.10 (s, 3H), 1.75-1.35 (m, 7H), 1.25-1.05 (m, 3H).

Example 4

Synthesis of Compound 4: 5-bromo-N-((4,6-dimethyl-2-oxo-1,2-dihydropyridin-3-yl)methyl)-2-methyl-3-(methyl(1-pivaloylpiperidin-4-yl)amino)benzamide Compound 4

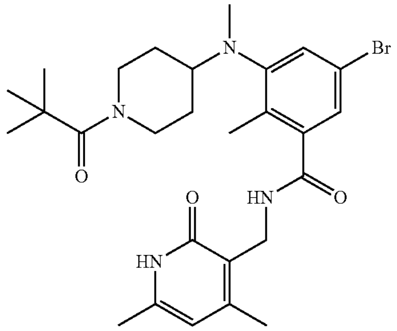

To a stirred solution of 5-bromo-N-((4,6-dimethyl-2-oxo-1,2-dihydropyridin-3-yl)methyl)-2-methyl-3-(methyl(piperidine-4-yl)amino)benzamide (0.05 g, 0.112 mmol) in DMF (2 mL), EDCI.HCl (0.064 g, 0.336 mmol), HOBt (0.03 g, 0.22 mmol), triethyl amine (0.03 g, 0.336 mmol) and pivalic acid (0.023 g, 0.224 mmol) were added at room temperature and stirred at same temperature for 18 h. On completion, water was added and extracted with 10% MeOH/DCM. Combined organic layers were dried, concentrated giving crude material; which then purified by column chromatography to afford the desired compound (0.03 g, 56%). LCMS: 545.20 $(M+1)^+$; HPLC: 98.60% (@ 254 nm) ($R_t$; 6.355; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate.: 1.4 mL/min.; Gradient: 5% B to 95% B in 8 min, Hold for 1.5 min, 9.51-12 min 5% B); $^1H$ NMR (DMSO-$d_6$, 400 MHz) δ 11.46 (s, 1H), 8.20 (t, 1H, J=4.4 Hz), 7.25 (d, 1H, J=2.8 Hz), 7.05 (d, 1H, J=1.2 Hz), 5.85 (s, 1H), 4.23-4.25 (m, 4H), 3.00 (m, 1H), 2.76 (t, 2H, J=12.4 Hz), 2.54 (s, 3H), 2.18 (s, 3H), 2.14 (s, 3H), 2.10 (s, 3H), 1.62-1.65 (m, 2H), 1.42-1.48 (m, 2H), 1.18 (s, 9H).

Example 5

Synthesis of Compound 5: 5-bromo-3-(cyclopentyl(ethyl)amino)-N-((4,6-dimethyl-2-oxo-1,2-dihydropyridin-3-yl)methyl)-2-methylbenzamide Compound 5

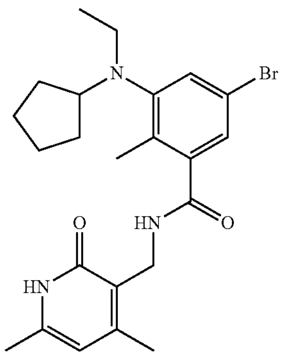

Step 1: 5-bromo-2-methyl-3-nitrobenzoic acid

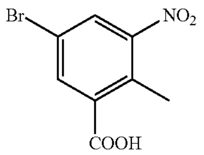

To a mixture of 2-methyl-3-nitrobenzoic acid (15 g, 82.80 mmol) in conc. $H_2SO_4$ (60 mL), 1,3-dibromo-5,5-dimethyl 2,4-imidazolidinedione (13.07 g, 45.71 mmol) was added and reaction mixture was stirred at room temperature for 5 h. Then reaction mixture was slowly poured in to 400 mL of ice cold water. Solid that precipitated out was filtered, washed and dried under vacuum the desired compound (21 g, 98.22%).

Step 2: methyl 3-bromo-5-nitrobenzoate (3)

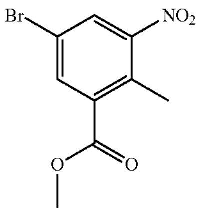

To a stirred solution of 5-bromo-2-methyl-3-nitrobenzoic acid (16 g, 61.54 mmol) in DMF (160 mL), iodomethane (35.72 g, 248 mmol) and sodium carbonate (26.28 g, 248 mmol) were added. Resulting reaction mass was stirred at 60° C. for 8 h. On completion, reaction mass was filtered and inorganic solid residue washed with ethyl acetate. Combined filtrates were concentrated under vacuum till dryness. The residue was re-dissolved in ethyl acetate and washed with 5% sodium bicarbonate solution (700 mL) followed by 5M HCl solution (300 mL). Organic layer was finally washed with brine, dried over sodium sulfate and concentrated to afford desired compound (16 g, 95%).

Step 3: ethyl 3-amino-5-bromobenzoate

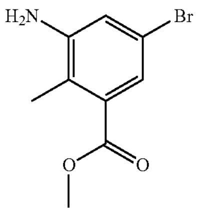

To a stirred solution of methyl 3-bromo-5-nitrobenzoate (17 g, 62.04 mmol) in ethanol (85 mL), was added $NH_4Cl$ solution (17 g in 85 mL water, 317.8 mmol) followed by Fe powder (27.82 g, 498.12 mmol). Resulting reaction mass was stirred at 90° C. for 1 h. On completion, reaction mass was filtered and filtrate concentrated till dryness to get solid which was dissolved in sat. sodium bicarbonate solution. Aqueous layer was extracted with ethyl acetate (3×50 mL). Combined organic layers were dried over sodium sulfate and concentrated to afford the desired compound (15 g, 99.14%).

Step 4: methyl 3-bromo-5-(cyclopentylamino)benzoate

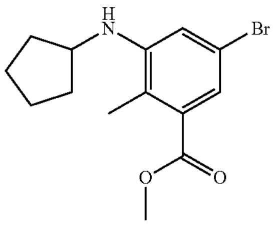 [SMILES: COC(=O)c1cc(Br)cc(NC2CCCC2)c1C]

To a stirred solution of ethyl 3-amino-5-bromobenzoate (2 g, 8.73 mmol) and cyclopentanone (2.2 g, 26.1 mmol) in methanol (20 mL), acetic acid (1.04 g, 17.4 mmol) was added and reaction stirred at room temperature for 3 h. Then sodium cyanoborohydride (1.37 g, 21.83 mmol) was added and reaction stirred overnight. On completion, solvent was removed under reduced pressure and crude material was purified by column chromatography to afford desired compound (1.6 g, 61%).

Step 5: methyl 5-bromo-3-(cyclopentyl(ethyl)amino)-2-methylbenzoate

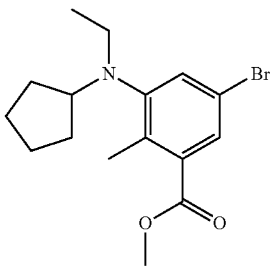 [SMILES: CCN(c1cc(Br)cc(C(=O)OC)c1C)C1CCCC1]

To a stirred solution of methyl 3-bromo-5-(cyclopentylamino)benzoate (0.3 g, 0.96 mmol) in DMF (5 mL), cesium carbonate (0.628 g, 1.92 mmol) and ethyl iodide (0.748 g, 4.8 mmol) were added; resulting reaction mass was heated at 80° C. for 24 h. On completion, reaction mass was cooled to room temperature and filtered, residue was washed with ethyl acetate and filtrate was concentrated and then purified by column chromatography to afford desired compound (0.150 g, 46%).

Step 6: 5-bromo-3-(cyclopentyl(ethyl)amino)-N-((4,6-dimethyl-2-oxo-1,2-dihydropyridin-3-yl)methyl)-2-methylbenzamide

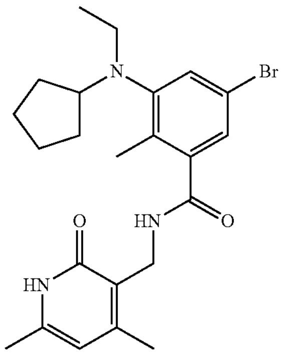

Aqueous NaOH (0.03 g, 0.75 mmol) was added to a solution of methyl 5-bromo-3-(cyclopentyl(ethyl)amino)-2-methylbenzoate (0.170 g, 0.75 mmol) in EtOH (10 mL) and stirred at 60° C. for 1 h. After completion of the reaction, ethanol was removed under reduced pressure and acidified using dilute HCl up to pH 6. Extraction was carried out using ethyl acetate. Combined organic layers were dried concentrated giving respective acid (0.15 g, 92.59%).

The acid (0.15 g, 0.461 mmol) was then dissolved in DMSO (5 mL) and 3-(amino methyl)-4,6-dimethylpyridin-2(1H)-one (0.14 g, 0.923 mmol) was added to it. The reaction mixture was stirred at room temperature for 15 min before PYBOP (0.35 g, 0.692 mmol) was added to it and stirring was continued for overnight. After completion of the reaction, reaction mass was poured into ice to obtain solid, this was filtered and washed with acetonitrile followed by HPLC purification to provide the title compound (0.050 g, 24%) as the TFA salt.: LCMS: 460.10 $(M+1)^+$; HPLC: 99.22% (@ 254 nm) ($R_t$; 5.115; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.47 (s, 1H), 8.24 (s, 1H), 7.32 (s, 1H), 7.09 (s, 1H), 5.86 (s, 1H), 4.24 (d, 2H, J=4.8 Hz), 3.47-3.48 (m, 1H), 2.96 (m, 2H), 2.18 (s, 3H), 2.15 (s, 3H), 2.10 (s, 3H), 1.33-1.63 (m, 8H), 0.78 (t, 3H, J=6.4 Hz).

Example 6

Synthesis of Compound 7: 5-chloro-3-(cyclopentyl(methyl)amino)-N-((4,6-dimethyl-2-oxo-1,2-dihydropyridin-3-yl)methyl)-2-methylbenzamide Compound 7

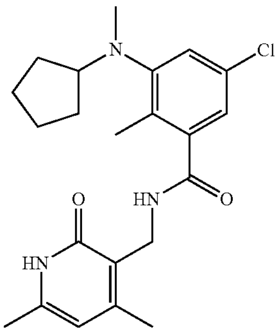

Step 1: Synthesis of 5-chloro-2-methyl-3-nitrobenzoic acid

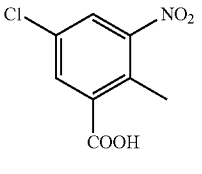

5-chloro-2-methylbenzoic acid (4 g, 23.4 mmol) was added to cooled conc. $H_2SO_4$ (27 mL) at −10° C. in small portions and stirred for 10 minutes. Nitrating mixture {prepared by mixing Conc. HNO3 (3.3 g, 52.68 mmol) with conc.$H_2SO_4$ (4.4 mL)} was added drop wise at −10° C. The resulting mixture was stirred at −10° C. for 30 minutes. On completion, the reaction mixture was poured into ice cold water, the solid was collected by filtration, washed with water and dried under vacuum to give 5-chloro-2-methyl-3-nitrobenzoic acid (4.95 g, 99%).

Step 2: Synthesis of methyl 5-chloro-2-methyl-3-nitrobenzoate

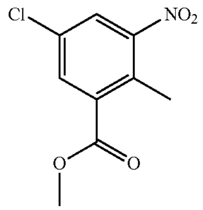

To a stirred solution of 5-chloro-2-methyl-3-nitrobenzoic acid, prepared analogously to above, (6.75 g, 31.3 mmol) in DMF (33 mL) was added sodium carbonate (13.2 g, 125 mmol) and methyl iodide (17.8 g, 125 mmol). The resulting mixture was heated at 60° C. for 4 h. On completion, water was added to the mixture and extraction was carried out using DCM. Combined organic layers were dried, concentrated under reduced pressure and purified by column chromatography over silica to give methyl 5-chloro-2-methyl-3-nitrobenzoate (6 g, 83.6%).

Step 3: Synthesis of methyl 3-amino-5-chloro-2-methyl benzoate

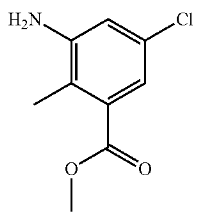

To a stirred solution of methyl 5-chloro-2-methyl-3-nitrobenzoate (6 g, 26.1 mmol) in ethanol (60 mL), was added ammonium chloride (6 g, 112 mmol) dissolved in water (60 mL) and iron powder (11.9 g, 208 mmol). The resulting mixture was heated at 80° C. for 1 h. On completion, water was added to mixture and reaction mixture was filtered through celite, and the filtrate was extracted with ethyl acetate. Combined organic layers were washed with water, dried, and concentrated under reduced pressure to give methyl 3-amino-5-chloro-2-methyl benzoate.

Step 4: Synthesis of methyl 5-chloro-3-(cyclopentylamino)-2-methylbenzoate

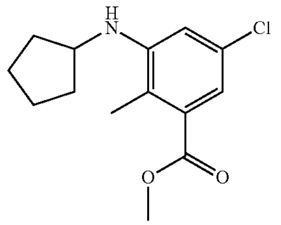 [SMILES: COC(=O)c1cc(Cl)cc(NC2CCCC2)c1C]

To a stirred solution of methyl 3-amino-5-chloro-2-methyl benzoate (1 g, 5.0 mmol) and cyclopentanone (2.1 g, 25.0 mmol) in methanol (10 mL) was added acetic acid (0.6 g, 5.0 mmol), and the mixture was stirred at room temperature for 3 h. Then sodium cyanoborohydride (0.78 g, 12.5 mmol) was added and the reaction stirred overnight. On completion, solvent was removed under reduced pressure and crude material was purified by column silica chromatography to afford methyl 5-chloro-3-(cyclopentylamino)-2-methylbenzoate (1.2 g, 89%).

Step 5: Synthesis of methyl 5-chloro-3-(cyclopentyl(methyl)amino)-2-methylbenzoate

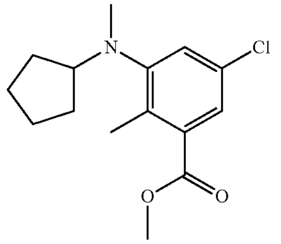 [SMILES: COC(=O)c1cc(Cl)cc(N(C)C2CCCC2)c1C]

To a stirred solution of methyl 5-chloro-3-(cyclopentylamino)-2-methylbenzoate (0.5 g, 1.86 mmol) in acetonitrile (5 mL) was added cesium carbonate (1.22 g, 3.7 mmol) and methyl iodide (1.32 g, 9.33 mmol). The resulting mixture was heated at 80° C. for 12 h. On completion, the mixture was cooled to room temperature and filtered, the residue was washed with ethyl acetate and the filtrate was concentrated and then purified by column chromatography to afford methyl 5-chloro-3-(cyclopentyl(methyl)amino)-2-methylbenzoate (0.5 g, 95%).

Step 6: Synthesis of 5-chloro-3-(cyclopentyl(methyl)amino)-N-((4,6-dimethyl-2-oxo-1,2-dihydropyridin-3-yl)methyl)-2-methylbenzamide Aqueous NaOH (0.106 g, 2.66 mmol) was added to a solution of methyl 5-chloro-3-(cyclopentyl(methyl)amino)-2-methylbenzoate (0.5 g, 1.77 mmol) in MeOH (5 mL) and stirred at 60° C. for 1 h. After completion of the reaction, methanol was removed under reduced pressure and acidified using dilute HCl up to pH 6 and pH 4 was adjusted using citric acid. Extraction was carried out using ethyl acetate. Combined organic layers were dried concentrated giving respective acid (0.4 g, 84%).

The acid (0.1 g, 0.37 mmol) was then dissolved in DMSO (0.5 mL) and 3-(amino methyl)-4,6-dimethylpyridin-2(1H)-one (0.114 g, 0.74 mmol) was added to it. The reaction mixture was stirred at room temperature for 15 min before PYBOP (0.29 g, 0.56 mmol) was added to it and stirring was continued for overnight. After completion of the reaction, mixture was poured into ice to obtain a solid, this was filtered and washed with acetonitrile followed column purification to provide 5-chloro-3-(cyclopentyl(methyl)amino)-N-((4,6-dimethyl-2-oxo-1,2-dihydropyridin-3-yl)methyl)-2-methylbenzamide (100 mg, 66%). LCMS: 402.15 $(M+1)^+$; HPLC: 96.46% (@ 254 nm) ($R_t$; 5.289; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min B); $^1H$ NMR (DMSO-$d_6$, 400 MHz) δ 11.45 (s, 1H), 8.19 (t, 1H, J=4.8 Hz), 7.13 (d, 1H, J=2 Hz), 6.91 (d, 1H, J=2 Hz), 5.85 (s, 1H), 4.23 (d, 2H, J=5.2 Hz), 3.41-3.45 (m, 1H), 2.50 (3H merged in solvent peak), 2.18 (s, 3H), 2.15 (s, 3H), 2.10 (s, 3H), 1.38-1.67 (m, 8H).

Example 7

Synthesis of Compound 8: 5-chloro-N-((4,6-dimethyl-2-oxo-1,2-dihydropyridin-3-yl)methyl)-2-methyl-3-(methyl(piperidin-4-yl)amino)benzamide Compound 8

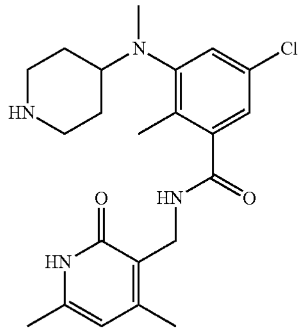

Step 1: 5-chloro-2-methyl-3-nitrobenzoic acid

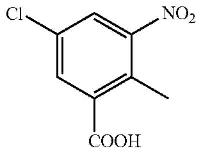

5-Chloro-2-methylbenzoic acid (4 g, 23.39 mmol) was added to cooled conc. $H_2SO_4$ (27 mL) at −10° C. lot wise. After 10 minutes nitrating mixture {prepared as mixing Conc. HNO3 (3.3 g, 52.68 mmol) with conc.$H_2SO_4$ (4.4 mL)} was added drop wise at −10° C. Resulting reaction mass was stirred at −10° C. for 30 minutes. On completion, reaction mixture was poured on ice cold water, solid precipitated was filtered, washed with water and dried under vacuum giving desired compound (4.95 g, 99%).

Step 2: methyl 5-chloro-2-methyl-3-nitrobenzoate

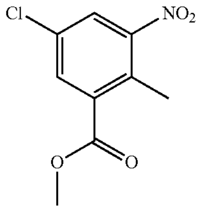

To stirred solution of 5-chloro-2-methyl-3-nitrobenzoic acid (6.75 g, 31.25 mmol) in DMF (33 mL), sodium carbonate (13.23 g, 125.18 mmol) and methyl iodide (17.77 g, 125.2 mmol) were added. Resulting reaction mass was heated at 60° C. for 4 h. On completion, water was added to the reaction mass and extraction was carried out using DCM. Combined organic layers were dried, concentrated under reduced pressure and purified by column chromatography over silica (60-120 mesh size) giving desired compound (6 g, 84%).

Step 3: methyl 3-amino-5-chloro-2-methyl benzoate

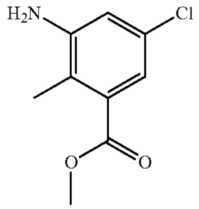

To stirred solution of methyl 5-chloro-2-methyl-3-nitrobenzoate (6 g, 26.13 mmol) in ethanol (60 mL), ammonium chloride (6 g, 112.1 mmol) dissolved in water (60 mL) and iron powder (11.88 g, 208.4 mmol) were added under stirring. Resulting reaction mass was heated at 80° C. for 1 h. On completion, water was added to reaction mass and reaction mixture was filtered through celite, filtrate was extracted with ethyl acetate. Combined organic layers were washed with water, dried, concentrated under reduced pressure giving the desired compound.

Step 4: tert-butyl 4-((5-chloro-3-(methoxycarbonyl)-2-methylphenyl)amino)piperidine-1-carboxylate

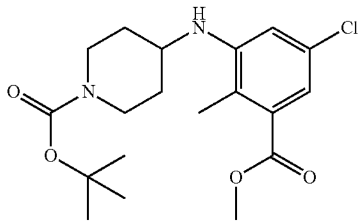 [SMILES: COC(=O)c1cc(Cl)cc(NC2CCN(C(=O)OC(C)(C)C)CC2)c1C]

To a stirred solution of methyl 3-amino-5-chloro-2-methyl benzoate (6 g, 30.15 mmol) and tert-butyl 4-oxopiperidine-1-carboxylate (29 g, 150 mmol) in methanol (10 mL), acetic acid (1.8 g, 30.1 mmol) was added and reaction stirred at room temperature for 3 h. Then sodium cyanoborohydride (4.7 g, 75.3 mmol) was added and reaction stirred overnight. On completion, solvent was removed under reduced pressure and crude material was purified by column chromatography to afford the desired compound (4 g, 30%).

Step 5: tert-butyl 4-((5-chloro-3-(methoxycarbonyl)-2-methylphenyl)(methyl)amino)piperidine-1-carboxylate

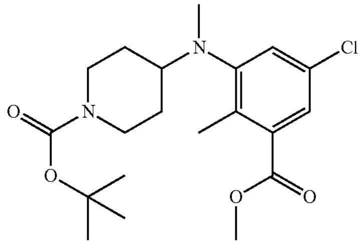 [SMILES: COC(=O)c1cc(Cl)cc(N(C)C2CCN(C(=O)OC(C)(C)C)CC2)c1C]

To a stirred solution of tert-butyl 4-((5-chloro-3-(methoxycarbonyl)-2-methylphenyl)amino)piperidine-1-carboxylate (4 g, 9.09 mmol) in acetonitrile (50 mL), cesium carbonate (5.9 g, 18.09 mmol) and methyl iodide (6.95 g, 48.94 mmol) were added; resulting reaction mass was heated at 80° C. for 12 h. On completion, reaction mass was cooled to room temperature and filtered, residue was washed with ethyl acetate and filtrate was concentrated and then purified by column chromatography to afford the desired compound (2.2 g, 53%).

Step 6: tert-butyl 4-((5-chloro-3-(((4,6-dimethyl-2-oxo-1,2-dihydropyridin-3-yl)methyl)carbamoyl)-2-methylphenyl)(methyl)amino)piperidine-1-carboxylate

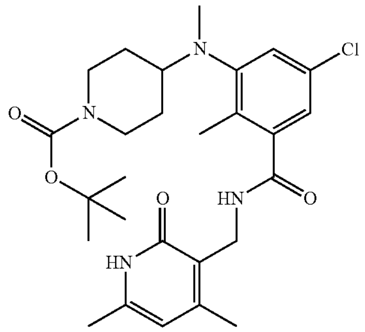 [SMILES: Cc1cc(C)c(CNC(=O)c2cc(Cl)cc(N(C)C3CCN(C(=O)OC(C)(C)C)CC3)c2C)c(=O)[nH]1]

Aqueous NaOH (0.75 g, 1.86 mmol) was added to a solution of tert-butyl 4-((5-chloro-3-(methoxycarbonyl)-2-methylphenyl)(methyl)amino)piperidine-1-carboxylate (0.5 g, 1.26 mmol) in MeOH (5 mL) and stirred at 60° C. for 1 h. After completion of the reaction, ethanol was removed under reduced pressure and acidified using dilute HCl up to pH 6 and pH 4 was adjusted using citric acid. Extraction was carried out using ethyl acetate. Combined organic layers were dried concentrated giving respective acid (0.4 g, 84%).

The acid (0.4 g, 1.04 mmol) was then dissolved in DMSO (1 mL) and 3-(amino methyl)-4,6-dimethylpyridin-2(1H)-one (0.316 g, 2.09 mmol) was added to it. The reaction mixture was stirred at room temperature for 15 min before PYBOP (0.816 g, 1.56 mmol) was added to it and stirring was continued for overnight. After completion of the reaction, reaction mass was poured into ice to obtain solid, this was filtered and washed with acetonitrile followed column purification to provide the desired compound (0.225 g, 41%).

Step 7: 5-chloro-N-((4,6-dimethyl-2-oxo-1,2-dihydropyridin-3-yl)methyl)-2-methyl-3-(methyl(piperidin-4-yl)amino)benzamide

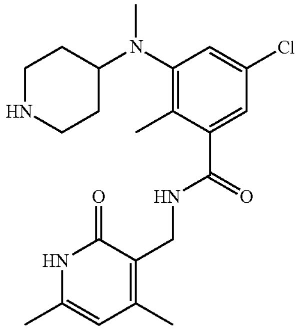 [SMILES: Cc1cc(C)c(CNC(=O)c2cc(Cl)cc(N(C)C3CCNCC3)c2C)c(=O)[nH]1]

A stirred solution of tert-butyl 4-((5-chloro-3-(((4,6-dimethyl-2-oxo-1,2-dihydropyridin-3-yl)methyl)carbamoyl)-2-methylphenyl)(methyl)amino)piperidine-1-carboxylate (0.2 g, 0.632 mmol) in DCM (5 mL) was cooled to 0° C. and TFA (0.15 mL) was added to it. Reaction mass was stirred at room temperature for 1 h. On completion, reaction was concentrated to dryness. Residue was purified by solvent washings to afford the desired compound (0.14 g, 53%) as its TFA salt. LCMS: 417.25 $(M+1)^+$; HPLC: 96.16% (@ 254 nm) ($R_t$; 4.677; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-$d_6$, 400 MHz) δ 11.47 (s, 1H), 8.49 (bs, 1H), 8.20 (t, 1H), 8.18 (bs, 1H), 7.19 (s, 1H), 6.96 (s, 1H), 5.86 (s, 1H), 4.25 (d, 2H, J=4.4 Hz), 3.25 (d, 2H, J=12 Hz), 3.08 (m, 1H), 2.88 (bs, 2H), 2.56 (s, 3H), 2.18 (s, 3H), 2.17 (s, 3H), 2.10 (s, 3H), 1.76 (bs, 4H).

Example 8

Synthesis of Compound 10: 5-bromo-N-((4,6-dimethyl-2-oxo-1,2-dihydropyridin-3-yl)methyl)-2-methyl-3-(methyl(tetrahydro-2H-pyran-4-yl)amino)benzamide Compound 10

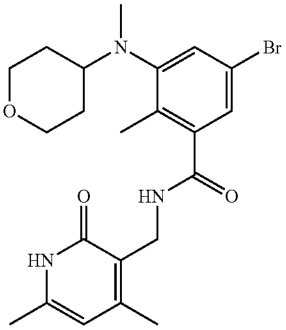

Step 1: Synthesis of 5-bromo-2-methyl-3-nitrobenzoic acid

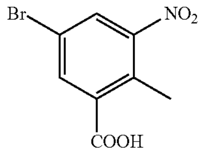

To stirred solution of 2-methyl-3-nitrobenzoic acid (50 g, 276 mmol) in conc. $H_2SO_4$ (200 mL), 1,3-dibromo-5,5-dimethyl-2,4-imidazolidinedione (43.4 g, 152 mmol) was added portion wise at room temperature, and stirring was continued at room temperature for 5 h. On completion, the mixture was poured into ice cold water, the resulting solid was filtered, washed with water and dried under vacuum to give 5-bromo-2-methyl-3-nitrobenzoic acid (71.7 g, 99.9%).

Step 2: Synthesis of methyl 5-bromo-2-methyl-3-nitrobenzene

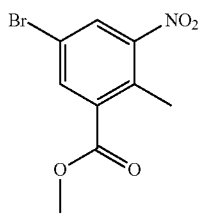

To stirred solution of 5-bromo-2-methyl-3-nitrobenzoic acid, prepared analogously to above, (287 g, 1103 mmol) in DMF (150 mL), sodium carbonate (468 g, 4415 mmol) and methyl iodide (626.6 g, 4415 mmol) were added. Resulting mixture was heated at 60° C. for 8 h. On completion, solid was remove by filtration, and the residue washed with diethyl ether (5 times). The combined organic layers were dried, concentrated under reduced pressure to give methyl 5-bromo-2-methyl-3-nitrobenzene (302 g, 99%).

Step 3: Synthesis of methyl 3-amino-5-bromo-2-methylbenzoate

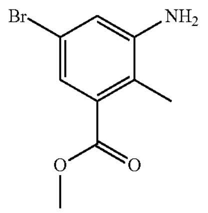

To a stirred solution of 5-bromo-2-methyl-3-nitrobenzene (150 g, 544 mmol) in ethanol (750 mL) was added a solution of ammonium chloride (150 g, 2777 mmol) in water (750 mL) and iron powder (93.3 g, 1636 mmol). The resulting mixture was heated at 80° C. for 7 h. On completion, mixture was filtered through celite; the celite was washed with water and ethyl acetate and the filtrate was extracted with ethyl acetate. Combined organic layers were dried, concentrated under reduced pressure to give methyl 3-amino-5-bromo-2-methylbenzoate.

Step 4: Synthesis of methyl 5-bromo-2-methyl-3-((tetrahydro-2H-pyran-4-yl)amino)benzoate

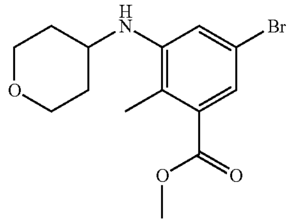 [SMILES: COC(=O)c1cc(Br)cc(NC2CCOCC2)c1C]

To a stirred solution of methyl 3-amino-5-bromo-2-methylbenzoate (2 g, 8.23 mmol) and dihydro-2H-pyran-4(3)-one (1.06 g, 10.6 mmol) in methanol (20 mL), acetic acid (0.5 g, 8.23 mmol) was added and the reaction stirred at room temperature for 3 h. Then sodium cyanoborohydride (0.622 g, 9.87 mmol) was added at 0° C. and reaction stirred overnight at room temperature. On completion, the solvent was removed under reduced pressure and the crude material was purified by column chromatography to afford methyl 5-bromo-2-methyl-3-((tetrahydro-2H-pyran-4-yl)amino) benzoate (1.6 g, 61%).

Step 5: Synthesis of methyl 5-bromo-2-methyl-3-(methyl(tetrahydro-2H-pyran-4-yl)amino)benzoate

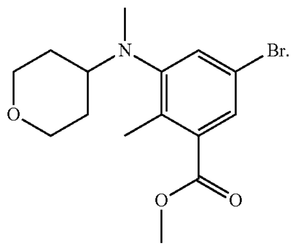 [SMILES: COC(=O)c1cc(Br)cc(N(C)C2CCOCC2)c1C]

To a stirred solution of methyl 5-bromo-2-methyl-3-((tetrahydro-2H-pyran-4-yl)amino)benzoate (0.4 g, 1.26 mmol) in acetonitrile (15 mL), cesium carbonate (0.79 g, 2.44 mmol) and methyl iodide (0.86 g, 6.11 mmol) were added; resulting mixture was heated at 80° C. for 7 h. On completion, the mixture was cooled to room temperature and filtered, the residue was washed with ethyl acetate and the filtrate was concentrated and then purified by column chromatography to afford Synthesis of methyl 5-bromo-2-methyl-3-(methyl(tetrahydro-2H-pyran-4-yl)amino)benzoate (0.33 g, 80%).

Step 6: Synthesis of 5-bromo-N-((4,6-dimethyl-2-oxo-1,2-dihydropyridin-3-yl)methyl)-2-methyl-3-(methyl(tetrahydro-2H-pyran-4-yl)amino)benzamide

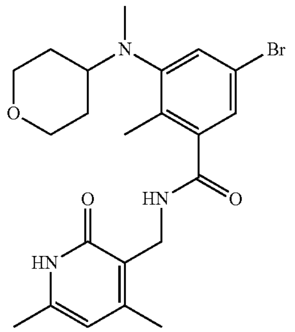 [SMILES: Cc1cc(C)c(CNC(=O)c2cc(Br)cc(N(C)C3CCOCC3)c2C)c(=O)[nH]1]

Aqueous NaOH (0.19 g, 4.89 mmol) was added to a solution of compound 6 (0.8 g, 2.4 mmol) in MeOH (20 mL) and stirred at 60° C. for 1 h. After completion of the reaction, ethanol was removed under reduced pressure and acidified using dilute HCl up to pH 6 and pH 4 was adjusted using citric acid. Extraction was carried out using ethyl acetate. Combined organic layers were dried concentrated giving respective acid (0.70 g, 92%).

The acid (0.7 g, 2.24 mmol) was then dissolved in DMSO (3 mL) and 3-(amino methyl)-4,6-dimethylpyridin-2(1H)-one (0.74 g, 4.89 mmol) was added to it. The reaction mixture was stirred at room temperature for 15 min before PYBOP (1.9 g, 3.6 mmol) was added to it and stirring was continued for overnight. After completion, mixture was poured into ice to obtain a solid. The solid was filtered and washed with acetonitrile followed by purification with column chromatography to afford 5-bromo-N-((4,6-dimethyl-2-oxo-1,2-dihydropyridin-3-yl)methyl)-2-methyl-3-(methyl(tetrahydro-2H-pyran-4-yl)amino)benzamide (0.53 g, 54%). LCMS: 462.23 $(M+1)^+$; HPLC: 98.57% (@ 254 nm) ($R_t$; 5.276; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.46 (s, 1H), 8.20 (t, 1H, J=4.8 Hz), 7.24 (d, 1H, J=2 Hz), 7.04 (d, 1H, J=2 Hz), 5.85 (s, 1H), 4.24 (d, 2H, J=4.8 Hz), 3.84 (d, 2H, J=10.8 Hz), 3.22-3.28 (m, 2H), 2.96 (m, 1H), 2.56 (s, 3H), 2.18 (s, 3H), 2.13 (s, 3H), 2.10 (s, 3H), 1.52-1.61 (m, 4H).

Example 9

Synthesis of Compound 13: 2,5-dichloro-3-(cyclopentyl(methyl)amino)-N-((4,6-dimethyl-2-oxo-1,2-dihydropyridin-3-yl)methyl)benzamide Compound 13

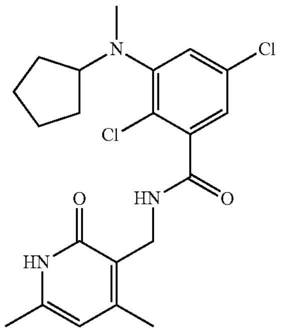

Step 1: Synthesis of 2,5-dichloro-3-nitrobenzoic acid

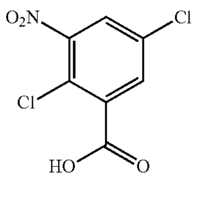 [SMILES: O=C(O)c1cc(Cl)cc([N+](=O)[O-])c1Cl]

2,5-dichlorobenzoic acid (5 g, 26.2 mmol) was added to cooled conc. $H_2SO_4$ (50 mL) at −10° C. in small portions. After 10 minutes nitrating mixture {prepared by mixing Conc. $HNO_3$ (2.5 mL) with conc. $H_2SO_4$ (10 mL)} was added drop wise at −10° C. The resulting reaction mixture was stirred at −10° C. for 2 h. On completion, the reaction mixture was poured into ice cold water and a solid precipitated. The solid was collected by filtration, washed with water and dried under vacuum to give 2,5-dichloro-3-nitrobenzoic acid (3.4 g, 65%).

Step 2: Synthesis of methyl 2,5-dichloro-3-nitrobenzoate

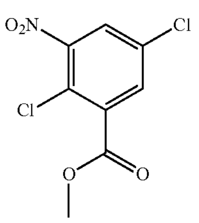

To stirred solution of 2,5-dichloro-3-nitrobenzoic acid (3.2 g, 13.67 mmol) in DMF (30 mL) was added sodium carbonate (4.3 g, 40.56 mmol) and methyl iodide (9.7 g, 68.30 mmol). The reaction mixture was heated at 60° C. for 18 h. On completion, water was added to the reaction mixture, and the product was extracted using DCM. The combined organic layers were dried and concentrated under reduced pressure to give methyl 2,5-dichloro-3-nitrobenzoate (3 g, 90%).

Step 3: Synthesis of methyl 3-amino-2,5-dichlorobenzoate

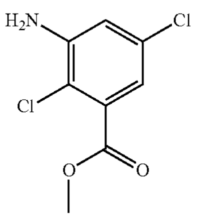

To stirred solution of methyl 2,5-dichloro-3-nitrobenzoate (3.3 g, 13.1 mmol) in ethanol (20 mL) was added ammonium chloride (3.5 g, 64.81 mmol) dissolved in water (20 mL) and iron powder (7 g, 82.35 mmol). The reaction mixture was heated at 80° C. for 3 h. On completion, water was added to the reaction mixture and the solids removed by filtration through celite. The filtrate was extracted with ethyl acetate. The combined organic layers were washed with water, dried, and concentrated under reduced pressure to give methyl 3-amino-2,5-dichlorobenzoate (2.5 g, 66%).

Step 4: Synthesis of methyl 2,5-dichloro-3-(cyclopentylamino)benzoate

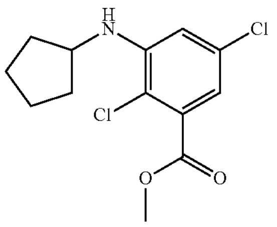 [SMILES: COC(=O)c1cc(Cl)cc(NC2CCCC2)c1Cl]

To a stirred solution of methyl 3-amino-2,5-dichlorobenzoate (2.5 g, 11.5 mmol) and cyclopentanone (4.8 g, 57.1 mmol) in methanol (5 mL) was added acetic acid (0.6 g, 11.3 mmol) and stirring was continued at room temperature for 3 h. Then sodium cyanoborohydride (1.4 g, 22.2 mmol) was added and the reaction stirred overnight. On completion, the solvent was removed under reduced pressure and the product was purified by column chromatography to afford methyl 2,5-dichloro-3-(cyclopentylamino)benzoate (0.275 g, 8%).

Step 5: Synthesis of methyl 2,5-dichloro-3-(cyclopentyl(methyl)amino)benzoate

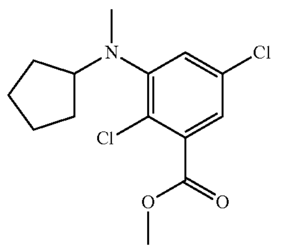 [SMILES: COC(=O)c1cc(Cl)cc(N(C)C2CCCC2)c1Cl]

To a stirred solution of methyl 2,5-dichloro-3-(cyclopentylamino)benzoate (0.275 g, 0.958 mmol) in acetonitrile (5 mL) was added cesium carbonate (0.622 g, 1.9 mmol) and methyl iodide (0.689 g, 4.78 mmol). The reaction mixture was heated at 80° C. for 18 h. On completion, the reaction was cooled to room temperature and filtered. The residue was washed with ethyl acetate and the filtrate was concentrated to afford methyl 2,5-dichloro-3-(cyclopentyl(methyl)amino) benzoate (0.27 g, 93%).

Step 6: Synthesis of 2,5-dichloro-3-(cyclopentyl(methyl)amino)-N-((4,6-dimethyl-2-oxo-1,2-dihydropyridin-3-yl)methyl)benzamide

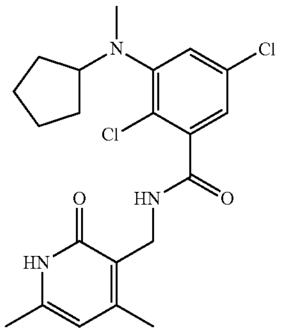 [SMILES: Cc1cc(C)c(CNC(=O)c2cc(Cl)cc(N(C)C3CCCC3)c2Cl)c(=O)[nH]1]

Aqueous NaOH (0.50 g, 1.24 mmol) was added to a solution of methyl 2,5-dichloro-3-(cyclopentyl(methyl)amino) benzoate (0.25 g, 0.83 mmol) in MeOH (5 mL) and stirred at 60° C. for 1 h. After completion of the reaction, methanol was removed under reduced pressure and acidified using dilute HCl up to pH 6 and to pH 4 using citric acid. The product was extracted using ethyl acetate. The combined organic layers were dried and concentrated to give the desired acid (021 g, 88%).

The acid (0.21 g, 0.755 mmol) was then dissolved in DMSO (3 mL) and 3-(amino methyl)-4,6-dimethylpyridin-2(1H)-one (0.3 g, 1.97 mmol) was added to it. The reaction mixture was stirred at room temperature for 15 min before PYBOP (0.757 g, 1.45 mmol) was added to it and stirring was continued for overnight. After completion of the reaction, reaction mixture was poured into ice to obtain a solid. The solid was filtered and washed with acetonitrile. The compound was further purified by prep. HPLC to afford 2,5-dichloro-3-(cyclopentyl(methyl)amino)-N-((4,6-dimethyl-2-oxo-1,2-dihydropyridin-3-yl)methyl)benzamide (0.1 g, 36%) as TFA salt. LCMS: 422.10 $(M+1)^+$; HPLC: 97.58% (@ 254 nm) ($R_t$; 6.973; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.46 (s, 1H), 8.35 (t, 1H), 7.23 (s, 1H), 6.98 (s, 1H), 5.85 (s, 1H), 4.24 (d, 2H, J=4.4 Hz), 3.66 (m, 1H), 2.59 (s, 3H), 2.18 (s, 3H), 2.10 (s, 3H), 1.70 (bs, 2H), 1.61 (bs, 2H), 1.48 (bs, 4H).

Example 10

Synthesis of Compound 14: 5-chloro-N-((4,6-dimethyl-2-oxo-1,2-dihydropyridin-3-yl)methyl)-2-methyl-3-(methyl(tetrahydro-2H-pyran-4-yl)amino) benzamide Compound 14

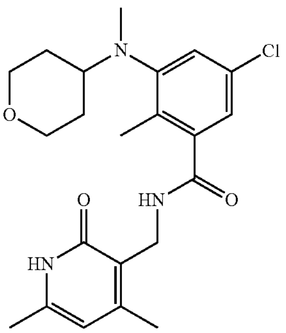

Step 1: 5-chloro-2-methyl-3-nitrobenzoic acid

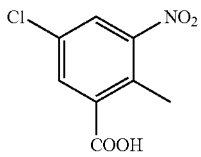

2-Methyl-3-nitrobenzoic acid (4 g, 23.39 mmol) was added to cooled conc. $H_2SO_4$ (27 mL) at −10° C. lot wise. After 10 minutes nitrating mixture {prepared as mixing Conc. HNO3 (3.3 g, 52.68 mmol) with conc.$H_2SO_4$ (4.4 mL)} was added drop wise at −10° C. Resulting reaction mass was stirred at −10° C. for 30 minutes. On completion, reaction mixture was poured on ice cold water, solid precipitated was filtered, washed with water and dried under vacuum giving desired compound (4.95 g, 99%).

Step 2: methyl 5-chloro-2-methyl-3-nitrobenzoate

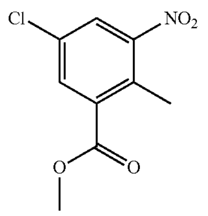

To a stirred solution of 5-chloro-2-methyl-3-nitrobenzoic acid (6.75 g, 31.25 mmol) in DMF (33 mL), sodium carbonate (13.23 g, 125.18 mmol) and methyl iodide (17.77 g, 125.2 mmol) were added. Resulting reaction mass was heated at 60° C. for 4 h. On completion, water was added to the reaction mass and extraction was carried out using DCM. Combined organic layers were dried, concentrated under reduced pressure and purified by column chromatography over silica (60-120 mesh size) giving desired compound (6 g, 84%).

Step 3: methyl 3-amino-5-chloro-2-methyl benzoate

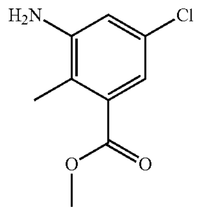

To stirred solution of methyl 5-chloro-2-methyl-3-nitrobenzoate (6 g, 26.13 mmol) in ethanol (60 mL), ammonium chloride (6 g, 112.1 mmol) dissolved in water (60 mL) and iron powder (11.88 g, 208.4 mmol) were added under stirring. Resulting reaction mass was heated at 80° C. for 1 h. On completion, water was added to reaction mass and reaction mixture was filtered through celite, filtrate was extracted with ethyl acetate. Combined organic layers were washed with water, dried, concentrated under reduced pressure giving desired compound which was used as is.

Step 4: methyl 5-chloro-2-methyl-3-((tetrahydro-2H-pyran-4-yl)amino)benzoate

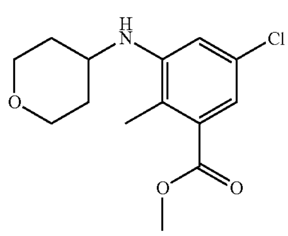 [SMILES: COC(=O)c1cc(Cl)cc(NC2CCOCC2)c1C]

To a stirred solution of methyl 3-amino-5-chloro-2-methyl benzoate (1 g, 5.025 mmol) and dihydro-2H-pyran-4(3H)-one (753 mg, 7.537 mmol) in methanol (10 mL), acetic acid (301 mg, 5.025 mmol) was added and reaction stirred at room temperature for 3 h. Then sodium cyanoborohydride (373 mg, 6.03 mmol) was added and reaction stirred overnight. On completion, solvent was removed under reduced pressure and crude material was purified by column chromatography to afford the desired compound (700 mg, 49%).

Step 5: methyl 5-chloro-2-methyl-3-(methyl(tetrahydro-2H-pyran-4-yl)amino)benzoate

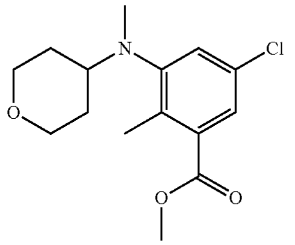 [SMILES: COC(=O)c1cc(Cl)cc(N(C)C2CCOCC2)c1C]

To a stirred solution of methyl 5-chloro-2-methyl-3-((tetrahydro-2H-pyran-4-yl)amino)benzoate (700 mg, 2.473 mmol) in acetonitrile (10 mL), cesium carbonate (1.61 g, 4.946 mmol) and methyl iodide (1.82 g, 0.8 ml, 12.36 mmol) were added; resulting reaction mass was heated at 80° C. for 13 h. On completion, reaction mass was cooled to room temperature and filtered, residue was washed with ethyl acetate and filtrate was concentrated and then purified by column chromatography to afford desired compound (480 mg, 65%).

Step 6: 5-chloro-N-((4,6-dimethyl-2-oxo-1,2-dihydropyridin-3-yl)methyl)-2-methyl-3-(methyl(tetrahydro-2H-pyran-4-yl)amino)benzamide

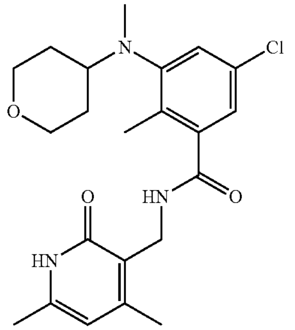 [SMILES: Cc1cc(C)c(CNC(=O)c2cc(Cl)cc(N(C)C3CCOCC3)c2C)c(=O)[nH]1]

Aqueous NaOH (96 mg, 2.424 mmol) was added to a solution of methyl 5-chloro-2-methyl-3-(methyl(tetrahydro-2H-pyran-4-yl)amino)benzoate (0.48 g, 1.616 mmol) in EtOH (2 mL) and stirred at 60° C. for 1 h. After completion of the reaction, ethanol was removed under reduced pressure and acidified using dilute HCl up to pH 6 and pH 4 was adjusted using citric acid. Extraction was carried out using ethyl acetate. Combined organic layers were dried concentrated giving respective acid (0.4 g, 87%).

The acid (0.4 g, 1.41 mmol) was then dissolved in DMSO (1 mL) and 3-(amino methyl)-4,6-dimethylpyridin-2(1H)-one (0.429 g, 2.82 mmol) was added to it. The reaction mixture was stirred at room temperature for 15 min before PYBOP (1.10 g, 2.12 mmol) was added to it and stirring was continued for overnight. After completion of the reaction, reaction mass was poured into ice to obtain solid, this was filtered and washed with acetonitrile followed column purification to provide the title compound (0.17 g, 29%): LCMS: 418.25 $(M+1)^+$; HPLC: 97.72% (@ 254 nm) ($R_t$; 5.022; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-$d_6$, 400 MHz) δ 11.48 (s, 1H), 8.21 (t, 1H, J=4.4 Hz), 7.13 (s, 1H), 6.92 (s, 1H), 5.85 (s, 1H), 4.24 (d, 2H, J=4.4 Hz), 3.84 (d, 2H, J=10.8 Hz), 3.25 (t, 2H, J=11.2 Hz), 2.96 (m, 1H), 2.56 (s, 3H), 2.18 (s, 3H), 2.15 (s, 3H), 2.10 (s, 3H), 1.65-1.52 (m, 4H).

Example 11

Synthesis of Compound 15: tert-butyl (4-((5-bromo-3-(((4,6-dimethyl-2-oxo-1,2-dihydropyridin-3-yl) methyl)carbamoyl)-2-methylphenyl)(methyl)amino) cyclohexyl)carbamate Compound 15

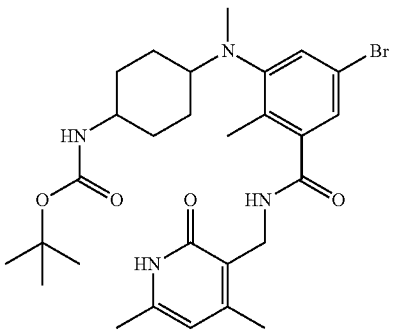

Step 1: Synthesis of methyl 5-bromo-3-((4-((tert-butoxycarbonyl)amino)cyclohexyl)amino)-2-methylbenzoate

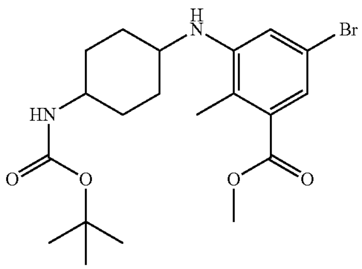 [SMILES: COC(=O)c1cc(Br)cc(NC2CCC(NC(=O)OC(C)(C)C)CC2)c1C]

To a stirred solution of methyl 3-amino-5-bromo-2-methylbenzoate (5 g, 20.6 mmol) and tert-butyl (4-oxocyclohexyl) carbamate (5.6 g, 26.7 mmol) in methanol (50 mL) was added acetic acid (1.2 g, 20.6 mmol) and the mixture was stirred at room temperature for 3 h. Then sodium cyanoborohydride (1.6 g, 26.7 mmol) was added and the reaction stirred overnight. On completion, the solvent was removed under reduced pressure and the product purified by column chromatography to afford compound methyl 5-bromo-3-((4-((tert-butoxycarbonyl)amino)cyclohexyl)amino)-2-methylbenzoate (3 g, 33.3%).

Step 2: Synthesis of methyl 5-bromo-3-((4-((tert-butoxycarbonyl)amino)cyclohexyl)(methyl)amino)-2-methylbenzoate

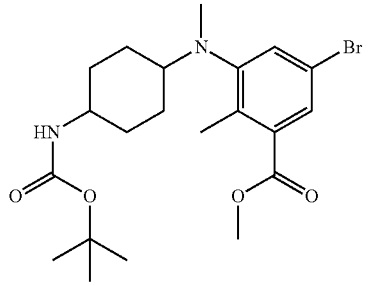 [SMILES: COC(=O)c1cc(Br)cc(N(C)C2CCC(NC(=O)OC(C)(C)C)CC2)c1C]

To a stirred solution of methyl 5-bromo-3-((4-((tert-butoxycarbonyl)amino)cyclohexyl)amino)-2-methylbenzoate (1.5 g, 4.6 mmol) in acetonitrile (15 mL) was added cesium carbonate (2.63 g, 8.1 mmol) and methyl iodide (2.86 g, 20.32 mmol). The mixture was heated at 80° C. for 7 h. On completion, the reaction was cooled to room temperature, filtered, and the residue was washed with ethyl acetate. The filtrate was concentrated to afford methyl 5-bromo-3-((4-((tert-butoxycarbonyl)amino)cyclohexyl)(methyl)amino)-2-methylbenzoate (1.5 g).

Step 3: Synthesis of tert-butyl (4-((5-bromo-3-((4,6-dimethyl-2-oxo-1,2-dihydropyridin-3-yl)methyl) carbamoyl)-2-methylphenyl)(methyl)amino)cyclohexyl)carbamate

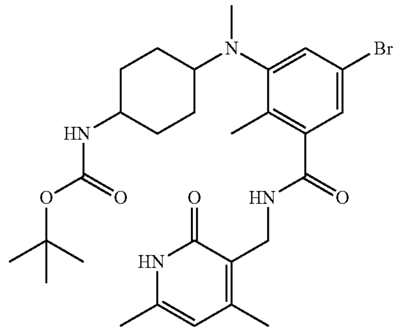 [SMILES: Cc1cc(C)c(CNC(=O)c2cc(Br)cc(N(C)C3CCC(NC(=O)OC(C)(C)C)CC3)c2C)c(=O)[nH]1]

Aqueous NaOH (0.26 g, 6.62 mmol) was added to a solution of methyl 5-bromo-3-((4-((tert-butoxycarbonyl)amino) cyclohexyl)(methyl)amino)-2-methylbenzoate (1.5 g, 3.3 mmol) in MeOH (20 mL) and stirred at 60° C. for 1 h. After completion of the reaction, methanol was removed under reduced pressure and the mixture was acidified using dilute HCl up to pH 6 and to pH 4 using citric acid. The product was extracted with ethyl acetate. Combined organic layers were dried and concentrated to give the desired acid (1.33 g, 92%).

The acid (1.3 g, 2.96 mmol) was then dissolved in DMSO (10 mL) and 3-(amino methyl)-4,6-dimethylpyridin-2(1H)-one (0.34 g, 2.2 mmol) was added to it. The reaction mixture was stirred at room temperature for 15 min before PYBOP (0.88 g, 1.7 mmol) was added to it and stirring was continued for overnight. After completion of the reaction, the mixture was poured onto ice to obtain solid. The solid was filtered and washed with acetonitrile followed by purification with column chromatography to afford tert-butyl (4-((5-bromo-3-(((4,6-dimethyl-2-oxo-1,2-dihydropyridin-3-yl)methyl)carbamoyl)-2-methylphenyl)(methyl)amino)cyclohexyl) carbamate. (0.5 g, 26%). LCMS: 575.80 $(M+1)^+$; HPLC: 99.99% (@ 254 nm) ($R_t$; 6.094, 7.065 [mixture of diastereomers]; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-$d_6$, 400 MHz) δ 11.45 (s, 1H), 8.20 (d, 1H, J=3.6 Hz), 7.21 (s, 1H), 7.18 (s, 1H), 7.01 (s, 1H), 6.66 (d, 1H, J=7.2 Hz), 5.85 (s, 1H), 4.23 (d, 2H, J=3.2 Hz), 3.44 (bs, 1H), 3.15 (bs, 1H), 2.55-2.66 (m, 3H), 2.18 (s, 3H), 2.10 (s, 6H), 1.76-1.79 (m, 2H), 1.51-1.63 (m, 3H), 1.36-1.38 (m, 11H), 1.07-1.16 (m, 1H).

Example 12

Synthesis of Compound 16: 3-(cyclopentyl(methyl)amino)-N-((4,6-dimethyl-2-oxo-1,2-dihydropyridin-3-yl)methyl)-2-methyl-5-(1-methyl-1,2,3,6-tetrahydropyridin-4-yl)benzamide Compound 16

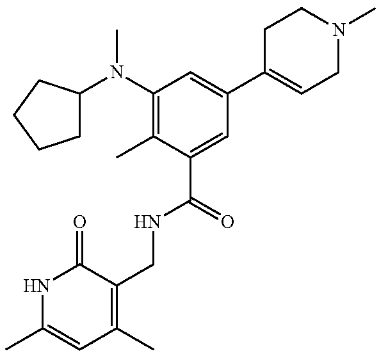

Step 1: 5-bromo-2-methyl-3-nitrobenzoic acid

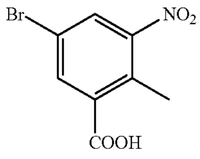

To stirred solution of 2-methyl-3-nitrobenzoic acid (50 g, 276.2 mmol) in conc. $H_2SO_4$ (200 mL), 1,3-dibromo-5,5-dimethyl-2,4-imidazolidinedione (43.4 g, 151.8 mmol) was added portion wise at room temperature and reaction mass was stirred at room temperature for 5 h. On completion, reaction mass was poured on ice cold water, solid precipitated was filtered, resulting residue was washed with water and dried under vacuum giving the desired compound (71.7 g, 100%)

Step 2: methyl 5-bromo-2-methyl-3-nitrobenzene

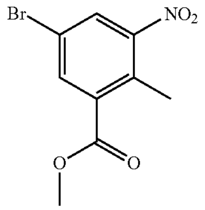

To stirred solution of 5-bromo-2-methyl-3-nitrobenzoic acid (287 g, 1103 mmol) in DMF (150 mL), sodium carbonate (468 g, 4415 mmol) and methyl iodide (626.63 g, 4415 mmol) were added. Resulting reaction mass was heated at 60° C. for 8 h. On completion, solid precipitated was filtered, residue washed with diethyl ether (5 times). Combined organic layers were dried, concentrated under reduced pressure giving the desired crude compound (302 g, 99%) which was used without further purification.

Step 3: methyl 3-amino-5-bromo-2-methylbenzoate

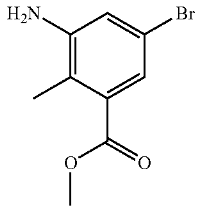

To a stirred solution of methyl 5-bromo-2-methyl-3-nitrobenzene (150 g, 544 mmol) in ethanol (750 mL), ammonium chloride (150 g, 2777 mmol) dissolved in water (750 mL) and iron powder (93.3 g, 1636 mmol) were added under stirring. Resulting reaction mass was heated at 80° C. for 7 h. On completion, reaction mass was filtered through celite giving washing of water and ethyl acetate, filtrate was extracted with ethyl acetate. Combined organic layers were dried, concentrated under reduced pressure giving the desired compound which was used further as is.

Step 4: methyl 5-bromo-3-(cyclopentylamino)-2-methylbenzoate

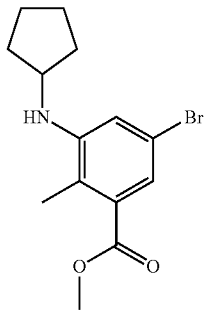 [SMILES: COC(=O)c1cc(Br)cc(NC2CCCC2)c1C]

To a stirred solution of methyl 3-amino-5-bromo-2-methylbenzoate (0.3 g, 1.33 mmol) and cyclopentanone (0.56 g, 6.6 mmol) in methanol (3 mL), acetic acid (0.159 g, 2.6 mmol) was added and reaction stirred at room temperature for 3 h. Then sodium cyanoborohydride (0.208 g, 3.3 mmol) was added and reaction stirred overnight. On completion, solvent was removed under reduced pressure and crude material was used as is in the next step.

Step 5: Synthesis of methyl 5-bromo-3-(cyclopentyl(methyl)amino)-2-methylbenzoate

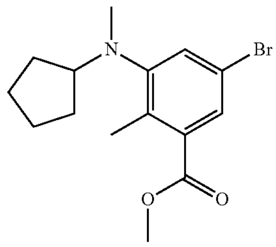 [SMILES: COC(=O)c1cc(Br)cc(N(C)C2CCCC2)c1C]

A solution of methyl 5-bromo-3-(cyclopentylamino)-2-methylbenzoate (1 g, 3.22 mmol), $Cs_2CO_3$ (2.10 g, 6.45 mmol) and methyl iodide (2.3 g, 16.12 mmol) in acetonitrile (15 mL) was heated at 80° C. for 14 h. After complete consumption of starting material reaction mixture was filtered. The filtrate was concentrated and the obtained residue was purified by column chromatography to provide the desired compound (0.9 g, 86%).

Step 6: 5-bromo-3-(cyclopentylamino)-N-((4,6-dimethyl-2-oxo-1,2-dihydropyridin-3-yl)methyl)-2-methylbenzamide

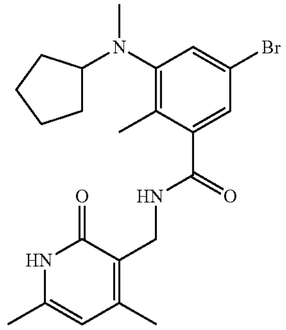 [SMILES: Cc1cc(C)c(CNC(=O)c2cc(Br)cc(N(C)C3CCCC3)c2C)c(=O)[nH]1]

Aqueous NaOH (0.166 g, 4.15 mmol) was added to a solution of methyl 5-bromo-3-(cyclopentyl(methyl)amino)-2-methylbenzoate (0.9 g, 2.76 mmol) in EtOH (9 mL) and water (2.2 mL) and stirred at 60° C. for 1 h. After completion of the reaction, ethanol was removed under reduced pressure and acidified using dilute HCl up to pH 6 and pH 4 was adjusted using citric acid. Extraction was carried out using ethyl acetate. Combined organic layers were dried concentrated giving respective acid (0.85 g, 98%).

The acid (0.85 g, 2.73 mmol) was then dissolved in DMSO (10 mL) and 3-(amino methyl)-4,6-dimethylpyridin-2(1H)-one (0.83 g, 5.46 mmol) was added to it. The reaction mixture was stirred at room temperature for 15 min before PYBOP (2.13 g, 4.09 mmol) was added to it and stirring was continued for overnight. After completion of the reaction, reaction mass was poured into ice to obtain solid, this was filtered and washed with acetonitrile followed by ether to provide the desired compound (0.450 g, 37%).

Step 7: tert-butyl 4-(3-(cyclopentyl(methyl)amino)-5-(((4,6-dimethyl-2-oxo-1,2-dihydropyridin-3-yl)methyl)carbamoyl)-4-methylphenyl)-5,6-dihydropyridine-1(2H)-carboxylate

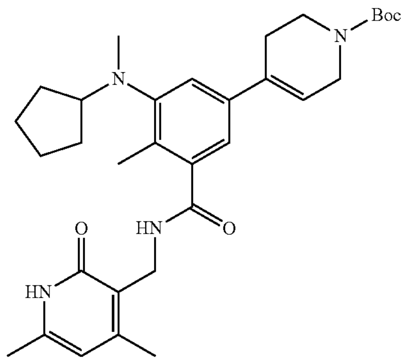 [SMILES: Cc1cc(C)c(CNC(=O)c2cc(C3=CCN(C(=O)OC(C)(C)C)CC3)cc(N(C)C3CCCC3)c2C)c(=O)[nH]1]

To a degassed solution of 5-bromo-3-(cyclopentylamino)-N-((4,6-dimethyl-2-oxo-1,2-dihydropyridin-3-yl)methyl)-2-methylbenzamide (1.0 g, 2.24 mmol) and boronic acid (0.833 g, 2.69 mmol) in dioxane (20 mL) was added $Pd(PPh_3)_4$ (0.260 g, 0.224 mmol, 0.1 eq) and the solution was again purged with argon for 20 min. To the reaction mixture Aq $Na_2CO_3$ (0.857, 8.08 mmol) solution in 1 mL water was added and reaction mixture was again purged with argon for 20 min. The reaction was heated at 100° C. for 90 min. The reaction mixture was then cooled to room temperature and poured in to cold water and extracted with dichloromethane. Crude compound purified by column chromatography to provide the desired compound (0.900 g, 64%).

Step 8: 3-(cyclopentyl(methyl)amino)-N-((4,6-dimethyl-2-oxo-1,2-dihydropyridin-3-yl)methyl)-2-methyl-5-(1,2,3,6-tetrahydropyridin-4-yl)benzamide

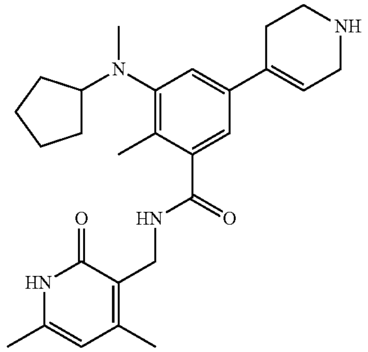 [SMILES: Cc1cc(C)c(CNC(=O)c2cc(C3=CCNCC3)cc(N(C)C3CCCC3)c2C)c(=O)[nH]1]

To a stirred solution of tert-butyl 4-(3-(cyclopentyl(methyl)amino)-5-(((4,6-dimethyl-2-oxo-1,2-dihydropyridin-3-yl)methyl)carbamoyl)-4-methylphenyl)-5,6-dihydropyridine-1(2H)-carboxylate (0.800 g, 1.45 mmol) in DCM was added TFA (3 mL) and the reaction mixture was stirred at RT for 2 h. On completion, reaction was concentrated to dryness. Residue was basified with aqueous sodium bicarbonate till pH 8 and aqueous layer extracted with 20% MeOH/DCM. Combined organic layers were dried over sodium sulfate and concentrated to afford crude material which was purified by preparative HPLC to afford the desired compound (0.620 g, 95%).

Step 9: 3-(cyclopentyl(methyl)amino)-N-((4,6-dimethyl-2-oxo-1,2-dihydropyridin-3-yl)methyl)-2-methyl-5-(1-methyl-1,2,3,6-tetrahydropyridin-4-yl)benzamide

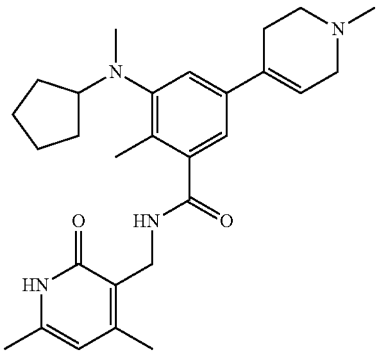

3-(Cyclopentyl(methyl)amino)-N-((4,6-dimethyl-2-oxo-1,2-dihydropyridin-3-yl)methyl)-2-methyl-5-(1,2,3,6-tetrahydropyridin-4-yl)benzamide (0.100 g, 0.223 mmol) was dissolved in methanol (5 mL) and cooled to 0° C., formalin (0.067 g, 0.19 mL, 2.23 mmol) was added. Resulting reaction mass was stirred at same temperature for 30 minutes. Sodium cyanoborohydride (0.041 g, 0.66 mmol) was added to above reaction mass and stirred at room temperature for 4 h. After completion, solvent were removed under reduced pressure and water was added to the residue, extraction was carried out using DCM. Combined organic layers were dried, concentrated and purified by column chromatography to provide the desired compound (0.065 g, 63%): LCMS: 463.40 $(M+1)^+$; HPLC: 98.79% (@ 254 nm) ($R_t$; 3.911; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.43 (s, 1H), 8.04 (t, 1H, J=4.8 Hz), 7.17 (s, 1H), 6.95 (s, 1H), 6.07 (s, 1H), 5.85 (s, 1H), 4.25 (d, 2H, J=4.8 Hz), 3.45 (m, 1H), 2.98 (bs, 2H), 2.53 (m, 2H), 2.42 (bs, 2H), 2.26 (s, 3H), 2.18 (s, 3H), 2.17 (s, 3H), 2.10 (s, 3H), 1.67 (m, 2H), 1.59 (m, 2H), 1.49 (m, 2H), 1.40 (m, 2H).

Example 13

Synthesis of Compound 17: 3-((1-acetylpiperidin-4-yl)(methyl)amino)-5-bromo-N-((4,6-dimethyl-2-oxo-1,2-dihydropyridin-3-yl)methyl)-2-methylbenzamide Compound 17

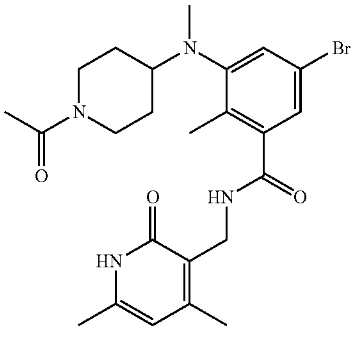

The 5-bromo-N-((4,6-dimethyl-2-oxo-1,2-dihydropyridin-3-yl)methyl)-2-methyl-3-(methyl(piperidine-4-yl)amino)benzamide (0.2 g, 0.447 mmol) dissolved in DMSO (2 mL) and acetic acid (0.054 g, 0.896 mmol) were added to it. The reaction mixture was stirred at room temperature for 15 min before PYBOP (0.342 g, 0.672 mmol) was added to it and stirring was continued for overnight. After completion, reaction mass was poured into ice, and extracted using 10% MeOH/DCM. Combined organic layers were dried, concentrated to provide crude material, which then purified with column chromatography using silica (100-200 mesh size) to afford the desired compound (0.15 g, 17%). LCMS: 503.20 $(M+1)^+$; HPLC: 96.06% (@ 254 nm) ($R_t$; 5.143; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.48 (s, 1H), 8.21 (t, 1H, J=4.8 Hz), 7.23 (d, 1H, J=1.6 Hz), 7.04 (d, 1H, J=1.6 Hz), 5.85 (s, 1H), 4.32 (d, 1H, J=12.4 Hz), 4.23 (d, 2H, J=4.8 Hz), 3.77 (d, 1H, J=13.2 Hz), 2.98 (t, 2H, J=11.2 Hz), 2.54 (s, 3H), 2.18 (s, 3H), 2.13 (s, 3H), 2.10 (s, 3H), 1.97 (s, 3H), 1.53-1.60 (m, 4H), 1.38-1.41 (m, 1H).

Example 14

Synthesis of Compound 18: 3-(cyclopentyl(methyl)amino)-N-((4,6-dimethyl-2-oxo-1,2-dihydropyridin-3-yl)methyl)-2-methyl-5-(1-methylpiperidin-4-yl)benzamide Compound 18

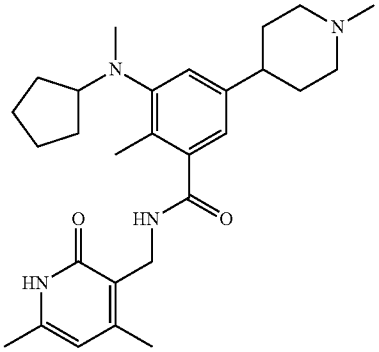

To a solution of 3-(cyclopentyl(methyl)amino)-N-((4,6-dimethyl-2-oxo-1,2-dihydropyridin-3-yl)methyl)-2-methyl-5-(1-methyl-1,2,3,6-tetrahydropyridin-4-yl)benzamide (0.045 g, 0.097 mmol) in ethanol added 10% Pd/C and the reaction was stirred under $H_2$ at bladder pressure. After complete consumption of the starting material reaction mixture was filtered through celite. The filtrate was concentrated and triturated in acetonitrile and filtered to provide the desired compound (0.030 g, 66%): LCMS: 465.40 $(M+1)^+$; HPLC: 95.39% (@ 254 nm) ($R_t$; 3.884; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.44 (s, 1H), 7.98 (t, 1H), 7.00 (s, 1H), 6.77 (s, 1H), 5.85 (s, 1H), 4.25 (d, 2H, J=4.4 Hz), 3.42 (m, 1H), 2.84 (d, 2H, J=11.2 Hz), 2.47 (s, 3H), 2.37 (m, 1H), 2.18 (s, 6H), 2.15 (s, 3H), 2.10 (s, 3H), 1.93 (t, 2H, J=10.8 Hz), 1.70-1.55 (m, 8H), 1.48 (m, 2H), 1.38 (m, 2H).

Example 15

Synthesis of Compound 20: 3-(cyclopentyl(methyl) amino)-N-((4,6-dimethyl-2-oxo-1,2-dihydropyridin-3-yl)methyl)-2-methyl-5-(trifluoromethyl)benzamide Compound 20

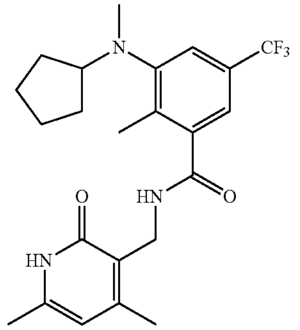

Step 1: Synthesis of 2-methyl-3-nitro-5-(trifluoromethyl)benzoic acid

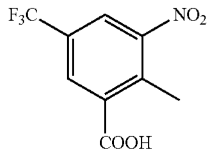 [SMILES: Cc1c(C(=O)O)cc(C(F)(F)F)cc1[N+](=O)[O-]]

2-methyl-5-(trifluoromethyl)benzoic acid (4 g, 19.6 mmol) was added to cooled conc. $H_2SO_4$ (27 mL) at −10° C. in small portions. After 10 minutes nitrating mixture {prepared by mixing conc. $HNO_3$ (2.77 g, 44.44 mmol) with conc.$H_2SO_4$ (3.6 mL)} was added drop wise at −10° C. The resulting solution was stirred at −10° C. for 30 minutes. On completion, the reaction mixture was poured into ice cold water. The solid was filtered, washed with water and dried under vacuum to give 2-methyl-3-nitro-5-(trifluoromethyl) benzoic acid (4.95 g, 99%).

Step 2: Synthesis of methyl 2-methyl-3-nitro-5-(trifluoromethyl)benzoate

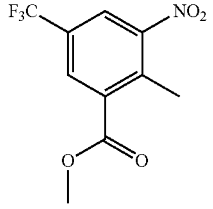 [SMILES: COC(=O)c1cc(C(F)(F)F)cc([N+](=O)[O-])c1C]

To stirred solution of 2-methyl-3-nitro-5-(trifluoromethyl) benzoic acid (1 g, 4.01 mmol) in DMF (3 mL) was added sodium carbonate (0.63 g, 6.02 mmol) and methyl iodide (1.14 g, 8.03 mmol). The resulting mixture was heated at 60° C. for 4 h. On completion, water was added to the reaction, and the product extracted using DCM. Combined organic layers were dried, concentrated under reduced pressure and purified by column chromatography over silica to give methyl 2-methyl-3-nitro-5-(trifluoromethyl)benzoate (1 g, 95.2%).

Step 3: Synthesis of methyl 3-amino-2-methyl-5-(trifluoromethyl)benzoate

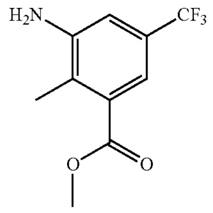 [SMILES: COC(=O)c1cc(C(F)(F)F)cc(N)c1C]

To a stirred solution of methyl 2-methyl-3-nitro-5-(trifluoromethyl)benzoate (5.6 g, 20.97 mmol) in ethanol (40 mL) was added ammonium chloride (5.6 g, 104.6 mmol) dissolved in water (30 mL) and iron powder (4.67 g, 85.16 mmol). The resulting mixture was heated at 80° C. for 1 h. On completion, water was added to the reaction then the mixture was filtered through celite. The filtrate was extracted with ethyl acetate. The combined organic layers were dried then concentrated under reduced pressure to give methyl 3-amino-2-methyl-5-(trifluoromethyl)benzoate.

Step 4: Synthesis of methyl 3-(cyclopentylamino)-2-methyl-5-(trifluoromethyl)benzoate

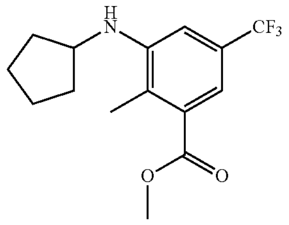 [SMILES: COC(=O)c1cc(C(F)(F)F)cc(NC2CCCC2)c1C]

To a stirred solution of methyl 3-amino-2-methyl-5-(trifluoromethyl)benzoate (2.5 g, 10.7 mmol) and cyclopentanone (4.5 g, 53.49 mmol) in methanol (25 mL) was added acetic acid (1.98 g, 21.44 mmol). After 3 h, sodium cyanoborohydride (1.68 g, 24.3 mmol) was added and the reaction stirred overnight. On completion, the solvent was removed under reduced pressure and crude material was purified by column chromatography to afford methyl 3-(cyclopentylamino)-2-methyl-5-(trifluoromethyl)benzoate (1.8 g, 55.9%).

Step 5: Synthesis of methyl 3-(cyclopentyl(methyl) amino)-2-methyl-5-(trifluoromethyl)benzoate

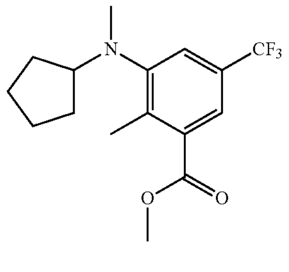 [SMILES: COC(=O)c1cc(C(F)(F)F)cc(N(C)C2CCCC2)c1C]

To a stirred solution of methyl 3-(cyclopentylamino)-2-methyl-5-(trifluoromethyl)benzoate (1.6 g, 5.38 mmol) in acetonitrile (25 mL) was added cesium carbonate (3.5 g, 10.7 mmol) and methyl iodide (3.8 g, 26.8 mmol). The mixture was heated at 80° C. for 8 h. On completion, the reaction was cooled to room temperature and filtered. The residue was washed with ethyl acetate and the filtrate was concentrated to give methyl 3-(cyclopentyl(methyl)amino)-2-methyl-5-(trifluoromethyl)benzoate.

Step 6: Synthesis of 3-(cyclopentyl(methyl)amino)-N-((4,6-dimethyl-2-oxo-1,2-dihydropyridin-3-yl)methyl)-2-methyl-5-(trifluoromethyl)benzamide

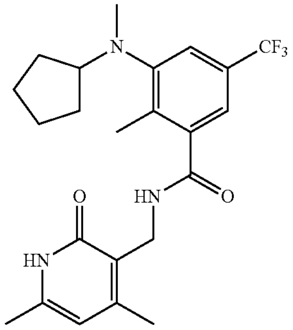 [SMILES: Cc1cc(C)c(CNC(=O)c2cc(C(F)(F)F)cc(N(C)C3CCCC3)c2C)c(=O)[nH]1]

Aqueous NaOH (0.762 g, 15.4 mmol) was added to a solution of methyl 3-(cyclopentyl(methyl)amino)-2-methyl-5-(trifluoromethyl)benzoate (2 g, 6.34 mmol) in MeOH (20 mL) and the mixture was stirred at 60° C. for 1 h. After completion of the reaction, methanol was removed under reduced pressure and the residue acidified using dilute HCl up to pH 6 and to pH 4 using citric acid. The product was extracted using ethyl acetate. The combined organic layers were dried and concentrated to give the desired acid (1.5 g, 78%).

The acid (0.5 g, 1.69 mmol) was then dissolved in DMSO (3 mL) and 3-(amino methyl)-4,6-dimethylpyridin-2(1H)-one (0.505 g, 3.32 mmol) was added to it. The reaction mixture was stirred at room temperature for 15 min before PYBOP (1.29 g, 2.49 mmol) was added and stirring was continued overnight. After completion of the reaction, the mixture was poured onto ice to obtain a solid. The solid was filtered and washed with acetonitrile followed by ether to provide compound 3-(cyclopentyl(methyl)amino)-N-((4,6-dimethyl-2-oxo-1,2-dihydropyridin-3-yl)methyl)-2-methyl-5-(trifluoromethyl)benzamide (100 mg, 14%). Analytical Data: LCMS: 436.20 $(M+1)^+$; HPLC: 89.22% (@ 254 nm) ($R_t$; 6.094; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-$d_6$, 400 MHz) δ 11.47 (s, 1H), 8.30 (t, 1H), 7.37 (s, 1H), 7.18 (s, 1H), 5.86 (s, 1H), 4.26 (d, 2H, J=4.4 Hz), 3.51 (m, 1H), 2.53 (s, 3H), 2.25 (s, 3H), 2.19 (s, 3H), 2.10 (s, 3H), 1.41-1.69 (m, 8H).

Example 16

Synthesis of Compound 21: 3-(cyclopentyl(methyl)amino)-N-((4,6-dimethyl-2-oxo-1,2-dihydropyridin-3-yl)methyl)-2-methylbenzamide Compound 21

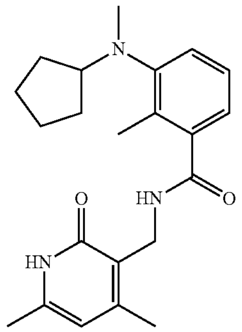

Step 1: Synthesis of methyl 3-amino-2-methylbenzoate

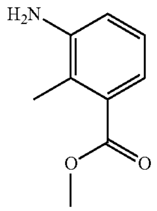

To stirred solution of methyl 3-amino-2-methylbenzoic acid (5 g, 33.1 mmol) in methanol (50 mL), was added conc. $H_2SO_4$ (5 mL) at 0° C. and the mixture was heated at 70° C. for 22 h. On completion, methanol was removed under reduced pressure, and then sat. sodium bicarbonate solution was added and the product extracted with 10% MeOH/DCM. Combined organic layers were dried, concentrated to yield methyl 3-amino-2-methylbenzoate (5 g, 91%).

Step 2: Synthesis of methyl 3-(cyclopentylamino)-2-methylbenzoate

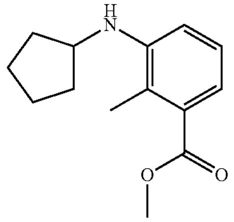 [SMILES: COC(=O)c1cccc(NC2CCCC2)c1C]

To a stirred solution of methyl 3-amino-2-methylbenzoate (2 g, 12.1 mmol) and cyclopentanone (5 g, 60.6 mmol) in methanol (20 mL) was added acetic acid (0.72 g, 12.12 mmol) and the reaction stirred at room temperature for 3 h. Sodium cyanoborohydride (1.13 g, 18.2 mmol) was added and the reaction stirred overnight. On completion, the solvent was removed under reduced pressure and the product was purified by column chromatography to afford methyl 3-(cyclopentylamino)-2-methylbenzoate (2.2 g, 78%).

Step 3: Synthesis of methyl 3-(cyclopentyl(methyl)amino)-2-methylbenzoate

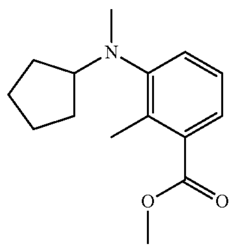 [SMILES: COC(=O)c1cccc(N(C)C2CCCC2)c1C]

To a stirred solution of methyl 3-(cyclopentylamino)-2-methylbenzoate (2.2 g, 9.44 mmol) in acetonitrile (20 mL) was added cesium carbonate (6.13 g, 18.8 mmol) and methyl iodide (6.7 g, 47.2 mmol). The resulting mixture was heated at 80° C. for 12 h. On completion, the mixture was cooled to room temperature and filtered, washing with ethyl acetate. The filtrate was concentrated and then purified by column chromatography to afford methyl 3-(cyclopentyl(methyl)amino)-2-methylbenzoate (2 g, 85%).

Step 4: Synthesis of 3-(cyclopentyl(methyl)amino)-N-((4,6-dimethyl-2-oxo-1,2-dihydropyridin-3-yl)methyl)-2-methylbenzamide

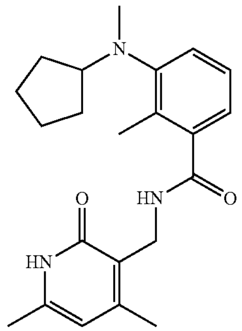 [SMILES: Cc1cc(C)c(CNC(=O)c2cccc(N(C)C3CCCC3)c2C)c(=O)[nH]1]

Aqueous NaOH (0.48 g, 12.14 mmol) was added to a solution of methyl 3-(cyclopentyl(methyl)amino)-2-methylbenzoate (2 g, 8.09 mmol) in MeOH (20 mL) and stirred at 60° C. for 1 h. After completion of the reaction, methanol was removed under reduced pressure and acidified using dilute HCl up to pH 6 and pH 4 was adjusted using citric acid. Extraction was carried out using ethyl acetate. Combined organic layers were dried and concentrated to give the desired acid (1.3 g, 69%).

The acid (0.3 g, 1.28 mmol) was then dissolved in DMSO (5 mL) and 3-(amino methyl)-4,6-dimethylpyridin-2(1H)-one (0.39 g, 2.5 mmol) was added to it. The reaction mixture was stirred at room temperature for 15 min before PYBOP (0.99 g, 1.92 mmol) was added to it and stirring was continued for overnight. After completion of the reaction, mixture was poured into ice to obtain solid, this was filtered and washed with acetonitrile followed column purification to provide 3-(cyclopentyl(methyl)amino)-N-((4,6-dimethyl-2-oxo-1,2-dihydropyridin-3-yl)methyl)-2-methylbenzamide (0.020 g, 4%).

Analytical Data: LCMS: 368.15 $(M+1)^+$; HPLC: 99.49% (@ 254 nm) ($R_t$; 4.186; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.43 (s, 1H), 8.00 (t, 1H, J=4 Hz), 7.09-7.16 (m, 2H), 6.90 (d, 1H, J=6.8 Hz), 5.84 (s, 1H), 4.25 (d, 2H, J=5.2 Hz), 3.41 (t, 1H, J=6.8 Hz), 2.47 (s, 3H), 2.18 (d, 6H, J=4.4 Hz), 2.10 (s, 3H), 1.58-1.67 (m, 4H), 1.37-1.52 (m, 4H).

Example 17

Synthesis of Compound 23: 5-chloro-N-((4,6-dimethyl-2-oxo-1,2-dihydropyridin-3-yl)methyl)-2-methyl-3-(methyl(1-methylpiperidin-4-yl)amino)benzamide Compound 23

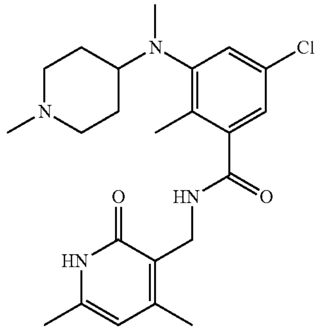

5-Chloro-N-((4,6-dimethyl-2-oxo-1,2-dihydropyridin-3-yl)methyl)-2-methyl-3-(methyl(piperidin-4-yl)amino)benzamide (0.08 g, 0.192 mmol) was dissolved in methanol (5 mL) and cooled to 0° C., formalin (0.028 g, 0.965 mmol) was added. Resulting reaction mass was stirred at same temperature for 30 minutes. Sodium cyanoborohydride (0.023 g, 0.38 mmol) was added to above reaction mass and stirred at room temperature for 4 h. After completion, solvent were removed under reduced pressure and water was added to the residue, extraction was carried out using DCM. Combined organic layers were dried, concentrated and purified by column chromatography giving the desired compound (0.02 g, 24%): LCMS: 431.25 $(M+1)^+$; HPLC: 98.80% (@ 254 nm) ($R_t$; 4.757; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.46 (s, 1H), 8.20 (t, 1H), 7.15 (d, 1H, J=1.2 Hz), 6.94 (d, 1H, J=2 Hz), 5.85 (s, 1H), 4.25 (d, 2H, J=4.8 Hz), 3.05 (bs, 2H), 2.88 (bs, 1H), 2.55 (s, 3H), 2.44 (bs, 2H), 2.18 (s, 3H), 2.14 (s, 3H), 2.10 (s, 3H), 1.68 (bs, 4H).

Example 18

Synthesis of Compound 25: 3-(cyclopentyl(methyl)amino)-N-((4,6-dimethyl-2-oxo-1,2-dihydropyridin-3-yl)methyl)-2-methyl-5-(2,2,6,6-tetramethyl-1,2,3,6-tetrahydropyridin-4-yl)benzamide Compound 25

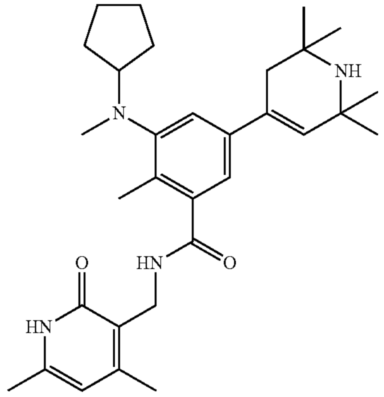

Step 1: 5-bromo-2-methyl-3-nitrobenzoic acid

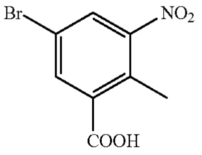

To stirred solution of 2-methyl-3-nitrobenzoic acid (50 g, 276.2 mmol) in conc. $H_2SO_4$ (200 mL), 1,3-dibromo-5,5-dimethyl-2,4-imidazolidinedione (43.4 g, 151.8 mmol) was added portion wise at room temperature and reaction mass was stirred at room temperature for 5 h. On completion, reaction mass was poured on ice cold water, solid precipitated was filtered, resulting residue was washed with water and dried under vacuum to give the desired compound (71.7 g, 100%).

Synthesis of methyl 5-bromo-2-methyl-3-nitrobenzene

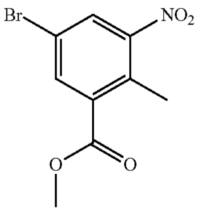

To a stirred solution of 5-bromo-2-methyl-3-nitrobenzoic acid (287 g, 1103 mmol) in DMF (150 mL), sodium carbonate (468 g, 4415 mmol) and methyl iodide (626.63 g, 4415 mmol) were added. Resulting reaction mass was heated at 60° C. for 8 h. On completion, solid precipitated was filtered, residue washed with diethyl ether (5 times). Combined organic layers were dried, concentrated under reduced pressure giving the desired crude compound (302 g, 99%).

Step 2: methyl 3-amino-5-bromo-2-methylbenzoate

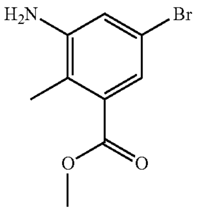

To stirred solution of methyl 5-bromo-2-methyl-3-nitrobenzene (150 g, 544 mmol) in ethanol (750 mL), ammonium chloride (150 g, 2777 mmol) dissolved in water (750 mL) and iron powder (93.3 g, 1636 mmol) were added under stirring. Resulting reaction mass was heated at 80° C. for 7 h. On completion, reaction mass was filtered through celite giving washing of water and ethyl acetate, filtrate was extracted with ethyl acetate. Combined organic layers were dried, concentrated under reduced pressure giving the desired compound.

Step 3: methyl 5-bromo-3-(cyclopentylamino)-2-methylbenzoate

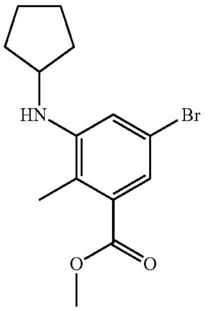 [SMILES: COC(=O)c1cc(Br)cc(NC2CCCC2)c1C]

To a stirred solution of methyl 3-amino-5-bromo-2-methylbenzoate (0.3 g, 1.33 mmol) and cyclopentanone (0.56 g, 6.6 mmol) in methanol (3 mL), acetic acid (0.159 g, 2.6 mmol) was added and reaction stirred at room temperature for 3 h. Then sodium cyanoborohydride (0.208 g, 3.3 mmol) was added and reaction stirred overnight. On completion, solvent was removed under reduced pressure to give the desired compound.

Step 4: methyl 5-bromo-3-(cyclopentyl(methyl)amino)-2-methylbenzoate

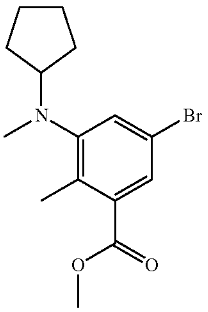 [SMILES: COC(=O)c1cc(Br)cc(N(C)C2CCCC2)c1C]

To a stirred solution of the crude methyl 5-bromo-3-(cyclopentylamino)-2-methylbenzoate (0.7 g, 2.25 mmol) in acetonitrile (15 mL), cesium carbonate (1.47 g, 4.50 mmol) and methyl iodide (1.6 g, 11.26 mmol) were added; resulting reaction mass was heated at 80° C. for 7 h. On completion, reaction mass was cooled to room temperature and filtered, residue was washed with ethyl acetate and filtrate was concentrated and then purified by column chromatography to afford the desired compound (0.6 g, 82%).

Step 5: 5-bromo-3-(cyclopentyl(methyl)amino)-N-((4,6-dimethyl-2-oxo-1,2-dihydropyridin-3-yl)methyl)-2-methylbenzamide

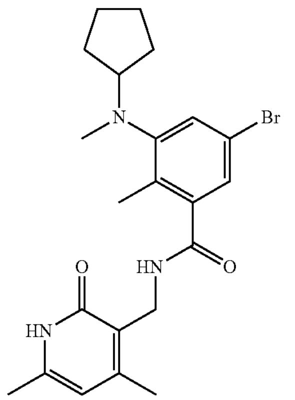 [SMILES: Cc1cc(C)c(CNC(=O)c2cc(Br)cc(N(C)C3CCCC3)c2C)c(=O)[nH]1]

Aqueous NaOH (0.11 g, 2.75 mmol) was added to a solution of methyl 5-bromo-3-(cyclopentyl(methyl)amino)-2-methylbenzoate (0.6 g, 1.8 mmol) in MeOH (1.5 mL) and stirred at 60° C. for 1 h. After completion of the reaction, ethanol was removed under reduced pressure and acidified using dilute HCl up to pH 6 and pH 4 was adjusted using citric acid. Extraction was carried out using ethyl acetate. The combined organic layers were dried and concentrated to give the respective acid (0.5 g, 87%).

The acid (0.5 g, 1.60 mmol) was then dissolved in DMSO (3 mL) and 3-(amino methyl)-4,6-dimethylpyridin-2(1H)-one (0.49 g, 3.22 mmol) was added to it. The reaction mixture was stirred at room temperature for 15 min before PYBOP (1.25 g, 2.41 mmol) was added to it and stirring was continued for overnight. After completion of the reaction, reaction mass was poured into ice to obtain solid, this was filtered and washed with acetonitrile followed by ether to provide the desired compound (0.315 g, 44%).

Step 6: 3-(cyclopentyl(methyl)amino)-N-((4,6-dimethyl-2-oxo-1,2-dihydropyridin-3-yl)methyl)-2-methyl-5-(2,2,6,6-tetramethyl-1,2,3,6-tetrahydropyridin-4-yl)benzamide

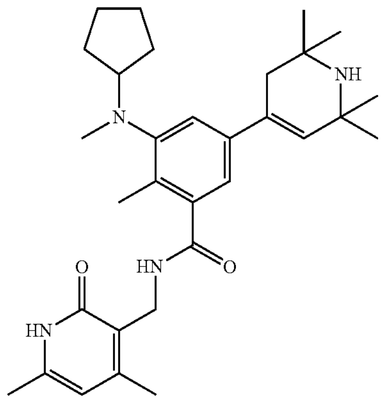

A solution of 5-bromo-3-(cyclopentyl(methyl)amino)-N-((4,6-dimethyl-2-oxo-1,2-dihydropyridin-3-yl)methyl)-2-methylbenzamide (1 equiv.), (2,2,6,6-tetramethyl-1,2,3,6-tetrahydropyridin-4-yl)boronic acid (1.2 equiv.) and Pd $(PPh_3)_4$ (0.1 equiv.) in 1,4-dioxane (4 mL) was purged with argon for 10 min. Then, 2 M $Na_2CO_3$ solution (3.6 equiv.) was added to it and argon was purged again for 10 min. The reaction mixture was stirred at 100° C. for 2 h. After completion of the reaction, water was added to it and extraction was carried out using DCM. The combined organic layers were washed with water, dried over anhydrous $Na_2SO_4$, filtered and concentrated under reduced pressure to afford crude material which was purified preparative HPLC to give the desired compound as its TFA salt (0.045, 23%). LCMS: 505.39 $(M+1)^+$; HPLC: 99.95% (@ 254 nm) ($R_t$; 4.091; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (MeOD, 400 MHz) δ 7.70 (s, 1H), 7.46 (s, 1H), 6.21 (s, 1H), 6.13 (s, 1H), 4.48 (s, 2H), 4.23 (bs, 1H), 3.14 (s, 3H), 2.69 (s, 2H), 2.42 (s, 3H), 2.39 (s, 3H), 2.24 (s, 3H), 1.92 (, 2H), 1.81 (m, 2H), 1.67 (m, 4H), 1.60 (s, 6H), 1.53 (s, 6H).

Example 19

Synthesis of Compound 26: tert-butyl (4-((5-bromo-3-(((4,6-dimethyl-2-oxo-1,2-dihydropyridin-3-yl)methyl)carbamoyl)-2-methylphenyl)amino)cyclohexyl)carbamate Compound 26

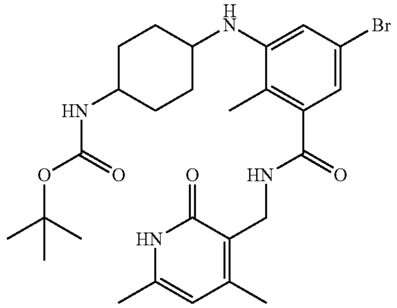

Step 1: 5-bromo-2-methyl-3-nitrobenzoic acid

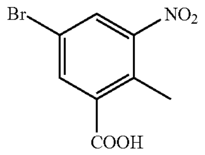

To a mixture of 2-methyl-3-nitrobenzoic acid (15 g, 82.80 mmol) in conc. $H_2SO_4$ (60 mL), 1,3-dibromo-5,5-dimethyl-2,4-imidazolidinedione (13.07 g, 45.71 mmol) was added and reaction mixture was stirred at room temperature for 5 h. After completion of reaction, reaction mixture was slowly poured onto ice cold water (400 mL). The precipitate was collected by filtration to give the desired compound (21 g, 98.22%).

Step 2: methyl 5-bromo-2-methyl-3-nitrobenzoate

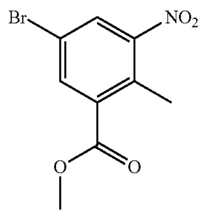

To a stirred solution of 5-bromo-2-methyl-3-nitrobenzoic acid (16 g, 61.54 mmol) in DMF (160 mL), iodomethane (35.72 g, 248 mmol) and sodium carbonate (26.28 g, 248 mmol) were added. Resulting reaction mass was stirred at 60° C. for 8 h. On completion, reaction mass was filtered and inorganic solid residue washed with ethyl acetate. Combined filtrate was concentrated under vacuum till dryness. The residue was re-dissolved in ethyl acetate and washed with 5% sodium bicarbonate solution (700 mL) followed by 5M HCl solution (300 mL). Organic layer was finally washed with brine, dried over sodium sulfate, filtered and concentrated to afford the desired compound (16 g. 94.50%).

Step 3: methyl 3-amino-5-bromo-2-methylbenzoate

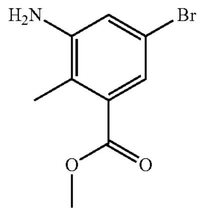

To a stirred solution of methyl 5-bromo-2-methyl-3-nitrobenzoate (17 g, 62.04 mmol) in ethanol (85 mL), was added $NH_4Cl$ solution (17 g in 85 mL water, 317.8 mmol) followed by Fe powder (27.82 g, 498.11 mmol). Resulting reaction mass was stirred at 90° C. for 1 h. On completion, reaction mass was filtered and filtrate was concentrated till dryness to get solid which was dissolved in saturated sodium bicarbonate solution. The aqueous layer was extracted with ethyl acetate. Combined organic layers were dried over sodium sulfate and concentrated to afford the desired compound 4 (15 g, 99%).

Step 4: methyl 5-bromo-3((4-((tert-butoxycarbonyl) amino)cyclohexyl)amino)-2-methylbenzoate

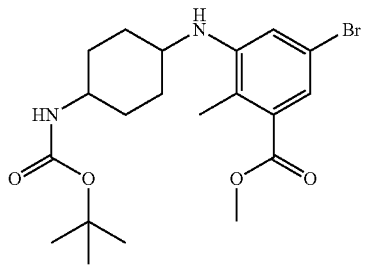 [SMILES: COC(=O)c1cc(Br)cc(NC2CCC(NC(=O)OC(C)(C)C)CC2)c1C]

To a stirred solution of methyl 3-amino-5-bromo-2-methylbenzoate (5 g, 20.57 mmol) and tert-butyl (4-oxocyclohexyl)carbamate (5.67 g, 26.74 mmol) in methanol (50 mL), acetic acid (1.2 g, 20.57 mmol) was added and reaction stirred at room temperature for 4 h. Then sodium cyanoborohydride (1.68 g, 26.74 mmol) was added and reaction stirred 18 h. On completion, solvent was removed under reduced pressure; water was added and extracted with DCM. Combined organic were dried, concentrated and purified by column chromatography using silica (100-200 mesh size) to afford the desired compound (3 g, 33%).

Step 5: tert-butyl (4-((5-bromo-3-(((4,6-dimethyl-2-oxo-1,2-dihydropyridin-3-yl)methyl)carbamoyl)-2-methylphenyl)amino)cyclohexyl)carbamate

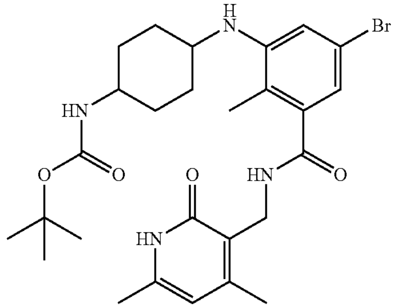 [SMILES: Cc1cc(C)c(CNC(=O)c2cc(Br)cc(NC3CCC(NC(=O)OC(C)(C)C)CC3)c2C)c(=O)[nH]1]

Aqueous NaOH (0.247 g, 6.83 mmol) was added to a solution of methyl 5-bromo-3-((4-((tert-butoxycarbonyl) amino)cyclohexyl)amino)-2-methylbenzoate (1.5 g, 3.41 mmol) in MeOH (20 mL) and stirred at 60° C. for 1 h. After completion of the reaction, ethanol was removed under reduced pressure and acidified using dilute HCl up to pH 6 and pH 4 was adjusted using citric acid. Extraction was carried out using DCM. Combined organic layers were dried concentrated giving respective acid (1.28 g, 89%).

The acid (1.28 g, 3.01 mmol) was then dissolved in DMSO (10 mL) and 3-(amino methyl)-4,6-dimethylpyridin-2(1H)-one (1.03 g, 6.83 mmol) was added to it. The reaction mixture was stirred at room temperature for 15 min before PYBOP (2.6 g, 5.12 mmol) was added to it and stirring was continued for overnight. After completion of the reaction, reaction mass was poured into ice and extracted with 5% MeOH/DCM. The combined organic layers were dried and concentrated to obtain a crude solid, which was purified by column chromatography to afford the desired compound (0.75 g, 45%). LCMS: 561.15 $(M+1)^+$; HPLC: 99.99% (@ 254 nm) ($R_t$; 6.876, 7.080 [mixture of diastereomers]; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-$d_6$, 400 MHz) δ 11.44 (s, 1H), 8.07 (t, 1H, J=4.8 Hz), 6.77 (d, 1H, J=7.6 Hz), 6.66 (s, 1H), 6.51-6.54 (m, 1H), 5.84 (s, 1H), 4.71 (d, 1H, J=7.6 Hz), 4.21-4.22 (m, 2H), 3.44 (bs, 1H), 3.19 (bs, 1H), 2.16 (s, 3H), 2.10 (s, 3H), 1.93-2.03 (m, 5H), 1.78 (s, 1H), 1.56-1.72 (m, 3H), 1.37 (s, 9H), 1.26-1.31 (m, 2H).

Example 20

Synthesis of Compound 28: 5-bromo-3-(cyclohexylamino)-N-((4,6-dimethyl-2-oxo-1,2-dihydropyridin-3-yl)methyl)-2-methylbenzamide Compound 28

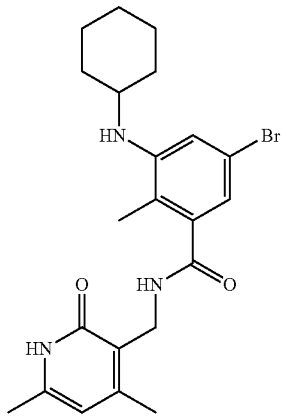

Step 1: 5-bromo-2-methyl-3-nitrobenzoic acid

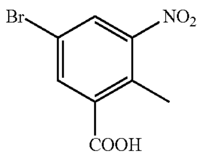

To stirred solution of 2-methyl-3-nitrobenzoic acid (50 g, 276.2 mmol) in conc. $H_2SO_4$ (200 mL), 1,3-dibromo-5,5-dimethyl-2,4-imidazolidinedione (43.4 g, 151.8 mmol) was added portion wise at room temperature and reaction mass was stirred at room temperature for 5 h. On completion, reaction mass was poured on ice cold water, solid precipitated was filtered, resulting residue was washed with water and dried under vacuum giving the desired compound (71.7 g, 100%).

Step 2: methyl 5-bromo-2-methyl-3-nitrobenzene

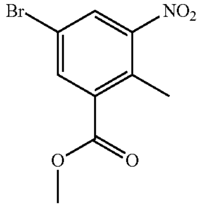

To stirred solution of 5-bromo-2-methyl-3-nitrobenzoic acid (287 g, 1103 mmol) in DMF (150 mL), sodium carbonate (468 g, 4415 mmol) and methyl iodide (626.63 g, 4415 mmol) were added. Resulting reaction mass was heated at 60° C. for 8 h. On completion, solid precipitated was filtered, residue washed with diethyl ether (5 times). Combined organic layers were dried, concentrated under reduced pressure giving the desired compound (302 g, 99%).

Step 3: methyl 3-amino-5-bromo-2-methylbenzoate

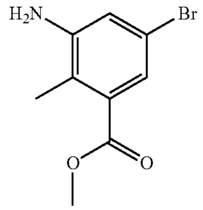

To a stirred solution of methyl 5-bromo-2-methyl-3-nitrobenzene (150 g, 544 mmol) in ethanol (750 mL), ammonium chloride (150 g, 2777 mmol) dissolved in water (750 mL) and iron powder (93.3 g, 1636 mmol) were added under stirring. Resulting reaction mass was heated at 80° C. for 7 h. On completion, reaction mass was filtered through celite giving washing of water and ethyl acetate, filtrate was extracted with ethyl acetate. Combined organic layers were dried, concentrated under reduced pressure to give the desired compound which was used directly in the next step.

Step 4: methyl 5-bromo-3-(cyclohexylamino)-2-methylbenzoate

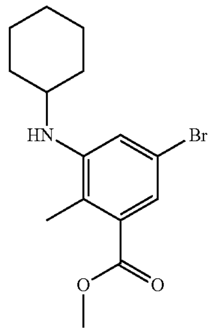 [SMILES: COC(=O)c1cc(Br)cc(NC2CCCCC2)c1C]

To a stirred solution of methyl 3-amino-5-bromo-2-methylbenzoate (0.3 g, 1.33 mmol) and cyclohexanone (0.64 g, 6.6 mmol) in methanol (3 mL), acetic acid (0.159 g, 2.6 mmol) was added and reaction stirred at room temperature for 3 h. Then sodium cyanoborohydride (0.208 g, 3.3 mmol) was added and reaction stirred overnight. On completion, solvent was removed under reduced pressure and was used directly in the next step.

Step 5: 5-bromo-3-(cyclohexylamino)-N-((4,6-dimethyl-2-oxo-1,2-dihydropyridin-3-yl)methyl)-2-methylbenzamide

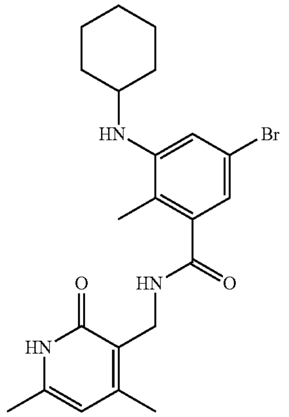 [SMILES: Cc1cc(C)c(CNC(=O)c2cc(Br)cc(NC3CCCCC3)c2C)c(=O)[nH]1]

Aqueous NaOH (0.049 g, 1.23 mmol) was added to a solution of methyl 5-bromo-3-(cyclohexylamino)-2-methylbenzoate (0.2 g, 0.61 mmol) in MeOH (5 mL) and stirred at 60° C. for 1 h. After completion of the reaction, ethanol was removed under reduced pressure and acidified using dilute HCl up to pH 6 and pH 4 was adjusted using citric acid. Extraction was carried out using ethyl acetate. Combined organic layers were dried concentrated giving respective acid (0.17 g, 89%).

The acid (0.17 g, 0.54 mmol) was then dissolved in DMSO (3 mL) and 3-(amino methyl)-4,6-dimethylpyridin-2(1H)-one (0.099 g, 0.65 mmol) was added to it. The reaction mixture was stirred at room temperature for 15 min before PYBOP (0.42 g, 0.817 mmol) was added to it and stirring was continued for overnight. After completion of the reaction, reaction mass was poured into ice to obtain solid, this was purified by preparative HPLC to provide the desired compound as its TFA salt (0.042 g, 15%). LCMS: 446.16 $(M+1)^+$; HPLC: 99.85% (@ 254 nm) ($R_t$; 6.918; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-$d_6$, 400 MHz) δ 11.45 (s, 1H), 8.08 (s, 1H), 6.66 (s, 1H), 6.51 (d, 1H, J=0.8 Hz), 5.84 (s, 1H), 4.70 (s, 1H), 4.21 (d, 2H, J=4.4 Hz), 3.24 (s, 1H), 2.16 (s, 3H), 2.10 (s, 3H), 1.94 (s, 3H), 1.88 (d, 2H, J=10 Hz), 1.69-1.72 (m, 3H), 1.22-1.36 (m, 5H).

Example 21

Synthesis of Compound 30: 5-bromo-N-((4,6-dimethyl-2-oxo-1,2-dihydropyridin-3-yl)methyl)-2-methyl-3-(methyl(1-methylpiperidin-4-yl)amino)benzamide Compound 30

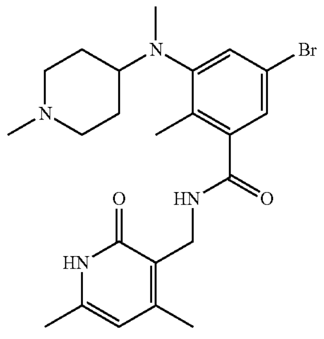

Step 1: 5-bromo-2-methyl-3-nitrobenzoic acid

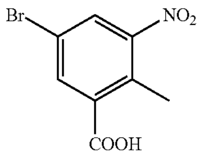

To stirred solution of 2-methyl-3-nitrobenzoic acid (50 g, 276.2 mmol) in conc. $H_2SO_4$ (200 mL), 1,3-dibromo-5,5-dimethyl-2,4-imidazolidinedione (43.4 g, 151.8 mmol) was added portion wise at room temperature and reaction mass was stirred at room temperature for 5 h. On completion, reaction mass was poured on ice cold water, solid precipitated was filtered, resulting residue was washed with water and dried under vacuum giving the desired compound (71.7 g, 99.9%) which was used for further reaction.

Step 2: methyl 5-bromo-2-methyl-3-nitrobenzene

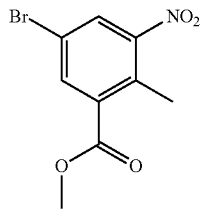

To stirred solution of 5-bromo-2-methyl-3-nitrobenzoic acid (287 g, 1103 mmol) in DMF (150 mL), sodium carbonate (468 g, 4415 mmol) and methyl iodide (626.63 g, 4415 mmol) were added. Resulting reaction mass was heated at 60° C. for 8 h. On completion, solid precipitated was filtered, residue washed with diethyl ether (5 times). Combined organic layers were dried, concentrated under reduced pressure giving the desired compound (302 g, 99).

Step 3: methyl 3-amino-5-bromo-2-methylbenzoate

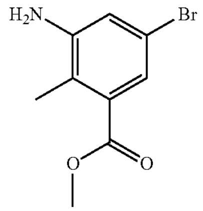

To a stirred solution of methyl 5-bromo-2-methyl-3-nitrobenzene (150 g, 544 mmol) in ethanol (750 mL), ammonium chloride (150 g, 2777 mmol) dissolved in water (750 mL) and iron powder (93.3 g, 1636 mmol) were added under stirring. Resulting reaction mass was heated at 80° C. for 7 h. On completion, reaction mass was filtered through celite giving washing of water and ethyl acetate, filtrate was extracted with ethyl acetate. The combined organic layers were dried, concentrated under reduced pressure giving the desired compound.

Step 4: methyl 5-bromo-2-methyl-3((1-methylpiperidin-4-yl)amino)benzoate

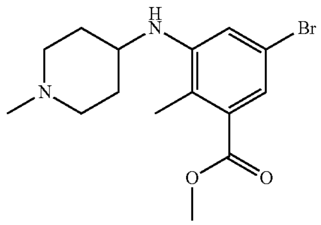 [SMILES: COC(=O)c1cc(Br)cc(NC2CCN(C)CC2)c1C]

To a stirred solution of methyl 3-amino-5-bromo-2-methylbenzoate (2 g, 8.23 mmol) and 1-methylpiperidin-4-one (1.86 g, 16.46 mmol) in methanol (20 mL), acetic acid (0.5 g, 8.23 mmol) was added and reaction stirred at room temperature for 3 h. Then sodium cyanoborohydride (0.622 g, 9.87 mmol) was added and reaction stirred overnight. On completion, solvent was removed under reduced pressure and crude material was purified by column chromatography to afford the desired compound (0.9 g, 33%).

Step 5: methyl 5-bromo-2-methyl-3-(methyl(1-methylpiperidin-4-yl)amino)benzoate

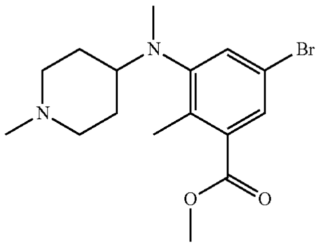 [SMILES: COC(=O)c1cc(Br)cc(N(C)C2CCN(C)CC2)c1C]

To a stirred solution of methyl 5-bromo-2-methyl-3-((1-methylpiperidin-4-yl)amino)benzoate (0.6 g, 1.76 mmol) in acetonitrile (15 mL), cesium carbonate (1.14 g, 3.52 mmol) and methyl iodide (1.2 g, 8.8 mmol) were added; resulting reaction mass was heated at 80° C. for 7 h. On completion, reaction mass was cooled to room temperature and filtered, residue was washed with ethyl acetate and filtrate was concentrated and then purified by column chromatography to afford the desired compound (0.5 g, 80%).

Step 6: 5-bromo-N-((4,6-dimethyl-2-oxo-1,2-dihydropyridin-3-yl)methyl)-2-methyl-3-(methyl(1-methylpiperidin-4-yl)amino)benzamide

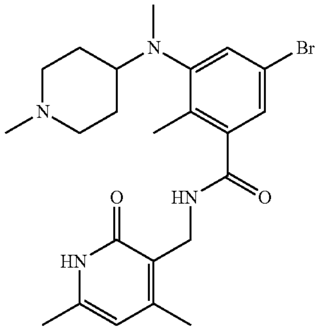 [SMILES: Cc1cc(C)c(CNC(=O)c2cc(Br)cc(N(C)C3CCN(C)CC3)c2C)c(=O)[nH]1]

Aqueous NaOH (0.11 g, 2.75 mmol) was added to a solution of methyl 5-bromo-2-methyl-3-(methyl(1-methylpiperidin-4-yl)amino)benzoate (0.5 g, 1.4 mmol) in MeOH (20 mL) and stirred at 60° C. for 1 h. After completion of the reaction, ethanol was removed under reduced pressure and acidified using dilute HCl up to pH 6 and pH 4 was adjusted using citric acid. Extraction was carried out using ethyl acetate. Combined organic layers were dried concentrated giving respective acid (0.42 g, 90%).

The acid (0.5 g, 0.974 mmol) was then dissolved in DMSO (3 mL) and 3-(amino methyl)-4,6-dimethylpyridin-2(1H)-one (0.45 g, 2.8 mmol) was added to it. The reaction mixture was stirred at room temperature for 15 min before PYBOP (1.1 g, 2.1 mmol) was added to it and stirring was continued for overnight. After completion of the reaction, reaction mass was poured into ice to obtain solid, this was filtered and washed with acetonitrile followed by purification with column chromatography to afford the desired compound (0.2 g, 30%). LCMS: 475.02 $(M+1)^+$; HPLC: 94.25% (@ 254 nm) ($R_t$; 4.570; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.45 (s, 1H), 8.13 (t, 1H, J=4.8 Hz), 6.78 (d, 1H, J=0.8 Hz), 6.60 (d, 1H, J=1.6 Hz), 5.85 (s, 1H), 4.94 (d, 1H, J=8.8 Hz), 4.22 (d, 2H, J=4.8 Hz), 3.62-3.64 (m, 1H), 3.37-3.46 (m, 3H), 3.11 (s, 3H), 3.09 (s, 3H), 2.17 (s, 3H), 2.10 (s, 3H), 1.99-2.09 (m, 2H), 1.98 (s, 3H), 1.86-1.93 (m, 2H).

Example 22

Synthesis of Compound 31: 5-bromo-N-((4,6-dimethyl-2-oxo-1,2-dihydropyridin-3-yl)methyl)-3-(isopropyl(methyl)amino)-2-methylbenzamide Compound 31

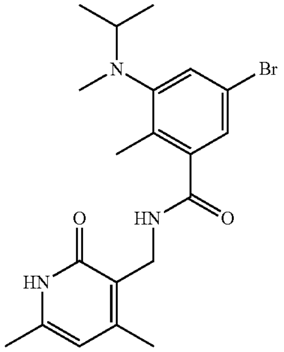

Step 1: Synthesis of methyl 5-bromo-3-(isopropylamino)-2-methylbenzoate

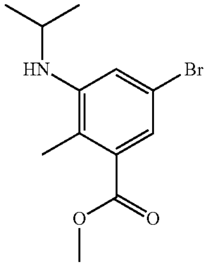 [SMILES: COC(=O)c1cc(Br)cc(NC(C)C)c1C]

To a stirred solution of methyl 3-amino-5-bromo-2-methylbenzoate (1 equiv.) in methanol (5 mL), acetone (5 equiv.) and acetic acid (2 equiv.) were added and reaction mixture stirred at room temperature for 2 h. Then $NaBH_3CN$ (3 equiv.) was added at 0° C. The resulting reaction mixture was stirred further for 16 h at room temperature. On completion, solvent was evaporated and water added to the residue and the extracted with ethyl acetate. The combined organic layers were dried over sodium sulfate and concentrated to afford crude product which was used in next step without further purification (yield 80-90%).

Step 2: Synthesis of methyl 5-bromo-3-(isopropyl(methyl)amino)-2-methylbenzoate

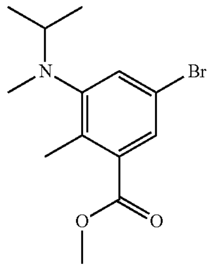 [SMILES: COC(=O)c1cc(Br)cc(N(C)C(C)C)c1C]

To a stirred solution of methyl 5-bromo-3-(isopropylamino)-2-methylbenzoate (0.5 g, 1.75 mmol) in acetonitrile (10 mL), $Cs_2CO_3$ (1.02 g, 2.63 mmol) and methyl iodide (1.45 g, 3.5 mmol) were added to it. The resulting reaction mixture was stirred at 80° C. for 4 h. Upon completion, the solvent was removed under reduced pressure and residue dissolved in water and extracted with ethyl acetate. Crude material obtained was purified by column chromatography over silica gel affording the desired compound product without further purification (0.39 g)

Step 3: 5-bromo-N-((4,6-dimethyl-2-oxo-1,2-dihydropyridin-3-yl)methyl)-3-(isopropyl(methyl)amino)-2-methylbenzamide

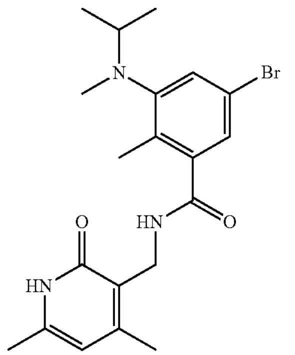 [SMILES: Cc1cc(C)c(CNC(=O)c2cc(Br)cc(N(C)C(C)C)c2C)c(=O)[nH]1]

To a stirred solution of methyl 5-bromo-3-(isopropyl(methyl)amino)-2-methylbenzoate (1 equiv.) in ethanol (5 mL), aqueous NaOH solution (1 equiv.) was added and reaction stirred at 60° C. for 4 h. On completion, ethanol was removed under reduced pressure and residue acidified with 1N HCl to pH 6. The aqueous phase was extracted with 10% MeOH/DCM. Combined organic layers were dried over sodium sulfate and solvent removed under reduced pressure affording pure acid (yield 50-60%). To a solution of this acid (1 equiv.) in DMSO (1.5 mL), PyBOP (1.5 equiv.) was added and reaction stirred at room temperature for 15 min. Then 3-(aminomethyl)-4,6-dimethylpyridin-2(1H)-one (2 equiv.) was added and reaction stirred overnight. On completion, water was added and the resulting solid precipitate filtered and washed with water. Then this solid was stirred with acetonitrile for 10 min and filtered again to obtain pure target molecule (yield 50-60%).

LCMS: 420.15 $(M+1)^+$; HPLC: 93.04% (@ 254 nm) ($R_t$; 4.791); $^1$H NMR (DMSO-$d_6$, 400 MHz) δ 11.47 (s, 1H), 8.19 (t, 1H, J=4.8 Hz), 7.14 (d, 1H, J=1.6 Hz), 7.00 (d, 1H, J=1.2 Hz), 5.85 (s, 1H), 4.23 (d, 2H, J=4.4 Hz), 3.16-3.20 (m, 1H), 2.52 (s, 3H), 2.17 (s, 3H), 2.10 (s, 6H), 1.01 (d, 6H, J=6.4 Hz).

Example 23

Synthesis of Compound 32: 5-bromo-N-((4,6-dihydro-2-oxo-1,2-dihydropyridin-3-yl)methyl)-2-methyl-3-((tetrahydro-2H-pyran-4-yl)amino)benzoate Compound 32

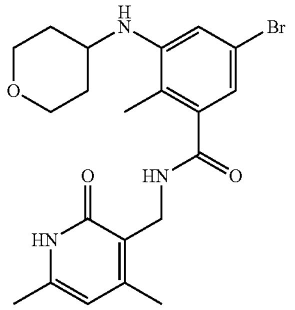

Step 1: 5-bromo-2-methyl-3-nitrobenzoic acid

To a mixture of 2-methyl-3-nitrobenzoic acid (15 g, 82.80 mmol) in conc. $H_2SO_4$ (60 mL), 1,3-dibromo-5,5-dimethyl-2,4-imidazolidinedione (13.07 g, 45.71 mmol) was added and reaction mixture was stirred at room temperature for 5 h. After completion of reaction, reaction mixture was slowly poured onto ice cold water (400 mL). Solid that precipitated out was filtered and dried under vacuum to obtain the desired compound (21 g, 98%).

Step 2: methyl 5-bromo-2-methyl-3-nitrobenzoate

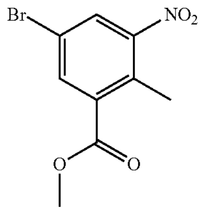

To a stirred solution of 5-bromo-2-methyl-3-nitrobenzoic acid (16 g, 61.54 mmol) in DMF (160 mL), iodomethane (35.72 g, 248 mmol) and sodium carbonate (26.28 g, 248 mmol) were added. Resulting reaction mass was stirred at 60° C. for 8 h. On completion, reaction mass was filtered and inorganic solid residue washed with ethyl acetate. Combined filtrate was concentrated under vacuum till dryness. The residue was re-dissolved in ethyl acetate and washed with 5% sodium bicarbonate solution (700 mL) followed by 5M HCl solution (300 mL). Organic layer was finally washed with brine, dried over sodium sulfate and concentrated to afford the desired compound (16 g, 95%).

Step 3: methyl 3-amino-5-bromo-2-methylbenzoate

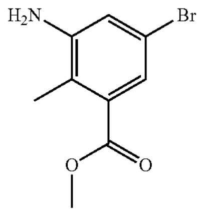

To a stirred solution of methyl 5-bromo-2-methyl-3-nitrobenzoate (17 g, 62.04 mmol) in ethanol (85 mL), was added $NH_4Cl$ solution (17 g in 85 mL water, 317.8 mmol) followed by Fe powder (27.82 g, 498.11 mmol). Resulting reaction mass was stirred at 90° C. for 1 h. On completion, reaction mass was filtered and filtrate was concentrated till dryness to get solid which was dissolved in saturated sodium bicarbonate solution. Aqueous layer was extracted with ethyl acetate. Combined organic layers were dried over sodium sulfate and concentrated to afford the desired compound (15 g, 99%).

Step 4: methyl 5-bromo-2-methyl-3-((tetrahydro-2H-pyran-4-yl)amino)benzoate

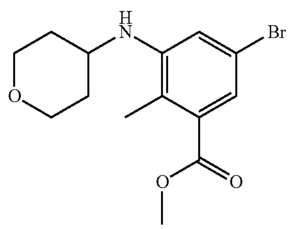 [SMILES: COC(=O)c1cc(Br)cc(NC2CCOCC2)c1C]

To a stirred solution of methyl 3-amino-5-bromo-2-methylbenzoate (2 g, 8.23 mmol) and tetrahydro pyran-4-one (1.06 g, 10.66 mmol) in methanol (20 mL), acetic acid (0.5 g, 8.23 mmol) was added and reaction stirred at room temperature for 18 h. Then sodium cyanoborohydride (0.62 g, 9.83 mmol) was added and reaction stirred 3 h. On completion, solvent was removed under reduced pressure; water was added and extracted with DCM. Combined organic were dried, concentrated and purified by column chromatography using silica (100-200 mesh size) to afford the desired compound (1.6 g, 62%).

Step 5: 5-bromo-N-((4,6-dihydro-2-oxo-1,2-dihydropyridin-3-yl)methyl)-2-methyl-3-((tetrahydro-2H-pyran-4-yl)amino)benzoate

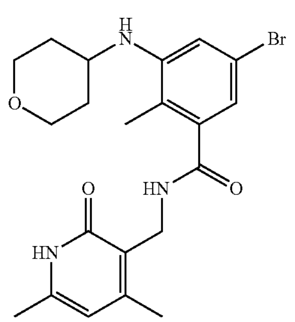 [SMILES: Cc1cc(C)c(CNC(=O)c2cc(Br)cc(NC3CCOCC3)c2C)c(=O)[nH]1]

Aqueous NaOH (0.146 g, 3.66 mmol) was added to a solution of methyl 5-bromo-2-methyl-3-((tetrahydro-2H-pyran-4-yl)amino)benzoate (0.6 g, 1.88 mmol) in MeOH (8 mL) and stirred at 60° C. for 1 h. After completion of the reaction, ethanol was removed under reduced pressure and acidified using dilute HCl up to pH 6 and pH 4 was adjusted using citric acid. Extraction was carried out using DCM. Combined organic layers were dried concentrated giving respective acid (0.515 g, 90%).

The acid (0.515 g, 1.67 mmol) was then dissolved in DMSO (3 mL) and 3-(amino methyl)-4,6-dimethylpyridin-2(1H)-one (0.50 g, 3.3 mmol) was added to it. The reaction mixture was stirred at room temperature for 15 min before PYBOP (1 g, 1.98 mmol) was added to it and stirring was continued for overnight. After completion of the reaction, reaction mass was poured into ice and extracted with 5% MeOH/DCM. Combined organic layers were dried and concentrated to obtain crude solid, this was purified by column chromatography to afford the desired compound (0.30 g, 37%). LCMS: 447.84 $(M+1)^+$; HPLC: 99.78% (@ 254 nm) ($R_t$; 5.753; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-$d_6$, 400 MHz) δ 11.45 (s, 1H), 8.09 (t, 1H, J=4.8 Hz), 6.76 (s, 1H), 6.53 (d, 1H, J=1.6 Hz), 5.84 (s, 1H), 4.82 (d, 1H, J=8 Hz), 4.42 (d, 2H, J=4.8 Hz), 3.85 (d, 2H, J=11.2 Hz), 3.37-3.53 (m, 3H), 2.16 (s, 3H), 2.10 (s, 3H), 1.95 (s, 3H), 1.81 (d, 2H, J=12.8 Hz), 1.44-1.54 (m, 2H).

Example 24

Synthesis of Compound 33: 5-bromo-3-(cyclopentylamino)-N-((4,6-dimethyl-2-oxo-1,2-dihydropyridin-3-yl)methyl)-2-methylbenzamide Compound 33

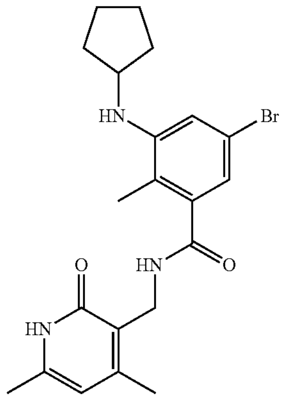

Step 1: Synthesis of methyl 5-bromo-3-(cyclopentylamino)-2-methylbenzoate

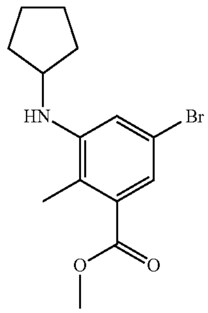 [SMILES: COC(=O)c1cc(Br)cc(NC2CCCC2)c1C]

To a stirred solution of methyl 3-amino-5-bromo-2-methylbenzoate (1 equiv.) in methanol (5 mL), cyclopentanone (5 equiv.) and acetic acid (2 equiv.) were added and reaction mixture stirred at room temperature for 2 h. Then $NaBH_3CN$ (3 equiv.) was added at 0° C. The resulting reaction mixture was stirred further for 16 h at room temperature. On completion, solvent was evaporated and water added to the residue and the extracted with ethyl acetate. The combined organic layers were dried over sodium sulfate and concentrated to afford crude product which was used in next step without further purification (yield 80-90%).

Step 2: Synthesis of 5-bromo-3-(cyclopentylamino)-N-((4,6-dimethyl-2-oxo-1,2-dihydropyridin-3-yl)methyl)-2-methylbenzamide

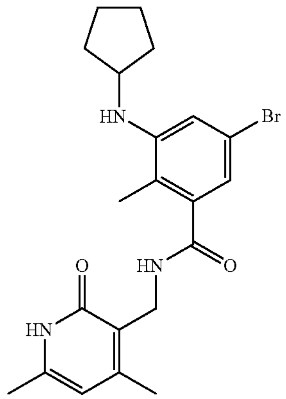 [SMILES: Cc1cc(C)c(CNC(=O)c2cc(Br)cc(NC3CCCC3)c2C)c(=O)[nH]1]

To a stirred solution of methyl 5-bromo-3-(cyclopentylamino)-2-methylbenzoate (1 equiv.) in ethanol (5 mL), aqueous NaOH solution (1 equiv.) was added and reaction stirred at 60° C. for 4 h. On completion, ethanol was removed under reduced pressure and residue acidified with 1N HCl to pH 6. Aqueous phase was extracted with 10% MeOH/DCM. Combined organic layers were dried over sodium sulfate and solvent removed under reduced pressure affording pure acid (yield 50-60%). To a solution of this acid (1 equiv.) in DMSO (1.5 mL), PyBOP (1.5 equiv.) was added and reaction stirred at room temperature for 15 min. Then 3-(aminomethyl)-4,6-dimethylpyridin-2(1H)-one (2 equiv.) was added and reaction stirred overnight. On completion, water was added and the solid precipitate filtered and washed with water. This solid was then stirred with acetonitrile for 10 min and filtered again to obtain the pure target molecule (50-60% yield).

LCMS: 432.10 $(M+1)^+$; HPLC: 97.15% (@ 254 nm) ($R_t$; 6.834); $^1$H NMR (DMSO-$d_6$, 400 MHz) δ 11.45 (s, 1H), 8.09 (t, 1H, J=4.4 & 5.2 Hz), 6.65 (d, 1H, J=1.6 Hz), 6.54 (d, 1H, J=1.6 Hz), 5.84 (s, 1H), 4.85 (d, 1H, J=6 Hz), 4.22 (d, 2H, J=5.2 Hz), 3.73 (m, 1H), 2.16 (s, 3H), 2.10 (s, 3H), 1.95 (s, 3H), 1.91 (m 2H), 1.70-1.62 (m, 2H), 1.60-1.45 (m, 4H).

Example 25

Synthesis of Compound 36: 5-bromo-3-(cyclopentyl(methyl)amino)-N-((4,6-dimethyl-2-oxo-1,2-dihydropyridin-3-yl)methyl)-2,4-dimethylbenzamide Compound 36

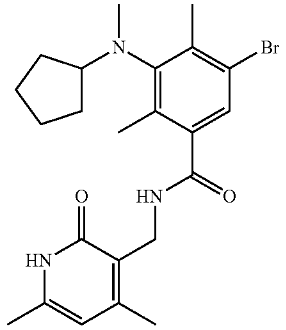

Step 1: 5-bromo-2,4-dimethylbenzoic acid

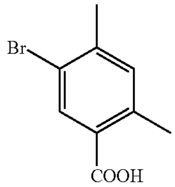

To the stirred solution of NaOH (60 g) in water (1152 ml) was added bromine (36 ml) dropwise at 0° C. and stirred the reaction mixture for 45 min. at same temperature. 2,4-dimethylbenzoic acid (12 g, 79.9 mmol) was added in above reaction mixture at 0° C. portion wise and stirred the reaction at room temperature for 3 h. After completion of reaction of reaction (TLC) reaction mixture was acidified using conc. HCl, solid was filtered through Buchner funnel and wash with water and dried to afford the desired compound (12 g, 65%) which was used without further purification.

Step 2: 5-bromo-2,4-dimethyl-3-nitrobenzoic acid

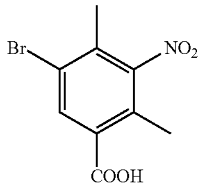

5-Bromo-2,4-dimethylbenzoic acid (12 g, 52.17 mmol) was added to cooled conc. $H_2SO_4$ (48 mL) at −10° C. lot wise. After 10 minutes nitrating mixture {prepared as mixing Conc. $HNO_3$ (6 mL) with conc.$H_2SO_4$ (24 mL)} was added drop wise at −10° C. Resulting reaction mass was stirred at −10° C. for 30 minutes. On completion, reaction mixture was poured on ice cold water, solid precipitated was filtered, washed with water and dried under vacuum giving desired compound (13 g, 91%).

Step 3: methyl 3-bromo-5-nitrobenzoate

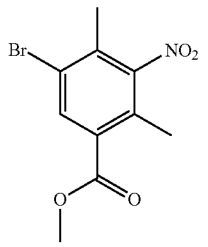 [SMILES: COC(=O)c1cc(Br)c(C)c([N+](=O)[O-])c1C]

To stirred solution of 5-bromo-2,4-dimethyl-3-nitrobenzoic acid (13 g, 47.44 mmol) in DMF (120 mL), sodium carbonate (15 g, 142.2 mmol) and methyl iodide (4.4 ml, 71.16 mmol) were added. Resulting reaction mass was heated at 60° C. for 8 h. On completion, water was added to the reaction mass and extraction was carried out using ethyl acetate. Combined organic layers were washed with sat. bicarbonate solution and 5 N HCl, dried over sodium sulphate, concentrated under reduced pressure giving desired compound (12.9 g, 86%).

Step 4: methyl 3-amino-5-bromo-2,4-dimethylbenzoate

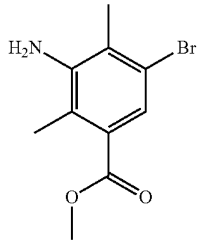

To stirred solution of methyl 3-bromo-5-nitrobenzoate (12.9 g, 44.79 mmol) in ethanol (65 mL), ammonium chloride (13 g, 223.95 mmol) dissolved in water (65 mL) and iron powder (20 g, 358.33 mmol) were added under stirring. Resulting reaction mass was heated at 80° C. for 1 h. On completion, reaction mixture was filtered through celite bed, celite bed was washed with ethanol, filtrate was extracted with ethyl acetate. Combined organic layers were washed with water, dried, concentrated under reduced pressure giving desired compound (11.0 g, 95%).

Step 5: methyl 5-bromo-3-(cyclopentylamino)-2,4-dimethylbenzoate

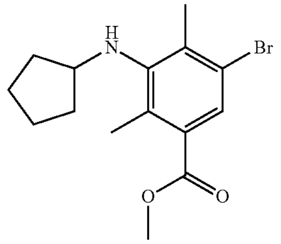 [SMILES: COC(=O)c1cc(Br)c(C)c(NC2CCCC2)c1C]

To a stirred solution of methyl 3-amino-5-bromo-2,4-dimethylbenzoate (1.4 g, 5.42 mmol) and cyclopentanone (2.4 mL, 27.13 mmol) in methanol (20 mL), acetic acid (0.650 g, 10.84 mmol) was added and reaction stirred at room temperature for 3 h. Then sodium cyanoborohydride (0.85 g, 13.56 mmol) was added and reaction was stirred for overnight. On completion, solvent was removed water was added and compound was extracted with ethyl acetate. Combined organic layer was collected, dried over $Na_2SO_4$ and concentrate under reduced pressure and crude material was purified by column chromatography to afford the desired compound (1.2 g, 68%).

Step 6: methyl 5-bromo-3-(cyclopentyl(methyl)amino)-2,4-dimethylbenzoate

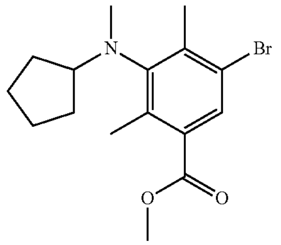 [SMILES: COC(=O)c1cc(Br)c(C)c(N(C)C2CCCC2)c1C]

To a stirred solution of methyl 5-bromo-3-(cyclopentylamino)-2,4-dimethylbenzoate (0.3 g, 1.07 mmol) in DMF (5 mL), cesium carbonate (0.697 g, 2.14 mmol) and ethyl iodide (0.3 mL, 5.38 mmol) were added; resulting reaction mass was heated at 80° C. for 12 h. On completion, reaction mass was cooled to room temperature and filtered, residue was washed with ethyl acetate and filtrate was concentrated and then purified by column chromatography to afford desired compound (0.3 g, 82%).

Step 7: 5-bromo-3-(cyclopentyl(methyl)amino)-N-((4,6-dimethyl-2-oxo-1,2-dihydropyridin-3-yl)methyl)-2,4-dimethylbenzamide

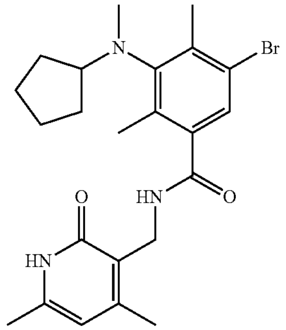 [SMILES: Cc1cc(C)c(CNC(=O)c2cc(Br)c(C)c(N(C)C3CCCC3)c2C)c(=O)[nH]1]

Aqueous NaOH (0.022 g, 0.553 mmol) was added to a solution of methyl 5-bromo-3-(cyclopentyl(methyl)amino)-2,4-dimethylbenzoate (0.125 g, 0.368 mmol) in EtOH (10 mL) and $H_2O$ (1 mL) and stirred at 60° C. for 1 h. After completion of the reaction, ethanol was removed under reduced pressure and acidified using dilute HCl up to pH 6. Extraction was carried out using ethyl acetate. Combined organic layers were dried over $Na_2SO_4$, concentrated under reduced pressure to give respective acid (0.1 g, 84.03%).

The acid (0.1 g, 0.308 mmol) was then dissolved in DMSO (3 mL) and 3-(amino methyl)-4,6-dimethylpyridin-2(1H)-one (0.07 g, 0.462 mmol) was added to it. The reaction mixture was stirred at room temperature for 15 min before PYBOP (0.320 g, 0.616 mmol) was added to it and stirring was continued for overnight. After completion of the reaction, reaction mass was poured into ice to obtain solid, this was filtered and washed with acetonitrile followed by HPLC purification to provide the title compound (0.018 g, 12.7%) as its TFA salt: LCMS: 460.10 $(M+1)^+$; HPLC: 98.10% (@ 254 nm) ($R_t$; 8.291; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.46 (s, 1H), 8.18 (t, 1H, J=4.4 Hz), 7.20 (s, 1H), 5.85 (s, 1H), 4.26 (d, 2H, J=4.8 Hz), 3.51-3.52 (m, 1H), 2.64 (s, 3H), 2.30 (s, 3H), 2.17 (s, 3H), 2.14 (s, 3H), 2.10 (s, 3H), 1.48-1.59 (m, 6H), 1.31-1.32 (m, 2H).

Example 26

Synthesis of Compound 48: 5-chloro-N-((4,6-dimethyl-2-oxo-1,2-dihydropyridin-3-yl)methyl)-2-methyl-3-(N-methylcyclopentanecarboxamido)benzamide Compound 48

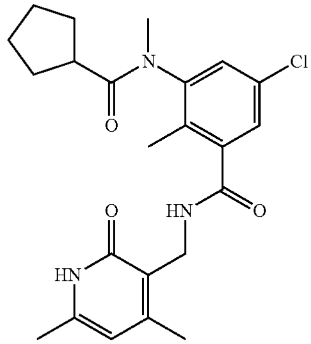

Step 1: Synthesis of 5-chloro-2-methyl-3-nitrobenzoic acid

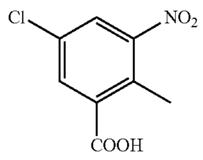

To a stirred ice cold (−10 to −15° C.) conc. $H_2SO_4$ (136 mL) was added 5-chloro-2-methylbenzoic acid (20 g, 0.117 mmol) in portions. The nitrating mixture [Conc. $H_2SO_4$ (22 mL) and $HNO_3$ (11.05 mL] was added dropwise at −10 to −15° C. and resulting mixture was allowed stir for 30 min.

The obtained precipitate was filtered and dried. The solid was the dissolved in ethyl acetate and dried ($Na_2SO_4$) and concentrated to provide desired product (23.6 g, 93%) as a white solid.

Step 2: Synthesis of methyl 5-chloro-2-methyl-3-nitrobenzoate

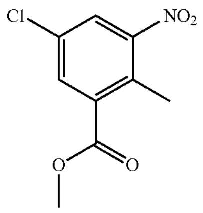

To a solution of 5-chloro-2-methyl-3-nitrobenzoic acid (23.5 g, 0.109 mmol) in DMF (120 mL) was added sodium carbonate (46.21, 0.436 mmol) and methyl iodide (27.2 mL, 0.43 mmol) at room temperature. The reaction mixture was heated at 60° C. for 3 h. After complete consumption of starting material the reaction mixture was filtered and the residue washed with ethyl acetate. The filtrate was concentrated under reduced pressure and the crude product purified by column chromatography to provide the desired compound (16 g, 64%) as thick oil which solidified on standing.

Step 3: Synthesis of methyl 3-amino-5-chloro-2-methylbenzoate

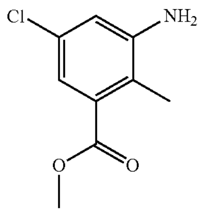

To stirred solution of methyl 5-chloro-2-methyl-3-nitrobenzoate (16 g, 69 mmol) in ethanol (160 mL), ammonium chloride (16 g, 53.4 mmol) dissolved in water (160 mL) and iron powder (31.2 g, 55.85 mmol) were added under stirring. The resulting reaction mixture was heated at 80° C. for 1 h. On completion, water was added to and the reaction mixture filtered through celite. The filtrate was extracted with ethyl acetate and the combined organic layers washed with water, dried and concentrated under reduced pressure giving desired compound (12.10 g, 86%) without further purification.

Step 4: Synthesis of methyl 5-chloro-3-(cyclopentanecarboxamido)-2-methylbenzoate

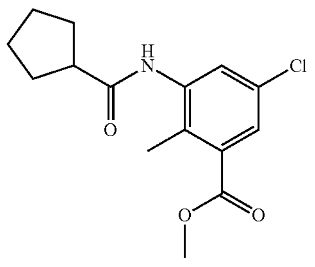 [SMILES: COC(=O)c1cc(Cl)cc(NC(=O)C2CCCC2)c1C]

To a stirred solution of methyl 3-amino-5-chloro-2-methylbenzoate (0.4 g, 2.0 mmol) in pyridine (2 mL), cyclopentyl chloride (0.39 mL, 3.00 mmol) was added at 0° C. The reaction mixture was stirred at room temperature for 2 h. After complete consumption of the starting material the reaction was quenched with ice water. The resulting precipitate was filtered of to provide desired product (0.5 g, 84%).

Step 5: Synthesis of methyl 5-chloro-2-methyl-3-(N-methylcyclopentanecarboxamido)benzoate

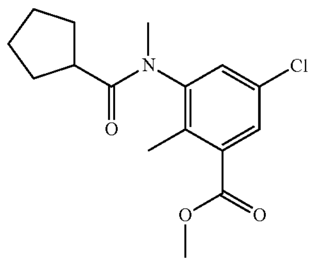 [SMILES: COC(=O)c1cc(Cl)cc(N(C)C(=O)C2CCCC2)c1C]

To a stirred solution of methyl 5-chloro-3-(cyclopentanecarboxamido)-2-methylbenzoate (0.3 g, 1.01 mmol) in DMF, sodium hydride (0.060 g, 0.0015 mmol) was added at 0° C. and reaction mixture was allowed to stir for 15 min. Methyl iodide (0.32 mL, 0.50 mmol) was added and reaction mixture and was stirred at room temperature. After complete consumption of starting material, the reaction was quenched with addition of water and extracted with ethyl acetate. The combined organic layer was the washed with brine, dried ($Na_2SO_4$) and concentrated. The crude compound was used for the next step.

Step 6: Synthesis of 5-chloro-N-((4,6-dimethyl-2-oxo-1,2-dihydropyridin-3-yl)methyl)-2-methyl-3-(N-methylcyclopentanecarboxamido)benzamide

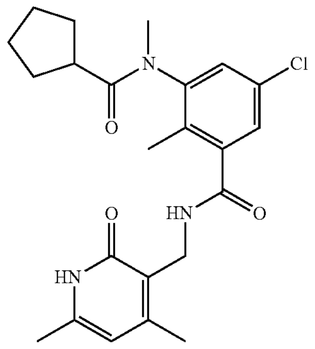 [SMILES: Cc1cc(C)c(CNC(=O)c2cc(Cl)cc(N(C)C(=O)C3CCCC3)c2C)c(=O)[nH]1]

Aq. NaOH (0.077 g, 1.94 mmol) was added to a solution of methyl 5-chloro-2-methyl-3-(N-methylcyclopentanecarboxamido)benzoate (0.4 g, 1.2 mmol) in 4:1 EtOH:Water (15 mL) and stirred at 65° C. for 1 h. After completion of the reaction, ethanol was removed under reduced pressure and acidified with 1N HCl. The reaction mixture was extracted with ethyl acetate. Combined organic layers were washed with brine, dried and concentrated to provide respective acid (0.35 g, 91%).

The acid (0.3 g, 0.10 mmol) was then dissolved in DMSO (3 mL) and 3-(amino methyl)-4,6-dimethylpyridin-2(1H)-one (0.309 g, 0.20 mmol) was added to it. The reaction mixture was stirred at room temperature for 15 min before PYBOP (0.826 g, 0.155 mmol) was added to it and stirring was continued overnight. After completion the reaction mixture was poured into ice to obtain a solid which was filtered and washed with acetonitrile. Final purification was performed using prep. HPLC purification to the desired product as the TFA salt (0.120 g, 27%).

LCMS: 430.20 $(M+1)^+$; HPLC: 99.79% (@ 254 nm) ($R_t$; 6.086); $^1H$ NMR (DMSO-$d_6$, 400 MHz) δ 11.55 (bs, 1H), 8.43 (t, 1H), 7.46 (s, 1H), 7.29 (s, 1H), 5.87 (s, 1H), 4.25 (s, 2H), 3.01 (s, 3H), 2.35 (m, 1H), 2.19 (s, 3H), 2.10 (s, 3H), 2.06 (s, 3H), 1.70-1.45 (m, 6H), 1.35 (m, 2H).

Example 27

Synthesis of Compound 49: 3-((2-aminoethyl)(methyl)amino)-5-chloro-N-((4,6-dimethyl-2-oxo-1,2-dihydropyridin-3-yl)methyl)-2-methylbenzamide Compound 49

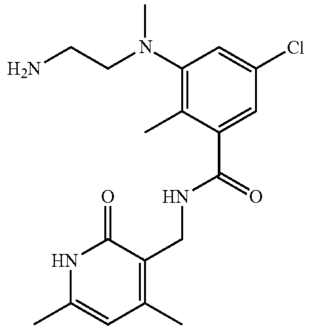

A stirred solution of tert-butyl (2-((5-chloro-3-(((4,6-dimethyl-2-oxo-1,2-dihydropyridin-3-yl)methyl)carbamoyl)-2-methylphenyl)(methyl)amino)ethyl)carbamate (0.2 g, 4.2 mmol) in DCM (5 mL) was cooled to 0° C. and TFA (1 mL) was added to it. The reaction mixture was stirred at room temperature for 1 h. On completion, the reaction was concentrated to dryness. Half of the material was purified by solvent washings giving pure 3-((2-aminoethyl)(methyl)amino)-5-chloro-N-((4,6-dimethyl-2-oxo-1,2-dihydropyridin-3-yl)methyl)-2-methylbenzamide as the TFA salt (0.060 g, 76%).

LCMS: 377.15 $(M+1)^+$; HPLC: 97.57% (@ 254 nm) ($R_t$; 4.611); $^1H$ NMR (DMSO-$d_6$, 400 MHz) δ 11.47 (s, 1H), 8.21 (t, 1H), 7.69 (bs, 3H), 7.16 (s, 1H), 6.97 (s, 1H), 5.86 (s, 1H), 4.25 (d, 2H, J=4.4 Hz), 3.07 (t, 2H), 2.96 (m, 2H), 2.59 (s, 3H), 2.18 (s, 6H), 2.10 (s, 3H).

Remaining material was basified with aqueous sodium bicarbonate till pH 8 and aqueous layer extracted with 20% MeOH/DCM. Combined organic layers were dried over sodium sulfate and concentrated to afford desired compound as free base which used for further reaction (0.075 g).

Example 28

Synthesis of Compound 50: tert-butyl (2-((5-chloro-3-(((4,6-dimethyl-2-oxo-1,2-dihydropyridin-3-yl)methyl)carbamoyl)-2-methylphenyl)(methyl)amino)ethyl)carbamate Compound 50

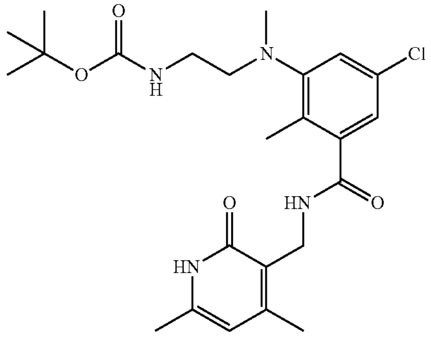

Step 1: Synthesis of methyl 3-((2-((tert-butoxycarbonyl)amino)ethyl)amino)-5-chloro-2-methylbenzoate

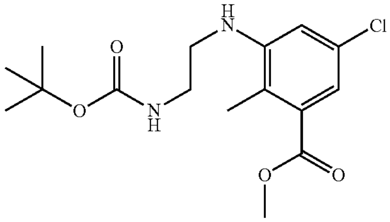 [SMILES: COC(=O)c1cc(Cl)cc(NCCNC(=O)OC(C)(C)C)c1C]

To a stirred solution of methyl 3-amino-5-chloro-2-methylbenzoate (1 g, 4.6 mmol) and tert-butyl (2-oxoethyl)carbamate (1.4 g, 8.8 mmol) in methanol (10 mL), acetic acid (0.027 g, 4.6 mmol) was added and reaction stirred at room temperature for 3 h. Then sodium cyanoborohydride (0.352 g, 4.68 mmol) was added and reaction stirred overnight. On completion, solvent was removed under reduced pressure and crude material was purified by column chromatography to afford the desired product (0.62 g, 38%).

Step 2: Synthesis of methyl 3-((2-((tert-butoxycarbonyl)amino)ethyl)(methyl)amino)-5-chloro-2-methylbenzoate

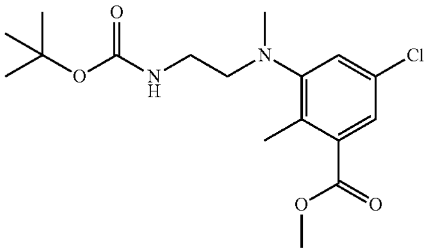 [SMILES: COC(=O)c1cc(Cl)cc(N(C)CCNC(=O)OC(C)(C)C)c1C]

To a stirred solution of methyl 3-((2-((tert-butoxycarbonyl)amino)ethyl)amino)-5-chloro-2-methylbenzoate (0.5 g, 1.46 mmol) in acetonitrile (10 mL), cesium carbonate (0.95 g, 2.92 mmol) and methyl iodide (1 g, 7.3 mmol) were added and the resulting reaction mixture heated at 80° C. for 12 h. On completion, the reaction mixture was cooled to room temperature and filtered, the residue washed with ethyl acetate and the filtrate concentrated before purification by column chromatography to afford desired product (0.325 g, 62%).

Step 3: Synthesis of tert-butyl (2-((5-chloro-3-(((4,6-dimethyl-2-oxo-1,2-dihydropyridin-3-yl)methyl)carbamoyl)-2-methylphenyl)(methyl)amino)ethyl)carbamate

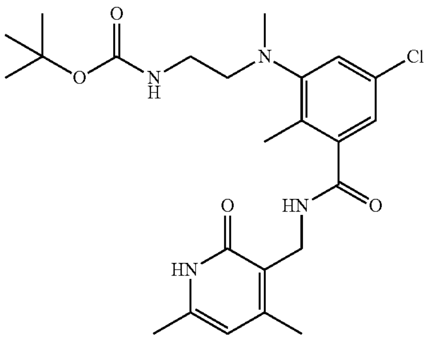 [SMILES: Cc1cc(C)c(CNC(=O)c2cc(Cl)cc(N(C)CCNC(=O)OC(C)(C)C)c2C)c(=O)[nH]1]

Aqueous NaOH (0.071 g, 1.79 mmol) was added to a solution of methyl 3-((2-((tert-butoxycarbonyl)amino)ethyl)(methyl)amino)-5-chloro-2-methylbenzoate (0.425 g, 1.19 mmol) in MeOH (5 mL) and stirred at 60° C. for 1 h. After completion of the reaction, ethanol was removed under reduced pressure and acidified using dilute HCl up to pH 6 and pH 4 and adjusted using citric acid. Extraction was carried out using ethyl acetate and the combined organic layers dried and concentrated giving respective acid (0.34 g, 84%).

The acid (0.34 g, 0.99 mmol) was then dissolved in DMSO (1.5 mL) and 3-(amino methyl)-4,6-dimethylpyridin-2(1H)-one (0.300 g, 1.98 mmol) was added to it. The reaction mixture was stirred at room temperature for 15 min before PYBOP (0.77 g, 1.48 mmol) was added to it and stirring was continued for overnight. After completion of the reaction, the reaction mixture was poured into ice to obtain solid, this was filtered and washed with acetonitrile followed column purification to provide tert-butyl (2-((5-chloro-3-(((4,6-dimethyl-2-oxo-1,2-dihydropyridin-3-yl)methyl)carbamoyl)-2-methylphenyl)(methyl)amino)ethyl)carbamate (0.27 g, 58%).

LCMS: 477.25 $(M+1)^+$; HPLC: 97.92% (@ 254 nm) ($R_t$; 6.229); $^1H$ NMR (DMSO-$d_6$, 400 MHz) δ 11.46 (s, 1H), 8.17 (t, 1H), 7.07 (s, 1H), 6.88 (s, 1H), 6.78 (bs, 1H), 5.85 (s, 1H), 4.24 (d, 2H, J=4.4 Hz), 3.07 (t, 2H), 2.84 (t, 2H), 2.62 (s, 3H), 2.17 (s, 3H), 2.13 (s, 3H), 2.10 (s, 3H), 1.35 (s, 9H).

Example 29

Synthesis of Compound 51: 5-chloro-N-((4,6-dimethyl-2-oxo-1,2-dihydropyridin-3-yl)methyl)-3-((2-(dimethylamino)ethyl)(methyl)amino)-2-methylbenzamide Compound 51

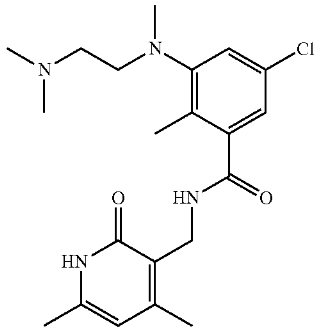

3-((2-Aminoethyl)(methyl)amino)-5-chloro-N-((4,6-dimethyl-2-oxo-1,2-dihydropyridin-3-yl)methyl)-2-methylbenzamide (0.075 g, 0.199 mmol) was dissolved in methanol (5 mL) and cooled to 0° C., formaldehyde (0.056 g, 1.86 mmol) was added. The resulting reaction mixture was stirred at the same temperature for 30 minutes then sodium cyanoborohydride (0.023 g, 0.366 mmol) was added to above reaction mixture and stirred at room temperature for 4 h. After completion, solvent was removed under reduced pressure and water added before extraction with DCM. The combined organic layers were dried, concentrated and purified by column chromatography to provide 5-chloro-N-((4,6-dimethyl-2-oxo-1,2-dihydropyridin-3-yl)methyl)-3-((2-(dimethylamino)ethyl)(methyl)amino)-2-methylbenzamide (0.040 g, 50%). LCMS: 405.25 $(M+1)^+$; HPLC: 89.93% (@ 254 nm) ($R_t$; 4.634); $^1H$ NMR (DMSO-$d_6$, 400 MHz) δ 11.47 (s, 1H), 8.21 (s, 1H), 7.08 (s, 1H), 5.85 (s, 1H), 4.24 (bs, 2H), 2.91 (t, 2H), 2.63 (s, 3H), 2.33-2.35 (m, 2H), 2.11-2.18 (m, 15H).

Example 30

Synthesis of Compound 52: 3-(allyl(cyclopentyl)amino)-5-chloro-N-((4,6-dimethyl-2-oxo-1,2-dihydropyridin-3-yl)methyl)-2-methylbenzamide Compound 52

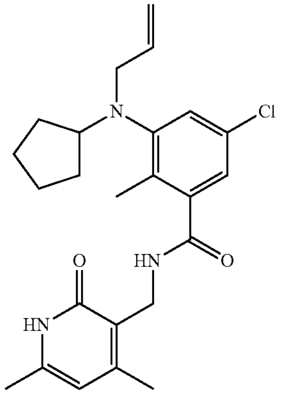

Step 1: Synthesis of methyl 3-(allyl(cyclopentyl)amino)-5-chloro-2-methylbenzoate

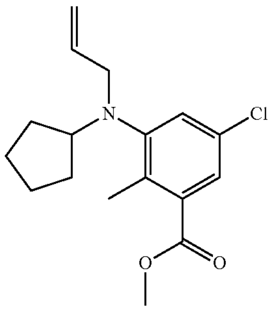 [SMILES: C=CCN(c1cc(Cl)cc(C(=O)OC)c1C)C1CCCC1]

Methyl 5-chloro-3-(cyclopentylamino)-2-methylbenzoate (1.2 g, 4.46 mmol) was dissolved in DMF (12 mL) and cooled to 0° C. NaH (0.21 g, 8.92 mmol) was added after 10 minutes and allyl bromide (1.07 g, 8.9 mmol) was added. The reaction mixture was stirred at room temperature for 4 h and then heated at 80 0° C. for 18 h. The reaction was quenched with ice water and extracted with ethyl acetate. Combined organic layers were dried, concentrated giving crude methyl 3-(allyl(cyclopentyl)amino)-5-chloro-2-methylbenzoate (0.4 g, 29.4%).

Step 2: Synthesis of 3-(allyl(cyclopentyl)amino)-5-chloro-N-((4,6-dimethyl-2-oxo-1,2-dihydropyridin-3-yl)methyl)-2-methylbenzamide

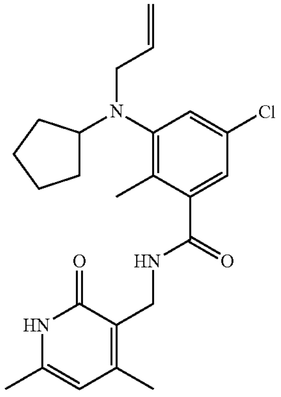 [SMILES: C=CCN(c1cc(Cl)cc(C(=O)NCc2c(C)cc(C)[nH]c2=O)c1C)C1CCCC1]

Aqueous NaOH (0.078 g, 1.95 mmol) was added to a solution of methyl 3-(allyl(cyclopentyl)amino)-5-chloro-2-methylbenzoate (0.4 g, 1.30 mmol) in MeOH (5 mL) and stirred at 60° C. for 1 h. After completion of the reaction, ethanol was removed under reduced pressure and acidified using dilute HCl up to pH 6 and pH 4 was adjusted using citric acid. Extraction was carried out using ethyl acetate and the combined organic layers concentrated giving respective acid (0.37 g, 97.6%).

The acid (0.25 g, 0.85 mmol) was then dissolved in DMSO (3 mL) and 3-(amino methyl)-4,6-dimethylpyridin-2(1H)-one (0.259 g, 1.74 mmol) was added to it. The reaction mixture was stirred at room temperature for 15 min before PYBOP (0.66 g, 1.27 mmol) was added to it and stirring was continued for overnight. After completion of the reaction, reaction mixture was poured into ice to obtain a solid, which was filtered and washed with acetonitrile followed column purification to provide the desired 3-(allyl(cyclopentyl)amino)-5-chloro-N-((4,6-dimethyl-2-oxo-1,2-dihydropyridin-3-yl)methyl)$_2$-methylbenzamide (0.175 g, 48N.

LCMS: 428.30 $(M+1)^+$; HPLC: 96.37% (@ 254 nm) ($R_t$; 6.357); $^1$H NMR (DMSO-$d_6$, 400 MHz) δ 11.47 (s, 1H), 8.21 (t, 1H), 7.16 (s, 1H), 6.92 (s, 1H), 5.85 (s, 1H), 5.63-5.69 (m, 1H), 4.98 (m, 2H), 4.23 (d, 2H, J=4 Hz), 3.54 (d, 2H, J=5.6 Hz), 3.46-3.50 (m, 1H), 2.18 (s, 3H), 2.16 (s, 3H), 2.10 (s, 3H), 1.67 (m, 2H), 1.59 (m, 2H), 1.47 (m, 2H), 1.36 (m, 2H).

Example 31

Synthesis of Compound 53: 3-(cyclopentyl(methyl)amino)-N-((4,6-dimethyl-2-oxo-1,2-dihydropyridin-3-yl)methyl)-2-methyl-5-(piperazin-1-yl)benzamide Compound 53

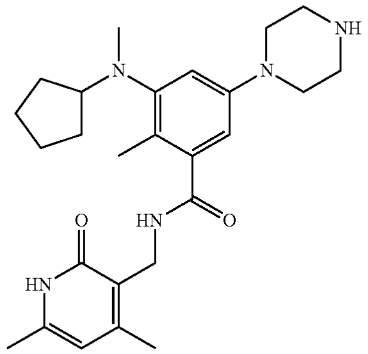

Step 1: Synthesis of methyl 5-bromo-3-(cyclopentylamino)-2-methylbenzoate

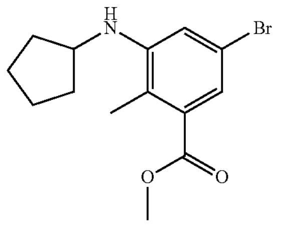

To a stirred solution of methyl 3-amino-5-bromo-2-methylbenzoate (3 g, 13.3 mmol) and cyclopentanone (5.6 g, 66 mmol) in methanol (30 mL), acetic acid (1.59 g, 26.6 mmol) was added and reaction stirred at room temperature for 3 h. Then sodium cyanoborohydride (2.08 g, 29.4 mmol) was added and reaction stirred overnight. On completion, solvent was removed under reduced pressure and crude material was used without further purification.

Step 2: Synthesis of methyl 5-bromo-3-(cyclopentyl(methyl)amino)-2-methylbenzoate

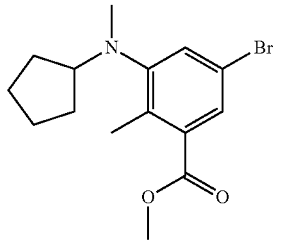

To a stirred solution of methyl 5-bromo-3-(cyclopentylamino)-2-methylbenzoate (1.6 g, 5.38 mmol) in acetonitrile (20 mL), cesium carbonate (3.5 g, 10.73 mmol) and methyl iodide (3.87 g, 27.25 mmol) were added and the resulting reaction mixture heated at 80° C. for 12 h. On completion, the reaction mixture was cooled to room temperature and filtered. The residue was washed with ethyl acetate and filtrate concentrated and purified by column chromatography to afford desired compound (1.6 g, 95%).

Step 3: Synthesis of tert-butyl 4-(3-(cyclopentyl(methyl)amino)-5-(methoxycarbonyl)-4-methylphenyl)piperazine-1-carboxylate

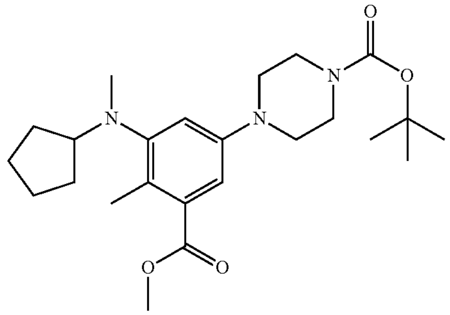 [SMILES: COC(=O)c1cc(N2CCN(C(=O)OC(C)(C)C)CC2)cc(N(C)C2CCCC2)c1C]

A solution of methyl 5-bromo-3-(cyclopentyl(methyl)amino)-2-methylbenzoate (1 g, 3.07 mmol), tert-butyl piperazine-1-carboxylate (0.85 g, 4.61 mmol) and $Cs_2CO_3$ (0.5 g, 1.53 mmol) in toluene (25 mL) was purged with argon for 10 min. Then, $Pd_2(dba)_3$ (0.31 g, 0.307 mmol) and BINAP (0.038 g, 0.061 mmol) was added to it and argon purged again for 10 min. The reaction mixture was stirred at 100° C. for 8 h. After completion, water was added to it and extracted with ethyl acetate. The combined organic layers were washed with water, dried over anhydrous $Na_2SO_4$, filtered and concentrated under reduced pressure to afford crude material which was purified by column chromatography to afford the title compound (0.44 g, 33.3%).

Step 4: Synthesis tert-butyl 4-(3-(cyclopentyl(methyl)amino)-5-(((4,6-dimethyl-2-oxo-1,2-dihydropyridin-3-yl)methyl)carbamoyl)-4-methylphenyl)piperazine-1-carboxylate

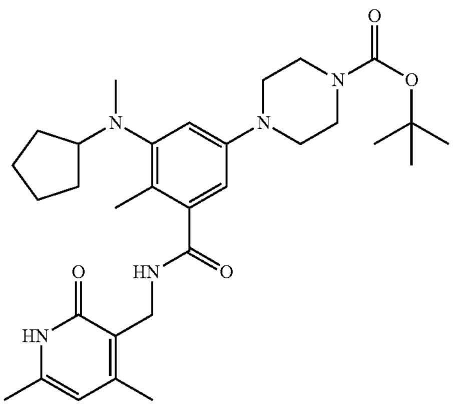 [SMILES: Cc1cc(C)c(CNC(=O)c2cc(N3CCN(C(=O)OC(C)(C)C)CC3)cc(N(C)C3CCCC3)c2C)c(=O)[nH]1]

Aqueous NaOH (0.061 g, 1.53 mmol) was added to a solution of tert-butyl 4-(3-(cyclopentyl(methyl)amino)-5-(methoxycarbonyl)-4-methylphenyl)piperazine-1-carboxylate (0.44 g, 1.02 mmol) in MeOH (10 mL) and stirred at 60° C. for 1 h. After completion of the reaction, ethanol was removed under reduced pressure and acidified using dilute HCl up to pH 6 and pH 4 was adjusted using citric acid. Extraction was carried out using ethyl acetate. Combined organic layers were dried concentrated giving respective acid (0.3 g, 70%).

The acid (0.3 g, 0.71 mmol) was then dissolved in DMSO (3 mL) and 3-(amino methyl)-4,6-dimethylpyridin-2(1H)-one (0.215 g, 1.43 mmol) was added to it. The reaction mixture was stirred at room temperature for 15 min before PYBOP (0.56 g, 1.07 mmol) was added to it and stirring was continued for overnight. After completion of the reaction, reaction mixture was poured into ice to obtain solid, which was filtered and washed with acetonitrile followed by ether to provide tert-butyl 4-(3-(cyclopentyl(methyl)amino)-5-(((4,6-dimethyl-2-oxo-1,2-dihydropyridin-3-yl)methyl)carbamoyl)-4-methylphenyl)piperazine-1-carboxylate (0.30 g, 75.7%).

Step 5: Synthesis of 3-(cyclopentyl(methyl)amino)-N-((4,6-dimethyl-2-oxo-1,2-dihydropyridin-3-yl)methyl)-2-methyl-5-(piperazin-1-yl)benzamide

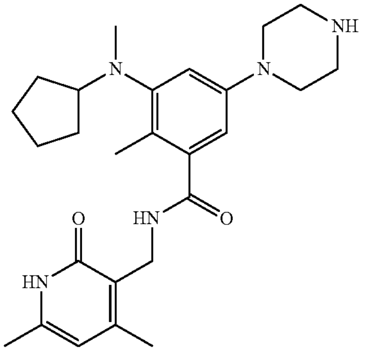 [SMILES: Cc1cc(C)c(CNC(=O)c2cc(N3CCNCC3)cc(N(C)C3CCCC3)c2C)c(=O)[nH]1]

A stirred solution of tert-butyl 4-(3-(cyclopentyl(methyl)amino)-5-(((4,6-dimethyl-2-oxo-1,2-dihydropyridin-3-yl)methyl)carbamoyl)-4-methylphenyl)piperazine-1-carboxylate (0.30, 0.54 mmol) in DCM (10 mL) was cooled to 0° C. and TFA (3 mL) was added to it. The reaction mixture was stirred at room temperature for 1 h. Upon completion, the mixture was concentrated to dryness. Half crude was purified by solvent washing giving the title compound as TFA salt (0.01 g, 8.33%).

LCMS: 452.39 $(M+1)^+$; HPLC: 83.92% (@ 254 nm) ($R_t$; 3.825); $^1$H NMR (DMSO-$d_6$, 400 MHz) δ 11.45 (s, 1H), 8.71 (s, 2H), 7.98 (s, 1H), 6.79 (s, 1H), 6.55 (s, 1H), 5.85 (s, 1H), 4.24 (d, 2H, J=3.2 Hz), 3.46 (1H in solvent peak), 3.22-3.26 (m, 8H), 2.50 (3H in solvent peak), 2.18 (s, 3H), 2.10 (s, 6H), 1.41-1.67 (m, 8H).

Half of the crude was basified with aqueous sodium bicarbonate till pH 8 and aqueous layer extracted with 20% MeOH/DCM. Combined organic layers were dried over sodium sulfate and concentrated to afford the title compound as free base.

Example 32

Synthesis of Compound 54: 3-(cyclopentyl(methyl)amino)-N-((4,6-dimethyl-2-oxo-1,2-dihydropyridin-3-yl)methyl)-2-methyl-5-(4-methylpiperazin-1-yl)benzamide Compound 54

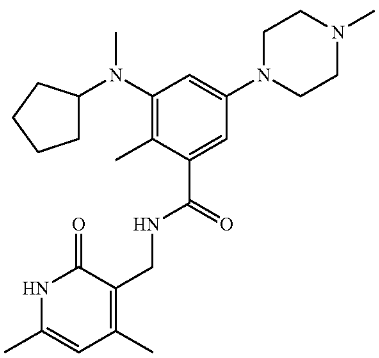

3-(Cyclopentyl(methyl)amino)-N-((4,6-dimethyl-2-oxo-1,2-dihydropyridin-3-yl)methyl)-2-methyl-5-(piperazin-1-yl)benzamide (free base) (0.100 g, 0.223 mmol) was dissolved in methanol (5 mL) and cooled to 0° C. before formalin (0.033 g, 1.1 mL, 2.23 mmol) was added. The resulting reaction mixture was stirred at same temperature for 30 minutes. Sodium cyanoborohydride (0.013 g, 0.22 mmol) was added to above reaction mixture and stirred at room temperature for 4 h. After completion, solvent was removed under reduced pressure and water added to the residue, with extraction carried out using DCM. The combined organic layers were dried, concentrated and purified by column chromatography to provide desired 3-(cyclopentyl(methyl)amino)-N-((4,6-dimethyl-2-oxo-1,2-dihydropyridin-3-yl)methyl)-2-methyl-5-(4-methylpiperazin-1-yl)benzamide (0.037 g, 36%).

LCMS: 466.40 $(M+1)^+$; HPLC: 99.18% (@ 254 nm) ($R_t$; 3.871); $^1$H NMR (DMSO-$d_6$, 400 MHz) δ 11.45 (s, 1H), 7.94 (t, 1H), 6.71 (s, 1H), 6.48 (s, 1H), 5.85 (s, 1H), 4.24 (d, 2H, J=3.2 Hz), 3.39-3.43 (m, 1H), 3.07 (bs, 4H), 2.46 (s, 3H), 2.31 (s, 3H), 2.18 (s, 3H), 2.10 (s, 3H), 2.08 (s, 3H), 1.66 (m, 2H), 1.59 (m, 2H), 1.39-1.48 (m, 4H).

Example 33

Synthesis of Compound 55: 5-chloro-3-(cyclohexyl(ethyl)amino)-N-((4,6-dimethyl-2-oxo-1,2-dihydropyridin-3-yl)methyl)-2-methylbenzamide Compound 55

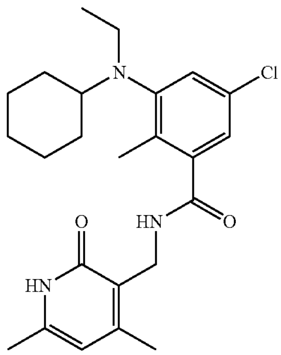

Step 1: Synthesis of methyl 5-chloro-3-(cyclohexylamino)-2-methylbenzoate

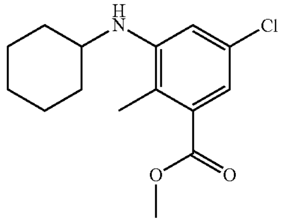 [SMILES: COC(=O)c1cc(Cl)cc(NC2CCCCC2)c1C]

To a stirred solution of methyl 3-amino-5-chloro-2-methylbenzoate (1 g, 5.02 mmol) and cyclohexanone (2.45 g, 25 mmol) in methanol (10 mL), acetic acid (0.3 g, 5.02 mmol) was added and reaction stirred at room temperature for 3 h. Then sodium cyanoborohydride (0.63 g, 10.05 mmol) was added and reaction stirred overnight. On completion, solvent was removed under reduced pressure and crude material was purified by column chromatography to afford methyl 5-chloro-3-(cyclohexylamino)-2-methylbenzoate (1.2 g, 89.92%).

Step 2: Synthesis of methyl 5-chloro-3-(cyclohexyl(ethyl)amino)-2-methylbenzoate

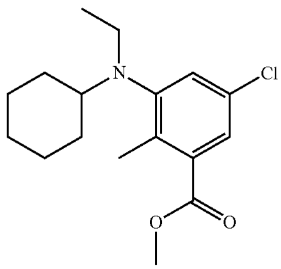 [SMILES: CCN(c1cc(Cl)cc(C(=O)OC)c1C)C1CCCCC1]

To a stirred solution of methyl 5-chloro-3-(cyclohexylamino)-2-methylbenzoate (1.2 g, 4.3 mmol) in dry DMF (15 mL), cesium carbonate (2.78 g, 8.5 mmol) and ethyl iodide (3.35 g, 21.47 mmol) were added. The resulting reaction mixture was heated at 80° C. for 18 h. On completion, the reaction mixture was cooled to room temperature and filtered, and the residue washed with ethyl acetate. The filtrate was concentrated and purified by column chromatography to afford methyl 5-chloro-3-(cyclohexyl(ethyl)amino)-2-methylbenzoate (0.25 g, 22.7%).

Step 3: Synthesis of 5-chloro-3-(cyclohexyl(ethyl) amino)-N-((4,6-dimethyl-2-oxo-1,2-dihydropyridin-3-yl)methyl)-2-methylbenzamide

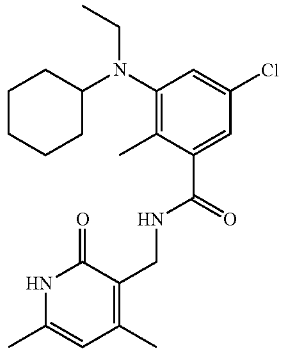 [SMILES: CCN(c1cc(Cl)cc(C(=O)NCc2c(C)cc(C)[nH]c2=O)c1C)C1CCCCC1]

Aqueous NaOH (0.065 g, 1.61 mmol) was added to a solution of methyl 5-chloro-3-(cyclohexyl(ethyl)amino)-2-methylbenzoate (0.25 g, 0.809 mmol) in EtOH (5 mL) and stirred at 60° C. for 1 h. After completion of the reaction, ethanol was removed under reduced pressure and acidified using dilute HCl up to pH 6 and pH 4 was adjusted using citric acid. Extraction was carried out using ethyl acetate. Combined organic layers were dried concentrated giving respective acid (0.22 g, 92%).

The acid (0.22 g, 0.745 mmol) was then dissolved in DMSO (2 mL) and 3-(amino methyl)-4,6-dimethylpyridin-2(1H)-one (0.246 g, 1.49 mmol) was added to it. The reaction mixture was stirred at room temperature for 15 min before PYBOP (0.58 g, 1.11 mmol) was added to it and stirring was continued for overnight. After completion of the reaction, the mixture was poured into ice to obtain a solid which was filtered and washed with acetonitrile. Final purification by column purification gave 5-chloro-3-(cyclohexyl(ethyl) amino)-N-((4,6-dimethyl-2-oxo-1,2-dihydropyridin-3-yl) methyl)-2-methylbenzamide (0.200 g, 46.6%). LCMS: 430.20 $(M+1)^+$; HPLC: 92.49% (@ 254 nm) ($R_t$; 5.264); $^1H$ NMR (DMSO-$d_6$, 400 MHz) δ 11.45 (s, 1H), 8.21 (t, 1H), 7.12 (s, 1H), 6.91 (s, 1H), 5.85 (s, 1H), 4.23 (d, 2H, J=4.4 Hz), 3.01-3.03 (m, 2H), 2.64-2.66 (m, 1H), 2.18 (s, 3H), 2.13 (s, 3H), 2.10 (s, 3H), 1.68 (m, 4H), 1.51-1.53 (m, 1H), 1.07-1.34 (m, 5H), 0.78 (t, 3H, J=6.8 Hz).

Example 34

Synthesis of Compound 56: 5-chloro-N-((4,6-dimethyl-2-oxo-1,2-dihydropyridin-3-yl)methyl)-3-(ethyl(tetrahydro-2H-pyran-4-yl)amino)-2-methylbenzamide Compound 56

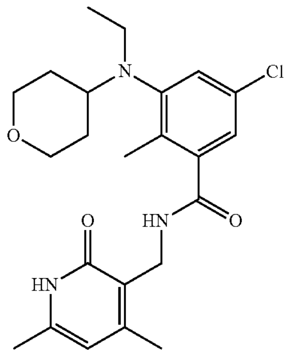

Step 1: Synthesis of methyl 5-chloro-2-methyl-3-((tetrahydro-2H-pyran-4-yl)amino)benzoate To a stirred solution of methyl 3-amino-5-chloro-2-methylbenzoate (1 g, 5.02 mmol) and tetrahydropyran-4-one (2.5 g, 25 mmol) in methanol (10 mL), acetic acid (0.3 g, 5.02 mmol) was added and reaction stirred at room temperature for 3 h. Then sodium cyanoborohydride (0.63 g, 10.05 mmol) was added and reaction stirred overnight. On completion, solvent was removed under reduced pressure and crude material was purified by column chromatography to afford methyl 5-chloro-2-methyl-3-((tetrahydro-2H-pyran-4-yl)amino) benzoate (0.5 g, 35.5%).

Step 2: Synthesis of methyl 5-chloro-3-(ethyl(tetrahydro-2H-pyran-4-yl)amino)-2-methylbenzoate

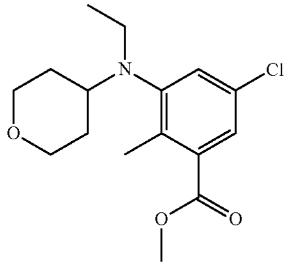 [SMILES: CCN(c1cc(Cl)cc(C(=O)OC)c1C)C1CCOCC1]

To a stirred solution of methyl 5-chloro-2-methyl-3-((tetrahydro-2H-pyran-4-yl)amino)benzoate (0.5 g, 1.76 mmol) in dry CAN (15 mL), cesium carbonate (1.2 g, 3.68 mmol) and ethyl iodide (2.7 g, 17.3 mmol) were added and the resulting reaction mixture was heated at 80° C. for 18 h. On completion, the mixture was cooled to room temperature and filtered with the residue washed with ethyl acetate. The filtrate was concentrated and then purified by column chromatography to afford desired methyl 5-chloro-3-(ethyl(tetrahydro-2H-pyran-4-yl)amino)-2-methylbenzoate (0.180 g, 34%).

Step 3: Synthesis of 5-chloro-N-((4,6-dimethyl-2-oxo-1,2-dihydropyridin-3-yl)methyl)-3-(ethyl(tetrahydro-2H-pyran-4-yl)amino)-2-methylbenzamide

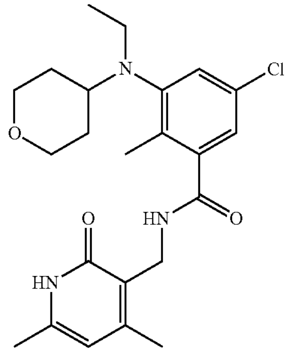 [SMILES: CCN(c1cc(Cl)cc(C(=O)NCc2c(C)cc(C)[nH]c2=O)c1C)C1CCOCC1]

Aqueous NaOH (0.05 g, 1.22 mmol) was added to a solution of methyl 5-chloro-3-(ethyl(tetrahydro-2H-pyran-4-yl)amino)-2-methylbenzoate (0.18 g, 0.608 mmol) in EtOH (5 mL) and stirred at 60° C. for 1 h. After completion of the reaction, ethanol was removed under reduced pressure and acidified using dilute HCl up to pH 6 and pH 4 and adjusted using citric acid. Extraction was carried out using ethyl acetate and the combined organic layers were dried and concentrated giving respective acid (0.15 g, 87%).

The acid (0.15 g, 0.530 mmol) was then dissolved in DMSO (1 mL) and 3-(amino methyl)-4,6-dimethylpyridin-2(1H)-one (0.160 g, 1.06 mmol) was added to it. The reaction mixture was stirred at room temperature for 15 min before PYBOP (0.413 g, 0.79 mmol) was added to it and stirring was continued for overnight. After completion of the reaction, reaction mixture was poured into ice and extraction was carried out using 10% MeOH/DCM. Combined organic layers were dried, concentrated and purified by silica gel column to afford 5-chloro-N-((4,6-dimethyl-2-oxo-1,2-dihydropyridin-3-yl)methyl)-3-(ethyl(tetrahydro-2H-pyran-4-yl)amino)-2-methylbenzamide (0.100 g, 43.88%). LCMS: 432.25 $(M+1)^+$; HPLC: 90.46% (@ 254 nm) ($R_t$; 4.833); $^1H$ NMR (DMSO-$d_6$, 400 MHz) δ 11.46 (s, 1H), 8.22 (t, 1H), 7.19 (s, 1H), 6.96 (s, 1H), 5.85 (s, 1H), 4.23 (d, 2H, J=4 Hz), 3.81 (d, 2H, J=10 Hz), 3.20-3.21 (m, 2H), 2.94-3.02 (m, 3H), 2.18 (s, 3H), 2.15 (s, 3H), 2.10 (s, 3H), 1.48-1.61 (m, 4H), 0.78 (t, 3H, J=6.4 Hz).

Example 35

Synthesis of Compound 57: 5-chloro-3-(cycloheptyl(ethyl)amino)-N-((4,6-dimethyl-2-oxo-1,2-dihydropyridin-3-yl)methyl)-2-methylbenzamide Compound 57

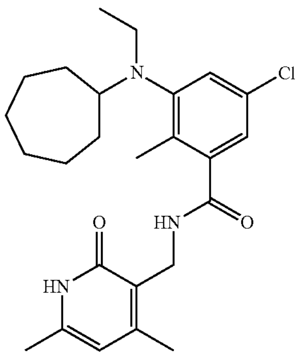

Step 1: Synthesis of methyl 5-chloro-3-(cycloheptylamino)-2-methylbenzoate

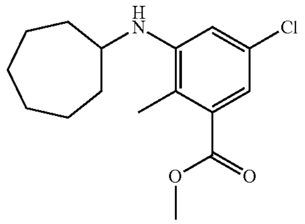 [SMILES: COC(=O)c1cc(Cl)cc(NC2CCCCCC2)c1C]

To a stirred solution of methyl 3-amino-5-chloro-2-methylbenzoate (1 g, 5.02 mmol) and cycloheptanone (2.81 g, 25 mmol) in methanol (10 mL), acetic acid (0.3 g, 5.02 mmol) was added and reaction stirred at room temperature for 3 h. Then sodium cyanoborohydride (0.65 g, 10.05 mmol) was added and reaction stirred overnight. On completion, solvent was removed under reduced pressure and crude material was purified by column chromatography to afford 5-chloro-3-(cycloheptylamino)-2-methylbenzoate (0.8 g, 56.2%).

Step 2: Synthesis of methyl 5-chloro-3-(cycloheptyl(ethyl)amino)-2-methylbenzoate

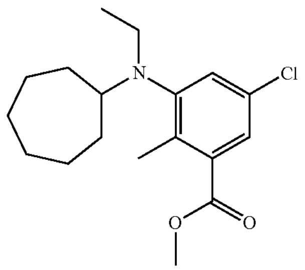 [SMILES: CCN(c1cc(Cl)cc(C(=O)OC)c1C)C1CCCCCC1]

To a stirred solution of 5-chloro-3-(cycloheptylamino)-2-methylbenzoate (0.8 g, 2.70 mmol) in dry DMF (10 mL), cesium carbonate (1.76 g, 5.4 mmol) and ethyl iodide (2.11 g, 13.5 mmol) were added and the resulting reaction mixture heated at 80° C. for 18 h. On completion, the mixture was cooled to room temperature and filtered, the residue washed with ethyl acetate and the filtrate concentrated before purification by column chromatography to afford the desired methyl 5-chloro-3-(cycloheptyl(ethyl)amino)-2-methylbenzoate (0.220 g, 25%).

Step 3: Synthesis of 5-chloro-3-(cycloheptyl(ethyl)amino)-N-((4,6-dimethyl-2-oxo-1,2-dihydropyridin-3-yl)methyl)-2-methylbenzamide

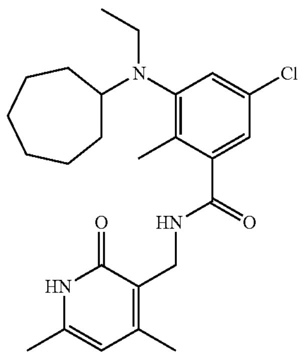 [SMILES: CCN(c1cc(Cl)cc(C(=O)NCc2c(C)cc(C)[nH]c2=O)c1C)C1CCCCCC1]

Aqueous NaOH (0.04 g, 1.02 mmol) was added to a solution of methyl 5-chloro-3-(cycloheptyl(ethyl)amino)-2-methylbenzoate (0.22 g, 0.68 mmol) in EtOH (5 mL) and stirred at 60° C. for 1 h. After completion of the reaction, ethanol was removed under reduced pressure and acidified using dilute HCl up to pH 6 and pH 4 and adjusted using citric acid. Extraction was carried out using ethyl acetate. With the combined organic layers dried and concentrated giving the respective acid (0.18 g, 85%).

The acid (0.18 g, 0.585 mmol) was then dissolved in DMSO (1.5 mL) and 3-(amino methyl)-4,6-dimethylpyridin-2(1H)-one (0.177 g, 1.16 mmol) was added to it. The reaction mixture was stirred at room temperature for 15 min before PYBOP (0.45 g, 0.87 mmol) was added to it and stirring was continued for overnight. After completion of the reaction, the reaction mixture was poured into ice to obtain solid, which was filtered and washed with acetonitrile before column purification to 5-chloro-3-(cycloheptyl(ethyl)amino)-N-((4,6-dimethyl-2-oxo-1,2-dihydropyridin-3-yl)methyl)-2-methylbenzamide (0.100 g, 38.7%). LCMS: 444.25 $(M+1)^+$; HPLC: 89.74% (@ 254 nm) ($R_t$; 5.933); $^1$H NMR (DMSO-$d_6$, 400 MHz) δ 11.46 (s, 1H), 8.21 (t, 1H), 7.07 (s, 1H), 6.88 (s, 1H), 5.85 (s, 1H), 4.23 (d, 2H, J=4 Hz), 3.02-3.03 (m, 2H), 2.77 (bs, 1H), 2.18 (s, 3H), 2.13 (s, 3H), 2.10 (s, 3H), 1.76 (m, 2H), 1.59-1.62 (m, 4H), 1.46 (m, 4H), 1.28 (m, 2H), 0.78 (t, 3H, J=6 Hz).

Example 36

Synthesis of Compound 58: Cis-3-((4-aminocyclohexyl)(methyl)amino)-5-bromo-N-((4,6-dimethyl-2-oxo-1,2-dihydropyridin-3-yl)methyl)-2-methylbenzamide Compound 58

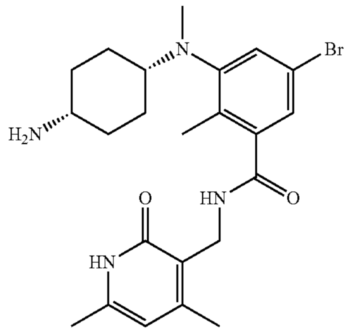

Step 1: Synthesis of 5-bromo-2-methyl-3-nitrobenzoic acid

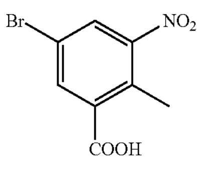

To stirred solution of 2-methyl-3-nitrobenzoic acid (50 g, 276.2 mmol) in conc. $H_2SO_4$ (200 mL), 1,3-dibromo-5,5-dimethyl-2,4-imidazolidinedione (43.4 g, 151.8 mmol) was added portion wise at room temperature and reaction mass was stirred at room temperature for 5 h. On completion, reaction mixture was poured onto ice cold water, solid precipitated was filtered, resulting residue was washed with water and dried under vacuum giving desired compound (71.7 g, 100%) which was used as is in subsequent steps.

Step 2: Synthesis of methyl 5-bromo-2-methyl-3-nitrobenzene

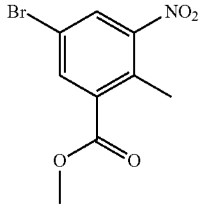

To stirred solution of 5-bromo-2-methyl-3-nitrobenzoic acid (287 g, 1103 mmol) in DMF (150 mL), sodium carbonate (468 g, 4415 mmol) and methyl iodide (626.63 g, 4415 mmol) were added. The resulting reaction mixture was heated at 60° C. for 8 h. On completion, a solid precipitated was filtered, residue washed with diethyl ether (5 times). The combined organic layers were dried, concentrated under reduced pressure giving desired compound (302 g, 99%) which was used as is in subsequent steps.

Step 3: Synthesis of methyl 3-amino-5-bromo-2-methylbenzoate

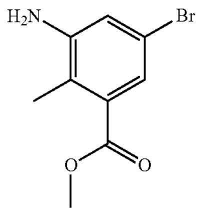

To a stirred solution of methyl 5-bromo-2-methyl-3-nitrobenzene (150 g, 544 mmol) in ethanol (750 mL), ammonium chloride (150 g, 2777 mmol) dissolved in water (750 mL) and iron powder (93.3 g, 1636 mmol) were added under stirring. The resulting reaction mixture was heated at 80° C. for 7 h. On completion, reaction mass was filtered through celite; giving washings of water and ethyl acetate to the residue, filtrate was extracted with ethyl acetate. Combined organic layers were dried, concentrated under reduced pressure giving desired compound which was used in subsequent steps without further purification.

Step 4: Synthesis of cis and trans methyl 5-bromo-3-((4-((tert-butoxycarbonyl)amino)cyclohexyl)amino)-2-methylbenzoate

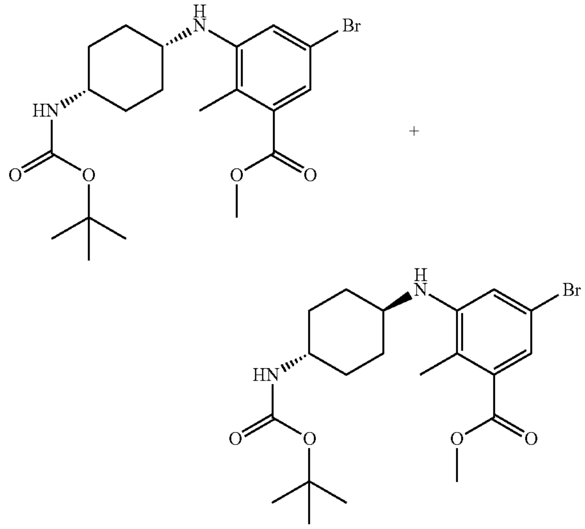

To a stirred solution of methyl 3-amino-5-bromo-2-methylbenzoate (5 g, 20.57 mmol) and tert-butyl (4-oxocyclohexyl)carbamate (5.6 g, 26.7 mmol) in methanol (50 mL), acetic acid (1.2 g, 20.57 mmol) was added and reaction stirred at room temperature for 8 h. Then sodium cyanoborohydride (1.6 g, 26.74 mmol) was added at 0° C. and reaction stirred overnight. On completion, solvent was removed under reduced pressure and crude material was purified by column chromatography twice eluting with ethyl acetate:hexane to afford (4 g, 44%) of less polar cis isomer and (3 g, 33%) of the pure more polar trans isomer.

Step 5: Synthesis of Cis-methyl 5-bromo-3-((4-((tert-butoxycarbonyl)amino)cyclohexyl)(methyl)amino)-2-methylbenzoate

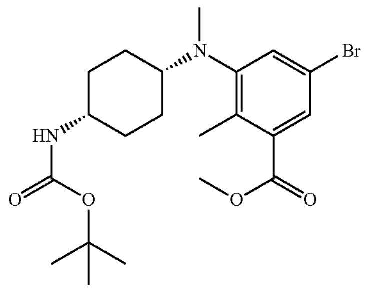 [SMILES: COC(=O)c1cc(Br)cc(N(C)[C@H]2CC[C@@H](NC(=O)OC(C)(C)C)CC2)c1C]

To a stirred solution of mixture of cis isomer of methyl 5-bromo-3-((4-((tert-butoxycarbonyl)amino)cyclohexyl)amino)-2-methylbenzoate (4 g, 9.09 mmol) in acetonitrile (50 mL) was added cesium carbonate (5.9 g, 18.18 mmol) and methyl iodide (6.45 g, 45.45 mmol). The resulting reaction mixture was heated at 80° C. for 7 h. On completion, the reaction mixture was cooled to room temperature and filtered, the residue was washed with ethyl acetate and filtrate was concentrated to afford desired crude compound which then purified by column chromatography giving desired compound (1.4 g, 34%).

Step 6: Synthesis of Cis-tert-butyl (4-((5-bromo-3-(((4,6-dimethyl-2-oxo-1,2-dihydropyridin-3-yl)methyl)carbamoyl)-2-methylphenyl)(methyl)amino)cyclohexyl)carbamate

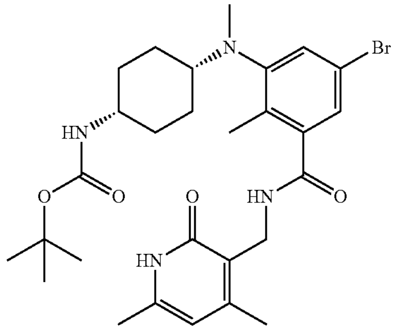 [SMILES: Cc1cc(C)c(CNC(=O)c2cc(Br)cc(N(C)[C@H]3CC[C@@H](NC(=O)OC(C)(C)C)CC3)c2C)c(=O)[nH]1]

Aqueous NaOH (0.23 g, 5.72 mmol) was added to a solution of cis-methyl 5-bromo-3-((4-((tert-butoxycarbonyl)amino)cyclohexyl)(methyl)amino)-2-methylbenzoate (1.3 g, 2.86 mmol) in MeOH (20 mL) and stirred at 60° C. for 1 h. After completion of the reaction, ethanol was removed under reduced pressure and acidified using dilute HCl up to pH 6 and pH 4 was adjusted using citric acid. Extraction was carried out using ethyl acetate. Combined organic layers were dried concentrated giving respective acid (1.13 g, 90.1%).

The acid (1.13 g, 2.57 mmol) was then dissolved in DMSO (10 mL) and 3-(amino methyl)-4,6-dimethylpyridin-2(1H)-one (0.87 g, 5.72 mmol) was added to it. The reaction mixture was stirred at room temperature for 15 min before PYBOP (2.23 g, 4.28 mmol) was added to it and stirring was continued for overnight. After completion of the reaction, reaction mass was poured into ice to obtain solid, this was filtered and washed with acetonitrile followed by purification with column chromatography to afford the desired compound (0.8 g, 49%).

Step 7: Synthesis of Cis-3-((4-aminocyclohexyl)(methyl)amino)-5-bromo-N-((4,6-dimethyl-2-oxo-1,2-dihydropyridin-3-yl)methyl)-2-methylbenzamide

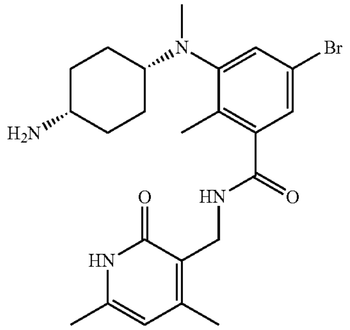 [SMILES: Cc1cc(C)c(CNC(=O)c2cc(Br)cc(N(C)[C@H]3CC[C@@H](N)CC3)c2C)c(=O)[nH]1]

A stirred solution of cis-tert-butyl (4-((5-bromo-3-(((4,6-dimethyl-2-oxo-1,2-dihydropyridin-3-yl)methyl)carbamoyl)-2-methylphenyl)(methyl)amino)cyclohexyl)carbamate (0.8 g, 1.39 mmol) in DCM (25 mL) was cooled to 0° C. and TFA (5 mL) was added to it. The reaction mixture was stirred at room temperature for 1 h. Upon completion, reaction was concentrated to dryness. Residue was basified with aqueous sodium bicarbonate till pH 8 and aqueous layer extracted with 20% MeOH/DCM. The combined organic layers were dried over sodium sulfate, filtered and concentrated to afford the desired compound (600 mg, 91% yield). LCMS: 475.15 $(M+1)^+$; HPLC % 95.88 (@ 254 nm) ($R_t$; 4.832; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-$d_6$, 400 MHz) δ 8.22 (t, 1H), 7.20 (s, 1H), 7.01 (s, 1H), 5.85 (s, 1H), 4.23 (d, 2H, J=3.6 Hz), 2.82-2.86 (m, 2H), 2.53 (s, 3H), 2.18 (s, 3H), 2.13 (s, 3H), 2.10 (s, 3H), 1.82-1.84 (m, 2H), 1.34-1.44 (m, 6H).

100 mg of cis-3-((4-aminocyclohexyl)(methyl)amino)-5-bromo-N-((4,6-dimethyl-2-oxo-1,2-dihydropyridin-3-yl)methyl)-2-methylbenzamide (free base) was then dissolved in methanolic HCl (5 mL) and stirred at room temperature for 1 h. On completion of salt formation solvent was removed under reduced pressure and resulting solid was purified by washing with diethyl ether to afford the corresponding HCl salt. Analytical Data of HCl salt: LCMS: 475.20 $(M+1)^+$; HPLC % 96.09 (@ 254 nm) ($R_t$; 4.818; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-$d_6$, 400 MHz) δ 11.51 (s, 1H), 8.28 (t, 1H), 8.08 (s, 3H), 7.31 (s, 1H), 7.08 (s, 1H), 5.90 (s, 1H), 4.24 (d, 2H, J=4.4 Hz), 3.05-3.13 (m, 2H), 2.54 (s, 3H), 2.19 (s 6H), 2.12 (s, 3H), 1.83 (m, 2H), 1.66 (m, 2H), 1.59-1.60 (m, 2H), 1.46 (m, 2H).

Example 37

Synthesis of Compounds 59: Trans-3-((4-aminocyclohexyl)(methyl)amino)-5-bromo-N-((4,6-dimethyl-2-oxo-1,2-dihydropyridin-3-yl)methyl)-2-methylbenzamide Compound 59

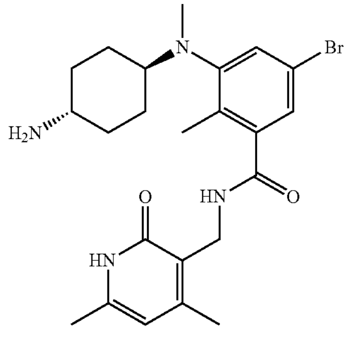

Step 1: Synthesis of Trans-methyl 5-bromo-3-((4-((tert-butoxycarbonyl)amino)cyclohexyl)(methyl)amino)-2-methylbenzoate

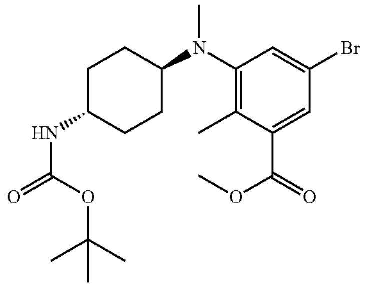 [SMILES: COC(=O)c1cc(Br)cc(N(C)[C@H]2CC[C@H](NC(=O)OC(C)(C)C)CC2)c1C]

To a stirred solution of trans-methyl 5-bromo-3-((4-((tert-butoxycarbonyl)amino)cyclohexyl)amino)-2-methylbenzoate (3 g, 6.81 mmol) in acetonitrile (40 mL), cesium carbonate (4.4 g, 13.62 mmol) and methyl iodide (4.83 g, 34.05 mmol) were added; the resulting reaction mixture was heated at 80° C. for 7 h. Upon completion, the reaction mixture was cooled to room temperature and filtered, the residue was washed with ethyl acetate and filtrate was concentrated to afford desired crude compound which then purified by column chromatography giving the desired compound (1.3 g, 43%).

Step 2: Synthesis of Trans-tert-butyl (4-((5-bromo-3-(((4,6-dimethyl-2-oxo-1,2-dihydropyridin-3-yl)methyl)carbamoyl)-2-methylphenyl)(methyl)amino)cyclohexyl)carbamate

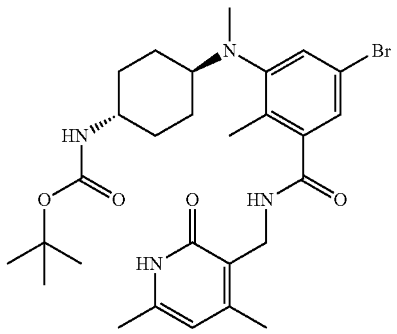 [SMILES: Cc1cc(C)c(CNC(=O)c2cc(Br)cc(N(C)[C@H]3CC[C@H](NC(=O)OC(C)(C)C)CC3)c2C)c(=O)[nH]1]

Aqueous NaOH (0.23 g, 5.72 mmol) was added to a solution of trans-methyl 5-bromo-3-((4-((tert-butoxycarbonyl)amino)cyclohexyl)(methyl)amino)-2-methylbenzoate (1.3 g, 2.86 mmol) in MeOH (20 mL) and was stirred at 60° C. for 1 h. After completion of the reaction, ethanol was removed under reduced pressure and the residue was acidified using dilute HCl up to pH 6 and to pH 4 using citric acid. The mixture was extracted was with ethyl acetate. The combined organic layers were dried, filtered and concentrated to give the respective acid (1 g, 83%).

The acid (1 g, 2.27 mmol) was then dissolved in DMSO (5 mL) and 3-(amino methyl)-4,6-dimethylpyridin-2(1H)-one (0.65 g, 4.54 mmol) was added to it. The reaction mixture was stirred at room temperature for 15 min before PYBOP (1.7 g, 3.4 mmol) was added to it and stirring was continued for overnight. After completion of the reaction, reaction mass was poured into ice to obtain solid, this was filtered and washed with acetonitrile followed by purification with column chromatography to afford the desired compound (0.7 g, 54%).

Step 3: Synthesis of Trans-3-((4-aminocyclohexyl)(methyl)amino)-5-bromo-N-((4,6-dimethyl-2-oxo-1,2-dihydropyridin-3-yl)methyl)-2-methylbenzamide

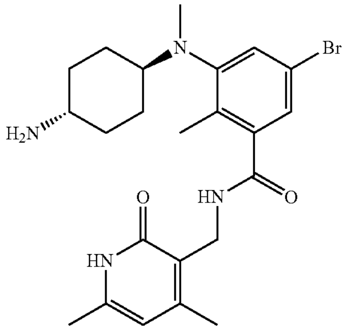 [SMILES: Cc1cc(C)c(CNC(=O)c2cc(Br)cc(N(C)[C@H]3CC[C@H](N)CC3)c2C)c(=O)[nH]1]

A stirred solution of trans-tert-butyl (4-((5-bromo-3-(((4,6-dimethyl-2-oxo-1,2-dihydropyridin-3-yl)methyl)carbamoyl)-2-methylphenyl)(methyl)amino)cyclohexyl)carbamate (0.7 g, 1.21 mmol) in DCM (8 mL) was cooled to 0° C. and TFA (2.5 mL) was added to it. Reaction mass was stirred at room temperature for 1 h. On completion, reaction was concentrated to dryness. Residue was basified with aqueous sodium bicarbonate till pH 8 and aqueous layer extracted with 20% MeOH/DCM. The combined organic layers were dried over sodium sulfate, filtered and concentrated to afford crude material which was then purified by solvent washings giving desired compound (0.5 g, 86%). LCMS: 475.20 $(M+1)^+$; HPLC % 92.35 (@ 254 nm) ($R_t$; 4.416; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-$d_6$, 400 MHz) δ 8.21 (t, 1H), 7.18 (s, 1H), 7.01 (s, 1H), 5.85 (s, 1H), 4.23 (d, 2H), 2.63-2.66 (m, 2H), 2.55 (s, 3H), 2.17 (s, 3H), 2.10 (s, 6H), 1.79-1.82 (m, 2H), 1.60 (m, 2H), 1.46-1.49 (m, 2H), 1.06-1.09 (m, 2H).

100 mg of trans-3-((4-aminocyclohexyl)(methyl)amino)-5-bromo-N-((4,6-dimethyl-2-oxo-1,2-dihydropyridin-3-yl)methyl)-2-methylbenzamide (free base) was then dissolved in methanolic HCl (5 mL) and stirred at room temperature for 1 h. On completion of salt formation, the solvent was removed under reduced pressure and resulting solid was purified by washing with diethyl ether to afford the corresponding HCl salt. Analytical data of HCl salt: LCMS: 475.20 $(M+1)^+$; HPLC % 91.40 (@ 254 nm) ($R_t$; 4.408; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 ml/min.; Gradient: 5% B to 95% B in 8 min, Hold for 1.5 min, 9.51-12 min 5% B); $^1H$ NMR (DMSO-$d_6$, 400 MHz) δ 11.51 (s, 1H), 8.28 (t, 1H), 8.06 (s, 3H), 7.31 (s, 1H), 7.08 (s, 1H), 5.89 (s, 1H), 4.24 (d, 2H, J=4.4 Hz), 2.92 (bs, 1H), 2.62-2.91 (m, 4H), 2.19 (s, 3H), 2.13 (s, 3H), 2.11 (s, 3H), 1.97 (d, 2H, J=10.8 Hz), 1.70 (m, 2H), 1.53-1.56 (m, 2H), 1.31-1.34 (m, 2H).

Example 38

Synthesis of Compound 60: Cis-3-((4-acetamidocyclohexyl)(methyl)amino)-5-bromo-N-((4,6-dimethyl-2-oxo-1,2-dihydropyridin-3-yl)methyl)-2-methylbenzamide Compound 60

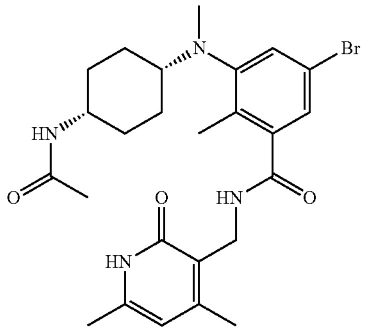

To a stirred solution of compound cis-3-((4-aminocyclohexyl)(methyl)amino)-5-bromo-N-((4,6-dimethyl-2-oxo-1,2-dihydropyridin-3-yl)methyl)-2-methylbenzamide (free base) (0.225, 0.474 mmol) in DMF (3 mL), EDCI.HCl (0.138 g, 0.718 mmol), HOBt (0.064 g, 0.47 mmol), triethyl amine (0.1 g, 0.99 mmol) and acetic acid (0.057 g, 0.949 mmol) were added at room temperature and stirred at same temperature for 18 h. On completion, water was added and extracted with 10% MeOH/DCM. Combined organic layers were dried, concentrated giving crude material; which then purified by column chromatography to afford the desired compound (0.17 g, 72%). LCMS: 517.25 $(M+1)^+$; HPLC % 95.83 (@ 254 nm) ($R_t$; 4.894; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-$d_6$, 400 MHz) δ 11.46 (s, 1H), 8.22 (t, 1H), 7.76 (d, 1H, J=7.2 Hz), 7.23 (s, 1H), 7.03 (s, 1H), 5.85 (s, 1H), 4.23 (d, 2H, J=3.6 Hz), 3.71 (bs, 1H), 2.89 (m, 1H), 2.53 (s, 3H), 2.18 (s, 3H), 2.16 (s, 3H), 2.10 (s, 3H), 1.81 (s, 3H), 1.74-1.76 (m, 2H), 1.53 (m, 2H), 1.39 (m, 4H).

Example 39

Synthesis of Compounds 61: Trans-3-((4-acetamidocyclohexyl)(methyl)amino)-5-bromo-N-((4,6-dimethyl-2-oxo-1,2-dihydropyridin-3-yl)methyl)-2-methylbenzamide Compound 61

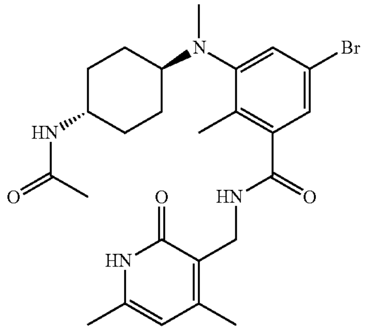

To a stirred solution of trans-3-((4-aminocyclohexyl)(methyl)amino)-5-bromo-N-((4,6-dimethyl-2-oxo-1,2-dihydropyridin-3-yl)methyl)-2-methylbenzamide (0.225, 0.474 mmol) in DMF (3 mL), EDCI.HCl (0.138 g, 0.718 mmol), HOBt (0.064 g, 0.47 mmol), triethyl amine (0.1 g, 0.99 mmol) and acetic acid (0.057 g, 0.949 mmol) were added at room temperature and stirred at same temperature for 18 h. On completion, water was added and extracted with 10% MeOH/DCM. Combined organic layers were dried, concentrated giving crude material; which then purified by column chromatography to afford desired compound (0.13 g, 53%).

LCMS: 517.20 $(M+1)^+$; HPLC % 93.92 (@ 254 nm) ($R_t$; 4.713; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-$d_6$, 400 MHz) δ 11.45 (s, 1H), 8.20 (t, 1H), 7.65 (d, 1H, J=7.6 Hz), 7.18 (s, 1H), 7.01 (s, 1H), 5.85 (s, 1H), 4.23 (d, 2H, J=3.6 Hz), 3.42-3.44 (m, 1H), 2.68-2.71 (m, 1H), 2.56 (s, 3H), 2.18 (s, 3H), 2.10 (s, 6H), 1.77-1.80 (m, 2H), 1.74 (s, 3H), 1.62-1.65 (m, 2H), 1.46-1.54 (m, 2H), 1.07-1.23 (m, 2H).

Example 40

Synthesis of Compound 62: 2-bromo-3-(cyclopentyl(methyl)amino)-N-((4,6-dimethyl-2-oxo-1,2-dihydropyridin-3-yl)methyl)benzamide Compound 62

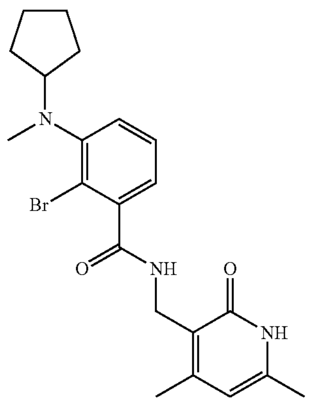

Step 1: methyl 2-bromo-3-nitrobenzoate

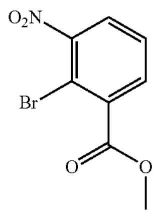

To a stirred solution of 2-bromo-3-nitrobenzoate (3 g, 12.19 mmol) in DMF (33 mL), sodium carbonate (5.16 g, 48.67 mmol) and methyl iodide (6.92 g, 48.67 mmol) were added. Resulting reaction mixture was heated at 60° C. for 4 h. On completion, water was added to the mixture and extraction carried out using DCM. The combined organic layers were dried and concentrated under reduced pressure to obtain crude methyl 2-bromo-3-nitrobenzoate (4 g, crude).

Step 2: Synthesis of methyl 3-amino-2-bromobenzoate

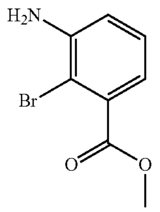

To a stirred solution of methyl 2-bromo-3-nitrobenzoate (4 g, 15.38 mmol) in ethanol (20 mL), ammonium chloride (4 g, 74.07 mmol) dissolved in water (20 mL) and iron powder (6.88 g, 123 mmol) were added under stirring. Resulting reaction mixture was heated at 80° C. for 1 h. On completion, water was added to the mixture and filtered through celite. The filtrate was extracted with ethyl acetate and the combined organic layers washed with water and sodium bicarbonate solution, dried and concentrated under reduced pressure giving the desired methyl 3-amino-2-bromobenzoate (3 g, 85%) which was used without further purification.

Step 3: Synthesis of methyl 2-bromo-3-(cyclopentylamino)benzoate

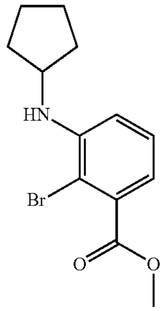 [SMILES: COC(=O)c1cccc(NC2CCCC2)c1Br]

To a stirred solution of methyl 3-amino-2-bromobenzoate (3 g, 13.0 mmol) and cyclopentanone (5.4 g, 64.28 mmol) in methanol (20 mL), acetic acid (1.56 g, 26 mmol) was added and reaction stirred at room temperature for 3 h. Then sodium cyanoborohydride (2 g, 31.7 mmol) was added and reaction stirred overnight. On completion, solvent was removed under reduced pressure and crude material purified by column chromatography to afford methyl 2-bromo-3-(cyclopentylamino)benzoate (1.4 g, 36%).

Step 4: Synthesis of methyl 2-bromo-3-(cyclopentyl(methyl)amino)benzoate

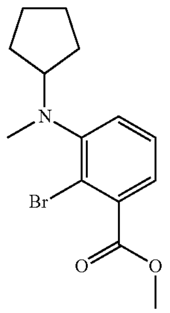

To a stirred solution of methyl 2-bromo-3-(cyclopentylamino)benzoate (1.4 g, 4.69 mmol) in acetonitrile (10 mL), cesium carbonate (3 g, 9.2 mmol) and methyl iodide (3.38 g, 23.3 mmol) were added and the resulting reaction mixture heated at 80° C. for 12 h. On completion, the mixture was cooled to room temperature and filtered and the residue was washed with ethyl acetate. The filtrate was concentrated and purified by column chromatography to afford methyl 2-bromo-3-(cyclopentyl(methyl)amino)benzoate (1.1 g, 75%).

Step 5: Synthesis of 2-bromo-3-(cyclopentyl(methyl)amino)-N-((4,6-dimethyl-2-oxo-1,2-dihydropyridin-3-yl)methyl)benzamide

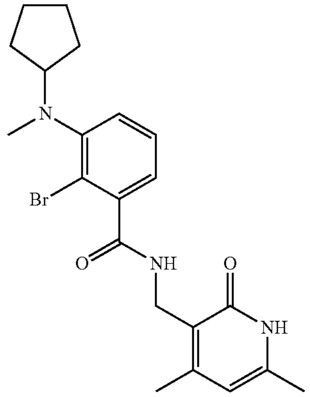

Aqueous NaOH (0.064 g, 1.6 mmol) was added to a solution of methyl 2-bromo-3-(cyclopentyl(methyl)amino)benzoate (0.25 g, 0.801 mmol) in MeOH (5 mL) and stirred at 60° C. for 1 h. After completion of the reaction, ethanol was removed under reduced pressure and acidified using dilute HCl up to pH 6 and pH 4 was adjusted using citric acid. Extraction was carried out using ethyl acetate. Combined organic layers were dried concentrated giving respective acid (0.2 g, 84%).

The acid (0.2 g, 0.67 mmol) was then dissolved in DMSO (1.5 mL) and 3-(amino methyl)-4,6-dimethylpyridin-2(1H)-one (0.204 g, 1.34 mmol) was added to it. The reaction mixture was stirred at room temperature for 15 min before PYBOP (0.516 g, 1.00 mmol) was added to it and stirring was continued for overnight. After completion of the reaction, the mixture was poured into ice to obtain a solid, which was filtered and washed with acetonitrile. Final purification by preparative HPLC provided 2-bromo-3-(cyclopentyl(methyl)amino)-N-((4,6-dimethyl-2-oxo-1,2-dihydropyridin-3-yl)methyl)benzamide as the TFA salt (0.02 g, 6.89%). LCMS: 432.10 $(M+1)^+$; HPLC % 96.05 (@ 254 nm) ($R_t$; 4.908); $^1H$ NMR (DMSO-$d_6$, 400 MHz) δ 11.47 (s, 1H), 8.21 (t, 1H), 7.26-7.29 (m, 2H), 6.94 (d, 1H, J=8 Hz), 5.86 (s, 1H), 4.25 (d, 2H), 3.59 (m, 1H), 2.56 (s, 3H), 2.19 (s, 3H), 2.10 (s, 3H), 1.61-1.67 (m, 4H), 1.46 (bs, 4H).

Example 41

Synthesis of Compound 63: 3-(cyclopentyl(methyl)amino)-N-((4,6-dimethyl-2-oxo-1,2-dihydropyridin-3-yl)methyl)-2-vinylbenzamide Compound 63

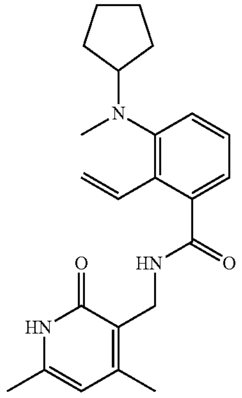

Step 1: Synthesis of methyl 2-bromo-3-nitrobenzoate

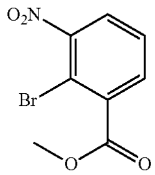

To a stirred solution of 2-bromo-3-nitrobenzoic acid (3 g, 12.19 mmol) in DMF (30 mL), sodium carbonate (5.16 g, 48.6 mmol) and methyl iodide (6.92 g, 48.7 mmol) were added. Resulting reaction mixture was heated at 60° C. for 8 h. On completion, solid precipitated was filtered, residue washed with ethyl acetate (5 times). Combined organic layers were dried, concentrated under reduced pressure giving desired crude 2-bromo-3-nitrobenzoate (4 g, 99%) which was used without further purification.

Step 2: Synthesis of methyl 3-amino-2-bromobenzoate

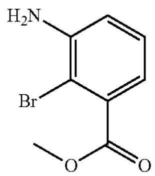

To stirred solution of above crude 2-bromo-3-nitrobenzoate (4 g, 15.38 mmol) in ethanol (20 mL), ammonium chloride (4 g, 74.0 mmol) dissolved in water (20 mL) and iron powder (6.87 g, 123 mmol) were added under stirring. The resulting reaction mixture was heated at 80° C. for 7 h. On completion, the reaction mixture was filtered through celite, washing with water and ethyl acetate and the filtrate extracted with ethyl acetate. The combined organic layers were dried and concentrated under reduced pressure giving the desired crude product (3 g).

Step 3: Synthesis of methyl 2-bromo-3-(cyclopentylamino)benzoate

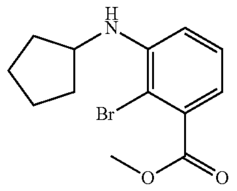 [SMILES: COC(=O)c1cccc(NC2CCCC2)c1Br]

To a stirred solution of methyl 3-amino-2-bromobenzoate (3 g, 13.01 mmol) and cyclopentanone (5.6 g, 66 mmol) in methanol (30 mL), acetic acid (1.59 g, 26.6 mmol) was added and the reaction stirred at room temperature for 3 h. Then sodium cyanoborohydride (2.08 g, 29.4 mmol) was added and the mixture stirred overnight. On completion, solvent was removed under reduced pressure and crude material was purified by column chromatography to afford methyl 2-bromo-3-(cyclopentylamino)benzoate (1.4 g, 36%).

Step 4: Synthesis of methyl 2-bromo-3-(cyclopentyl(methyl)amino)benzoate

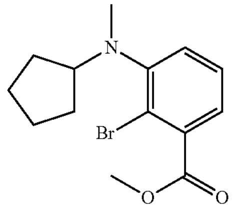 [SMILES: COC(=O)c1cccc(N(C)C2CCCC2)c1Br]

To a stirred solution of methyl 2-bromo-3-(cyclopentylamino)benzoate (1.4 g, 4.69 mmol) in acetonitrile (20 mL), cesium carbonate (3.0 g, 9.2 mmol) and methyl iodide (3.38 g, 23.4 mmol) were added and the resulting reaction mixture heated at 80° C. for 12 h. On completion, the mixture was cooled to room temperature and filtered and the residue washed with ethyl acetate. The filtrate was concentrated and then purified by column chromatography to afford desired methyl 2-bromo-3-(cyclopentyl(methyl)amino)benzoate (1.1 g, 75%).

Step 5: Synthesis of methyl 3-(cyclopentyl(methyl)amino)-2-vinylbenzoate

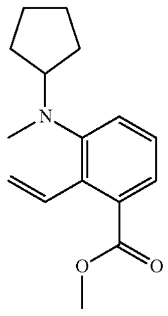 [SMILES: C=Cc1c(C(=O)OC)cccc1N(C)C1CCCC1]

To a stirred solution of methyl 2-bromo-3-(cyclopentyl(methyl)amino)benzoate (1 equiv.) and 4,4,5,5-tetramethyl-2-vinyl-1,3,2-dioxaborolane (1.2 equiv.) in dioxane/water mixture (5 mL+1 mL), $Na_2CO_3$ (3.6 equiv.) was added and solution purged with argon for 15 min. Then, $Pd(PPh_3)_4$ (0.1 equiv.) was added and argon purged for 10 min. and the reaction mixture heated at 100° C. for 2 h. On completion, the reaction mixture was diluted with water and extracted with 10% MeOH/DCM. The combined organic layers were dried over $Na_2SO_4$ and solvent removed under reduced pressure to afford crude material which was purified by column chromatography over silica gel to afford the desired methyl 3-(cyclopentyl(methyl)amino)-2-vinylbenzoate.

Step 6: Synthesis of 3-(cyclopentyl(methyl)amino)-N-((4,6-dimethyl-2-oxo-1,2-dihydropyridin-3-yl)methyl)-2-vinylbenzamide

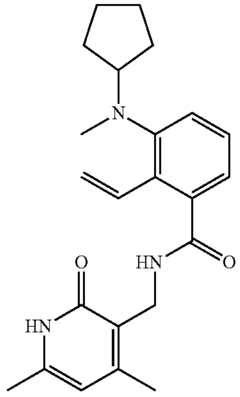 [SMILES: C=Cc1c(C(=O)NCc2c(C)cc(C)[nH]c2=O)cccc1N(C)C1CCCC1]

To a stirred solution of methyl 3-(cyclopentyl(methyl)amino)-2-vinylbenzoate (1 equiv.) in ethanol (10 mL), aqueous NaOH solution (1.5 equiv. in 10 mL water) was added and reaction stirred at 60° C. for 4 h. On completion, ethanol was removed under reduced pressure and residue acidified with 1N HCl to pH 6. The precipitate was filtered, washed with water and dried to obtain pure corresponding acid.

To a solution of this respective acid (1 equiv.) in DMSO (10 mL), PyBOP (1.5 equiv.) was added and reaction stirred at rt for 15 min. Then 3-(amino methyl)-4,6-dimethylpyridin-2(1H)-one (2 equiv.) was added and reaction stirred overnight. On completion, water was added and the resulting solid filtered and washed with water. This solid was stirred with acetonitrile for 10 min and filtered again to obtain 3-(cyclopentyl(methyl)amino)-N-((4,6-dimethyl-2-oxo-1,2-dihydropyridin-3-yl)methyl)-2-vinylbenzamide which was purified by preparative HPLC yielding the TFA salt (0.045 g, 10.39%). LCMS: 380.25 $(M+1)^+$; HPLC % 98.00 (@ 254 nm) ($R_t$; 4.323); $^1H$ NMR (DMSO-$d_6$, 400 MHz) δ 11.51 (s, 1H), 8.01 (s, 1H), 7.25 (bs, 2H), 6.81-6.88 (m, 2H), 5.85 (s, 1H), 5.49 (d, 1H, J=18 Hz), 5.40 (bs, 1H), 4.34 (3H merged in solvent peak), 4.19 (d, 3H, J=4.8 Hz), 2.17 (s, 3H), 2.10 (s, 3H), 1.61 (m, 4H), 1.47 (bs, 4H).

Example 42

Synthesis of Compound 64: 5-chloro-3-(cyclopentyl(ethyl)amino)-N-((4,6-dimethyl-2-oxo-1,2-dihydropyridin-3-yl)methyl)-2-methylbenzamide Compound 64

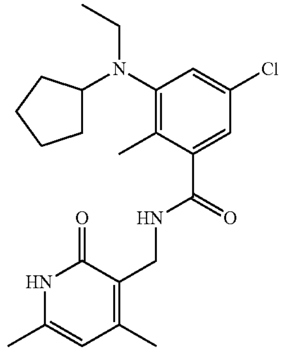

Step 1: Synthesis of 5-chloro-2-methyl-3-nitrobenzoic acid

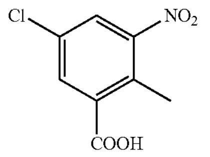

5-Chloro-2-methylbenzoic acid (4 g, 23.39 mmol) was added to cooled conc. $H_2SO_4$ (27 mL) at −10° C. lot wise. After 10 minutes nitrating mixture [Prepared by mixing Conc. HNO3 (3.3 g, 52.68 mmol) with conc.$H_2SO_4$ (4.4 mL)] was added drop wise at −10° C. Resulting reaction mixture was stirred at −10° C. for 30 minutes. On completion, the mixture was poured on ice cold water and the resulting solid precipitated was filtered, washed with water and dried under vacuum giving the desired chloro-2-methyl-3-nitrobenzoic acid (4.95 g, 99%).

Step 2: Synthesis of methyl 5-chloro-2-methyl-3-nitrobenzoate

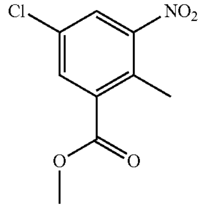

To a stirred solution of chloro-2-methyl-3-nitrobenzoic acid (6.75 g, 31.25 mmol) in DMF (33 mL), sodium carbonate (13.23 g, 125.18 mmol) and methyl iodide (17.77 g, 125.2 mmol) were added. The resulting reaction mixture was heated at 60° C. for 4 h. On completion, water was added and extracted out using DCM. Combined organic layers were dried, concentrated under reduced pressure and purified by column chromatography over silica (60-120 mesh size) giving methyl 5-chloro-2-methyl-3-nitrobenzoate (6 g, 83.65%).

Step 3: Synthesis of methyl 3-amino-5-chloro-2-methyl benzoate

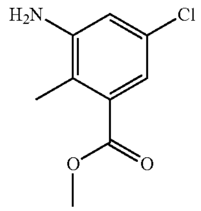

To a stirred solution of methyl 5-chloro-2-methyl-3-nitrobenzoate (6 g, 26.13 mmol) in ethanol (60 mL), ammonium chloride (6 g, 112.1 mmol) dissolved in water (60 mL) and iron powder (11.88 g, 208.4 mmol) were added under stirring. The resulting reaction mixture was heated at 80° C. for 1 h. On completion, water was added to reaction and the mixture was filtered through celite. The filtrate was extracted with ethyl acetate and the combined organic layers were washed with water, dried, concentrated under reduced pressure giving methyl 3-amino-5-chloro-2-methyl benzoate which was used without further purification.

Step 4: Synthesis of methyl 5-chloro-3-(cyclopentylamino)-2-methylbenzoate

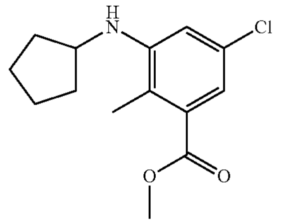 [SMILES: COC(=O)c1cc(Cl)cc(NC2CCCC2)c1C]

To a stirred solution of methyl 3-amino-5-chloro-2-methyl benzoate (1 g, 5.02 mmol) and cyclopentanone (2.1 g, 25 mmol) in methanol (10 mL), acetic acid (0.3 g, 5.02 mmol) was added and reaction stirred at room temperature for 3 h. Then sodium cyanoborohydride (0.37 g, 5.90 mmol) was added and reaction stirred overnight. On completion, solvent was removed under reduced pressure and crude material was purified by column chromatography to afford methyl 5-chloro-3-(cyclopentylamino)-2-methylbenzoate (0.62 g, 46.2%).

Step 5: Synthesis of methyl 5-chloro-3-(cyclopentyl(ethyl)amino)-2-methylbenzoate

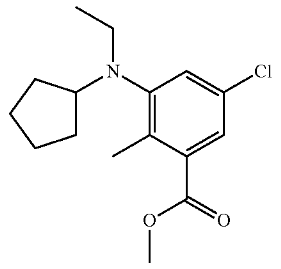 [SMILES: CCN(c1cc(Cl)cc(C(=O)OC)c1C)C1CCCC1]

To a stirred solution of methyl 5-chloro-3-(cyclopentylamino)-2-methylbenzoate (0.62 g, 2.32 mmol) in dry DMF (10 mL), cesium carbonate (3.78 g, 11.6 mmol) and ethyl iodide (5.43 g, 34.8 mmol) were added and the resulting reaction mass was heated at 80° C. for 18 h. On completion, reaction mixture was cooled to room temperature and filtered. The residue was washed with ethyl acetate and filtrate concentrated and purified by column chromatography to afford desired methyl 5-chloro-3-(cyclopentyl(ethyl)amino)-2-methylbenzoate (0.101 g, 15%).

Step 6: Synthesis of 5-chloro-3-(cyclopentyl(ethyl)amino)-N-((4,6-dimethyl-2-oxo-1,2-dihydropyridin-3-yl)methyl)-2-methylbenzamide

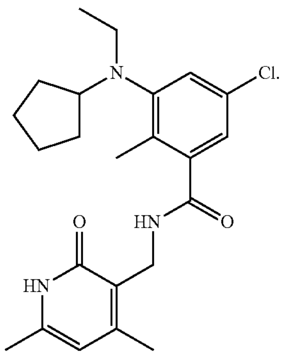 [SMILES: CCN(c1cc(Cl)cc(C(=O)NCc2c(C)cc(C)[nH]c2=O)c1C)C1CCCC1]

Aqueous NaOH (0.1 g, 2.5 mmol) was added to a solution of methyl 5-chloro-3-(cyclopentyl(ethyl)amino)-2-methylbenzoate (0.5 g, 1.69 mmol) in EtOH (10 mL) and stirred at 60° C. for 1 h. After completion of the reaction, ethanol was removed under reduced pressure and acidified using dilute HCl up to pH 6 and pH 4 was adjusted using citric acid. Extraction was carried out using ethyl acetate and the combined organic layers were dried concentrated giving respective acid (0.41 g, 86%).

The acid (0.10 g, 0.355 mmol) was then dissolved in DMSO (1.5 mL) and 3-(amino methyl)-4,6-dimethylpyridin-2(1H)-one (0.104 g, 0.77 mmol) was added to it. The reaction mixture was stirred at room temperature for 15 min before PYBOP (0.277 g, 0.533 mmol) was added to it and stirring was continued for overnight. After completion of the reaction, the mixture was poured into ice and the resulting solid filtered and washed with acetonitrile followed by additional solvent washings to yield 5-chloro-3-(cyclopentyl(ethyl)amino)-N-((4,6-dimethyl-2-oxo-1,2-dihydropyridin-3-yl)methyl)-2-methylbenzamide (0.107 g, 72%). LCMS: 416.25 $(M+1)^+$; HPLC % 91.83 (@ 254 nm) ($R_t$; 5.021); $^1$H NMR (DMSO-$d_6$, 400 MHz) δ 11.45 (s, 1H), 8.21 (t, 1H), 7.19 (s, 1H), 6.95 (s, 1H), 5.85 (s, 1H), 4.23 (d, 2H, J=4 Hz), 3.45 (t, 1H), 2.94-2.96 (m, 2H), 2.18 (s, 3H), 2.15 (s, 3H), 2.10 (s, 3H), 1.58-1.64 (m, 4H), 1.47 (m, 2H), 1.32 (m, 2H), 0.77 (t, 3H, J=6.8 Hz).

Example 43

Synthesis of Compound 19: 5-bromo-2-chloro-3-(cyclopentyl(methyl)amino)-N-((4,6-dimethyl-2-oxo-1,2-dihydropyridin-3-yl)methyl)benzamide Compound 19

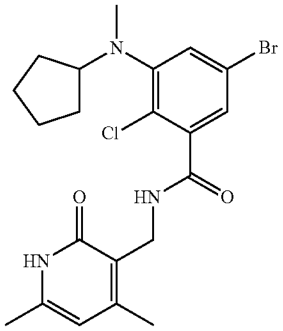

Step 1: Synthesis of 5-bromo-2-chloro-3-nitrobenzoic acid

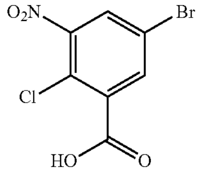 [SMILES: O=C(O)c1cc(Br)cc([N+](=O)[O-])c1Cl]

5-bromo-2-chlorobenzoic acid: (5 g, 27.3 mmol) was added to cooled conc. $H_2SO_4$ (20 mL) at −10° C. in small portions. After 10 minutes nitrating mixture {prepared by mixing conc. $HNO_3$ (2.5 mL) with conc. $H_2SO_4$ (10 mL)} was added drop wise at −10° C. The reaction mixture was stirred at −10° C. for 30 minutes. On completion, the reaction mixture was poured into ice cold water and the solid collected by filtration. The solid was washed with water and dried under vacuum to give 5-bromo-2-chloro-3-nitrobenzoic acid: (3.6 g, 60.5%).

Step 2: Synthesis of methyl 5-bromo-2-chloro-3-nitrobenzoate

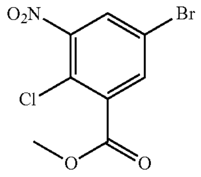

To stirred solution of -bromo-2-chloro-3-nitrobenzoic acid (3.6 g, 12.9 mmol) in DMF (40 mL) was added sodium carbonate (4.1 g, 38.6 mmol) and methyl iodide (4 mL, 64.3 mmol). The reaction mixture was heated at 60° C. for 8 h. On completion, water was added to the reaction mixture and the product was extracted with ethyl acetate. The combined organic layers were washed with sat. bicarbonate solution and 5 N HCl. The organics were dried and concentrated under reduced pressure to afford methyl 5-bromo-2-chloro-3-nitrobenzoate (3.4 g, 89.9%).

Step 3: Synthesis of methyl 3-amino-5-bromo-2-chlorobenzoate

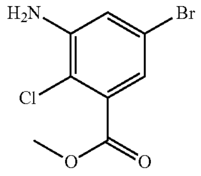

To stirred solution of methyl 5-bromo-2-chloro-3-nitrobenzoate (3.4 g, 11.6 mmol) in ethanol (19 mL) was added ammonium chloride (3.4 g, 57.8 mmol) dissolved in water (30 mL) and iron powder (5.16 g, 92.5 mmol). The reaction mixture was heated at 80° C. for 1 h. On completion, the reaction mixture was filtered through celite washing with ethanol and ethylacetate. The filtrate was extracted with ethyl acetate and the combined organic layers were washed with water, dried and concentrated under reduced pressure to give methyl 3-amino-5-bromo-2-chlorobenzoate (2.8 g, 92.1%).

Step 4: Synthesis of methyl 5-bromo-2 chloro-3-(cyclopentylamino)benzoate

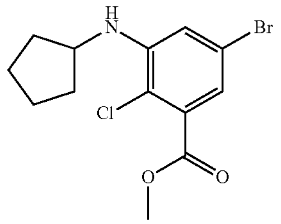 [SMILES: COC(=O)c1cc(Br)cc(NC2CCCC2)c1Cl]

To a stirred solution of methyl 3-amino-5-bromo-2-chlorobenzoate (2.8 g, 10.6 mmol) and cyclopentanone (4.47 g, 53.2 mmol) in methanol (20 mL) was added acetic acid (1.3 mL, 21.2 mmol) and the reaction stirred at room temperature for 3 h. Then sodium cyanoborohydride (1.7 g, 26.6 mmol) was added and the reaction stirred overnight. On completion, the solvent was removed under reduced pressure and the product was purified by column chromatography to afford methyl 5-bromo-2-chloro-3-(cyclopentylamino)benzoate (0.5 g, 14.2%).

Step 5: Synthesis of methyl 5-bromo-2-chloro-3-(cyclopentyl(methyl)amino)benzoate

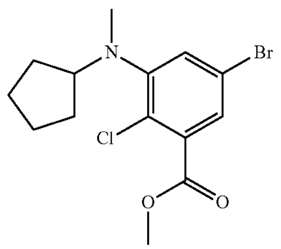 [SMILES: COC(=O)c1cc(Br)cc(N(C)C2CCCC2)c1Cl]

To a stirred solution of methyl 5-bromo-2-chloro-3-(cyclopentylamino)benzoate (0.550 g, 1.65 mmol) in acetonitrile (20 mL) was added cesium carbonate (1.08 g, 3.31 mmol) and methyl iodide (1.17 g, 8.25 mmol). The reaction mixture was heated at 80° C. for 12 h. On completion, the reaction mixture was cooled to room temperature and filtered. The residue was washed with ethyl acetate and the filtrate was concentrated and purified by column chromatography to afford methyl 5-bromo-2-chloro-3-(cyclopentyl(methyl)amino)benzoate (0.350 g, 61%).

Step 6: Synthesis of 5-bromo-2-chloro-3-(cyclopentyl(methyl)amino)-N-((4,6-dimethyl-2-oxo-1,2-dihydropyridin-3-yl)methyl)benzamide

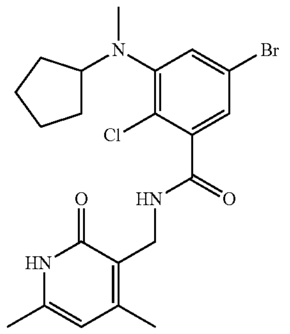 [SMILES: Cc1cc(C)c(CNC(=O)c2cc(Br)cc(N(C)C3CCCC3)c2Cl)c(=O)[nH]1]

Aqueous NaOH (0.06 g, 152 mmol) was added to a solution of methyl 5-bromo-2-chloro-3-(cyclopentyl(methyl)amino)benzoate (0.350 g, 1.01 mmol) in EtOH (4 mL) and water (1 mL) and stirred at 60° C. for 1 h. After completion of the reaction, ethanol was removed under reduced pressure and acidified using dilute HCl up to pH 6 and to pH 4 with citric acid. The product was extracted with ethyl acetate. The combined organic layers were dried and concentrated to give the desired acid (0.266 g, 79.4%).

The acid (0.265 g, 0.80 mmol) was then dissolved in DMSO (3 mL) and 3-(amino methyl)-4,6-dimethylpyridin-2(1H)-one (0.243 g, 1.60 mmol) was added to it. The reaction mixture was stirred at room temperature for 15 min before PYBOP (0.624 g, 1.20 mmol) was added and stirring was continued overnight. After completion of the reaction, the reaction mixture was poured into ice to obtain a solid. The solid was filtered and washed with acetonitrile followed by purification by column chromatography and prep. HPLC to give 5-bromo-2-chloro-3-(cyclopentyl(methyl)amino)-N-((4,6-dimethyl-2-oxo-1,2-dihydropyridin-3-yl)methyl)benzamide (0.012 g, 3.22%).

Analytical Data: LCMS: 466.05 $(M+1)^+$; HPLC: 99.28% (@ 254 nm) ($R_t$; 6.917; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (CD3OD, 400 MHz) δ 7.42 (d, 1H, J=2 Hz), 7.24 (d, 1H, J=1.6 Hz), 6.16 (s, 1H), 4.66 (s, 2H), 3.71 (m, 1H), 2.70 (s, 3H), 2.37 (s, 3H), 2.25 (s, 3H), 1.79 (m, 2H), 1.70 (m, 2H), 1.56 (m, 4H).

Example 44

Syntheses of Compounds 91, 92, 97, 98, 102, 104, 105, 117-123, 126, 127, 137, 144, 157, 191, 192, 205-209, 212, 213, 222, 243-245, 268, 269, 273, 276-279, 282-287, 290, 301, 302, 306, 308-311, 313, 315, 319-322, 328, 332-336, 339, 340, 344, 347-349, 356, 386, 387, 389, 390, and 392-417

Compounds 91, 92, 97, 98, 102, 104, 105, 117-123, 126, 127, 137, 144, 157, 191, 192, 205-209, 212, 213, 222, 243-245, 268, 269, 273, 276-279, 282-287, 290, 301, 302, 306, 308-311, 313, 315, 319-322, 328, 332-336, 339, 340, 344, 347-349, 356, 386, 387, 389, 390, and 392-417 were synthesized as described below.

Compound 91: 3-(allyl(piperidin-4-yl)amino)-5-chloro-N-((4,6-dimethyl-2-oxo-1,2-dihydropyridin-3-yl)methyl)-2-methylbenzamide

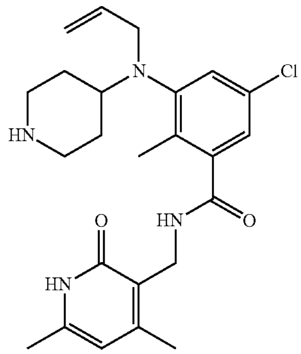 [SMILES: C=CCN(c1cc(Cl)cc(C(=O)NCc2c(C)cc(C)[nH]c2=O)c1C)C1CCNCC1]

Step 1: Synthesis of 5-chloro-2-methyl-3-nitrobenzoic acid

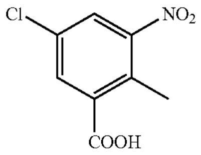

5-Chloro-2-methylbenzoic acid (4.0 g, 23 mmol) was added portionwise to cooled conc. $H_2SO_4$ (27 mL) at −10° C. After 10 minutes the nitrating mixture {consisting of concentrated HNO3 (3.3 g, 52 mmol) and concentrated $H_2SO_4$ (4.4 mL)} was added dropwise at −10° C. The mixture was stirred at −10° C. for 30 minutes and poured on ice cold water. The solid precipitate was filtered, washed with water and dried under vacuum to give the title compound (4.95 g, 99%).

Step 2: Synthesis of methyl 5-chloro-2-methyl-3-nitrobenzoate

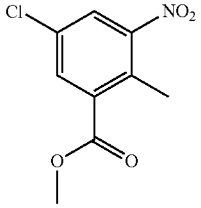

To a stirred solution of 5-chloro-2-methyl-3-nitrobenzoic acid (6.75 g, 31.3 mmol) in DMF (33 mL), were added sodium carbonate (13.23 g, 125 mmol) and methyl iodide (17.77 g, 125 mmol). The mixture was heated at 60° C. for 4 h. On completion, water was added to the reaction mass and extraction was carried out using DCM. The combined organic layers were dried, concentrated under reduced pressure, and purified by column chromatography over silica gel (to afford the title compound (6.0 g, 83%).

Step 3: Synthesis of methyl 3-amino-5-chloro-2-methyl benzoate

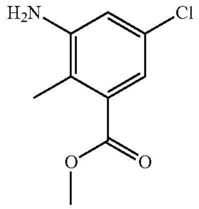

To a stirred solution of methyl 5-chloro-2-methyl-3-nitrobenzoate (6.0 g, 26 mmol) in ethanol (60 mL) were added ammonium chloride (6.0 g, 110 mmol) dissolved in water (60 mL) and iron powder (11.9 g, 208 mmol) under stirring. The mixture was heated at 80° C. for 1 h. On completion, water was added and the reaction mixture was filtered through celite. The filtrate was extracted with ethyl acetate. The combined organic layers were washed with water, dried, concentrated under reduced pressure to afford the title compound which was used without further purification.

Step 4: Synthesis of tert-butyl 4-((5-chloro-3-(methoxycarbonyl)-2-methylphenyl)amino)piperidine-1-carboxylate

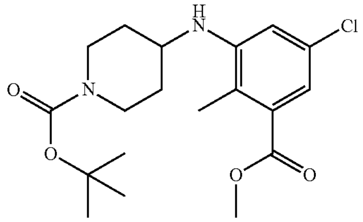 [SMILES: COC(=O)c1cc(Cl)cc(NC2CCN(C(=O)OC(C)(C)C)CC2)c1C]

To a stirred solution of methyl 3-amino-5-chloro-2-methyl benzoate (5.0 g, 25 mmol) and tert-butyl 4-oxopiperidine-1-carboxylate (25.3 g, 127 mmol) in methanol (50 mL), acetic acid (1.5 g, 25 mmol) was added and the reaction stirred at room temperature for 8 h. Then sodium cyanoborohydride (1.89 g, 30.1 mmol) was added at 0° C. and the reaction stirred overnight at room temperature. On completion, the solvent was removed under reduced pressure and the crude material was purified by column chromatography to afford the title compound (5.0 g, 52%).

Step 5: Synthesis of tert-butyl 4-(allyl(5-chloro-3-(methoxycarbonyl)-2-methylphenyl)amino)piperidine-1-carboxylate

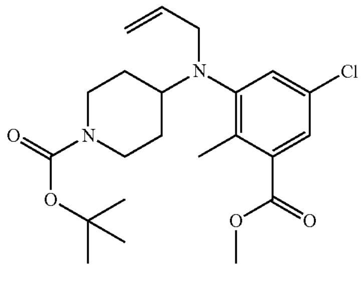 [SMILES: C=CCN(c1cc(Cl)cc(C(=O)OC)c1C)C1CCN(C(=O)OC(C)(C)C)CC1]

To a stirred solution of tert-butyl 4-((5-chloro-3-(methoxycarbonyl)-2-methylphenyl)amino)piperidine-1-carboxylate (0.70 g, 1.82 mmol) in DMF (7 mL), was added NaH (0.052 g, 2.19 mmol) at 0° C. After stirring for 20 minutes, 3-bromoprop-1-ene (0.44 g, 3.64 mmol) was added and the mixture was heated at 80° C. for 15 h. On completion, the reaction mass was quenched with ice cold water and extraction was carried out using DCM. The combined organic layers were dried, concentrated under reduced pressure and the residue was purified by column chromatography to afford the title compound (0.3 g, 39%).

Step 6: Synthesis of tert-butyl 4-(allyl (5-chloro-3-(((4,6-dimethyl-2-oxo-1,2-dihydropyridin-3-yl)methyl)carbamoyl)-2-methylphenyl)amino)piperidine-1-carboxylate

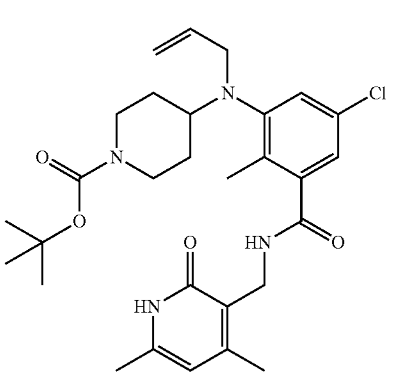 [SMILES: C=CCN(c1cc(Cl)cc(C(=O)NCc2c(C)cc(C)[nH]c2=O)c1C)C1CCN(C(=O)OC(C)(C)C)CC1]

Aqueous NaOH (0.113 g, 2.83 mmol) was added to a solution of tert-butyl 4-(allyl(5-chloro-3-(methoxycarbonyl)-2-methylphenyl)amino)piperidine-1-carboxylate (0.60 g, 1.41 mmol) in ethanol (15 mL). After stirring at 60° C. for 1 h ethanol was removed under reduced pressure and the mixture acidified using dilute HCl up to pH 6 and pH 4 was adjusted using citric acid. Extraction was carried out using DCM. The combined organic layers were dried and concentrated giving respective acid (0.5 g, 86%). The above acid (0.5 g, 1.22 mmol) was then dissolved in DMSO (5 mL) and 3-(amino methyl)-4,6-dimethylpyridin-2(1H)-one (0.37 g, 2.44 mmol) was added to it. The reaction mixture was stirred at room temperature for 15 min before PYBOP (0.95 g, 1.83 mmol) was added to it and stirring was continued overnight. The mixture was poured into ice and extracted with 10% MeOH/DCM. The combined organic layers were dried, concentrated, and purified by column chromatography to afford the title compound (0.2 g, 30%).

Step 7: Synthesis of 3-(allyl(piperidin-4-yl)amino)-5-chloro-N-((4,6-dimethyl-2-oxo-1,2-dihydropyridin-3-yl)methyl)-2-methylbenzamide

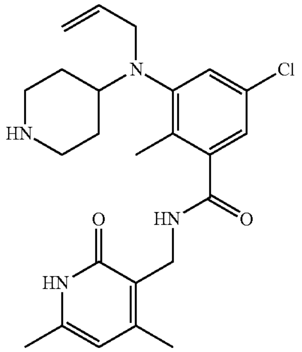 [SMILES: C=CCN(c1cc(Cl)cc(C(=O)NCc2c(C)cc(C)[nH]c2=O)c1C)C1CCNCC1]

A stirred solution of compound tert-butyl 4-(allyl (5-chloro-3-(((4,6-dimethyl-2-oxo-1,2-dihydropyridin-3-yl) methyl)carbamoyl)-2-methylphenyl)amino)piperidine-1-carboxylate (0.2 g, 0.36 mmol) in DCM (5 mL) was cooled to 0° C. and TFA (0.5 mL) was added. The mixture was stirred at room temperature for 18 h. and concentrated to dryness. The residue was washed with diethyl ether and then purified by preparative HPLC to afford the title compound as TFA salt (0.06 g, 37%). LCMS: 443.25 $(M+1)^+$; HPLC: 97.14% (@ 254 nm) ($R_t$; 5.074; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.46 (s, 1H), 8.38 (bs, 1H), 8.21 (t, 1H), 8.05 (d, 1H), 7.21 (d, 1H, J=4.4 Hz), 6.97 (d, 1H, J=1.6 Hz), 5.86 (s, 1H), 5.56-5.64 (m, 1H), 4.97-5.09 (m, 2H), 4.24 (d, 2H, J=4.4 Hz), 3.62 (d, 2H, J=5.2 Hz), 3.23 (m, 2H), 3.10-3.16 (m, 1H), 2.85-2.88 (m, 2H), 2.19 (s, 3H), 2.18 (s, 3H), 2.10 (s, 3H), 1.83-1.86 (m, 2H), 1.68-1.73 (m, 2H).

Compound 97: 5-chloro-N-((4,6-dimethyl-2-oxo-1,2-dihydropyridin-3-yl)methyl)-2-methyl-3-(piperidin-4-yl(propyl)amino)benzamide

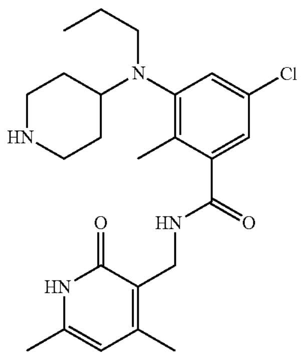 [SMILES: CCCN(c1cc(Cl)cc(C(=O)NCc2c(C)cc(C)[nH]c2=O)c1C)C1CCNCC1]

To a stirred solution of 3-(allyl(piperidin-4-yl)amino)-5-chloro-N-((4,6-dimethyl-2-oxo-1,2-dihydropyridin-3-yl) methyl)-2-methylbenzamide (0.04 g, 0.09 mmol) in MeOH (3 mL) was added 10% Pd/C (0.01 g) and reaction stirred at room temperature under hydrogen (balloon pressure) for 2 h. The mixture was filtered through celite and the filtrate was concentrated under reduced pressure to obtain a crude solid which was purified by preparative HPLC to afford the title compound as TFA salt (0.012 g, 40%). LCMS: 445.25 $(M+1)^+$; HPLC: 95.52% (@ 254 nm) ($R_t$; 5.102; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.46 (s, 1H), 8.39 (bs, 1H), 8.22 (t, 1H), 8.03 (bs, 1H), 7.25 (s, 1H), 6.98 (s, 1H), 5.86 (s, 1H), 4.24 (d, 2H, J=4.8 Hz), 3.24-3.27 (m, 2H), 3.00 (m, 1H), 2.92 (m, 2H), 2.83-2.86 (m, 2H), 2.18 (s, 3H), 2.17 (s, 3H), 2.10 (s, 3H), 1.79-1.82 (m, 2H), 1.67-1.71 (m, 2H), 1.18-1.23 (m, 2H), 0.75 (t, 3H, J=8 Hz).

Compound 144: 3,6-dichloro-N-[(4,6-dimethyl-2-oxo-1,2-dihydropyridin-3-yl)methyl]-4-[methyl (piperidin-4-yl)amino]pyridine-2-carboxamide

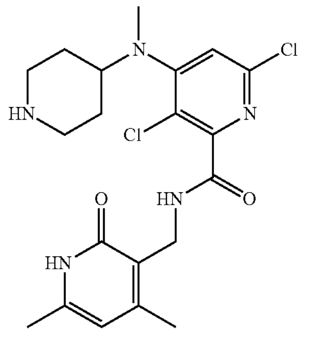

Step 1: Synthesis of methyl 3,4,6-trichloropyridine-2-carboxylate

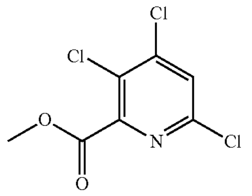

To a stirred solution of methyl 3,6-dichloropyridine-2-carboxylate (0.96 g, 4.66 mmol) in TFA (5 ml) was added hydrogen peroxide (30% w/w aqueous solution, 435 μl, 2.5 mmol) and the reaction mixture was heated at 60° C. for 20 h. The reaction mixture was then cooled and slowly poured onto saturated $K_2CO_3$ solution (100 ml), followed by extraction of the aqueous layer with EtOAc (2×200 ml), washing of the combined organic phases with brine (2×50 ml), drying ($Na_2SO_4$) and evaporation. The desired 3,6-dichloro-2-(methoxycarbonyl)pyridin-1-ium-1-olate was used crude in the next stage of the synthesis without any further purification. To the crude 3,6-dichloro-2-(methoxycarbonyl)pyridin-1-ium-1-olate (~70% purity, 2.40 g, 7.7 mmol) was added $POCl_3$ (3.5 ml, 38 mmol) and the solution was heated to 100° C. for 4 h. After cooling the $POCl_3$ was removed in vacuo to give a white solid which was chromatographed over silica gel eluting with 0% to 10% of EtOAc in heptane to afford the title compound as colourless needles (340 mg, 30% over two steps). LC-MS 100%, 2.20 min (3.5 minute LC-MS method), m/z=239.8/241.7, $^1$H NMR (500 MHz, Chloroform-d) δ 7.51 (1H, s), 3.92 (3H, s).

Step 2: Synthesis of methyl 4-({1-[(tert-butoxy)carbonyl]piperidin-4-yl}(methyl)amino)-3,6-dichloropyridine-2-carboxylate

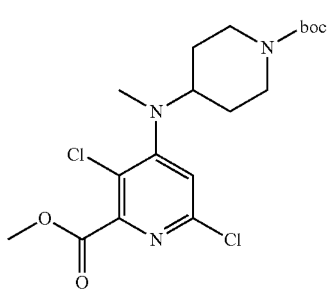

To a stirred solution of methyl 3,4,6-trichloropyridine-2-carboxylate (310 mg, 1.29 mmol) in DMF (5 ml) was added TEA (359 μl, 2.58 mmol) followed by tert-butyl 4-(methylamino)piperidine-1-carboxylate (276 mg, 1.29 mmol) and the reaction mixture was heated at 100° C. for 4 h. The reaction mixture was then cooled to room temperature and poured onto water (50 ml), followed by extraction of the product into TBME (3×50 ml), washing of the combined organics with brine (50 ml), drying with $Na_2SO_4$ and evaporation. The crude product was then purified over a 10 g silica Isolute column eluting with a gradient of 0% to 50% EtOAc in heptane to afford the title compound as a white solid (95 mg, 18%). LC-MS 95%, 2.29 min (3.5 minute LC-MS method), m/z=418.1/419.8, $^1$H NMR (500 MHz, Chloroform-d) δ 6.87 (s, 1H) 4.12-4.34 (m, 2H) 3.99 (s, 3H) 3.69-3.80 (m, 1H) 2.79 (s, 3H) 2.64-2.77 (m, 2H) 1.75 (br. s., 4H) 1.48 (s, 9H).

Step 3: Synthesis of 4-({1-[(tert-butoxy)carbonyl]piperidin-4-yl}(methyl)amino)-3,6-dichloropyridine-2-carboxylic acid

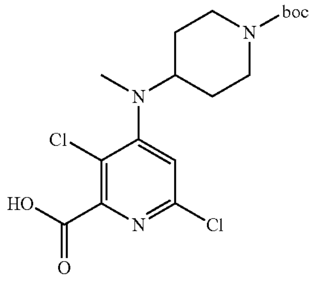

To a stirred solution of methyl 4-({1-[(tert-butoxy)carbonyl]piperidin-4-yl}(methyl)amino)-3,6-dichloropyridine-2-carboxylate (95 mg, 0.23 mmol) in THF (5 ml) was added 2M aqueous NaOH (2.3 ml, 4.54 mmol) and the reaction mixture was left to stir at room temperature for 16 h after which time the THF was evaporated in vacuo. The aqueous phase was then treated with an aqueous 10% citric acid solution to pH 5-6 and then extracted with EtOAc (3×50 ml), the combined organic phases were then dried with $Na_2SO_4$ and evaporated to give the title compound as a white powder (77 mg, 84%). LC-MS 100%, 2.02 min (3.5 minute LC-MS method), m/z=403.9/405.6, $^1$H NMR (500 MHz, Methanol-d4) δ 7.09 (s, 1H) 4.14-4.22 (m, 2H) 3.80-3.89 (m, 1H) 2.84 (s, 5H) 1.74-1.81 (m, 4H) 1.46 (s, 9H).

Step 4: Synthesis of tert-butyl 4-[(3,6-dichloro-2-{[(4,6-dimethyl-2-oxo-1,2-dihydropyridin-3-yl)methyl]carbamoyl}pyridin-4-yl)(methyl)amino]piperidine-1-carboxylate

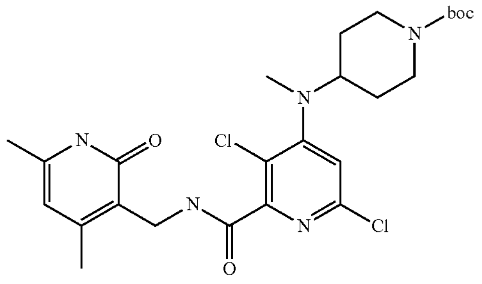

To a stirred solution of 4-({1-[(tert-butoxy)carbonyl]piperidin-4-yl}(methyl)amino)-3,6-dichloropyridine-2-carboxylic acid (75 mg, 0.19 mmol) in DMF (2 ml) cooled to 0° C. h was added DIPEA (48 µl, 0.28 mmol) followed by PyBOP (116 mg, 0.22 mmol) and 3-(aminomethyl)-4,6-dimethyl-1,2-dihydropyridin-2-one (89% purity, 35 mg, 0.2 mmol). The reaction mixture was then stirred at room temperature for 16 h after which the reaction was poured onto water (30 ml) and extracted with EtOAc (3×50 ml) after which the combined organics were washed with brine (50 ml) and dried ($Na_2SO_4$) and evaporated. The crude product was purified using a 5 g silica Isolute column eluting with a gradient of 0% to 100% EtOAc in heptane to afford the title compound as a white solid which contained ~45% w/w tripyrrolidinophosphene oxide by NMR—this compound was used in the next stage of the synthesis without any further purification. LC-MS 93%, 1.97 min (3.5 minute LC-MS method), m/z=538.0/539.45/542.05, $^{1}$H NMR (500 MHz, Chloroform-d) δ 10.03 (br. s, 1H), 8.13-7.97 (m, 1H), 6.79 (s, 1H), 5.87 (s, 1H), 4.50 (d, J=6.1 Hz, 2H), 4.16 (br. m, 2H), 3.78-3.62 (m, 1H), 2.72 (s, 3H), 2.65 (br. m, 2H), 2.35 (s, 3H), 2.22 (s, 3H), 1.73-1.63 (m, 4H), 1.44 (s, 9H).

Step 5: Synthesis of 3,6-dichloro-N-[(4,6-dimethyl-2-oxo-1,2-dihydropyridin-3-yl)methyl]-4-[methyl(piperidin-4-yl)amino]pyridine-2-carboxamide hydrochloride

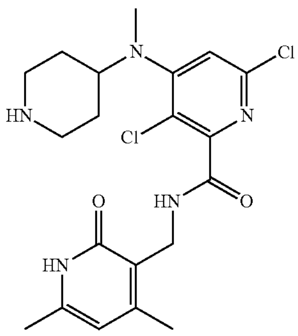 [SMILES: Cc1cc(C)c(CNC(=O)c2nc(Cl)cc(N(C)C3CCNCC3)c2Cl)c(=O)[nH]1]

Tert-butyl4-[(3,6-dichloro-2-{[(4,6-dimethyl-2-oxo-1,2-dihydropyridin-3-yl)methyl]carbamoyl}pyridin-4-yl)(methyl)amino]piperidine-1-carboxylate (310 mg, 1.29 mmol) was dissolved in 4M HCl in dioxane solution (3 ml) and stirred at room temperature for 16 h after which the solvent was evaporated and the compound purified by preparative HPLC to afford the title compound as a beige powder (13 mg, 14%). LC-MS 100%, 2.41 min (7 minute LC-MS method), m/z=438.1/439.8, $^{1}$H NMR (500 MHz, Methanol-d4) δ 7.12 (s, 1H), 6.11 (s, 1H), 4.46 (s, 2H), 4.01-3.81 (m, 1H), 3.45 (d, J=12.9 Hz, 2H), 3.12-2.97 (m, 2H), 2.82 (s, 3H), 2.35 (s, 3H), 2.22 (s, 3H), 2.13-1.93 (m, 4H).

Compound 386: 3,6-dichloro-n-[(4,6-dimethyl-2-oxo-1,2-dihydropyridin-3-yl)methyl]-4-[methyl(oxan-4-yl)amino]pyridine-2-carboxamide

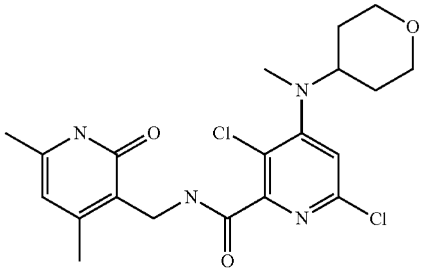 [SMILES: Cc1cc(C)c(CNC(=O)c2nc(Cl)cc(N(C)C3CCOCC3)c2Cl)c(=O)[nH]1]

Step 1: Synthesis of methyl 3,6-dichloro-4-[methyl(oxan-4-yl)amino]pyridine-2-carboxylate To a stirred solution of methyl 3,4,6-trichloropyridine-2-carboxylate (600 mg, 2.50 mmol) in DMF (12 ml) was added TEA (696 µl, 4.99 mmol) followed by N-methyloxan-4-amine (287 mg, 2.50 mmol) and the reaction mixture was heated at 100° C. for 20 h. The reaction mixture was then cooled to room temperature and poured onto water (100 ml), followed by extraction of the product into EtOAc (3×100 ml), washing of the combined organics with brine (50 ml), drying with $Na_2SO_4$ and evaporation. The crude product was then purified over a 10 g silica Isolute column eluting with a gradient of 0% to 60% EtOAc in heptane to afford the title compound as a white solid (114 mg, 14%). LC-MS 100%, 1.91 min (3.5 minute LC-MS method), m/z=319.3/320.9, $^{1}$H NMR (500 MHz, Chloroform-d) δ 6.87 (s, 1H), 4.15-4.00 (m, 2H), 3.98 (s, 3H), 3.93-3.71 (m, 1H), 3.54-3.24 (m, 2H), 2.82 (s, 3H), 1.94 (dd, J=12.1, 4.7 Hz, 2H), 1.70 (d, J=10.2 Hz, 2H). (br. s., 4H) 1.48 (s, 9H)

Step 2: Synthesis of 3,6-dichloro-4-[methyl(oxan-4-yl)amino]pyridine-2-carboxylic acid

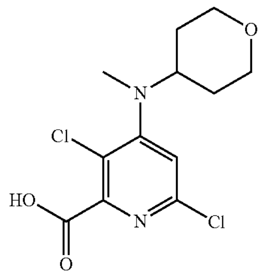 [SMILES: CN(c1cc(Cl)nc(C(=O)O)c1Cl)C1CCOCC1]

To a stirred solution of methyl 3,6-dichloro-4-[methyl(oxan-4-yl)amino]pyridine-2-carboxylate (114 mg, 0.36 mmol) in THF (5 ml) was added 2M aqueous NaOH (0.89 ml, 1.79 mmol) and the reaction mixture was left to stir at room temperature for 20 h after which time the THF was evaporated in vacuo. The aqueous phase was then treated with an aqueous 10% citric acid solution to pH 5-6 and then extracted with EtOAc (3×50 ml) followed by a solution of 1:1 IPA/$CHCl_3$ (2×50 ml), the combined organic phases were then washed with brine (50 ml) dried with $Na_2SO_4$ and evaporated to give the title compound as a white solid (85 mg, 78%). LC-MS 100%, 1.47 min (3.5 minute LC-MS method), m/z=305.5/306.9, $^{1}$H NMR (500 MHz, Methanol-d4) δ 7.10 (s, 1H), 4.03 (dd, J=11.5, 4.4 Hz, 2H), 3.99-3.86 (m, 1H), 3.47 (t, J=11.0 Hz, 2H), 2.90 (s, 3H), 2.05-1.90 (m, 2H), 1.74 (d, J=12.4 Hz, 2H).

Step 3: Synthesis of 3,6-dichloro-N-[(4,6-dimethyl-2-oxo-1,2-dihydropyridin-3-yl)methyl]-4-[methyl(oxan-4-yl)amino]pyridine-2-carboxamide

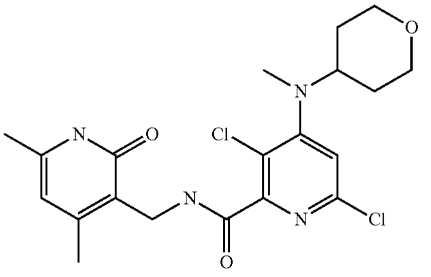 [SMILES: Cc1cc(C)c(CNC(=O)c2nc(Cl)cc(N(C)C3CCOCC3)c2Cl)c(=O)[nH]1]

To a stirred solution of 3,6-dichloro-4-[methyl(oxan-4-yl)amino]pyridine-2-carboxylic acid (85 mg, 0.28 mmol) in DMF (2 ml) was added DIPEA (73 μl, 0.42 mmol) and HATU (127 mg, 0.33 mmol). The reaction was stirred at room temperature for 5 min after which time 3-(aminomethyl)-4,6-dimethyl-1,2-dihydropyridin-2-one (89%, 52 mg, 0.31 mmol) was added and the reaction was stirred at room temperature for 16 h. The reaction mixture was then poured onto 50 ml of water and the aqueous phase was extracted with EtOAc (3×50 ml), washed with brine (50 ml) dried ($Na_2SO_4$) and evaporated to give an oil. The product was then purified using a 5 g silica Isolute column eluting with 0% to 5% MeOH in DCM and evaporated to give a glassy solid which was triturated with diethyl ether and filtered to afford the title compound as a white powder (50 mg, 41%). LC-MS 95%, m/z=439.0/440.8, $^1H$ NMR (500 MHz, Chloroform-d) δ 11.33 (br. s, 1H), 8.20 (br. s, 1H), 6.79 (s, 1H), 5.93 (s, 1H), 4.51 (s, 2H), 4.02 (dd, J=11.4, 3.8 Hz, 2H), 3.92-3.72 (m, 1H), 3.39 (t, J=11.3 Hz, 2H), 2.78 (s, 3H), 2.38 (s, 3H), 2.27 (s, 3H), 1.89 (tt, J=12.0, 6.2 Hz, 2H), 1.83-1.52 (m, 2H).

Compound 387: 3-bromo-6-chloro-N-[(4,6-dimethyl-2-oxo-1,2-dihydropyridin-3-yl)methyl]-4-[methyl(oxan-4-yl)amino]pyridine-2-carboxamide

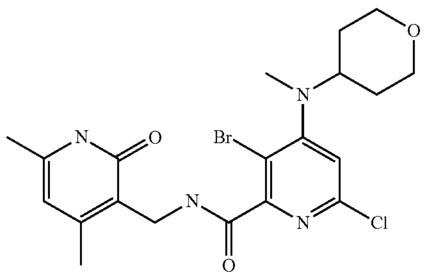 [SMILES: Cc1cc(C)c(CNC(=O)c2nc(Cl)cc(N(C)C3CCOCC3)c2Br)c(=O)[nH]1]

Step 1: Synthesis of methyl 3-bromo-6-chloropyridine-2-carboxylate

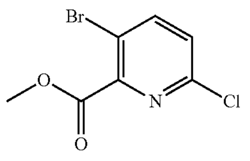

To a stirred solution of 3-bromo-6-chloropyridine-2-carboxylic acid (2.00 g, 8.46 mmol) in MeOH (40 ml) was added $H_2SO_4$ (189 μl, 3.55 mmol) and the solution was heated to reflux for 16 h. The reaction was cooled and the MeOH removed under reduced pressure, the resulting solid was dissolved in EtOAc (100 ml) and washed with saturated $NaHCO_3$ solution (2×50 ml) followed by brine (50 ml), dried ($Na_2SO_4$) and evaporated under reduced pressure to afford the title compound as an off-white solid (1.97 g, 93%) which was used without any further purification. LC-MS 98%, m/z=249.8/251.7/253.7

Step 2: Synthesis of methyl 3-bromo-4,6-dichloropyridine-2-carboxylate

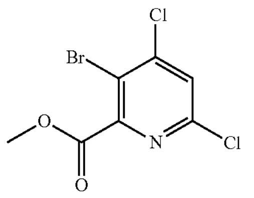

To a stirred solution of methyl 3-bromo-6-chloropyridine-2-carboxylate (1.92 g, 7.67 mmol) in TFA (18 ml) was added hydrogen peroxide (30% w/w aqueous solution, 5.22 ml, 53.7 mmol) and the reaction mixture was heated at 60° C. for 21 h. The reaction mixture was then cooled and slowly poured onto saturated $K_2CO_3$ solution (100 ml), followed by extraction of the aqueous layer with EtOAc (3×100 ml), washing of the combined organic phases with brine (2×50 ml), drying ($Na_2SO_4$) and evaporation. The desired 3-bromo-6-chloro-2-(methoxycarbonyl)pyridin-1-ium-1-olate (2.61 g, ~75% purity) was used crude in the next stage of the synthesis without any further purification. To the crude 3-bromo-6-chloro-2-(methoxycarbonyl)pyridin-1-ium-1-olate (~75% purity, 2.61 g, 7.35 mmol) was added $POCl_3$ (3.42 ml, 36.7 mmol) and the solution was heated to 100° C. for 4 h. After cooling the $POCl_3$ was remove in vacuo to give a white solid which was columned over silica eluting with 0% to 10% of EtOAc in heptane to afford the title compound as a pale yellow powder (1.07 g, 49% over two steps). LC-MS 99%, 2.02 min (3.5 minute LC-MS method), m/z=283.7/285.7/287.7, $^1H$ NMR (500 MHz, Chloroform-d) δ ppm 7.56 (s, 1H) 4.00 (s, 3H).

Step 3: Synthesis of methyl 3-bromo-6-chloro-4-[methyl(oxan-4-yl)amino]pyridine-2-carboxylate

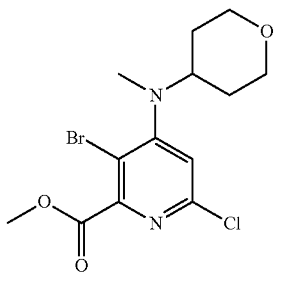 [SMILES: COC(=O)c1nc(Cl)cc(N(C)C2CCOCC2)c1Br]

To a stirred solution of methyl 3-bromo-4,6-dichloropyridine-2-carboxylate (600 mg, 2.1 mmol) in DMF (5 ml) was added TEA (587 μl, 4.21 mmol) followed by N-methyloxan-4-amine (240 mg, 2.1 mmol) and the reaction mixture was heated at 80° C. for 20 h. The reaction mixture was then cooled to room temperature and poured onto water (100 ml), followed by extraction of the product into EtOAc (3×100 ml), washing of the combined organics with brine (50 ml), drying with $Na_2SO_4$ and evaporation. The crude product was then purified over a 10 g silica Isolute column eluting with a gradient of 0% to 100% EtOAc in heptane to afford the title compound as a white solid (110 mg, 14%). LC-MS 100%, 1.94 min (3.5 minute LC-MS method), m/z=362.8/365.2/346.8, $^1$H NMR (250 MHz, Chloroform-d) δ 6.87 (s, 1H), 4.17-3.99 (m, 2H), 3.98 (s, 3H), 3.93-3.70 (m, 1H), 3.41 (t, J=10.9 Hz, 2H), 2.81 (s, 3H), 1.93 (dd, J=11.9, 4.6 Hz, 2H), 1.71 (d, J=10.3 Hz, 2H).

Step 4: Synthesis of 3-bromo-6-chloro-4-[methyl (oxan-4-yl)amino]pyridine-2-carboxylic acid

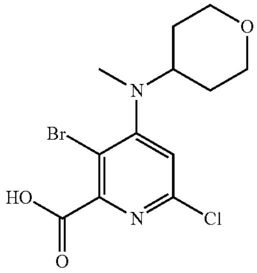

To a stirred solution of methyl 3-bromo-6-chloro-4-[methyl(oxan-4-yl)amino]pyridine-2-carboxylate (102 mg, 0.28 mmol) in THF (2 ml) was added 2M aqueous NaOH (0.70 ml, 1.40 mmol) and the reaction mixture was left to stir at room temperature for 18 h after which time the THF was evaporated in vacuo. The aqueous phase was then treated with an aqueous 10% citric acid solution to 5-6 and then extracted with EtOAc (3×50 ml) followed by a solution of 1:1 IPA/$CHCl_3$ (2×50 ml), the combined organic phases were then washed with brine (50 ml) dried with $Na_2SO_4$ and evaporated to give the title compound as a white solid (72 mg, 73%). LC-MS 100%, 1.49 min (3.5 minute LC-MS method), m/z=349.0/351.0/352.9, $^1$H NMR (500 MHz, Methanol-d4) δ 7.07 (s, 1H), 4.02 (dd, J=11.3, 4.3 Hz, 2H), 3.96-3.87 (m, 1H), 3.46 (t, J=11.0 Hz, 2H), 2.85 (s, 3H), 1.96 (dd, J=12.3, 4.3 Hz, 2H), 1.77 (s, 2H).

Step 5: Synthesis of 3-bromo-6-chloro-N-[(4,6-dimethyl-2-oxo-1,2-dihydropyridin-3-yl)methyl]-4-[methyl(oxan-4-yl)amino]pyridine-2-carboxamide

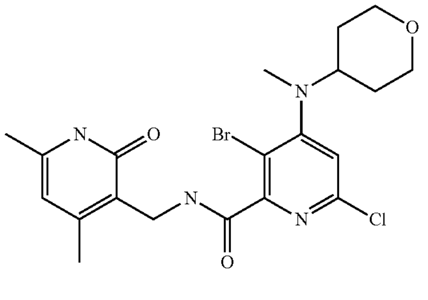

To a stirred solution of 3-bromo-6-chloro-4-[methyl(oxan-4-yl)amino]pyridine-2-carboxylic acid (73 mg, 0.21 mmol) in DMF (2 ml) were added DIPEA (56 µl, 0.31 mmol) and HATU (95 mg, 0.25 mmol) at 0° C. The reaction was stirred at 0° C. for 5 min after which time 3-(aminomethyl)-4,6-dimethyl-1,2-dihydropyridin-2-one (89%, 52 mg, 0.31 mmol) was added and the reaction was stirred at room temperature for 16 h. The reaction mixture was then poured onto 50 ml of water, the aqueous phase was extracted with EtOAc (3×50 ml), washed with brine (50 ml) dried ($Na_2SO_4$) and evaporated to give an oil. The product was then purified using a 5 g silica Isolute column eluting with 0% to 4% MeOH in DCM and evaporated to give a glassy solid which was triturated with diethyl ether and filtered and dried in a vacuum oven at 40° C. for 24 h to afford the title compound as a white powder (50 mg, 41%). LC-MS 99%, m/z=483.1/485.0/486.9, $^1$H NMR (500 MHz, $CDCl_3$) δ 10.94 (br. s, 1H), 8.14-7.98 (m, 1H), 6.83 (s, 1H), 5.92 (s, 1H), 4.55 (d, J=6.1 Hz, 2H), 4.15-3.94 (m, 2H), 3.93-3.70 (m, 1H), 3.40 (t, J=11.0 Hz, 2H), 2.78 (s, 3H), 2.39 (s, 3H), 2.28 (s, 3H), 1.99-1.82 (m, 2H), 1.79-1.64 (m, 2H).

Compound 213: 5-(azetidin-3-yl)-N-[(4,6-dimethyl-2-oxo-1,2-dihydropyridin-3-yl)methyl]-3-[ethyl (oxan-4-yl)amino]-2-methylbenzamide

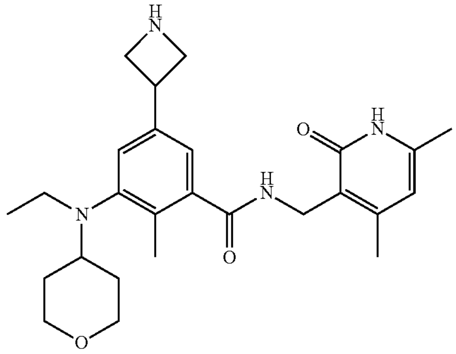 [SMILES: CCN(c1cc(C2CNC2)cc(C(=O)NCc2c(C)cc(C)[nH]c2=O)c1C)C1CCOCC1]

Step 1: Synthesis of methyl 5-bromo-2-methyl-3-[(oxan-4-yl)amino]benzoate

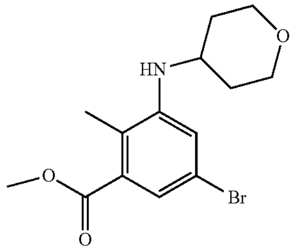 [SMILES: COC(=O)c1cc(Br)cc(NC2CCOCC2)c1C]

To a stirred solution of methyl 3-amino-2-methyl-5-bromobenzoate (4.06 g, 16.6 mmol) in DCE (60 ml) under a nitrogen atmosphere was added oxan-4-one (3.07 ml, 33.3 mmol) followed by acetic acid (5.71 ml, 99.8 mmol) and the reaction was left to stir for 5 min before the addition of sodium triacetoxyborohydride (10.6 g, 49.9 mmol). The reaction was stirred for 3 h at room temperature whereupon distilled water (50 ml) was added and the solution was neutralised with solid NaHCO3. The phases were separated and then the aqueous phase was washed with EtOAc (2×100 ml), the combined organics were then dried using Na2SO4, filtered and evaporated. The residue was purified by FCC using silica and eluting with a 10% to 40% EtOAc in heptane gradient to afford the title compound as an off-white solid (3.88 g, 71%). LC-MS 100%, 2.10 min (3.5 minute LC-MS method), m/z=327.9/329.8, $^1$H NMR (500 MHz, Chloroform-d) δ 7.23 (d, J=1.9 Hz, 1H), 6.84 (d, J=1.7 Hz, 1H), 4.02 (dt, J=11.7, 3.5 Hz, 2H), 3.87 (s, 3H), 3.65 (d, J=7.2 Hz, 1H), 3.59-3.45 (m, 3H), 2.23 (s, 3H), 2.05 (d, J=13.8 Hz, 2H), 1.51 (ddd, J=24.1, 10.8, 4.2 Hz, 2H).

Step 2: Synthesis of methyl 5-bromo-3-[ethyl(oxan-4-yl)amino]-2-methylbenzoate

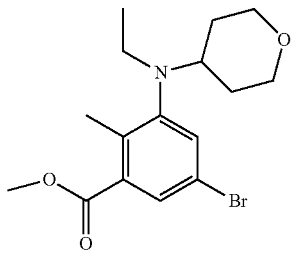 [SMILES: CCN(c1cc(Br)cc(C(=O)OC)c1C)C1CCOCC1]

To a stirred solution of methyl 5-bromo-2-methyl-3-[(oxan-4-yl)amino]benzoate (2.0 g, 6.1 mmol) in DCE (10 ml) under a nitrogen atmosphere was added acetaldehyde (1.0 ml, 18 mmol) followed by acetic acid (2.1 ml, 37 mmol) and the reaction was left to stir for 5 min before the addition of sodium triacetoxyborohydride (6.6 g, 31 mmol). The reaction was stirred for 16 h at room temperature after which time additional acetaldehyde (1.0 ml, 22 mmol) and sodium triacetoxyborohydride (3.0 g, 14 mmol) were added and the reaction was stirred for a further 6 h whereupon distilled water (100 ml) was added and the phases were separated. The aqueous phase was washed with EtOAc (3×100 ml), the combined organics were then dried using $Na_2SO_4$, filtered and evaporated to afford the title compound as a colourless oil (2.10 g, 93%) which was suitable for use without any further purification. LC-MS 96%, 2.38 min (3.5 minute LC-MS method), m/z=356.1/357.9, $^1$H NMR (500 MHz, Chloroform-d) δ 7.70 (d, J=2.0 Hz, 1H), 7.36 (d, J=2.0 Hz, 1H), 3.95 (d, J=11.3 Hz, 2H), 3.88 (d, J=9.1 Hz, 3H), 3.32 (td, J=11.5, 2.5 Hz, 2H), 3.04 (q, J=7.1 Hz, 2H), 2.98-2.87 (m, 1H), 2.44 (s, 3H), 1.77-1.55 (m, 4H), 0.86 (t, J=7.1 Hz, 3H).

Step 3: Synthesis of tert-butyl 3-{3-[ethyl(oxan-4-yl)amino]-5-(methoxycarbonyl)-4-methylphenyl}azetidine-1-carboxylate

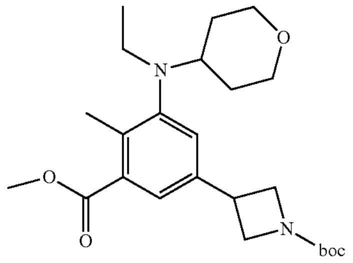

To a dry flask was added zinc dust (40 mg, 0.61 mmol) followed by anhydrous DMA (2 ml) and the vessel was flushed with nitrogen whilst stirring vigorously and heating to 65° C. TMS-Cl (9 μl, 0.07 mmol) and 1,2-dibromoethane (6 μl, 0.07 mmol) were added and the reaction was stirred at 65° C. for 30 mins, followed by the dropwise addition of N-Boc-3-iodoazetidine (133 mg, 0.47 mmol) as a solution in anhydrous DMA (1 ml). The reaction was then cooled to room temperature and methyl 5-bromo-3-[ethyl(oxan-4-yl)amino]-2-methylbenzoate (100 mg, 0.28 mmol) was added as a solution in anhydrous DMA (2 ml). The resulting solution was degassed with nitrogen for 5 mins after which Pd(dppf)$Cl_2$.DCM (7 mg, 0.01 mmol) and copper (I) iodide (3 mg, 0.02 mmol) were added as solids. The reaction was heated to 80° C. for 16 h and then cooled to room temperature followed by the addition of saturated $NH_4Cl$ solution (50 ml). The aqueous phase was extracted with EtOAc (3×100 ml), and then the combined organic phases were washed with brine (2×50 ml), dried with $Na_2SO_4$, filtered and evaporated. The residue was purified over a 5 g Isolute column using 10-30% EtOAc in heptane as the eluent to afford the title compound as a colourless oil (77 mg, 62%). LC-MS 98%, 2.19 min (3.5 minute LC-MS method), m/z=433.2, $^1$H NMR (500 MHz, $CDCl_3$) δ 7.49 (d, J=1.6 Hz, 1H), 7.16 (d, J=1.6 Hz, 1H), 4.31 (t, J=8.7 Hz, 2H), 3.94 (dd, J=14.4, 5.5 Hz, 4H), 3.89 (s, 3H), 3.77-3.64 (m, 1H), 3.31 (td, J=11.4, 2.7 Hz, 2H), 3.06 (q, J=7.0 Hz, 2H), 2.99-2.87 (m, 1H), 2.46 (s, 3H), 1.65 (ddd, J=11.1, 8.6, 6.0 Hz, 4H), 1.46 (s, 9H), 0.85 (dd, J=13.1, 6.1 Hz, 3H).

Step 4: Synthesis of 5-{1-[(tert-butoxy)carbonyl]azetidin-3-yl}-3-[ethyl(oxan-4-yl)amino]-2-methylbenzoic acid

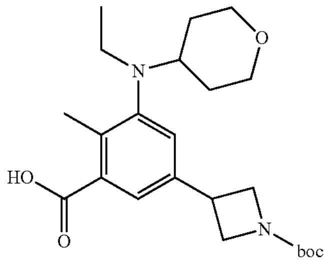

To a stirred solution of tert-butyl 3-{3-[ethyl(oxan-4-yl)amino]-5-(methoxycarbonyl)-4-methylphenyl}azetidine-1-carboxylate (78 mg, 0.18 mmol) in THF (2 ml) and MeOH (0.1 ml) was added 2M NaOH solution (0.9 ml, 1.8 mmol) and the reaction was stirred at room temperature for 16 h followed by heating at 50° C. for 22 h. The reaction was cooled to room temperature and the solvent removed in vacuo after which the aqueous solution was adjusted to pH5 using 1M HCl. The product was extracted into DCM (2×50 ml), dried with $Na_2SO_4$ and filtered to afford the title compound as a colourless oil (54 mg, 72%). LC-MS 100%, 1.70 min (3.5 minute LC-MS method), m/z=419.2, 1H NMR (500 MHz, MeOD) δ 7.77 (s, 1H), 7.55 (s, 1H), 4.36 (t, J=8.2 Hz, 2H), 3.90 (d, J=27.0 Hz, 5H), 3.71 (t, J=6.5 Hz, 1H), 3.36 (t, J=11.3 Hz, 3H), 2.55 (s, 3H), 1.92-1.81 (m, 1H), 1.64 (d, J=55.8 Hz, 3H), 1.49-1.42 (m, 10H), 0.93 (s, 3H).

Step 5: Synthesis of 5-(azetidin-3-yl)-N-[(4,6-dimethyl-2-oxo-1,2-dihydropyridin-3-yl)methyl]-3-[ethyl(oxan-4-yl)amino]-2-methylbenzamide

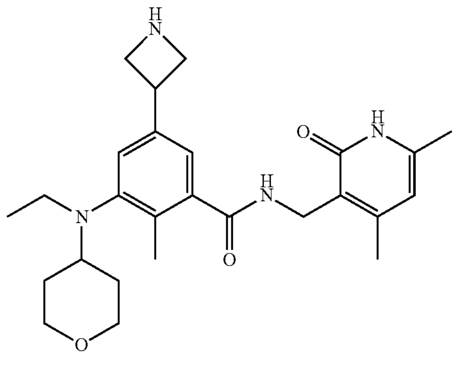 [SMILES: CCN(c1cc(C2CNC2)cc(C(=O)NCc2c(C)cc(C)[nH]c2=O)c1C)C1CCOCC1]

To a stirred solution of 5-{1-[(tert-butoxy)carbonyl]azetidin-3-yl}-3-[ethyl(oxan-4-yl)amino]-2-methylbenzoic acid (54 mg, 0.13 mmol) in DMF (2 ml) and the reaction was cooled using an ice bath followed by the addition of DIPEA (45 μl, 0.26 mmol) and HATU (59 mg, 0.15 mmol)). The reaction was stirred at 0° C. for 5 min after which time 3-(aminomethyl)-4,6-dimethyl-1,2-dihydropyridin-2-one (89%, 24 mg, 0.14 mmol) was added and the reaction was warmed room temperature for 16 h. The reaction mixture was then poured onto 50 ml of water and the aqueous phase was extracted with EtOAc (3×50 ml), washed with brine (50 ml) dried ($Na_2SO_4$), filtered and evaporated to give an oil. The product was then purified using a 5 g silica Isolute column eluting with 0% to 2.5% MeOH in DCM and evaporated to afford tert-butyl 3-(3-{[(4,6-dimethyl-2-oxo-1,2-dihydropyridin-3-yl)methyl]carbamoyl}-5-[ethyl(oxan-4-yl)amino]-4-methylphenyl)azetidine-1-carboxylate as a colourless oil (29 mg). LC-MS 90%, m/z=553.3. This material was dissolved in 4M HCl in dioxane solution (3 ml) and stirred at room temperature for 90 min after which the solvent was evaporated to dryness and the compound purified by preparative HPLC to afford the title compound as a white solid (11 mg, 8% over 2 steps). LC-MS 97%, 2.17 min (7 minute LC-MS method), m/z=453.2, 1H NMR (500 MHz, MeOD) δ 7.26 (s, 1H), 7.18 (s, 1H), 6.14 (s, 1H), 4.48 (s, 2H), 4.39 (s, 2H), 4.22 (s, 3H), 3.93 (d, J=10.5 Hz, 2H), 3.40-3.33 (m, 2H), 3.29-2.90 (m, 3H), 2.40 (s, 3H), 2.31 (s, 3H), 2.26 (s, 3H), 1.68 (d, J=26.3 Hz, 4H), 0.87 (s, 3H).

Compound 245: 5-(azetidin-3-yl)-N-[(4,6-dimethyl-2-oxo-1,2-dihydropyridin-3-yl)methyl]-2-methyl-3-[methyl(oxan-4-yl)amino]benzamide

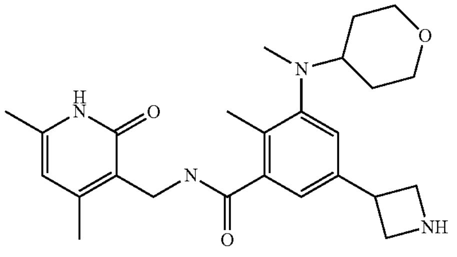 [SMILES: Cc1cc(C)c(CNC(=O)c2cc(C3CNC3)cc(N(C)C3CCOCC3)c2C)c(=O)[nH]1]

Step 1: Synthesis of methyl 5-bromo-2-methyl-3-[methyl(oxan-4-yl)amino]benzoate

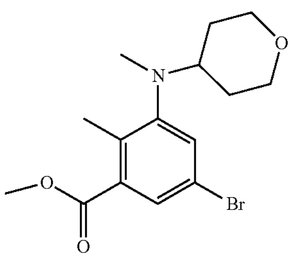 [SMILES: COC(=O)c1cc(Br)cc(N(C)C2CCOCC2)c1C]

To a stirred solution of methyl 5-bromo-2-methyl-3-[(oxan-4-yl)amino]benzoate (1.20 g, 3.66 mmol) in DCE (10 ml) under a nitrogen atmosphere was added paraformaldehyde (659 mg, 21.9 mmol) followed by acetic acid (1.26 ml, 21.9 mmol) and the reaction was left to stir for 5 min before the addition of sodium triacetoxyborohydride (4.65 g, 21.9 mmol). The reaction was stirred for 16 h at room temperature after which time additional paraformaldehyde (325 mg, 10.8 mmol) and sodium triacetoxyborohydride (2.40 g, 11.3 mmol) was added and the reaction was stirred for a further 18 h whereupon distilled water (30 ml) was added and solid $NaHCO_3$ was added until the aqueous phase was pH7 and the phases were separated, the aqueous phase was washed with EtOAc (3×50 ml), the combined organics were then washed with brine (50 ml), dried using $Na_2SO_4$, filtered and evaporated. The crude residue was purified using FCC over silica eluting with 0-10% EtOAc in heptane to afford the title compound as a colourless oil (728 mg, 52%). LC-MS 87%, m/z=341.9/343.9, 1H NMR (500 MHz, Chloroform-d) δ 7.60 (d, J=2.0 Hz, 1H), 7.25 (d, J=1.9 Hz, 1H), 3.92 (d, J=11.1 Hz, 2H), 3.82 (s, 3H), 3.27 (td, J=11.5, 2.0 Hz, 2H), 2.94-2.79 (m, 1H), 2.57 (s, 3H), 2.36 (s, 3H), 1.74-1.52 (m, 4H).

Step 2: Synthesis of 5-{1-[(tert-butoxy)carbonyl]azetidin-3-yl}-2-methyl-3-[methyl(oxan-4-yl)amino]benzoic acid

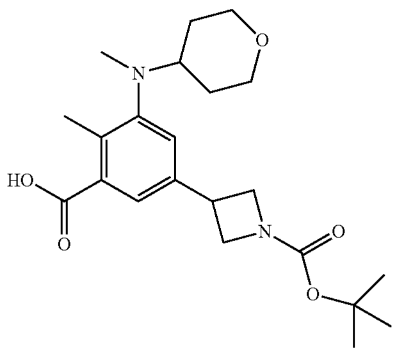 [SMILES: Cc1c(C(=O)O)cc(C2CN(C(=O)OC(C)(C)C)C2)cc1N(C)C1CCOCC1]

To a dry flask was added zinc dust (436 mg, 6.67 mmol) and the flask was heated using a heat gun for a few minutes. Then anhydrous DMA (20 ml) was added under nitrogen whilst stirring vigorously and heating to 65° C. TMS-Cl (102 μl, 0.8 mmol) and 1,2-dibromoethane (70 μl, 0.8 mmol) were added and the reaction was stirred at 65° C. for 30 min followed by the dropwise addition of N-Boc-3-iodoazetidine (1.46 g, 5.16 mmol) as a solution in anhydrous DMA (15 ml). The reaction was then cooled to room temperature and methyl 5-bromo-2-methyl-3-[methyl(oxan-4-yl)amino]benzoate (1.06 g, 3.09 mmol) was added as a solution in anhydrous DMA (15 ml). The resulting solution was degassed with nitrogen for 10 mins after which $Pd(dppf)Cl_2$.DCM (76 mg, 0.09 mmol) and copper (I) iodide (35 mg, 0.19 mmol) were added as solids. The reaction was heated to 80° C. for 90 min and then cooled to room temperature followed by the addition of distilled water (100 ml) and saturated $NH_4Cl$ solution (10 ml). The aqueous phase was extracted with TBME (3×50 ml), and then the combined organic phases were dried with $Na_2SO_4$, filtered and evaporated. The residue was purified over a 25 g Isolute column using 0%-40% EtOAc in heptane as the eluent to afford the title compound as a pale brown oil (507 mg). LC-MS 97%, m/z=420.0. To a stirred solution of tert-butyl 3-[3-(methoxycarbonyl)-4-methyl-5-[methyl(oxan-4-yl)amino]phenyl]azetidine-1-carboxylate (85 mg, 0.2 mmol) in THF (2 ml) and MeOH (0.1 ml) was added 2M NaOH solution (1.02 ml, 2.03 mmol) and the reaction was stirred at 50°

C. for 16 h after which time 4M NaOH solution (0.5 ml, 2.0 mmol) was added and the reaction was heated for a further 24 h. The reaction was cooled to room temperature and the solvent removed in vacuo after which the aqueous solution was adjusted to pH3 using 1M HCl. The product was extracted into DCM (2×50 ml), washed with brine (20 ml), dried with $Na_2SO_4$ and filtered to afford the title compound as an off-white solid (47 mg, 21% over two steps). LC-MS 95%, m/z=405.1, 1H NMR (500 MHz, Chloroform-d) δ 7.66 (t, J=7.0 Hz, 1H), 7.19 (d, J=1.3 Hz, 1H), 4.34 (t, J=8.7 Hz, 2H), 3.98 (dd, J=16.6, 10.2 Hz, 4H), 3.79-3.69 (m, 2H), 3.35 (dd, J=11.5, 10.0 Hz, 2H), 2.97 (td, J=10.8, 5.3 Hz, 1H), 2.67 (s, 3H), 2.55 (d, J=6.6 Hz, 3H), 1.74 (ddd, J=15.5, 12.1, 4.3 Hz, 2H), 1.66 (d, J=11.1 Hz, 2H), 1.48 (s, 9H).

Step 3: Synthesis of tert-butyl 3-(3-{[(4,6-dimethyl-2-oxo-1,2-dihydropyridin-3-yl)methyl]carbamoyl}-4-methyl-5-[methyl(oxan-4-yl)amino]phenyl)azetidine-1-carboxylate

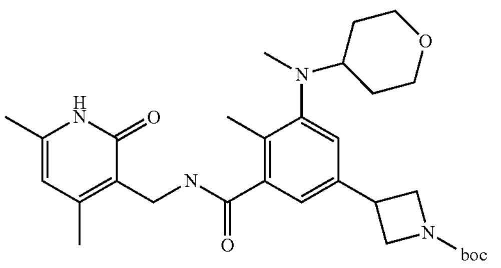

To a stirred solution of 5-{1-[(tert-butoxy)carbonyl]azetidin-3-yl}-2-methyl-3-[methyl(oxan-4-yl)amino]benzoic acid (47 mg, 0.12 mmol) in DMF (2 ml) were added DIPEA (40 μl, 0.23 mmol) and HATU (53 mg, 0.14 mmol) at 0° C. The reaction was stirred at 0° C. for 5 min after which time 3-(aminomethyl)-4,6-dimethyl-1,2-dihydropyridin-2-one (89%, 22 mg, 0.13 mmol) was added and the reaction was warmed room temperature for 16 h. The reaction mixture was then poured onto distilled water (50 ml) and the aqueous phase was extracted with DCM (3×50 ml), washed with brine (50 ml) dried ($Na_2SO_4$), filtered and evaporated to give an oil. The product was then purified using a 5 g silica Isolute column eluting with 0% to 5% MeOH in DCM and evaporated to afford the title compound as a colourless oil (44 mg, 67%). LC-MS 96%, m/z=539.4, $^1$H NMR (500 MHz, Chloroform-d) δ 11.68 (s, 1H), 6.95 (t, J=5.8 Hz, 1H), 6.92 (d, J=4.2 Hz, 2H), 5.88 (s, 1H), 4.47 (d, J=5.8 Hz, 2H), 4.20 (t, J=8.7 Hz, 2H), 3.90 (d, J=11.2 Hz, 2H), 3.86-3.73 (m, 2H), 3.62-3.50 (m, 1H), 3.26 (t, J=10.8 Hz, 2H), 2.89 (ddd, J=14.6, 10.8, 3.7 Hz, 1H), 2.55 (s, 3H), 2.33 (s, 3H), 2.20 (s, 3H), 2.14 (s, 3H), 1.75-1.47 (m, 4H), 1.39 (d, J=5.7 Hz, 9H).

Step 4: Synthesis of 5-(azetidin-3-yl)-N-[(4,6-dimethyl-2-oxo-1,2-dihydropyridin-3-yl)methyl]-2-methyl-3-[methyl(oxan-4-yl)amino]benzamide

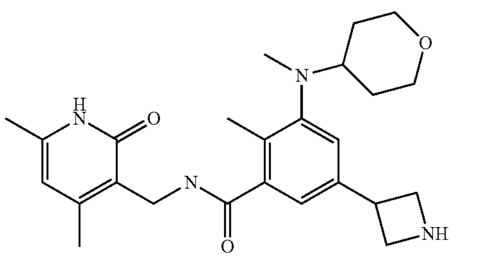 [SMILES: Cc1cc(C)c(CNC(=O)c2cc(C3CNC3)cc(N(C)C3CCOCC3)c2C)c(=O)[nH]1]

To a stirred solution of tert-butyl 3-(3-{[(4,6-dimethyl-2-oxo-1,2-dihydropyridin-3-yl)methyl]carbamoyl}-4-methyl-5-[methyl(oxan-4-yl)amino]phenyl)azetidine-1-carboxylate (29 mg, 1.29 mmol) in DCM (4 ml) was added TFA (1 ml) and the solution was stirred at room temperature for 90 min after which the solvent was evaporated and saturated aqueous $NaHCO_3$ was added until pH7-8. The aqueous phase was extracted with a 1:1 mixture IPA:$CHCl_3$ (2×50 ml), and the combined organic phases washed with brine (30 ml, dried with $Na_2SO_4$, filtered and evaporated. The residue was purified by preparative HPLC to afford the title compound as a white solid (15 mg, 42%). LC-MS 100%, m/z=439.3, 1H NMR (500 MHz, MeOD) δ 7.19 (d, J=1.4 Hz, 1H), 7.10 (d, J=1.5 Hz, 1H), 6.12 (s, 1H), 4.46 (s, 2H), 4.41-4.27 (m, 2H), 4.26-4.13 (m, 3H), 3.93 (d, J=11.4 Hz, 2H), 3.36 (td, J=11.3, 3.3 Hz, 2H), 3.06 (dq, J=14.6, 5.0 Hz, 1H), 2.65 (s, 3H), 2.39 (s, 3H), 2.26 (s, 3H), 2.24 (s, 3H), 1.75-1.60 (m, 4H).

Compound 269: N-[(4,6-dimethyl-2-oxo-1,2-dihydropyridin-3-yl)methyl]-2-methyl-3-[methyl(oxan-4-yl)amino]-5-(1-methylazetidin-3-yl)benzamide

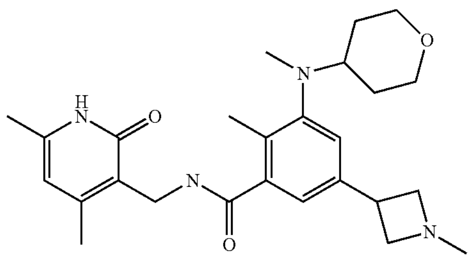

Step 1: Synthesis of methyl 5-(azetidin-3-yl)-2-methyl-3-[methyl(oxan-4-yl)amino]benzoate

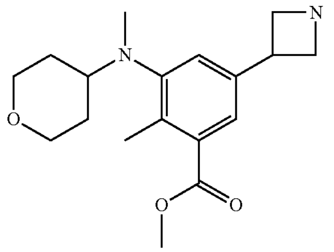 [SMILES: COC(=O)c1cc(C2CNC2)cc(N(C)C2CCOCC2)c1C]

To a stirred solution of tert-butyl 3-[3-(methoxycarbonyl)-4-methyl-5-[methyl(oxan-4-yl)amino]phenyl]azetidine-1-carboxylate (400 mg, 0.96 mmol) in DCM (4 ml) was added TFA (1 ml) and the solution was stirred at room temperature for 45 min after which the solvent was evaporated to dryness and saturated aqueous $NaHCO_3$ was added until pH7-8. The aqueous phase was extracted with DCM (3×30 ml), washed with brine (30 ml), dried with $MgSO_4$, filtered and evaporated to afford the title compound as an orange oil (370 mg, 95%). LC-MS 96%, m/z=319.1, $^1$H NMR (500 MHz, Chloroform-d) δ 7.49 (d, J=1.4 Hz, 1H), 7.20 (d, J=1.3 Hz, 1H), 4.32-4.10 (m, 5H), 3.98 (d, J=11.0 Hz, 2H), 3.90 (d, J=8.4 Hz, 3H), 3.34 (t, J=10.8 Hz, 2H), 2.99 (ddd, J=14.7, 10.9, 3.8 Hz, 1H), 2.65 (d, J=8.3 Hz, 3H), 2.51-2.41 (m, 3H), 1.73 (ddd, J=15.7, 12.1, 4.3 Hz, 2H), 1.64 (d, J=11.2 Hz, 2H).

Step 2: Synthesis of methyl 2-methyl-3-[methyl (oxan-4-yl)amino]-5-(1-methylazetidin-3-yl)benzoate

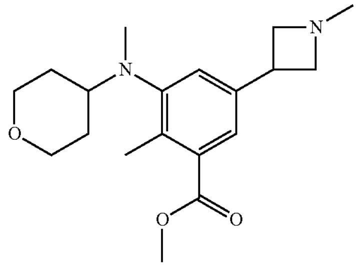 [SMILES: COC(=O)c1cc(C2CN(C)C2)cc(N(C)C2CCOCC2)c1C]

To a stirred solution of methyl 5-(azetidin-3-yl)-2-methyl-3-[methyl(oxan-4-yl)amino]benzoate (320 mg, 1.01 mmol) in DCE (10 ml) under a nitrogen atmosphere was added paraformaldehyde (151 mg, 5.03 mmol) followed by acetic acid (0.115 ml, 2.01 mmol) and the reaction was left to stir for 5 min before the addition of sodium triacetoxyborohydride (852 mg, 4.02 mmol). The reaction was stirred for 16 h at room temperature after which time additional paraformaldehyde (21 mg) and sodium triacetoxyborohydride (98 mg) was added and the reaction was stirred for a further 4 h whereupon distilled water (20 ml) was added and solid $NaHCO_3$ was added until the aqueous phase was pH7. The phases were separated, the aqueous phase was washed with DCM (3×20 ml), the combined organic phases were then washed with brine (50 ml), dried using $MgSO_4$, filtered and evaporated to afford the title compound as an oil (296 mg, 89%). LC-MS 100%, m/z=333.1, 1H NMR (500 MHz, Chloroform-d) δ 7.42 (d, J=1.4 Hz, 1H), 7.09 (s, 1H), 3.96 (d, J=11.2 Hz, 2H), 3.92-3.82 (m, 5H), 3.74 (d, J=7.2 Hz, 1H), 3.30 (dt, J=22.2, 15.0 Hz, 4H), 3.00-2.89 (m, 1H), 2.62 (s, 3H), 2.49-2.39 (m, 6H), 1.75-1.59 (m, 4H).

Step 3: Synthesis of N-[(4,6-dimethyl-2-oxo-1,2-dihydropyridin-3-yl)methyl]-2-methyl-3-[methyl (oxan-4-yl)amino]-5-(1-methylazetidin-3-yl)benzamide

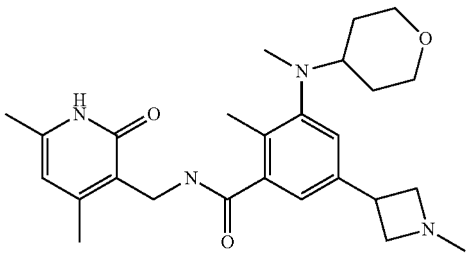

To a stirred solution of methyl 2-methyl-3-[methyl(oxan-4-yl)amino]-5-(1-methylazetidin-3-yl)benzoate (296 mg, 0.89 mmol) in THF (10 ml) and MeOH (1 ml) was added 2M NaOH solution (4.5 ml, 8.9 mmol) and the reaction was stirred at 50° C. for 16 h after which time 4M NaOH solution (1 ml, 4.5 mmol) was added and the reaction was heated for a further 24 h. The reaction was cooled to room temperature and the product was neutralised with 1M HCl and evaporated to dryness followed by azeotrope with toluene to remove residual water. The crude acid was taken through to the next stage without any purification. The crude residue of 2-methyl-3-[methyl(oxan-4-yl)amino]-5-(1-methylazetidin-3-yl) benzoic acid was suspended in DMF (10 ml) and the solution was cooled using an ice bath followed by the addition of DIPEA (433 μl, 2.49 mmol) and HATU (567 mg, 1.49 mmol). The reaction was stirred at 0° C. for 5 min after which time 3-(aminomethyl)-4,6-dimethyl-1,2-dihydropyridin-2-one (89%, 221 mg, 1.29 mmol) was added and the reaction was warmed room temperature for 16 h. The reaction mixture was then poured onto distilled water (50 ml) and the aqueous phase was extracted with DCM (3×50 ml), washed with brine (50 ml) dried ($Na_2SO_4$), filtered and evaporated to give an oil. The product was then purified using preparative HPLC method (and evaporated to dryness followed by trituration with ether and filtration to afford the title compound as an off-white solid (51 mg, 10%). LC-MS 91%, m/z=453.2, 1H NMR (500 MHz, MeOD) δ 7.14 (d, J=1.7 Hz, 1H), 7.09 (d, J=1.7 Hz, 1H), 6.12 (s, 1H), 4.46 (s, 2H), 4.41 (t, J=9.2 Hz, 2H), 4.22 (t, J=9.3 Hz, 2H), 4.14 (dd, J=17.4, 8.5 Hz, 1H), 3.98-3.89 (m, 2H), 3.36 (td, J=11.3, 3.4 Hz, 2H), 3.06 (ddd, J=14.6, 9.8, 4.9 Hz, 1H), 2.97 (s, 3H), 2.64 (s, 3H), 2.39 (s, 3H), 2.26 (s, 3H), 2.24 (s, 3H), 1.73-1.62 (m, 4H).

Compound 389: N-[(4,6-dimethyl-2-oxo-1,2-dihydropyridin-3-yl)methyl]-5-[ethyl(oxan-4-yl)amino]-4-methylpyridine-3-carboxamide

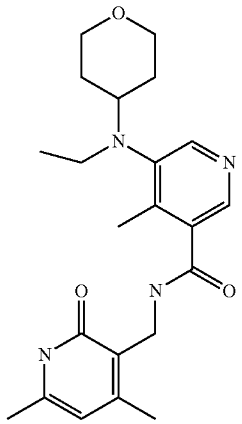 [SMILES: CCN(c1cncc(C(=O)NCc2c(C)cc(C)[nH]c2=O)c1C)C1CCOCC1]

Step 1: Synthesis of methyl 5-amino-4-methylpyridine-3-carboxylate

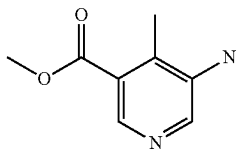

To a stirred solution of 5-amino-4-methylpyridine-3-carboxylic acid (0.94 g, 6.18 mmol) in MeOH (20 ml at 0° C. was added thionyl chloride drop-wise. The solution was then heated to 50° C. for 3.5 h, a further 10 ml of MeOH was added and the reaction heated at 50° C. for 5 h followed by stirring at room temperature for 64 h. The solvent was then evaporated under reduced pressure and saturated $NaHCO_3$ solution was added until pH7-8. The product was extracted into EtOAc (2×50 ml) and the combined organics were washed with brine (50 ml) dried using $Na_2SO_4$, filtered and evaporated to afford the title compound as an off-white powder (824 mg, 80%) which was suitable for use in the next stage without any purification. LC-MS m/z=167.0, 1H NMR (500 MHz, Chloroform-d) δ 8.52 (d, J=34.2 Hz, 1H), 8.16 (s, 1H), 3.95 (d, J=4.8 Hz, 3H), 3.78 (s, 2H), 2.42 (s, 3H).

Step 2: Synthesis of methyl 4-methyl-5-[(oxan-4-yl)amino]pyridine-3-carboxylate

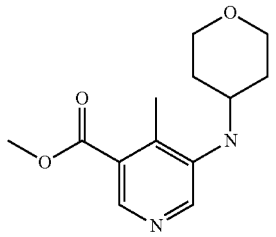 [SMILES: COC(=O)c1cncc(NC2CCOCC2)c1C]

To a stirred solution of methyl 5-amino-4-methylpyridine-3-carboxylate (805 mg, 4.84 mmol) in DCE (20 ml) under a nitrogen atmosphere was added oxan-4-one (537 μl, 5.80 mmol) followed by trifluoroacetic acid (742 μl, 9.69 mmol) and the reaction was left to stir for 5 min before the addition of sodium triacetoxyborohydride (1.54 g, 7.27 mmol). The reaction was stirred for 16 h at room temperature after which time more oxan-4-one (100 μl) and sodium triacetoxyborohydride (300 mg) were added and the reaction stirred for a further 6 h. Distilled water (20 ml) was added and solid $NaHCO_3$ was added until pH8. The phases were separated and then the aqueous phase was washed with EtOAc (2×50 ml), the combined organics were washed with brine (50 ml), dried using $Na_2SO_4$, filtered and evaporated to afford the title compound as a pale yellow solid (1.11 g, 88%) which was used in the next stage without any further purification. LC-MS 96%, m/z=251.0, 1H NMR (500 MHz, Chloroform-d) δ 8.40 (s, 1H), 8.10 (s, 1H), 4.03 (dt, J=11.9, 3.5 Hz, 2H), 3.92 (s, 3H), 3.68-3.58 (m, 1H), 3.54 (tt, J=8.1, 4.1 Hz, 3H), 2.35 (s, 3H), 2.12-2.05 (m, 2H), 1.53 (ddd, J=23.8, 11.0, 4.3 Hz, 2H).

Step 3: Synthesis of methyl 5-[ethyl(oxan-4-yl)amino]-4-methylpyridine-3-carboxylate

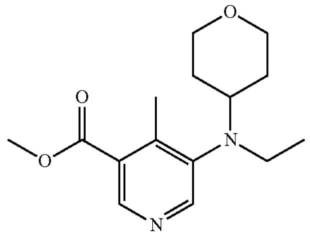 [SMILES: CCN(c1cncc(C(=O)OC)c1C)C1CCOCC1]

To a stirred solution of methyl 4-methyl-5-[(oxan-4-yl)amino]pyridine-3-carboxylate (600 mg, 2.40 mmol) in DCE (20 ml) under a nitrogen atmosphere was added acetaldehyde (1.07 ml, 19.2 mmol) followed by trifluoroacetic acid (367 μl, 4.79 mmol) and the reaction was left to stir for 5 min before the addition of sodium triacetoxyborohydride (3.05 g, 14.4 mmol). The reaction was stirred for 16 h at room temperature after which time more acetaldehyde (500 μl) and sodium triacetoxyborohydride (1.0 g) were added and the reaction stirred for a further 16 h. Distilled water (20 ml) was added and solid $NaHCO_3$ was added until pH8. The phases were separated and then the aqueous phase was washed with DCM (2×50 ml), the combined organics were washed with brine (50 ml), dried using $Na_2SO_4$, filtered and evaporated. The residue was purified using a 25 g Isolute silica column using a gradient of 0% to 50% EtOAc in heptane to afford the title compound as a pale yellow oil (418 mg, 60%). LC-MS 96%, m/z=279.1, 1H NMR (500 MHz, Chloroform-d) δ 8.76 (s, 1H), 8.44 (s, 1H), 3.97 (d, J=11.0 Hz, 2H), 3.93 (s, 3H), 3.33 (td, J=11.6, 2.1 Hz, 2H), 3.13 (q, J=7.1 Hz, 2H), 3.04 (tt, J=10.9, 4.0 Hz, 1H), 2.54 (s, 3H), 1.76-1.59 (m, 4H), 0.89 (t, J=7.1 Hz, 3H).

Step 4: Synthesis of 5-[ethyl(oxan-4-yl)amino]-4-methylpyridine-3-carboxylic acid

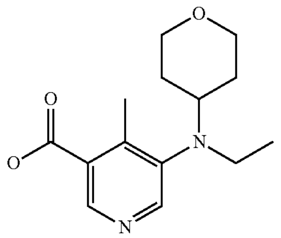 [SMILES: CCN(c1cncc(C(=O)O)c1C)C1CCOCC1]

To a stirred solution of methyl 5-[ethyl(oxan-4-yl)amino]-4-methylpyridine-3-carboxylate (415 mg, 1.49 mmol) in THF (7 ml) and MeOH (3 ml) was added 4M NaOH solution (932 μl, 3.73 mmol). The reaction was stirred at room temperature for 4.5 h after which the solution was neutralised via the addition of 1M HCl and the solvent was removed under reduced pressure, followed by the addition of saturated brine (10 ml). The aqueous phase was extracted with 1:1 IPA: $CHCl_3$ (3×50 ml), the combined organics washed with brine (30 ml), dried using $Na_2SO_4$, filtered and evaporated to afford the title compound as an off-white solid (305 mg, 77%) which was suitable for use in the next stage without any further purification. LC-MS 99%, m/z=265.1, 1H NMR (500 MHz, DMSO-d6) δ 8.57 (s, 1H), 8.46 (s, 1H), 3.82 (d, J=11.6 Hz, 2H), 3.25 (t, J=10.9 Hz, 2H), 3.16-2.99 (m, 3H), 2.45 (s, 3H), 1.64 (d, J=11.0 Hz, 2H), 1.48 (dt, J=11.9, 5.7 Hz, 2H), 0.81 (t, J=7.0 Hz, 3H).

Step 5: Synthesis of N-[(4,6-dimethyl-2-oxo-1,2-dihydropyridin-3-yl)methyl]-5-[ethyl(oxan-4-yl)amino]-4-methylpyridine-3-carboxamide

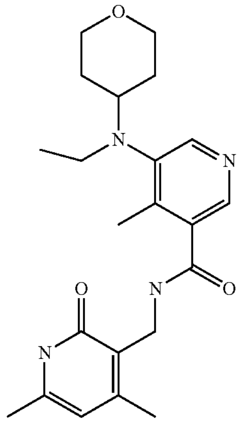 [SMILES: CCN(c1cncc(C(=O)NCc2c(C)cc(C)[nH]c2=O)c1C)C1CCOCC1]

To a stirred solution of 5-[ethyl(oxan-4-yl)amino]-4-methylpyridine-3-carboxylic acid (300 mg, 1.13 mmol) in DMF (10 ml) was added DIPEA (395 μl, 2.27 mmol) and HATU (518 mg, 1.36 mmol). The reaction was stirred at room temperature for 5 min after which time 3-(aminomethyl)-4,6-dimethyl-1,2-dihydropyridin-2-one (89%, 214 mg, 1.25 mmol) was added and the reaction was stirred at room temperature for 18 h. The reaction mixture was then poured onto 500 ml of water and the product was extracted into EtOAc (3×200 ml), the combined organic phase was washed with brine (2×100 ml), dried ($Na_2SO_4$) and evaporated. The crude product was then purified using preparative-HPLC and the resulting solid was triturated with diethyl ether and isolated by filtration to afford the title compound as an off white solid (115 mg, 25%). LC-MS 100%, m/z=399.2, $^1$H NMR (500 MHz, Acetone) δ 10.97 (s, 1H), 8.32 (s, 1H), 8.22 (s, 1H), 7.73 (s, 1H), 5.92 (s, 1H), 4.41 (d, J=5.3 Hz, 2H), 3.85 (dd, J=11.3, 3.0 Hz, 2H), 3.28 (td, J=11.7, 1.9 Hz, 2H), 3.15 (q, J=7.1 Hz, 2H), 3.09 (ddd, J=11.1, 7.2, 3.9 Hz, 1H), 2.32 (d, J=1.5 Hz, 6H), 2.23 (s, 3H), 1.69 (dd, J=12.6, 1.7 Hz, 2H), 1.55 (ddd, J=24.3, 12.2, 4.4 Hz, 2H), 0.85 (t, J=7.1 Hz, 3H).

Compound 322: N-[(4,6-dimethyl-2-oxo-1,2-dihydropyridin-3-yl)methyl]-3-[ethyl(oxan-4-yl)amino]-2-methyl-5-(1-methylazetidin-3-yl)benzamide

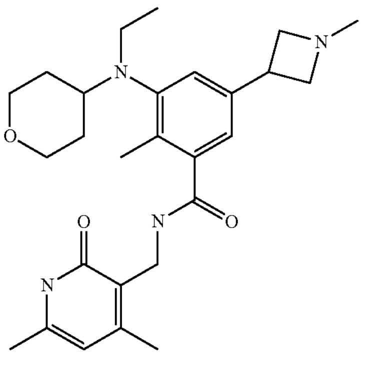

Step 1: Synthesis of methyl 5-bromo-3-[ethyl(oxan-4-yl)amino]-2-methylbenzoate

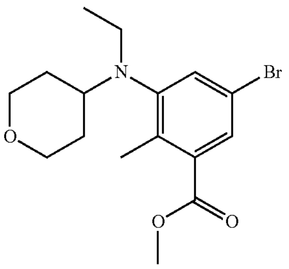 [SMILES: CCN(c1cc(Br)cc(C(=O)OC)c1C)C1CCOCC1]

To a stirred solution of methyl 5-bromo-3-[ethyl(oxan-4-yl)amino]-2-methylbenzoate (622 mg, 1.90 mmol) in DCE (10 ml) under a nitrogen atmosphere was added acetaldehyde (318 μl, 5.69 mmol) followed by acetic acid (650 μl, 11.4 mmol) and the reaction was left to stir for 5 min before the addition of sodium triacetoxyborohydride (2.00 g, 9.48 mmol). The reaction was stirred for 16 h at room temperature after which time additional acetaldehyde (300 μl) and sodium triacetoxyborohydride (1.2 g) were added. The reaction was stirred for a further 6 h whereupon distilled water (100 ml) was added and solid $NaHCO_3$ was added until the aqueous phase was pH7. The phases were separated, the aqueous phase was washed with DCM (2×50 ml), the combined organic phases were then washed with brine (100 ml), dried using $Na_2SO_4$, filtered and evaporated. The crude residue was purified using FCC over silica eluting with 0-5% EtOAc in heptane to afford the title compound as a pale yellow oil (47 0 mg, 70%). LC-MS 100 m/z=356.0/357.9. 1H NMR (500 MHz, Chloroform-d) δ 7.64 (d, J=2.0 Hz, 1H), 7.29 (d, J=2.0 Hz, 1H), 3.89 (d, J=11.3 Hz, 2H), 3.83 (s; 3H), 3.26 (td, J=11.5, 2.6 Hz, 2H), 2.98 (q, J=7.1 Hz, 2H), 2.86 (dd, J=9.7, 5.2 Hz, 1H), 2.38 (s, 3H), 1.67-1.52 (m, 4H), 0.80 (t, J=7.1 Hz, 3H).

Step 2: Synthesis of methyl 5-(azetidin-3-yl)-3-[ethyl(oxan-4-yl)amino]-2-methylbenzoate

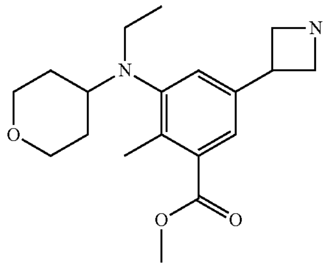 [SMILES: CCN(c1cc(C2CNC2)cc(C(=O)OC)c1C)C1CCOCC1]

To a dry flask was added zinc dust (186 mg, 2.85 mmol) and the flask was heated using a heat gun for a few minutes. Then anhydrous DMA (15 ml) was added under nitrogen whilst stirring vigorously and heating to 65° C. TMSCl (44 μl, 0.34 mmol) and 1,2-dibromoethane (30 μl, 0.34 mmol) were added and the reaction was stirred at 65° C. for 30 mins followed by the dropwise addition of N-Boc-3-iodoazetidine (624 mg, 2.20 mmol) as a solution in anhydrous DMA (5 ml). The reaction was then cooled to room temperature methyl 5-bromo-3-[ethyl(oxan-4-yl)amino]-2-methylbenzoate (470 mg, 1.32 mmol) was added as a solution in anhydrous DMA (10 ml). The resulting solution was degassed with nitrogen for 10 mins after which Pd(dppf)$Cl_2$.DCM (32 mg, 0.04 mmol) and copper (I) iodide (15 mg, 0.08 mmol) were added as solids. The reaction was heated to 80° C. for 60 min and then cooled to room temperature followed by the addition of distilled water (50 ml) and saturated $NH_4Cl$ solution (10 ml). The aqueous phase was extracted with EtOAc (3×50 ml) and then the combined organics were washed with brine (20 ml), dried with $Na_2SO_4$, filtered and evaporated to dryness followed by heptane azeotrope to remove any residual DMA. The residue was purified over a 10 g Isolute column using 0%-25% EtOAc in heptane as the eluent to afford the title compound as a pale brown oil (565 mg). LC-MS 100%, 2.12 min (3.5 minute LC-MS method), m/z=433.2. To this oil was added DCM (4 ml) followed by TFA (1 ml) and the solution was stirred at room temperature for 2 h after which the solvent was evaporated and saturated aqueous $NaHCO_3$ was added until pH7-8. The aqueous phase was extracted with DCM (3×30 ml), washed with brine (30 ml), dried with MgSO4, filtered and evaporated to afford the title compound yellow oil (440 mg). LC-MS 100%, m/z=333.1.

Step 3: Synthesis of N-[(4,6-dimethyl-2-oxo-1,2-dihydropyridin-3-yl)methyl]-3-[ethyl(oxan-4-yl)amino]-2-methyl-5-(1-methylazetidin-3-yl)benzamide

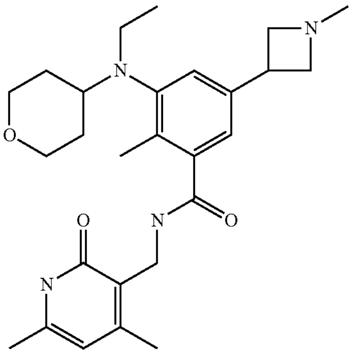 [SMILES: CCN(c1cc(C2CN(C)C2)cc(C(=O)NCc2c(C)cc(C)[nH]c2=O)c1C)C1CCOCC1]

To a stirred solution of methyl 5-(azetidin-3-yl)-3-[ethyl(oxan-4-yl)amino]-2-methylbenzoate (440 mg, 1.32 mmol) in DCE (10 ml) under a nitrogen atmosphere was added paraformaldehyde (278 mg, 9.27 mmol) followed by acetic acid (0.15 ml, 2.65 mmol) and the reaction was left to stir for 5 min before the addition of sodium triacetoxyborohydride (1.40 g, 6.62 mmol). The reaction was stirred for 16 h at room temperature after which time distilled water (20 ml) was added and solid $NaHCO_3$ was added until the aqueous phase was pH8 and the phases were separated, the aqueous phase was washed with DCM (3×30 ml), the combined organics were then washed with brine (50 ml), dried using $Na_2SO_4$, filtered and evaporated. The residue was purified by chromatography over a 10 g Isolute (elution with 0% to 5% MeOH in DCM) and evaporated followed by purification over alumina (elution with 0% to 1% MeOH in DCM) to afford the title compound as a yellow oil which was used directly in the next stage of the synthesis. LC-MS 77%, 1 m/z=347.1.

Methyl 3-[ethyl(oxan-4-yl)amino]-2-methyl-5-(1-methylazetidin-3-yl)benzoate (103 mg, 0.30 mmol) was dissolved in THF (20 ml) and MeOH (5 ml) and 2M NaOH (1.49 ml, 2.97 mmol) was added. The reaction was stirred at 50° C. for 16 h, cooled, acidified to pH4 using 6M HCl and the solvent evaporated under reduced pressure, and the residue dried in a vacuum oven at 40° C. for 5 h to afford the crude acid. To the acid in DMF (10 ml) were added HATU (170 mg, 0.45 mmol) and DIPEA (130 μl, 0.74 mmol). The mixture was stirred at room temperature for 5 min and then 3-(aminomethyl)-4,6-dimethyl-1,2-dihydropyridin-2-one (89%, 66 mg, 0.39 mmol) was added. The reaction was stirred for 16 h after which additional HATU (80 mg) and 3-(aminomethyl)-4,6-dimethyl-1,2-dihydropyridin-2-one (30 mg) and the mixture stirred a further 5 h. The reaction mixture was poured onto distilled after (50 ml), extracted with EtOAc (3×50 ml), washed with brine (2×20 ml), dried with $Na_2SO_4$, filtered and evaporated. The crude residue was purified using preparative HPLC and evaporated to afford the title compound as an off-white solid (28 mg, 5% over three steps). LC-MS 95%, m/z=467.3, 1H NMR (500 MHz, Acetone-$d_6$) δ 10.73 (s, 1H), 7.61 (s, 1H), 7.30 (s, 1H), 7.26 (s, 1H), 5.97 (s, 1H), 4.74 (t, J=9.9 Hz, 2H), 4.60 (t, J=9.6 Hz, 2H), 4.38 (q, J=6.2 Hz, 3H), 3.83 (d, J=11.6 Hz, 2H), 3.27 (s, 3H), 3.23 (t, J=11.6 Hz, 2H), 3.10 (dd, J=14.1, 7.0 Hz, 2H), 3.04-2.97 (m, 1H), 2.34 (s, 3H), 2.31 (s, 3H), 2.25 (s, 3H), 1.67 (d, J=11.1 Hz, 2H), 1.56 (td, J=11.8, 4.1 Hz, 2H), 0.83 (t, J=7.0 Hz, 3H).

Compound 332: 3-[benzyl(methyl)amino]-N-[(4,6-dimethyl-2-oxo-1,2-dihydropyridin-3-yl)methyl]-2-(trifluoromethyl)benzamide

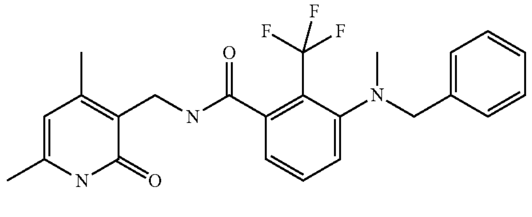 [SMILES: Cc1cc(C)c(CNC(=O)c2cccc(N(C)Cc3ccccc3)c2C(F)(F)F)c(=O)[nH]1]

Step 1: Synthesis of N-[(4,6-dimethyl-2-oxo-1,2-dihydropyridin-3-yl)methyl]-3-fluoro-2-(trifluoromethyl)benzamide

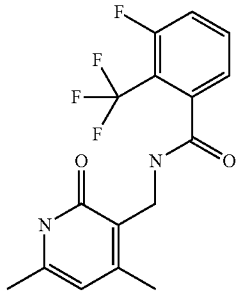 [SMILES: Cc1cc(C)c(CNC(=O)c2cccc(F)c2C(F)(F)F)c(=O)[nH]1]

To a stirred solution of 3-fluoro-2-(trifluoromethyl)benzoic acid (1.00 g, 4.81 mmol) in DMF (25 ml) cooled in an ice bath was added HATU (2.19 g, 5.77 mmol) and DIPEA (1.67 ml, 9.61 mmol). The reaction was stirred at 0° C. for 5 min after which time 3-(aminomethyl)-4,6-dimethyl-1,2-dihydropyridin-2-one (89%, 904 mg, 5.29 mmol) was added and the reaction was warmed room temperature for 4 h. The reaction mixture was then poured onto distilled water (300 ml) and stirred for 1 h after which time the precipitate was collected via vacuum filtration using microfibre paper. The resulting solid was triturated using diethyl ether and filtered to afford the title compound as a pale brown solid (1.19 g, 72%). LC-MS 100%, m/z=343.0, 1H NMR (500 MHz, DMSO) δ 11.48 (s, 1H), 8.54 (t, J=4.8 Hz, 1H), 7.71 (dd, J=13.3, 8.0 Hz, 1H), 7.56-7.45 (m, 1H), 7.20 (d, J=7.6 Hz, 1H), 5.86 (s, 1H), 4.25 (d, J=4.9 Hz, 2H), 2.18 (s, 3H), 2.11 (s, 3H).

Step 2: Synthesis of 3-(benzylamino)-N-[(4,6-dimethyl-2-oxo-1,2-dihydropyridin-3-yl)methyl]-2-(trifluoromethyl)benzamide

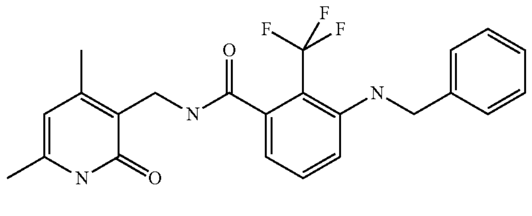 [SMILES: Cc1cc(C)c(CNC(=O)c2cccc(NCc3ccccc3)c2C(F)(F)F)c(=O)[nH]1]

A suspension of N-[(4,6-dimethyl-2-oxo-1,2-dihydropyridin-3-yl)methyl]-3-fluoro-2-(trifluoro methyl)benzamide (0.80 g, 2.34 mmol) in benzylamine (2.6 ml, 23.4 mmol) was heated in a microwave reactor at 210° C. for 4 h. After cooling distilled water (20 ml) was added to the slurry and 2M HCl was added until the suspension was at pH5. and the mixture was extracted using EtOAc (3×50 ml). The combined organics were washed with pH5 HCl solution (2×50 ml), brine (30 ml), dried using $Na_2SO_4$ filtered and evaporated. The resultant oil was purified using a 50 g Isolute silica column eluting with a gradient of 0% to 5% MeOH in DCM to afford the title compound as an off-white solid (313 mg, 29%). LC-MS 94%, m/z=430.2, 1H NMR (500 MHz, Acetone-d6) δ 7.41-7.16 (m, 8H), 6.69 (d, J=8.5 Hz, 1H), 6.50 (d, J=7.4 Hz, 1H), 5.87 (s, 1H), 5.84 (s, 1H), 4.53 (d, J=5.7 Hz, 2H), 4.35 (d, J=5.6 Hz, 2H), 2.28, (d, J=4.0 Hz, 3H), 2.21 (s, 3H).

Step 3: Synthesis of 3-[benzyl(methyl)amino]-N-[(4,6-dimethyl-2-oxo-1,2-dihydropyridin-3-yl)methyl]-2-(trifluoromethyl)benzamide

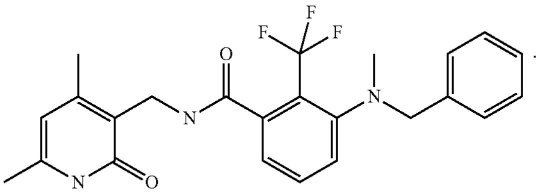 [SMILES: Cc1cc(C)c(CNC(=O)c2cccc(N(C)Cc3ccccc3)c2C(F)(F)F)c(=O)[nH]1]

To a solution of 3-(benzylamino)-N-[(4,6-dimethyl-2-oxo-1,2-dihydropyridin-3-yl)methyl]-2-(trifluoromethyl)benzamide (100 mg, 0.23 mmol) in DCE (5 ml) was added acetic acid (27 μl, 0.47 mmol) followed by paraformaldehyde (7 mg, 0.23 mmol) after which the reaction was stirred at room temperature for 10 min. Then sodium triacetoxyborohydride (74 mg, 0.35 mmol) was added in one portion and the reaction was stirred at room temperature for 16 h. Further treatment with acetaldehyde (35 mg), sodium triacetoxyborohydride (250 mg) and AcOH (100 ml) was performed. After a further 24 h further acetaldehyde (445 mg) and sodium triacetoxyborohydride (250 mg) were added and the reaction was stirred for a further 3 h. Water (20 ml) was then added to the reaction mixture and the aqueous phase was neutralised by the portionwise addition of $NaHCO_3$. The aqueous phase was extracted with DCM (2×50 ml), then the combined organic phases were washed with brine, dried ($Na_2SO_4$) and evaporated. The product was purified using FCC over a 5 g Isolute, eluting with 0-5% MeOH in DCM to afford the title compound as an off-white powder (24 mg, 22%). LC-MS 95%, 4.12 min (7 minute LC-MS method), m/z=444.2, 1H NMR (500 MHz, Chloroform-d) δ 11.10 (br. s, 1H), 7.44 (t, J=7.8 Hz, 1H), 7.38-7.29 (m, 5H), 7.27-7.23 (m, 1H), 7.12 (d, J=7.4 Hz, 1H), 7.04 (t, J=5.6 Hz, 1H), 5.92 (s, 1H), 4.52 (d, J=5.9 Hz, 2H), 4.09 (s, 2H), 2.60 (s, 3H), 2.38 (s, 3H), 2.19 (s, 3H).

Compound 333: 3-[benzyl(ethyl)amino]-N-[(4,6-dimethyl-2-oxo-1,2-dihydropyridin-3-yl)methyl]-2-(trifluoromethyl)benzamide

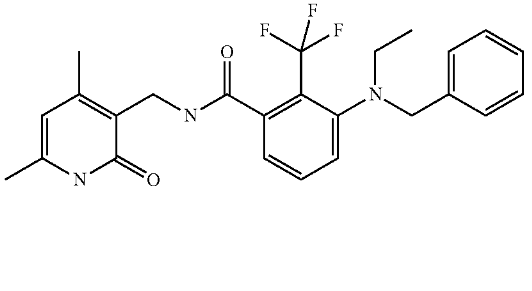 [SMILES: CCN(Cc1ccccc1)c1cccc(C(=O)NCc2c(C)cc(C)[nH]c2=O)c1C(F)(F)F]

To a solution of 3-(benzylamino)-N-[(4,6-dimethyl-2-oxo-1,2-dihydropyridin-3-yl)methyl]-2-(trifluoromethyl)benzamide (198 mg, 0.46 mmol) in DCE (5 ml) was added acetic acid (80 μl, 1.38 mmol) followed by acetaldehyde (129 μl, 2.31 mmol) after which the reaction was stirred at room temperature for 10 min. Then sodium triacetoxyborohydride (490 mg, 2.31 mmol) was added in one portion and the reaction was stirred at room temperature for 16 h. Further 4×130 uL treatments with acetaldehyde and 4×0.5 g sodium triacetoxyborohydride were performed over 3 days to completed the reaction. Water (100 ml) was then added to the reaction mixture and the aqueous phase was neutralized by the portionwise addition of $NaHCO_3$. The aqueous phase was extracted with DCM (2×50 ml), then the combined organic phases washed with brine, dried ($Na_2SO_4$) and evaporated. The product was purified using FCC over a 5 g Isolute, eluting with 0-5% MeOH in DCM followed by purification via RP-HPLC to give the title compound as an off-white powder (76 mg, 34%). LC-MS 100%, m/z=458.3, 1H NMR (500 MHz, Chloroform-d) δ 11.70 (s, 1H), 7.42 (t, J=7.8 Hz, 1H), 7.36-7.27 (m, 5H), 7.24 (d, J=7.1 Hz, 1H), 7.12 (d, J=7.4 Hz, 1H), 7.03 (d, J=5.4 Hz, 1H), 5.90 (s, 1H), 4.50 (d, J=5.7 Hz, 2H), 4.05 (s, 2H), 2.96 (q, J=7.1 Hz, 2H), 2.36 (s, 3H), 2.15 (s, 3H), 0.89 (t, J=7.1 Hz, 3H).

Compound 334: 3-[benzyl(ethyl)amino]-N-[(4,6-dimethyl-2-oxo-1,2-dihydropyridin-3-yl)methyl]-2-methylbenzamide

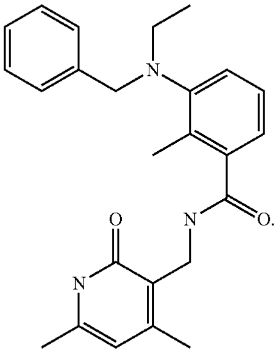 [SMILES: CCN(Cc1ccccc1)c1cccc(C(=O)NCc2c(C)cc(C)[nH]c2=O)c1C]

Step 1: Synthesis of ethyl 3-(benzylamino)-2-methylbenzoate

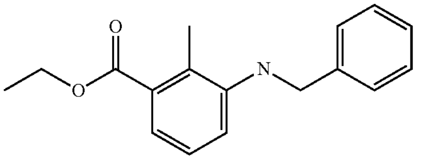 [SMILES: CCOC(=O)c1cccc(NCc2ccccc2)c1C]

To a stirred solution of ethyl 3-amino-2-methylbenzoate (1.00 g, 5.58 mmol) in DCE (20 ml) was added benzaldehyde (569 μl, 5.58 mmol) followed by acetic acid (0.64 ml, 11.2 mmol). The reaction was stirred at room temperature for 1 h and then sodium triacetoxyborohydride (1.77 g, 8.37 mmol) was added and the reaction stirred for 2 h. Distilled water (20 ml) was added and solid $NaHCO_3$ was added until the aqueous phase was pH7 and the phases were separated. The aqueous phase was washed with DCM (2×5 0 ml), the combined organics were then washed with brine (50 ml), dried using $Na_2SO_4$, filtered and evaporated to afford the title compound as a yellow oil (1.52 g, 96%) which was used in the next stage without any further purification. LC-MS 95%, m/z=270.0, 1H NMR (500 MHz, Chloroform-d) δ 7.42-7.32 (m, 4H), 7.32-7.28 (m, 1H), 7.17-7.06 (m, 2H), 6.73 (dd, J=7.8, 1.1 Hz, 1H), 4.40 (s, 2H), 4.36 (q, J=14.3, 5.3 Hz, 2H), 4.08 (br. s, 1H), 2.35, (s, 3H), 1.39 (t, 3H).

Step 2: Synthesis of ethyl 3-[benzyl(ethyl)amino]-2-methylbenzoate

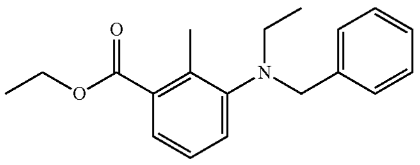 [SMILES: CCOC(=O)c1cccc(N(CC)Cc2ccccc2)c1C]

To a stirred solution of ethyl 3-(benzylamino)-2-methylbenzoate (396 mg, 1.47 mmol) in DCE (10 ml) was added acetaldehyde (164 µl, 2.94 mmol) followed by acetic acid (0.17 ml, 2.94 mmol) The reaction was stirred at room temperature for 10 min and then sodium triacetoxyborohydride (0.62 g, 2.94 mmol) was added and the reaction stirred for 16 h. Distilled water (30 ml) was added and solid $NaHCO_3$ was then added until the aqueous phase was pH7, the phases were separated, the aqueous phase was washed with DCM (2×50 ml), the combined organics were then washed with brine (50 ml), dried using $Na_2SO_4$, filtered and evaporated. The resultant residue was then purified using a 25 g silica Isolute column eluting using a gradient of 0% to 5% EtOAc in heptane to afford the title compound as a colourless oil (372 mg, 81%). LC-MS 94%, m/z=298.1, 1H NMR (500 MHz, Chloroform-d) δ 7.48 (dd, J=7.5, 1.3 Hz, 1H), 7.29-7.08 (m, 8H), 4.32 (q, J=7.1 Hz, 2H), 4.05 (s, 2H), 2.92 (q, J=7.1 Hz, 2H), 2.56 (s, 3H), 1.35 (t, J=7.1 Hz, 3H), 0.92 (t, J=7.1 Hz, 3H).

Step 3: Synthesis of 3-[benzyl(ethyl)amino]-2-methylbenzoic acid

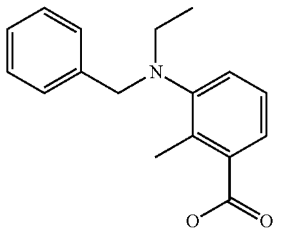 [SMILES: CCN(Cc1ccccc1)c1cccc(C(=O)O)c1C]

To a stirred solution of ethyl 3-[benzyl(ethyl)amino]-2-methylbenzoate (370 mg, 1.24 mmol) in THF (20 ml) and MeOH (5 ml) was added 2M NaOH (3.11 ml, 6.22 mmol) and the reaction was stirred at 50° C. for 16 h. The reaction was cooled to room temperature and the solvent removed in vacuo after which the aqueous solution was adjusted to pH1 using 1M HCl. The product was extracted into DCM (3×50 ml), washed with brine (20 ml), dried with $Na_2SO_4$ concentrated and filtered to afford the title compound as an orange oil (296 mg, 80%) which was used in the next stage without any further purification. LC-MS 91%, m/z=270.0, 1H NMR (500 MHz, Chloroform-d) δ 7.73 (d, J=7.5 Hz, 1H), 7.34-7.30 (m, 4H), 7.23 (dt, J=15.4, 6.9 Hz, 3H), 4.12 (d, J=13.5 Hz, 2H), 3.04-2.94 (m, 2H), 2.69 (s, 3H), 0.99 (t, J=7.0 Hz, 3H).

Step 4: Synthesis of 3-[benzyl(ethyl)amino]-N-[(4,6-dimethyl-2-oxo-1,2-dihydropyridin-3-yl)methyl]-2-methylbenzamide

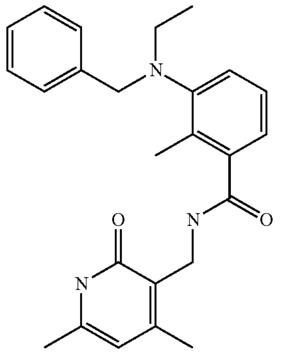 [SMILES: CCN(Cc1ccccc1)c1cccc(C(=O)NCc2c(C)cc(C)[nH]c2=O)c1C]

To a stirred solution of (3-[benzyl(ethyl)amino]-2-methylbenzoic acid (91% purity, 296 mg, 1.0 mmol) in DMF (10 ml) was added DIPEA (440 µl, 2.5 mmol) and HATU (570 mg, 1.5 mmol). The reaction was stirred at room temperature for 5 min after which time 3-(aminomethyl)-4,6-dimethyl-1,2-dihydropyridin-2-one (89%, 222 mg, 1.3 mmol) was added and the reaction was stirred at room temperature for 16 h. The reaction mixture was then poured onto 150 ml of water and stirred for 20 min. The product was filtered, air dried under vacuum and then purified using RP-HPLC. The resulting solid was triturated with diethyl ether and isolated by filtration to afford the title compound as an off white solid (86 mg, 21%). LC-MS 99%, m/z=404.3, $^1$H NMR (500 MHz, Chloroform-d) δ 12.04 (s, 1H), 7.33-7.23 (m, 4H), 7.21 (t, J=6.8 Hz, 1H), 7.14-7.05 (m, 3H), 7.05-6.99 (m, 1H), 5.92 (s, 1H), 4.53 (d, J=5.9 Hz, 2H), 4.06 (s, 2H), 2.92 (q, J=6.9 Hz, 2H), 2.41 (s, 3H), 2.39 (s, 3H), 2.16 (s, 3H), 0.92 (t, J=7.0 Hz, 3H).

Compound 191: 2-bromo-5-chloro-N-((4,6-dimethyl-2-oxo-1,2-dihydropyridin-3-yl)methyl)-3-(ethyl(tetrahydro-2H-pyran-4-yl)amino)benzamide

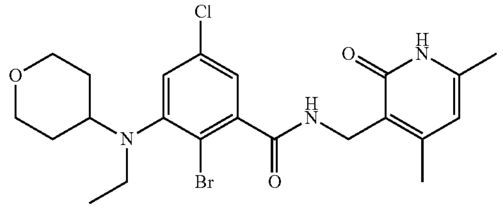 [SMILES: CCN(c1cc(Cl)cc(C(=O)NCc2c(C)cc(C)[nH]c2=O)c1Br)C1CCOCC1]

Step 1: Synthesis of methyl 2-bromo-5-chloro-3-nitrobenzoate

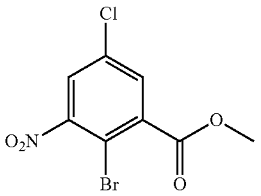

A solution of methyl 2-bromo-5-chlorobenzoate (10 g, 40 mmol) in concentrated $H_2SO_4$ (48 ml, 910 mmol) was cooled to −5° C. in an acetone/ice bath in air. A mixture of concentrated nitric acid (3.35 ml, 52 mmol) and concentrated $H_2SO_4$ (3.4 ml, 64 mmol) was added dropwise to the reaction mixture at 0° C. over 30 minutes. The yellow reaction mixture was stirred at 0° C. for 1.5 hours before being poured onto ice. EtOAc (150 ml) was added and the phases were separated. The organic phase was washed with deionized water (3×50 ml) followed by brine (50 ml). The organic phase was dried over MgSO4, filtered and concentrated under reduced pressure to give 12.0 g (60%) of the title compound material as a pale yellow oil which solidified upon standing. This material contained 40% of the 6-nitro isomer. This material was used without further purification. LC-MS 91%, m/z=no ionisation, $^1$H NMR (500 MHz, Chloroform-d) δ 7.86 (1H, d, J=2.52 Hz), 7.77 (1H, d, J=2.52 Hz), 3.99 (3H, s).

Step 2: Synthesis of methyl 3-amino-2-bromo-5-chlorobenzoate

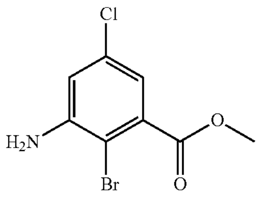

To a solution of methyl 2-bromo-5-chloro-3-nitrobenzoate (4.0 g, 14 mmol) in methanol (130 ml) at room temperature was added ammonium chloride (7.13 g, 136 mmol) followed by deionized water (65 ml). The mixture was heated to 70° C. in air before the addition of iron (4.55 g, 81.5 mmol). The reaction was stirred at 70° C. for 3 hours, allowed to cool to room temperature and filtered through Kieselgel. The filter pad was washed with MeOH (65 ml) and the filtrate concentrated under reduced pressure. The residue was dissolved in saturated $NaHCO_3$ (50 ml) and EtOAc (100 ml). The phases were separated and the organic phase was washed with saturated $NaHCO_3$(aq) (3×50 ml) before being dried over $MgSO_4$, filtered and concentrated under reduced pressure. The residue was purified by FCC (50 g silica, Isolute cartridge, gradient of eluents; 95:5 Heptane:EtOAc to 7:3 Heptane:EtOAc) to give 1.92 g (48%) of the title compound as a colourless oil. LC-MS 92%, m/z=268.8/265.8/267.6, $^1$H NMR (500 MHz, Chloroform-d) δ 7.08 (1H, d, J=2.36 Hz), 6.86 (1H, d, J=2.36 Hz), 4.34-4.49 (2H, m), 3.93 (3H, s).

Step 3: Synthesis of methyl 2-bromo-5-chloro-3-(oxan-4-ylamino)benzoate

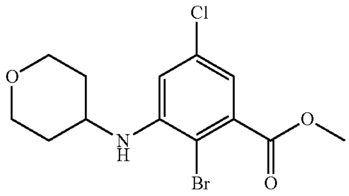 [SMILES: COC(=O)c1cc(Cl)cc(NC2CCOCC2)c1Br]

To a solution of methyl 3-amino-2-bromo-5-chlorobenzoate (1.0 g, 3.8 mmol) in 1,2-dichloroethane (15 ml) at room temperature under nitrogen was added oxan-4-one (0.7 ml, 7.6 mmol) followed by acetic acid (1.3 ml, 23 mmol). This solution was stirred for 5 minutes before the addition of sodium triacetoxyborohydride (2.4 g, 11 mmol) at room temperature. After 21 h, additional oxan-4-one (0.7 ml, 7.6 mmol) was added to the reaction mixture, with stirring for 10 minutes before adding sodium triacetoxyborohydride (2.4 g, 11 mmol). After stirring for 20 h, deionized water (30 ml) was added and the mixture was neutralised with solid $NaHCO_3$. The phases were separated and the aqueous layer was extracted with EtOAc (2×30 ml). The combined organic extracts were dried over $MgSO_4$, filtered and concentrated under reduced pressure. The residue was purified by FCC (25 g silica, Isolute cartridge, gradient of eluents; 9:1 Heptane: EtOAc to 8:2 Heptane:EtOAc) to give 903 mg (68%) of the title compound as a white solid. LC-MS 92%, 2.11 min (3 minute LC-MS method), m/z=348.2/350.2/351.9, $^1$H NMR (500 MHz, Chloroform-d) δ 6.94-7.07 (1H, m), 6.70 (1H, d, J=2.36 Hz), 4.72 (1H, d, J=7.57 Hz), 3.96-4.15 (2H, m), 3.87-3.96 (3H, m), 3.40-3.67 (3H, m), 2.05 (2H, d, J=13.08 Hz), 1.49-1.69 (2H, m).

Step 4: Synthesis of methyl 2-bromo-5-chloro-3-[ethyl(oxan-4-yl)amino]benzoate

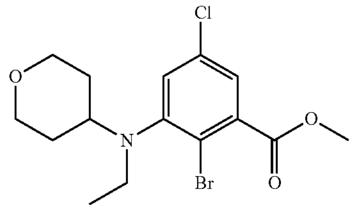 [SMILES: CCN(c1cc(Cl)cc(C(=O)OC)c1Br)C1CCOCC1]

To a solution of methyl 2-bromo-5-chloro-3-(oxan-4-ylamino)benzoate (300 mg, 0.86 mmol) in 1,2-dichloroethane (3 ml) at room temperature under nitrogen was added acetaldehyde (96 μl, 1.7 mmol) followed by acetic acid (0.3 ml, 5.16 mmol). This solution was stirred for 5 minutes before the addition of sodium triacetoxyborohydride (0.55 g, 2.6 mmol) at room temperature with reaction monitoring by LCMS. After 22 h, further acetaldehyde (96 μl, 1.7 mmol) was added to the reaction mixture and this was stirred for 10 minutes before the addition of sodium triacetoxyborohydride (0.55 g, 2.6 mmol). After 3 days, the reaction mixture was diluted with 1,2-dichloroethane (5 ml). Acetaldehyde (962 μl, 17.2 mmol) was added to the reaction mixture and this was stirred for 10 minutes before the addition of sodium triacetoxyborohydride (1.82 g, 8.6 mmol). After 15 h, further acetaldehyde (960 μl, 17.2 mmol) was added to the reaction mixture and this was stirred for 10 minutes before the addition of sodium triacetoxyborohydride (1.82 g, 8.6 mmol). The reaction mixture was then stirred at room temperature for a further 22 hours before deionized water (25 ml) was added and the mixture was neutralised with solid $NaHCO_3$. EtOAc (25 ml) was added and the phases were separated. The aqueous layer was then extracted with EtOAc (2×25 ml) and the combined organic extracts were dried over $MgSO_4$, filtered and concentrated under reduced pressure. The residue was purified by FCC (10 g silica, Isolute cartridge, gradient of eluents; 99:1 Heptane:EtOAc to 8:2 Heptane:EtOAc) to give 122 mg (38%) of the title compound as a colourless oil. LC-MS 85%, m/z=376.3/378.2/379.9, $^1$H NMR (500 MHz, Chloroform-d) δ 7.31 (d, J=2.5 Hz, 1H), 7.18 (d, 12.4 Hz, 1H), 3.98 (dd, J=8.7, 5.5 Hz, 2H), 3.94 (s, 3H), 3.35 (td, J=11.6, 5.5 Hz, 2H), 3.19 (t, J=7.1 Hz, 1H), 3.12 (q, J=7.1 Hz, 2H), 1.75 (td, J=10.1, 8.8, 3.9 Hz, 4H), 0.92 (t, J=7.1 Hz, 3H).

Step 5: Synthesis of 2-bromo-5-chloro-3-[ethyl(oxan-4-yl)amino]benzoic acid

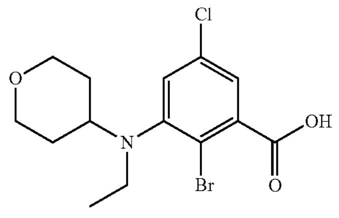 [SMILES: CCN(c1cc(Cl)cc(C(=O)O)c1Br)C1CCOCC1]

To a solution of methyl 2-bromo-5-chloro-3-[ethyl(oxan-4-yl)amino]benzoate (122 mg, 0.32 mmol) in tetrahydrofuran (3 ml) was added 4M NaOH (3.2 ml). The reaction mixture was stirred at 50° C. for 20 hours. The reaction mixture was acidified to pH 2-3 with 6M HCl and extracted with DCM (3×100 ml). The combined organic extracts were dried over $MgSO_4$, filtered and concentrated under reduced pressure to give 109 mg (93%, 83% corrected yields) of 2-bromo-5-chloro-3-[ethyl(oxan-4-yl)amino]benzoic acid as a pale yellow foam. LC-MS 89%, m/z=361.9/364.2/365.8, $^1H$ NMR (500 MHz, Chloroform-d) δ 7.50 (d, J=2.4 Hz, 1H), 7.23 (d, J=2.4 Hz, 1H), 4.00 (d, J=11.5 Hz, 2H), 3.49-3.27 (m, 2H), 3.21 (t, J=7.4 Hz, 1H), 3.14 (q, J=7.0 Hz, 2H), 1.78 (dd, J=7.4, 3.4 Hz, 4H), 0.93 (t, J=7.0 Hz, 3H).

Step 6: Synthesis of 2-bromo-5-chloro-N-((4,6-dimethyl-2-oxo-1,2-dihydropyridin-3-yl)methyl)-3-(ethyl(tetrahydro-2H-pyran-4-yl)amino)benzamide

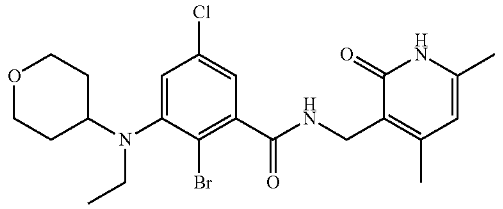 [SMILES: CCN(c1cc(Cl)cc(C(=O)NCc2c(C)cc(C)[nH]c2=O)c1Br)C1CCOCC1]

To a solution of 2-bromo-5-chloro-3-[ethyl(oxan-4-yl)amino]benzoic acid (109 mg, 0.3 mmol) in DMF (3 ml) at room temperature under nitrogen was added PyBOP (187 mg, 0.36 mmol) followed by N-ethyl-N-(propan-2-yl)propan-2-amine (78 μl, 0.45 mmol) and 3-(aminomethyl)-4,6-dimethyl-1,2-dihydropyridin-2-one (89%, 56 mg, 0.33 mmol). After stirring for 1 hour at room EtOAc (30 ml) was added to the reaction mixture and this was then washed with deionized water (2×10 ml) followed by saturated $NaHCO_3$(aq) (2×10 ml). The organic phase was dried over $MgSO_4$, filtered and concentrated under reduced pressure. The residue was purified twice by FCC (5 g silica, Isolute cartridge, gradient of eluents; 100% DCM to 98:2 DCM:MeOH). The sample was dried in a vacuum oven for 18 hours to give 103 mg (65%) of the title compound as a pale yellow solid. LC-MS 94%, m/z=496.0/498.0/500.0, $^1H$ NMR (500 MHz, Chloroform-d) δ 11.00 (s, 1H), 7.20-7.10 (m, 1H), 7.10-7.05 (m, 2H), 5.94 (s, 1H), 4.54 (d, J=5.9 Hz, 2H), 3.96 (d, J=11.4 Hz, 2H), 3.42-3.26 (m, 2H), 3.28-3.12 (m, 1H), 3.09 (q, J=7.0 Hz, 2H), 2.39 (s, 3H), 2.23 (s, 3H), 1.72 (td, J=8.5, 3.8 Hz, 4H), 0.90 (t, J=7.0 Hz, 3H).

Compound 102: 5-chloro-N-[(4,6-dimethyl-2-oxo-1,2-dihydropyridin-3-yl)methyl]-3-[ethyl(piperidin-4-yl)amino]-2-methylbenzamide

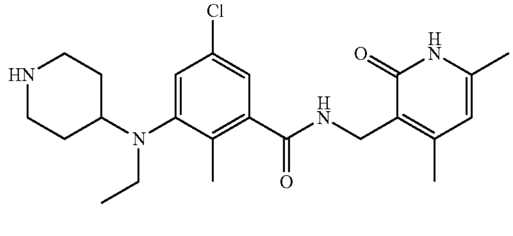 [SMILES: CCN(c1cc(Cl)cc(C(=O)NCc2c(C)cc(C)[nH]c2=O)c1C)C1CCNCC1]

Step 1: Synthesis of 5-chloro-2-methyl-3-nitrobenzoic acid

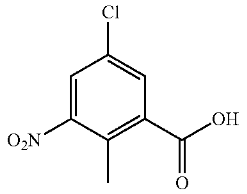

A solution of 5-chloro-2-methylbenzoic acid (9.9 g, 58 mmol) in concentrated $H_2SO_4$ (70 ml, 1310 mmol) was cooled to −5° C. in an acetone/ice bath. A mixture of concentrated nitric acid (4.9 ml, 75 mmol) and concentrated $H_2SO_4$ (5.0 ml, 94 mmol) was added dropwise to the reaction mixture at −5° C. over 30 minutes. The reaction mixture was stirred at −5° C. for 2 hours before being poured onto ice (150 g) and the precipitate collected by filtration. The precipitate was dissolved in EtOAc (100 ml) and washed with brine (100 ml) before being dried over $MgSO_4$, filtered and concentrated under reduced pressure to give 11.9 g of the title compound as an off-white solid. This material was used without further purification. LC-MS 57%, m/z=214.0/216.0, $^1H$ NMR (500 MHz, Chloroform-d) δ 10.37 (1H, br. s.), 8.19 (1H, d, J=2.21 Hz), 7.91 (1H, d, J=2.21 Hz), 2.67 (2H, s).

Step 2: Synthesis of methyl 5-chloro-2-methyl-3-nitrobenzoate

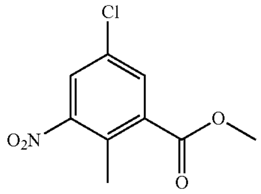

To a solution of 5-chloro-2-methyl-3-nitrobenzoic acid (1.17 g, 5.43 mmol) in DMF (11 ml) at room temperature and nitrogen was added $Na_2CO_3$ (862 mg, 8.14 mmol) followed by iodomethane (0.51 ml, 8.14 mmol). The reaction mixture was stirred at room temperature for 19 hours before being diluted with deionized water (30 ml) and extracted with EtOAc (3×30 ml). The combined organic phases were washed with saturated $NaHCO_3$(aq) (30 ml), dried over $MgSO_4$, filtered and concentrated under reduced pressure. The residue was purified by FCC (10 g silica, Isolute cartridge, gradient of eluents; 99:1 Heptane:EtOAc to 95:5 Heptane:EtOAc) to give 900 of the title compound as a pale yellow oil. LC-MS 89%, m/z=no ionisation, $^1H$ NMR (500 MHz, Chloroform-d) δ 8.00 (1H, d, J=2.21 Hz), 7.86 (1H, d, J=2.21 Hz), 3.96 (3H, s), 2.60 (3H, s).

Step 3: Synthesis of methyl 3-amino-5-chloro-2-methylbenzoate

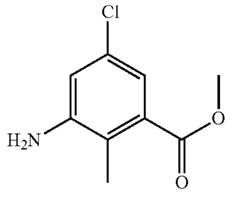

To a solution of methyl 5-chloro-2-methyl-3-nitrobenzoate (9.19 g, 40 mmol) in methanol (200 ml) at room temperature was added ammonium chloride (21 g, 400 mmol) followed by deionized water (100 ml). The mixture was heated to 70° C. before the addition of iron (13.4 g, 240 mmol). The reaction turned to a dark colour over the 2.5 hours it was stirred at 70° C. This mixture was allowed to cool to room temperature and was filtered through Kieselgel. The filter pad was washed with MeOH (100 ml) and the filtrate concentrated under reduced pressure. The residue was dissolved in deionized water (100 ml) and EtOAc (100 ml). The phases were separated and the aqueous phase was extracted with EtOAc (2×100 ml). The combined organic extracts were washed with brine (100 ml), dried over $MgSO_4$, filtered and concentrated under reduced pressure to give 7.6 g of the title compound as a viscous orange oil that solidified upon standing. This material was used without further purification. LC-MS 63%, m/z=200.3/202.0, $^1H$ NMR (500 MHz, Chloroform-d) δ 7.20 (1H, d, J=2.21 Hz), 6.80 (1H, d, J=2.05 Hz), 3.89 (3H, s), 3.74-3.87 (2H, m), 2.30 (3H, s).

Step 4: Synthesis of tert-butyl 4-{[5-chloro-3-(methoxycarbonyl)-2-methylphenyl]amino}piperidine-1-carboxylate

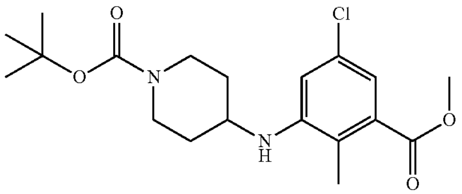 [SMILES: COC(=O)c1cc(Cl)cc(NC2CCN(C(=O)OC(C)(C)C)CC2)c1C]

To a solution of methyl 3-amino-5-chloro-2-methylbenzoate (100 mg, 0.50 mmol) in 1,2-dichloroethane (2.5 ml) at room temperature and under nitrogen was added tert-butyl 4-oxopiperidine-1-carboxylate (200 mg, 1.0 mmol) followed by acetic acid (0.17 ml, 3.0 mmol). This solution was stirred for 5 minutes before the addition of sodium triacetoxyborohydride (0.32 g, 1.5 mmol) at room temperature. The resulting mixture was stirred for 20 hours under nitrogen. Deionized water (5 ml) was added and the mixture was neutralised with solid $NaHCO_3$. The phases were separated and the aqueous layer was extracted with EtOAc (2×5 ml). The combined organic extracts were dried over $MgSO_4$, filtered and concentrated under reduced pressure. The residue was purified by FCC (10 g silica, Isolute cartridge, gradient of eluents; 99:1 Heptane:EtOAc to 7:3 Heptane:EtOAc) to give 131 mg (68%) of the title compound as a white solid. LC-MS 98%, m/z=405.4/406.9 (M+Na), $^1H$ NMR (500 MHz, Chloroform-d) δ ppm 7.10 (1H, d, J=2.05 Hz), 6.70 (1H, d, J=1.89 Hz), 3.98-4.16 (2H, m), 3.88 (3H, s), 3.58-3.72 (1H, m), 3.37-3.52 (1H, m), 2.97 (2H, br. t, J=11.50, 11.50 Hz), 2.24 (3H, s), 2.06 (2H, br. d, J=10.60 Hz), 1.44-1.51 (9H, m), 1.32-1.44 (2H, m).

Step 5: Synthesis of tert-butyl 4-{[5-chloro-3-(methoxycarbonyl)-2-methylphenyl](ethyl)amino}piperidine-1-carboxylate

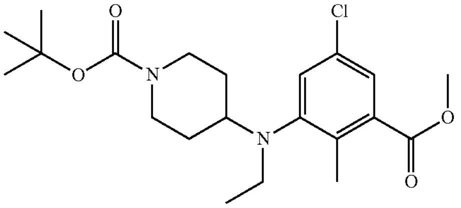 [SMILES: CCN(c1cc(Cl)cc(C(=O)OC)c1C)C1CCN(C(=O)OC(C)(C)C)CC1]

To a solution of tert-butyl 4-{[5-chloro-3-(methoxycarbonyl)-2-methylphenyl]amino}piperidine-1-carboxylate (125 mg, 0.33 mmol) in 1,2-dichloroethane (1.6 ml) at room temperature under nitrogen was added acetaldehyde (37 µl, 0.65 mmol) followed by acetic acid (0.11 ml, 1.96 mmol). This solution was stirred for 5 minutes before adding sodium triacetoxyborohydride (0.21 g, 0.98 mmol) at room temperature. The reaction was monitored by LCMS and after 4.5 h a further acetaldehyde (73 µl, 1.31 mmol) and sodium triacetoxyborohydride (0.28 g, 1.31 mmol) were added to the reaction mixture. The mixture was stirred for a further 18 hours after which deionized water (10 ml) was added and the mixture was neutralised with solid $NaHCO_3$. The phases were separated and the aqueous layer was extracted with EtOAc (2×10 ml). The combined organic extracts were dried over $MgSO_4$, filtered and concentrated under reduced pressure. The residue was purified by FCC (10 g silica, Isolute cartridge, gradient of eluents; 99:1 Heptane:EtOAc to 8:2 Heptane:EtOAc) to give 131 mg (98%) of the title compound as a thick colourless oil. LC-MS 98%, m/z=433.5/435.1 (M+Na), $^1H$ NMR (500 MHz, Chloroform-d) δ ppm 7.57 (1H, d, J=2.21 Hz), 7.22 (1H, d, J=2.05 Hz), 3.97-4.14 (2H, m), 3.90 (3H, s), 3.04 (2H, q, J=6.99 Hz), 2.81-2.91 (1H, m), 2.70 (2H, br. t, J=11.50, 11.50 Hz), 2.45 (3H, s), 1.69-1.80 (2H, m), 1.47-1.56 (2H, m), 1.46 (9H, s), 0.87 (3H, t, J=7.09 Hz).

Step 6: Synthesis of 3-({1-[(tert-butoxy)carbonyl]piperidin-4-yl}(ethyl)amino)-5-chloro-2-methylbenzoic acid

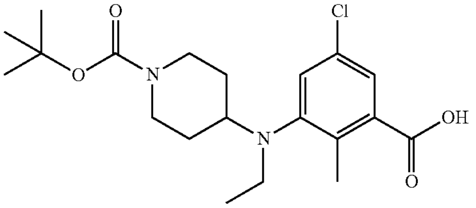 [SMILES: CCN(c1cc(Cl)cc(C(=O)O)c1C)C1CCN(C(=O)OC(C)(C)C)CC1]

To a solution of tert-butyl 4-{[5-chloro-3-(methoxycarbonyl)-2-methylphenyl](ethyl)amino}piperidine-1-carboxylate (131 mg, 0.32 mmol) in tetrahydrofuran (2 ml) was added LiOH (8.4 mg, 0.35 mmol) in deionized water (2 ml). The reaction mixture was stirred in air at room temperature for 24 hours. 1M NaOH (3.19 ml) was added to the reaction mixture and this was stirred for a further 24 hours. The reaction mixture was then warmed to 40° C. for 25 h. The reaction mixture was acidified to pH 2-3 with 1M HCl and extracted with EtOAc (3×20 ml). The combined organic extracts were dried over $MgSO_4$, filtered and concentrated under reduced pressure to give 122 mg of the title compound as a thick orange oil. LC-MS 76%, m/z=397.5/399.4, $^1H$ NMR (500 MHz, Chloroform-d) δ ppm 7.74 (1H, s), 7.20-7.35 (2H, m), 3.92-4.11 (2H, m), 2.97-3.13 (2H, m), 2.81-2.95 (1H, m), 2.62-2.79 (2H, m), 2.53 (3H, s), 1.75 (2H, br. s.), 1.48-1.61 (2H, m), 1.46 (9H, s), 0.89 (3H, t, J=6.86 Hz).

Step 7: Synthesis of tert-butyl 4-[(5-chloro-3-{[(4,6-dimethyl-2-oxo-1,2-dihydropyridin-3-yl)methyl]carbamoyl}-2-methylphenyl)(ethyl)amino]piperidine-1-carboxylate

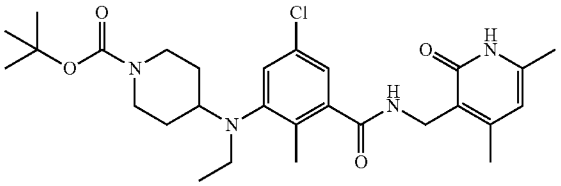 [SMILES: CCN(c1cc(Cl)cc(C(=O)NCc2c(C)cc(C)[nH]c2=O)c1C)C1CCN(C(=O)OC(C)(C)C)CC1]

To a solution of 3-({1-[(tert-butoxy)carbonyl]piperidin-4-yl}(ethyl)amino)-5-chloro-2-methylbenzoic acid (60 mg, 0.15 mmol) in DMF (2 ml) at room temperature under nitrogen was added PyBOP (94 mg, 0.18 mmol) followed by N-ethyl-N-(propan-2-yl)propan-2-amine (40 µl, 0.23 mmol) and 3-(aminomethyl)-4,6-dimethyl-1,2-dihydropyridin-2-one (89%, 28 mg, 0.17 mmol). After stirring for 1 hour at room temperature EtOAc (30 ml) was added to the reaction mixture and this was then washed with deionized water (5 ml) followed by saturated $NaHCO_3$(aq) (3×5 ml). The organic phase was dried over MgSO4, filtered and concentrated under reduced pressure. The residue was purified by FCC (2 g silica, Isolute cartridge, gradient of eluents; 100% EtOAc to 96:4 EtOAc:MeOH) to give 71 mg (88%) of the title compound as a pale yellow solid. LC-MS 97%, m/z=531.1/533.1, $^1H$ NMR (250 MHz, Chloroform-d) δ ppm 11.17 (1H, br. s.), 7.11-7.18 (1H, m), 7.06 (2H, dd, J=7.46, 2.28 Hz), 5.96 (1H, s), 4.53 (2H, d, J=5.94 Hz), 3.93-4.14 (2H, m), 2.97-3.08 (2H, m), 2.78-2.88 (1H, m), 2.68 (2H, t, J=11.57 Hz), 2.39 (3H, s), 2.26 (3H, s), 2.24 (3H, s), 1.71 (2H, d, J=11.27 Hz), 1.52 (2H, br. s.), 1.45 (9H, s), 0.86 (3H, t, J=6.93 Hz).

Step 8: Synthesis of 5-chloro-N-[(4,6-dimethyl-2-oxo-1,2-dihydropyridin-3-yl)methyl]-3-[ethyl(piperidin-4-yl)amino]-2-methylbenzamide

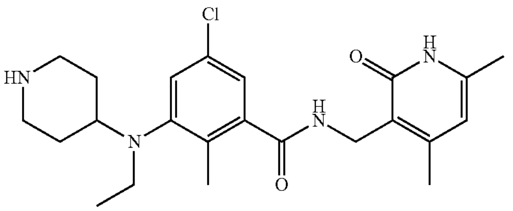 [SMILES: CCN(c1cc(Cl)cc(C(=O)NCc2c(C)cc(C)[nH]c2=O)c1C)C1CCNCC1]

To a solution of tert-butyl 4-[(5-chloro-3-{[(4,6-dimethyl-2-oxo-1,2-dihydropyridin-3-yl)methyl]carbamoyl}-2-methylphenyl)(ethyl)amino]piperidine-1-carboxylate (140 mg, 0.26 mmol) in 1,4-dioxane (5 ml) at room temperature was added HCl (4M in dioxane) (1.32 ml). A gum formed after stirring for a short time which then dissolved upon the addition of deionized water (2 ml). The reaction was stirred for 21 h before being concentrated under reduced pressure to give a thick oil. DCM (3 ml) was added and a solid formed. This mixture was concentrated to give 105 mg of a yellow solid which was stirred in DCM (10 ml) for 1 hour before being filtered and dried under high vacuum in a vacuum oven for 24 hours. The sample was then dissolved in deionized water (0.2 ml) and lyophilized to give 86 mg (70%) of the title compound as a beige solid. LC-MS 100%, m/z=431.2/433.2, $^1H$ NMR (500 MHz, Chloroform-d) δ ppm 7.44 (bs, 1H), 7.26 (bs, 1H), 6.69 (bs, 1H), 4.55 (s, 2H), 3.53-3.34 (m, 3H), 3.28-3.08 (m, 2H), 3.01 (t, J=11.8 Hz, 2H), 2.51 (s, 3H), 2.43 (s, 3H), 2.33 (s, 3H), 2.16-1.96 (m, 2H), 1.91-1.76 (m, 2H), 0.92 (t, J=6.9 Hz, 3H).

Compound 192: 5-chloro-N-[(4,6-dimethyl-2-oxo-1,2-dihydropyridin-3-371)methyl]-3-[ethyl(oxan-4-yl)amino]-2-methoxybenzamide

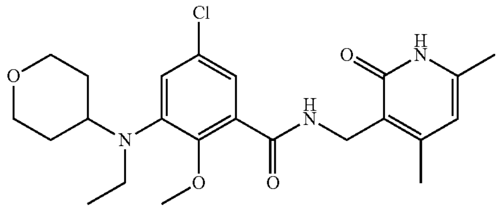 [SMILES: CCN(c1cc(Cl)cc(C(=O)NCc2c(C)cc(C)[nH]c2=O)c1OC)C1CCOCC1]

Step 1: Synthesis of methyl 5-chloro-2-methoxy-3-nitrobenzoate

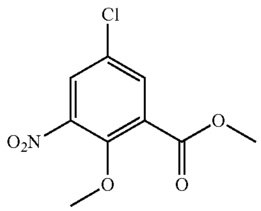 [SMILES: COC(=O)c1cc(Cl)cc([N+](=O)[O-])c1OC]

To concentrated $H_2SO_4$ (90 mL) was added portionwise 5-chloro-2-methylbenzoic acid (13.2 g, 77.6 mmol) at 0° C. Then a mixture of conc. $HNO_3$ (10.5 g, 1740 mmol) in conc. $H_2SO_4$ (15 mL) was added dropwise at 0° C. over a period of about 1.5 hr. After the addition, the mixture was stirred at this temperature for 2 hr. The mixture was poured into ice water with vigorous stirring and the precipitate was collected by filtration. The precipitate was dissolved in EtOAc, washed with brine, dried over anhydrous $Na_2SO_4$, and concentrated to give a crude title compound (13.2 g), which was used in the next step without further purification. LC-MS 95%, m/z=245.9/247.9, $^1$H NMR (500 MHz, Chloroform-d) δ ppm 8.01 (1H, d, J=2.68 Hz), 7.91 (1H, d, J=2.68 Hz), 4.01 (3H, s), 3.97-3.99 (3H, s).

Step 2: Synthesis of methyl 3-amino-5-chloro-2-methoxybenzoate

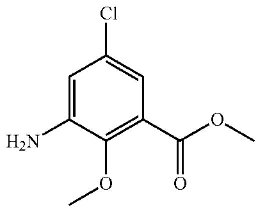

To a solution of methyl 5-chloro-2-methoxy-3-nitrobenzoate (1.21 g, 4.93 mmol) in methanol (50 ml) at room temperature was added ammonium chloride (2.59 g, 49.2 mmol) followed by deionized water (25 ml). The mixture was heated to 70° C. before the addition of iron (1.65 g, 29.6 mmol). The reaction turned to a dark color over the 2 hours it was stirred at 70° C. This mixture was allowed to cool to room temperature and was filtered through Kieselgel. The filter pad was washed with MeOH (50 ml) and the filtrate concentrated under reduced pressure. The residue was dissolved in deionized water (25 ml) and EtOAc (25 ml). The phases were separated and the aqueous phase was extracted with EtOAc (2×25 ml). The combined organic extracts were washed with brine (25 ml), dried over $MgSO_4$, filtered and concentrated under reduced pressure to give 892 mg (67%) of the title compound as a viscous brown oil. This material was used without further purification. LC-MS 89%, 1.75 min (3 minute LC-MS method), m/z=216.3/218.0, $^1$H NMR (500 MHz, Chloroform-d) δ ppm 7.16 (1H, d, J=2.52 Hz), 6.87 (1H, d, J=2.52 Hz), 4.03 (2H, br. s.), 3.89-3.94 (3H, m), 3.84 (3H, s).

Step 3: Synthesis of methyl 5-chloro-2-methoxy-3-[(oxan-4-yl)amino]benzoate

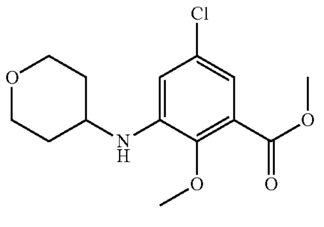 [SMILES: COC(=O)c1cc(Cl)cc(NC2CCOCC2)c1OC]

To a solution of methyl 3-amino-5-chloro-2-methoxybenzoate (440 mg, 2 mmol) in 1,2-dichloroethane (8 ml) at temperature under nitrogen was added oxan-4-one (0.38 ml, 4.0 mmol) followed by acetic acid (0.7 ml, 12 mmol). This solution was stirred for 5 minutes before the addition of sodium triacetoxyborohydride (1.3 g, 6.1 mmol) at room temperature. After stirring for 23 hours deionized water (16 ml) was added and the mixture was neutralized with solid $NaHCO_3$. The phases were separated and the aqueous layer was extracted with EtOAc (2×16 ml). The combined organic extracts were dried over $MgSO_4$, filtered and concentrated under reduced pressure. The residue was purified by FCC (10 g silica, Isolute cartridge, gradient of eluents; 9:1 Heptane:EtOAc to 7:3 Heptane:EtOAc) to give 439 mg (72%) of the title compound as a white solid. LC-MS 97%, m/z=300.3/302.0, $^1$H NMR (500 MHz, Chloroform-d) δ ppm 7.06 (1H, d, J=2.52 Hz), 6.73 (1H, d, J=2.52 Hz), 4.38-4.45 (1H, m), 4.02 (2H, dt, J=11.78, 3.49 Hz), 3.91 (3H, s), 3.81 (3H, s), 3.54 (2H, td, J=11.47, 2.13 Hz), 3.40-3.50 (1H, m), 2.03 (2H, br. d, J=13.70 Hz), 1.48-1.55 (2H, m).

Step 4: Synthesis of methyl 5-chloro-3-[ethyl(oxan-4-yl)amino]-2-methoxybenzoate

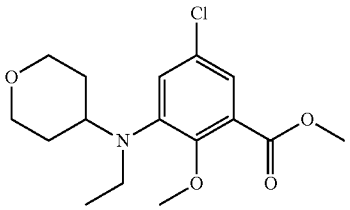 [SMILES: CCN(c1cc(Cl)cc(C(=O)OC)c1OC)C1CCOCC1]

To a solution of methyl 5-chloro-2-methoxy-3-[(oxan-4-yl)amino]benzoate (220 mg, 0.73 mmol) in 1,2-dichloroethane (2 ml) at room temperature under nitrogen was added acetaldehyde (82 μl, 1.47 mmol) followed by acetic acid (0.25 ml, 4.4 mmol). This solution was stirred for 5 minutes before the addition of sodium triacetoxyborohydride (0.47 g, 2.2 mmol) at room temperature. After stirring for 16 hours acetaldehyde (82 μl, 1.47 mmol) was added to the reaction mixture and stirred for 5 minutes before the addition of sodium triacetoxyborohydride (0.47 g, 2.2 mmol). After stirring for 24 hours, a further acetaldehyde (82 μl, 1.47 mmol) was added to the reaction mixture and stirred for 5 minutes before the addition of sodium triacetoxyborohydride (0.47 g, 2.2 mmol). The reaction was stirred for 24 h after which deionized water (10 ml) was added and the mixture was neutralized with solid $NaHCO_3$. The phases were separated and the aqueous layer was extracted with EtOAc (2×10 ml). The combined organic extracts were dried over $MgSO_4$, filtered and concentrated under reduced pressure. The residue was purified by FCC (10 g silica, Isolute cartridge, gradient of eluents; 95:5 Heptane:EtOAc to 7:3 Heptane:EtOAc) to give 127 mg (53%) of the title compound as a yellow oil. LC-MS 93%, m/z=328.4/330.0, $^1$H NMR (500 MHz, Chloroform-d) δ ppm 7.35 (d, J=2.6 Hz, 1H), 7.09 (d, J=2.6 Hz, 1H), 3.98 (dd, J=11.3, 4.2 Hz, 2H), 3.91 (s, 3H), 3.85 (s, 3H), 3.48 (tt, J=11.6, 4.0 Hz, 1H), 3.36 (td, J=11.8, 1.9 Hz, 2H), 3.15 (q, J=7.0 Hz, 2H), 1.78 (qd, J=12.2, 4.6 Hz, 2H), 1.72-1.59 (m, 2H), 0.99 (t, J=7.0 Hz, 3H).

Step 5: Synthesis of 5-chloro-3-[ethyl(oxan-4-yl)amino]-2-methoxybenzoic acid

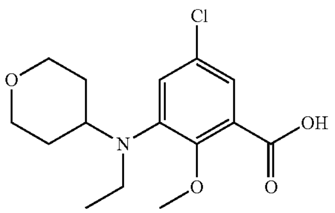 [SMILES: CCN(c1cc(Cl)cc(C(=O)O)c1OC)C1CCOCC1]

To a solution of methyl 5-chloro-3-[ethyl(oxan-4-yl)amino]-2-methoxybenzoate (127 mg, 0.39 mmol) in THF (4 ml) was added 4M NaOH (3.87 ml). The reaction mixture was stirred at 50° C. for 24 hours. The reaction mixture was acidified to pH 2-3 with 6M HCl and extracted with DCM (5×15 ml). The combined organic extracts were dried over MgSO4, filtered and concentrated under reduced pressure to give 111 mg (91%) of the title compound as a yellow oil. LC-MS 80%, 1.25 min (3 minute LC-MS method), m/z=314.4/315.9, $^{1}$H NMR (500 MHz, Chloroform-d) δ ppm 10.02-9.55 (m, 1H), 8.01-7.47 (m, 1H), 7.36-6.96 (m, 1H), 4.15-3.86 (m, 5H), 3.76 (t, J=6.6 Hz, 2H), 3.55-3.12 (m, 3H), 1.95-1.59 (m, 4H), 1.15-0.88 (m, 3H).

Step 6: Synthesis of 5-chloro-N-[(4,6-dimethyl-2-oxo-1,2-dihydropyridin-3-yl)methyl]-3-[ethyl(oxan-4-yl)amino]-2-methoxybenzamide

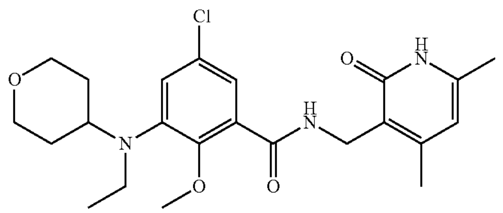

To a solution of 5-chloro-3-[ethyl(oxan-4-yl)amino]-2-methoxybenzoic acid (111 mg, 0.35 mmol) in DMF (3 ml) at room temperature under nitrogen was added PyBOP (220 mg, 0.42 mmol) followed by N-ethyl-N-(propan-2-yl)propan-2-amine (92 μl, 0.53 mmol) and 3-(aminomethyl)-4,6-dimethyl-1,2-dihydropyridin-2-one (89%, 66 mg, 0.39 mmol). After stirring for 1.5 hours at room temperature no starting material was observed by LCMS. Deionized water (20 ml) was added to the reaction mixture and the resultant precipitate was collected by filtration. The solid was washed with deionized water (3×5 ml) before being air dried. The solid was further purified by FCC (5 g silica, Isolute cartridge, gradient of eluents; 100% DCM to 97:3 DCM:MeOH). The sample was dried in a vacuum oven for 18 hours to give 105 mg (64%) the title compound as an off-white solid. LC-MS 98%, m/z=449.5/452.1, $^{1}$H NMR (500 MHz, Chloroform-d) δ ppm 11.47 (s, 1H), 8.79 (t, J=5.8 Hz, 1H), 7.73 (d, J=2.6 Hz, 1H), 7.05 (d, J=2.6 Hz, 1H), 5.92 (s, 1H), 4.55 (d, J=6.0 Hz, 2H), 3.98 (dd, J=11.3, 3.8 Hz, 2H), 3.78 (s, 3H), 3.35 (t, J=11.6 Hz, 3H), 3.12 (q, J=7.0 Hz, 2H), 2.42 (s, 3H), 2.28 (s, 3H), 1.92-1.61 (m, 4H), 0.94 (t, J=7.0 Hz, 3H).

Compound 212: 5-chloro-N-[(4,6-dimethyl-2-oxo-1,2-dihydropyridin-3-yl)methyl]-2-methoxy-3-[methyl(oxan-4-yl)amino]benzamide

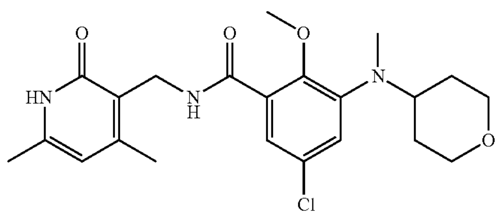 [SMILES: COc1c(C(=O)NCc2c(C)cc(C)[nH]c2=O)cc(Cl)cc1N(C)C1CCOCC1]

Step 1: Synthesis of methyl 5-chloro-2-methoxy-3-[methyl(oxan-4-yl)amino]benzoate

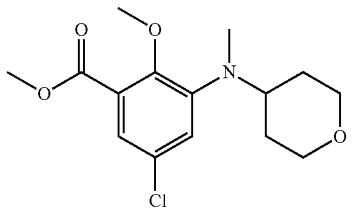 [SMILES: COC(=O)c1cc(Cl)cc(N(C)C2CCOCC2)c1OC]

To a solution of methyl 5-chloro-2-methoxy-3-[(oxan-4-yl)amino]benzoate (500 mg, 1.67 mmol) in 1,2-dichloroethane (16 ml) at room temperature under nitrogen was added paraformaldehyde (300 mg, 10 mmol) followed by acetic acid (0.57 ml, 10 mmol). This mixture was stirred for 5 minutes before the addition of sodium triacetoxyborohydride (2.12 g, 10 mmol). After stirring for 64 hours deionized water (30 ml) was added and the mixture was neutralized with solid $NaHCO_3$ and the phases were separated. The aqueous layer was extracted with EtOAc (3×15 ml) and the combined organic extracts were dried over $MgSO_4$, filtered and concentrated under reduced pressure. The residue was purified by FCC (10 g silica, Isolute cartridge, gradient of eluents; 9:1 Heptane:EtOAc to 7:3 Heptane:EtOAc) to give 431 mg (82%) of the title compound as a colorless oil. LC-MS 98%, m/z=314.0/316.0, $^{1}$H NMR (500 MHz, Chloroform-d) δ ppm 7.30 (d, J=2.5 Hz, 1H), 7.04 (d J=2.5 Hz, 1H), 4.00 (dd, J=11.3, 4.3 Hz, 2H), 3.90 (s, 3H), 3.82 (s, 3H), 3.70 (ddt, J=11.7, 7.7, 3.8 Hz, 1H), 3.39 (t, J=11.1 Hz, 2H), 2.71 (s, 3H), 1.84 (qd, J=12.3, 4.6 Hz, 2H), 1.66-1.55 (m, 2H).

Step 2: Synthesis of 5-chloro-2-methoxy-3-[methyl(oxan-4-yl)amino]benzoic acid

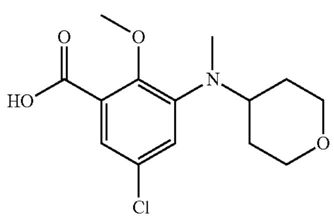 [SMILES: COc1c(C(=O)O)cc(Cl)cc1N(C)C1CCOCC1]

To a solution of methyl 5-chloro-2-methoxy-3-[methyl(oxan-4-yl)amino]benzoate (413 mg, 1.32 mmol) in THF (13 ml) and MeOH (2 ml) was added 4M NaOH (13.16 ml). The reaction mixture was stirred at 50° C. for 16 hours. The reaction mixture was acidified to pH 2-3 with 6M HCl and extracted with DCM (5×10 ml). The combined organic extracts were dried over $MgSO_4$, filtered and concentrated under reduced pressure to give 385 mg (98%) of the title compound as a thick yellow oil. LC-MS 94%, m/z=300.0/302.0, $^{1}$H NMR (500 MHz, Chloroform-d) δ ppm 7.74 (d, J=2.0 Hz, 1H), 7.30-7.12 (m, 1H), 4.11-4.02 (m, 2H), 4.01 (s, 3H), 3.54 (t, J=11.6 Hz, 1H), 3.40 (t, J=11.3 Hz, 2H), 2.76 (s, 3H), 1.97-1.78 (m, 2H), 1.63 (d, J=11.8 Hz, 2H).

Step 3: Synthesis of 5-chloro-N-[(4,6-dimethyl-2-oxo-1,2-dihydropyridin-3-yl)methyl]-2-methoxy-3-[methyl(oxan-4-yl)amino]benzamide

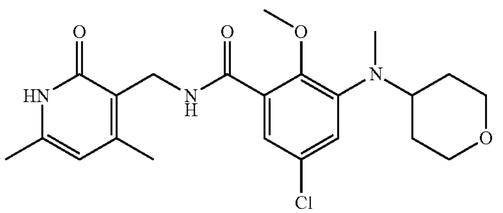 [SMILES: COc1c(C(=O)NCc2c(C)cc(C)[nH]c2=O)cc(Cl)cc1N(C)C1CCOCC1]

To a solution of 5-chloro-2-methoxy-3-[methyl(oxan-4-yl)amino]benzoic acid (200 mg, 0.67 mmol) in DMF (2 ml) at room temperature under nitrogen was added HBTU (304 mg, 0.80 mmol) followed by N-ethyl-N-(propan-2-yl)propan-2-amine (174 μl, 1.0 mmol) and 3-(aminomethyl)-4,6-dimethyl-1,2-dihydropyridin-2-one (89%, 125 mg, 0.73 mmol). After stirring for 2 hours at room temperature EtOAc (30 ml) was added to the reaction mixture and this was then washed with deionized water (5 ml) followed by saturated $NaHCO_3$ (aq) (3×5 ml). The organic phase was dried over $MgSO_4$, filtered and concentrated under reduced pressure. The residue was purified by FCC (10 g silica, Isolute cartridge, gradient of eluents; 100% DCM to 96:4 DCM:MeOH) to give 182 mg (63%) of the title compound as an off-white solid. LC-MS 98%, m/z=434.1/436.1, $^1$H NMR (500 MHz, Chloroform-d) δ ppm 12.52 (br s, 1H), 8.76 (t, J=5.8 Hz, 1H), 7.69 (d, J=2.6 Hz, 1H), 7.01 (d, J=2.6 Hz, 1H), 5.94 (s, 1H), 4.56 (d, J=6.0 Hz, 2H), 3.99 (dd, J=11.2, 3.9 Hz, 2H), 3.72 (s, 3H), 3.49 (tt, J=11.5, 3.7 Hz, 1H), 3.36 (t, J=11.2 Hz, 2H), 2.67 (s, 3H), 2.42 (s, 3H), 2.31 (s, 3H), 1.93-1.73 (m, 2H), 1.64-1.52 (m, 2H).

Compound 205: 5-chloro-N-[(4,6-dimethyl-2-oxo-1,2-dihydropyridin-3-yl)methyl]-2-ethyl-3-[methyl(oxan-4-yl)amino]benzamide

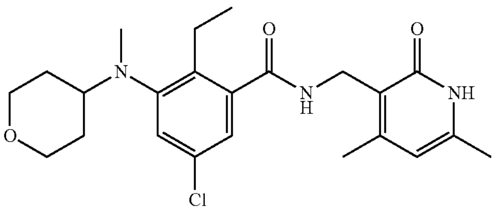 [SMILES: CCc1c(C(=O)NCc2c(C)cc(C)[nH]c2=O)cc(Cl)cc1N(C)C1CCOCC1]

Step 1: Synthesis of methyl 5-chloro-2-[2-(trimethylsilyl)ethynyl]benzoate

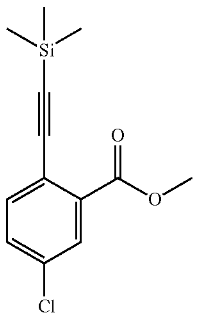 [SMILES: COC(=O)c1cc(Cl)ccc1C#C[Si](C)(C)C]

To a solution of methyl 2-bromo-5-chlorobenzoate (14.8 g, 59 mmol) in TEA (124 ml, 890 mmol) was added copper(I) iodide (338 mg, 1:78 mmol) and triphenylphosphine (778 mg, 2.97 mmol) at room temperature under nitrogen. This mixture had nitrogen bubbled through it for 10 minutes before the addition of ethynyl(trimethyl)silane (12.45 ml, 89 mmol) and $Pd(OAc)_2$ (266 mg, 1.19 mmol). The reaction mixture was stirred at 50° C. for 20 hours before being concentrated under reduced pressure. The residue was dissolved in deionized water (50 ml) and EtOAc (50 ml) and filtered through celite. The filter cake was washed with EtOAc (50 ml) before the phases were separated and the aqueous layer was extracted with EtOAc (2×50 ml). The combined organic extracts were dried over $MgSO_4$, filtered and concentrated under reduced pressure. The residue was purified by FCC (10 g silica, Isolute cartridge, gradient of eluents; 99:1 Heptane:EtOAc to 85:15 Heptane:EtOAc) to give 16.2 g (102.4%) of the title compound as an orange oil that solidified upon standing and contained residual heptane. LC-MS 91%, m/z=267.4/268.9, $^1$H NMR (500 MHz, Chloroform-d) δ ppm 7.89 (d, J=2.2 Hz, 1H), 7.51 (d, J=8.3 Hz, 1H), 7.41 (dd, J=8.3, 2.3 Hz, 1H), 3.92 (s, 3H), 0.27 (s, 9H).

Step 2: Synthesis of methyl 5-chloro-2-ethynylbenzoate

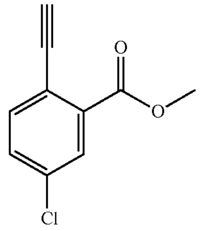

To a solution of methyl 5-chloro-2-[2-(trimethylsilyl)ethynyl]benzoate (10 g, 37.5 mmol) in MeOH (150 ml) was added $K_2CO_3$ (10.4 g, 75 mmol) at room temperature. The reaction mixture was stirred for 1 hour before being concentrated under reduced pressure. The residue was dissolved in deionized water (50 ml) and EtOAc (50 ml). The phases were separated and the aqueous layer was extracted with EtOAc (2×50 ml). The combined organic extracts were dried over $MgSO_4$, filtered and concentrated under reduced pressure. The residue was purified by FCC (50 g silica, Isolute cartridge, gradient of eluents; 95:5 Heptane:EtOAc to 9:1 Heptane:EtOAc) to give 5.75 g (55%) of the title compound as an orange oil that solidified upon standing. This material contained 30% of ethyl ester and was suitable for use without any further purification. LC-MS 38%, m/z=195.0/196.9, $^1$H NMR (500 MHz, Chloroform-d) δ ppm 7.93 (d, J=2.2 Hz, 1H), 7.55 (d, J=8.3 Hz, 1H), 7.45 (dd, J=8.3, 2.3 Hz, 1H), 3.94 (s, 3H), 3.43 (s, 1H).

Step 3: Synthesis of methyl 5-chloro-2-ethylbenzoate

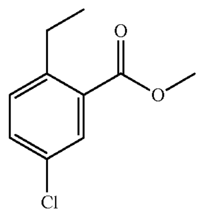

To a solution of methyl 5-chloro-2-ethynylbenzoate (5.34 g, 27 mmol) in ethyl acetate (135 ml) was added Pd/C (10%) (50% water, 2.92 g, 1.37 mmol). The reaction mixture was stirred under a hydrogen atmosphere at room temperature for 3 hours. The mixture was filtered through Celite. The filter cake washed with EtOAc (50 ml) and the filtrate was concentrated under reduced pressure to give 5.12 g (94%) of the title compound as a brown oil which was suitable for use without any further purification. LC-MS 56%, m/z=198.9/200.9, $^1$H NMR (500 MHz, Chloroform-d) δ ppm 7.84 (d, J=2.3 Hz, 1H), 7.39 (dd, J=8.3, 2.3 Hz, 1H), 7.21 (d, J=8.3 Hz, 1H), 3.90 (s, 3H), 2.94 (q, J=7.5 Hz, 2H), 1.21 (t, J=7.5 Hz, 3H).

Step 4: Synthesis of methyl 5-chloro-2-ethyl-3-nitrobenzoate

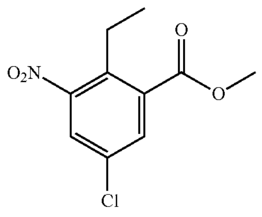 [SMILES: CCc1c(C(=O)OC)cc(Cl)cc1[N+](=O)[O-]]

A solution of methyl 5-chloro-2-ethylbenzoate (5.12 g, 25.8 mmol) in concentrated $H_2SO_4$ (31 ml, 587 mmol) was cooled to −5° C. in an acetone/ice bath. A mixture of concentrated nitric acid (2.15 ml, 33.5 mmol) and concentrated $H_2SO_4$ (2.0 ml, 37.5 mmol) was added dropwise to the reaction mixture at −5° C. over 15 minutes. The pale yellow reaction mixture was stirred at −5° C. for 1 hour before being poured onto ice (500 ml) and this was extracted with EtOAc (3×100 ml). The combined organic phases were washed with deionized water (100 ml) and then brine (100 ml). The organic phase was dried over $MgSO_4$, filtered and concentrated under reduced pressure. LCMS and NMR showed ~30% hydrolysis of the ester. The crude material was dissolved in methanol (30 ml) and cooled to 0° C. under nitrogen where $SOCl_2$ (2.25 ml, 30.93 mmol) was added slowly. The reaction mixture was then heated to reflux for 6 hours before being concentrated under reduced pressure to give 6.18 g (98%) of the title compound containing material as an orange oil which was a 1:1 mixture of 3-nitro:6-nitro isomers along with some ethyl ester. The material was suitable for use in the next step without any further purification.

Step 5: Synthesis of methyl 3-amino-5-chloro-2-ethylbenzoate

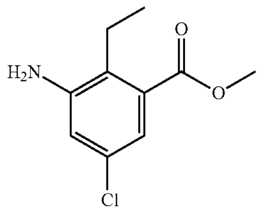

To a solution of methyl 5-chloro-2-ethyl-3-nitrobenzoate (6.18 g, 25.4 mmol) in methanol (250 ml) at room temperature was added ammonium chloride (13.3 g, 253 mmol) followed by deionized water (125 ml). The mixture was heated to 70° C. before the addition of iron (8.50 g, 152 mmol). The reaction turned to a dark color over the 2.5 hours it was stirred at 70° C. This mixture was allowed to cool to room temperature and was filtered through Kieselgel. The filter pad was washed with MeOH (250 ml) and the filtrate concentrated under reduced pressure. The residue was dissolved in saturated $NaHCO_3$(aq) (50 ml) and EtOAc (150 ml). The phases were separated and the organic phase was washed with saturated $NaHCO_3$(aq) (2×50 ml) before being dried over $MgSO_4$, filtered and concentrated under reduced pressure. The residue was purified by FCC (50 g silica, Isolute cartridge, gradient of eluents; 95:5 Heptane:EtOAc to 75:25 Heptane:EtOAc) to give 2.42 g of crude methyl 3-amino-5-chloro-2-ethylbenzoate as a yellow oil. The material was taken through the next step without further purification. LC-MS 31%, m/z=295.0, $^1$H NMR (500 MHz, Chloroform-d) δ ppm 7.17 (d, J=2.1 Hz, 1H), 6.79 (d, J=2.1 Hz, 1H), 3.87 (s, 3H), 3.86-3.81 (m, 2H), 2.74 (q, J=7.5 Hz, 2H), 1.20 (t, J=7.5 Hz, 3H).

Step 6: Synthesis of methyl 5-chloro-2-ethyl-3-[(oxan-4-yl)amino]benzoate

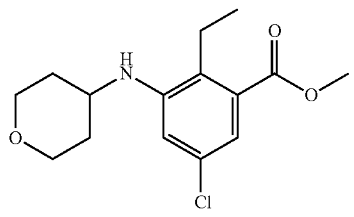 [SMILES: CCc1c(NC2CCOCC2)cc(Cl)cc1C(=O)OC]

To a solution of methyl 3-amino-5-chloro-2-ethylbenzoate (1.5 g, 7.02 mmol) in 1,2-dichloroethane (28 ml) at room temperature under nitrogen was added oxan-4-one (1.3 ml, 14. mmol) followed by acetic acid (2.41 ml, 42 mmol). This solution was stirred for 5 minutes before the addition of sodium triacetoxyborohydride (4.46 g, 21 mmol) at room temperature. After stirring for 20 hours, deionized water (28 ml) was added and the mixture was neutralized with solid $NaHCO_3$. The phases were separated and the aqueous layer was extracted with EtOAc (2×28 ml). The combined organic extracts were dried over $MgSO_4$, filtered and concentrated under reduced pressure. The residue was purified by FCC (50 g silica, Isolute cartridge, gradient of eluents; 95:5 Heptane: EtOAc to 8:2 Heptane:EtOAc) to give 1.76 g of crude methyl 5-chloro-2-ethyl-3-[(oxan-4-yl)amino]benzoate as a white solid. The material was taken through the next step without further purification. LC-MS 60%, m/z=298.0/300.0, $^1$H NMR (500 MHz, Chloroform-d) δ ppm 7.07 (d, J=2.0 Hz, 1H), 6.71 (d, J=1.9 Hz, 1H), 4.01 (dt, J=11.8, 3.4 Hz, 2H), 3.87 (s, 3H), 3.82-3.76 (m, 1H), 3.64-3.47 (m, 3H), 2.79-2.63 (m, 2H), 2.06 (d, J=13.2 Hz, 2H), 1.55-1.46 (m, 2H), 1.18 (t, J=7.5 Hz, 3H).

Step 7: Synthesis of methyl 5-chloro-2-ethyl-3-[methyl(oxan-4-yl)amino]benzoate

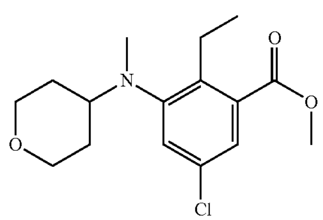 [SMILES: CCc1c(C(=O)OC)cc(Cl)cc1N(C)C1CCOCC1]

To a solution of methyl 5-chloro-2-ethyl-3-[(oxan-4-yl)amino]benzoate (350 mg, 1.18 mmol) in 1,2-dichloroethane (10 ml) at room temperature under nitrogen was added paraformaldehyde (212 mg, 7.05 mmol) followed by acetic acid (0.4 ml, 7.05 mmol). This mixture was stirred for 5 minutes before the addition of sodium triacetoxyborohydride (1.49 g, 7.05 mmol). After stirring for 23 hours, further paraformaldehyde (212 mg, 7.05 mmol) was added to the reaction mixture and this was stirred for 10 minutes before the addition of sodium triacetoxyborohydride (1.49 g, 7.05 mmol). After stirring for 3 hours, deionized water (15 ml) was added and the mixture was neutralized with solid $NaHCO_3$ and the phases were separated. The aqueous layer was extracted with EtOAc (2×15 ml) and the combined organic extracts were dried over $MgSO_4$, filtered and concentrated under reduced pressure. The residue was purified by FCC (10 g silica, Isolute cartridge, gradient of eluents; 99:1 Heptane:EtOAc to 85:15 Heptane:EtOAc) to give 334 mg of the title compound as a colorless oil. The product contains ~22% ethyl ester. The material was taken through the next step without further purification. LC-MS 56%, m/z=312.0/314.0, $^1$H NMR (500 MHz, Chloroform-d) δ ppm 7.52 (d, J=2.2 Hz, 1H), 7.24 (d, J=2.2 Hz, 1H), 4.01-3.93 (m, 2H), 3.89 (s, 3H), 3.34 (td, J=11.7, 2.3 Hz, 2H), 3.06-2.96 (m, 2H), 2.94-2.85 (m, 1H), 2.61 (s, 3H), 1.76-1.59 (m, 4H), 1.10 (t, J=7.4 Hz, 3H).

Step 8: Synthesis of 5-chloro-2-ethyl-3-[methyl(oxan-4-yl)amino]benzoic acid

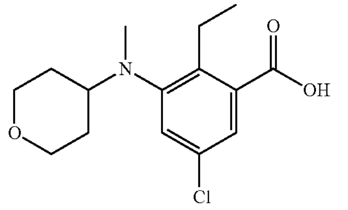 [SMILES: CCc1c(C(=O)O)cc(Cl)cc1N(C)C1CCOCC1]

To a solution of methyl 5-chloro-2-ethyl-3-[methyl(oxan-4-yl)amino]benzoate (334 mg, 1.07 mmol) in THF (11 ml) was added 4M NaOH (10.7 ml). The reaction mixture was stirred at 50° C. for 27 hours. MeOH (5 ml) was added to the reaction mixture and this was stirred for a further 21 hours at 50° C. The reaction mixture was acidified to pH 2-3 with 6M HCl and extracted with DCM (5×10 ml). The combined organic extracts were dried over $MgSO_4$, filtered and concentrated under reduced pressure to give 311 mg of the title compound as an orange oil that solidified upon standing. The material was taken through the next step without further purification. LC-MS 79%, 2.01 min (3 minute LC-MS method), m/z=298.0/300.0, $^1$H NMR (500 MHz, Chloroform-d) δ ppm 7.72 (d, J=2.1 Hz, 1H), 7.37-7.27 (m, 1H), 4.00 (brd, J=11.1 Hz, 2H), 3.36 (td, J=11.6, 2.0 Hz, 2H), 3.11 (q, J=7.4 Hz, 2H), 2.94 (t, J=10.6 Hz, 1H), 2.64 (s, 3H), 1.78-1.56 (m, 4H), 1.15 (t, J=7.4 Hz, 3H).

Step 9: Synthesis of 5-chloro-N-[(4,6-dimethyl-2-oxo-1,2-dihydropyridin-3-yl)methyl]-2-ethyl-3-[methyl(oxan-4-yl)amino]benzamide

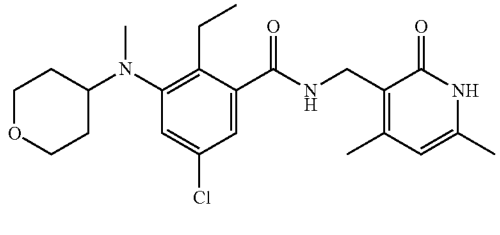 [SMILES: CCc1c(C(=O)NCc2c(C)cc(C)[nH]c2=O)cc(Cl)cc1N(C)C1CCOCC1]

To a solution of 5-chloro-2-ethyl-3-[methyl(oxan-4-yl)amino]benzoic acid (100 mg, 0.34 mmol) in DMF (2 ml) at room temperature under nitrogen was added HBTU (153 mg, 0.4 mmol) followed by N-ethyl-N-(propan-2-yl)propan-2-amine (88 μl, 0.5 mmol) and 3-(aminomethyl)-4,6-dimethyl-1,2-dihydropyridin-2-one (89%, 63 mg, 0.37 mmol). After stirring for 3 hours at room temperature EtOAc (30 ml) was added to the reaction mixture and this was then washed with deionized water (5 ml) followed by saturated $NaHCO_3$(aq) (3×5 ml). The organic phase was dried over MgSO4, filtered and concentrated under reduced pressure. The residue was purified by FCC (5 g silica, Isolute cartridge, gradient of eluents; 100% DCM to 96:4 DCM:MeOH) to give 94 mg (65%) of the title compound as an off-white solid. LC-MS 95%, m/z=432.1/434.1, $^1$H NMR (500 MHz, Chloroform-d) δ ppm 11.34 (s, 1H), 7.14-7.08 (m, 2H), 7.03 (d, J=2.0 Hz, 1H), 5.95 (s, 1H), 4.52 (d, J=5.8 Hz, 2H), 3.96 (d, J=11.2 Hz, 2H), 3.33 (td, J=11.4, 2.3 Hz, 2H), 2.96-2.85 (m, 1H), 2.79 (q, J=7.4 Hz, 2H), 2.58 (s, 3H), 2.39 (s, 3H), 2.23 (s, 3H), 1.73-1.62 (m, 4H), 1.05 (t, J=7.4 Hz, 3H).

Compound 206: 5-chloro-N-[(4,6-dimethyl-2-oxo-1,2-dihydropyridin-3-yl)methyl]-2-ethyl-3-[ethyl(oxan-4-yl)amino]benzamide

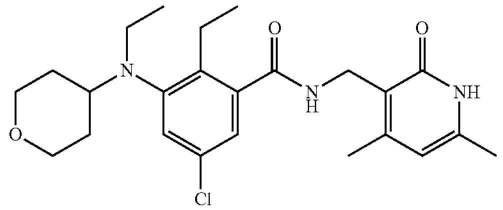 [SMILES: CCc1c(C(=O)NCc2c(C)cc(C)[nH]c2=O)cc(Cl)cc1N(CC)C1CCOCC1]

Step 1: Synthesis of methyl 5-chloro-2-ethyl-3-[ethyl(oxan-4-yl)amino]benzoate

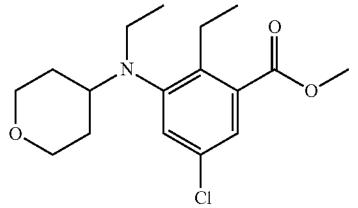 [SMILES: CCc1c(C(=O)OC)cc(Cl)cc1N(CC)C1CCOCC1]

To a solution of methyl 5-chloro-2-ethyl-3-[(oxan-4-yl)amino]benzoate (350 mg, 1.18 mmol) in 1,2-dichloroethane (10 ml) at room temperature under nitrogen was added acetaldehyde (0.66 ml, 11.8 mmol) followed by acetic acid (0.4 ml, 7.05 mmol). This solution was stirred for 5 minutes before the addition of sodium triacetoxyborohydride (2.49 g, 11.8 mmol) at room temperature. After stirring for 23 hours acetaldehyde (0.66 ml, 11.8 mmol) was added to the dark reaction mixture and this was stirred for 10 minutes before the addition of sodium triacetoxyborohydride (2.49 g, 11.8 mmol). After stirring for 3 hours deionized water (15 ml) was added and the mixture was neutralized with solid $NaHCO_3$. The phases were separated and the aqueous layer was extracted with EtOAc (2×15 ml). The combined organic extracts were dried over $MgSO_4$, filtered and concentrated under reduced pressure. The residue was purified by FCC (10 g silica, Isolute cartridge, gradient of eluents; 99:1 Heptane:EtOAc to 85:15 Heptane:EtOAc) to give 317 mg of the title compound as a colorless oil. The product contains ~25% ether ester. The material was taken through the next step without further purification. LC-MS 55%, 2 m/z=326.0/328.0, $^1$H NMR (500 MHz, Chloroform-d) δ ppm 7.52 (d, J=2.2 Hz, 1H), 7.23 (d, J=2.2 Hz, 1H), 3.97 (d, J=11.1 Hz, 2H), 3.90 (s, 3H), 3.32 (td, J=11.6, 2.5 Hz, 2H), 3.04 (q, J=7.1 Hz, 4H), 2.93 (ddd, J=15.1, 10.8, 4.3 Hz, 1H), 1.76-1.62 (m, 4H), 1.08 (t, J=7.4 Hz, 3H), 0.88 (t, J=7.1 Hz, 3H).

Step 2: Synthesis of 5-chloro-N-[(4,6-dimethyl-2-oxo-1,2-dihydropyridin-3-yl)methyl]-2-ethyl-3-[ethyl(oxan-4-yl)amino]benzamide

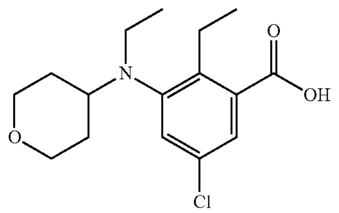 [SMILES: CCc1c(C(=O)O)cc(Cl)cc1N(CC)C1CCOCC1]

To a solution of methyl 5-chloro-2-ethyl-3-[ethyl(oxan-4-yl)amino]benzoate (317 mg, 0.97 mmol) in THF (10 ml) was added 4M NaOH (9.73 ml). The reaction mixture was stirred at 50° C. for 27 hours. MeOH (5 ml) was added to the reaction mixture and this was stirred for a further 21 hours at 50° C. The reaction mixture was acidified to pH 2-3 with 6M HCl and extracted with DCM (5×10 ml). The combined organic extracts were dried over $MgSO_4$, filtered and concentrated under reduced pressure to give 289 mg of the title compound as an orange oil that solidified upon standing. The material was taken through the next step without further purification. LC-MS 79%, m/z=311.95/313.95, $^1$H NMR (500 MHz, Chloroform-d) δ ppm 7.73 (d, J=1.7 Hz, 1H), 7.29 (d, J=1.8 Hz, 1H), 3.99 (d, J=11.0 Hz, 2H), 3.38-3.29 (m, 2H), 3.20-3.03 (m, 4H), 3.02-2.91 (m, 1H), 1.78-1.61 (m, 4H), 1.13 (t, J=7.4 Hz, 3H), 0.91 (t, J=7.0 Hz, 3H).

Step 3: Synthesis of 5-chloro-N-[(4,6-dimethyl-2-oxo-1,2-dihydropyridin-3-yl)methyl]-2-ethyl-3-[ethyl(oxan-4-yl)amino]benzamide

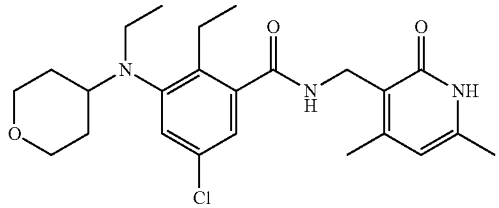 [SMILES: CCc1c(C(=O)NCc2c(C)cc(C)[nH]c2=O)cc(Cl)cc1N(CC)C1CCOCC1]

To a solution of 5-chloro-2-ethyl-3-[ethyl(oxan-4-yl)amino]benzoic acid (100 mg, 0.32 mmol) in DMF (2 ml) at room temperature under nitrogen was added HBTU (146 mg, 0.38 mmol) followed by N-ethyl-N-(propan-2-yl)propan-2-amine (84 μl, 0.48 mmol) and 3-(aminomethyl)-4,6-dimethyl-1,2-dihydropyridin-2-one (89%, 60.3 mg, 0.35 mmol). After stirring for 3 hours at room EtOAc (30 ml) was added to the reaction mixture and this was then washed with deionized water (5 ml) followed by saturated $NaHCO_3$(aq) (3×5 ml). The organic phase was dried over $MgSO_4$, filtered and concentrated under reduced pressure. The residue was purified by FCC (5 g silica, Isolute cartridge, gradient of eluents; 100% EtOAc to 97:3 EtOAc:MeOH) to give 90 mg (63%) of the title compound as a white solid. LC-MS 97%, m/z=446.1/448.2, $^1$H NMR (500 MHz, Chloroform-d) δ ppm 11.93 (s, 1H), 7.14 (t, J=5.7 Hz, 1H), 7.10 (d, J=2.0 Hz, 1H), 7.04 (d, J=2.0 Hz, 1H), 5.95 (s, 1H), 4.52 (d, J=5.8 Hz, 2H), 3.95 (d, J=11.2 Hz, 2H), 3.30 (td, J=11.3, 3.6 Hz, 2H), 3.01 (q, J=7.0 Hz, 2H), 2.93 (ddd, J=15.3, 10.0, 5.3 Hz, 1H), 2.83 (q, J=7.4 Hz, 2H), 2.38 (s, 3H), 2.22 (s, 3H), 1.71-1.63 (m, 4H), 1.02 (t, J=7.5 Hz, 3H), 0.86 (t, J=7.0 Hz, 3H).

Compound 243: 5-bromo-N-[(4,6-dimethyl-2-oxo-1,2-dihydropyridin-3-yl)methyl]-2-methyl-3-[(oxan-4-yl)(2,2,2-trifluoroethyl)amino]benzamide

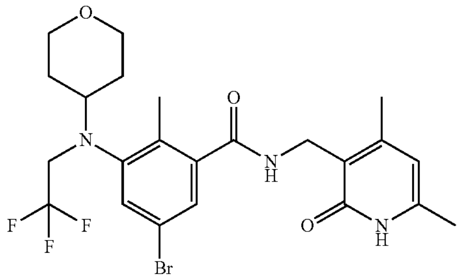 [SMILES: Cc1cc(C)c(CNC(=O)c2cc(Br)cc(N(CC(F)(F)F)C3CCOCC3)c2C)c(=O)[nH]1]

Step 1: Synthesis of 5-bromo-2-methyl-3-nitrobenzoic acid

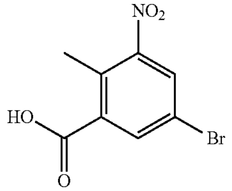

A solution of 5-bromo-2-methylbenzoic acid (5.0 g, 23 mmol) in concentrated $H_2SO_4$ (27 ml, 512 mmol) was cooled to 5° C. in an acetone/ice bath. A mixture of concentrated nitric acid (1.9 ml, 30 mmol) and concentrated $H_2SO_4$ (2.8 ml, 52 mmol) was added dropwise to the reaction mixture at −5 t0° C. over 15 minutes. The yellow reaction mixture was stirred at −5° C. for 2 hours during which time a yellow precipitate formed. The reaction mixture was poured onto ice (150 g) and the precipitate was then collected by filtration. The precipitate was air dried to give the title compound (5.5 g, 52%) as a pale yellow solid.; $^1$HNMR (500 MHz, DMSO-$d_6$) δ ppm 8.29 (s, 1H) 8.13 (d, J=1.58 Hz, 1H) 2.43 (s, 3H).

Step 2: Synthesis of methyl 5-bromo-2-methyl-3-nitrobenzoate

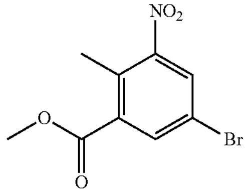

To a solution of 5-bromo-2-methyl-3-nitrobenzoic acid (5.5 g, 21 mmol) in DMF (42 ml) under nitrogen, was added $Na_2CO_3$ (3.4 g, 32 mmol) followed by iodomethane (2.0 ml, 32 mmol). The reaction mixture was stirred at room temperature for 2 hours. The mixture was diluted with deionized water (150 ml) and extracted with EtOAc (4×50 ml). The combined organic phases were washed with saturated $NaHCO_3$(aq) (2×50 ml), dried over $MgSO_4$, filtered and concentrated in-vacuo to give the title compound (6.3 g, 61%) as a yellow oil. $^1$H NMR (500 MHz, Chloroform-d) δ ppm 7.38 (d, J=2.05 Hz, 1H) 7.23 (d, J=2.05 Hz, 1H) 3.20 (s, 3H) 1.82 (s, 3H).

Step 3: Synthesis of methyl 3-amino-5-bromo-2-methylbenzoate

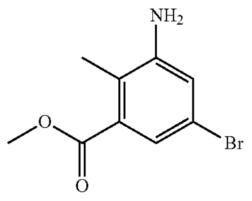

To a solution of methyl 5-bromo-2-methyl-3-nitrobenzoate (6.3 g, 21 mmol) in methanol (150 ml) was added ammonium chloride (11.0 g, 210 mmol) followed by deionized water (75 ml). The mixture was heated to 70° C. before the addition of iron (7.0 g, 125 mmol). The reaction mixture was stirred at 70° C. for 2 hours, before being allowed to cool to room temperature and filtered through Kieselgel. The filter pad was washed with MeOH (150 ml) and the filtrate concentrated in-vacuo. The residue was dissolved in saturated $NaHCO_3$ (aq) (50 ml) and EtOAc (150 ml). The phases were separated and the organic phase was washed with saturated $NaHCO_3$ (aq) (3×50 ml), dried over $MgSO_4$, filtered and concentrated in-vacuo. The residue was purified by flash column chromatography (50 g silica Isolute cartridge, 5-20% EtOAc:Heptanes) to give the title compound (3.0 g, 51%) as a thick pale yellow oil. LC-MS 87%, m/z=243.9, 244.9, 245.9, 246.9; $^1$H NMR (500 MHz, Chloroform-d) δ ppm 7.34 (d, J=1.89 Hz, 1H) 6.95 (d, J=1.89 Hz, 1H) 3.88 (s, 3H) 3.80 (br. s., 2H) 2.29 (s, 3H).

Step 4: Synthesis of methyl 5-bromo-2-methyl-3-[(oxan-4-yl)amino]benzoate

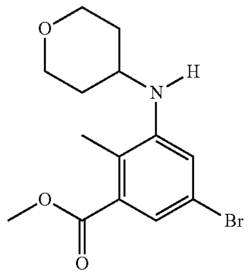 [SMILES: COC(=O)c1cc(Br)cc(NC2CCOCC2)c1C]

To a solution of methyl 3-amino-5-bromo-2-methylbenzoate (3.0 g, 12 mmol) in 1,2-dichloroethane (48 ml) under nitrogen, was added oxan-4-one (2.3 ml, 25 mmol) followed by acetic acid (4.2 ml, 74 mmol). The reaction mixture was stirred for 5 minutes before the addition of sodium triacetoxyborohydride (7.8 g, 37 mmol). After stirring for 64 hours, deionized water (100 ml) was added and the mixture was neutralized with solid $NaHCO_3$. The phases were separated and the aqueous layer was extracted with EtOAc (4×50 ml). The combined organic extracts were dried over $MgSO_4$, filtered and concentrated in-vacuo. The residue was purified by flash column chromatography (50 g silica, Isolute cartridge, 10-30% EtOAc:Heptanes) to give the title compound (3.5 g 85%) as a white solid. LC-MS 99.8 m/z=327.9, 328.9, 329.9, 330.9; $^1$H NMR (500 MHz, Chloroform-d) δ ppm 7.24 (d, J=1.73 Hz, 1H) 6.85 (d, J=1.58 Hz, 1H) 4.03 (dt, J=11.82, 3.31 Hz, 2H) 3.88 (s, 3H) 3.66 (br. s., 1H) 3.56 (td, J=11.55, 1.97 Hz, 2H) 3.47-3.55 (m, 1H) 2.24 (s, 3H) 2.06 (d, J=13.56 Hz, 2H) 1.47-1.60 (m, 2H).

Step 5: Synthesis of methyl 5-bromo-2-methyl-3-[(oxan-4-yl)(2,2,2-trifluoroethyl)amino]benzoate

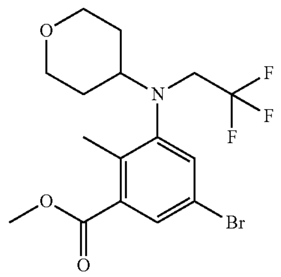 [SMILES: COC(=O)c1cc(Br)cc(N(CC(F)(F)F)C2CCOCC2)c1C]

To a solution of methyl 5-bromo-2-methyl-3-[(oxan-4-yl)amino]benzoate (500 mg, 1.5 mmol) and TFA (15 ml), was added $NaBH_4$ (1.0 g, 26 mmol) portionwise over 5 minutes. The reaction mixture was stirred at room temperature for 2 hours and then heated to 50° C. for 3 hours and treated with a further aliquot of $NaBH_4$ (300 mg) over 25 minutes. The reaction mixture was then heated to 60° C. for 2 hours and left to stir at room temperature for 17 hours. The reaction mixture was treated with TFA (5 ml) and $NaBH_4$ (200 mg) and heated back up to 60° C. for 3.5 hours. A further aliquot of $NaBH_4$ (200 mg) was added over 15 minutes, along with TFA (5 ml) and heating continued for a further 3 hours, before being left to stand at room temperature overnight. The reaction mixture was poured over ice (75 ml) and stirred until the ice had melted. The reaction mixture was then basified by the addition of 6M NaOH (aq) (40 ml) and re-adjusted to pH 7 using 1M HCl (aq) (40 ml). The resulting white suspension was collected by filtration, the solid washed with water (20 ml) and dried in-vacuo at 40° C. for 3 hours to give the title compound (577 mg, 91%) as a white solid. LC-MS 98%,), m/z=409.90, 410.9, 411.90, 412.9; $^1$H NMR (500 MHz, Chloroform-d) δ ppm 7.80 (d, J=1.73 Hz, 1H) 7.41 (d, J=1.73 Hz, 1H) 4.01 (dd, J=11.51, 4.10 Hz, 2H) 3.91 (s, 3H) 3.64 (d, J=5.20 Hz, 2H) 3.32 (t, J=11.82 Hz, 2H) 2.99 (tt, J=11.43, 3.63 Hz, 1H) 2.48 (s, 3H) 1.80 (dd, J=12.53, 1.50 Hz, 2H) 1.54-1.62 (m, 2H).

Step 6: Synthesis of 5-bromo-2-methyl-3-[(oxan-4-yl)(2,2,2-trifluoroethyl)amino]benzoic acid

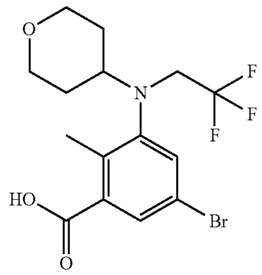 [SMILES: Cc1c(C(=O)O)cc(Br)cc1N(CC(F)(F)F)C1CCOCC1]

To a stirred solution of methyl 5-bromo-2-methyl-3-[(oxan-4-yl)(2,2,2-trifluoroethyl)amino]benzoate (572 mg, 1.4 mmol) in a mixture of THF (14 ml) and MeOH (2.1 ml), was added 4M NaOH (aq) (13.9 ml). The reaction mixture was stirred at 50° C. for 5.5 hours and then stirred at room temperature for 17 hours. The THF was removed by concentrating in-vacuo and the aqueous residue was acidified to pH 4 with 6M HCl (9.5 ml). The resulting suspension was allowed to stand at room temperature for 20 minutes before collecting the solid by filtration. The solid cake was washed with water (20 ml) and dried under high vacuum for 2 hours to give the title compound (507 mg, 90%) as a white solid. LC-MS 98%, m/z=395.9, 396.9, 397.9, 398.9; $^1$H NMR (500 MHz, Chloroform-d) δ ppm 7.97 (d, J=1.73 Hz, 1H) 7.48 (d, J=1.73 Hz, 1H) 4.02 (dd, J=11.35, 3.94 Hz, 2H) 3.65 (br. s, 2H) 3.33 (t, J=11.59 Hz, 2H) 3.00 (tt, J=11.49, 3.80 Hz, 1H) 2.55 (s, 3H) 1.82 (d, J=11.98 Hz, 2H) 1.55-1.69 (m, 2H). OH not visible.

Step 7: Synthesis of 5-bromo-N-[(4,6-dimethyl-2-oxo-1,2-dihydropyridin-3-yl)methyl]-2-methyl-3-[(oxan-4-yl)(2,2,2-trifluoroethyl)amino]benzamide

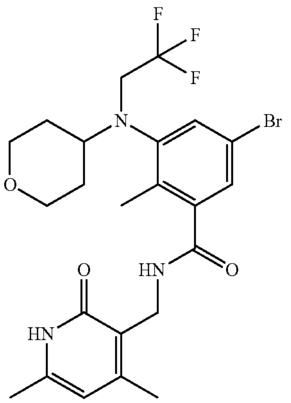 [SMILES: Cc1cc(C)c(CNC(=O)c2cc(Br)cc(N(CC(F)(F)F)C3CCOCC3)c2C)c(=O)[nH]1]

A stirred solution of methyl 5-bromo-2-methyl-3-[(oxan-4-yl)(2,2,2-trifluoroethyl)amino]benzoate (250 mg, 0.63 mmol) in dry DMF (3.0 ml) at 0° C. under nitrogen, was treated with HATU (288 mg, 0.76 mmol) and DIPEA (220 μl, 1.3 mmol) dropwise. The resulting solution was stirred for 5 minutes and then treated with 3-(aminomethyl)-4,6-dimethyl-1,2-dihydropyridin-2-one (89%, 119 mg, 0.69 mmol). The resulting suspension was stirred at 0° C. for 20 minutes and then stirred at room temperature for 16.5 hours. The reaction mixture was treated with 3-(aminomethyl)-4,6-dimethyl-1,2-dihydropyridin-2-one (30 mg). Stirring was continued for 23 hours and the reaction mixture was then partitioned between water (30 ml) and $CH_2Cl_2$ (20 ml). The layers were separated and the aqueous phase was extracted with $CH_2Cl_2$ (3×20 ml). The combined organics were washed with a saturated solution of $NaHCO_3$) (50 ml), water (60 ml), brine (2×40 ml), dried over $MgSO_4$, filtered and concentrated in-vacuo. The crude residue was purified by flash column chromatography (10 g SNAP cartridge, Isolera, 0-10% MeOH/$CH_2Cl_2$) and triturated from ether (10 ml) with sonication. The resulting precipitate was collected by filtration and dried in-vacuo to give the title compound (249 mg, 74%) as a white solid. LC-MS 100%, m/z=530.0, 531.0, 532.0, 533.0; $^1$H NMR (500 MHz, Acetone) δ 10.67 (s, 1H), 7.55 (d, J=1.8 Hz, 2H), 7.27 (d, J=1.9 Hz, 1H), 5.90 (s, 1H), 4.40 (d, J=5.5 Hz, 2H), 3.90 (dd, J=11.2, 4.6 Hz, 4H), 3.28 (t, J=11.6 Hz, 2H), 3.07-2.97 (m, 1H), 2.32 (s, 3H), 2.29 (s, 3H), 2.24 (s, 3H), 1.76 (dd, J=12.3, 1.6 Hz, 2H), 1.61 (qd, J=12.0, 4.5 Hz, 2H).

Compound 244: 5-bromo-3-[(2,2-difluoroethyl)(oxan-4-yl)amino]-N-[(4,6-dimethyl-2-oxo-1,2-dihydropyridin-3-yl)methyl]-2-methylbenzamide

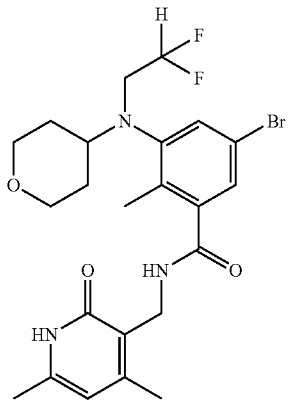

Step 1: Synthesis of methyl 5-bromo-3-[(2,2-difluoroethyl)(oxan-4-yl)amino]-2-methylbenzoate

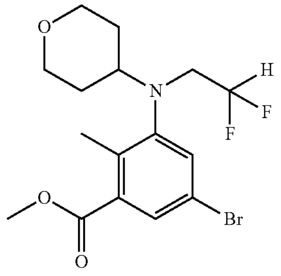 [SMILES: COC(=O)c1cc(Br)cc(N(CC(F)F)C2CCOCC2)c1C]

A stirred solution of methyl 5-bromo-2-methyl-3-[(oxan-4-yl)amino]benzoate (500 mg, 1.5 mmol) in difluoroacetic acid (15 ml), was treated with sodium tetrahydroborate (1000 mg, 26 mmol) portionwise over 12 minutes. The reaction mixture was warmed to 50° C. and stirred for 4 hours. The reaction mixture was allowed to reach room temperature and then poured over ice (130 ml) and left for 5 minutes. The mixture was basified by the addition of 6M NaOH (aq) (35 ml) and the pH adjusted to 7 using 1M HCl (aq) (20 ml). The resulting suspension was allowed to stand until the solution was clear and the resulting solid collected by filtration and dried in-vacuo at 40° C. to give the title compound (572 mg, 96%) as a white solid. LC-MS 100%, m/z=391.9, 392.9, 393.9, 394.9; $^1$H NMR (500 MHz, Chloroform-d) δ ppm 7.79 (d, J=1.89 Hz, 1H) 7.44 (d, J=1.89 Hz, 1H) 5.44-5.71 (m, 1H) 4.00 (dd, J=11.51, 4.10 Hz, 2H) 3.91 (s, 3H) 3.41 (td, J=13.99, 4.18 Hz, 2H) 3.32 (t, J=11.27 Hz, 2H) 2.97 (tt, J=11.37, 3.84 Hz, 1H) 2.47 (s, 3H) 1.72-1.81 (m, 2H) 1.59-1.67 (m, 2H).

Step 2: Synthesis of 5-bromo-3-[(2,2-difluoroethyl)(oxan-4-yl)amino]-2-methylbenzoic acid

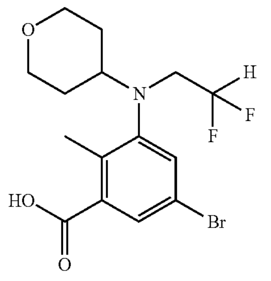 [SMILES: Cc1c(C(=O)O)cc(Br)cc1N(CC(F)F)C1CCOCC1]

To a stirred solution of methyl 5-bromo-3-[(2,2-difluoroethyl)(oxan-4-yl)amino]-2-methylbenzoate (571 mg, 1.5 mmol) in a mixture of THF (14.6 ml) and MeOH (2.2 ml), was added 4M NaOH (14.6 ml). The reaction mixture was stirred at 50° C. for 7 hours. The heat was switched off and the reaction mixture was stirred at room temperature for 16.5 hours. THF was removed in-vacuo and the aqueous residue was acidified to pH 4 by the addition of 6M HCl (aq) (10 ml) with ice cooling. The resulting solid was collected by filtration, washed with water (20 ml), and dried in-vacuo to give the title compound (526 mg, 96%) as a light beige solid. LC-MS 100%, m/z=377.9, 378.9, 379.9, 380.9; $^1$H NMR (500 MHz, Chloroform-d) δ ppm 7.91 (d, J=1.58 Hz, 1H) 7.49 (d, J=1.58 Hz, 1H) 5.43-5.75 (m, 1H) 4.01 (dd, J=11.43, 3.55 Hz, 2H) 3.42 (td, J=13.95, 3.78 Hz, 2H) 3.32 (t, J=11.35 Hz, 2H) 2.98 (tt, J=11.37, 3.53 Hz, 1H) 2.52 (s, 3H) 1.77 (d, J=10.88 Hz, 2H) 1.56-1.69 (m, 2H). OH not visible.

Step 3: Synthesis of 5-bromo-3-[(2,2-difluoroethyl)(oxan-4-yl)amino]-N-[(4,6-dimethyl-2-oxo-1,2-dihydropyridin-3-yl)methyl]-2-methylbenzamide

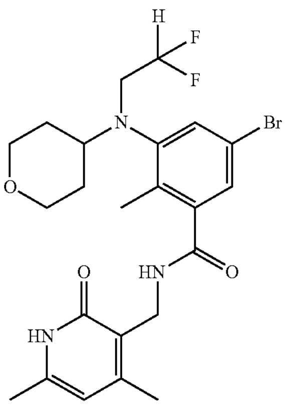 [SMILES: Cc1cc(C)c(CNC(=O)c2cc(Br)cc(N(CC(F)F)C3CCOCC3)c2C)c(=O)[nH]1]

A stirred solution of 5-bromo-3-[(2,2-difluoroethyl)(oxan-4-yl)amino]-2-methylbenzoic acid (250 mg, 0.66 mmol) in dry DMF (3.0 ml) at 0° C. under nitrogen, was treated with HATU (327 mg, 0.86 mmol) and DIPEA (230 μl, 1.3 mmol) dropwise. The resulting solution was stirred for 5 minutes and then treated with 3-(aminomethyl)-4,6-dimethyl-1,2-dihydropyridin-2-one (89%, 136 mg, 0.79 mmol). The resulting suspension was stirred at 0° C. for 20 minutes and then stirred at room temperature overnight. After 18 hours, 3-(aminomethyl)-4,6-dimethyl-1,2-dihydropyridin-2-one (25 mg) was added and stirring continued for a further 25 hours. The reaction mixture was diluted with water (30 ml) and $CH_2Cl_2$ (30 ml). The layers were separated and the aqueous phase was extracted with $CH_2Cl_2$ (3×15 ml). The combined organic phases were washed with a saturated solution of $NaHCO_3$ (aq) (45 ml), water (2×50 ml), brine (2×50 ml), dried ($MgSO_4$), filtered and concentrated in-vacuo. The residue was purified by column chromatography (10 g SNAP cartridge, Isolera, 0-3% MeOH:$CH_2Cl_2$) and then triturated with ether. The resulting solid was collected by filtration and dried in-vacuo at 40° C. to give the title compound (259 mg, 77%) as an off white solid. LC-MS 100%, m/z=512.0, 513.0, 514.0, 515.0; $^1$H NMR (500 MHz, Acetone) δ 10.71 (s, 1H), 7.57-7.49 (m, 2H), 7.25 (d, J=1.9 Hz, 1H), 5.91 (s, 1H), 5.76 (tt, J=56.2, 4.3 Hz, 1H), 4.40 (d, J=5.5 Hz, 2H), 3.88 (dd, J=11.3, 4.2 Hz, 2H), 3.52 (td, J=14.6, 4.2 Hz, 2H), 3.33-3.23 (m, 2H), 3.02 (tt, J=11.6, 3.9 Hz, 1H), 2.32 (s, 3H), 2.28 (s, 3H), 2.24 (s, 3H), 1.73 (dd, J=12.4, 1.9 Hz, 2H), 1.59 (qd, J=12.2, 4.5 Hz, 2H).

Compound 328: N-[(4,6-dimethyl-2-oxo-1,2-dihydropyridin-3-yl)methyl]-2-[ethyl(oxan-4-yl)amino]-3-methylpyridine-4-carboxamide

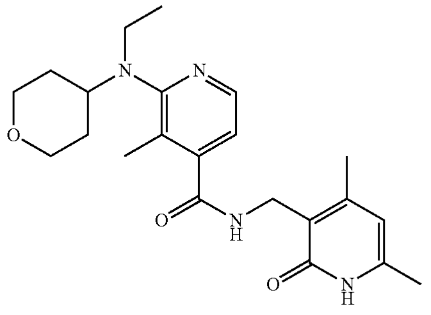 [SMILES: CCN(c1nccc(C(=O)NCc2c(C)cc(C)[nH]c2=O)c1C)C1CCOCC1]

Step 1: Synthesis of 2-chloro-N-phenylpyridine-4-carboxamide

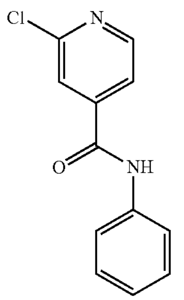 [SMILES: O=C(Nc1ccccc1)c1ccnc(Cl)c1]

To a stirred suspension of 2-chloroisonicotinic acid (5.0 g, 0.03 mol) in dry toluene (100 ml) and 4 drops of DMF, was added dropwise thionyl chloride (7.4 ml, 0.10 mol) under nitrogen. The reaction mixture was stirred at 60° C. for 2.5 hours and the temperature was gradually increased to 100° C. over 1.5 hours and held at this temperature for 2 hours. The reaction mixture was stirred at room temperature for 65 hours, before being treated with another equivalent of thionyl chloride (2.3 ml) and heated to 95° C. for 40 minutes. The reaction was allowed to cool to room temperature and was then concentrated to dryness in-vacuo and azeotroped with dry toluene (2×10 ml) to give a yellow mobile oil which was used directly in the next step without further purification.

To a stirred solution of aniline (2.9 ml, 0.03 mol) and N-ethyl-N-(propan-2-yl)propan-2-amine (13.6 ml, 83 mmol) in dry THF (50 ml) was added the acid chloride prepared above dropwise. The reaction mixture was stirred under nitrogen for 19 hours. The reaction mixture was then quenched by the addition of a saturated solution of sodium hydrogen carbonate (aq) (100 ml) and stirred for 35 minutes. The layers were separated and the aqueous phase extracted with ethyl acetate (3×55 ml). The combined organic extracts were washed with water (3×66 ml), brine (80 ml), dried ($MgSO_4$), filtered and concentrated in-vacuo. The residue was suspended in diethyl ether (100 ml), briefly sonicated and the product collected by filtration. It was dried under high vacuum for 3 hours at room temperature, then left under vacuum overnight to give the title compound (6.1 g, 83%) as a white solid. LC-MS 100%, m/z=233.0, 234.9; $^1$H NMR (500 MHz, Chloroform-d) δ ppm 8.58 (d, J=5.04 Hz, 1H) 7.81 (br. s., 1H) 7.77 (s, 1H) 7.63 (d, J=7.41 Hz, 3H) 7.42 (t, J=7.96 Hz, 2H) 7.19-7.26 (m, 1H).

Step 2: Synthesis of 2-chloro-N,3-dimethyl-N-phenylpyridine-4-carboxamide

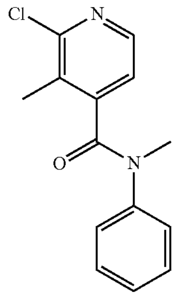 [SMILES: Cc1c(C(=O)N(C)c2ccccc2)ccnc1Cl]

To a stirred solution of 2-chloro-N-phenylpyridine-4-carboxamide (2.0 g, 8.6 mmol) in dry THF (40 ml) at −78° C. under nitrogen, was added dropwise 1.6M butyl lithium in n-hexanes (11.8 ml, 18.9 mmol) over 24 minutes. The reaction mixture was stirred at −78° C. for 50 minutes and then treated with iodomethane (1.8 ml, 28 mmol) dropwise over 8 minutes. The reaction mixture was stirred at −78° C. for 1 hour and then left to slowly reach room temperature and stirred for 20 hours. The reaction mixture was quenched with water (20 ml), and the layers were separated. The aqueous phase was extracted with $CH_2Cl_2$ (3×20 ml). The combined organic phases were washed with brine (60 ml), dried ($MgSO_4$), filtered, concentrated in-vacuo and to give the title compound (2.2 g, 93%) as a thick brown oil. LC-MS 95%, m/z=261.0, 263.0; $^1$H NMR (500 MHz, Chloroform-d) δ ppm 8.03 (d, J=4.89 Hz, 1H) 7.23 (d, J=7.88 Hz, 2H) 7.16-7.21 (m, 1H) 7.02 (d, J=7.25 Hz, 2H) 6.89 (d, J=4.89 Hz, 1H) 3.51 (s, 3H) 2.34 (s, 3H).

Step 3: Synthesis of 2-chloro-3-methylpyridine-4-carboxylic acid

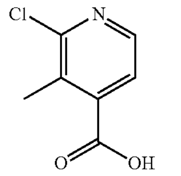

2-chloro-N,3-dimethyl-N-phenylpyridine-4-carboxamide (2.2 g, 8.5 mmol) was treated with a mixture of concentrated $H_2SO_4$ (23.2 ml) and water (16.8 ml) and then heated to 130° C. for 46 hours. After which time, the reaction mixture was allowed to reach room temperature and poured onto ice (200 ml) and stirred until the ice had melted. The mixture was made alkaline (pH 8) by the addition of solid $Na_2CO_3$ (50.3 g) portionwise. The suspension was filtered and the filtrate acidified to pH 3 by the addition of 6M HCl (aq) (~1.5 ml). The resulting solid was collected by filtration, washed with water (20 ml) and dried in-vacuo at 40° C. for 10 hours to give the title compound (779 mg, 54%) as a pink solid. LC-MS 100%, m/z=171.9, 173.9; $^1$H NMR (500 MHz, MeOD) δ ppm 8.30 (d, J=4.89 Hz, 1H) 7.64 (d, J=5.04 Hz, 1H) 2.58 (s, 3H).

Step 4: Synthesis of methyl 2-chloro-3-methylpyridine-4-carboxylate

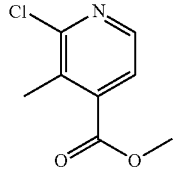

To a stirred solution of 2-chloro-3-methylpyridine-4-carboxylic acid (780 mg, 4.5 mmol) in anhydrous DMF (5.0 ml), was added potassium carbonate (1.25 g, 9.1 mmol), followed by methyl iodide (0.42 ml, 6.8 mmol) dropwise. A further 4 ml of DMF was added and the reaction mixture was stirred at room temperature under nitrogen for 18.5 hours. The solvent was removed in-vacuo and the residue was then partitioned between $CH_2Cl_2$ (20 ml) and water (20 ml). The layers were separated and the aqueous layer was extracted with $CH_2Cl_2$ (3×15 ml). The combined organic layers were washed with water (2×30 ml), brine (40 ml), dried ($MgSO_4$), filtered and concentrated in-vacuo. The residue was purified by column chromatography (10 g SNAP cartridge, Isolera, 0-6% ethyl acetate:heptanes) to give the title compound (591 mg, 59%) as a colourless oil. LC-MS 84%, m/z=185.9, 187.9; $^1$H NMR (500 MHz, Chloroform-d) δ ppm 8.33 (d, J=5.04 Hz, 1H) 7.54 (d, J=5.04 Hz, 1H) 3.95 (s, 3H) 2.60 (s, 3H).

Step 5: Synthesis of methyl 3-methyl-2-[(oxan-4-yl) amino]pyridine-4-carboxylate

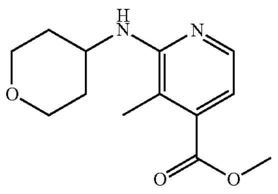 [SMILES: COC(=O)c1ccnc(NC2CCOCC2)c1C]

A nitrogen purged suspension of $Pd(OAc)_2$ (77 mg, 0.34 mmol) and 1,1'-binaphthalene-2,2'-diylbis(diphenylphosphane) (430 mg, 0.69 mmol) in 1,4-dioxane (11 ml) was heated at 40° C. for 1 hour. Oxan-4-amine (237 μl, 2.3 mmol), a solution of methyl 2-chloro-3-methylpyridine-4-carboxylate (213 mg, 1.2 mmol) in degassed dioxane (2 ml) and $Cs_2CO_3$ (562 mg, 1.7 mmol) were then added and the red suspension was heated at 100° C. for 6 hours. After cooling to room temperature, the mixture was diluted with $CH_2Cl_2$ (30 ml) and water (20 ml). The layers were separated and the aqueous phase was extracted with $CH_2Cl_2$ (3×15 ml). The combined organic phases were washed with brine (25 ml), dried ($MgSO_4$), filtered and concentrated in-vacuo. The crude residue was purified by column chromatography (25 g SNAP cartridge, Isolera, 0-28% ethyl acetate:heptanes) followed by prep-HPLC (MeCN/Water) to give the title compound (112 mg, 39%) as a white crystalline solid. LC-MS 100%, m/z=251.0; $^1H$ NMR (500 MHz, MeOD) δ ppm 7.91 (d, J=5.20 Hz, 1H) 6.77 (d, J=5.36 Hz, 1H) 4.07-4.17 (m, 1H) 3.98 (dd, J=12.06, 1.81 Hz, 2H) 3.88 (s, 3H) 3.55 (td, J=11.78, 1.66 Hz, 2H) 2.22 (s, 3H) 1.97 (dd, J=12.69, 1.97 Hz, 2H) 1.62 (qd, J=12.03, 4.41 Hz, 2H). NH not observed.

Step 6: Synthesis of 2-[ethyl(oxan-4-yl)amino]-3-methylpyridine-4-carboxylic acid

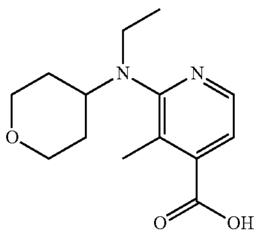 [SMILES: CCN(c1nccc(C(=O)O)c1C)C1CCOCC1]

A solution of methyl 3-methyl-2-[(oxan-4-yl)amino]pyridine-4-carboxylate (67 mg, 0.27 mmol) in dry DMF (1.0 ml), was added to a stirred suspension of sodium hydride (60% dispersion in mineral oil, 16 mg, 0.4 mmol) in DMF (0.3 ml) at 0° C. under nitrogen. The reaction mixture was allowed to warm to room temperature and stirred for 30 minutes. The reaction was then treated with iodoethane (16 μl, 0.20 mmol) and stirred for 30 minutes, and then treated again with iodoethane (16 μl, 0.20 mmol) and stirred for a further 30 minutes. The reaction mixture was added to a suspension of sodium hydride (16 mg, 0.4 mmol) in DMF (0.3 ml) at 0° C. Once addition was complete, the reaction mixture was allowed to reach room temperature and stirred for 1 hour before treating with iodoethane (2×16 μl, 0.40 mmol). The reaction mixture was stirred for a further 30 minutes. Sodium hydride (16 mg, 0.4 mmol) was added to the reaction mixture and the mixture stirred for 45 minutes before treating with iodoethane (2×16 μl, 0.40 mmol) and stirred for 15 minutes before adding under nitrogen to a solution of 4M HCl/dioxane (5.0 ml) with cooling.

The reaction mixture was then concentrated in-vacuo at 40° C. was treated with 1M NaOH (aq) (5 ml) and basified by the addition of 10 NaOH pellets to pH 12 with cooling. The pH was adjusted back to pH 10 by the addition of 6M HCl. The resulting solution was stirred at room temperature for 18 hours. The reaction mixture was then acidified to pH 5 by the addition of 1M HCl (80 drops). The resulting solution was extracted with $CHCl_3$/IPA (1:1) (6×10 ml). The combined extracts were concentrated in-vacuo to give the crude title compound (207 mg) as a yellow oil. LC-MS 100%, m/z=265.1. This material was used directly in the coupling reaction as described below.

Step 7: Synthesis of N-[(4,6-dimethyl-2-oxo-1,2-dihydropyridin-3-yl)methyl]-2-[ethyl(oxan-4-yl)amino]-3-methylpyridine-4-carboxamide

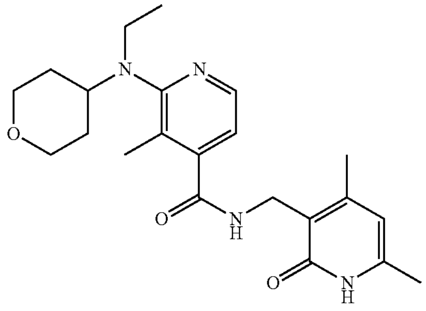 [SMILES: CCN(c1nccc(C(=O)NCc2c(C)cc(C)[nH]c2=O)c1C)C1CCOCC1]

A stirred solution of 2-[ethyl(oxan-4-yl)amino]-3-methylpyridine-4-carboxylic acid (20 mg, 0.08 mmol) in dry DMF (1.0 ml) at 0° C. under nitrogen, was treated with HATU (37 mg, 0.1 mmol) and DIPEA (26 μl, 0.15 mmol) dropwise. The resulting solution was stirred for 10 minutes and then treated with 3-(aminomethyl)-4,6-dimethyl-1,2-dihydropyridin-2-one (89%, 15 mg, 0.09 mmol). The resulting suspension was stirred at 0° C. for 20 minutes and then stirred at room temperature for 18.5 hours. The reaction mixture was cooled to 0° C. and retreated with HATU (120 mg, 0.31 mmol) and DIPEA (84 μl, 0.48 mmol). After stirring for 10 minutes, 3-(aminomethyl)-4,6-dimethyl-1,2-dihydropyridin-2-one (89%, 49 mg, 0.29 mmol) was added. The reaction mixture was stirred for 1 hour at 0° C. and was then lifted out of the ice bath stirred at room temperature for 48 hours. The reaction mixture was diluted with water (20 ml) and $CH_2Cl_2$ (20 ml). The layers were separated and the aqueous phase was extracted with $CH_2Cl_2$ (3×15 ml). The combined organic phases were washed with water (2×25 ml), brine (2×25 ml), dried ($MgSO_4$), filtered and concentrated in-vacuo. The crude residue was purified by column chromatography (10 g SNAP cartridge, Isolera, 0-40% MeOH:$CH_2Cl_2$ and 0-25% MeOH (containing 10% $NH_4OH$):$CH_2Cl_2$) to give 6.7 mg (22% Yield) of the title compound as an off white solid. LC-MS 100%, m/z=399.1; $^1H$ NMR (250 MHz, DMSO) δ 11.49 (s, 1H), 8.32 (t, J=4.9 Hz, 1H), 8.14 (d, J=4.9 Hz, 1H), 6.84 (d, J=4.9 Hz, 1H), 5.86 (s, 1H), 4.26 (d, J=4.7 Hz, 2H), 3.84 (dd, J=10.3, 3.5 Hz, 2H), 3.21 (dt, J=13.6, 4.6 Hz, 5H), 2.19 (s, 3H), 2.15 (s, 3H), 2.11 (s, 3H), 1.62 (dt, J=21.1, 6.6 Hz, 4H), 0.80 (t, J=6.9 Hz, 3H).

Compound 356: 5-chloro-3-{ethyl[(1r,4r)-4-(dimethylamino)cyclohexyl]amino}-N-[(5-fluoro-4,6-dimethyl-2-oxo-1,2-dihydropyridin-3-yl)methyl]-2-methylbenzamide

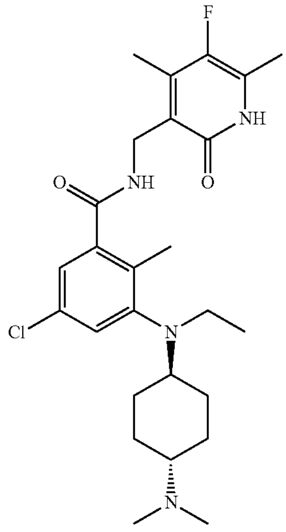 [SMILES: CCN(c1cc(Cl)cc(C(=O)NCc2c(C)c(F)c(C)[nH]c2=O)c1C)[C@H]1CC[C@H](N(C)C)CC1]

Step 1: Synthesis of 5-fluoro-4,6-dimethyl-2-oxo-1,2-dihydropyridine-3-carbonitrile

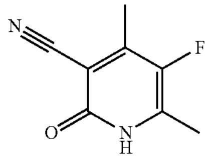

To a stirred solution of 2-cyanoacetamide (689 mg, 8.2 mmol) in anhydrous EtOH (7.0 ml) at 75° C., was added 3-fluoropentane-2,4-dione (880 mg, 7.5 mmol), followed by piperidine (96 μl, 0.97 mmol). The reaction mixture was stirred at this temperature for 3 hours and the reaction mixture left to reach room temperature before being stored in the refrigerator for 4 days. The beige solid was collected by filtration and rinsed with cold EtOH (4×0.4 ml) until the filtrate ran clear. The resulting beige solid was dried in-vacuo at 40° C. for 5 hours to give the title compound (733 mg, 58%) as a beige solid. LC-MS 97%, m/z=166.9, $^1$H NMR (500 MHz, Chloroform-d) δ ppm 13.67 (br. s., 1H) 2.46 (d, J=2.05 Hz, 3H) 2.45 (d, J=2.84 Hz, 3H).

Step 2: Synthesis of 3-(aminomethyl)-5-fluoro-4,6-dimethyl-1,2-dihydropyridin-2-one

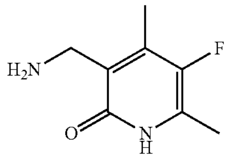

A solution of 0.05M 5-fluoro-4,6-dimethyl-2-oxo-1,2-dihydropyridine-3-carbonitrile (731 mg, 4.4 mmol) in 1.75M $NH_3$/MeOH (87 ml) was passed through the H-Cube flow hydrogenator at 80° C. and 50 bar at a flow rate of 1 ml/min. The resulting solution was concentrated in-vacuo. The resulting solid was split into 2 batches and 350 mg of the crude product was purified by column chromatography (25 g SNAP cartridge, Isolera, 0-25% MeOH (containing 10% $NH_4OH$): $CH_2Cl_2$) to give the title compound (307 mg, 20%) as an off white solid and a 1:1 mixture of product:starting material. LC-MS (ELS) 100%, m/z=170.9, $^1$H NMR (500 MHz, Chloroform-d) δ ppm 3.79 (s, 2H) 2.31 (d, J=2.84 Hz, 3H) 2.25 (d, J=2.05 Hz, 3H).

Step 3: Synthesis of 5-chloro-3-{ethyl[(1r,4r)-4-(dimethylamino)cyclohexyl]amino}-2-methylbenzoic acid

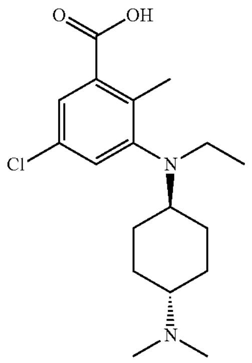 [SMILES: CCN(c1cc(Cl)cc(C(=O)O)c1C)[C@H]1CC[C@H](N(C)C)CC1]

To a stirred solution of methyl 5-chloro-3-{ethyl[(1r,4r)-4-(dimethylamino)cyclohexyl]amino}-2-methylbenzoate (1.0 g, 2.8 mmol) in THF (21 ml), was added a solution of 4M NaOH (aq) (21.3 ml, 85.0 mmol), followed by MeOH (8.0 ml). The resulting solution was stirred at 50° C. for 16.5 hours and cooled to room temperature. The organic solvents were removed in-vacuo and the remaining aqueous phase was treated with a solution of 6M HCl (aq) (14 ml) to adjust the pH to 7 and then 0.1 M HCl (aq) (24 ml) to adjust the pH to 4. The mixture was extracted with ethyl acetate (3×35 ml). The aqueous extract was further extracted with a mixture of $CHCl_3$:IPA (1:1) (3×30 ml). The combined $CHCl_3$:IPA extracts were dried ($MgSO_4$), filtered and concentrated in-vacuo and then thoroughly dried on the high vac line. The resulting solid was azeotroped with toluene (3×20 ml). $CH_2Cl_2$ (10 ml) was then added to the sample, concentrated in-vacuo and further dried on the high vac line for several hours. This gave the title compound (831 mg, 88%) as a white solid. LC-MS 92 m/z=339.0, 341.0; $^1$H NMR (500 MHz, Chloroform-d) δ ppm 12.21 (s, 1H) 7.69 (d, J=2.05 Hz, 1H) 7.22-7.26 (m, 1H) 2.99-3.11 (m, 3H) 2.69-2.79 (m, 7H) 2.47 (s, 3H) 2.28 (d, J=11.98 Hz, 2H) 2.05 (d, J=13.08 Hz, 2H) 1.35-1.65 (m, 4H) 0.88 (t, J=7.01 Hz, 3H).

Step 4: Synthesis of 5-chloro-3-{ethyl[(1r,4r)-4-(dimethylamino)cyclohexyl]amino}-N-[(5-fluoro-4,6-dimethyl-2-oxo-1,2-dihydropyridin-3-yl)methyl]-2-methylbenzamide

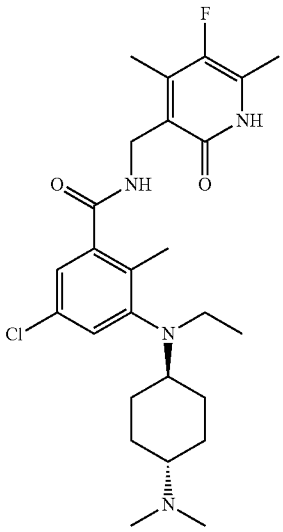 [SMILES: CCN(c1cc(Cl)cc(C(=O)NCc2c(C)c(F)c(C)[nH]c2=O)c1C)[C@H]1CC[C@H](N(C)C)CC1]

To a stirred solution of 5-chloro-3-{ethyl[(1r,4r)-4-(dimethylamino)cyclohexyl]amino}-2-methylbenzoic acid (100 mg, 0.27 mmol) in anhydrous DMF (2.0 ml) at 0° C. under a f nitrogen, was treated with HATU (121 mg, 0.32 mmol) and DIPEA (93 μl, 0.53 mmol) dropwise. The resulting solution was stirred for 10 minutes and then treated with 3-(aminomethyl)-5-fluoro-4,6-dimethyl-1,2-dihydropyridin-2-one (50%, 99 mg, 0.29 mmol). The resulting suspension was stirred at 0° C. for 1 hour and then stirred for 17 hours at room temperature. The reaction mixture was partitioned between water (15 ml) and $CH_2Cl_2$ (20 ml). The layers were separated and the aqueous phase was extracted with $CH_2Cl_2$ (2×15 ml). The combined organics were washed with a saturated solution of $NaHCO_3$ (aq) (30 ml), water (2×25 ml), brine (20 ml), dried ($MgSO_4$), filtered and concentrated in-vacuo. The crude residue was purified by flash column chromatography (10 g SNAP cartridge, Isolera, 0-29% MeOH:$CH_2Cl_2$) to give the title compound (68 mg, 52%) as a beige solid. LC-MS 99%, m/z=491.1, 493.1; $^1$H NMR (500 MHz, Methanol-$d_4$) δ 7.17 (d, J=1.9 Hz, 1H), 7.02 (d, J=2.0 Hz, 1H), 4.59 (s, 1H), 4.44 (s, 2H), 3.06 (q, J=7.0 Hz, 2H), 2.69 (tt, J=12.1, 3.2 Hz, 1H), 2.41-2.29 (m, 10H), 2.24 (d, J=2.8 Hz, 3H), 2.20 (s, 3H), 1.91 (dd, J=27.7, 12.2 Hz, 4H), 1.44 (q, J=12.3, 11.1 Hz, 2H), 1.30-1.20 (m, 2H), 0.83 (t, J=7.0 Hz, 3H). One proton assumed to be coincident with a solvent peak.

Compound 347: 5-chloro-N-[(4,6-dimethyl-2-oxo-1,2-dihydropyridin-3-yl)methyl]-2-ethyl-3-{ethyl[(1r,4r)-4-(dimethylamino)cyclohexyl]amino}benzamide and Compound 348: 5-chloro-N-[(4,6-dimethyl-2-oxo-1,2-dihydropyridin-3-yl)methyl]-2-ethyl-3-{ethyl[(1s,4s)-4-(dimethylamino)cyclohexyl]amino}benzamide

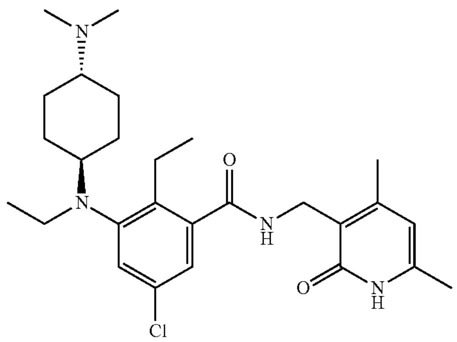

and

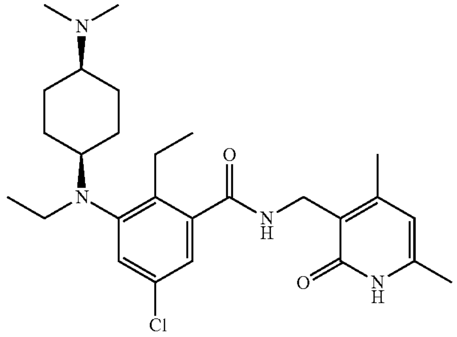

Step 1: Synthesis of methyl 5-chloro-2-[2-(trimethylsilyl)ethynyl]benzoate

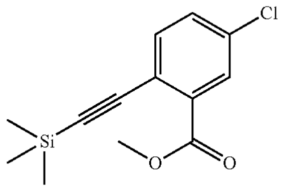 [SMILES: COC(=O)c1cc(Cl)ccc1C#C[Si](C)(C)C]

To a stirred solution of methyl 2-bromo-5-chlorobenzoate (14.8 g, 59 mmol) in triethylamine (124 ml, 890 mmol) was added copper iodide (339 mg, 1.8 mmol) and triphenylphosphine (778 mg, 3.0 mmol) at room temperature, under nitrogen. This mixture was purged with nitrogen before the addition of ethynyl(trimethyl)silane (12.5 ml, 89 mmol) and $Pd(OAc)_2$ (266 mg, 1.2 mmol). The reaction mixture was stirred at 50° C. for 20 hours and concentrated in-vacuo. The residue was dissolved in deionized water (50 ml) and EtOAc (50 ml) and filtered through Celite. The filter cake was washed with EtOAc (50 ml) before the phases were separated and the aqueous layer was extracted with EtOAc (2×50 ml).

The combined organic extracts were dried over $MgSO_4$, filtered and concentrated in vacuo. The residue was purified by flash column chromatography (10 g Silica Isolute cartridge, 1-15% EtOAc:Heptanes) to give the title compound (16.2 g, 93%) as an orange solid. LC-MS 91%, m/z=267.4, 268.9; $^1H$ NMR (500 MHz, Chloroform-d) δ ppm 7.90 (d, J=2.21 Hz, 1H) 7.52 (d, J=8.35 Hz, 1H) 7.42 (dd, J=8.28, 2.29 Hz, 1H) 3.93 (s, 3H) 0.28 (s, 9H).

Step 2: Synthesis of methyl 5-chloro-2-ethynylbenzoate

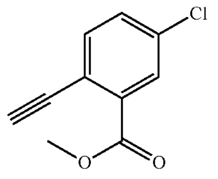

A suspension of potassium carbonate (5.0 g, 36 mmol) in methanol (20 ml) was stirred under nitrogen whilst adding a solution of methyl 5-chloro-2-[2-(trimethylsilyl)ethynyl]benzoate (4.8 g, 18.0 mmol) in methanol (50 ml). The resulting mixture was stirred at 20° C. for 2 hours. The reaction mixture was filtered, and the solid washed with methanol. The filtrate was concentrated in-vacuo and then re-dissolved in methanol (50 ml) and carefully treated with acetyl chloride (4.0 ml). The reaction mixture was stirred overnight and concentrated in-vacuo. TBME (50 ml) was added to the residue and the resulting suspension filtered. The filtrate was washed with a saturated solution of $NaHCO_3$ (40 ml). The layers were separated and the aqueous phase was extracted with TBME (3×40 ml). The combined organics were dried over $MgSO_4$, filtered and concentrated in-vacuo. The crude residue was purified by flash column chromatography (50 g Isolute cartridge, 0-10% TBME:Heptanes) to give the title compound (1.2 g, 33%) as a white solid. LC-MS 93%, m/z=194.9, 196.9; $^1H$ NMR (500 MHz, Chloroform-d) δ ppm 7.94 (s, 1H), 7.56 (d, J=8.4 Hz, 1H), 7.46 (d, J=8.4 Hz, 1H), 3.95 (s, 3H), 3.44 (s, 1H).

Step 3: Synthesis of methyl 5-chloro-2-ethylbenzoate

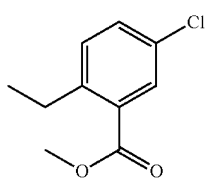

To a solution of methyl 5-chloro-2-ethynylbenzoate (1.13 g, 5.8 mmol) in TBME (50 ml) was added Pd/C (10%) (50% water, 0.61 g, 0.29 mmol). The reaction mixture was stirred under a hydrogen atmosphere for 130 minutes. The mixture was filtered through Celite and the filter cake was washed with TBME. The filtrate was concentrated in-vacuo to give the title compound (1.08 g, 74%) as a pale brown oil. LC-MS 79%, m/z=198.9/200.9; $^1H$ NMR (500 MHz, Chloroform-d) δ ppm 7.85 (s, 1H) 7.40 (d, J=8.20 Hz, 1H) 7.22 (d, J=8.20 Hz, 1H) 3.91 (s, 3H) 2.95 (q, J=7.46 Hz, 2H) 1.22 (t, J=7.49 Hz, 3H).

Step 4: Synthesis of methyl 5-chloro-2-ethyl-3-nitrobenzoate

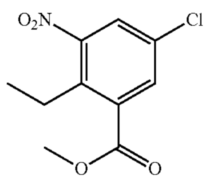 [SMILES: CCc1c(C(=O)OC)cc(Cl)cc1[N+](=O)[O-]]

A solution of methyl 5-chloro-2-ethylbenzoate (1.08 g, 5.4 mmol) in concentrated sulphuric acid (7.0 ml) was cooled to −5° C. in an acetone/ice bath. A mixture of 70% nitric acid (0.45 ml, 7.1 mmol) and concentrated sulphuric acid (0.5 ml) was added dropwise to the reaction mixture at −5° C. over 15 minutes. The resulting pale yellow reaction mixture was stirred at −5° C. for 1 hour before being poured onto ice (100 ml) and extracted with $CH_2Cl_2$ (3×20 ml). The combined organic phases were washed with deionized water (20 ml), brine (20 ml), dried over $Na_2SO_4$, filtered and concentrated in-vacuo. The resulting oil was added to a solution containing methanol (25 ml) and thionyl chloride (0.75 ml) at 0° C. Following addition, the mixture was heated under gentle reflux for 6 hours, before cooling to room temperature and concentrating in-vacuo to give the title compound (1.2 g) as an orange oil which was used without further purification in the next step.

Step 5: Synthesis of methyl 3-amino-5-chloro-2-ethylbenzoate

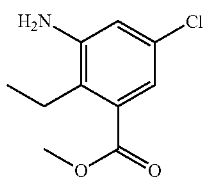

To a solution of methyl 5-chloro-2-ethyl-3-nitrobenzoate (1.2 g, 5.0 mmol) in methanol (50 ml) and deionised water (25 ml), was added ammonium chloride (2.6 g, 50 mmol). The mixture was heated to 70° C. before the addition of iron (1.7 g, 30 mmol). The reaction mixture was stirred at 70° C. for 3.5 hours, hot filtered through Celite and the filter pad was washed with MeOH (20 ml). The filtrate was concentrated in-vacuo and the aqueous residue was dissolved in a saturated solution of $NaHCO_3$(aq) (50 ml) and EtOAc (100 ml). The phases were separated and the organic phase was washed with saturated $NaHCO_3$(aq) (2×65 ml), brine (30 ml), dried over $MgSO_4$, filtered and concentrated in-vacuo. The residue was purified by column chromatography (25 g SNAP cartridge, Isolera, 0-11% ethyl acetate/heptanes) to give the title compound (372 mg, 33%) as a yellow oil. LC-MS 94%, m/z=213.9, 215.9; $^1H$ NMR (500 MHz, Chloroform-d) d ppm 7.18 (d, J=2.21 Hz, 1H) 6.80 (d, J=2.05 Hz, 1H) 3.88 (s, 3H) 3.85 (d, J=2.52 Hz, 2H) 2.75 (q, J=7.57 Hz, 2H) 1.21 (t, J=7.49 Hz, 3H).

Step 6: Synthesis of methyl 3-[(4-{[(tert-butoxy) carbonyl]amino}cyclohexyl)amino]-5-chloro-2-ethylbenzoate

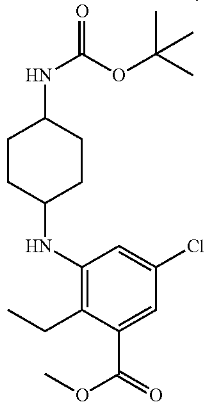 [SMILES: CCc1c(NC2CCC(NC(=O)OC(C)(C)C)CC2)cc(Cl)cc1C(=O)OC]

To a stirred solution of methyl 3-amino-5-chloro-2-ethylbenzoate (365 mg, 1.7 mmol) in 1,2-dichloroethane (20 ml) under nitrogen, was added tert-butyl (4-oxocyclohexyl)carbamate (364 mg, 1.7 mmol) followed by acetic acid (587 µl, 10.3 mmol). The solution was stirred for 10 minutes before the portionwise addition of sodium triacetoxyborohydride (1.09 g, 5.1 mmol) over 1 hour. The resulting solution was stirred at room temperature for 17 hours, before treating with tert-butyl (4-oxocyclohexyl)carbamate (364 mg, 1.7 mmol). The reaction mixture was stirred for 30 minutes and then treated with sodium triacetoxyborohydride (1.09 g, 5.1 mmol) over 2.5 hours. The reaction mixture was stirred at room temperature for a further 26 hours before addition of deionized water (40 ml). The mixture was neutralised with solid $NaHCO_3$ (2.95 g) and was extracted with ethyl acetate (3×50 ml). The combined organic extracts were washed with brine (35 ml), dried ($MgSO_4$), filtered and concentrated in-vacuo. The crude residue was purified by column chromatography (25 g SNAP cartridge, Isolera, 0-18% EtOAc/Heptanes) to give as an oil the title compound (623 mg, 85%) as a mixture of cis/trans isomers. LC-MS 46.1%, 2.61 min (3.5 minute LC-MS method), m/z=411.1, 413.1 and 50.2%, 2.66 min (3.5 minute LC-MS method), m/z=411.1, 413.1; $^{1}$H NMR (500 MHz, Chloroform-d) d ppm 7.05 (dd, J=7.09, 2.05 Hz, 1H) 6.68 (t, J=2.36 Hz, 1H) 4.36-4.63 (m, 1H) 3.88 (d, J=3.31 Hz, 3H) 3.62-3.78 (m, 1H) 3.49 (br. s., 1H) 3.23 (br. s., 1H) 2.63-2.76 (m, 2H) 2.07-2.18 (m, 2H) 1.77-1.89 (m, 2H) 1.69 (br. s., 1H) 1.46 (s, 9H) 1.27 (m, 3H) 1.13-1.24 (m, 3H).

Step 7: Synthesis of methyl 3-[(4-{[(tert-butoxy) carbonyl]amino}cyclohexyl)(ethyl)amino]-5-chloro-2-ethylbenzoate

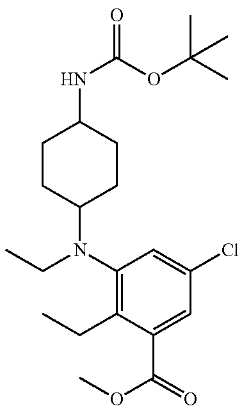 [SMILES: CCc1c(C(=O)OC)cc(Cl)cc1N(CC)C1CCC(NC(=O)OC(C)(C)C)CC1]

To a stirred solution of methyl 3-[(4-{[(tert-butoxy)carbonyl]amino}cyclohexyl)amino]-5-chloro-2-ethylbenzoate (200 mg, 0.49 mmol) in dry 1,2-dichloroethane (5.0 ml), was added acetaldehyde (54 µl, 1.0 mmol), followed by acetic acid (167 µl, 2.9 mmol). The reaction mixture was stirred for 50 minutes, sodium triacetoxyborohydride (309 mg, 1.5 mmol) was added over 2 hours and the reaction was stirred for 20 hours. The reaction mixture was treated with acetaldehyde (54 µl, 1.0 mmol) stirred for 1 hour and sodium triacetoxyborohydride (309 mg, 1.5 mmol) was added portionwise over 2 hours. The reaction mixture was stirred for a further 22 hours and then treated with acetaldehyde (136 µl, 2.4 mmol) and stirred for 1 hour, followed by sodium triacetoxyborohydride (516 mg, 2.4 mmol) over 1.5 hours and stirred for 22 hours. The reaction mixture was treated with acetaldehyde (109 µl, 2.0 mmol) and stirred for 1.5 hours before sodium triacetoxyborohydride (413 mg, 2.0 mmol) was added over 2 hours, along with dichloroethane (5.0 ml) to aid stirring. The reaction mixture was stirred for 19 hours before the addition of acetaldehyde (82 µl, 1.5 mmol), stirred for 1.5 hours, followed by sodium triacetoxyborohydride (309 mg, 1.5 mmol) over 45 minutes. The reaction mixture was stirred for a further 70 hours before being diluted with water (20 ml) and the pH was adjusted to 8 by the gradual addition of solid $NaHCO_3$ (2.53 g). The layers were separated and the aqueous layer was extracted with $CH_2Cl_2$ (3×20 ml). The combined organic phases were washed with brine (60 ml), dried ($MgSO_4$), filtered and concentrated in-vacuo. The crude residue was purified by flash column chromatography (10 g SNAP cartridge, Isolera, 0-30% EtOAc/Heptanes) to give the title compound (163 mg, 73%) as a yellow oil and a mixture of cis/trans-isomers. LC-MS 100%, 5.83 min (7 minute LC-MS method), m/z=439.2, 441.2; $^{1}$H NMR (500 MHz, Chloroform-d) δ ppm 7.45-7.55 (m, 1H) 7.22 (dd, J=4.33, 2.13 Hz, 1H) 4.25-4.67 (m, 1H) 3.90 (d, J=2.21 Hz, 3H) 3.29-3.76 (m, 1H) 2.95-3.11 (m, 4H) 2.58-2.96 (m, 1H) 1.62-2.03 (m, 4H) 1.38-1.53 (m, 11H) 1.01-1.14 (m, 4H) 0.81-0.94 (m, 4H).

Step 8: Synthesis of 3-[(4-{[(tert-butoxy)carbonyl] amino}cyclohexyl)(ethyl)amino]-5-chloro-2-ethylbenzoic acid

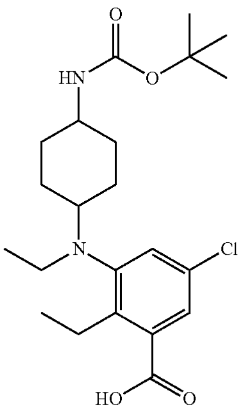 [SMILES: CCc1c(C(=O)O)cc(Cl)cc1N(CC)C1CCC(NC(=O)OC(C)(C)C)CC1]

To a stirred solution of methyl 3-[(4-{[(tert-butoxy)carbonyl]amino}cyclohexyl)(ethyl)amino]-5-chloro-2-ethylbenzoate (156 mg, 0.36 mmol) in THF (4.0 ml) and MeOH (0.29 ml), was added a solution of 4M NaOH (aq) (2.7 ml, 10.7 mmol). The resulting solution was stirred at 50° C. for 17 hours. The reaction mixture was treated with 4M NaOH (aq) (0.5 ml, 2.0 mmol) and stirring was continued at 50° C. for 32 hours. The heat was removed and the reaction mixture was left to stir at room temperature for 65 hours. The reaction mixture was treated with 4M NaOH (aq) (1.0 ml, 4.0 mmol) and heated back up to 50° C. for 24 hours. The organic solvents were removed in-vacuo and the aqueous phase was treated with a solution of 0.5M citric acid (20 ml) to adjust the pH to 4/5. The product was extracted with ethyl acetate (3×25 ml). The combined organic phases were washed with brine (30 ml), dried ($MgSO_4$), filtered and concentrated in-vacuo and then further dried on the high vac line for 4 hours to give the title compound (142 mg, 92%) as a white solid and a mixture of cis/trans isomers. LC-MS 98%, 5.49 min (7 minute LC-MS method), m/z=425.1, 427.1. $^1$H NMR shows a mixture of cis/trans isomers.

Step 9: Synthesis of tert-butyl N-{4-[(5-chloro-3-{[(4,6-dimethyl-2-oxo-1,2-dihydropyridin-3-yl)methyl]carbamoyl}-2-ethylphenyl)(ethyl)amino]cyclohexyl}carbamate

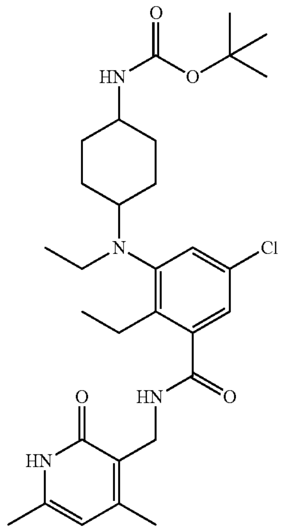 [SMILES: CCc1c(C(=O)NCc2c(C)cc(C)[nH]c2=O)cc(Cl)cc1N(CC)C1CCC(NC(=O)OC(C)(C)C)CC1]

A stirred solution of 3-[(4-{[(tert-butoxy)carbonyl]amino}cyclohexyl)(ethyl)amino]-5-chloro-2-ethylbenzoic acid (139 mg, 0.33 mmol) in anhydrous DMF (2.0 ml) at 0° C. under nitrogen, was treated with HATU (149 mg, 0.39 mmol) and DIPEA (114 μl, 0.65 mmol). The resulting solution was stirred for 10 minutes and then treated with 3-(aminomethyl)-4,6-dimethyl-1,2-dihydropyridin-2-one (89%, 61 mg, 0.36 mmol). The resulting suspension was stirred at 0° C. for 1 hour and then stirred at room temperature for 98.5 hours. The reaction mixture was treated with HATU (37 mg, 0.1 mmol), stirred for 1 hour and then 3-(aminomethyl)-4,6-dimethyl-1,2-dihydropyridin-2-one (89%, 11 mg, 0.07 mmol). The reaction mixture was stirred at room temperature for a further 23 hours and then partitioned between water (20 ml) and $CH_2Cl_2$ (20 ml). The layers were separated and the aqueous phase was extracted with $CH_2Cl_2$ (3×10 ml). The combined organics were washed with a saturated solution of $NaHCO_3$ (aq) (40 ml), water (20 ml), brine (2×20 ml), dried ($MgSO_4$), filtered and concentrated in-vacuo. The crude residue was purified by flash column chromatography (10 g SNAP cartridge, Isolera, 0-13% MeOH/$CH_2Cl_2$) and triturated from ether/heptane (2.0 ml) with sonication and the liquor decanted. The remaining solid was dried under high vacuum to give the title compound (101 mg, 52%) as a beige solid. LC-MS 93%, 4.54 min (7 minute LC-MS method), m/z=559.2, 561.2. $^1$H NMR shows a mixture of cis/trans isomers.

Step 10: Synthesis of 3-[(4-aminocyclohexyl)(ethyl)amino]-5-chloro-N-[(4,6-dimethyl-2-oxo-1,2-dihydropyridin-3-yl)methyl]-2-ethylbenzamide

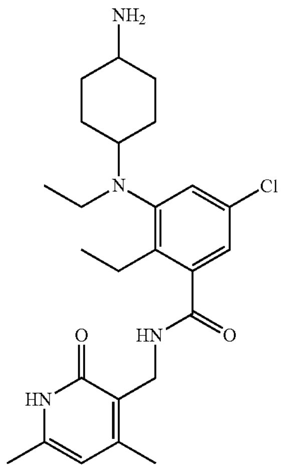 [SMILES: CCc1c(C(=O)NCc2c(C)cc(C)[nH]c2=O)cc(Cl)cc1N(CC)C1CCC(N)CC1]

To a stirred solution of tert-butyl N-{4-[(5-chloro-3-{[(4,6-dimethyl-2-oxo-1,2-dihydropyridin-3-yl)methyl]carbamoyl}-2-ethylphenyl)(ethyl)amino]cyclohexyl}carbamate (100 mg, 0.18 mmol) in $CH_2Cl_2$ (4.0 ml) at 0° C., was added trifluoroacetic acid (1.0 ml). The reaction mixture was stirred at 0° C. for 40 minutes and then stirred for 2 hours at room temperature. The reaction mixture was concentrated in-vacuo and the residue was basified with a saturated solution of $NaHCO_3$ (aq) (10 ml) until the pH was 8. The aqueous residue was extracted with 20% MeOH/$CH_2Cl_2$ (4×15 ml). The combined organic layers were dried ($MgSO_4$), filtered and concentrated in-vacuo to give the title compound (108 mg, 113%) as a yellow solid. LC-MS 48%, 2.88 min (7 minute LC-MS method), m/z=459.1 and 39%, 2.96 min (7 minute LC-MS method), m/z=459.1. $^1$H NMR shows a mixture of cis/trans isomers.

Step 11: Synthesis of 5-chloro-N-[(4,6-dimethyl-2-oxo-1,2-dihydropyridin-3-yl)methyl]-2-ethyl-3-{ethyl[(1r,4r)-4-(dimethylamino)cyclohexyl]amino}benzamide and 5-chloro-N-[(4,6-dimethyl-2-oxo-1,2-dihydropyridin-3-yl)methyl]-2-ethyl-3-{ethyl[(1s,4s)-4-(dimethylamino)cyclohexyl]amino}benzamide

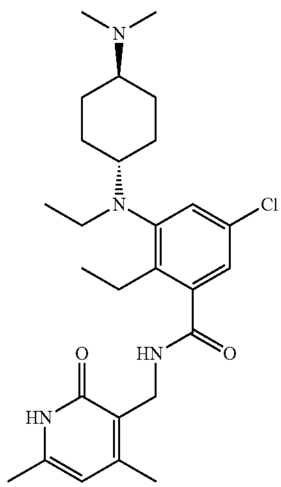

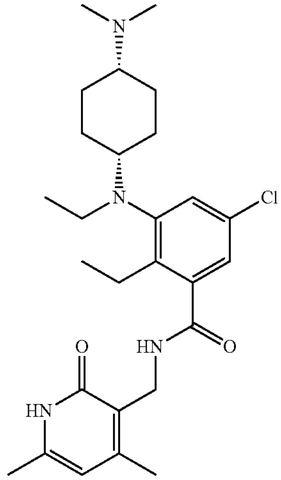

A stirred solution of 3-[(4-aminocyclohexyl)(ethyl)amino]-5-chloro-N-[(4,6-dimethyl-2-oxo-1,2-dihydropyridin-3-yl)methyl]-2-ethylbenzamide (80 mg, 0.18 mmol) in 1,2-dichloroethane (3.0 ml), was treated with acetic acid (60 µl, 1.0 mmol) and paraformaldehyde (31 mg, 1.0 mmol). The reaction mixture was stirred for 35 minutes under nitrogen before the addition of sodium triacetoxyborohydride (222 mg, 1.0 mmol). The reaction mixture was stirred for 16.5 hours before paraformaldehyde (16 mg, 0.52 mmol) was added and stirring was continued for 1 hour prior to the addition of sodium triacetoxyborohydride (111 mg, 0.52 mmol). The reaction mixture was stirred for a further 6 hours and then treated with paraformaldehyde (10 mg, 0.35 mmol), stirred for 10 minutes before the addition of sodium triacetoxyborohydride (74 mg, 0.35 mmol) and 1,2-dichloroethane (1.0 ml) and stirred for a further 89 hours. The reaction mixture was diluted with water (20 ml) and basified to pH 8 by the addition of solid $NaHCO_3$ (1.45 g). $CH_2Cl_2$ (20 ml) was added and the layers were separated. The aqueous phase was extracted with $CH_2Cl_2$ (3×10 ml). The combined organic phases were washed with brine (30 ml), dried ($MgSO_4$), filtered and concentrated in-vacuo. The crude residue was purified by preparative-HPLC (MeCN/water+0.2% ammonium hydroxide) to give pure trans isomer title compound 347: 5-chloro-N-[(4,6-dimethyl-2-oxo-1,2-dihydropyridin-3-yl)methyl]-2-ethyl-3-{ethyl[(1r,4r)-4-(dimethylamino)cyclohexyl]amino}benzamide (22 mg, 26%) as a white solid and pure cis isomer title compound 348: 5-chloro-N-[(4,6-dimethyl-2-oxo-1,2-dihydropyridin-3-yl)methyl]-2-ethyl-3-{ethyl[(1s,4s)-4-(dimethylamino)cyclohexyl]amino}benzamide-(18 mg, 21%) as a white solid.

5-chloro-N-[(4,6-dimethyl-2-oxo-1,2-dihydropyridin-3-yl)methyl]-2-ethyl-3-{ethyl[(1r,4r)-4-(dimethylamino)cyclohexyl]amino}benzamide LC-MS 100%, 3.07 min (7 minute LC-MS method), m/z=487.2, 489.2; $^1$H NMR (500 MHz, Chloroform-d) δ 11.09 (s, 1H), 7.11-7.04 (m, 2H), 7.00 (d, J=2.1 Hz, 1H), 5.94 (s, 1H), 4.51 (d, J=5.9 Hz, 2H), 3.00 (q, J=7.0 Hz, 2H), 2.79 (q, J=7.4 Hz, 2H), 2.65 (t, J=11.5 Hz, 1H), 2.38 (s, 3H), 2.24 (s, 6H), 2.22 (s, 3H), 2.14 (t, J=11.4 Hz, 1H), 1.87 (d, J=10.3 Hz, 4H), 1.37 (q, J=12.1 Hz, 2H), 1.17 (q, J=11.5 Hz, 2H), 1.02 (t, J=7.4 Hz, 3H), 0.85 (t, J=7.0 Hz, 3H).

5-chloro-N-[(4,6-dimethyl-2-oxo-1,2-dihydropyridin-3-yl)methyl]-2-ethyl-3-{ethyl[(1s,4s)-4-(dimethylamino)cyclohexyl]amino}benzamide LC-MS 100%, 3.13 min (7 minute LC-MS method), m/z=487.2, 489.2; $^1$H NMR (500 MHz, chloroform-d) δ 10.72 (s, 1H), 7.09 (d, J=2.0 Hz, 2H), 7.01 (d, J=2.1 Hz, 1H), 5.93 (s, 1H), 4.51 (d, J=5.9 Hz, 2H), 3.01 (q, J=6.7 Hz, 3H), 2.89 (q, J=7.4 Hz, 2H), 2.39 (s, 3H), 2.23 (s, 9H), 2.06 (s, 1H), 1.87-1.72 (m, 4H), 1.43 (td, J=8.3, 3.8 Hz, 2H), 1.33 (dd, J=12.6, 9.2 Hz, 2H), 1.01 (t, J=7.5 Hz, 3H), 0.84 (t, J=7.0 Hz, 3H).

Compound 92: 3-(allyl(tetrahydro-2H-pyran-4-yl)amino)-5-chloro-N-((4,6-dimethyl-2-oxo-1,2-dihydropyridin-3-yl)methyl)-2-methylbenzamide

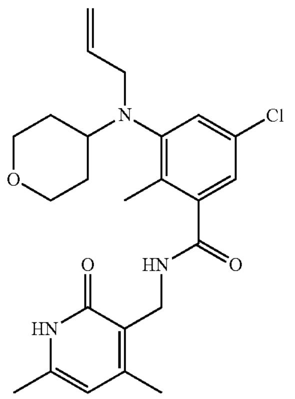 [SMILES: C=CCN(c1cc(Cl)cc(C(=O)NCc2c(C)cc(C)[nH]c2=O)c1C)C1CCOCC1]

Step 1: Synthesis of 5-chloro-2-methyl-3-nitrobenzoic acid

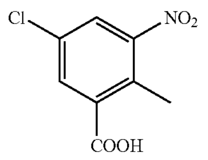

5-chloro-2-methylbenzoic acid (4.0 g, 23 mmol) was added portionwise to cooled conc. $H_2SO_4$ (27 mL) at −10° C. After 10 minutes a nitrating mixture {prepared by mixing conc. HNO3 (3.3 g, 52.68 mmol) with conc. $H_2SO_4$ (4.4 mL)} was added dropwise at −10° C. The resulting reaction mass was stirred at −10° C. for 30 minutes. On completion, the reaction mixture was poured on ice cold water, the solid precipitate was filtered, washed with water and dried under vacuum giving the title compound (4.95 g, 99%).

Step 2: Synthesis of methyl 5-chloro-2-methyl-3-nitrobenzoate

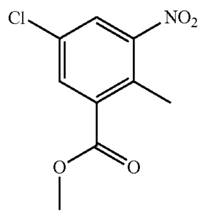

To a stirred solution of 5-chloro-2-methyl-3-nitrobenzoic acid (6.75 g, 31.3 mmol) in DMF (33 mL), sodium carbonate (13.2 g, 125 mmol) and methyl iodide (17.8 g, 125 mmol) were added. The mixture was heated at 60° C. for 4 h. On completion, water was added to the reaction mass and extraction was carried out using DCM. The combined organic layers were dried, concentrated under reduced pressure and purified by column chromatography over silica gel giving the title compound (6.0 g, 83%).

Step 3: Synthesis of methyl 3-amino-5-chloro-2-methyl benzoate

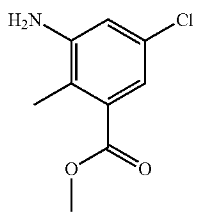

To stirred solution of methyl 5-chloro-2-methyl-3-nitrobenzoate (6.0 g, 26 mmol) in ethanol (60 mL), ammonium chloride (6.0 g, 110 mmol) dissolved in water (60 mL) and iron powder (11.9 g, 208 mmol) were added under stirring. The resulting reaction mass was heated at 80° C. for 1 h. On completion, water was added to reaction mass and reaction mixture was filtered through celite, the filtrate was extracted with ethyl acetate. The combined organic layers were washed with water, dried, and concentrated under reduced pressure giving the title compound which was used as is.

Step 4: Synthesis of methyl 5-chloro-2-methyl-3-((tetrahydro-2H-pyran-4-yl)amino)benzoate

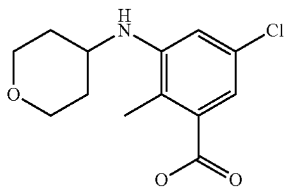 [SMILES: Cc1c(NC2CCOCC2)cc(Cl)cc1C(=O)O]

To a stirred solution of methyl 3-amino-5-chloro-2-methyl benzoate (5.0 g, 19 mmol) and dihydro-2H-pyran-4(3H)-one (2.86 g, 28.6 mmol) in methanol (50 mL), acetic acid (2.3 g, 38 mmol) was added and reaction stirred at room temperature for 8 h. Then sodium cyanoborohydride (3.0 g, 48 mmol) was added at 0° C. and reaction stirred overnight at room temperature. On completion, the solvent was removed under reduced pressure and crude material was purified by column chromatography to afford the title compound (3.0 g, 42%).

Step 5: Synthesis of methyl 3-(allyl(tetrahydro-2H-pyran-4-yl)amino)-5-chloro-2-methylbenzoate

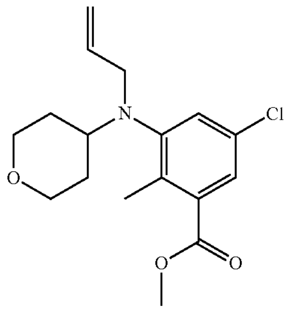 [SMILES: C=CCN(c1cc(Cl)cc(C(=O)OC)c1C)C1CCOCC1]

To a stirred solution of methyl 5-chloro-2-methyl-3-((tetrahydro-2H-pyran-4-yl)amino)benzoate (1.0 g, 3.3 mmol) in DMF (10 mL), NaH (0.25 g, 10 mmol) was added at 0° C. and the mixture stirred for 20 minutes. 3-bromoprop-1-ene (1.7 g, 14.13 mmol) was added and the mixture was heated at 80° C. for 15 h. On completion, the reaction was quenched with ice cold water and extraction was carried out using DCM. The combined organic layers were dried, concentrated and resulting crude was purified by column chromatography giving the title compound (0.50 g, 44%).

Step 6: Synthesis of 3-(allyl(tetrahydro-2H-pyran-4-yl)amino)-5-chloro-N-((4,6-dimethyl-2-oxo-1,2-dihydropyridin-3-yl)methyl)-2-methylbenzamide

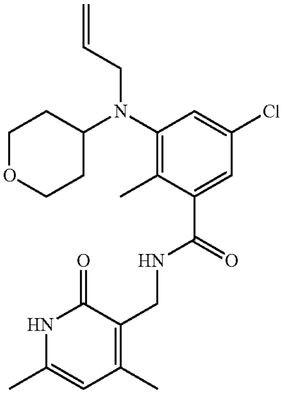 [SMILES: C=CCN(c1cc(Cl)cc(C(=O)NCc2c(C)cc(C)[nH]c2=O)c1C)C1CCOCC1]

Aqueous NaOH (0.092 g, 2.32 mmol) was added to a solution of methyl 3-(allyl(tetrahydro-2H-pyran-4-yl)amino)-5-chloro-2-methylbenzoate (0.50 g, 1.54 mmol) in ethanol (15 mL) and the mixture stirred at 60° C. for 1 h. After completion of the reaction, ethanol was removed under reduced pressure and acidified using dilute HCl up to pH 6 and pH 4 was adjusted using citric acid. Extraction was carried out using DCM. The combined organic layers were dried and concentrated giving respective acid (0.47 g, 98%).

The above acid (0.47 g, 1.52 mmol) was then dissolved in DMSO (5 mL) and 3-(amino methyl)-4,6-dimethylpyridin-2(1H)-one (0.462 g, 3.04 mmol) was added. The reaction mixture was stirred at room temperature for 15 min before PYBOP (1.18 g, 2.28 mmol) was added to it and stirring was continued overnight. After completion of the reaction, reaction mass was poured into ice to obtain a solid which was filtered and dried to afford the title compound (0.40 g, 59%). LCMS: 444.25 $(M+1)^+$; HPLC: 96.85% (@ 254 nm) ($R_t$; 6.310; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-$d_6$, 400 MHz) δ 11.47 (s, 1H), 8.22 (t, 1H), 7.16 (s, 1H), 6.93 (s, 1H), 5.85 (s, 1H), 5.56-5.62 (m, 1H), 5.02-5.07 (m, 1H), 4.94-4.96 (m, 1H), 4.23 (d, 2H, J=3.6 Hz), 3.83 (d, 2H, J=9.6 Hz), 3.64 (d, 2H, J=4 Hz), 3.23 (t, 2H, J=10 Hz), 2.97 (m, 1H), 2.18 (s, 3H), 2.17 (s, 3H), 2.10 (s, 3H), 1.54-1.60 (m, 4H).

Compound 98: 5-chloro-N-((4,6-dimethyl-2-oxo-1,2-dihydropyridin-3-yl)methyl)-2-methyl-3-(propyl(tetrahydro-2H-pyran-4-yl)amino)benzamide

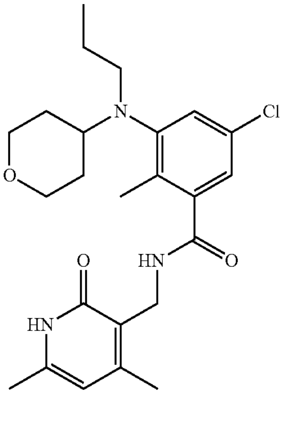 [SMILES: CCCN(c1cc(Cl)cc(C(=O)NCc2c(C)cc(C)[nH]c2=O)c1C)C1CCOCC1]

To a stirred solution of 3-(allyl(tetrahydro-2H-pyran-4-yl)amino)-5-chloro-N-((4,6-dimethyl-2-oxo-1,2-dihydropyridin-3-yl)methyl)-2-methylbenzamide (0.10 g) in MeOH (10 mL) was added 10% Pd/C (0.03 g) and the reaction stirred at room temperature under hydrogen (balloon pressure) for 2 h. On completion, the reaction mixture was filtered through celite and the filtrate was concentrated under reduced pressure to obtain crude solid which was purified by column chromatography to afford the title compound (0.02 g, 20%). LCMS: 445.25 $(M+1)^+$; HPLC: 90.40% (@ 254 nm) ($R_t$; 5.609; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-$d_6$, 400 MHz) δ 11.47 (s, 1H), 8.23 (t, 1H), 7.19 (s, 1H), 6.93 (d, 1H, J=1.6 Hz), 5.88 (s, 1H), 4.24 (d, 2H, J=4.4 Hz), 3.83 (d, 2H, J=10.4 Hz), 3.22-3.25 (m, 2H), 2.94 (t, 2H, J=7.2 Hz), 2.88-2.90 (m, 1H), 2.18 (s, 3H), 2.15 (s, 3H), 2.10 (s, 3H), 1.56 (m, 4H), 1.14-1.23 (m, 2H), 0.75 (t, 3H, J=8 Hz).

Compound 104: 5-chloro-N-((4,6-dimethyl-2-oxo-1,2-dihydropyridin-3-yl)methyl)-3-(isobutylmethyl)amino)-2-methylbenzamide

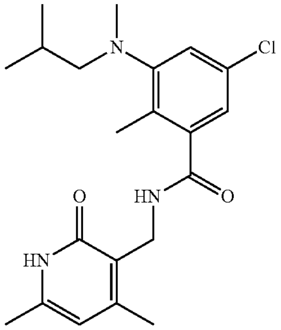 [SMILES: Cc1cc(C)c(CNC(=O)c2cc(Cl)cc(N(C)CC(C)C)c2C)c(=O)[nH]1]

Step 1: Synthesis of methyl 5-chloro-3-(isobutyl amino)-2-methylbenzoate

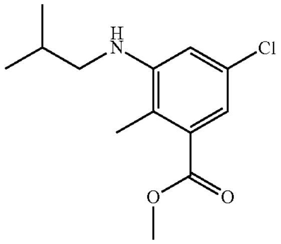 [SMILES: COC(=O)c1cc(Cl)cc(NCC(C)C)c1C]

To a stirred solution of methyl 3-amino-5-chloro-2-methyl benzoate (5.0 g, 25 mmol) and isobutyraldehyde (4.5 g, 62 mmol) in methanol (50 mL), acetic acid (3.0 g, 50 mmol) was added and reaction stirred at room temperature for 2 h. Then sodium cyanoborohydride (3.94 g, 62 mmol) was added at 0° C. and reaction stirred overnight at room temperature. On completion, the solvent was removed under reduced pressure and the crude material was purified by column chromatography to afford the title compound (6.0 g, 94%).

Step 2: Synthesis of methyl 5-chloro-3-(isobutyl(methyl)amino)-2-methylbenzoate

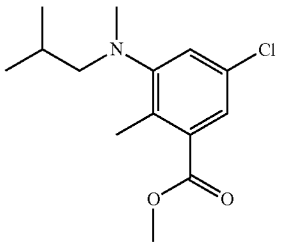 [SMILES: COC(=O)c1cc(Cl)cc(N(C)CC(C)C)c1C]

To a stirred solution of methyl 5-chloro-3-(isobutyl amino)-2-methylbenzoate (1.0 g, 3.9 mmol) in dry acetonitrile (10 mL), cesium carbonate (2.55 g, 7.8 mmol) and methyl iodide (5.55 g, 39 mmol) were added. The mixture was heated at 80° C. for 12 h. On completion, the mixture was cooled to room temperature and filtered. The residue was washed with ethyl acetate and the filtrate was concentrated to the title compound (1.0 g, 95%).

Step 3: Synthesis of 5-chloro-N-((4,6-dimethyl-2-oxo-1,2-dihydropyridin-3-yl)methyl)-3-(isobutyl (methyl)amino)-2-methylbenzamide

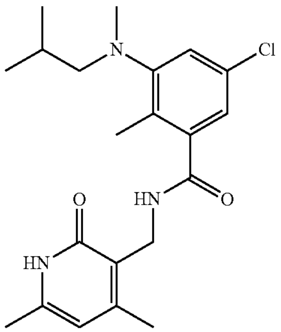 [SMILES: Cc1cc(C)c(CNC(=O)c2cc(Cl)cc(N(C)CC(C)C)c2C)c(=O)[nH]1]

Aqueous NaOH (0.22 g, 5.5 mmol) was added to a solution of methyl 5-chloro-3-(isobutyl(methyl)amino)-2-methylbenzoate (1.0 g, 3.7 mmol) in EtOH (5 mL) and the mixture stirred at 60° C. for 1 h. After completion of the reaction, ethanol was removed under reduced pressure. The residue was acidified using dilute HCl up to pH 6 and pH 4 was adjusted using citric acid. Extraction was carried out using ethyl acetate. The combined organic layers were dried and concentrated giving the respective acid (0.900 g, 95%). The acid (0.30 g, 1.17 mmol) was then dissolved in DMSO (1.5 mL) and 3-(amino methyl)-4,6-dimethylpyridin-2(1H)-one (0.357 g, 2.34 mmol) was added. The reaction mixture was stirred at room temperature for 15 min before PYBOP (0.915 g, 1.76 mmol) was added to it and stirring was continued overnight. After completion of the reaction, the reaction mass was poured into ice to obtain a solid, this was filtered and purified by column chromatography to afford the title compound (0.245 g, 53%). LCMS: 390.25 $(M+1)^+$; HPLC: 97.59% (@ 254 nm) ($R_t$; 6.063; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^{1}H$ NMR (DMSO-$d_6$, 400 MHz) δ 11.47 (s, 1H), 8.20 (t, 1H), 7.07 (s, 1H), 6.90 (s, 1H), 5.85 (s, 1H), 4.23 (d, 2H, J=4.4 Hz), 2.63 (d, 2H, J=7.2 Hz), 2.54 (s, 3H), 2.18 (s, 3H), 2.16 (s, 3H), 2.10 (s, 3H), 1.75-1.78 (m, 1H), 0.85 (d, 611, J=6 Hz).

Compound 105: 5-chloro-N-((4,6-dimethyl-2-oxo-1,2-dihydropyridin-3-yl)methyl)-3-(ethyl(isobutyl) amino)-2-methylbenzamide

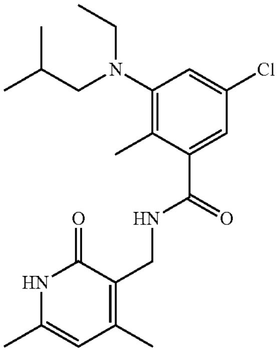 [SMILES: CCN(CC(C)C)c1cc(Cl)cc(C(=O)NCc2c(C)cc(C)[nH]c2=O)c1C]

Step 1: Synthesis of methyl 5-chloro-3-(ethyl(isobutyl)amino)-2-methylbenzoate

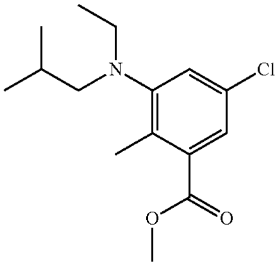 [SMILES: CCN(CC(C)C)c1cc(Cl)cc(C(=O)OC)c1C]

To a stirred solution of methyl 5-chloro-3-(isobutyl amino)-2-methylbenzoate (1.0 g, 3.9 mmol) in dry DMF (10 mL), cesium carbonate (2.55 g, 7.82 mmol) and ethyl iodide (6.09 g, 39.1 mmol) were added. The resulting reaction mass was heated at 80° C. for 12 h. On completion, the reaction mass was cooled to room temperature and filtered. The residue was washed with ethyl acetate and the filtrate was concentrated to give crude material which then used for next step as is (10 g, 91%).

Step 2: Synthesis of 5-chloro-N-((4,6-dimethyl-2-oxo-1,2-dihydropyridin-3-yl)methyl)-3-(ethyl(isobutyl)amino)-2-methylbenzamide

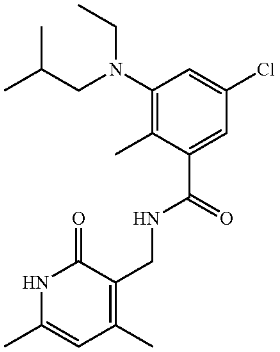 [SMILES: CCN(CC(C)C)c1cc(Cl)cc(C(=O)NCc2c(C)cc(C)[nH]c2=O)c1C]

Aqueous NaOH (0.212 g, 5.28 mmol) was added to a solution of compound 7 (1.0 g, 3.50 mmol) in EtOH (5 mL) and stirred at 60° C. for 1 h. After completion of the reaction, ethanol was removed under reduced pressure and acidified using dilute HCl up to pH 6 and pH 4 was adjusted using citric acid. Extraction was carried out using ethyl acetate. The combined organic layers were dried concentrated giving the respective acid (0.900 g).

The acid (0.90 g, 3.33 mmol) was then dissolved in DMSO (4.5 mL) and 3-(amino methyl)-4,6-dimethylpyridin-2(1H)-one (1.01 g, 6.67 mmol) was added to it. The reaction mixture was stirred at room temperature for 15 min before PYBOP (2.60 g, 4.9 mmol) was added and stirring was continued for overnight. The mixture was poured into ice to give a solid, this was filtered and purified by acetonitrile and diethyl ether washings to afford the title compound (1.0 g, 75%). LCMS: 404.25 $(M+1)^+$; HPLC: 90.28% (@ 254 nm) ($R_t$; 6.063; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-$d_6$, 400 MHz) δ 11.45 (s, 1H), 8.19 (t, 1H), 7.10 (s, 1H), 6.90 (s, 1H), 5.85 (s, 1H), 4.24 (d, 2H, J=4.8 Hz), 2.86 (q, 2H, J=7.2 Hz), 2.73 (d, 2H, J=7.6 Hz), 2.18 (s, 3H), 2.16 (s, 3H), 2.10 (s, 3H), 1.57-1.61 (m, 1H), 0.91 (t, 3H, J=6.8 Hz), 0.82 (d, 6H, J=6.4 Hz).

Compound 117: 5-chloro-3-((cyclopentylmethyl)(methyl)amino)-N-((4,6-dimethyl-2-oxo-1,2-dihydropyridin-3-yl)methyl)-2-methylbenzamide

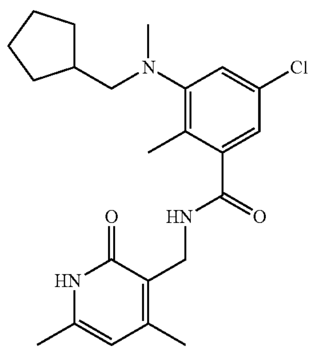 [SMILES: Cc1cc(C)c(CNC(=O)c2cc(Cl)cc(N(C)CC3CCCC3)c2C)c(=O)[nH]1]

Step 1: Synthesis of methyl 5-chloro-3-((cyclopentylmethyl)amino)-2-methylbenzoate

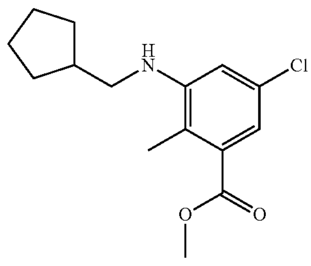 [SMILES: COC(=O)c1cc(Cl)cc(NCC2CCCC2)c1C]

To a stirred solution of methyl 3-amino-5-chloro-2-methyl benzoate (3.0 g, 15 mmol) and cyclopentanecarbaldehyde (2.2 g, 22 mmol) in methanol (30 mL), acetic acid (1.8 g, 30 mmol) was added and reaction stirred at room temperature for 8 h. Then sodium cyanoborohydride (2.4 g, 37 mmol) was added at 0° C. and the reaction stirred overnight at room temperature. On completion, the solvent was removed under reduced pressure and the crude material was purified by column chromatography to afford the title compound (4.2 g, 99%).

Step 2: Synthesis of methyl 5-chloro-3-((cyclopentylmethyl)(methyl)amino)-2-methylbenzoate

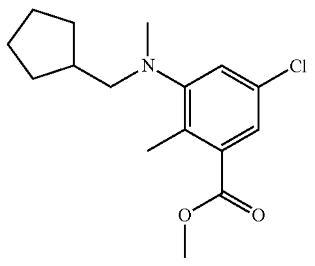 [SMILES: COC(=O)c1cc(Cl)cc(N(C)CC2CCCC2)c1C]

To a stirred solution of methyl 5-chloro-3-((cyclopentylmethyl)amino)-2-methylbenzoate (1.0 g, 3.5 mmol) in acetonitrile (10 mL), cesium carbonate (2.3 g, 7.1 mmol) and methyl iodide (5.0 g, 35 mmol) were added. The mixture was heated at 80° C. for 12 h. cooled to room temperature and filtered. The residue was washed with ethyl acetate and the filtrate was concentrated and then purified by column chromatography to afford the title compound (1.0 g, 95%).

Step 3: Synthesis of 5-chloro-3-((cyclopentylmethyl)(methyl)amino)-N-((4,6-dimethyl-2-oxo-1,2-dihydropyridin-3-yl)methyl)-2-methylbenzamide

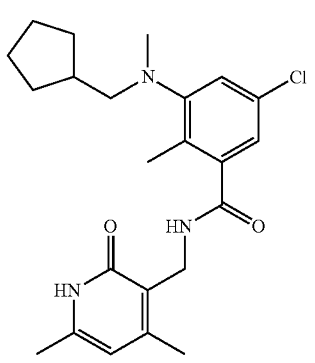 [SMILES: Cc1cc(C)c(CNC(=O)c2cc(Cl)cc(N(C)CC3CCCC3)c2C)c(=O)[nH]1]

Aqueous NaOH (0.206 g, 15.1 mmol) was added to a solution of methyl 5-chloro-3-((cyclopentylmethyl)(methyl)amino)-2-methylbenzoate (1.0 g, 3.38 mmol) in ethanol (10 mL) and the mixture stirred at 60° C. for 1 h. The ethanol was removed under reduced pressure and the residue acidified using dilute HCl up to pH 6 and pH 4 was adjusted using citric acid. Extraction was carried out using DCM. The combined organic layers were dried and concentrated giving the respective acid (0.9 g) The above acid (0.3 g, 1.06 mmol) was then dissolved in DMSO (1.5 mL) and 3-(amino methyl)-4,6-dimethylpyridin-2(1H)-one (0.324 g, 2.12 mmol) was added. The reaction mixture was stirred at room temperature for 15 min before PYBOP (0.831 g, 1.57 mmol) was added and stirring was continued overnight. The mixture was poured into ice to obtain a solid, this was filtered and washed with acetonitrile to provide the title compound (0.25 g, 56%). LCMS: 416.15 $(M+1)^+$; HPLC: 92.58% (@ 254 nm) ($R_t$; 6.169; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.45 (s, 1H), 8.19 (t, 1H), 7.08 (s, 1H), 6.89 (s, 1H), 5.85 (s, 1H), 4.23 (d, 2H, J=4.4 Hz), 2.77 (d, 2H, J=7.2 Hz), 2.57 (s, 3H), 2.18 (s, 3H), 2.15 (s, 3H), 2.10 (s, 3H), 2.04-2.06 (m, 1H), 1.63-1.65 (m, 2H), 1.49-1.52 (m, 2H), 1.45-1.46 (m, 2H), 1.15-1.18 (m, 2H).

Compound 118: 5-chloro-3-((cyclopentylmethyl)(ethyl)amino)-N-((4,6-dimethyl-2-oxo-1,2-dihydropyridin-3-yl)methyl)-2-methylbenzamide

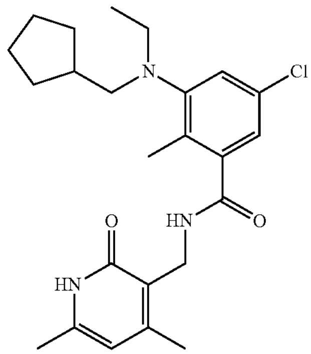 [SMILES: CCN(CC1CCCC1)c1cc(Cl)cc(C(=O)NCc2c(C)cc(C)[nH]c2=O)c1C]

Step 1: Synthesis of methyl 5-chloro-3-((cyclopentylmethyl)(ethyl)amino)-2-methylbenzoate

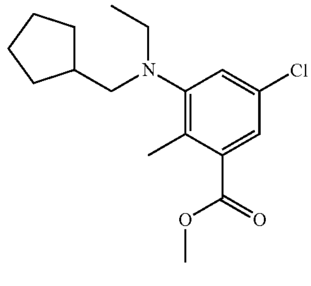 [SMILES: CCN(CC1CCCC1)c1cc(Cl)cc(C(=O)OC)c1C]

To a stirred solution of methyl 5-chloro-3-((cyclopentylmethyl)amino)-2-methylbenzoate (1.0 g, 3.54 mmol) in DMF (10 mL), cesium carbonate (2.31 g, 7.09 mmol) and ethyl iodide (5.53 g, 35.4 mmol) were added. The resulting reaction mass was heated at 80° C. for 12 h. The mixture was cooled to room temperature and filtered. The residue was washed with ethyl acetate and the filtrate was concentrated to a residue which was purified by column chromatography to afford the title compound (1.0 g, 91%).

Step 2: Synthesis of 5-chloro-3-((cyclopentylmethyl)(ethyl)amino)-N-((4,6-dimethyl-2-oxo-1,2-dihydropyridin-3-yl)methyl)-2-methylbenzamide

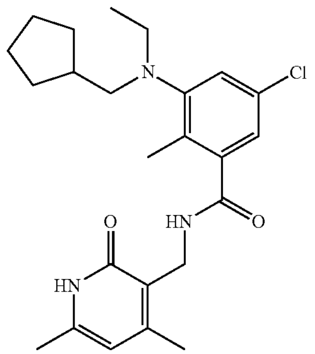 [SMILES: CCN(CC1CCCC1)c1cc(Cl)cc(C(=O)NCc2c(C)cc(C)[nH]c2=O)c1C]

Aqueous NaOH (0.193 g, 15.1 mmol) was added to a solution of methyl 5-chloro-3-((cyclopentylmethyl)(ethyl)amino)-2-methylbenzoate (1.0 g, 3.22 mmol) in ethanol (10 mL) and the mixture stirred at 60° C. for 1 h. After completion of the reaction, ethanol was removed under reduced pressure and the residue acidified using dilute HCl up to pH 6 and pH 4 was adjusted using citric acid. Extraction was carried out using DCM. The combined organic layers were dried concentrated giving respective acid (0.9 g).

The above acid (0.3 g, 1.01 mmol) was then dissolved in DMSO (1.5 mL) and 3-(amino methyl)-4,6-dimethylpyridin-2(1H)-one (0.308 g, 2.12 mmol) was added. The reaction mixture was stirred at room temperature for 15 min before PYBOP (0.791 g, 1.52 mmol) was added and stirring was continued overnight. After completion of the reaction, the reaction mass was poured into ice to obtain a solid, this was filtered and washed with acetonitrile to provide the title compound (0.25 g, 57%). LCMS: 430.2 $(M+1)^+$; HPLC: 91.54% (@ 210 nm) ($R_t$; 9.378; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.46 (s, 1H), 8.20 (t, 1H), 7.12 (s, 1H), 6.91 (s, 1H), 5.85 (s, 1H), 4.23 (d, 2H, J=3.6 Hz), 2.83-2.89 (m, 4H), 2.18 (s, 3H), 2.14 (s, 3H), 2.10 (s, 3H), 1.85-1.89 (m, 1H), 1.51-1.58 (m, 4H), 1.41-1.46 (m, 2H), 1.14-1.15 (m 2H), 0.91 (t, 3H, J=8 Hz).

Compound 123: 5-chloro-3-(cyclobutyl(methyl)amino)-N-((4,6-dimethyl-2-oxo-1,2-dihydropyridin-3-yl)methyl)-2-methylbenzamide

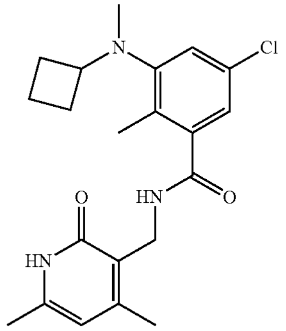 [SMILES: Cc1cc(C)c(CNC(=O)c2cc(Cl)cc(N(C)C3CCC3)c2C)c(=O)[nH]1]

Step 1: Synthesis of methyl 5-chloro-3-(cyclobutylamino)-2-methylbenzoate

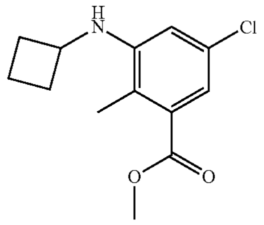 [SMILES: COC(=O)c1cc(Cl)cc(NC2CCC2)c1C]

To a stirred solution of methyl 3-amino-5-chloro-2-methylbenzoate (2.0 g, 10 mmol) and cyclobutanone (1.4 g, 20 mmol) in dichloroethane (20 mL), acetic acid (3.6 g, 60 mmol) was added and reaction stirred at room temperature for 10 minutes. Then sodium triacetoxyborohydride (6.3 g, 30 mmol) was added at 0° C. and the reaction stirred for 3 h at room temperature. On completion, the solvent was removed under reduced pressure and the crude material was purified by column chromatography to afford the title compound (1.4 g, 56%).

Step 2: Synthesis of methyl 5-chloro-3-(cyclobutyl (methyl)amino)-2-methylbenzoate

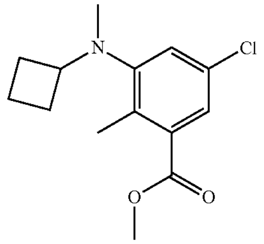 [SMILES: COC(=O)c1cc(Cl)cc(N(C)C2CCC2)c1C]

To a stirred solution of methyl 5-chloro-3-(cyclobutylamino)-2-methylbenzoate (0.7 g, 2.8 mmol) in acetonitrile-(10 mL), cesium carbonate (2.2 g, 6.8 mmol) and methyl iodide (3.9 g, 28 mmol) were added. The resulting reaction mass was heated at 80° C. for 8 h. On completion, the reaction mass was cooled to room temperature and filtered. The residue was washed with ethyl acetate and the filtrate was concentrated to give the title compound (0.62 g, 84%).

Step 3: Synthesis of 5-chloro-3-(cyclobutyl(methyl) amino)-N-((4,6-dimethyl-2-oxo-1,2-dihydropyridin-3-yl)methyl)-2-methylbenzamide

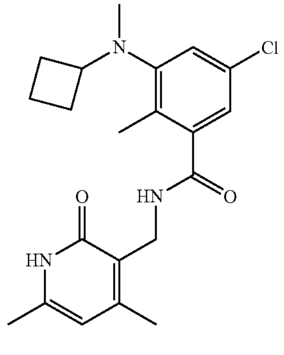 [SMILES: Cc1cc(C)c(CNC(=O)c2cc(Cl)cc(N(C)C3CCC3)c2C)c(=O)[nH]1]

Aqueous NaOH (0.134 g, 3.34 mmol) was added to a solution of methyl 5-chloro-3-(cyclobutyl(methyl)amino)-2-methylbenzoate (0.60 g, 2.23 mmol) in ethanol (10 mL) and the mixture stirred at 60° C. for 1 h. After completion of the reaction, ethanol was removed under reduced pressure and acidified using dilute HCl up to pH 6 and pH 4 was adjusted using citric acid. Extraction was carried out using DCM. The combined organic layers were dried concentrated giving respective acid (0.5 g).

The above acid (0.25 g, 0.98 mmol) was then dissolved in DMSO (5 mL) and 3-(amino methyl)-4,6-dimethylpyridin-2(1H)-one (0.22 g, 1.41 mmol) was added. The reaction mixture was stirred at room temperature for 15 min before PYBOP (0.767 g, 1.47 mmol) was added and stirring was continued overnight. After completion of the reaction, the reaction mass was poured into ice and extraction was carried out using 10% MeOH/DCM. The combined organic layers were dried over sodium sulphate and concentrated under reduced pressure to obtain crude material which was then purified by column chromatography giving the title compound (0.36 g, 95%). LCMS: 388.09 $(M+1)^+$; HPLC: 96.62% (@ 254 nm) ($R_t$; 5.461; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.44 (s, 1H), 8.18 (t, 1H), 6.90 (d, 2H, J=7.2 Hz), 5.85 (s, 1H), 4.24 (d, 2H, J=4.4 Hz), 3.65 (m, 1H), 2.45 (s, 3H), 2.18 (s, 3H), 2.15 (s, 3H), 2.10 (s, 3H), 2.03 (bs, 2H), 1.76-1.81 (m, 2H), 1.61-1.62 (m, 2H).

Compound 137: 5-chloro-3-(cyclobutyl(ethyl) amino)-N-((4,6-dimethyl-2-oxo-1,2-dihydropyridin-3-yl)methyl)-2-methylbenzamide

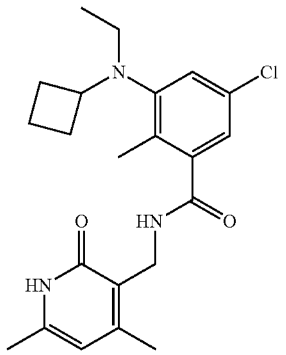 [SMILES: CCN(c1cc(Cl)cc(C(=O)NCc2c(C)cc(C)[nH]c2=O)c1C)C1CCC1]

Step 1: Synthesis of methyl 5-chloro-3-(cyclobutyl (ethyl)amino)-2-methylbenzoate

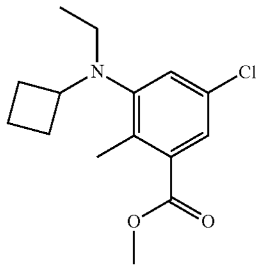 [SMILES: CCN(c1cc(Cl)cc(C(=O)OC)c1C)C1CCC1]

To a stirred solution of methyl 5-chloro-3-(cyclobutylamino)-2-methylbenzoate (0.70 g, 2.73 mmol) and acetaldehyde (0.36 g, 8.20 mmol) in dichloroethane (15 mL), acetic acid (0.98 g, 16.4 mmol) was added and the reaction stirred at room temperature for 10 minutes. Then sodium triacetoxyborohydride (1.7 g, 8.2 mmol) was added at 0° C. and the reaction stirred for 3 h at room temperature. On completion, the solvent was removed under reduced pressure to give title compound (0.71 g, 91%).

Step 2: Synthesis of 5-chloro-3-(cyclobutyl(ethyl)amino)-N-((4,6-dimethyl-2-oxo-1,2-dihydropyridin-3-yl)methyl)-2-methylbenzamide

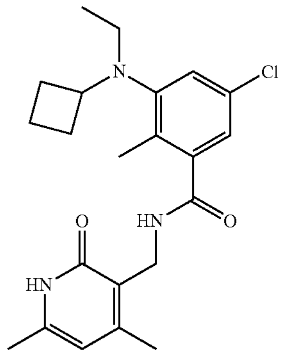 [SMILES: CCN(c1cc(Cl)cc(C(=O)NCc2c(C)cc(C)[nH]c2=O)c1C)C1CCC1]

Aqueous NaOH (0.149 g, 3.7 mmol) was added to a solution of methyl 5-chloro-3-(cyclobutyl(ethyl)amino)-2-methylbenzoate (0.70 g, 2.48 mmol) in ethanol (10 mL) and the mixture stirred at 60° C. for 1 h. After completion of the reaction, ethanol was removed under reduced pressure and the residue acidified using dilute HCl up to pH 6 and pH 4 was adjusted using citric acid. Extraction was carried out using DCM. The combined organic layers were dried and concentrated giving respective acid (0.6 g,).

The above acid (0.6 g, 2.2 mmol) was then dissolved in DMSO (5 mL) and 3-(amino methyl)-4,6-dimethylpyridin-2(1H)-one (0.67 g, 4.44 mmol) was added. The reaction mixture was stirred at room temperature for 15 min before PYBOP (1.7 g, 3.33 mmol) was added and stirring was continued overnight. After completion of the reaction, the reaction mass was poured into ice; extraction was carried out using 10% MeOH/DCM. The combined organic layers were dried over sodium sulphate and concentrated under reduced pressure to obtain crude material which was then purified by solvent washings giving the title compound (0.45 g, 50%). LCMS: 402.20 $(M+1)^+$; HPLC: 98.73% (@ 254 nm) ($R_t$; 4.096; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.47 (s, 1H), 8.22 (t, 1H, J=4.4 Hz), 6.97 (s, 1H), 6.92 (s, 1H), 5.85 (s, 1H), 4.23 (d, 2H, J=4.4 Hz), 3.75-3.79 (m, 1H), 2.87-2.93 (m, 2H), 2.18 (s, 3H), 2.15 (s, 3H), 2.10 (s, 3H), 1.99 (m, 2H), 1.58-1.69 (m, 4H), 0.77 (t, 3H, J=6.8 Hz).

Compound 126: 5-chloro-N-((4,6-dimethyl-2-oxo-1,2-dihydropyridin-3-yl)methyl)-2-methyl-3-(methyl((tetrahydro-2H-pyran-4-yl)methyl)amino)benzamide

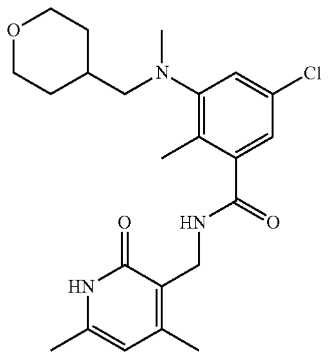 [SMILES: Cc1cc(C)c(CNC(=O)c2cc(Cl)cc(N(C)CC3CCOCC3)c2C)c(=O)[nH]1]

Step 1: Synthesis of methyl 5-chloro-2-methyl-3-(((tetrahydro-2H-pyran-4-yl)methyl)amino)benzoate

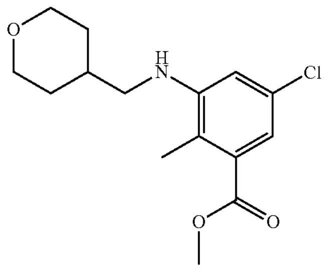 [SMILES: COC(=O)c1cc(Cl)cc(NCC2CCOCC2)c1C]

To a stirred solution of methyl 3-amino-5-chloro-2-methyl benzoate (2.0 g, 10 mmol) and tetrahydro-2H-pyran-4-carbaldehyde (1.71 g, 15 mmol) in methanol (20 mL), acetic acid (1.2 g, 20 mmol) was added and the reaction stirred at room temperature for 8 h. Then sodium cyanoborohydride (2.11 g, 25.1 mmol) was added at 0° C. and the reaction stirred overnight at room temperature. On completion, the solvent was removed under reduced pressure and the crude material was purified by column chromatography to afford the title compound (1.8 g, 60%).

Step 2: Synthesis of methyl 5-chloro-2-methyl-3-(methyl((tetrahydro-2H-pyran-4-yl)methyl)amino) benzoate

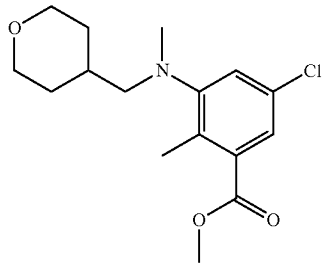 [SMILES: COC(=O)c1cc(Cl)cc(N(C)CC2CCOCC2)c1C]

To a stirred solution of methyl 5-chloro-2-methyl-3-(((tetrahydro-2H-pyran-4-yl)methyl)amino)benzoate (0.80 g, 2.71 mmol) in acetonitrile (20 mL), cesium carbonate (1.75 g, 5.42 mmol) and methyl iodide (1.93 g, 13.6 mmol) were added. The resulting reaction mass was heated at 80° C. for 8 h. On completion, the mixture was cooled to room temperature and filtered. The residue was washed with ethyl acetate and the filtrate was concentrated to give crude material which was purified by column chromatography to give the title compound (0.70 g, 84%).

Step 3: Synthesis of 5-chloro-N-((4,6-dimethyl-2-oxo-1,2-dihydropyridin-3-yl)methyl)-2-methyl-3-(methyl((tetrahydro-2H-pyran-4-yl)methyl)amino) benzamide

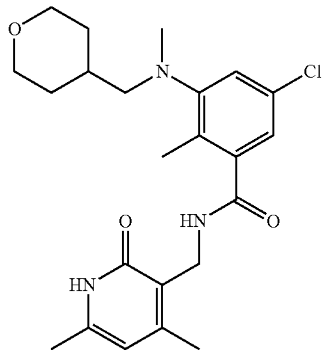 [SMILES: Cc1cc(C)c(CNC(=O)c2cc(Cl)cc(N(C)CC3CCOCC3)c2C)c(=O)[nH]1]

Aqueous NaOH (0.18 g, 4.5 mmol) was added to a solution of methyl 5-chloro-2-methyl-3-(methyl((tetrahydro-2H-pyran-4-yl)methyl)amino)benzoate (0.70 g, 2.25 mmol) in ethanol (10 mL) and the mixture stirred at 60° C. for 1 h. The ethanol was removed under reduced pressure and the residue acidified using dilute HCl up to pH 6 and pH 4 was adjusted using citric acid. Extraction was carried out using DCM. The combined organic layers were dried and concentrated giving the respective acid (0.2 g).

The above acid (0.2 g, 0.68 mmol) was then dissolved in DMSO (0.5 mL) and 3-(amino methyl)-4,6-dimethylpyridin-2(1H)-one (0.206 g, 1.35 mmol) was added. The reaction mixture was stirred at room temperature for 15 min before PYBOP (0.528 g, 1.01 mmol) was added t and stirring was continued overnight. The mixture was poured into ice and extraction was carried out using 10% MeOH/DCM. The combined organic layers were dried over sodium sulphate and concentrated under reduced pressure to obtain crude material which was purified by column chromatography giving the title compound (0.2 g, 69%). LCMS: 432.25 $(M+1)^+$; HPLC: 99.95% (@ 254 nm) ($R_t$; 5.750; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-$d_6$, 400 MHz) δ 11.45 (s, 1H), 8.19 (t, 1H), 7.10 (d, 1H, J=1.6 Hz), 6.90 (d, 1H, J=2 Hz), 5.85 (s, 1H), 4.23 (d, 2H, J=4.8 Hz), 3.80 (d, 2H, J=8.4 Hz), 3.21-3.27 (m, 2H), 2.73 (d, 2H, J=7.2 Hz), 2.55 (s, 3H), 2.18 (s, 3H), 2.15 (s, 3H), 2.10 (s, 3H), 1.74-1.75 (m, 1H), 1.58-1.61 (m, 2H), 1.07-1.16 (m, 2H).

Compound 127: 5-chloro-N-((4,6-dimethyl-2-oxo-1,2-dihydropyridin-3-yl)methyl)-3-(ethyl((tetrahydro-2H-pyran-4-yl)methyl)amino)-2-methylbenzamide

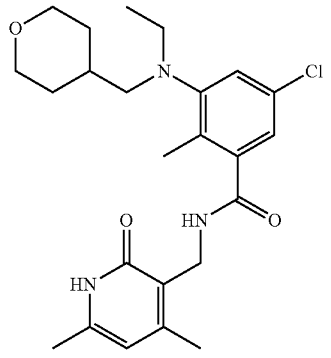 [SMILES: CCN(CC1CCOCC1)c1cc(Cl)cc(C(=O)NCc2c(C)cc(C)[nH]c2=O)c1C]

Step 1: Synthesis of methyl 5-chloro-3-(ethyl((tetrahydro-2H-pyran-4-yl)methyl)amino)-2-methylbenzoate

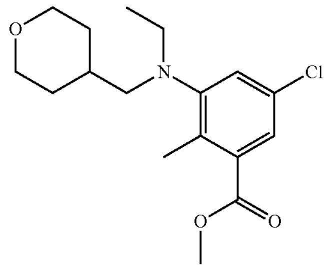 [SMILES: CCN(CC1CCOCC1)c1cc(Cl)cc(C(=O)OC)c1C]

To a stirred solution of methyl 5-chloro-2-methyl-3-(((tetrahydro-2H-pyran-4-yl)methyl)amino)benzoate (0.40 g, 1.35 mmol) and acetaldehyde (0.120 g, 2.71 mmol) in dichloroethane (5 mL), acetic acid (0.48 g, 8.1 mmol) was added and the reaction stirred at room temperature for 10 minutes.

Then sodium triacetoxyborohydride (0.663 g, 4.05 mmol) was added at 0° C. and the reaction stirred for 3 h at room temperature. On completion, the solvent was removed under reduced pressure and the crude material purified by column chromatography to the title compound (0.38 g, 86%).

Step 2: Synthesis of 5-chloro-N-((4,6-dimethyl-2-oxo-1,2-dihydropyridin-3-yl)methyl)-3-(ethyl((tetrahydro-2H-pyran-4-yl)methyl)amino)-2-methylbenzamide

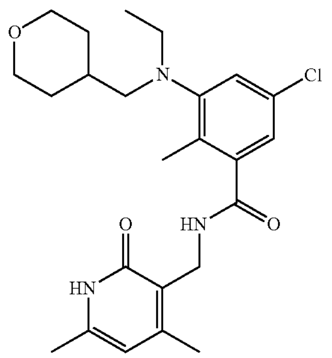 [SMILES: CCN(CC1CCOCC1)c1cc(Cl)cc(C(=O)NCc2c(C)cc(C)[nH]c2=O)c1C]

Aqueous NaOH (0.099 g, 2.46 mmol) was added to a solution of methyl 5-chloro-3-(ethyl((tetrahydro-2H-pyran-4-yl)methyl)amino)-2-methylbenzoate (0.38 g, 1.2 mmol) in ethanol (20 mL) and the mixture stirred at 60° C. for 1 h. After completion of the reaction, ethanol was removed under reduced pressure and the residue acidified using dilute HCl up to pH 6 and pH 4 was adjusted using citric acid. Extraction was carried out using DCM. The combined organic layers were dried concentrated giving the respective acid (0.2 g).

The above acid (0.2 g, 0.64 mmol) was then dissolved in DMSO (2 mL) and 3-(amino methyl)-4,6-dimethylpyridin-2 (1H)-one (0.196 g, 1.29 mmol) was added. The reaction mixture was stirred at room temperature for 15 min before PYBOP (0.504 g, 0.97 mmol) was added and stirring was continued overnight. The mixture was poured into ice and extraction was carried out using 10% MeOH/DCM. The combined organic layers were dried over sodium sulphate and concentrated under reduced pressure to obtain crude material which was purified by column chromatography to afford the title compound (0.15 g, 52%). LCMS: 446.20 $(M+1)^+$; HPLC: 99.89% (@ 254 nm) ($R_t$; 5.381; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.47 (s, 1H), 8.21 (t, 1H), 7.14 (s, 1H), 6.91 (s, 1H), 5.85 (s, 1H), 4.23 (d, 2H, J=4.4 Hz), 3.78 (d, 2H, J=8.8 Hz), 3.18 (t, 2H, J=11.6 Hz), 2.82-2.89 (m, 4H), 2.18 (s, 3H), 2.13 (s, 3H), 2.10 (s, 3H), 1.54-1.57 (m, 3H), 1.09-1.15 (m, 2H), 0.91 (t, 3H, J=6.8 Hz).

Compound 157: N-((4,6-dimethyl-2-oxo-1,2-dihydropyridin-3-yl)methyl)-3-(ethyl(tetrahydro-2H-pyran-4-yl)amino)-2,5-dimethylbenzamide

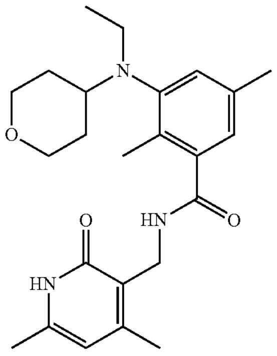

Step 1: Synthesis of 5-bromo-2-methyl-3-nitrobenzoic acid

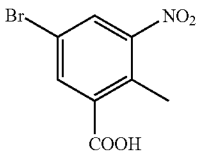

To stirred solution of 2-methyl-3-nitrobenzoic acid (50 g, 276 mmol) in conc. $H_2SO_4$ (200 mL), 1,3-dibromo-5,5-dimethyl-2,4-imidazolidinedione (43.4 g, 152 mmol) was added portionwise at room temperature. The mixture was stirred at room temperature for 5 h. and poured on ice cold water. The precipitate was filtered, washed with water and dried under vacuum giving the title compound (71 g, 99%).

Step 2: Synthesis of methyl 5-bromo-2-methyl-3-nitrobenzene

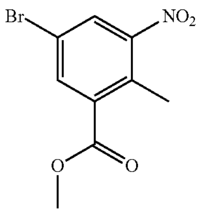

To a stirred solution of 5-bromo-2-methyl-3-nitrobenzoic acid (287 g, 1100 mmol) in DMF (150 mL), were added sodium carbonate (468 g, 4415 mmol) and methyl iodide (627 g, 4415 mmol). The mixture was heated at 60° C. for 8 h. The precipitate was filtered and washed with diethyl ether (5 times). The combined organic layers were dried, concentrated under reduced pressure giving the title compound (302 g, 99%) which was used directly without further purification.

Step 3: Synthesis of methyl 3-amino-5-bromo-2-methylbenzoate

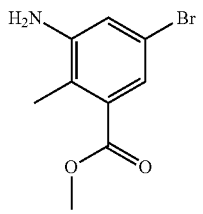

To a stirred solution of methyl 5-bromo-2-methyl-3-nitrobenzene (150 g, 544 mmol) in ethanol (750 mL), ammonium chloride (150 g, 2777 mmol) dissolved in water (750 mL) and iron powder (93.3 g, 1636 mmol) were added under stirring. The mixture was heated at 80° C. for 7 h. and filtered through celite.; The solids were washed with water and ethyl acetate and the combined filtrates were extracted with ethyl acetate. The combined organic layers were dried and concentrated under reduced pressure to give the title compound (175 g) which was used without further purification.

Step 4: Synthesis of methyl 5-bromo-2-methyl-3-((tetrahydro-2H-pyran-4-yl)amino)benzoate

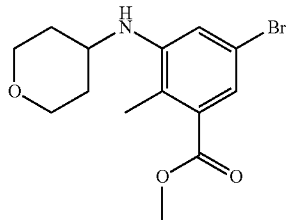 [SMILES: COC(=O)c1cc(Br)cc(NC2CCOCC2)c1C]

To a stirred solution of methyl 3-amino-5-bromo-2-methylbenzoate (15 g, 61 mmol) and dihydro-2H-pyran-4(3H)-one (9.2 g, 92 mmol) in dichloroethane (300 mL), acetic acid (22 g, 368.4 mmol) was added and the reaction stirred at room temperature for 2 h. Then sodium triacetoxyborohydride (39 g, 184 mmol) was added at 0° C. and the reaction stirred overnight at room temperature. The solvent was removed under reduced pressure and the crude material was purified by column chromatography to afford the title compound (14 g, 69%).

Step 5: Synthesis of methyl 5-bromo-3-(ethyl(tetrahydro-2H-pyran-4-yl)amino)-2-methylbenzoate

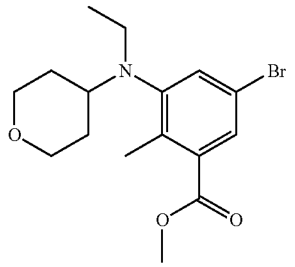 [SMILES: CCN(c1cc(Br)cc(C(=O)OC)c1C)C1CCOCC1]

To a stirred solution of methyl 5-bromo-2-methyl-3-((tetrahydro-2H-pyran-4-yl)amino)benzoate (14 g, 43 mmol) and acetaldehyde (3.75 g, 85 mmol) in dichloroethane (150 mL), was added acetic acid (15.4 g, 256 mmol) and the reaction stirred at room temperature for 20 minutes. Then sodium triacetoxyborohydride (27.0 g, 128 mmol) was added at 0° C. and the reaction stirred at room temperature for 2 h. The solvent was removed under reduced pressure and water added to the residue. Extraction was carried out using DCM and the combined organic layers were dried over sodium sulphate and concentrated under reduced pressure to give crude material was purified by column chromatography to afford the title compound (14 g, 93%).

Step 6: Synthesis of 5-bromo-N-((4,6-dimethyl-2-oxo-1,2-dihydropyridin-3-yl)methyl)-3-(ethyl(tetrahydro-2H-pyran-4-yl)amino)-2-methylbenzamide

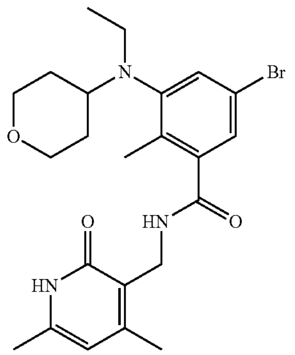 [SMILES: CCN(c1cc(Br)cc(C(=O)NCc2c(C)cc(C)[nH]c2=O)c1C)C1CCOCC1]

Aqueous NaOH (2.36 g, 59 mmol) was added to a solution of methyl 5-bromo-3-(ethyl(tetrahydro-2H-pyran-4-yl)amino)-2-methylbenzoate (14 g, 39 mmol) in ethanol (100 mL) and the mixture stirred at 60° C. for 1 h. The ethanol was removed under reduced pressure and the residue acidified using dilute HCl up to pH 6 and pH 4 was adjusted using citric acid. Extraction was carried out using ethyl acetate. The combined organic layers were dried and concentrated giving the respective acid (13.9 g).

The above acid (10 g, 29 mmol) was then dissolved in DMSO (25 mL) and 3-(amino methyl)-4,6-dimethylpyridin-2(1H)-one (8.8 g, 58 mmol) and triethyl amine (5.6 g, 58 mmol) was added. The reaction mixture was stirred at room temperature for 15 min before PYBOP (22 g, 43.8 mmol) was added and stirring was continued overnight. The mixture was poured into ice and extracted with 10% MeOH/DCM. The combined organic layers were dried and concentrated to obtain crude material which was purified by solvent washings to afford the title compound (14 g, 74%).

Step 7: Synthesis of N-((4,6-dimethyl-2-oxo-1,2-dihydropyridin-3-yl)methyl)-3-(ethyl(tetrahydro-2H-pyran-4-yl)amino)-2,5-dimethylbenzamide

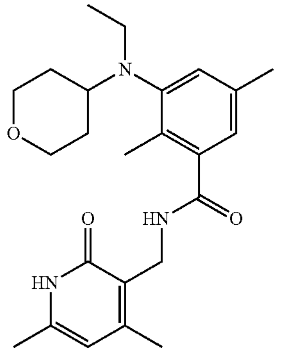 [SMILES: CCN(c1cc(C)cc(C(=O)NCc2c(C)cc(C)[nH]c2=O)c1C)C1CCOCC1]

To stirred solution of 5-bromo-N-((4,6-dimethyl-2-oxo-1,2-dihydropyridin-3-yl)methyl)-3-(ethyl(tetrahydro-2H-pyran-4-yl)amino)-2-methylbenzamide (0.30 g, 0.63 mmol) in DMF (2 mL), was added dichlorobis(triphenylphosphine) palladium (II) (0.028 g, 0.034 mmol) followed by tetramethyl tin (0.124 g, 0.69 mmol). The mixture was heated at 160° C. for 30 minutes in a microwave reactor. The reaction mass was quenched with water and extraction was carried out using 10% MeOH/DCM. The combined organic layers were dried and concentrated giving crude material. Purification by column chromatography and then by preparative HPLC gave the title compound as the corresponding TFA salt (0.15 g, 57.7%). LCMS: 412.15 $(M+1)^+$; HPLC: 94.29% (@ 254 nm) ($R_t$; 4.245; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (CD3OD, 400 MHz) δ 7.54 (s, 1H), 7.33 (s, 1H), 6.13 (s, 1H), 4.47 (s, 2H), 3.95-3.98 (m, 4H), 3.74 (bs, 2H), 3.37 (m, 1H), 2.42 (s, 3H), 2.38 (s, 3H), 2.37 (s, 3H), 2.24 (s, 3H), 1.61-1.91 (bs, 4H), 1.01 (t, 3H, J=3.2 Hz).

Compound 222: 5-chloro-N-((4,6-dimethyl-2-oxo-1,2-dihydropyridin-3-3-yl)methyl)-3-(((1s,4s)-4-(dimethylamino)cyclohexyl)(ethyl)amino)-2-methylbenzamide

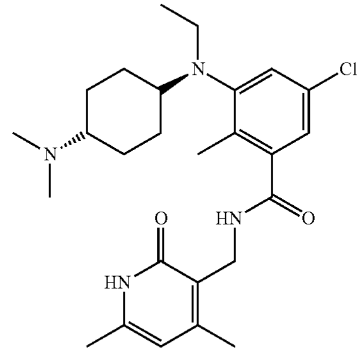

Step 1: Synthesis of methyl 3-(((1r,4r)-4-((tert-butoxycarbonyl)amino)cyclohexyl)amino)-5-chloro-2-methylbenzoate

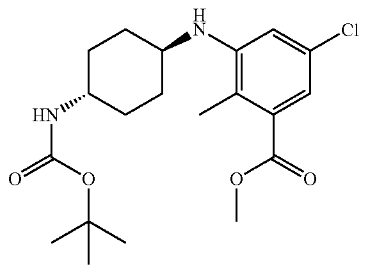 [SMILES: COC(=O)c1cc(Cl)cc(N[C@H]2CC[C@H](NC(=O)OC(C)(C)C)CC2)c1C]

To a stirred solution of methyl 3-amino-5-chloro-2-methyl benzoate (5.0 g, 25 mmol) and tert-butyl (4-oxocyclohexyl) carbamate (6.95 g, 32.6 mmol) in 25 ml of dichloroethane, was added acetic acid (9.0 mL, 450.75 mmol) at room temperature. The reaction mixture was cooled and sodium triacetoxyborohydride (22.8 g, 108 mmol) was added and the mixture stirred at room temperature overnight. The mixture was neutralized with sat. $NaHCO_3$ and extracted with DCM. The combined organic phases were dried over $Na_2SO_4$, concentrated under reduced pressure and the product isomers separated by silica gel (100-200) column chromatography to give the less polar as cis-isomer, methyl 3-(((1s,4s)-4-((tert-butoxycarbonyl)amino)cyclohexyl)amino)-5-chloro-2-methylbenzoate (5.2 g, 52%) and the more polar title compound trans-isomer, methyl 3-(((1r,4r)-4-((tert-butoxycarbonyl)amino)cyclohexyl)amino)-5-chloro-2-methylbenzoate (3.5 g, 35%).

Step 2: Synthesis of methyl 3-(((1r,4r)-4-((tert-butoxycarbonyl)amino)cyclohexyl)(ethyl)amino)-5-chloro-2-methylbenzoate

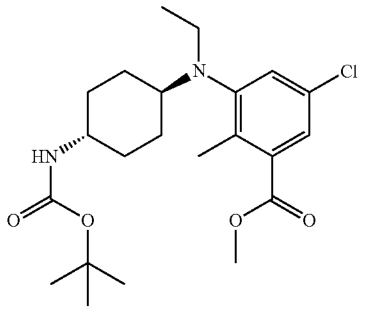 [SMILES: CCN(c1cc(Cl)cc(C(=O)OC)c1C)[C@H]1CC[C@H](NC(=O)OC(C)(C)C)CC1]

To a stirred solution of methyl 3-(((1r,4r)-4-((tert-butoxycarbonyl)amino)cyclohexyl)amino)-5-chloro-2-methylbenzoate (3.0 g, 7.6 mmol) and acetaldehyde (0.66 g, 15 mmol) in 15 ml of dichloroethane, was added acetic acid (2.72 mL, 45.45 mmol) and the mixture stirred at room temperature for 20 minutes. The reaction mixture was cooled to 0° C. and sodium triacetoxyborohydride (4.81 g, 22.72 mmol) was added and the mixture stirred at room temperature overnight. The reaction mixture was neutralized with sat. $NaHCO_3$ extracted with DCM. The combined organic phases were dried over $Na_2SO_4$, concentrated under reduced pressure and the crude material purified by silica gel (100-200) column chromatography to yield the title compound (3.5 g, 96%).

Step 3: Synthesis of tert-butyl((1r,rs)-4-(5-chloro-3-(((4,6-dimethyl-2-oxo-1,2-dihydropyridin-3-yl)methyl)carbamoyl)-2-methylphenyl)(ethyl)amino)cyclohexyl)carbamate

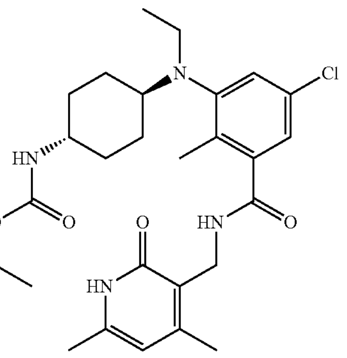

A mixture of methyl 3-(((1r,4r)-4-((tert-butoxycarbonyl)amino)cyclohexyl)(ethyl)amino)-5-chloro-2-methylbenzoate (3.5 g, 8.2 mmol) and NaOH (0.49 g, 12 mmol) in 20 ml of ethanol:water (4:1) was heated at 70° C. for 2 h. The reaction mixture was cooled to 0° C. and acidified to pH 6 by using 1N HCl. The mixture was concentrated and the residue partitioned between water and ethyl acetate. The organic layer was dried over $Na_2SO_4$ and concentrated under reduced pressure to afford 3.2 g of crude acid. A mixture of the crude acid (3.2 g, 7.8 mmol), 3-(aminomethyl)-4,6-dimethylpyridin-2(1H)-one (2.36 mg, 15.5 mmol) and PyBOP (6.07 mg, 11.7 mmol) was stirred in 15 ml of DMSO at room temperature overnight. The reaction mixture was diluted with water and extracted with 10% MeOH in DCM. The organic layer was dried over $Na_2SO_4$, concentrated under reduced pressure and the residue purified by silica gel (100-200) column chromatography to give the title compound (3.0 g, 71%).

Step 4: Synthesis of 3-(((1r,4r)-4-aminocyclohexyl)(ethyl)amino)-5-chloro-N-((4,6-dimethyl-2-oxo-1,2-dihydropyridin-3-yl)methyl)-2-methylbenzamide

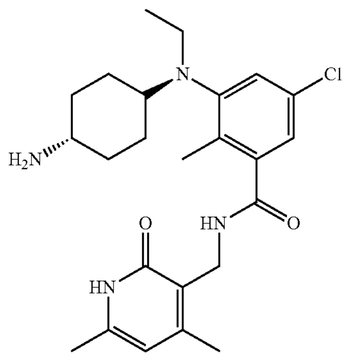

To a cooled solution of tert-butyl((1r,4r)-4-((5-chloro-3-(((4,6-dimethyl-2-oxo-1,2-dihydropyridin-3-yl)methyl)carbamoyl)-2-methylphenyl)(ethyl)amino)cyclohexyl)carbamate (400 mg, 0.73 mmol) in 5 ml of DCM, 2 ml of TFA was added and the reaction mixture stirred at room temperature for 2 h. The reaction mixture was concentrated to dryness under reduced pressure. The crude product was dissolved in 10% MeOH in DCM and washed with sat $NaHCO_3$, water and brine. The organic phase was dried over $Na_2SO_4$, concentrated under reduced pressure to afford the title compound (320 mg, 98%).

Step 5: Synthesis of 5-chloro-N-((4,6-dimethyl-2-oxo-1,2-dihydropyridin-3-yl)methyl)-3-(((1r,4r)-4-(dimethylamino)cyclohexyl)(ethyl)amino)-2-methylbenzamide

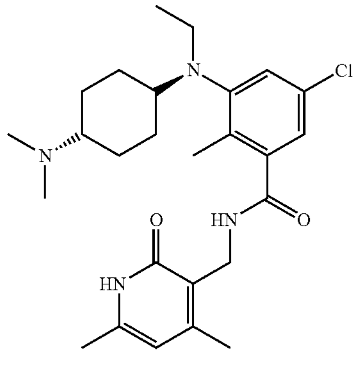

To a stirred solution of 3-(((1r,4r)-4-aminocyclohexyl)(ethyl)amino)-5-chloro-N-((4,6-dimethyl-2-oxo-1,2-dihydropyridin-3-yl)methyl)-2-methylbenzamide (300 mg, 0.67 mmol) and formaldehyde (0.5 ml of 38% solution, 6.75 mmol) in 3 ml of methanol, sodium triacetoxyborohydride (83.0 mg, 1.35 mmol) was added at 0° C. and the mixture stirred at room temperature for 3 h. The reaction mixture was concentrated to dryness and partitioned between water and 10% MeOH in DCM. The organic layer was dried over $Na_2SO_4$, concentrated under reduced pressure and the crude material was purified over basic alumina to yield the title compound (120 mg, 32%).

Compound 268: N-((4,6-dimethyl-2-oxo-1,2-dihydropyridin-3-yl)methyl)-3-(((1r,4r)-4-(dimethylamino)cyclohexyl)(ethyl)amino)-2-methylbenzamide

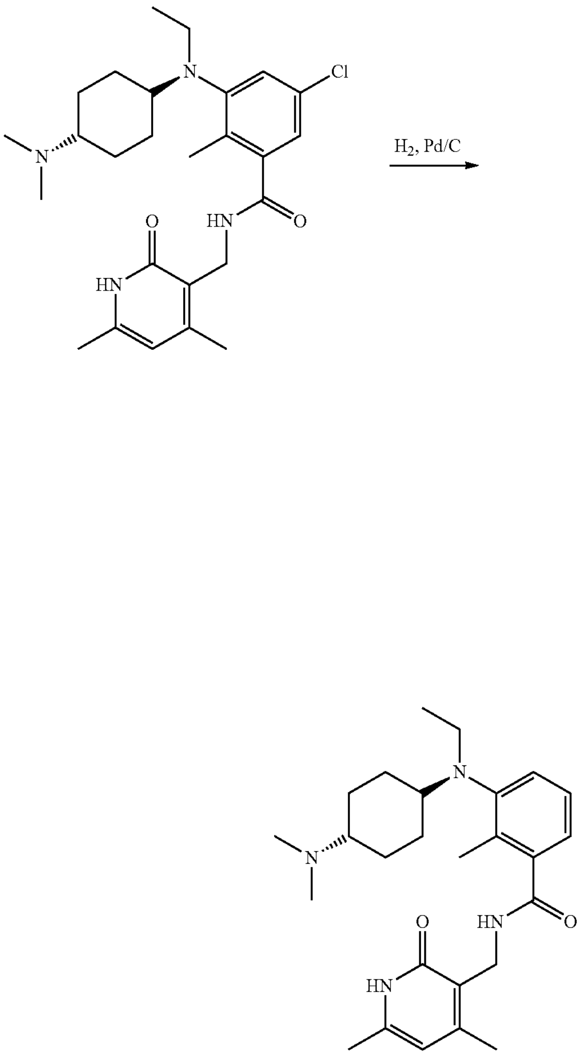

To a solution of 5-chloro-N-((4,6-dimethyl-2-oxo-1,2-dihydropyridin-3-yl)methyl)-3-(((1r,4r)-4-(dimethylamino)cyclohexyl)(ethyl)amino)-2-methylbenzamide (80 mg, 0.16 mmol) in 5 mL of methanol, was added a catalytic amount of 10% palladium on carbon. The mixture was stirred under hydrogen atmosphere at balloon pressure for 13 h. The reaction mixture was filtered through a bed of celite, concentrated under reduced pressure to a viscous oil which on ether washing afforded the title compound (40 mg, 54%) as an off-white solid.

LCMS: 439.25 $(M+1)^+$; HPLC: 88.61% (@ 254 nm) ($R_t$ 4.084; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.46 (bs, 1H), 8.03 (t, 1H), 7.15-7.13 m, 2H), 6.94 (d, 1H), 4.26 (d, 2H, J=4.4 Hz), 3.02 (d, 2H, J=6.8 Hz), 2.61 (s, 6H), 2.18 (s 6H), 2.10 (s, 3H), 1.97-1.83 (m, 4H), 1.39 (m, 4H), 0.8 (t, 3H, J=6.8 Hz), (3H merged in solvent peak).

Compound 273: 5-chloro-3-(((1s,4s)-4-(diethylamino)cyclohexyl)(ethyl)amino)-N-((4,6-dimethyl-2-oxo-1,2-dihydropyridin-3-yl)methyl)-2-methylbenzamide

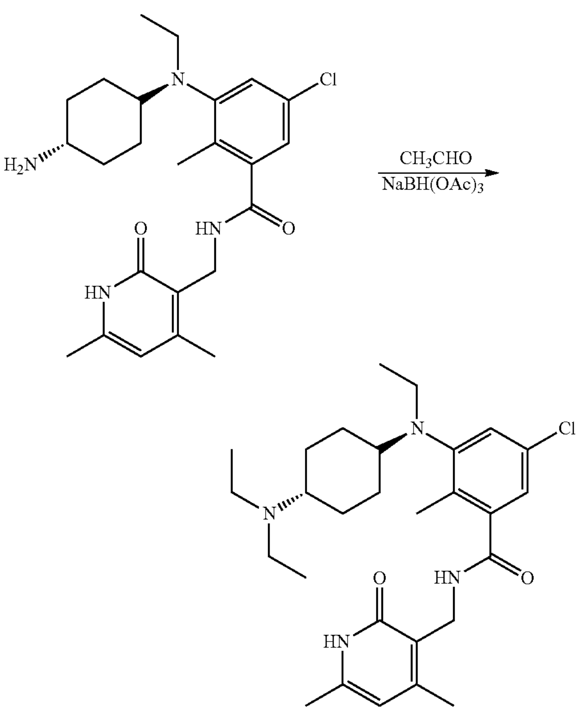

To a stirred solution of 3-(((1r,4r)-4-aminocyclohexyl)(ethyl)amino)-5-chloro-N-((4,6-dimethyl-2-oxo-1,2-dihydropyridin-3-yl)methyl)-2-methylbenzamide (150 mg, 0.33 mmol) and acetaldehyde (0.15 ml, 2.70 mmol) in 5 ml of dichloroethane, acetic acid (0.14 mL, 2.36 mmol) was added and the mixture stirred at room temperature for 20 minutes. The reaction mixture was cooled to 0° C. and sodium triacetoxyborohydride (286 mg, 1.35 mmol) was added and the mixture stirred at room temperature overnight. The reaction mixture was neutralized with sat. $NaHCO_3$ and extracted with DCM, dried over $Na_2SO_4$ and concentrated under reduced pressure to a residue. Purification by prep. HPLC gave the title compound (100 mg, 59%). LCMS: 501.50 $(M+1)^+$; HPLC: 93.90% (@ 210-370 nm) ($R_t$; 4.543; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.45 (bs, 1H), 8.21 (t, 1H), 7.13 (s, 1H), 6.92 (s, 1H), 5.85 (s, 1H), 4.25 (d, 2H, J=3.6 Hz), 3.03-3.01 (m, 2H), 2.67-2.61 (m, 2H), 2.42-2.33 (m, 4H), 2.19 (s, 3H), 2.14 (s, 3H), 2.11 (s, 3H), 1.73 (m, 4H), 1.39-1.19 (m, 4H), 0.92 (m, 6H), 0.78 (t, 3H).

Compound 277: N-((4,6-dimethyl-2-oxo-1,2-dihydropyridin-3-yl)methyl)-3-(((1r,4r)-4-(dimethylamino)cyclohexyl)(ethyl)amino)-5-ethynyl-2-methylbenzamide

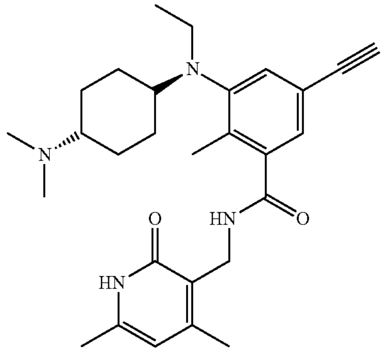

Step 1: Synthesis of methyl 5-bromo-3-(((1r,4r)-4-((tert-butoxycarbonyl)amino)cyclohexyl)(ethyl)amino)-2-methylbenzoate

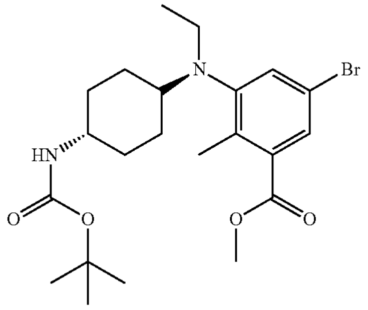

To a stirred solution of methyl 5-bromo-3-(((1r,4r)-4-((tert-butoxycarbonyl)amino)cyclohexyl)amino)-2-methylbenzoate 6.0 g, 13.0 mmol) and acetaldehyde (1.5 ml, 27.0 mmol) in dichloroethane (60 mL), was added acetic acid (5.4 ml, 82 mmol) and the mixture was stirred at room temperature for 20 minutes. Sodium triacetoxyborohydride (8.6 g, 41 mmol) was added at 0° C. and the mixture stirred at room temperature for 2 h. The reaction mixture was neutralized with sat. $NaHCO_3$ and was extracted with DCM. The combined organic phases were dried over $Na_2SO_4$ and concentrated under reduced pressure. The crude material was purified by silica gel (100-200) column chromatography to afford the title compound (5.0 g, 79%).

Steps 2 and 3: Synthesis of methyl 3-(((1r,4r)-4-((tert-butoxycarbonyl)amino)cyclohexyl)(ethyl)amino)-5-ethynyl-2-methylbenzoate

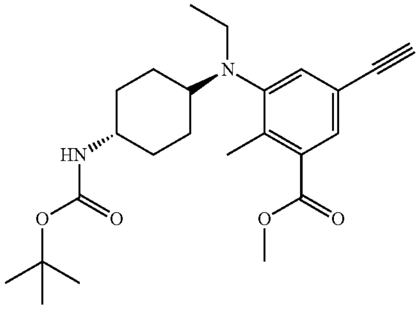

A solution of methyl 5-bromo-3-(((1r,4r)-4-((tert-butoxycarbonyl)amino)cyclohexyl)(ethyl)amino)-2-methylbenzoate (1.5 g, 3.20 mmol), trimethylsilyl acetylene (0.52 ml, 3.84 mmol), copper iodide (12 mg, 0.06 mmol) and N,N-diisopropyl amine (1.0 ml, 8.38 mmol) in 20 ml of toluene was purged with argon. Dichloro-bis(triphenyl phosphine) palladium (II) (44 mg, 0.06 mmol) was added the reaction mixture heated at 80° C. for 16 h. The reaction mixture was cooled to room temperature, diluted with ethyl acetate and washed with water. The organic layer was dried over $Na_2SO_4$ and concentrated under reduced pressure to obtain 1.8 g of crude silyl protected compound. This was dissolved in 15 ml of THF and tetra-butylammonium fluoride (7.5 ml of 1M solution in THF, 7.40 mmol) was added at room temperature. The mixture stirred for 2 h, diluted with ethyl acetate and washed with water. The organic layer was dried over $Na_2SO_4$, concentrated under reduced pressure, and the residue purified by silica gel (100-200) column chromatography to give the title compound (800 mg, 52%).

Steps 4 and 5: Synthesis of tert-butyl ((1r,4r)-4-((3-(((4,6-dimethyl-2-oxo-1,2-dihydropyridin-3-yl)methyl)carbamoyl)-5-ethynyl-2-methylphenyl)(ethyl)amino)cyclohexyl)carbamate

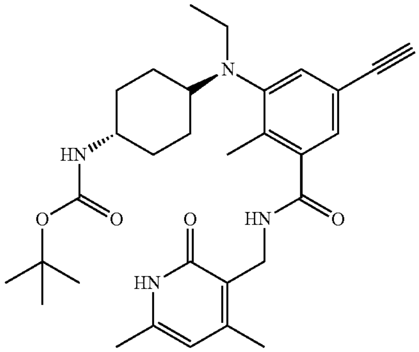

A mixture of methyl 3-(((1r,4r)-4-((tert-butoxycarbonyl)amino)cyclohexyl)(ethyl)amino)-5-ethynyl-2-methylbenzoate (800 mg, 1.92 mmol) and NaOH (115 mg, 2.89 mmol) in 12 ml of ethanol:water (3:1) was heated at 70° C. for 2 h. The reaction mixture was concentrated to dryness and the residue was partitioned between water and DCM. The organic layer was dried over $Na_2SO_4$ and concentrated under reduced pressure to afford 700 mg of the crude acid. The crude acid (700 mg, 1.75 mmol), 3-(aminomethyl)-4,6-dimethylpyridin-2(1H)-one (532 mg, 3.5 mmol) and PyBOP (1.36 g, 2.6: mmol) were stirred in 7 ml of DMSO at room temperature overnight. The reaction mixture was diluted with water, and the precipitated product was filtered and purified by silica gel column chromatography to give the title compound (750 mg, 80%).

Step 6: Synthesis of 3-(((1r,4r)-4-aminocyclohexyl)(ethyl)amino)-N-((4,6-dimethyl-2-oxo-1,2-dihydropyridin-3-yl)methyl)-5-ethynyl-2-methylbenzamide

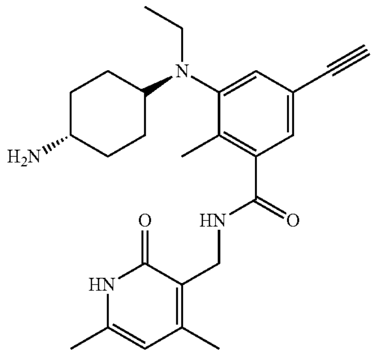

To a cooled solution of tert-butyl ((1r,4r)-4-((3-(((4,6-dimethyl-2-oxo-1,2-dihydropyridin-3-yl)methyl)carbamoyl)-5-ethynyl-2-methylphenyl)(ethyl)amino)cyclohexyl)carbamate (750 mg, 1.40 mmol) in 10 ml of DCM, was added 3 ml of TFA The mixture was stirred at rt for 2 h and was concentrated to dryness under reduced pressure. The residue was dissolved in 10% MeOH in DCM an washed with sat $NaHCO_3$, water and brine. The organic phase was dried over $Na_2SO_4$ and concentrated under reduced pressure to give the crude title compound (600 mg, 98%).

Step 7: Synthesis of N-((4,6-dimethyl-2-oxo-1,2-dihydropyridin-3-yl)methyl)-3-(((1r,4r)-4-(dimethylamino)cyclohexyl)(ethyl)amino)-5-ethynyl-2-methylbenzamide

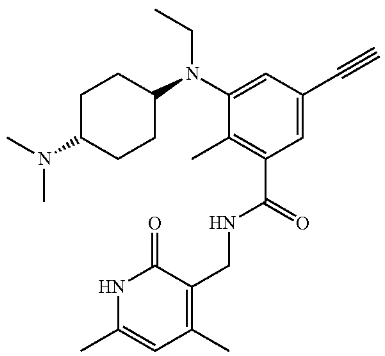

To a stirred solution of crude 3-(((1r,4r)-4-aminocyclohexyl)(ethyl)amino)-N-((4,6-dimethyl-2-oxo-1,2-dihydropyridin-3-yl)methyl)-5-ethynyl-2-methylbenzamide (600 mg, 1.38 mmol) and formaldehyde (0.4 ml of 38% solution, 6.75 mmol) in 10 ml of dichloroethane was added sodium triacetoxyborohydride (731 mg, 3.45 mmol) at 0° C. The reaction mixture was stirred at room temperature for 3 h and partitioned between water and 10% MeOH in DCM The organic layer was separated, dried over $Na_2SO_4$ and concentrated under reduced pressure. The residue was purified over basic alumina to give the title compound (450 mg, 70%).

Analytical Data for N-((4,6-dimethyl-2-oxo-1,2-dihydropyridin-3-yl)methyl)-3-(((1r,4r)-4-(dimethylamino)cyclohexyl)(ethyl)amino)-5-ethynyl-2-methylbenzamide-TFA salt: LCMS: 463.65 $(M+1)^+$; HPLC: 92.65% (@ 254 nm) ($R_t$; 4.748; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-$d_6$, 400 MHz) δ 11.46 (bs, 9.43 (bs, 1H), 8.23 (t, 1H), 7.36 (s, 1H), 7.12 (s, 1H), 5.87 (s, 1H), 4.26 (d, 2H, J=4.0 Hz), 3.17-3.03 (m, 4H), 2.69-2.68 (m, 6H), 2.50 (1H merged in solvent peak), 2.21 (s, 3H), 2.19 (s, 3H), 2.11 (s, 3H), 1.96-1.84 (m, 4H), 1.43 (m, 4H), 0.79 (t, 3H).

Compound 278: 5-cyano-N-((4,6-dimethyl-2-oxo-1,2-dihydropyridin-3-yl)methyl)-3-(((1r,4r)-4-(dimethylamino)cyclohexyl)(ethyl)amino)-2-methylbenzamide

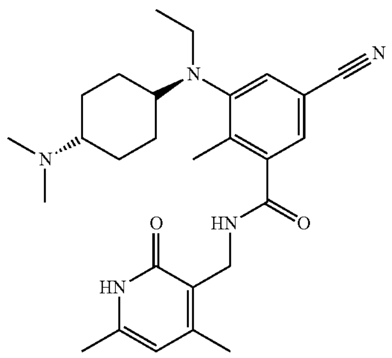

Step 1: Synthesis of methyl 3-(((1s,4s)-4-((tert-butoxycarbonyl)amino)cyclohexyl)(ethyl)amino)-5-cyano-2-methylbenzoate

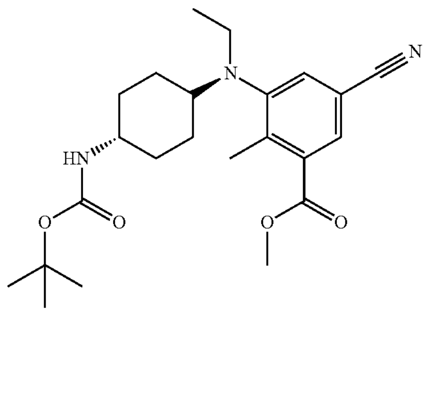

A solution of compound methyl 5-bromo-3-(((1r,4r)-4-((tert-butoxycarbonyl)amino)cyclohexyl)(ethyl)amino)-2-methylbenzoate (1.0 gm, 2.13 mmol) and $Zn(CN)_2$ (370 mg, 3.19 mmol) in 6 ml of DMF was degassed with argon for 20 min followed by addition of $Pd(PPh_3)_4$ (240 mg, 0.21 mmol). The mixture was heated at 100° C. overnight, diluted with water and was extracted with ethyl acetate. The combined organic layers were dried over $Na_2SO_4$, concentrated and the residue purified by silica gel column chromatography to give the title compound (280 mg, 82%).

Steps 2 and 3: Synthesis of tert-butyl ((1r,4r)-4-((5-cyano-3-(((4,6-dimethyl-2-oxo-1,2-dihydropyridin-3-yl)methyl)carbamoyl)-2-methylphenyl)(ethyl)amino)cyclohexyl)carbamate

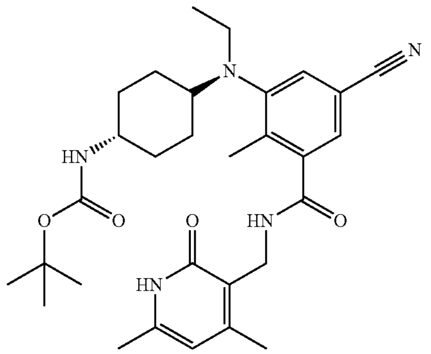

A mixture of methyl 3-(((1r,4r)-4-((tert-butoxycarbonyl)amino)cyclohexyl)(ethyl)amino)-5-cyano-2-methylbenzoate (735 mg, 1.78 mmol) and NaOH (85 mg, 2.13 mmol) in 12 ml of ethanol:water (3:1) was heated at 70° C. for 2 h. The mixture was concentrated to dryness and the crude product was partitioned between water and DCM. The organic layer was dried over $Na_2SO_4$ and concentrated under reduced pressure to afford 380 mg of crude acid. A mixture of the crude acid (380 mg, 0.94 mmol), 3-(aminomethyl)-4,6-dimethylpyridin-2(1H)-one (287 mg, 1.89 mmol) and PyBOP (737 mg, 1.41 mmol) in 4 ml of DMSO was stirred at room temperature overnight. The reaction mixture was diluted with water and was extracted with 10% MeOH in DCM. The combined organic phases were dried over Na2SO4, concentrated under reduced pressure and the residue purified by silica column chromatography to afford the title compound (350 mg, 75%).

Step 4: Synthesis of 3-(((1r,4r)-4-aminocyclohexyl)(ethyl)amino)-5-cyano-N-((4,6-dimethyl-2-oxo-1,2-dihydropyridin-3-yl)methyl)-2-methylbenzamide

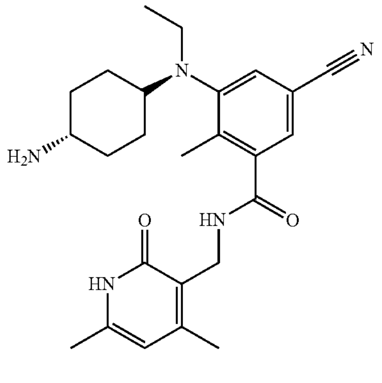

To a cooled solution of compound tert-butyl ((1r,4r)-4-((5-cyano-3-(((4,6-dimethyl-2-oxo-1,2-dihydropyridin-3-yl) methyl)carbamoyl)-2-methylphenyl)(ethyl)amino)cyclohexyl)carbamate (350 mg, 0.80 mmol) in 5 ml of DCM, was added 1 ml of TFA. The mixture was stirred at rt for 2 h. and concentrated to dryness under reduced pressure. The residue was dissolved in 10% MeOH in DCM and washed with sat $NaHCO_3$, water and brine. The organic phase was dried over $Na_2SO_4$, and concentrated under reduced pressure to obtain 284 mg of the crude title compound.

Step 5: Synthesis of 5-cyano-N-((4,6-dimethyl-2-oxo-1,2-dihydropyridin-3-yl)methyl)-3-(((1r,4r)-4-(dimethylamino)cyclohexyl)(ethyl)amino)-2-methylbenzamide

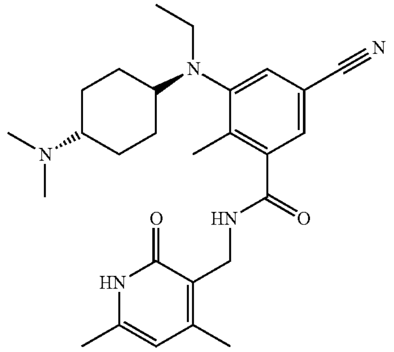

To a stirred solution of crude 3-(((1r,4r)-4-aminocyclohexyl)(ethyl)amino)-5-cyano-N-((4,6-dimethyl-2-oxo-1,2-dihydropyridin-3-yl)methyl)-2-methylbenzamide (325 mg, 0.74 mmol) and formaldehyde (0.3 ml of 38% solution, 3.72 mmol) in 10 ml of methanol, sodium cyanoborohydride (100 mg, 1.49 mmol) was added at 0° C. The mixture was stirred at room temperature for 4 h and partitioned between water and 10% MeOH in DCM. The organic layer was dried over $Na_2SO_4$, concentrated under reduced pressure and the residue was purified by basic alumina column purification to give the title compound (75 mg, 22%).

Analytical Data of 5-cyano-N-((4,6-dimethyl-2-oxo-1,2-dihydropyridin-3-yl)methyl)-3-(((1s,4s)-4-(dimethylamino) cyclohexyl)(ethyl)amino)-2-methylbenzamide: LCMS: 464.30 $(M+1)^+$; HPLC: 87.24% (@ 254 nm) ($R_t$; 4.540; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-$d_6$, 400 MHz) δ 11.47 (bs, 1H), 8.31 (t, 1H), 7.61 (s, 1H), 7.35 (s, 1H), 5.87 (s, 1H), 4.26 (d, 2H, J=4.4 Hz), 3.07-3.05 (m, 3H), 2.73-2.63 (m, 7H), 2.25 (s, 3H), 2.20 (s, 3H), 2.11 (s, 3H), 1.96-1.82 (m, 4H), 1.41-1.37 (m, 4H), 0.78 (t, 3H).

Compound 279: 5-chloro-N-((4,6-dimethyl-2-oxo-1,2-dihydropyridin-3-yl)methyl)-3-(ethyl((1r,4r)-4-(methyl(tetrahydro-2H-pyran-4-yl)amino)cyclohexyl)amino)-2-methylbenzamide

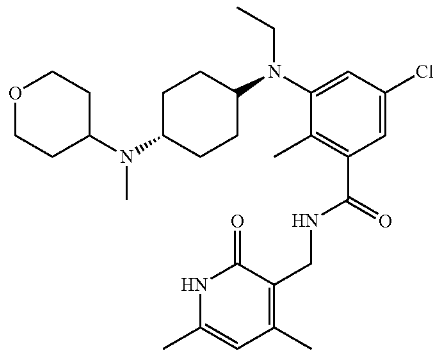

Step 1: Synthesis of 5-chloro-N-((4,6-dimethyl-2-oxo-1,2-dihydropyridin-3-yl)methyl)-3-(ethyl((1r,4r)-4-(methyl(tetrahydro-2H-pyran-4-yl)amino)cyclohexyl)amino)-2-methylbenzamide

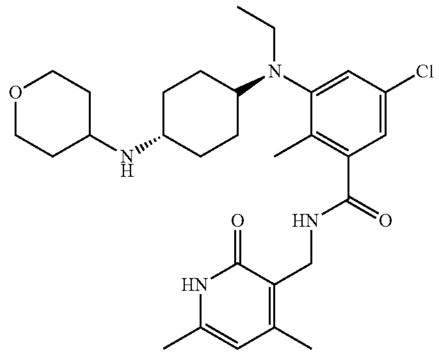

To a stirred solution of 3-(((1r,4r)-4-aminocyclohexyl) (ethyl)amino)-5-chloro-N-((4,6-dimethyl-2-oxo-1,2-dihydropyridin-3-yl)methyl)-2-methylbenzamide (300 mg, 0.67 mmol) and dihydro-2H-pyran-4(3H)-one (99 mg, 1.01 mmol) in 5 ml of dichloroethane, was added acetic acid (0.24 mL, 4.05 mmol) and the mixture stirred at room temperature for 20 minutes. The mixture was cooled to 0° C. and sodium triacetoxyborohydride (429 mg, 2.02 mmol) was added and the reaction stirred at room temperature overnight. The reaction mixture was neutralized with sat. $NaHCO_3$ and extracted with DCM. The combined organic phases were dried over $Na_2SO_4$, concentrated under reduced pressure and the residue purified by silica gel column chromatography to give the title compound (175 mg, 57%).

Step 2: Synthesis of 5-chloro-N-((4,6-dimethyl-2-oxo-1,2-dihydropyridin-3-yl)methyl)-3-(ethyl((1r,4r)-4-(methyl(tetrahydro-2H-pyran-4-yl)amino)cyclohexyl)amino)-2-methylbenzamide

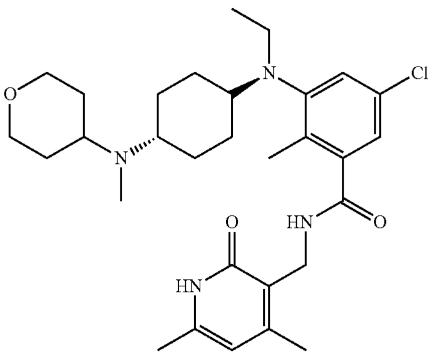

To a stirred solution of 5-chloro-N-((4,6-dimethyl-2-oxo-1,2-dihydropyridin-3-yl)methyl)-3-(ethyl((1r,4r)-4-((tetrahydro-2H-pyran-4-yl)amino)cyclohexyl)amino)-2-methylbenzamide (175 mg, 0.33 mmol) and formalin (99 mg, 3.31 mmol) in 2 ml of methanol was added sodium cyanoborohydride (41 mg, 0.66 mmol) at 0° C. The mixture was stirred at room temperature overnight, neutralized with sat. $NaHCO_3$ and extracted with DCM. The combined organic phases were dried over $Na_2SO_4$, concentrated under reduced pressure and the residue purified by preparative HPLC to afford the title compound (70 mg, 39%).

LCMS: 543.65 $(M+1)^+$; HPLC: 98.19% (@ 210-370 nm) ($R_t$; 4.515; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.45 (bs, 1H), 8.21 (t, 1H), 7.13 (s, 1H), 6.92 (s, 1H), 5.85 (s, 1H), 4.25 (d, 2H, J=4 Hz), 3.84-3.82 (m, 2H), 3.26-3.23 (m, 3H), 3.03-3.01 (m, 2H), 2.67-2.53 (m, 2H), 2.19 (s, 3H), 2.14 (s, 3H), 2.11 (s, 6H), 1.75-1.57 (m, 6H), 1.41-1.24 (m, 6H), 0.78 (t, 3H).

Compound 276: Synthesis of compound 5-bromo-N-((4,6-dimethyl-2-oxo-1,2-dihydropyridin-3-yl)methyl)-3-(((1r,4r)-4-(dimethylamino)cyclohexyl)(ethyl)amino)-2-methylbenzamide

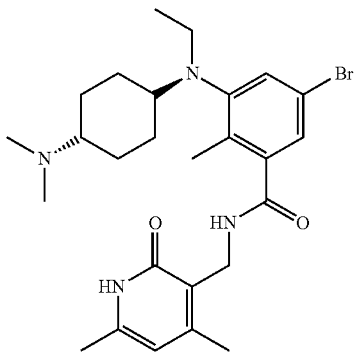

Step 1: Synthesis of 5-bromo-2-methyl-3-nitrobenzoic acid

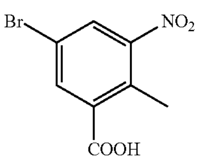

To stirred solution of compound 2-methyl-3-nitrobenzoic acid (50.0 g, 276 mmol) in conc. $H_2SO_4$ (200 mL), 1,3-dibromo-5,5-dimethyl-2,4-imidazolidinedione (43.4 g, 152 mmol) was added portionwise at room temperature and stirring was continued for 5 h. On completion, the reaction mass was poured on ice cold water, the solid precipitate was filtered, washed with water and dried under vacuum giving the crude title compound (71.7 g, 99.9%) which was used without further purification.

Step 2: Synthesis of methyl 5-bromo-2-methyl-3-nitrobenzoate

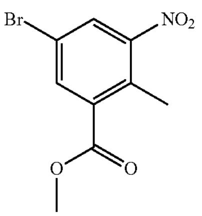

To a stirred solution of crude 5-bromo-2-methyl-3-nitrobenzoic acid (287 g, 1103 mmol) in DMF (150 mL), sodium carbonate (468 g, 4415 mmol) and methyl iodide (626 g, 4415 mmol) were added. The mixture was heated at 60° C. for 8 h, cooled to room temperature. The solid precipitate was filtered and washed with diethyl ether (5 times). The combined organic layers were dried and concentrated under reduced pressure to give the title compound (302 g, 99%) which was used directly.

Step 3: Synthesis of methyl 3-amino-5-bromo-2-methylbenzoate

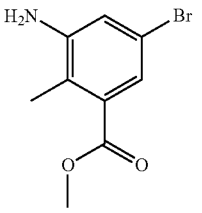

To a stirred solution of above crude compound methyl 5-bromo-2-methyl-3-nitrobenzoate (150 g, 0.54 mol) in ethanol (750 mL), ammonium chloride (150 g, 2.78 mol) dissolved in 750 ml of water was added followed by iron powder (93.3 g, 1.64 mol) with vigorous stirring. The mixture was heated at 80° C. for 7 hand filtered through celite. The filter pad was washed with water and ethyl acetate and the filtrates were extracted with ethyl acetate. The combined organic layers were dried over $Na_2SO_4$ and concentrated under reduced pressure to give the title compound (175 g crude).

Step 4: Synthesis of methyl 5-bromo-3-(((1r,4r)-4-((tert-butoxycarbonyl)amino)cyclohexyl)amino)-2-methylbenzoate

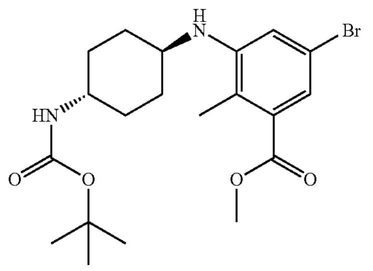 [SMILES: COC(=O)c1cc(Br)cc(N[C@H]2CC[C@H](NC(=O)OC(C)(C)C)CC2)c1C]

To a stirred solution of crude compound methyl 3-amino-5-bromo-2-methylbenzoate (15 g, 62 mmol) and tert-butyl (4-oxocyclohexyl)carbamate (17 g, 8 mmol) in dichloroethane (200 mL), was added acetic acid (23 ml, 368 mmol) and the reaction stirred at room temperature for 10 min. Sodium triacetoxyborohydride (40 g, 185 mmol) was added at 0° C. and the mixture stirred at room temperature for overnight. The reaction mixture was neutralized with sat. $NaHCO_3$ and extracted with DCM. The combined organic phases were dried over $Na_2SO_4$, and concentrated under reduced pressure. Separation by column chromatography of the crude isomeric mixture gave desired the title compound (6.0 g, 22%).

Step 5: Synthesis of methyl 5-bromo-3-(((1r,4r)-4-((tert-butoxycarbonyl)amino)cyclohexyl)(ethyl)amino)-2-methylbenzoate

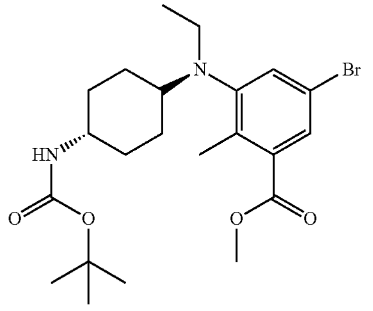

To a stirred solution of compound methyl 5-bromo-3-(((1r,4r)-4-((tert-butoxycarbonyl)amino)cyclohexyl)amino)-2-methylbenzoate (6.0 g, 13.0 mmol) and acetaldehyde (1.5 ml, 27.0 mmol) in dichloroethane (60 mL) was added acetic acid (5.4 ml, 82 mmol) and the mixture was stirred at room temperature for 20 minutes. Sodium triacetoxyborohydride (8.6 g, 40.9 mmol) was added at 0° C. and the mixture stirred at room temperature for 2 h. The reaction mixture was neutralized with sat. $NaHCO_3$ and extracted with DCM. The combined organic phases were dried over $Na_2SO_4$ and concentrated under reduced pressure. The crude material was purified by silica gel column chromatography to afford the title compound (5.0 g, 79%).

Steps 6 and 7: Synthesis of tert-butyl ((1r,4r)-4-((5-bromo-3-(((4,6-dimethyl-2-oxo-1,2-dihydropyridin-3-yl)methyl)carbamoyl)-2-methylphenyl)(ethyl)amino)cyclohexyl)carbamate

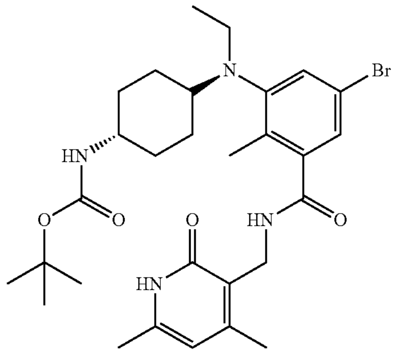

A mixture of methyl 5-bromo-3-(((1r,4r)-4-((tert-butoxycarbonyl)amino)cyclohexyl)(ethyl)amino)-2-methylbenzoate (1.00 g, 2.13 mmol) and NaOH (102 mg, 2.56 mmol) in 6 ml of ethanol:water (2:1) was heated at 70° C. for 2 h. The reaction mixture was concentrated to dryness and the residue was partitioned between water and DCM. The organic layer was dried over $Na_2SO_4$ and concentrated under reduced pressure to afford 1.0 g of crude acid. The crude acid (1.0 g, 2.20 mmol), 3-(aminomethyl)-4,6-dimethylpyridin-2(1H)-one (669 mg, 4.40 mmol), PyBOP (1.71 g, 3.30 mmol) and 1 ml of triethyl amine were stirred in 2 ml of DMSO at room temperature overnight. The reaction mixture was diluted with water and extracted with DCM. The combined organic layers were dried over $Na_2SO_4$, concentrated under reduced pressure and the residue purified by silica gel column chromatography to give the title compound (1.0 g, 83%).

Step 8: Synthesis of 3-(((1r,4r)-4-aminocyclohexyl)(ethyl)amino)-5-bromo-N-((4,6-dimethyl-2-oxo-1,2-dihydropyridin-3-yl)methyl)-2-methylbenzamide

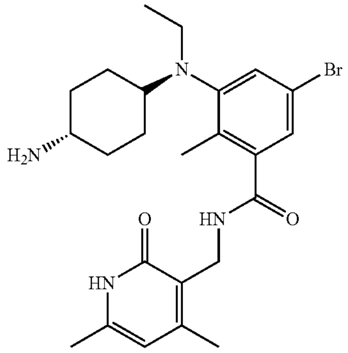

To a cooled solution of compound tert-butyl ((1r,4r)-4-((5-bromo-3-(((4,6-dimethyl-2-oxo-1,2-dihydropyridin-3-yl)methyl)carbamoyl)-2-methylphenyl)(ethyl)amino)cyclohexyl)carbamate (1.0 g, 1.60 mmol) in 10 ml of DCM, was added 2 ml of TFA. The reaction mixture was stirred at rt for 2 h, and concentrated to dryness under reduced pressure. The residue was dissolved in 10% MeOH in DCM and washed with sat $NaHCO_3$, water and brine. The organic phase was dried over $Na_2SO_4$ and concentrated under reduced pressure to give the crude title compound (650 mg, 81%).

Step 9: Synthesis of 5-bromo-N-((4,6-dimethyl-2-oxo-1,2-dihydropyridin-3-yl)methyl)-3-(((1r,4r)-4-(dimethylamino)cyclohexyl)(ethyl)amino)-2-methylbenzamide

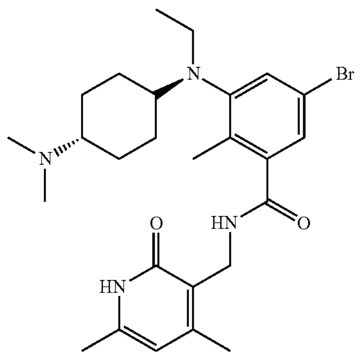

To a stirred solution of crude 3-(((1r,4r)-4-aminocyclohexyl)(ethyl)amino)-5-bromo-N-((4,6-dimethyl-2-oxo-1,2-dihydropyridin-3-yl)methyl)-2-methylbenzamide (650 mg, 1.32 mmol) and formaldehyde (0.5 ml of 38% solution, 13.3 mmol) in 10 ml of methanol, was added sodium cyanoborohydride (82 mg, 1.32 mmol at 0° C. and the mixture stirred at room temperature overnight. The reaction mixture was partitioned between water and 10% MeOH in DCM. The organic layer was dried over $Na_2SO_4$ and concentrated under reduced pressure. The residue was purified by basic alumina column purification to give the title compound (450 mg, 65%). Analytical data of 5-bromo-N-((4,6-dimethyl-2-oxo-1,2-dihydropyridin-3-yl)methyl)-3-(((1r,4r)-4-(dimethylamino)cyclohexyl)(ethyl)amino)-2-methylbenzamide: LCMS: 519.30 $(M+1)^+$; HPLC: 98.35% (@ 254 nm) ($R_t$; 4.392); Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.46 (bs, 1H), 9.39 (bs, 1H), 8.23 (t, 1H), 7.30 (s, 1H), 7.09 (s, 1H), 5.86 (s, 1H), 4.25 (d, 2H, J=4.0 Hz), 3.03-3.01 (m, 3H), 2.69-2.69 (m, 6H), 2.50 (1H merged in solvent peak), 2.18 (s, 3H), 2.14 (s, 3H), 2.11 (s, 3H), 1.94-1.84 (m, 4H), 1.42 (m, 4H), 0.79 (t, 3H, J=6.8 Hz).

Compound 282: N-((4,6-dimethyl-2-oxo-1,2-dihydropyridin-3-yl)methyl)-3-(((1r,4r)-4-(dimethylamino)cyclohexyl)(ethyl)amino)-5-ethyl-2-methylbenzamide

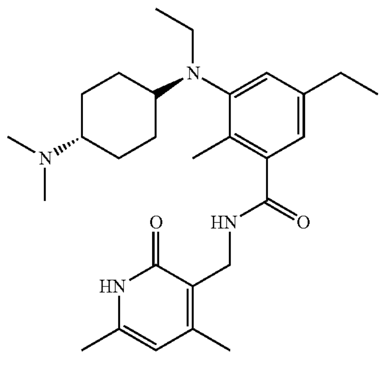

Step 1: Synthesis of N-((4,6-dimethyl-2-oxo-1,2-dihydropyridin-3-yl)methyl)-3-(((1r,4r)-4-(dimethylamino)cyclohexyl)(ethyl)amino)-2-methyl-5-vinylbenzamide

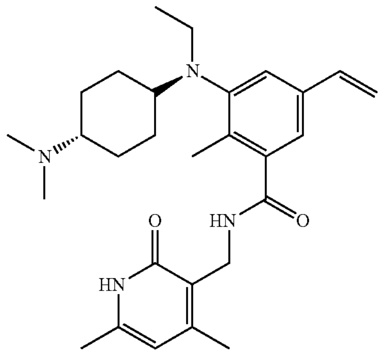

A mixture of 5-bromo-N-((4,6-dimethyl-2-oxo-1,2-dihydropyridin-3-yl)methyl)-3-(((1r,4r)-4-(dimethylamino)cyclohexyl)(ethyl)amino)-2-methylbenzamide (200 mg, 0.38 mmol), 4,4,5,5-tetramethyl-2-vinyl-1,3,2-dioxaborolane (71 mg, 0.46 mmol) and sodium carbonate (147 mg, 1.39 mmol) in 10 ml of dioxane was degassed with argon for 20 min, $Pd(PPh_3)_4$ (44 mg, 0.04 mmol) was added and the mixture heated at 100° C. overnight. The reaction was cooled to room temperature and diluted with water. The mixture was extracted with 10% MeOH in DCM, the combined organic phases dried over $Na_2SO_4$ and concentrated. The residue was purified by silica gel chromatography to obtain the title compound (150 mg, 83%).

Step 2: Synthesis of N-((4,6-dimethyl-2-oxo-1,2-dihydropyridin-3-yl)methyl)-3-(((1r,4r)-4-(dimethylamino)cyclohexyl)(ethyl)amino)-5-ethyl-2-methylbenzamide

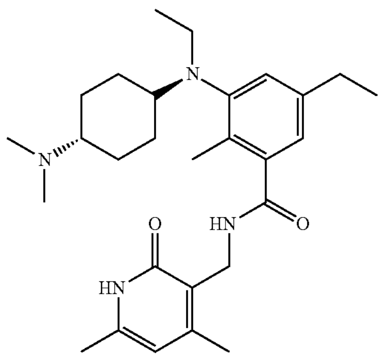

To a solution of compound N-((4,6-dimethyl-2-oxo-1,2-dihydropyridin-3-yl)methyl)-3-(((1r,4r)-4-(dimethylamino) cyclohexyl)(ethyl)amino)-2-methyl-5-vinylbenzamide (150 mg, 0.32 mmol) in 5 mL of methanol, was added a catalytic amount of 10% palladium on carbon The mixture was stirred under hydrogen atmosphere at balloon pressure for 12 h, filtered through celite, and concentrated under reduced pressure. The residue was purified by prep. HPLC to give the title compound as a TFA salt (65 mg, 43%).

LCMS: 467.35 $(M+1)^+$; HPLC: 93.41% (@ 254 nm) ($R_t$; 10.946; Method: Column: YMC ODS-A 150 mm×4.6 mm×5μ; Mobile Phase: A; 10 m M ammonium formate in water+0.1% $NH_3$, B; Acetonitrile+5% solvent A+0.1% $NH_3$; Inj. Vol: 10 μL, Col. Temp.: 30° C.; Flow rate: 1.0 mL/min.; Gradient: 15% B to 95% B in 6.0 min, Hold till 8.0 min, 15% B at 8.5 min hold up to 15 min); $^1H$ NMR (DMSO-$d_6$, 400 MHz) δ 11.47 (bs, 1H), 9.45 (s, 1H), 8.38 (s, 1H), 8.03 (s, 2H), 7.26-6.84 (m, 2H), 5.87 (s, 1H), 4.26 (d, J=4.0 Hz, 2H), 3.17-2.89 (m, 3H), 2.70, 2.68 (2s, 6H), 2.19, 2.11 (3s, 9H), 1.96-1.87 (m, 4H), 1.42 (m, 4H), 1.15 (t, J=7.2 Hz, 3H), 0.80 (s, 3H).

Compound 283: N-((4,6-dimethyl-2-oxo-1,2-dihydropyridin-3-yl)methyl)-3-(((1r,4r)-4-(dimethylamino)cyclohexyl)(ethyl)amino)-2-methyl-5-(3-(4-methylpiperazin-1-yl)prop-1-yn-1-yl)benzamide

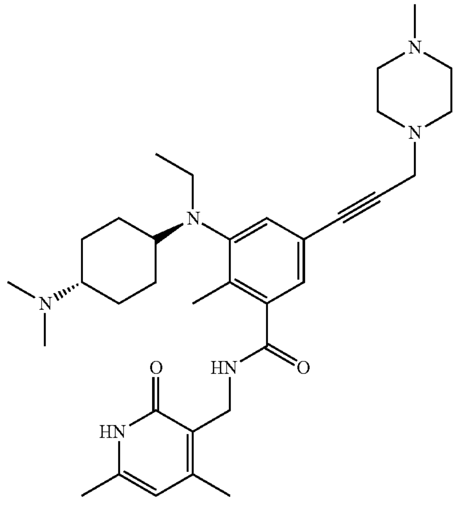

Step 1 Synthesis of methyl 3-(((1r,4r)-4-((tert-butoxycarbonyl)amino)cyclohexyl)(ethyl)amino)-2-methyl-5-(3-(4-methylpiperazin-1-yl)prop-1-yn-1-yl) benzoate

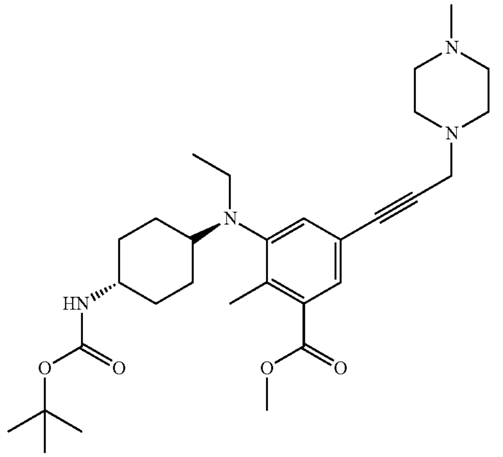

A solution of methyl 5-(3-bromoprop-1-yn-1-yl)-3-(((1r,4r)-4-((tert-butoxycarbonyl)amino)cyclohexyl)(ethyl) amino)-2-methylbenzoate (500 mg, 1.0 mmol) and 1-methylpiperazine (0.49 ml, 4.9 mmol) in 5 ml of DMF was stirred at room temperature overnight. The reaction mixture was diluted with water and extracted with DCM. The combined organic phases were dried over $Na_2SO_4$, and concentrated under vacuum to give the title compound (550 mg).

Steps 2 and 3: Synthesis of tert-butyl ((1r,4r)-4-((3-(((4,6-dimethyl-2-oxo-1,2-dihydropyridin-3-yl)methyl)carbamoyl)-2-methyl-5-(3-(4-methylpiperazin-1-yl)prop-1-yn-1-yl)phenyl) (ethyl)amino) cyclohexyl)carbamate

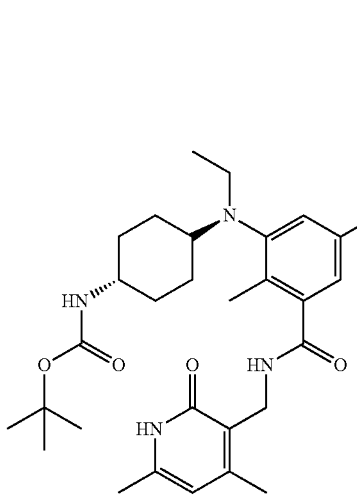

A mixture of compound methyl 3-(((1r,4r)-4-((tert-butoxycarbonyl)amino)cyclohexyl)(ethyl)amino)-2-methyl-5-(3-(4-methylpiperazin-1-yl)prop-1-yn-1-yl)benzoate (550 mg, 1.0 mmol) and NaOH (83 mg, 2.1 mmol) in 8 ml of ethanol:water (3:1) was heated at 70° C. for 2 h. The reaction mixture was concentrated to dryness and the residue was partitioned between water and DCM. The organic layer was dried over $Na_2SO_4$, concentrated under reduced pressure to afford 470 mg of acid. The crude acid (470 mg, 0.92 mmol), 3-(aminomethyl)-4,6-dimethylpyridin-2(1H)-one (279 mg, 1.83 mmol), PyBOP (716 mg, 1.37 mmol) and triethyl amine (0.38 ml, 2.75 mmol) mixture were stirred in 5 ml of DMSO at room temperature overnight. The reaction mixture was diluted with water and the compound was extracted into 10% MeOH in DCM. The organic layer was dried over $Na_2SO_4$, concentrated under reduced pressure and the residue purified by silica gel column chromatography to give the title compound (350 mg, 50%).

Step 4: Synthesis of 3-(((1r,4r)-4-aminocyclohexyl) (ethyl)amino)-N-((4,6-dimethyl-2-oxo-1,2-dihydropyridin-3-yl)methyl)-2-methyl-5-(3-(4-methylpiperazin-1-yl)prop-1-yn-1-yl)benzamide

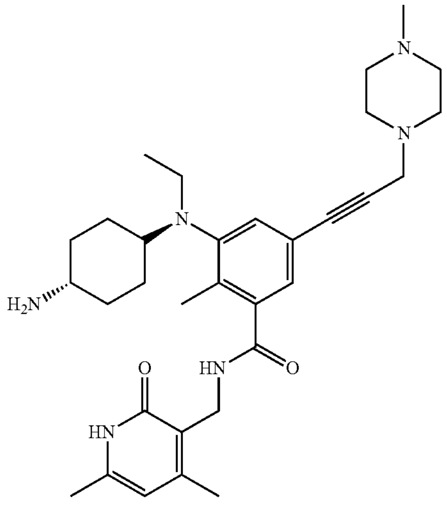

To a cooled solution of tert-butyl ((1r,4r)-4-((3-(((4,6-dimethyl-2-oxo-1,2-dihydropyridin-3-yl)methyl)carbamoyl)-2-methyl-5-(3-(4-methylpiperazin-1-yl)prop-1-yn-1-yl)phenyl)(ethyl)amino)cyclohexyl)carbamate (350 mg, 0.54 mmol) in 5 ml of DCM, were added 2 ml of TFA. The reaction mixture was stirred at rt for 2 h, concentrated to dryness under reduced pressure. The residue was dissolved in 10% MeOH in DCM and washed with sat $NaHCO_3$, water and brine. The organic phase was dried over $Na_2SO_4$ and concentrated under reduced pressure to obtain the crude title compound (250 mg, 84%).

Step 5: Synthesis of N-((4,6-dimethyl-2-oxo-1,2-dihydropyridin-3-yl)methyl)-3-(((1r,4r)-4-(dimethylamino)cyclohexyl)(ethyl)amino)-2-methyl-5-(3-(4-methylpiperazin-1-yl)prop-1-yn-1-yl)benzamide

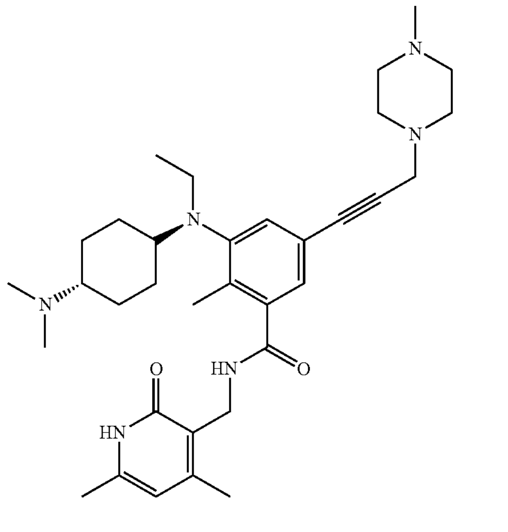

To a stirred solution of crude 3-(((1r,4r)-4-aminocyclohexyl)(ethyl)amino)-N-((4,6-dimethyl-2-oxo-1,2-dihydropyridin-3-yl)methyl)-2-methyl-5-(3-(4-methylpiperazin-1-yl)prop-1-yn-1-yl)benzamide (250 mg, 0.45 mmol) and formaldehyde (0.35 ml of 38% solution, 4.56 mmol) in 3 ml of methanol was added sodium cyanoborohydride (85 mg, 1.37 mmol) at 0° C. The mixture was stirred at room temperature for 4 hand partitioned between water and 10% MeOH in DCM. The organic layer was separated, dried over $Na_2SO_4$, and concentrated under reduced pressure. The residue was purified by prep. HPLC to afford the title compound as a TFA salt (40 mg, 15%).

LCMS: 575.45 $(M+1)^+$; HPLC: 99.30% (@ 254 nm) ($R_t$; 3.849; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR ($D_2O$, 400 MHz) δ 7.75 (s, 1H), 7.60 (s, 1H), 6.28 (s, 1H), 4.45 (d, J=4.0 Hz, 2H), 3.80-3.63 (m, 5H), 3.40-3.21 (m, 9H), 2.92 (s, 3H), 2.79 (2s, 6H), 2.35 (m, 3H), 2.32 (s, 3H), 2.26 (s, 3H), 2.19-2.05 (m, 4H), 1.65-1.57 (m, 4H), 0.97 (t, J=7.2 Hz, 3H).

Compound 284: 5-chloro-N-((4,6-dimethyl-2-oxo-1,2-dihydropyridin-3-yl)methyl)-3-(ethyl((1r,4r)-4-(methylamino)cyclohexyl)amino)-2-methylbenzamide

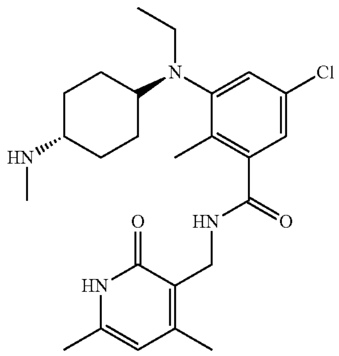

Step 1: Synthesis of methyl 3-(((1r,4r)-4-((tert-butoxycarbonyl)amino)cyclohexyl)amino)-5-chloro-2-methylbenzoate

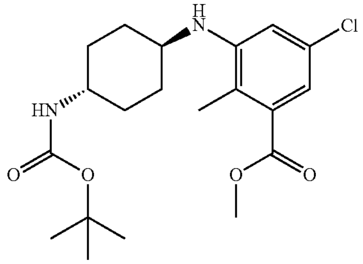 [SMILES: COC(=O)c1cc(Cl)cc(N[C@H]2CC[C@H](NC(=O)OC(C)(C)C)CC2)c1C]

To a stirred solution of compound methyl 3-amino-5-chloro-2-methylbenzoate (5.0 g, 25 mmol) and tert-butyl (4-oxocyclohexyl)carbamate (6.95 g, 32.7 mmol) in 25 ml of dichloroethane was added acetic acid (9.0 mL, 450 mmol) and the mixture stirred at room temperature for 10 min. The mixture was cooled and sodium triacetoxyborohydride (22.8 g, 108 mmol) was added and the mixture stirred at room temperature overnight. The mixture was neutralized with sat. $NaHCO_3$ and was extracted with DCM. The combined organic phases were dried over $Na_2SO_4$, concentrated under reduced pressure and the residue was purified by silica gel column chromatography to give (3.5 g, 35%) of the more polar trans-isomer title compound 3-(((1r,4r)-4-((tert-butoxycarbonyl)amino)cyclohexyl)amino)-5-chloro-2-methylbenzoate, along with (5.2 g, 52%) of the less polar cis-isomer 3-(((1s,4s)-4-((tert-butoxycarbonyl)amino)cyclohexyl)amino)-5-chloro-2-methylbenzoate.

Step 2: Synthesis of methyl 3-(((1r,4r)-4-((tert-butoxycarbonyl)amino)cyclohexyl)(ethyl)amino)-5-chloro-2-methylbenzoate

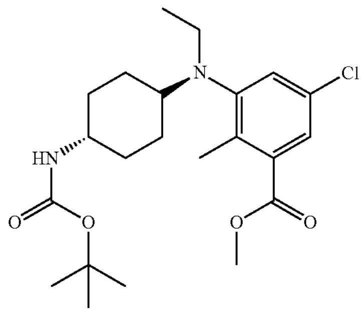

To a stirred solution of methyl 3-(((1r,4r)-4-((tert-butoxycarbonyl)amino)cyclohexyl)amino)-5-chloro-2-methylbenzoate (3.0 g, 7.6 mmol) and acetaldehyde (0.66 g, 15 mmol) in 15 ml of dichloroethane, was added acetic acid (2.7 mL, 45 mmol) and the mixture was stirred at room temperature for 20 minutes. The mixture was cooled to 0° C., sodium triacetoxyborohydride (4.8 g, 22 mmol) was added and the mixture stirred at room temperature overnight. The mixture was neutralized with sat. $NaHCO_3$ and was extracted with DCM. The combined organic phases were dried over $Na_2SO_4$, concentrated under reduced pressure and the residue purified by silica gel column chromatography to give the title compound (3.5 g, 96%).

Step 3: Synthesis of methyl 3-(((1r,4r)-4-((tert-butoxycarbonyl)(methyl)amino)cyclohexyl)(ethyl)amino)-5-chloro-2-methylbenzoate

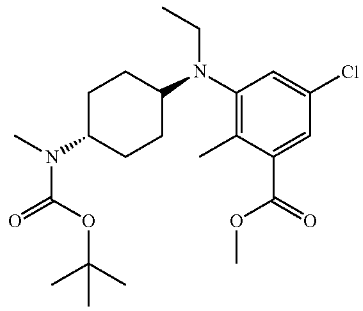

To a cooled solution of methyl 3-(((1r,4r)-4-((tert-butoxycarbonyl)amino)cyclohexyl)(ethyl)amino)-5-chloro-2-methylbenzoate (1.1 g, 3.3 mmol) in 12 ml of THF, was added sodium hydride (410 mg, 10 mmol) followed by methyl iodide (2.1 ml, 34 mmol), The mixture was stirred at room temperature overnight, quenched by slow addition of ice water and acidified with citric acid solution. Extraction with 10% MeOH in DCM followed by drying and concentration of the combined organic phases under reduced pressure gave the title compound (1.0 g, 88%).

Steps 4 and 5: Synthesis of tert-butyl ((1r,4r)-4-((5-chloro-3-(((4,6-dimethyl-2-oxo-1,2-dihydropyridin-3-yl)methyl)carbamoyl)-2-methylphenyl)(ethyl)amino)cyclohexyl)(methyl)carbamate

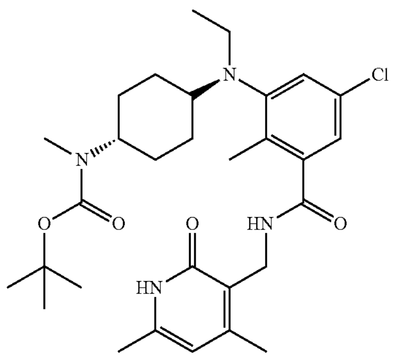

A mixture of methyl 3-(((1r,4r)-4-((tert-butoxycarbonyl)(methyl)amino)cyclohexyl)(ethyl)amino)-5-chloro-2-methylbenzoate (1.0 g, 2.4 mmol) and NaOH (140 mg, 3.5 mmol) in 10 ml of ethanol:water (4:1) was heated at 70° C. for 2 h. The reaction mixture was concentrated to dryness and the residue was partitioned between water and DCM. The organic layer was dried over $Na_2SO_4$, and concentrated under reduced pressure to afford 1.0 g of crude acid. A mixture of the crude acid (1.0 g, 2.4 mmol), 3-(aminomethyl)-4,6-dimethylpyridin-2(1H)-one (716 mg, 4.71 mmol), PyBOP (1.83 g, 3.53 mmol) and 2 ml of triethyl amine was stirred in 5 ml of DMSO at room temperature overnight. The mixture was diluted with water and extracted with 10% MeOH in DCM. The combined organic layers were dried over $Na_2SO_4$, concentrated under reduced pressure and the residue purified by silica gel column chromatography to give the title compound (700 mg, 53%).

Step 6: Synthesis of 5-chloro-N-((4,6-dimethyl-2-oxo-1,2-dihydropyridin-3-yl)methyl)-3-(ethyl((1r,4r)-4-(methylamino)cyclohexyl)amino)-2-methylbenzamide

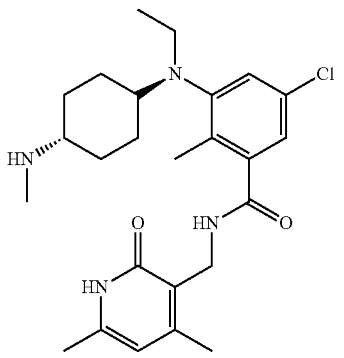

To a cooled solution of tert-butyl ((1s,4s)-4-(5-chloro-3-(((4,6-dimethyl-2-oxo-1,2-dihydropyridin-3-yl)methyl)carbamoyl)-2-methylphenyl)(ethyl)amino)cyclohexyl)(methyl) carbamate (700 mg, 1.25 mmol) in 20 ml of DCM, were added 3 ml of TFA. The reaction mixture was stirred at room temperature for 2 h, and concentrated to dryness under reduced pressure. The residue was dissolved in 10% MeOH in DCM and washed with sat $NaHCO_3$, water and brine. The organic phase was dried over $Na_2SO_4$, concentrated under reduced pressure and the residue purified by preparative HPLC to obtain the title compound as its TFA salt (500 mg, 87%).

LCMS: 459.35 $(M+1)^+$; HPLC: 97.63% (@ 254 nm) ($R_t$; 4.565; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-$D_6$, 400 MHz) δ 11.46 (bs, 1H), 8.32 (s, 2H), 8.22 (m, 1H), 7.20 (s, 1H), 7.00 (s, 1H), 5.86 (s, 1H), 4.25 (d, J=4.0 Hz, 2H), 3.74 (m, 3H), 3.03-3.01 (m, 3H), 2.67 (m, 1H), 2.19 (s, 3H), 2.14 (s, 3H), 2.11 (s, 3H), 1.33 (m, 2H), 1.82-1.80 (m, 2H), 1.42-1.23 (m, 2H+2H), 0.78 (t, J=7.2 Hz, 3H).

Compound 285: 5-chloro-N-((4,6-dimethyl-2-oxo-1,2-dihydropyridin-3-yl)methyl)-3-(ethyl((1r,4r)-4-(ethyl(methyl)amino)cyclohexyl)amino)-2-methylbenzamide

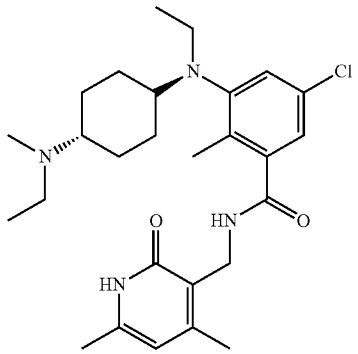

Step 1: Synthesis of 5-chloro-N-((4,6-dimethyl-2-oxo-1,2-dihydropyridin-3-yl)methyl)-3-(ethyl((1r,4r)-4-(ethyl(methyl)amino)cyclohexyl)amino)-2-methylbenzamide

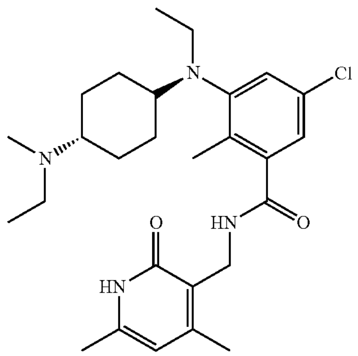

To a stirred solution of compound 5-chloro-N-((4,6-dimethyl-2-oxo-1,2-dihydropyridin-3-yl)methyl)-3-(ethyl((1r,4r)-4-(methylamino)cyclohexyl)amino)-2-methylbenzamide (200 mg, 0.43 mmol) and acetaldehyde (0.03 ml, 0.43 mmol) in 5 ml of dichloroethane, was added acetic acid (0.15 mL, 2.62 mmol) and the mixture stirred at room temperature for 20 minutes. The mixture was cooled to 0° C. and sodium triacetoxyborohydride (0.28 g, 1.31 mmol) was added and the mixture stirred at room temperature overnight. The reaction mixture was neutralized with sat. $NaHCO_3$ and was extracted with DCM. The combined organic layers were dried over $Na_2SO_4$, concentrated under reduced pressure, and the residue purified by prep. HPLC to give the title compound as a TFA salt (80 mg, 37%). LCMS: 487.35 $(M+1)^+$; HPLC: 99.87% (@ 254 nm) ($R_t$; 4.711; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-$D_6$, 400 MHz) δ 11.47 (bs, 1H), 9.15 (s, 1H), 8.22 (s, 1H), 7.19 (s, 1H), 6.97 (s, 1H), 5.86 (s, 1H), 4.24 (d, J=4.0 Hz, 2H), 3.16-3.01 (m, 5H), 2.64-2.63 (m, 4H), 2.19 (s, 3H), 2.15 (s, 3H), 2.10 (s, 3H), 1.91-1.83 (m, 4H), 1.47 (m, 4H), 1.19 (m, 3H), 0.79 (t, J=7.2 Hz, 3H).

Compound 286: 5-chloro-3-(((1r,4r)-4-((cyclopropylmethyl)(methyl)amino)cyclohexyl)(ethyl)amino)-N-((4,6-dimethyl-2-oxo-1,2-dihydropyridin-3-yl)methyl)-2-methylbenzamide

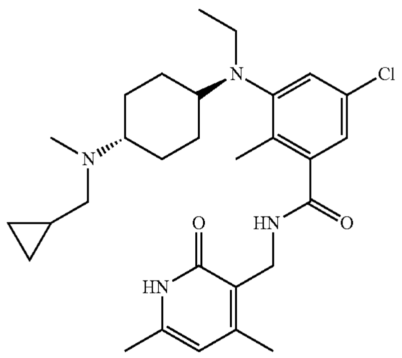

Step 1: Synthesis of 5-chloro-3-(((1r,r)-4-((cyclopropylmethyl)(methyl)amino)cyclohexyl)(ethyl)amino)-N-((4,6-dimethyl-2-oxo-1,2-dihydropyridin-3-yl)methyl)-2-methylbenzamide

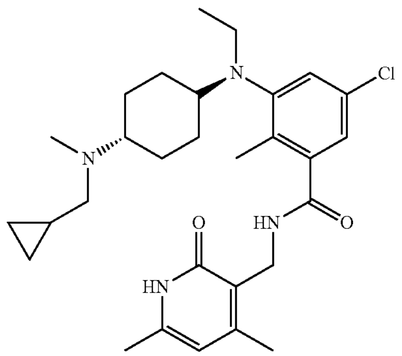

To a stirred solution of d 5-chloro-N-((4,6-dimethyl-2-oxo-1,2-dihydropyridin-3-yl)methyl)-3-(ethyl((1r,4r)-4-(methylamino)cyclohexyl)amino)-2-methylbenzamide (200 mg, 0.43 mmol) and cyclopropanecarbaldehyde (0.03 gm, 0.43 mmol) in 5 ml of dichloroethane, was added acetic acid (0.15 mL, 2.62 mmol) and the mixture stirred at room temperature for 20 minutes. The mixture was cooled to 0° C. and sodium triacetoxyborohydride (0.277 g, 1.31 mmol) was added and the mixture stirred at room temperature overnight. The mixture was neutralized with sat. $NaHCO_3$ and was extracted with DCM. The combined organic phases were dried over $Na_2SO_4$, concentrated under reduced pressure, and the residue purified by prep. HPLC to give the title compound as a TFA salt (100 mg, 44%). LCMS: 513.40 $(M+1)^+$; HPLC: 94.81% (@ 254 nm) ($R_t$; 4.924; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-$D_6$, 400 MHz) δ 11.47 (bs, 1H), 9.09 (s, 1H), 8.21 (s, 1H), 7.18 (s, 1H), 6.97 (s, 1H), 5.86 (s, 1H), 4.25 (d, J=4.0 Hz, 2H), 3.24 (m, 1H), 3.03-3.01 (m, 3H), 2.89-2.87 (m, 1H), 2.71-2.70 (m, 4H), 2.18 (s, 3H), 2.15 (s, 3H), 2.10 (s, 3H), 1.93-1.83 (m, 4H), 1.46-1.44 (m, 4H), 1.05 (m, 1H), 0.79 (t, J=7.2 Hz, 3H), 0.63 (m, 2H), 0.38-0.31 (m, 2H).

Compound 287: Synthesis of compound 5-chloro-3-(((1r,4r)-4-(cyclobutyl(methyl)amino)cyclohexyl)(ethyl)amino)-N-((4,6-dimethyl-2-oxo-1,2-dihydropyridin-3-yl)methyl)-2-methylbenzamide

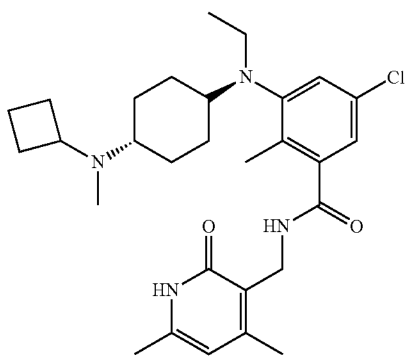

Steps 1 and 2: Synthesis of tert-butyl((1r,4r)-4-((5-chloro-3-(((4,6-dimethyl-2-oxo-1,2-dihydropyridin-3-yl)methyl)carbamoyl)-2-methylphenyl)(ethyl)amino)cyclohexyl)carbamate

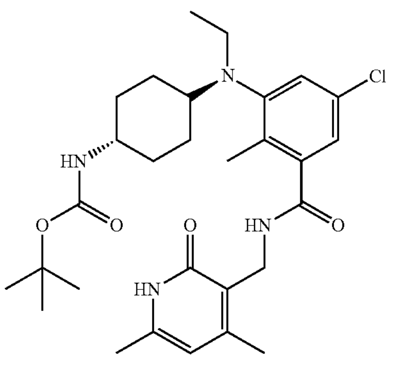

A mixture of compound methyl 3-(((1r,4r)-4-((tert-butoxycarbonyl)amino)cyclohexyl)(ethyl)amino)-5-chloro-2-methylbenzoate (3.5 g, 8.2 mmol) and NaOH (0.5 g, 12 mmol) in 20 ml of ethanol:water (4:1) was heated at 70° C. for 2 h. The reaction mixture was cooled to 0° C. and acidified to pH 6 by using 1N HCl and concentrated. The residue was partitioned between water and ethyl acetate, the organic layer was dried over $Na_2SO_4$ and concentrated under reduced pressure to afford 3.2 g of crude acid. The crude acid (3.2 g, 7.8 mmol), 3-(aminomethyl)-4,6-dimethylpyridin-2(1H)-one (2.36 mg, 15.6 mmol) and PyBOP (6.1 mg, 11 mmol) were stirred in 15 ml of DMSO at room temperature overnight. The reaction mixture was diluted with water and extracted with 10% MeOH in DCM. The combined organic layers were dried over $Na_2SO_4$, concentrated under reduced pressure and the residue purified by silica gel column chromatography to give the title compound (3.0 g, 71%).

Step 3: Synthesis of 3-(((1r,4r)-4-aminocyclohexyl)(ethyl)amino)-5-chloro-N-((4,6-dimethyl-2-oxo-1,2-dihydropyridin-3-yl)methyl)-2-methylbenzamide

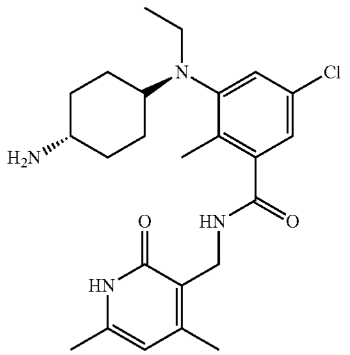

To a cooled solution of tert-butyl((1s,4s)-4-((5-chloro-3-(((4,6-dimethyl-2-oxo-1,2-dihydropyridin-3-yl)methyl)carbamoyl)-2-methylphenyl)(ethyl)amino)cyclohexyl)carbamate (400 mg, 0.73 mmol) in 5 ml of DCM, were added 2 ml of TFA. The reaction mixture was stirred at room temperature for 2 h and concentrated to dryness under reduced pressure. The residue was dissolved in 10% MeOH in DCM and washed with sat $NaHCO_3$, water and brine. The organic phase was dried over $Na_2SO_4$ and concentrated under reduced pressure to give the title compound (320 mg, 98%).

Step 4: Synthesis of 5-chloro-3-(((1r,4r)-4-(cyclobutylamino)cyclohexyl)(ethyl)amino)-N-((4,6-dimethyl-2-oxo-1,2-dihydropyridin-3-yl)methyl)-2-methylbenzamide

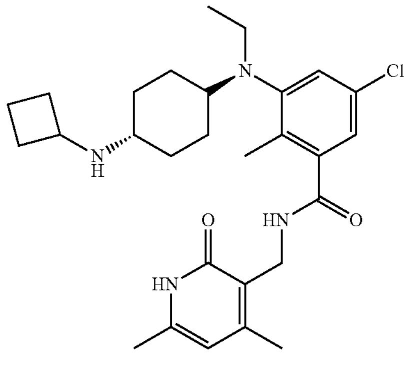

To a stirred solution of 3-(((1r,4r)-4-aminocyclohexyl)(ethyl)amino)-5-chloro-N-((4,6-dimethyl-2-oxo-1,2-dihydropyridin-3-yl)methyl)-2-methylbenzamide (300 mg, 0.67 mmol) and cyclobutanone (141 mg, 2.02 mmol) in 20 ml of methanol, was added sodium cyanoborohydride (127 mg, 2.02 mmol) at 0° C. The mixture was stirred at rt overnight, neutralized with sat. $NaHCO_3$ and extracted with DCM. The combined organic phases were dried over $Na_2SO_4$ and concentrated under reduced pressure to obtain crude title compound (260 mg, 77%).

Step 5: Synthesis of 5-chloro-3-(((1r,4r)-4-(cyclobutyl(methyl)amino)cyclohexyl)(ethyl)amino)-N-((4,6-dimethyl-2-oxo-1,2-dihydropyridin-3-yl)methyl)-2-methylbenzamide

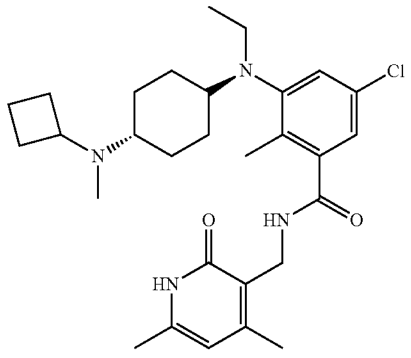

To a stirred solution of 5-chloro-3-(((1r,4r)-4-(cyclobutylamino)cyclohexyl) (ethyl)amino)-N-((4,6-dimethyl-2-oxo-1,2-dihydropyridin-3-yl)methyl)-2-methylbenzamide (230 mg, 0.46 mmol) and formalin (138 mg, 4.61 mmol) in 10 ml of methanol, was added sodium cyanoborohydride (43 mg, 0.69 mmol) at 0° C. The mixture was stirred at rt for overnight neutralized with sat. $NaHCO_3$ and extracted with DCM. The combined organic phases were dried over $Na_2SO_4$, concentrated under reduced pressure and the residue purified by silica gel column chromatography to give the title compound (150 mg, 63%).

Analytical Data of 5-chloro-3-(((1r,4r)-4-(cyclobutyl(methyl)amino)cyclohexyl)(ethyl)amino)-N-((4,6-dimethyl-2-oxo-1,2-dihydropyridin-3-yl)methyl)-2-methylbenzamide-TFA salt: LCMS: 513.25 $(M+1)^+$; HPLC: 96.89% (@ 254 nm) ($R_t$; 4.886; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-$D_6$, 400 MHz) δ 11.45 (bs, 1H), 9.40 (s, 1H), 8.21 (s, 1H), 7.18 (s, 1H), 6.97 (s, 1H), 5.86 (s, 1H), 4.25 (d, J=4.0 Hz, 2H), 3.77-3.75 (m, 1H), 3.12-3.02 (m, 3H), 2.69 (m, 1H), 2.50 (4H merged in solvent peak), 2.18, 2.15, 2.11 (3s, 6H+3H+3H), 1.83-1.44 (m, 10H), 0.78 (t, 3H).

Compound 290: N-((4,6-dimethyl-2-oxo-1,2-dihydropyridin-3-yl)methyl)-3-(((1r,4r)-4-(dimethylamino)cyclohexyl)(ethyl)amino)-5-(3-(dimethylamino)prop-1-yn-1-yl)-2-methylbenzamide

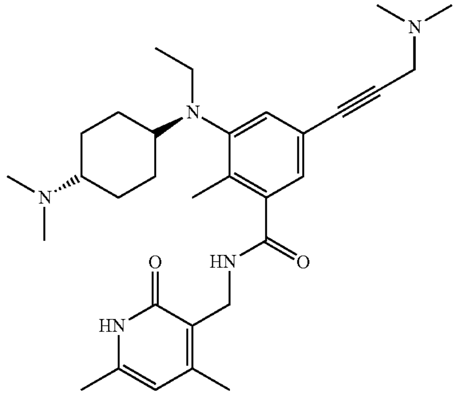

Steps 1 and 2: Synthesis of methyl 3-(((1r,4r)-4-((tert-butoxycarbonyl)amino)cyclohexyl)(ethyl)amino)-5-(3-hydroxyprop-1-yn-1-yl)-2-methylbenzoate

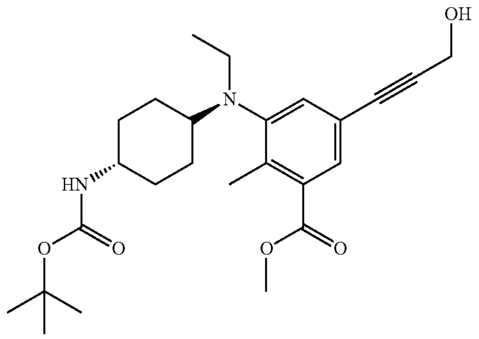

A solution of methyl 5-bromo-3-(((1r,4r)-4-((tert-butoxycarbonyl)amino)cyclohexyl)(ethyl)amino)-2-methylbenzoate (1.5 g, 3.2 mmol), tert-butyldimethyl(prop-2-yn-1-yloxy)silane (1.6 g, 9.6 mmol), copper iodide (183 mg, 0.96 mmol) and triethyl amine (1.30 ml, 9.60 mmol) in 10 ml of DMF was purged with argon gas for 20 min. Tetrakis-(triphenylphosphine)palladium (369 mg, 0.32 mmol) was added to the reaction mixture and the mixture heated at 100° C. for 5 h and cooled to room temperature. The mixture was diluted with ethyl acetate, washed with water, and the organic layer was dried over $Na_2SO_4$ and concentrated under reduced pressure to obtain crude 1.9 g of the silyl protected intermediate product. The product was dissolved in 15 ml of THF and tetra-butyl ammonium fluoride (6.81 ml of 1M solution in THF, 6.81 mmol) was added at room temperature and the mixture stirred for 2 h. The reaction mixture was diluted with ethyl acetate and washed with water. The organic layer was dried over $Na_2SO_4$, concentrated under reduced pressure, and the residue purified by silica gel column chromatography to give the title compound (950 mg, 630%).

Step 3: Synthesis of methyl 5-(3-bromoprop-1-yn-1-yl)-3-(((1r,4r)-4-((tert-butoxycarbonyl)amino)cyclohexyl)(ethyl)amino)-2-methylbenzoate

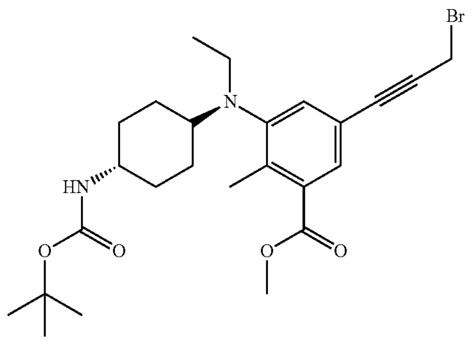

To a solution of methyl 3-(((1r,4r)-4-((tert-butoxycarbonyl)amino)cyclohexyl)(ethyl)amino)-5-(3-hydroxyprop-1-yn-1-yl)-2-methylbenzoate (950 mg, 2.14 mmol) in 13 ml of DCM, triphenylphosphine (840 mg, 3.21 mmol) and carbon tetrabromide (1.06 gm, 3.21 mmol) were added at room temperature. The mixture was stirred for 3 h, diluted with DCM and washed with water. The organic layer was dried over $Na_2SO_4$, concentrated under reduce pressure and the residue column purified over silica gel to give the title compound (900 mg, 82%).

Step 4: Synthesis of methyl 3-(((1r,4r)-4-((tert-butoxycarbonyl)amino)cyclohexyl)(ethyl)amino)-5-(3-(dimethylamino)prop-1-yn-1-yl)-2-methylbenzoate

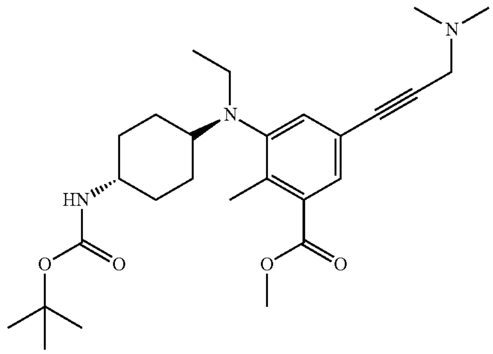

A solution of methyl 5-(3-bromoprop-1-yn-1-yl)-3-(((1r,4r)-4-((tert-butoxycarbonyl)amino)cyclohexyl)(ethyl)amino)-2-methylbenzoate (500 mg, 0.98 mmol) and a 2M solution in THF of N,N-dimethylamine (2.5 ml, 4.9 mmol) in 5 ml of DMF was stirred at room temperature overnight. The mixture was concentrated under reduced pressure, diluted with water and extracted with DCM. The combined organic phases were dried over $Na_2SO_4$ and concentrated under vacuum to afford the title compound (450 mg, 96%).

Steps 5 and 6: Synthesis of tert-butyl ((1r,4r)-4-((3-(((4,6-dimethyl-2-oxo-1,2-dihydropyridin-3-yl)methyl)carbamoyl)-5-(3-(dimethylamino)prop-1-yn-1-yl)-2-methylphenyl)(ethyl)amino)cyclohexyl) carbamate

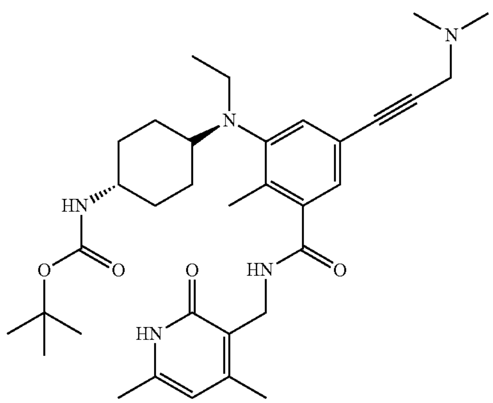

A mixture of methyl 3-(((1r,4r)-4-((tert-butoxycarbonyl)amino)cyclohexyl)(ethyl)amino)-5-(3-(dimethylamino)prop-1-yn-1-yl)-2-methylbenzoate (450 mg, 0.95 mmol) and NaOH (57 mg, 1.40 mmol) in 10 ml of ethanol:water (4:1) was heated at 70° C. for 2 h. The reaction mixture was concentrated to dryness and the residue partitioned between water and DCM. The organic layer was dried over $Na_2SO_4$ cand concentrated under reduced pressure to afford 430 mg of acid. The crude acid (430 mg, 0.94 mmol), 3-(aminomethyl)-4,6-dimethylpyridin-2(1H)-one (280 mg, 1.88 mmol), PyBOP (733 mg, 1.40 mmol) and triethyl amine (0.1 ml, 0.94 mmol) were stirred in 7 ml of DMSO at rt overnight. The reaction mixture was diluted with water, the precipitated compound was filtered and dried under vacuum to obtain the crude title compound (450 mg, 81%).

Step 7: Synthesis of 3-(((1r,4r)-4-aminocyclohexyl)(ethyl)amino)-N-((4,6-dimethyl-2-oxo-1,2-dihydropyridin-3-yl)methyl)-5-(3-(dimethylamino)prop-1-yn-1-yl)-2-methylbenzamide

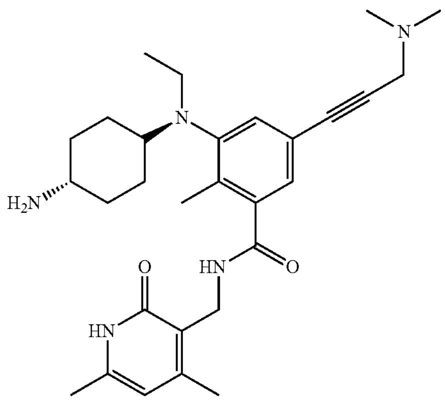

To a cooled solution of methyl 3-(((1r,4r)-4-((tert-butoxycarbonyl)amino)cyclohexyl)(ethyl)amino)-5-(3-(dimethylamino)prop-1-yn-1-yl)-2-methylbenzoate (450 mg, 0.76 mmol) in 6 ml of DCM, was added 1 ml of TFA. The reaction mixture was stirred at rt for 2 h, and concentrated to dryness under reduced pressure. The residue was dissolved in 10% MeOH in DCM and washed with sat $NaHCO_3$, water and brine. The organic phase was dried over $Na_2SO_4$, concentrated under reduced pressure to obtain the crude title compound (350 mg, 93%).

Step 8: Synthesis of N-((4,6-dimethyl-2-oxo-1,2-dihydropyridin-3-yl)methyl)-3-(((1r,4r)-4-(dimethylamino)cyclohexyl)(ethyl)amino)-5-(3-(dimethylamino)prop-1-yn-1-yl)-2-methylbenzamide

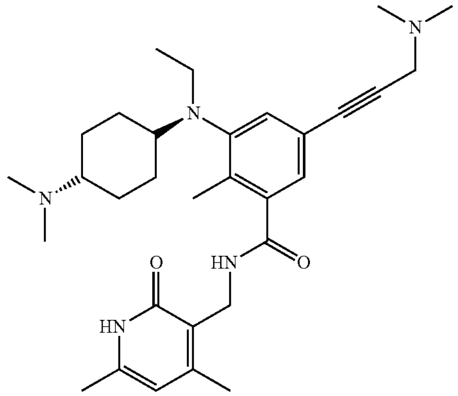

To a stirred solution of crude compound 3-(((1r,4r)-4-aminocyclohexyl)(ethyl)amino)-N-((4,6-dimethyl-2-oxo-1,2-dihydropyridin-3-yl)methyl)-5-(3-(dimethylamino)prop-1-yn-1-yl)-2-methylbenzamide (350 mg, 0.71 mmol) and formaldehyde (0.56 ml of 38% solution, 7.10 mmol) in 8 ml of methanol, was added sodium cyanoborohydride (132 mg, 2.10 mmol) at 0° C. The mixture was stirred at room temperature for 4 h, and partitioned between water and 10% MeOH in DCM. The organic layer was dried over $Na_2SO_4$ and concentrated under reduced pressure. The residue was purified by basic alumina column chromatography to afford the title compound (120 mg, 32%).

LCMS: 520.6 $(M+1)^+$; HPLC: 92.27% (@ 254 nm) ($R_t$; 3.886; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-$d_6$, 400 MHz) δ 11.45 (bs, 1H), 8.18 (t, 1H), 7.15 (s, 1H), 6.96 (s, 1H), 5.86 (s, 1H), 4.25 (d, 2H), 3.02-3.00 (m, 2H), 2.50 (13 protons merged in solvent peak), 2.33 (s, 3H), 2.23 (s, 3H), 2.18 (s, 3H), 2.11 (s, 3H), 1.82 (m, 4H), 1.39-1.28 (m, 4H), 0.77 (t, 3H).

Compound 301: N-((1-benzyl-4,6-dimethyl-2-oxo-1,2-dihydropyridin-3-yl)methyl)-5-chloro-3-(((1r,4r)-4-(dimethylamino)cyclohexyl)(ethyl)amino)-2-methylbenzamide

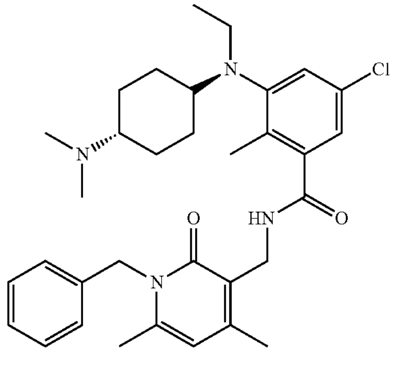

5-Chloro-3-(((1r,4r)-4-(dimethylamino)cyclohexyl)(ethyl)amino)-2-methylbenzoic acid (1 eq) was dissolved in DMSO and 3-(aminomethyl)-1-(2-hydroxyethyl)-4,6-dimethylpyridin-2(1H)-one (2 eq) and triethylamine (1 eq) was added to it. The reaction mixture was stirred at room temperature for 15 min, PYBOP (1.5 eq) was added and stirring was continued overnight. The reaction mixture was poured into ice and extracted with 10% MeOH/DCM. The combined organic layers were dried and concentrated to obtain crude product which was purified by prep. HPLC to afford the title compound (0.011 g, 16%) as the TFA salt. LCMS: 563.40 $(M+1)^+$; HPLC: 90.27% (@ 210 nm-370 nm) ($R_t$; 6.122; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (MeOD, 400 MHz) δ, 7.31-7.26 (m, 2H), 7.24-7.04 (m, 5H), 6.23 (s, 1H), 5.40 (d, 2H), 4.50 (s, 2H), 3.34 (1 Protons merged in solvent peak), 3.11-3.08 (m, 2H+1H), 2.81 (s, 3H+3H), 2.42 (s, 3H), 2.29 (s, 3H), 2.21 (s, 3H), 2.08-1.99 (m, 2H+2H), 1.52-1.49 (m, 4H), 0.86 (t, 3H J=7.2 Hz).

Compound 302: 5-chloro-3-(((1r,4r)-4-(dimethylamino)cyclohexyl)(ethyl)amino)-N-((1-(2-hydroxyethyl)-4,6-dimethyl-2-oxo-1,2-dihydropyridin-3-yl)methyl)-2-methylbenzamide

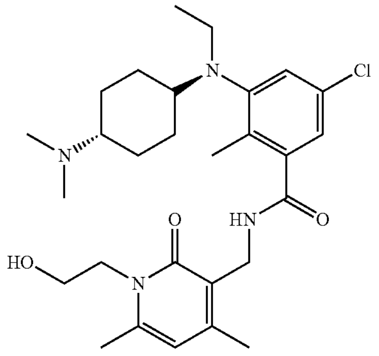

Step 1: Synthesis of methyl 5-chloro-3-(((1r,4r)-4-(dimethylamino)cyclohexyl)(ethyl)amino)-2-methylbenzoate

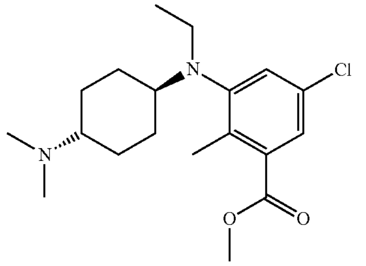

To a stirred solution of ethyl 3-(((1r,4r)-4-((tert-butoxycarbonyl)amino)cyclohexyl)(ethyl)amino)-5-chloro-2-methylbenzoate (3.4 g, 8.0 mmol) in DCM (35 mL) was added TFA (10 mL). The mixture was stirred at room temperature for 1 hour, the solvent was removed under reduced pressure and saturated $NaHCO_3$ solution was added. Extraction was carried out using 10% MeOH/DCM and the combined organic layers were washed with water and brine and dried over anhydrous $Na_2SO_4$. Evaporation of the solvent under reduced pressure gave methyl 3-(((1r,4r)-4-aminocyclohexyl)(ethyl)amino)-5-chloro-2-methylbenzoate (2.5 g, 96%).

The above compound (2.4 g, 7.4 mmol) was dissolved in methanol (25 mL) and the mixture cooled to 0° C. Formalin (2.21 g, 73.95 mmol) was added and the resulting reaction mixture was stirred at same temperature for 20 minutes. Sodium cyanoborohydride (0.92 g, 14.8 mmol) was added and the mixture stirred at room temperature for 1 hour. The solvent was removed under reduced pressure, water added to the residue, and extraction was carried out using 10% MeOH/DCM. The combined organic layers were dried and concentrated under reduced pressure giving the title compound (2.3 g, 88) which was used further without further purification.

Step 2: Synthesis of 5-chloro-3-(((1r,4r)-4-(dimethylamino)cyclohexyl)(ethyl)amino)-2-methylbenzoic acid

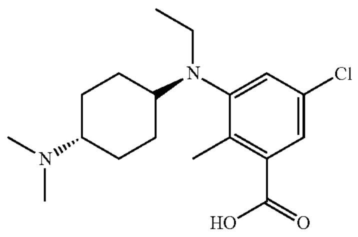

Aqueous NaOH (0.73 g, 18.35 mmol) was added to a solution of ethyl 5-chloro-3-(((1r,4r)-4-(dimethylamino)cyclohexyl)(ethyl)amino)-2-methylbenzoate (2.3 g, 9.1 mmol) in ethanol (25 mL) and the mixture stirred at 60° C. for 1 hour. The ethanol was removed under reduced pressure and the residue acidified using dilute HCl up to pH 6 and adjusted to pH 4 using citric acid. Extraction was carried out using ethyl acetate. The combined organic layers were dried and concentrated giving the title compound (2.0 g, 92%).

Step 3: Synthesis of 5-chloro-3-(((1r,4r)-4-(dimethylamino)cyclohexyl)(ethyl)amino N-((1-(2-hydroxyethyl)-4,6-dimethyl-2-oxo-1,2-dihydropyridin-3-yl)methyl)-2-methylbenzamide

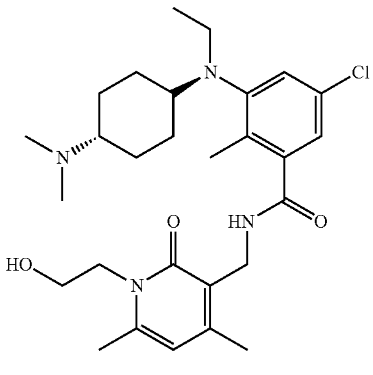

5-Chloro-3-(((1r,4r)-4-(dimethylamino)cyclohexyl)(ethyl)amino)-2-methylbenzoic acid (1 eq) was dissolved in DMSO and 3-(aminomethyl)-1-(2-hydroxyethyl)-4,6-dimethylpyridin-2(1H)-one (2 eq) and triethylamine (1 eq) was added. The reaction mixture was stirred at room temperature for 15 min, PYBOP (1.5 eq) was added and stirring was continued overnight. After completion, the reaction mixture was poured into ice and extracted with 10% MeOH/DCM. The combined organic layers were dried and concentrated to obtain a crude product which was purified by prep. HPLC to afford the title compound (0.07 g, 20%) as the TFA salt. LCMS: 517.35 $(M+1)^+$; HPLC: 91.15% (@ 254 nm) ($R_t$; 5.134; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-$D_2O$ Exchange, 400 MHz) δ 7.17 (s, 1H), 6.94 (s, 1H), 6.01 (s, 1H), 4.26 (m, 2H), 3.99 (s, 2H), 3.01-2.99 (m, 3H), 2.67 (s, 3H+3H), 2.35 (1 Protons merged in solvent peak), 2.33 (m, 2H+2H), 2.19 (s, 3H), 2.12 (s, 3H), 1.94-1.81 (m, 5H) 1.40 (m, 4H), 0.77 (t, 3H).

Compound 306: N-((4,6-dimethyl-2-oxo-1,2-dihydropyridin-3-yl)methyl)-3-(((1r,4r)-4-(dimethylamino)cyclohexyl)(ethyl)amino)-2-methyl-5-(trifluoromethyl)benzamide

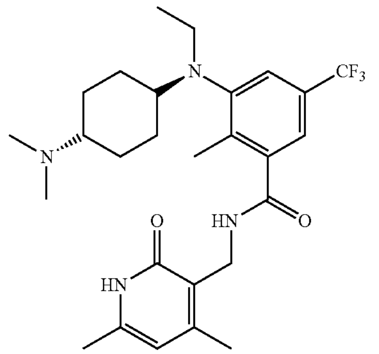

Step 1: Synthesis of methyl 3-(((1r,4r)-4-((tert-butoxycarbonyl)amino)cyclohexyl)amino)-2-methyl-5-(trifluoromethyl)benzoate

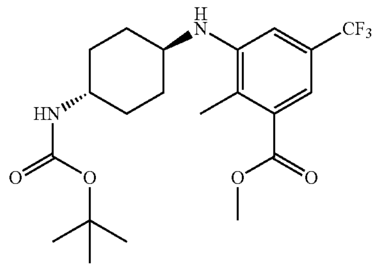 [SMILES: COC(=O)c1cc(C(F)(F)F)cc(N[C@H]2CC[C@H](NC(=O)OC(C)(C)C)CC2)c1C]

Acetic acid (3.28 g, 54.8 mmol) was added to a stirred solution of methyl 3-amino-2-methyl-5-(trifluoromethyl)benzoate (2.0 g, 9.1 mmol) and tert-butyl (4-oxocyclohexyl)carbamate (2.52 g, 11.87 mmol) in dichloroethane (20 mL) and the reaction mixture was stirred at room temperature for 10 minutes. Then sodium triacetoxyborohydride (5.80 g, 27.4 mmol) was added at 0° C. and the reaction mixture was stirred overnight at room temperature. On completion the reaction was quenched with aqueous sodium bicarbonate. The organic phase was separated and the aqueous phase extracted with dichloromethane. The combined organic layers were washed with water, dried, and concentrated under reduced pressure. The crude material was purified by column chromatography to afford the title compound (2.8 g, 82%).

Step 2: Synthesis of methyl 3-(((1r,4r)-4-((tert-butoxycarbonyl)amino)-cyclohexyl)(ethyl)amino)-2-methyl-5-(trifluoromethyl)benzoate

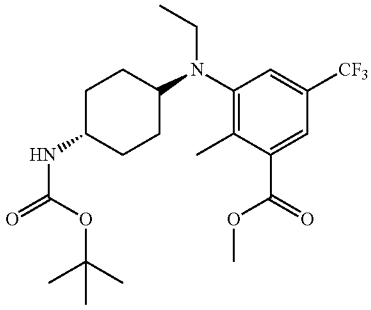

Acetic acid (0.85 g, 14.2 mmol) was added to a stirred solution of methyl 3-(((1r,4r)-4-((tert-butoxycarbonyl)amino)cyclohexyl)amino)-2-methyl-5-(trifluoromethyl)benzoate (0.9 g, 2.40 mmol) and acetaldehyde (0.21 g, 4.80 mmol) in dichloroethane (10 mL) and the reaction mixture stirred at room temperature for 20 minutes. Then sodium triacetoxyborohydride (1.53 g, 7.21 mmol) was added at 0° C. and the reaction mixture stirred overnight at room temperature. The reaction was quenched with aqueous sodium bicarbonate, the organic phase separated and the aqueous phase extracted with dichloromethane. The combined organic layers were washed with water, dried, concentrated under reduced pressure, and the crude material was purified by column chromatography to afford the title compound (0.8 g, 83%).

Step 3: Synthesis of tert-butyl ((1r,4r)-4-((3-(((4,6-dimethyl-2-oxo-1,2-dihydropyridin-3-yl)methyl)carbamoyl)-2-methyl-5-(trifluoromethyl)phenyl)(ethyl)amino)cyclohexyl)carbamate

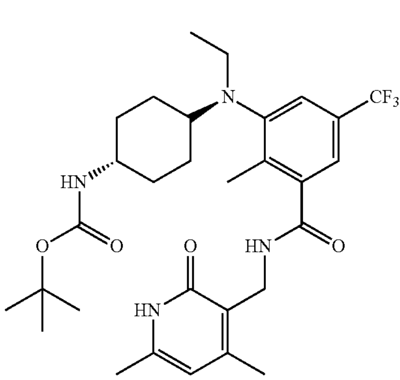

Aqueous sodium hydroxide (0.12 g, 2.97 mmol) was added to a solution of compound methyl 3-(((1r,4r)-4-((tert-butoxycarbonyl)amino)cyclohexyl)(ethyl)amino)-2-methyl-5-(trifluoromethyl)benzoate (0.80 g, 1.98 mmol) in ethanol (8 mL) and the mixture was stirred at 60° C. for 1 hour. After completion of the reaction, ethanol was removed under reduced pressure and the residue acidified using dilute HCl up to pH 6 and then adjusted to pH 4 using citric acid. Extraction was carried out using 10% MeOH/DCM. The combined organic layers were dried and concentrated giving the respective acid (0.7 g,) The acid (0.7 g, 1.8 mmol) was then dissolved in DMSO (10 mL) and 3-(amino methyl)-4,6-dimethylpyridin-2(1H)-one (0.54 g, 3.59 mmol) was added. The reaction mixture was stirred at room temperature for 15 min, PYBOP (1.40 g, 2.69 mmol) was added and stirring was continued overnight. After completion of the reaction, the reaction mixture was poured into ice and extracted with 10% MeOH/DCM. The combined organic layers were dried, concentrated to obtain crude product which was then purified by washing with acetonitrile to afford the title compound (0.7 g, 74%).

Step 4: Synthesis of 3-(((1r,4r)-4-aminocyclohexyl)(ethyl)amino)-N-((4,6-dimethyl-2-oxo-1,2-dihydropyridin-3-yl)methyl)-2-methyl-5-(trifluoromethyl)benzamide

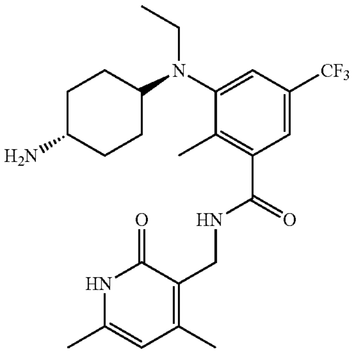

To a solution of tert-butyl ((1r,4r)-4-((3-(((4,6-dimethyl-2-oxo-1,2-dihydropyridin-3-yl)methyl)carbamoyl)-2-methyl-5-(trifluoromethyl)phenyl)(ethyl)amino)cyclohexyl)carbamate (0.7 g, 1.3 mmol) in DCM (10 mL) was added TFA (3 mL) and the reaction mixture stirred at room temperature for 1 h. After completion of reaction, the solvent was removed under reduced pressure and saturated $NaHCO_3$ solution was added. Extraction was carried out using 10% MeOH/DCM; the combined organic layers were washed with water and brine; dried over anhydrous $Na_2SO_4$; filtered and concentrated under reduced pressure to give the title compound (0.56 g, 98%) which was used directly in the next step.

Step 5: Synthesis of N-((4,6-dimethyl-2-oxo-1,2-dihydropyridin-3-yl)methyl)-3-(((1r,4r)-4-(dimethylamino)cyclohexyl)(ethyl)amino)-2-methyl-5-(trifluoromethyl)benzamide

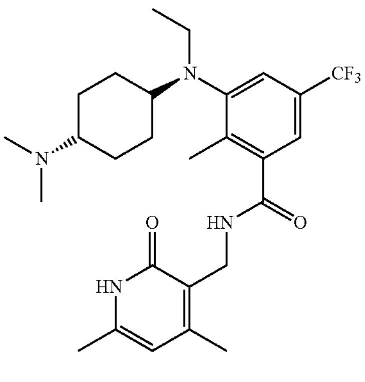

To a solution of 3-(((1r,4r)-4-aminocyclohexyl)(ethyl) amino)-N-((4,6-dimethyl-2-oxo-1,2-dihydropyridin-3-yl) methyl)-2-methyl-5-(trifluoromethyl)benzamide (0.5 g, 1.2 mmol) in DCM (5 mL) at 0° C. was added formalin (0.124 g, 4.13 mmol). The reaction mixture was stirred at 0° C. for 20 minutes. Sodium triacetoxyborohydride (0.63 g, 2.95 mmol) was added and the reaction mixture was stirred at room temperature for 1 h. After completion, water was added and extraction was carried out using 10% MeOH/DCM. The combined organic layers were dried and concentrated under reduced pressure. The crude solid obtained was washed with acetonitrile and ether to afford the title compound (0.4 g, 67%). LCMS: 507.45 $(M+1)^+$; HPLC: 96.81% (@ 210-370 nm) ($R_t$; 4.857; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-d6, 400 MHz) δ 11.46 (bs, 1H), 8.34 (s, 1H), 7.38 (s, 1H), 7.20 (s, 1H), 5.86 (s, 1H), 4.27 (d, 2H), 3.08 (m, 2H), 2.67 (m, 1H), 2.40 (s, 6H), 2.24 (s, 3H), 2.19 (s, 3H), 2.10 (s, 3H), 1.85 (m, 2H), 1.80 (m, 2H), 1.42 (m, 2H), 1.25 (m, 2H), 0.78 (t, 3H).

Compound 390: N-((4,6-dimethyl-2-oxo-1,2-dihydropyridin-3-yl)methyl)-5-(((1r,4r)-4-(dimethylamino)cyclohexyl)(ethyl)amino)-4-methylnicotinamide

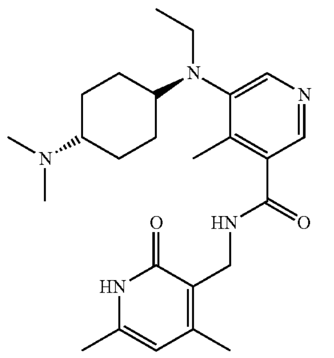

Step 1: Synthesis of methyl 5-amino-4-methylnicotinate

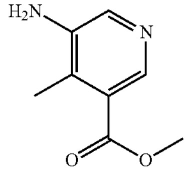

To a stirred solution of 5-amino-4-methylnicotinic acid (5.0 g, 32 mmol) in methanol (75 mL), was added conc. $H_2SO_4$ (5 mL) slowly at room temperature. The mixture was stirred at 70° C. for 12 h. On completion, the solvent was removed under reduced pressure and the residue was neutralized with saturated $NaHCO_3$ solution. Extraction was carried out using EtOAc; the combined organic layers were washed with water, brine and dried over anhydrous $Na_2SO_4$ and concentrated under reduced pressure to give the title compound (4.1 g, 75%) which used without further purification.

Step 2: Synthesis of methyl 5-(((1r,4r)-4-((tert-butoxycarbonyl)amino)cyclohexyl)amino)-4-methylnicotinate

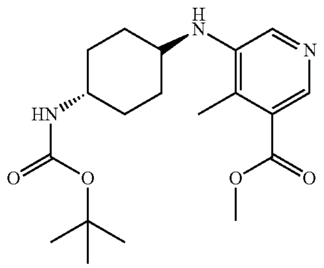

To a stirred solution of methyl 5-amino-4-methylnicotinate (1.20 g, 7.22 mmol) and tert-butyl (4-oxocyclohexyl)carbamate (2.30 g, 10.8 mmol) in dichloroethane (20 mL), was added acetic acid (2.59 g, 43 mmol) and the mixture stirred at room temperature for 10 minutes. Then sodium triacetoxyborohydride (4.59 g, 21.56 mmol) was added at 0° C. and the reaction stirred overnight at room temperature. On completion, the reaction was quenched with aqueous sodium bicarbonate, the organic phase separated and the aqueous phase extracted with dichloromethane. The combined organic layers were dried over anhydrous sodium sulphate and concentrated under reduced pressure. The crude compound was purified by silica gel column chromatography to afford the title compound (0.65 g, 25%).

Step 3: Synthesis of methyl 5-(((1r,4r)-4-((tert-butoxycarbonyl)-amino)-cyclohexyl)-(ethyl)-amino)-4-methylnicotinate

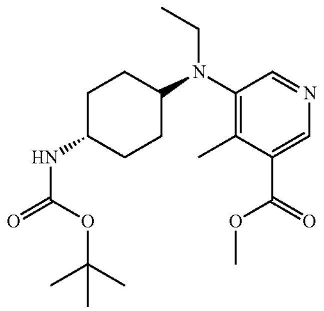

To a stirred solution of methyl 5-(((1r,4r)-4-((tert-butoxycarbonyl)amino)cyclohexyl)amino)-4-methylnicotinate (0.65 g, 1.79 mmol) and acetaldehyde (0.39 g, 8.95 mmol) in dichloroethane (20 mL) was added acetic acid (0.64 g, 10.7 mmol) and the mixture stirred at room temperature for 10 minutes. Then sodium triacetoxyborohydride (1.13 g, 5.33 mmol) was added at 0° C. and the reaction stirred overnight at room temperature. On completion, the reaction was quenched with aqueous sodium bicarbonate, the organic phase separated and the aqueous phase extracted with dichloromethane.

The combined organic layers were dried over anhydrous sodium sulphate and concentrated under reduced pressure to afford the title compound (0.55 g, 79%).

Step 4: Synthesis of tert-butyl ((1r,4r)-4-((5-(((4,6-dimethyl-2-oxo-1,2-dihydropyridin-3-yl)methyl) carbamoyl)-4-methylpyridin-3-yl)(ethyl)amino)cyclohexyl)carbamate

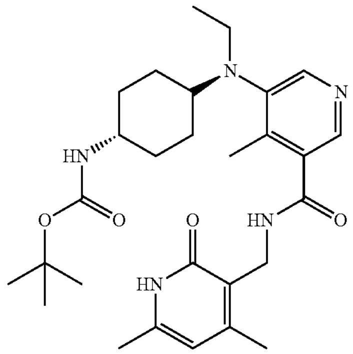

Aqueous NaOH (0.11 g, 2.81 mmol) was added to a solution of methyl 5-(((1r,4r)-4-((tert-butoxycarbonyl)-amino)-cyclohexyl)-(ethyl)-amino)-4-methylnicotinate (0.55 g, 1.40 mmol) in ethanol (7 mL) and the mixture stirred at 60° C. for 1 h. After completion of the reaction, ethanol was removed under reduced pressure and the mixture acidified using dilute HCl up to pH 6 and pH 4 was adjusted using citric acid. Extraction was carried out using ethyl acetate. The combined organic layers were dried concentrated giving respective acid (0.5 g). The above acid (0.5 g, 1.3 mmol) was then dissolved in DMSO (5 mL) and 3-(amino methyl)-4,6-dimethylpyridin-2(1H)-one (0.48 g, 2.65 mmol) was added. The reaction mixture was stirred at room temperature for 15 min, PYBOP (1.02 g, 1.58 mmol) was added and stirring was continued overnight. After completion of the reaction, the mixture was poured into ice and extracted with 10% MeOH/DCM. The combined organic layers were dried and concentrated to a residue which was purified by silica gel chromatography to afford the title compound (0.5 g, 74%).

Step 5: Synthesis of 5-(((1r,r)-4-aminocyclohexyl) (ethyl)amino)-N-((4,6-dimethyl-2-oxo-1,2-dihydropyridin-3-yl)methyl)-4-methylnicotinamide

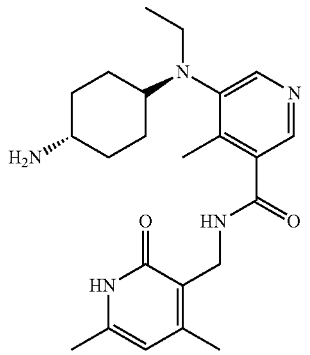

To a stirred solution of tert-butyl ((1r,4r)-4-((5-(((4,6-dimethyl-2-oxo-1,2-dihydropyridin-3-yl)methyl)carbamoyl)-4-methylpyridin-3-yl)(ethyl)amino)cyclohexyl)carbamate (0.5 g, 0.97 mmol) in DCM (10 mL) was added TFA (2 mL). The mixture was stirred at rt for 1 the solvent was removed under reduced pressure. Saturated $NaHCO_3$ solution was added to The residue and extraction was carried out using 10% MeOH/DCM. The combined organic layers were washed with water and brine; dried over anhydrous $Na_2SO_4$; filtered and concentrated under reduced pressure to give the title compound (0.35 g, 88%).

Step 6: Synthesis of N-((4,6-dimethyl-2-oxo-1,2-dihydropyridin-3-yl)methyl)-5-(((1r,4r)-4-(dimethylamino)cyclohexyl)(ethyl)amino)-4-methylnicotinamide

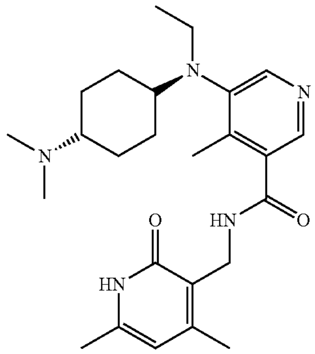

5-(((1r,4r)-4-aminocyclohexyl)(ethyl)amino)-N-((4,6-dimethyl-2-oxo-1,2-dihydropyridin-3-yl)methyl)-4-methylnicotinamide (0.35 g, 0.85 mmol) was dissolved in DCM (5 mL) and formalin (0.089 g, 2.96 mmol) was added at 0° C. The mixture was stirred for 20 minutes, sodium triacetoxyborohydride (0.45 g, 2.12 mmol) was added and the mixture stirred at room temperature for 1 h. After completion, the mixture was diluted with water and extraction was carried out using 10% MeOH/DCM. The combined organic layers were dried and concentrated under reduced pressure. The solid obtained was further purified by washings with acetonitrile and ether to afford the title compound (0.3 g, 80%). LCMS: 440.45 $(M+1)^+$; HPLC: 73.44% & 21.34% (@ 210-370 nm) ($R_t$; 3.769 & 3.965); Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-d6, 400 MHz) δ 11.45 (bs, 1H), 8.34 (s, 1H), 8.29 (s, 1H), 8.07 (s, 1H), 5.86 (s, 1H), 4.27 (d, 2H), 3.18 (m, 1H), 3.01 (m, 2H), 2.22 (s, 3H), 2.19 (s, 3H), 2.12 (s, 6H), 2.10 (s, 3H), 1.74 (m, 2H), 1.64 (m, 2H), 1.40-1.20 (m, 4H), 0.81 (t, 3H).

Compound 308: N-((4,6-dimethyl-2-oxo-1,2-dihydropyridin-3-yl)methyl)-3-(((1r,4r)-4-(dimethylamino)cyclohexyl)(ethyl)amino)-5-methoxy-2-methylbenzamide

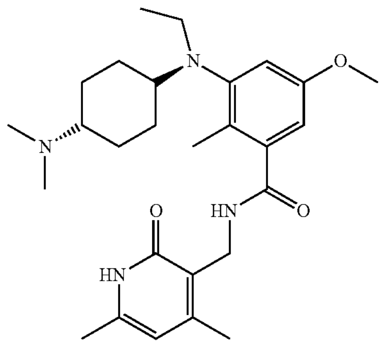

Step 1: Synthesis of methyl 5-methoxy-2-methyl-3-nitrobenzoate

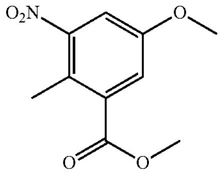

To a stirred solution of 5-hydroxy-2-methyl-3-nitrobenzoic acid (1.50 g, 7.61 mmol) in DMF (15 mL) was added sodium carbonate (3.23 g, 30.5 mmol) and methyl iodide (1.88 mL, 30.5 mmol). The resulting reaction mixture was heated at 60° C. for 8 h. On completion, the reaction mixture was diluted with water and extraction was carried out using ethyl acetate. The combined organic layers were dried and concentrated under reduced pressure to give the crude title compound (1.7 g) which was used directly in the next step.

Step 2: Synthesis of methyl 3-amino-5-methoxy-2-methylbenzoate

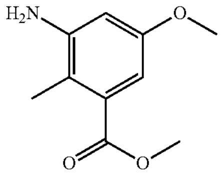

To a stirred solution of methyl 5-methoxy-2-methyl-3-nitrobenzoate (1.7 g, 7.6 mmol) in ethanol (20 mL) was added ammonium chloride (1.7 g, 32 mmol) dissolved in water (20 mL) and iron powder (3.38 g, 60.44 mmol). The mixture was heated at 80° C. for 3 h, filtered and the residue washed well with hot ethanol. The filtrate was concentrated and the residue was basified with aqueous sodium bicarbonate. The aqueous phase was extracted with ethyl acetate. The combined organic layers were washed with water, dried, and concentrated under reduced pressure to give the crude title compound (1.2 g) which was used directly in the next step.

Step 3: Synthesis methyl 3-(((1r,4r)-4-((tert-butoxycarbonyl)amino)cyclohexyl)amino)-5-methoxy-2-methylbenzoate

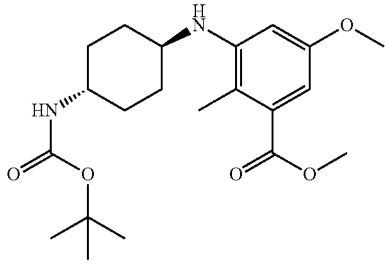 [SMILES: COC(=O)c1cc(OC)cc(N[C@H]2CC[C@H](NC(=O)OC(C)(C)C)CC2)c1C]

To a stirred solution of methyl 3-amino-5-methoxy-2-methylbenzoate (1.2 g, 6.15 mmol) and tert-butyl (4-oxocyclohexyl)carbamate (1.70 g, 7.99 mmol) in dichloroethane (20 mL) was added acetic acid (2.21 g, 36.8 mmol). The reaction was stirred at room temperature for 20 minutes. Sodium triacetoxyborohydride (3.91 g, 18.4 mmol) was added at 0° C. and the reaction mixture was stirred at room temperature overnight. On completion, the reaction was quenched with aqueous sodium bicarbonate, the organic phase separated and the aqueous phase extracted with dichloromethane. The combined organic layers were washed with water, dried, and concentrated under reduced pressure. The crude material obtained was purified by column chromatography to afford the title compound (0.35 g, 14%).

Step 4: Synthesis of methyl 3-(((1r,4r)-4-((tert-butoxycarbonyl)amino)cyclohexyl)-(ethyl)amino)-5-methoxy-2-methylbenzoate

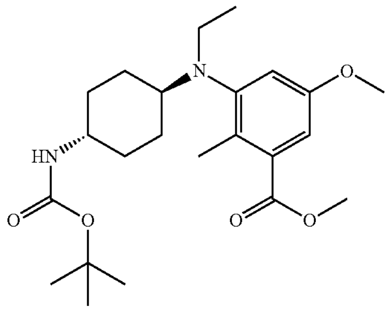 [SMILES: CCN(c1cc(OC)cc(C(=O)OC)c1C)[C@H]1CC[C@H](NC(=O)OC(C)(C)C)CC1]

To a stirred solution of 3-(((1r,4r)-4-((tert-butoxycarbonyl)amino)cyclohexyl)amino)-5-methoxy-2-methylbenzoate (0.35 g, 0.89 mmol) and acetaldehyde (0.2 g, 4.46 mmol) in dichloroethane (5 mL) was added acetic acid (0.32 g, 5.35 mmol) and the reaction mixture stirred at room temperature for 20 minutes. Then sodium triacetoxyborohydride (0.57 g, 2.67 mmol) was added at 0° C. and the reaction mixture was stirred at room temperature for 2 h. On completion, the reaction was quenched with aqueous sodium bicarbonate, the organic phase separated and the aqueous phase extracted with dichloromethane. The combined organic layers were washed with water, dried, and concentrated under reduced pressure. The crude material was purified by column chromatography to afford the title compound (0.3 g, 80%).

Step 5: Synthesis of tert-butyl ((1r,4r)-4-((3-(((4,6-dimethyl-2-oxo-1,2-dihydropyridin-3-yl)methyl)carbamoyl)-5-methoxy-2-methylphenyl)(ethyl)amino)cyclohexyl)carbamate

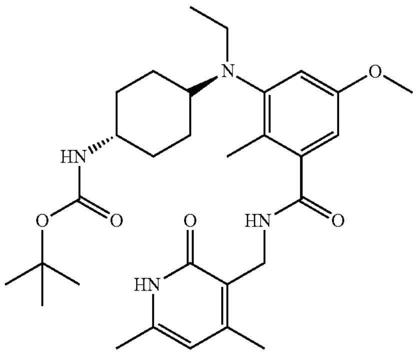

Aqueous NaOH (0.06 g, 1.42 mmol) was added to a solution of methyl 3-(((1r,4r)-4-tert-butoxycarbonyl)amino)cyclohexyl)-(ethyl)amino)-5-methoxy-2-methylbenzoate (0.3 g, 0.71 mmol) in ethanol (4 mL) and the mixture stirred at 60° C. for 1 h. After completion of the reaction, ethanol was removed under reduced pressure and the residue acidified using dilute HCl up to pH 6 and pH 4 was adjusted using citric acid. Extraction was carried out using ethyl acetate. The combined organic layers were dried concentrated to give the crude acid (0.25 g).

The acid (0.25 g, 0.62 mmol) was dissolved in DMSO (3 mL) and 3-(amino methyl)-4,6-dimethylpyridin-2(1H)-one (0.19 g, 1.23 mmol) was added. The reaction mixture was stirred at room temperature for 15 min, PYBOP (0.48 g, 0.92 mmol) was added and the mixture was stirred overnight. The reaction was quenched by pouring into ice, and the mixture was extracted with 10% MeOH/DCM. The combined organic layers were washed with water, dried over anhydrous $Na_2SO_4$, filtered and concentrated under reduced pressure to afford crude material which was purified by column chromatography to give the title compound (0.2 g, 60%).

Step 6: Synthesis of N-((4,6-dimethyl-2-oxo-1,2-dihydropyridin-3-yl)methyl)-3-(((1r,4r)-4-(dimethylamino)cyclohexyl)(ethyl)amino)-5-methoxy-2-methylbenzamide

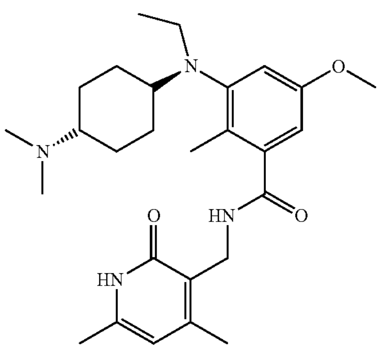

To a solution of tert-butyl ((1r,4r)-4-((3-(((4,6-dimethyl-2-oxo-1,2-dihydropyridin-3-yl)methyl)carbamoyl)-5-methoxy-2-methylphenyl)(ethyl)amino)cyclohexyl)carbamate (0.2 g, 0.37 mmol) in DCM (4 mL) was added TFA (2 mL) and the reaction mixture was stirred at rt for 1 h. After completion of reaction the solvent was removed under reduced pressure and saturated $NaHCO_3$ solution was added. Extraction was carried out using 10% MeOH/DCM; the combined organic layers were washed with water and brine; dried over anhydrous $Na_2SO_4$; filtered and concentrated under reduced pressure to give Boc-deprotected compound (0.15 g,).

The Boc deprotected compound (0.15 g, 0.34 mmol) was dissolved in DCM (2 mL) and formalin (0.035 g, 1.19 mmol) was added to it at 0° C. The resulting reaction mixture was stirred at 0° C. for 10 minutes. Sodium triacetoxyborohydride (0.18 g, 0.85 mmol) was the added and the mixture stirred at temperature carried for 1 h. After reaction completion, water was added and extraction was carried out using 10% MeOH/DCM. The combined organic layers were dried and concentrated under reduced pressure to afford crude material which was purified by prep. HPLC to give the title compound as a TFA salt (0.02 g, 12%). LCMS: 469.80 $(M+1)^+$; HPLC: 96.80% (@ 210-370 nm) ($R_t$; 3.802); Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-d6, 400 MHz) δ 11.46 (s, 1H), 9.42 (s, 1H), 8.06 (s, 1H), 6.75 (s, 1H), 6.58 (s, 1H), 5.86 (s, 1H), 4.26 (d, 2H, J=4 Hz), 3.72 (s, 3H), 3.09 (m, 3H), 2.69 (s, 3H), 2.68 (s, 3H), 2.19 (s, 3H), 2.10 (s, 6H), 1.95 (m, 2H), 1.87 (m, 2H), 1.41 (m, 4H), 0.801 (t, 3H).

Compound 309: N-(((4,6-dimethyl-2-oxo-1,2-dihydropyridin-3-yl)methyl)-3-((4-(dimethylamino)cyclohexyl)(ethyl)amino)-5-(2-hydroxyethoxy)-2-methylbenzamide

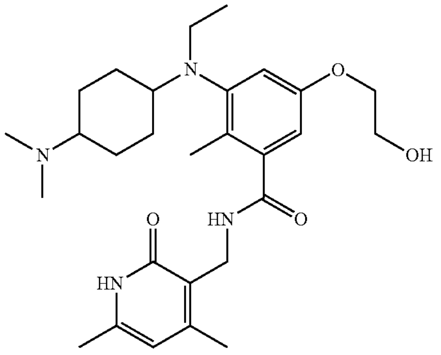 [SMILES: CCN(c1cc(OCCO)cc(C(=O)NCc2c(C)cc(C)[nH]c2=O)c1C)C1CCC(N(C)C)CC1]

Step 1: synthesis of methyl 5-hydroxy-2-methyl-3-nitrobenzoate

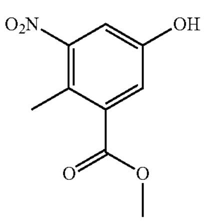

To a stirred solution of 5-hydroxy-2-methyl-3-nitrobenzoic acid (3.50 g, 17.8 mmol) in methanol (40 mL) was added thionyl chloride (3.9 mL, 53 mmol) at 0° C. The reaction mixture was heated at reflux for 3 h. On completion, the solvent was removed under reduced pressure. Aqueous sodium bicarbonate was added, followed by extraction with ethyl acetate. The combined organic layers were washed with water, dried and concentrated under reduced pressure. The crude material was purified by column chromatography to afford the title compound (3.0 g, 80%).

Step 2: synthesis of methyl 5-(2-hydroxyethoxy)-2-methyl-3-nitrobenzoate

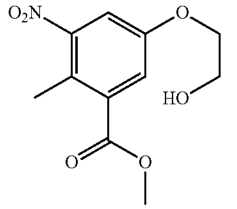

To a stirred solution of methyl 5-hydroxy-2-methyl-3-nitrobenzoate (1.5 g, 7.1 mmol) in ACN (15 mL), were added cesium carbonate (4.6 g, 14 mmol) and 2-bromoethanol (2.5 mL, 35 mmol). The resulting reaction mixture was heated at 80° C. overnight. On completion, the reaction mixture was diluted with water and extraction was carried out using ethyl acetate. The combined organic layers were washed with water, dried and concentrated under reduced pressure. The crude material was purified by silica gel column chromatography to afford the title compound (1.35 g, 74%).

Step 3: synthesis of methyl 3-amino-5-(2-hydroxyethoxy)-2-methylbenzoate

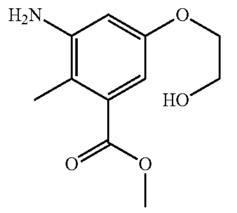 [SMILES: COC(=O)c1cc(OCCO)cc([N+](=O)[O-])c1C]

To a stirred solution of methyl 5-(2-hydroxyethoxy)-2-methyl-3-nitrobenzoate (1.5 g, 5.88 mmol) in ethanol (20 mL), were added ammonium chloride (1.5 g, 28 mmol) dissolved in water (20 mL) and iron powder (1.3 g, 23 mmol). The resulting reaction mixture was heated at 80° C. for 3 h. On completion, the reaction mixture was filtered and the residue washed well with hot ethanol. The filtrate was concentrated and the residue was basified by aqueous sodium bicarbonate. The aqueous phase was extracted with ethyl acetate. The combined organic layers were washed with water, dried, and concentrated under reduced pressure giving the crude title compound (1.3 g) which was used directly.

Step 4: synthesis of methyl 3-((4-((tert-butoxycarbonyl)amino)cyclohexyl)amino)-5-(2-hydroxyethoxy)-2-methyl benzoate

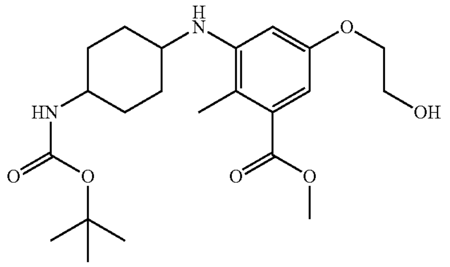 [SMILES: COC(=O)c1cc(OCCO)cc(NC2CCC(NC(=O)OC(C)(C)C)CC2)c1C]

To a stirred solution of methyl 3-amino-5-(2-hydroxyethoxy)-2-methylbenzoate (1.3 g, 5.77 mmol) and tert-butyl (4-oxocyclohexyl)carbamate (1.6 g, 7.5 mmol) in dichloroethane (20 mL) was added acetic acid (2.07 g, 34.66 mmol) and the reaction mixture stirred at room temperature for 20 minutes. Then sodium triacetoxyborohydride (3.7 g, 17 mmol) was added at 0° C. and the reaction mixture was stirred at room temperature overnight. On completion, the reaction was quenched with aqueous sodium bicarbonate, the organic phase separated and the aqueous phase extracted with dichloromethane. The combined organic layers were washed with water, dried, and concentrated under reduced pressure. The crude material was purified by silica gel column chromatography to afford the title compound (2.0 g, 82%) as a mixture of cis/trans-isomers which was carried forward as a mixture through to the final compound 309 which was also isolate as a mixture of cis/trans-isomers.

Step 5: synthesis of methyl 3-((4-((tert-butoxycarbonyl)amino)cyclohexyl)-(ethyl)amino)-5-(2-hydroxyethoxy)-2-methylbenzoate

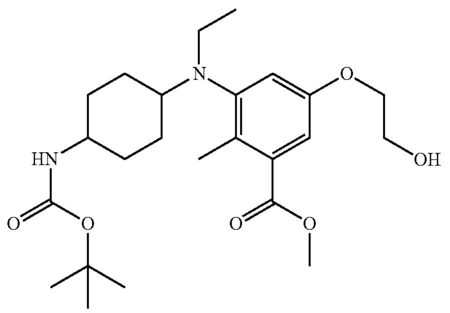 [SMILES: CCN(c1cc(OCCO)cc(C(=O)OC)c1C)C1CCC(NC(=O)OC(C)(C)C)CC1]

To a stirred solution of methyl 3-((4-((tert-butoxycarbonyl)amino)cyclohexyl)amino)-5-(2-hydroxyethoxy)-2-methylbenzoate (2.0 g, 4.7 mmol) and acetaldehyde (0.63 g, 14.2 mmol) in dichloroethane (20 mL) was added acetic acid (1.7 g, 28 mmol) and the reaction mixture stirred at room temperature for 20 minutes. Then sodium triacetoxyborohydride (3.0 g, 14.2 mmol) was added at 0° C. and reaction was stirred at room temperature for 2 h. On completion, the reaction was quenched with aqueous sodium bicarbonate, the organic phase was separated and the aqueous phase extracted with dichloromethane. The combined organic layers were washed with water, dried, concentrated under reduced pressure; Crude material was purified by column chromatography to afford the title compound (1.9 g, 89%).

Step 6: synthesis of tert-butyl (4-((3-(((4,6-dimethyl-2-oxo-1,2-dihydropyridin-3-yl)methyl)carbamoyl)-5-(2-hydroxyethoxy)-2-methylphenyl)-(ethyl)-amino) cyclohexyl)carbamate

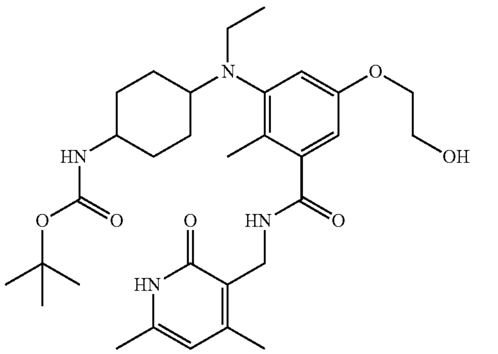 [SMILES: CCN(c1cc(OCCO)cc(C(=O)NCc2c(C)cc(C)[nH]c2=O)c1C)C1CCC(NC(=O)OC(C)(C)C)CC1]

Aqueous NaOH (0.25 g, 6.33 mmol) was added to a solution of methyl 3-((4-((tert-butoxycarbonyl)amino)cyclohexyl)-(ethyl)amino)-5-(2-hydroxyethoxy)-2-methylbenzoate (1.9 g, 4.2 mmol) in ethanol (20 mL) and the mixture stirred at 60° C. for 1 h. After completion of the reaction, ethanol was removed under reduced pressure and acidified using dilute HCl up to pH 6 and pH 4 was adjusted using citric acid. Extraction was carried out using ethyl acetate. The combined organic layers were dried and concentrated giving the corresponding crude acid (1.8 g).

The acid (1.8 g, 4.1 mmol) was then dissolved in DMSO (15 mL) and 3-(amino methyl)-4,6-dimethylpyridin-2(1H)-one (1.25 g, 8.25 mmol) was added. The reaction mixture was stirred at room temperature for 15 min, PYBOP (3.22 g, 6.19 mmol) was added and stirring was continued overnight. After completion of the reaction, the reaction mixture was poured into ice and extracted with 10% MeOH/DCM. The combined organic layers were washed with water, dried over anhydrous $Na_2SO_4$, filtered and concentrated under reduced pressure to afford crude material which was purified by column chromatography to give the title compound (1.4 g, 59%).

Step 7: synthesis of 3-((4-aminocyclohexyl)-(ethyl)-amino)-N-((4,6-dimethyl-2-oxo-1,2-dihydropyridin-3-yl)methyl)-5-(2-hydroxyethoxy)-2-methylbenzamide

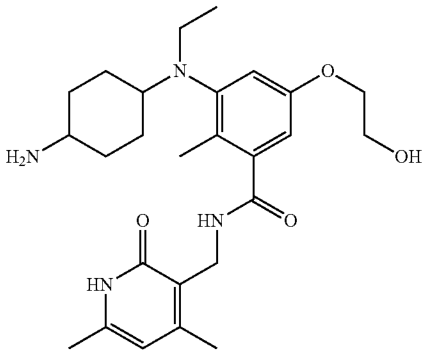 [SMILES: CCN(c1cc(OCCO)cc(C(=O)NCc2c(C)cc(C)[nH]c2=O)c1C)C1CCC(N)CC1]

To a solution of tert-butyl (4-((3-(((4,6-dimethyl-2-oxo-1,2-dihydropyridin-3-yl)methyl)carbamoyl)-5-(2-hydroxyethoxy)-2-methylphenyl)-(ethyl)-amino)cyclohexyl)carbamate (0.80 g, 1.40 mmol) in DCM (5 mL) was added TFA (2 mL) and the reaction mixture was stirred at rt for 1 h. After completion of reaction, the solvent was removed under reduced pressure and saturated $NaHCO_3$ solution was added. Extraction was carried out using 10% MeOH/DCM; the combined organic layers were washed with water and brine; dried over anhydrous $Na_2SO_4$; filtered and concentrated under reduced pressure to give the title compound (0.5 g, 76%).

Step 8: synthesis of N-((4,6-dimethyl-2-oxo-1,2-dihydropyridin-3-yl)methyl)-3-((4-(dimethylamino) cyclohexyl)(ethyl)amino)-5-(2-hydroxyethoxy)-2-methylbenzamide

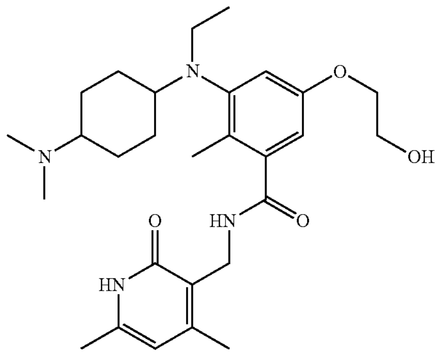 [SMILES: CCN(c1cc(OCCO)cc(C(=O)NCc2c(C)cc(C)[nH]c2=O)c1C)C1CCC(N(C)C)CC1]

To a solution of 3-((4-aminocyclohexyl)-(ethyl)-amino)-N-((4,6-dimethyl-2-oxo-1,2-dihydropyridin-3-yl)methyl)-5-(2-hydroxyethoxy)-2-methylbenzamide (0.30 g, 0.63 mmol) in DCM (3 mL) was added formalin (0.07 g, 2.23 mmol) at 0° C. The resulting reaction mixture was stirred at 0° C. for 20 minutes. Sodium triacetoxyborohydride (0.34 g, 1.59 mmol) was added and the reaction mixture stirred at room temperature for 1 h. After completion, solvent was removed under reduced pressure and water was added to the residue and extraction was carried out using 10% MeOH/DCM. The combined organic layers were dried and concentrated under reduced pressure. The solid obtained was further purified by washings with acetonitrile and ether to afford the title compound N-((4,6-dimethyl-2-oxo-1,2-dihydropyridin-3-yl)methyl)-3-((4-(dimethylamino)cyclohexyl)(ethyl)amino)-5-(2-hydroxyethoxy)-2-methylbenzamide as a mixture of cis/trans-isomers (0.25 g, 78%). LCMS: 499.55 $(M+1)^+$; HPLC: 51.61 & 47.78% (@ 210-370 nm) ($R_t$; 3.539 & 3.751); Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-d6, 400 MHz). δ 11.45 (bs, 1H), 8.04 (s, 1H), 6.68 (s, 1H), 6.51 (s, 1H), 5.85 (s, 1H), 4.25 (d, 2H), 3.92 (t, 2H), 3.67 (t, 2H), 2.97 (m, 2H), 2.18 (s, 3H), 2.16 (s, 3H), 2.12 (s, 3H), 2.10 (s, 3H), 2.08 (s, 3H), 1.89 (s, 3H), 1.76 (m, 3H), 1.65 (bs, 1H), 1.33 (m, 3H), 1.10 (m, 1H), 0.788 (bs, 3H).

Compound 310: N-((4,6-dimethyl-2-oxo-1,2-dihydropyridin-3-yl)methyl)-3-((4-(dimethylamino)cyclohexyl)-(ethyl)-amino)-5-(2-methoxyethoxy)-2-methylbenzamide

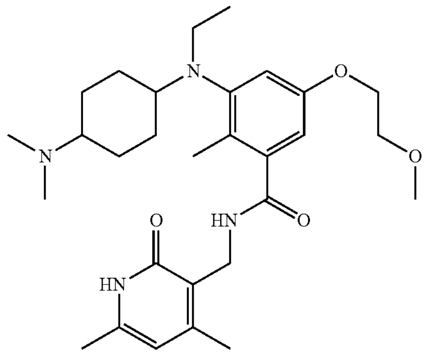

Step 1: synthesis of methyl 5-(2-methoxyethoxy)-2-methyl-3-nitrobenzoate

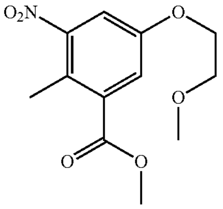 [SMILES: COCCOc1cc(C(=O)OC)c(C)c([N+](=O)[O-])c1]

To stirred solution of methyl 5-hydroxy-2-methyl-3-nitrobenzoate (1.50 g, 7.61 mmol) in ACN (15 mL) was added cesium carbonate (4.96 g, 15.2 mmol) and 1-bromo-2-methoxyethane (1.57 g, 11.4 mmol). The resulting reaction mixture was heated at 80° C. overnight. On completion, the reaction mixture was diluted with water and extraction was carried out using ethyl acetate. The combined organic layers were washed with water, dried, and concentrated under reduced pressure. The crude material was purified by column chromatography to afford the title compound (1.3 g, 68).

Step 2: synthesis of methyl 3-amino-5-(2-methoxyethoxy)-2-methylbenzoate

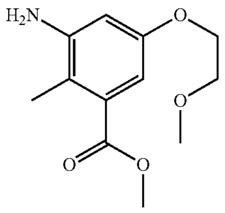

To stirred solution of methyl 5-(2-methoxyethoxy)-2-methyl-3-nitrobenzoate (1.35 g, 4.83 mmol) in ethanol (20 mL) were added ammonium chloride (1.35 g, 25.0 mmol) dissolved in water (20 mL) and iron powder (1.07 g, 19.3 mmol). The resulting reaction mixture was heated at 80° C. for 3 h. On completion, the reaction mixture was filtered and the residue washed well with hot ethanol. The filtrate was concentrated and the residue was basified by aqueous sodium bicarbonate. The aqueous phase was extracted with ethyl acetate. The combined organic layers were washed with water, dried, concentrated under reduced pressure to give the crude title compound (1.23 g) which was used directly in the next step.

Step 3: synthesis of methyl 3-((4-((tert-butoxycarbonyl)amino)cyclohexyl)amino)-5-(2-methoxyethoxy)-2-methyl benzoate

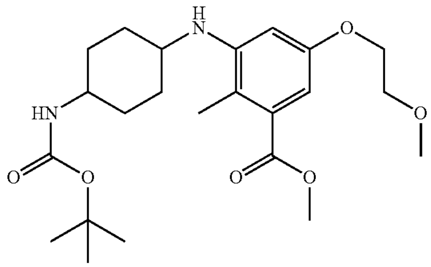 [SMILES: COCCOc1cc(NC2CCC(NC(=O)OC(C)(C)C)CC2)c(C)c(C(=O)OC)c1]

To a stirred solution of methyl 3-amino-5-(2-methoxyethoxy)-2-methylbenzoate (1.23 g, 5.14 mmol) and tert-butyl (4-oxocyclohexyl)carbamate (1.42 g, 6.69 mmol) in dichloroethane (15 mL) was added acetic acid (1.8 g, 31 mmol) and the reaction mixture stirred at room temperature for 20 minutes. Then sodium triacetoxyborohydride (3.2 g, 15 mmol) was added at 0° C. and the reaction was stirred at room temperature overnight. On completion, the reaction was quenched with aqueous sodium bicarbonate, the organic phase separated and the aqueous phase extracted with dichloromethane. The combined organic layers were washed with water, dried and concentrated under reduced pressure. The crude material was purified by column chromatography to afford methyl the title compound (1.6 g, 72%) as a mixture of cis/trans-isomers which was carried forward through to the final compound as a cis/trans-isomer mixture.

Step 4: synthesis of methyl 3-((4-((tert-butoxycarbonyl)amino)cyclohexyl)-(ethyl)-amino)-5-(2-methoxyethoxy)-2-methylbenzoate

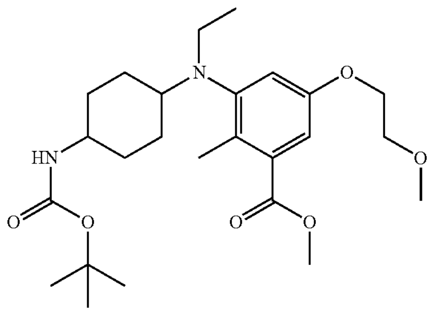 [SMILES: CCN(c1cc(OCCOC)cc(C(=O)OC)c1C)C1CCC(NC(=O)OC(C)(C)C)CC1]

To a stirred solution of methyl 3-((4-((tert-butoxycarbonyl)amino)cyclohexyl)amino)-5-(2-methoxyethoxy)-2-methylbenzoate (1.60 g, 3.67 mmol) and acetaldehyde (0.48 g, 10.9 mmol) in dichloroethane (20 mL) was added acetic acid (1.3 g, 22 mmol) and the reaction mixture stirred at room temperature for 20 minutes. Then sodium triacetoxyborohydride (2.33 g. 11.0 mmol) was added at 0° C. and the reaction was stirred at room temperature for 2 h. The reaction was quenched with aqueous sodium bicarbonate, the organic phase separated and the aqueous phase extracted with dichloromethane. The combined organic layers were washed with water, dried, concentrated under reduced pressure, the crude material was purified by column chromatography to afford the title compound (1.6 g, 94%).

Step 5: synthesis of tert-butyl (4-((3-(((4,6-dimethyl-2-oxo-1,2-dihydropyridin-3-yl)methyl)carbamoyl)-5-(2-methoxyethoxy)-2-methylphenyl)-(ethyl)-amino)-cyclohexyl)carbamate

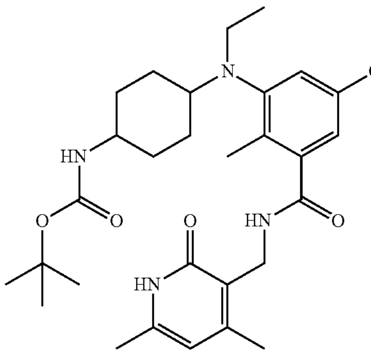

Aqueous NaOH (0.2 g, 5.3 mmol) was added to a solution of methyl 3-((4-((tert-butoxycarbonyl)amino)cyclohexyl)-(ethyl)-amino)-5-(2-methoxyethoxy)-2-methylbenzoate (1.6 g, 3.5 mmol) in ethanol (20 mL) and stirred at 60° C. for 1 h. After completion of the reaction, ethanol was removed under reduced pressure and acidified using dilute HCl up to pH 6 and pH 4 was adjusted using citric acid. Extraction was carried out using ethyl acetate. The combined organic layers were concentrated to give the corresponding crude acid (1.4 g).

The acid (1.4 g, 3.1 mmol) was then dissolved in DMSO (15 mL) and 3-(amino methyl)-4,6-dimethylpyridin-2(1H)-one (0.95 g, 6.2 mmol) was added. The reaction mixture was stirred at room temperature for 15 min, PYBOP (2.4 g, 4.6 mmol) was added and stirring was continued overnight. The reaction mixture was poured into ice and extracted with 10% MeOH/DCM. The combined organic layers were washed with water, dried over anhydrous $Na_2SO_4$, filtered and concentrated under reduced pressure to afford crude material which was purified by column chromatography to afford the title compound (1.9 g, 95%).

Step 5: synthesis of N-((4,6-dimethyl-2-oxo-1,2-dihydropyridin-3-yl)methyl)-3-((4-(dimethylamino)cyclohexyl)-(ethyl)-amino)-5-(2-methoxyethoxy)-2-methylbenzamide

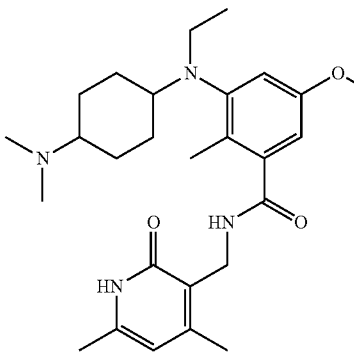

To a solution of methyl 3-((4-((tert-butoxycarbonyl)amino)cyclohexyl)-(ethyl)-amino)-5-(2-methoxyethoxy)-2-methylbenzoate (1.2 g, 2.67 mmol) in DCM (10 mL) was added TFA (2 mL) and the reaction mixture stirred at rt for 1 h. After completion of reaction, the solvent was removed under reduced pressure and saturated $NaHCO_3$ solution was added to the residue. Extraction was carried out using 10% MeOH/DCM; the combined organic layers were washed with water and brine; dried over anhydrous $Na_2SO_4$; filtered and concentrated under reduced pressure to give the Boc deprotected-compound (0.78 g,).

The Boc deprotected compound (0.30 g, 0.62 mmol) was dissolved in DCM (3 mL) and formalin (0.07 g, 2.33 mmol) was added at 0° C. The resulting reaction mixture was stirred at 0° C. for 20 minutes. Sodium triacetoxyborohydride (0.33 g, 1.56 mmol) was added and the reaction mixture was stirred at room temperature for 1 h. After completion, the solvent was removed under reduced pressure and water was added to the residue, extraction was carried out using 10% MeOH/DCM. The combined organic layers were dried and concentrated under reduced pressure to afford crude material which was purified by prep. HPLC to give the title compound N-((4,6-dimethyl-2-oxo-1,2-dihydropyridin-3-yl)methyl)-3-((4-(dimethylamino)cyclohexyl)-(ethyl)-amino)-5-(2-methoxyethoxy)-2-methylbenzamide as a mixture of cis/trans-isomers (0.02 g, 6.3%). LCMS: 513.60 $(M+1)^+$; HPLC: 44.48% & 50.77% (@ 210-370 nm) ($R_t$; 3.879 & 4.316); Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-d6, 400 MHz) δ 11.45 (s, 1H), 8.04 (s, 1H), 6.68 (s, 1H), 6.52 (s, 1H), 5.85 (s, 1H), 4.25 (d, 2H, J=4.4 Hz), 4.03 (bs, 2H), 3.61 (bs, 2H), 3.28 (s, 3H), 3.10 (m, 1H), 2.95 (m, 2H), 2.18 (s, 6H), 2.12 (s, 3H), 2.10 (s, 3H), 2.08 (s, 3H), 1.77 (m, 2H), 1.65 (bs, 2H), 1.33 (m, 3H), 1.15 (m, 1H), 0.78 (t, 3H, J=4 Hz).

Compound 311: N-((4,6-dimethyl-2-oxo-1,2-dihydropyridin-3-yl)methyl)-3-(((1r,4r)-4-(dimethylamino)cyclohexyl)-(ethyl)-amino)-5-(ethylthio)-2-methylbenzamide

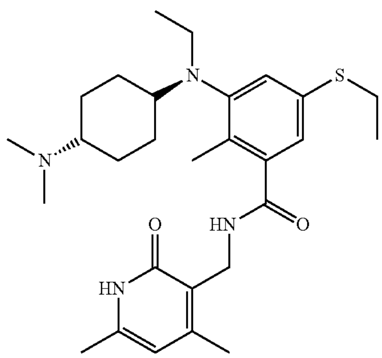

Step 1: synthesis of 5-bromo-2-methyl-3-nitrobenzoic acid

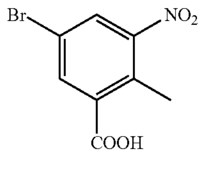

To stirred solution of 2-methyl-3-nitrobenzoic acid (50.0 g, 276 mmol) in conc. $H_2SO_4$ (200 mL) was added 1,3-dibromo-5,5-dimethyl-2,4-imidazolidinedione (43.4 g, 151.8 mmol) portion-wise at room temperature and the reaction mixture was stirred at room temperature for 5 h. On completion, the reaction mixture was poured on ice cold water, the resulting precipitate was filtered, washed with water, and dried under vacuum giving desired crude title compound (71.7 g, 99.9%) which was used directly in the next step.

Step 2: synthesis of methyl 5-bromo-2-methyl-3-nitrobenzoate

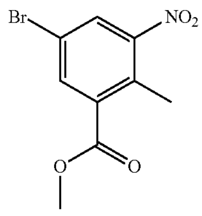

To stirred solution of 5-bromo-2-methyl-3-nitrobenzoic acid (285 g, 1104 mmol) in DMF (2.8 L) was added sodium carbonate (468 g, 4415 mmol) followed by addition of methyl iodide (626 g, 4415 mmol) at room temperature. The resulting reaction mixture was heated at 60° C. for 8 h. After completion, the reaction mixture was filtered and washed with ethyl acetate. The combined filtrates were washed with water and the aqueous phase was back extracted with ethyl acetate. The combined organic layers were dried over anhydrous sodium sulphate, filtered and concentrated under reduced pressure to afford the title compound as an off-white solid (290 g, 97% yield). The isolated compound was taken directly into the next step.

Step 3: synthesis of methyl 3-amino-5-bromo-2-methylbenzoate

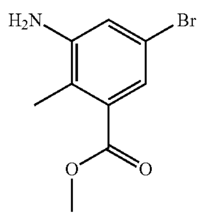

To stirred solution of methyl 5-bromo-2-methyl-3-nitrobenzoate (290 g, 1060 mmol) in ethanol (1.5 L) was added aqueous ammonium chloride (283 g, 5290 mmol dissolved in 1.5 L water). The resulting mixture was stirred and heated at 80° C. followed by addition of iron powder (472 g, 8450 mmol) in portions at 80° C. The resulting reaction mixture was heated at 80° C. for 12 h. After completion, the reaction mixture was hot filtered over celite and the celite bed was washed with methanol (5 L) followed by washing with 30% MeOH in DCM (5 L). The combined filtrate was concentrated in-vacuo, the residue obtained was diluted with aqueous bicarbonate and extracted with ethyl acetate. The combined organic layers were dried over anhydrous sodium sulphate, filtered and concentrated under reduced pressure to afford the title compound as brown solid (220 g, 89% yield).

Step 4: synthesis of methyl 5-bromo-3-(((1R,4R)-4-((tert-butoxycarbonyl)-amino)-cyclohexyl)amino)-2-methylbenzoate

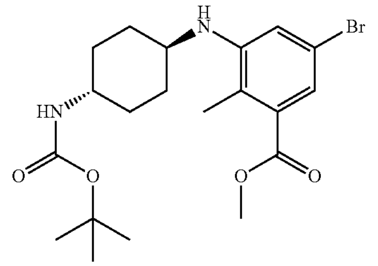 [SMILES: COC(=O)c1cc(Br)cc(N[C@H]2CC[C@H](NC(=O)OC(C)(C)C)CC2)c1C]

To a stirred solution of methyl 3-amino-5-bromo-2-methylbenzoate (15.0 g, 617 mmol) and tert-butyl (4-oxocyclohexyl)carbamate (17.1 g, 80.2 mmol) in dichloroethane (150 mL) was added acetic acid (22.2 g, 370 mmol) and the reaction mixture stirred at room temperature for 10 minutes. Then sodium triacetoxyborohydride (39.3 g, 185 mmol) was added at 0° C. and the reaction stirred overnight at room temperature. On completion, the reaction was quenched with aqueous sodium bicarbonate, the organic phase separated and the aqueous phase extracted with dichloromethane. The combined organic layers were washed with water, dried, and concentrated under reduced pressure. The crude material was purified by column chromatography to afford the title compound methyl 5-bromo-3-(((1r,4r)-4-((tert-butoxycarbonyl)-amino)-cyclohexyl)amino)-2-methylbenzoate (10.5 g, 39%).

Step 5: synthesis of methyl 5-bromo-3-(((1r,4r)-4-((tert-butoxycarbonyl)-amino)-cyclohexyl)-(ethyl)-amino)-2-methylbenzoate

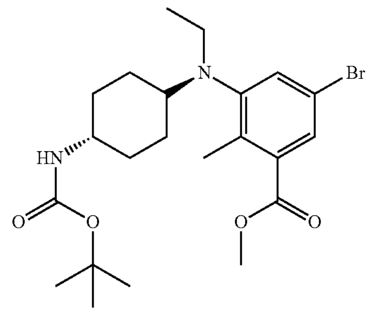

To a stirred solution of 5-bromo-3-(((1r,4r)-4-((tert-butoxycarbonyl)-amino)-cyclohexyl)amino)-2-methylbenzoate (10.0 g, 22.7 mmol) and acetaldehyde (2.99 g, 68 mmol) in dichloroethane (100 mL) was added acetic acid (8.18 g, 136 mmol) and the reaction mixture was stirred at room temperature for 20 minutes. Then sodium triacetoxyborohydride (14.5 g, 68.1 mmol) was added at 0° C. and the reaction stirred overnight at room temperature. On completion, the reaction was quenched with aqueous sodium bicarbonate, the organic phase separated and the aqueous phase extracted with dichloromethane. The combined organic layers were washed with water, dried, concentrated under reduced pressure, crude material was purified by column chromatography to afford the title compound (9.0 g, 84%).

Step 6: synthesis of tert-butyl ((1r,4r)-4-((5-bromo-3-(((4,6-dimethyl-2-oxo-1,2-dihydropyridin-3-yl)methyl)carbamoyl)-2-methylphenyl)-(ethyl)-amino)-cyclohexyl)carbamate

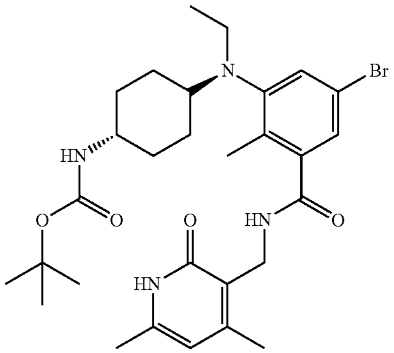

Aqueous NaOH (1.15 g, 28.8 mmol) was added to a solution of methyl 5-bromo-3-(((1r,4r)-4-((tert-butoxycarbonyl)-amino)-cyclohexyl)-(ethyl)-amino)-2-methylbenzoate (9.0 g, 19 mmol) in ethanol (100 mL) and the mixture stirred at 60° C. for 1 h. After completion of the reaction, ethanol was removed under reduced pressure and the residue was acidified using dilute HCl up to pH 6 and adjusted to pH 4 with citric acid. Extraction was carried out using 10% MeOH/DCM. The combined organic layers were dried and concentrated to give the crude acid (8.6 g,).

The acid (8.6 g, 19 mmol) was then dissolved in DMSO (10 mL) and 3-(amino methyl)-4,6-dimethylpyridin-2(1H)-one (5.74 g, 37.8 mmol) was added. The reaction mixture was stirred at room temperature for 15 min, PYBOP (14.7 g, 2845 mmol) was added and stirring was continued overnight. The reaction mixture was poured into ice and extracted with 10% MeOH/DCM. The combined organic layers were dried, concentrated to obtain crude material which was purified by washing with acetonitrile to afford the title compound (10.2 g, 92%).

Step 7: synthesis of 3-(((1r,4r)-4-aminocyclohexyl)-(ethyl)-amino)-5-bromo-N-((4,6-dimethyl-2-oxo-1,2-dihydropyridin-3-yl)methyl)-2-methylbenzamide

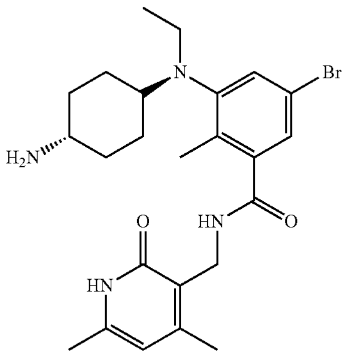

To a solution of tert-butyl ((1r,4r)-4-((5-bromo-3-(((4,6-dimethyl-2-oxo-1,2-dihydropyridin-3-yl)methyl)carbamoyl)-2-methylphenyl)-(ethyl)-amino)-cyclohexyl)carbamate (3.0 g, 5.10 mmol) in DCM (20 mL) was added TFA (5 mL) and the reaction mixture was stirred at rt for 1 h. After completion of reaction, the solvent was removed under reduced pressure and saturated $NaHCO_3$ solution was added to the residue. Extraction was carried out using 10% MeOH/DCM; the combined organic layers were washed with water and brine; dried over anhydrous $Na_2SO_4$; filtered and concentrated under reduced pressure to give the title compound (2.2 g, 88%) which was used directly in the next step.

Step 8: synthesis of 5-bromo-N-((4,6-dimethyl-2-oxo-1,2-dihydropyridin-3-yl)methyl)-3-(((1r,4r)-4-(dimethylamino)cyclohexyl)-(ethyl)-amino)-2-methylbenzamide

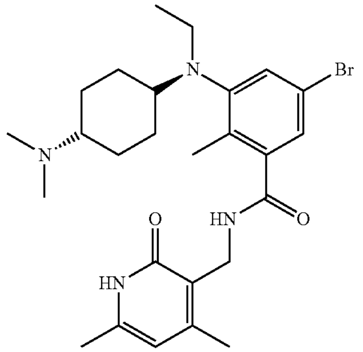

To a solution of 3-(((1r,4r)-4-aminocyclohexyl)-(ethyl)-amino)-5-bromo-N-((4,6-dimethyl-2-oxo-1,2-dihydropyridin-3-yl)methyl)-2-methylbenzamide (2.20 g, 4.50 mmol) in DCM (25 mL) was added formalin (0.49 g, 16.3 mmol) at 0° C. The resulting reaction mixture was stirred at 0° C. for 20 minutes. Sodium triacetoxyborohydride (2.39 g, 11.2 mmol) was added and the reaction mixture was stirred at room temperature for 1 h. After completion, water was added and extraction was carried out using 10% MeOH/DCM. The combined organic layers were dried and concentrated under reduced pressure to give the title compound (2.3 g, 98%) which was used directly in the next step.

Step 9: synthesis of N-((4,6-dimethyl-2-oxo-1,2-dihydropyridin-3-yl)methyl)-3-(((1r,4r)-4-(dimethylamino)cyclohexyl)-(ethyl)-amino)-5-(ethylthio)-2-methylbenzamide

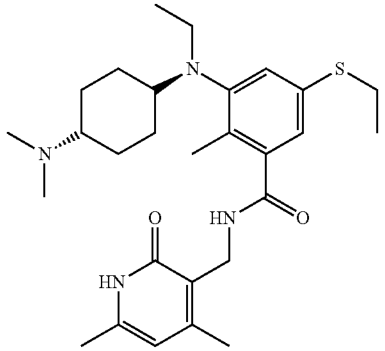

To a stirred solution of 5-bromo-N-((4,6-dimethyl-2-oxo-1,2-dihydropyridin-3-yl)methyl)-3-(((1r,4r)-4-(dimethylamino)cyclohexyl)-(ethyl)-amino)-2-methylbenzamide (0.40 g, 0.77 mmol) in dioxane was added ethanethiol (0.048 g, 0.77 mmol) and DIPEA (2.70 mL, 1.55 mmol) and the reaction mixture then purged with argon for 10 min. Then, Pd $(OAc)_2$ (0.009 g, 0.038 mmol) and Xantphos (0.045 g, 0.077 mmol) were added and the reaction mixture was stirred at 100° C. overnight. After completion of the reaction, water was added and extraction was carried out using ethyl acetate. The combined organic layers were washed with water, dried over anhydrous $Na_2SO_4$, filtered and concentrated under reduced pressure to afford crude material which was purified by column chromatography to give the title compound (0.17 g, 44%). LCMS: 499.55 $(M+1)^+$; HPLC: 99.30% (at 210-370 nm) ($R_t$; 4.264); Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-d6, 400 MHz) δ 11.46 (bs, 1H), 9.37 (s, 1H), 8.14 (s, 1H), 7.08 (s, 1H), 6.89 (s, 1H), 5.86 (s, 1H), 4.25 (d, 2H, J=4 Hz), 3.15-2.90 (m, 6H), 2.69 (s, 3H), 2.68 (s, 3H), 2.18 (s, 3H), 2.14 (s, 3H), 2.10 (s, 3H), 1.94 (m, 2H), 1.85 (m, 2H), 1.41 (m, 4H), 1.20 (t, 3H, J=7.2), 0.78 (t, 3H, J=6 Hz).

Compound 313: 5-chloro-N-((4,6-dimethyl-2-oxo-1,2-dihydropyridin-3-yl)methyl)-3-(ethyl(4-hydroxycyclohexyl)-amino)-2-methylbenzamide

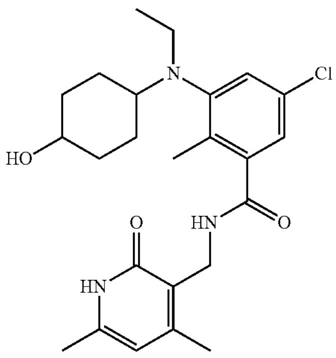 [SMILES: CCN(c1cc(Cl)cc(C(=O)NCc2c(C)cc(C)[nH]c2=O)c1C)C1CCC(O)CC1]

Step 1: synthesis of methyl 3-(1,4-dioxaspiro[4.5]decan-8-ylamino)-5-chloro-2-methylbenzoate

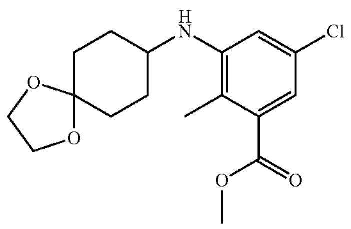 [SMILES: COC(=O)c1cc(Cl)cc(NC2CCC3(CC2)OCCO3)c1C]

To a stirred solution of methyl 3-amino-5-chloro-2-methylbenzoate (5.0 g, 25 mmol) and 1,4-dioxaspiro[4.5]decan-8-one (5.86 g, 37.8 mmol) in dichloroethane (50 mL) was added acetic acid (9.0 g, 150 mmol) and the reaction mixture stirred at room temperature for 10 minutes. Then sodium triacetoxyborohydride (15.9 g, 752 mmol) was added at 0° C. and the reaction stirred overnight at room temperature. On completion, the reaction was quenched with aqueous sodium bicarbonate, the organic phase separated and the aqueous phase extracted with dichloromethane. The combined organic layers were dried over anhydrous sodium sulphate and concentrated under reduced pressure. The crude material was purified by silica gel column chromatography to afford the title compound (6.6 g, 76%).

Step 2: synthesis of methyl 5-chloro-3-(ethyl(1,4-dioxaspiro[4.5]decan-8-yl)amino)-2-methylbenzoate

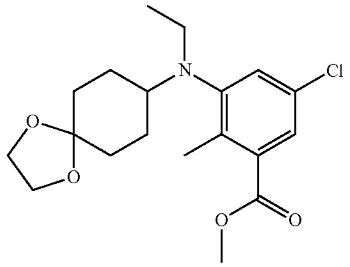 [SMILES: CCN(c1cc(Cl)cc(C(=O)OC)c1C)C1CCC2(CC1)OCCO2]

To a stirred solution of methyl 3-(1,4-dioxaspiro[4.5]decan-8-ylamino)-5-chloro-2-methylbenzoate (6.6 g, 19 mmol) and acetaldehyde (2.56 g, 58.4 mmol) in dichloroethane (70 mL) was added acetic acid (7.0 g, 120 mmol) and the reaction mixture stirred at room temperature for 10 minutes. Then sodium triacetoxyborohydride (12 g, 57 mmol) was added at 0° C. and the reaction stirred overnight at room temperature. On completion, the reaction was quenched with aqueous sodium bicarbonate, the organic phase separated and the aqueous phase extracted with dichloromethane. The combined organic layers were dried over anhydrous sodium sulphate and concentrated under reduced pressure. The residue was purified by silica gel column chromatography to afford the title compound (4.0 g, 56%).

Step 3: synthesis of 5-chloro-N-((4,6-dimethyl-2-oxo-1,2-dihydropyridin-3-yl)methyl)-3-(ethyl(1,4-dioxaspiro[4.5]decan-8-yl)amino)-2-methylbenzamide

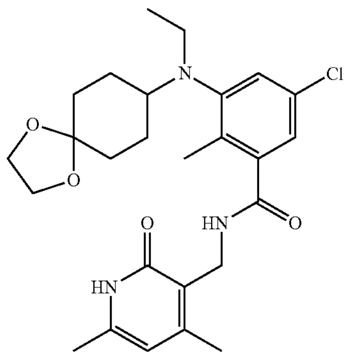 [SMILES: CCN(c1cc(Cl)cc(C(=O)NCc2c(C)cc(C)[nH]c2=O)c1C)C1CCC2(CC1)OCCO2]

Aqueous NaOH (1.5 g, 38 mmol) was added to a solution of methyl 5-chloro-3-(ethyl(1,4-dioxaspiro[4.5]decan-8-yl)amino)-2-methylbenzoate (6.9 g, 19 mmol) in ethanol (70 mL) and the mixture stirred at 60° C. for 1 h. After completion of the reaction, ethanol was removed under reduced pressure and acidified using dilute HCl up to pH 6 and adjusted to pH 4 with citric acid. Extraction was carried out using ethyl acetate. The combined organic layers were dried concentrated to give the crude acid (6.5 g).

The crude acid (6.5 g, 18 mmol) was dissolved in DMSO (50 mL) and 3-(amino methyl)-4,6-dimethylpyridin-2(1H)-one (5.6 g, 37 mmol) was added. The reaction mixture was stirred at room temperature for 15 min, PYBOP (14.3 g, 27.5 mmol) was added and stirring was continued overnight. The reaction mixture was poured into ice and extracted with 10% MeOH/DCM. The combined organic layers were washed with water, dried, concentrated under reduced pressure to give the title compound (5.9 g 66%) which was used directly in the next step.

Step 4: synthesis of 5-chloro-N-((4,6-dimethyl-2-oxo-1,2-dihydropyridin-3-yl)methyl)-3-(ethyl(4-oxocyclohexyl)amino)-2-methylbenzamide

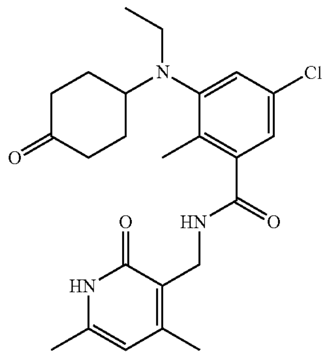 [SMILES: CCN(c1cc(Cl)cc(C(=O)NCc2c(C)cc(C)[nH]c2=O)c1C)C1CCC(=O)CC1]

To a stirred solution of 5-chloro-N-((4,6-dimethyl-2-oxo-1,2-dihydropyridin-3-yl)methyl)-3-(ethyl(1,4-dioxaspiro[4.5]decan-8-yl)amino)-2-methylbenzamide (2.0 g, 4.1 mmol) in acetone: water (14 mL+6 mL) was added PTSA (3.1 g, 16 mmol). The resulting reaction mixture was stirred at 70° C. overnight. On completion, the solvent was removed under reduced pressure and the residue was basified with aqueous sodium bicarbonate. The aqueous phase was extracted with ethyl acetate. The combined organic layers were washed with water, dried, concentrated under reduced pressure to give the title compound (1.5 g, 83%) which was used directly in the next step.

Step 5: synthesis of 5-chloro-N-((4,6-dimethyl-2-oxo-1,2-dihydropyridin-3-yl)methyl)-3-(ethyl(4-hydroxycyclohexyl)-amino)-2-methylbenzamide

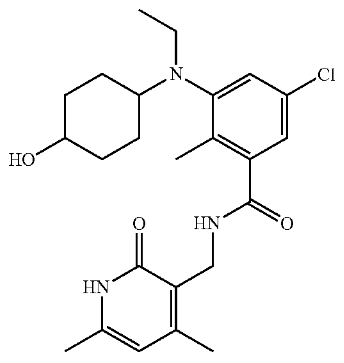 [SMILES: CCN(c1cc(Cl)cc(C(=O)NCc2c(C)cc(C)[nH]c2=O)c1C)C1CCC(O)CC1]

To a stirred solution of 5-chloro-N-((4,6-dimethyl-2-oxo-1,2-dihydropyridin-3-yl)methyl)-3-(ethyl(4-oxocyclohexyl)amino)-2-methylbenzamide (0.30 g, 0.68 mmol) in MeOH was added $NaBH_4$ (0.038 g, 1.01 mmol) slowly at 0° C. The resulting reaction mixture was stirred at 0° C. for 2 h. On completion, the reaction was quenched with water and extracted with ethyl acetate. The combined organic layers were washed with water, dried, concentrated under reduced pressure and the crude material obtained was purified by acetonitrile and ether washings to afford the title compound as a mixture of isomers (175 mg, 58%). LCMS: 446.35 $(M+1)^+$; HPLC: 74.32% & 24.18% (@ 210-370 nm) ($R_t$; 5.157 & 5.276); Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-d6, 400 MHz) δ 11.49 (s, 1H), 8.25 (s, 1H), 7.17 (s, 1H), 6.96 (s, 1H), 5.86 (s, 1H), 4.25 (d, 2H, J=4 Hz), 3.33 (m, 1H), 3.04 (m, 2H), 2.19 (s, 3H), 2.14 (s, 3H), 2.10 (s, 3H), 1.78 (m, 2H), 1.66 (m, 2H), 1.38 (m, 3H), 1.10 (m, 2H), 0.78 (t, 3H).

Compound 315: N-((4,6-dimethyl-2-oxo-1,2-dihydropyridin-3-yl)methyl)-3-(((1r,4r)-4-(dimethylamino)cyclohexyl)(ethyl)amino)-2-methyl-5-(tetrahydro-2H-pyran-4-yl)benzamide

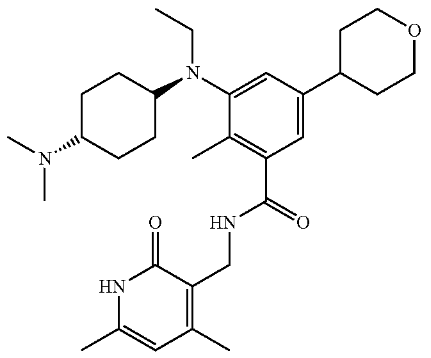

Step 1: Synthesis of 5-(3,6-dihydro-2H-pyran-4-yl)-N-((4,6-dimethyl-2-oxo-1,2-dihydropyridin-3-yl)methyl)-3-(((1r,4r)-4-(dimethylamino)cyclohexyl)(ethyl)amino)-2-methylbenzamide

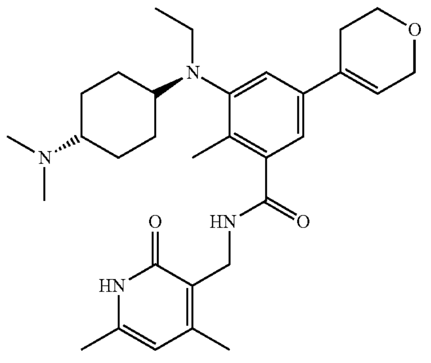

To a stirred solution of 5-bromo-N-((4,6-dimethyl-2-oxo-1,2-dihydropyridin-3-yl)methyl)-3-(((1r,4r)-4-(dimethylamino)cyclohexyl)(ethyl)amino)-2-methylbenzamide (0.30 g, 0.58 mmol) and 2-(3,6-dihydro-2H-pyran-4-yl)-4,4,5,5-tetramethyl-1,3,2-dioxaborolane (0.18 g, 0.88 mmol) in dioxane-water mixture was added $Na_2CO_3$ (0.22 g, 2.07 mmol). The solution was purged with argon for 15 min, Pd $(PPh_3)_4$ (0.067 g, 0.05 mmol) was added and the solution was purged again with argon for 10 min. The reaction mixture was heated at 100° C. for 3 hours. On completion, the reaction mixture was diluted with water and extracted with 10% MeOH/DCM. The combined organic layers were dried over $Na_2SO_4$ and the solvent removed under reduced pressure to afford the title compound (0.30 g, 98%).

Step 2: Synthesis of N-((4,6-dimethyl-2-oxo-1,2-dihydropyridin-3-yl)methyl)-3-(((1r,4r)-4-(dimethylamino)cyclohexyl)(ethyl)amino)-2-methyl-5-(tetrahydro-2H-pyran-4-yl)benzamide

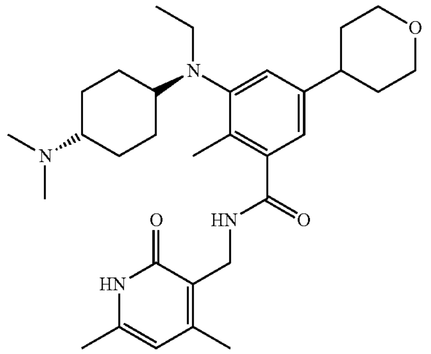

To a stirred solution of 5-(3,6-dihydro-2H-pyran-4-yl)-N-((4,6-dimethyl-2-oxo-1,2-dihydropyridin-3-yl)methyl)-3-(((1r,4r)-4-(dimethylamino)cyclohexyl)(ethyl)amino)-2-methylbenzamide (0.3 g, 0.576 mmol) in methanol, was added a catalytic amount of 10% Pd/C. The reaction mixture was stirred at room temperature under hydrogen balloon pressure for 1 hour. On completion, the reaction mixture was filtered through a celite bed, the celite washed with methanol and the filtrate concentrated under reduced pressure, to yield a crude compound which was purified by prep. HPLC to afford the target compound N-((4,6-dimethyl-2-oxo-1,2-dihydropyridin-3-yl)methyl)-3-(((1s,4s)-4-(dimethylamino)cyclohexyl)(ethyl)amino)-2-methyl-5-(tetrahydro-2H-pyran-4-yl)benzamide as the TFA salt (0.08 g, 26%).

LCMS: 523.60 $(M+1)^+$; HPLC: 48.41+51.05% (@ 210 nm-370 nm) ($R_t$; 3.93& 3.99); Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-$d_6$, 400 MHz) δ 11.47 (bs, 1H), 8.39 (t, 1H), 8.08 (s, 1H), 7.07 (s, 1H), 6.86 (s, 1H), 5.87 (s, 1H), 4.26 (d, 2H, J=2.8 Hz), 3.94-3.92 (m, 2H), 3.41 (m, 2H), 3.09-2.89 (m, 3H), 2.69 (s, 3H+3H), 2.19 (s, 3H+3H), 2.11 (s, 3H), 1.99-1.86 (m, 5H), 1.64 (m, 4H), 1.42 (m, 3H), 1.25 (m, 2H), 0.79 (t, 3H).

Compound 319: N-((4,6-dimethyl-2-oxo-1,2-dihydropyridin-3-yl)methyl)-3-(((1r,4r)-4-(dimethylamino)cyclohexyl)(ethyl)amino)-5-(ethylsulfonyl)-2-methylbenzamide

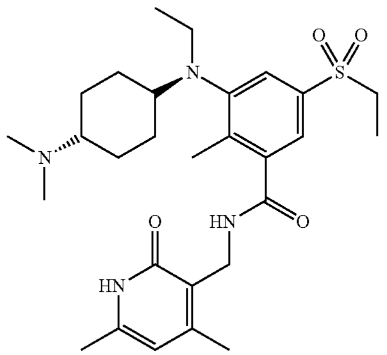

Step 1: Synthesis of N-((4,6-dimethyl-2-oxo-1,2-dihydropyridin-3-yl)methyl)-3-(((1r,4r)-4-(dimethylamino)cyclohexyl)(ethyl)amino)-5-(ethylthio)-2-methylbenzamide To a stirred solution of 5-bromo-N-((4,6-dimethyl-2-oxo-1,2-dihydropyridin-3-yl)methyl)-3-(((1r,4r)-4-(dimethylamino)cyclohexyl)(ethyl)amino)-2-methylbenzamide (0.4 g, 0.77 mmol.) in dioxane was added ethanethiol (0.048 g, 0.77 mmol) and DIPEA (2.7 mL, 1.55 mmol). The solution was purged with argon for 10 min, Pd $(OAc)_2$ (0.009 g, 0.038 mmol) and Xantphos (0.045 g, 0.077 mmol) were added to it and argon was purged again for 10 min. The reaction mixture was stirred at 100° C. for overnight, water was and extraction was carried out using ethyl acetate. The combined organic layers were washed with water, dried over anhydrous $Na_2SO_4$, filtered and concentrated under reduced pressure to afford crude material which was purified by column chromatography to afford compound the title compound (0.17 g, 44%). LCMS: 499.55 $(M+1)^+$; HPLC: 99.30% (@ 210-370 nm) ($R_t$; 4.264); Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-d6, 400 MHz) δ 11.46 (bs, 1H), 9.37 (s, 1H), 8.14 (s, 1H), 7.08 (s, 1H), 6.89 (s, 1H), 5.86 (s, 1H), 4.25 (d, 2H, J=4 Hz), 3.15-2.90 (m, 6H), 2.69 (s, 3H), 2.68 (s, 3H), 2.18 (s, 3H), 2.14 (s, 3H), 2.10 (s, 3H), 1.94 (m, 2H), 1.85 (m, 2H), 1.41 (m, 4H), 1.20 (t, 3H, J=7.2), 0.78 (t, 3H, J=6 Hz).

Step 2: Synthesis of N-((4,6-dimethyl-2-oxo-1,2-dihydropyridin-3-yl)methyl)-3-(((1r,4r)-4-(dimethylamino)cyclohexyl)(ethyl)amino)-5-(ethylsulfonyl)-2-methylbenzamide

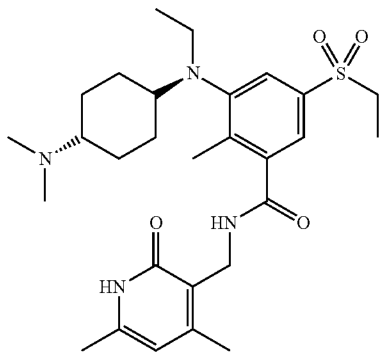

To a stirred solution of N-((4,6-dimethyl-2-oxo-1,2-dihydropyridin-3-yl)methyl)-3-(((1r,4r)-4-(dimethylamino)cyclohexyl)(ethyl)amino)-5-(ethylthio)-2-methylbenzamide (0.085 g, 0.17 mmol.) in methanol was added oxone (0.105 g, 0.34 mmol) at room temperature. The reaction mixture was stirred at room temperature for 4 h, water was added and extraction was carried out using 10% MeOH/DCM. The combined organic layers were washed with water, dried over anhydrous $Na_2SO_4$, filtered and concentrated under reduced pressure to afford crude material which was purified by prep. HPLC to afford the title compound as the TFA salt (0.07 g, 77%). LCMS: 531.60 $(M+1)^+$; HPLC: 89.24% (@ 210 nm-370 nm) ($R_t$; 4.082; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.47 (s, 1H), 9.36 (s, 1H), 8.36 (s, 1H), 7.53 (s, 1H), 7.38 (s, 1H), 7.22 (m, 1H), 7.09 (s, 1H), 6.96 (s, 1H), 5.87 (s, 1H), 4.29-4.28 (d, 2H, J=4.8 Hz), 3.0-3.20 (m, 4H), 2.60-2.80 (m, 8H), 2.27 (s, 9H), 2.20 (s, 3H), 2.11 (s, 3H), 1.90-2.0 (m, 2H), 1.80-1.90 (m, 2H), 1.40-1.50 (m, 4H), 1.05-1.15 (t, 3H, J=7.6 Hz), 0.75-0.85 (t, 3H, J=6.8 Hz).

Compound 320: N-((4,6-dimethyl-2-oxo-1,2-dihydropyridin-3-yl)methyl)-3-(((1r,4r)-4-(dimethylamino)cyclohexyl)(ethyl)amino)-5-isopropyl-2-methylbenzamide

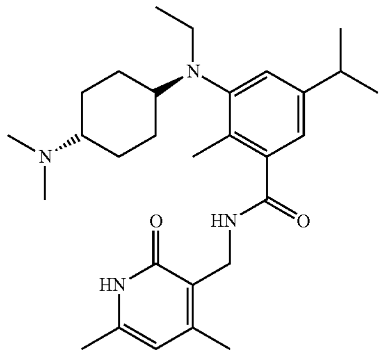

Step 1: Synthesis of N-((4,6-dimethyl-2-oxo-1,2-dihydropyridin-3-yl)methyl)-3-(((1r,4r)-4-(dimethylamino)cyclohexyl)(ethyl)amino)-2-methyl-5-(prop-1-en-2-yl)benzamide

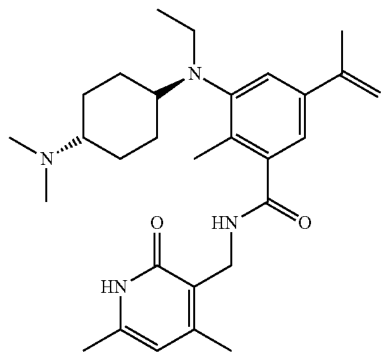

To a stirred solution of 5-bromo-N-((4,6-dimethyl-2-oxo-1,2-dihydropyridin-3-yl)methyl)-3-(((1r,4r)-4-(dimethylamino)cyclohexyl)(ethyl)amino)-2-methylbenzamide (0.30 g, 0.58 mmol) and 4,4,5,5-tetramethyl-2-(prop-1-en-2-yl)-1,3,2-dioxaborolane (0.147 g, 0.875 mmol) in dioxane/water mixture was added $Na_2CO_3$ (0.22 g, 2.07 mmol) and the solution purged with argon for 15 min. Then Pd $(PPh_3)_4$ (0.067 g, 0.058 mmol) was added and argon was purged again for 10 min. The reaction mixture was heated at 100° C. for 2 hours diluted with water and extracted with 10% MeOH/DCM. The combined organic layers were dried over $Na_2SO_4$ and the solvent removed under reduced pressure to afford crude material which was purified by column chromatography over silica gel to afford the title compound (0.20 g, 71%).

Step 2: N-((4,6-dimethyl-2-oxo-1,2-dihydropyridin-3-yl)methyl)-3-(((1r,4r)-4-(dimethylamino)cyclohexyl)(ethyl)amino)-5-isopropyl-2-methylbenzamide

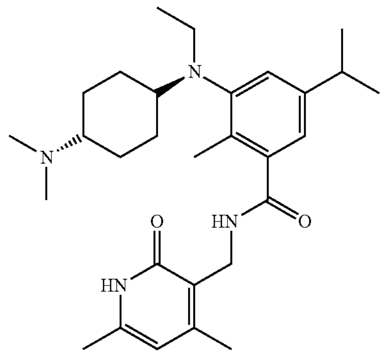

To a stirred solution of N-((4,6-dimethyl-2-oxo-1,2-dihydropyridin-3-yl)methyl)-3-(((1r,4r)-4-(dimethylamino)cyclohexyl)(ethyl)amino)-2-methyl-5-(prop-1-en-2-yl)benzamide (0.20 g, 0.41 mmol) in methanol was added a catalytic amount of 10% Pd/C. The reaction mixture was stirred at room temperature under hydrogen pressure (balloon pressure) for 2 h. The mixture was filtered through a celite bed, washed with methanol and the filtrate was concentrated under reduced pressure. The resulting crude compound was purified by prep. HPLC to afford the title compound as the TFA salt (0.07 g, 35%). LCMS: 481.40 $(M+1)^+$; HPLC: 97.01% (@ 210 nm-370 nm) ($R_t$; 3.996; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-$d_6$, 400 MHz) δ 11.46 (bs, 1H), 9.37 (bs, 1H), 8.00 (s, 1H), 7.01 (s, 1H), 6.83 (s, 1H), 5.86 (s, 1H), 4.26-4.25 (d, 2H, J=4.0 Hz), 3.0-3.25 (m, 3H), 2.70-2.8 (m, 1H), 2.60-2.75 (m, 6H), 2.19 (s, 3H), 2.15 (s, 3H), 2.10 (s, 3H), 1.90-2.0 (m, 2H), 1.80-1.90 (m, 2H), 1.35-1.50 (m, 4H), 1.16-1.20 (d, 6H, J=6.8 Hz), 0.75-0.85 (t, 3H).

Compound 321: 5-chloro-3-(((1r,4r)-4-(dimethylamino)cyclohexyl)-(ethyl)-amino)-N-((4-ethyl-6-methyl-2-oxo-1,2-dihydropyridin-3-yl)methyl)-2-methylbenzamide

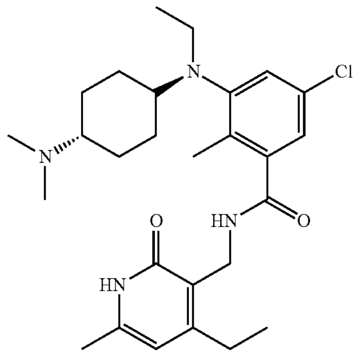

Step 1: synthesis of methyl 5-chloro-2-methyl-3-nitrobenzoate

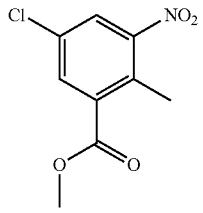

To stirred solution of 5-chloro-2-methyl-3-nitrobenzoic acid (126 g, 0.59 mol) in DMF (1.0 L) was added sodium carbonate (249 g, 2.34 mol) and methyl iodide (145 mL, 2.34 mol). The reaction mixture was heated at 60° C. for 4 h. On completion, the reaction mixture was filtered and the residue washed with DCM. The aqueous phase was separated and extracted with DCM. The combined organic layers were dried, concentrated under reduced pressure and purified by column chromatography over silica eluting with ethyl acetate:hexane to afford the title compound (85 g, 63%). $^1H$ NMR (DMSO-$d_6$, 400 MHz): δ 8.25 (d, 1H), 8.05 (s, 1H), 3.9 (s, 1H), 2.4 (s, 1H).

Step 2: synthesis of methyl 3-amino-5-chloro-2-methyl benzoate

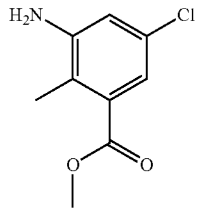

To stirred solution of methyl 5-chloro-2-methyl-3-nitrobenzoate (85 g, 0.37 mol) in ethanol (425 mL) were added ammonium chloride (85 g, 112 mmol) dissolved in water (425 mL) and iron powder (169 g, 2.96 mol) with stirring. The resulting reaction mixture was heated at 80° C. for 16 h filtered and the residue washed well with hot ethanol. The filtrate was concentrated and the residue was basified with aqueous sodium bicarbonate. The aqueous phase was extracted with ethyl acetate. The combined organic layers were washed with water, dried, concentrated under reduced pressure to give the crude title compound (70 g) which was used directly. $^1H$ NMR (DMSO-$d_6$, 400 MHz): δ 6.8 (s, 2H), 5.45 (s, 2H), 3.75 (s, 3H), 2.15 (s, 3H)

Step 3: synthesis of methyl 3-(((1r,4r)-4-((tert-butoxy-carbonyl)amino)cyclohexyl)amino)-5-chloro-2-methylbenzoate

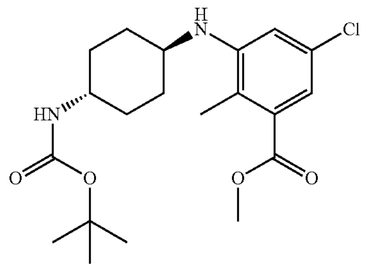 [SMILES: COC(=O)c1cc(Cl)cc(N[C@H]2CC[C@H](NC(=O)OC(C)(C)C)CC2)c1C]

To a stirred solution of methyl 3-amino-5-chloro-2-methyl benzoate (12 g, 60 mmol) and tert-butyl (4-oxocyclohexyl) carbamate (15.4 g, 72 mmol) in dichloroethane (120 mL) was added acetic acid (21 g, 360 mmol) and the reaction mixture was stirred at room temperature for 10 minutes. Then sodium triacetoxyborohydride (38.2 g, 180 mmol) was added and the reaction stirred for 2 h at room temperature. On completion, water was added to the reaction mixture and extraction was carried out using DCM. The combined organic layers were washed with bicarbonate solution, dried over sodium sulphate and concentrated under reduced pressure to give crude material which was then column purified to give trans-isomer title compound methyl 3-(((1r,4rs)-4-((tert-butoxycarbonyl) amino)cyclohexyl)amino)-5-chloro-2-methylbenzoate (8.0 g, 33%).

Step 4: synthesis of methyl 3-(((1r,4r)-4-((tert-butoxycarbonyl)amino)-cyclohexyl)-(ethyl)amino)-5-chloro-2-methylbenzoate

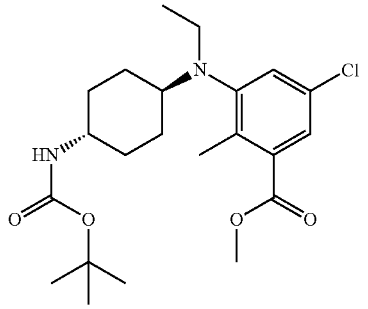 [SMILES: CCN(c1cc(Cl)cc(C(=O)OC)c1C)[C@H]1CC[C@H](NC(=O)OC(C)(C)C)CC1]

To a stirred solution of methyl 3-(((1r,4r)-4-((tert-butoxycarbonyl)amino)cyclohexyl)amino)-5-chloro-2-methylbenzoate (11.4 g, 28.8 mmol) and acetaldehyde (2.5 g, 56 mmol) in dichloroethane (120 mL) was added acetic acid (10.7 g, 169 mmol) and the reaction mixture was stirred at room temperature for 10 minutes. Then sodium triacetoxyborohydride (17.95 g, 84.6 mmol) was added and reaction stirred for 2 h at room temperature. On completion, water was added to the reaction mixture and extraction was carried out using DCM. Combined organic layers were washed with bicarbonate solution, dried over sodium sulphate and concentrated under reduced pressure to give crude material which was then column purified to give the title compound (9.8 g, 80%).

Step 5: synthesis of methyl 5-chloro-3-(((1r,4r)-4-(dimethylamino)-cyclohexyl)-(ethyl)amino)-2-methylbenzoate

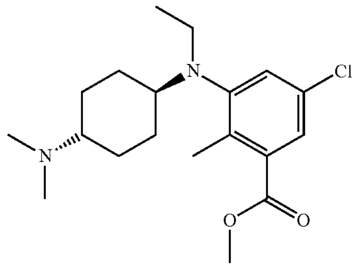

To a stirred solution of methyl 3-(((1r,4r)-4-((tert-butoxycarbonyl)amino)cyclohexyl)amino)-5-chloro-2-methylbenzoate (9.8 g, 23 mmol) in DCM (50 mL) at 0° C. was added TFA (10 mL) and the reaction mixture was stirred for 2 h at room temperature. After completion, the reaction was concentrated to dryness. The residue was then basified with aqueous sat. bicarbonate solution (100 mL) to pH 8 and the aqueous layer extracted with 20% methanol in DCM (100 mL×4). The combined organic layers were dried over $Na_2SO_4$ and the solvent removed under reduced pressure to afford crude amine (7.4 g) which was used as such for next reaction.

To a stirred solution of the amine (7.4 g, 23 mmol) in DCM (70 mL) at 0° C., was added 37-41% aq. formalin solution (2.4 g, 81 mmol) and the reaction mixture stirred at room temperature for 10 min. $NaBH(OAc)_3$ (12.1 g, 57 mmol) was then added and the reaction stirred for 2 h. On completion, the reaction mixture was quenched with water. MeOH (8 mL) was added and the layers were separated. Extraction was performed with 10% MeOH in DCM and the combined organic phases were dried and concentrated. The residue was column purified over basic alumina to afford the title compound (8.0 g, 99%).

Step 6: synthesis of 5-chloro-3-(((1r,4r)-4-(dimethylamino)cyclohexyl)-(ethyl)-amino)-2-methyl-benzoic acid

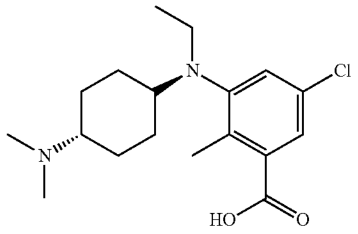

Aqueous NaOH (1.8 g, 45 mmol in 7 mL $H_2O$) was added to a solution of compound methyl 3-(((1r,4r)-4-((tert-butoxycarbonyl)amino)-cyclohexyl)-(ethyl)amino)-5-chloro-2-methylbenzoate (8.0 g, 23 mmol) in ethanol (70 mL) and stirred at 60° C. for 1 h. After completion of the reaction, ethanol was removed under reduced pressure and the residue acidified using dilute HCl up to pH 6 and adjusted to pH 4 with citric acid. Extraction was carried out using 10% MeOH in DCM. The combined organic layers were dried over $Na_2SO_4$ and concentrated to afford the title compound (7.6 g, 99%).

Step 7: synthesis of 3-(aminomethyl)-4-ethyl-6-methylpyridin-2(1H)-one

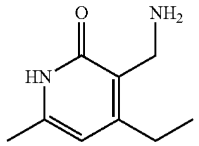

To a solution of 4-ethyl-6-methyl-2-oxo-1,2-dihydropyridine-3-carbonitrile (1 eq) in methanol and aq. ammonia solution (9:1) was added a catalytic amount of Raney Nickel. The reaction mixture was stirred at room temperature under hydrogen pressure (balloon pressure) for 2-5 h. On completion of reaction, it was filtered through a celite bed and the filtrate was concentrated under reduced pressure to afford the title compound.

Step 8: synthesis of 5-chloro-3-(((1r,4r)-4-(dimethylamino)cyclohexyl)-(ethyl)-amino)-N-((4-ethyl-6-methyl-2-oxo-1,2-dihydropyridin-3-yl)methyl)-2-methylbenzamide

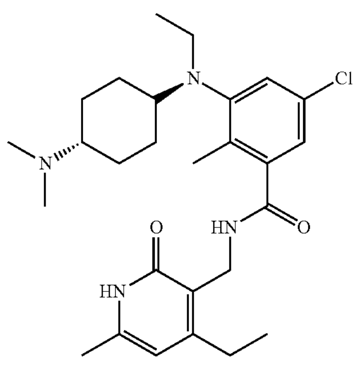

The above acid, 5-chloro-3-(((trans)-4-(dimethylamino)cyclohexyl)-(ethyl)-amino)-2-methyl-benzoic acid, (1 eq) was dissolved in DMSO and 3-(aminomethyl)-4-ethyl-6-methylpyridin-2(1H)-one (2 eq.) was added. The reaction mixture was stirred at room temperature for 15 min, PYBOP (1.5 eq.) and triethylamine (1 eq.) were added. The reaction mixture was stirred overnight. The reaction mixture was then poured into ice, and extracted with 10% MeOH/DCM. The combined organic layers were dried, and concentrated to obtain which was purified by column chromatography followed by prep. HPLC to afford the title compound as a TFA salt (0.1 g, 70%). LCMS: 487.45 $(M+1)^+$; HPLC: 96.17% (@ 254 nm) ($R_t$; 6.026; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-$d_6$, 400 MHz) δ 11.46 (bs, 1H), 9.33 (s, 1H), 8.22 (s, 1H), 7.19 (s, 1H), 6.97 (s, 1H), 5.88 (s, 1H), 4.20-4.25 (d, 2H), 3.0-3.15 (m, 1H+2H), 2.60-2.75 (m, 1H+3H+3H), 2.35-2.45 (m, 2H), 2.20 (s, 3H), 2.15 (s, 3H), 1.90-2.0 (m, 2H), 1.80-1.90 (m, 2H), 1.35-1.50 (m, 4H), 1.10-1.20 (t, 3H, J=7.2 Hz), 0.75-0.85 (t, 3H).

Compound 335: 5-chloro-N-#4,6-dimethyl-2-oxo-1,2-dihydropyridin-3-yl)methyl)-3-((4-(dimethylamino)cyclohexyl)thio)-2-methylbenzamide

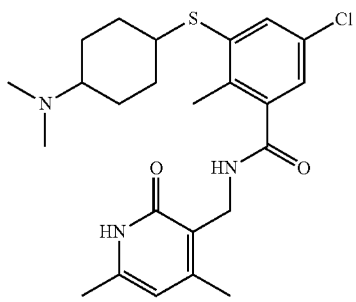 [SMILES: Cc1cc(C)c(CNC(=O)c2cc(Cl)cc(SC3CCC(N(C)C)CC3)c2C)c(=O)[nH]1]

Step 1: Synthesis of methyl 3-bromo-5-chloro-2-methylbenzoate

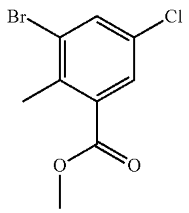

To stirred solution of $CuBr_2$ (12.3 g, 55.3 mmol) in acetonitrile (150 mL), tert-butyl nitrite (7.77 g, 75.4 mmol) was added at 0° C. and then methyl 3-amino-5-chloro-2-methylbenzoate (10.0 g, 50.3 mmol) dissolved in acetonitrile was added to it. The resulting reaction mixture was stirred at 0° C. for 2 hours and then at room temperature for 18 h. On completion, the reaction mixture was diluted with water and extracted with ethyl acetate. The combined organic layers were dried, concentrated under reduced pressure and purified by silica gel column chromatography giving the title compound (6.6 g, 50%).

Step 2: Synthesis of 3-bromo-5-chloro-N-((4,6-dimethyl-2-oxo-1,2-dihydropyridin-3-yl)-methyl)-2-methylbenzamide

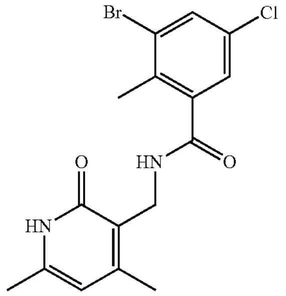 [SMILES: Cc1cc(C)c(CNC(=O)c2cc(Cl)cc(Br)c2C)c(=O)[nH]1]

Aqueous NaOH (0.45 g, 11.4 mmol) was added to a solution of methyl 3-bromo-5-chloro-2-methylbenzoate (2.0 g, 7.6 mmol) in EtOH (20 mL) and the mixture stirred at 60° C. for 1 hour. After completion of the reaction, ethanol was removed under reduced pressure and the residue acidified using dilute HCl up to pH 8 and then with citric acid till pH 6. The aqueous phase was extracted with 10% methanol in DCM. The combined organic layers were dried and concentrated to give respective crude acid intermediate (1.5 g).

The acid (1.5 g, 6.2 mmol) was dissolved in DMSO (15 mL) and 3-(amino methyl)-4,6-dimethylpyridin-2(1H)-one (1.67 g, 12.43 mmol) and triethylamine (0.61 g, 6.01 mmol) was added. The reaction mixture was stirred at room temperature for 15 min, PyBop (4.81 g, 9.26 mmol) was added and stirring was continued overnight at room temperature. After completion, the reaction mixture was poured into ice water. The suspended solid was collected by filtration, washed well with water and dried. The solid obtained was further purified by washings with acetonitrile to afford the title compound (2.18 g, 92%).

Step 3: Synthesis of 5-chloro-N-((4,6-dimethyl-2-oxo-1,2-dihydropyridin-3-yl)methyl)-2-methyl-3-((4-oxocyclohexyl)thio)benzamide

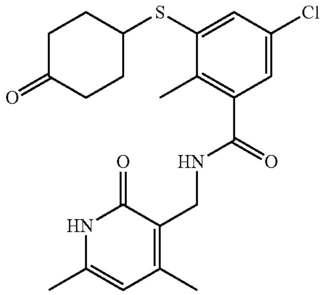 [SMILES: Cc1cc(C)c(CNC(=O)c2cc(Cl)cc(SC3CCC(=O)CC3)c2C)c(=O)[nH]1]

A solution of 3-bromo-5-chloro-N-((4,6-dimethyl-2-oxo-1,2-dihydropyridin-3-yl)-methyl)-2-methylbenzamide (0.35 g, 0.91 mmol.), 4-mercaptocyclohexanone (0.142 g, 1.09 mmol) and DIPEA (0.235 g, 1.82 mmol) in dioxane was purged with argon for 10 min. Then, $Pd(OAc)_2$ (0.01 g, 0.044 mmol) and Xantphos (0.052 g, 0.089 mmol) were added and argon was purged again for 10 min. The reaction mixture was stirred at 100° C. overnight. After completion of the reaction, water was added and extraction was carried out using ethyl acetate. The combined organic layers were washed with water, dried over anhydrous $Na_2SO_4$, filtered and concentrated under reduced pressure to afford crude material which was purified by column chromatography to afford the title compound (0.50 g, 88%).

Step 4: Synthesis of 5-chloro-N-((4,6-dimethyl-2-oxo-1,2-dihydropyridin-3-yl)methyl)-3-((4-(dimethylamino)cyclohexyl)thio)-2-methylbenzamide

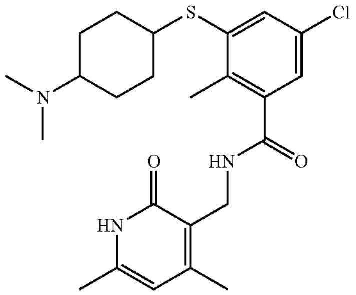 [SMILES: Cc1cc(C)c(CNC(=O)c2cc(Cl)cc(SC3CCC(N(C)C)CC3)c2C)c(=O)[nH]1]

To a stirred solution of 5-chloro-N-((4,6-dimethyl-2-oxo-1,2-dihydropyridin-3-yl)methyl)-2-methyl-3-((4-oxocyclohexyl)thio)benzamide (0.45 g, 1.03 mmol) and dimethylamine (0.14 g, 3.11 mmol) in dichloroethane (5 mL) was added acetic acid (0.37 g, 6.16 mmol) and the mixture stirred at room temperature for 20 minutes. Then sodium triacetoxyborohydride (0.66 g, 3.11 mmol) was added at 0° C. and the mixture stirred overnight at room temperature. On completion of the reaction, the solvent was removed under reduced pressure. Water was added to the residue and extraction was performed using 5% MeOH/DCM. The combined organic layers were dried and concentrated to afford crude material which was purified by column chromatography to afford the title compound (0.016 g, 3.3%). Analytical Data: LCMS: 462.35 $(M+1)^+$; HPLC: 89.00% (@ 210-370 nm) ($R_t$; 4.949;

Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 7.44 (s, 1H), 7.16 (s, 1H), 6.10 (s, 1H), 4.44 (s, 2H), 3.63 (m, 1H), 3.13 (m, 1H), 2.38 (s, 3H), 2.36 (s, 3H), 2.35 (s, 3H), 2.31 (s, 3H), 2.24 (s, 3H), 1.75-2.08 (m, 8H).

Compound 336: 5-chloro-N-((4,6-dimethyl-2-oxo-1,2-dihydropyridin-3-yl)methyl)-3-((4-hydroxycyclohexyl)thio)-2-methylbenzamide

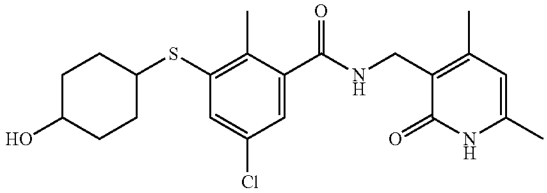 [SMILES: Cc1cc(C)c(CNC(=O)c2cc(Cl)cc(SC3CCC(O)CC3)c2C)c(=O)[nH]1]

This compound was also isolated as an additional product from the purification of compound 335 (0.235 g, 50%) Analytical Data of: LCMS: 435.30 $(M+1)^+$; HPLC: 99.37% (@ 210-370 nm) ($R_t$; 5.900; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.46 (bs, 1H), 8.31 (t, 1H), 7.72-7.68 (m, 1H), 7.41 (s, 1H), 7.07 (s, 1H), 5.85 (s, 1H), 4.58 (d, 1H, J=4 Hz), 4.24 (d, 2H, J=4 Hz), 4.13 (m, 1H), 3.43 (m, 1H), 2.20 (s, 3H), 2.18 (s, 3H), 2.10 (s, 3H), 1.95-1.80 (m, 1H), 1.75-1.55 (m, 1H), 1.40-1.20 (m, 4H), 0.87 (m, 2H).

Compound 339: N-((4,6-dimethyl-2-oxo-1,2-dihydropyridin-3-yl)methyl)-3-(ethyl(4-hydroxy-4-methylcyclohexyl)amino)-2-methylbenzamide

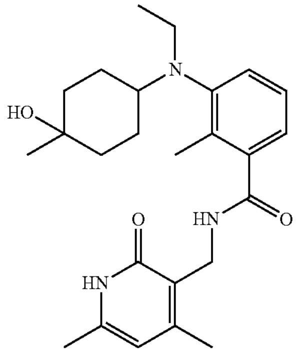 [SMILES: CCN(c1cccc(C(=O)NCc2c(C)cc(C)[nH]c2=O)c1C)C1CCC(C)(O)CC1]

Step 1: synthesis of methyl 2-methyl-3-nitrobenzoate

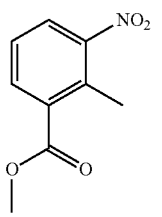

To a solution of 2-methyl-3-nitrobenzoic acid (10.0 g, 55.0 mmol) in 120 ml of methanol, was added conc. $H_2SO_4$ (15 ml) at room temperature and the mixture stirred at 60° C. overnight. The mixture was concentrated under reduced pressure, the crude material was neutralized with sat. $NaHCO_3$, and extracted with ethyl acetate. The organic phase was dried over $Na_2SO_4$, and concentrated under reduced pressure to afford the title compound (10 g).

Step 2: synthesis of methyl 3-amino-2-methylbenzoate

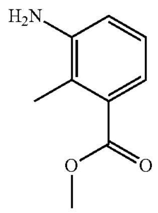

To a stirred solution of methyl 2-methyl-3-nitrobenzoate (10.0 g, 56.4 mmol) in 60 ml of ethanol were added ammonium chloride (18.0 g, 338 mmol) dissolved in 60 mL of water and iron powder (18.8 g, 338.2 mmol). The resulting reaction mixture was heated at 80° C. for 3 h. Water was added to the reaction mixture and then it was filtered through celite. The filtrate was extracted with ethyl acetate. The combined organic layers were washed with water, dried over $Na_2SO_4$, concentrated under reduced pressure to give the title compound (7.0 g, 83%).

Step 3: synthesis of methyl 3-((4-hydroxy-4-methylcyclohexyl)amino)-2-methylbenzoate

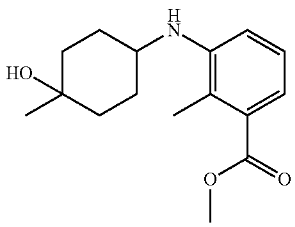 [SMILES: COC(=O)c1cccc(NC2CCC(C)(O)CC2)c1C]

To a stirred solution of methyl 3-amino-2-methylbenzoate (1.5 g, 9.1 mmol) and 4-hydroxy-4-methylcyclohexanone (1.51 ml, 11.8 mmol) in 10 ml of dichloroethane was added acetic acid (3.2 mL, 55 mmol) and the reaction mixture stirred at room temperature for 20 minutes. The reaction mixture was cooled to 0° C. and sodium triacetoxyborohydride (5.78 g, 27.3 mmol) was added and the mixture stirred at room temperature overnight. The reaction mixture was neutralized with sat. $NaHCO_3$, extracted with DCM, dried over $Na_2SO_4$, concentrated under reduced pressure, and purified by silica gel column chromatography to afford the title compound which was carried forward as a mixture of cis and trans isomers (1.4 g, 56%).

Step 4: synthesis of methyl 3-(ethyl(4-hydroxy-4-methylcyclohexyl)amino)-2-methylbenzoate

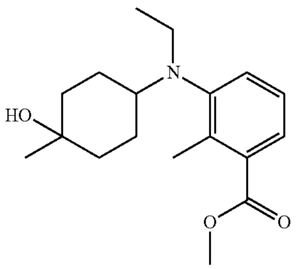 [SMILES: CCN(c1cccc(C(=O)OC)c1C)C1CCC(C)(O)CC1]

To a stirred solution of methyl 3-((4-hydroxy-4-methylcyclohexyl)amino)-2-methylbenzoate (1.4 g, 5.05 mmol) and acetaldehyde (0.7 ml, 13 mmol) in 20 ml of dichloroethane was added acetic acid (1.7 mL, 30 mmol) and the reaction mixture was stirred at room temperature for 20 minutes. The reaction mixture was cooled to 0° C. and sodium triacetoxyborohydride (3.2 g, 15 mmol) was added and the mixture was stirred at room temperature for overnight. The reaction mixture was neutralized with sat. $NaHCO_3$ and extracted with DCM. The combined organic layers were dried over $Na_2SO_4$, concentrated under reduced pressure, and the residue purified by silica gel column chromatography to afford the title compound (1.42 g, 94%).

Step 5: synthesis of N-((4,6-dimethyl-2-oxo-1,2-dihydropyridin-3-yl)methyl)-3-(ethyl(4-hydroxy-4-methylcyclohexyl)amino)-2-methylbenzamide

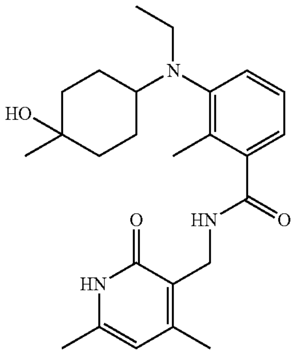 [SMILES: CCN(c1cccc(C(=O)NCc2c(C)cc(C)[nH]c2=O)c1C)C1CCC(C)(O)CC1]

A mixture of methyl 3-(ethyl(4-hydroxy-4-methylcyclohexyl)amino)-2-methylbenzoate (300 mg, 0.98 mmol) and NaOH (58 mg, 1.47 mmol) in 5 ml of ethanol and water (3:2) was heated at 70° C. for 2 h. The reaction mixture was concentrated to dryness and the residue was partitioned between water and ethyl acetate. The organic layer was dried over $Na_2SO_4$ and concentrated under reduced pressure to afford 270 mg of the crude acid. The crude acid (270 g, 0.92 mmol), 3-(aminomethyl)-4,6-dimethylpyridin-2(1H)-one (282 mg, 1.85 mmol), PyBOP (717 mg, 1.38 mmol) and triethylamine (0.12 ml, 0.92 mmol) were stirred in 3 ml of DMSO at room temperature overnight. The reaction mixture was diluted with water and extracted with 10% MeOH in DCM. The combined organic phases were dried over $Na_2SO_4$, concentrated and the residue purified by silica gel column chromatography to give the title compound N-((4,6-dimethyl-2-oxo-1,2-dihydropyridin-3-yl)methyl)-3-(ethyl(4-hydroxy-4-methylcyclohexyl)amino)-2-methylbenzamide as a mixture of isomers (120 mg, 30%). LCMS: 426.45 $(M+1)^+$; HPLC: 62.09 & 33.24% (@ 210-370 nm) ($R_t$; 3.982 & 4.164; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-$d_6$, 400 MHz) δ 11.44 (s, 1H), 8.04 (m, 1H), 7.12 (s, 2H), 6.91 (m, 1H), 5.85 (s, 1H), 4.25 (d, 2H, J=4 Hz), 4.15 (m, 1H), 3.00 (m, 2H), 2.84 (m, 1H), 2.18 (s, 6H), 2.10 (s, 3H), 1.75-1.60 (m, 2H), 1.55-1.35 (m, 4H), 1.35-1.15 (m, 4H), 1.08 & 1.03 (s, 3H), 0.87 & 0.77 (t, 3H).

Compound 340: N-#4,6-dimethyl-2-oxo-1,2-dihydropyridin-3-yl)methyl)-3-(ethyl(4-methoxy-4-methylcyclohexyl)amino)-2-methylbenzamide

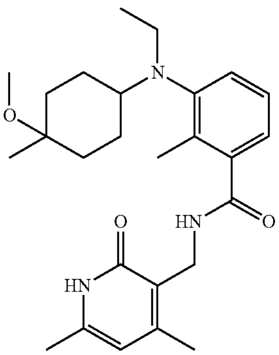 [SMILES: CCN(c1cccc(C(=O)NCc2c(C)cc(C)[nH]c2=O)c1C)C1CCC(C)(OC)CC1]

Step 1: synthesis of methyl 3-(ethyl(4-methoxy-4-methylcyclohexyl)amino)-2-methylbenzoate

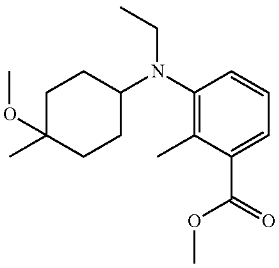 [SMILES: CCN(c1cccc(C(=O)OC)c1C)C1CCC(C)(OC)CC1]

To a cooled solution of methyl 3-(ethyl(4-hydroxy-4-methylcyclohexyl)amino)-2-methylbenzoate (300 mg, 0.98 mmol) in THF (5 ml), was added sodium hydride (235 mg, 5.89 mmol) portion-wise followed by methyl iodide (0.61 ml, 9.8 mmol). The mixture was stirred at room temperature for 1 h, cooled to 0° C. quenched with ice cold water and extracted with ethyl acetate. The combined organic layers were dried over $Na_2SO_4$ and concentrated under reduced pressure to give 300 mg of the crude title compound.

Step 2: Synthesis of N-((4,6-dimethyl-2-oxo-1,2-dihydropyridin-3-yl)methyl)-3-(ethyl(4-methoxy-4-methylcyclohexyl)amino)-2-methylbenzamide

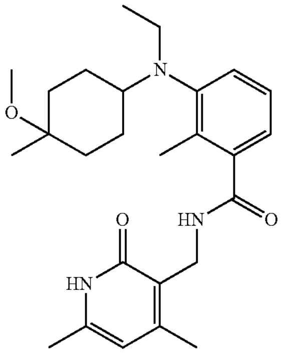 [SMILES: CCN(c1cccc(C(=O)NCc2c(C)cc(C)[nH]c2=O)c1C)C1CCC(C)(OC)CC1]

A mixture of 3-(ethyl(4-methoxy-4-methylcyclohexyl)amino)-2-methylbenzoate (300 mg, 0.94 mmol) and NaOH (56 mg, 1.41 mmol) in 5 ml of ethanol and water (4:1) was heated at 70° C. for 2 h. The reaction mixture was concentrated to dryness and the crude material was partitioned between water and ethyl acetate. The organic layer was dried over $Na_2SO_4$, and concentrated under reduced pressure to afford 280 mg of the crude acid. A mixture of the crude acid (280 mg, 0.91 mmol), 3-(aminomethyl)-4,6-dimethylpyridin-2(1H)-one (279 mg, 1.83 mmol), PyBOP (716 mg, 1.37 mmol) and triethylamine (0.12 ml, 0.91 mmol) in DMSO (3 ml) was stirred at room temperature overnight. The reaction mixture was diluted with water, extracted with 10% MeOH in DCM, dried over $Na_2SO_4$, and concentrated to a residue which was purified by silica gel column chromatography to afford the title compound N-((4,6-dimethyl-2-oxo-1,2-dihydropyridin-3-yl)methyl)-3-(ethyl(4-methoxy-4-methylcyclohexyl)amino)-2-methylbenzamide as a mixture of isomers (70 mg, 17%). LCMS: 440.45 $(M+1)^+$; HPLC: 45.77 & 48.47% (@ 210-370 nm) ($R_t$; 4.297 & 4.430; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-$d_6$, 400 MHz) δ 11.45 (s, 1H), 8.03 (bs, 1H), 7.15 (bs, 2H), 6.91 (s, 1H), 5.85 (s, 1H), 4.25 (d, 2H, J=2.8 Hz), 3.10-2.90 (m, 7H), 2.19 (s, 6H), 2.10 (s, 3H), 1.72-1.10 (m, 8H), 1.08 & 0.99 (s, 3H), 0.77 (t, 3H).

Compound 344: 5-chloro-N-((4,6-dimethyl-2-oxo-1,2-dihydropyridin-3-yl)methyl)-3-(ethyl((1s,4s)-4-methoxycyclohexyl)amino)-2-methylbenzamide

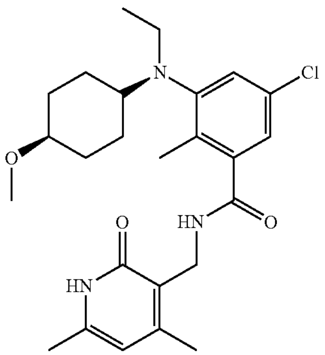

Step 1: Synthesis of methyl 5-chloro-3-(((1s,4s)-4-methoxycyclohexyl)amino)-2-methylbenzoate

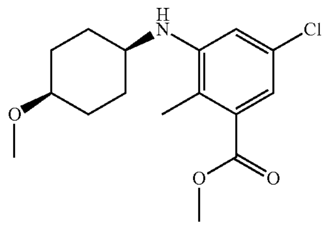 [SMILES: COC(=O)c1cc(Cl)cc(N[C@H]2CC[C@@H](OC)CC2)c1C]

To a stirred solution of methyl 3-amino-5-chloro-2-methylbenzoate (1.0 g, 5.0 mmol) and 4-methoxycyclohexanone (1.28 g, 10.0 mmol) in dichloroethane (10 mL) was added acetic acid (1.8 g, 30 mmol) and the mixture stirred at room temperature for 10 minutes. Then sodium triacetoxyborohydride (3.2 g, 15 mmol) was added at 0° C. and the reaction stirred overnight at room temperature. On completion, the reaction was quenched with aqueous sodium bicarbonate, the organic phase separated and the aqueous phase extracted with dichloromethane. The combined organic layers were dried over anhydrous sodium sulphate and concentrated under reduced pressure. The crude material obtained was purified by silica gel column chromatography and the cis-isomer title compound was isolated as the less polar product isomer (0.60 g, 38%). The trans isomer can also be carried forward to produce the corresponding trans final product, compound 343.

Step 2: Synthesis of methyl 5-chloro-3-(ethyl((1s,4s)-4-methoxycyclohexyl)amino)-2-methylbenzoate

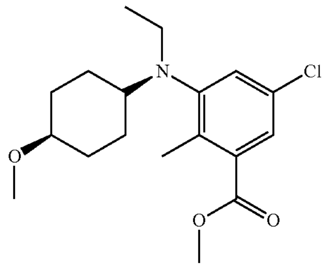

To a stirred solution of methyl 5-chloro-3-(((1s,4s)-4-methoxycyclohexyl)amino)-2-methylbenzoate (0.60 g, 1.92 mmol) and acetaldehyde (0.25 g, 5.78 mmol) in dichloroethane (10 mL), was added acetic acid (0.69 g, 11.6 mmol) and the mixture stirred at room temperature for 10 minutes. Then sodium triacetoxyborohydride (1.22 g, 5.78 mmol) was added at 0° C. and the reaction stirred overnight at room temperature. On completion, the reaction was quenched with aqueous sodium bicarbonate, the organic phase separated and the aqueous phase extracted with dichloromethane. The combined organic layers were dried over anhydrous sodium sulphate and concentrated under reduced pressure and the crude product purified by silica gel column chromatography to afford the title compound (0.60 g, 92%).

Step 3: Synthesis of 5-chloro-N-((4,6-dimethyl-2-oxo-1,2-dihydropyridin-3-yl)methyl)-3-(ethyl((1s,4s)-4-methoxycyclohexyl)amino)-2-methylbenzamide

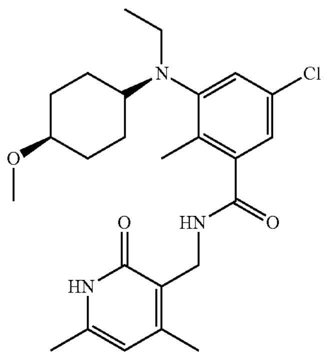

Aqueous NaOH (0.07 g, 1.76 mmol) was added to a solution of methyl 5-chloro-3-(ethyl((1r,4r)-4-methoxycyclohexyl)amino)-2-methylbenzoate (0.4 g, 1.17 mmol) in ethanol (5 mL) and the mixture was stirred at 60° C. for 1 h. After completion of the reaction, ethanol was removed under reduced pressure and acidified using dilute HCl up to pH 6 and adjusted using to pH 4 citric acid. Extraction was carried out using ethyl acetate and the combined organic layers were dried concentrated giving the respective crude acid (0.35 g).

The above crude acid (0.35 g, 1.1 mmol) was dissolved in DMSO (4 mL) and 3-(amino methyl)-4,6-dimethylpyridin-2(1H)-one (0.33 g, 2.14 mmol) was added. The reaction mixture was stirred at room temperature for 15 min, PYBOP (0.84 g, 1.61 mmol) was added and stirring was continued overnight. After completion of the reaction, the mixture was poured into ice and extracted with 10% MeOH/DCM. The combined organic layers were dried over anhydrous sodium sulphate and concentrated under reduced pressure to yield a crude product which was purified by silica gel column chromatography to afford the title compound (0.55 g, 79%). LCMS: 460.30 $(M+1)^+$; HPLC: 97.37% (@ 210-370 nm) ($R_t$; 5.026; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.44 (bs, 1H), 8.21 (t, 1H), 7.13 (s, 1H), 6.93 (s, 1H), 5.85 (s, 1H), 4.25 (d, 2H, J=3.2 Hz), 3.27 (m, 1H), 3.18 (s, 3H), 2.99 (q, 2H), 2.79 (m, 1H), 2.18 (s, 3H), 2.14 (s, 3H), 2.10 (s, 3H), 1.77 (m, 2H), 1.60 (m, 2H), 1.45 (m, 2H), 1.33 (m, 2H), 0.78 (t, 3H, J=6 Hz).

Compound 349: N-((4,6-dimethyl-2-oxo-1,2-dihydropyridin-3-yl)methyl)-3-((4-(dimethylamino)cyclohexyl)(ethyl)amino)-2-methyl-5-((1-methylazetidin-3-yl)oxy)benzamide

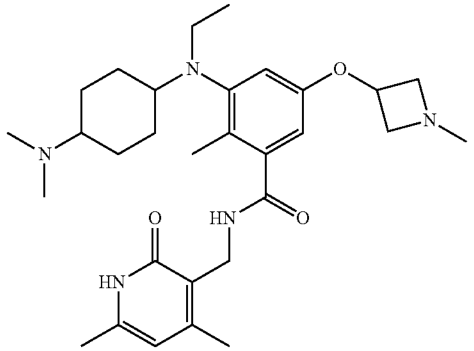

Step 1: Synthesis of methyl 5-hydroxy-2-methyl-3-nitrobenzoate

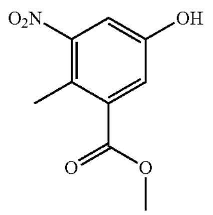

To a stirred solution of 5-hydroxy-2-methyl-3-nitrobenzoic acid (3.50 g, 17.8 mmol) in methanol (40 mL), was added thionyl chloride (3.9 mL, 53 mmol) at 0° C. The mixture was heated under reflux for 3 hours and concentrated under reduced pressure. Aqueous sodium bicarbonate was added to the residue which was extracted with ethyl acetate. The combined organic layers were washed with water, dried and concentrated under reduced pressure. The crude material was purified by column chromatography to afford the title compound (3.0 g, 80%).

Step 2: Synthesis of tert-butyl 3-(3-(methoxycarbonyl)-4-methyl-5-nitrophenoxy)azetidine-1-carboxylate

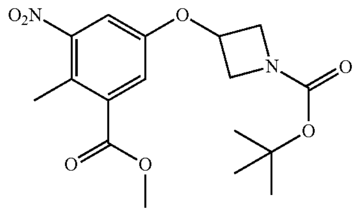

To stirred solution of 5-hydroxy-2-methyl-3-nitrobenzoate (1.5 g, 7.1 mmol) in ACN (15 mL) were added cesium carbonate (4.64 g, 14.2 mmol) and tert-butyl 3-iodoazetidine-1-carboxylate (3.0 g, 11 mmol). The resulting mixture was heated at 80° C. overnight. On completion, the reaction mixture was diluted with water and extraction was carried out using ethyl acetate. The combined organic layers were washed with water, dried and concentrated under reduced pressure. The crude material was purified by column chromatography to afford the title compound (1.2 g, 46%).

Step 3: Synthesis of tert-butyl 3-(3-amino-5-(methoxycarbonyl)-4-methylphenoxy)azetidine-1-carboxylate

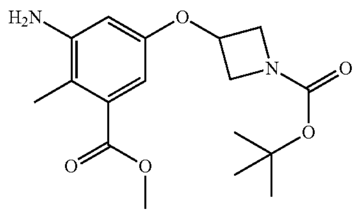 [SMILES: COC(=O)c1cc(OC2CN(C(=O)OC(C)(C)C)C2)cc([N+](=O)[O-])c1C]

To stirred solution of tert-butyl 3-(3-(methoxycarbonyl)-4-methyl-5-nitrophenoxy)azetidine-1-carboxylate (1.0 g, 2.7 mmol) in methanol (10 mL) was added a catalytic amount of 10% Pd/C. The mixture was stirred at room temperature under a hydrogen atmosphere (balloon pressure) for 3 hours. On completion, the reaction mixture was filtered through a celite bed which was further washed with methanol. The combined filtrates were concentrated under reduced pressure to afford the title compound (0.90 g, 98%).

Step 4: Synthesis of tert-butyl 3-(3-((4-((tert-butoxycarbonyl)amino)cyclohexyl)amino)-5-(methoxycarbonyl)-4-methylphenoxy)azetidine-1-carboxylate

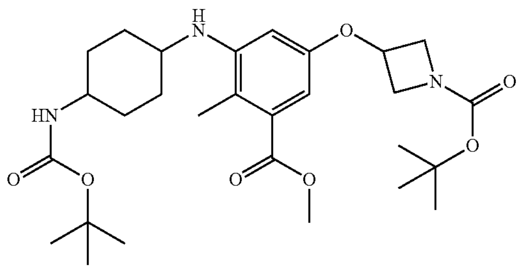 [SMILES: COC(=O)c1cc(OC2CN(C(=O)OC(C)(C)C)C2)cc(NC2CCC(NC(=O)OC(C)(C)C)CC2)c1C]

To a stirred solution of tert-butyl 3-(3-amino-5-(methoxycarbonyl)-4-methylphenoxy)azetidine-1-carboxylate (0.90 g, 2.67 mmol) and tert-butyl (4-oxocyclohexyl)carbamate (0.741 g, 3.47 mmol) in dichloroethane (10 mL) was added acetic acid (0.96 g, 16.1 mmol) and the mixture stirred at room temperature for 20 minutes. Then sodium triacetoxyborohydride (1.7 g, 8.0 mmol) was added at 0° C. and the reaction stirred at room temperature for 2 h. On completion, the reaction was quenched with aqueous sodium bicarbonate, the organic phase separated and the aqueous phase extracted with dichloromethane. The combined organic layers were washed with water, dried, concentrated under reduced pressure and the crude material purified by column chromatography to afford the title compound (0.9 g, 63%) as a mixture of cis/trans isomers.

Step 5: Synthesis of tert-butyl 3-(3-((4-((tert-butoxycarbonyl)amino)cyclohexyl)(ethyl)amino)-5-(methoxycarbonyl)-4-methylphenoxy)azetidine-1-carboxylate

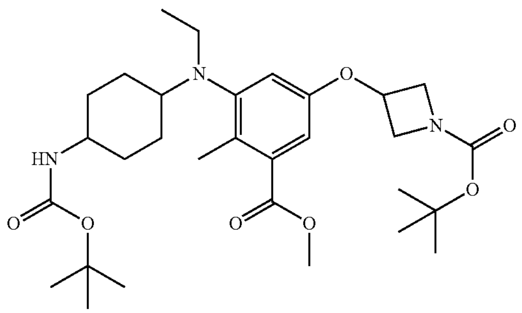 [SMILES: CCN(c1cc(OC2CN(C(=O)OC(C)(C)C)C2)cc(C(=O)OC)c1C)C1CCC(NC(=O)OC(C)(C)C)CC1]

To a stirred solution of tert-butyl 3-(3-((4-((tert-butoxycarbonyl)amino)cyclohexyl)amino)-5-(methoxycarbonyl)-4-methylphenoxy)azetidine-1-carboxylate (0.90 g, 1.69 mmol) and acetaldehyde (0.22 g, 5.06 mmol) in dichloroethane (10 mL), was added acetic acid (0.61 g, 10 mmol) and the reaction stirred at room temperature for 20 minutes. Then sodium triacetoxyborohydride (1.07 g, 5.05 mmol) was added at 0° C. and the reaction was stirred at room temperature for 2 h. On completion, the reaction was quenched with aqueous sodium bicarbonate, the organic phase separated and the aqueous phase extracted with dichloromethane. The combined organic layers were washed with water, dried, concentrated under reduced pressure giving the title compound which was used without further purification (0.85 g).

Step 6: Synthesis of tert-butyl 3-(3-((4-((tert-butoxycarbonyl)amino)cyclohexyl)(ethyl)amino)-5-(((4,6-dimethyl-2-oxo-1,2-dihydropyridin-3-yl)methyl)carbamoyl)-4-methylphenoxy)azetidine-1-carboxylate

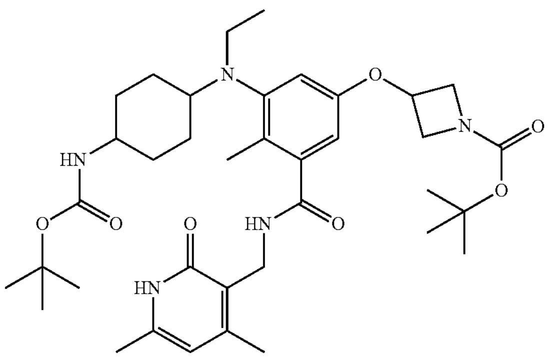 [SMILES: CCN(c1cc(OC2CN(C(=O)OC(C)(C)C)C2)cc(C(=O)NCc2c(C)cc(C)[nH]c2=O)c1C)C1CCC(NC(=O)OC(C)(C)C)CC1]

Aqueous NaOH (0.12 g, 3.03 mmol) was added to a solution of tert-butyl 3-(3-((4-((tert-butoxycarbonyl)amino)cyclohexyl)(ethyl)amino)-5-(methoxycarbonyl)-4-methylphenoxy)azetidine-1-carboxylate (0.85 g, 1.52 mmol) in ethanol (10 mL) and the mixture stirred at 60° C. for 1 h. After completion of the reaction, ethanol was removed under reduced pressure and acidified using dilute HCl up to pH 6 and adjusted using citric acid to pH 4. Extraction was carried out using ethyl acetate. The combined organic layers were dried and concentrated giving the respective acid (0.75 g).

The above acid (0.75 g, 1.37 mmol) was then dissolved in DMSO (7 mL) and 3-(amino methyl)-4,6-dimethylpyridin-2(1H)-one (0.42 g, 2.74 mmol) was added to it. The reaction mixture was stirred at room temperature for 15 min, PYBOP (1.06 g, 2.05 mmol) was added to it and stirring was continued overnight. After completion, the reaction mixture was poured into ice, extracted with 10% MeOH/DCM. The combined organic layers were washed with water, dried over anhydrous $Na_2SO_4$, filtered and concentrated under reduced pressure to afford the title compound (0.80 g, 85%).

Step 7: Synthesis of N-((4,6-dimethyl-2-oxo-1,2-dihydropyridin-3-yl)methyl)-3-((4-(dimethylamino)cyclohexyl)(ethyl)amino)-2-methyl-5-((1-methylazetidin-3-yl)oxy)benzamide

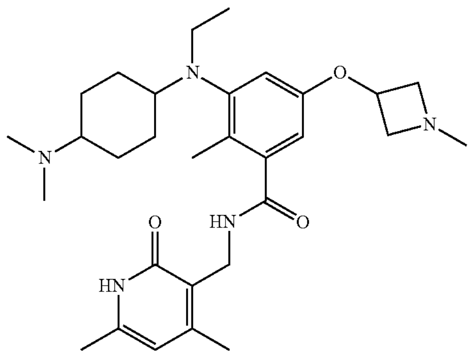

To a cooled stirred solution of tert-butyl 3-(3-((4-((tert-butoxycarbonyl)amino)cyclohexyl)(ethyl)amino)-5-(((4,6-dimethyl-2-oxo-1,2-dihydropyridin-3-yl)methyl)carbamoyl)-4-methylphenoxy)azetidine-1-carboxylate (0.80 g, 1.17 mmol) in DCM (10 mL) was added TFA (2 mL). The mixture was stirred at rt for 1 h, concentrated under reduced pressure and saturated $NaHCO_3$ solution was added to the residue. Extraction was carried out using 10% MeOH/DCM and the combined organic layers were washed with water and brine and dried over anhydrous $Na_2SO_4$. The solvent was removed under reduced pressure to give the Boc deprotected intermediate compound (0.5 g).

The above intermediate (0.5 g, 1.0 mmol) was dissolved in MeOH (3 mL) and formalin (0.16 g, 5.33 mmol) was added at 0° C. The mixture was stirred at same temperature for 20 minutes. Sodium triacetoxyborohydride (0.55 g, 2.59 mmol) was added and the mixture stirred at room temperature for 1 h. After completion, the solvent was removed under reduced pressure and water added to the residue. Extraction was carried out using 10% MeOH/DCM. The combined organic layers were dried and concentrated under reduced pressure to afford crude material which was purified by column chromatography to afford the title compound (0.03 g, 5.5%).

LCMS: 524.55 $(M+1)^+$; HPLC: 37.93+61.46% (@ 210-370 nm) ($R_t$; 3.462 and 3.810; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-$d_6$, 400 MHz) δ 11.45 (bs, 1H), 8.05 (bs, 1H), 6.56 (s, 1H), 6.36 (s, 1H), 5.85 (s, 1H), 4.69 (bs, 1H), 4.24 (bs, 2H), 3.67 (m, 2H), 3.08-2.92 (m, 4H), 2.33-2.11 (m, 20H), 1.73-1.65 (m, 4H), 1.35-1.29 (m, 4H), 0.77 (t, 3H).

Compound 119: 3-(((1s,4s)-4-aminocyclohexyl)(ethyl)amino)-5-chloro-N-((4,6-dimethyl-2-oxo-1,2-dihydropyridin-3-yl)methyl)-2-methylbenzamide

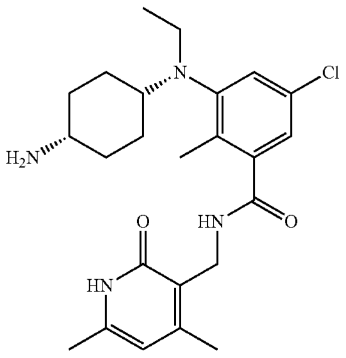

Step 1: synthesis of 5-chloro-2-methyl-3-nitrobenzoic acid

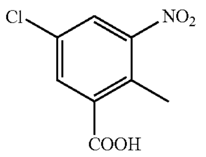

To a stirred solution of 5-chloro-2-methylbenzoic acid (4.0 g, 24 mmol) in concentrated $H_2SO_4$ (27 mL) at −10° C. was added a nitrating solution comprised of concentrated $HNO_3$ (3.3 g, 53 mmol) dissolved in concentrated $H_2SO_4$ (4.4 mL). The resulting mixture was stirred at −10° C. for 3 h and poured onto ice water. The resulting precipitate was filtered, washed with water and dried under vacuum to give the title compound (4.95 g, 99%).

Step 2: synthesis of methyl 5-chloro-2-methyl-3-nitrobenzoate

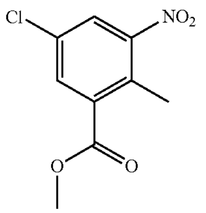

To a stirred solution of 5-chloro-2-methyl-3-nitrobenzoic acid (6.75 g, 31.3 mmol) in DMF (33 mL), were added sodium carbonate (13.2 g, 125 mmol) and methyl iodide (17.8 g, 125 mmol). The mixture was heated at 60° C. for 4 h. Water was added to the reaction mixture followed by extraction with dichloromethane. The combined organic extracts were dried over sodium sulfate, filtered and concentrated under reduced pressure. The crude product was purified by column chromatography over silica gel to afford the title compound (6.0 g, 84%).

Step 3: synthesis of methyl 3-amino-5-chloro-2-methyl benzoate

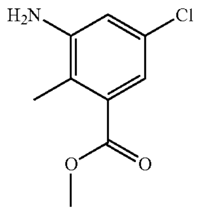

To stirred solution of methyl 5-chloro-2-methyl-3-nitrobenzoate (6.0 g, 26 mmol) in ethanol (60 mL), were added a solution of ammonium chloride (6.0 g, 112 mmol) in water (60 mL) and iron powder (11.9 g, 208 mmol). The mixture was heated at 80° C. for 1 h. Water was added and the resulting mixture was filtered through celite followed by extraction with ethyl acetate. The combined organic layers were washed with water, dried over sodium sulfate and concentrated under reduced pressure to afford the crude title compound (5.0 g).

Step 4: synthesis of methyl 3-(((1s,4s)-4-((tert-butoxycarbonyl)amino)cyclohexyl)amino)-5-chloro-2-methylbenzoate

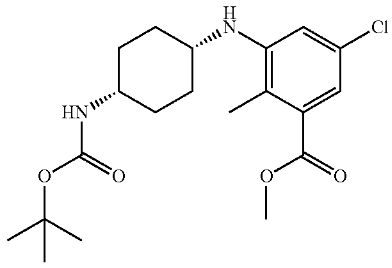 [SMILES: COC(=O)c1cc(Cl)cc(N[C@H]2CC[C@@H](NC(=O)OC(C)(C)C)CC2)c1C]

To a stirred solution of 3-amino-5-chloro-2-methyl benzoate (5.0 g, 25 mmol) and tert-butyl (4-oxocyclohexyl)carbamate (6.95 g, 32.7 mmol) in dichloroethane (25 mL), was added acetic acid (9.0 g, 150 mmol) at room temperature. Sodium triacetoxyborohydride (15.97 g, 75.4 mmol) was added and reaction stirred 1 h at room temperature. The solvent was removed under reduced pressure and the crude material was purified by column chromatography over silica gel to afford to afford 5.2 g (52%) of the first eluting title compound cis-isomer product methyl 3-(((1s,4s)-4-((tert-butoxycarbonyl)amino)cyclohexyl)amino)-5-chloro-2-methylbenzoate and 3.5 g (35%) the more polar isomer trans-isomer product methyl 3-(((1r,4r)-4-((tert-butoxycarbonyl)amino) cyclohexyl)amino)-5-chloro-2-methylbenzoate.

Step 5: synthesis of methyl 3-(((1s,4s)-4-((tert-butoxycarbonyl)amino)cyclohexyl)(ethyl)amino)-5-chloro-2-methylbenzoate

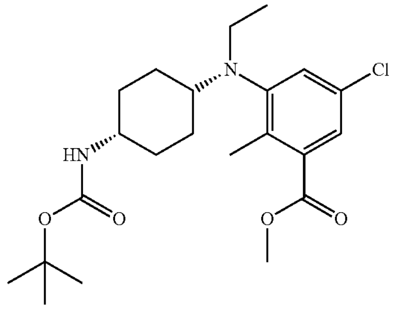

To a stirred solution of 3-(((1s,4s)-4-((tert-butoxycarbonyl)amino)cyclohexyl)amino)-5-chloro-2-methylbenzoate (5.20 g, 13.1 mmol) and acetaldehyde (1.15 g, 26.3 mmol) in dichloroethane (15 mL), was added acetic acid (4.72 g, 78.8 mmol) at room temperature. Sodium triacetoxyborohydride (8.35 g, 39.4 mmol) was added and the mixture was stirred for 1 h. Water was added the mixture was extracted with dichloromethane. The combined organic layers were dried over sodium sulfate and concentrated under reduced pressure. The crude product was purified by column chromatography over silica gel to afford the title compound (5.3 g, 99%).

Step 6: synthesis of tert-butyl ((1s,4s)-4-((5-chloro-3-(((4,6-dimethyl-2-oxo-1,2-dihydropyridin-3-yl) methyl)carbamoyl)-2-methylphenyl)(ethyl)amino) cyclohexyl)carbamate

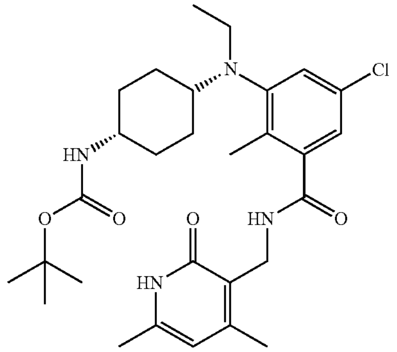

To a stirred solution of 3-(((1s,4s)-4-((tert-butoxycarbonyl)amino)-cyclohexyl)(ethyl)amino)-5-chloro-2-methylbenzoate (5.20 g, 12.2 mmol) in ethanol (15 mL) was added an aqueous solution of NaOH (0.73 g, 18.4 mmol). The mixture was stirred at 60° C. for 1 h, concentrated under reduced pressure and then acidified to pH 4 by addition of dilute HCl followed by citric acid. The resulting mixture was extracted with ethyl acetate and the combined extracts were dried and concentrated under reduced pressure to afford the corresponding crude acid (4.4 g). To a stirred solution of the acid (4.4 g, 10.7 mmol), 3-(aminomethyl)-4,6-dimethylpyridin-2(1H)-one (3.25 g, 21.4 mmol) and triethylamine (1.08 g, 10.70 mmol) in DMSO (15 mL) was added PYBOP (8.34 g, 16.05 mmol) at 0° C. After stirring overnight at room temperature, the mixture was poured onto ice and extracted with 10% MeOH/$CH_2Cl_2$. The combined organic layers were dried over sodium sulfate and concentrated under reduced pressure to obtain crude material which was purified by column chromatography over silica gel to afford the title compound (4.20 g, 72%). LCMS: 548.40 $(M+1)^+$; HPLC: 98.62% (@ 254 nm) ($R_t$; 5.736; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.45 (s, 1H), 8.20 (t, 1H), 7.13 (s, 1H), 6.91 (m, 2H), 5.85 (s, 1H), 4.22 (d, 2H), 3.47 (bs, 1H), 3.00-3.02 (m, 3H), 2.18 (s, 3H), 2.16 (s, 3H), 2.10 (s, 3H), 1.71 (m, 2H), 1.53 (m, 2H), 1.39 (m, 4H), 1.37 (s, 9H), 0.78 (t, 3H, J=6.8 Hz).

Step 7: synthesis of 3-(((1s,4s)-4-aminocyclohexyl) (ethyl)amino)-5-chloro-N-((4,6-dimethyl-2-oxo-1,2-dihydropyridin-3-yl)methyl)-2-methylbenzamide

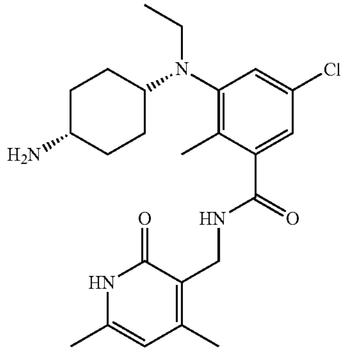

To a stirred solution of tert-butyl ((1s,4s)-4-(5-chloro-3-(((4,6-dimethyl-2-oxo-1,2-dihydropyridin-3-yl)methyl)carbamoyl)-2-methylphenyl)(ethyl)amino)cyclohexyl)carbamate (0.60 g, 1.10 mmol) in $CH_2Cl_2$ (10 mL) was added trifluoroacetic acid (2 mL) at 0° C. The mixture was stirred at room temperature for 2 h and concentrated to dryness. The residue was dissolved in aqueous sodium bicarbonate followed by extraction with 20% MeOH/$CH_2Cl_2$. The combined organic layers were dried over sodium sulfate and concentrated under reduced pressure to afford a residue which was triturated to afford the title compound (0.5 g, 100%). LCMS: 445.30 $(M+1)^+$; HPLC: 99.3% (@ 254 nm) ($R_t$; 4.524; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 8.21 (t, 1H), 7.13 (s, 1H), 6.91 (d, 1H, J=1.6 Hz), 5.85 (s, 1H), 4.24 (d, 2H, J=4.8 Hz), 2.99-3.04 (m, 2H), 2.82-2.85 (m, 2H), 2.18 (s, 3H), 2.15 (s, 3H), 2.10 (s, 3H), 1.75-1.77 (m, 2H), 1.36-1.39 (m, 6H), 0.79 (t, 3H, J=6.8 Hz).

Compound 121: 3-(((1s,4s)-4-acetamidocyclohexyl)(ethyl)amino)-5-chloro-N-((4,6-dimethyl-2-oxo-1,2-dihydropyridin-3-yl)methyl)-2-methylbenzamide

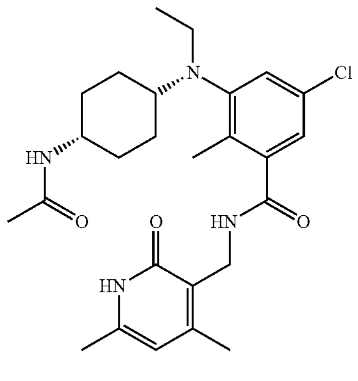

To a stirred solution of 3-(((1s,4s)-4-aminocyclohexyl)(ethyl)amino)-5-chloro-N-((4,6-dimethyl-2-oxo-1,2-dihydropyridin-3-yl)methyl)-2-methylbenzamide (0.30 g, 0.68 mmol) and EDCI.HCl (0.194 g, 1.01 mmol) in DMF (5 mL) were added HOBt (0.091 g, 0.675 mmol) and acetic acid (0.081 g, 1.35 mmol) at room temperature. After stirring for 18 h water was added and the mixture was extracted with 10% MeOH/$CH_2Cl_2$. The combined organic layers were dried over sodium sulfate and concentrated to a residue which was purified by column chromatography over silica gel to afford the title compound (0.10 g, 30%). LCMS: 487.30 $(M+1)^+$; HPLC: 91.72% (@ 254 nm) ($R_t$; 4.585; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-$d_6$, 400 MHz) δ 8.22 (t, 1H), 7.75 (d, 1H, J=7.2 Hz), 7.15 (s, 1H), 6.93 (s, 1H), 5.85 (s, 1H), 4.24 (d, 2H, J=4.4 Hz), 3.69 (bs, 1H), 3.01-3.03 (m, 2H), 2.94 (m, 1H), 2.18 (s, 6H), 2.10 (s, 3H), 1.80 (s, 3H), 1.69-1.71 (m, 2H), 1.37-1.51 (m, 6H), 0.79 (t, 3H, J=6.8. Hz).

Compound 120: 3-(((1r,4r)-4-aminocyclohexyl)(ethyl)amino)-5-chloro-N-((4,6-dimethyl-2-oxo-1,2-dihydropyridin-3-yl)methyl)-2-methylbenzamide

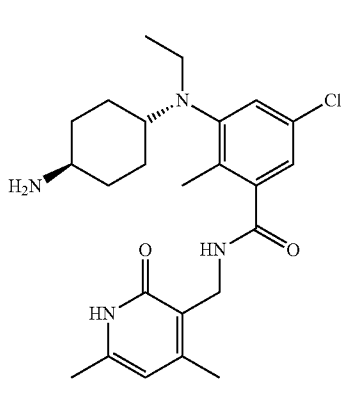

Step 1: synthesis of methyl 3-(((1r,4r)-4-((tert-butoxycarbonyl)amino)cyclohexyl)(ethyl)amino)-5-chloro-2-methylbenzoate

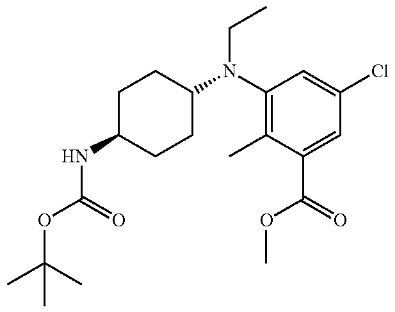

To a stirred solution of methyl 3-(((1r,4r)-4-((tert-butoxycarbonyl)amino)cyclohexyl)amino)-5-chloro-2-methylbenzoate (3.5 g, 8.8 mmol) prepared as described above and acetaldehyde (0.77 g, 17.7 mmol) in dichloroethane (15 mL), was added acetic acid (3.17 g, 53 mmol) at room temperature. After stirring for 10 minutes, sodium triacetoxyborohydride (5.61 g, 26.5 mmol) was added and the reaction was stirred for 1 h at room temperature. Water was added and the mixture was extracted with dichloromethane. The combined organic layers were dried over sodium sulfate and concentrated under reduced pressure to give crude material which was purified by column chromatography over silica gel to afford the title compound (3.5 g, 93%).

Step 2: synthesis of tert-butyl ((1r,4r)-4-((5-chloro-3-(((4,6-dimethyl-2-oxo-1,2-dihydropyridin-3-yl)methyl)carbamoyl)-2-methylphenyl)(ethyl)amino)cyclohexyl)carbamate

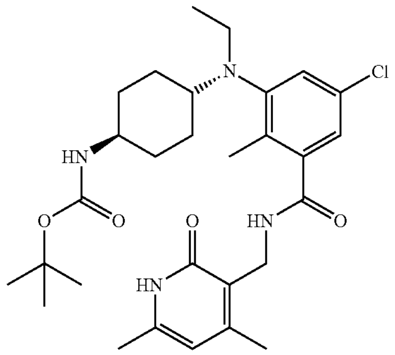

To a stirred solution of 3-(((1r,4r)-4-((tert-butoxycarbonyl)amino)cyclohexyl)(ethyl)amino)-5-chloro-2-methylbenzoate (3.50 g, 8.23 mmol) in ethanol (15 mL) was added an aqueous solution of NaOH (0.49 g, 12.4 mmol). The mixture was stirred at 60° C. for 1 h, concentrated under reduced pressure and acidified to pH 4 by addition of dilute HCl followed by citric acid solution. The resulting mixture was extracted with ethyl acetate, and the combined organic layers were dried under reduced pressure to give the corresponding crude acid (3.2 g). To a stirred solution of the acid (3.2 g, 7.8 mmol), 3-(aminomethyl)-4,6-dimethylpyridin-2(1H)-one (2.36 g, 15.6 mmol) and triethylamine (0.79 g, 7.8 mmol) in DMSO (15 mL) was added PYBOP (6.07 g, 11.7 mmol) at 0° C. After stirring overnight at room temperature, the mixture was poured onto ice and extracted with 10% MeOH/$CH_2Cl_2$. The combined organic layers were dried over sodium sulfate and concentrated under reduced pressure to obtain crude material which was purified by column chromatography over silica gel to afford the title compound (3.0 g, 70%). Analytical Data: LCMS: 545.25 $(M+1)^+$; HPLC: 99.92% (@ 254 nm) ($R_t$; 5.677; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-$d_6$, 400 MHz) δ 11.46 (s, 1H), 8.23 (t, 1H), 7.14 (s, 1H), 6.92 (s, 1H), 6.65 (d, 1H, J=7.2 Hz), 5.85 (s, 1H), 4.23 (d, 2H, J=4 Hz), 3.14 (bs, 1H), 3.00-3.02 (m, 2H), 2.18 (s, 3H), 2.11 (s, 3H), 2.10 (s, 3H), 1.67-1.76 (m, 4H), 1.40 (m, 2H) 1.35 (m, 9H), 1.04-1.13 (m, 2H), 0.77 (t, 3H, J=6 Hz).

Step 3: synthesis of 3-(((1r,4r)-4-aminocyclohexyl)(ethyl)amino)-5-chloro-N-((4,6-dimethyl-2-oxo-1,2-dihydropyridin-3-yl)methyl)-2-methylbenzamide

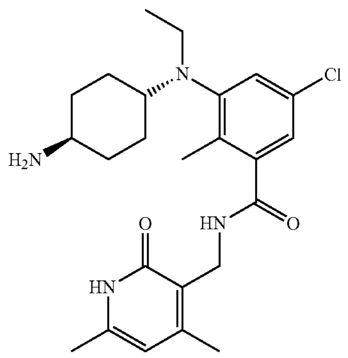

To a stirred solution of tert-butyl ((1r,4r)-4-((5-chloro-3-(((4,6-dimethyl-2-oxo-1,2-dihydropyridin-3-yl)methyl)carbamoyl)-2-methylphenyl)(ethyl)amino)cyclohexyl)carbamate (0.6 g, 1.10 mmol) in dichloromethane (2 mL) was added TFA (2 mL) at 0° C. The mixture was stirred at room temperature for 2 h and concentrated to dryness. The residue was dissolved in aqueous sodium bicarbonate and extracted with 20% MeOH/$CH_2Cl_2$. The combined organic layers were dried over sodium sulfate and concentrated under reduced pressure to afford crude product which was purified by column chromatography over silica get to afford the title compound (0.40 g, 81%). LCMS: 445.18 $(M+1)^+$; HPLC: 98.13% (@ 254 nm) ($R_t$; 4.096; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-$d_6$, 400 MHz) δ 8.22 (t, 1H), 7.13 (s, 1H), 6.92 (s, 1H), 5.85 (s, 1H), 4.23 (d, 2H, J=4 Hz), 3.00-3.01 (m, 2H), 2.59 (m, 1H), 2.18 (s, 3H), 2.12 (s, 3H), 2.10 (s, 3H), 1.73-1.76 (m, 2H), 1.65-1.68 (m, 2H), 1.36-1.39 (m, 2H), 0.97-1.00 (m, 2H), 0.77 (t, 3H, J=6 Hz). [1H merged in solvent peak].

Compound 122: 3-(((1r,4r)-4-acetamidocyclohexyl)(ethyl)amino)-5-chloro-N-((4,6-dimethyl-2-oxo-1,2-dihydropyridin-3-yl)methyl)-2-methylbenzamide

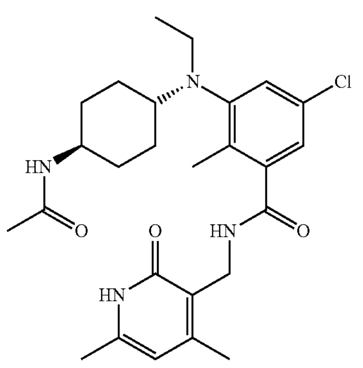

To a stirred solution of 3-(((1r,4r)-4-aminocyclohexyl)(ethyl)amino)-5-chloro-N-((4,6-dimethyl-2-oxo-1,2-dihydropyridin-3-yl)methyl)-2-methylbenzamide (0.30 g, 0.68 mmol) and EDCI.HCl (0.19 g, 1.0 mmol) in DMF (5 mL) were added HOBt (0.09 g, 0.68 mmol) and acetic acid (0.081 g, 1.35 mmol) at room temperature. After stirring for 18 h, water was added and the mixture was extracted with 10% MeOH/DCM. The combined organic layers were dried and concentrated giving crude material which was then purified by column chromatography over silica get to afford the title compound (0.10 g, 30%). LCMS: 487.25 $(M+1)^+$; HPLC: 92.95% (@ 254 nm) ($R_t$; 4.445; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-$d_6$, 400 MHz) δ11.45 (s, 1H), 8.21 (t, 1H), 7.64 (d, 1H, J=7.6 Hz), 7.14 (s, 1H), 6.92 (s, 1H), 5.85 (s, 1H), 4.24 (d, 2H, J=4.8 Hz), 3.41-3.43 (m, 1H), 3.01-3.03 (m, 2H), 2.61 (m, 1H), 2.18 (s, 3H), 2.13 (s, 3H), 2.10 (s, 3H), 1.74 (t, 7H, J=18 Hz), 1.40-1.43 (m, 2H), 1.07-1.12 (m, 2H), 0.77 (t, 3H, J=6.8 Hz).

Compound 207: 5-chloro-3-(cyclohexylthio)-N-((4,6-dimethyl-2-oxo-1,2-dihydropyridin-3-yl)methyl)-2-methylbenzamide

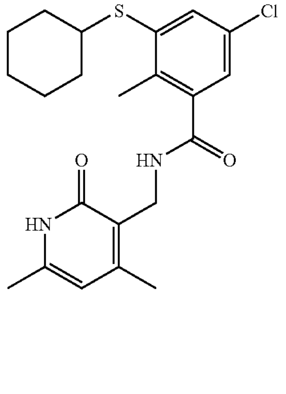 [SMILES: Cc1cc(C)c(CNC(=O)c2cc(Cl)cc(SC3CCCCC3)c2C)c(=O)[nH]1]

Step 1: Synthesis of methyl 3-bromo-5-chloro-2-methylbenzoate

To a stirred solution of $CuBr_2$ (12.3 g, 55.3 mmol) in acetonitrile (100 mL), t-butyl nitrite (7.79 g, 75.4 mmol) was added at 0° C. To this solution, methyl 3-amino-5-chloro-2-methylbenzoate (10 g, 50.3 mmol) in acetonitrile (50 mL) was added and stirred at 0° C. for 2 h and at rt for overnight. On completion, water added and the product extracted with ethyl acetate. The organic layer was washed with aq. $NH_4Cl$ solution and dried over sodium sulphate, then concentrated under reduced pressure. Silica gel column purification afforded the title compound (6.6 g, 50%).

Step 2: Synthesis of methyl 5-chloro-3-(cyclohexylthio)-2-methylbenzoate

To a stirred solution of methyl 3-bromo-5-chloro-2-methylbenzoate (1.0 g, 3.79 mmol) in 1,4-dioxane was added N,N-diisopropyl ethylamine (0.98 g, 7.59 mmol). The reaction mixture was purged with argon for 20 min. then $Pd(OAc)_2$ (0.042 g, 0.189 mmol), Xanthphos (0.22 g, 0.38 mmol) and cyclohexylthiol (0.44 g, 3.79 mmol) was added to it sequentially and again purged with argon for 10 min. The reaction mixture was then refluxed for 16 h. On completion, water was added, and the product extracted with ethyl acetate. The organic layer was dried over sodium sulphate and the product was purified by silica gel column to afford the title compound (1.0 g, 83%)

Step 3: Synthesis of 5-chloro-3-(cyclohexylthio)-N-((4,6-dimethyl-2-oxo-1,2-dihydropyridin-3-yl)methyl)-2-methylbenzamide Aqueous NaOH (0.2 g in 2.5 mL $H_2O$, 5.02 mmol) was added to a solution of methyl 5-chloro-3-(cyclohexylthio)-2-methylbenzoate (1.0 g, 3.35 mmol) in ethanol (10 mL) and the solution stirred at 60° C. for 1 h. After completion of the reaction, ethanol was removed under reduced pressure and the aqueous layer was acidified using dilute HCl to pH 6 and then citric acid to pH 4. The product was extracted was using 10% methanol in DCM. The combined organic layers were dried and concentrated to give the respective acid (0.91 g, 95%).

The above acid (0.91 g, 3.2 mmol) was then dissolved in DMSO (2 mL) and 3-(amino methyl)-4,6-dimethylpyridin-2(1H)-one (0.974 g, 6.41 mmol) and triethyl amine (0.65 g, 3.2 mmol) was added to it. The reaction mixture was stirred at room temperature for 15 min before PyBOP (2.5 g, 4.8 mmol) was added to it and stirring was continued for overnight. After completion of the reaction, the solution was poured into ice and the product was extracted with 10% MeOH in DCM. The combined organic layers were dried, concentrated to obtain crude product. Purification by solvent washings afforded the title compound (1.3 g, 93%).

Analytical Data: LCMS: 419.2 $(M+1)^+$; HPLC: 98.38% (@ 254 nm) ($R_t$; 7.989; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient 5% B to 95% B in 8 min, Hold for 1.5 min, 9.51=12-min 5% B); $^1H$ NMR (DMSO-$d_6$, 400 MHz) δ 11.47 (bs, 1H), 8.32 (t, 1H), 7.40 (s, 1H), 7.07 (s, 1H), 5.85 (s, 1H), 4.24-4.25 (d, 1H, J=4 Hz), 2.21 (s, 3H), 2.18 (s, 3H), 2.11 (s, 3H), 1.88-1.91 (m, 2H), 1.56-1.69 (m, 3H), 1.25-1.38 (m, 5H), 2 protons merged in solvent peak.

Compound 208: 5-chloro-3-(cyclohexylsulfinyl)-N-((4,6-dimethyl-2-oxo-1,2-dihydro-pyridin-3-yl)methyl)-2-methylbenzamide

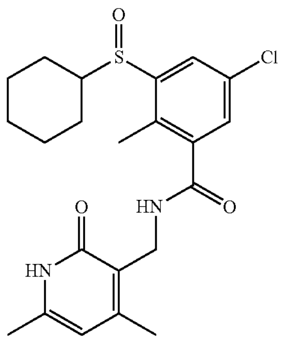 [SMILES: Cc1cc(C)c(CNC(=O)c2cc(Cl)cc(S(=O)C3CCCCC3)c2C)c(=O)[nH]1]

To a stirred solution of 5-chloro-3-(cyclohexylthio)-N-((4,6-dimethyl-2-oxo-1,2-dihydropyridin-3-yl)methyl)-2-methylbenzamide (0.2 g, 0.48 mmol) in DCM (7 mL) at 0° C., m-CPBA (0.098 g, 0.57 mmol) was added and stirred at 0° C. for 2 h. Reaction was monitored by TLC. After completion, the reaction mixture was diluted with DCM and washed with aqs. $NaHCO_3$. The product was purified by solvent washings to afford the title compound (0.17 g, 82.3%).

Analytical Data: LCMS: 435.1 $(M+1)^+$; HPLC: 92.68% (@ 220 nm) ($R_t$; 5.996; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (CDCl3, 400 MHz) δ 11.44 (bs, 1H), 7.82 (s, 1H), 7.45 (t, 1H), 7.39 (s, 1H), 5.97 (s, 1H), 4.52 (bs, 2H), 2.53-2.59 (m, 1H), 2.38 (s, 3H), 2.34 (s, 3H), 2.23 (s, 3H), 1.85-1.93 (m, 3H), 1.65 (m, 2H), 1.20-1.29 (m, 3H).

Compound 209: 5-chloro-3-(cyclohexylsulfonyl)-N-((4,6-dimethyl-2-oxo-1,2-dihydro-pyridin-3-yl)methyl)-2-methylbenzamide

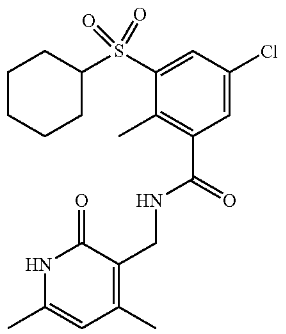 [SMILES: Cc1cc(C)c(CNC(=O)c2cc(Cl)cc(S(=O)(=O)C3CCCCC3)c2C)c(=O)[nH]1]

To a stirred solution of 5-chloro-3-(cyclohexylthio)-N-((4,6-dimethyl-2-oxo-1,2-dihydropyridin-3-yl)methyl)-2-methylbenzamide (0.1 g, 0.238 mmol) in DCM (4 mL) at 0° C., m-CPBA (0.082 g, 0.48 mmol) was added and stirred at rt for 2 h. Reaction was monitored by TLC. After completion reaction mixture was diluted with DCM and washed with aqs. $NaHCO_3$. The product was purified by prep. HPLC to afford the title compound (0.075 g, 23%).

Analytical Data: LCMS: 451.1 $(M+1)^+$; HPLC: 83.44% (@ 254 nm) ($R_t$; 6.547; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (CDCl3, 400 MHz) δ 11.44 (bs, 1H), 7.98 (s, 1H), 7.50 (s, 1H), 7.45 (t, 1H), 5.97 (s, 1H), 4.51 (d, 2H, J=4 Hz), 2.94-3.00 (m, 1H), 2.62 (s, 3H), 2.38 (s, 3H), 2.21 (s, 3H), 1.88-1.95 (m, 4H), 1.70 (m, 1H), 1.52-1.55 (m, 2H), 1.21 (m, 3H).

Compound 416: 5-chloro-N-((4,6-dimethyl-2-oxo-1,2-dihydropyridin-3-yl)methyl)-3-(ethyl((1s,4s)-4-(methylsulfonyl)cyclohexyl)amino)-2-methylbenzamide

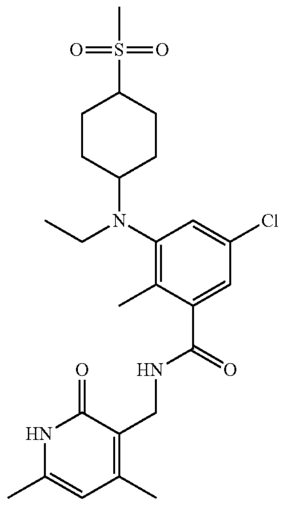 [SMILES: CCN(c1cc(Cl)cc(C(=O)NCc2c(C)cc(C)[nH]c2=O)c1C)C1CCC(S(C)(=O)=O)CC1]

Step 1: Synthesis of 4-methanesulfonylcyclohexan-1-one

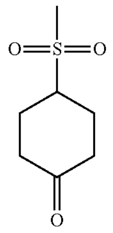

A solution containing (buta-1,3-dien-2-yloxy)(trimethyl)silane (12.5 ml, 70.7 mmol) in toluene (50 ml), was treated with (methylsulfonyl)ethene (4.1 ml, 47.1 mmol) and heated under reflux for 76 hours. After which time, the reaction mixture was cooled to room temperature and concentrated in-vacuo to give a yellow oil. The oil was dissolved in $CH_2Cl_2$ (120 ml) and filtered through Celite®. The filtrate was concentrated in-vacuo and the resulting residue was then dissolved in MeOH (8 ml) with cooling (ice/water). It was then treated with TFA (2.0 ml). The reaction mixture was stirred at 0° C. for a further 10 minutes and then at room temperature for 25 hours. The reaction mixture was concentrated in-vacuo and the residue was purified by flash column chromatography (0-10% $MeOH/CH_2Cl_2$) 100 g SNAP cartridge on the Biotage Isolera to give the title compound 1.2 g (14%) as a thick yellow oil. LC-MS 94%, 0.39 min (3.5 minute LC-MS method), m/z=177.0 (ELS visible only). $^1H$ NMR (500 MHz, CHLOROFORM-d) δ ppm 3.24-3.32 (m, 1H) 2.94 (s, 3H) 2.62-2.70 (m, 2H) 2.50-2.56 (m, 2H) 2.38-2.45 (m, 2H) 2.07-2.18 (m, 2H).

Step 2: Synthesis of methyl 5-chloro-2-methyl-3-(((1s,4s)-4-(methylsulfonyl)cyclohexyl)amino)benzoate

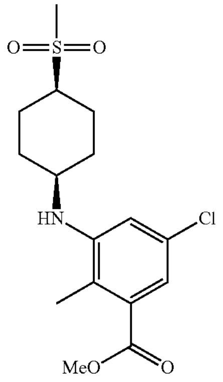 [SMILES: COC(=O)c1cc(Cl)cc(N[C@H]2CC[C@@H](S(C)(=O)=O)CC2)c1C]

To a stirred solution of 4-methanesulfonylcyclohexan-1-one (94%, 0.56 g, 3.0 mmol) in 1,2-dichloroethane (10 ml) under a balloon of nitrogen, was added methyl 3-amino-5-chloro-2-methylbenzoate (0.60 g, 3.0 mmol), followed by acetic acid (1.0 ml, 18.0 mmol). The solution was stirred for 50 minutes before the portionwise addition of sodium triacetoxyborohydride (1.9 g, 9.0 mmol) over 4 hours. The resulting suspension was stirred overnight before the addition of 4-methanesulfonylcyclohexan-1-one (0.28 g, 1.5 mmol) in 1,2-dichloroethane (1.5 ml) and sodium triacetoxyborohydride (0.96 g, 4.5 mmol) over 2.5 hours. The reaction mixture was stirred for a further 67 hours before the addition of deionized water (40 ml) to the reaction mixture and neutralisation (pH 8) by the gradual addition of solid $NaHCO_3$ (4.8 g). The mixture was extracted with $CH_2Cl_2$ (3×25 ml). The combined organic extracts were washed with brine (40 ml), dried over $MgSO_4$, filtered and concentrated in-vacuo. The residue was pre-absorbed onto silica and purified by flash column chromatography (0-55% ethyl acetate/heptanes) 100 g SNAP cartridge on the Biotage Isolera to give the title compound (131 mg, 12%). LC-MS 96%, 2.09 min (3.5 minute LC-MS method), m/z=359.85, 360.85, 361.90, 362.85; $^1H$ NMR (500 MHz, CHLOROFORM-d) δ ppm 7.12 (br. s., 1H) 6.68 (br. s., 1H) 3.89 (s, 3H) 3.82 (br. s., 1H) 3.71 (br. s., 1H) 2.93-3.02 (m, 1H) 2.89 (s, 3H) 2.29 (s, 3H) 2.03-2.18 (m, 4H) 1.91-2.02 (m, 2H) 1.71-1.83 (m, 2H).

The other isomer methyl 5-chloro-2-methyl-3-(((1r,4r)-4-(methylsulfonyl)cyclohexyl)amino)benzoate was also isolated

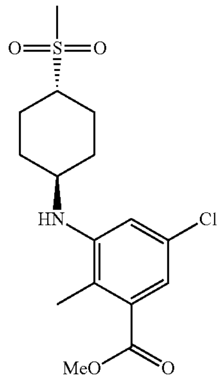 [SMILES: COC(=O)c1cc(Cl)cc(N[C@H]2CC[C@H](S(C)(=O)=O)CC2)c1C]

(92 mg, 8%), LC-MS 96%, 2.06 min (3.5 minute LC-MS method), m/z=359.85, 360.90, 361.90, 362.85; $^1$H NMR (500 MHz, CHLOROFORM-d) δ ppm 7.11 (br. s, 1H) 6.68 (br. s., 1H) 3.89 (s, 3H) 3.62 (br. s., 1H) 3.27-3.36 (m, 1H) 2.84-2.95 (m, 4H) 2.32-2.42 (m, 4H) 2.24 (br. s., 3H) 1.72-1.85 (m, 2H) 1.27-1.35 (m, 2H).

The assignment of cis and trans from further NMR experiments could not be made and assignment is arbitrary.

Step 3: Synthesis of methyl 5-chloro-3-(ethyl((1s, 4s)-4-(methylsulfonyl)cyclohexyl)amino)-2-methylbenzoate

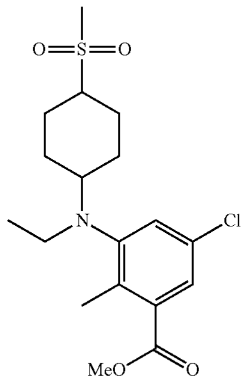 [SMILES: CCN(c1cc(Cl)cc(C(=O)OC)c1C)C1CCC(S(C)(=O)=O)CC1]

To a stirred solution of methyl 5-chloro-2-methyl-3-(((1s, 4s)-4-(methylsulfonyl)cyclohexyl)amino)benzoate (246 mg, 0.68 mmol) in dry 1,2-dichloroethane (6.0 ml), was added acetaldehyde (115 μl, 2.1 mmol), followed by acetic acid (235 μl, 4.1 mmol). The reaction was stirred for 35 minutes before sodium triacetoxyborohydride (435 mg, 2.1 mmol) was added in portions over 50 minutes and the reaction was stirred overnight and then treated with acetaldehyde (115 μl, 2.1 mmol). The reaction mixture was stirred for 1 hour before addition of sodium triacetoxyborohydride (435 mg, 2.1 mmol) in portions over 1 hour and the reaction mixture stirred overnight. Acetaldehyde (229 μl, 4.1 mmol) was added and the reaction stirred for 2.5 hours, followed by the addition of sodium triacetoxyborohydride (869 mg, 4.1 mmol) in portions over 1.5 hours and stirring was continued overnight. Acetaldehyde (229 μl, 4.1 mmol) was added along with 1,2-dichloroethane (4.0 ml) to aid solution and the reaction stirred for 4 hours. Sodium triacetoxyborohydride (869 mg, 4.1 mmol) was added in portions over 2 hours and stirring was continued over the weekend. Acetaldehyde (229 μl, 4.1 mmol) was added and the reaction stirred for 1.5 hours, followed by the addition of sodium triacetoxyborohydride (869 mg, 4.1 mmol) in equal portions over 1 hour, along with 1,2-dichloroethane (5.0 ml) and stirring was continued overnight. Acetaldehyde (382 μl, 6.8 mmol) was added and the reaction stirred for 2.5 hours, followed by the addition of sodium triacetoxyborohydride (1.4 g, 6.8 mmol) in equal portions over 4 hours, along with 1,2-dichloroethane (10 ml) and stirring was continued overnight. The reaction mixture was diluted with water (40 ml) and neutralised (to pH 8) by the gradual addition of solid $NaHCO_3$ (5.79 g). The layers were separated and the aqueous layer was extracted with $CH_2Cl_2$ (3×25 ml). The combined organic phases were washed with brine (20 ml), dried ($MgSO_4$), filtered and concentrated in-vacuo. The crude residue was pre-absorbed onto silica and purified by column chromatography (0-50% EtOAc/Heptanes) 10 g SNAP cartridge on the Biotage Isolera to give the title compound (140 mg, 51%) as a colourless glassy solid. LC-MS 97%, 2.29 min (3 minute LC-MS method), m/z=387.95, 388.95, 389.90, 390.95. $^1$H NMR (500 MHz, CHLOROFORM-d) δ ppm 7.59 (d, J=1.89 Hz, 1H) 7.21 (d, J=1.89 Hz, 1H) 3.91 (s, 3H) 3.45 (br. s., 1H) 3.01 (m, 2H) 2.86-2.95 (m, 1H) 2.82 (s, 3H) 2.52 (s, 3H) 2.08 (br. s., 2H) 1.94 (br. s., 2H) 1.86 (br. s., 2H) 1.46-1.54 (m, 2H) 0.89 (t, J=7.01 Hz, 3H).

Step 4: Synthesis of 5-chloro-3-(ethyl((1s,4s)-4-(methylsulfonyl)cyclohexyl)amino)-2-methylbenzoic acid

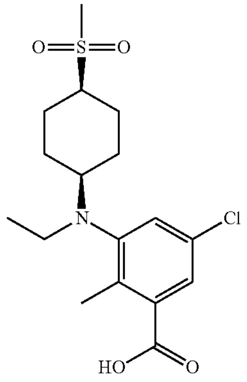 [SMILES: CCN(c1cc(Cl)cc(C(=O)O)c1C)[C@H]1CC[C@@H](S(C)(=O)=O)CC1]

To a stirred solution of methyl 5-chloro-3-(ethyl((1s,4s)-4-(methylsulfonyl)cyclohexyl)amino)-2-methylbenzoate (140 mg, 0.36 mmol) in THF (5.0 ml) and MeOH (0.3 ml), was added a solution of 4M NaOH (2.7 ml). The resulting solution was stirred at 50° C. for 21 hours and then treated with 4M NaOH (0.9 ml, 3.6 mmol) and heating was continued for a further 4 hours. After which time, the reaction mixture was left to reach room temperature and then concentrated in-vacuo. The resulting aqueous residue was extracted with $CH_2Cl_2$ (20 ml) and ether (20 ml). The pH of the aqueous phase was then adjusted to 3-4 by the addition of 1M HCl (aq) (13 ml) and extracted with ethyl acetate (3×25 ml). The combined ethyl acetate extracts were dried over $MgSO_4$, filtered and concentrated in-vacuo to give the title compound (122 mg, 80% yield) as a light yellow solid. LC-MS 89%, 4.03 min (7 minute LC-MS method), m/z=373.95, 374.90, 375.95, 377.00. $^1$H NMR (500 MHz, CHLOROFORM-d) δ ppm 7.77 (d, J=1.89 Hz, 1H) 3.47 (br. s., 1H) 3.03 (br. s., 2H) 2.88-2.97

(m, 1H) 2.84 (s, 3H) 2.60 (s, 3H) 2.12 (br. s, 2H) 1.96 (br. s, 2H) 1.88 (br. s., 2H) 1.55 (br. s., 2H) 0.91 (t, J=7.01 Hz, 3H). 1×ArH assumed to be under the $CDCl_3$ peak and the $CO_2H$ peak also not visible.

Step 5: Synthesis of 5-chloro-N-((4,6-dimethyl-2-oxo-1,2-dihydropyridin-3-yl)methyl)-3-(ethyl((1s, 4s)-4-(methylsulfonyl)cyclohexyl)amino)-2-methylbenzamide

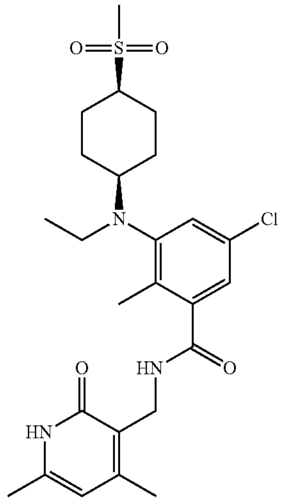

A stirred solution of 5-chloro-3-(ethyl((1s,4s)-4-(methylsulfonyl)cyclohexyl)amino)-2-methylbenzoic acid (90%, 122 mg, 0.29 mmol) in anhydrous DMF (2.0 ml) at 0° C. under a balloon of $N_2$, was treated with HATU (134 mg, 0.35 mmol) and DIPEA (102 μl, 0.59 mmol) dropwise. The resulting solution was stirred for 10 minutes and then treated with 3-(aminomethyl)-4,6-dimethyl-1,2-dihydropyridin-2-one (89%, 60 mg, 0.35 mmol). The resulting suspension was stirred at 0° C. for 15 minutes and then stirred at room temperature over the weekend. The reaction mixture was partitioned between water (10 ml) and $CH_2Cl_2$ (10 ml). The layers were separated and the aqueous phase was extracted with $CH_2Cl_2$ (3×15 ml). The combined organics were washed with a saturated solution of $NaHCO_3$ (aq) (10 ml), water (40 ml), brine (2×25 ml), dried ($MgSO_4$), filtered and concentrated in-vacuo. The residue was purified by flash column chromatography (0-9% MeOH/$CH_2Cl_2$) 10 g SNAP cartridge on the Biotage Isolera to give the title compound (120 mg, 76% yield) as an off-white solid. LC-MS: 95%, 3.71 min (7 minute LC-MS method), m/z=508.10, 509.10, 510.10, 511.10. $^1H$ NMR (500 MHz, Chloroform-d) δ 10.84 (s, 1H), 7.07 (s, 2H), 7.00 (m, 1H), 6.10 (s, 1H), 4.53 (d, J=5.8 Hz, 2H), 3.45 (s, 1H), 3.07-2.95 (m, 2H), 2.93-2.85 (m, 1H), 2.81 (s, 3H), 2.45 (s, 3H), 2.31 (s, 3H), 2.29 (s, 3H), 2.14-2.01 (m, 2H), 1.97-1.89 (m, 2H), 1.87-1.80 (m, 2H), 1.50 (br s, 2H), 0.88 (t, J=5.9 Hz, 3H).

Compound 417: 5-chloro-N-((4,6-dimethyl-2-oxo-1, 2-dihydropyridin-3-yl)methyl)-3-(ethyl((1r,4r)-4-(methylsulfonyl)cyclohexyl)amino)-2-methylbenzamide This compound was prepared in an analogous manner to that of compound 416 using the other isomer obtained in step 2

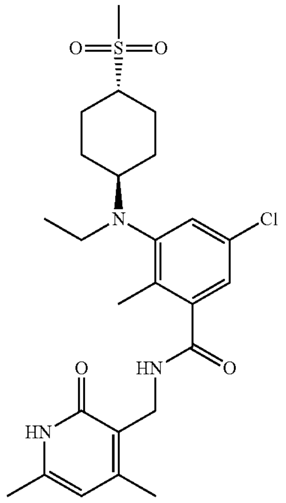 [SMILES: CCN(c1cc(Cl)cc(C(=O)NCc2c(C)cc(C)[nH]c2=O)c1C)[C@H]1CC[C@H](S(C)(=O)=O)CC1]

Compound 392: N-[(4,6-Dimethyl-2-oxo-1,2-dihydropyridin-3-yl)methyl]-3-[ethyl(1-methylpiperidin-4-yl)amino]-2-methyl-5-(trifluoromethyl)benzamide

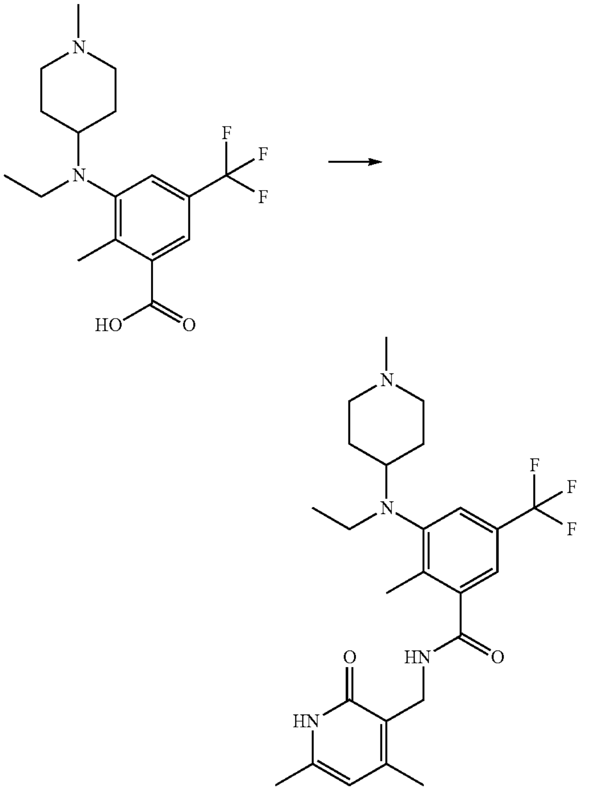

To a stirred solution of 3-[ethyl(1-methylpiperidin-4-yl)amino]-2-methyl-5-(trifluoromethyl)benzoic acid (crude material, 580 mg, 1.68 mmol) and 3-(aminomethyl)-4,6-dimethyl-1,2-dihydropyridin-2-one HCl salt (477 mg, 2.53 mmol) in DMSO (6 mL) was added PyBOP (1.57 g, 3.02 mmol) and hunig base (650 mg, 5.04 mmol). The reaction mixture was stirred at 23° C. for 20 hours. The reaction mixture was quenched with water and resulting precipitate was collected. The solid was purified by silica gel column chromatography (NH—$SiO_2$ ethylacetate/MeOH=25/1) to give the titled compound as a white amorphous (386 mg, 48% yield). $^1$HNMR (400 MHz, $CDCl_3$) δppm; 7.31 (s, 1H), 7.27 (s, 1H), 7.18 (t, J=5.7 Hz, 1H), 5.95 (s, 1H), 4.55 (d, J=5.9 Hz, 2H), 3.17 (dq, J=6.4, 3.3 Hz, 2H), 3.08 (q, J=7.0 Hz, 2H), 2.81 (m, 2H), 2.70 (m, 1H), 2.40 (s, 3H), 2.33 (s, 3H), 2.23 (s, 3H), 2.21 (s, 3H), 1.78-1.93 (m, 2H), 1.70 (m, 2H), 0.84 (t, J=7.0 Hz, 3H); MS (ES) [M+H] 479.2, [M+Na] 501.3; HPLC 96.8% purity.

Compound 393: 3-[Ethyl(1-methylpiperidin-4-yl)amino]-2-methyl-N-[(6-methyl-2-oxo-4-propyl-1,2-dihydropyridin-3-yl)methyl]-5-(trifluoromethyl)benzamide

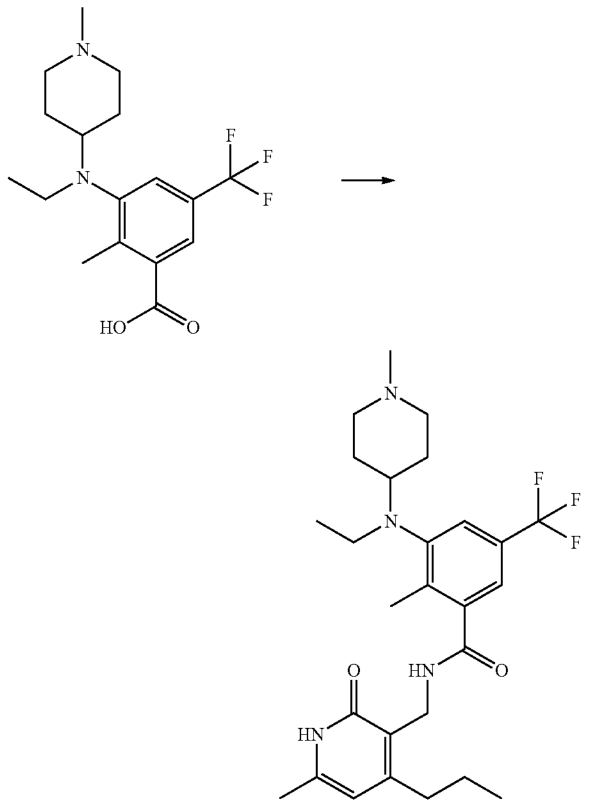

To a stirred solution of 3-[ethyl(1-methylpiperidin-4-yl)amino]-2-methyl-5-(trifluoromethyl)benzoic acid (crude material, 680 mg, 1.97 mmol) and 3-(aminomethyl)-6-methyl-4-propyl-1,2-dihydropyridin-2-one HCl salt (642 mg, 2.96 mmol) in DMSO (7 mL) was added PyBOP (1.85 g, 3.55 mmol) and hunig base (764 mg, 5.91 mmol). The reaction mixture was stirred at 23° C. for 20 hours. The reaction mixture was quenched with water and resulting precipitate was collected. The solid was purified by silica gel column chromatography (NH—$SiO_2$ ethylacetate/MeOH=20/1) to give the titled compound as a white solid (224 mg, 22% yield). $^1$H-NMR (400 MHz, $CDCl_3$) δppm; 7.31 (s, 1H), 7.26 (s, 1H), 7.16 (m, 1H), 5.94 (s, 1H), 4.55 (d, J=5.9 Hz, 2H), 3.08 (q, J=7.0 Hz, 2H), 2.82 (m, 2H), 2.66-2.73 (m, 3H), 2.33 (s, 3H), 2.24 (s×2, 6H), 1.79-1.98 (m, 2H), 1.67-1.75 (m, 4H), 1.59-1.66 (m, 2H), 1.02 (t, J=7.2 Hz, 3H), 0.84 (t, J=7.0 Hz, 3H); MS (ES) [M−H] 505.2; HPLC 98.1% purity.

Compound 394: 3-[Ethyl(1-methylpiperidin-4-yl)amino]-2-methyl-N-{[6-methyl-2-oxo-4-(propan-2-yl)-1,2-dihydropyridin-3-yl]methyl}-5-(trifluoromethyl)benzamide

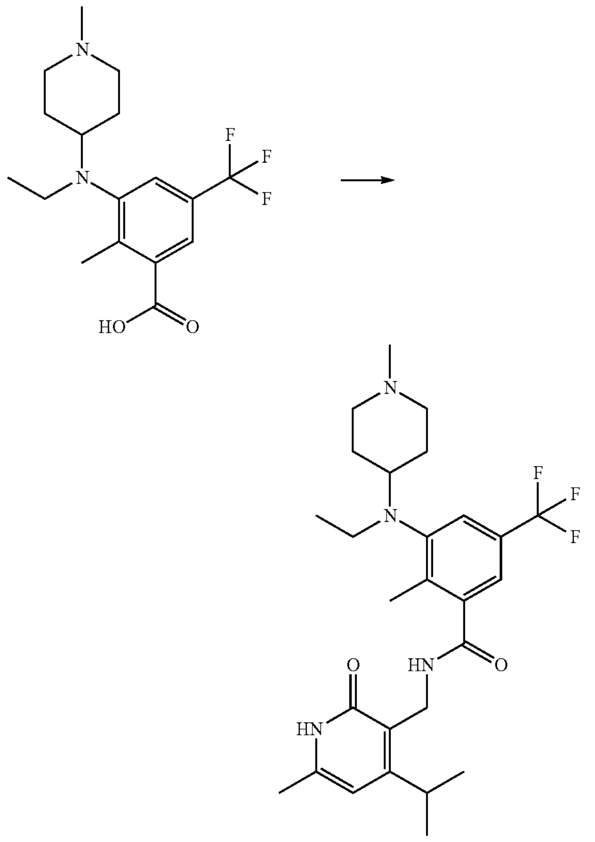

To a stirred solution of 3-[ethyl(1-methylpiperidin-4-yl)amino]-2-methyl-5-(trifluoromethyl)benzoic acid (crude material, ~0.313 mmol) and 3-(aminomethyl)-6-methyl-4-(propan-2-yl)-1,2-dihydropyridin-2-one HCl salt (88.0 mg, 0.407 mmol) in DMSO (2.4 mL) was added PyBOP (244 mg, 0.470 mmol) and hunig base (164 ul, 0.939 mmol). The reaction mixture was stirred at rt for 16 hours. The reaction mixture was quenched with water and diluted with ethylacetate. The aqueous layer was extracted with dichloromethane. The combined organic layer was washed with brine, dried over $Na_2SO_4$, filtered and concentrated. The residue was purified by silica gel column chromatography (NH—$SiO_2$ ethylacetate/MeOH=20/1+5% triethylamine). The crude compound was dissolved with DMSO, diluted with water. The precipitated solid was collected and triturated with ethylacetate/TBME/hexane to give the titled compound as a white solid (80.0 mg, 51% yield). $^1$H-NMR (400 MHz, $CDCl_3$) δppm; 7.31 (s, 1H), 7.26 (s, 1H), 7.03-7.10 (m, 1H), 6.04 (s, 1H), 4.59 (d, J=6.0 Hz, 2H), 3.49-3.55 (m, 1H), 3.09 (q, J=6.8 Hz, 2H), 2.81-2.84 (m, 2H), 2.70-2.78 (m, 1H), 2.32 (s, 3H), 2.26 (s, 3H), 2.24 (s, 3H), 1.86-1.89 (m, 2H), 1.68-1.71 (m, 4H), 1.22 (d, J=6.4 Hz, 6H), 0.84 (t, J=6.8 Hz, 3H); MS (ES) [M+H] 507.2, [M+Na] 529.2; HPLC 97.7% purity.

Compound 395: 3-[Ethyl(1-methylpiperidin-4-yl)amino]-2-methyl-N-{[6-methyl-2-oxo-4-(trifluoromethyl)-1,2-dihydropyridin-3-yl]methyl}-5-(trifluoromethyl)benzamide

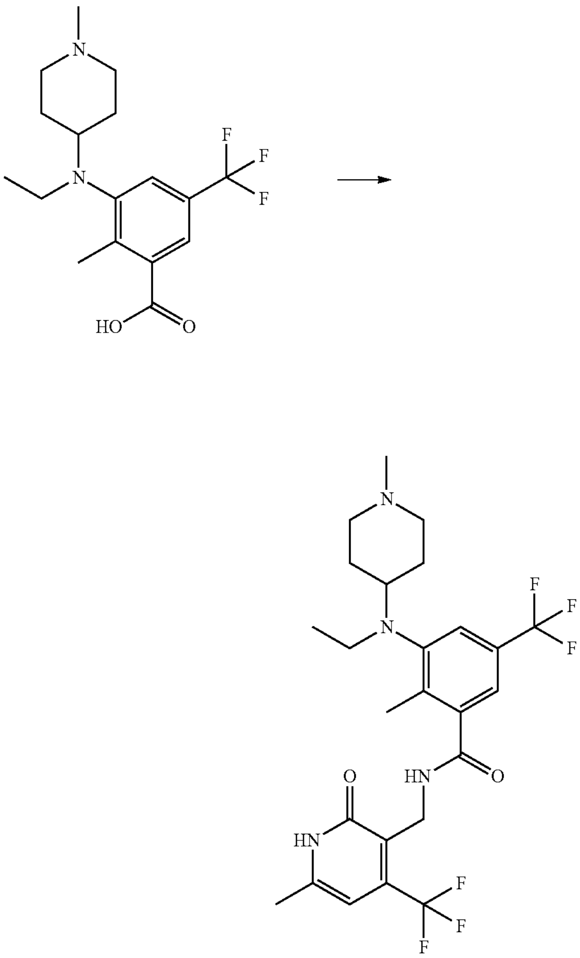

To a stirred solution of 3-[ethyl(1-methylpiperidin-4-yl)amino]-2-methyl-5-(trifluoromethyl)benzoic acid (crude material, ~0.313 mmol) and 3-(aminomethyl)-6-methyl-4-(trifluoromethyl)-1,2-dihydropyridin-2-one hydrochloride HCl salt (100 mg, 0.91 mmol) in DMSO (2.4 mL) was added PyBOP (248 mg, 1.05 mmol) and hunig base (166 ul, 2.10 mmol). The reaction mixture was stirred at rt for 16 hours. The reaction mixture was quenched with water and resulting precipitate was collected. The solid was triturated from ethylacetate/hexane. The resulting solid was purified by silica gel column chromatography (NH—$SiO_2$ ethylacetate/MeOH=10/1+10% triethylamine). The crude compound was triturated from ethylacetate/hexane, and dried to give the titled compound as a white solid (75.0 mg, 44% yield). $^1$H-NMR (400 MHz, $CDCl_3$) δppm; 7.32 (s, 1H), 7.26 (s, 1H), 6.86-6.89 (m, 1H), 6.34 (s, 1H), 4.73 (d, J=6.4 Hz, 2H), 3.08 (q, J=7.2 Hz, 2H), 2.80-2.85 (m, 2H), 2.70-2.78 (m, 1H), 2.37 (s, 3H), 2.35 (s, 3H), 2.24 (s, 3H), 1.85-1.89 (m, 2H), 1.69-1.72 (m, 4H), 0.84 (t, J=7.2 Hz, 3H); MS (ES) [M+H] 533.1, [M+Na] 555.2; HPLC 95.8% purity.

Compound 395: 3-(ethyl(1-methylpiperidin-4-yl)amino)-2-methyl-N-((6-methyl-2-oxo-4-(trifluoromethyl)-1,2-dihydropyridin-3-yl)methyl)-5-(trifluoromethyl)benzamide diformate

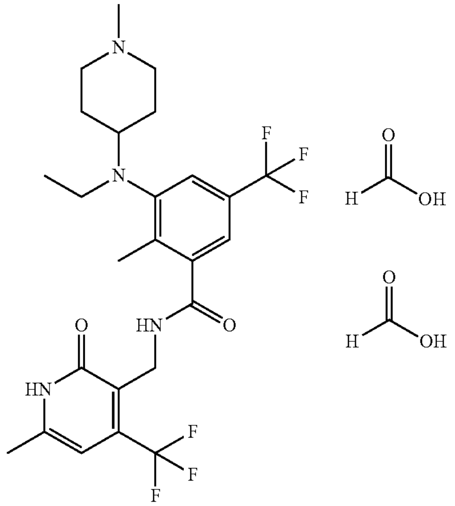

$^1$H NMR (400 MHz, $CD_3OD$) δ ppm 8.39 (s, 2H), 7.48 (s, 1H), 7.36 (s, 1H), 6.36 (s, 1H), 4.52 (s, 2H), 3.38 (br, 2H), 3.18 (br, m, 1H), 3.11 (q, J=7.2 Hz, 2H), 2.96 (br, m, 2H), 2.77 (s, 3H), 2.35 (s, 3H), 2.31 (s, 3H), 1.97 (br, d, J=12.0 Hz, 2H), 1.83 (br, m, 2H), 0.84 (t, J=7.2 Hz, 3H); MS (ES) (M+H) =533.53.

Following the same preparation method above of 3-[Ethyl(1-methylpiperidin-4-yl)amino]-2-methyl-N-{[6-methyl-2-oxo-4-(trifluoromethyl)-1,2-dihydropyridin-3-yl]methyl}-5-(trifluoromethyl)benzamide, the following analogs have been prepared using the corresponding carboxylic acid and amine, and purified by reverse phase HPLC (ACN-$H_2O$ containing 0.1% formic acid).

Compound 396: 3-(ethyl(1-methylpiperidin-4-yl)amino)-N-((5-fluoro-6-methyl-2-oxo-4-propyl-1,2-dihydropyridin-3-yl)methyl)-2-methyl-5-(trifluoromethyl)benzamide formate

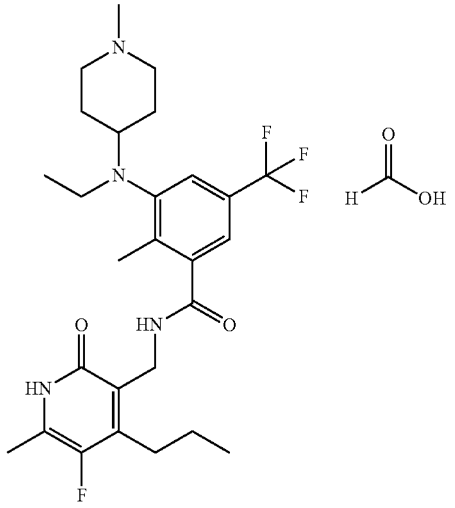

$^1$H NMR (400 MHz, $CD_3OD$) δ ppm 8.31 (s, 1H), 7.49 (s, 1H), 7.34 (s, 1H), 4.45 (s, 2H), 3.39 (br, 2H), 3.17 (br, 1H), 3.10 (q, J=7.2 Hz, 2H), 2.97 (br, m, 2H), 2.77 (s, 3H), 2.74 (br, m, 2H), 2.33 (s, 3H), 2.22 (d, J=2.8 Hz, 3H), 1.97 (br, m, 2H), 1.85 (br, m, 2H), 1.60 (m, 2H), 1.02 (t, J=7.2 Hz, 3H), 0.84 (t, J=6.8 Hz, 3H); MS (ES) (M+H)=525.58.

Compound 397: 3-(ethyl(1-methylpiperidin-4-yl)amino)-N-((5-fluoro-4-isopropyl-6-methyl-2-oxo-1,2-dihydropyridin-3-yl)methyl)-2-methyl-5-(trifluoromethyl)benzamide formate

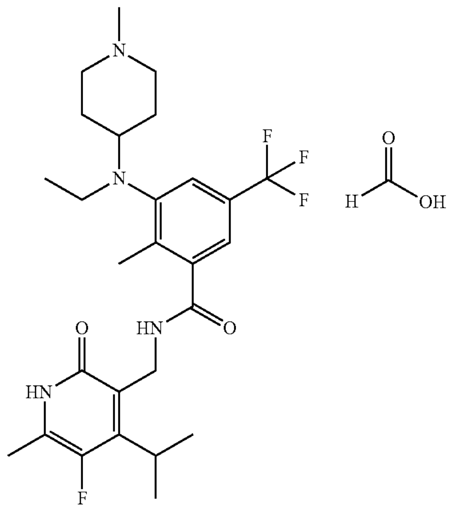

LCMS ES+ (M+1)=525.58. $^1$H NMR (400 MHz, $CD_3OD$) δ ppm 8.31 (s, 1H), 7.50 (s, 1H), 7.34 (s, 1H), 4.49 (s, 2H), 3.48 (m, 1H), 3.39 (br, 2H), 3.18 (br, m, 1H), 3.09 (q, J=6.8 Hz, 2H), 2.97 (br, m, 2H), 2.78 (s, 3H), 2.34 (s, 3H), 2.21 (d, J=3.2 Hz, 3H), 1.96 (br, d, J=12.0 Hz, 2H), 1.86 (br, m, 2H), 1.32 (dd, J=1.6 Hz, J=7.2 Hz, 6H), 0.84 (t, J=6.8 Hz, 3H); MS (ES) (M+H)=525.58.

Compound 398: 3-(ethyl(1-methylpiperidin-4-yl)amino)-N-((5-fluoro-4,6-dimethyl-2-oxo-1,2-dihydropyridin-3-yl)methyl)-2-methyl-5-(trifluoromethyl)benzamide formate

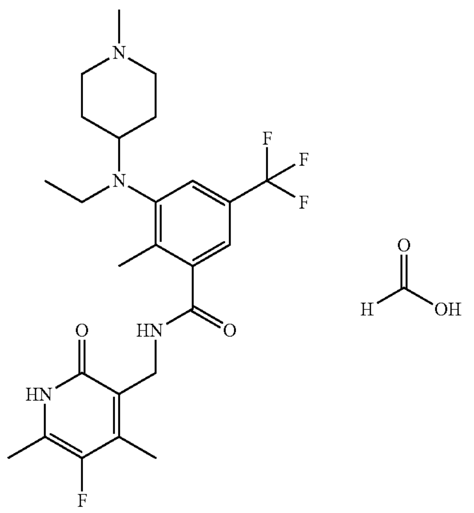 [SMILES: CCN(c1cc(C(F)(F)F)cc(C(=O)NCc2c(C)c(F)c(C)[nH]c2=O)c1C)C1CCN(C)CC1 ; O=CO]

$^1$H NMR (400 MHz, $CD_3OD$) δ ppm 8.29 (s, 1H), 7.49 (s, 1H), 7.35 (s, 1H), 4.45 (s, 2H), 3.39 (br, 2H), 3.19 (br, 1H), 3.09 (q, J=7.2 Hz, 2H), 2.97 (br, m, 2H), 2.77 (s, 3H), 2.34 (d, J=2.4 Hz, 3H), 2.33 (s, 3H), 2.22 (d, J=3.2 Hz, 3H), 1.97 (br, m, 2H), 1.86 (br, m, 2H), 0.84 (t, J=6.8 Hz, 3H); MS (ES) (M+H)=497.51.

Compound 399: 3-(ethyl(1-methylpiperidin-4-yl)amino)-N-((5-fluoro-6-methyl-2-oxo-4-(trifluoromethyl)-1,2-dihydropyridin-3-yl)methyl)-2-methyl-5-(trifluoromethyl)benzamide diformate

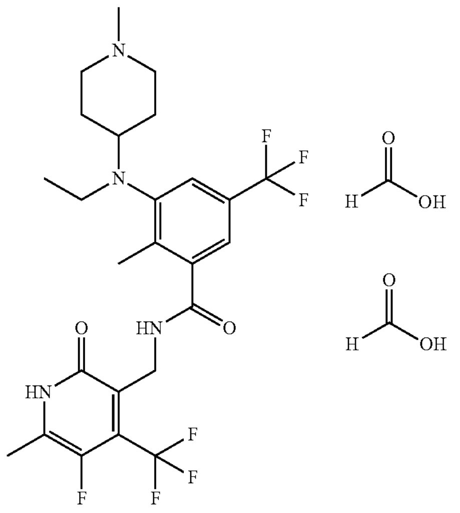

$^1$H NMR (400 MHz, $CD_3OD$) δ ppm 8.32 (s, 2H), 7.50 (s, 1H), 7.34 (s, 1H), 4.59 (s, 2H), 3.40 (br, 2H), 3.18 (br, m, 2H), 3.09 (q, J=6.8, 2H), 2.96 (br, m, 2H), 2.78 (s, 3H), 2.35 (s, 3H), 2.29 (d, J=3.2 Hz, 3H), 1.98 (br, d, J=13.2 Hz, 2H), 1.86 (m, 1H), 1.80 (br, m, 2H), 0.84 (t, J=6.8 Hz, 3H); MS (ES) (M+H)=551.53.

Compound 399: 3-(ethyl(1-methylpiperidin-4-yl)amino)-N-((5-fluoro-6-methyl-2-oxo-4-(trifluoromethyl)-1,2-dihydropyridin-3-yl)methyl)-2-methyl-5-(trifluoromethyl)benzamide diformate

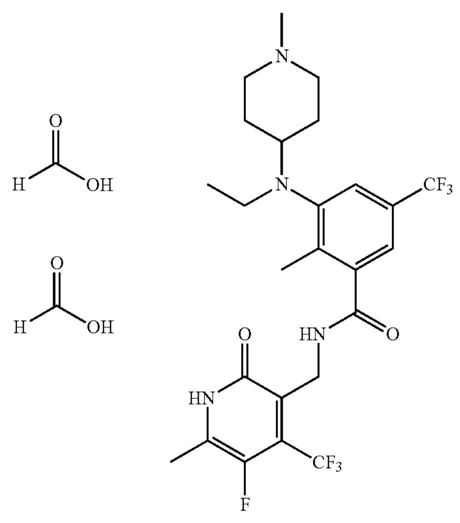 [SMILES: O=CO ; O=CO ; CCN(c1cc(C(F)(F)F)cc(C(=O)NCc2c(C(F)(F)F)c(F)c(C)[nH]c2=O)c1C)C1CCN(C)CC1]

6-Methyl-2-oxo-4-(trifluoromethyl)-1,2-dihydropyridine-3-carbonitrile was fluorinated as described for 5-fluoro-4-isopropyl-6-methyl-2-oxo-1,2-dihydropyridine-3-carbonitrile. The product was isolated as a 3:1 mixture of 6-methyl-2-oxo-4-(trifluoromethyl)-1,2-dihydropyridine-3-carbonitrile (starting material) and 5-fluoro-6-methyl-2-oxo-4-(trifluoromethyl)-1,2-dihydropyridine-3-carbonitrile. For 5-fluoro-6-methyl-2-oxo-4-(trifluoromethyl)-1,2-dihydropyridine-3-carbonitrile, LCMS E-S (M+H)=221.2. This mixture of nitriles was subjected to the reduction conditions as described above for 3-(Aminomethyl)-5-fluoro-4-isopropyl-6-methylpyridin-2(1H)-one. For fluorinated compound LCMS (ES) (M+H) showed 225.2 and for non-fluorinated analog LCMS (ES) (M+H) showed 207.2. Subsequent coupling reaction was performed with the crude mixture of amines without further purifications. For 3-(ethyl(1-methylpiperidin-4-yl)amino)-N-((5-fluoro-6-methyl-2-oxo-4-(trifluoromethyl)-1,2-dihydropyridin-3-yl)methyl)-2-methyl-5-(trifluoromethyl)benzamide diformate; $^1$HNMR (400 MHz, $CD_3OD$) δ ppm 8.32 (s, 2H), 7.50 (s, 1H), 7.34 (s, 1H), 4.59 (s, 2H), 3.40 (br, 2H), 3.18 (br, m, 1H), 3.09 (q, J=6.8, 2H), 2.96 (br, m, 2H), 2.78 (s, 3H), 2.35 (s, 3H), 2.29 (d, J=3.2 Hz, 3H), 1.98 (br, d, J=13.2 Hz, 2H), 1.80 (br, m, 2H), 0.84 (t, J=6.8 Hz, 3H); MS (ES) (M+H) 551.5.

Compound 400: N-[(4,6-Eimethyl-2-oxo-1,2-dihydropyridin-3-yl)methyl]-3-{ethyl[1-(propan-2-yl)piperidin-4-yl]amino}-2-methyl-5-(trifluoromethyl)benzamide

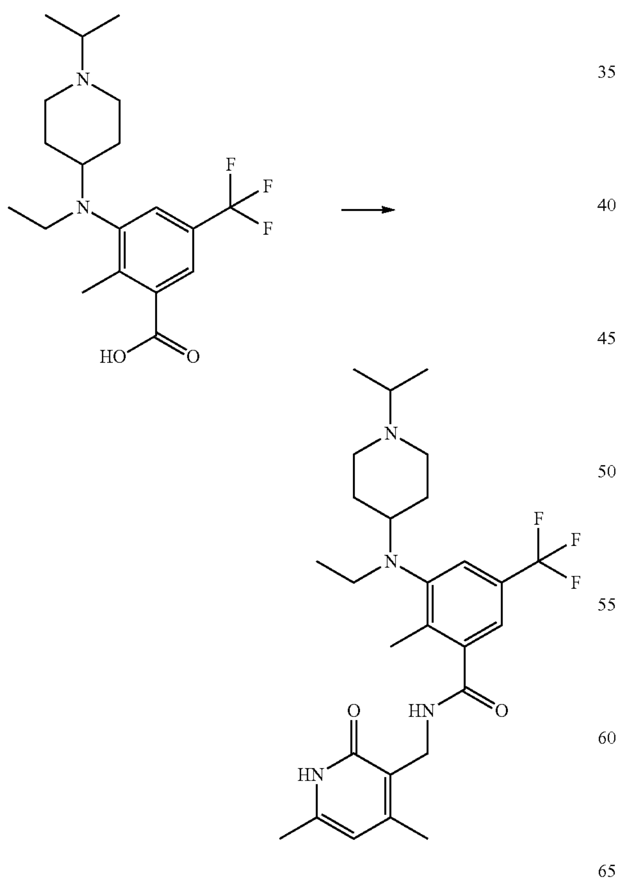

To a stirred solution of 3-{ethyl[1-(propan-2-yl)piperidin-4-yl]amino}-2-methyl-5-(trifluoromethyl)benzoic acid (crude material, 510 mg, 0.569 mmol) and 3-(aminomethyl)-4,6-dimethyl-1,2-dihydropyridin-2-one HCl salt (161 mg, 0.854 mmol) in DMSO (2 mL) was added PyBOP (534 mg, 1.02 mmol) and hunig base (220 mg, 1.71 mmol). The reaction mixture was stirred at 23° C. for 20 hours. The reaction mixture was quenched with water and resulting precipitate was collected. The solid was purified by silica gel column chromatography (NH—$SiO_2$ ethylacetate/MeOH=20/1) to give the titled compound as a white solid (129 mg, 44% yield). $^1$H-NMR (400 MHz, $CDCl_3$) δppm; 7.30 (s, 1H), 7.26 (s, 1H), 7.22 (t, J=5.9 Hz, 1H), 5.95 (s, 1H), 4.54 (d, J=5.9 Hz, 2H), 3.16 (m, 2H), 3.08 (q, J=7.0 Hz, 2H), 2.85 (m, 2H), 2.62-2.74 (m, 1H), 2.38 (s, 3H), 2.33 (s, 3H), 2.19 (s, 3H), 2.00-2.09 (m, 1H), 1.81 (m, 2H), 1.58-1.76 (m, 2H), 0.99 (s×2, 6H), 0.83 (t, J=7.0 Hz, 3H); MS (ES) [M+H] 507.2, [M+Na] 529.3; HPLC 97.2% purity.

Compound 401: N-[(4,6-Dimethyl-2-oxo-1,2-dihydropyridin-3-yl)methyl]-3-{[(2R*,6R*)-2,6-dimethylpiperidin-4-yl](ethyl)amino}-2-methyl-5-(trifluoromethyl)benzamide

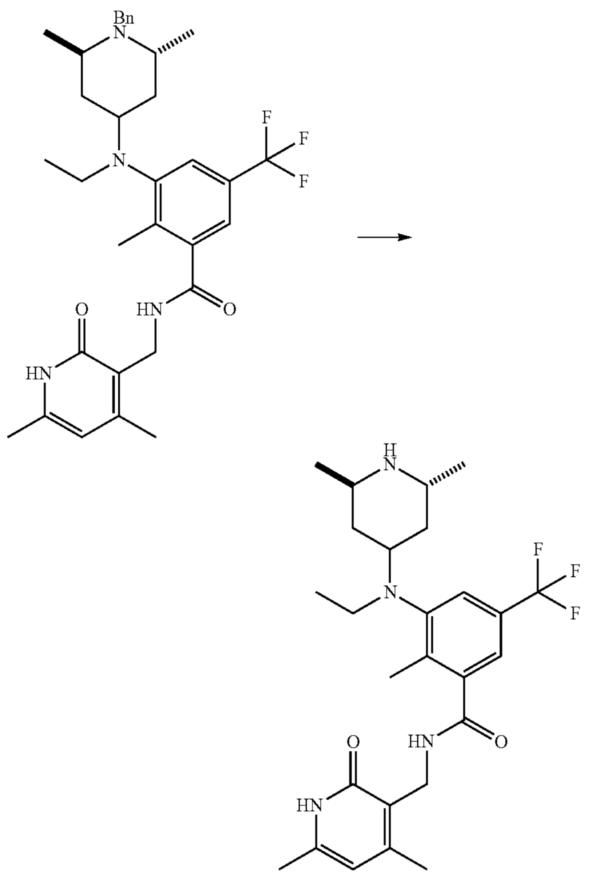

To a stirred solution of 3-{[(2R,6R)-1-benzyl-2,6-dimethylpiperidin-4-yl](ethyl)amino}-N-[(4,6-dimethyl-2-oxo-1,2-dihydropyridin-3-yl)methyl]-2-methyl-5-(trifluoromethyl)benzamide (267 mg, 0.459 mmol) in MeOH (5 mL) was added Pd/C (250 mg). The reaction mixture was stirred at et for 2 hour under hydrogen atmosphere. The reaction mixture was filtered and the filtrate was concentrated in vacuo. The residue was purified by silica gel column chromatography (1.

NAM-300H silica gel produced by Nagara Science Co., Ltd., ethylacetate/MeOH=4/1 to ethylacetate/MeOH/triethylamine=1/1/0.01, 2. NH—$SiO_2$, heptane/ethylacetate=30/1 to 8/1) to give the titled compound as a white solid (127 mg, 56% yield). $^1$H-NMR (400 MHz, $CDCl_3$) δppm; 7.30 (s, 1H), 7.26 (s, 1H), 7.14 (t, J=6.1 Hz, 1H), 5.94 (s, 1H), 4.54 (dd, J=5.9, 1.6 Hz, 2H), 3.41-3.49 (m, 1H), 3.01-3.13 (m, 3H), 2.85-2.92 (m, 1H), 2.40 (s, 3H), 2.32 (s, 3H), 2.22 (s, 3H), 1.63-1.80 (m 4H), 1.13 (d, J=7.0 Hz, 3H), 1.02 (d, J=6.2 Hz, 3H), 0.83 (t, J=7.0 Hz, 3H); LC-MS: m/z [M+H] 493.1, [M+Na] 515.3; HPLC; 97.2% purity.

Compound 402: N-[(4,6-Dimethyl-2-oxo-1,2-dihydropyridin-3-yl)methyl]-3-{[(2R*,4R*,6S*)-2,6-dimethylpiperidin-4-yl](ethyl)amino}-2-methyl-5-(trifluoromethyl)benzamide

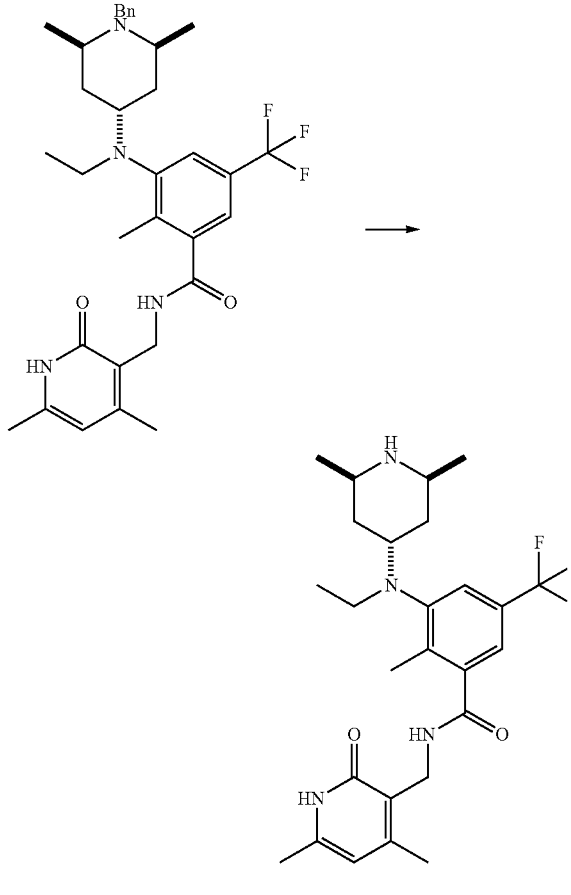

To a stirred solution of 3-{[(2R,4R,6S)-1-benzyl-2,6-dimethylpiperidin-4-yl](ethyl)amino}-N-[(4,6-dimethyl-2-oxo-1,2-dihydropyridin-3-yl)methyl]-2-methyl-5-(trifluoromethyl)benzamide (35.6 mg, 0.0611 mmol) in MeOH (3.0 ml) was added Pd/C (120 mg). The reaction mixture was stirred for 30 minutes under hydrogen atmosphere. After purging with nitrogen, the mixture was filtered and the filtrate was concentrated in vacuo. The residue was purified by preparative TLC (TLC silica gel 60F254, MERCK, MeOH/$Et_3N$=100/1) twice to give title compound as a white solid (4.4 mg, 15% yield). $^1$HNMR (400 MHz, $CDCl_3$) δ ppm; 7.33 (s, 1H), 7.30 (s, 1H), 7.18 (m, 1H), 5.96 (s, 1H), 4.54 (d, J=6.0 Hz, 2H), 3.73 (m, 1H), 3.26-2.69 (m, 4H), 2.40 (s, 3H), 2.38 (s, 3H), 2.23 (s, 3H), 1.90-1.10 (m, 4H), 1.10-0.86 (m, 6H), 0.83 (t, J=7.2 Hz, 3H). (−2H); LC-MS: m/z [M+H] 493.2, [M+Na] 515.3; HPLC; 88.8% purity.

Compound 403: 3-(ethyl(1-methylazetidin-3-yl)amino)-2-methyl-N-((6-methyl-2-oxo-4-propyl-1,2-dihydropyridin-3-yl)methyl)-5-(trifluoromethyl)benzamide formate

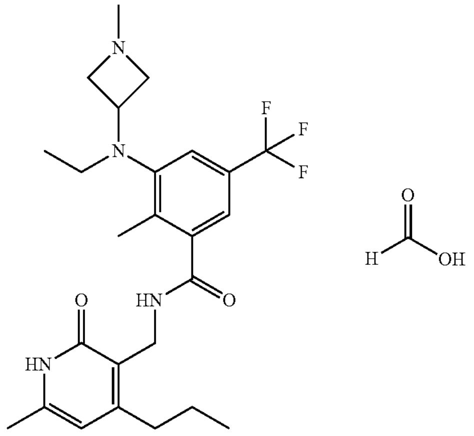 [SMILES: CCCc1cc(C)[nH]c(=O)c1CNC(=O)c1cc(C(F)(F)F)cc(N(CC)C2CN(C)C2)c1C ; O=CO]

$^1$H NMR (400 MHz, $CD_3OD$) δ ppm 8.33 (s, 1H), 7.37 (s, 1H), 7.26 (s, 1H), 6.11 (s, 1H), 4.46 (s, 2H), 4.42 (br, m, 1H), 4.21 (br, 2H), 3.82 (br, 2H), 3.00 (q, J=6.8 Hz, 2H), 2.88 (s, 3H), 2.65 (m, 2H), 2.40 (s, 3H), 2.22 (s, 3H), 1.61 (m, 2H), 0.99 (t, J=7.2 Hz, 3H), 0.86 (t, J=6.8 Hz, 3H); MS (ES) (M+1) 480.53.

Compound 404: 3-(ethyl(1-methylazetidin-3-yl)amino)-N-((4-isopropyl-6-methyl-2-oxo-1,2-dihydropyridin-3-yl)methyl)-2-methyl-5-(trifluoromethyl)benzamide formate

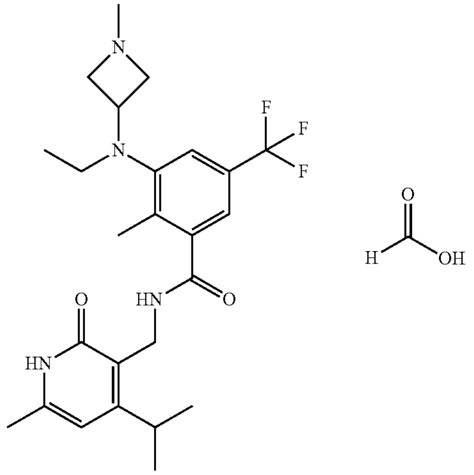 [SMILES: CCN(c1cc(C(F)(F)F)cc(C(=O)NCc2c(C(C)C)cc(C)[nH]c2=O)c1C)C1CN(C)C1 ; O=CO]

$^1$H NMR (400 MHz, $CD_3OD$) δ ppm 8.31 (s, 1H), 7.37 (s, 1H), 7.27 (s, 1H), 6.21 (s, 1H), 4.50 (s, 2H), 4.41 (br, 1H0, 4.21 (br, 2H), 3.81 (br, 2H), 3.38 (m, 1H), 3.00 (q, J=6.8 Hz, 2H), 2.87 (s, 3H), 2.40 (s, 3H), 2.24 (s, 3H), 1.20 (d, J=6.4 Hz, 6H), 0.86 (t, J=6.8 Hz, 3H); MS (ES) (M+1) 479.54.

Compound 405: N-((4,6-dimethyl-2-oxo-1,2-dihydropyridin-3-yl)methyl)-3-(ethyl(1-methylazetidin-3-yl)amino)-2-methyl-5-(trifluoromethyl)benzamide formate

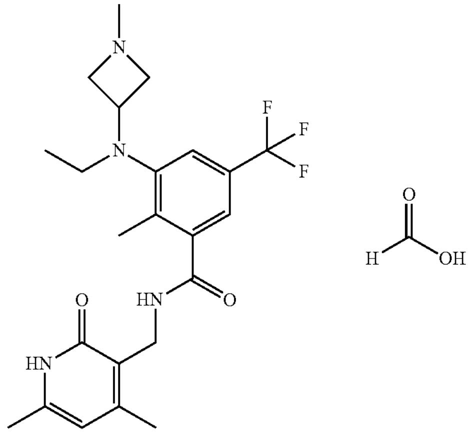 [SMILES: CCN(c1cc(C(F)(F)F)cc(C(=O)NCc2c(C)cc(C)[nH]c2=O)c1C)C1CN(C)C1 ; O=CO]

$^1$H NMR (400 MHz, $CD_3OD$) δ ppm 8.32 (s, 1H), 7.39 (s, 1H), 7.26 (s, 1H), 6.08 (s, 1H), 4.44 (s, 2H), 4.41 (br, m, 1H), 4.21 (br, 2H), 3.82 (br, 2H), 3.00 (q, J=6.8 Hz, 2H), 2.88 (s, 3H), 2.39 (s, 3H), 2.34 (d, J=1.2 Hz, 3H), 2.21 (s, 3H), 0.86 (t, J=6.8 Hz, 3H); MS (ES) (M+1) 451.49.

Compound 406: 5-Chloro-3-[ethyl(1-methylpiperidin-4-yl)amino]-2-methyl-N-[(6-methyl-2-oxo-4-propyl-1,2-dihydropyridin-3-yl)methyl]benzamide

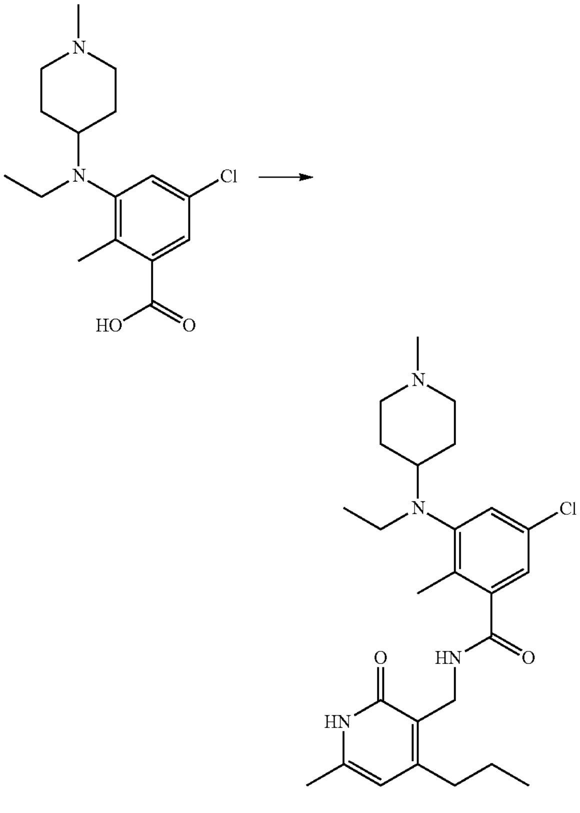

To a stirred solution of 5-chloro-3-[ethyl(1-methylpiperidin-4-yl)amino]-2-methylbenzoic acid (crude material, 1.80 g, 3.26 mmol) and 3-(aminomethyl)-6-methyl-4-propyl-1,2-dihydropyridin-2-one HCl salt (916 mg, 4.24 mmol) in DMSO (10 mL) was added PyBOP (3.10 g, 5.87 mmol) and hunig base (1.20 g, 9.78 mmol). The reaction mixture was stirred at 23° C. for 16 hours. The reaction mixture was quenched with water and resulting precipitate was collected. The solid was purified by silica gel column chromatography (NH—$SiO_2$ Ethylacetate/MeOH=10/1) to give the titled compound as a white solid (264 mg, 17% yield). $^1$H-NMR (400 MHz, $CDCl_3$) δppm; 7.20 (t, J=5.9 Hz, 1H), 7.06 (d, J=2.0 Hz, 1H), 7.02 (d, J=2.0 Hz, 1H), 5.96 (s, 1H), 4.54 (d, J=5.9 Hz, 2H), 3.02 (q, J=7.0 Hz, 2H), 2.81 (m, 2H), 2.64-2.71 (m, 3H), 2.21-2.27 (s×3, 9H), 1.84-1.94 (m, 2H), 1.55-1.65 (m, 6H), 1.00 (t, J=7.4 Hz, 3H), 0.84 (t, J=7.0 Hz, 3H); MS (ES) [M+H] 473.1, [M+Na] 495.3; HPLC 94.7% purity.

Compound 407: 5-Chloro-3-[ethyl(1-methylpiperidin-4-yl)amino]-2-methyl-N-{[6-methyl-2-oxo-4-(propan-2-yl)-1,2-dihydropyridin-3-yl]methyl}benzamide

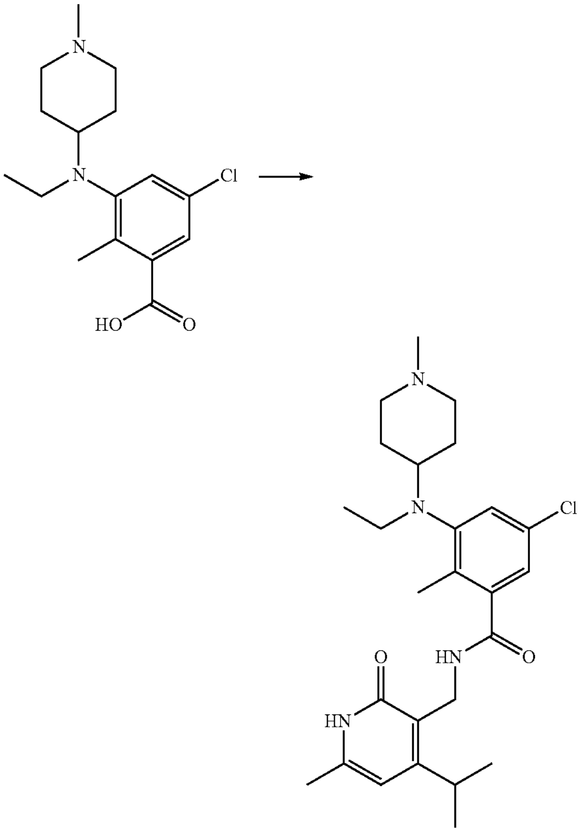

To a stirred solution of 5-chloro-3-[ethyl(1-methylpiperidin-4-yl)amino]-2-methylbenzoic acid (crude material, ~0.7 mmol) and 3-(aminomethyl)-6-methyl-4-(propan-2-yl)-1,2-dihydropyridin-2-one hydrochloride HCl salt (200 mg, 0.91 mmol) in DMSO (5.3 mL) was added PyBOP (550 mg, 1.05 mmol) and hunig base (366 ul, 2.10 mmol). The reaction mixture was stirred at 23° C. for 7 hours. The reaction mixture was quenched with water and resulting precipitate was collected. The solid was purified by silica gel column chromatography (NH—$SiO_2$ Ethylacetate/MeOH=10/1+10% triethylamine). The crude compound was triturated from ethylacetate/hexane, and dried to give the titled compound as a white solid (166 mg, 50% yield). $^1$H-NMR (400 MHz, $CDCl_3$) δppm; 7.06 (d, J=2.4 Hz, 1H), 7.01-7.05 (m, 1H), 7.00 (d, J=2.4 Hz, 1H), 6.04 (s, 1H), 4.57 (d, J=6.0 Hz, 2H), 3.49-3.57 (m, 1H), 3.02 (q, J=6.8 Hz, 2H), 2.80-2.84 (m, 2H), 2.61-2.69 (m, 1H), 2.29 (s, 3H), 2.23 (s, 3H), 2.23 (s, 3H), 1.86-1.90 (m, 2H), 1.66-1.70 (m, 4H), 1.21 (d, J=6.8 Hz, 6H), 0.84 (t, J=6.8 Hz, 3H); MS (ES) [M+Na] 495.2; HPLC 95.7% purity.

Compound 408: 5-Chloro-3-[ethyl(1-methylpiperidin-4-yl)amino]-2-methyl-N-{[6-methyl-2-oxo-4-(trifluoromethyl)-1,2-dihydropyridin-3-yl]methyl}benzamide

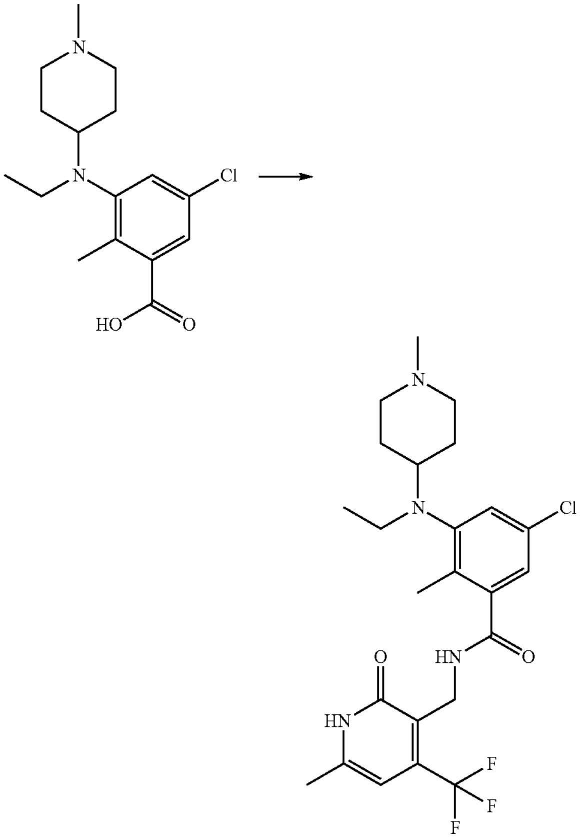

To a stirred solution of 5-chloro-3-[ethyl(1-methylpiperidin-4-yl)amino]-2-methylbenzoic acid (crude material, ~0.7 mmol) and 3-(aminomethyl)-6-methyl-4-(trifluoromethyl)-1,2-dihydropyridin-2-one hydrochloride HCl salt (200 mg, 0.91 mmol) in DMSO (5.3 mL) was added PyBOP (550 mg, 1.05 mmol) and hunig base (366 ul, 2.10 mmol). The reaction mixture was stirred at 23° C. for 7 hours. The reaction mixture was quenched with water and diluted with ethylacetate. The aqueous layer was extracted with dichloromethane. The combined organic layer was washed with brine, dried over $Na_2SO_4$, filtered and concentrated. The residue was purified by silica gel column chromatography ($SiO_2$ Ethylacetate/MeOH=10/1+5% triethylamine). The crude compound was triturated with ethylacetate/hexane, and dried to give the titled compound as a white solid (145 mg, 42% yield). $^1$H-NMR (400 MHz, $CDCl_3$) δppm; 7.08 (d, J=2.4 Hz, 1H), 7.03 (d, J=2.4 Hz, 1H), 6.81-6.85 (m, 1H), 6.35 (s, 1H), 4.71 (d, J=5.2 Hz, 2H), 3.03 (q, J=6.8 Hz, 2H), 2.81-2.85 (m, 2H), 2.68-2.72 (m, 1H), 2.39 (s, 3H), 2.27 (s, 3H), 2.24 (s, 3H), 1.88-1.94 (m, 2H), 1.67-1.72 (m, 4H), 0.85 (t, J=6.8 Hz, 3H); MS (ES) [M+H] 499.1, [M+Na] 521.1; HPLC 96.0% purity.

Following the same preparation method described above for 5-chloro-3-[ethyl(1-methylpiperidin-4-yl)amino]-2-methyl-N-{[6-methyl-2-oxo-4-(trifluoromethyl)-1,2-dihydropyridin-3-yl]methyl}benzamide, the following analogs were prepared using the corresponding pyridone fragments described earlier, and purified by reverse HPLC/MS (ACN-$H_2O$, containing 0.1% formic acid).

Compound 409: 5-chloro-3-(ethyl(1-methylpiperidin-4-yl)amino)-N-((5-fluoro-4,6-dimethyl-2-oxo-1,2-dihydropyridin-3-yl)methyl)-2-methylbenzamide formate

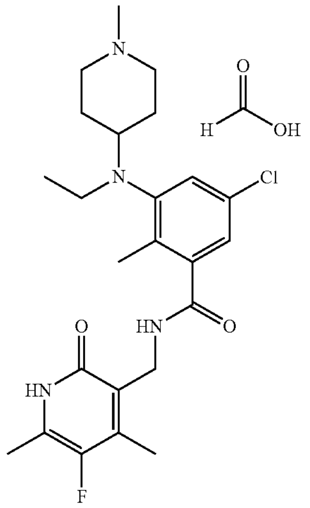

$^1$H-NMR (500 MHz, $CD_3OD$) δ ppm 8.45-8.25 (br, 1H), 7.30 (d, J=2.0 Hz, 1H), 7.13 (d, J=2.0 Hz, 1H), 4.47 (s, 2H), 3.50-3.38 (br, 2H), 3.25-3.15 (br, 1H), 3.08 (q, J=7.0 Hz, 2H), 3.06-2.98 (br, 2H), 2.83 (s, 3H), 2.38 (d, J=2.0 Hz, 3H), 2.27 (s, 3H), 2.26 (d, J=2.0 Hz, 3H), 2.03 (bd, J=14.75 Hz, 2H), 1.90-1.77 (br, 2H), 0.89 (t, J=7.0 Hz, 3H); MS (ES) (M+H) 463.50.

Compound 410: 5-chloro-3-(ethyl(1-methylpiperidin-4-yl)amino)-N-((5-fluoro-6-methyl-2-oxo-4-propyl-1,2-dihydropyridin-3-yl)methyl)-2-methylbenzamide formate

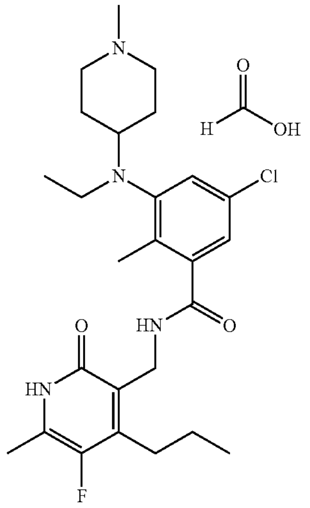

$^1$H-NMR (500 MHz, $CD_3OD$) δ ppm 8.43-8.26 (br, 1H), 7.30 (d, J=2.0 Hz, 1H), 7.12 (d, J=2.0 Hz, 1H), 4.47 (s, 2H), 3.47-3.39 (br, 2H), 3.23-3.15 (br, 1H), 3.08 (q, J=7.0 Hz, 2H), 3.05-2.96 (br, 2H), 2.82 (s, 3H), 2.79 (bd, J=8.2 Hz, 2H), 2.28-2.26 (br, 6H), 2.06-1.99 (br, 2H), 1.93-1.82 (br, 2H), 1.68-1.59 (m, 2H), 1.06 (t, J=7.5 Hz, 3H), 0.89 (t, J=7.0 Hz, 3H); MS (ES) (M+H) 491.52.

Compound 411: 5-chloro-3-(ethyl(1-methylpiperidin-4-yl)amino)-N-((5-fluoro-4-isopropyl-6-methyl-2-oxo-1,2-dihydropyridin-3-yl)methyl)-2-methylbenzamide formate

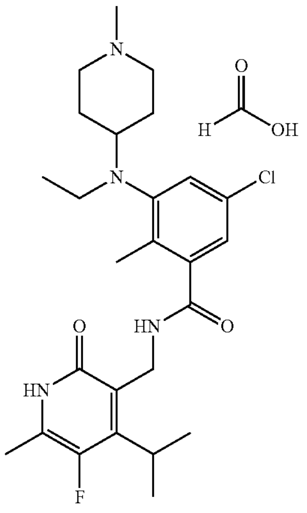

$^1$H-NMR (500 MHz, $CD_3OD$) δ ppm 8.48-8.34 (br, 1H), 7.35 (d, J=2.0 Hz, 1H), 7.16 (d, J=2.0 Hz, 1H), 4.57 (s, 2H), 3.61-3.53 (m, 1H), 3.52-3.44 (br, 2H), 3.30-3.20 (br, 1H), 3.13 (q, J=7.0 Hz, 2H), 3.10-3.01 (br, 2H), 2.87 (s, 3H), 2.33 (s, 3H), 2.31 (d, J=2.8 Hz, 3H), 2.10-2.04 (br, 2H), 1.98-1.87 (br, 2H), 1.41 (d, J=6.5 Hz, 6H), 0.93 (t, J=7.0 Hz, 3H); MS (ES) (M+H) 491.51.

Compound 412: 5-chloro-3-(ethyl(1-methylazetidin-3-yl)amino)-2-methyl-N-((6-methyl-2-oxo-4-propyl-1,2-dihydropyridin-3-yl)methyl)benzamide formate

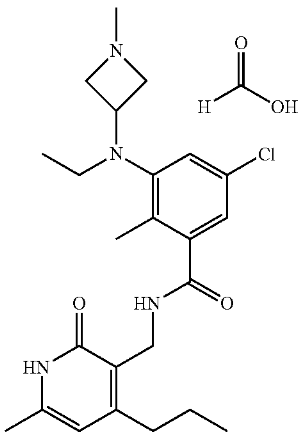

Methyl 5-chloro-3-(ethyl(1-methylazetidin-3-yl)amino)-2-methylbenzoate was hydrolyzed to 5-chloro-3-(ethyl(1-methylazetidin-3-yl)amino)-2-methylbenzoic acid following the same preparation method for 3-{Ethyl[1-(propan-2-yl)piperidin-4-yl]amino}-2-methyl-5-(trifluoromethyl)benzoic acid from its corresponding carboxylate. The crude 5-chloro-3-(ethyl(1-methylazetidin-3-yl)amino)-2-methylbenzoic acid was then coupled with 3-(Aminomethyl)-6-methyl-4-propyl-1,2-dihydropyridin-2-one HCl salt prepared earlier following the preparation method described for N-[(4,6-Dimethyl-2-oxo-1,2-dihydropyridin-3-yl)methyl]-3-[ethyl(1-methylpiperidin-4-yl)amino]-2-methyl-5-(trifluoromethyl)benzamide. After purification by reverse phase HPLC/MS (CAN-$H_2O$ containing 0.1% formic acid), the titled compound was obtained. $^1$H-NMR (500 MHz, $CD_3OD$) δ ppm 8.58-8.24 (br, 1H), 7.15 (d, J=2.0 Hz, 1H), 7.08 (d, J=2.0 Hz, 1H), 6.14 (s, 1H), 4.48 (s, 2H), 4.41-4.34 (m, 1H), 4.25 (br, 2H), 3.85 (br, 2H), 3.00 (q, J=7.0 Hz, 2H), 2.92 (s, 3H), 2.72-2.66 (m, 2H), 2.34 (s, 3H), 2.26 (s, 3H), 1.70-1.61 (m, 2H), 1.04 (t, J=7.2 Hz, 3H), 0.91 (t, J=7.0 Hz, 3H); MS (ES) (M+H) 445.48.

Compound 413: 5-chloro-3-(ethyl(1-methylazetidin-3-yl)amino)-N-((4-isopropyl-6-methyl-2-oxo-1,2-dihydropyridin-3-yl)methyl)-2-methylbenzamide formate

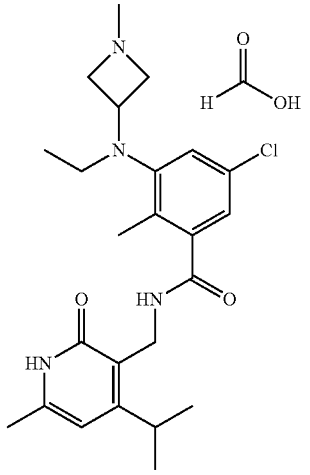

The same way for the previous compound 5-chloro-3-(ethyl(1-methylazetidin-3-yl)amino)-2-methyl-N-((6-methyl-2-oxo-4-propyl-1,2-dihydropyridin-3-yl)methyl)benzamide formate prepared, the titled compound prepared using 5-chloro-3-(ethyl(1-methylazetidin-3-yl)amino)-2-methylbenzoic acid and 3-(Aminomethyl)-6-methyl-4-(propan-2-yl)-1,2-dihydropyridin-2-one HCl salt. After purification by reverse phase HPLC/MS (CAN-$H_2O$ containing 0.1% formic acid), the titled compound was obtained. $^1$H-NMR (500 MHz, $CD_3OD$) δ ppm 8.43-8.25 (br, 1H), 7.15 (d, J=2.0 Hz, 1H), 7.08 (d, J=2.0 Hz, 1H), 6.25 (s, 1H), 4.52 (s, 2H), 4.40-4.34 (m, 1H), 4.29-4.21 (br, 2H), 3.90-3.79 (br, 2H), 3.48-3.40 (m, 1H), 3.00 (q, J=7.0 Hz, 2H), 2.92 (s, 3H), 2.34 (s, 3H), 2.28 (s, 3H), 1.24 (d, J=7.0 Hz, 6H), 0.90 (t, J=7.0 Hz, 3H). MS (ES) (M+H) 445.47.

Compound 414: N-[(4,6-Dimethyl-2-oxo-1,2-dihydropyridin-3-yl)methyl]-3-{[(2R,6R)-2,6-dimethylpiperidin-4-yl](ethyl)amino}-5-fluoro-2-methylbenzamide

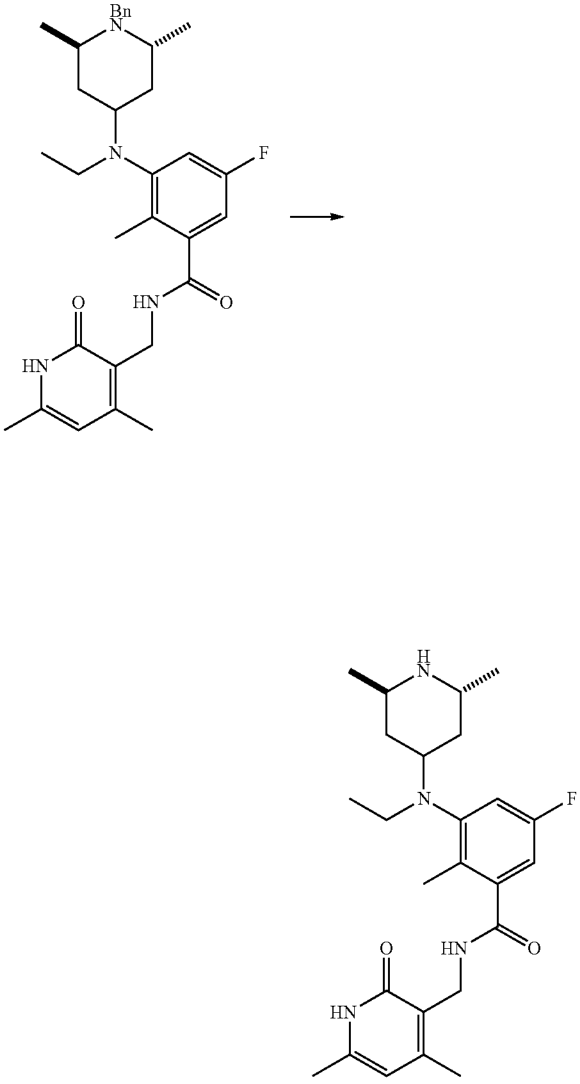

To a stirred solution of 3-{[(2R,6R)-1-benzyl-2,6-dimethylpiperidin-4-yl](ethyl)amino}-N-[(4,6-dimethyl-2-oxo-1,2-dihydropyridin-3-yl)methyl]-5-fluoro-2-methylbenzamide (378 mg, 0.709 mmol) in MeOH (7 mL) was added Pd/C (150 mg). The reaction mixture was stirred at 23° C. for 1 hour under hydrogen atmosphere. The reaction mixture was filtered and the filtrate was concentrated in vacuo. The residue was purified by silica gel column chromatography (1. NAM-300H silica gel produced by Nagara Science Co., Ltd., ethylacetate/MeOH=4/1 to ethylacetate/MeOH/triethylamine=1/1/0.01, 2. NH—$SiO_2$, heptane/ethylacetate=30/1 to 8/1) to give title compound as a white solid (235 mg, 75% yield). $^1$HNMR (400 MHz, $CDCl_3$) δppm; 7.08 (t, J=6.2 Hz, 1H), 6.82 (dd, J=10.7, 2.5 Hz, 1H), 6.75 (dd, J=8.2, 2.7 Hz, 1H), 5.93 (s, 1H), 4.51 (d, J=6.2 Hz, 2H), 3.40-3.48 (m, 1H), 2.95-3.09 (m, 3H), 2.83-2.92 (m, 1H), 2.39 (s, 3H), 2.22 (s×2, 6H), 1.63-1.78 (m, 4H), 1.13 (d, J=7.0 Hz, 3H), 1.02 (d, J=6.2 Hz, 3H), 0.84 (t, J=7.0 Hz, 3H); MS (ES) [M+H] 443.1, [M+Na] 465.2; HPLC; 99.3% purity.

Compound 415: N-[(4,6-Dimethyl-2-oxo-1,2-dihydropyridin-3-yl)methyl]-3-{[(2R,4R,6S)-2,6-dimethylpiperidin-4-yl](ethyl)amino}-5-fluoro-2-methylbenzamide

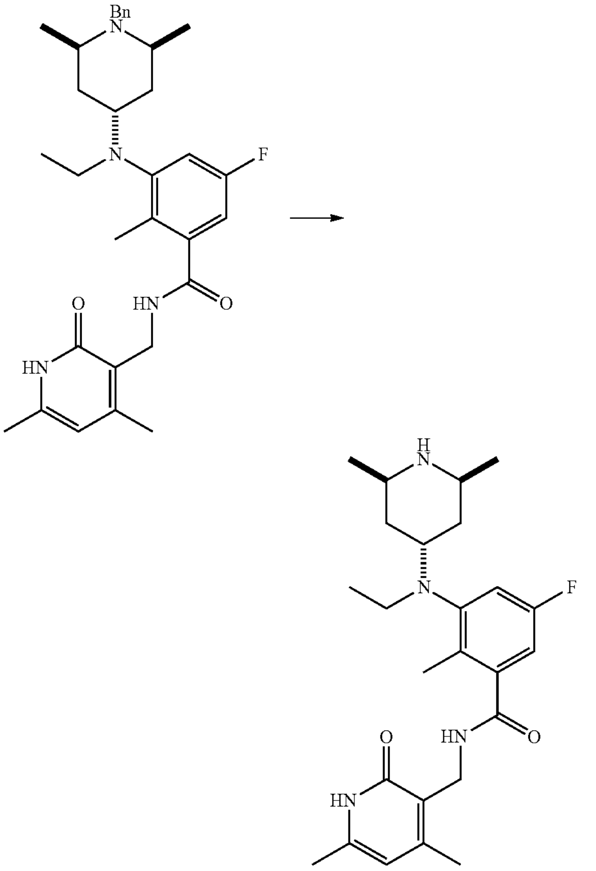

To a stirred solution of 3-{[(2R,4R,6S)-1-benzyl-2,6-dimethylpiperidin-4-yl](ethyl)amino}-N-[(4,6-dimethyl-2-oxo-1,2-dihydropyridin-3-yl)methyl]-5-fluoro-2-methylbenzamide (50.1 mg, 0.0860 mmol) in MeOH (2 ml) was added Pd/C (100 mg). The reaction mixture was stirred for 3 hours under hydrogen atmosphere at 23° C. After purging with nitrogen, the mixture was filtered and the filtrate was concentrated in vacuo. The residue was purified by silica gel column chromatography (NAM-300H silica gel produced by Nagara Science Co., Ltd., ethylacetate/MeOH=4/1 to ethylacetate/MeOH/triethylamine=1/1/0.01). The target fractions were collected and concentrated in vacuo. The residue was purified by silica gel column chromatography (NH—$SiO_2$, ethylacetate/MeOH=30/1 to 20/1 to 8/1). The target fractions were collected and concentrated in vacuo. The residue was purified with preparative TLC (TLC silica gel $60F_{254}$, MERCK, MeOH/$Et_3N$=100/1) to give the titled compound as a white solid (17.2 mg, 45% yield). $^1$HNMR (400 MHz, $CDCl_3$) δppm; 7.10 (m, 1H), 6.81 (m, 2H), 5.91 (s, 1H), 4.52 (d, J=6.0 Hz, 2H), 3.61 (m, 1H), 3.23-2.73 (m, 4H), 2.40 (s, 3H), 2.28 (s, 3H), 2.24 (s, 3H), 1.64-1.05 (m, 4H), 1.05-0.86 (m, 6H), 0.82 (t, J=7.2 Hz, 3H). (−2H); LC-MS: m/z [M+H] 443.2, [M+Na] 465.3; HPLC; 97.4% purity.

Example 45

Syntheses of Compounds 6, 9, 11-12, 19, 22, 24, 27, 29, 34-35, 37-47, 65-90, 93-96, 99-101, 103, 106-116, 124, 125, 128-136, 138-143, 145-156, 158-190, 193-204, 210, 211, 214-221, 223-242, 244-267, 270-272, 274, 275, 280, 281, 288, 289, 291-300, 303-305, 307, 312, 314, 316-318, 323-327, 329-331, 337, 338, 341-343, 345, 346, 350-355, 357-385, 388, 391, and 418

Compounds 6, 9, 11-12, 19, 22, 24, 27, 29, 34-35, 37-47, 65-90, 93-96, 99-101, 103, 106-116, 124, 125, 128-136, 138-143, 145-156, 158-190, 193-204, 210, 211, 214-221, 223-242, 244-267, 270-272, 274, 275, 280, 281, 288, 289, 291-300, 303-305, 307, 312, 314, 316-318, 323-327, 329-331, 337, 338, 341-343, 345, 346, 350-355, 357-385, 388, 391, and 418 were synthesized by methods similar to those described for Examples 1-44 or by reaction schemes depicted in the general schemes.

Example 46

Bioassay Protocol and General Methods

Protocol for Wild-Type and Mutant PRC2 Enzyme Assays

General Materials.

S-adenosylmethionine (SAM), S-adenosylhomocyteine (SAH), bicine, KCl, Tween20, dimethylsulfoxide (DMSO) and bovine skin gelatin (BSG) were purchased from Sigma-Aldrich at the highest level of purity possible. Dithiothreitol (DTT) was purchased from EMD. $^3$H-SAM was purchased from American Radiolabeled Chemicals with a specific activity of 80 Ci/mmol. 384-well streptavidin Flashplates were purchased from PerkinElmer.

Substrates.

Peptides representative of human histone H3 residues 21-44 containing either an unmodified lysine 27 (H3K27me0) or dimethylated lysine 27 (H3K27me2) were synthesized with a C-terminal G(K-biotin) linker-affinity tag motif and a C-terminal amide cap by 21$^{st}$ Century Biochemicals. The peptides were high-performance liquid chromatography (HPLC) purified to greater than 95% purity and confirmed by liquid chromatography mass spectrometry (LC-MS). The sequences are listed below.

```
H3K27me0:
                                        (SEQ ID NO: 1)
ATKAARKSAPATGGVKKPHRYRPGGK(biotin)-amide

H3K27me2:
                                        (SEQ ID NO: 2)
ATKAARK(me2)SAPATGGVKKPHRYRPGGK(biotin)-amide
```

Chicken erythrocyte oligonucleosomes were purified from chicken blood according to established procedures.

Recombinant PRC2 Enzymes.

Human PRC2 enzymes were purified as 4-component enzyme complexes co-expressed in *Spodoptera frugiperda* (sf9) cells using a baculovirus expression system. The subunits expressed were wild-type EZH2 (NM_004456) or EZH2 Y641F, N, H, S or C mutants generated from the wild-type EZH2 construct, EED (NM_003797), Suz12 (NM_015355) and RbAp48 (NM_005610). The EED subunit contained an N-terminal FLAG tag that was used to purify the entire 4-component complex from sf9 cell lysates. The purity of the complexes met or exceeded 95% as determined by SDS-PAGE and Agilent Bioanalyzer analysis. Concentrations of enzyme stock concentrations (generally 0.3-1.0 mg/mL) was determined using a Bradford assay against a bovine serum albumin (BSA) standard.

General Procedure for PRC2 Enzyme Assays on Peptide Substrates.

The assays were all performed in a buffer consisting of 20 mM bicine (pH=7.6), 0.5 mM DTT, 0.005% BSG and 0.002% Tween20, prepared on the day of use. Compounds in 100% DMSO (1 μL) were spotted into polypropylene 384-well V-bottom plates (Greiner) using a Platemate 2×3 outfitted with a 384-channel pipet head (Thermo). DMSO (1 μL) was added to columns 11, 12, 23, 24, rows A-H for the maximum signal control, and SAH, a known product and inhibitor of PRC2 (1 μL) was added to columns 11, 12, 23, 24, rows I-P for the minimum signal control. A cocktail (40 μL) containing the wild-type PRC2 enzyme and H3K27me0 peptide or any of the Y641 mutant enzymes and H3K27me2 peptide was added by Multidrop Combi (Thermo). The compounds were allowed to incubate with PRC2 for 30 min at 25° C., then a cocktail (10 μL) containing a mixture of non-radioactive and $^3$H-SAM was added to initiate the reaction (final volume=51 μL). In all cases, the final concentrations were as follows: wild-type or mutant PRC2 enzyme was 4 nM, SAH in the minimum signal control wells was 1 mM and the DMSO concentration was 1%. The final concentrations of the rest of the components are indicated in Table 2, below. The assays were stopped by the addition of non-radioactive SAM (10 μL) to a final concentration of 600 μM, which dilutes the $^3$H-SAM to a level where its incorporation into the peptide substrate is no longer detectable. 50 μL of the reaction in the 384-well polypropylene plate was then transferred to a 384-well Flashplate and the biotinylated peptides were allowed to bind to the streptavidin surface for at least 1 h before being washed three times with 0.1% Tween20 in a Biotek ELx405 plate washer. The plates were then read in a PerkinElmer TopCount platereader to measure the quantity of $^3$H-labeled peptide bound to the Flashplate surface, measured as disintegrations per minute (dpm) or alternatively, referred to as counts per minute (cpm).

TABLE 2

Final concentrations of components for each assay variation based upon EZH2 identity (wild-type or Y641 mutant EZH2)

| PRC2 Enzyme (denoted by EZH2 identity) | Peptide (nM) | Non-radioactive SAM (nM) | $^3$H-SAM (nM) |
|---|---|---|---|
| Wild-type | 185 | 1800 | 150 |
| Y641F | 200 | 850 | 150 |
| Y641N | 200 | 850 | 150 |
| Y641H | 200 | 1750 | 250 |
| Y641S | 200 | 1300 | 200 |
| Y641C | 200 | 3750 | 250 |

General Procedure for Wild-Type PRC2 Enzyme Assay on Oligonucleosome Substrate.

The assays was performed in a buffer consisting of 20 mM bicine (pH=7.6), 0.5 mM DTT, 0.005% BSG, 100 mM KCl and 0.002% Tween20, prepared on the day of use. Compounds in 100% DMSO (1 μL) were spotted into polypropylene 384-well V-bottom plates (Greiner) using a Platemate 2×3 outfitted with a 384-channel pipet head (Thermo). DMSO (1 μL) was added to columns 11, 12, 23, 24, rows A-H for the maximum signal control, and SAH, a known product and inhibitor of PRC2 (1 μL) was added to columns 11, 12, 23, 24, rows I-P for the minimum signal control. A cocktail (40 μL) containing the wild-type PRC2 enzyme and chicken erythrocyte oligonucleosome was added by Multidrop Combi (Thermo). The compounds were allowed to incubate with PRC2 for 30 min at 25° C., then a cocktail (10 μL) containing a mixture of non-radioactive and $^3$H-SAM was added to initiate the reaction (final volume=51 μL). The final concentrations were as follows: wild-type PRC2 enzyme was 4 nM, non-radioactive SAM was 430 nM, $^3$H-SAM was 120 nM, chicken erythrocyte oligonucleosome was 120 nM, SAH in the minimum signal control wells was 1 mM and the DMSO concentration was 1%. The assay was stopped by the addition of non-radioactive SAM (10 μL) to a final concentration of 600 μM, which dilutes the $^3$H-SAM to a level where its incorporation into the chicken erythrocyte oligonucleosome substrate is no longer detectable. 50 μL of the reaction in the 384-well polypropylene plate was then transferred to a 384-well Flashplate and the chicken erythrocyte nucleosomes were immobilized to the surface of the plate, which was then washed three times with 0.1% Tween20 in a Biotek ELx405 plate washer. The plates were then read in a PerkinElmer TopCount platereader to measure the quantity of $^3$H-labeled chicken erythrocyte oligonucleosome bound to the Flashplate surface, measured as disintegrations per minute (dpm) or alternatively, referred to as counts per minute (cpm).

% Inhibition Calculation $$\% \ inh = 100 - \left(\frac{dpm_{cmpd} - dpm_{min}}{dpm_{max} - dpm_{min}}\right) \times 100$$

Where dpm=disintegrations per minute, cmpd=signal in assay well, and min and max are the respective minimum and maximum signal controls.

Four-Parameter $IC_{50}$ Fit $$Y = \text{Bottom} + \frac{(\text{Top} - \text{Bottom})}{1 + \left(\frac{X}{IC_{50}}\right)^{Hill\ Coefficeint}}$$

Where top and bottom are the normally allowed to float, but may be fixed at 100 or 0 respectively in a 3-parameter fit. The Hill Coefficient normally allowed to float but may also be fixed at 1 in a 3-parameter fit. Y is the % inhibition and X is the compound concentration.

$IC_{50}$ values for the PRC2 enzyme assays on peptide substrates (e.g., EZH2 wild type and Y641F) are presented in Table 3 below.

WSU-DLCL2 Methylation Assay

WSU-DLCL2 suspension cells were purchased from DSMZ (German Collection of Microorganisms and Cell Cultures, Braunschweig, Germany). RPMI/Glutamax Medium, Penicillin-Streptomycin, Heat Inactivated Fetal Bovine Serum, and D-PBS were purchased from Life Technologies, Grand Island, N.Y., USA. Extraction Buffer and Neutralization Buffer (5×) were purchased from Active Motif, Carlsbad, Calif., USA. Rabbit anti-Histone H3 antibody was purchased from Abcam, Cambridge, Mass., USA. Rabbit anti-H3K27me3 and HRP-conjugated anti-rabbit-IgG were purchased from Cell Signaling Technology, Danvers, Mass., USA. TMB "Super Sensitive" substrate was sourced from BioFX Laboratories, Owings Mills, Md., USA. IgG-free Bovine Serum Albumin was purchased from Jackson ImmunoResearch, West Grove, Pa., USA. PBS with Tween (10× PBST) was purchased from KPL, Gaithersburg, Md., USA. Sulfuric Acid was purchased from Ricca Chemical, Arlington, Tex., USA. Immulon ELISA plates were purchased from Thermo, Rochester, N.Y., USA. V-bottom cell culture plates were purchased from Corning Inc., Corning, N.Y., USA. V-bottom polypropylene plates were purchased from Greiner Bio-One, Monroe, N.C., USA.

WSU-DLCL2 suspension cells were maintained in growth medium (RPMI 1640 supplemented with 10% v/v heat inactivated fetal bovine serum and 100 units/mL penicillin-streptomycin) and cultured at 37° C. under 5% $CO_2$. Under assay conditions, cells were incubated in Assay Medium (RPMI 1640 supplemented with 20% v/v heat inactivated fetal bovine serum and 100 units/mL penicillin-streptomycin) at 37° C. under 5% $CO_2$ on a plate shaker.

WSU-DLCL2 cells were seeded in assay medium at a concentration of 50,000 cells per mL to a 96-well V-bottom cell culture plate with 200 μL per well. Compound (1 μL) from 96 well source plates was added directly to V-bottom cell plate. Plates were incubated on a titer-plate shaker at 37° C., 5% CO2 for 96 hours. After four days of incubation, plates were spun at 241×g for five minutes and medium was aspirated gently from each well of cell plate without disturbing cell pellet. Pellet was resuspended in 200 μL DPBS and plates were spun again at 241×g for five minutes. The supernatant was aspirated and cold (4° C.) Extraction buffer (100 μL) was added per well. Plates were incubated at 4° C. on orbital shaker for two hours. Plates were spun at 3427×g×10 minutes. Supernatant (80 μL per well) was transferred to its respective well in 96 well V-bottom polypropylene plate. Neutralization Buffer 5× (20 μL per well) was added to V-bottom polypropylene plate containing supernatant. V-bottom polypropylene plates containing crude histone preparation (CHP) were incubated on orbital shaker×five minutes. Crude Histone Preparations were added (24 per well) to each respective well into duplicate 96 well ELISA plates containing 100 μL Coating Buffer (1×PBS+BSA 0.05% w/v). Plates were sealed and incubated overnight at 4° C. The following day, plates were washed three times with 300 μL per well 1×PBST. Wells were blocked for two hours with 300 μL per well ELISA Diluent ((PBS (1×) BSA (2% w/v) and Tween20 (0.05% v/v)). Plates were washed three times with 1×PBST. For the Histone H3 detection plate, 100 μl per well were added of anti-Histone-H3 antibody (Abcam, ab1791) diluted 1:10,000 in ELISA Diluent. For H3K27 trimethylation detection plate, 100 μL per well were added of anti-H3K27me3 diluted 1:2000 in ELISA diluent. Plates were incubated for 90 minutes at room temperature. Plates were washed three times with 300 μL 1×PBST per well. For Histone H3 detection, 100 μL of HRP-conjugated anti-rabbit IgG antibody diluted to 1:6000 in ELISA diluent was added per well. For H3K27me3 detection, 100 μL of HRP conjugated anti-rabbit IgG antibody diluted to 1:4000 in ELISA diluent was added per well. Plates were incubated at room temperature for 90 minutes. Plates were washed four times with 1×PBST 300 μL per well. TMB substrate 100 μL was added per well. Histone H3 plates were incubated for five minutes at room temperature. H3K27me3 plates were incubated for 10 minutes at room temperature. The reaction was stopped with sulfuric acid 1N (100 μL per well). Absorbance for each plate was read at 450 nm.

First, the ratio for each well was determined by:

$$\left(\frac{H3K27me3\ OD450\ \text{value}}{\text{Histone}\ H3\ OD450\ \text{value}}\right)$$

Each plate included eight control wells of DMSO only treatment (Minimum Inhibition) as well as eight control wells for maximum inhibition (Background wells).

The average of the ratio values for each control type was calculated and used to determine the percent inhibition for each test well in the plate. Test compound was serially diluted three-fold in DMSO for a total of ten test concentrations, beginning at 25 μM. Percent inhibition was determined and $IC_{50}$ curves were generated using duplicate wells per concentration of compound. $IC_{50}$ values for this assay are presented in Table 3 below.

$$\text{Percent Inhibition} = 100 - \left(\left(\frac{(\text{Individual Test Sample Ratio}) - (\text{Background } Avg \text{ Ratio})}{(\text{Minimum Inhibition Ratio}) - (\text{Background Average Ratio})}\right) * 100\right)$$

Cell Proliferation Analysis

WSU-DLCL2 suspension cells were purchased from DSMZ (German Collection of Microorganisms and Cell Cultures, Braunschweig, Germany). RPMI/Glutamax Medium, Penicillin-Streptomycin, Heat Inactivated Fetal Bovine Serum were purchased from Life Technologies, Grand Island, N.Y., USA. V-bottom polypropylene 384-well plates were purchased from Greiner Bio-One, Monroe, N.C., USA. Cell culture 384-well white opaque plates were purchased from Perkin Elmer, Waltham, Mass., USA. Cell-Titer Glo® was purchased from Promega Corporation, Madison, Wis., USA. SpectraMax M5 plate reader was purchased from Molecular Devices LLC, Sunnyvale, Calif., USA.

WSU-DLCL2 suspension cells were maintained in growth medium (RPMI 1640 supplemented with 10% v/v heat inactivated fetal bovine serum and cultured at 37° C. under 5% $CO_2$. Under assay conditions, cells were incubated in Assay Medium (RPMI 1640 supplemented with 20% v/v heat inactivated fetal bovine serum and 100 units/mL penicillin-streptomycin) at 37° C. under 5% $CO_2$.

For the assessment of the effect of compounds on the proliferation of the WSU-DLCL2 cell line, exponentially growing cells were plated in 384-well white opaque plates at a density of 1250 cell/ml in a final volume of 50 μl of assay medium. A compound source plate was prepared by performing triplicate nine-point 3-fold serial dilutions in DMSO, beginning at 10 mM (final top concentration of compound in the assay was 20 μM and the DMSO was 0.2%). A 100 mL aliquot from the compound stock plate was added to its respective well in the cell plate. The 100% inhibition control consisted of cells treated with 200 nM final concentration of staurosporine and the 0% inhibition control consisted of DMSO treated cells. After addition of compounds, assay plates were incubated for 6 days at 37° C., 5% $CO_2$, relative humidity >90% for 6 days. Cell viability was measured by quantization of ATP present in the cell cultures, adding 35 μl of Cell Titer Glo® reagent to the cell plates. Luminescence was read in the SpectraMax M5. The concentration inhibiting cell viability by 50% was determined using a 4-parametric fit of the normalized dose response curves. $IC_{50}$ values for this assay are also presented in Table 3 below.

TABLE 3

| Cpd # | WT EZH2 $IC_{50}$ (μM) | Mutant Y641F $IC_{50}$ (μM) | H3K27Me3 ELISA $IC_{50}$ (μM) | WSU proliferation $IC_{50}$ (μM) |
|---|---|---|---|---|
| 1 | 0.0199 | | | 3.09728 |
| 2 | 0.02348 | | | 0.62109 |
| 3 | 0.04011 | | | |
| 4 | 0.02231 | | | 0.54412 |
| 5 | 0.02389 | | | 2.19558 |
| 6 | 0.02703 | | | 0.50577 |
| 7 | 0.03317 | | | |
| 8 | 0.03622 | 0.02506 | | |
| 9 | 0.03501 | | | |
| 10 | 0.03978 | | | |
| 11 | 0.04682 | | | |
| 12 | 0.05026 | | | |
| 13 | 0.06396 | | | |
| 14 | 0.04353 | | | |
| 15 | 0.07173 | | | |
| 16 | 0.10471 | | | |
| 17 | 0.08438 | | | |
| 18 | 0.1603 | | | |
| 19 | 0.10845 | | | |
| 20 | 0.16251 | | | |
| 21 | 0.17104 | | | |
| 22 | 0.20549 | | | |
| 23 | 0.17755 | | | |
| 24 | 0.22919 | | | |
| 25 | 0.23 | | | |
| 26 | 0.29374 | | | |
| 27 | 0.48381 | | | |
| 28 | 0.54889 | | | |
| 29 | 0.62173 | | | |
| 30 | 0.62615 | | | |
| 31 | 0.6324 | | | |
| 32 | 0.63441 | | | |
| 33 | 0.65963 | | | |
| 35 | 0.82442 | | | |
| 36 | 0.91712 | | | |
| 37 | 1.00379 | | | |
| 38 | 1.0545 | | | |
| 39 | 1.07137 | | | |
| 40 | 1.09168 | | | |
| 41 | 1.13408 | | | |
| 42 | 2.59043 | | | |
| 43 | 2.67651 | | | |
| 44 | 4.32369 | | | |
| 45 | 25.22746 | | | |
| 46 | 26.53597 | | | |
| 47 | 39.133 | | | |
| 48 | 0.24998 | | | |
| 49 | 3.59887 | | | |
| 50 | 0.30813 | | | |
| 51 | 0.37599 | | | |
| 52 | 0.04814 | | | |
| 53 | 0.41267 | | | |
| 54 | 0.50073 | | | |
| 55 | 0.01626 | | | 3.91279 |
| 56 | 0.01519 | | | 0.21216 |
| 57 | 0.02987 | | | 7.72974 |
| 58 | 0.05639 | | | |
| 59 | 0.03149 | | | |
| 60 | 0.05852 | | | |
| 61 | 0.01585 | | | 0.33187 |
| 62 | 0.09429 | | | |
| 63 | 0.05709 | | | |
| 64 | 0.02472 | | | 2.06774 |
| 65 | 1.07044 | | | |
| 66 | 1.71172 | | | |
| 67 | 3.61905 | | | |
| 68 | 1.3267 | | | |
| 69 | 4.71695 | | | |
| 70 | 0.90608 | | | |
| 71 | 1.21512 | | | |
| 72 | 1.01436 | | | |
| 73 | 4.14125 | | | |
| 74 | 0.07113 | | | |
| 75 | 0.3843 | | | |
| 76 | 1.24461 | | | |

TABLE 3-continued

| Cpd # | WT EZH2 $IC_{50}$ (μM) | Mutant Y641F $IC_{50}$ (μM) | H3K27Me3 ELISA $IC_{50}$ (μM) | WSU prolifer-ation $IC_{50}$ (μM) |
|---|---|---|---|---|
| 77 | 0.14901 | | | |
| 78 | 0.14362 | | | |
| 79 | 0.02465 | 0.02116 | | |
| 80 | 1.64878 | | | |
| 82 | 4.20192 | | | |
| 83 | 0.18011 | 0.09576 | | |
| 84 | 0.11391 | 0.10243 | | |
| 85 | 0.10754 | 0.07626 | | |
| 86 | 2.57252 | | | |
| 87 | 0.09019 | 0.10057 | | |
| 88 | 0.03758 | 0.02817 | | |
| 89 | 0.07342 | 0.08298 | | |
| 90 | 0.0998 | 0.1002 | | |
| 91 | 0.02271 | 0.0176 | | 2.5696 |
| 92 | 0.01655 | 0.02341 | | 1.23721 |
| 93 | 1.18036 | 1.08352 | | |
| 94 | 3.80992 | 5.5015 | | |
| 95 | 0.35125 | 0.33255 | | |
| 96 | 0.38143 | 0.40305 | | |
| 97 | 0.02024 | 0.0292 | | 2.4644 |
| 98 | 0.0174 | 0.03732 | | 1.75896 |
| 99 | 0.01481 | 0.01028 | | 3.86397 |
| 100 | 0.03203 | 0.01966 | | |
| 101 | 0.00711 | 0.00717 | | 1.07296 |
| 102 | 0.01545 | 0.00727 | | 0.61272 |
| 103 | 0.072 | 0.06724 | | |
| 104 | 0.03077 | 0.0318 | | 9.05638 |
| 105 | 0.01728 | 0.01229 | | 6.47052 |
| 106 | 0.2446 | 0.19119 | | |
| 107 | 0.05396 | 0.10057 | | |
| 108 | 0.02003 | 0.0175 | | 4.42418 |
| 109 | 0.01112 | 0.01094 | | 0.44691 |
| 110 | 0.04792 | 0.06226 | | |
| 111 | 0.05328 | 0.02875 | | |
| 112 | 0.0587 | 0.02666 | | |
| 113 | 0.18895 | 0.17503 | | |
| 114 | 0.1051 | 0.11091 | | |
| 115 | 0.06117 | 0.05267 | | |
| 116 | 0.06276 | 0.0452 | | |
| 117 | 0.02807 | 0.02213 | | |
| 118 | 0.01759 | 0.01615 | | 8.60536 |
| 119 | 0.00951 | 0.00748 | | 1.40617 |
| 120 | 0.00911 | 0.01085 | | 0.36889 |
| 121 | 0.01385 | 0.0133 | | 0.5035 |
| 122 | 0.01511 | 0.01932 | | 0.18096 |
| 123 | 0.09153 | 0.06041 | | |
| 124 | 0.16779 | 0.11113 | | |
| 125 | 0.04721 | 0.0315 | | |
| 126 | 0.04784 | 0.03472 | | |
| 127 | 0.01691 | 0.01923 | | 1.50101 |
| 128 | 0.04911 | 0.0438 | | |
| 129 | 0.11098 | 0.08998 | | |
| 130 | 0.01722 | 0.01508 | | 2.3697 |
| 131 | 0.02287 | 0.00778 | | 1.65122 |
| 132 | 0.06337 | 0.0717 | | |
| 133 | 0.04829 | 0.03059 | | |
| 134 | 0.02562 | 0.02189 | | 1.08958 |
| 135 | 0.04667 | 0.02555 | | 4.14394 |
| 136 | 0.11517 | 0.0957 | | |
| 137 | 0.01602 | 0.00604 | | 3.29434 |
| 138 | 0.03495 | 0.04493 | | >20.0 uM |
| 139 | 0.0204 | 0.01392 | | 1.79898 |
| 140 | 1.66626 | 0.91482 | | |
| 141 | 0.06632 | 0.18147 | | |
| 142 | 0.02672 | 0.02005 | | 3.72097 |
| 143 | 0.13711 | 0.05828 | | |
| 144 | 2.294 | 1.3667 | | |
| 145 | 0.10444 | 0.07112 | | |
| 146 | 0.32313 | 0.28854 | | |
| 147 | 0.14779 | 0.25593 | | |
| 148 | 0.10411 | 0.0887 | | |
| 149 | 0.04469 | 0.03168 | | |
| 150 | 0.02894 | 0.02965 | | 0.57037 |
| 151 | 0.01594 | 0.0157 | | 0.52874 |
| 152 | 0.02585 | 0.02197 | | 1.40549 |
| 153 | 0.08502 | 0.09128 | | |
| 154 | 0.013 | 0.01062 | | 1.16887 |
| 155 | 0.02133 | 0.02385 | | 0.46034 |
| 156 | 0.0588 | 0.01936 | | |
| 157 | 0.00315 | 0.02001 | | 0.71676 |
| 158 | 0.00901 | 0.00955 | | 0.65779 |
| 159 | 0.02579 | 0.02495 | | 0.58237 |
| 160 | 0.01766 | 0.02255 | | 6.6023 |
| 161 | 0.01969 | 0.01299 | | 1.59243 |
| 162 | 0.01532 | 0.01819 | | 1.18391 |
| 163 | 0.46447 | 0.26959 | | |
| 164 | 0.0546 | 0.06284 | | |
| 165 | 0.02452 | 0.01895 | | 0.84174 |
| 166 | 0.01495 | 0.01835 | | 0.69533 |
| 167 | 0.0131 | 0.00987 | | 0.10896 |
| 168 | 0.00808 | 0.00611 | | 0.82333 |
| 169 | 0.09611 | 0.1054 | | |
| 170 | 0.01635 | 0.01145 | | 4.16823 |
| 171 | 0.07652 | 0.0652 | | |
| 172 | 0.65963 | | | |
| 173 | 1.13408 | | | |
| 174 | 0.0199 | | | 3.09728 |
| 175 | 15.49647 | | | |
| 176 | 35.36685 | | | |
| 177 | 4.13196 | | | |
| 178 | 4.13196 | | | |
| 179 | 2.875 | | | |
| 180 | 2.31858 | | | |
| 181 | 1.18357 | | | |
| 182 | 0.13256 | | | |
| 183 | 7.67584 | | | |
| 184 | 1.07044 | | | |
| 186 | 1.64878 | | | |
| 187 | 2.57252 | | | |
| 188 | 0.15624 | 0.16162 | | |
| 189 | 3.80992 | 5.5015 | | |
| 190 | 0.2839 | 0.21448 | | |
| 191 | 0.0109 | 0.00548 | | 0.43262 |
| 192 | 0.13004 | 0.09414 | | |
| 193 | 0.0822 | 0.05193 | | |
| 194 | 0.01771 | 0.00919 | | 0.41697 |
| 195 | 0.01654 | 0.01113 | | 1.45306 |
| 196 | 0.01817 | 0.01479 | | 0.35933 |
| 197 | 0.01822 | 0.00537 | | 1.05176 |
| 198 | 0.20387 | 0.13976 | | |
| 199 | 1.38563 | 0.99179 | | |
| 200 | 0.00624 | 0.00596 | | 0.2826 |
| 201 | 1.33026 | 1.11031 | | |
| 202 | 0.04811 | 0.03758 | | 3.12395 |
| 203 | 0.02138 | 0.0142 | | 0.47667 |
| 204 | 0.22175 | 0.21976 | | |
| 205 | 0.0077 | 0.00479 | 0.82074 | |
| 206 | 0.01284 | 0.01106 | | 0.63322 |
| 207 | 0.10198 | 0.11905 | | >20.0 uM |
| 208 | 1.31405 | 1.19521 | | |
| 209 | 1.487 | 1.18544 | | |
| 210 | | | | 1.26697 |
| 211 | 0.00679 | 0.0147 | | 0.54832 |
| 212 | 1.05201 | 0.98451 | | |
| 213 | 0.05325 | 0.0438 | | 14.71083 |
| 214 | 0.07475 | 0.06722 | | 2.45231 |
| 215 | 0.01551 | 0.02167 | | 0.80033 |
| 216 | 0.02489 | 0.04884 | | 1.54705 |
| 217 | 0.18259 | 0.34753 | | |
| 218 | 0.02083 | 0.02903 | | 1.27027 |
| 219 | 0.1748 | 0.16449 | | |
| 220 | 0.0205 | 0.04357 | | 1.04201 |
| 221 | 0.0191 | 0.01616 | | 1.11978 |
| 222 | 0.00078 | 0.00225 | 0.18533 | 0.13712 |
| 223 | 0.0136 | 0.02689 | | 1.54605 |
| 224 | 0.03257 | 0.03334 | | 1.76879 |
| 225 | 0.00695 | 0.01342 | | 0.20778 |
| 226 | 0.03426 | 0.06624 | | 0.23132 |
| 227 | 0.00365 | 0.00622 | | 0.21515 |
| 228 | 0.0144 | 0.02015 | | 1.27869 |

TABLE 3-continued

| Cpd # | WT EZH2 $IC_{50}$ (μM) | Mutant Y641F $IC_{50}$ (μM) | H3K27Me3 ELISA $IC_{50}$ (μM) | WSU prolifer-ation $IC_{50}$ (μM) |
|---|---|---|---|---|
| 229 | 0.02235 | 0.02847 | | 1.54848 |
| 230 | 0.34423 | 0.25475 | | |
| 231 | 0.29712 | 0.15945 | | >20.0 uM |
| 232 | 0.15485 | 0.0881 | | 8.04526 |
| 233 | 1.42344 | 0.5799 | | |
| 234 | 1.97267 | 1.62693 | | |
| 235 | 0.0632 | 0.05138 | | 3.79895 |
| 236 | 0.61213 | 0.83099 | | 14.62129 |
| 237 | 2.18156 | 1.47293 | | |
| 238 | 1.40428 | 0.80506 | | |
| 239 | 4.95504 | 4.77826 | | |
| 240 | 6.94031 | 6.8594 | | |
| 241 | 6.57787 | | | |
| 242 | 0.1998 | 0.12679 | | 8.4057 |
| 243 | 0.06318 | | | 6.47336 |
| 244 | 0.03749 | | | 3.06427 |
| 245 | 0.33295 | | | |
| 246 | | | | |
| 247 | 0.01787 | 0.02136 | | 3.19941 |
| 248 | 0.03458 | 0.0601 | | 4.57081 |
| 249 | | | | 11.45613 |
| 250 | 0.15959 | 0.20744 | | 4.58295 |
| 251 | | | | 13.11386 |
| 252 | | | | >20.0 uM |
| 253 | 0.45669 | 0.28936 | | 14.42495 |
| 254 | | | | |
| 255 | 0.01095 | 0.009 | | 1.63338 |
| 256 | 0.00648 | 0.00738 | | 1.69149 |
| 257 | 0.02224 | 0.07406 | | 4.49758 |
| 258 | 1.90754 | | | |
| 259 | 0.58066 | 0.60207 | | >20.0 uM |
| 260 | 0.01282 | 0.01164 | | 1.08525 |
| 261 | 0.01426 | 0.02069 | | 0.9055 |
| 262 | 0.00961 | 0.00523 | | 1.89119 |
| 263 | 0.03631 | 0.02181 | | 4.89099 |
| 264 | 0.04094 | 0.04072 | | 8.72536 |
| 265 | 0.02507 | 0.01843 | | 5.09483 |
| 266 | 0.19847 | 0.08014 | | 8.72547 |
| 267 | 0.16128 | | | >20.0 uM |
| 268 | 0.00131 | 0.0024 | | 0.38531 |
| 269 | 0.09984 | 0.11108 | | 14.2318 |
| 270 | 9.47417 | >10.0 uM | | |
| 271 | 0.05109 | 0.02565 | | 5.32683 |
| 272 | 0.11472 | 0.06925 | | |
| 273 | 0.00328 | 0.00537 | | 0.28489 |
| 274 | 7.76353 | >10.0 uM | | >20.0 uM |
| 275 | 0.90643 | 3.32337 | | >20.0 uM |
| 276 | 0.00152 | 0.00407 | | 0.18228 |
| 277 | 0.0023 | 0.00264 | | 2.47797 |
| 278 | 0.00493 | 0.01117 | | 0.61255 |
| 279 | 0.01143 | 0.01999 | | 0.78715 |
| 280 | 0.00139 | 0.00556 | | 0.43228 |
| 281 | >10.0 uM | >10.0 uM | | |
| 282 | 0.00492 | 0.00985 | | 0.21356 |
| 283 | 0.00316 | 0.0177 | | 0.27638 |
| 284 | 0.008 | 0.0119 | | 0.26282 |
| 285 | 0.00211 | 0.00506 | | 0.21307 |
| 286 | 0.00122 | 0.00272 | | 0.46721 |
| 287 | 0.00882 | 0.01141 | | 1.35674 |
| 288 | 0.00694 | 0.00732 | | 0.53484 |
| 289 | 0.14621 | 0.09339 | | |
| 290 | 0.00743 | | | 0.53732 |
| 291 | 0.00951 | | | 0.71974 |
| 292 | 0.01046 | | | 1.21021 |
| 293 | 0.01737 | 0.01158 | | 1.29406 |
| 294 | 0.02412 | | | 2.16178 |
| 295 | 0.01161 | 0.01056 | | 2.51445 |
| 296 | 0.00655 | 0.01825 | | 4.33357 |
| 297 | 0.03337 | 0.02251 | | 11.2951 |
| 298 | 0.0371 | 0.04303 | | 6.54579 |
| 299 | 0.00324 | 0.00307 | | 0.25937 |
| 300 | 0.02277 | 0.01709 | | 4.94656 |
| 301 | 0.00497 | 0.00507 | | |
| 302 | 0.01217 | 0.01607 | | 1.97477 |
| 303 | 0.03293 | 0.04119 | | 3.89541 |
| 304 | 0.01722 | 0.0126 | | 2.14418 |
| 305 | 0.00254 | 0.00785 | | 0.28787 |
| 306 | 0.00942 | 0.00922 | | 0.17284 |
| 307 | 0.0402 | 0.10188 | | 3.85437 |
| 308 | 0.00997 | 0.01169 | | 0.16744 |
| 309 | 0.00817 | | | |
| 310 | 0.00596 | | | 0.60994 |
| 311 | 0.00323 | | | 0.16549 |
| 312 | 0.01507 | | | |
| 313 | 0.00818 | | | |
| 314 | 2.90826 | 4.7092 | | |
| 315 | 0.00973 | 0.00922 | | |
| 316 | | 0.01202 | | 1.40268 |
| 317 | 1.37527 | 1.96382 | | |
| 318 | 1.06978 | 0.91775 | | 9.7596 |
| 319 | 0.0108 | 0.01137 | | 2.95728 |
| 320 | 0.01694 | 0.01579 | | 0.17566 |
| 321 | 0.00783 | 0.01144 | | |
| 322 | 0.03101 | 0.02239 | | 3.59961 |
| 323 | 0.05148 | 0.03445 | | 4.15894 |
| 324 | 0.40349 | 0.15525 | | 16.80211 |
| 325 | 0.13585 | 0.21534 | | 13.3829 |
| 326 | 0.0206 | 0.0095 | | 1.43256 |
| 327 | 0.23134 | 0.09407 | | 3.11887 |
| 328 | 0.84894 | | | >20.0 uM |
| 329 | 0.00755 | 0.00371 | | 0.88119 |
| 330 | 0.03576 | 0.0368 | | 1.20313 |
| 331 | 0.03891 | 0.01805 | | 0.19105 |
| 332 | 0.27993 | 0.45426 | | >20.0 uM |
| 333 | 0.30257 | 0.54098 | | >20.0 uM |
| 334 | 0.05384 | 0.11977 | | |
| 335 | 0.01004 | 0.0027 | | 0.97124 |
| 336 | 0.03144 | 0.02075 | | |
| 337 | 4.32339 | 3.56167 | | >20.0 uM |
| 338 | 0.49234 | 0.19347 | | >20.0 uM |
| 339 | 0.00858 | 0.00734 | | 0.97312 |
| 340 | 0.01056 | 0.00412 | | 1.59354 |
| 341 | 0.00592 | 0.00552 | | 2.28944 |
| 342 | 0.03972 | 0.01592 | | 1.9859 |
| 343 | 0.01081 | 0.00912 | | 0.63289 |
| 344 | 0.00623 | 0.00396 | | 1.30672 |
| 345 | 0.02228 | 0.01819 | | 1.2346 |
| 346 | 0.00428 | 0.00245 | | 0.12639 |
| 347 | 0.00654 | 0.00328 | | 0.13526 |
| 348 | 0.00566 | 0.00363 | | 0.32865 |
| 349 | 0.00872 | 0.00153 | | |
| 350 | 0.01244 | 0.00357 | | 0.38084 |
| 351 | 0.00911 | 0.00138 | | 4.85151 |
| 352 | 0.13195 | | | 5.54765 |
| 353 | 0.00792 | 0.00463 | | 0.14599 |
| 354 | 0.01312 | 0.01039 | 0.14232 | 0.15832 |
| 355 | 0.08966 | 0.06081 | | |
| 356 | 0.03629 | 0.00721 | | |
| 357 | 0.00437 | 0.00456 | 0.14928 | |
| 358 | 0.17315 | 0.06636 | | |
| 359 | 0.00729 | 0.00554 | | |
| 360 | 0.00883 | 0.00841 | | |
| 361 | 0.00661 | 0.00423 | | |
| 362 | 0.01388 | 0.00491 | | |
| 363 | 0.00394 | 0.00206 | | |
| 364 | 0.00943 | 0.00687 | | |
| 365 | 0.00609 | 0.00665 | 0.23299 | |
| 366 | 0.03483 | 0.02934 | >25.0 uM | |
| 367 | 0.33336 | 0.16784 | >25.0 uM | |
| 368 | 0.02799 | 0.03855 | >25.0 uM | |
| 369 | 0.07146 | 0.02755 | 3.7881 | |
| 370 | 0.02998 | 0.01113 | | |
| 371 | 0.01181 | 0.00537 | | |
| 372 | 0.00801 | 0.0081 | 0.3659 | |
| 373 | 0.00694 | 0.00369 | | |
| 374 | 0.00319 | 0.00831 | | |
| 375 | 0.01661 | 0.04182 | | |
| 376 | 0.01641 | 0.01977 | | |
| 377 | 0.07647 | 0.02552 | | |
| 378 | 0.00296 | 0.0031 | >25.0 uM | |

TABLE 3-continued

| Cpd # | WT EZH2 $IC_{50}$ (μM) | Mutant Y641F $IC_{50}$ (μM) | H3K27Me3 ELISA $IC_{50}$ (μM) | WSU proliferation $IC_{50}$ (μM) |
|---|---|---|---|---|
| 379 | 0.00516 | 0.00322 | >25.0 uM | |
| 380 | 0.02778 | 0.04196 | >25.0 uM | |
| 381 | 0.05627 | 0.05243 | >25.0 uM | |
| 382 | 0.00341 | 0.02167 | 4.16185 | |
| 383 | 0.03974 | 0.04428 | >25.0 uM | |
| 384 | 0.00206 | 0.00156 | 1.53716 | |
| 385 | 0.06573 | 0.03511 | >25.0 uM | |
| 386 | 2.42146 | 1.15144 | | |
| 387 | 0.74351 | 0.39771 | | |
| 388 | 0.00728 | 0.00396 | 2.29835 | |
| 389 | 0.01564 | 0.0177 | | |
| 390 | 0.01251 | 0.01037 | | 1.32773 |
| 391 | 0.04809 | 0.06404 | >25.0 uM | |
| 392 | 0.048 | 0.039 | | |
| 393 | 0.12932 | 0.10995 | | |
| 394 | 0.29421 | 0.23058 | | |
| 395 | 0.30434 | 0.17359 | | |
| 396 | 4.42445 | 6.6822 | | |
| 397 | 3.37221 | 2.39173 | | |
| 398 | 2.61756 | 2.00394 | | |
| 399 | >10.0 uM | 8.31018 | | |
| 400 | 0.025 | 0.018 | | |
| 401 | 0.01466 | 0.01426 | | |
| 402 | >10.0 uM | 8.0921 | | |
| 403 | 0.53602 | 0.58786 | | |
| 404 | 2.27552 | 1.40203 | | |
| 405 | 0.172 | 0.107 | | |
| 406 | 0.017 | 0.053 | | |
| 407 | 0.0861 | 0.04069 | | |
| 408 | 0.1656 | 0.0936 | | |
| 409 | 0.45616 | 0.3404 | | |
| 410 | 2.28273 | 2.85881 | | |
| 411 | 1.19988 | 1.40119 | | |
| 412 | 0.22183 | 0.21475 | | |
| 413 | 0.76484 | 0.64167 | | |
| 414 | 0.00692 | 0.0084 | | |
| 415 | 1.5555 | 0.89979 | | |
| 416 | 0.016 | 0.015 | | |

Example 47

Derivation of the Lowest Cytotoxic Concentration (LCC)

It is well established that cellular proliferation proceeds through cell division that results in a doubling of the number of cells after division, relative to the number of cells prior to division. Under a fixed set of environmental conditions (e.g., pH, ionic strength, temperature, cell density, medium content of proteins and growth factors, and the like) cells will proliferate by consecutive doubling (i.e., division) according to the following equation, provided that sufficient nutrients and other required factors are available.

$$N_t = N_0 \times 2^{\frac{t}{t_D}} \quad (A.1)$$

where $N_t$ is the cell number at a time point (t) after initiation of the observation period, $N_0$ is the cell number at the initiation of the observation period, t is the time after initiation of the observation period and $t_D$ is the time interval required for cell doubling, also referred to as the doubling time. Equation A.1 can be converted into the more convenient form of an exponential equation in base e, taking advantage of the equality, 0.693=ln(2).

$$N_t = N_0 e^{\frac{0.693t}{t_D}} \quad (A.2)$$

The rate constant for cell proliferation ($k_p$) is inversely related to the doubling time as follows.

$$k_p = \frac{0.693}{t_D} \quad (A.3)$$

Combining equation A.2 and A.3 yields, $$N_t = N_0 e^{k_p t} \quad (A.4)$$

Thus, according to equation A.4 cell number is expected to increase exponentially with time (FIG. 1 A) during the early period of cell growth referred to as log-phase growth. Exponential equations like equation A.4 can be linearized by taking the natural logarithm of each side.

$$\ln(N_t) = \ln(N_0) + k_p t \quad (A.5)$$

Figure 1:
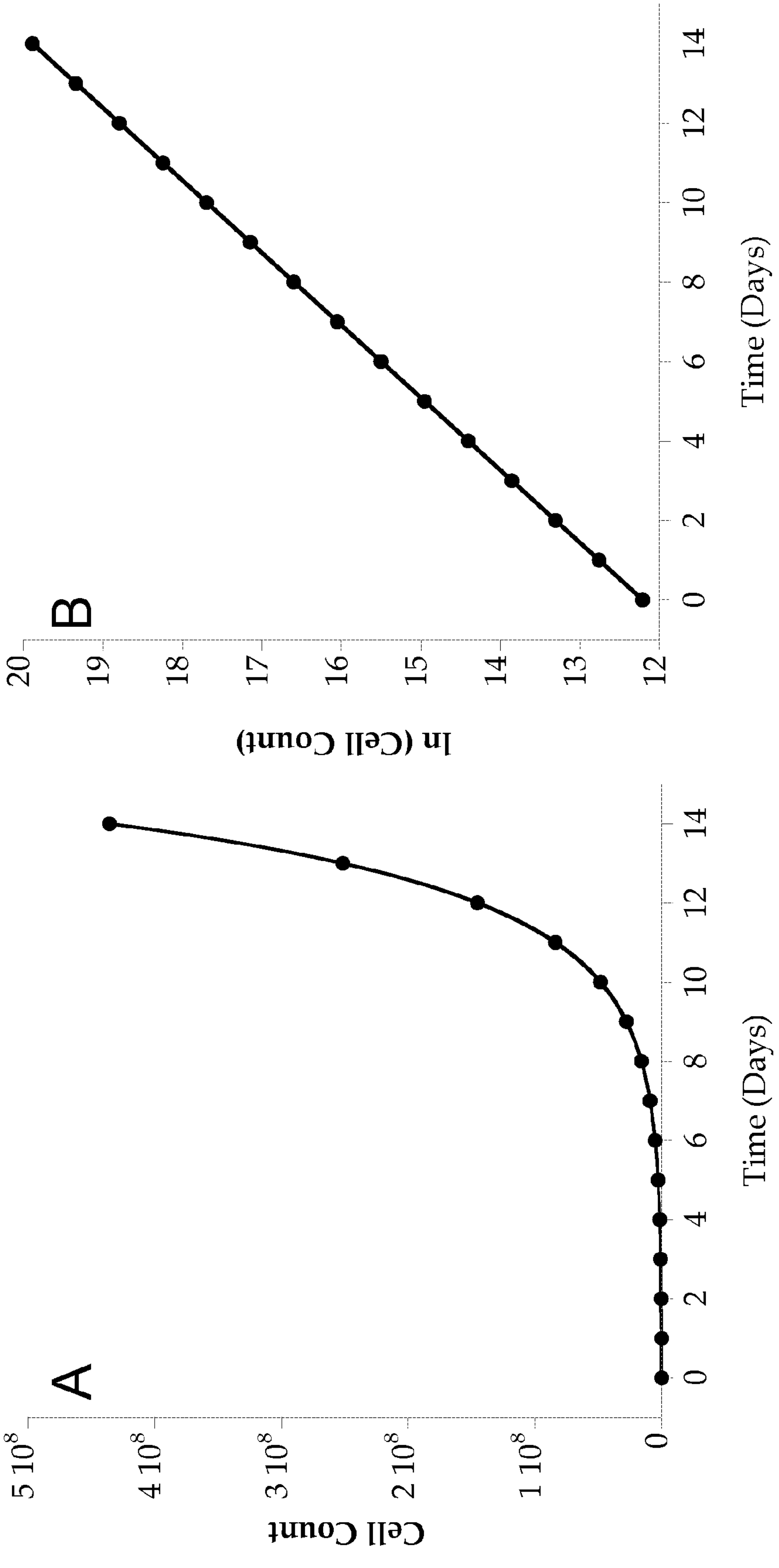
FIG. 1 (A) is an idealized plot of cell count (i.e., cell number) as a function of time showing exponential proliferation during log-phase cell growth.

Thus a plot of $\ln(N_t)$ as a function of time is expected to yield an ascending straight line with slope equal to $k_p$ and y-intercept equal to $\ln(N_0)$, as illustrated in FIG. 1 B.

Changes in environmental conditions can result in a change in the rate of cellular proliferation that is quantifiable as changes in the proliferation rate constant $k_p$. Among conditions that may result in a change in proliferation rate is the introduction to the system of an antiproliferative compound at the initiation of the observation period (i.e., at t=0). When an antiproliferative compound has an immediate impact on cell proliferation, one expects that plots of $\ln(N_t)$ as a function of time will continue to be linear at all compound concentrations, with diminishing values of $k_p$ at increasing concentrations of compound.

Depending on the mechanistic basis of antiproliferative action, some compounds may not immediately effect a change in proliferation rate. Instead, there may be a period of latency before the impact of the compound is realized. In such cases a plot of $\ln(N_t)$ as a function of time will appear biphasic, and a time point at which the impact of the compound begins can be identified as the breakpoint between phases (FIG. 2). Regardless of whether a compound's impact on proliferation is immediate or begins after a latency period, the rate constant for proliferation at each compound concentration is best defined by the slope of the $\ln(N_t)$ vs. time curve from the time point at which compound impact begins to the end of the observation period of the experiment.

A compound applied to growing cells may affect the observed proliferation in one of two general ways: by inhibiting further cell division (cytostasis) or by cell killing (cytotoxicity). If a compound is cytostatic, increasing concentration of compound will reduce the value of $k_p$ until there is no further cell division. At this point, the rate of cell growth, and therefore the value of $k_p$, will be zero. If, on the other hand, the compound is cytotoxic, then the value of $k_p$ will be composed of two rate constants: a rate constant for continued cell growth in the presence of the compound ($k_g$) and a rate constant for cell killing by the compound ($k_d$). The overall rate constant for proliferation at a fixed concentration of compound will thus be the difference between the absolute values of these opposing rate constants.

$$k_p = |k_g| - |k_d| \quad (A.6)$$

At compound concentrations for which the rate of cell growth exceeds that of cell killing, the value of $k_p$ will have a positive value (i.e., $k_p>0$). At compound concentrations for which the rate of cell growth is less than that for cell killing, the value of $k_p$ will have a negative value (i.e., $k_p<0$) and the cell number will decrease with time, indicative of robust cytotoxicity. When $k_g$ exactly matches $k_d$ then the overall proliferation rate constant, $k_p$, will have a value of zero. We can thus define the lowest cytotoxic concentration (LCC) as that concentration of compound that results in a value of $k_p$ equal to zero, because any concentration greater than this will result in clearly observable cytotoxicity. Nota bene: at concentrations below the LCC there is likely to be cell killing occurring, but at a rate that is less than that of residual cell proliferation. The treatment here is not intended to define the biological details of compound action. Rather, the goal here is to merely define a practical parameter with which to objectively quantify the concentration of compound at which the rate of cell killing exceeds new cell growth. Indeed, the LCC represents a breakpoint or critical concentration above which frank cytotoxicity is observed, rather than a cytotoxic concentration per se. In this regard, the LCC can be viewed similar to other physical breakpoint metrics, such as the critical micelle concentration (CMC) used to define the concentration of lipid, detergent or other surfactant species above which all molecules incorporate into micellar structures.

Traditionally, the impact of antiproliferative compounds on cell growth has been most commonly quantified by the $IC_{50}$ value, which is defined as that concentration of compound that reduces the rate of cell proliferation to one half that observed in the absence of compound (i.e., for the vehicle or solvent control sample; FIG. 2). The $IC_{50}$, however, does not allow the investigator to differentiate between cytostatic and cytotoxic compounds. The LCC, in contrast, readily allows one to make such a differentiation and to further quantify the concentration at which the transition to robust cytotoxic behavior occurs.

If one limits the observation time window to between the start of impact (as defined above and in FIG. 2) and the end of the experiment, then the data will generally fit well to a linear equation when plotted as $\ln(N_t)$ as a function of time (vide supra). From fits of this type, the value of $k_p$ can be determined at each concentration of compound tested. A replot of the value of $k_p$ as a function of compound concentration ([I]) will have the form of a descending isotherm, with a maximum value at [I]=0 of $k_{max}$ (defined by the vehicle or solvent control sample) and a minimum value at infinite compound concentration of $k_{min}$(FIG. 3).

$$k_p = \frac{(k_{max} - k_{min})}{1 + \frac{[I]}{I_{mid}}} + k_{min} \quad (A.7)$$

where $I_{mid}$ is the concentration of compound yielding a value of $k_p$ that is midway between the values of $k_{max}$ and $k_{min}$ (note that the value of $I_{mid}$ is not the same as the $IC_{50}$, except in the case of a complete and purely cytostatic compound). Thus, fitting the replot data to equation A.7 provides estimates of $k_{max}$, $k_{min}$, and $I_{mid}$. If a compound is cytostatic (as defined here), the value of $k_{min}$ cannot be less than zero. For cytotoxic compounds, $k_{min}$ will be less than zero and the absolute value of $k_{min}$ will relate directly to the effectiveness of the compound in killing cells.

The fitted values derived from equation A.7 can also be used to determine the value of the LCC. By definition, when [I]=LCC, $k_p$=0. Thus, under these conditions equation A.7 becomes.

$$0 = \frac{(k_{max} - k_{min})}{1 + \frac{LCC}{I_{mid}}} + k_{min} \quad (A.8)$$

Algebraic rearrangement of equation A.8 yields an equation for the LCC.

$$LCC = I_{mid}\left[\left(\frac{k_{max} - k_{min}}{-k_{min}}\right) - 1\right] \quad (A.9)$$

This analysis is simple to implement with nonlinear curve fitting software and may be applied during cellular assays of compound activity throughout the drug discovery and development process. In this manner, the LCC may provide a valuable metric for the assessment of compound SAR (structure-activity relationship).

Table 4 below provides LCC and $IC_{50}$ data for certain compounds of the invention on WSU-DLCL2 cells.

TABLE 4

| Cpd # | WSU-DLCL2 11-day LCC (μM) | WSU-DLCL2 11-day IC50 (μM) |
|---|---|---|
| 8 | 0.207 | 0.076 |
| 56 | 0.442 | 0.0097 |
| 88 | 1.27 | 0.035 |
| 101 | 2.59 | 0.25 |
| 120 | 0.343 | 0.006 |
| 121 | 0.0597 | 0.0094 |
| 222 | 0.0268 | 0.0043 |
| 261 | 0.556 | 0.051 |
| 277 | 0.037 | 0.0024 |
| 354 | 0.043 | 0.013 |
| 357 | 0.026 | 0.0095 |

Example 48

In Vivo Assay

Mice

Female Fox Chase SCID® Mice (CB17/Icr-Prkdcscid/IcrIcoCrl, Charles River Laboratories) or athymic nude mice (Crl:NU(Ncr)-Foxn1nu, Charles River Laboratories) were 8 weeks old and had a body-weight (BW) range of 16.0-21.1 g on D1 of the study. The animals were fed ad libitum water (reverse osmosis 1 ppm Cl) and NIH 31 Modified and Irradiated Lab Diet® consisting of 18.0% crude protein, 5.0% crude fat, and 5.0% crude fiber. The mice were housed on irradiated Enrich-o'Cobs™ bedding in static microisolators on a 12-hour light cycle at 20-22° C. (68-72° F.) and 40-60% humidity. All procedures comply with the recommendations of the Guide for Care and Use of Laboratory Animals with respect to restraint, husbandry, surgical procedures, feed and fluid regulation, and veterinary care.

Tumor Cell Culture

Human lymphoma cell lines line were obtained from different sources (ATCC, DSMZ) and maintained at Piedmont as suspension cultures in RPMI-1640 medium containing 100 units/mL penicillin G sodium salt, 100 g/mL streptomycin, and 25 g/mL gentamicin. The medium was supplemented with 10% fetal bovine serum and 2 mM glutamine. The cells were cultured in tissue culture flasks in a humidified incubator at 37° C., in an atmosphere of 5% CO2 and 95% air.

In Vivo Tumor Implantation

Human lymphoma cell lines were harvested during mid-log phase growth, and resuspended in PBS with 50% Matrigel™ (BD Biosciences). Each mouse received $1\times10^7$ cells (0.2 mL cell suspension) subcutaneously in the right flank. Tumors were calipered in two dimensions to monitor growth as the mean volume approached the desired 80-120 $mm^3$ range. Tumor size, in $mm^3$, was calculated from:

$$\text{Tumor volume} = \frac{w^2 \times l}{2}$$

where w=width and l=length, in mm, of the tumor. Tumor weight can be estimated with the assumption that 1 mg is equivalent to 1 mm3 of tumor volume. After 10-30 days (depending on the cell line used) mice with 108-126 $mm^3$ tumors were sorted into eight groups with mean tumor volumes of 117-119 mm3.

Test Articles

Test compounds were stored at room temperature and protected from light. On each treatment day, a fresh compound formulations were prepared by suspending the powders in 0.5% sodium carboxymethylcellulose (NaCMC) and 0.1% Tween® 80 in deionized water. The EM10 vehicle, 0.5% NaCMC and 0.1% Tween® 80 in deionized water, Was used to treat the control groups at the same schedules. Formulations were stored away from light at 4° C. prior to administration.

Treatment Plan

Mice were treated at compound doses ranging from 1-1000 mg/kg and at TID (3 times a day every 8 h), BID (twice a day every 12 h) or QD (once a day) schedules for various amount of days by oral gavage or injections via the intravenous, intraperitoneal or subcutaneous routes. Each dose was delivered in a volume of 0.2 mL/20 g mouse (10 mL/kg), and adjusted for the last recorded weight of individual animals. The maximal treatment length was 28 days.

Median Tumor Volume (MTV) and Tumor Growth Inhibition (TGI) Analysis

Treatment efficacy was determined on the last treatment day. MTV(n), the median tumor volume for the number of animals, n, evaluable on the last day, was determined for each group. Percent tumor growth inhibition (% TGI) can be defined several ways. First, the difference between the MTV (n) of the designated control group and the MTV(n) of the drug-treated group is expressed as a percentage of the MTV (n) of the control group:

$$\%\ TGI = \left(\frac{MTV(n)_{control} - MTV(n)_{treated}}{MTV(n)_{control}}\right) \times 100$$

Another way of calculating % TGI is taking the change of the tumor size from day 1 to day n into account with n being the last treatment day.

$$\%\ TGI = \left(\frac{\Delta MTV_{control} - \Delta MTV_{treated}}{\Delta MTV_{control}}\right) \times 100$$

$$\Delta MTV_{control} = MTV(n)_{control} - MTV(1)_{control}$$

-continued $$\Delta MTV_{treated} = MTV(n)_{treated} - MTV(1)_{treated}$$

Tumor Growth Delay Analysis

Alternatively, mice were kept alive after the last treatment day for tumor growth delay analysis. Tumors were callipered twice-weekly and each test animal was euthanized when its neoplasm reached the endpoint volume of 2000 $mm^3$ or on the pre-specified last day of the study, whichever came first. The time-to-endpoint (TTE) for each mouse was calculated from the following equation:

$$TTE(\text{days}) = \frac{\log_{10}(\text{endpoint volume, mm}^3) - b}{m}$$

where b is the intercept and m is the slope of the line obtained by linear regression of a log-transformed tumor growth data set. The data sets were composed of the first observation that exceeded the study endpoint volume and the three consecutive observations that immediately preceded the attainment of the endpoint volume. Animals that did not reach the volume endpoint were assigned a TTE value equal to the last day of the study (prespecified). Any animal classified as a treatment-related (TR) death was to be assigned a TTE value equal to the day of death. Any animal classified as a nontreatment-related (NTR) death was excluded from TTE calculations and all further analyses.

Treatment outcome was determined from tumor growth delay (TGD), defined as the increase in the median TTE in a treatment group compared to the control group:

$$\text{TGD}=T-C$$

expressed in days, or as a percentage of the median TTE of the control group:

$$\%\ TGD = \frac{T - C}{C} \times 100$$

where:

T=median TTE for a treatment group

C=median TTE for the control group

Toxicity

Animals were weighed daily on Days 1-5, and then twice weekly until the completion of the study. The mice were examined frequently for overt signs of any adverse, treatment related side effects, which were documented. Acceptable toxicity for the maximum tolerated dose (MTD) was defined as a group mean BW loss of less than 20% during the test, and not more than 10% mortality due to TR deaths. A death was to be classified as TR if it was attributable to treatment side effects as evidenced by clinical signs and/or necropsy, or due to unknown causes during the dosing period. A death was to be classified as NTR if there was evidence that the death was unrelated to treatment side effects. NTR deaths during the dosing interval would typically be categorized as NTRa (due to an accident or human error) or NTRm (due to necropsy-confirmed tumor dissemination by invasion and/or metastasis). Orally treated animals that die from unknown causes during the dosing period may be classified as NTRu when group performance does not support a TR classification and necropsy, to rule out a dosing error, is not feasible.

Sampling

On several days during the study mice were sampled in a pre-specified fashion. Sampling included non-terminal bleeds (0.25 mL) from the mandibular vein without anesthesia and full volume blood collection via terminal cardiac puncture under $CO_2$ anesthesia. Blood samples were processed for plasma, with K2-EDTA as anti-coagulant. The plasma samples were frozen at −80° C. and stored prior to bioanalysis of compound levels.

Tumors were harvested from specified mice under RNAse free conditions and bisected. A 2 mm thick slice from one half of each tumor was formalin-fixed for 24 h and transferred to 70% ethanol. The fixed tumor tissues were paraffin embedded. The remaining tumor tissue from each animal was snap frozen in liquid $N_2$ and pulverized with a mortar and pestle.

Specified mice were sampled for the surrogate tissues including spleen, skin, bone marrow, and whiskers. Each tissue was isolated and fixed and/or snap frozen.

Statistical and Graphical Analyses

All statistical and graphical analyses were performed with Prism 3.03 (GraphPad) for Windows. Several analyses methods were applied. Median D29 tumor volumes were compared with the Kruskal-Wallis test, and a post hoc Dunn's multiple comparison test. These tests were performed three times.

The two-tailed statistical analyses were conducted at P=0.05. Prism reports results as non-significant (ns) at P>0.05, significant (symbolized by "*") at 0.01<P<0.05, very significant ("") at 0.001<P<0.01 and extremely significant ("*") at P<0.001.

To test statistical significance between the control and treated groups over the whole treatment time course, either a repeated measures ANOVA test followed by Dunnets multiple comparison post test or a 2 way ANOVA test was employed.

For graphical representations s "box and whiskers" diagram was constructed to show the distribution of individual tumor volumes for each group. The box represents the 25th to 75th percentile of observations, the horizontal line corresponds to the median value, and the "whiskers" indicate the maximum and minimum values. Median or mean (±SEM) tumor volumes were graphed on a semilog or linear plot as functions of time. Group mean BW changes during the study were plotted as percent change, ±SEM, from D1.

A scatter plot was constructed to show TTE values, by group. The TTE plot includes NTR deaths, which are excluded from all other graphical analyses. When an animal exited the study because of tumor size, the final tumor volume recorded for the animal was included with the data used to calculate the median volume at subsequent time points. The percentage of animals in each group remaining in the study versus time was presented in a Kaplan-Meier survival plot.

Histone Extraction

For isolation of histones, 60-90 mg tumor tissue was homogenized in 1.5 ml nuclear extraction buffer (10 mM Tris-HCl, 10 mM MgCl2, 25 mM KCl, 1% Triton X-100, 8.6% Sucrose, plus a Roche protease inhibitor tablet 1836145) and incubated on ice for 5 minutes. Nuclei were collected by centrifugation at 600 g for 5 minutes at 4° C. and washed once in PBS. Supernatant was removed and histones extracted for one hour, with vortexing every 15 minutes, with 0.4 N cold sulfuric acid. Extracts were clarified by centrifugation at 10000 g for 10 minutes at 4° C. and transferred to a fresh microcentrifuge tube containing 10× volume of ice cold acetone. Histones were precipitated at −20° C. for 2 hours-overnight, pelleted by centrifugation at 10000 g for 10 minutes and resuspended in water.

Western Blot Analysis

Protein concentrations for acid extracted histones were determined by BCA assay (Pierce). 400-800 ng of each lysate was fractionated on 10-20% Tris-Glycine gel (Biorad), transferred using iBlot (7 minutes on program 3, using Nitrocellulose transfer stacks), and probed with the following antibodies in Odyssey blocking buffer: rabbit anti-H3K27me3 (CST 9733; 1:20000 dilution) and mouse anti-Total H3 (CST 3638; 1:20000 dilution). Following primary Ab incubation, membranes were probed with IRDye 800CW Donkey-anti-mouse IgG (LiCOR #926-32212) and Alexa Fluor 680 goat-anti-rabbit IgG (Invitrogen #A-21076) secondary Ab and imaged using the LiCOR Odyssey system.

ELISA

Histones were prepared in equivalent concentrations in coating buffer (PBS+0.05% BSA) yielding 0.5 ng/ul of sample, and 100 ul of sample or standard was added in duplicate to 2 96-well ELISA plates (Thermo Labsystems, Immulon 4HBX #3885). The plates were sealed and incubated overnight at 4° C. The following day, plates were washed 3× with 300 ul/well PBST (PBS+0.05% Tween 20; 10×PBST, KPL #51-14-02) on a Bio Tek plate washer. Plates were blocked with 300 ul/well of diluent (PBS+2% BSA+0.05% Tween 20), incubated at RT for 2 hours, and washed 3× with PBST. All antibodies were diluted in diluent. 100 ul/well of anti-H3K27me3 (CST #9733, 50% glycerol stock 1:1,000) or anti-total H3 (Abcam ab1791, 50% glycerol 1:10,000) was added to each plate. Plates were incubated for 90 min at RT and washed 3× with PBST. 100 ul/well of anti-Rb-IgG-HRP (Cell Signaling Technology, 7074) was added 1:2,000 to the H3K27Me3 plate and 1:6,000 to the H3 plate and incubated for 90 min at RT. Plates were washed 4× with PBST. For detection, 100 ul/well of TMB substrate (BioFx Laboratories, #TMBS) was added and plates incubated in the dark at RT for 5 min. Reaction was stopped with 100 ul/well 1N $H_2SO_4$ Absorbance at 450 nm was read on SpectaMax M5 Microplate reader.

The in vivo results for Compound 222 were shown in FIGS. 4 and 5. FIG. 4 shows tumor growth of WSU-DLCL2 xenograft bearing mice treated with Compound 222 over 27 days. Tumor growth inhibition was observed at all 3 doses 100 mg/kg (b.i.d., 27 days), 200 mg/kg (b.i.d., 27 days) and 400 mg/kg (400 mg/kg b.i.d. 7 days, 0 mg/kg for 7 days and 300 mg/kg b.i.d., 13 days days). FIG. 5 shows global H3K27me3 methylation in WSU-DLCL2 tumors from mice treated with compound 222 or vehicle for 27 days. This figure shows a reduction in the H3K27Me3 mark for each of the dose groups.

INCORPORATION BY REFERENCE

The entire disclosure of each of the patent documents and scientific articles referred to herein is incorporated by reference for all purposes.

EQUIVALENTS

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A compound of Formula (Ie) or a pharmaceutically acceptable salt thereof:

(Ie)

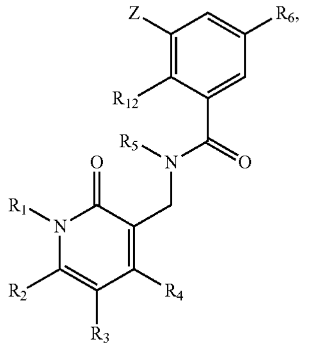

wherein

Z is $NR_7R_8$ or $S(O)_aR_7$, in which a is 0;

$R_1$ is H or $C_1$-$C_6$ alkyl optionally substituted with one or more substituents selected from hydroxyl, $C_1$-$C_6$ alkoxyl, amino, mono-$C_1$-$C_6$ alkylamino, di-$C_1$-$C_6$ alkylamino, and $C_6$-$C_{10}$ aryl;

each of $R_2$ and $R_4$ independently, is -$Q_1$-$T_1$, in which $Q_1$ is a bond or $C_1$-$C_3$ alkyl linker optionally substituted with one or more substituents selected from halo and hydroxyl, and $T_1$ is H, halo, or azido;

$R_3$ is H or halo;

$R_5$ is H or $C_1$-$C_6$ alkyl;

$R_6$ is H, halo, cyano, azido, $OR_a$, —$NR_aR_b$, —C(O)$NR_aR_b$, —$S(O)_bR_a$, or $R_{S2}$; wherein $R_{S2}$ is $C_1$-$C_6$ alkyl, $C_2$-$C_6$ alkenyl, $C_2$-$C_6$ alkynyl, or 4 to 12-membered heterocycloalkyl, wherein b is 0, 1, or 2, and wherein each of $R_a$ and $R_b$, independently is H, $C_1$-$C_6$ alkyl, or 4 to 12-membered heterocycloalkyl; or $R_a$ and $R_b$, together with the N atom to which they are attached, form a 4 to 12-membered heterocycloalkyl ring having 0 or 1 additional heteroatom; and each of $R_a$, $R_{S2}$ and the 4 to 12-membered heterocycloalkyl ring formed by $R_a$ and $R_b$, is optionally substituted with one or more -$Q_2$-$T_2$; wherein $Q_2$ is a bond or $C_1$-$C_3$ alkyl linker, and $T_2$ is H, halo, —$OR_e$, —$NR_cR_d$, —C(O)$OR_c$, $C_1$-$C_6$ alkyl, or $R_{S4}$, in which each of $R_c$ and $R_d$, independently is H or $C_1$-$C_6$ alkyl, $R_{S4}$ is $C_3$-$C_8$ cycloalkyl, $C_6$-$C_{10}$ aryl, 4 to 12-membered heterocycloalkyl, or 5- or 6-membered heteroaryl, and $R_{S4}$ is optionally substituted with one or more -$Q_3$-$T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_e$, $COOR_e$, —$S(O)_2R_e$, —$NR_eR_f$, and —$C(O)NR_eR_f$, each of $R_e$ and $R_f$ independently being H or $C_1$-$C_6$ alkyl, or $R_c$ and $R_d$, together with the N atom to which they are attached, form a 4 to 12-membered heterocycloalkyl ring having 0 or 1 additional heteroatom and optionally substituted with $C_1$-$C_6$ alkyl;

$R_7$ is -$Q_4$-$T_4$, in which $Q_4$ is a bond or $C_1$-$C_4$ alkyl linker and $T_4$ is H, $C_1$-$C_6$ alkyl, $C_3$-$C_8$ cycloalkyl, $C_6$-$C_{10}$ aryl, C(O)—$C_{1-6}$ alkyl, C(O)—$C_{3-6}$ cycloalkyl, or 4 to 14-membered heterocycloalkyl, each optionally substituted with one or more -$Q_5$-$T_5$, wherein $Q_5$ is a bond, C(O), C(O)$NR_k$, $NR_k$C(O), $S(O)_2$, or $C_1$-$C_3$ alkyl linker, $R_k$ being H or $C_1$-$C_6$ alkyl, and $T_5$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or $S(O)_qR_q$ in which q is 0, 1, or 2 and $R_q$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_5$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_5$ is H, halo, hydroxyl, or cyano; or -$Q_5$-$T_5$ is oxo;

$R_8$ is H, $C_1$-$C_6$ alkyl optionally substituted with halo, hydroxyl or $C_1$-$C_6$ alkoxyl, $C_2$-$C_6$ alkenyl, $C_3$-$C_8$ cycloalkyl, or 4 to 7-membered heterocycloalkyl; or $R_7$ and $R_8$, together with the N atom to which they are attached, form a 4 to 12-membered heterocycloalkyl ring having 0 to 2 additional heteroatoms, and the 4 to 12-membered heterocycloalkyl ring formed by $R_7$ and $R_8$ is optionally substituted with one or more -$Q_6$-$T_6$, wherein $Q_6$ is a bond, C(O), C(O)$NR_m$, $NR_m$C(O), $S(O)_2$, or $C_1$-$C_3$ alkyl linker, $R_m$ being H or $C_1$-$C_6$ alkyl, and $T_6$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or $S(O)_pR_p$ in which p is 0, 1, or 2 and $R_p$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_6$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_6$ is H, halo, hydroxyl, or cyano; or -$Q_6$-$T_6$ is oxo; and $R_{12}$ is halo, $C_1$-$C_6$ alkoxyl, or $C_1$-$C_6$ alkyl optionally substituted with halo or $C_2$-$C_6$ alkenyl.

2. The compound of claim 1, wherein the compound is of Formula (II):

(II)

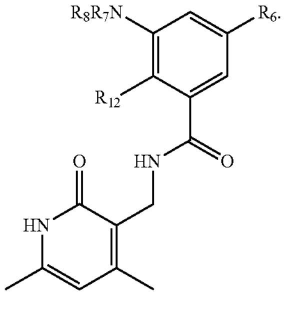

3. The compound of claim 1, wherein the compound is of Formula (IIA):

(IIA)

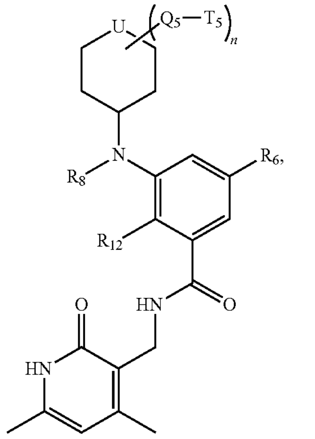

wherein n is 0, 1, or 2; U is O, S, N-$Q_5$-$T_5$, or CH-$Q_5$-$T_5$; and $R_{12}$ is Cl, Br, or methyl.

4. A pharmaceutical composition comprising a compound of claim 1, N-(5-(((4,6-dimethyl-2-oxo-1,2-dihydropyridin-3-yl)methyl)carbamoyl)-2-methylphenyl)furan-2-carboxamide, N,N'-(5-(((4,6-dimethyl-2-oxo-1,2-dihydropyridin-3-yl)methyl)carbamoyl)-1,3-phenylene)diacetamide, N-((4,6-dimethyl-2-oxo-1,2-dihydropyridin-3-yl)methyl)-3-pivalamidobenzamide, 3-(3,4-dihydro-2H-benzo[b][1,4]dioxepine-7-sulfonamido)-N-((4,6-dimethyl-2-oxo-1,2-dihydropyridin-3-yl)methyl)benzamide, N-((4,6-dimethyl-2-oxo-1,2-dihydropyridin-3-yl)methyl)-3,5-dimethoxybenzamide, N-((4,6-dimethyl-2-oxo-1,2-dihydropyridin-3-yl)methyl)-3,4,5-trimethoxybenzamide, 3-allyl-N-((4,6-dimethyl-2-oxo-1,2-dihydropyridin-3-yl)methyl)-4,5-dimethoxybenzamide, 4-(2-amino-2-oxoethoxy)-3-chloro-N-((4,6-dimethyl-2-oxo-1,2-dihydropyridin-3-yl)methyl)-5-methoxybenzamide, 3-chloro-N-((4,6-dimethyl-2-oxo-1,2-dihydropyridin-3-yl)methyl)-4-hydroxy-5-methoxybenzamide, or 3-bromo-N-((4,6-dimethyl-2-oxo-1,2-dihydropyridin-3-yl)methyl)-5-methoxy-4-propoxybenzamide, or a pharmaceutically acceptable salt thereof and a pharmaceutically acceptable carrier.

5. The compound of claim 1, wherein $R_1$ is H or $C_1$-$C_6$ alkyl optionally substituted one or more times with a substituent selected from hydroxyl, $C_1$-$C_6$ alkoxyl and $C_6$-$C_{10}$ aryl;

$R_7$ is -$Q_4$-$T_4$, in which $Q_4$ is a bond or a $C_1$-$C_4$ alkyl linker, and $T_4$ is $C_1$-$C_6$ alkyl, $C_3$-$C_8$ cycloalkyl, $C_6$-$C_{10}$ aryl, C(O)—$C_1$-$C_6$ alkyl, C(O)—$C_3$-$C_6$ cycloalkyl, dihydropyranyl, tetrahydropyranyl, tetrahydrothiopyranyl, piperidinyl, pyrrolidinyl, azetidinyl and oxetanyl, each optionally substituted with one or more substituents independently selected from oxo and -$Q_5$-$T_5$;

$R_8$ is H, $C_1$-$C_6$ alkyl, $C_1$-$C_6$ haloalkyl, $C_2$-$C_6$ alkenyl or $C_3$-$C_8$ cycloalkyl; and $R_{12}$ is halo, $C_1$-$C_6$ alkyl, $C_1$-$C_6$ haloalkyl or $C_1$-$C_6$ alkoxyl.

6. The compound of claim 1, wherein

Z is $NR_7R_8$ or $SR_7$;

$R_6$ is H, halo, cyano, $OR_a$, —C(O)$NR_aR_b$, —$S(O)_2R_a$, or $R_{S2}$; wherein $R_{S2}$ is $C_1$-$C_6$ alkyl, $C_2$-$C_6$ alkenyl, $C_2$-$C_6$ alkynyl, or 4 to 12-membered heterocycloalkyl, and wherein each of $R_a$ and $R_b$, independently is H or $C_1$-$C_6$ alkyl; or $R_a$ and $R_b$, together with the N atom to which they are attached, form a 4 to 12-membered heterocycloalkyl ring having 0 or 1 additional heteroatom; and each of $R_{S2}$ and the 4 to 12-membered heterocycloalkyl ring formed by $R_a$ and $R_b$, is optionally substituted with one or more -$Q_2$-$T_2$; wherein $Q_2$ is a bond or $C_1$-$C_3$ alkyl linker, and $T_2$ is H, halo, —$OR_c$, —$NR_cR_d$, —C(O)O$C_1$-$C_6$ alkyl, or $C_1$-$C_6$ alkyl, in which each of $R_c$ and $R_d$, independently is H or $C_1$-$C_6$ alkyl, or $R_c$ and $R_d$, together with the N atom to which they are attached, form a 4 to 12-membered heterocycloalkyl ring having 0 or 1 additional heteroatom and 0 or 1 $C_1$-$C_6$ alkyl substituents;

$R_7$ is $C_1$-$C_6$ alkyl, $C_3$-$C_8$ cycloalkyl, dihydropyranyl, tetrahydropyranyl, tetrahydrothiopyranyl, piperidinyl, pyrrolidinyl, azetidinyl and oxetanyl, each optionally substituted with one or more substituents independently selected from oxo and -$Q_5$-$T_5$; and $R_{12}$ is halo or $C_1$-$C_6$ alkyl.

7. The compound of claim 1, wherein $R_2$, $R_4$ and $R_{12}$ are each independently $C_1$-$C_6$ alkyl and $R_5$ is H.

8. The compound of claim 1, wherein $R_7$ is cyclohexyl, dihydropyranyl, tetrahydropyranyl, tetrahydrothiopyranyl, piperidinyl, pyrrolidinyl, azetidinyl oxetanyl, 1,4-dioxaspiro[4.5]decan-8-yl, 1-oxaspiro[4.5]decan-8-yl, 3'H-spiro[cyclohexane-1,1'-isobenzofuran]-4-yl, 7'H-spiro[cyclohexane-1,5'-furo[3,4-b]pyridin]-4-yl, 3'H-spiro[cyclohexane-1,1'-furo[3,4-c]pyridin]-4-yl, or 1-azaspiro[4.5]decan-8-yl, each substituted with one or more -$Q_5$-$T_5$.

9. The compound of claim 1, wherein Z is selected from the group consisting of piperidinyl, morpholinyl, piperazinyl, azetidinyl, pyrrolidinyl, 2-oxa-5-azabicyclo[2.2.1]heptan-5-yl, and 1,4-dioxa-8-azaspiro[4.5]decan-8-yl, each optionally substituted with one -$Q_6$-$T_6$.

10. The compound of claim 1, wherein (i) $R_6$ is halo and Z is $SR_7$, in which $R_7$ is $C_1$-$C_6$ alkyl, $C_3$-$C_8$ cycloalkyl or 4 to 7-membered heterocycloalkyl and $R_7$ is optionally substituted with one or more -$Q_5$-$T_5$; or (ii) $R_6$ is —$S(O)_bR_a$ or azido, in which b is 0, 1, or 2 and $R_a$ is $C_1$-$C_6$ alkyl; and Z is $NR_7R_8$, in which $R_7$ is $C_3$-$C_8$ cycloalkyl or 4 to 14-membered heterocycloalkyl, each optionally substituted with one or more -$Q_5$-$T_5$; and $R_8$ is H or $C_1$-$C_6$ alkyl.

11. The compound of claim 1, wherein (i) $Q_5$ is a bond and $T_5$ is H, $C_1$-$C_6$ alkyl, $C_3$-$C_8$ cycloalkyl, 4 to 12-membered heterocycloalkyl, 5- or 6-membered heteroaryl, amino, mono-$C_1$-$C_6$ alkylamino, or di-$C_1$-$C_6$ alkylamino, $T_5$ being optionally substituted with one or more substituents selected from the group consisting of halo, hydroxyl, $C_1$-$C_6$ alkoxyl, or $C_3$-$C_8$ cycloalkyl; (ii) $Q_5$ is CO, $S(O)_2$, or NHC(O); and $T_5$ is $C_1$-$C_6$ alkyl, $C_1$-$C_6$ alkoxyl, $C_3$-$C_8$ cycloalkyl, or 4 to 12-membered heterocycloalkyl; or (iii) $Q_5$ is $C_1$-$C_3$ alkyl linker and $T_5$ is H, $C_6$-$C_{10}$ aryl, $C_3$-$C_8$ cycloalkyl, 4 to 12-membered heterocycloalkyl, or $S(O)_qR_q$.

12. The compound of claim 1, wherein one or more -$Q_5$-$T_5$ are oxo.

13. The compound of claim 3, wherein U is CH-$Q_5$-$T_5$ and n is 0.

14. The compound of claim 1, wherein (i) one or more -$Q_6$-$T_6$ are oxo; or (ii) $Q_6$ is a bond or C(O) and $T_6$ is $C_1$-$C_6$ alkyl or $C_1$-$C_6$ alkoxy.

15. The compound of claim 1, wherein $R_6$ is halo or $R_6$ is $C_2$-$C_6$ alkynyl optionally substituted with one or more -$Q_2$-$T_2$.

16. The compound of claim 15, wherein $R_{12}$ is $C_1$-$C_6$ alkyl or halo.

17. The compound of claim 15, wherein -Q-$T_2$ is 4 to 12-membered heterocycloalkyl optionally substituted with one or more -$Q_3$-$T_3$.

18. The compound of claim 1, wherein one Z is $NR_7R_8$ in which $R_8$ is H and $R_7$ is $C_1$-$C_6$ alkyl optionally substituted with $C_1$-$C_6$ alkoxyl.

19. A compound selected from

| Compound Number | Structure |
|---|---|
| 1 | 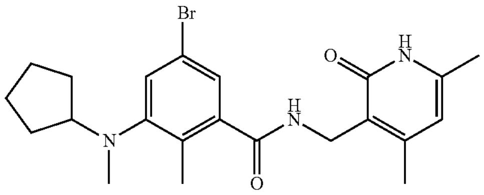 [SMILES: Cc1cc(C)c(CNC(=O)c2cc(Br)cc(N(C)C3CCCC3)c2C)c(=O)[nH]1] |
| 2 | 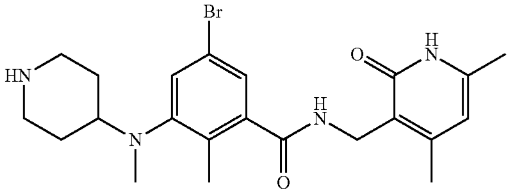 [SMILES: Cc1cc(C)c(CNC(=O)c2cc(Br)cc(N(C)C3CCNCC3)c2C)c(=O)[nH]1] |
| 3 | 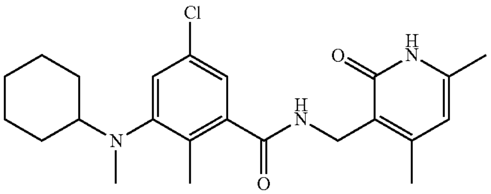 [SMILES: Cc1cc(C)c(CNC(=O)c2cc(Cl)cc(N(C)C3CCCCC3)c2C)c(=O)[nH]1] |

-continued
| Compound Number | Structure |
|---|---|
| 4 | 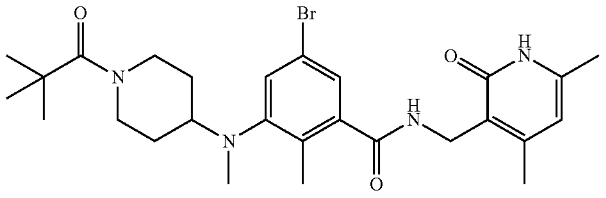 [SMILES: Cc1cc(C)c(CNC(=O)c2cc(Br)cc(N(C)C3CCN(C(=O)C(C)(C)C)CC3)c2C)c(=O)[nH]1] |
| 5 | 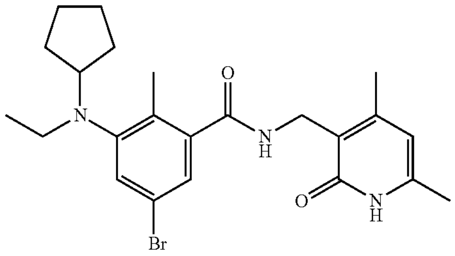 [SMILES: CCN(c1cc(Br)cc(C(=O)NCc2c(C)cc(C)[nH]c2=O)c1C)C1CCCC1] |
| 6 | 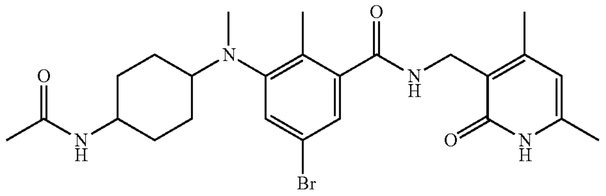 |
| 7 | 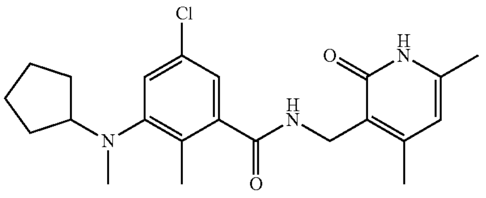 [SMILES: Cc1cc(C)c(CNC(=O)c2cc(Cl)cc(N(C)C3CCCC3)c2C)c(=O)[nH]1] |
| 8 | 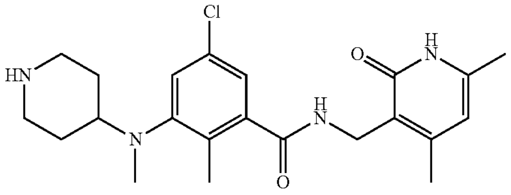 [SMILES: Cc1cc(C)c(CNC(=O)c2cc(Cl)cc(N(C)C3CCNCC3)c2C)c(=O)[nH]1] |
| 9 | 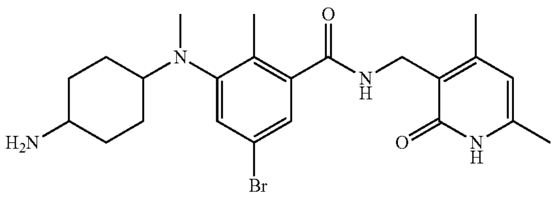 [SMILES: Cc1cc(C)c(CNC(=O)c2cc(Br)cc(N(C)C3CCC(N)CC3)c2C)c(=O)[nH]1] |
| 10 | 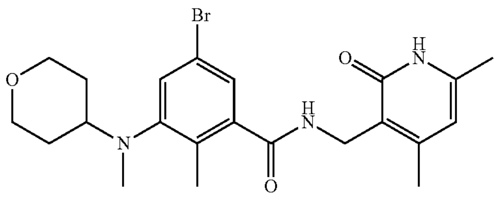 |

-continued
| Compound Number | Structure |
| --- | --- |
| 11 | 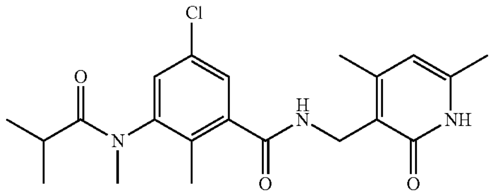 [SMILES: Cc1cc(C)c(CNC(=O)c2cc(Cl)cc(N(C)C(=O)C(C)C)c2C)c(=O)[nH]1] |
| 12 | 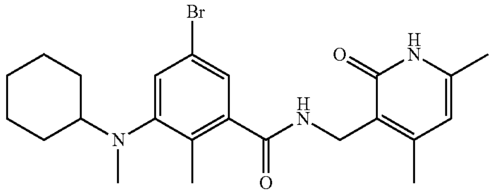 [SMILES: Cc1cc(C)c(CNC(=O)c2cc(Br)cc(N(C)C3CCCCC3)c2C)c(=O)[nH]1] |
| 13 | 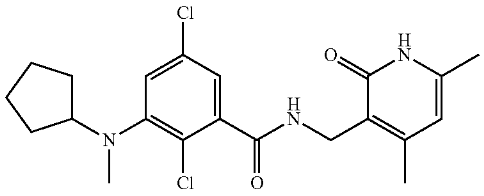 [SMILES: Cc1cc(C)c(CNC(=O)c2cc(Cl)cc(N(C)C3CCCC3)c2Cl)c(=O)[nH]1] |
| 14 | 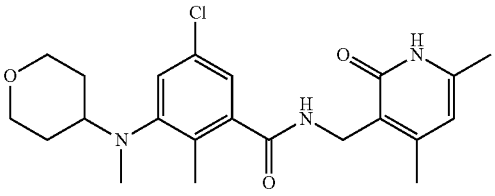 |
| 15 | 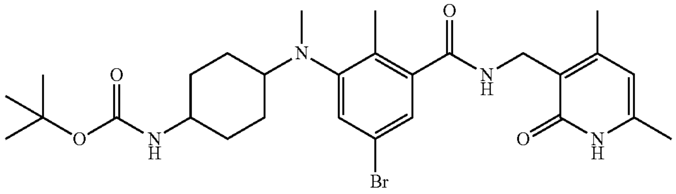 [SMILES: Cc1cc(C)c(CNC(=O)c2cc(Br)cc(N(C)C3CCC(NC(=O)OC(C)(C)C)CC3)c2C)c(=O)[nH]1] |
| 16 | 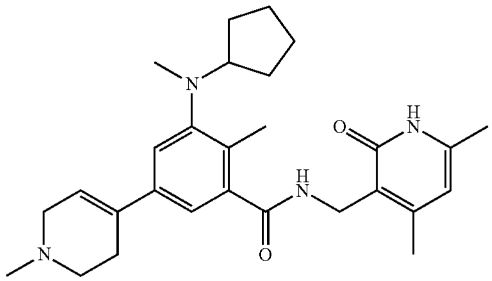 |
| 17 | 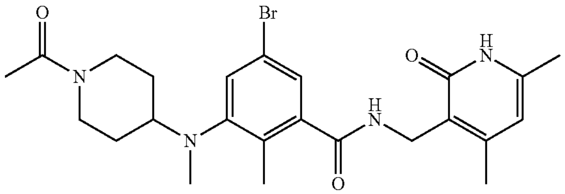 [SMILES: CC(=O)N1CCC(N(C)c2cc(Br)cc(C(=O)NCc3c(C)cc(C)[nH]c3=O)c2C)CC1] |

-continued
| Compound Number | Structure |
|---|---|
| 18 | 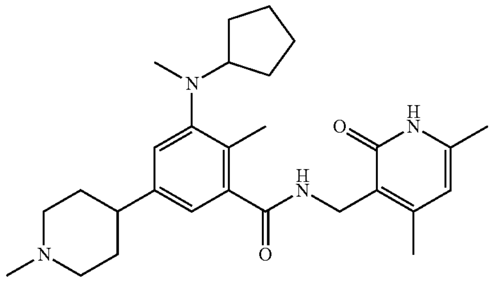 |
| 19 | 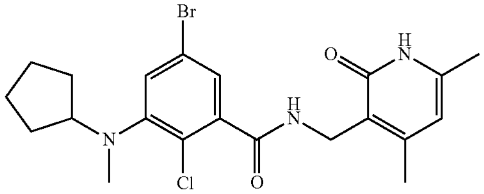 [SMILES: Cc1cc(C)c(CNC(=O)c2cc(Br)cc(N(C)C3CCCC3)c2Cl)c(=O)[nH]1] |
| 20 | 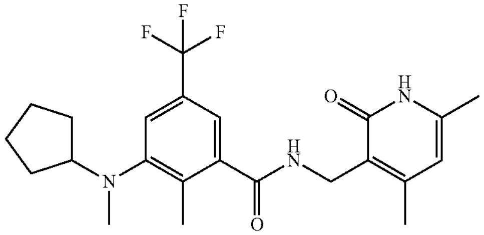 [SMILES: Cc1cc(C)c(CNC(=O)c2cc(C(F)(F)F)cc(N(C)C3CCCC3)c2C)c(=O)[nH]1] |
| 21 | 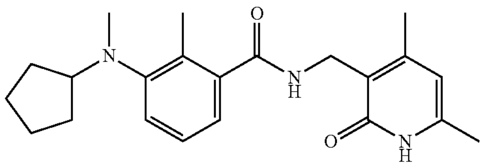 [SMILES: Cc1cc(C)c(CNC(=O)c2cccc(N(C)C3CCCC3)c2C)c(=O)[nH]1] |
| 22 | 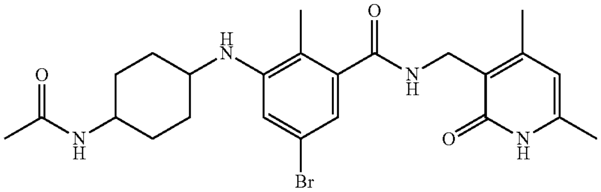 [SMILES: CC(=O)NC1CCC(Nc2cc(Br)cc(C(=O)NCc3c(C)cc(C)[nH]c3=O)c2C)CC1] |
| 23 | 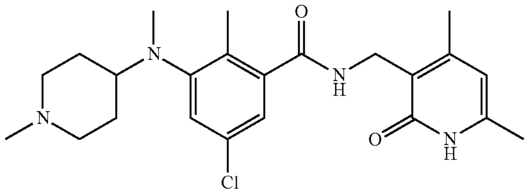 |
| 24 | 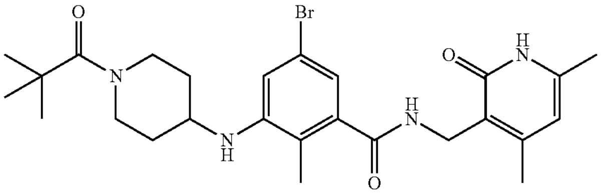 |

-continued
| Compound Number | Structure |
|---|---|
| 25 | 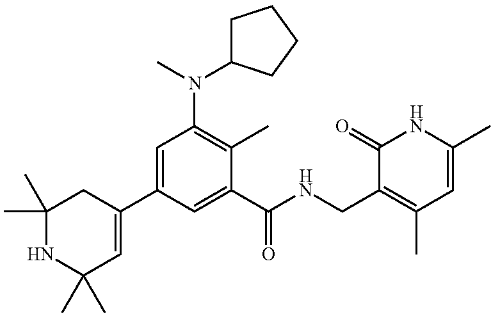 |
| 26 | 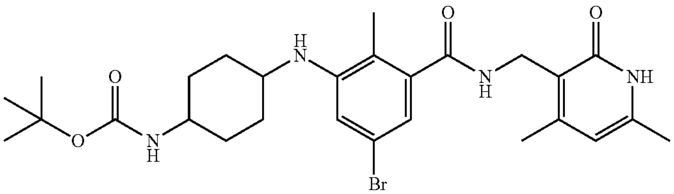 [SMILES: Cc1cc(C)c(CNC(=O)c2cc(Br)cc(NC3CCC(NC(=O)OC(C)(C)C)CC3)c2C)c(=O)[nH]1] |
| 27 | 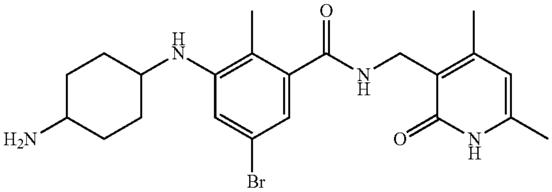 [SMILES: Cc1cc(C)c(CNC(=O)c2cc(Br)cc(NC3CCC(N)CC3)c2C)c(=O)[nH]1] |
| 28 | 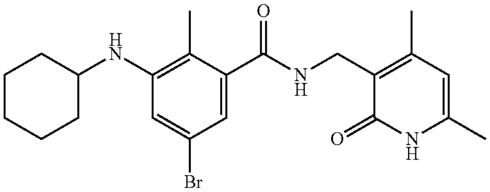 [SMILES: Cc1cc(C)c(CNC(=O)c2cc(Br)cc(NC3CCCCC3)c2C)c(=O)[nH]1] |
| 29 | 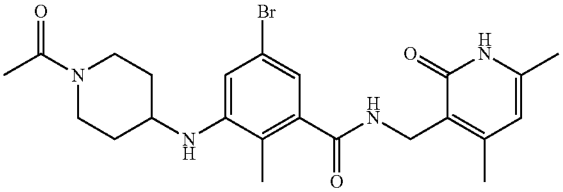 |
| 30 | 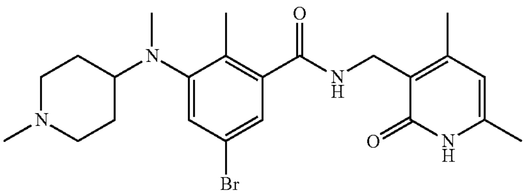 |
| 31 | 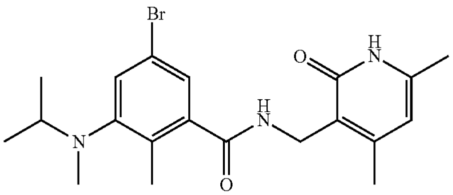 |

-continued
| Compound Number | Structure |
|---|---|
| 32 | 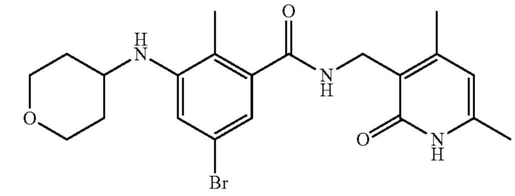 [SMILES: Cc1cc(C)c(CNC(=O)c2cc(Br)cc(NC3CCOCC3)c2C)c(=O)[nH]1] |
| 33 | 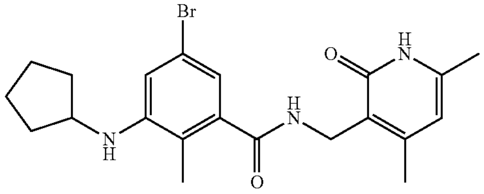 |
| 34 | 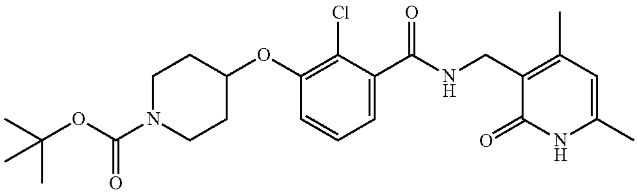 [SMILES: Cc1cc(C)c(CNC(=O)c2cccc(OC3CCN(C(=O)OC(C)(C)C)CC3)c2Cl)c(=O)[nH]1] |
| 35 | 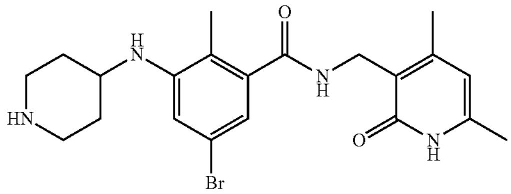 [SMILES: Cc1cc(C)c(CNC(=O)c2cc(Br)cc(NC3CCNCC3)c2C)c(=O)[nH]1] |
| 36 | 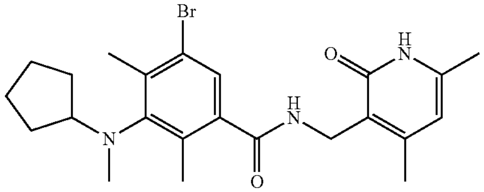 [SMILES: Cc1cc(C)c(CNC(=O)c2cc(Br)c(C)c(N(C)C3CCCC3)c2C)c(=O)[nH]1] |
| 37 | 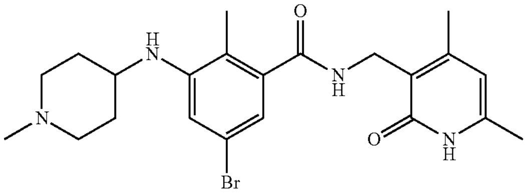 |
| 38 | 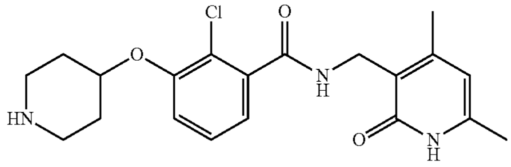 [SMILES: Cc1cc(C)c(CNC(=O)c2cccc(OC3CCNCC3)c2Cl)c(=O)[nH]1] |

-continued
| Compound Number | Structure |
|---|---|
| 39 | 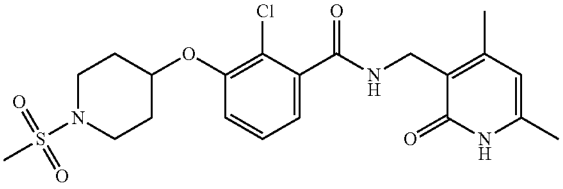 |
| 40 | 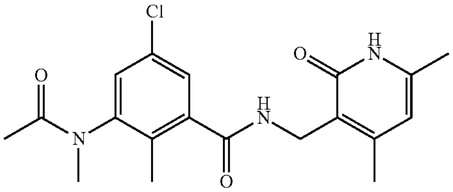 [SMILES: CC(=O)N(C)c1cc(Cl)cc(C(=O)NCc2c(C)cc(C)[nH]c2=O)c1C] |
| 41 | 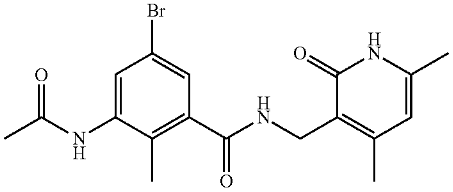 |
| 42 | 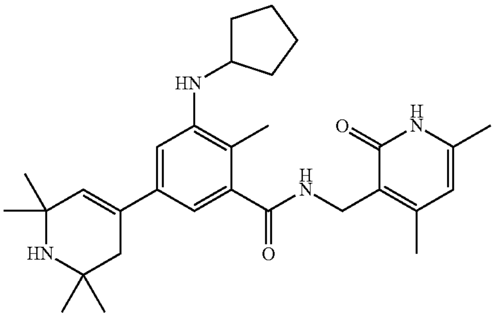 |
| 43 | 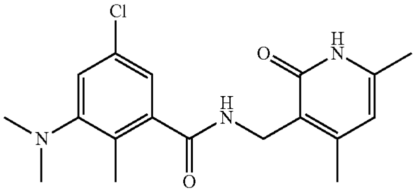 |
| 44 | 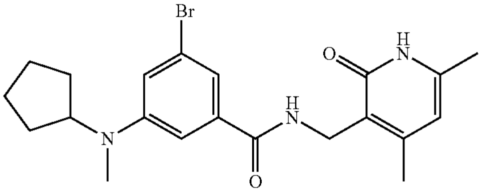 [SMILES: Cc1cc(C)c(CNC(=O)c2cc(Br)cc(N(C)C3CCCC3)c2)c(=O)[nH]1] |

-continued
| Compound Number | Structure |
|---|---|
| 45 | 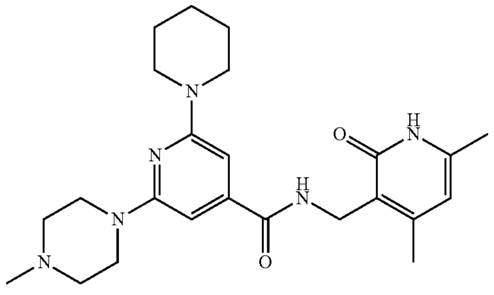 |
| 46 | 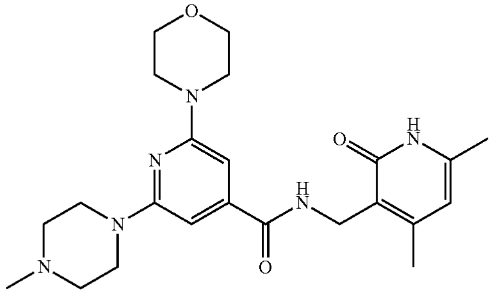 |
| 47 | 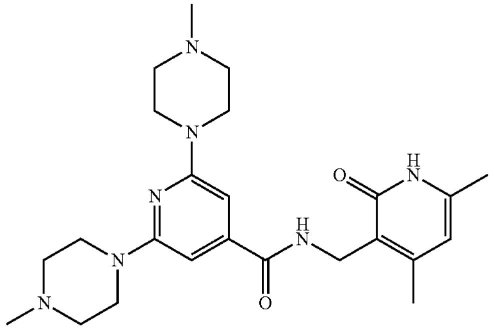 |
| 48 | 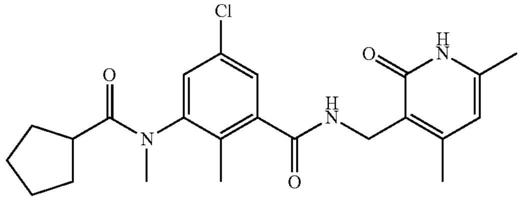 [SMILES: Cc1cc(C)c(CNC(=O)c2cc(Cl)cc(N(C)C(=O)C3CCCC3)c2C)c(=O)[nH]1] |
| 49 | 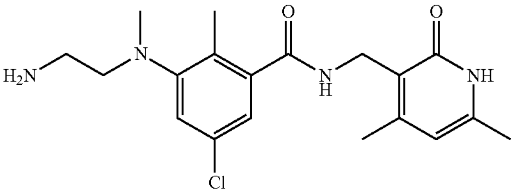 [SMILES: Cc1cc(C)c(CNC(=O)c2cc(Cl)cc(N(C)CCN)c2C)c(=O)[nH]1] |
| 50 | 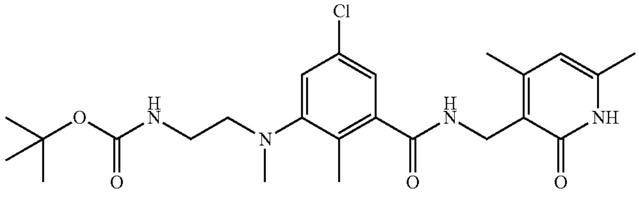 [SMILES: Cc1cc(C)c(CNC(=O)c2cc(Cl)cc(N(C)CCNC(=O)OC(C)(C)C)c2C)c(=O)[nH]1] |

-continued
| Compound Number | Structure |
|---|---|
| 51 | 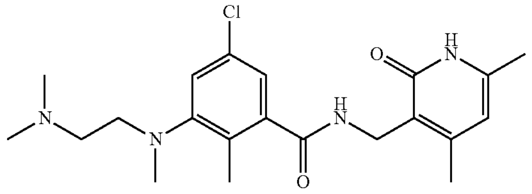 |
| 52 | 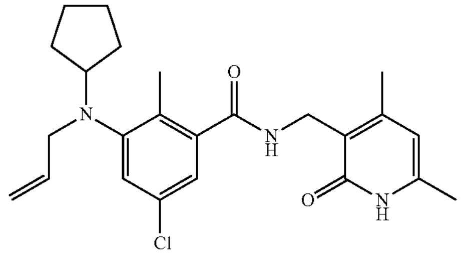 [SMILES: C=CCN(c1cc(Cl)cc(C(=O)NCc2c(C)cc(C)[nH]c2=O)c1C)C1CCCC1] |
| 53 | 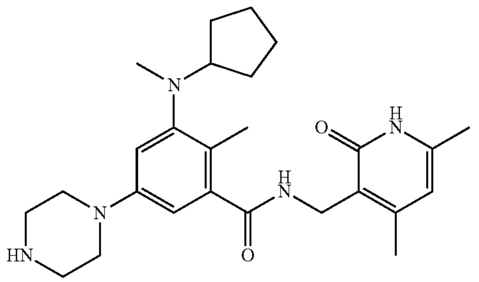 [SMILES: Cc1cc(C)c(CNC(=O)c2cc(N3CCNCC3)cc(N(C)C3CCCC3)c2C)c(=O)[nH]1] |
| 54 | 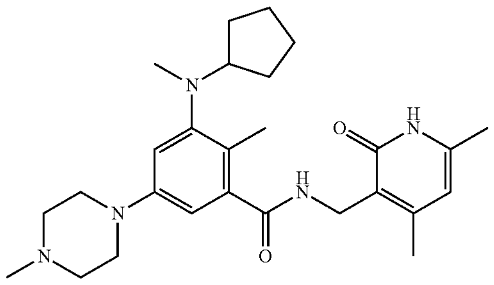 |
| 55 | 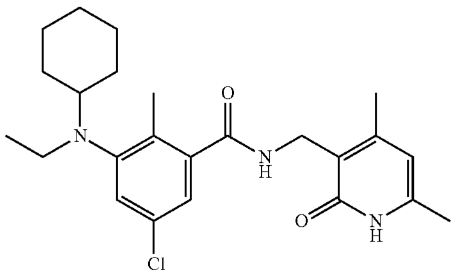 [SMILES: CCN(c1cc(Cl)cc(C(=O)NCc2c(C)cc(C)[nH]c2=O)c1C)C1CCCCC1] |

-continued
| Compound Number | Structure |
|---|---|
| 56 | 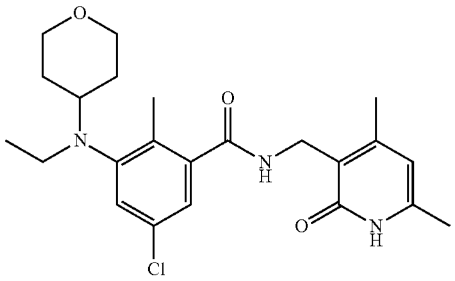 [SMILES: CCN(c1cc(Cl)cc(C(=O)NCc2c(C)cc(C)[nH]c2=O)c1C)C1CCOCC1] |
| 57 | 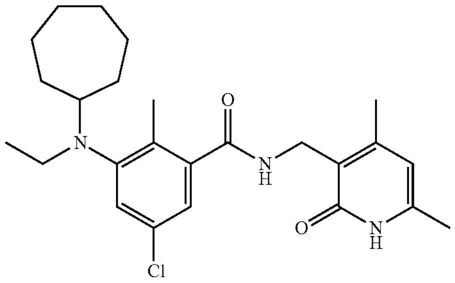 [SMILES: CCN(c1cc(Cl)cc(C(=O)NCc2c(C)cc(C)[nH]c2=O)c1C)C1CCCCCC1] |
| 58 | 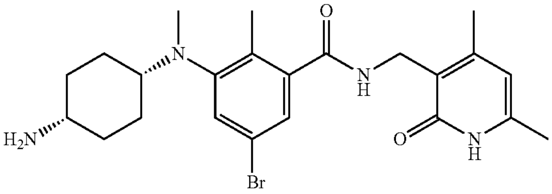 [SMILES: Cc1cc(C)c(CNC(=O)c2cc(Br)cc(N(C)[C@H]3CC[C@@H](N)CC3)c2C)c(=O)[nH]1] |
| 59 | 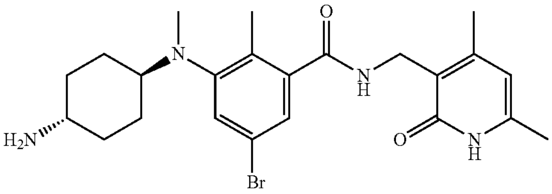 [SMILES: Cc1cc(C)c(CNC(=O)c2cc(Br)cc(N(C)[C@H]3CC[C@H](N)CC3)c2C)c(=O)[nH]1] |
| 60 | 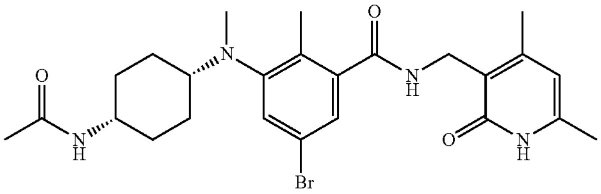 [SMILES: CC(=O)N[C@H]1CC[C@@H](N(C)c2cc(Br)cc(C(=O)NCc3c(C)cc(C)[nH]c3=O)c2C)CC1] |
| 61 | 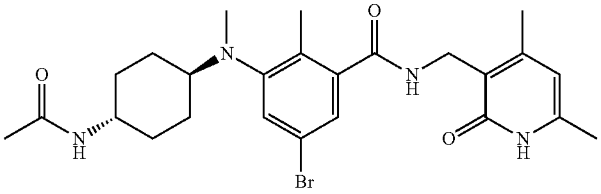 [SMILES: CC(=O)N[C@H]1CC[C@H](N(C)c2cc(Br)cc(C(=O)NCc3c(C)cc(C)[nH]c3=O)c2C)CC1] |
| 62 | 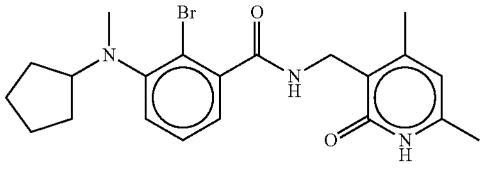 |

-continued
| Compound Number | Structure |
|---|---|
| 63 | 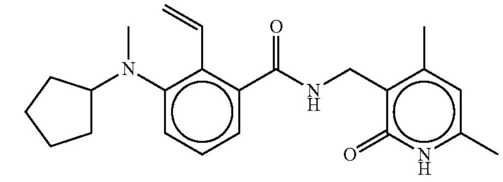 |
| 64 | 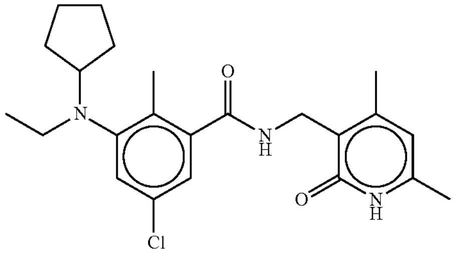 |
| 65 | 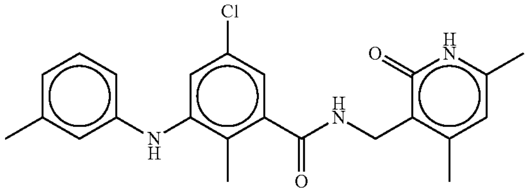 |
| 66 | 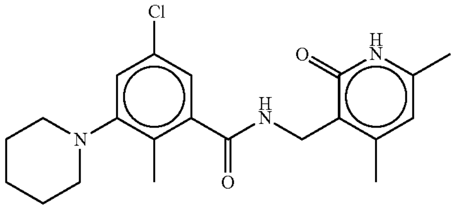 |
| 67 | 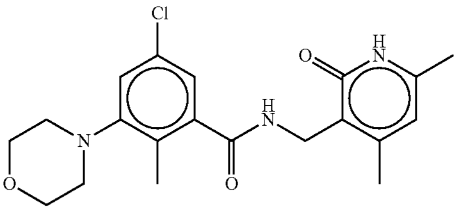 |
| 68 | 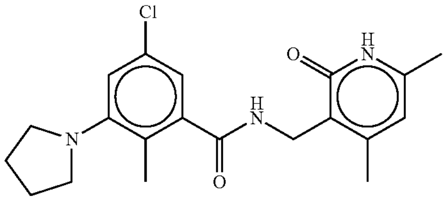 |
| 69 | 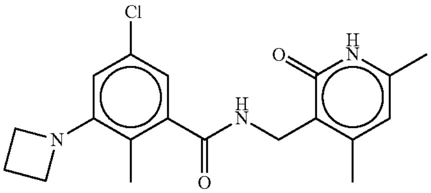 |

-continued
| Compound Number | Structure |
|---|---|
| 70 | 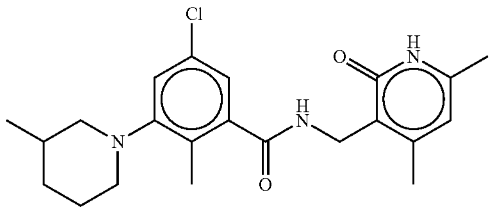 |
| 71 | 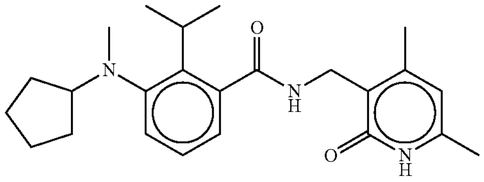 |
| 72 | 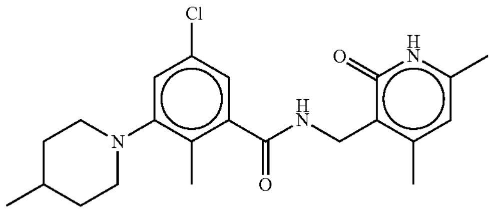 |
| 73 | 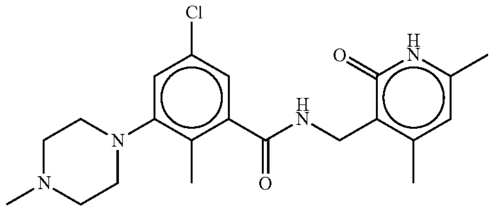 |
| 74 | 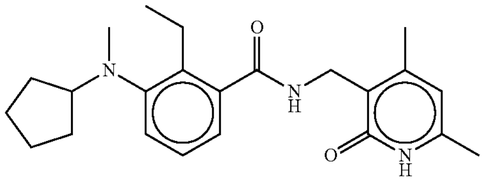 |
| 75 | 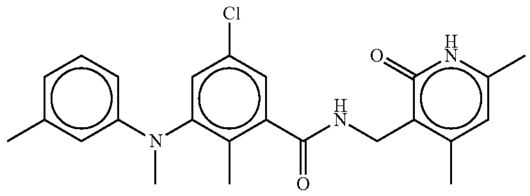 |
| 76 | 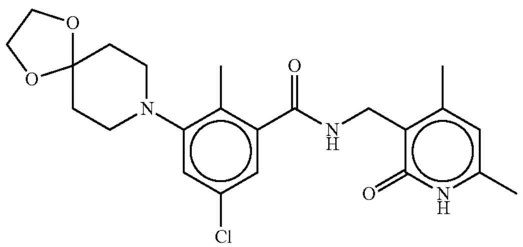 |

-continued
| Compound Number | Structure |
|---|---|
| 77 | 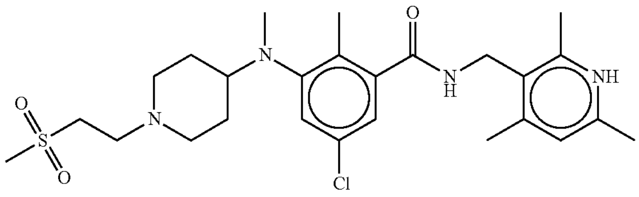 |
| 78 | 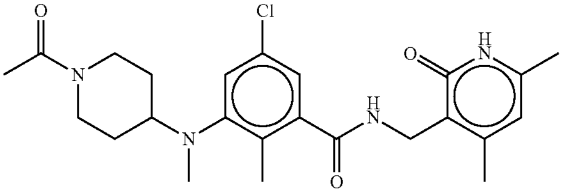 |
| 79 | 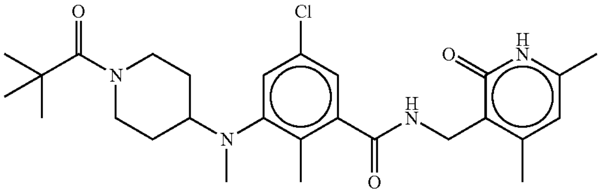 |
| 80 | 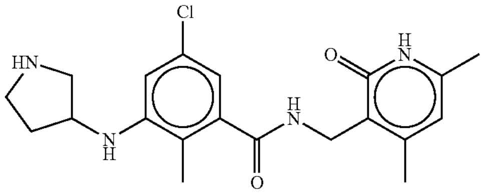 |
| 81 | |
| 82 | 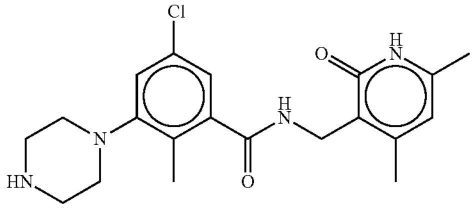 |
| 83 | 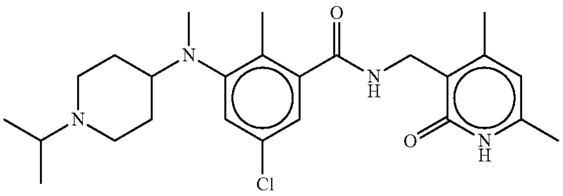 |
| 84 | 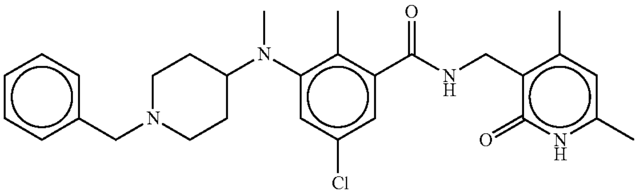 |

-continued
| Compound Number | Structure |
|---|---|
| 85 | 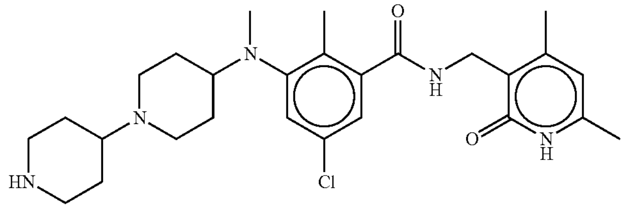 |
| 86 | 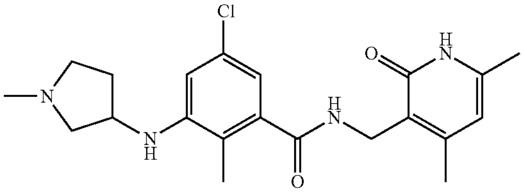 |
| 87 | 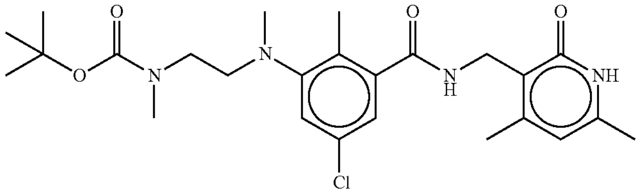 |
| 88 | 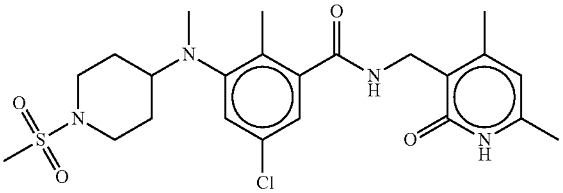 |
| 89 | 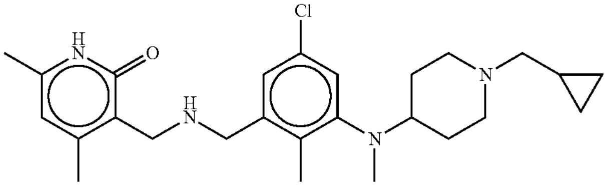 |
| 90 | 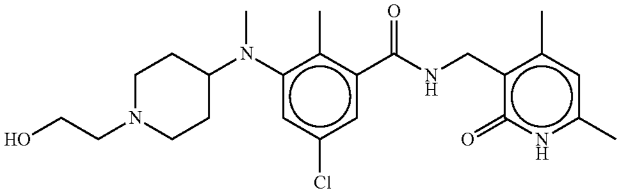 |
| 91 | 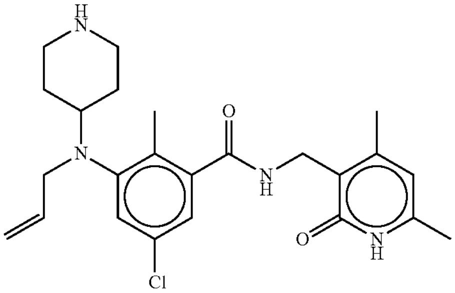 |

-continued
| Compound Number | Structure |
| --- | --- |
| 92 | 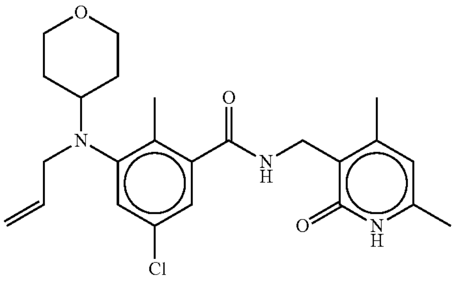 |
| 93 | 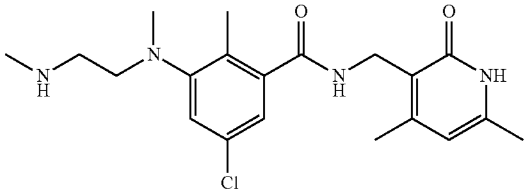 |
| 94 | 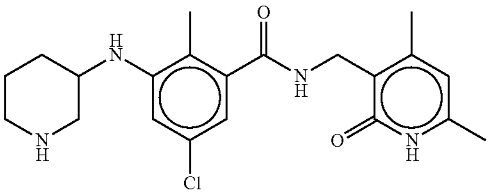 |
| 95 | 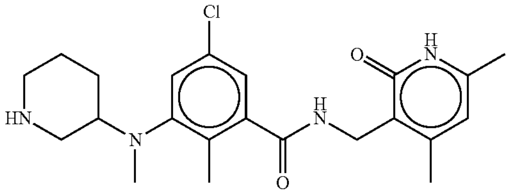 |
| 96 | 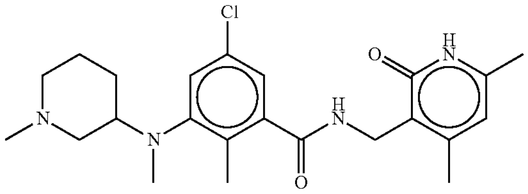 |
| 97 | 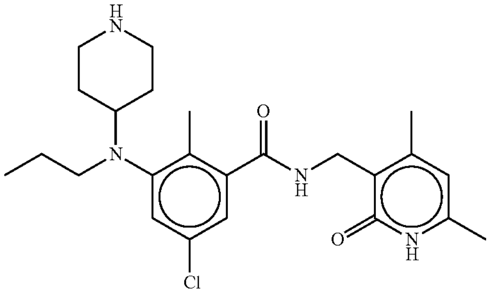 |

-continued
| Compound Number | Structure |
|---|---|
| 98 | 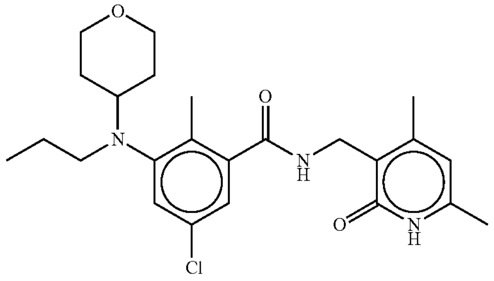 |
| 99 | 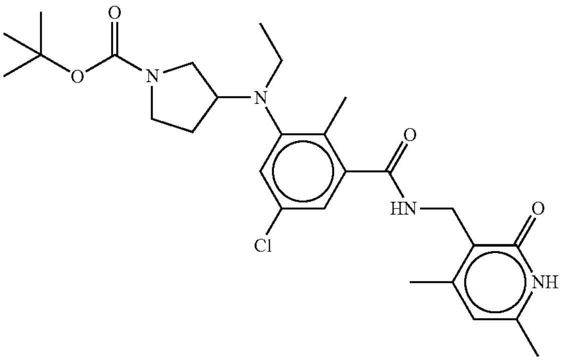 |
| 100 | 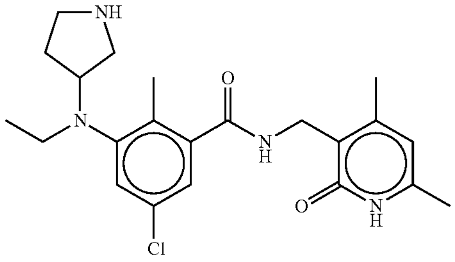 |
| 101 | 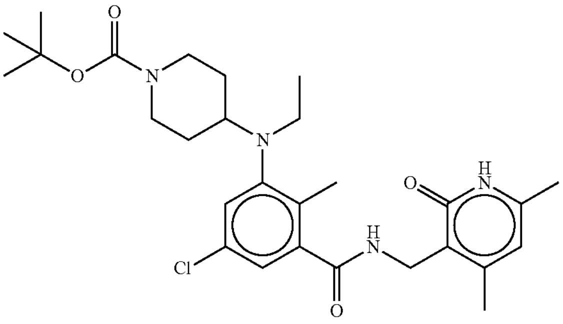 |
| 102 | 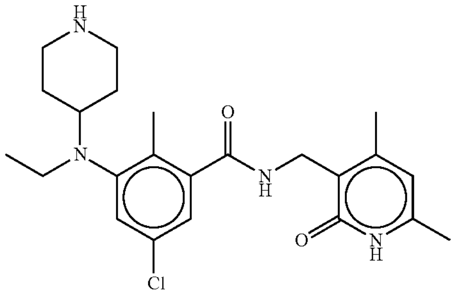 |

-continued
| Compound Number | Structure |
|---|---|
| 103 | 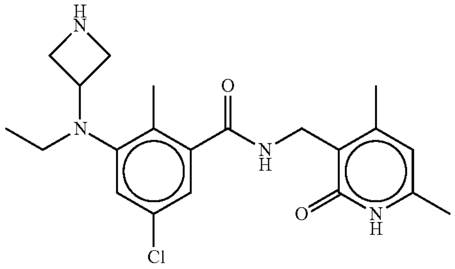 |
| 104 | 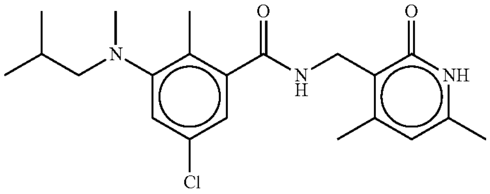 |
| 105 | 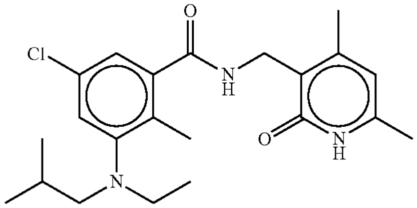 |
| 106 | 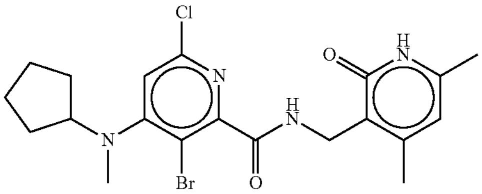 |
| 107 | 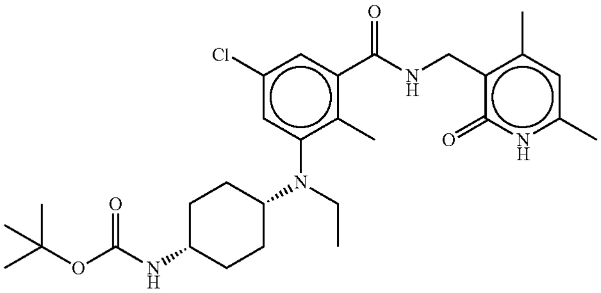 |
| 108 | 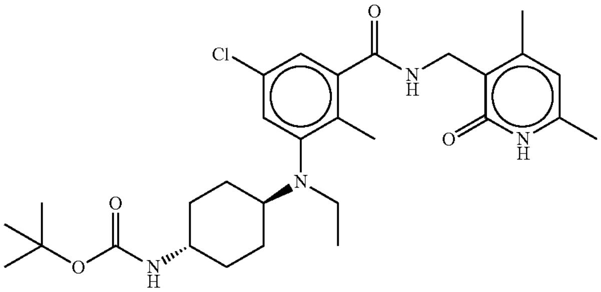 |

-continued
| Compound Number | Structure |
| --- | --- |
| 109 | 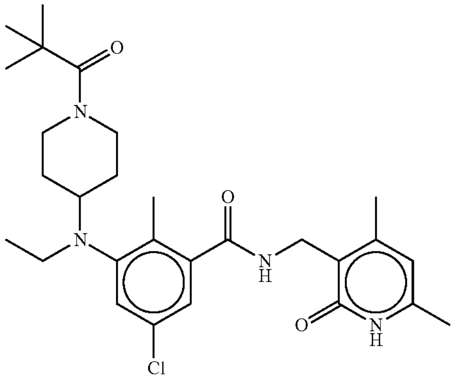 |
| 110 | 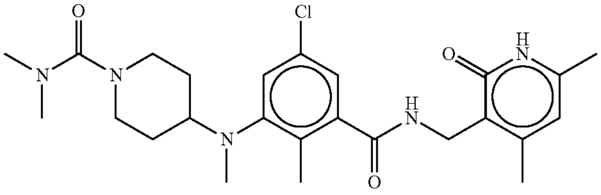 |
| 111 | 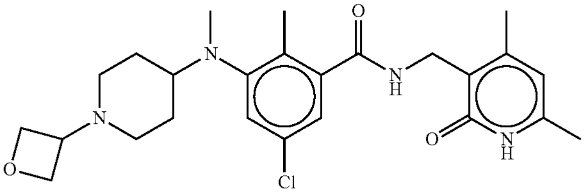 |
| 112 | 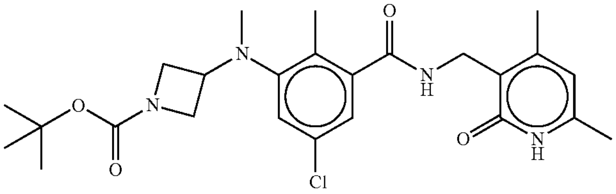 |
| 113 | 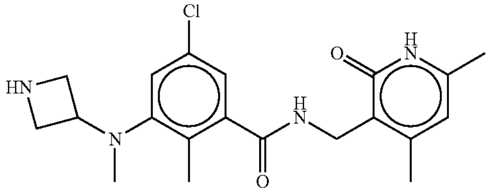 |
| 114 | 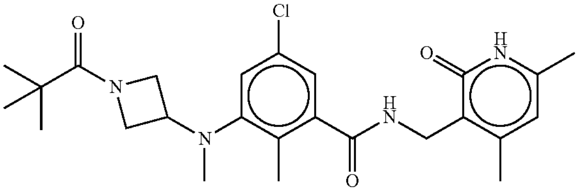 |

-continued
| Compound Number | Structure |
|---|---|
| 115 | 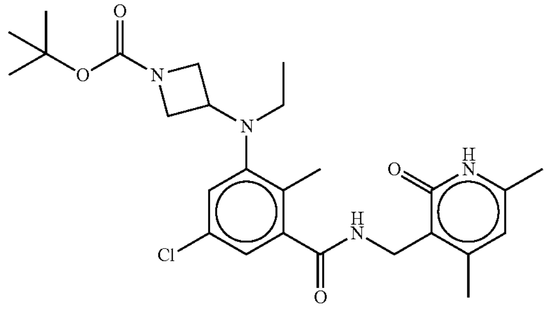 |
| 116 | 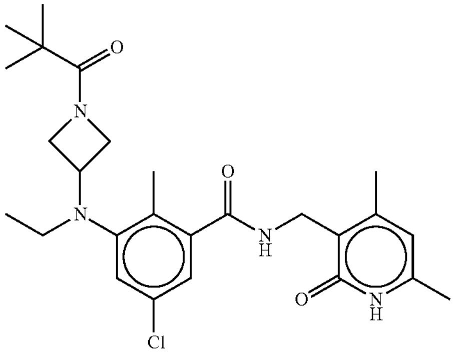 |
| 117 | 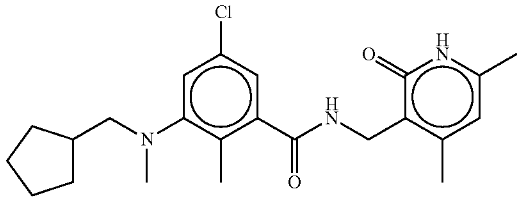 |
| 118 | 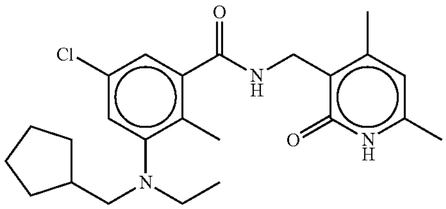 |
| 119 | 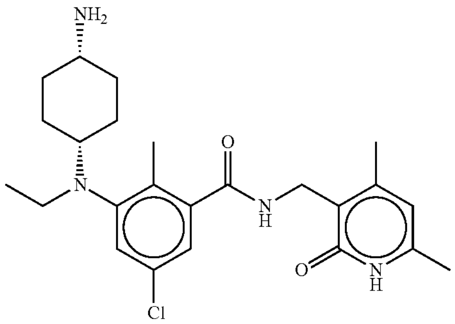 |

-continued
| Compound Number | Structure |
| --- | --- |
| 120 | 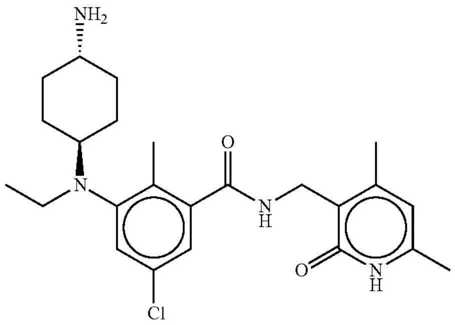 |
| 121 | 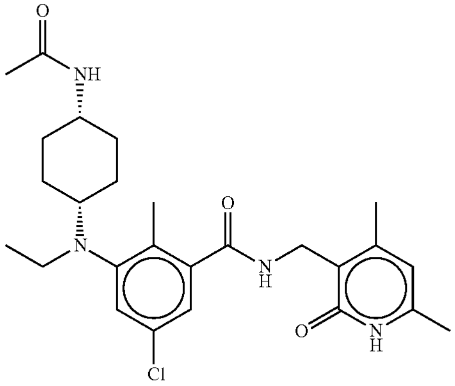 |
| 122 | 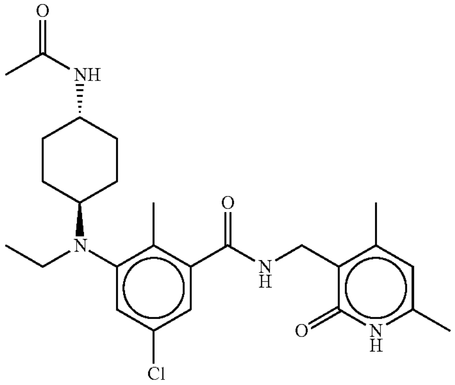 |
| 123 | 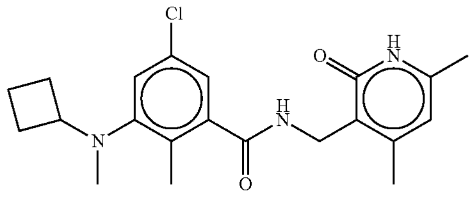 |
| 124 | 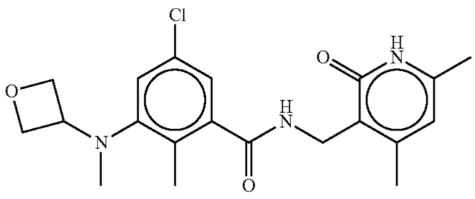 |

-continued
| Compound Number | Structure |
|---|---|
| 125 | 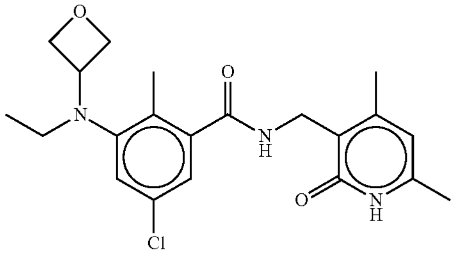 |
| 126 | 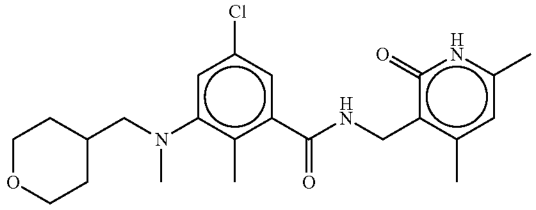 |
| 127 | 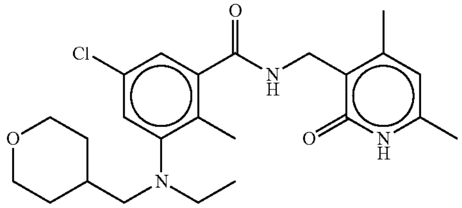 |
| 128 | 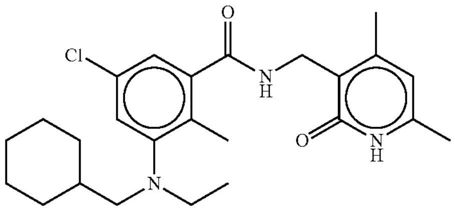 |
| 129 | 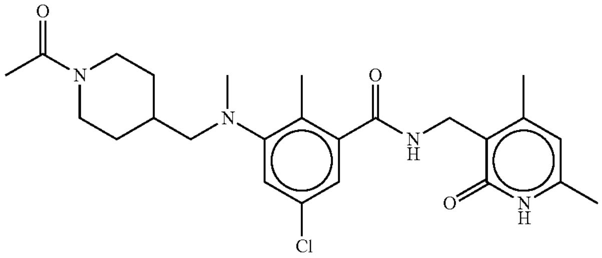 |
| 130 | 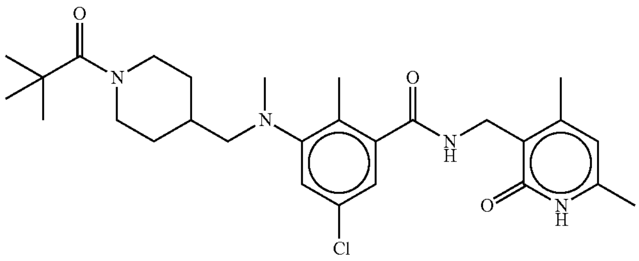 |

-continued
| Compound Number | Structure |
|---|---|
| 131 | 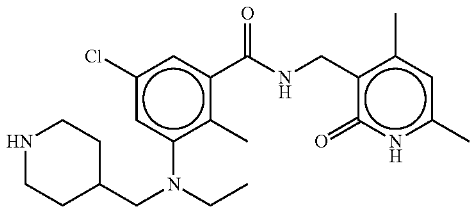 |
| 132 | 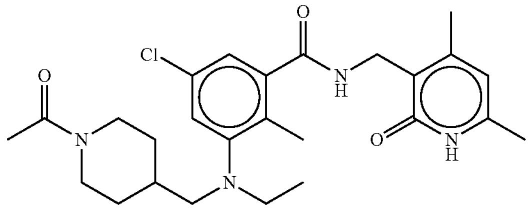 |
| 133 | 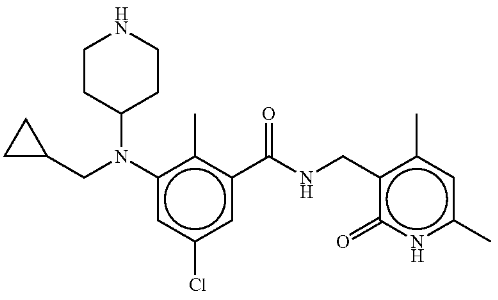 |
| 134 | 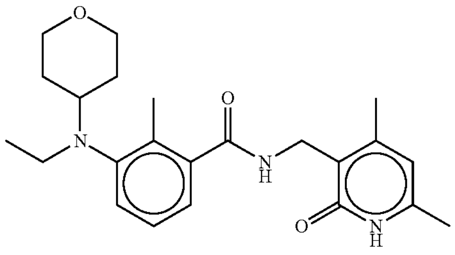 |
| 135 | 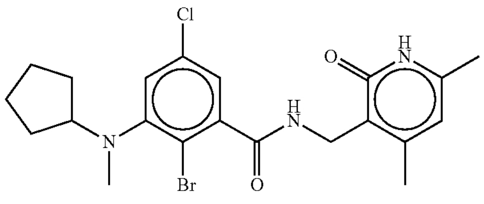 |
| 136 | 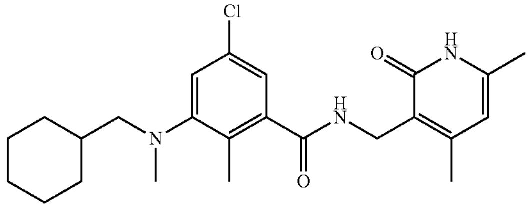 [SMILES: Cc1cc(C)c(CNC(=O)c2cc(Cl)cc(N(C)CC3CCCCC3)c2C)c(=O)[nH]1] |

-continued
| Compound Number | Structure |
|---|---|
| 137 | 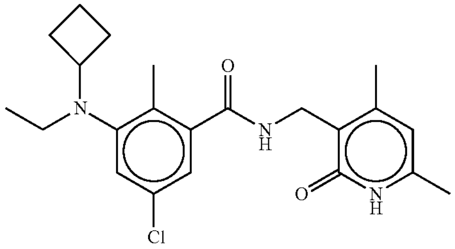 |
| 138 | 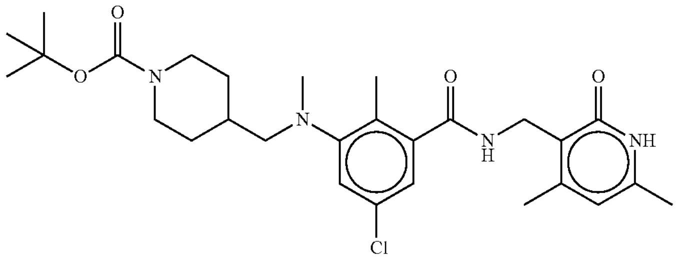 |
| 139 | 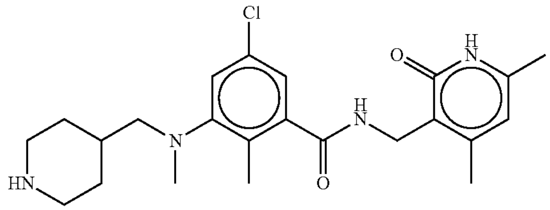 |
| 140 | 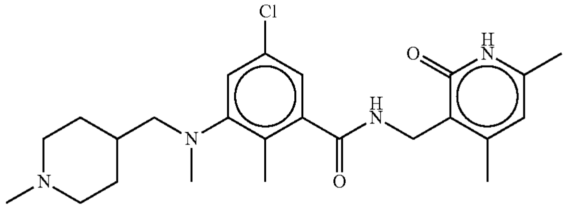 |
| 141 | 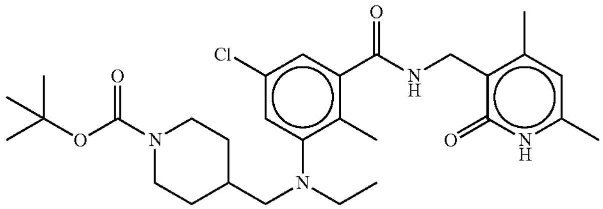 |
| 142 | 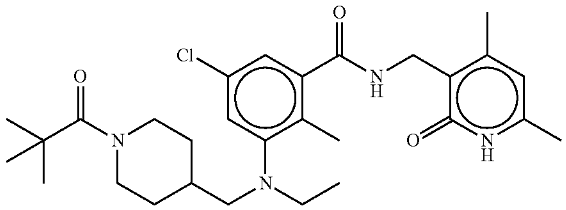 |

-continued
| Compound Number | Structure |
|---|---|
| 143 | 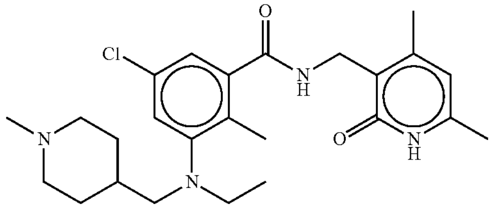 |
| 144 | 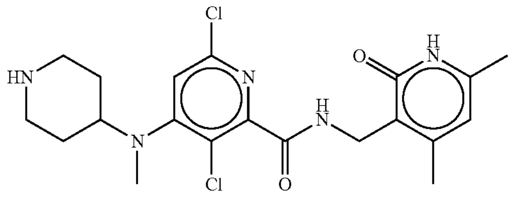 |
| 145 | 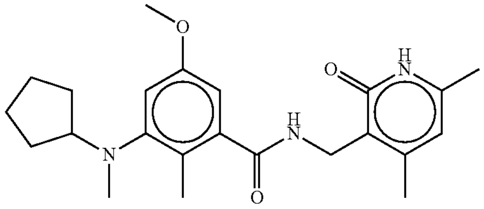 |
| 146 | 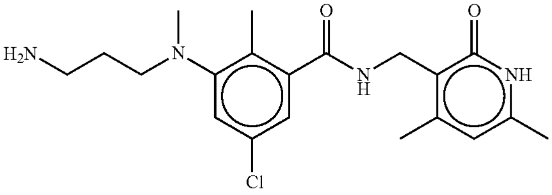 |
| 147 | 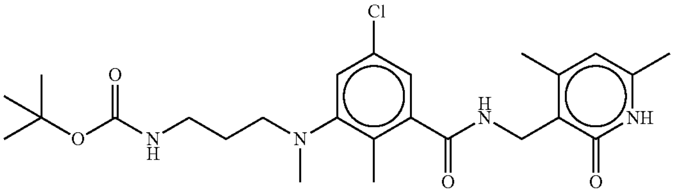 |
| 148 | 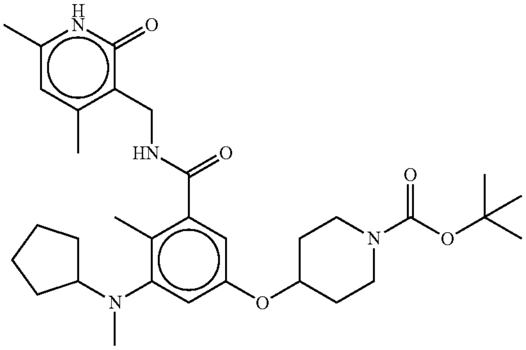 |

-continued
| Compound Number | Structure |
|---|---|
| 149 | 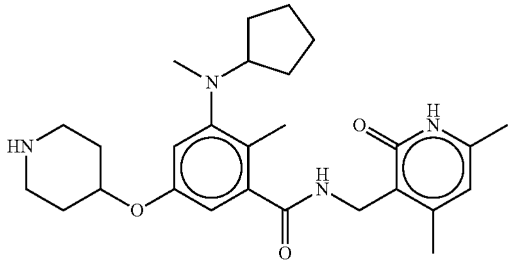 |
| 150 | 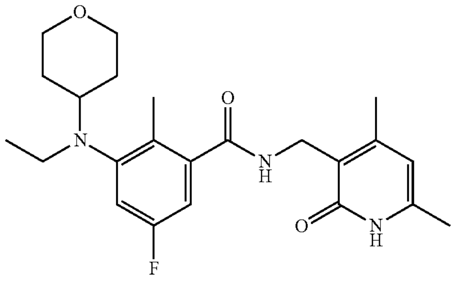 [SMILES: CCN(c1cc(F)cc(C(=O)NCc2c(C)cc(C)[nH]c2=O)c1C)C1CCOCC1] |
| 151 | 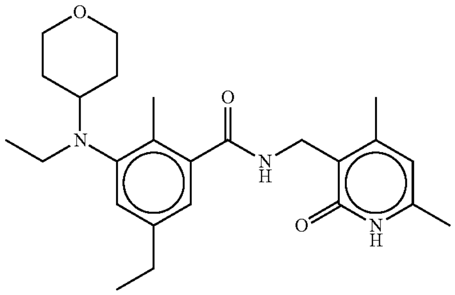 |
| 152 | 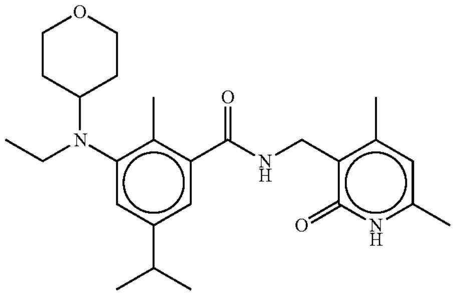 |
| 153 | 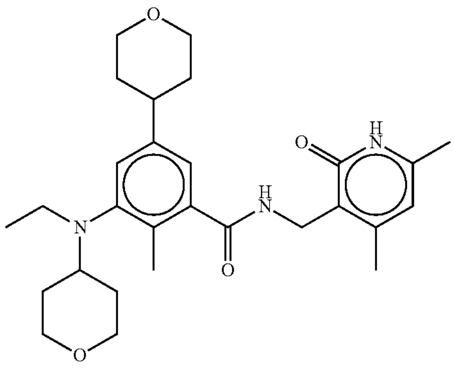 |

-continued
| Compound Number | Structure |
|---|---|
| 154 | 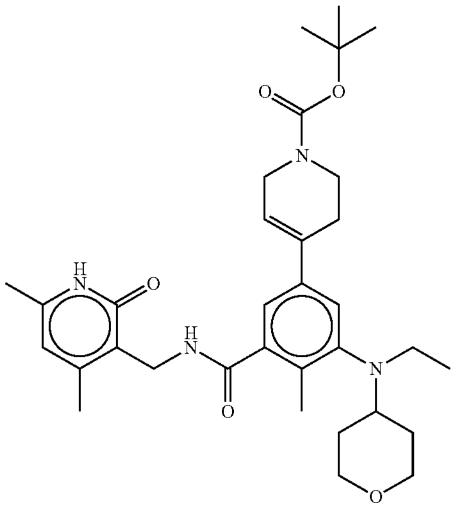 |
| 155 | 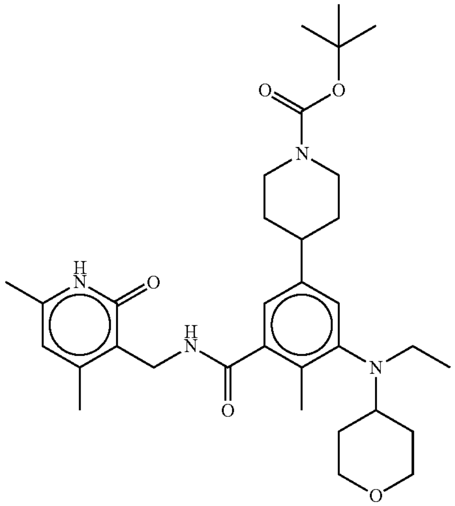 |
| 156 | 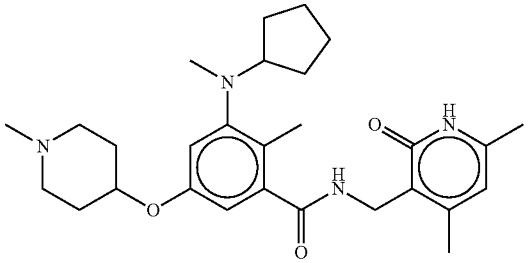 |
| 157 | 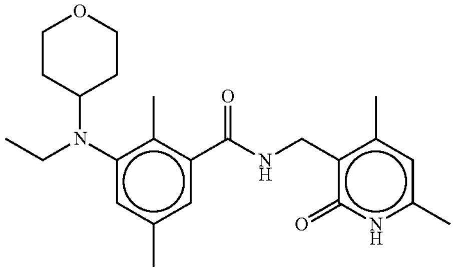 |

-continued
| Compound Number | Structure |
|---|---|
| 158 | 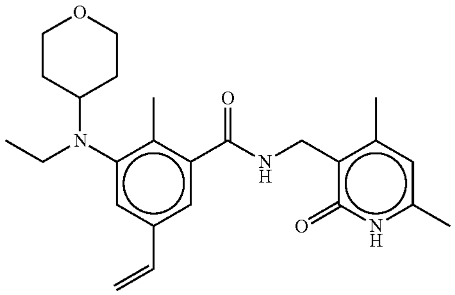 |
| 159 | 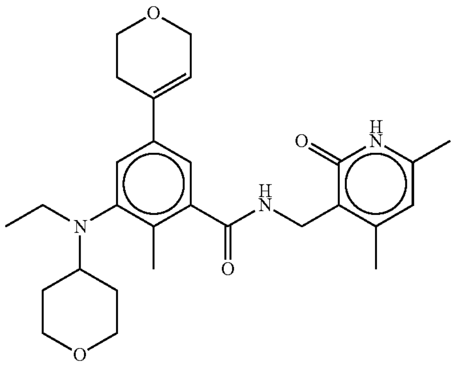 |
| 160 | 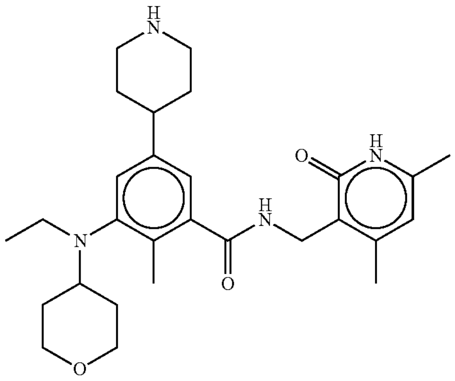 |
| 161 | 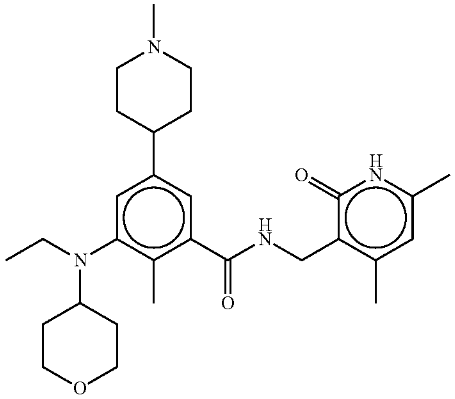 |

-continued
| Compound Number | Structure |
| --- | --- |
| 162 | 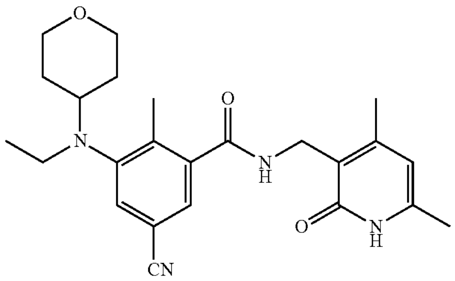 [SMILES: CCN(c1cc(C#N)cc(C(=O)NCc2c(C)cc(C)[nH]c2=O)c1C)C1CCOCC1] |
| 163 | 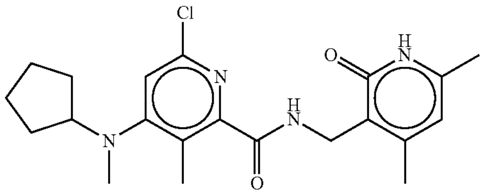 |
| 164 | 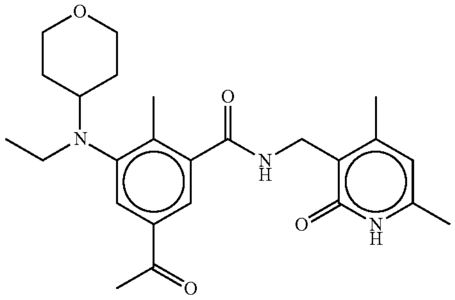 |
| 165 | 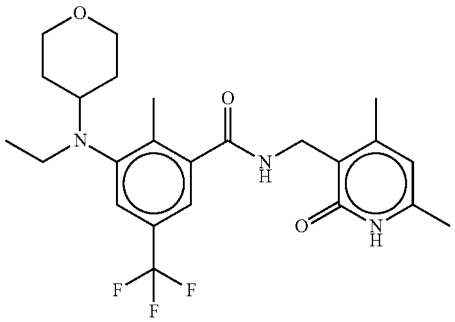 |
| 166 | 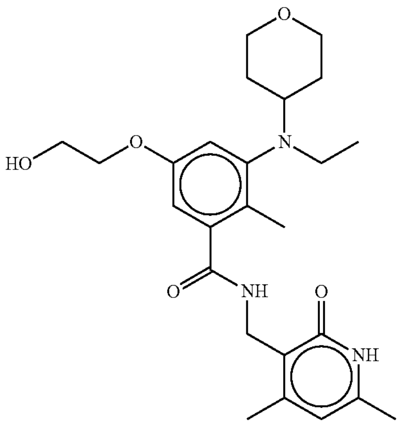 |

-continued
| Compound Number | Structure |
|---|---|
| 167 | 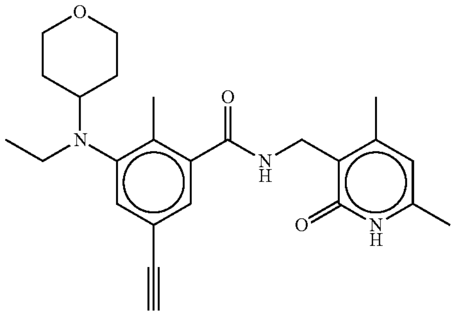 |
| 168 | 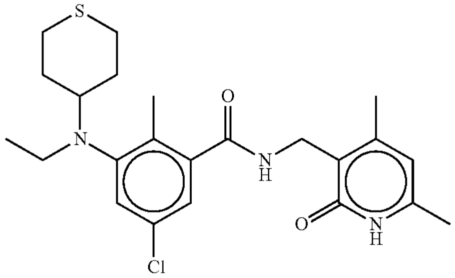 |
| 169 | 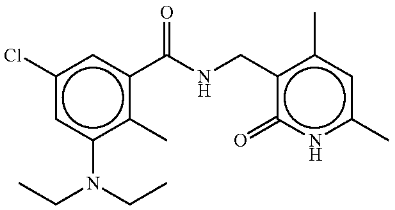 |
| 170 | 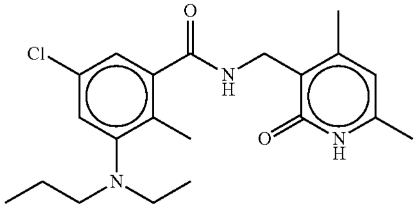 |
| 171 | 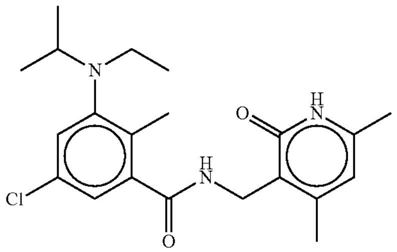 |
| 172 | 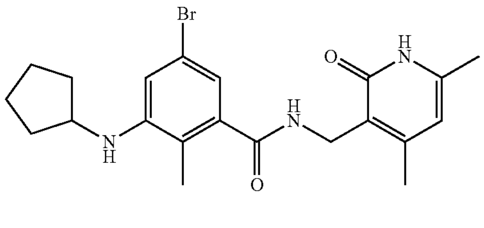 [SMILES: Cc1cc(C)c(CNC(=O)c2cc(Br)cc(NC3CCCC3)c2C)c(=O)[nH]1] |

-continued
| Compound Number | Structure |
| --- | --- |
| 173 | 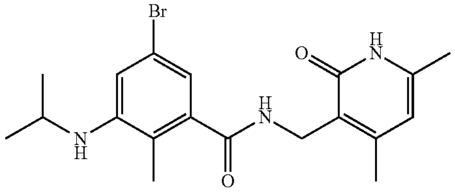 [SMILES: Cc1cc(C)c(CNC(=O)c2cc(Br)cc(NC(C)C)c2C)c(=O)[nH]1] |
| 174 | 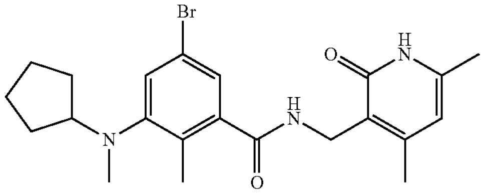 [SMILES: Cc1cc(C)c(CNC(=O)c2cc(Br)cc(N(C)C3CCCC3)c2C)c(=O)[nH]1] |
| 175 | 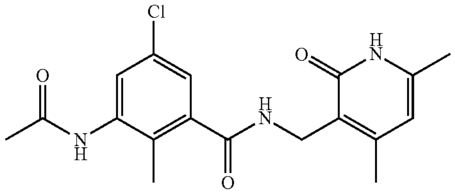 |
| 176 | 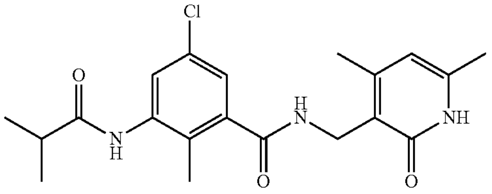 [SMILES: Cc1cc(C)c(CNC(=O)c2cc(Cl)cc(NC(=O)C(C)C)c2C)c(=O)[nH]1] |
| 177 | 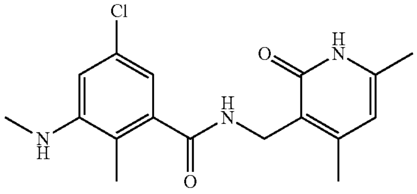 |
| 178 | 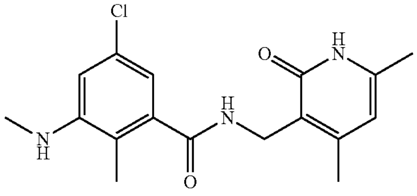 |
| 179 | 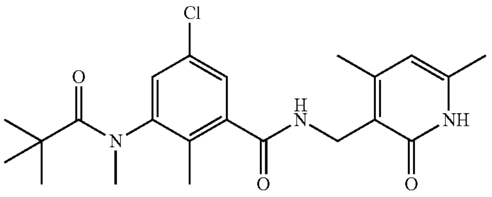 [SMILES: Cc1cc(C)c(CNC(=O)c2cc(Cl)cc(N(C)C(=O)C(C)(C)C)c2C)c(=O)[nH]1] |

-continued
| Compound Number | Structure |
|---|---|
| 180 | 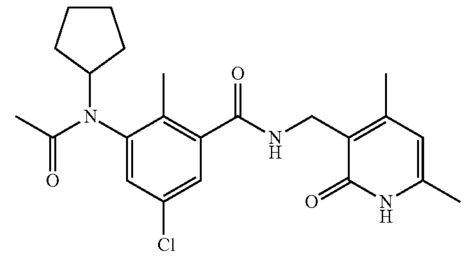 [SMILES: CC(=O)N(c1cc(Cl)cc(C(=O)NCc2c(C)cc(C)[nH]c2=O)c1C)C1CCCC1] |
| 181 | 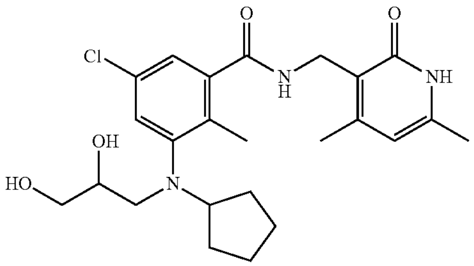 [SMILES: Cc1cc(C)c(CNC(=O)c2cc(Cl)cc(N(CC(O)CO)C3CCCC3)c2C)c(=O)[nH]1] |
| 182 | 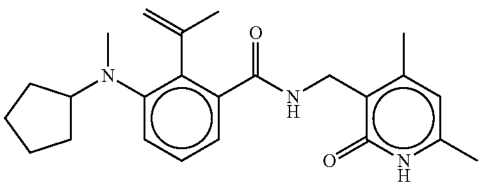 |
| 183 | 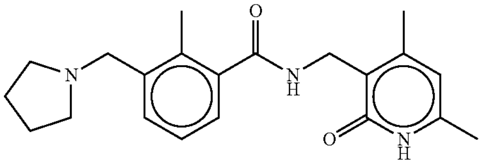 |
| 184 | 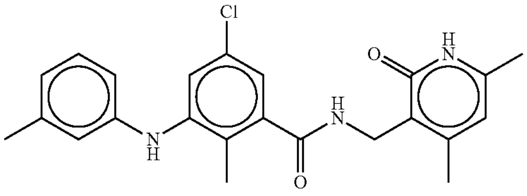 |
| 185 | |
| 186 | 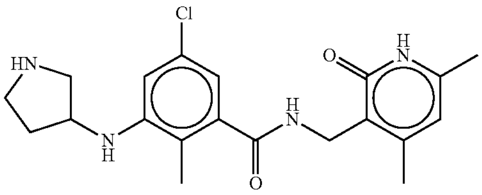 |
| 187 | 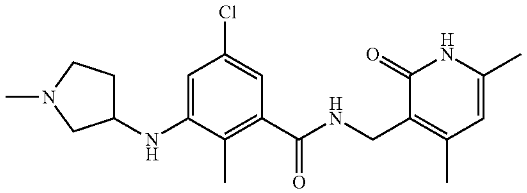 |

-continued
| Compound Number | Structure |
|---|---|
| 188 | 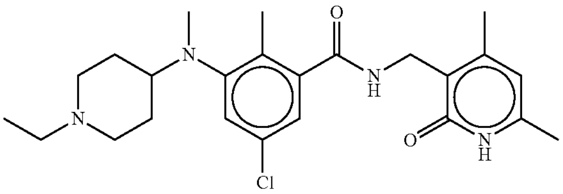 |
| 189 | 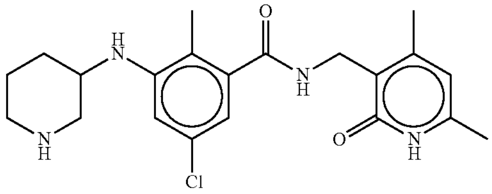 |
| 190 | 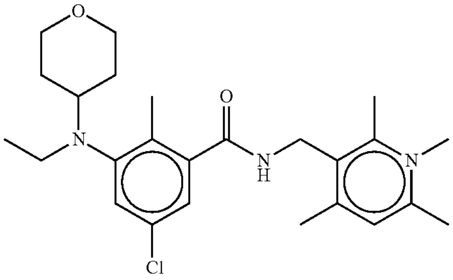 |
| 191 | 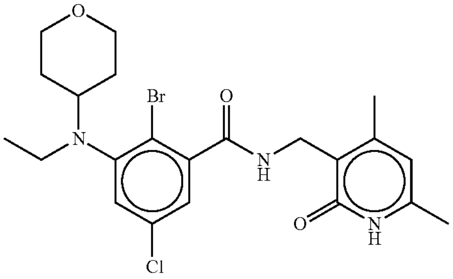 |
| 192 | 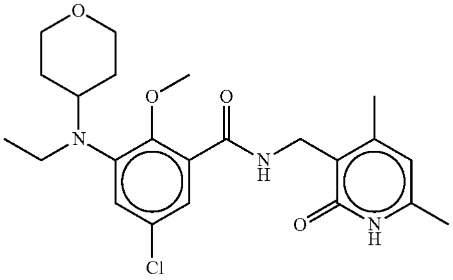 |
| 193 | 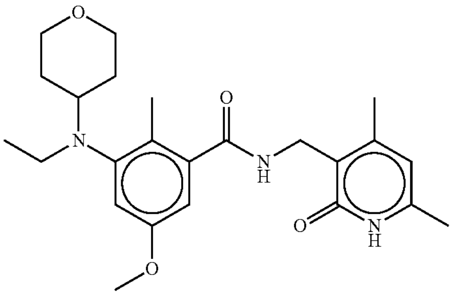 |

-continued
| Compound Number | Structure |
| --- | --- |
| 194 | 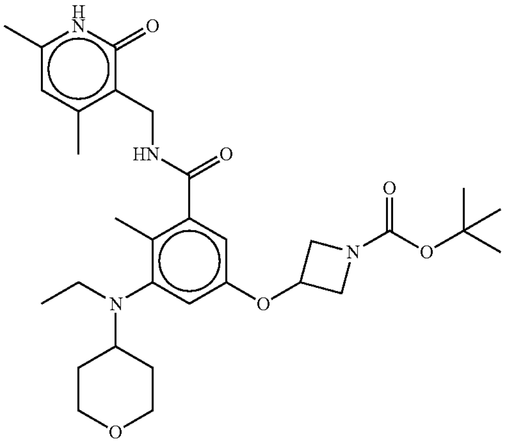 |
| 195 | 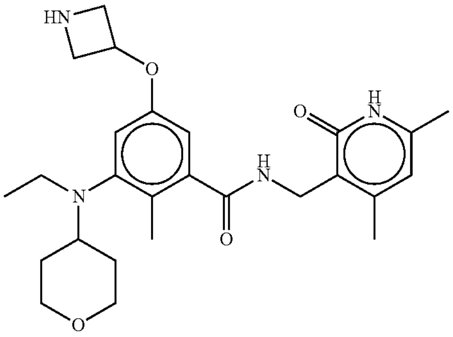 |
| 196 | 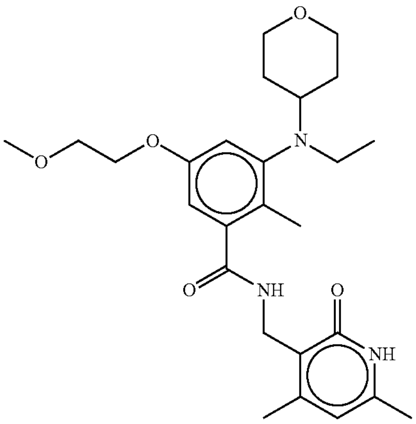 |
| 197 | 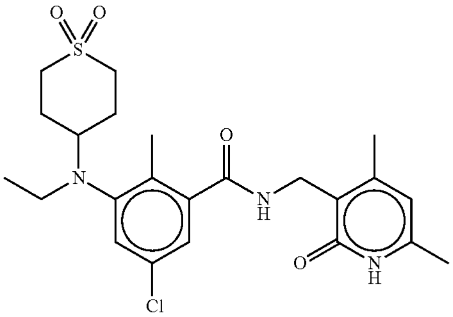 |

-continued
| Compound Number | Structure |
| --- | --- |
| 198 | 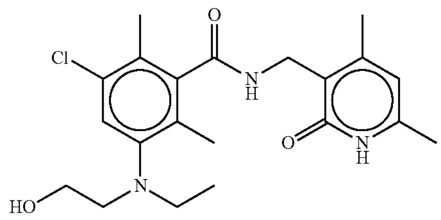 |
| 199 | 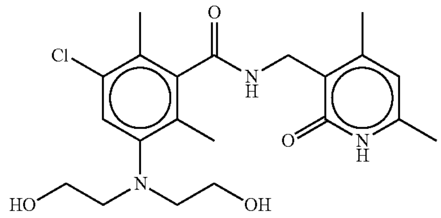 |
| 200 | 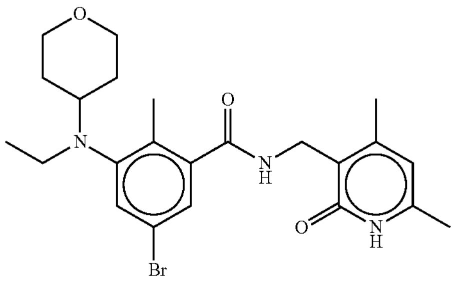 |
| 201 | 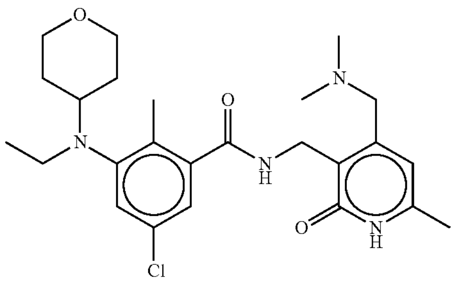 |
| 202 | 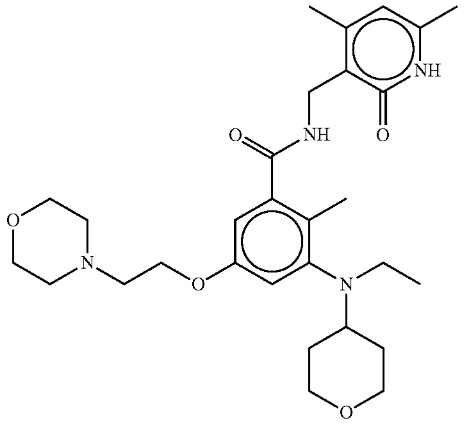 |

-continued
| Compound Number | Structure |
|---|---|
| 203 | 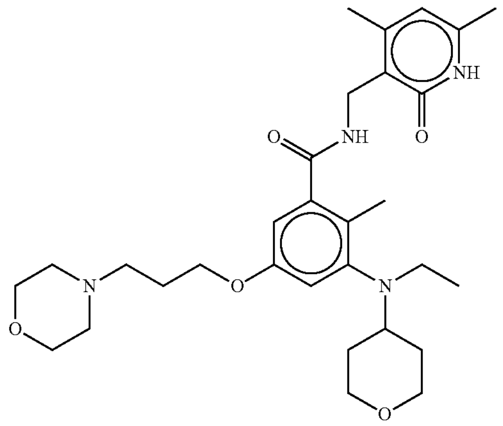 |
| 204 | 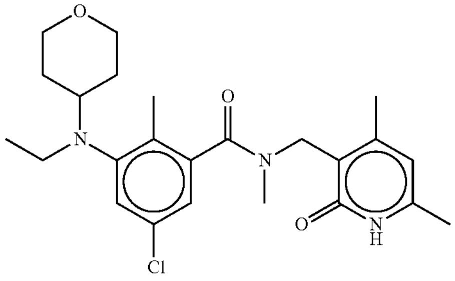 |
| 205 | 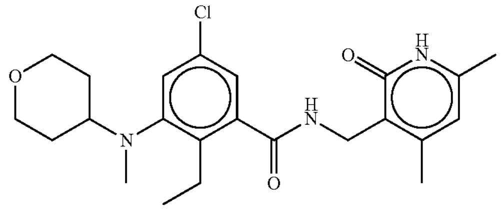 |
| 206 | 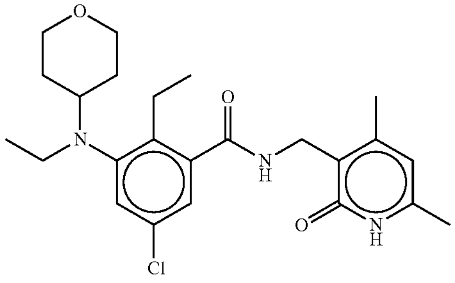 |
| 207 | 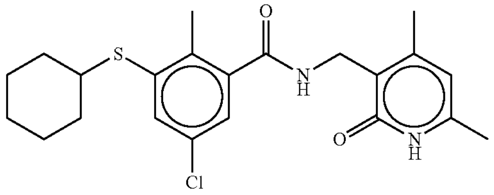 |

-continued
| Compound Number | Structure |
|---|---|
| 208 | 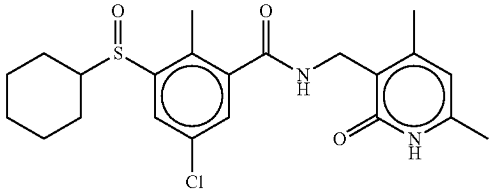 |
| 209 | 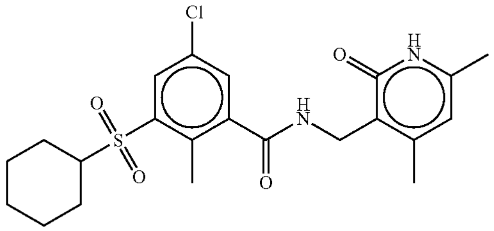 |
| 210 | 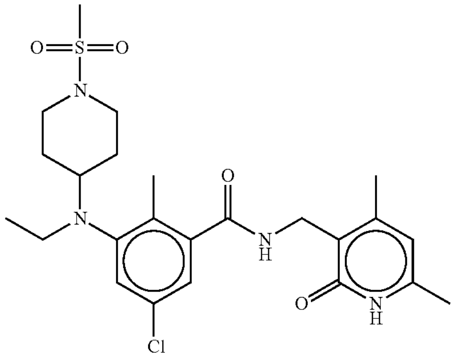 |
| 211 | 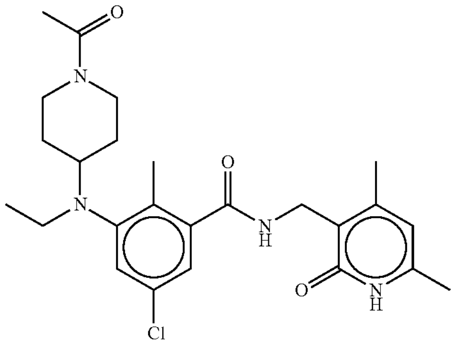 |
| 212 | 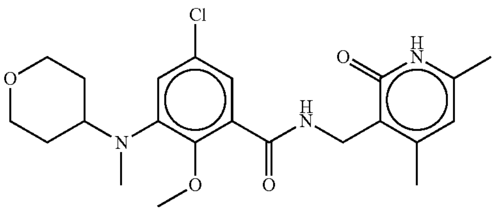 |

-continued
| Compound Number | Structure |
|---|---|
| 213 | 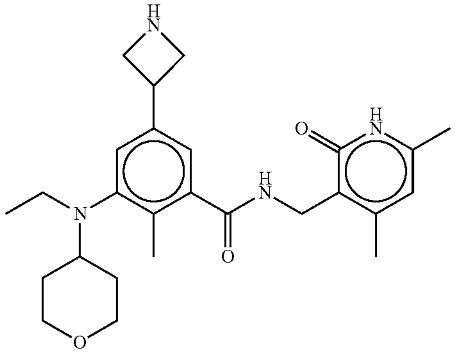 |
| 214 | 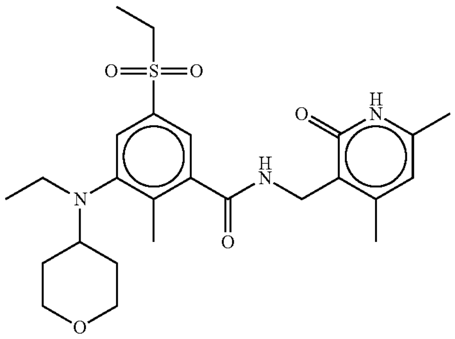 |
| 215 | 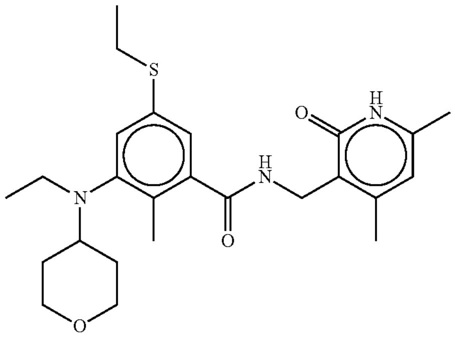 |
| 216 | 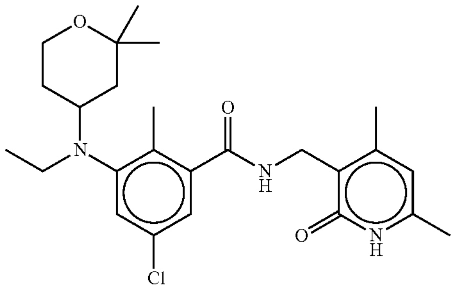 |

-continued
| Compound Number | Structure |
|---|---|
| 217 | 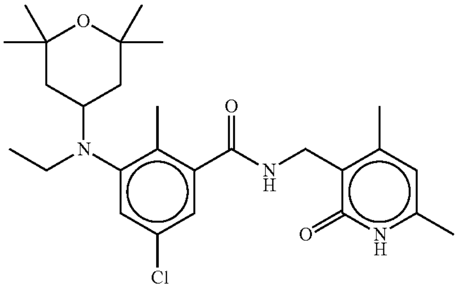 |
| 218 | 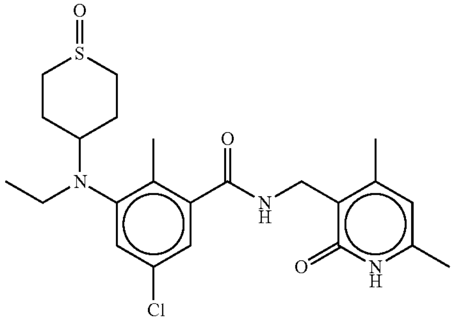 |
| 219 | 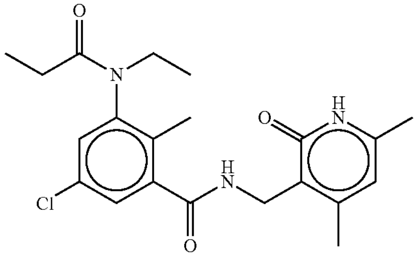 |
| 220 | 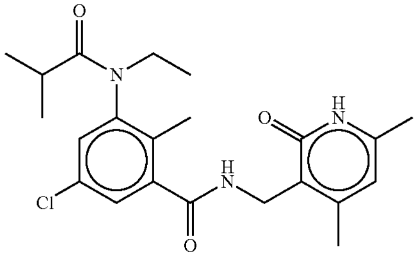 |
| 221 | 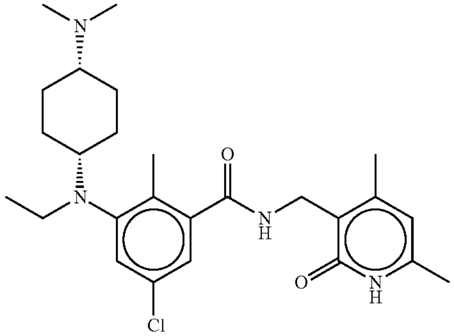 |

-continued
| Compound Number | Structure |
|---|---|
| 222 | 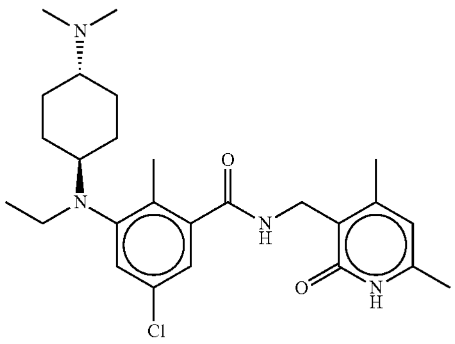 |
| 223 | 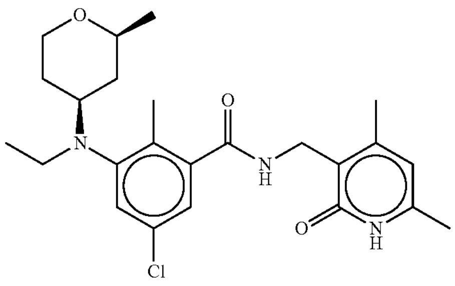 |
| 224 | 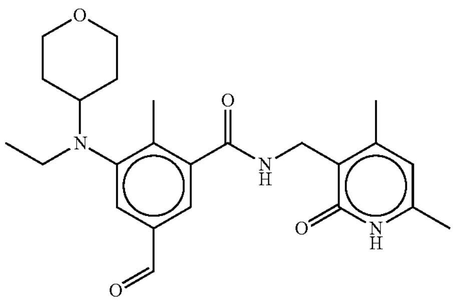 |
| 225 | 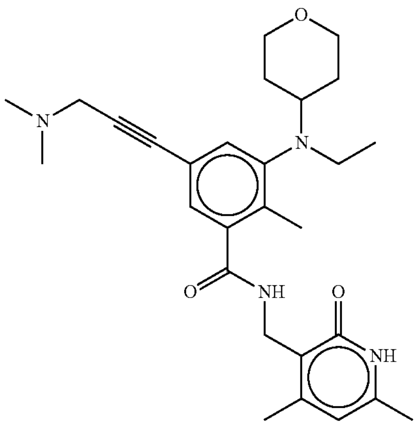 |

-continued
| Compound Number | Structure |
|---|---|
| 226 | 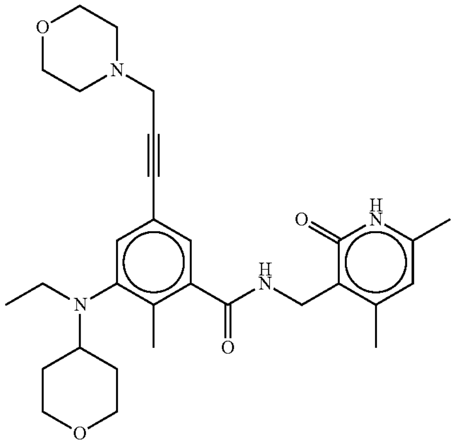 |
| 227 | 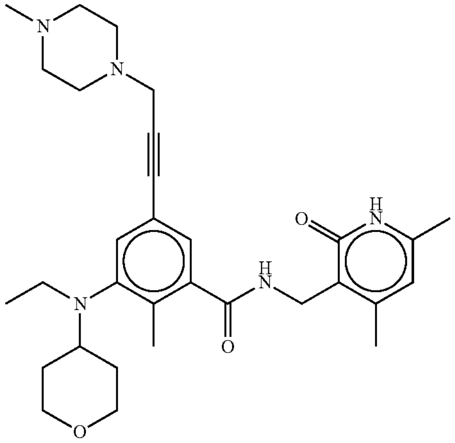 |
| 228 | 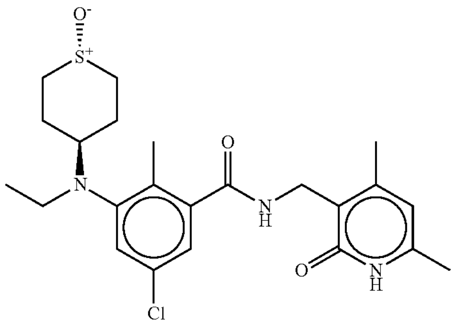 |
| 229 | 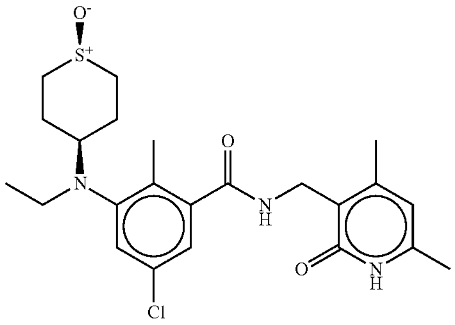 |

-continued
| Compound Number | Structure |
|---|---|
| 230 | 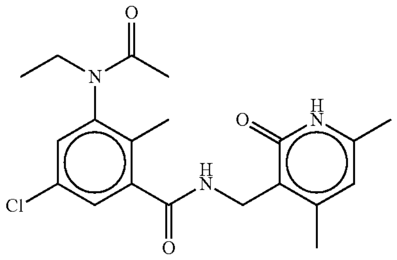 |
| 231 | 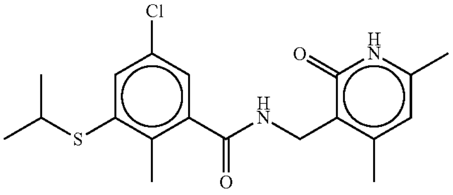 |
| 232 | 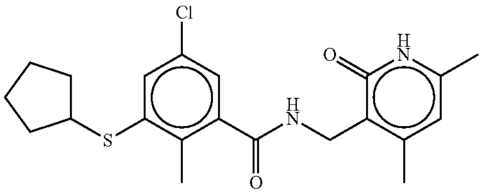 |
| 233 | 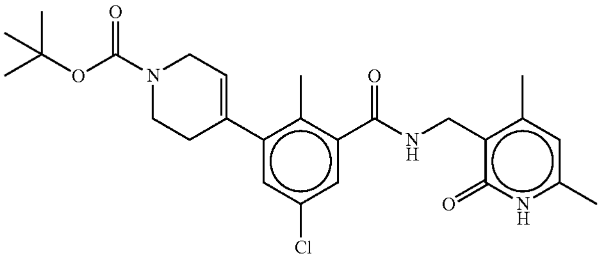 |
| 234 | 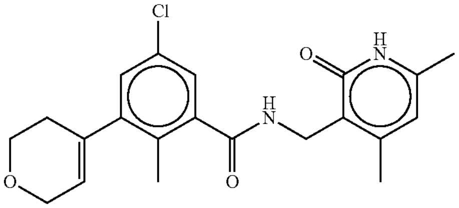 |
| 235 | 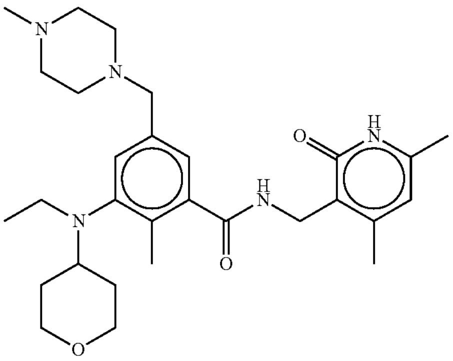 |

-continued
| Compound Number | Structure |
|---|---|
| 236 | 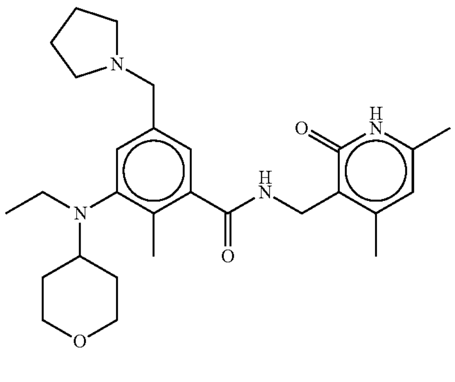 |
| 237 | 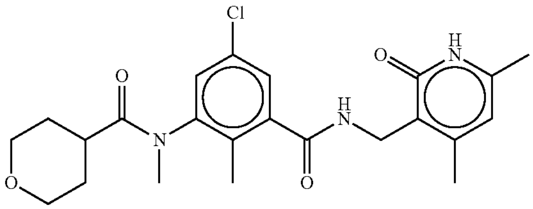 |
| 238 | 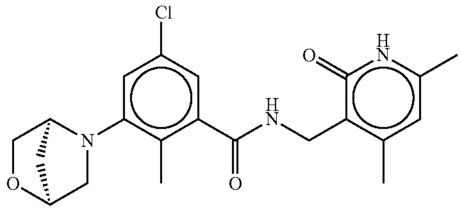 |
| 239 | 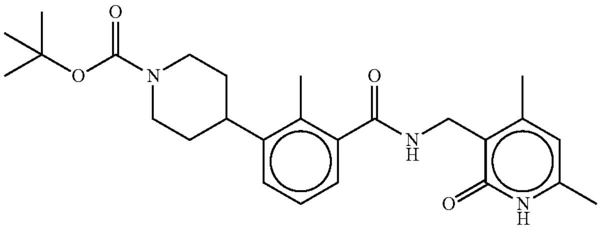 |
| 240 | 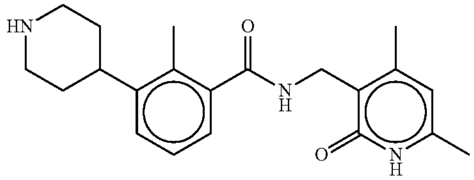 |
| 241 | 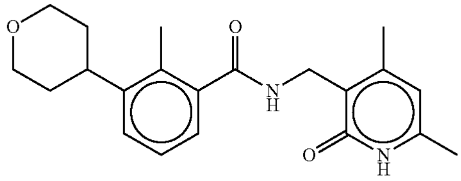 |

-continued
| Compound Number | Structure |
| --- | --- |
| 242 | 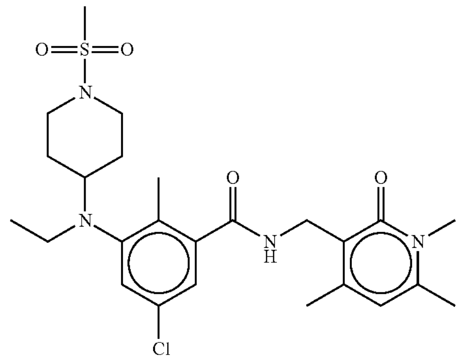 |
| 243 | 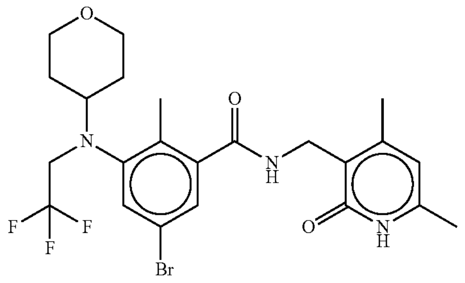 |
| 244 | 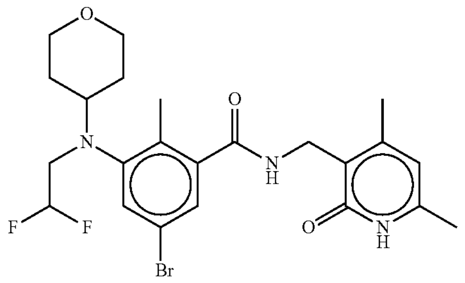 |
| 245 | 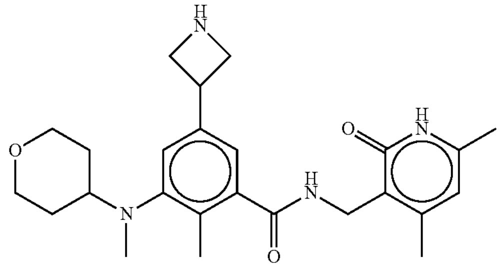 |
| 246 | 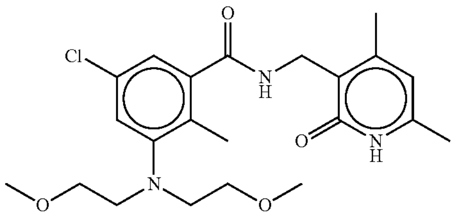 |

-continued
| Compound Number | Structure |
| --- | --- |
| 247 | 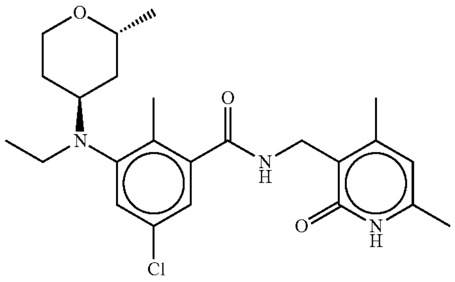 |
| 248 | 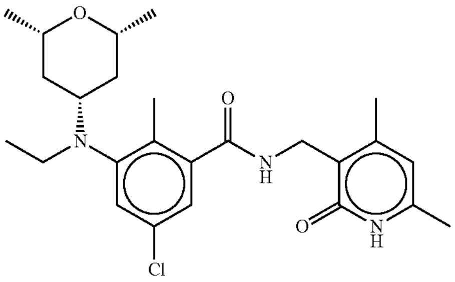 |
| 249 | 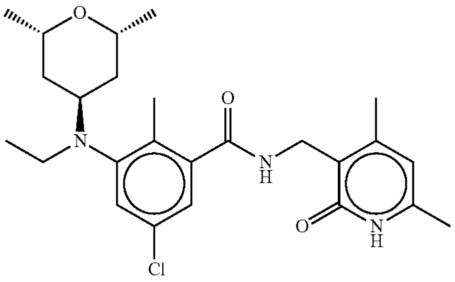 |
| 250 | 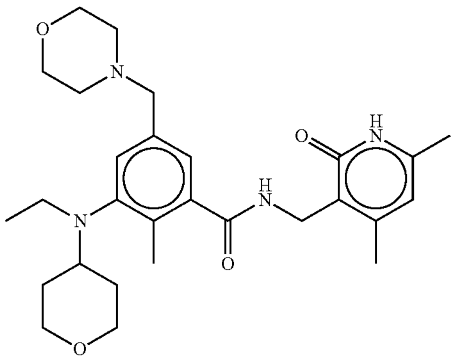 |
| 251 | 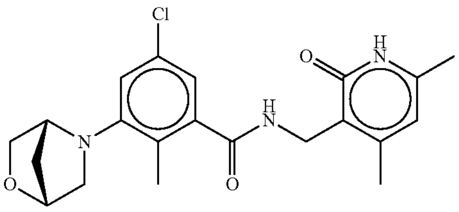 |

-continued
| Compound Number | Structure |
| --- | --- |
| 252 | 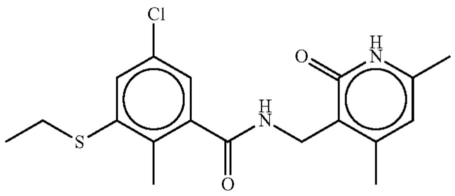 |
| 253 | 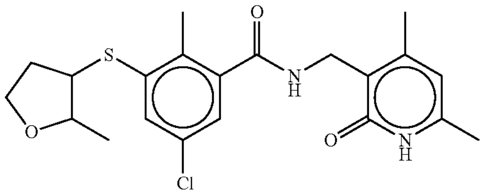 |
| 254 | 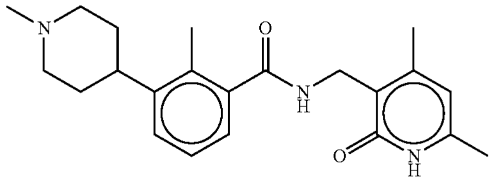 |
| 255 | 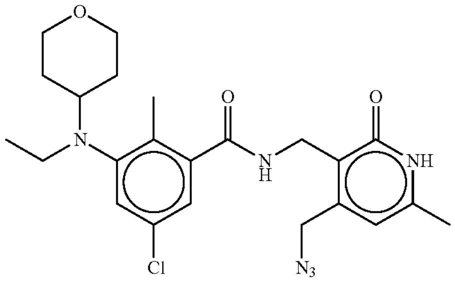 |
| 256 | 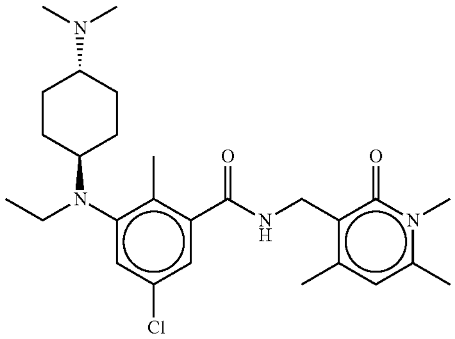 |
| 257 | 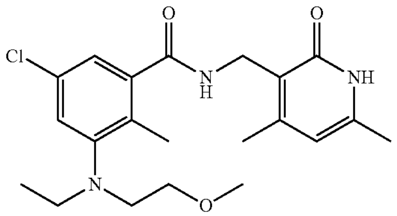 [SMILES: CCN(CCOC)c1cc(Cl)cc(C(=O)NCc2c(C)cc(C)[nH]c2=O)c1C] |

-continued
| Compound Number | Structure |
| --- | --- |
| 258 | 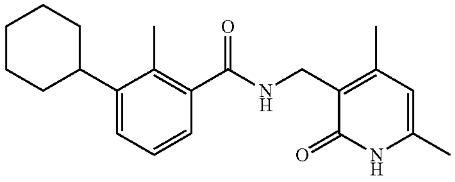 [SMILES: Cc1cc(C)c(CNC(=O)c2cccc(C3CCCCC3)c2C)c(=O)[nH]1] |
| 259 | 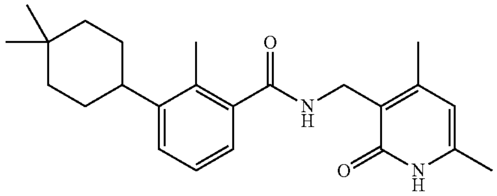 |
| 260 | 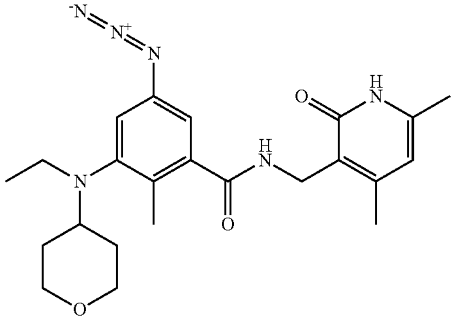 |
| 261 | 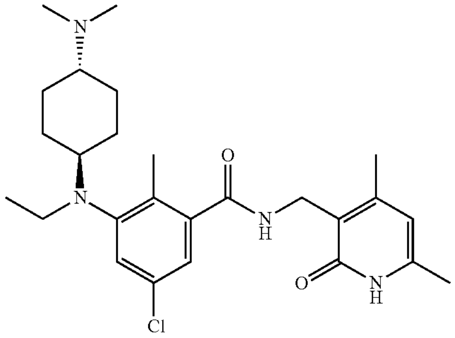 [SMILES: CCN(c1cc(Cl)cc(C(=O)NCc2c(C)cc(C)[nH]c2=O)c1C)[C@H]1CC[C@H](N(C)C)CC1] |
| 262 | 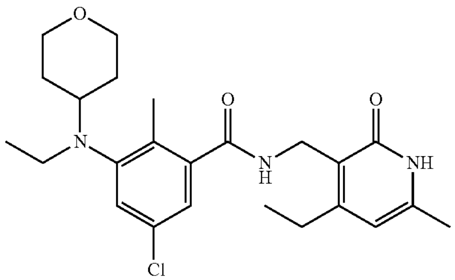 [SMILES: CCc1cc(C)[nH]c(=O)c1CNC(=O)c1cc(Cl)cc(N(CC)C2CCOCC2)c1C] |
| 263 | 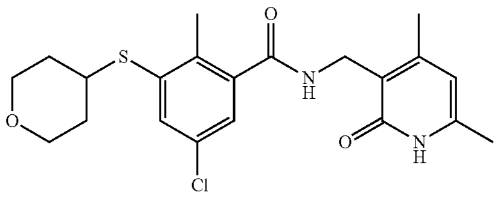 |

-continued
| Compound Number | Structure |
|---|---|
| 264 | 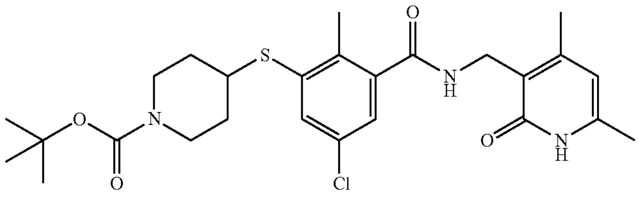 [SMILES: Cc1cc(C)c(CNC(=O)c2cc(Cl)cc(SC3CCN(C(=O)OC(C)(C)C)CC3)c2C)c(=O)[nH]1] |
| 265 | 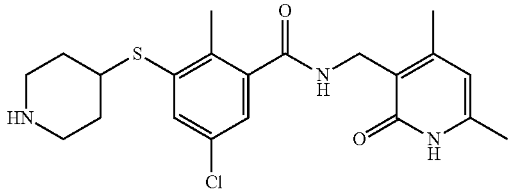 [SMILES: Cc1cc(C)c(CNC(=O)c2cc(Cl)cc(SC3CCNCC3)c2C)c(=O)[nH]1] |
| 266 | 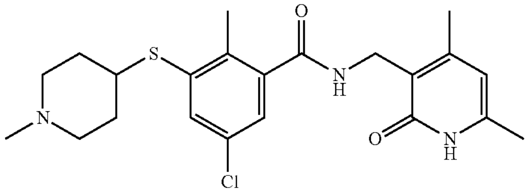 |
| 267 | 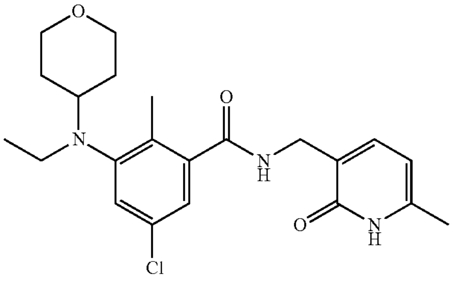 [SMILES: CCN(c1cc(Cl)cc(C(=O)NCc2ccc(C)[nH]c2=O)c1C)C1CCOCC1] |
| 268 | 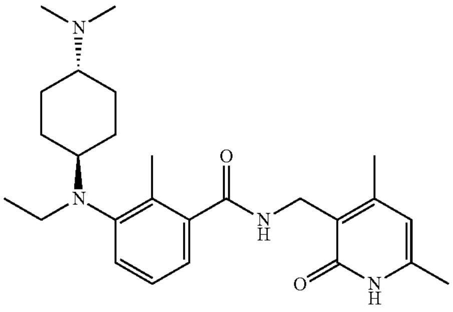 |
| 269 | 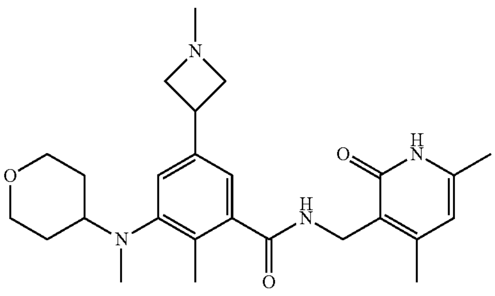 [SMILES: Cc1cc(C)c(CNC(=O)c2cc(C3CN(C)C3)cc(N(C)C3CCOCC3)c2C)c(=O)[nH]1] |

-continued
| Compound Number | Structure |
|---|---|
| 270 | 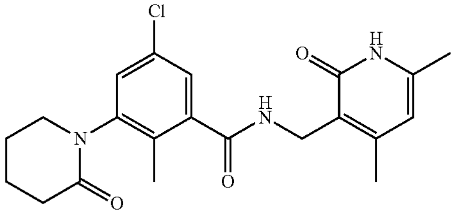 [SMILES: Cc1cc(C)c(CNC(=O)c2cc(Cl)cc(N3CCCCC3=O)c2C)c(=O)[nH]1] |
| 271 | 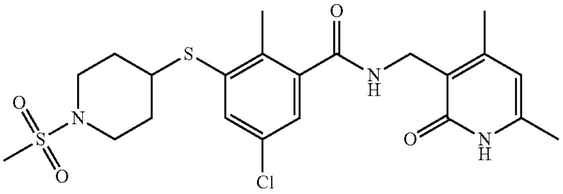 |
| 272 | 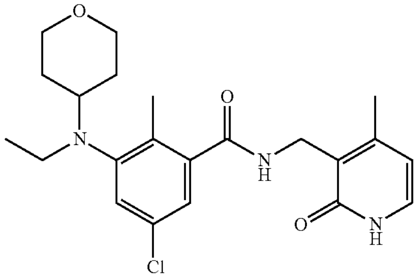 [SMILES: CCN(c1cc(Cl)cc(C(=O)NCc2c(C)cc[nH]c2=O)c1C)C1CCOCC1] |
| 273 | 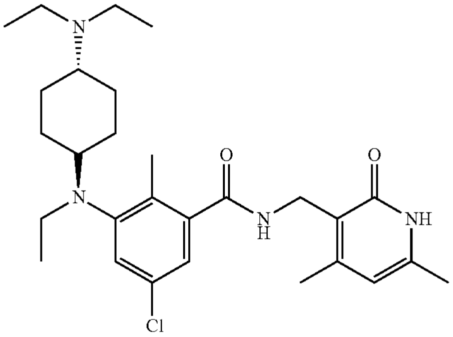 |
| 274 | 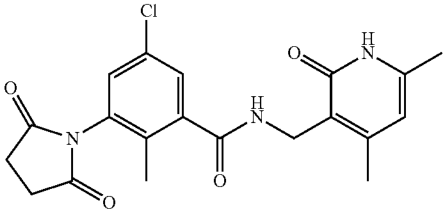 [SMILES: Cc1cc(C)c(CNC(=O)c2cc(Cl)cc(N3C(=O)CCC3=O)c2C)c(=O)[nH]1] |
| 275 | 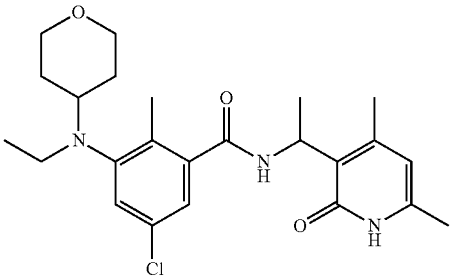 |

-continued
| Compound Number | Structure |
|---|---|
| 276 | 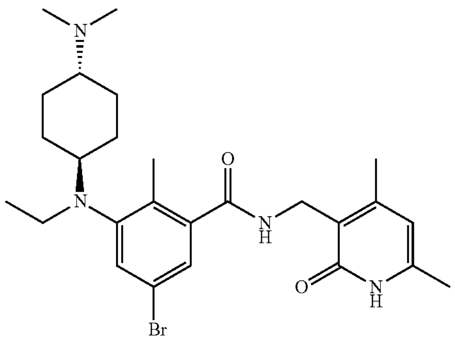 [SMILES: CCN(c1cc(Br)cc(C(=O)NCc2c(C)cc(C)[nH]c2=O)c1C)[C@H]1CC[C@H](N(C)C)CC1] |
| 277 | 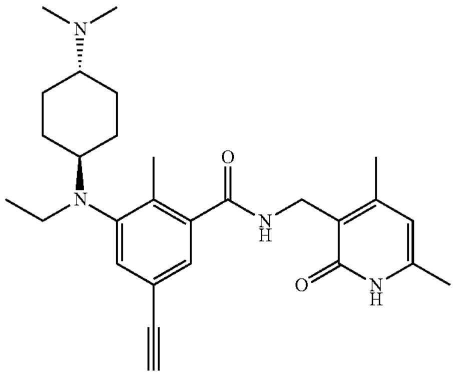 [SMILES: C#Cc1cc(C(=O)NCc2c(C)cc(C)[nH]c2=O)c(C)c(N(CC)[C@H]2CC[C@H](N(C)C)CC2)c1] |
| 278 | 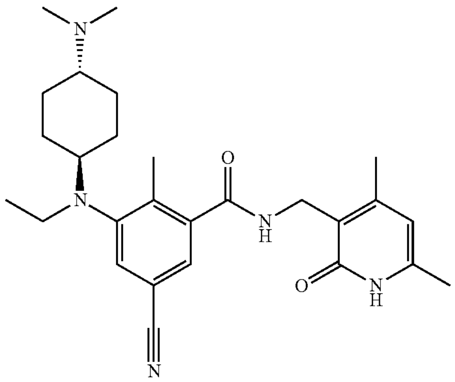 [SMILES: CCN(c1cc(C#N)cc(C(=O)NCc2c(C)cc(C)[nH]c2=O)c1C)[C@H]1CC[C@H](N(C)C)CC1] |
| 279 | 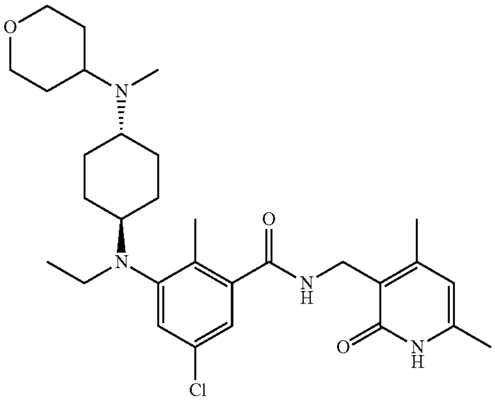 [SMILES: CCN(c1cc(Cl)cc(C(=O)NCc2c(C)cc(C)[nH]c2=O)c1C)[C@H]1CC[C@H](N(C)C2CCOCC2)CC1] |

-continued
| Compound Number | Structure |
|---|---|
| 280 | 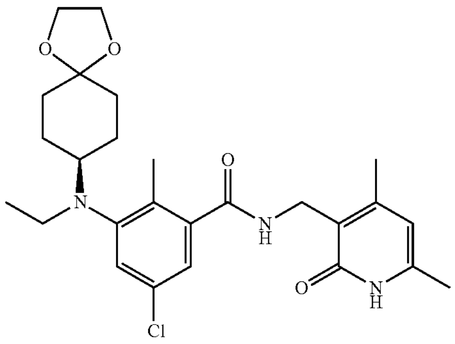 |
| 281 | 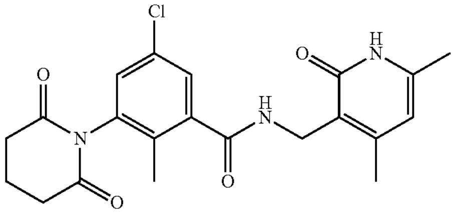 [SMILES: Cc1cc(C)c(CNC(=O)c2cc(Cl)cc(N3C(=O)CCCC3=O)c2C)c(=O)[nH]1] |
| 282 | 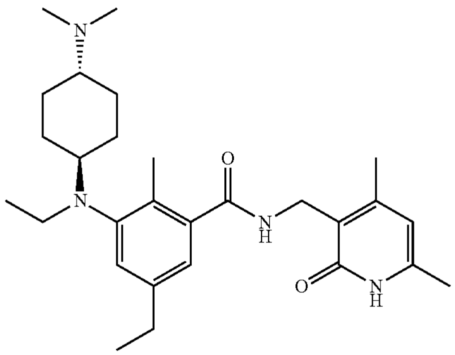 [SMILES: CCc1cc(C(=O)NCc2c(C)cc(C)[nH]c2=O)c(C)c(N(CC)[C@H]2CC[C@H](N(C)C)CC2)c1] |
| 283 | 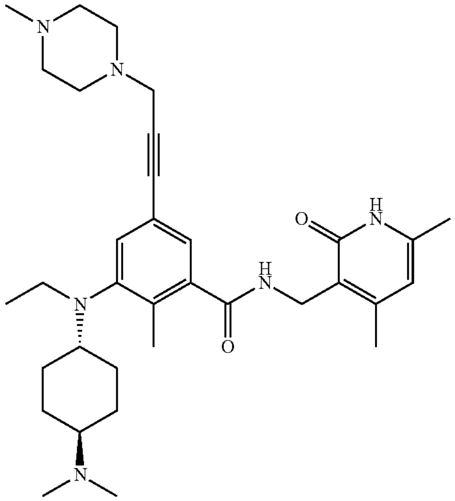 [SMILES: CCN(c1cc(C#CCN2CCN(C)CC2)cc(C(=O)NCc2c(C)cc(C)[nH]c2=O)c1C)[C@H]1CC[C@H](N(C)C)CC1] |

-continued
| Compound Number | Structure |
| --- | --- |
| 284 | 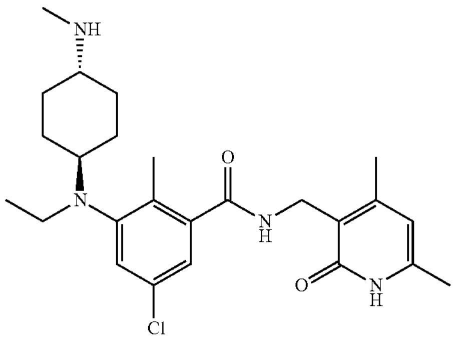 [SMILES: CCN(c1cc(Cl)cc(C(=O)NCc2c(C)cc(C)[nH]c2=O)c1C)[C@H]1CC[C@H](NC)CC1] |
| 285 | 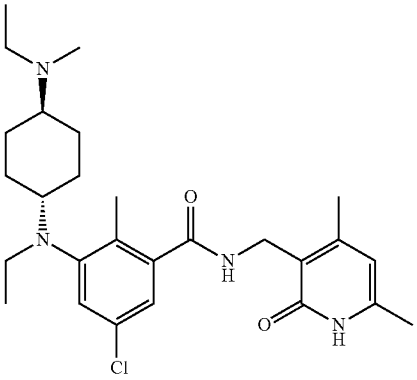 [SMILES: CCN(C)[C@H]1CC[C@H](N(CC)c2cc(Cl)cc(C(=O)NCc3c(C)cc(C)[nH]c3=O)c2C)CC1] |
| 286 | 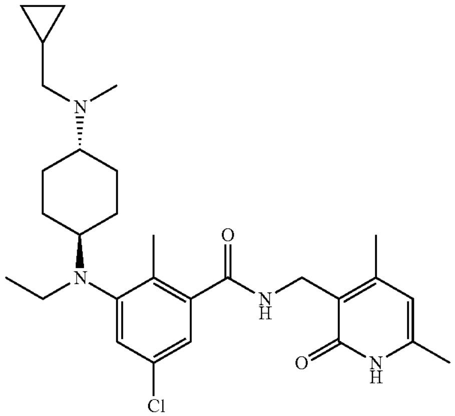 [SMILES: CCN(c1cc(Cl)cc(C(=O)NCc2c(C)cc(C)[nH]c2=O)c1C)[C@H]1CC[C@H](N(C)CC2CC2)CC1] |
| 287 | 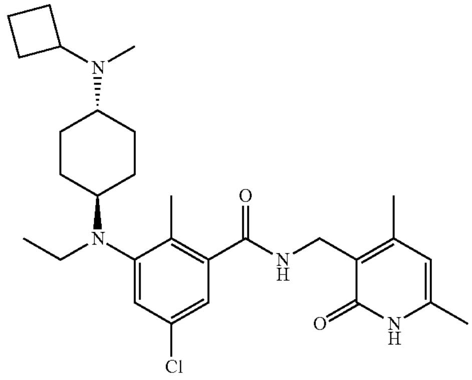 [SMILES: CCN(c1cc(Cl)cc(C(=O)NCc2c(C)cc(C)[nH]c2=O)c1C)[C@H]1CC[C@H](N(C)C2CCC2)CC1] |

-continued
| Compound Number | Structure |
|---|---|
| 288 | 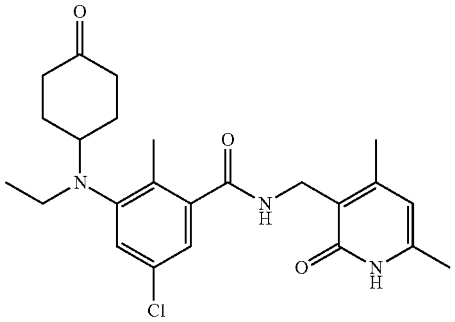 [SMILES: CCN(c1cc(Cl)cc(C(=O)NCc2c(C)cc(C)[nH]c2=O)c1C)C1CCC(=O)CC1] |
| 289 | 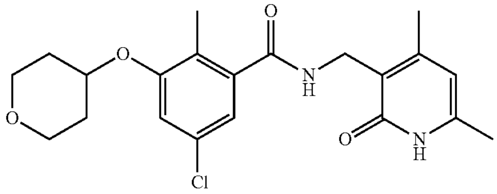 |
| 290 | 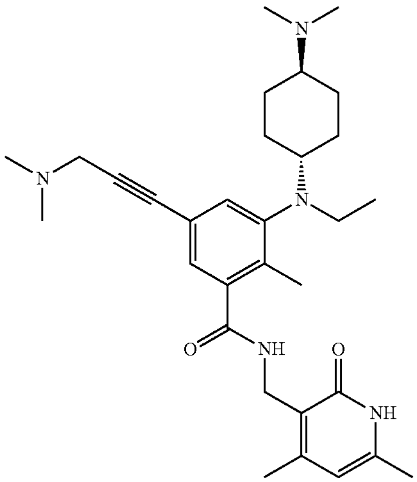 |
| 291 | 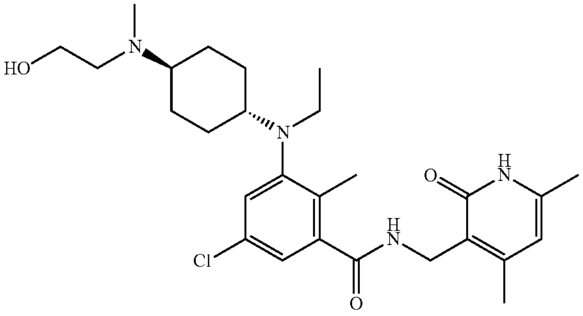 [SMILES: CCN(c1cc(Cl)cc(C(=O)NCc2c(C)cc(C)[nH]c2=O)c1C)[C@H]1CC[C@H](N(C)CCO)CC1] |

-continued
| Compound Number | Structure |
| --- | --- |
| 292 | 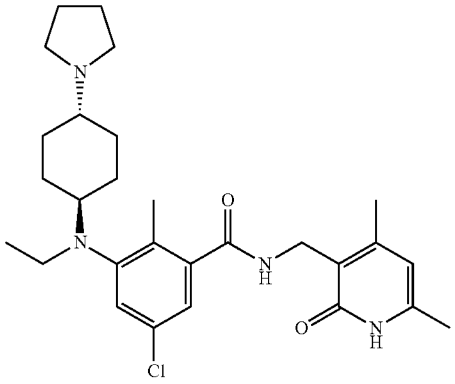 [SMILES: CCN(c1cc(Cl)cc(C(=O)NCc2c(C)cc(C)[nH]c2=O)c1C)[C@H]1CC[C@H](N2CCCC2)CC1] |
| 293 | 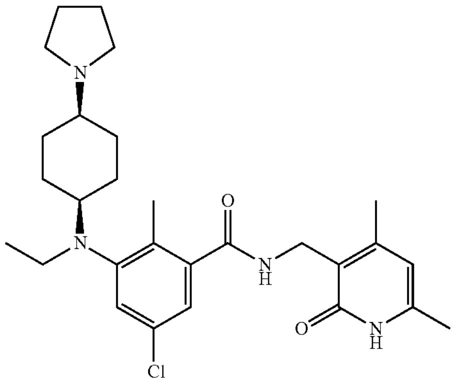 [SMILES: CCN(c1cc(Cl)cc(C(=O)NCc2c(C)cc(C)[nH]c2=O)c1C)[C@H]1CC[C@@H](N2CCCC2)CC1] |
| 294 | 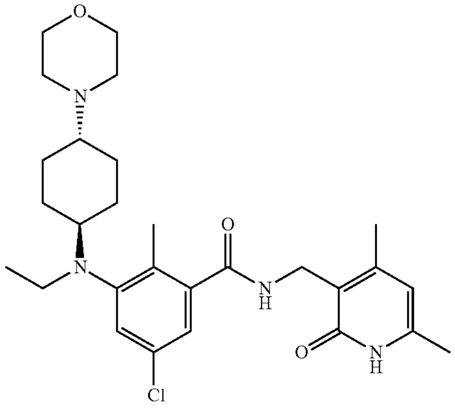 [SMILES: CCN(c1cc(Cl)cc(C(=O)NCc2c(C)cc(C)[nH]c2=O)c1C)[C@H]1CC[C@H](N2CCOCC2)CC1] |
| 295 | 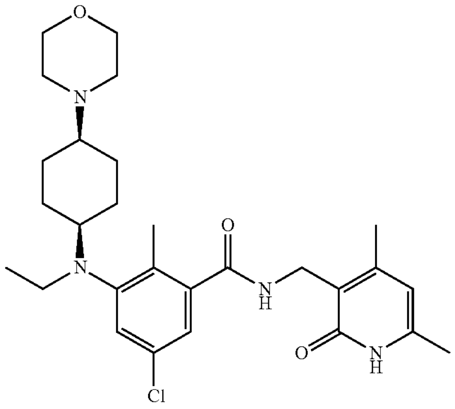 [SMILES: CCN(c1cc(Cl)cc(C(=O)NCc2c(C)cc(C)[nH]c2=O)c1C)[C@H]1CC[C@@H](N2CCOCC2)CC1] |

-continued
| Compound Number | Structure |
|---|---|
| 296 | 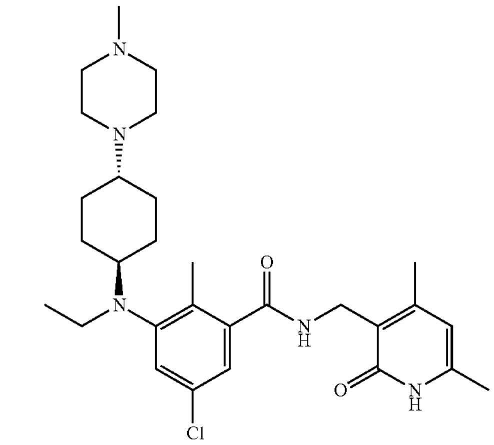 [SMILES: CCN(c1cc(Cl)cc(C(=O)NCc2c(C)cc(C)[nH]c2=O)c1C)[C@H]1CC[C@H](N2CCN(C)CC2)CC1] |
| 297 | 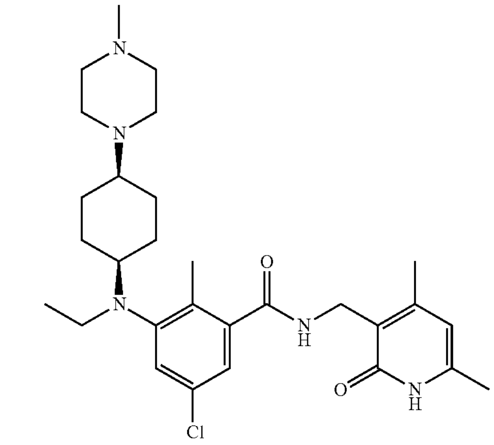 [SMILES: CCN(c1cc(Cl)cc(C(=O)NCc2c(C)cc(C)[nH]c2=O)c1C)[C@H]1CC[C@@H](N2CCN(C)CC2)CC1] |
| 298 | 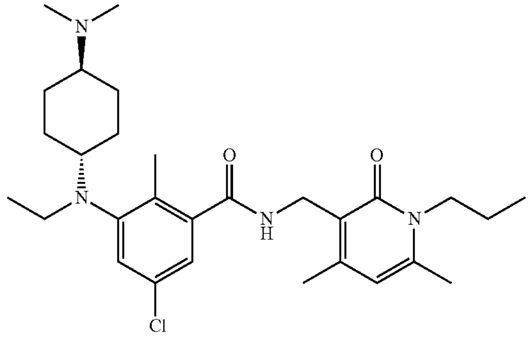 [SMILES: CCCn1c(C)cc(C)c(CNC(=O)c2cc(Cl)cc(N(CC)[C@H]3CC[C@H](N(C)C)CC3)c2C)c1=O] |
| 299 | 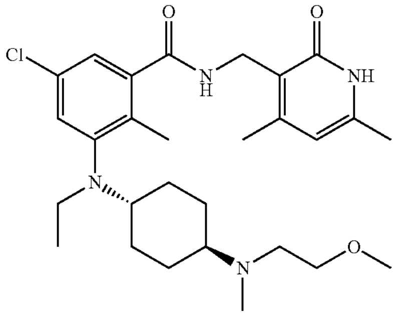 [SMILES: CCN(c1cc(Cl)cc(C(=O)NCc2c(C)cc(C)[nH]c2=O)c1C)[C@H]1CC[C@H](N(C)CCOC)CC1] |

-continued
| Compound Number | Structure |
|---|---|
| 300 | 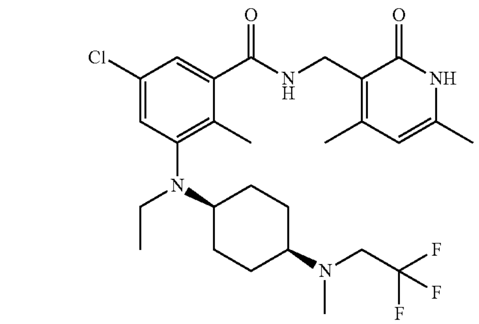 [SMILES: CCN(c1cc(Cl)cc(C(=O)NCc2c(C)cc(C)[nH]c2=O)c1C)[C@H]1CC[C@@H](N(C)CC(F)(F)F)CC1] |
| 301 | 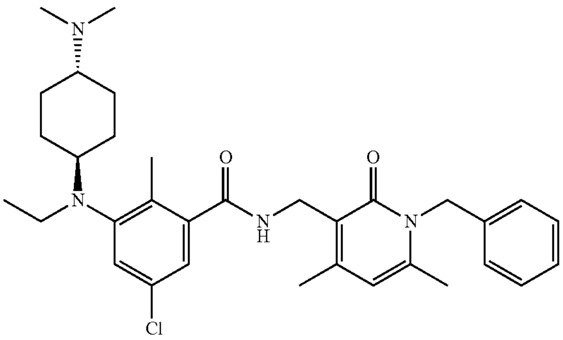 [SMILES: CCN(c1cc(Cl)cc(C(=O)NCc2c(C)cc(C)n(Cc3ccccc3)c2=O)c1C)[C@H]1CC[C@H](N(C)C)CC1] |
| 302 | 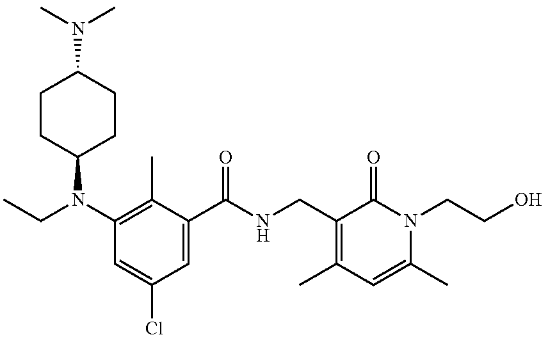 [SMILES: CCN(c1cc(Cl)cc(C(=O)NCc2c(C)cc(C)n(CCO)c2=O)c1C)[C@H]1CC[C@H](N(C)C)CC1] |
| 303 | 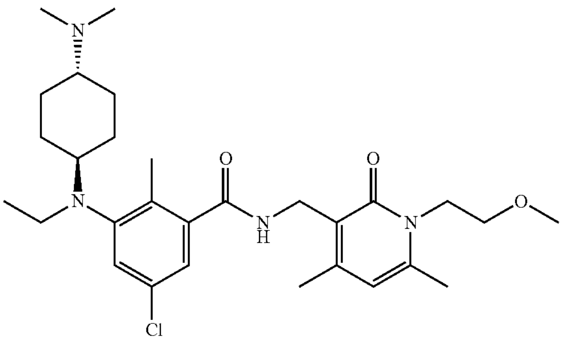 [SMILES: CCN(c1cc(Cl)cc(C(=O)NCc2c(C)cc(C)n(CCOC)c2=O)c1C)[C@H]1CC[C@H](N(C)C)CC1] |

-continued
| Compound Number | Structure |
|---|---|
| 304 | 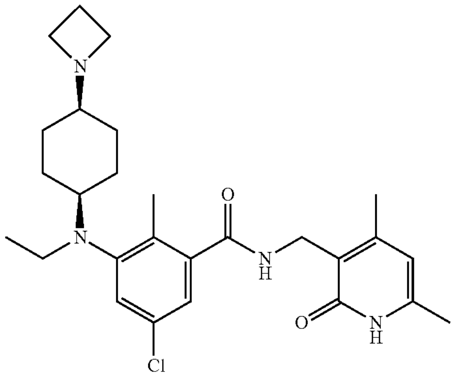 [SMILES: CCN(c1cc(Cl)cc(C(=O)NCc2c(C)cc(C)[nH]c2=O)c1C)[C@H]1CC[C@@H](N2CCC2)CC1] |
| 305 | 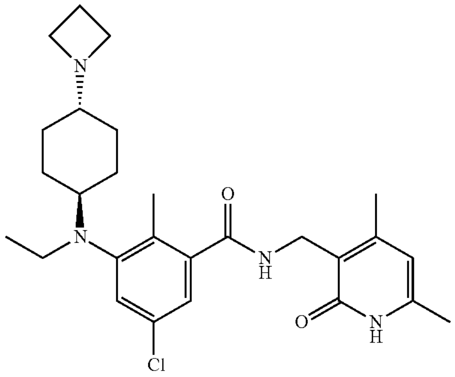 [SMILES: CCN(c1cc(Cl)cc(C(=O)NCc2c(C)cc(C)[nH]c2=O)c1C)[C@H]1CC[C@H](N2CCC2)CC1] |
| 306 | 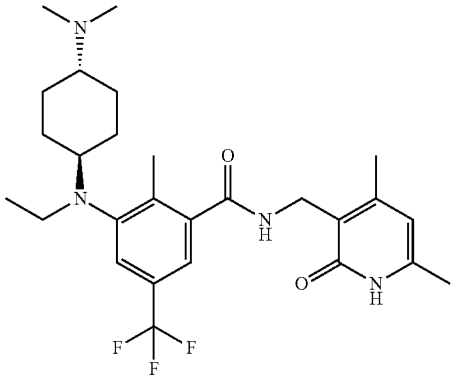 [SMILES: CCN(c1cc(C(F)(F)F)cc(C(=O)NCc2c(C)cc(C)[nH]c2=O)c1C)[C@H]1CC[C@H](N(C)C)CC1] |
| 307 | 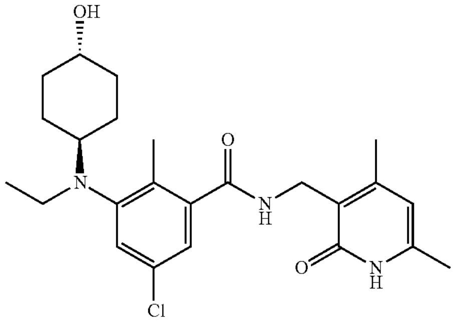 [SMILES: CCN(c1cc(Cl)cc(C(=O)NCc2c(C)cc(C)[nH]c2=O)c1C)[C@H]1CC[C@H](O)CC1] |

-continued
| Compound Number | Structure |
|---|---|
| 308 | 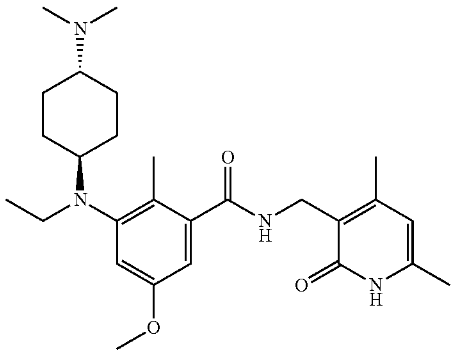 [SMILES: CCN(c1cc(OC)cc(C(=O)NCc2c(C)cc(C)[nH]c2=O)c1C)[C@H]1CC[C@H](N(C)C)CC1] |
| 309 | 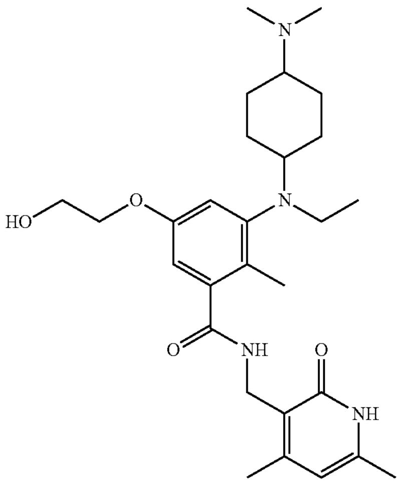 [SMILES: CCN(c1cc(OCCO)cc(C(=O)NCc2c(C)cc(C)[nH]c2=O)c1C)C1CCC(N(C)C)CC1] |
| 310 | 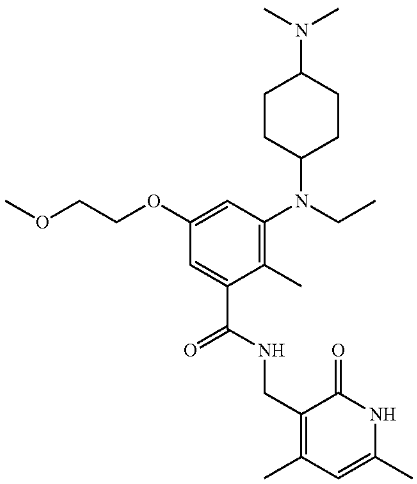 |

-continued
| Compound Number | Structure |
|---|---|
| 311 | 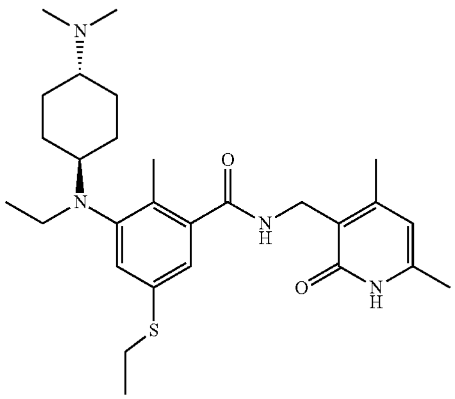 [SMILES: CCSc1cc(C(=O)NCc2c(C)cc(C)[nH]c2=O)c(C)c(N(CC)[C@H]2CC[C@H](N(C)C)CC2)c1] |
| 312 | 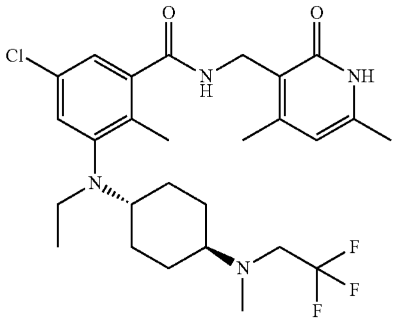 [SMILES: CCN(c1cc(Cl)cc(C(=O)NCc2c(C)cc(C)[nH]c2=O)c1C)[C@H]1CC[C@H](N(C)CC(F)(F)F)CC1] |
| 313 | 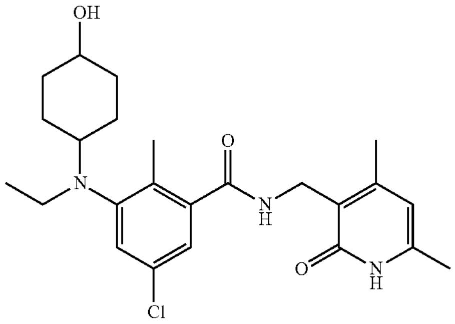 [SMILES: CCN(c1cc(Cl)cc(C(=O)NCc2c(C)cc(C)[nH]c2=O)c1C)C1CCC(O)CC1] |
| 314 | 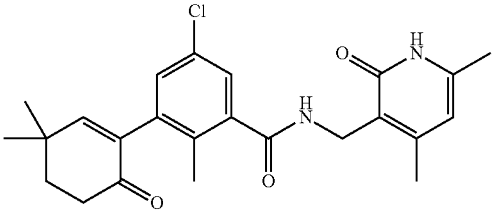 |

-continued
| Compound Number | Structure |
|---|---|
| 315 | 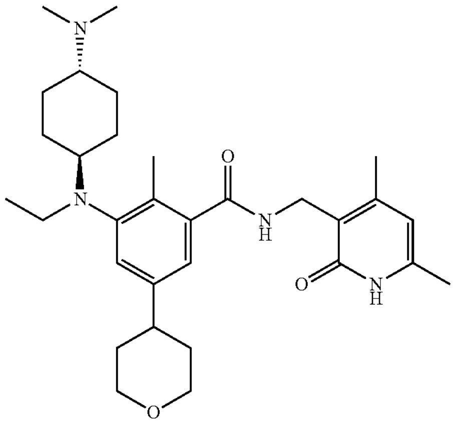 [SMILES: CCN(c1cc(C2CCOCC2)cc(C(=O)NCc2c(C)cc(C)[nH]c2=O)c1C)[C@H]1CC[C@H](N(C)C)CC1] |
| 316 | 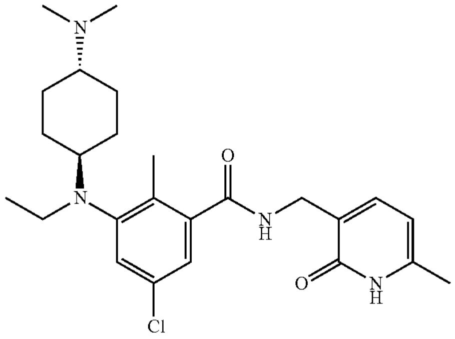 [SMILES: CCN(c1cc(Cl)cc(C(=O)NCc2ccc(C)[nH]c2=O)c1C)[C@H]1CC[C@H](N(C)C)CC1] |
| 317 | 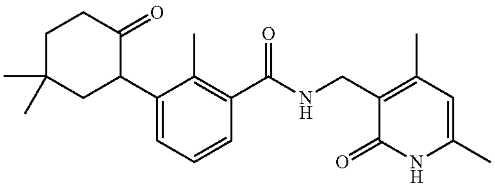 |
| 318 | 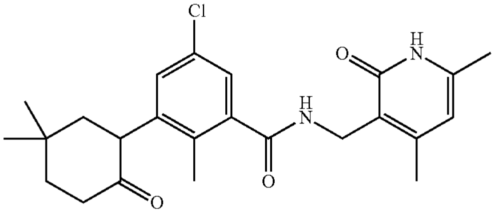 |
| 319 | 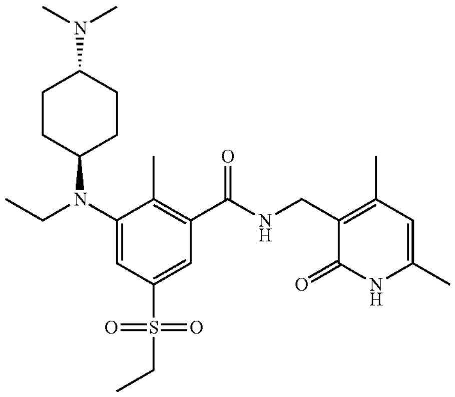 [SMILES: CCN(c1cc(S(=O)(=O)CC)cc(C(=O)NCc2c(C)cc(C)[nH]c2=O)c1C)[C@H]1CC[C@H](N(C)C)CC1] |

-continued
| Compound Number | Structure |
|---|---|
| 320 | 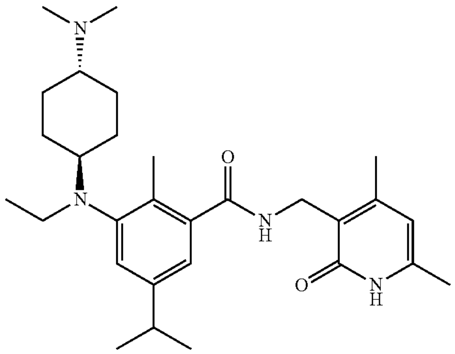 [SMILES: CCN(c1cc(C(C)C)cc(C(=O)NCc2c(C)cc(C)[nH]c2=O)c1C)[C@H]1CC[C@H](N(C)C)CC1] |
| 321 | 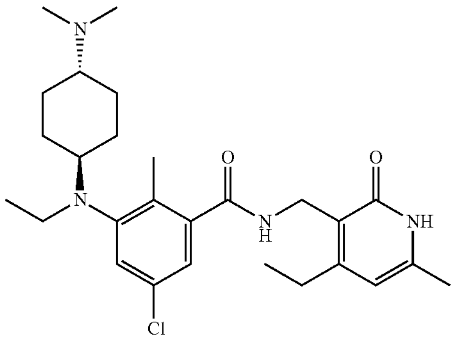 [SMILES: CCc1cc(C)[nH]c(=O)c1CNC(=O)c1cc(Cl)cc(N(CC)[C@H]2CC[C@H](N(C)C)CC2)c1C] |
| 322 | 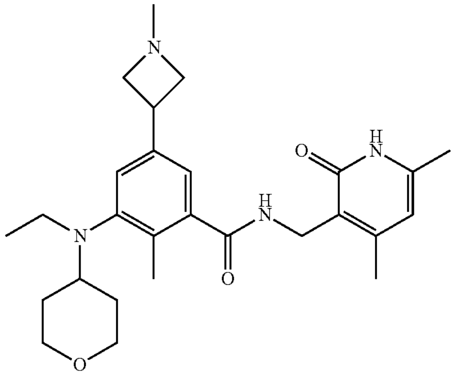 [SMILES: CCN(c1cc(C2CN(C)C2)cc(C(=O)NCc2c(C)cc(C)[nH]c2=O)c1C)C1CCOCC1] |
| 323 | 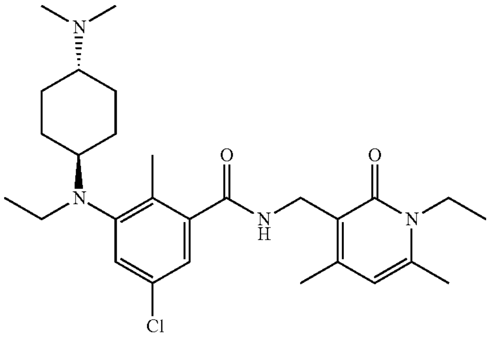 [SMILES: CCn1c(C)cc(C)c(CNC(=O)c2cc(Cl)cc(N(CC)[C@H]3CC[C@H](N(C)C)CC3)c2C)c1=O] |

-continued
| Compound Number | Structure |
| --- | --- |
| 324 | 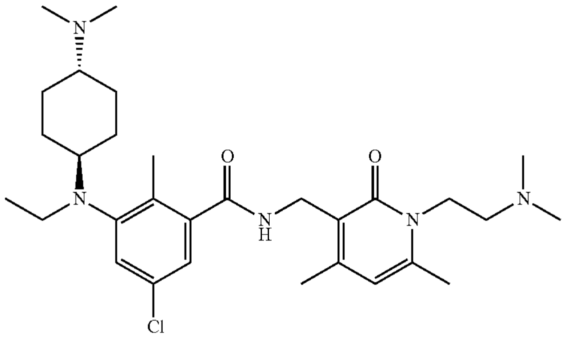 [SMILES: CCN(c1cc(Cl)cc(C(=O)NCc2c(C)cc(C)n(CCN(C)C)c2=O)c1C)[C@H]1CC[C@H](N(C)C)CC1] |
| 325 | 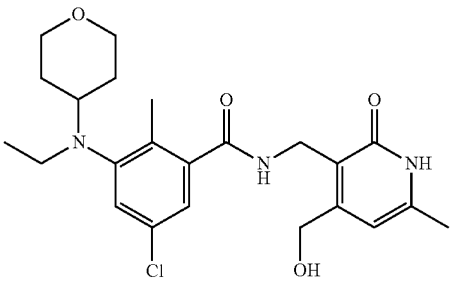 [SMILES: CCN(c1cc(Cl)cc(C(=O)NCc2c(CO)cc(C)[nH]c2=O)c1C)C1CCOCC1] |
| 326 | 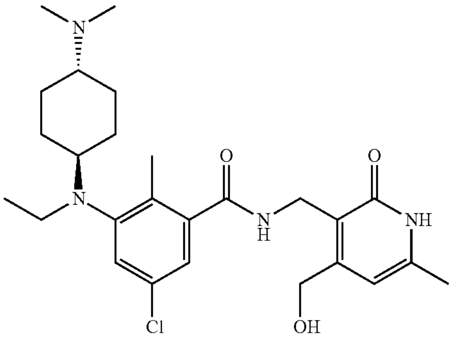 [SMILES: CCN(c1cc(Cl)cc(C(=O)NCc2c(CO)cc(C)[nH]c2=O)c1C)[C@H]1CC[C@H](N(C)C)CC1] |
| 327 | 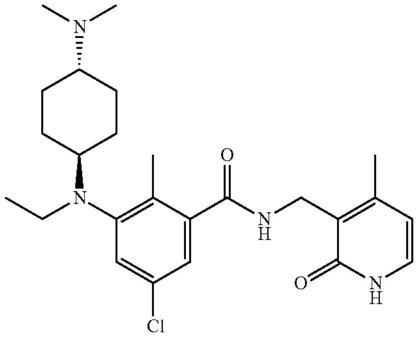 [SMILES: CCN(c1cc(Cl)cc(C(=O)NCc2c(C)cc[nH]c2=O)c1C)[C@H]1CC[C@H](N(C)C)CC1] |
| 328 | 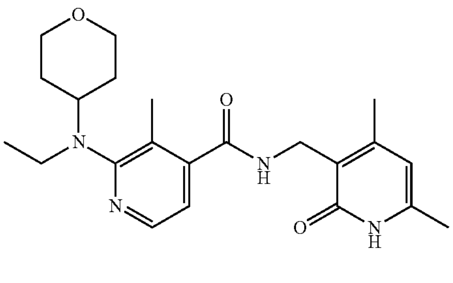 [SMILES: CCN(c1nccc(C(=O)NCc2c(C)cc(C)[nH]c2=O)c1C)C1CCOCC1] |

-continued
| Compound Number | Structure |
|---|---|
| 329 | 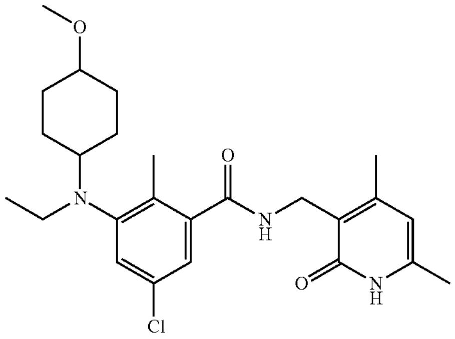 |
| 330 | 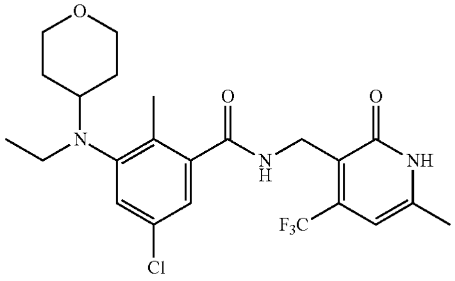 [SMILES: CCN(c1cc(Cl)cc(C(=O)NCc2c(C(F)(F)F)cc(C)[nH]c2=O)c1C)C1CCOCC1] |
| 331 | 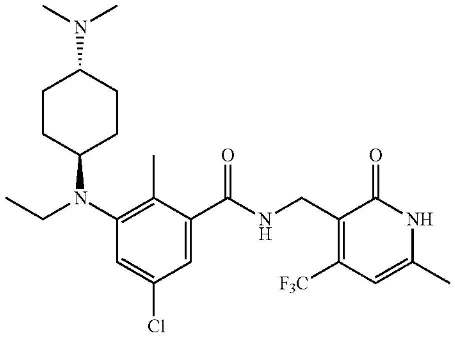 [SMILES: CCN(c1cc(Cl)cc(C(=O)NCc2c(C(F)(F)F)cc(C)[nH]c2=O)c1C)[C@H]1CC[C@H](N(C)C)CC1] |
| 332 | 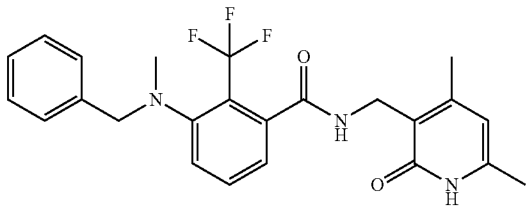 [SMILES: Cc1cc(C)c(CNC(=O)c2cccc(N(C)Cc3ccccc3)c2C(F)(F)F)c(=O)[nH]1] |
| 333 | 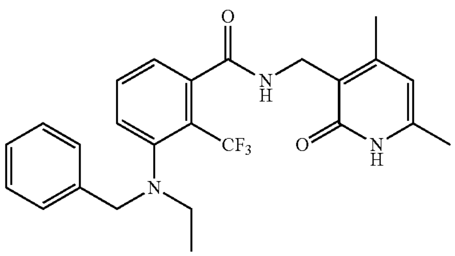 [SMILES: CCN(Cc1ccccc1)c1cccc(C(=O)NCc2c(C)cc(C)[nH]c2=O)c1C(F)(F)F] |

-continued
| Compound Number | Structure |
|---|---|
| 334 | 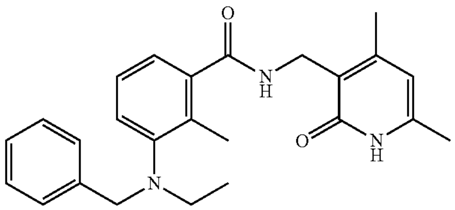 [SMILES: CCN(Cc1ccccc1)c1cccc(C(=O)NCc2c(C)cc(C)[nH]c2=O)c1C] |
| 335 | 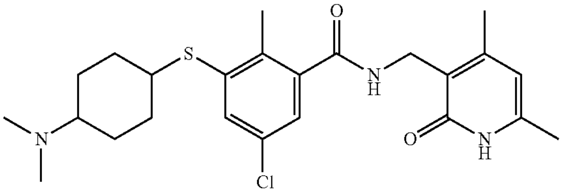 |
| 336 | 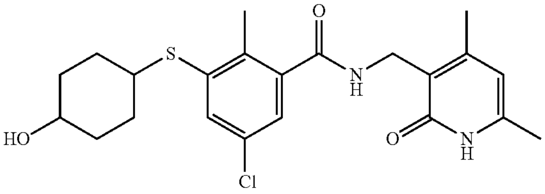 [SMILES: Cc1cc(C)c(CNC(=O)c2cc(Cl)cc(SC3CCC(O)CC3)c2C)c(=O)[nH]1] |
| 337 | 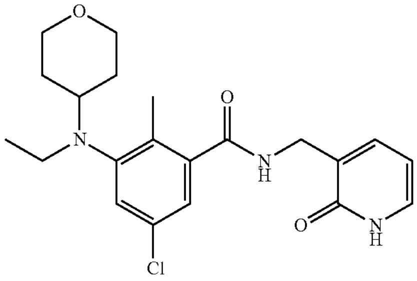 [SMILES: CCN(c1cc(Cl)cc(C(=O)NCc2ccc[nH]c2=O)c1C)C1CCOCC1] |
| 338 | 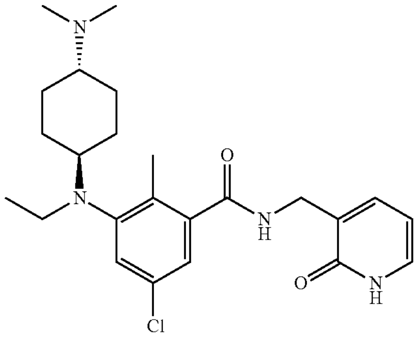 [SMILES: CCN(c1cc(Cl)cc(C(=O)NCc2ccc[nH]c2=O)c1C)[C@H]1CC[C@H](N(C)C)CC1] |
| 339 | 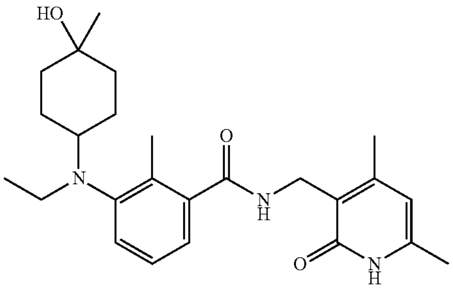 |

-continued
| Compound Number | Structure |
|---|---|
| 340 | 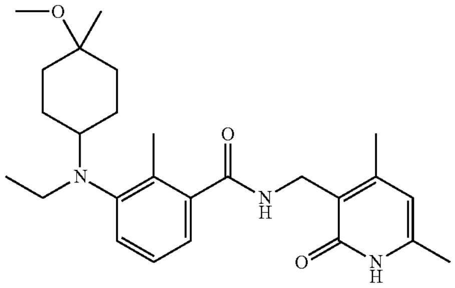 [SMILES: CCN(c1cccc(C(=O)NCc2c(C)cc(C)[nH]c2=O)c1C)C1CCC(C)(OC)CC1] |
| 341 | 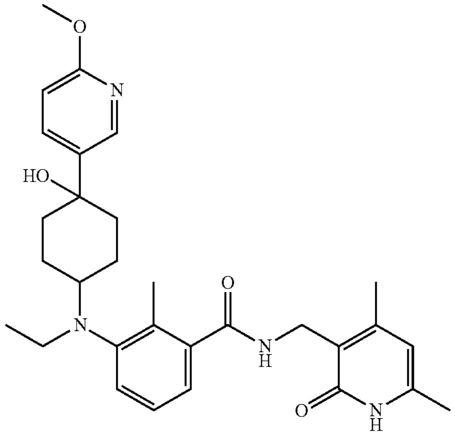 [SMILES: CCN(c1cccc(C(=O)NCc2c(C)cc(C)[nH]c2=O)c1C)C1CCC(O)(c2ccc(OC)nc2)CC1] |
| 342 | 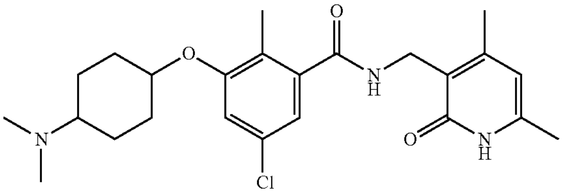 |
| 343 | 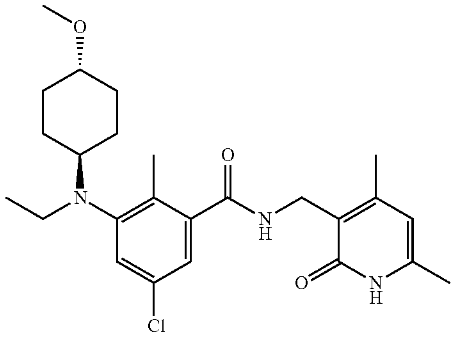 [SMILES: CCN(c1cc(Cl)cc(C(=O)NCc2c(C)cc(C)[nH]c2=O)c1C)[C@H]1CC[C@H](OC)CC1] |

-continued
| Compound Number | Structure |
|---|---|
| 344 | 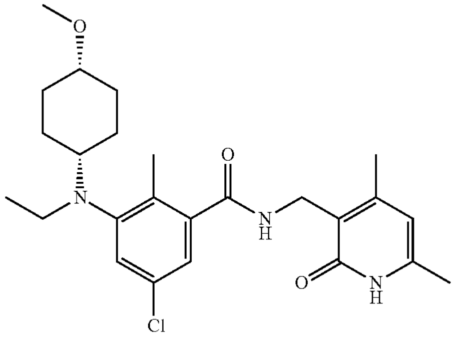 [SMILES: CCN(c1cc(Cl)cc(C(=O)NCc2c(C)cc(C)[nH]c2=O)c1C)[C@H]1CC[C@@H](OC)CC1] |
| 345 | 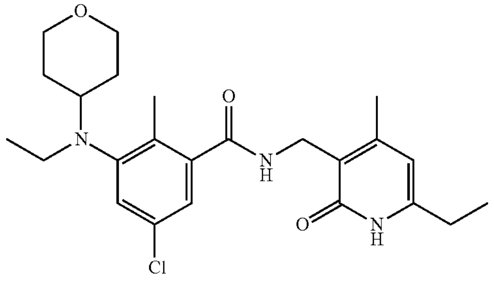 [SMILES: CCc1cc(C)c(CNC(=O)c2cc(Cl)cc(N(CC)C3CCOCC3)c2C)c(=O)[nH]1] |
| 346 | 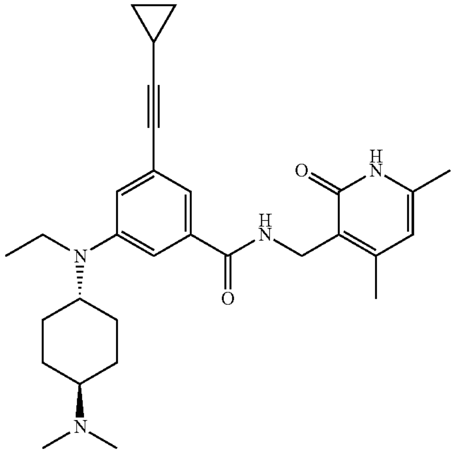 |
| 347 | 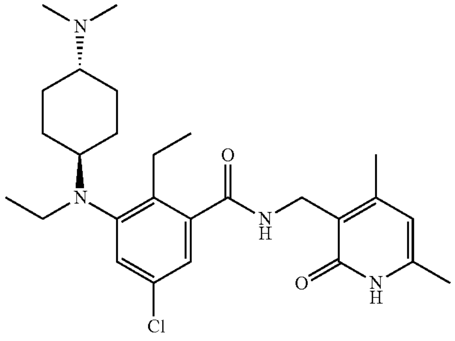 [SMILES: CCc1c(C(=O)NCc2c(C)cc(C)[nH]c2=O)cc(Cl)cc1N(CC)[C@H]1CC[C@H](N(C)C)CC1] |

-continued
| Compound Number | Structure |
|---|---|
| 348 | 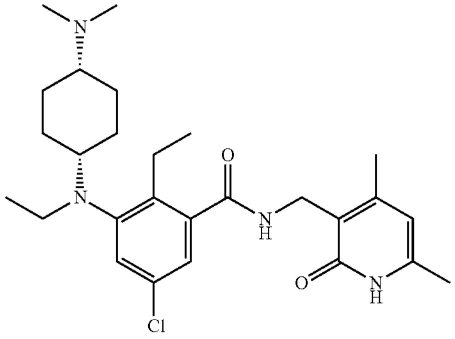 [SMILES: CCc1c(C(=O)NCc2c(C)cc(C)[nH]c2=O)cc(Cl)cc1N(CC)[C@H]1CC[C@@H](N(C)C)CC1] |
| 349 | 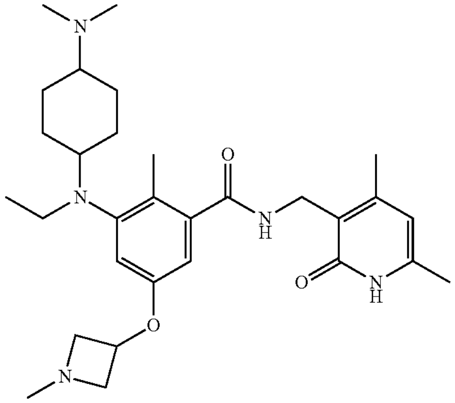 [SMILES: CCN(c1cc(OC2CN(C)C2)cc(C(=O)NCc2c(C)cc(C)[nH]c2=O)c1C)C1CCC(N(C)C)CC1] |
| 350 | 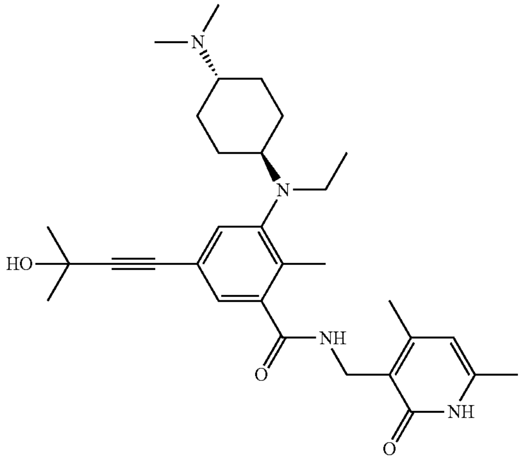 [SMILES: CCN(c1cc(C#CC(C)(C)O)cc(C(=O)NCc2c(C)cc(C)[nH]c2=O)c1C)[C@H]1CC[C@H](N(C)C)CC1] |

-continued
| Compound Number | Structure |
|---|---|
| 351 | 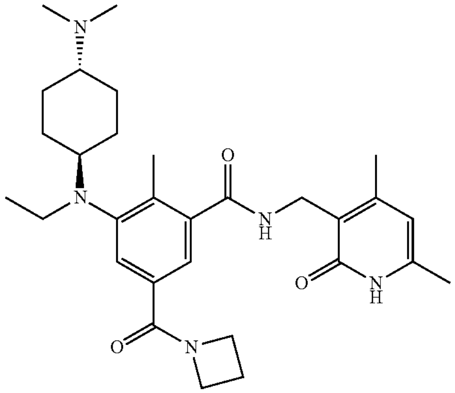 [SMILES: CCN(c1cc(C(=O)N2CCC2)cc(C(=O)NCc2c(C)cc(C)[nH]c2=O)c1C)[C@H]1CC[C@H](N(C)C)CC1] |
| 352 | 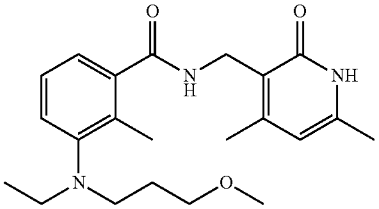 [SMILES: CCN(CCCOC)c1cccc(C(=O)NCc2c(C)cc(C)[nH]c2=O)c1C] |
| 353 | 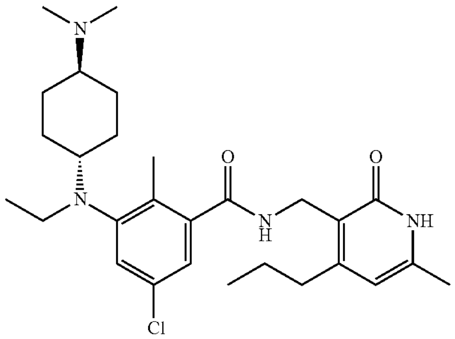 [SMILES: CCCc1cc(C)[nH]c(=O)c1CNC(=O)c1cc(Cl)cc(N(CC)[C@H]2CC[C@H](N(C)C)CC2)c1C] |
| 354 | 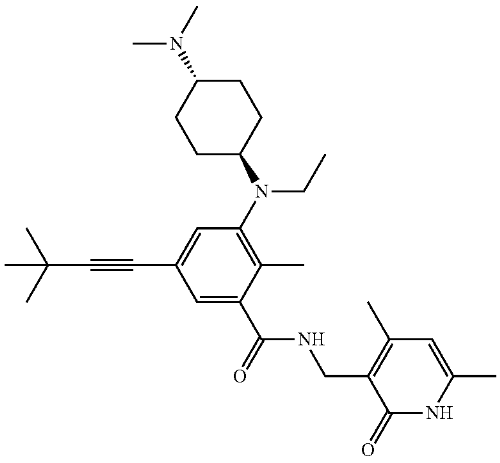 [SMILES: CCN(c1cc(C#CC(C)(C)C)cc(C(=O)NCc2c(C)cc(C)[nH]c2=O)c1C)[C@H]1CC[C@H](N(C)C)CC1] |

-continued
| Compound Number | Structure |
|---|---|
| 355 | 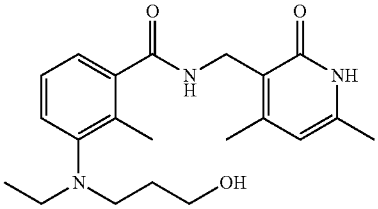 [SMILES: CCN(CCCO)c1cccc(C(=O)NCc2c(C)cc(C)[nH]c2=O)c1C] |
| 356 | 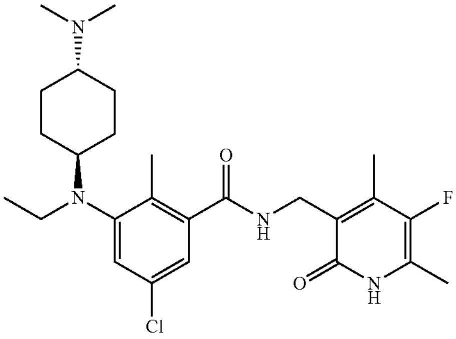 [SMILES: CCN(c1cc(Cl)cc(C(=O)NCc2c(C)c(F)c(C)[nH]c2=O)c1C)[C@H]1CC[C@H](N(C)C)CC1] |
| 357 | 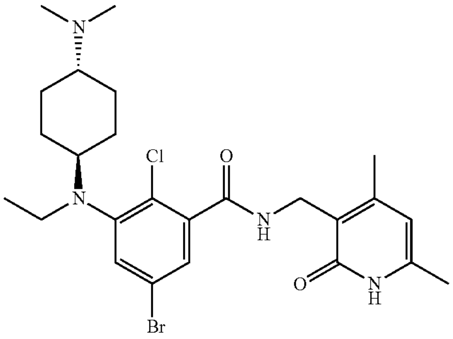 |
| 358 | 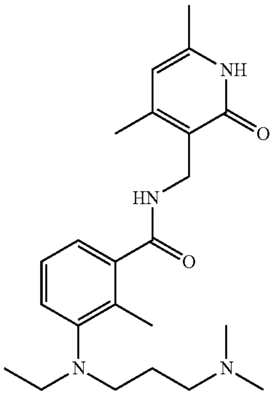 [SMILES: CCN(CCCN(C)C)c1cccc(C(=O)NCc2c(C)cc(C)[nH]c2=O)c1C] |

-continued
| Compound Number | Structure |
| --- | --- |
| 359 | 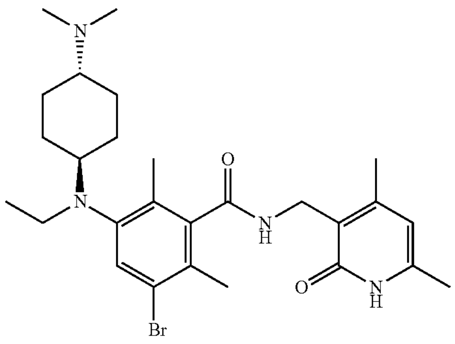 [SMILES: CCN(c1cc(Br)c(C)c(C(=O)NCc2c(C)cc(C)[nH]c2=O)c1C)[C@H]1CC[C@H](N(C)C)CC1] |
| 360 | 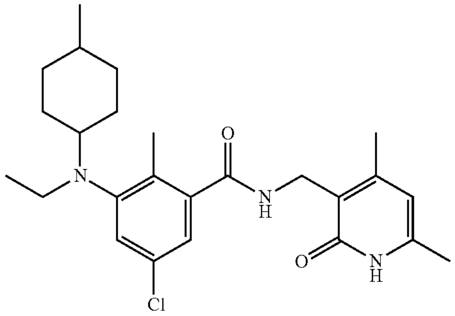 |
| 361 | 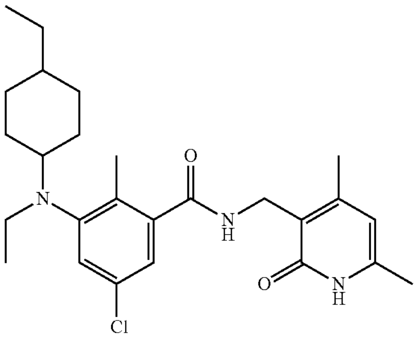 [SMILES: CCC1CCC(N(CC)c2cc(Cl)cc(C(=O)NCc3c(C)cc(C)[nH]c3=O)c2C)CC1] |
| 362 | 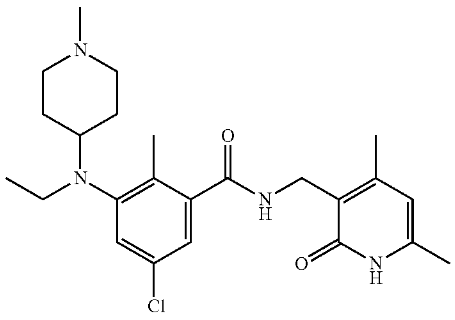 |

-continued
| Compound Number | Structure |
|---|---|
| 363 | 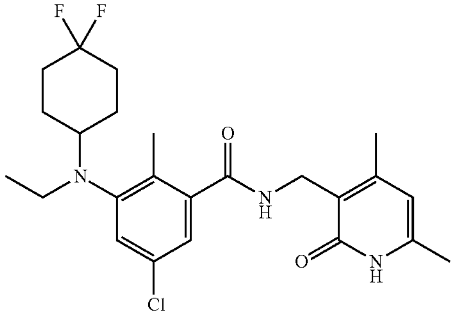 [SMILES: CCN(c1cc(Cl)cc(C(=O)NCc2c(C)cc(C)[nH]c2=O)c1C)C1CCC(F)(F)CC1] |
| 364 | 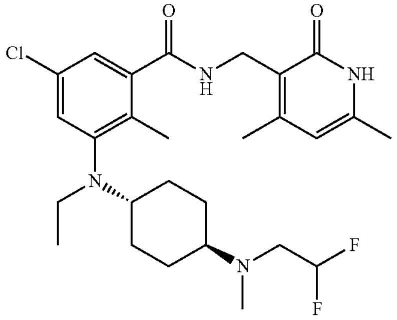 [SMILES: CCN(c1cc(Cl)cc(C(=O)NCc2c(C)cc(C)[nH]c2=O)c1C)[C@H]1CC[C@H](N(C)CC(F)F)CC1] |
| 365 | 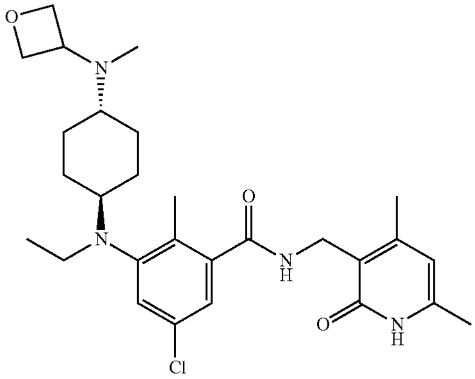 [SMILES: CCN(c1cc(Cl)cc(C(=O)NCc2c(C)cc(C)[nH]c2=O)c1C)[C@H]1CC[C@H](N(C)C2COC2)CC1] |
| 366 | 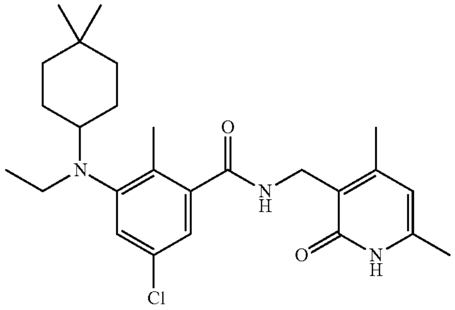 [SMILES: CCN(c1cc(Cl)cc(C(=O)NCc2c(C)cc(C)[nH]c2=O)c1C)C1CCC(C)(C)CC1] |

-continued
| Compound Number | Structure |
|---|---|
| 367 | 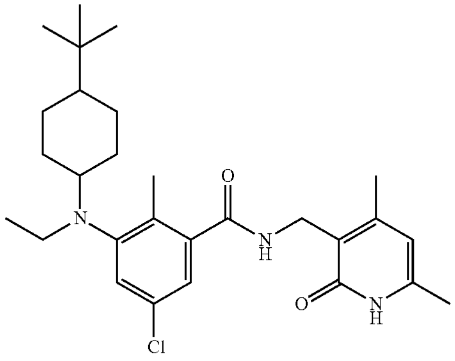 [SMILES: CCN(c1cc(Cl)cc(C(=O)NCc2c(C)cc(C)[nH]c2=O)c1C)C1CCC(C(C)(C)C)CC1] |
| 368 | 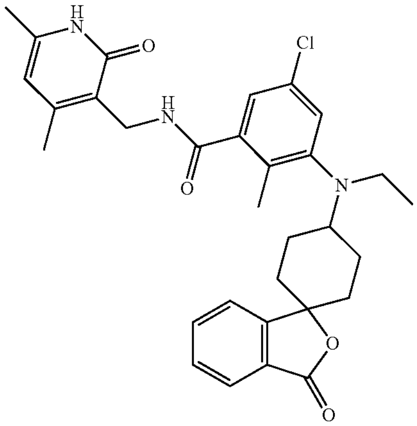 |
| 369 | 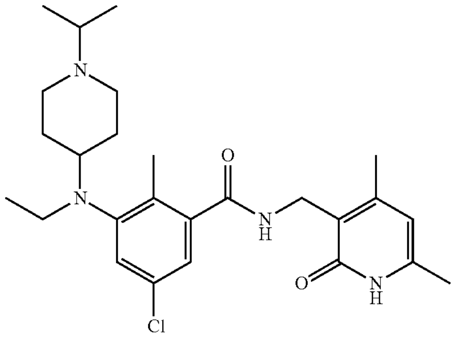 [SMILES: CCN(c1cc(Cl)cc(C(=O)NCc2c(C)cc(C)[nH]c2=O)c1C)C1CCN(C(C)C)CC1] |
| 370 | 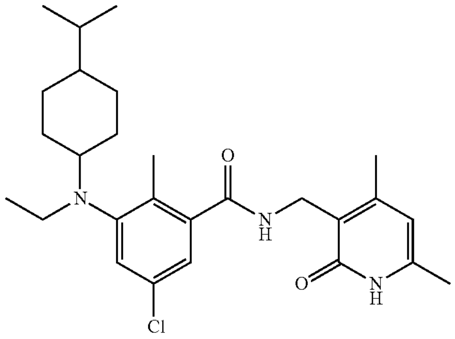 [SMILES: CCN(c1cc(Cl)cc(C(=O)NCc2c(C)cc(C)[nH]c2=O)c1C)C1CCC(C(C)C)CC1] |

-continued
| Compound Number | Structure |
|---|---|
| 371 | 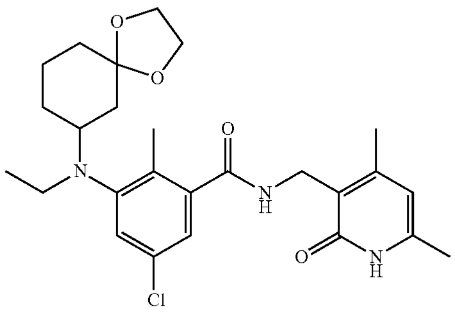 [SMILES: CCN(c1cc(Cl)cc(C(=O)NCc2c(C)cc(C)[nH]c2=O)c1C)C1CCCC2(C1)OCCO2] |
| 372 | 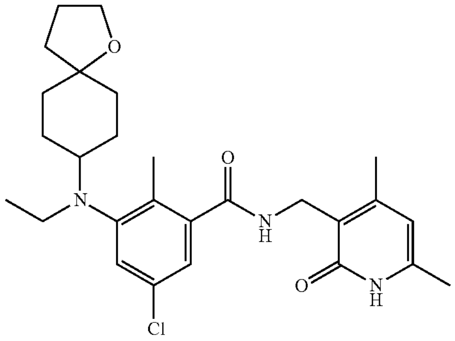 [SMILES: CCN(c1cc(Cl)cc(C(=O)NCc2c(C)cc(C)[nH]c2=O)c1C)C1CCC2(CCCO2)CC1] |
| 373 | 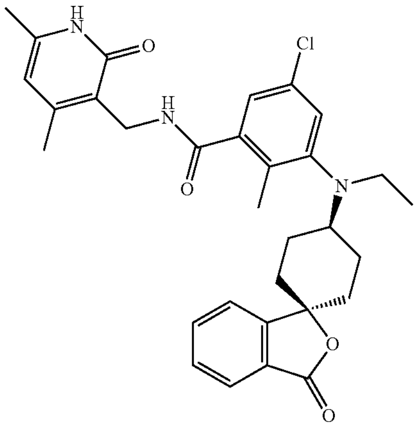 [SMILES: CCN(c1cc(Cl)cc(C(=O)NCc2c(C)cc(C)[nH]c2=O)c1C)[C@H]1CC[C@]2(CC1)OC(=O)c1ccccc12] |
| 374 | 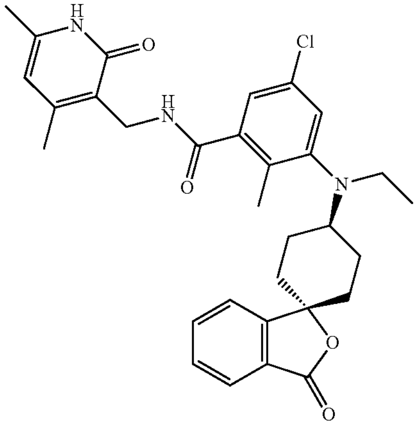 [SMILES: CCN(c1cc(Cl)cc(C(=O)NCc2c(C)cc(C)[nH]c2=O)c1C)[C@H]1CC[C@@]2(CC1)OC(=O)c1ccccc12] |

-continued
| Compound Number | Structure |
|---|---|
| 375 | 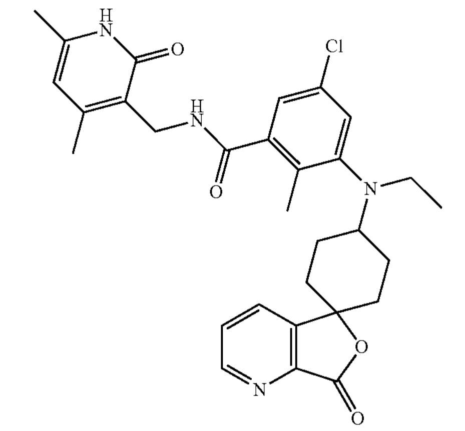 [SMILES: CCN(c1cc(Cl)cc(C(=O)NCc2c(C)cc(C)[nH]c2=O)c1C)C1CCC2(CC1)OC(=O)c1ncccc12] |
| 376 | 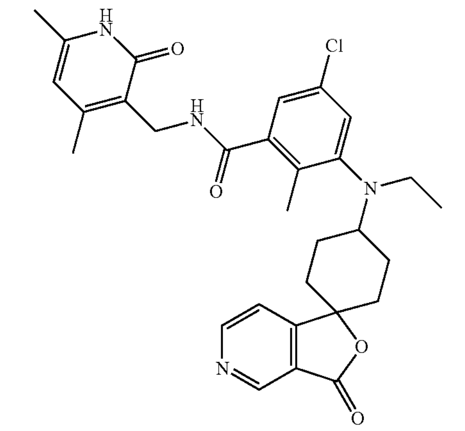 [SMILES: CCN(c1cc(Cl)cc(C(=O)NCc2c(C)cc(C)[nH]c2=O)c1C)C1CCC2(CC1)OC(=O)c1cnccc12] |
| 377 | 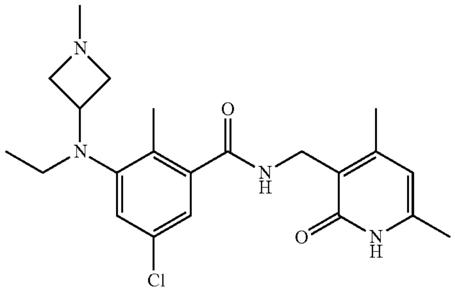 [SMILES: CCN(c1cc(Cl)cc(C(=O)NCc2c(C)cc(C)[nH]c2=O)c1C)C1CN(C)C1] |
| 378 | 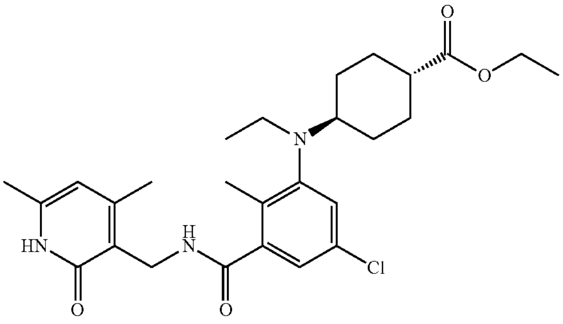 [SMILES: CCOC(=O)[C@H]1CC[C@H](N(CC)c2cc(Cl)cc(C(=O)NCc3c(C)cc(C)[nH]c3=O)c2C)CC1] |

-continued
| Compound Number | Structure |
|---|---|
| 379 | 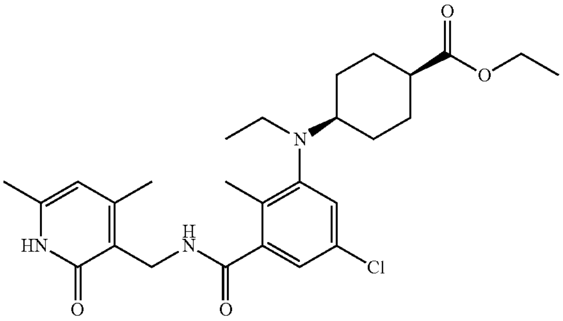 [SMILES: CCOC(=O)[C@H]1CC[C@@H](N(CC)c2cc(Cl)cc(C(=O)NCc3c(C)cc(C)[nH]c3=O)c2C)CC1] |
| 380 | 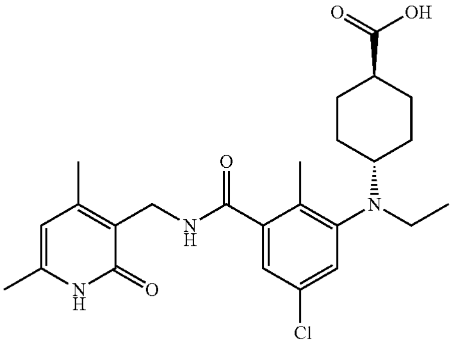 |
| 381 | 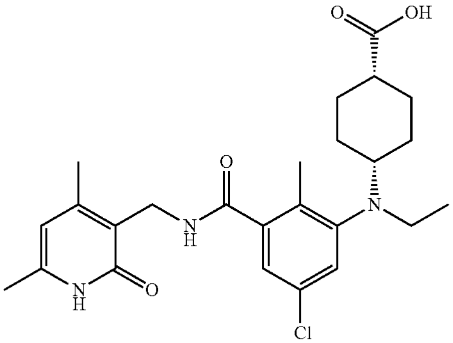 [SMILES: CCN(c1cc(Cl)cc(C(=O)NCc2c(C)cc(C)[nH]c2=O)c1C)[C@H]1CC[C@@H](C(=O)O)CC1] |
| 382 | 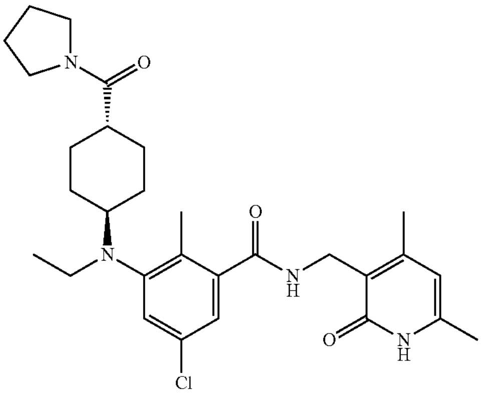 [SMILES: CCN(c1cc(Cl)cc(C(=O)NCc2c(C)cc(C)[nH]c2=O)c1C)[C@H]1CC[C@H](C(=O)N2CCCC2)CC1] |

-continued
| Compound Number | Structure |
|---|---|
| 383 | 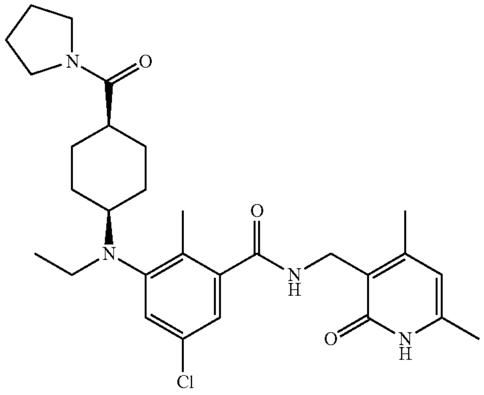 [SMILES: CCN(c1cc(Cl)cc(C(=O)NCc2c(C)cc(C)[nH]c2=O)c1C)[C@H]1CC[C@@H](C(=O)N2CCCC2)CC1] |
| 384 | 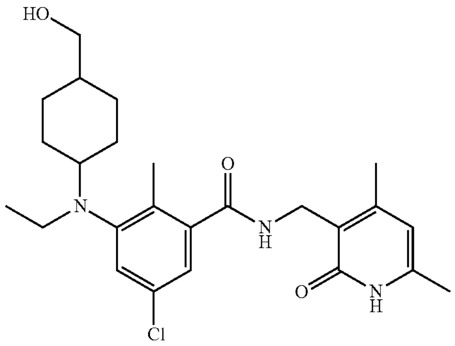 [SMILES: CCN(c1cc(Cl)cc(C(=O)NCc2c(C)cc(C)[nH]c2=O)c1C)C1CCC(CO)CC1] |
| 385 | 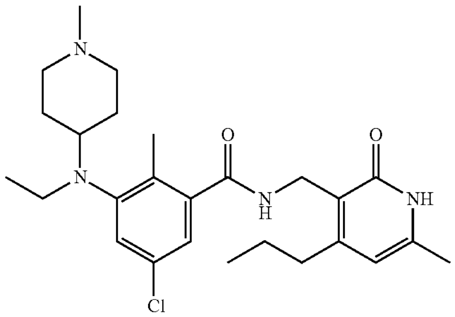 [SMILES: CCCc1cc(C)[nH]c(=O)c1CNC(=O)c1cc(Cl)cc(N(CC)C2CCN(C)CC2)c1C] |
| 386 | 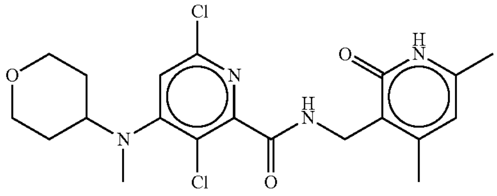 |
| 387 | 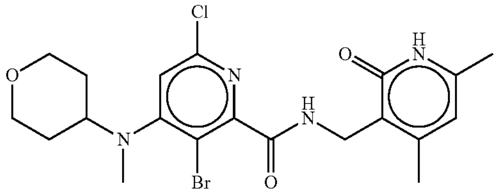 |

-continued
| Compound Number | Structure |
|---|---|
| 388 | 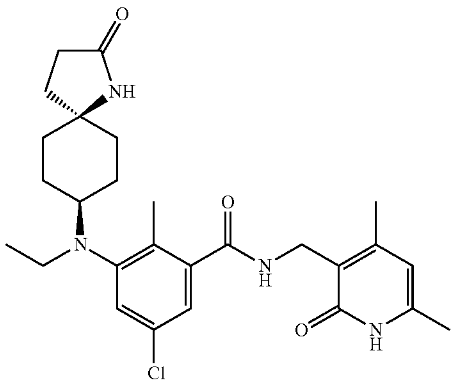 [SMILES: CCN(c1cc(Cl)cc(C(=O)NCc2c(C)cc(C)[nH]c2=O)c1C)[C@H]1CC[C@]2(CCC(=O)N2)CC1] |
| 389 | 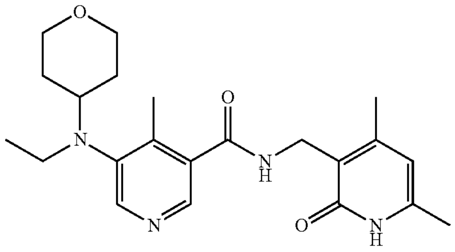 [SMILES: CCN(c1cncc(C(=O)NCc2c(C)cc(C)[nH]c2=O)c1C)C1CCOCC1] |
| 390 | 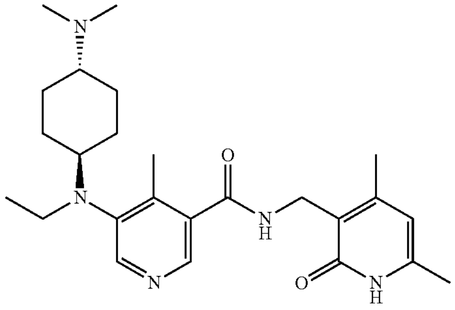 [SMILES: CCN(c1cncc(C(=O)NCc2c(C)cc(C)[nH]c2=O)c1C)[C@H]1CC[C@H](N(C)C)CC1] |
| 391 | 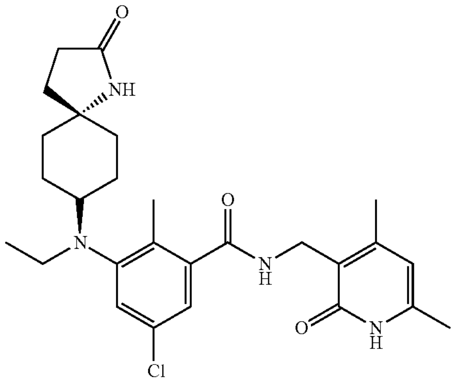 |

-continued
| Compound Number | Structure |
|---|---|
| 392 | 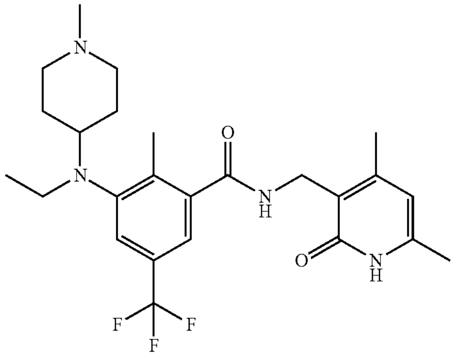 [SMILES: CCN(c1cc(C(F)(F)F)cc(C(=O)NCc2c(C)cc(C)[nH]c2=O)c1C)C1CCN(C)CC1] |
| 393 | 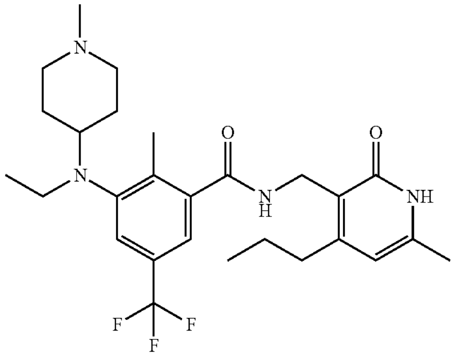 |
| 394 | 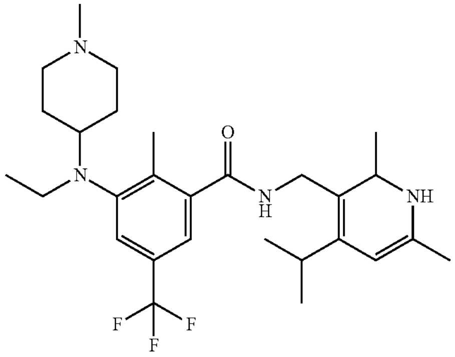 [SMILES: CCN(c1cc(C(F)(F)F)cc(C(=O)NCC2=C(C(C)C)C=C(C)NC2C)c1C)C1CCN(C)CC1] |
| 395 | 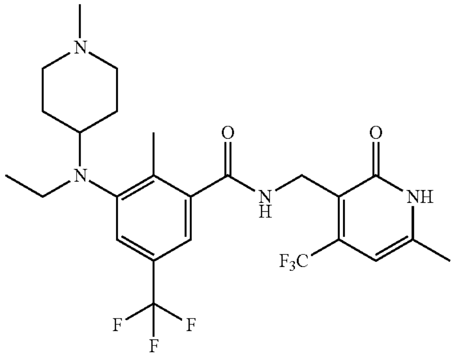 |

-continued
| Compound Number | Structure |
|---|---|
| 396 | 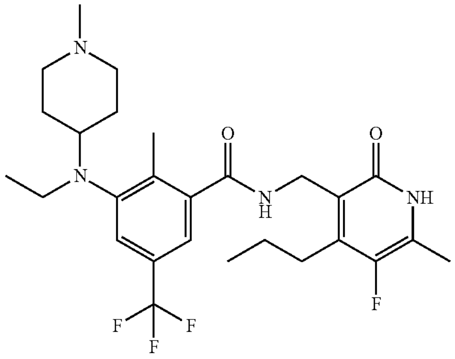 [SMILES: CCCc1c(F)c(C)[nH]c(=O)c1CNC(=O)c1cc(C(F)(F)F)cc(N(CC)C2CCN(C)CC2)c1C] |
| 397 | 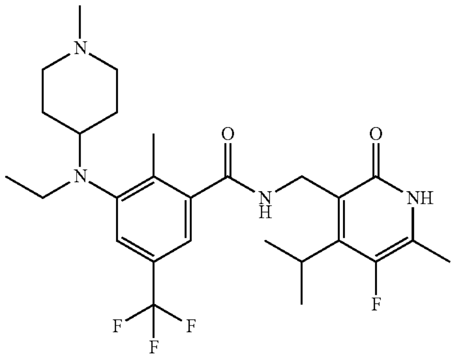 [SMILES: CCN(c1cc(C(F)(F)F)cc(C(=O)NCc2c(C(C)C)c(F)c(C)[nH]c2=O)c1C)C1CCN(C)CC1] |
| 398 | 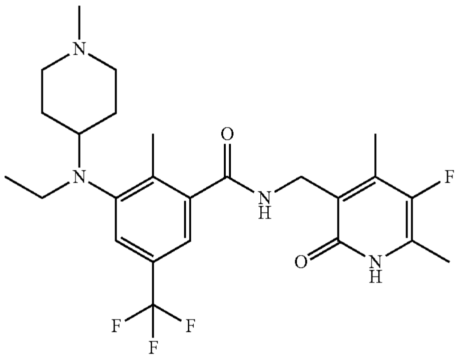 [SMILES: CCN(c1cc(C(F)(F)F)cc(C(=O)NCc2c(C)c(F)c(C)[nH]c2=O)c1C)C1CCN(C)CC1] |
| 399 | 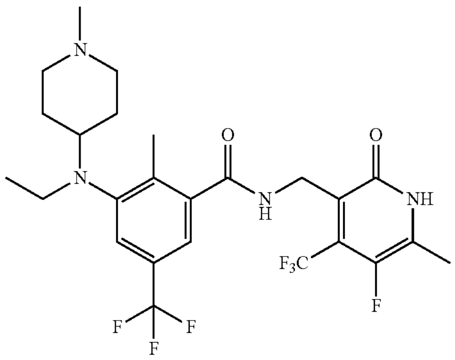 [SMILES: CCN(c1cc(C(F)(F)F)cc(C(=O)NCc2c(C(F)(F)F)c(F)c(C)[nH]c2=O)c1C)C1CCN(C)CC1] |

-continued
| Compound Number | Structure |
|---|---|
| 400 | 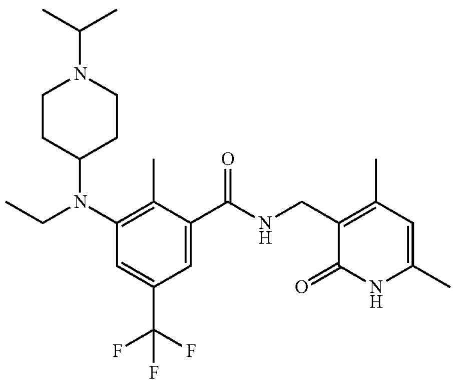 [SMILES: CCN(c1cc(C(F)(F)F)cc(C(=O)NCc2c(C)cc(C)[nH]c2=O)c1C)C1CCN(C(C)C)CC1] |
| 401 | 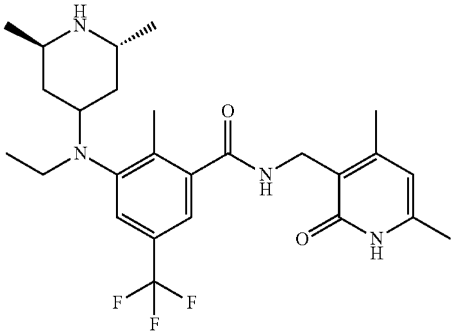 [SMILES: CCN(c1cc(C(F)(F)F)cc(C(=O)NCc2c(C)cc(C)[nH]c2=O)c1C)C1C[C@@H](C)N[C@H](C)C1] |
| 402 | 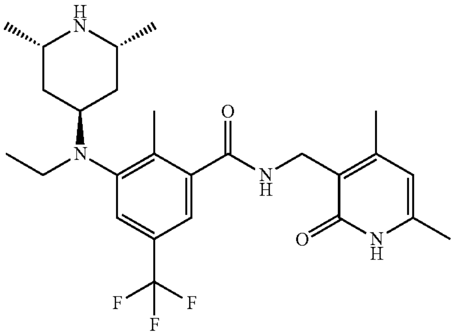 [SMILES: CCN(c1cc(C(F)(F)F)cc(C(=O)NCc2c(C)cc(C)[nH]c2=O)c1C)[C@@H]1C[C@@H](C)N[C@@H](C)C1] |
| 403 | 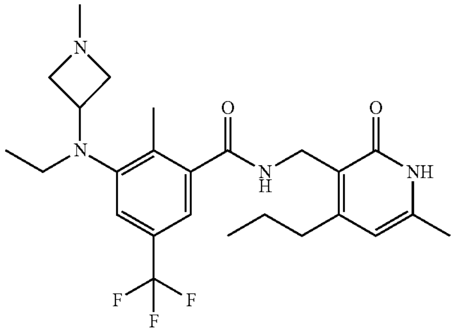 [SMILES: CCCc1cc(C)[nH]c(=O)c1CNC(=O)c1cc(C(F)(F)F)cc(N(CC)C2CN(C)C2)c1C] |

-continued
| Compound Number | Structure |
|---|---|
| 404 | 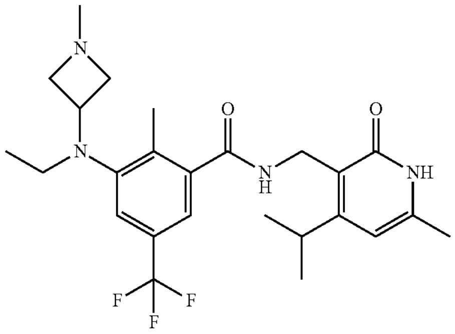 [SMILES: CCN(c1cc(C(F)(F)F)cc(C(=O)NCc2c(C(C)C)cc(C)[nH]c2=O)c1C)C1CN(C)C1] |
| 405 | 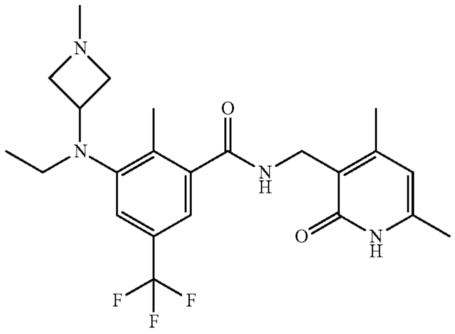 [SMILES: CCN(c1cc(C(F)(F)F)cc(C(=O)NCc2c(C)cc(C)[nH]c2=O)c1C)C1CN(C)C1] |
| 406 | 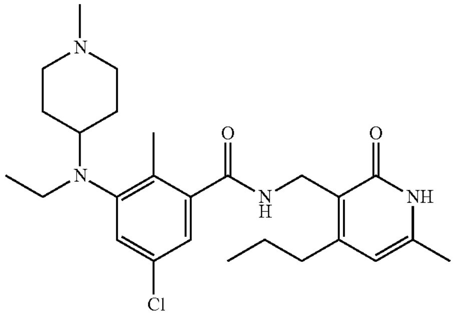 [SMILES: CCCc1cc(C)[nH]c(=O)c1CNC(=O)c1cc(Cl)cc(N(CC)C2CCN(C)CC2)c1C] |
| 407 | 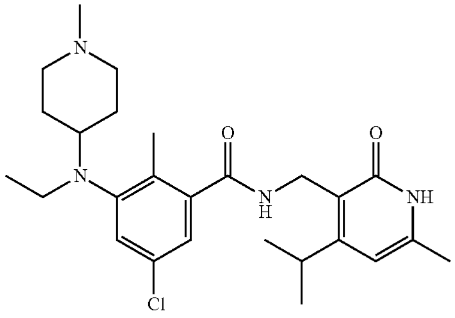 [SMILES: CCN(c1cc(Cl)cc(C(=O)NCc2c(C(C)C)cc(C)[nH]c2=O)c1C)C1CCN(C)CC1] |

-continued
| Compound Number | Structure |
|---|---|
| 408 | 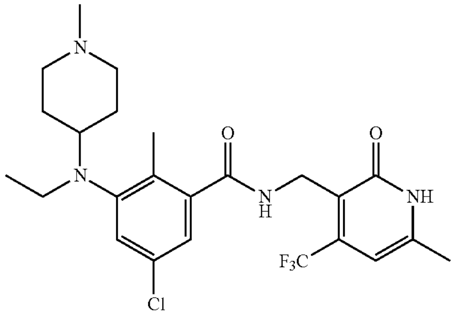 [SMILES: CCN(c1cc(Cl)cc(C(=O)NCc2c(C(F)(F)F)cc(C)[nH]c2=O)c1C)C1CCN(C)CC1] |
| 409 | 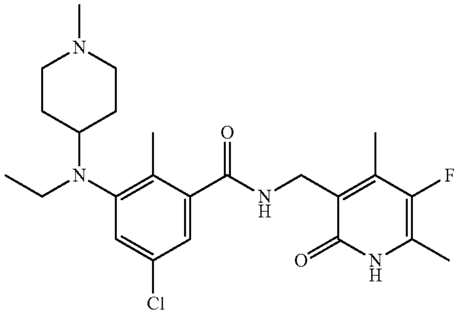 [SMILES: CCN(c1cc(Cl)cc(C(=O)NCc2c(C)c(F)c(C)[nH]c2=O)c1C)C1CCN(C)CC1] |
| 410 | 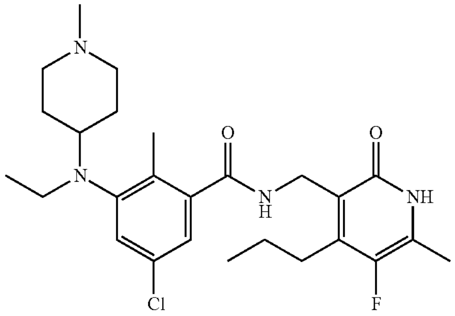 [SMILES: CCCc1c(F)c(C)[nH]c(=O)c1CNC(=O)c1cc(Cl)cc(N(CC)C2CCN(C)CC2)c1C] |
| 411 | 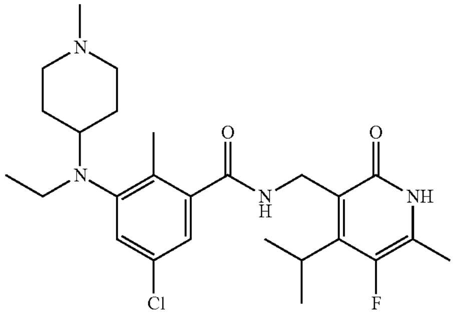 [SMILES: CCN(c1cc(Cl)cc(C(=O)NCc2c(C(C)C)c(F)c(C)[nH]c2=O)c1C)C1CCN(C)CC1] |
| 412 | 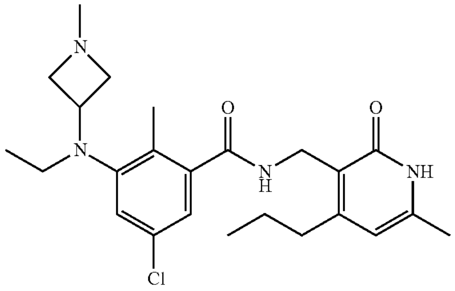 [SMILES: CCCc1cc(C)[nH]c(=O)c1CNC(=O)c1cc(Cl)cc(N(CC)C2CN(C)C2)c1C] |

-continued
| Compound Number | Structure |
|---|---|
| 413 | 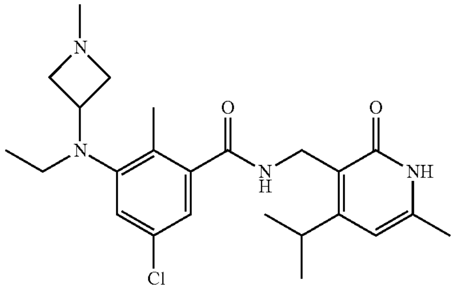 [SMILES: CCN(c1cc(Cl)cc(C(=O)NCc2c(C(C)C)cc(C)[nH]c2=O)c1C)C1CN(C)C1] |
| 414 | 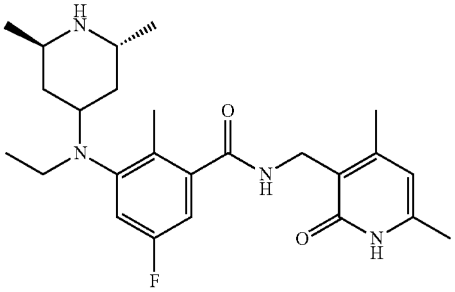 [SMILES: CCN(c1cc(F)cc(C(=O)NCc2c(C)cc(C)[nH]c2=O)c1C)C1C[C@@H](C)N[C@H](C)C1] |
| 415 | 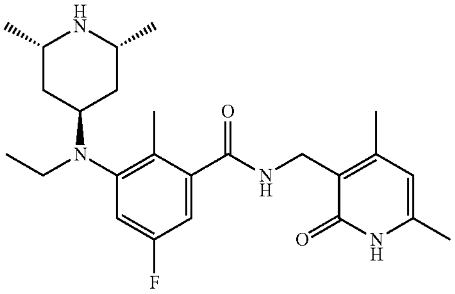 [SMILES: CCN(c1cc(F)cc(C(=O)NCc2c(C)cc(C)[nH]c2=O)c1C)[C@@H]1C[C@@H](C)N[C@@H](C)C1] |
| 416 | 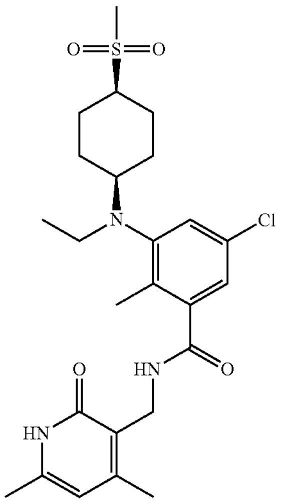 [SMILES: CCN(c1cc(Cl)cc(C(=O)NCc2c(C)cc(C)[nH]c2=O)c1C)[C@H]1CC[C@@H](S(C)(=O)=O)CC1] |

-continued
| Compound Number | Structure |
|---|---|
| 417 | 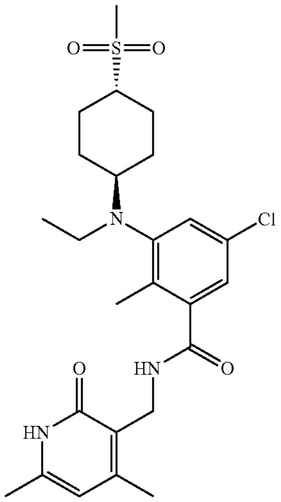 [SMILES: CCN(c1cc(Cl)cc(C(=O)NCc2c(C)cc(C)[nH]c2=O)c1C)[C@H]1CC[C@H](S(C)(=O)=O)CC1] |
| 418 | 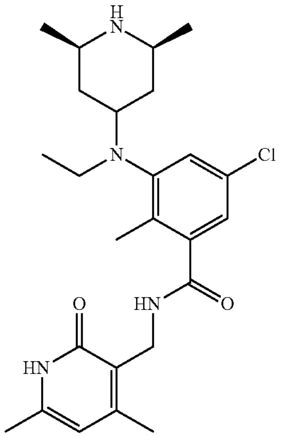 [SMILES: CCN(c1cc(Cl)cc(C(=O)NCc2c(C)cc(C)[nH]c2=O)c1C)C1C[C@@H](C)N[C@@H](C)C1] |
and pharmaceutically acceptable salts thereof.
* * * * *